US008916370B2

(12) United States Patent
Bott et al.

(10) Patent No.: US 8,916,370 B2
(45) Date of Patent: *Dec. 23, 2014

(54) ISOPRENE SYNTHASE VARIANTS FOR IMPROVED MICROBIAL PRODUCTION OF ISOPRENE

(75) Inventors: Richard R. Bott, Burlingame, CA (US); Marguerite A. Cervin, Redwood City, CA (US); James T. Kellis, Jr., Woodside, CA (US); Joseph C. McAuliffe, Sunnyvale, CA (US); Andrei Miasnikov, Mountain View, CA (US); Caroline M. Peres, Palo Alto, CA (US); Christopher Lee Rife, Redwood City, CA (US); Derek H. Wells, Palo Alto, CA (US); Walter Weyler, San Francisco, CA (US); Gregory M. Whited, Belmont, CA (US)

(73) Assignees: Danisco US Inc., Palo Alto, CA (US); The Goodyear Tire & Rubber Company, Akron, OH (US)

( * ) Notice: Subject to any disclaimer, the term of this patent is extended or adjusted under 35 U.S.C. 154(b) by 333 days.

This patent is subject to a terminal disclaimer.

(21) Appl. No.: 13/436,612

(22) Filed: Mar. 30, 2012

(65) Prior Publication Data

US 2013/0260432 A1 Oct. 3, 2013

Related U.S. Application Data

(63) Continuation of application No. 12/429,143, filed on Apr. 23, 2009, now Pat. No. 8,173,410.

(60) Provisional application No. 61/125,336, filed on Apr. 23, 2008.

(51) Int. Cl.
| C12N 9/88 | (2006.01) |
| C12P 21/06 | (2006.01) |
| C12N 15/00 | (2006.01) |
| C12P 5/02 | (2006.01) |
| C12N 1/20 | (2006.01) |
| C12N 1/00 | (2006.01) |
| C07H 21/04 | (2006.01) |
| C07K 1/00 | (2006.01) |
| C12P 5/00 | (2006.01) |

(52) U.S. Cl.
CPC .. *C12N 9/88* (2013.01); *C12P 5/007* (2013.01)
USPC ....... 435/232; 435/69.1; 435/320.1; 435/167; 435/252.3; 435/252.33; 435/254.11; 435/254.2; 435/254.21; 435/254.6; 536/23.1; 536/23.2; 530/350

(58) Field of Classification Search
USPC .............. 435/232, 69.1, 320.1, 167, 252.3, 435/252.33, 254.11, 254.2, 254.21, 254.6; 536/23.1, 23.2; 530/350
See application file for complete search history.

(56) References Cited

U.S. PATENT DOCUMENTS

| 1,344,713 A | 6/1920 | Peters |
| 3,686,349 A | 8/1972 | Schliebs et al. |
| 4,570,029 A | 2/1986 | Kulprathipanja et al. |
| 4,647,344 A | 3/1987 | Lindner et al. |
| 4,683,195 A | 7/1987 | Mullis et al. |
| 4,683,202 A | 7/1987 | Mullis |
| 4,703,007 A | 10/1987 | Mulholland et al. |
| 4,846,872 A | 7/1989 | Kamuro et al. |
| 4,965,188 A | 10/1990 | Mullis et al. |
| 5,322,770 A | 6/1994 | Gelfand |
| 5,349,126 A | 9/1994 | Chappell et al. |
| 5,380,831 A | 1/1995 | Adang et al. |
| 5,436,391 A | 7/1995 | Fujimoto et al. |
| 5,545,816 A | 8/1996 | Ausich et al. |
| 5,849,970 A | 12/1998 | Fall et al. |
| 5,874,276 A | 2/1999 | Fowler et al. |
| 6,022,725 A | 2/2000 | Fowler et al. |
| 6,106,888 A | 8/2000 | Dale et al. |
| 6,176,176 B1 | 1/2001 | Dale et al. |
| 6,268,328 B1 | 7/2001 | Mitchinson et al. |
| 6,270,739 B1 | 8/2001 | Barnicki et al. |
| 6,294,653 B1 | 9/2001 | Mayfield |
| 6,582,914 B1 | 6/2003 | Caldwell et al. |
| 6,806,076 B1 | 10/2004 | Miyake et al. |
| 6,989,257 B2 | 1/2006 | Berry et al. |
| 6,998,471 B2 | 2/2006 | Hallahan et al. |
| 7,129,392 B2 | 10/2006 | Hahn et al. |
| 7,132,268 B2 | 11/2006 | Miyake et al. |
| 7,132,527 B2 | 11/2006 | Payne et al. |
| 7,172,886 B2 | 2/2007 | Keasling et al. |

(Continued)

FOREIGN PATENT DOCUMENTS

| DE | 196 29 568 C1 | 1/1998 |
| EP | 0 215 594 A2 | 3/1987 |

(Continued)

OTHER PUBLICATIONS

Albrecht, M. et al. (Aug. 2000). "Novel Hydroxycarotenoids with Improved Antioxidative Properties Produced by Gene Combination in *Escherichia coli*," *Nature Biotechnology* 18:843-846.

(Continued)

*Primary Examiner* — Ganapathirama Raghu

(74) *Attorney, Agent, or Firm* — Morrison & Foerster LLP

(57) ABSTRACT

The present invention provides methods and compositions comprising at least one isoprene synthase enzyme with improved catalytic activity and/or solubility. In particular, the present invention provides variant plant isoprene synthases for increased isoprene production in microbial host cells. Biosynthetically produced isoprene of the present invention finds use in the manufacture of rubber and elastomers.

21 Claims, 156 Drawing Sheets

(56) References Cited

U.S. PATENT DOCUMENTS

| | | | |
|---|---|---|---|
| 7,183,089 | B2 | 2/2007 | Keasling et al. |
| 7,208,298 | B2 | 4/2007 | Miyake et al. |
| 7,241,587 | B2 | 7/2007 | Dodge et al. |
| 7,262,041 | B2 | 8/2007 | Baldwin et al. |
| 7,364,885 | B2 | 4/2008 | Miyake et al. |
| 7,371,558 | B2 | 5/2008 | Cervin et al. |
| 7,531,333 | B2 | 5/2009 | Miyake et al. |
| 8,173,410 | B2 * | 5/2012 | Bott et al. ............... 435/232 |
| 8,288,148 | B2 | 10/2012 | Cervin et al. |
| 8,420,759 | B2 | 4/2013 | Feher et al. |
| 8,518,686 | B2 | 8/2013 | Beck et al. |
| 8,709,785 | B2 | 4/2014 | Cervin et al. |
| 2002/0095818 | A1 | 7/2002 | Jain et al. |
| 2003/0033626 | A1 | 2/2003 | Hahn et al. |
| 2004/0005678 | A1 | 1/2004 | Kleasling et al. |
| 2004/0219629 | A1 | 11/2004 | Cheng et al. |
| 2005/0287655 | A1 | 12/2005 | Tabata et al. |
| 2006/0009647 | A1 | 1/2006 | Yeates et al. |
| 2006/0020095 | A1 | 1/2006 | Gandon-Pain |
| 2008/0038805 | A1 | 2/2008 | Melis |
| 2008/0178354 | A1 | 7/2008 | Chappell |
| 2009/0155874 | A1 | 6/2009 | Clark et al. |
| 2010/0048964 | A1 | 2/2010 | Calabria et al. |
| 2010/0086978 | A1 | 4/2010 | Beck et al. |
| 2010/0113846 | A1 | 5/2010 | McAuliffe et al. |
| 2010/0196982 | A1 | 8/2010 | Anderson |
| 2010/0285549 | A1 | 11/2010 | Muramatsu et al. |
| 2011/0045563 | A1 | 2/2011 | Melis |
| 2013/0045891 | A1 | 2/2013 | Beck et al. |
| 2013/0071908 | A1 | 3/2013 | Cervin et al. |
| 2013/0078699 | A1 | 3/2013 | Cervin et al. |
| 2013/0252303 | A1 | 9/2013 | Beck et al. |

FOREIGN PATENT DOCUMENTS

| | | |
|---|---|---|
| EP | 0 215 594 A3 | 3/1987 |
| EP | 0 215 594 B1 | 3/1987 |
| EP | 0 215 594 B2 | 3/1987 |
| EP | 0 238 023 A2 | 9/1987 |
| EP | 0 238 023 A3 | 9/1987 |
| EP | 0 238 023 B1 | 9/1987 |
| EP | 0 238 023 B2 | 9/1987 |
| EP | 0 244 234 A2 | 11/1987 |
| EP | 0 244 234 A3 | 11/1987 |
| EP | 0 244 234 B1 | 11/1987 |
| EP | 0 244 234 B2 | 11/1987 |
| EP | 1 118 855 A2 | 7/2001 |
| EP | 1 118 855 A3 | 7/2001 |
| JP | 2006-271379 A | 10/2006 |
| JP | 2008-035831 A | 2/2008 |
| JP | 2008-061506 A | 3/2008 |
| JP | 2008-182950 A | 8/2008 |
| JP | 2009-207402 A | 9/2009 |
| KR | 2001-0084864 A | 9/2001 |
| RU | 2 197 461 C2 | 1/2003 |
| WO | WO-95/04134 A1 | 2/1995 |
| WO | WO-95/11913 A1 | 5/1995 |
| WO | WO-96/35796 A1 | 11/1996 |
| WO | WO-98/02550 A2 | 1/1998 |
| WO | WO-98/02550 A3 | 1/1998 |
| WO | WO-00/17327 A2 | 3/2000 |
| WO | WO-00/17327 A3 | 3/2000 |
| WO | WO-00/17327 A9 | 3/2000 |
| WO | WO-01/58839 A1 | 8/2001 |
| WO | WO-02/076189 A1 | 10/2002 |
| WO | WO-02/099095 A2 | 12/2002 |
| WO | WO-02/099095 A3 | 12/2002 |
| WO | WO-2004/033646 A2 | 4/2004 |
| WO | WO-2004/033646 A3 | 4/2004 |
| WO | WO-2004/111214 A1 | 12/2004 |
| WO | WO-2005/001036 A2 | 1/2005 |
| WO | WO-2005/001036 C1 | 1/2005 |
| WO | WO-2005/007682 A2 | 1/2005 |
| WO | WO-2005/007682 A3 | 1/2005 |
| WO | WO-2005/078074 A2 | 8/2005 |
| WO | WO-2005/078074 A3 | 8/2005 |
| WO | WO-2006/063752 A1 | 6/2006 |
| WO | WO-2006/085899 A2 | 8/2006 |
| WO | WO-2006/085899 A3 | 8/2006 |
| WO | WO-2007/018062 A1 | 2/2007 |
| WO | WO-2007/136847 A2 | 11/2007 |
| WO | WO-2007/136847 A3 | 11/2007 |
| WO | WO-2007/140339 A2 | 12/2007 |
| WO | WO-2007/140339 A3 | 12/2007 |
| WO | WO-2007/140339 A8 | 12/2007 |
| WO | WO-2008/002472 A2 | 1/2008 |
| WO | WO-2008/002472 A3 | 1/2008 |
| WO | WO-2008/003078 A2 | 1/2008 |
| WO | WO-2008/003078 A3 | 1/2008 |
| WO | WO-2008/003078 A8 | 1/2008 |
| WO | WO-2008/137092 A2 | 11/2008 |
| WO | WO-2008/137092 A3 | 11/2008 |
| WO | WO-2008/153925 A2 | 12/2008 |
| WO | WO-2008/153925 A3 | 12/2008 |
| WO | WO-2008/153925 A9 | 12/2008 |
| WO | WO-2008/153934 A2 | 12/2008 |
| WO | WO-2008/153934 A3 | 12/2008 |
| WO | WO-2008/153935 A2 | 12/2008 |
| WO | WO-2008/153935 A3 | 12/2008 |
| WO | WO-2009/036067 A2 | 3/2009 |
| WO | WO-2009/036067 A3 | 3/2009 |
| WO | WO-2009/036067 A2 | 5/2009 |
| WO | WO-2009/036067 A3 | 5/2009 |
| WO | WO-2009/076676 A2 | 6/2009 |
| WO | WO-2009/076676 A3 | 6/2009 |
| WO | WO-2009/100231 A2 | 8/2009 |
| WO | WO-2009/100231 A3 | 8/2009 |
| WO | WO-2009/132220 A2 | 10/2009 |
| WO | WO-2009/132220 A3 | 10/2009 |
| WO | WO-2009/132220 A9 | 10/2009 |
| WO | WO-2010/003007 A2 | 1/2010 |
| WO | WO-2010/003007 A3 | 1/2010 |
| WO | WO-2010/005525 A1 | 1/2010 |
| WO | WO-2010/031062 A1 | 3/2010 |
| WO | WO-2010/031068 A1 | 3/2010 |
| WO | WO-2010/031076 A2 | 3/2010 |
| WO | WO-2010/031076 A3 | 3/2010 |
| WO | WO-2010/031077 A1 | 3/2010 |
| WO | WO-2010/031079 A1 | 3/2010 |
| WO | WO-2010/078457 A2 | 7/2010 |
| WO | WO-2010/078457 A3 | 7/2010 |
| WO | WO-2010/124146 A2 | 10/2010 |
| WO | WO-2010/124146 A3 | 10/2010 |
| WO | WO-2010/148150 A1 | 12/2010 |
| WO | WO-2011/000026 A1 | 1/2011 |

OTHER PUBLICATIONS

Allison, R. et al. (1986). "The Nucleotide Sequence of the Coding Region of Tobacco Etch Virus Genomic RNA: Evidence for the Synthesis of a Single Polyprotein," *Virology* 154:9-20.

Alper, H. et al. (2008). "Uncovering the Gene Knockout Landscape for Improved Lycopene Production in *E. coli*," *Appl. Microbiol. Biotechnol.* 10 pages.

Alterthum, F. et al. (Aug. 1989). "Efficient Ethanol Production from Glucose, Lactose, and Xylose by Recombinant *Escherichia coli*," *Applied Environmental Microbiology* 55(8):1943-1948.

Altschul, S.F. et al. (1990). "Basic Local Alignment Search Tool," *J Mol. Biol.* 215:403-410.

Altschul, S.F. et al. (1996). "Local Alignment Statistics," Chapter 27 in *Multiple Alignment and Phylogenetic Trees*, American Press, Inc. 266:460-480.

Altschul, S.F. et al. (1997). "Gapped BLAST and PSI-BLAST: A New Generation of Protein Database Search Programs," *Nucleic Acids Research* 25(17):3389-3402.

Alves, R. et al. (Nov. 2000). "Effect of Overall Feedback Inhibition in Unbranched Biosynthetic Pathways," *Biophysical Journal* 79(5):2290-2304.

Anderson, M.S. et al. (Nov. 15, 1989). "Isopentenyl Diphosphate: Dimethylallyl Diphosphate Isomerase. An Improved Purification of

(56) References Cited

OTHER PUBLICATIONS the Enzyme and Isolation of the Gene from *Saccharomyces cerevisiae*," *J. Biol. Chem.* 264(32):19169-19175.
Andreassi, J.L. et al. (2004, e-pub. Dec. 4, 2004). "*Streptococcus pneumoniae* Isoprenoid Biosynthesis Is Downregulated by Diphosphomevalonate: An Antimicrobial Target," *Biochemistry* 43(51):16461-16466.
Andreassi, J.L. et al. (2007, e-pub. Mar. 30, 2007). "Crystal Structure of the *Streptococcus pneumoniae* Mevalonate Kinase in Complex with Diphosphomevalonate," *Protein Science* 16:983-989.
Aon, J.C. et al. (Feb. 2008, e-pub. Dec. 14, 2007). "Suppressing Posttranslational Gluconoylation of Heterologous Proteins by Metabolic Engineering of *Escherichia coli*," *Applied and Environmental Microbiology* 74(4):950-958.
Arai, Y. et al. (2004). "Production of Polyhydroxybutyrate by Polycistronic Expression of Bacterial Genes in Tobacco Plastid," *Plant Cell Physiol.* 45(9):1176-1184.
Ashby, M.N. et al. (Aug. 5, 1990). "Elucidation of the Deficiency in Two Yeast Coenzyme Q Mutants: Characterization of the Structural Gene Encoding Hexaprenyl Pyrophosphate Synthetase," *The Journal of Biological Chemistry* 265(22):13157-13164.
Ausubel, F. M. et al. eds. (1987). "Introduction of DNA into Mammalian Cells," Chapter 9 in *Current Protocols in Molecular Biology*.
Baba, T. et al. (Feb. 21, 2006). "Construction of *Escherichia coli* K-12 In-Frame, Single-Gene Knockout Mutants: The Keio Collection," *Molecular Systems Biology* pp. 1-11.
Ballas, N. et al. (1989). "Efficient Functioning of Plant Promoters and Poly(A) Sites in *Xenopus* Oocytes," *Nucleic Acids Research* 17(19):7891-7903.
Barkovich, R. et al. (2001, e-pub. Dec. 1, 2000). "Metabolic Engineering of Isoprenoids," *Metabolic Engineering* 3:27-39.
Beaucage, S.L. et al. (1981). "Deoxynucleoside Phosphoramidites—A New Class of Key Intermediates for Deoxypolynucleotide Synthesis," *Tetrahedron Letters* 22(20):1859-1862.
Bellion, E. et al. (1993). "Methylamine Utilization in Yeast and Bacteria: Studies Using in vivo NMR," Chapter 32 in *Microbial Growth on $C_1$ Compounds*, Murrell, J.C. et al. eds, Intercept Ltd: Andover, UK, pp. 415-432.
Berman, H. et al. (2007, e-pub. Nov. 16, 2006). "The Worldwide Protein Data Bank (wwPDB): Ensuring a Single, Uniform Archive of PDB Data," *Nucleic Acids Research* 35:D301-D303.
Beytia, E. et al. (Oct. 25, 1970). "Purification and Mechanism of Action of Hog Liver Mevalonic Kinase," *The Journal of Biological Chemistry* 245(20):5450-5458.
Bock, R. et al. (2000). "Extranuclear Inheritance: Plastid Genetics: Manipulation of Plastid Genomes and Biotechnological Applications," *Progress in Botany* 61:76-90.
Bock, R. (2001). "Transgenic Plastids in Basic Research and Plant Biotechnology," *J. Mol. Biol.* 312:425-438.
Bock, R. et al. (Jun. 2004). "Taming Plastids for a Green Future," *Trends in Biotechnology* 22(6):311-318.
Boel, E. et al. (1984). "Two Different Types of Intervening Sequences in the Glucoamylase Gene from *Aspergillus niger*," *The EMBO Journal* 3(7):1581-1585.
Bouvier, F. et al. (2005). "Biogenesis, Molecular Regulation and Function of Plant Isoprenoids," *Progress in Lipid Research* 44:357-429.
Boynton, J.E. et al. (1993). "Chloroplast Transformation in *Chlamydomonas*," *Methods in Enzymology* 217(37):510-536.
Broun, P. et al. (Nov. 13, 1998). "Catalytic Plasticity of Fatty Acid Modification Enzymes Underlying Chemical Diversity of Plant Lipids," *Science* 282:1315-1317.
Brünger, A.T. et al. (1998). "*Crystallography & NMR System*: A New Software Suite for Macromolecular Structure Determination," *Acta Cryst.* D54:905-921.
Bubunenko, M. et al. (Apr. 2007). "Essentiality of Ribosomal and Transcription Antitermination Proteins Analyzed by Systematic Gene Replacement in *Escherichia coli*," *Journal of Bacteriology* 189(7):2844-2853.

Campbell, E.I. et al. (1989). "Improved Transformation Efficiency of *Aspergillus niger* Using the Homologous niaD Gene for Nitrate Reductase," *Curr. Genet.* 16:53-56.
Campbell, J.W. et al. (Oct. 2001). "*Escherichia coli* FadR Positively Regulates Transcription of the fabB Fatty Acid Biosynthetic Gene," *J. Bacteriol.* 183(20):5982-5990.
Campos, N. et al. (2001). "*Escherichia coli* Engineering to Synthesize Isopentenyl Diphosphate and Dimethylallyl Diphosphate from Mevalonate: A Novel System for the Genetic Analysis of the 2-*C*-Methyl-D-Erythritol 4-Phospate Pathway for Isoprenoid Biosynthesis," *Biochem. J.* 353:59-67.
Cao, Q.-N. et al. (2000). "Penicillopepsin-JT2, a Recombinant Enzyme from *Penicillium janthinellum* and the Contribution of a Hydrogen Bond in Subsite $S_3$ to $k_{cat}$," *Protein Science* 9:991-1001.
Chamberlin, M. et al. (Oct. 17, 1970). "New RNA Polymerase from *Escherichia coli* Infected with Bacteriophage T7," *Nature* 228:227-231.
Champenoy, S. et al. (1998). "Expression of the Yeast Mevalonate Kinase Gene in Transgenic Tobacco," *Molecular Breeding* 4:291-300.
Chan, W. et al. (2007, e-pub. Apr. 10, 2007). "A Recombineering Based Approach for High-Throughput Conditional Knockout Targeting Vector Construction," *Nucleic Acids Research* 35(8):e64, 13 pages.
Chappell, J. et al. (1995). "Is the Reaction Catalyzed by 3-Hydroxy-3-Methylglutaryl—Coenzyme A Reductase a Rate-Limiting Step for Isoprenoid Biosynthesis in Plants?" *Plant Physiology* 109:1337-1343.
Chemler, J.A. et al. (May 23, 2006). "Biosynthesis of Isoprenoids, Polyunsaturated Fatty Acids and Flavonoids in *Saccharomyces cerevisiae*," *Microbial Cell Factories* 5:20, 9 pages.
Cherepanov, P.P. et al. (1995). "Gene Disruption in *Escherichia coli*: $Tc^H$ and $Km^H$ Cassettes with the Option of Flp-Catalyzed Excision of the Antibiotic-Resistance Determinant," *Gene* 158(1):9-14.
Chica, R.A. et al. (2005). "Semi-Rational Approaches to Engineering Enzyme Activity: Combining the Benefits of Directed Evolution and Rational Design," *Current Opinion in Biotechnology* 16:378-384.
Cho, H.-J. et al. (1995). "Expression Pattern of Bacterial Polycistronic Genes in Tobacco Cells," *Journal of Fermentation and Bioengineering* 80(2):111-117.
Clarke, S. (1992). "Protein Isoprenylation and Methylation at Carboxyl-Terminal Cysteine Residues," *Annu. Rev. Biochem.* 61:355-386.
Clough, S.J. et al. (1998). "Floral Dip: A Simplified Method for *Agrobacterium*-Mediated Transformation of *Arabidopsis thaliana*," *The Plant Journal* 16(6):735-743.
Collaborative Computational Project, No. 4. (1994). "The CCP4 Suite: Programs for Protein Crystallography," *Acta Cryst.* D50:760-763.
Cordier, H. et al. (1999). "Heterologous Expression in *Saccharomyces cerevisiae* of an *Arabidopsis thaliana* cDNA Encoding Mevalonate Diphosphate Decarboxylase," *Plant Molecular Biology* 39:953-967.
Cunningham, F.X. et al. (1998). "Genes and Enzymes of Carotenoid Biosynthesis in Plants," *Ann. Rev. Plant Physiol. Plant Mol. Biol.* 49:557-583.
Cunningham, F.X. et al. (Oct. 2000). "Evidence of a Role for LytB in the Nonmevalonate Pathway of Isoprenoid Biosynthesis," *Journal of Bacteriology* 182(20):5841-5848.
Dale, P.J. (1992). "Spread of Engineered Genes to Wild Relatives," *Plant Physiol.* 100:13-15.
Dale, G.E. et al. (2003). "The Protein as a Variable in Protein Crystallization," *Journal of Structural Biology* 142:88-97.
Daniell, H. (1997). "Transformation and Foreign Gene Expression in Plants Mediated by Microprojectile Bombardment," Chapter 35 in *Methods in Molecular Biology, Recombinant Gene Expression Protocols*, Tuan, R. ed., Humana Press, Inc., Totowa, NJ, 62:463-489.
Daniell, H. et al. (Apr. 1998) "Containment of Herbicide Resistance Through Genetic Engineering of the Chloroplast Genome," *Nature Biotechnology* 16:345-348.
Datsenko, K.A. et al. (Jun. 6, 2000). "One-Step Inactivation of Chromosomal Genes in *Escherichia coli* K-12 Using PCR Products," *PNAS* 97(12):6640-6645.

(56) References Cited

OTHER PUBLICATIONS

Datta, S. et al. (2006). "A Set of Recombineering Plasmids for Gram-Negative Bacteria," *Gene* 379:109-115.

Datukishvili, N.T. et al. (2001). "Isolation and Purification of Protein Responsible for the Conversion of Dimethylallylpyrophosphate from Poplar Leaves into Isoprene," *Russian Journal of Plant Physiology* 48(2):222-225.

Davidson, S. (Oct.-Dec. 2003). "Light Factories," located at <http://www.publish.csiro.au/?act=view_file&file_id=EC117p10.pdf>, last visited on Oct. 2, 2008.

Davis, I.W. et al. (2007). "MolProbity: All-Atom Contacts and Structure Validation for Proteins and Nucleic Acids," *Nucleic Acids Research* 35:W375-W383.

De Cosa, B. et al. (Jan. 2001). "Overexpression of the Bt cry2Aa2operon in Chloroplasts Leads to Formation of Insecticidal Crystals," *Nature Biotechnology* 19:71-74.

Del Campo, E. M. et al. (1997). "Plastid ndhD Gene of Barley, Sequence and Transcript Editing (Accesion No. Y12258) (PGR 97-090)," *Plant Physiol.* 114:747-749.

Della-Cioppa, G. et al. (1987). "Protein Trafficking in Plant Cells," *Plant Physiol.* 84:965-968.

Deppenmeier, U. et al. (2002). "The Genome of *Methanosarcina mazei*: Evidence for Lateral Gene Transfer Between Bacteria and Archaea," *J. Mol. Microbiol. Biotechnol.* 4(4):453-461.

Deroles, S.C. et al. (1988). "Expression and Inheritance of Kanamycin Resistance in a Large Number of Transgenic Petunias Generated by *Agrobacterium*-Mediated Transformation," *Plant Molecular Biology* 11:355-364.

Dettmer, K. et al. (2000). "Stability of Reactive Low Boiling Hydrocarbons on Carbon Based Adsorbents Typically Used for Adsorptive Enrichment and Thermal Desorption," *Fresenius J. Anal. Chem.* 366:70-78.

Devereux, J. et al. (1984). "A Comprehensive Set of Sequence Analysis Programs for the VAX," *Nucleic Acids Research* 12(1):387-395.

Devos, D. et al. (2000). "Practical Limits of Function Prediction," *Proteins: Structure, Function, and Genetics* 41:98-107.

Dewick, P.M. et al. (2002, e-pub. Jan. 22, 2002). "The Biosynthesis of $C_5$—$C_{25}$ Terpenoid Compounds," *Nat. Prod. Rep.* 19:181-222.

Dhe-Paganon, S. et al. (1994). "Mechanism of Mevalonate Pyrophosphate Decarboxylase: Evidence for a Carbocationic Transition State," *Biochemistry* 33(45):13355-13362.

Dorsey, J.K. et al. (Sep. 25, 1968). "The Inhibition of Mevalonic Kinase by Geranyl and Farnesyl Pyrophosphates," *The Journal of Biological Chemistry* 243(18):4667-4670.

Doumith, M. et al. (2000, e-pub. Aug. 25, 2000). "Analysis of Genes Involved in 6-Deoxyhexose Biosynthesis and Transfer in *Saccharopolyspora erythraea*," *Mol. Gen Genet.* 264:477-485.

Dynan, W.S. et al. (Aug. 29, 1985). "Control of Eukaryotic Messenger RNA Synthesis by Sequence-Specific DNA-Binding Proteins," *Nature* 316:774-778.

Eisenreich, W. et al. (Sep. 1998). "The Deoxyxylulose Phosphate Pathway of Terpenoid Biosynthesis in Plants and Microorganisms," *Chemistry and Biology* 5(9):R221-R233.

Eisenreich, W. et al, (Feb. 2001). "Deoxyxylulose Phosphate Pathway to Terpenoids," *Trends in Plant Science* 6(2):78-84.

Elroy-Stein, O. et al. (Aug. 1989). "Cap-Independent Translation of mRNA Conferred by Encephalomyocarditis Virus 5' Sequence Improves the Performance of the Vaccinia Virus/Bacteriophage T7 Hybrid Expression System," *PNAS USA* 86:6126-6130.

EMBL-EBI Accession No. A0PFK2, last updated on Mar. 2, 2010, located at <http://srs.ebi.ac.uk/srsbin/cgi-bin/wgetz?-e+[UNIPROT:A0PFK2_POPNI]+-newId>, last visited on Jun. 2, 2010, 2 pages.

EMBL-EBI Accession No. A9PGR5, last updated on Mar. 2, 2010, located at <http://srs.ebi.ac.uk/srsbin/cgi-bin/wgetz?-e+[UNIPROT:A9PGR5_POPTR]+-newId>, last visited on Jun. 2, 2010, 2 pages.

EMBL-EBI Accession No. AB198180, last updated May 10, 2005, located at <http://www.ebi.ac.uk/cgi-bin/dbfetch?db=embl&id=ab198180&Subm . . . >, last visited on Jul. 8, 2009, 2 pages.

EMBL-EBI Accession No. AY341431, last updated Apr. 16, 2005, located at <http://www.ebi.ac.uk/cgi-bin/dbfetch?db=embl&id=AY341431∈ . . . >, last visited on Nov. 26, 2009, 2 pages.

Emsley, P. et al. (2004). "Coot: Model-Building Tools for Molecular Graphics," *Acta Crystallographica* D60:2126-2132.

Emsley, P. et al. (2010). "Features and Development of Coot," *Acta Crystallographica* D66:486-501.

Extended European Search Report mailed on Jun. 14, 2011, for EP Patent Application No. 08860589.4, filed on Dec. 15, 2008, 10 pages.

Fall, R. (Sep. 12, 2003). "Final Technical Report: DE-FG03-97ER20274, Microbial Production of Isoprene. Dates Covered: Jun. 15, 2000 to Jun. 14, 2003," located at <http://www.osti.gov/scitech/servlets/purl/814920>, last visited on Nov. 11, 2013, 4 pages.

Farmer, W.R. et al. (May 2000). "Improving Lycopene Production in *Escherichia coli* by Engineering Metabolic Control," *Nature Biotechnology* 18:533-537.

Feng, D.-F. et al. (1987). "Progressive Sequence Alignment as a Prerequisite to Correct Phylogenetic Trees," *Journal of Molecular Evolution* 25:351-360.

Finkelstein, D.B. (1992). "Transformation," Chapter 6 in *Biotechnology of Filamentous Fungi*, Butterworth-Heinemann: Boston, MA, pp. 113-156.

Flores, S. et al. (Aug. 20, 2004, e-pub. Jul. 23, 2004). "Growth-Rate Recovery of *Escherichia coli* Cultures Carrying a Multicopy Plasmid, by Engineering of the Pentose-Phosphate Pathway," *Biotechnology and Bioengineering* 87(4):485-494.

Fu, Z. et al. (2008, e-pub. Feb. 27, 2008). "Biochemical and Structural Basis for Feedback Inhibition of Mevalonate Kinase and Isoprenoid Metabolism," *Biochemistry* 47:3715-3724.

Gallie, D.R. et al. (1989). "Eukaryotic Viral 5'-Leader Sequences Act as Translational Enhancers in Eukaryotes and Prokaryotes," in *Molecular Biology of RNA*, Cech, T.R. ed., Alan R. Liss, Inc: New York, NY, pp. 237-256.

Garret, T.A. et al. (May 15, 1998). "Accumulation of a Lipid A Precursor Lacking the 4'-Phosphate Following Inactivation of the *Escherichia coli* IpxK Gene," *The Journal of Biological Chemistry* 273(20):12457-12465.

GenBank Accession No. AB198180, last updated on May 10, 2005, located at <http://www.ncbi.nlm.nih.gov/nuccore/63108309>, last visited on Jun. 2, 2010, 2 pages.

GenBank Accession No. AJ294819.1, last updated Apr. 15, 2005, located at <http://www.ncbi.nlm.nih.gov/nuccore/AJ294819.1>, last visited on Dec. 7, 2011, 2 pages.

GenBank Accession No. AJ457070, last updated on Apr. 15, 2005, located at <http://www.ncbi.nlm.nih.gov/nuccore/38092202>, last visited on Jun. 2, 2010, 2 pages.

GenBank Accession No. AM410988.1, last updated Aug. 14, 2008, located at <http://www.ncbi.nlm.nih.gov/nuccore/AM410988.1>, last visited on Dec. 7, 2011, 2 pages.

GenBank Accession No. AY182241, last updated on May 4, 2004, located at <http://www.ncbi.nlm.nih.gov/nuccore/32265057>, last visited on Jun. 2, 2010, 2 pages.

GenBank Accession No. AY279379, last updated on Mar. 11, 2005, located at <http://www.ncbi.nlm.nih.gov/nuccore/30984014>, last visited on Jun. 2, 2010, 2 pages.

GenBank Accession No. AY316691, last updated on Feb. 15, 2005, located at <http://www.ncbi.nlm.nih.gov/nuccore/35187003>, last visited on Jun. 2, 2010, 2 pages.

GenBank Accession No. AY341431, last updated on Feb. 15, 2005, located at <http://www.ncbi.nlm.nih.gov/nuccore/33358228>, last visited on Jun. 2, 2010, 3 pages.

GenBank Accession No. EF147555.1, last updated Mar. 24, 2009, located at <http://www.ncbi.nlm.nih.gov/nuccore/EF147555.1>, last visited on Dec. 7, 2011, 2 pages.

GenBank Accession No. EF638224.1, last updated May 3, 2010, located at <http://www.ncbi.nlm.nih.gov/nuccore/EF638224.1>, last visited on Dec. 7, 2011, 2 pages.

GenBank Accession No. EU693027, last updated on May 27, 2008, located at <http://www.ncbi.nlm.nih.gov/nuccore/189017053>, last visited on Jun. 2, 2010, 2 pages.

GenBank Accession No. CAC35696, last updated Apr. 15, 2005, located at <http://www.ncbi.nlm.nih.gov/protein/CAC35696>, last visited on Nov. 1, 2011, 1 page.

(56) References Cited

OTHER PUBLICATIONS

Geneseq Database Accession No. AFB74822, "Monoterpene synthetase protein SEQ ID No. 4." Retrieved from EBI accession No. GSP:AFB74822 (Apr. 19, 2007), located at http://ibis/exam/dbfetch.jsp?id=GSP:AFB74822, last visited on Apr. 17, 2012, 2 pages.
Goedegebuur, F. et al. (2002, e-pub. May 7, 2002). "Cloning and Relational Analysis of 15 Novel Fungal Endoglucanases from Family 12 Glycosyl Hydrolase," *Curr. Genet.* 41:89-98.
Goldschmidt-Clermont, M. (1991). "Transgenic Expression of Aminoglycoside Adenine Transferase in the Chloroplast: A Selectable Marker for Site-Directed Transformation of Chlamydomonas," *Nucleic Acids Res.* 19(15):4083-4089.
Goodwin, T.W. (1971). "Biosynthesis of Carotenoids and Plant Triterpenes: The Fifth CIBA Medal Lecture," *Biochem. J.* 123(3):293-329.
Gräwert, T. et al. (2004, e-pub. Sep. 21, 2004). "IspH Protein of *Escherichia coli*: Studies on Iron-Sulfur Cluster Implementation and Catalysis," *Journal American Chemistry Society* 126:12847-12855.
Greenberg, J.P. et al. (1993). "Sub-Parts Per Billion Detection of Isoprene Using a Reduction Gas Detector with a Portable Gas Chromatograph," *Atmospheric Environment* 27A(16):2689-2692.
Grochowski, L.L. et al. (May 2006). "*Methanocaldococcus jannaschii* Uses a Modified Mevalonate Pathway for Biosynthesis of Isopentenyl Diphosphate," *Journal of Bacteriology* 188(9):3192-3198.
Guda, C. et al. (2000). "Stable Expression for a Biodegradable Protein-Based Polymer in Tobacco Chloroplasts," *Plant Cell Reports* 19:257-262.
Guerineau, F. et al. (1991). "Effect of Deletions in the Cauliflower Mosaic Virus Polyadenylation Sequence on the Choice of the Polyadenylation Sites in Tobacco Protoplasts," *Mol. Gen. Genet.* 226:141-144.
Guo, D.-A. et al. (1995). "Developmental Regulation of Sterol Biosynthesis in *Zea mays*," *Lipids* 30(3):203-219.
Hahn, F.M. et al. (May 12, 1995). "Isolation of *Schizosaccharomyces pombe* Isopentenyl Diphosphate Isomerase in cDNA Clones by Complementation and Synthesis of the Enzyme in *Escherichia coli*," *The Journal of Biological Chemistry* 270(19):11298-11303.
Hahn, F.M. et al. (Feb. 1996). "Open Reading Frame 176 in the Photosynthesis Gene Cluster of *Rhodobacter capsulatus* Encodes idi, a Gene for Isopentenyl Diphosphate Isomerase," *Journal of Bacteriology* 178(3):619-624.
Hahn, F.M. et al. (Aug. 1999). "*Escherichia coli* Open Reading Frame 696 Is idi, a Nonessential Gene Encoding Isopentenyl Diphosphate Isomerase," *Journal of Bacteriology* 181(15):4499-4504.
Hahn, F.M. et al. (Jan. 2001). "1-Deoxy D-Xylulose 5-Phosphate Synthase, the Gene Product of Open Reading Frame (ORF) 2816 and ORF 2895 in *Rhodobacter capsulatus*," *Journal of Bacteriology* 183(1):1-11.
Hamano, Y. et al. (2001). "Cloning of a Gene Cluster Encoding Enzymes Responsible for the Mevalonate Pathway from a Terpenoid-Antibiotic-Producing *Streptomyces* Strain," *Biosci. Biotechnol. Biochem.* 65(7):1627-1635.
Hamilton, C.M. et al. (Sep. 1989). "New Method for Generating Deletions and Gene Replacements in *Escherichia coli*," *Journal of Bacteriology* 171(9):4617-4622.
Hanai, T. et al. (Dec. 2007). "Engineered Synthetic Pathway for Isopropanol Production in *Escherichia coli*," *Applied and Environmental Microbiology* 73(24):7814-7818.
Harker, M. et al. (1999). "Expression of Prokaryotic 1-Deoxy-D-Xylulose-5-Phosphatases in *Escherichia coli* Increases Carotenoid and Ubiquinone Biosynthesis," *FEBS Letters* 448:115-119.
Harkki, A. et al. (Jun. 1989). "A Novel Fungal Expression System: Secretion of Active Calf Chymosin from the Filamentous Fungus *Trichoderma reesei*," *Bio/Technology* 7:596-603.
Hedl, M. et al. (Apr. 2002). "*Enterococcus faecalis* Acetoacetyl-Coenzyme A Thiolase/3-Hydroxy-3-Methyglutaryl-Coenzyme A Reductase, a Dual-Function Protein of Isopentenyl Diphosphate Biosynthesis," *Journal of Bacteriology* 184(8):2116-2122.

Hedl, M. et al. (Apr. 2004). "Class II 3-Hydroxy-3-Methylglutaryl Coenzyme A Reductases," *Journal of Bacteriology* 186(7):1927-1932.
Hellman, U. et al. (1995). "Improvement of an "In-Gel" Digestion Procedure for the Micropreparation of Internal Protein Fragments for Amino Acid Fragments for Amino Acid Sequencing," *Analytical Biochemistry* 224:451-455.
Henikoff, S. (Nov. 1992). "Amino Acid Substitution Matrices from Protein Blocks," *Proc. Natl. Acad. Sci. USA* 89:10915-10919.
Herbers, K. et al. (Jun. 1996). "Manipulating Metabolic Partitioning in Transgenic Plants", *TIBTECH* 14:198-205.
Herz, S. et al. (Mar. 14, 2000). "Biosynthesis of Terpenoids: YgbB Protein Converts 4- Diphosphocytidyl-2C-Methyl-D-Erythritol 2-Phosphate to 2C-Methyl-D-Erythritol 2,4-Cyclodiphosphate," *PNAS* 97(6):2486-2490.
Higgins, D.G. et al. (1989). "Fast and Sensitive Multiple Sequence Alignments on a Microcomputer," *Cabios Communications* 5(2):151-153.
Hinson, D.D. et al. (1997). "Post-Translation Regulation of Mevalonate Kinase by Intermediates of the Cholesterol and Nonsterol Isoprene Biosynthetic Pathways," *Journal of Lipid Research* 38:2216-2223.
Hoeffler, J-F. et al. (2002). "Isoprenoid Biosynthesis Via the Methylerythritol Phosphate Pathway. Mechanistic Investigations of the 1-Deoxy-D-Xylulose 5-Phosphate Reductoisomerase," *Eur. J. Biochem.* 269:4446-4457.
Huang, K.-X. et al. (1999). "Overexpression, Purification, and Characterization of the Thermostable Mevalonate Kinase from *Methanococcus jannaschii*," *Protein Expression and Purification* 17:33-40.
Hunter, B.K. (1985). "Formaldehyde Metabolism by *Escherichia coli*. Carbon and Solvent Deuterium Incorporation into Glycerol, 1,2-Propanediol, and 1,3-Propanediol," *Biochemistry* 24(15):4148-4155.
Hyatt, D.C. et al. (Mar. 27, 2007). "Structure of Limonene Synthase, A Simple Model for Terpenoid Cyclase Catalysis," *PNAS* 104(13):5360-5365.
Ilmén, M. et al. (Apr. 1997). "Regulation of Cellulase Gene Expression in the Filamentous Fungus *Trichoderma reesei*," *Appl. Environ. Microbiol.* 63(4):1298-1306.
Innis, M.A. et al. (Apr. 5, 1985). "Expression, Glycosylation, and Secretion of an *Aspergillus* Glucoamylase by *Saccharomyces cerevisiae*," *Science* 228:21-26.
Jenkins, L.S. et al. (Jan. 1987). "Genetic and Molecular Characterization of the Genes Involved in Short-Chain Fatty Acid Degradation in *Escherichia coli*:The ato System," *Journal of Bacteriology* 169(1):42-52.
Jeong, S-W. et al. (2004, e-pub. Jan. 21, 2004). "Dicistronic Expression of the Green Fluorescent Protein and Antibiotic Resistance Genes in the Plastid for Selection and Tracking of Plastid-Transformed Cells in Tobacco," *Plant Cell Rep* 22:747-751.
Jeong, D-W. et al. (2007). "Cloning and Characterization of a Gene Encoding Phosphoketolase in a *Lactobacillus paraplantarum* Isolated from Kimchi," *Journal of Microbiology and Biotechnology* 17(5):822-829.
Jobling, S.A. et al. (Feb. 12, 1987). "Enhanced Translation of Chimaeric Messenger RNAs Containing a Plant Viral Untranslated Leader Sequence," *Nature* 235:622-625.
Jones, K.L. et al. (2000). "Low-Copy Plasmids Can Perform as Well as or Better Than High-Copy Plasmids for Metabolic Engineering of Bacteria," *Metabolic Engineering* 2:238-338.
Jones, E.Y. et al. (1991). "Methodology Employed for the Structure Determination of Tumour Necrosis Factor, a Case of High Non-Crystallographic Symmetry," *Acta Cryst* A47:753-770.
Joshi, C.P. (1987). "Putative Polyadenylation Signals in Nuclear Genes of Higher Plants: A Compilation and Analysis," *Nucleic Acids Research* 15(23):9627-9640.
Julsing, M.K. et al. (Jul. 2007, e-pub. Apr. 26, 2007). "Functional Analysis of Genes Involved in the Biosynthesis of Isoprene in *Bacillus subtilis*," *Applied Microbiol. Biotechnol.* 75(6):1377-1384.
Kacian, D.L. et al. (Oct. 1972). "A Replicating RNA Molecule Suitable for a Detailed Analysis of Extracellular Evolution and Replication," *Proc. Natl. Acad. Sci. USA* 69(10):3038-3042.

(56) References Cited

OTHER PUBLICATIONS

Kajiwara, S. et al. (1997). "Expression of an Exogenous Isopentenyl Diphosphate Isomerase Gene Enhances Isoprenoid Biosynthesis in *Escherichia coli*," *Biochem. J.* 324:421-426.

Kampranis, S.C. et al. (Jun. 2007). "Rational Conversion of Substrate and Product Specificity in a Salvia Monoterpene Synthase: Structural Insights into the Evolution of Terpene Synthase Function," *The Plant Cell* 19:1994-2005.

Kaneda, K. et al. (Jan. 30, 2001). "An Unusual Isopentenyl Diphosphate Isomerase Found in the Mevalonate Pathway Gene Cluster from *Streptomyces* sp. Strain CL190," *PNAS* 98(3):932-937.

Karl, T. et al. (2003). "Dynamic Measurements of Partition Coefficients Using Proton-Transfer-Reaction Mass Spectrometry (PTR-MS)," *International Journal of Mass Spectrometry* 223-224:383-395.

Karlin, S. (Jun. 1993). "Applications and Statistics for Multiple High-Scoring Segments in Molecular Sequences," *Proc. Natl. Acad. Sci. USA* 90:5873-5787.

Kavanagh, T.A. et al. (Jul. 1999). "Homeologous Plastid DNA Transformation in Tobacco Is Mediated by Multiple Recombination Events," *Genetics* 152(3):1111-1122.

Keasling, J.D. (Mar. 29, 2004). "Genetic Tools for Metabolic Enzyme Production in *Escherichia coli*," presented at NIGMS 2004 PSI Protein Production & Crystallization Workshop, Bethesda, MD, Mar. 29-31, 2004, located at <http://www-nmr.cabm.rutgers.edu/labdocuments/workshops/psi_ppcw_32904/ppcw_32904.html>, last visited on Jun. 4, 2010, 66 pages.

Keasling, J.D. (May 7, 2005). "Drugs from Bugs: Engineering Microorganisms to Produce New Drugs," presented at Engineering a Better World: *Our Environment, Our Health*, Berkeley, CA, May 7, 2005, 62 pages.

Keasling, J.D. (Sep. 23, 2007). "Engineering Microbes for Production of Low-Cost, Effective, Anti-Malarial Drugs," presented at *Enzyme Engineering XIX*, Harrison Hot Springs, British Columbia, Canada, Sep. 23-28, 2007, 152 pages.

Keegan, R.M. et al. (2007). "Automated Search-Model Discovery and Preparation for Structure Solution by Molecular Replacement," *Acta Crystallographica* D63:447-457.

Keeler, K.H. et al. (1996). "Movement of Crop Transgenes into Wild Plants," Chapter 20 in *Herbicide Resistant Crops: Agricultural, Environmental, Economic, Regulatory, and Technical Aspects*, Duke, S.O. ed., Lewis Publishers: Boca Raton, FL., pp. 303-330.

Kelly, J.M. et al. (1985). "Transformation of *Aspergillus niger* by the amdS Gene of *Aspergillus nidulans*," *The EMBO Journal* 4(2):475-479.

Khan, M.S. et al. (Sep. 1999). "Fluorescent Antibiotic Resistance Marker for Tracking Plastid Transformation in Higher Plants," *Nature Biotechnology* 17:910-914.

Kieser, T. eds. et al. (Jul. 2000). "Introduction of DNA into *Streptomyces*," Chapter 10 in *Practical Streptomyces Genetics*, pp. 229-252.

Kisselev, L. (Jan. 2002). "Polypeptide Release Factors in Prokaryotes and Eukaryotes: Same Function, Different Structure," *Structure* 10:8-9.

Klein-Marcuschamer, D. et al. (2007, e-pub. Aug. 2, 2007). "Engineering Microbial Cell Factories for Biosynthesis of Isoprenoid Molecules: Beyond Lycopene," *TRENDS in Biotechnology* 25(9):417-424.

Klein-Marcuschamer, D. et al. (Feb. 19, 2008). "Assessing the Potential of Mutational Strategies to Elicit New Phenotypes in Industrial Strains," *PNAS* 105(7):2319-2324.

Koga, Y. et al. (Mar. 2007). "Biosynthesis of Ether-Type Polar Lipids in Archaea and Evolutionary Considerations," *Microbiology and Molecular Biology Reviews* 71(1):97-120.

Köksal, M. et al. (2010, e-pub. Jul. 17, 2010). "Structure of Isoprene Synthase Illuminates the Chemical Mechanism of Teragram Atmospheric Carbon Emission," *J. Mol. Biol.* pp. 1-11.

Kooter, J. M., et al. (Sep. 1999). "Listening to the Silent Genes: Transgene Silencing, Gene Regulation and Pathogen Control," *Trends in Plant Science* 4(9):340-347.

Kota, M. et al. (Mar. 1999). "Overexpression of the *Bacillus thuringiensis* (Bt) Cry2Aa2 Protein in Chloroplasts Confers Resistance to Plants Against Susceptible and Bt-Resistant Insects," *Proc. Natl. Acad. Sci. USA* 96:1840-1845.

Kozak, M. (Oct. 25, 1991). "Structural Features in Eukaryotic mRNAs That Modulate the Initiation of Translation," *The Journal of Biological Chemistry* 266(30):19867-19870.

Kozak, M. (1999). "Initiation of Translation in Prokaryotes and Eukaryotes," *Gene* 234:187-208.

Kunkel, T. A. (Jan. 1985). "Rapid and Efficient Site-Specific Mutagenesis without Phenotypic Selection," *Proc. Natl. Acad. Sci. USA* 82:488-492.

Kuzma, J. et al. (1995). "Bacteria Produce the Volatile Hydrocarbon Isoprene," *Current Microbiology* 30:97-103.

Kuzuyama, T. et al. (1998). "Direct Formation of 2-C Methyl-D-Erythritol 4-Phosphate from 1-Deoxy-D-Xylulose 5-Phosphate by 1-Deoxy-D-Xylulose 5-Phosphate Reductoisomerase, a New Enzyme in the Non-Mevalonate Pathway to Isopentenyl Diphosphate," *Tetrahedron Letters* 39:4509-4512.

Kuzuyama, T. et al. (1998). "Fosmidomycin, a Specific Inhibitor of 1-Deoxy-D-Xylulose 5-Phosphate Reductoisomerase in the Nonmevalonate Pathway for Terpenoid Biosynthesis," *Tetrahedron Letters* 39:7913-7916.

Lange, B.M. et al. (Nov. 23, 1999). "Isopentenyl Diphosphate Biosynthesis Via a Mevalonate-Independent Pathway: Isopentenyl Monophosphate Kinase Catalyzes the Terminal Enzymatic Step," *PNAS* 96(24):13714-13719.

Lange, B.M. et al. (Sep. 2001). "Isoprenoid Biosynthesis. Metabolite Profiling of Peppermint Oil Gland Secretory Cells and Application to Herbicide Target Analysis," *Plant Physiology* 127:305-314.

Law, C.K. (1984). "Heat and Mass Transfer in Combustion: Fundamental Concepts and Analytical Techniques," *Progress in Energy and Combustion Science* 10:295-318.

Lehning, A. et al. (1999). "Isoprene Synthase Activity and Its Relation to Isoprene Emission in *Quercus robur* L. Leaves," *Plant, Cell and Environment* 22:495-504.

Lerner, C.G. et al. (1990). "Low Copy Number Plasmids for Regulated Low-Level Expression of Cloned Genes in *Escherichia coli* with Blue/White Insert Screening Capability," *Nucleic Acids Research* 18(15):4631.

Li, W. et al. (2010, e-pub. Nov. 1, 2009). "Non-Redundant Patent Sequence Databases with Value-Added Annotations at Two Levels," *Nucleic Acids Research* 38:D52-D56.

Lichtenthaler, H.K. et al. (1997). "Biosynthesis of Isoprenoids in Higher Plant Chloroplasts Proceeds Via a Mevalonate-Independent Pathway," *FEBS Letters* 400:271-274.

Lichtenthaler, H.K. (1999). "The 1-Deoxy-D-Xylulose-5-Phosphate Pathway of Isoprenoid Biosynthesis in Plants," *Annu. Rev. Plant Physiol. Plant Mol. Biol.* 50:47-65.

Lin, X.-M. et al. (2008, e-pub. Apr. 26, 2008). "Proteomic Analysis of Nalidixic Acid Resistance in *Escherichia coli*: Identification and Functional Characterization of OM Proteins," *Journal of Proteome Research* pp. A-G.

Lluch, M.A. et al. (2000). "Molecular Cloning and Expression Analysis of the Mevalonate Kinase Gene from *Arabidopsis thaliana*," *Plant Molecular Biology* 42:365-376.

Lois, L.M. et al. (Mar. 1998). "Cloning and Characterization of a Gene from *Escherichia coli* Encoding a Transketolase-Like Enzyme that Catalyzes the Synthesis of D-1-Deoxyxylulose 5-Phosphate, a Common Precursor for Isoprenoid, Thiamin, and Pyridoxol Biosynthesis," *Proc. Natl. Acad. Sci. USA* 95:2105-2110.

Loivamäki, M. et al. (Jun. 2007). "*Arabidopsis*, a Model to Study Biological Functions of Isoprene Emission?" *Plant Physiology* 144:1066-1078.

Lommel, S.A. et al. (1991). "Identification of the Maize Chlorotic Mottle Virus Capsid Protein Cistron and Characterization of its Subgenomic Messenger RNA," *Virology* 181:382-385.

Lücker, J. et al. (2002). "Monoterpene Biosynthesis in Lemon (*Citrus limon*). cDNA Isolation and Functional Analysis of Four Monoterpene Synthases," *European Journal of Biochemistry* 269:3160-3171.

(56) References Cited

OTHER PUBLICATIONS

Luli, G.W. et al. (Apr. 1990). "Comparison of Growth, Acetate Production, and Acetate Inhibition of *Escherichia coli* in Batch and Fed-Batch Fermentations," *Applied and Environmental Microbiology* 56(4):1004-1011.

Lüttgen, H. et al. (Feb. 1, 2000). "Biosynthesis of Terpenoids: YchB Protein *Escherichia coli* Phosphorylates the 2-Hydroxy Group of 4-Diphosphocytidyl-2C-Methyl-D-Erythritol," *PNAS* 97(3):1062-1067.

Macejak, D.G. et al. (Sep. 5, 1991). "Internal Initiation of Translation Mediated by the 5' Leader of a Cellular mRNA," *Nature* 353:90-94.

Mahmoud, S.S. et al. (Jul. 17, 2001). "Metabolic Engineering of Essential Oil Yield and Composition in Mint by Altering Expression of Deoxyxylulose Phosphate Reductoisomerase and Menthofuran Synthase," *PNAS* 98(15):8915-8920.

Maldonado-Mendoza, I.E. et al. (Jul. 1997). "Molecular Characterization of Three Differentially Expressed Members of the *Camptotheca acuminata* 3-Hydroxy-3-Methylglutaryl CoA Reductase (HMGR) Gene Family," *Plant Molecular Biology* 34(5):781-790.

Mann, V. et al. (Aug. 2000). "Metabolic Engineering of Astaxanthin Production in Tobacco Flowers," *Nature Biotechnology* 18:888-892.

Martin, V.J.J. et al. (Dec. 5, 2001). "The in Vivo Synthesis of Plant Sesquiterpenes by *Escherichia coli*," *Biotechnology and Bioengineering* 75(5):497-503.

Martin, V.J.J. et al. (Jul. 2003). "Engineering a Mevalonate Pathway in *Escherichia coli* for Production of Terpenoids," *Nature Biotechnology* 21(7):796-802.

Martin, W. et al. (May 14, 1998). "Gene Transfer to the Nucleus and the Evolution of Chloroplasts," *Nature* 393:162-165.

Mashego, M.R. et al. (2007, e-pub. Nov. 8, 2006). "Microbial Metabolomics: Past, Present and Future Methodologies," *Biotechnol. Lett.* 29:1-16.

Matsuoka, S. et al. (Feb. 25, 1991). "Variable Product Specificity of Microsomal Dehydrodolichyl Diphosphate Synthase from Rat Liver," *The Journal of Biological Chemistry* 266(6):3464-3468.

Matteucci, M.D. et al. (1981). "Synthesis of Deoxyoligonucleotides on a Polymer Support," *J. American Chemical Society* 103(11):3185-3191.

Matthews, P.D. et al. (2000). "Metabolic Engineering of Carotenoid Accumulation in *Escherichia coli* by Modulation of the Isoprenoid Precursor Pool with Expression of Deoxyxylulose Phosphate Synthase," *Appl. Microbiol. Biotechnol.* 53:396-400.

Maury, J. et al. (2005, e-pub. Jul. 5, 2005). "Microbial Isoprenoid Production: An Example of Green Chemistry through Metabolic Engineering," *Adv. Biochem. Engin/Biotechnol.* 100:19-51.

McPherson, A. (2004). "Introduction to Protein Crystallization," *Methods* 34:254-265.

Meile, L. et al. (May 2001). "Characterization of the D-Xylulose 5-Phosphate/D-Fructose 6-Phosphate Phosphoketolase Gene (xfp) from *Bifidobacterium lactis*," *Journal of Bacteriology* 183(9):2929-2936.

Meinkoth, J. et al. (1984). "Hybridization of Nucleic Acids Immobilized on Solid Supports," *Analytical Biochemistry* 138:267-284.

Meyer, P. et al. (1996). "Homology-Dependent Gene Silencing in Plants," *Ann. Rev. Plant Physiol. Plant Mol. Biol.* 47:23-48.

Millen, R.S. et al. (Mar. 2001). "Many Parallel Losses of infA from Chloroplast DNA During Angiosperm Evolution with Multiple Independent Transfers to the Nucleus," *The Plant Cell* 13:645-658.

Miller, B. (2001). "Erstmalige Isolierung Eines Isoprenysthase-Gens und Heterologe Expression Des Aus Der Pappel Stammenden Gens Sowie Charakterisierung der Eingangsgene des Mevalonat-unabhängigen Isoprenoidbiosyntheseweges aus dem Cyanobakterium Synechococcus leopoliensis," located at <http://kups.ub.uni-koeln.de/883/>, last visited on Jun. 23, 2011, English Translation included, 2 pages.

Miller, B. et al. (2001, e-pub. May 10, 2001). "First Isolation of an Isoprene Synthase Gene from Poplar and Successful Expression of the Gene in *Escherichia coli*," *Planta* 213:483-487.

Miller, J. "High-Throughput Screening for Protein Engineering of Industrial Enzymes," published by Genencor on Jun. 5, 2009, Online document-retrieved on Apr. 17, 2012, XP002673697, 29 pages.

Milne, P.J. et al. (1995). "Measurement of Vertical Distribution of Isoprene in Surface Seawater, its Chemical Fate, and its Emission from Several Phytoplankton Monocultures," *Marine Chemistry* 48:237-244.

Mo, H. et al. (2004). "Studies of the Isoprenoid-Mediated Inhibition of Mevalonate Synthesis Applied to Cancer Chemotherapy and Chemoprevention," *Exp. Biol. Med.* 229:567-585.

Mogen, B.D. et al. (Dec. 1990). "Upstream Sequences Other than AAUAAA are Required for Efficient Messenger RNA 3'-End Formation in Plants," *The Plant Cell* 2:1261-1272.

Monson, R.K. et al. (1992). "Relationships Among Isoprene Emission Rate, Photosynthesis, and Isoprene Synthase Activity as Influenced by Temperature," *Plant Physiol.* 98:1175-1180.

Munroe, D. et al. (1990). "Tales of Poly(A): a Review," *Gene* 91:151-158.

Murray, E.E. et al. (1989). "Codon Usage in Plant Genes," *Nucleic Acids Research* 17(2): 477-498.

Nakamura, C.E. et al. (2003). "Metabolic Engineering for the Microbial Production of 1,3-Propanediol," *Current Opinion in Biotechnology* 14:454-459.

Nanchen, A. et al. (Apr. 2008, e-pub. Jan. 25, 2008). "Cyclic AMP-Dependent Catabolite Repression Is the Dominant Control Mechanism of Metabolic Fluxes Under Glucose Limitation in *Escherichia coli*," *Journal of Bacteriology* 190(7):2323-2330.

Nawrath, C. et al. (Dec. 1994). "Targeting of the Polyhydroxybutyrate Biosynthetic Pathway to the Plastids of *Arabidopsis thaliana* Results in High Levels of Polymer Accumulation," *Proc. Natl. Acad. Sci. USA* 91:12760-12764.

Needleman, S. B. et al. (1970). "A General Method Applicable to the Search for Similarities in the Amino Acid Sequence of Two Proteins," *J. Mol. Biol.* 48:443-453.

Neidhardt, F.C. et al. (Sep. 1974). "Culture Medium for Enterobacteria," *Journal of Bacteriology* 119(3):736-747.

Neidhardt, F.C. et al. (1990). "Table 1. Overall Macromolecular Composition of an Average *E. coli* B/r Cell$^a$," Chapter 1 in *Physiology of the Bacterial Cell: A Molecular Approach*, Sinauer Associates, Inc., Sunderland, MA, pp. 4.

Nevalainen, K.M.H. et al. (1992). "The Molecular Biology of *Trichoderma* and Its Application to the Expression of Both Homologous and Heterologous Genes," Chapter 6 in *Molecular Industrial Mycology, Systems and Applications for Filamentous Fungi*, Leong, S.A. et al. eds., Marcel Dekker Inc., New York, NY, pp. 129-148.

Newman, J.D. et al. (Nov. 5, 2006, e-pub. Jul. 28, 2006). "High-Level Production of Amorpha-4,11-Diene in a Two-Phase Partitioning Bioreactor of Metabolically Engineered *Escherichia coli*," *Biotechnology and Bioengineering* 95(4):684-691.

Newman, T. et al. (1994). "Genes Galore: A Summary of Methods for Accessing Results from Large-Scale Partial Sequencing of Anonymous *Arabidopsis* cDNA Clones," *Plant Physiology* 106:1241-1255.

Nielsen, K.M. et al. (1997). "Analysis and Developmental Profile of Carotenoid Pigments in Petals of Three Yellow Petunia Cultivars," *Scientia Horticulturae* 71:257-266.

Niinemets, Ü. et al. (Nov. 2002). "Stomatal Constraints May Affect Emission of Oxygenated Monoterpenoids from the Foliage of *Pinus pinea*," *Plant Physiology* 130:1371-1385.

Noronha, S.B. et al. (May 5, 2000). "Investigation of the TCA Cycle and the Glyoxylate Shunt in *Escherichia coli* BL21 and JM109 Using $^{13}$C-NMR/MS," *Biotechnology and Bioengineering* 68(3):316-327.

Nunberg, J.H. et al. (Nov. 1984). "Molecular Cloning and Characterization of the Glucoamylase Gene of *Aspergillus awamori*," *Mol. Cell. Biol.* 4(11):2306-2315.

Oh, M.-K. et al. (Apr. 12, 2002). "Global Expression Profiling of Acetate-Grown *Escherichia coli*," *The Journal of Biological Chemistry* 277(15):13175-13183.

Okamura, E. et al. (Jun. 22, 2010). "Unprecedented Acetoacetyl-coenzyme a Synthesizing Enzyme of the Thiolase Superfamily Involved in the Mevalonate Pathway," *PNAS* 107(25):11265-11270.

Ondrey, G. et al. (Oct. 2008). "Bio-Based Isoprene," *Chemical Engineering, Access Intelligence Association*, Rockville, MD, 115(1):14.

(56) References Cited

OTHER PUBLICATIONS

Oulmouden, A. et al. (1991). "Nucleotide Sequence of the ERG12 Gene of *Saccharomyces cerevisiae* Encoding Mevalonate Kinase," *Curr. Genet.* 19:9-14.

Pachuk, C.J. et al. (2000). "Chain Reaction Cloning: A One-Step Method for Directional Ligation of Multiple DNA Fragments," *Gene* 243:19-25.

Pearson, W.R. et al. (Apr. 1988). "Improved Tools for Biological Sequence Comparison," *Proc. Natl. Acad. Sci. USA* 85:2444-2448.

Pegg, S.C.-H. et al. (2006). "Leveraging Enzyme Structure-Function Relationships for Functional Inference and Experimental Design: The Structure-Function Linkage Database," *Biochemistry* 45:2545-2555.

Penttila, M. et al. (1987). "A Versatile Transformation System for the Cellulolytic Filamentous Fungus *Trichoderma reesei*," *Gene* 61:155-164.

Perego, M. (1993). "Integrational Vectors for Genetic Manipulation in *Bacillus subtilis*," Chapter 42 in *Bacillus subtilis and Other Gram-Positive Bacteria: Biochemistry, Physiology, and Molecular Genetics*, Sonenshein et al. eds., American Society for Microbiology: Washington, D.C., pp. 615-624.

Phan, R.M. et al. (2001, e-pub. Sep. 13, 2001). "Synthesis of (*S*)-Isoprenoid Thiodiphosphates as Substrates and Inhibitors," *J. Org. Chem.* 66(20):6705-6710.

Phillips, T.A. et al. (Jul. 1984). "Ion Gene Product of *Escherichia coli* Is a Heat-Shock Protein," *Journal of Bacteriology* 159(1):283-287.

Phue, J.-N. et al. (2004). "Transcription Levels of Key Metabolic Genes are the Cause for Different Glucose Utilization Pathways in *E. coli* B (BL21) and *E. coli* K (JM109)," *Journal of Biotechnology* 109:21-30.

Phue, J.-N. et al. (2005, e-pub. Aug. 11, 2005). "Impact of Dissolved Oxygen Concentration on Acetate Accumulation and Physiology of *E. coli* BL21, Evaluating Transcription Levels of Key Genes at Different Dissolved Oxygen Conditions," *Metabolic Engineering* 7:353-363.

Pilloff, D. et al. (Feb. 14, 2003). "The Kinetic Mechanism of Phosphomevalonate Kinase," *The Journal of Biological Chemistry* 278(7):4510-4515.

Pitera, D.J. et al. (2007, e-pub. Nov. 23, 2006). "Balancing a Heterologous Mevalonate Pathway for Improved Isoprenoid Production in *Escherichia coli*," *Metabolic Engineering* 9:193-207.

Pommer, H. et al. (1975). "Industrial Synthesis of Terpene Compounds," *Pure and Applied Chemistry* 43(3-4):527-551.

Potter, D. et al. (Oct. 10, 1997). "Identification of Catalytic Residues in Human Mevalonate Kinase," *The Journal of Biological Chemistry* 272(41):25449-25454.

Pourquié, J. et al. (1988). "Scale Up of Cellulase Production and Utilization," in *Biochemistry and Genetics of Cellulose Degradation*, Aubert, J.-P. et al. eds., Academic Press: San Diego, CA, pp. 71-86.

Proudfoot, N. (Feb. 22, 1991). "Poly(A) Signals," *Cell* 64:671-674.

Ramos-Valdivia, A.C. et al. (1997). "Isopentenyl Diphosphate Isomerase: A Core Enzyme in Isoprenoid Biosynthesis: A Review of its Biochemistry and Function," *Natural Product Reports* 6:591-603.

Raschke, M. et al. (2004, e-pub. Oct. 28, 2004). "A High-Performance Liquid Chromatography Methods for the Analysis of Intermediates of the Deoxyxylulose Phosphate Pathway," *Analytical Biochemistry* 335:235-243.

Re, E.B. et al. (1995). "Co-Expression of Native and Introduced Genes Reveals Cryptic Regulation of HMG CoA Reductase Expression in *Arabidopsis*," *The Plant Journal* 7(5):771-784.

Reiling, K.K. et al. (Jul. 20, 2004, e-pub. Jun. 18, 2004). "Mono and Diterpene Production in *Escherichia coli*," *Biotechnology and Bioengineering* 87(2):200-212.

Rodríguez-Concepción, M. et al. (2000). "Genetic Evidence of Branching in the Isoprenoid Pathway for the Production of Isopentenyl Diphosphate and Dimethylallyl Diphosphate in *Escherichia coli*," *FEBS Letters* 473:328-332.

Rodríguez-Concepción, M. et al. (Nov. 2002). "Elucidation of the Methylerythritol Phosphate Pathway for Isoprenoid Biosynthesis in Bacteria and Plastids. A Metabolic Milestone Achieved Through Genomics," *Plant Physiology* 130:1079-1089.

Rodríguez-Villalón, A. et al. (2008). "Carotenoid Accumulation in Bacteria with Enhanced Supply of Isoprenoid Precursors by Upregulation of Exogenous or Endogenous Pathways," *Journal of Biotechnology* 135:78-84.

Rohdich, F. et al. (Oct. 12, 1999). "Cytidine 5'-Triphosphate-Dependent Biosynthesis of Isoprenoids: YgbP Protein of *Escherichia coli* Catalyzes the Formation of 4-Diphosphocytidyl-2-*C*-Methylerythritol," *PNAS* 96(21):11758-11763.

Rohdich, F. et al. (Jun. 6, 2000). "Biosynthesis of Terpenoids: 4-Diphosphocytidyl-2C-Methyl-D-Erythritol Synthase of *Arabidopsis thaliana*," *PNAS* 97(12):6451-6456.

Rohmer, M. (1998). "Isoprenoid Biosynthesis Via the Mevalonate-Independent Route, A Novel Target for Antibacterial Drugs?" *Progress in Drug Research* 50:137-154.

Röhrich, R.C. et al. (2005, e-pub. Nov. 2, 2005). "Reconstitution of an Apicoplast-Localised Electron Transfer Pathway Involved in the Isoprenoid Biosynthesis of *Plasmodium falciparum*," *FEBS Letters* 579:6433-6438.

Rondon, M.R. et al. (May 1999). "Toward Functional Genomics in Bacteria: Analysis of Gene Expression in *Escherichia coli* from a Bacterial Artificial Chromosome Library of *Bacillus cereus*," *Proc. Natl. Acad. Sci. USA* 96:6451-6455.

Rosenfeld, J. et al. (1992). "In-Gel Digestion of Proteins for Internal Sequence Analysis After One- or Two-Dimensional Gel Electrophoresis," *Analytical Biochemistry* 203:173-179.

Rost, B. et al. (2004). "The PredictProtein Server," *Nucleic Acids Research* 32:W321-W326.

Sánchez, C. et al. (Apr. 2002). "The Biosynthetic Gene Cluster for the Antitumor Rebeccamycin: Characterization and Generation of Indolocarbazole Derivatives," *Chemistry and Biology* 9(4):519-531.

Sander, R. (Apr. 8, 1999). *Compilation of Henry's Law Constants for Inorganic and Organic Species of Potential Importance in Environmental Chemistry*, 3:1-107.

Sanfaçon, H. et al. (1991). "A Dissection of the Cauliflower Mosaic Virus Polyadenylation Signal," *Genes & Development* 5:141-149.

Sasaki, K. et al. (2005, e-pub. Apr. 7, 2005). "Gene Expression and Characterization of Isoprene Synthase from *Populus alba*," *FEBS Letters* 579:2514-2518.

Schneider, D. et al. (Jul. 9, 2002). "Genomic Comparisons Among *Escherichia coli* Strains B, K-12, and OI57:H7 Using IS Elements as Molecular Markers," *BMC Microbiology* 2:18, 8 pages.

Schnitzler, J.-P. et al. (2005, e-pub. Jul. 29, 2005). "Biochemical Properties of Isoprene Synthase in Poplar (*Populus* x *canescens*)," *Planta* 222(5):777-786.

Schöller, C. et al. (1997). "Volatile Metabolites from Some Gram-Negative Bacteria," *Chemosphere* 35(7):1487-1495.

Scott, E. et al. (2007, e-pub. Mar. 27, 2007). "Biomass in the Manufacture of Industrial Products—The Use of Proteins and Amino Acids," *Appl. Microbiol. Biotechnol.* 75:751-762.

Sen, S. et al. (2007). "Developments in Directed Evolution for Improving Enzyme Functions," *Appl. Biochem. Biotechnol.* 143:212-223.

Serino, G. et al. (1997). "A Negative Selection Scheme Based on the Expression of Cytosine Deaminase in Plastids," *The Plant Journal* 12(3):697-701.

Sharkey, T.D. et al. (Feb. 1, 2005). "Supplemental data for: Evolution of the Isoprene Biosynthetic Pathway in Kudzu," *Plant Physiology* 137(2):700-712.

Sharkey, T.D. et al. (Feb. 2005). "Evolution of the Isoprene Biosynthetic Pathway in Kudzu," *Plant Physiology* 137:700-712.

Sheir-Neiss, G. et al. (Jul. 1984). "Characterization of the Secreted Cellulases of *Trichoderma reesei* Wild Type and Mutants During Controlled Fermentations," *Appl. Microbiol. Biotechnol.* 20(1):46-53.

Shelton, D. et al. (2004, e-pub. Nov. 26, 2004). "Isolation and Partial Characterization of a Putative Monoterpene Synthase from *Melaleuca alternifolia*," *Plant Physiology and Biochemistry* 42:875-882.

Shinozaki, K. et al. (1986). "The Complete Nucleotide Sequence of the Tobacco Chloroplast Genome: its Gene Organization and Expression," *The EMBO Journal* 5(9):2043-2049.

(56) References Cited

OTHER PUBLICATIONS

Shirk, M.C. et al. (2002, e-pub. Jul. 27, 2002). "Isoprene Formation in *Bacillus subtilis*: A Barometer of Central Carbon Assimilation in a Bioreactor?" *Biotechnol. Prog.* 18(5):1109-1115.

Silver, G.M. et al. (1991). "Enzymatic Synthesis of Isoprene from Dimethylallyl Diphosphate in Aspen Leaf Extracts," *Plant Physiol.* 97:1588-1591.

Silver, G.M. et al. (Jun. 2, 1995). "Characterization of Aspen Isoprene Synthase, an Enzyme Responsible for Leaf Isoprene Emission to the Atmosphere," *The Journal of Biological Chemistry* 270(22):13010-13016.

Sivy, T.L. et al. (2002). "Isoprene Synthase Activity Parallels Fluctuations of Isoprene Release During Growth of *Bacillus subtilis*," *Biochemical and Biophysical Research Communications* 294:71-75.

Siwko, M.E. et al. (2007, e-pub. Oct. 4, 2006). "Does Isoprene Protect Plant Membranes from Thermal Shock? A Molecular Dynamics Study," *Biochimica et Biophysica Acta* 1768:198-206.

Slabinski, L. et al. (2007). "The Challenge of Protein Structure Determination—Lessons from Structural Genomics," *Protein Science* 16:2472-2482.

Slater, S. et al. (Apr. 1992). "Production of Poly-(3-Hydroxybutyrate-Co-3-Hydroxyvalerate) in a Recombinant *Escherichia coli* Strain," *Applied and Environmental Microbiology* 58(4):1089-1094.

Slater, S. et al. (Oct. 1999). "Metabolic Engineering of *Arabidopsis* and *Brassica* for Poly(3-Hydroxybutyrate-co-3-Hydroxyvalerate) Copolymer Production," *Nature Biotechnology* 17:1011-1016.

Smit, A. et al. (2000). "Biosynthesis of Isoprenoids Via Mevalonate in Archaea: The Lost Pathway," *Genome Research* 10:1468-1484.

Smith, T.F. et al. (1981). "Comparison of Biosequences," *Advances in Applied Mathematics* 2:482-489.

Sprenger, G.A. et al. (Nov. 1997). "Identification of a Thiamin-Dependent Synthase in *Escherichia coli* Required for the Formation of the 1-Deoxy-D-Xylulose 5-Phosphate Precursor to Isoprenoids, Thiamin, and Pyridoxol,"*Proc. Natl. Acad. Sci. USA* 94:12857-12862.

Starks, C.M. et al. (Sep. 19, 1997). "Structural Basis for Cyclic Terpene Biosynthesis by Tobacco 5-Epi-Aristolochene Synthase," *Science* 277:1815-1820.

Staub, J. M. et al. (1995). "Expression of a Chimeric uidA Gene Indicates that Polycistronic mRNAs are Efficiently Translated in Tobacco Plastids," *The Plant Journal* 7(5):845-848.

Staub, J. M. et al. (Mar. 2000). "High-Yield Production of a Human Therapeutic Protein in Tobacco Chloroplast," *Nature Biotechnology* 18:333-338.

Steinbüchel, A. (2003). "Production of Rubber-Like Polymers by Microorganisms," *Current Opinion in Microbiology* 6:261-270.

Steller, I. et al. (1997). "An Algorithm for Automatic Indexing of Oscillation Images using Fourier Analysis," *Journal of Applied Crystallography* 30:1036.1040.

Stermer, B.A. et al. (1994). "Regulation of HMG-CoA Reductase Activity in Plants," *Journal of Lipid Research* 35:1133-1140.

Stevens, D.R. et al. (1997). "Genetic Engineering of Eukaryotic Algae: Progress and Prospects," *J. Phycol.* 33:713-722.

Sulter, G.J. et al. (1990). "Proliferation and Metabolic Significance of Peroxisomes in *Candida boidinii* During Growth on D-Alanine or Oleic Acid as the Sole Carbon Source," *Arch. Microbiol.* 153:485-489.

Sutherlin, A. et al. (Aug. 2002). "*Enterococcus faecalis* 3-Hydroxy-3-Methylglutaryl Coenzyme A Synthase, an Enzyme of Isopentenyl Diphosphate Biosynthesis," *Journal of Bacteriology* 184(15):4065-4070.

Takagi, M. et al. (Aug. 2000). "A Gene Cluster for the Mevalonate Pathway from *Streptomyces* sp. Strain CL190," *Journal of Bacteriology* 182(15):4153-4157.

Takahashi, S. et al. (Feb. 1999). "Purification, Characterization, and Cloning of a Eubacterial 3-Hydroxy-3-Methylglutaryl Coenzyme A Reductase, a Key Enzyme Involved in Biosynthesis of Terpenoids," *Journal of Bacteriology* 181(4):1256-1263.

Takara Bio Inc. (Feb. 2008). "Chaperon Plasmid Set," Cat. # 3340, pp. 1-8.

Teymouri, F. et al. (2005, e-pub. Feb. 24, 2005). "Optimization of the Ammonia Fiber Explosion (AFEX) Treatment Parameters for Enzymatic Hydrolysis of Corn Stover," *Bioresource Technology* 96:2014-2018.

Thomas, F. et al. (1988). "Expression of the rp123, rp12 and rps19 Genes in Spinach Chloroplasts," *Nucleic Acids Research* 16(6):2461-2472.

Thomason, L.C. et al. (2007, e-pub. Apr. 16, 2007). "Multicopy Plasmid Modification with Phage λ Red Recombineering," *Plasmid* 58:148-158.

Thouvenot, B. et al. (2004). "The Strong Efficiency of the *Escherichia coli* gapA P1 Promoter Depends on a Complex Combination of Functional Determinants," *Biochem. J.* 383:371-382.

Timberlake, W.E. (1991). "Cloning and Analysis of Fungal Genes," Chapter 3 in *More Gene Manipulations in Fungi*, Bennett, J.W. et al. eds., Academic Press, San Diego, CA, pp. 70-76.

Tokuriki, N. et al. (2009, e-pub. Sep. 16, 2009). "Stability Effects of Mutations and Protein Evolvability," *Current Opinion in Structural Biology* 19(5):596-604.

Toriyama, K. et al. (1985). "Cell Suspension and Protoplast Culture in Rice," *Plant Science* 41:179-183.

Tsay, Y.H. et al. (Feb. 1991). "Cloning and Characterization of ERG8, an Essential Gene of *Saccharomyces cerevisiae* That Encodes Phosphomevalonate Kinase," *Molecular and Cellular Biology* 11(2):620-631.

Tsudsuki, T. (Apr. 27, 1998) "Direct submission, bases 1-155939", *Data Processing Center*, Submitted Feb. 27, 1998, Aichi-Gakuin University, Aichi, Japan, 12 pages.

UniProt Database Accession No. A2XGY9, last updated Jul. 27, 2011, located at <http://www.uniprot.org/jobs/201109112CDIG8GYZL.txt>, last visited on Sep. 11, 2011, 2 pages.

UniProt Database Accession No. A5AR04, last updated Jul. 27, 2011, located at <http://www.uniprot.org/jobs/20110911315BAWWKZ7.txt>, last visited on Sep. 11, 2011, 1 page.

UniProt Database Accession No. A5AV19, last updated on Oct. 16, 2013, located at http://www.uniprot.org/uniprot/A5AV19, last visited on Oct. 29, 2013, 3 pages.

UniProt Database Accession No. A5B7V4, last updated Jul. 27, 2011, located at <http://www.uniprot.org/jobs/201109115006CWCI3L.txt>, last visited on Sep. 11, 2011, 1 page.

UniProt Database Accession No. A5BKK1, last updated Jul. 27, 2011, located at <http://www.uniprot.org/jobs/20110911315BB1QWK6.txt>, last visited on Sep. 11, 2011, 1 page.

UniProt Database Accession No. A5BLS5, last updated Jul. 27, 2011, located at <http://www.uniprot.org/jobs/201109112CDIFUU28L.txt>, last visited on Sep. 11, 2011, 1 page.

UniProt Database Accession No. A7IZZ1, last updated on Oct. 16, 2013, located at http://www.uniprot.org/uniprot/A7IZZ1, last visited on Oct. 29, 2013, 5 pages.

UniProt Database Accession No. A9PGR5, last updated Jul. 27, 2011, located at <http://www.uniprot.org/jobs/201109112CDIFT06PL.txt>, last visited on Sep. 11, 2011, 1 page.

UniProt Database Accession No. A9Q7C9, last updated on Oct. 16, 2013, located at http://www.uniprot.org/uniprot/A9Q7C9, last visited on Oct. 29, 2013, 3 pages.

UniProt Database Accession No. B1P189, last updated Jul. 27, 2011, located at <http://www.uniprot.org/jobs/201109112CDIFXI7BK.txt>, last visited on Sep. 11, 2011, 1 page.

UniProt Database Accession No. B3GEM8, last updated Jul. 27, 2011, located at <http://www.uniprot.org/jobs/20110911315BAG9N17.txt>, last visited on Sep. 11, 2011, 1 page.

UniProt Database Accession No. B3TPQ7, "SubName: Full=Alpha-terpineol synthase." Retrieved from EBI accession No. UNIPROT:B3TPQ7 (Sep. 2, 2008), last updated on May 16, 2012, located at http://www.uniprot.org/uniprot/B3TPQ7, last visited on Jul. 23, 2012, 5 pages, (XP-002674045, XP-002674053).

UniProt Database Accession No. B6F137, last updated on Oct. 16, 2013, located at http://www.uniprot.org/uniprot/B6F137, last visited on Oct. 29, 2013, 3 pages.

(56) References Cited

OTHER PUBLICATIONS

UniProt Database Accession No. B7FLI6, last updated Jul. 27, 2011, located at <http://www.uniprot.org/jobs/20110911315BAXCRQU.txt>, last visited on Sep. 11, 2011, 1 page.
UniProt Database Accession No. B9HE95, last updated Jul. 27, 2011, located at <http://www.uniprot.org/jobs/201109112CDIFY9X6U.txt>, last visited on Sep. 11, 2011, 2 pages.
UniProt Database Accession No. B9MXU1, last updated Jul. 27, 2011, located at <http://www.uniprot.org/jobs/201109112CDIFV8DIC.txt>, last visited on Sep. 11, 2011, 2 pages.
UniProt Database Accession No. B9PAP5, last updated Jul. 27, 2011, located at <http://www.uniprot.org/jobs/201109112CDIG1HNFH.txt>, last visited on Sep. 11, 2011, 2 pages.
UniProt Database Accession No. B9RPM0, "SubName: Full=(R)-limonene synthase." Retrieved from EBI accession No. UNIPROT:B9RPM0 (Mar. 24, 2009), last updated on May 16, 2012, located at http://www.uniprot.org/uniprot/B9RPM0, last visited on Jul. 23, 2012, 3 pages.
UniProt Database Accession No. B9T537, last updated Nov. 30, 2010, located at <http://www.uniprot.org/jobs/20110911315BB065GR.txt>, last visited on Sep. 11, 2011, 1 page.
UniProt Database Accession No. B9T825, last updated Jul. 27, 2011, located at <http://www.uniprot.org/jobs/20110911315BALANC9.txt>, last visited on Sep. 11, 2011, 1 page.
UniProt Database Accession No. D7LHH0, last updated on Oct. 16, 2013, located at http://www.uniprot.org/uniprot/D7LHH0, last visited on Oct. 29, 2013, 4 pages.
UniProt Database Accession No. G1JUH1, last updated on Oct. 16, 2013, located at http://www.uniprot.org/uniprot/G1JUH1, last visited on Oct. 29, 2013, 5 pages.
UniProt Database Accession No. Q0PCI3, last updated Jul. 27, 2011, located at <http://www.uniprot.org/jobs/20110911315BAPL92C.txt>, last visited on Sep. 11, 2011, 1 page.
UniProt Database Accession No. Q0PCI4, last updated Jul. 27, 2011, located at <http://www.uniprot.org/jobs/20110911315BAQURQ8.txt>, last visited on Sep. 11, 2011, 1 page.
UniProt Database Accession No. Q50L36, last updated May 31, 2011, located at <http://www.uniprot.org/jobs/201109112CDIGBF1M4.txt>, last visited on Sep. 11, 2011, 2 pages.
UniProt Database Accession No. Q5SBP1, last updated Apr. 5, 2011, located at <http://www.uniprot.org/jobs/201109112CDIGFFR1Q.txt>, last visited on Sep. 11, 2011, 2 pages.
UniProt Database Accession No. Q5SBP2, last updated Apr. 5, 2011, located at <http://www.uniprot.org/jobs/201109112CDIG4W1U8.txt>, last visited on Sep. 11, 2011, 2 pages.
UniProt Database Accession No. Q5SBP4, last updated Jul. 27, 2011, located at <http://www.uniprot.org/jobs/2011091140O0OYGHJF.txt>, last visited on Sep. 11, 2011, 2 pages.
UniProt Database Accession No. Q5UB07, last updated Jul. 27, 2011, located at <http://www.uniprot.org/jobs/201109112CDIFZCWUC.txt>, last visited on Sep. 11, 2011, 1 page.
UniProt Database Accession No. Q672F7, last updated Jul. 27, 2011, located at <http://www.uniprot.org/jobs/201109112CDIFWBP6O.txt >, last visited on Sep. 11, 2011, 1 page.
UniProt Database Accession No. Q6EJ97, last updated Apr. 5, 2011, located at <http://www.uniprot.org/jobs/20110911315BARZM8D.txt>, last visited on Sep. 11, 2011, 2 pages.
UniProt Database Accession No. Q6PWU1, "SubName: Full=(-)-a-terpineol synthase." Retrieved from EBI accession No. UNIPROT:Q6PWU1 (Jul. 5, 2004), last updated on Jul. 11, 2012, located at http://www.uniprot.org/uniprot/Q6PWU1, last visited on Jul. 23, 2012, 4 pages.
UniProt Database Accession No. Q7Y1V1, last updated Jul. 27, 2011, located at <http://www.uniprot.org/jobs/201109112CDIG0LK2O.txt>, last visited on Sep. 11, 2011, 1 page.
UniProt Database Accession No. Q8L5K1, last updated on Oct. 16, 2013, located at http://www.uniprot.org/uniprot/Q8L5K1, last visited on Oct. 29, 2013, 3 pages.
UniProt Database Accession No. Q93X23, last updated on Oct. 16, 2013, located at http://www.uniprot.org/uniprot/Q93X23, last visited on Oct. 29, 2013, 5 pages.
UniProt Database Accession No. Q941H1, last updated Jul. 27, 2011, located at <http://www.uniprot.org/jobs/201109112CDIG6PW6Y.txt>, last visited on Sep. 11, 2011, 1 page.
UniProt Database Accession No. Q9AR86, last updated May 31, 2011, located at <http://www.uniprot.org/jobs/2011091140O0P1KMN7.txt>, last visited on Sep. 11, 2011, 2 pages.
UniProt Database Accession No. Q9LIA1; Q84UU7, last updated Jul. 27, 2011, located at <http://www.uniprot.org/jobs/20110911315BB4RI8G.txt>, last visited on Sep. 11, 2011, 3 pages.
UniProt Database Accession No. Q9LRZ6, "RecName: Full=Beta-myrcene/(E)-beta-ocimene synthase 2, chloroplastic; EC=4.2.3.15; AltName: Full=Terpenoid synthase 24; Short=AtTpS24; Flags: Precursor." Retrieved from EBI accession No. UNIPROT:Q9LRZ6 (Oct. 1, 2000); last updated on Jul. 11, 2012, located at http://www.uniprot.org/uniprot/Q9LRZ6, last visited on Jul. 23, 2012, 8 pages.
UniProt Database Accession No. Q7XAS7, last updated Apr. 5, 2011, located at <http://www.uniprot.org/jobs/201109112CDIGCK99G.txt>, last visited on Sep. 11, 2011, 2 pages.
UniProt Database Accession No. Q9FQ26, last updated Jul. 27, 2011, located at <http://www.uniprot.org/jobs/20110911315BB3SH2Y.txt>, last visited on Sep. 11, 2011, 1 page.
Vadali, R.V. et al. (2005, e-pub. Sep. 2, 2005). "Enhanced Lycopene Productivity by Manipulation of Carbon Flow to Isopentenyl Diphosphate in *Escherichia coli*," *Biotechnol. Prog.* 21(5):1558-1561.
Vagin, A. et al. (1997). "MOLREP: An Automated Program for Molecular Replacement," *Journal of Applied Crystallography* 30:1022-1025.
Vandamme, E.J. et al. (2002, e-pub. 2002). "Bioflavours and Fragrances Via Fermentation and Biocatalysis," *Journal of Chemical Technology and Biotechnology* 77:1323-1332.
Van Den Hondel, C.A.M.J.J. et al. (1991). "Heterologous Gene Expression in Filamentous Fungi," Chapter 18 in *More Gene Manipulations in Fungi*, Bennett, J.W. et al. eds., Academic Press, Inc.: San Diego, CA, pp. 396-428.
Van De Walle, M. et al. (Jan. 5, 1998). "Proposed Mechanism of Acetate Accumulation in Two Recombinant *Escherichia coli* Strains During High Density Fermentation," *Biotechnology and Bioengineering* 57(1):71-78.
Van Hylckama, J.E.T. et al. (Apr. 2000). "Characterization of the Gene Cluster Involved in Isoprene Metabolism in *Rhodococcus* sp. Strain AD45," *Journal of Bacteriology* 182(7):1956-1963.
Vane, L.M. (2005, e-pub. Apr. 21, 2005). "A Review of Pervaporation for Product Recovery from Biomass Fermentation Processes," *Journal of Chemical Technology and Biotechnology* 80:603-629.
Velikova, V. et al. (2005). "Consequences of Inhibition of Isoprene Synthesis in *Phragmites australis* Leaves Exposed to Elevated Temperatures," *Agriculture, Ecosystems & Environment* 106:209-217.
Vidal, M. et al. (2006, e-pub. Nov. 23, 2005). "Evaluation of Lower Flammability Limits of Fuel-Air-Diluent Mixtures Using Calculated Adiabatic Flame Temperatures," *Journal of Hazardous Materials* 130:21-27.
Voss, S. et al. (1997). "Mutagenesis of a Flexible Loop in Streptavidin Leads to Higher Affinity for the Strep-tag II Peptide and Improved Performance in Recombinant Protein Purification," *Protein Engineering* 10(8):975-982.
Voynova, N.E. et al. (Jan. 2004). "*Staphylococcus aureus* Mevalonate Kinase: Isolation and Characterization of an Enzyme of the Isoprenoid Biosynthetic Pathway," *Journal of Bacteriology* 186(1):61-67.
Wagner, W.P. et al. (Aug. 1999). "Three Distinct Phases of Isoprene Formation During Growth and Sporulation of *Bacillus subtilis*," *Journal of Bacteriology* 181(15):4700-4703.
Wagner, W.P. et al. (Jan. 2000, e-pub. Nov. 18, 1999). "Isoprene Biosynthesis in *Bacillus subtilis* Via the Methylerythritol Phosphate Pathway," *J. Nat. Prod.* 63(1):37-40.
Wang, C.-W. et al. (Jan. 20, 1999). "Engineered Isoprenoid Pathway Enhances Astaxanthin Production in *Escherichia coli*," *Biotechnology and Bioengineering* 62(2):235-241.

(56) References Cited

OTHER PUBLICATIONS

Ward, M. et al. (Aug. 1993). "Use of *Aspergillus* Overproducing Mutants, Cured for Integrated Plasmid, to Overproduce Heterologous Proteins," *Appl. Microbiol. Biotechnol.* 39(6):738-743.
Weissermel, K. et al. (2003). *Industrial Organic Chemistry, 4th, Completely Revised Edition*, translated by Lindley, C.R. et al., Wiley-VCH GmbH & Co. KGaA, Weinheim, Germany, pp. 117-222.
Whisstock, J.C. et al. (2003). "Prediction of Protein Function from Protein Sequence and Structure," *Quarterly Reviews of Biophysics* 36(3):307-340.
Whittington, D.A. et al. (Nov. 26, 2002). "Bornyl Diphosphate Synthase: Structure and Strategy for Carbocation Manipulation by a Terpenoid Cyclase," *PNAS* 99(24):15375-15380.
Wilde, R.J. et al. (1986). "Transcript Analysis of the Citrate Synthase and Succinate Dehydrogenase Genes of *Escherichia coli* K12," *Journal of General Microbiology* 132:3239-3251.
Wildermuth, M.C. et al. (1998). "Biochemical Characterization of Stromal and Thylakoid-Bound Isoforms of Isoprene Synthase in Willow Leaves," *Plant Physiology* 116:1111-1123.
Wilding, E.I. et al. (Aug. 2000). "Identification, Evolution, and Essentiality of the Mevalonate Pathway for Isopentenyl Diphosphate Biosynthesis in Gram-Positive Cocci," *Journal of Bacteriology* 182(15):4319-4327.
Wilkins, K. (1996). "Volatile Metabolites from Actinomycetes," *Chemosphere* 32(7):1427-1434.
Williams, D.C. et al. (1998). "Truncation of Limonene Synthase Preprotein Provides a Fully Active 'Pseudomature' Form of This Monoterpene Cyclase and Reveals the Function of the Amino-Terminal Arginine Pair," *Biochemistry* 37(35):12213-12220.
Wishart, M.J. et al. (Nov. 10, 1995). "A Single Mutation Converts a Novel Phosphotyrosine Binding Domain into a Dual-Specificity Phosphatase," *The Journal of Biological Chemistry* 270(45):26782-26785.
Withers, S.T. et al. (Oct. 2007, e-pub. Aug. 10, 2007). "Identification of Isopentenol Biosynthetic Genes from *Bacillus subtilis* by a Screening Method Based on Isoprenoid Precursor Toxicity," *Applied and Environmental Microbiology* 73(19):6277-6283.
Witkowski, A. et al. (1999, e-pub. Aug. 18, 1999). "Conversion of β-Ketoacyl Synthase to a Malonyl Decarboxylase by Replacement of the Active-Site Cysteine with Glutamine," *Biochemistry* 38(36):11643-11650.
Wolfertz, M. et al. (2003). "Biochemical Regulation of Isoprene Emission," *Plant, Cell and Environment* 26:1357-1364.
Wolfertz, M. et al. (Aug. 2004). "Rapid Regulation of the Methylerythritol 4-Phosphate Pathway During Isoprene Synthesis," *Plant Physiology* 135:1939-1945.
Wu, D.Y. et al. (1989). "The Ligation Amplification Reaction (LAR)- Amplification of Specific DNA Sequences Using Sequential Rounds of Template-Dependent Ligation," *Genomics* 4:560-569.

Xia, X.-X. et al. (2008). "Comparison of the Extracellular Proteomes of *Escherichia coli* B and K-12 Strains During High Cell Density Cultivation," *Proteomics* 8:1-15.
Yamada, K. et al. (1989). "Production of Glycerol from Methanol by a Mutant Strain of *Candida boidinii* No. 2201," *Agric. Biol. Chem.* 53(2):541-543.
Yang, D. et al. (Mar. 15, 2002, published ahead of print Dec. 19, 2001). "Structure of the *Methanococcus jannaschii* Mevalonate Kinase, a Member of the GHMP Kinase Superfamily," *The Journal of Biological Chemistry* 277(11):9462-9467.
Ye, X. et al. (Jan. 14, 2000). "Engineering the Provitamin A (β-Carotene) Biosynthetic Pathway into (Carotenoid-Free) Rice Endosperm," *Science* 287:303-305.
Yelton, M.M. et al. (Mar. 1984). "Transformation of *Aspergillus nidulans* by Using a trpC Plasmid," *Proc. Natl. Acad. Sci. USA* 81:1470-1474.
Yoon, S.-H. et al. (2007, e-pub. May 15, 2007). "Increased β-Carotene Production in Recombinant *Escherichia coli* Harboring an Engineered Isoprenoid Precursor Pathway with Mevalonate Addition," *Biotechnol. Prog.* 23(3):599-605.
Yoon, S.-H. et al. (2009). "Combinatorial Expression of Bacterial Whole Mevalonate Pathway for the Production of β-Carotene in *E. coli*," *Journal of Biotechnology* 140:218-226.
Zepeck, F. et al. (2005, e-pub. Oct. 14, 2005). "Biosynthesis of Isoprenoids. Purification and Properties of IspG Protein from *Escherichia coli*," *J. Org. Chem.* 70:9168-9174.
International Search Report mailed on Jun. 18, 2009, for PCT Patent Application No. PCT/US08/86869, filed on Dec. 15, 2008, one page.
International Search Report mailed on Dec. 8, 2009, for PCT Application No. PCT/US2009/041581, filed on Apr. 23, 2009, nine pages.
International Search Report mailed on Dec. 30, 2010, for PCT Application No. PCT/US2010/032134, filed on Apr. 22, 2010, 15 pages.
International Search Report mailed on Jul. 24, 2012, for PCT Patent Application No. PCT/US2011/058188, filed on Oct. 27, 2011, ten pages.
Miao, L. et al. (2006, e-pub. Mar. 15, 2006). "Effect of Culture Conditions on Mycelial Growth, Antibacterial Activity, and Metabolite Profiles of the Marine-derived Fungus *Arthrinium* c.f. *Saccharicola*," *Appl. Microbiol. Biotechnol.* 72:1063-1073.
Non-Final Office Action mailed on May 10, 2011, for U.S. Appl. No. 12/429,143, filed Apr. 23, 2009, 23 pages.
Response to Non-Final Office Action submitted to the U.S. PTO on Sep. 12, 2011, for U.S. Appl. No. 12/429,143, filed Apr. 23, 2009, 20 pages.
Final Office Action mailed on Oct. 24, 2011, for U.S. Appl. No. 12/429,143, filed Apr. 23, 2009, 13 pages.
Response to Final Office Action submitted to the U.S. PTO on Dec. 27, 2011, for U.S. Appl. No. 12/429,143, filed Apr. 23, 2009, 10 pages.
Notice of Allowance mailed on Jan. 19, 2012, for U.S. Appl. No. 12/429,143, filed Apr. 23, 2009, 8 pages.

\* cited by examiner

Figure. 1

Kudzu IspS DNA for *E. coli* (SEQ ID NO:1)

atgtgtgcgacctcttctcaatttactcagattaccgagcataattcccgtcgttccgcaaactatcagccaaacct
gtggaatttcgaattcctgcaatccctggagaacgacctgaaagtggaaaagctggaggagaaagcgaccaaactgg
aggaagaagttcgctgcatgatcaaccgtgtagacacccagccgctgtccctgctggagctgatcgacgatgtgcag
cgcctgggtctgacctacaaatttgaaaaagacatcattaaagccctggaaaacatcgtactgctggacgaaaacaa
aaagaacaaatctgacctgcacgcaaccgctctgtctttccgtctgctgcgtcagcacggtttcgaggtttctcagg
atgttttgagcgtttcaaggataaagaaggtggtttcagcggtgaactgaaaggtgacgtccaaggcctgctgagc
ctgtatgaagcgtcttacctgggtttcgagggtgagaacctgctggaggaggcgcgtacctttttccatcacccacct
gaagaacaacctgaaagaaggcattaataccaaggttgcagaacaagtgagccacgccctggaactgccatatcacc
agcgtctgcacgtctggaggcacgttggttcctggataaatacgaaccgaaagaaccgcatcaccagctgctgctg
gagctggcgaagctggattttaacatggtacagaccctgcaccagaaagagctgcaagatctgtcccgctggtggac
cgagatgggcctggctagcaaactggattttgtacgcgaccgcctgatggaagtttatttctgggcactgggtatgg
cgccagaccgcagtttggtgaatgtcgcaaagctgttactaaaatgtttggtctggtgacgatcatcgatgacgtg
tatgacgtttatggcactctggacgaactgcaactgttcaccgatgctgtagagcgctgggacgttaacgctattaa
caccctgccggactatatgaaactgtgtttcctggcactgtacaacaccgttaacgacacgtcctattctattctga
aagagaaaggtcataacaacctgtcctatctgacgaaaagctggcgtgaactgtgcaaagcctttctgcaagaggcg
aaatggtccaacaacaaaattatcccggcttttctccaagtacctggaaaacgccagcgtttcctcctccgtgtagc
gctgctggcgcgtctttactttccgtatgccagcagcaggaagacatctccgaccacgcgctgcgttccctgaccg
acttccatggtctggtgcgttctagctgcgttatcttccgcctgtgcaacgatctggccacctctgcggcggagctg
gaacgtggcgagactaccaattctatcattagctacatgcacgaaaacgatggtaccagcgaggaacaggcccgcga
agaactgcgtaaactgatcgacgccgaatggaaaaagatgaatcgtgaacgcgttagcgactccaccctgctgccta
aagcgttcatggaaatcgcagttaacatggcacgtgtttcccactgcacctaccagtatggcgatggtctgggtcgc
ccagactacgcgactgaaaaccgcatcaaactgctgctgattgacccttttccgattaaccagctgatgtatgtcta
a

Figure 2

Kudzu IspS protein (SEQ ID NO:2)

MCATSSQFTQITEHNSRRSANYQPNLWNFEFLQSLENDLKVEKLEEKATKLEEEVRCMINRVDTQPLSLLELIDDVQ
RLGLTYKFEKDIIKALENIVLLDENKKNKSDLHATALSFRLLRQHGFEVSQDVFERFKDKEGGFSGELKGDVQGLLS
LYEASYLGFEGENLLEEARTFSITHLKNNLKEGINTKVAEQVSHALELPYHQRLHRLEARWFLDKYEPKEPHHQLLL
ELAKLDFNMVQTLHQKELQDLSRWWTEMGLASKLDFVRDRLMEVYFWALGMAPDPQFGECRKAVTKMFGLVTIIDDV
YDVYGTLDELQLFTDAVERWDVNAINTLPDYMKLCFLALYNTVNDTSYSILKEKGHNNLSYLTKSWRELCKAFLQEA
KWSNNKIIPAFSKYLENASVSSSGVALLAPSYFSVCQQQEDISDHALRSLTDFHGLVRSSCVIFRLCNDLATSAAEL
ERGETTNSIISYMHENDGTSEEQAREELRKLIDAEWKKMNRERVSDSTLLPKAFMEIAVNMARVSHCTYQYGDGLGR
PDYATENRIKLLLIDPFPINQLMYV

Figure 3

Poplar IspS DNA for *E. coli* (SEQ ID NO:6)

atgtgctctgtttctaccgagaacgtttccttcactgagacggaaaccgaggcacgtcgtagcgcgaactacgagcc
gaatagctgggactacgatttcctgctgtcttccgatactgacgaatctattgaggtgtacaaagacaaagcaaaga
aactggaggctgaagtgcgccgcgaaattaacaacgagaaagctgaattcctgactctgctggagctgatcgataac
gtacagcgcctgggtctgggttaccgcttcgaatctgatatccgtcgcgcactggatcgtttcgtaagcagcggcgg
tttcgatggcgtgaccaaaacgagcctgcacgctaccgcgctgtccttccgtctgctgcgtcagcacggcttcgaag
tttctcaggaagcattctccggtttcaaagatcaaaacggtaacttcctggaaaacctgaaagaagacactaaggcg
atcctgagcctgtatgaggcaagctttctggccctggagggtgagaacatcctggatgaggcgcgcgtattcgccat
ctcccatctgaaagagctgtctgaagagaaaatcggtaaggaactggcagagcaggttaatcacgcactggaactgc
cgctgcatcgtcgtacccagcgtctggaggcggtttggtccatcgaagcgtaccgcaaaaaggaggatgctaaccag
gttctgctggaactggccatcctggactacaacatgatccagtccgtttaccagcgtgatctgcgtgaaacctcccg
ttggtggcgccgtgtgggcctggcgaccaaactgcacttcgctaaggaccgcctgattgagtcttttactgggcag
tcggcgttgcgttcgaacctcagtattctgactgccgtaacagcgttgcgaaaatgttcagcttcgttactattatc
gacgacatctacgacgtttacggtactctggacgagctggaactgtttaccgacgctgtcgaacgttgggatgttaa
cgccatcaacgatctgcctgactacatgaaactgtgcttcctggcactgtataacacgatcaacgaaattgcatacg
acaacctgaaagacaaaggtgaaaacatcctgccgtacctgactaaagcgtgggcggatctgtgtaacgcttttctg
caagaagcgaaatggctgtataacaaatccactccgaccttgacgattatttcggcaatgcctggaaatccagctc
tggcccgctgcaactgatcttcgcttattttgcggttgtccaaaacatcaaaaaggaggaaattgaaaacctgcaaa
aataccacgatatcattagccgtcctctctcatatctttcgcctgtgcaacgacctggcaagcgcgtccgcagagatc
gcacgtggcgaaaccgctaactctgtttcctgctacatgcgcaccaagggcatttccgaagagctggcaaccgagag
cgtaatgaatctgatcgacgaaacctgtaagaaaatgaacaaagaaaactggggtggctccctgttcgctaaaccgt
tcgtagagactgctattaacctggcacgtcagagccactgcacctaccacaatggtgacgcacatactagcccggat
gaactgactcgtaaacgtgtactgtctgttatcaccgaaccgattctgccgttcgaacgttaa

Figure 4

Poplar IspS protein (SEQ ID NO:7)

MCSVSTENVSFTETETEARRSANYEPNSWDYDFLLSSDTDESIEVYKDKAKKLEAEVRREINNEKAEFLTLLELIDN
VQRLGLGVRFESDIRRALDRFVSSGGFDGVTKTSLHATALSFRLLRQHGFEVSQEAFSGFKDQNGNFLENLKEDTKA
ILSLYEASFLALEGENILDEARVFAISHLKELSEEKIGKELAEQVNHALELPLHRRTQRLEAVWSIEAYRKKEDANQ
VLLELAILDYNMIQSVYQRDLRETSRWWRRVGLATKLHFAKDRLIESFYWAVGVAFEPQYSDCRNSVAKMFSFVTII
DDIYDVYGTLDELELFTDAVERWDVNAINDLPDYMKLCFLALYNTINEIAYDNLKDKGENILPYLTKAWADLCNAFL
QEAKWLYNKSTPTFDDYFGNAWKSSSGPLQLTFAYFAVVQNIKKEEIENLQKYHDIISRPSHIFRLCNDLASASAEI
ARGETANSVSCYMRTKGISEELATESVMNLIDETCKKMNKEKLGGSLFAKPFVETAINLARQSHCTYHNGDAHTSPD
ELTRKRVLSVITEPILPFER

Kudzu Isoprene Synthase

Figure 10A plasmid MCM93 = pCR2.1-Kudzu (SEQ ID NO:22)
aagggcgaattctgcagatatccatcacactggcggccgctcgagcatgcatctagagggcccaattcgccctatag
tgagtcgtattacaattcactggccgtcgttttacaacgtcgtgactgggaaaaccctggcgttacccaacttaatc
gccttgcagcacatccccctttcgccagctggcgtaatagcgaagaggcccgcaccgatcgcccttcccaacagttg
cgcagcctgaatggcgaatggacgcgccctgtagcggcgcattaagcgcggcgggtgtggtggttacgcgcagcgtg
accgctacacttgccagcgccctagcgcccgctcctttcgctttcttcccttcctttctcgccacgttcgccggctt
tccccgtcaagctctaaatcgggggctccctttagggttccgatttagtgctttacggcacctcgaccccaaaaaac
ttgattagggtgatggttcacgtagtgggccatcgccctgatagacggtttttcgccctttgacgttggagtccacg
ttctttaatagtggactcttgttccaaactggaacaacactcaacccatctcggtctattcttttgatttataagg
gattttgccgatttcggcctattggttaaaaaatgagctgatttaacaaaaatttaacgcgaattttaacaaaattc
agggcgcaagggctgctaaaggaagcggaacacgtagaaagccagtccgcagaaacggtgctgacccccggatgaatg
tcagctactgggctatctggacaagggaaaacgcaagcgcaaagagaaagcaggtagcttgcagtgggcttacatgg
cgatagctagactgggcggttttatggacagcaagcgaaccggaattgccagctggggcgccctctggtaaggttgg
gaagccctgcaaagtaaactggatggctttcttgccgccaaggatctgatggcgcaggggatcaagatctgatcaag
agacaggatgaggatcgtttcgcatgattgaacaagatggattgcacgcaggttctccggccgcttgggtggagagg
ctattcggctatgactgggcacaacagacaatcggctgctctgatgccgccgtgttccggctgtcagcgcaggggcg
cccggttctttttgtcaagaccgacctgtccggtgccctgaatgaactgcaggacgaggcagcgcggctatcgtggc
tggccacgacgggcgttccttgcgcagctgtgctcgacgttgtcactgaagcgggaagggactggctgctattgggc
gaagtgccggggcaggatctcctgtcatctcaccttgctcctgccgagaaagtatccatcatggctgatgcaatgcg
gcggctgcatacgcttgatccggctacctgcccattcgaccaccaagcgaaacatcgcatcgagcgagcacgtactc
ggatggaagccggtcttgtcgatcaggatgatctggacgaagagcatcaggggctcgcgccagccgaactgttcgcc
aggctcaaggcgcgcatgcccgacggcgaggatctcgtcgtgacccatggcgatgcctgcttgccgaatatcatggt
ggaaaatggccgcttttctggattcatcgactgtggccggctgggtgtggcggaccgctatcaggacatagcgttgg
ctacccgtgatattgctgaagagcttggcggcgaatgggctgaccgcttcctcgtgctttacggtatcgccgctccc
gattcgcagcgcatcgccttctatcgccttcttgacgagttcttctgaattgaaaaaggaagagtatgagtattcaa
catttccgtgtcgcccttattcccttttttgcggcattttgccttcctgtttttgctcacccagaaacgctggtgaa
agtaaaagatgctgaagatcagttgggtgcacgagtgggttacatcgaactggatctcaacagcggtaagatccttg
agagttttcgccccgaagaacgttttccaatgatgagcacttttaaagttctgctatgtggcgcggtattatcccgt
attgacgccgggcaagagcaactcggtcgccgcatacactattctcagaatgacttggttgagtactcaccagtcac
agaaaagcatcttacggatggcatgacagtaagagaattatgcagtgctgccataaccatgagtgataacactgcgg
ccaacttacttctgacaacgatcggaggaccgaaggagctaaccgcttttttgcacaacatgggggatcatgtaact
cgccttgatcgttgggaaccggagctgaatgaagccataccaaacgacgagcgtgacaccacgatgcctgtagcaat
ggcaacaacgttgcgcaaactattaactggcgaactacttactctagcttcccggcaacaattaatagactggatgg
aggcggataaagttgcaggaccacttctgcgctcggcccttccggctggctggtttattgctgataaatctggagcc
ggtgagcgtgggtctcgcggtatcattgcagcactggggccagatggtaagccctcccgtatcgtagttatctacac
gacgggagtcaggcaactatggatgaacgaaatagacagatcgctgagataggtgcctcactgattaagcattggt
aactgtcagaccaagtttactcatatatactttagattgatttaaaacttcatttttaatttaaaaggatctaggtg
aagatcctttttgataatctcatgaccaaaatcccttaacgtgagttttcgttccactgagcgtcagaccccgtaga
aaagatcaaaggatcttcttgagatccttttttctgcgcgtaatctgctgcttgcaaacaaaaaaaccaccgctac
cagcggtggtttgtttgccggatcaagagctaccaactcttttccgaaggtaactggcttcagcagagcgcagata
ccaaatactgttcttctagtgtagccgtagttaggccaccacttcaagaactctgtagcaccgcctacatacctcgc
tctgctaatcctgttaccagtggctgctgccagtggcgataagtcgtgtcttaccgggttggactcaagacgatagt
taccggataaggcgcagcggtcgggctgaacggggggttcgtgcacacagcccagcttggagcgaacgacctacacc
gaactgagatacctacagcgtgagctatgagaaagcgccacgcttcccgaagggagaaaggcggacaggtatccggt
aagcggcagggtcggaacaggagagcgcacgagggagcttccagggggaaacgcctggtatctttatagtcctgtcg
ggtttcgccacctctgacttgagcgtcgatttttgtgatgctcgtcaggggggcggagcctatggaaaaacgccagc
aacgcggcctttttacggttcctggccttttgctggccttttgctcacatgttctttcctgcgttatcccctgattc
tgtggataaccgtattaccgcctttgagtgagctgataccgctcgccgcagccgaacgaccgagcgcagcgagtcag
tgagcgaggaagcggaagagcgcccaatacgcaaaccgcctctccccgcgcgttggccgattcattaatgcagctgg
cacgacaggtttcccgactggaaagcgggcagtgagcgcaacgcaattaatgtgagttagctcactcattaggcacc
ccaggctttacactttatgcttccggctcgtatgttgtgtggaattgtgagcggataacaatttcacacaggaaaca
gctatgaccatgattacgccaagcttggtaccgagctcggatccactagtaacggccgccagtgtgctggaattcgc
ccttgatcatgcattcgcccttaggaggtaaaaaaacatgtgtgcgacctcttctcaatttactcagattaccgagc
ataattcccgtcgttccgcaaactatcagccaaacctgtggaatttcgaattcctgcaatccctggagaacgacctg

Figure 10B aaagtggaaaagctggaggagaaagcgaccaaactggaggaagaagttcgctgcatgatcaaccgtgtagacaccca
gccgctgtccctgctggagctgatcgacgatgtgcagcgcctgggtctgacctacaaatttgaaaaagacatcatta
aagccctggaaaacatcgtactgctggacgaaaacaaaaagaacaaatctgacctgcacgcaaccgctctgtctttc
cgtctgctgcgtcagcacggtttcgaggtttctcaggatgttttttgagcgtttcaaggataaagaaggtggtttcag
cggtgaactgaaaggtgacgtccaaggcctgctgagcctgtatgaagcgtcttacctgggtttcgagggtgagaacc
tgctggaggaggcgcgtacctttttccatcacccacctgaagaacaacctgaaagaaggcattaataccaaggttgca
gaacaagtgagccacgccctggaactgccatatcaccagcgtctgcacgtctggaggcacgttggttcctggataa
atacgaaccgaaagaaccgcatcaccagctgctgctggagctggcgaagctggattttaacatggtacagaccctgc
accagaaagagctgcaagatctgtcccgctggtggaccgagatgggcctggctagcaaactggattttgtacgcgac
cgcctgatggaagtttattctgggcactgggtatggcgccagacccgcagtttggtgaatgtcgcaaagctgttac
taaaatgtttggtctggtgacgatcatcgatgacgtgtatgacgtttatggcactctggacgaactgcaactgttca
ccgatgctgtagagcgctgggacgttaacgctattaacaccctgccggactatatgaaactgtgtttcctggcactg
tacaacaccgttaacgacacgtcctattctattctgaaagagaaaggtcataacaacctgtcctatctgacgaaaag
ctggcgtgaactgtgcaaagcctttctgcaagaggcgaaatggtccaacaacaaaattatcccggctttctccaagt
acctggaaaacgccagcgtttcctcctccggtgtagcgctgctggcgccgtcttacttttccgtatgccagcagcag
gaagacatctccgaccacgcgctgcgttccctgaccgacttccatggtctggtgcgttctagctgcgttatcttccg
cctgtgcaacgatctggccacctctgcggcggagctggaacgtggcgagactaccaattctatcattagctacatgc
acgaaaacgatggtaccagcgaggaacaggccgcgaagaactgcgtaaactgatcgacgccgaatggaaaaagatg
aatcgtgaacgcgttagcgactccaccctgctgcctaaagcgttcatggaaatcgcagttaacatggcacgtgtttc
ccactgcacctaccagtatggcgatggtctggtcgcccagactacgcgactgaaaaccgcatcaaactgctgctga
ttgaccctttcccgattaaccagctgatgtatgtctaactgcagggatccgtcgaccg

Figure 12A pET24D-Kudzu (SEQ ID NO:23) Kudzu IspS ORF 48-1742 (complementary)
gtgcggccgcaagcttgtcgacggagctcgaattcggatccctgcagttagacatacatcagctggttaatcgggaa
agggtcaatcagcagcagtttgatgcggttttcagtcgcgtagtctgggcgacccagaccatcgccatactggtagg
tgcagtgggaaacacgtgccatgttaactgcgatttccatgaacgctttaggcagcagggtggagtcgctaacgcgt
tcacgattcatcttttttccattcggcgtcgatcagtttacgcagttcttcgcgggcctgttcctcgctggtaccatc
gtttttcgtgcatgtagctaatgatagaattggtagtctcgccacgttccagctccgccgcagaggtggccagatcgt
tgcacaggcggaagataacgcagctagaacgcaccagaccatggaagtcggtcagggaacgcagcgcgtggtcgag
atgtcttcctgctgctggcatacggaaaagtaagacggcgcagcagcgctacaccggaggaggaaacgctggcgtt
tccaggtacttggagaaagccgggataatttttgttgttggaccatttcgcctcttgcagaaaggctttgcacagtt
cacgccagcttttcgtcagataggacaggttgttatgaccttctctttcagaatagaataggacgtgtcgttaacg
gtgttgtacagtgccaggaaacacagtttcatatagtccggcagggtgttaatagcgttaacgtcccagcgctctac
agcatcggtgaacagttgcagttcgtccagagtgccataaacgtcatacacgtcatcgatgatcgtcaccagaccaa
acattttagtaacagctttgcgacattcaccaaactgggggtctggcgccataccagtgcccagaaataaacttcc
atcaggcggtcgcgtacaaaatccagtttgctagccaggccatctcggtccaccagcgggacagatcttgcagctc
tttctggtgcagggtctgtaccatgttaaaatccagcttcgccagctccagcagcagctggtgatgcggttcttcg
gttcgtatttatccaggaaccaacgtgcctccagacggtgcagacgctggtgatatggcagttccagggcgtggctc
acttgttctgcaaccttggtattaatgccttcttcaggttgttcttcaggtgggtgatggaaaaggtacgcgctc
ctccagcaggttctcaccctcgaaacccaggtaagacgcttcatacaggctcagcaggcttggacgtcacctttca
gttcaccgctgaaaccaccttctttatccttgaaacgctcaaaaacatcctgagaaacctcgaaaccgtgctgacgc
agcagacggaaagacagagcggttgcgtgcaggtcgatttgttcttttgtttcgtccagcagtacgatgttttc
cagggctttaatgatgtcttttttcaaattttgtaggtcagaccaggcgctgcacatcgtcgatcagctccagcaggg
acagcggctgggttctctacacggttgatcatgcagcgaacttcttcccagtttggtcgctttctcctccagcttt
tccactttcaggtcgttctccagggattgcaggaattcgaaattccacaggtttggctgatagtttgcggaacgacg
ggaattatgctcggtaatctgagtaaattgagaagaggtcgcacacatggtatatctccttcttaaagttaaacaaa
attattctagaggggaattgttatccgctcacaattcccctatagtgagtcgtattaatttcgcgggatcgagatc
tcgatcctctacgccggacgcatcgtggccggcatcaccggcgccacaggtgcggttgctggcgctatatcgcga
catcaccgatggggaagatcgggctcgccacttcgggctcatgagcgcttgtttcggcgtggtggtatggtggcaggcc
ccgtggccggggactgttgggcgccatctccttgcatgcaccattcctgcggcggcggtgctcaacggcctcaac
ctactactgggctgcttcctaatgcaggagtcgcataagggagagcgtcgagatcccggacaccatcgaatggcgca
aaacctttcgcggtatggcatgatagcgcccggaagagagtcaattcagggtggtgaatgtgaaaccagtaacgtta
tacgatgtcgcagagtatgccggtgtctcttatcagaccgtttccgcgtggtgaaccaggccagccacgtttctgc
gaaaacgcgggaaaagtggaagcggcgatggcggagctgaattacattcccaaccgcgtggcacaacaactggcgg
gcaaacagtcgttgctgattggcgttgccacctccagtctggccctgcacgcgccgtcgcaaattgtcgcggcgatt
aaatctcgcgccgatcaactgggtgccagcgtggtggtgtcgatggtagaacgaagcggcgtcgaagcctgtaaagc
ggcggtgcacaatcttctcgcgcaacgcgtcagtgggctgatcattaactatccgctggatgaccaggatgccattg
ctgtggaagctgcctgcactaatgttccggcgttatttcttgatgtctctgaccagacacccatcaacagtattatt
ttctcccatgaagacggtacgcgactgggcgtggagcatctggtcgcattgggtcaccagcaaatcgcgctgttagc
gggcccattaagttctgtctcggcgcgtctgcgtctggctggctggcataaatatctcactcgcaatcaaattcagc
cgatagcggaacgggaaggcgactggagtgccatgtccggttttcaacaaaccatgcaaatgctgaatgagggcatc
gttcccactgcgatgctggttgccaacgatcagatggcgctgggcgcaatgcgcgccattaccgagtcggggctgcg
cgttggtgcggatatctcggtagtgggatacgacgataccgaagacagctcatgttatatcccgccgttaaccacca
tcaaacaggattttcgcctgctggggcaaaccagcgtggaccgcttgctgcaactctctcagggccaggcggtgaag
ggcaatcagctgttgcccgtctcactggtgaaaagaaaaaccaccctggcgcccaatacgcaaaccgcctctccccg
cgcgttggccgattcattaatgcagctggcacgacaggtttcccgactggaaagcgggcagtgagcgcaacgcaatt
aatgtaagttagctcactcattaggcaccgggatctcgaccgatgcccttgagagccttcaacccagtcagctcctt
ccggtgggcgcggggcatgactatcgtcgccgcacttatgactgtcttctttatcatgcaactcgtaggacaggtgc
cggcagcgctctgggtcattttcggcgaggaccgctttcgctggagcgcgacgatgatcggcctgtcgcttgcggta
ttcggaatcttgcacgccctcgctcaagccttcgtcactggtcccgccaccaaacgtttcggcgagaagcaggccat
tatcgccggcatggcggccccacgggtgcgcatgatcgtgctcctgtcgttgaggacccggctaggctggcggggtt
gccttactggttagcagaatgaatcaccgatacgcgagcgaacgtgaagcgactgctgctgcaaaacgtctgcgacc
tgagcaacaacatgaatggtcttcggtttccgtgtttcgtaaagtctggaaacgcggaagtcagcgccctgcaccat
tatgttccggatctgcatcgcaggatgctgctggctaccctgtggaacacctacatctgtattaacgaagcgctgg
attacccctgagtgatttttctctggtcccgccgcatccataccgccagttgtttaccctcacaacgttccagtaac
cgggcatgttcatcatcagtaacccgtatcgtgagcatcctctctcgtttcatcggtatcattaccccccatgaacag

Figure 12B

```
aaatcccccttacacggaggcatcagtgaccaaacaggaaaaaaccgcccttaacatggcccgctttatcagaagcc
agacattaacgcttctggagaaactcaacgagctggacgcggatgaacaggcagacatctgtaatcgcttcacgac
cacgctgatgagctttaccgcagctgcctcgcgcgtttcggtgatgacggtgaaaacctctgacacatgcagctcc
ggagacggtcacagcttgtctgtaagcggatgccggagcagacaagcccgtcagggcgcgtcagcgggtgttggcg
ggtgtcggggcgcagccatgacccagtcacgtagcgatagcggagtgtatactggcttaactatgcgggcatcagagc
agattgtactgagagtgcaccatatatgcggtgtgaaataccgcacagatgcgtaaggagaaaataccgcatcaggc
gctcttccgcttcctcgctcactgactcgctgcgctcggtcgttcggctgcggcgagcggtatcagctcactcaaag
gcggtaatacggttatccacagaatcaggggataacgcaggaaagaacatgtgagcaaaaggccagcaaaaggccag
gaaccgtaaaaaggccgcgttgctggcgtttttccataggctccgcccccctgacgagcatcacaaaaatcgacgct
caagtcagaggtggcgaaacccgacaggactataaagataccaggcgtttccccctggaagctccctcgtgcgctct
cctgttccgaccctgccgcttaccggatacctgtccgcctttctcccttcgggaagcgtggcgctttctcatagctc
acgctgtaggtatctcagttcggtgtaggtcgttcgctccaagctgggctgtgtgcacgaaccccccgttcagcccg
accgctgcgccttatccggtaactatcgtcttgagtccaacccggtaagacacgacttatcgccactggcagcagcc
actggtaacaggattagcagagcgaggtatgtaggcggtgctacagagttcttgaagtggtggcctaactacggcta
cactagaaggacagtatttggtatctgcgctctgctgaagccagttaccttcggaaaaagagttggtagctcttgat
ccggcaaacaaaccaccgctggtagcggtggtttttttgtttgcaagcagcagattacgcgcagaaaaaaaggatct
caagaagatcctttgatcttttctacggggtctgacgctcagtggaacgaaaactcacgttaagggattttggtcat
gaacaataaaactgtctgcttacataaacagtaatacaaggggtgttatgagccatattcaacgggaaacgtcttgc
tctaggccgcgattaaattccaacatggatgctgatttatatgggtataaatgggctcgcgataatgtcgggcaatc
aggtgcgacaatctatcgattgtatgggaagcccgatgcgccagagttgtttctgaaacatggcaaaggtagcgttg
ccaatgatgttacagatgagatggtcagactaaactggctgacggaatttatgcctcttccgaccatcaagcatttt
atccgtactcctgatgatgcatggttactcaccactgcgatcccgggaaaacagcattccaggtattagaagaata
tcctgattcaggtgaaaatattgttgatgcgctggcagtgttcctgcgccggttgcattcgattcctgtttgtaatt
gtccttttaacagcgatcgcgtatttcgtctcgctcaggcgcaatcacgaatgaataacggtttggttgatgcgagt
gattttgatgacgagcgtaatggctggcctgttgaacaagtctggaaagaaatgcataaacttttgccattctcacc
ggattcagtcgtcactcatggtgatttctcacttgataaccttatttttgacgaggggaaattaataggttgtattg
atgttggacgagtcggaatcgcagaccgataccaggatcttgccatcctatggaactgcctcggtgagttttctcct
tcattacagaaacggctttttcaaaaatatggtattgataatcctgatatgaataaattgcagtttcatttgatgct
cgatgagttttctaagaattaattcatgagcggatacatatttgaatgtatttagaaaaataaacaaatagggg
ccgcgcacatttccccgaaaagtgccacctgaaattgtaaacgttaatattttgttaaaattcgcgttaaatttttg
ttaaatcagctcattttttaaccaataggccgaaatcggcaaaatcccttataaatcaaaagaatagaccgagatag
ggttgagtgttgttccagtttggaacaagagtccactattaaagaacgtggactccaacgtcaaagggcgaaaaacc
gtctatcaggcgatggcccactacgtgaaccatcaccctaatcaagttttttggggtcgaggtgccgtaaagcact
aaatcggaaccctaaagggagcccccgatttagagcttgacggggaaagccggcgaacgtggcgagaaaggaaggga
agaaagcgaaaggagcgggcgctagggcgctggcaagtgtagcggtcacgctgcgcgtaaccaccacacccgccgcg
cttaatgcgccgctacagggcgcgtcccattcgccaatccggatatagttcctcctttcagcaaaaaaccccctcaag
acccgtttagaggccccaaggggttatgctagttattgctcagcggtggcagcagccaactcagcttcctttcgggc
tttgttagcagccggatctcagtggtggtggtggtggtgctcga
```

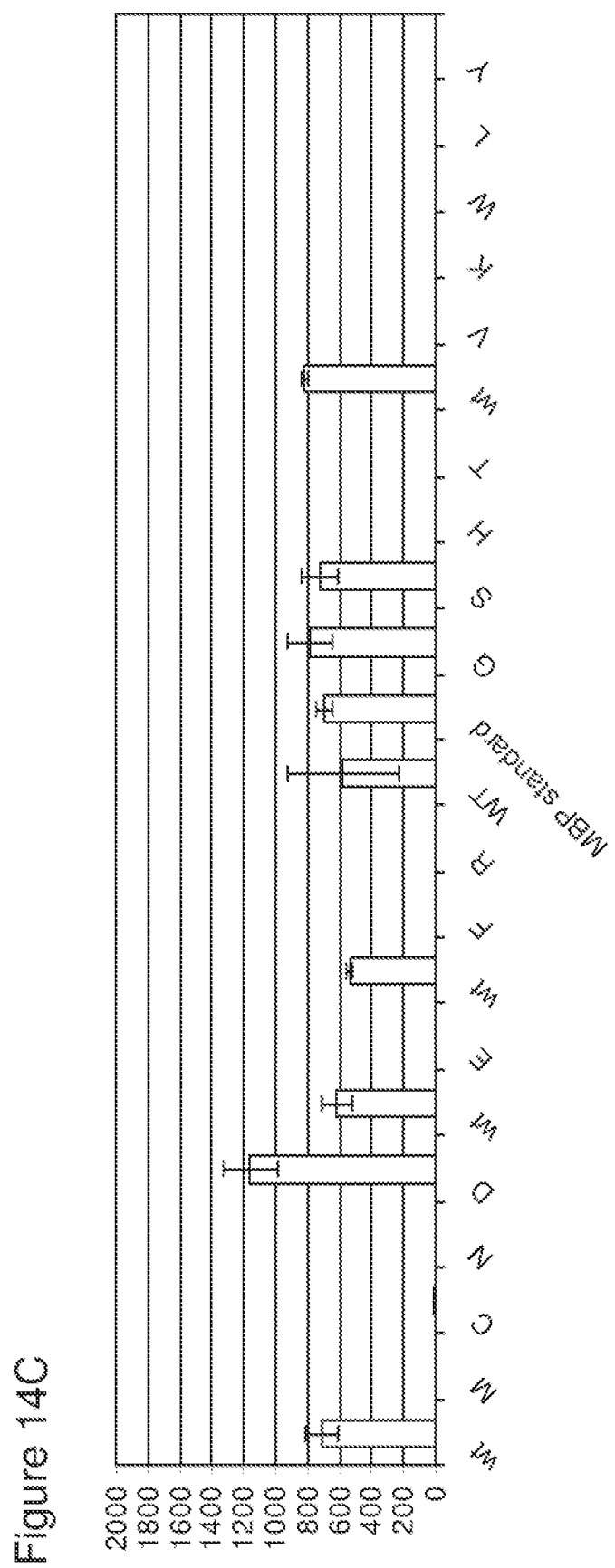

Figure 17

Amino acid sequence of 6XHis N-terminally tagged *P. alba* IspS (SEQ ID NO:118)

```
MRGSHHHHHHGMASMTGGQQMGRDLYDDDDKDHPFTMRCSVSTENVSFTETETEARRSANYEPN
SWDYDYLLSSDTDESIEVYKDKAKKLEAEVRREINNEKAEFLTLLELIDNVQRLGLGYRPESDI
RGALDRFVSSGGFDAVTKTSLHGTALSFRLLRQHGFEVSQEAFSGFKDQNGNFLENLKEDIKAI
LSLYEASFLALEGENILDEAKVFAISHLKELSEEKIGKELAEQVNHALELPLHRRTQRLEAVWS
IEAYRKKEDANQVLLELAILDYNMIQSVYQRDLRETSRWWRRVGLATKLHFARDRLIESFYWAV
GVAFEPQYSDCRNSVAKMFSFVTIIDDIYDVYGTLDELELFTDAVERWDVNAINDLPDYMKLCF
LALYNTINEIAYDNLKDKGENILPYLTKAWADLCNAFLQEAKWLYNKSTPTFDDYFGNAWKSSS
GPLQLVPAYFAVVQNIKKEEIENLQKYHDTISRPSHIFRLCNDLASASAEIARGETANSVSCYM
RTKGISEELATESVMNLIDETWKKMNKEKLGGSLFAKPFVETAINLARQSHCTYHNGDAHTSPD
ELTRKRVLSVITEPILPFER
```

Figure 18A

Nucleotide sequence of pDu27 (SEQ ID NO:119)

aagggcgagctcaacgatccggctgctaacaaagcccgaaaggaagctgagttggctgctgcca
ccgctgagcaataactagcataaccccttggggcctctaaacgggtcttgaggagttttttgct
gaaaggaggaactatatccggatatccgcaagaggccggcagtaccggcataaccaagccta
tgcctacagcatccagggtgacggtgccgaggatgacgatgagcgcattgttagatttcataca
cggtgcctgactgcgttagcaatttaactgtgataaactaccgcattaaagcttatcgatgata
agctgtcaaacatgagaattaattcttgaagacgaaagggcctcgtgatacgcctattttata
ggttaatgtcatgataataatggtttcttagacgtcaggtggcacttttcggggaaatgtgcgc
ggaacccctatttgtttatttttctaaatacattcaaatatgtatccgctcatgagacaataac
cctgataaatgcttcaataatattgaaaaaggaagagtatgattgaacaagatggattgcacgc
aggttctccggccgcttgggtggagaggctattcggctatgactgggcacaactgacaatcggc
tgctctgatgccgccgtgttccggctgtcagcgcaggggcgcccggttcttttgtcaagaccg
acctgtccggtgccctgaatgaactgcaggacgaggcagcgcggctatcgtggctggccacgac
gggcgttccttgcgcagctgtgctcgacgttgtcactgaagcgggaagggactggctgctattg
ggcgaagtgccggggcaggatctcctgtcatctcaccttgctcctgccgagaaagtatccatca
tggctgatgcaatgcggcggctgcatacgcttgatccggctacctgcccattcgaccaccaagc
gaaacatcgcatcgagcgggcacgtactcggatggaagccggtcttgtcgatcaggatgatctg
gacgaagagcatcaggggctcgcgccagccgaactgttcgccaggctcaaggcgcgcatgcccg
acggcgaggatctcgtcgtgacacatggcgatgcctgcttgccgaatatcatggtggaaaatgg
ccgcttttctggattcatcgactgtggccggctgggtgtggcggaccgctatcaggacatagcg
ttggctacccgtgatattgctgaagagcttggcggcgaatgggctgaccgcttcctcgtgcttt
acggtatcgccgctcccgattcgcagcgcatcgccttctatcgccttcttgacgagttcttctg
agcgggactctggggttcgaaatgaccgaccaagcgacgcctaactgtcagaccaagtttactc
atatatactttagattgatttaaaacttcattttaatttaaaaggatctaggtgaagatcctt
tttgataatctcatgaccaaaatcccttaacgtgagttttcgttccactgagcgtcagacccg
tagaaaagatcaaaggatcttcttgagatcctttttttctgcgcgtaatctgctgcttgcaaac
aaaaaaaccaccgctaccagcggtggtttgtttgccggatcaagagctaccaactctttttccg
aaggtaactggcttcagcagagcgcagataccaaatactgtccttctagtgtagccgtagttag
gccaccacttcaagaactctgtagcaccgcctacatacctcgctctgctaatcctgttaccagt
ggctgctgccagtggcgataagtcgtgtcttaccgggttggactcaagacgatagttaccggat
aaggcgcagcggtcgggctgaacggggggttcgtgcacacagcccagcttggagcgaacgacct
acaccgaactgagatacctacagcgtgagctatgagaaagcgccacgcttcccgaagggagaaa
ggcggacaggtatccggtaagcggcagggtcggaacaggagagcgcacgagggagcttccaggg
ggaaacgcctggtatctttatagtcctgtcgggtttcgccacctctgacttgagcgtcgatttt
tgtgatgctcgtcaggggggcggagcctatggaaaaacgccagcaacgcggcctttttacggtt
cctggccttttgctggccttttgctcacatgttctttcctgcgttatcccctgattctgtggat
aaccgtattaccgcctttgagtgagctgataccgctcgccgcagccgaacgaccgagcgcagcg
agtcagtgagcgaggaagcggaagagcgcctgatgcggtattttctccttacgcatctgtgcgg
tatttcacaccgcaatggtgcactctcagtacaatctgctctgatgccgcatagttaagccagt
atacactccgctatcgctacgtgactgggtcatggctgcgccccgacacccgccaacacccgct
gacgcgccctgacgggcttgtctgctcccggcatccgcttacagacaagctgtgaccgtctccg
ggagctgcatgtgtcagaggttttcaccgtcatcaccgaaacgcgcgaggcagctgcggtaaag
ctcatcagcgtggtcgtgaagcgattcacagatgtctgcctgttcatccgcgtccagctcgttg
agtttctccagaagcgttaatgtctggcttctgataaagcgggccatgttaagggcggttttt

Figure 18B

Nucleotide sequence of pDu27 cctgtttggtcactgatgcctccgtgtaaggggatttctgttcatggggtaatgataccgat
gaaacgagagaggatgctcacgatacgggttactgatgatgaacatgcccggttactggaacgt
tgtgagggtaaacaactggcggtatggatgcggcgggaccagagaaaaatcactcagggtcaat
gccagcgcttcgttaatacagatgtaggtgttccacagggtagccagcagcatcctgcgatgca
gatccggaacataatggtgcagggcgctgacttccgcgtttcagactttacgaaacacggaaa
ccgaagaccattcatgttgttgctcaggtcgcagacgttttgcagcagcagtcgcttcacgttc
gctcgcgtatcggtgattcattctgctaaccagtaaggcaacccgccagcctagccgggtcct
caacgacaggagcacgatcatgcgcacccgtggccaggacccaacgctgcccgagatgcgccgc
gtgcggctgctggagatggcggacgcgatggatatgttctgccaagggttggtttgcgcattca
cagttctccgcaagaattgattggctccaattcttggagtggtgaatccgttagcgaggtgccg
ccggcttccattcaggtcgaggtggcccggctccatgcaccgcgacgcaacgcggggaggcaga
caaggtatagggcggcgcctacaatccatgccaaccgttccatgtgctcgccgaggcggcata
aatcgccgtgacgatcagcggtccaatgatcgaagttaggctggtaagagccgcgagcgatcct
tgaagctgtccctgatggtcgtcatctacctgcctggacagcatggcctgcaacgcgggcatcc
cgatgccgccggaagcgagaagaatcataatggggaaggccatccagcctcgcgtcgcgaacgc
cagcaagacgtagcccagcgcgtcggccgccatgccggcgataatggcctgcttctcgccgaaa
cgtttggtggcgggaccagtgacgaaggcttgagcgagggcgtgcaagattccgaataccgcaa
gcgacaggccgatcatcgtcgcgctccagcgaaagcggtcctcgccgaaaatgacccagagcgc
tgccggcacctgtcctacgagttgcatgataaagaagacagtcataagtgcggcgacgatagtc
atgccccgcgcccaccggaaggagctgactgggttgaaggctctcaagggcatcggtcgagatc
ccggtgcctaatgagtgagctaacttacattaattgcgttgcgctcactgcccgctttccagtc
gggaaacctgtcgtgccagctgcattaatgaatcggccaacgcgcggggagaggcggtttgcgt
attgggcgccagggtggttttctcttttcaccagtgagacgggcaacagctgattgcccttcacc
gcctggccctgagagagttgcagcaagcggtccacgctggtttgcccagcaggcgaaaatcct
gtttgatggtggttaacggcgggatataacatgagctgtcttcggtatcgtcgtatcccactac
cgagatatccgcaccaacgcgcagcccggactcggtaatggcgcgcattgcgcccagcgccatc
tgatcgttggcaaccagcatcgcagtgggaacgatgccctcattcagcatttgcatggtttgtt
gaaaaccggacatggcactccagtcgccttcccgttccgctatcggctgaatttgattgcgagt
gagatatttatgccagccagccagacgcagacgcgccgagacagaacttaatgggcccgctaac
agcgcgatttgctggtgacccaatgcgaccagatgctccacgcccagtcgcgtaccgtcttcat
gggagaaaataatactgttgatgggtgtctggtcagagacatcaagaaataacgccggaacatt
agtgcaggcagcttccacagcaatggcatcctggtcatccagcggatagttaatgatcagccca
ctgacgcgttgcgcgagaagattgtgcaccgccgctttacaggcttcgacgccgcttcgttcta
ccatcgacaccaccacgctggcacccagttgatcggcgcgagatttaatcgccgcgacaatttg
cgacggcgcgtgcagggccagactggaggtggcaacgccaatcagcaacgactgtttgcccgcc
agttgttgtgccacgcggttgggaatgtaattcagctccgccatcgccgcttccacttttccc
gcgttttcgcagaaacgtggctggcctggttcaccacgcgggaaacggtctgataagagacacc
ggcatactctgcgacatcgtataacgttactggtttcacattcaccaccctgaattgactctct
tccgggcgctatcatgccataccgcgaaaggttttgcgccattcgatggtgtccgggatctcga
cgctctcccttatgcgactcctgcattaggaagcagcccagtagtaggttgaggccgttgagca
ccgccgccgaaggaatggtgcatgcaaggagatggcgcccaacagtccccggcacggggcc
tgccaccatacccacgccgaaacaagcgctcatgagcccgaagtggcgagcccgatcttcccca

Figure 18C

Nucleotide sequence of pDu27

```
tcggtgatgtcggcgatataggcgccagcaaccgcacctgtggcgccggtgatgccggccacga
tgcgtccggcgtagaggatcgagatctcgatcccgcgaaattaatacgactcactataggggaa
ttgtgagcggataacaattcccctctagaaataattttgtttaactttaagaaggagatataca
tatgcggggttctcatcatcatcatcatggtatggctagcatgactggtggacagcaaatg
ggtcgggatctgtacgacgatgacgataaggatcatcccttcaccatgcgttgtagcgtgtcca
ccgaaaatgtgtctttcaccgaaactgaaaccgaagctcgtcgttctgcgaactacgaacctaa
cagctgggactatgattacctgctgtcctccgacacggacgagtccatcgaagtatacaaagac
aaagcgaaaaagctggaagccgaagttcgtcgcgagattaataacgaaaaagcagaatttctga
ccctgctggaactgattgacaacgtccagcgcctgggcctgggttaccgtttcgagtctgatat
ccgtggtgcgctggatcgcttcgtttcctccggcggcttcgatgcggtaaccaagacttcctg
cacggtacggcactgtctttccgtctgctgcgtcaacacggttttgaggtttctcaggaagcgt
tcagcggcttcaaagaccaaaacggcaacttcctggagaacctgaaggaagatatcaaagctat
cctgagcctgtacgaggccagcttcctggctctggaaggcgaaaacatcctggacgaggcgaag
gttttcgcaatctctcatctgaaagaactgtctgaagaaagatcggtaaagagctggcagaac
aggtgaaccatgcactggaactgccactgcatcgccgtactcagcgtctggaagcagtatggtc
tatcgaggcctaccgtaaaaaggaggacgcgaatcaggttctgctggagctggcaattctggat
tacaacatgatccagtctgtataccagcgtgatctgcgtgaaacgtcccgttggtggcgtcgtg
tgggtctggcgaccaaactgcactttgctcgtgaccgcctgattgagagcttctactgggccgt
gggtgtagcattcgaaccgcaatactccgactgccgtaactccgtcgcaaaaatgttttcttt c
gtaaccattatcgacgatatctacgatgtatacggcaccctggacgaactggagctgtttactg
atgcagttgagcgttgggacgtaaacgccatcaacgacctgccggattacatgaaactgtgctt
tctggctctgtataacactattaacgaaatcgcctacgacaacctgaaagataaaggtgagaac
atcctgccgtatctgaccaaagcctgggctgacctgtgcaacgcttcctgcaagaagccaagt
ggctgtacaacaaatctactccgacctttgacgactacttcggcaacgcatggaaatcctcttc
tggcccgctgcaactggtgttcgcttacttcgctgtcgtgcagaacattaaaaaggaagagatc
gaaaacctgcaaaaataccatgacaccatctctcgtccttcccatatcttccgtctgtgcaatg
acctggctagcgcgtctgcggaaattgcgcgtggtgaaaccgcaaatagcgtttcttgttacat
gcgcactaaaggtatctccgaagaactggctaccgaaagcgtgatgaatctgatcgatgaaacc
tggaaaaagatgaacaaggaaaaactgggtggtagcctgttcgcgaaaccgttcgtggaaaccg
cgatcaacctggcacgtcaatctcactgcacttatcataacggcgacgcgcatacctctccgga
tgagctgacccgcaaacgcgttctgtctgtaatcactgaaccgattctgccgtttgaacgctaa
```

Figure 19

Amino acid sequence of full length *P. alba* IspS in P. alba (SEQ ID NO:120)

```
MRCSVSTENVSFTETETEARRSANYEPNSWDYDYLLSSDTDESIEVYKDKAKKLEAEVRREINN
EKAEFLTLLELIDNVQRLGLGYRFESDIRGALDRFVSSGGFDAVTKTSLHGTALSFRLLRQHGF
EVSQEAFSGFKDQNGNFLENLKEDIKAILSLYEASFLALEGENILDEAKVFAISHLKELSEEKI
GKELAEQVNHALELPLHRRTQRLEAVWSIEAYRKKEDANQVLLELAILDYNMIQSVYQRDLRET
SRWWRRVGLATKLHFARDRLIESFYWAVGVAFEPQYSDCRNSVAKMFSFVTIIDDIYDVYGTLD
ELELFTDAVERWDVNAINDLPDYMKLCFLALYNTINEIAYDNLKDKGENILPYLTKAWADLCNA
FLQEAKWLYNKSTPTFDDYFGNAWKSSSGPLQLVFAYFAVVQNIKKEEIENLQKYHDTISRPSH
IFRLCNDLASASAEIARGETANSVSCYMRTKGISEELATESVMNLIDETWKKMNKEKLGGSLPA
KPFVETAINLARQSHCTYHNGDAHTSPDELTRKRVLSVITEPILPFER
```

Figure 20A

Nucleotide sequence of P. alba pET24a (SEQ ID NO:121)

tggcgaatgggacgcgccctgtagcggcgcattaagcgcggcgggtgtggtggttacgcgcagc
gtgaccgctacacttgccagcgccctagcgccgtcctttcgtttcttcccttcctttctcg
ccacgttcgccggctttccccgtcaagctctaaatcggggctcccttttagggttccgatttag
tgctttacggcacctcgaccccaaaaaacttgattagggtgatggttcacgtagtgggccatcg
ccctgatagacggtttttcgccctttgacgttggagtccacgttctttaatagtggactcttgt
tccaaactggaacaacactcaaccctatctcggtctattcttttgatttataagggatttttgcc
gattcggcctattggttaaaaaatgagctgattaacaaaaatttaacgcgaattttaacaaa
atattaacgtttacaatttcaggtggcacttttcggggaaatgtgcgcggaacccctatttgtt
tattttctaaatacattcaaatatgtatccgctcatgaattaattcttagaaaaactcatcga
gcatcaaatgaaactgcaatttattcatatcaggattatcaataccatattttgaaaaagccg
tttctgtaatgaaggagaaaactcaccgaggcagttccataggatggcaagatcctggtatcgg
tctgcgattccgactcgtccaacatcaatacaacctattaatttccctcgtcaaaaataaggt
tatcaagtgagaaatcaccatgagtgacgactgaatccggtgagaatggcaaaagtttatgcat
ttctttccagacttgttcaacaggccagccattacgctcgtcatcaaaatcactcgcatcaacc
aaaccgttattcattcgtgattgcgcctgagcgagacgaaatacgcgatcgctgttaaaggac
aattacaaacaggaatcgaatgcaaccggcgcaggaacactgccagcgcatcaacaatatttc
acctgaatcaggatattcttctaataccctggaatgctgtttcccggggatcgcagtggtgagt
aaccatgcatcatcaggagtacggataaaatgcttgatggtcggaagaggcataaattccgtca
gccagtttagtctgaccatctcatctgtaacatcattggcaacgctacctttgccatgtttcag
aaacaactctggcgcatcgggcttcccatacaatcgatagattgtcgcacctgattgcccgaca
ttatcgcgagcccatttatacccatataaatcagcatccatgttggaatttaatcgcggcctag
agcaagacgtttcccgttgaatatggctcataacaccccttgtattactgtttatgtaagcaga
cagttttattgttcatgaccaaaatcccttaacgtgagttttcgttccactgagcgtcagaccc
cgtagaaaagatcaaaggatcttcttgagatcctttttttctgcgcgtaatctgctgcttgcaa
acaaaaaaaccaccgctaccagcggtggtttgtttgccggatcaagagctaccaactctttttc
cgaaggtaactggcttcagcagagcgcagataccaaatactgtccttctagtgtagccgtagtt
aggccaccacttcaagaactctgtagcaccgcctacatacctcgctctgctaatcctgttacca
gtggctgctgccagtggcgataagtcgtgtcttaccgggttggactcaagacgatagttaccgg
ataaggcgcagcggtcgggctgaacggggggttcgtgcacacagcccagcttggagcgaacgac
ctacaccgaactgagatacctacagcgtgagctatgagaaagcgccacgcttcccgaagggaga
aaggcggacaggtatccggtaagcggcagggtcggaacaggagagcgcacgagggagcttccag
ggggaaacgcctggtatctttatagtcctgtcgggtttcgccacctctgacttgagcgtcgatt
tttgtgatgctcgtcaggggggcggagcctatggaaaaacgccagcaacgcggcctttttacgg
ttcctggcctttgctggccttttgctcacatgttctttcctgcgttatcccctgattctgtgg
ataaccgtattaccgcctttgagtgagctgataccgctcgccgcagccgaacgaccgagcgcag
cgagtcagtgagcgaggaagcggaagagcgcctgatgcggtattttctccttacgcatctgtgc
ggtatttcacaccgcatatatggtgcactctcagtacaatctgctctgatgccgcatagttaag
ccagtatacactccgctatcgctacgtgactgggtcatggctgcgccccgacaccgccaacac
ccgctgacgcgccctgacggcttgtctgctcccggcatccgcttacagacaagctgtgaccgt
ctccgggagctgcatgtgtcagaggttttcaccgtcatcaccgaaacgcgcgaggcagctgcgg
taaagctcatcagcgtggtcgtgaagcgattcacagatgtctgcctgttcatccgcgtccagct
cgttgagtttctccagaagcgttaatgtctggcttctgataaagcgggccatgttaagggcggt
ttttcctgtttggtcactgatgcctccgtgtaagggggattctgttcatgggggtaatgata

Figure 20B

Nucleotide sequence of P. alba pET24a ccgatgaaacgagagaggatgctcacgatacgggttactgatgatgaacatgcccggttactgg
aacgttgtgagggtaaacaactggcggtatggatgcggcgggaccagagaaaaatcactcaggg
tcaatgccagcgcttcgttaatacagatgtaggtgttccacagggtagccagcagcatcctgcg
atgcagatccggaacataatggtgcagggcgctgacttccgcgtttccagactttacgaaacac
ggaaaccgaagaccattcatgttgttgctcaggtcgcagacgttttgcagcagcagtcgcttca
cgttcgctcgcgtatcggtgattcattctgctaaccagtaaggcaaccccgccagcctagccgg
gtcctcaacgacaggagcacgatcatgcgcacccgtgggccgccatgccggcgataatggcct
gcttctcgccgaaacgtttggtggcgggaccagtgacgaaggcttgagcgagggcgtgcaagat
tccgaatacccgcaagcgacaggccgatcatcgtcgcgctccagcgaaagcggtcctcgccgaaa
atgacccagagcgctgccggcacctgtcctacgagttgcatgataaagaagacagtcataagtg
cggcgacgatagtcatgccccgcgccaccggaaggagctgactgggttgaaggctctcaaggg
catcggtcgagatcccggtgcctaatgagtgagctaacttacattaattgcgttgcgctcactg
cccgctttccagtcgggaaacctgtcgtgccagctgcattaatgaatcggccaacgcgcgggga
gaggcggtttgcgtattgggcgccagggtggttttcttttcaccagtgagacgggcaacagct
gattgcccttcaccgcctggccctgagagagttgcagcaagcggtccacgctggtttgcccag
caggcgaaaatcctgtttgatggtggttaacggcgggatataacatgagctgtcttcggtatcg
tcgtatcccactaccgagatatccgcaccaacgcgcagcccggactcggtaatggcgcgcattg
cgccagcgccatctgatcgttggcaaccagcatcgcagtgggaacgatgccctcattcagcat
ttgcatggtttgttgaaaaccggacatggcactccagtcgccttcccgttccgctatcggctga
atttgattgcgagtgagatatttatgccagccagccagacgcagacgcgccgagacagaactta
atgggcccgctaacagcgcgatttgctggtgacccaatgcgaccagatgctccacgcccagtcg
cgtaccgtcttcatgggagaaaataatactgttgatgggtgtctggtcagagacatcaagaaat
aacgccggaacattagtgcaggcagcttccacagcaatggcatcctggtcatccagcggatagt
taatgatcagcccactgacgcgttgcgcgagaagattgtgcaccgccgctttacaggcttcgac
gccgcttcgttctaccatcgacaccaccacgctggcacccagttgatcggcgcgagatttaatc
gccgcgacaatttgcgacggcgcgtgcagggccagactggaggtggcaacgccaatcagcaacg
actgtttgcccgccagttgttgtgccacgcggttgggaatgtaattcagctccgccatcgccgc
ttccacttttcccgcgttttcgcagaaacgtggctggcctggttcaccacgcgggaaacggtc
tgataagagacaccggcatactctgcgacatcgtataacgttactggtttcacattcaccaccc
tgaattgactctcttccgggcgctatcatgccataccgcgaaaggttttgcgccattcgatggt
gtccgggatctcgacgctctcccttatgcgactcctgcattaggaagcagcccagtagtaggtt
gaggccgttgagcaccgccgccgcaaggaatggtgcatgcaaggagatggcgcccaacagtccc
ccggccacggggcctgccaccatacccacgccgaaacaagcgctcatgagcccgaagtggcgag
cccgatcttccccatcggtgatgtcggcgatataggcgccagcaacgcacctgtggcgccggt
gatgccggccacgatgcgtccggcgtagaggatcgagatctcgatcccgcgaaattaatacgac
tcactataggggaattgtgagcggataacaattcccctctagaaataattttgtttaactttaa
gaaggagatatacat<u>atgcgttgtagcgtgtccacgaaaatgtgtctttcaccgaaactgaaa
ccgaagctcgtcgtctctgcgaactacgaacctaacagctgggactatgattacctgctgtcctc
cgacacggacgagtccatcgaagtatacaaagacaaagcgaaaaagctggaagccgaagttcgt
cgcgagattaataacgaaaaagcagaatttctgacccctgctggaactgattgacaacgtccagc
gcctgggcctgggttaccgtttcgagtctgatatccgtggtgcgctggatcgcttcgtttcctc
cggcggcttcgatgcggtaaccaagacttccctgcacggtacggcactgtctttccgtctgctg
cgtcaacacggttttgaggtttctcaggaagcgttcagcggcttcaaagaccaaaacggcaact</u>

Figure 20C

Nucleotide sequence of P. alba pET24a tcctggagaacctgaaggaagatatcaaagctatcctgagcctgtacgaggccagcttcctggc
tctggaaggcgaaaacatcctggacgaggcgaaggttttcgcaatctctcatctgaaagaactg
tctgaagaaaagatcggtaaagagctggcagaacaggtgaaccatgcactggaactgccactgc
atcgccgtactcagcgtctggaagcagtatggtctatcgaggcctaccgtaaaaaggaggacgc
gaatcaggttctgctggagctggcaattctggattacaacatgatccagtctgtataccagcgt
gatctgcgtgaaacgtcccgttggtggcgtcgtgtgggtctggcgaccaaactgcactttgctc
gtgaccgcctgattgagagcttctactggccgtgggtgtagcattcgaaccgcaatactccga
ctgccgtaactccgtcgcaaaaatgttttctttcgtaaccattatcgacgatatctacgatgta
tacggcaccctggacgaactggagctgtttactgatgcagttgagcgttgggacgtaaacgcca
tcaacgacctgccggattacatgaaactgtgctttctggctctgtataacactattaacgaaat
cgcctacgacaacctgaaagataaaggtgagaacatcctgccgtatctgaccaaagcctgggct
gacctgtgcaacgcttcctgcaagaagccaagtggctgtacaacaaatctactccgaccttg
acgactactcggcaacgcatggaaatcctcttctggcccgctgcaactggtgttcgcttactt
cgctgtcgtgcagaacattaaaaaggaagagatcgaaaacctgcaaaaataccatgacaccatc
tctcgtccttcccatatcttccgtctgtgcaatgacctggctagcgcgtctgcggaaattgcgc
gtggtgaaaccgcaaatagccgtttcttgttacatgcgcactaaaggtatctccgaagaactggc
taccgaaagcgtgatgaatctgatcgatgaaacctggaaaaagatgaacaaggaaaaactgggt
ggtagcctgttcgcgaaaccgttcgtggaaaccgcgatcaacctggcacgtcaatctcactgca
cttatcataacggcgacgcgcataccctccggatgagctgacccgcaaacgcgttctgtctgt
aatcactgaacgattctgccgtttgaacgctaaggatccgaattcgagctccgtcgacaagct
tgcggccgcactcgagcaccaccaccaccaccactgagatccggctgctaacaaagcccgaaag
gaagctgagttggctgctgccaccgctgagcaataactagcataaccccttggggcctctaaac
gggtcttgaggggttttttgctgaaaggaggaactatatccggat

10% NUPAGE Bis-Tris Gel, Reduced

| Lane | Gel No. 1 Volume | Description |
|---|---|---|
| 1 | 10 | MW Marker |
| 2 | 1.5 | Purif IsoS 0.5 ug |
| 3 | 3.1 | Purif IsoS 1 ug |
| 4 | 6.3 | Purif IsoS 2 ug |
| 5 | 15 | P alba Uninduced |
| 6 | 15 | P alba Induced |
| 7 | 15 | P alba Lysate |
| 8 | 15 | P alba Supernatant |
| 9 | 15 | P alba Pellet |
| 10 | 0 | Blank |
| Function | | Coomassie Stain |

Figure 25

Amino acid sequence of "MEA" variant of *P. alba* IspS (SEQ ID NO:122)

```
MEARRSANYEPNSWDYDYLLSSDTDESIEVYKDKAKKLEAEVRREINNEKAEFLTLLELIDNVQ
RLGLGYRFESDIRGALDRFVSSGGFDAVTKTSLHGTALSFRLLRQHGFEVSQEAFSGFKDQNGN
FLENLKEDIKAILSLYEASFLALEGENILDEAKVFAISHLKELSEEKIGKELAEQVNHALELPL
HRRTQRLEAVWSIEAYRKKEDANQVLLELAILDYNMIQSVYQRDLRETSRWWRRVGLATKLHFA
RDRLIESFYWAVGVAPEPQYSDCRNSVAKMFSFVTIIDDIYDVYGTLDELELFTDAVERWDVNA
INDLPDYMKLCFLALYNTINEIAYDNLKDKGENILPYLTKAWADLCNAFLQEAKWLYNKSTPTF
DDYFGNAWKSSSGPLQLVFAYFAVVQNIKKEEIENLQKYHDTISRPSHIFRLCNDLASASAEIA
RGETANSVSCYMRTKGISEELATESVMNLIDETWKKMNKEKLGGSLFAKPFVETAINLARQSHC
TYHNGDAHTSPDELTRKRVLSVITEPILPFER
```

Figure 26A

Nucleotide sequence of pDu39 (SEQ ID NO:123)

```
tggcgaatgggacgcgccctgtagcggcgcattaagcgcggcgggtgtggtggttacgcgcagc
gtgaccgctacacttgccagcgccctagcgcccgctcctttcgctttcttcccttcctttctcg
ccacgttcgccggctttccccgtcaagctctaaatcgggggctccctttagggttccgatttag
tgctttacggcacctcgaccccaaaaaacttgattagggtgatggttcacgtagtgggccatcg
cctgatagacggttttcgccctttgacgttggagtccacgttctttaatagtggactcttgt
tccaaactggaacaacactcaaccctatctcggtctattcttttgatttataaggattttgcc
gatttcggcctattggttaaaaaatgagctgatttaacaaaatttaacgcgaattttaacaaa
atattaacgtttacaatttcaggtggcacttttcggggaaatgtgcgcggaaccctatttgtt
tatttttctaaatacattcaaatatgtatccgctcatgaattaattcttagaaaaactcatcga
gcatcaaatgaaactgcaatttattcatatcaggattatcaataccatattttgaaaaagccg
tttctgtaatgaaggagaaaactcaccgaggcagttccataggatggcaagatcctggtatcgg
tctgcgattccgactcgtccaacatcaatacaacctattaatttccctcgtcaaaaataaggt
tatcaagtgagaaatcaccatgagtgacgactgaatccggtgagaatggcaaaagtttatgcat
ttctttccagacttgttcaacaggccagccattacgctcgtcatcaaaatcactcgcatcaacc
aaaccgttattcattcgtgattgcgcctgagcgagacgaaatacgcgatcgctgttaaaaggac
aattacaaacaggaatcgaatgcaacggcgcaggaacactgccagcgcatcaacaatatttc
acctgaatcaggatattcttctaatacctggaatgctgtttccggggatcgcagtggtgagt
aaccatgcatcatcaggagtacggataaaatgcttgatggtcggaagaggcataaattccgtca
gccagtttagtctgaccatctcatctgtaacatcattggcaacgctacctttgccatgtttcag
aaacaactctggcgcatcgggcttcccatacaatcgatagattgtcgcacctgattgcccgaca
ttatcgcgagcccatttatacccatataaatcagcatccatgttggaatttaatcgcggcctag
agcaagacgtttcccgttgaatatggctcataacaccccttgtattactgtttatgtaagcaga
cagttttattgttcatgaccaaaatcccttaacgtgagttttcgttccactgagcgtcagaccc
cgtagaaaagatcaaaggatcttcttgagatcctttttttctgcgcgtaatctgctgcttgcaa
acaaaaaaaccaccgctaccagcggtggtttgtttgccggatcaagagctaccaactctttttc
cgaaggtaactggcttcagcagagcgcagataccaaatactgtccttctagtgtagccgtagtt
aggccaccacttcaagaactctgtagcaccgcctacatacctcgctctgctaatcctgttacca
gtggctgctgccagtggcgataagtcgtgtcttaccgggttggactcaagacgatagttaccgg
ataaggcgcagcggtcgggctgaacggggggttcgtgcacacagcccagcttggagcgaacgac
ctacaccgaactgagatacctacagcgtgagctatgagaaagcgccacgcttcccgaagggaga
aaggcggacaggtatccggtaagcggcagggtcggaacaggagagcgcacgagggagcttccag
ggggaaacgcctggtatctttatagtcctgtcgggtttcgccacctctgacttgagcgtcgatt
tttgtgatgctcgtcaggggggcggagcctatggaaaaacgccagcaacgcggcctttttacgg
ttcctggccttttgctggccttttgctcacatgttctttcctgcgttatcccctgattctgtgg
ataaccgtattaccgcctttgagtgagctgataccgctcgccgcagccgaacgaccgagcgcag
cgagtcagtgagcgaggaagcggaagagcgcctgatgcggtattttctccttacgcatctgtgc
ggtatttcacaccgcatatatggtgcactctcagtacaatctgctctgatgccgcatagttaag
ccagtatacactccgctatcgctacgtgactgggtcatggctgcgccccgacacccgccaacac
ccgctgacgcgccctgacgggcttgtctgctcccggcatccgcttacagacaagctgtgaccgt
ctccgggagctgcatgtgtcagaggttttcaccgtcatcaccgaaacgcgcgaggcagctgcgg
taaagctcatcagcgtggtcgtgaagcgattcacagatgtctgcctgttcatccgcgtccagct
cgttgagtttctccagaagcgttaatgtctggcttctgataaagcgggccatgttaagggcggt
ttttcctgtttggtcactgatgcctccgtgtaagggggatttctgttcatggggtaatgata
```

Figure 26B

Nucleotide sequence of pDu39 ccgatgaaacgagagaggatgctcacgatacgggttactgatgatgaacatgcccggttactgg
aacgttgtgagggtaaacaactggcggtatggatgcggcgggaccagagaaaaatcactcaggg
tcaatgccagcgcttcgttaatacagatgtaggtgttccacagggtagccagcagcatcctgcg
atgcagatccggaacataatggtgcagggcgctgacttccgcgtttccagactttacgaaacac
ggaaaccgaagaccattcatgttgttgctcaggtcgcagacgttttgcagcagcagtcgcttca
cgttcgctcgcgtatcggtgattcattctgctaaccagtaaggcaaccccgccagcctagccgg
gtcctcaacgacaggagcacgatcatgcgcacccgtggggccgccatgccggcgataatggcct
gcttctcgccgaaacgtttggtggcgggaccagtgacgaaggcttgagcgagggcgtgcaagat
tccgaataccgcaagcgacaggccgatcatcgtcgcgctccagcgaaagcggtcctcgccgaaa
atgacccagagcgctgccggcacctgtcctacgagttgcatgataaagaagacagtcataagtg
cggcgacgatagtcatgccccgcgccaccggaaggagctgactgggttgaaggctctcaaggg
catcggtcgagatcccggtgcctaatgagtgagctaacttacattaattgcgttgcgctcactg
cccgctttccagtcgggaaacctgtcgtgccagctgcattaatgaatcggccaacgcgcgggga
gaggcggtttgcgtattgggcgccagggtggttttcttttcaccagtgagacgggcaacagct
gattgcccttcaccgcctggccctgagagagttgcagcaagcggtccacgctggtttgccccag
caggcgaaaatcctgtttgatggtggttaacggcgggatataacatgagctgtcttcggtatcg
tcgtatcccactaccgagatatccgcaccaacgcgcagccggactcggtaatggcgcgcattg
cgcccagcgccatctgatcgttggcaaccagcatcgcagtgggaacgatgccctcattcagcat
ttgcatggtttgttgaaaaccggacatggcactccagtcgccttcccgttccgctatcggctga
atttgattgcgagtgagatatttatgccagccagccagacgcagacgcgccgagacagaactta
atgggccgctaacagcgcgatttgctggtgacccaatgcgaccagatgctccacgccagtcg
cgtaccgtcttcatgggagaaaataatactgttgatgggtgtctggtcagagacatcaagaaat
aacgccggaacattagtgcaggcagcttccacagcaatggcatcctggtcatccagcggatagt
taatgatcagcccactgacgcgttgcgcgagaagattgtgcaccgccgctttacaggcttcgac
gccgcttcgttctaccatcgacaccaccacgctggcacccagttgatcggcgcgagatttaatc
gccgcgacaatttgcgacggcgcgtgcagggcagactggaggtggcaacgccaatcagcaacg
actgtttgcccgccagttgttgtgccacgcggttgggaatgtaattcagctccgccatcgccgc
ttccacttttccgcgttttcgcagaaacgtggctggcctggttcaccacgcgggaaacggtc
tgataagagacaccggcatactctgcgacatcgtataacgttactggtttcacattcaccaccc
tgaattgactctcttccgggcgctatcatgccataccgcgaaaggttttgcgccattcgatggt
gtccgggatctcgacgctctcccttatgcgactcctgcattaggaagcagcccagtagtaggtt
gaggccgttgagcacgccgccgcaaggaatggtgcatgcaaggagatggcgcccaacagtccc
ccggccacggggcctgccaccatacccacgccgaaacaagcgctcatgagccgaagtggcgag
cccgatcttccccatcggtgatgtcggcgatataggcgccagcaacgcacctgtggcgccggt
gatgccggccacgatgcgtccggcgtagaggatcgagatctcgatcccgcgaattaatacgac
tcactatagggaattgtgagcggataacaattcccctctagaaataattttgtttaactttaa
gaaggagatatacat<u>atggaagctcgtcgttctgcgaactacgaacctaacagctgggactatg</u>
<u>attacctgctgtcctccgacacggacgagtccatcgaagtatacaaagacaaagcgaaaaagct</u>
<u>ggaagccgaagttcgtcgcgagattaataacgaaaagcagaatttctgaccctgctggaactg</u>
<u>attgacaacgtccagcgcctgggcctgggttaccgtttcgagtctgatatccgtggtgcgctgg</u>
<u>atcgcttcgtttcctccggcggcttcgatgcggtaaccaagacttcctgcacggtacggcact</u>
<u>gtctttccgtctgctgcgtcaacacggttttgaggtttctcaggaagcgttcagcggcttcaaa</u>
<u>gaccaaaacggcaacttcctggagaacctgaaggaagatatcaaagctatcctgagcctgtacg</u>

Figure 26C

Nucleotide sequence of pDu39

```
aggccagcttcctggctctggaaggcgaaaacatcctggacgaggcgaaggttttcgcaatctc
tcatctgaaagaactgtctgaagaaaagatcggtaaagagctggcagaacaggtgaaccatgca
ctggaactgccactgcatcgccgtactcagcgtctggaagcagtatggtctatcgaggcctacc
gtaaaaaggaggacgcgaatcaggttctgctggagctggcaattctggattacaacatgatcca
gtctgtataccagcgtgatctgcgtgaaacgtccgttgtggcgtcgtgtgggtctggcgacc
aaactgcactttgctcgtgaccgcctgattgagagcttctactgggccgtgggtgtagcattcg
aaccgcaatactccgactgccgtaactccgtcgcaaaaatgttttctttcgtaaccattatcga
cgatatctacgatgtatacggcaccctggacgaactggagctgttactgatgcagttgagcgt
tgggacgtaaacgccatcaacgacctgccggattacatgaaactgtgctttctggctctgtata
acactattaacgaaatcgcctacgacaacctgaaagataaaggtgagaacatcctgccgtatct
gaccaaagcctgggctgacctgtgcaacgctttcctgcaagaagccaagtggctgtacaacaaa
tctactccgacctttgacgactacttcggcaacgcatggaaatcctcttctggcccgctgcaac
tggtgttcgcttacttcgctgtcgtgcagaacattaaaaaggaagagatcgaaaacctgcaaaa
ataccatgacaccatctctcgtccttccatatcttccgtctgtgcaatgacctggctagcgcg
tctgcggaaattgcgcgtggtgaaaccgcaaatagcgtttcttgttacatgcgcactaaaggta
tctccgaagaactggctaccgaaagcgtgatgaatctgatcgatgaaacctggaaaaagatgaa
caaggaaaaactgggtggtagcctgttcgcgaaaccgttcgtggaaaccgcgatcaacctgca
cgtcaatctcactgcacttatcataacggcgacgcgcatacctctccggatgagctgacccgca
aacgcgttctgtctgtaatcactgaaccgattctgccgtttgaacgctaaggatccgaattcga
gctccgtcgacaagcttgcggccgcactcgagcaccaccaccaccaccactgagatccggctgc
taacaaagcccgaaggaagctgagttggctgctgccaccgctgagcaataactagcataaccc
cttggggcctctaaacgggtcttgaggggttttttgctgaaaggaggaactatatccggat
```

Figure 27

Amino acid sequence of truncated "MSV" variant of *P. alba* IspS (SEQ ID NO:124)

MSVSTENVSFTETETEARRSANYEPNSWDYDYLLSSDTDESIEVYKDKAKKLEAEVRREINNEK
AEFLTLLELIDNVQRLGLGYRFESDIRGALDRFVSSGGFDAVTKTSLHGTALSFRLLRQHGFEV
SQEAFSGFKDQNGNFLENLKEDIKAILSLYEASFLALEGENILDEAKVFAISHLKELSEEKIGK
ELAEQVNHALELPLHRRTQRLEAVWSIEAYRKKEDANQVLLELAILDYNMIQSVYQRDLRETSR
WWRRVGLATKLHFARDRLIESFYWAVGVAFEPQYSDCRNSVAKMFSFVTIIDDIYDVYGTLDEL
ELFTDAVERWDVNAINDLPDYMKLCFLALYNTINEIAYDNLKDKGENILPYLTKAWADLCNAPL
QEAKWLYNKSTPTFDDYFGNAWKSSSGPLQLVFAYFAVVQNIKKEEIENLQKYHDTISRPSHIF
RLCNDLASASAEIARGETANSVSCYMRTKGISEELATESVMNLIDETWKKMNKEKLGGSLFAKP
FVETAINLARQSHCTYHNGDAHTSPDELTRKRVLSVITEPILPFER

Figure 28A

Nucleotide sequence of pDu41 (pET24a-P.alba (MSV) Untagged) (SEQ ID NO:125)

```
tggcgaatgggacgcgccctgtagcggcgcattaagcgcggcgggtgtggtggttacgcgcagc
gtgaccgctacacttgccagcgccctagcgcccgctcctttcgcttcttcccttcctttctcg
ccacgttcgccggctttccccgtcaagctctaaatcgggggctcccttttagggttccgatttag
tgctttacggcacctcgaccccaaaaaacttgattagggtgatggttcacgtagtgggccatcg
ccctgatagacggttttcgccttgacgttggagtccacgttctttaatagtggactcttgt
tccaaactggaacaacactcaaccctatctcggtctattcttttgatttataagggattttgcc
gatttcggctattggttaaaaaatgagctgatttaacaaaaattaacgcgaattttaacaaa
atattaacgtttacaatttcaggtggcacttttcggggaaatgtgcgcggaaccctatttgtt
tatttttctaaatacattcaaatatgtatccgctcatgaattaattcttagaaaaactcatcga
gcatcaaatgaaactgcaatttattcatatcaggattatcaataccatattttgaaaaagccg
tttctgtaatgaaggagaaaactcaccgaggcagttccataggatggcaagatcctggtatcgg
tctgcgattccgactcgtccaacatcaatacaacctattaatttccctcgtcaaaaataaggt
tatcaagtgagaaatcaccatgagtgacgactgaatccggtgagaatggcaaaagtttatgcat
ttcttccagacttgttcaacaggccagccattacgctcgtcatcaaaatcactcgcatcaacc
aaaccgttattcattcgtgattgcgcctgagcgagacgaaatacgcgatcgctgttaaaaggac
aattacaaacaggaatcgaatgcaacggcgcaggaacactgccagcgcatcaacaatatttc
acctgaatcaggatattcttctaatacctggaatgctgttttccggggatcgcagtggtgagt
aaccatgcatcatcaggagtacggataaaatgcttgatggtcggaagaggcataaattccgtca
gccagtttagtctgaccatctcatctgtaacatcattggcaacgctacctttgccatgtttcag
aaacaactctggcgcatcgggcttcccatacaatcgatagattgtcgcacctgattgcccgaca
ttatcgcgagcccatttatacccatataaatcagcatccatgttggaatttaatcgcggcctag
agcaagacgtttcccgttgaatatggctcataacaccccttgtattactgtttatgtaagcaga
cagtttattgttcatgaccaaaatcccttaacgtgagttttcgttccactgagcgtcagaccc
cgtagaaaagatcaaaggatcttcttgagatcctttttttctgcgcgtaatctgctgcttgcaa
acaaaaaaaccaccgctaccagcggtggtttgtttgccggatcaagagctaccaactctttttc
cgaaggtaactggcttcagcagagcgcagataccaaatactgtccttctagtgtagccgtagtt
aggccaccacttcaagaactctgtagcaccgcctacatacctcgctctgctaatcctgttacca
gtggctgctgccagtggcgataagtcgtgtcttaccgggttggactcaagacgatagttaccgg
ataaggcgcagcggtcgggctgaacggggggttcgtgcacacagcccagcttggagcgaacgac
ctacaccgaactgagatacctacagcgtgagctatgagaaagcgccacgcttcccgaagggaga
aaggcggacaggtatccggtaagcggcagggtcggaacaggagagcgcacgagggagcttccag
gggaaacgcctggtatctttatagtcctgtcgggtttcgccacctctgacttgagcgtcgatt
tttgtgatgctcgtcaggggggcggagcctatggaaaaacgccagcaacgcggcctttttacgg
ttcctggccttttgctggccttttgctcacatgttctttcctgcgttatcccctgattctgtgg
ataaccgtattaccgcctttgagtgagctgataccgctcgccgcagccgaacgaccgagcgcag
cgagtcagtgagcgaggaagcggaagagcgcctgatgcggtattttctccttacgcatctgtgc
ggtatttcacaccgcatatatggtgcactctcagtacaatctgctctgatgccgcatagttaag
ccagtatacactccgctatcgctacgtgactgggtcatggctgcgccccgacacccgccaacac
ccgctgacgcgccctgacgggcttgtctgctcccggcatccgcttacagacaagctgtgaccgt
ctccgggagctgcatgtgtcagaggttttcaccgtcatcaccgaaacgcgcgaggcagctgcgg
taaagctcatcagcgtggtcgtgaagcgattcacagatgtctgcctgttcatccgcgtccagct
cgttgagtttctccagaagcgttaatgtctggcttctgataaagcgggccatgttaagggcggt
```

Figure 28B

Nucleotide sequence of pDu41 (pET24a-P.alba (MSV) Untagged)

ttttcctgtttggtcactgatgcctccgtgtaaggggattttctgttcatggggtaatgata
ccgatgaaacgagagaggatgctcacgatacggggttactgatgatgaacatgcccggttactgg
aacgttgtgagggtaaacaactggcggtatggatgcggcgggaccagagaaaaatcactcaggg
tcaatgccagcgcttcgttaatacagatgtaggtgttccacagggtagccagcagcatcctgcg
atgcagatccggaacataatggtgcagggcgctgacttccgcgtttccagactttacgaaacac
ggaaaccgaagaccattcatgttgttgctcaggtcgcagacgttttgcagcagcagtcgcttca
cgttcgctcgcgtatcggtgattcattctgctaaccagtaaggcaacccgccagcctagccgg
gtcctcaacgacaggagcacgatcatgcgcaccgtggggccgccatgccggcgataatggcct
gcttctcgccgaaacgtttggtggcgggaccagtgacgaaggcttgagcgagggcgtgcaagat
tccgaataccgaagcgacaggccgatcatcgtcgcgctccagcgaaagcggtcctcgccgaaa
atgacccagagcgctgccggcacctgtcctacgagttgcatgataaagaagacagtcataagtg
cggcgacgatagtcatgccccgcgccaccggaaggagctgactgggttgaaggctctcaaggg
catcggtcgagatcccggtgcctaatgagtgagctaacttacattaattgcgttgcgctcactg
cccgctttccagtcgggaaacctgtcgtgccagctgcattaatgaatcggccaacgcgcggga
gaggcggtttgcgtattgggcgccagggtggttttcttttcaccagtgagacgggcaacagct
gattgcccttcaccgcctggccctgagagagttgcagcaagcggtccacgctggtttgcccag
caggcgaaaatcctgtttgatggtggttaacggcgggatataacatgagctgtcttcggtatcg
tgtatccactaccgagatatccgcaccaacgcgcagcccggactcggtaatggcgcgcattg
cgccagcgccatctgatcgttggcaaccagcatcgcagtgggaacgatgccctcattcagcat
ttgcatggtttgttgaaaaccggacatggcactccagtcgccttcccgttccgctatcggctga
atttgattgcgagtgagatatttatgccagccagccagacgcagacgcgccgagacagaactta
atgggcccgctaacagcgcgatttgctggtgacccaatgcgaccagatgctccacgcccagtcg
cgtaccgtcttcatgggagaaaataatactgttgatgggtgtctggtcagagacatcaagaaat
aacgccggaacattagtgcaggcagcttccacagcaatggcatcctggtcatccagcggatagt
taatgatcagcccactgacgcgttgcgcgagaagattgtgcaccgccgctttacaggcttcgac
gccgcttcgttctaccatcgacaccaccacgctggcacccagttgatcggcgcgagatttaatc
gccgcgacaatttgcgacggcgcgtgcagggccagactggaggtggcaacgccaatcagcaacg
actgtttgcccgccagttgttgtgccacgcggttgggaatgtaattcagctccgccatcgccgc
ttccactttttccgcgttttcgcagaaacgtggctggcctggttcaccacgcgggaaacggtc
tgataagagacaccggcatactctgcgacatcgtataacgttactggtttcacattcaccaccc
tgaattgactctcttccgggcgctatcatgccataccgcgaaaggttttgcgccattcgatggt
gtccgggatctcgacgctctcccttatgcgactcctgcattaggaagcagccagtagtaggtt
gaggccgttgagcaccgccgccgcaaggaatggtgcatgcaaggagatggcgcccaacagtccc
cggccacgggcctgccaccataccacgccgaaacaagcgctcatgagcccgaagtggcgag
cccgatcttccccatcggtgatgtcggcgatataggcgccagcaaccgcacctgtggcgccggt
gatgccggccacgatgcgtccggcgtagaggatcgagatctcgatcccgcgaaattaatacgac
tcactatagggaattgtgagcggataacaattcccctctagaaataattttgtttaactttaa
gaaggagatatacatatgagcgtgtccaccgaaaatgtgtctttcaccgaaactgaaaccgaag
ctcgtcgttctgcgaactacgaacctaacagctgggactatgattacctgctgtcctccgacac
ggacgagtccatcgaagtatacaaagacaaagcgaaaaagctggaagccgaagttcgtcgcgag
attaataacgaaaaagcagaattctgacccctgctggaactgattgacaacgtccagcgcctgg
gcctgggttaccgtttcgagtctgatatccgtggtgcgctggatcgttcgtttcctccggcgg
cttcgatgcggtaaccaagacttccctgcacggtacggcactgtctttccgtctgctgcgtcaa

Figure 28C

Nucleotide sequence of pDu41 (pET24a-P.alba (MSV) Untagged)

cacggttttgaggtttctcaggaagcgttcagcggcttcaaagaccaaaacggcaacttcctgg
agaacctgaaggaagatatcaaagctatcctgagcctgtacgaggccagcttcctggctctgga
aggcgaaaacatcctggacgaggcgaaggttttcgcaatctctcatctgaaagaactgtctgaa
gaaaagatcggtaaagagctggcagaacaggtgaaccatgcactggaactgccactgcatcgcc
gtactcagcgtctggaagcagtatggtctatcgaggcctaccgtaaaaaggaggacgcgaatca
ggttctgctggagctggcaattctggattacaacatgatccagtctgtataccagcgtgatctg
cgtgaaacgtcccgttggtggcgtcgtgtgggtctggcgaccaaactgcactttgctcgtgacc
gcctgattgagagcttctactgggccgtgggtgtagcattcgaacgcaatactccgactgccg
taactccgtcgcaaaaatgttttctttcgtaaccattatcgacgatatctacgatgtatacggc
accctggacgaactggagctgtttactgatgcagttgagcgttgggacgtaaacgccatcaacg
acctgccggattacatgaaactgtgctttctggctctgtataacactattaacgaaatcgccta
cgacaacctgaaagataaaggtgagaacatcctgccgtatctgaccaaagcctgggctgacctg
tgcaacgctttcctgcaagaagccaagtggctgtacaacaaatctactccgaccttgacgact
actcggcaacgcatggaaatcctcttctggcccgctgcaactggtgttcgcttacttcgctgt
cgtgcagaacattaaaaaggaagagatcgaaaacctgcaaaaataccatgacaccatctctcgt
ccttccatatcttccgtctgtgcaatgacctggctagcgcgtctgcggaaattgcgcgtggtg
aaaccgcaaatagcgttcttgttacatgcgcactaaaggtatctccgaagaactggctaccga
aagcgtgatgaatctgatcgatgaaacctggaaaagatgaacaaggaaaaactgggtggtagc
ctgttcgcgaaaccgttcgtggaaaccgcgatcaacctggcacgtcaatctcactgcacttatc
ataacggcgacgcgcatacctctccggatgagctgacccgcaaacgcgttctgtctgtaatcac
tgaaccgattctgccgtttgaacgctaaggatccgaattcgagctccgtcgacaagcttgcgg
cgcactcgagcaccaccaccaccaccactgagatccggctgctaacaaagcccgaaaggaagct
gagttggctgctgccaccgctgagcaataactagcataacccttggggcctctaaacgggtct
tgaggggttttttgctgaaaggaggaactatatccggat

Figure 29

Amino acid sequence of truncated "MVS" Variant of *P. alba* IspS (SEQ ID NO:126)

MVSTENVSFTETETEARRSANYEPNSWDYDYLLSSDTDESIEVYKDKAKKLEAEVRREINNEKA
EFLTLLELIDNVQRLGLGYRPESDIRGALDRFVSSGGFDAVTKTSLHGTALSFRLLRQHGFEVS
QEAFSGFKDQNGNFLENLKEDIKAILSLYEASFLALEGENILDEAKVFAISHLKELSEEKIGKE
LAEQVNHALELPLHRRTQRLEAVWSIEAYRKKEDANQVLLELAILDYNMIQSVYQRDLRETSRW
WRRVGLATKLHFARDRLIESFYWAVGVAFEPQYSDCRNSVAKMFSFVTIIDDIYDVYGTLDELE
LFTDAVERWDVNAINDLPDYMKLCFLALYNTINEIAYDNLKDKGENILPYLTKAWADLCNAFLQ
EAKWLYNKSTPTFDDYFGNAWKSSSGPLQLVFAYFAVVQNIKKEEIENLQKYHDTISRPSHIFR
LCNDLASASAEIARGETANSVSCYMRTKGISEELATESVMNLIDETWKKMNKEKLGGSLFAKPF
VETAINLARQSHCTYHNGDAHTSPDELTRKRVLSVITEPILPFER

Figure 30A

Nucleotide sequence of pDu43 (pET24a-P.alba (MVS) Untagged) (SEQ ID NO:127)

```
tggcgaatgggacgcgccctgtagcggcgcattaagcgcggcgggtgtggtggttacgcgcagc
gtgaccgctacacttgccagcgccctagcgcccgctcctttcgctttcttcccttcctttctcg
ccacgttcgccggctttccccgtcaagctctaaatcgggggctccctttagggttccgatttag
tgctttacggcacctcgaccccaaaaaacttgattagggtgatggttcacgtagtgggccatcg
ccctgatagacggttttcgccctttgacgttggagtccacgttctttaatagtggactcttgt
tccaaactggaacaacactcaaccctatctcggtctattcttttgatttataagggattttgcc
gatttcggcctattggttaaaaaatgagctgatttaacaaaatttaacgcgaattttaacaaa
atattaacgtttacaatttcaggtggcacttttcggggaaatgtgcgcggaacccctatttgtt
tatttttctaaatacattcaaatatgtatccgctcatgaattaattcttagaaaaactcatcga
gcatcaaatgaaactgcaatttattcatatcaggattatcaataccatattttgaaaaagccg
tttctgtaatgaaggagaaaactcaccgaggcagttccataggatggcaagatcctggtatcgg
tctgcgattccgactcgtccaacatcaatacaacctattaatttccctcgtcaaaaataaggt
tatcaagtgagaaatcaccatgagtgacgactgaatccggtgagaatggcaaaagtttatgcat
ttctttccagacttgttcaacaggccagccattacgctcgtcatcaaaatcactcgcatcaacc
aaaccgttattcattcgtgattgcgcctgagcgagacgaaatacgcgatcgctgttaaaaggac
aattacaaacaggaatcgaatgcaaccggcgcaggaacactgccagcgcatcaacaatatttc
acctgaatcaggatattcttctaatacctggaatgctgttttcccggggatcgcagtggtgagt
aaccatgcatcatcaggagtacggataaaatgcttgatggtcggaagaggcataaattccgtca
gccagtttagtctgaccatctcatctgtaacatcattggcaacgctacctttgccatgtttcag
aaacaactctggcgcatcgggcttcccatacaatcgatagattgtcgcacctgattgcccgaca
ttatcgcgagcccatttatacccatataaatcagcatccatgttggaatttaatcgcggcctag
agcaagacgtttcccgttgaatatggctcataacaccccttgtattactgtttatgtaagcaga
cagttttattgttcatgaccaaaatcccttaacgtgagttttcgttccactgagcgtcagaccc
cgtagaaaagatcaaaggatcttcttgagatcctttttttctgcgcgtaatctgctgcttgcaa
acaaaaaaaccaccgctaccagcggtggtttgtttgccggatcaagagctaccaactctttttc
cgaaggtaactggcttcagcagagcgcagataccaaatactgtccttctagtgtagccgtagtt
aggccaccacttcaagaactctgtagcaccgcctacatacctcgctctgctaatcctgttacca
gtggctgctgccagtggcgataagtcgtgtcttaccgggttggactcaagacgatagttaccgg
ataaggcgcagcggtcgggctgaacggggggttcgtgcacacagcccagcttggagcgaacgac
ctacaccgaactgagatacctacagcgtgagctatgagaaagcgccacgcttcccgaagggaga
aaggcggacaggtatccggtaagcggcagggtcggaacaggagagcgcacgagggagcttccag
ggggaaacgcctggtatctttatagtcctgtcgggtttcgccacctctgacttgagcgtcgatt
tttgtgatgctcgtcaggggggcggagcctatggaaaaacgccagcaacgcggcctttttacgg
ttcctggccttttgctggccttttgctcacatgttctttcctgcgttatcccctgattctgtgg
ataaccgtattaccgcctttgagtgagctgataccgctcgccgcagccgaacgaccgagcgcag
cgagtcagtgagcgaggaagcggaagagcgcctgatgcggtattttctccttacgcatctgtgc
ggtatttcacaccgcatatatggtgcactctcagtacaatctgctctgatgccgcatagttaag
ccagtatacactccgctatcgctacgtgactgggtcatggctgcgccccgacacccgccaacac
ccgctgacgcgccctgacgggcttgtctgctcccggcatccgcttacagacaagctgtgaccgt
ctccgggagctgcatgtgtcagaggttttcaccgtcatcaccgaaacgcgcgaggcagctgcgg
taaagctcatcagcgtggtcgtgaagcgattcacagatgtctgcctgttcatccgcgtccagct
cgttgagtttctccagaagcgttaatgtctggcttctgataaagcgggccatgttaagggcggt
tttttcctgtttggtcactgatgcctccgtgtaaggggattctgttcatgggggtaatgata
```

Figure 30B

Nucleotide sequence of pDu43 (pET24a-P.alba (MVS) Untagged)

ccgatgaaacgagagaggatgctcacgatacgggttactgatgatgaacatgcccggttactgg
aacgttgtgagggtaaacaactggcggtatggatgcggcgggaccagagaaaaatcactcaggg
tcaatgccagcgcttcgttaatacagatgtaggtgttccacagggtagccagcagcatcctgcg
atgcagatccggaacataatggtgcagggcgctgacttccgcgtttccagactttacgaaacac
ggaaaccgaagaccattcatgttgttgctcaggtcgcagacgttttgcagcagcagtcgcttca
cgttcgctcgcgtatcggtgattcattctgctaaccagtaaggcaacccgccagcctagccgg
gtcctcaacgacaggagcacgatcatgcgcacccgtgggcgccatgccggcgataatggcct
gcttctcgccgaaacgtttggtggcgggaccagtgacgaaggcttgagcgagggcgtgcaagat
tccgaataccgcaagcgacaggccgatcatcgtcgcgctccagcgaaagcggtcctcgccgaaa
atgacccagagcgctgccggcacctgtcctacgagttgcatgataaagaagacagtcataagtg
cggcgacgatagtcatgccccgcgccaccggaaggagctgactgggttgaaggctctcaaggg
catcggtcgagatcccggtgcctaatgagtgagctaacttacattaattgcgttgcgctcactg
cccgctttccagtcgggaaacctgtcgtgccagctgcattaatgaatcggccaacgcgcgggga
gaggcggtttgcgtattgggcgccagggtggttttcttttcaccagtgagacgggcaacagct
gattgcccttcaccgcctggccctgagagagttgcagcaagcggtccacgctggtttgcccag
caggcgaaaatcctgtttgatggtggttaacggcgggatataacatgagctgtcttcggtatcg
tcgtatcccactaccgagatatccgcaccaacgcgcagcccggactcggtaatggcgcgcattg
cgcccagcgccatctgatcgttggcaaccagcatcgcagtgggaacgatgccctcattcagcat
ttgcatggtttgttgaaaaccggacatggcactccagtcgccttcccgttccgctatcggctga
atttgattgcgagtgagatatttatgccagccagccagacgcagacgcgccgagacagaactta
atgggcccgctaacagcgcgatttgctggtgacccaatgcgaccagatgctccacgccagtcg
cgtaccgtcttcatgggagaaaataatactgttgatgggtgtctggtcagagacatcaagaaat
aacgccggaacattagtgcaggcagcttccacagcaatggcatcctggtcatccagcggatagt
taatgatcagcccactgacgcgttgcgcgagaagattgtgcacgccgcgtttacaggcttcgac
gccgcttcgttctaccatcgacaccaccacgctggcacccagttgatcggcgcgagatttaatc
gccgcgacaatttgcgacggcgcgtgcagggccagactggaggtggcaacgccaatcagcaacg
actgtttgcccgccagttgttgtgccacgcggttgggaatgtaattcagctccgccatcgccgc
ttccacttttcccgcgttttcgcagaaacgtggctggcctggttcaccacgcgggaaacggtc
tgataagagacaccggcatactctgcgacatcgtataacgttactggtttcacattcaccaccc
tgaattgactctcttccgggcgctatcatgccataccgcgaaaggttttgcgccattcgatggt
gtccgggatctcgacgctctcccttatgcgactcctgcattaggaagcagcccagtagtaggtt
gaggccgttgagcaccgccgccgcaaggaatggtgcatgcaaggagatggcgcccaacagtccc
ccggccacggggcctgccaccatacccacgcgaaacaagcgctcatgagccgaagtggcgag
cccgatcttcccatcggtgatgtcggcgatataggcgccagcaacgcacctgtggcgccggt
gatgccggccacgatgcgtccggcgtagaggatcgagatctcgatcccgcgaaattaatacgac
tcactatagggaattgtgagcggataacaattcccctctagaaataattttgtttaactttaa
gaaggagatatacatatggtgtccaccgaaaatgtgtctttcaccgaaactgaaaccgaagctc
gtcgttctgcgaactacgaacctaacagctgggactatgattacctgctgtcctccgacacgga
cgagtccatcgaagtatacaaagacaaagcgaaaaagctggaagccgaagttcgtcgcgagatt
aataacgaaaagcagaatttctgaccctgctggaactgattgacaacgtccagcgcctgggcc
tgggttaccgtttcgagtctgatatccgtggtgcgctggatcgcttcgtttcctccggcggctt
cgatgcggtaaccaagacttccctgcacggtacggcactgtctttccgtctgctgcgtcaacac
ggttttgaggtttctcaggaagcgttcagcggcttcaaagaccaaaacggcaacttcctggaga

Figure 30C

Nucleotide sequence of pDu43 (pET24a-P.alba (MVS) Untagged)

```
acctgaaggaagatatcaaagctatcctgagcctgtacgaggccagcttcctggctctggaagg
cgaaaacatcctggacgaggcgaaggttttcgcaatctctcatctgaaagaactgtctgaagaa
aagatcggtaaagagctggcagaacaggtgaaccatgcactggaactgccactgcatcgccgta
ctcagcgtctggaagcagtatggtctatcgaggcctaccgtaaaaaggaggacgcgaatcaggt
tctgctggagctggcaattctggattacaacatgatccagtctgtataccagcgtgatctgcgt
gaaacgtccgttggtggcgtcgtgtgggtctggcgaccaaactgcactttgctcgtgaccgcc
tgattgagagcttctactgggccgtgggtgtagcattcgaaccgcaatactccgactgccgtaa
ctccgtcgcaaaaatgttttctttcgtaaccattatcgacgatatctacgatgtatacggcacc
ctggacgaactggagctgtttactgatgcagttgagcgttgggacgtaaacgccatcaacgacc
tgccggattacatgaaactgtgctttctggctctgtataacactattaacgaaatcgcctacga
caacctgaaagataaaggtgagaacatcctgccgtatctgaccaaagcctgggctgacctgtgc
aacgctttcctgcaagaagccaagtggctgtacaacaaatctactccgaccttgacgactact
tcggcaacgcatggaaatcctcttctggcccgtgcaactggtgttcgcttacttcgctgtcgt
gcagaacattaaaaaggaagagatcgaaaacctgcaaaaataccatgacaccatctctcgtcct
tcccatatcttccgtctgtgcaatgacctggctagcgcgtctgcggaaattgcgcgtggtgaaa
ccgcaaatagcgtttcttgttacatgcgcactaaaggtatctccgaagaactggctaccgaaag
cgtgatgaatctgatcgatgaaacctggaaaaagatgaacaaggaaaaactgggtggtagcctg
ttcgcgaaaccgttcgtggaaacgcgatcaacctggcacgtcaatctcactgcacttatcata
acggcgacgcgcatacctctccggatgagctgaccgcaaacgcgttctgtctgtaatcactga
accgattctgccgtttgaacgctaaggatccgaattcgagctccgtcgacaagcttgcggccgc
actcgagcaccaccaccaccaccactgagatccggctgctaacaaagcccgaaaggaagctgag
ttggctgctgccaccgctgagcaataactagcataaccccttggggcctctaaacgggtcttga
ggggttttttgctgaaaggaggaactatatccggat
```

Figure 31

Amino acid sequence of truncated "MTE" variant of *P. alba* IspS (SEQ ID NO:128)

```
MTENVSFTETETEARRSANYEPNSWDYDYLLSSDTDESIEVYKDKAKKLEAEVRREINNEKAEF
LTLLELIDNVQRLGLGYRFESDIRGALDRFVSSGGFDAVTKTSLHGTALSFRLLRQHGFEVSQE
AFSGFKDQNGNFLENLKEDIKAILSLYEASFLALEGENILDEAKVFAISHLKELSEEKIGKELA
EQVNHALELPLHRRTQRLEAVWSIEAYRKKEDANQVLLELAILDYNMIQSVYQRDLRETSRWWR
RVGLATKLHFARDRLIESFYWAVGVAFEPQYSDCRNSVAKMFSFVTIIDDIYDVYGTLDELELF
TDAVERWDVNAINDLPDYMKLCFLALYNTINEIAYDNLKDKGENILPYLTKAWADLCNAFLQEA
KWLYNKSTPTFDDYFGNAWKSSSGPLQLVFAYFAVVQNIKKEEIENLQKYHDTISRPSHIFRLC
NDLASASAEIARGETANSVSCYMRTKGISEELATESVMNLIDETWKKMNKEKLGGSLFAKPFVE
TAINLARQSHCTYHNGDAHTSPDELTRKRVLSVITEPILPFER
```

Figure 32A

Nucleotide sequence of pDu42 (pET24a-P.alba (MTE) Untagged) (SEQ ID NO:129)

```
tggcgaatgggacgcgcctgtagcggcgcattaagcgcggcgggtgtggtggttacgcgcagc
gtgaccgctacacttgccagcgccctagcgcccgctcctttcgctttcttcccttcctttctcg
ccacgttcgccggctttccccgtcaagctctaaatcgggggctccctttagggttccgatttag
tgctttacggcacctcgaccccaaaaaacttgattagggtgatggttcacgtagtgggccatcg
ccctgatagacggttttttcgccctttgacgttggagtccacgttctttaatagtggactcttgt
tccaaactggaacaacactcaaccctatctcggtctattcttttgatttataaggattttgcc
gatttcggcctattggttaaaaaatgagctgatttaacaaaatttaacgcgaattttaacaaa
atattaacgtttacaatttcaggtggcacttttcggggaaatgtgcgcggaacccctatttgtt
tattttttctaaatacattcaaatatgtatccgctcatgaattaattcttagaaaaactcatcga
gcatcaaatgaaactgcaatttattcatatcaggattatcaataccatattttgaaaaagccg
tttctgtaatgaaggagaaaactcaccgaggcagttccataggatggcaagatcctggtatcgg
tctgcgattccgactcgtccaacatcaatacaacctattaatttcccctcgtcaaaaataaggt
tatcaagtgagaaatcaccatgagtgacgactgaatccggtgagaatggcaaaagtttatgcat
ttctttccagacttgttcaacaggccagccattacgctcgtcatcaaaatcactcgcatcaacc
aaaccgttattcattcgtgattgcgcctgagcgagacgaaatacgcgatcgctgttaaaaggac
aattacaaacaggaatcgaatgcaaccggcgcaggaacactgccagcgcatcaacaatatttttc
acctgaatcaggatattcttctaatacctggaatgctgtttttccggggatcgcagtggtgagt
aaccatgcatcatcaggagtacggataaaatgcttgatggtcggaagaggcataaattccgtca
gccagtttagtctgaccatctcatctgtaacatcattggcaacgctacctttgccatgtttcag
aaacaactctggcgcatcgggcttcccatacaatcgatagattgtcgcacctgattgcccgaca
ttatcgcgagcccatttatacccatataaatcagcatccatgttggaatttaatcgcggcctag
agcaagacgtttcccgttgaatatggctcataacacccttgtattactgtttatgtaagcaga
cagttttattgttcatgaccaaaatcccttaacgtgagttttcgttccactgagcgtcagaccc
cgtagaaaagatcaaaggatcttcttgagatcctttttttctgcgcgtaatctgctgcttgcaa
acaaaaaaaccaccgctaccagcggtggtttgtttgccggatcaagagctaccaactctttttc
cgaaggtaactggcttcagcagagcgcagataccaaatactgtccttctagtgtagccgtagtt
aggccaccacttcaagaactctgtagcaccgcctacatacctcgctctgctaatcctgttacca
gtggctgctgccagtggcgataagtcgtgtcttaccgggttggactcaagacgatagttaccgg
ataaggcgcagcggtcgggctgaacggggggttcgtgcacacagcccagcttggagcgaacgac
ctacaccgaactgagatacctacagcgtgagctatgagaaagcgccacgcttcccgaagggaga
aaggcggacaggtatccggtaagcggcagggtcggaacaggagagcgcacgagggagcttccag
ggggaaacgcctggtatctttatagtcctgtcgggtttcgccacctctgacttgagcgtcgatt
tttgtgatgctcgtcaggggggcggagcctatggaaaaacgccagcaacgcggcctttttacgg
ttcctggccttttgctggccttttgctcacatgttctttcctgcgttatcccctgattctgtgg
ataaccgtattaccgcctttgagtgagctgataccgctcgccgcagccgaacgaccgagcgcag
cgagtcagtgagcgaggaagcggaagagcgcctgatgcggtattttctccttacgcatctgtgc
ggtatttcacaccgcatatatggtgcactctcagtacaatctgctctgatgccgcatagttaag
ccagtatacactccgctatcgctacgtgactgggtcatggctgcgccccgacacccgccaacac
ccgctgacgcgccctgacgggcttgtctgctcccggcatccgcttacagacaagctgtgaccgt
ctccgggagctgcatgtgtcagaggttttcaccgtcatcaccgaaacgcgcgaggcagctgcgg
taaagctcatcagcgtggtcgtgaagcgattcacagatgtctgcctgttcatccgcgtccagct
cgttgagtttctccagaagcgttaatgtctggcttctgataaagcgggccatgttaagggcggt
tttttcctgtttggtcactgatgcctccgtgtaaggggggattctgttcatggggtaatgata
```

Figure 32B

Nucleotide sequence of pDu42 (pET24a-P.alba (MTE) Untagged)

```
ccgatgaaacgagagaggatgctcacgatacgggttactgatgatgaacatgcccggttactgg
aacgttgtgagggtaaacaactggcggtatggatgcggcgggaccagagaaaaatcactcaggg
tcaatgccagcgcttcgttaatacagatgtaggtgttccacagggtagccagcagcatcctgcg
atgcagatccggaacataatggtgcagggcgctgacttccgcgtttccagactttacgaaacac
ggaaaccgaagaccattcatgttgttgctcaggtcgcagacgttttgcagcagtcgcttca
cgttcgctcgcgtatcggtgattcattctgctaaccagtaaggcaacccgccagcctagccgg
gtcctcaacgacaggagcacgatcatgcgcacccgtgggccgccatgccggcgataatggcct
gcttctcgccgaaacgtttggtggcgggaccagtgacgaaggcttgagcgagggcgtgcaagat
tccgaataccgcaagcgacaggccgatcatcgtcgcgctccagcgaaagcggtcctcgccgaaa
atgacccagagcgctgccggcacctgtcctacgagttgcatgataaagaagacagtcataagtg
cggcgacgatagtcatgccccgcgccaccggaaggagctgactgggttgaaggctctcaaggg
catcggtcgagatcccggtgcctaatgagtgagctaacttacattaattgcgttgcgctcactg
cccgctttccagtcgggaaacctgtcgtgccagctgcattaatgaatcggccaacgcgcggga
gaggcggtttgcgtattgggcgccagggtggttttcttttcaccagtgagacgggcaacagct
gattgcccttcaccgcctggccctgagagagttgcagcaagcggtccacgctggtttgcccag
caggcgaaaatcctgtttgatggtggttaacggcgggatataacatgagctgtcttcggtatcg
tcgtatcccactaccgagatatccgcaccaacgcgcagcccggactcggtaatggcgcgcattg
cgcccagcgccatctgatcgttggcaaccagcatcgcagtgggaacgatgccctcattcagcat
ttgcatggtttgttgaaaaccggacatggcactccagtcgccttcccgttccgctatcggctga
atttgattgcgagtgagatatttatgccagccagccagacgcagacgcgccgagacagaactta
atgggccgctaacagcgcgatttgctggtgacccaatgcgaccagatgctccacgccagtcg
cgtaccgtcttcatgggagaaaataatactgttgatgggtgtctggtcagagacatcaagaaat
aacgccggaacattagtgcaggcagcttccacagcaatggcatcctggtcatccagcggatagt
taatgatcagcccactgacgcgttgcgcgagaagattgtgcaccgccgctttacaggcttcgac
gccgcttcgttctaccatcgacaccaccacgctggcacccagttgatcggcgcgagatttaatc
gccgcgacaatttgcgacggcgcgtgcagggccagactggaggtggcaacgccaatcagcaacg
actgtttgcccgccagttgttgtgccacgcggttgggaatgtaattcagctccgccatcgccgc
ttccactttttcccgcgttttcgcagaaacgtggctggcctggttcaccacgcgggaaacggtc
tgataagagacaccggcatactctgcgacatcgtataacgttactggtttcacattcaccaccc
tgaattgactctcttccgggcgctatcatgccataccgcgaaaggttttgcgccattcgatggt
gtccgggatctcgacgctctcccttatgcgactcctgcattaggaagcagcccagtagtaggtt
gaggccgttgagcaccgccgccgcaaggaatggtgcatgcaaggagatggcgcccaacagtccc
ccggccacggggcctgccaccatacccacgccgaaacaagcgctcatgagcccgaagtggcgag
cccgatcttccccatcggtgatgtcggcgatataggcgccagcaaccgcacctgtggcgccggt
gatgccggccacgatgcgtccggcgtagaggatcgagatctcgatcccgcgaaattaatacgac
tcactatagggaattgtgagcggataacaattcccctctagaaataattttgtttaactttaa
gaaggagatatacatatgaccgaaaatgtgtctttcaccgaaactgaaaccgaagctcgtcgtt
ctgcgaactacgaacctaacagctgggactatgattacctgctgtcctccgacacggacgagtc
catcgaagtatacaaagacaaagcgaaaaagctggaagccgaagttcgtcgcgagattaataac
gaaaaagcagaatttctgaccctgctggaactgattgacaacgtccagcgcctgggcctgggtt
accgtttcgagtctgatatccgtggtgcgctggatcgcttcgtttcctccggcggcttcgatgc
ggtaaccaagacttccctgcacggtacggcactgtctttccgtctgctgcgtcaaacggttt
gaggtttctcaggaagcgttcagcggcttcaaagaccaaaacggcaacttcctggagaacctga
```

Figure 32C

Nucleotide sequence of pDu42 (pET24a-P.alba (MTE) Untagged)

aggaagatatcaaagctatcctgagcctgtacgaggccagcttcctggctctggaaggcgaaaa
catcctggacgaggcgaaggttttcgcaatctctcatctgaaagaactgtctgaagaaaagatc
ggtaaagagctggcagaacaggtgaaccatgcactggaactgccactgcatcgccgtactcagc
gtctggaagcagtatggtctatcgaggcctaccgtaaaaaggaggacgcgaatcaggttctgct
ggagctggcaattctggattacaacatgatccagtctgtataccagcgtgatctgcgtgaaacg
tcccgttggtggcgtcgtgtgggtctggcgaccaaactgcactttgctcgtgaccgctgattg
agagcttctactgggccgtgggtgtagcattcgaaccgcaatactccgactgccgtaactccgt
cgcaaaaatgttttctttcgtaaccattatcgacgatatctacgatgtatacggcaccctggac
gaactggagctgtttactgatgcagttgagcgttgggacgtaaacgccatcaacgacctgccgg
attacatgaaactgtgctttctggctctgtataacactattaacgaaatcgcctacgacaacct
gaaagataaggtgagaacatcctgccgtatctgaccaaagcctgggctgacctgtcaacgct
tcctgcaagaagccaagtggctgtacaacaaatctactccgacctttgacgactacttcggca
acgcatggaaatcctcttctggcccgctgcaactggtgttcgcttacttcgctgtcgtgcagaa
cattaaaaaggaagagatcgaaaacctgcaaaataccatgacaccatctctcgtccttccat
atcttccgtctgtgcaatgacctggctagcgcgtctgcggaaattgcgcgtggtgaaaccgcaa
atagcgtttcttgttacatgcgcactaaaggtatctccgaagaactggctaccgaaagcgtgat
gaatctgatcgatgaaacctggaaaagatgaacaaggaaaaactgggtggtagcctgttcgcg
aaaccgttcgtggaaaccgcgatcaacctggcacgtcaatctcactgcacttatcataacggcg
acgcgcataccctctccggatgagctgacccgcaaagcgcttctgtctgtaatcactgaaccgat
tctgccgtttgaacgctaaggatccgaattcgagctccgtcgacaagcttgcggccgcactcga
gcaccaccaccaccactgagatccggctgctaacaaagcccgaaaggaagctgagttggct
gctgccaccgctgagcaataactagcataaccccttggggcctctaaacgggtcttgagggtt
ttttgctgaaaggaggaactatatccggat

Figure 33

Amino acid Sequence of truncated "MNV" variant of *P. alba* IspS (SEQ ID NO:130)

MNVSFTETETEARRSANYEPNSWDYDYLLSSDTDESIEVYKDKAKKLEAEVRREINNEKAEFLT
LLELIDNVQRLGLGYRFESDIRGALDRFVSSGGFDAVTKTSLHGTALSFRLLRQHGFEVSQEAF
SGFKDQNGNFLENLKEDIKAILSLYEASFLALEGENILDEAKVFAISHLKELSEEKIGKELAEQ
VNHALELPLHRRTQRLEAVWSIEAYRKKEDANQVLLELAILDYNMIQSVYQRDLRETSRWWRRV
GLATKLHFARDRLIESFYWAVGVAFEPQYSDCRNSVAKMFSFVTIIDDIYDVYGTLDELELFTD
AVERWDVNAINDLPDYMKLCFLALYNTINEIAYDNLKDKGENILPYLTKAWADLCNAFLQEAKW
LYNKSTPTFDDYPGNAWKSSSGPLQLVFAYFAVVQNIKKEEIENLQKYHDTISRPSHIFRLCND
LASASAEIARGETANSVSCYMRTKGISEELATESVMNLIDETWKKMNKEKLGGSLFAKPFVETA
INLARQSHCTYHNGDAHTSPDELTRKRVLSVITEPILPFER

Figure 34A

Nucleotide sequence of pDu40 (pET24a-P.alba (MNV) Untagged) (SEQ ID NO:131)

```
tggcgaatgggacgcgccctgtagcggcgcattaagcgcggcgggtgtggtggttacgcgcagc
gtgaccgctacacttgccagcgccctagcgcccgctcctttcgctttcttcccttcctttctcg
ccacgttcgccggctttccccgtcaagctctaaatcgggggctcccttagggttccgatttag
tgctttacggcacctcgacccaaaaaacttgattagggtgatggttcacgtagtgggccatcg
ccctgatagacggttttcgccctttgacgttggagtccacgttctttaatagtggactcttgt
tccaaactggaacaacactcaaccctatctcggtctattcttttgatttataagggatttgcc
gattcggcctattggttaaaaaatgagctgatttaacaaaaatttaacgcgaattttaacaaa
atattaacgtttacaatttcaggtggcacttttcggggaaatgtgcgcggaacccctatttgtt
tatttttctaaatacattcaaatatgtatccgctcatgaattaattcttagaaaaactcatcga
gcatcaaatgaaactgcaatttattcatatcaggattatcaataccatattttgaaaaagccg
tttctgtaatgaaggagaaaactcaccgaggcagttccataggatggcaagatcctggtatcgg
tctgcgattccgactcgtccaacatcaatacaacctattaatttccctcgtcaaaaataaggt
tatcaagtgagaaatcaccatgagtgacgactgaatccggtgagaatggcaaaagtttatgcat
ttctttccagacttgttcaacaggccagccattacgctcgtcatcaaaatcactcgcatcaacc
aaaccgttattcattcgtgattgcgcctgagcgagacgaaatacgcgatcgctgttaaaaggac
aattacaaacaggaatcgaatgcaaccggcgcaggaacactgccagcgcatcaacaatattttc
acctgaatcaggatattcttctaataccctggaatgctgttttccggggatcgcagtggtgagt
aaccatgcatcatcaggagtacggataaaatgcttgatggtcggaagaggcataaattccgtca
gccagtttagtctgaccatctcatctgtaacatcattggcaacgctacctttgccatgtttcag
aaacaactctggcgcatcgggcttcccatacaatcgatagattgtcgcacctgattgcccgaca
ttatcgcgagcccatttatacccatataaatcagcatccatgttggaatttaatcgcggcctag
agcaagacgtttcccgttgaatatggctcataacaccccttgtattactgtttatgtaagcaga
cagttttattgttcatgaccaaaatcccttaacgtgagttttcgttccactgagcgtcagaccc
cgtagaaaagatcaaaggatcttcttgagatcctttttttctgcgcgtaatctgctgcttgcaa
acaaaaaaaccaccgctaccagcggtggtttgtttgccggatcaagagctaccaactctttttc
cgaaggtaactggcttcagcagagcgcagataccaaatactgtccttctagtgtagccgtagtt
aggccaccacttcaagaactctgtagcaccgcctacatacctcgctctgctaatcctgttacca
gtggctgctgccagtggcgataagtcgtgtcttaccgggttggactcaagacgatagttaccgg
ataaggcgcagcggtcgggctgaacggggggttcgtgcacacagcccagcttggagcgaacgac
ctacaccgaactgagatacctacagcgtgagctatgagaaagcgccacgcttcccgaagggaga
aaggcggacaggtatccggtaagcggcagggtcggaacaggagagcgcacgagggagcttccag
gggaaacgcctggtatctttatagtcctgtcgggtttcgccacctctgacttgagcgtcgatt
tttgtgatgctcgtcaggggggcggagcctatggaaaaacgccagcaacgcggcctttttacgg
ttcctggcctttgctggccttttgctcacatgttctttcctgcgttatcccctgattctgtgg
ataaccgtattaccgcctttgagtgagctgataccgctcgccgcagccgaacgaccgagcgcag
cgagtcagtgagcgaggaagcggaagagcgcctgatgcggtattttctccttacgcatctgtgc
ggtatttcacaccgcatatatggtgcactctcagtacaatctgctctgatgccgcatagttaag
ccagtatacactccgctatcgctacgtgactgggtcatggctgcgccccgacacccgccaacac
ccgctgacgcgccctgacggcttgtctgctcccggcatccgcttacagacaagctgtgaccgt
ctccgggagctgcatgtgtcagaggttttcaccgtcatcaccgaaacgcgcgaggcagctgcgg
taaagctcatcagcgtggtcgtgaagcgattcacagatgtctgcctgttcatccgcgtccagct
cgttgagtttctccagaagcgttaatgtctggcttctgataaagcgggccatgttaagggcggt
ttttcctgtttggtcactgatgcctccgtgtaaggggattctgttcatggggtaatgata
```

Figure 34B

Nucleotide sequence of pDu40 (pET24a-P.alba (MNV) Untagged)

ccgatgaaacgagagaggatgctcacgatacgggttactgatgatgaacatgcccggttactgg
aacgttgtgagggtaaacaactggcggtatggatgcggcgggaccagagaaaaatcactcaggg
tcaatgccagcgcttcgttaatacagatgtaggtgttccacagggtagccagcagcatcctgcg
atgcagatccggaacataatggtgcagggcgctgacttccgcgtttccagactttacgaaacac
ggaaaccgaagaccattcatgttgttgctcaggtcgcagacgttttgcagcagcagtcgcttca
cgttcgctcgcgtatcggtgattcattctgctaaccagtaaggcaacccgccagcctagccgg
gtcctcaacgacaggagcacgatcatgcgcacccgtggggccgccatgccggcgataatggcct
gcttctcgccgaaacgtttggtggcgggaccagtgacgaaggcttgagcgagggcgtgcaagat
tccgaataccgcaagcgacaggccgatcatcgtcgcgctccagcgaaagcggtcctcgccgaaa
atgacccagagcgctgccggcacctgtcctacgagttgcatgataaagaagacagtcataagtg
cggcgacgatagtcatgcccgcgccacggaaggagctgactgggttgaaggctctcaaggg
catcggtcgagatcccggtgcctaatgagtgagctaactcattaattgcgttgcgctcactg
cccgctttccagtcgggaaacctgtcgtgccagctgcattaatgaatcggccaacgcgcggga
gaggcggtttgcgtattgggcgccagggtggttttctttcaccagtgagacgggcaacagct
gattgcccttcaccgcctggccctgagagagttgcagcaagcggtccacgctggtttgccccag
caggcgaaaatcctgtttgatggtggttaacgcgggatataacatgagctgtcttcggtatcg
tcgtatcccactaccgagatatccgcaccaacgcgcagcccggactcggtaatggcgcgcattg
cgcccagcgccatctgatcgttggcaaccagcatcgcagtgggaacgatgccctcattcagcat
ttgcatggtttgttgaaaaccggacatggcactccagtcgccttcccgttccgctatcggctga
atttgattgcgagtgagatatttatgccagccagccagacgcagacgcgccgagacagaactta
atgggcccgctaacagcgcgatttgctggtgacccaatgcgaccagatgctccacgccagtcg
cgtaccgtcttcatgggagaaaataatactgttgatgggtgtctggtcagagacatcaagaaat
aacgccggaacattagtgcaggcagcttccacagcaatggcatcctggtcatccagcggatagt
taatgatcagcccactgacgcgttgcgcgagaagattgtgcaccgccgctttacaggcttcgac
gccgcttcgttctaccatcgacaccaccacgctggcacccagttgatcggcgcgagatttaatc
gccgcgacaatttgcgacggcgcgtgcagggccagactggaggtggcaacgccaatcagcaacg
actgtttgccgccagttgttgtgccacgcggttgggaatgtaattcagctccgccatcgccgc
ttccacttttttccgcgttttcgcagaaacgtggctggcctggttcaccacgcgggaaacggtc
tgataagagacaccggcatactctgcgacatcgtataacgttactggtttcacattcaccacc
tgaattgactctcttccgggcgctatcatgccataccgcgaaaggttttgcgccattcgatggt
gtccgggatctcgacgctctcccttatgcgactcctgcattaggaagcagcccagtagtaggtt
gaggccgttgagcaccgccgccgcaaggaatggtgcatgcaaggagatggcgcccaacagtccc
ccggccacggggcctgccaccatacccacgcgaaacaagcgctcatgagccgaagtggcgag
cccgatcttcccatcggtgatgtcggcgatataggcgccagcaaccgcacctgtggcgccggt
gatgccggccacgatgcgtccggcgtagaggatcgagatctcgatcccgcgaaattaatacgac
tcactatagggaattgtgagcggataacaattcccctctagaaataattttgtttaactttaa
gaaggagatatacatatgaatgtgtctttcaccgaaactgaaaccgaagctcgtcgttctgcga
actacgaaccctaacagctgggactatgattacctgctgtcctccgacacggacgagtccatcga
agtatacaaagacaaagcgaaaaagctggaagccgaagttcgtcgcgagattaataacgaaaaa
gcagaatttctgaccctgctggaactgattgacaacgtccagcgcctgggcctgggttaccgtt
tcgagtctgatatccgtggtgcgctggatcgcttcgtttcctccggcggcttcgatgcggtaac
caagactcccctgcacggtacggcactgtctttccgtctgctgcgtcaacacggttttgaggtt
tctcaggaagcgttcagcggcttcaaagaccaaaacggcaacttcctggagaacctgaaggaag

Figure 34C

Nucleotide sequence of pDu40 (pET24a-P.alba (MNV) Untagged)

```
atatcaaagctatcctgagcctgtacgaggccagcttcctggctctggaaggcgaaaacatcct
ggacgaggcgaaggttttcgcaatctctcatctgaaagaactgtctgaagaaaagatcggtaaa
gagctggcagaacaggtgaaccatgcactggaactgccactgcatcgccgtactcagcgtctgg
aagcagtatggtctatcgaggcctaccgtaaaaggaggacgcgaatcaggttctgctggagct
ggcaattctggattacaacatgatccagtctgtataccagcgtgatctgcgtgaaacgtcccgt
tggtggcgtcgtgtgggtctggcgaccaaactgcactttgctcgtgaccgcctgattgagagct
tctactgggccgtgggtgtagcattcgaaccgcaatactccgactgccgtaactccgtcgcaaa
aatgttttctttcgtaaccattatcgacgatatctacgatgtatacggcaccctggacgaactg
gagctgtttactgatgcagttgagcgttgggacgtaaacgccatcaacgacctgccggattaca
tgaaactgtgcttctggctctgtataacactattaacgaaatcgcctacgacaacctgaaaga
taaaggtgagaacatcctgccgtatctgaccaaagcctgggctgacctgtgcaacgcttcctg
caagaagccaagtggctgtacaacaaatctactccgacctttgacgactacttcggcaacgcat
ggaaatcctcttctggcccgctgcaactggtgttcgcttacttcgctgtcgtgcagaacattaa
aaaggaagagatcgaaaacctgcaaaaataccatgacaccatctctcgtccttcccatatcttc
cgtctgtgcaatgacctggctagcgcgtctcgcggaaattgcgcgtggtgaaaccgcaaatagcg
tttcttgttacatgcgcactaaaggtatctccgaagaactggctaccgaaagcgtgatgaatct
gatcgatgaaacctggaaaaagatgaacaaggaaaaactgggtggtagcctgttcgcgaaaccg
ttcgtggaaaccgcgatcaacctggcacgtcaatctcactgcacttatcataacggcgacgcgc
ataccctccggatgagctgaccgcaaacgcgttctgtctgtaatcactgaaccgattctgcc
gtttgaacgctaaggatccgaattcgagctccgtcgacaagcttgcggccgcactcgagcacca
ccaccaccaccactgagatccggctgctaacaaagcccgaaaggaagctgagttggctgctgcc
accgctgagcaataactagcataaccccttggggcctctaaacgggtcttgaggggttttttgc
tgaaggaggaactatatccggat
```

Figure 36

Amino acid sequence of *P. alba* MEA(+)TEV (SEQ ID NO:132)

MEARRSANYEPNSWDYDYLLSSDTDESIEVYKDKAKKLEAEVRREINNEKAEFLTLLELIDNVQ
RLGLGYRFESDIRGALDRFVSSGGFDAVTKTSLHGTALSFRLLRQHGFEVSQEAFSGFKDQNGN
FLENLKEDIKAILSLYEASFLALEGENILDEAKVFAISHLKELSEEKIGKELAEQVNHALELPL
HRRTQRLEAVWSIEAYRKKEDANQVLLELAILDYNMIQSVYQRDLRETSRWWRRVGLATKLHFA
RDRLIESFYWAVGVAFEPQYSDCRNSVAKMFSFVTIIDDIYDVYGTLDELELFTDAVERWDVNA
INDLPDYMKLCFLALYNTINEIAYDNLKDKGENILPYLTKAWADLCNAFLQEAKWLYNKSTPTF
DDYFGNAWKSSSGPLQLVFAYFAVVQNIKKEEIENLQKYHDTISRPSHIFRLCNDLASASAEIA
RGETANSVSCYMRTKGISEELATESVMNLIDETWKKMNKEKLGGSLFAKPFVETAINLARQSHC
TYHNGDAHTSPDELTRKVLSVITEPILPPERENLYFQGLEHHHHHH

Figure 37A

Nucleotide sequence of MD09-163 (pET24a-P. alba MEA(+)TEV) (SEQ ID NO:133)

tggcgaatgggacgcgccctgtagcggcgcattaagcgcggcgggtgtggtggttacgcgcagc
gtgaccgctacacttgccagcgccctagcgcccgctcctttcgctttcttcccttcctttctcg
ccacgttcgccggctttccccgtcaagctctaaatcgggggctccctttagggttccgatttag
tgctttacggcacctcgaccccaaaaaacttgattagggtgatggttcacgtagtgggccatcg
ccctgatagacggtttttcgccctttgacgttggagtccacgttctttaatagtggactcttgt
tccaaactggaacaacactcaaccctatctcggtctattcttttgatttataagggattttgcc
gatttcggcctattggttaaaaaatgagctgatttaacaaaaatttaacgcgaattttaacaaa
atattaacgtttacaatttcaggtggcacttttcggggaaatgtgcgcggaacccctatttgtt
tatttttctaaatacattcaaatatgtatccgctcatgaattaattcttagaaaaactcatcga
gcatcaaatgaaactgcaatttattcatatcaggattatcaataccatatttttgaaaaagccg
tttctgtaatgaaggagaaaactcaccgaggcagttccataggatggcaagatcctggtatcgg
tctgcgattccgactcgtccaacatcaatacaacctattaatttcccctcgtcaaaaataaggt
tatcaagtgagaaatcaccatgagtgacgactgaatccggtgagaatggcaaaagtttatgcat
ttctttccagacttgttcaacaggccagccattacgctcgtcatcaaaatcactcgcatcaacc
aaaccgttattcattcgtgattgcgcctgagcgagacgaaatacgcgatcgctgttaaaaggac
aattacaaacaggaatcgaatgcaaccggcgcaggaacactgccagcgcatcaacaatattttc
acctgaatcaggatattcttctaatacctggaatgctgtttttccggggatcgcagtggtgagt
aaccatgcatcatcaggagtacggataaaatgcttgatggtcggaagaggcataaattccgtca
gccagtttagtctgaccatctcatctgtaacatcattggcaacgctacctttgccatgtttcag
aaacaactctggcgcatcgggcttcccatacaatcgatagattgtcgcacctgattgcccgaca
ttatcgcgagcccatttataccatataaatcagcatccatgttggaatttaatcgcggcctag
agcaagacgtttcccgttgaatatggctcataacacccccttgtattactgtttatgtaagcaga
cagttttattgttcatgaccaaaatcccttaacgtgagttttcgttccactgagcgtcagaccc
cgtagaaaagatcaaaggatcttcttgagatcctttttttctgcgcgtaatctgctgcttgcaa
acaaaaaaaccaccgctaccagcggtggtttgtttgccggatcaagagctaccaactctttttc
cgaaggtaactggcttcagcagagcgcagataccaaatactgtccttctagtgtagccgtagtt
aggccaccacttcaagaactctgtagcaccgcctacataccctcgctctgctaatcctgttacca
gtggctgctgccagtggcgataagtcgtgtcttaccgggttggactcaagacgatagttaccgg
ataaggcgcagcggtcgggctgaacggggggttcgtgcacacagcccagcttggagcgaacgac
ctacaccgaactgagatacctacagcgtgagctatgagaaagcgccacgcttcccgaagggaga
aaggcggacaggtatccggtaagcggcagggtcggaacaggagagcgcacgagggagcttccag
ggggaaacgcctggtatctttatagtcctgtcgggtttcgccacctctgacttgagcgtcgatt
tttgtgatgctcgtcaggggggcggagcctatggaaaaacgccagcaacgcggcctttttacgg
ttcctggccttttgctggccttttgctcacatgttctttcctgcgttatcccctgattctgtgg
ataaccgtattaccgcctttgagtgagctgataccgctcgccgcagccgaacgaccgagcgcag
cgagtcagtgagcgaggaagcggaagagcgcctgatgcggtattttctccttacgcatctgtgc
ggtatttcacaccgcatatatggtgcactctcagtacaatctgctctgatgccgcatagttaag
ccagtatacactccgctatcgctacgtgactgggtcatggctgcgccccgacacccgccaacac
ccgctgacgcgccctgacgggcttgtctgctcccggcatccgcttacagacaagctgtgaccgt
ctccgggagctgcatgtgtcagaggttttcaccgtcatcaccgaaacgcgcgaggcagctgcgg
taaagctcatcagcgtggtcgtgaagcgattcacagatgtctgcctgttcatccgcgtccagct
cgttgagtttctccagaagcgttaatgtctggcttctgataaagcgggccatgttaagggcggt

Figure 37B

Nucleotide sequence of MD09-163 (pET24a-P. alba MEA(+)TEV)

```
tttttcctgtttggtcactgatgcctccgtgtaagggggattctgttcatgggggtaatgata
ccgatgaaacgagagaggatgctcacgatacgggttactgatgatgaacatgcccggttactgg
aacgttgtgagggtaaacaactggcggtatggatgcggcgggaccagagaaaaatcactcaggg
tcaatgccagcgcttcgttaatacagatgtaggtgttccacagggtagccagcagcatcctgcg
atgcagatccggaacataatggtgcagggcgctgacttccgcgtttccagactttacgaaacac
ggaaaccgaagaccattcatgttgttgctcaggtcgcagacgttttgcagcagcagtcgcttca
cgttcgctcgcgtatcggtgattcattctgctaaccagtaaggcaacccgccagcctagccgg
gtcctcaacgacaggagcacgatcatgcgcaccgtggggccgcatgccggcgataatggcct
gcttctcgccgaaacgtttggtggcgggaccagtgacgaaggcttgagcgagggcgtgcaagat
tccgaataccgcaagcgacaggccgatcatcgtcgcgctccagcgaaagcggtcctcgccgaaa
atgacccagagcgctgccggcacctgtcctacgagttgcatgataaagaagacagtcataagtg
cggcgacgatagtcatgccccgcgccaccggaaggagctgactgggttgaaggctctcaaggg
catcggtcgagatcccggtgcctaatgagtgagctaacttacattaattgcgttgcgctcactg
cccgctttccagtcgggaaacctgtcgtgccagctgcattaatgaatcggccaacgcgcgggga
gaggcggtttgcgtattgggcgccagggtggtttttcttttcaccagtgagacgggcaacagct
gattgccttcaccgcctggccctgagagagttgcagcaagcggtccacgctggtttgcccag
caggcgaaaatcctgtttgatggtggttaacggcgggatataacatgagctgtcttcggtatcg
tcgtatcccactaccgagatatccgcaccaacgcgcagcccggactcggtaatggcgcgcattg
cgccagcgccatctgatcgttggcaaccagcatcgcagtgggaacgatgccctcattcagcat
ttgcatggtttgttgaaaaccggacatggcactccagtcgccttccgttccgctatcggctga
atttgattgcgagtgagatatttatgccagccagccagacgcagacgcgcgagacagaactta
atgggcccgctaacagcgcgatttgctggtgacccaatgcgaccagatgctccacgccagtcg
cgtaccgtcttcatgggagaaaataatactgttgatgggtgtctggtcagagacatcaagaaat
aacgccggaacattagtgcaggcagcttccacagcaatggcatcctggtcatccagcggatagt
taatgatcagcccactgacgcgttgcgcgagaagattgtgcaccgccgctttacaggcttcgac
gccgcttcgttctaccatcgacaccaccacgctggcacccagttgatcggcgcgagatttaatc
gccgcgacaatttgcgacggcgcgtcagggccagactggaggtggcaacgccaatcagcaacg
actgtttgccgccagttgttgtgccacgcggttgggaatgtaattcagctccgccatcgccgc
ttccactttttcccgcgttttcgcagaaacgtggctggcctggttcaccacgcgggaaacggtc
tgataagagacaccggcatactctgcgacatcgtataacgttactggtttcacattcaccaccc
tgaattgactctcttccgggcgctatcatgccataccgcgaaaggttttgcgccattcgatggt
gtccgggatctcgacgctctcccttatgcgactcctgcattaggaagcagcccagtagtaggtt
gaggccgttgagcaccgccgccgcaaggaatggtgcatgcaaggagatggcgcccaacagtccc
ccggcacggggcctgccaccataccacgccgaaacaagcgctcatgagcccgaagtggcgag
cccgatcttcccatcggtgatgtcggcgatataggcgccagcaaccgcacctgtggcgccggt
gatgccggccacgatgcgtccggcgtagaggatcgagatctcgatcccgcgaaattaatacgac
tcactatagggaattgtgagcggataacaattcccctctagaaataattttgtttaactttaa
gaaggagatatacatatggaagctcgtcgttctgcgaactacgaacctaacagctgggactatg
attacctgctgtcctccgacacggacgagtccatcgaagtatacaaagacaaagcgaaaaagct
ggaagccgaagttcgtcgcgagattaataacgaaaagcagaatttctgaccctgctggaactg
attgacaacgtccagcgcctgggcctgggttaccgtttcgagtctgatatccgtggtgcgctgg
atcgcttcgttcctccggcggcttcgatgcggtaaccaagacttccctgcacggtacggact
gtcttccgtctgctgcgtcaacacggttttgaggtttctcaggaagcgttcagcggcttcaaa
```

Figure 37C

Nucleotide sequence of MD09-163 (pET24a-P. alba MEA(+)TEV)

```
gaccaaaacggcaacttcctggagaacctgaaggaagatatcaaagctatcctgagcctgtacg
aggccagcttcctggctctggaaggcgaaaacatcctggacgaggcgaaggttttcgcaatctc
tcatctgaaagaactgtctgaagaaaagatcggtaaagagctggcagaacaggtgaaccatgca
ctggaactgccactgcatcgccgtactcagcgtctggaagcagtatggtctatcgaggcctacc
gtaaaaaggaggacgcgaatcaggttctgctggagctggcaattctggattacaacatgatcca
gtctgtataccagcgtgatctgcgtgaaacgtcccgttggtggcgtcgtgtgggtctggcgacc
aaactgcactttgctcgtgaccgcctgattgagagcttctactgggccgtgggtgtagcattcg
aaccgcaatactccgactgccgtaactccgtcgcaaaaatgttttctttcgtaaccattatcga
cgatatctacgatgtatacggcacctggacgaactggagctgtttactgatgcagttgagcgt
tgggacgtaaacgccatcaacgacctgccggattacatgaaactgtgctttctggctctgtata
acactattaacgaaatcgcctacgacaacctgaaagataaggtgagaacatcctgccgtatct
gaccaaagcctgggctgacctgtgcaacgctttcctgcaagaagccaagtggctgtacaacaaa
tctactccgaccctttgacgactacttcggcaacgcatggaaatcctcttctggcccgctgcaac
tggtgttcgcttacttcgctgtcgtgcagaacattaaaaaggaagagatcgaaaacctgcaaaa
ataccatgacaccatctctcgtccttcccatatcttccgtctgtgcaatgacctggctagcgcg
tctgcggaaattgcgcgtggtgaaaccgcaaatagcgtttcttgttacatgcgcactaaaggta
tctccgaagaactggctaccgaaagcgtgatgaatctgatcgatgaaacctggaaaagatgaa
caaggaaaaactgggtggtagcctgttcgcgaaaccgttcgtggaaaccgcgatcaacctggca
cgtcaatctcactgcacttatcataacggcgacgcgcatacctctccggatgagctgaccccgca
aacgcgttctgtctgtaatcactgaaccgattctgccgtttgaacgcgaaaaacctgtatttca
gggcctcgagcaccaccaccaccaccactgagatccggctgctaacaaagcccgaaggaagct
gagttggctgctgccaccgctgagcaataactagcataaccccttggggcctctaaacgggtct
tgaggggttttttgctgaaaggaggaactatatccggat
```

Figure 38

Amino acid sequence of *P. alba* FL (+) TEV (SEQ ID NO:134)

```
MRCSVSTENVSFTETETEARRSANYEPNSWDYDYLLSSDTDESIEVYKDKAKKLEAEVRREINN
EKAEFLTLLELIDNVQRLGLGYRPESDIRGALDRFVSSGGFDAVTKTSLHGTALSFRLLRQHGP
EVSQEAPSGFKDQNGNFLENLKEDIKAILSLYEASPLALEGENILDEAKVFAISHLKELSEEKI
GKELAEQVNHALELPLHRRTQRLEAVWSIEAYRKKEDANQVLLELAILDYNMIQSVYQRDLRET
SRWWRRVGLATKLHPARDRLIESFYWAVGVAFEPQYSDCRNSVAKMFSFVTIIDDIYDVYGTLD
ELELFTDAVERWDVNAINDLPDYMKLCFLALYNTINEIAYDNLKDKGENILPYLTKAWADLCNA
FLQEAKWLYNKSTPTFDDYFGNAWKSSSGPLQLVFAYFAVVQNIKKEEIENLQKYHDTISRPSH
IFRLCNDLASASAEIARGETANSVSCYMRTKGISEELATESVMNLIDETWKMNKEKLGGSLFA
KPFVETAINLARQSHCTYHNGDAHTSPDELTRKRVLSVITEPILPFERENLYFQGLEHHHHHH
```

Figure 39A

Nucleotide sequence of MD09-161 (pET24a-P. alba FL(+)TEV) (SEQ ID NO:135)

```
tggcgaatgggacgcgccctgtagcggcgcattaagcgcggcgggtgtggtggttacgcgcagc
gtgaccgctacacttgccagcgccctagcgcccgctcctttcgctttcttcccttcctttctcg
ccacgttcgccggctttccccgtcaagctctaaatcgggggctccctttagggttccgatttag
tgctttacggcacctcgaccccaaaaaacttgattagggtgatggttcacgtagtgggccatcg
ccctgatagacggttttcgccctttgacgttggagtccacgttctttaatagtggactcttgt
tccaaactggaacaacactcaaccctatctcggtctattcttttgatttataaggggattttgcc
gatttcggcctattggttaaaaaatgagctgatttaacaaaaatttaacgcgaattttaacaaa
atattaacgtttacaatttcaggtggcacttttcggggaaatgtgcgcggaacccctatttgtt
tatttttctaaatacattcaaatatgtatccgctcatgaattaattcttagaaaaactcatcga
gcatcaaatgaaactgcaatttattcatatcaggattatcaataccatattttgaaaaagccg
tttctgtaatgaaggagaaaactcaccgaggcagttccataggatggcaagatcctggtatcgg
tctgcgattccgactcgtccaacatcaatacaacctattaatttcccctcgtcaaaaataaggt
tatcaagtgagaaatcaccatgagtgacgactgaatccggtgagaatggcaaaagtttatgcat
ttctttccagacttgttcaacaggccagccattacgctcgtcatcaaaatcactcgcatcaacc
aaaccgttattcattcgtgattgcgcctgagcgagacgaaatacgcgatcgctgttaaaaggac
aattacaaacaggaatcgaatgcaaccggcgcaggaacactgccagcgcatcaacaatatttc
acctgaatcaggatattcttctaatacctggaatgctgttttccggggatcgcagtggtgagt
aaccatgcatcatcaggagtacggataaaatgcttgatggtcggaagaggcataaattccgtca
gccagtttagtctgaccatctcatctgtaacatcattggcaacgctacctttgccatgtttcag
aaacaactctggcgcatcgggcttcccatacaatcgatagattgtcgcacctgattgcccgaca
ttatcgcgagcccatttatacccatataaatcagcatccatgttggaatttaatcgcggcctag
agcaagacgtttcccgttgaatatggctcataacaccccttgtattactgtttatgtaagcaga
cagttttattgttcatgaccaaaatcccttaacgtgagttttcgttccactgagcgtcagaccc
cgtagaaaagatcaaaggatcttcttgagatcctttttttctgcgcgtaatctgctgcttgcaa
acaaaaaaaccaccgctaccagcggtggtttgtttgccggatcaagagctaccaactcttttc
cgaaggtaactggcttcagcagagcgcagataccaaatactgtccttctagtgtagccgtagtt
aggccaccacttcaagaactctgtagcaccgcctacatacctcgctctgctaatcctgttacca
gtggctgctgccagtggcgataagtcgtgtcttaccgggttggactcaagacgatagttaccgg
ataaggcgcagcggtcgggctgaacggggggttcgtgcacacagcccagcttggagcgaacgac
ctacaccgaactgagatacctacagcgtgagctatgagaaagcgccacgcttcccgaagggaga
aaggcggacaggtatccggtaagcggcagggtcggaacaggagagcgcacgagggagcttccag
ggggaaacgcctggtatctttatagtcctgtcgggtttcgccacctctgacttgagcgtcgatt
tttgtgatgctcgtcaggggggcggagcctatggaaaaacgccagcaacgcggcctttttacgg
ttcctggccttttgctggccttttgctcacatgttctttcctgcgttatcccctgattctgtgg
ataaccgtattaccgcctttgagtgagctgataccgctcgccgcagccgaacgaccgagcgcag
cgagtcagtgagcgaggaagcggaagagcgcctgatgcggtattttctccttacgcatctgtgc
ggtatttcacaccgcatatatggtgcactctcagtacaatctgctctgatgccgcatagttaag
ccagtatacactccgctatcgctacgtgactgggtcatggctgcgccccgacacccgccaacac
ccgctgacgcgccctgacgggcttgtctgctcccggcatccgcttacagacaagctgtgaccgt
ctccgggagctgcatgtgtcagaggttttcaccgtcatcaccgaaacgcgcgaggcagctgcgg
taaagctcatcagcgtggtcgtgaagcgattcacagatgtctgcctgttcatccgcgtccagct
cgttgagtttctccagaagcgttaatgtctggcttctgataaagcgggccatgttaagggcggt
```

Figure 39B

Nucleotide sequence of MD09-161 (pET24a-P. alba FL(+)TEV)

ttttcctgtttggtcactgatgcctccgtgtaaggggggattctgttcatggggtaatgata
ccgatgaaacgagagaggatgctcacgatacgggttactgatgatgaacatgcccggttactgg
aacgttgtgagggtaaacaactggcggtatggatgcggcgggaccagagaaaaatcactcaggg
tcaatgccagcgcttcgttaatacagatgtaggtgttccacagggtagccagcagcatcctgcg
atgcagatccggaacataatggtgcaggcgctgacttccgcgtttccagactttacgaaacac
ggaaaccgaagaccattcatgttgttgctcaggtcgcagacgttttgcagcagcagtcgcttca
cgttcgctcgcgtatcggtgattcattctgctaaccagtaaggcaacccgccagcctagccgg
gtcctcaacgacaggagcacgatcatgcgcacccgtggggccgccatgccggcgataatggcct
gcttctcgccgaaacgtttggtggcgggaccagtgacgaaggcttgagcgagggcgtgcaagat
tccgaataccgcaagcgacaggccgatcatcgtcgcgctccagcgaaagcggtcctcgccgaaa
atgacccagagcgctgccggcacctgtcctacgagttgcatgataaagaagacagtcataagtg
cggcgacgatagtcatgccccgcgcccaccggaaggagctgactgggttgaaggctctcaaggg
catcggtcgagatcccggtgcctaatgagtgagctaacttacattaattgcgttgcgctcactg
cccgctttccagtcgggaaacctgtcgtgccagctgcattaatgaatcggccaacgcgcgggga
gaggcggtttgcgtattgggcgccagggtggttttctttcaccagtgagacgggcaacagct
gattgcccttcaccgcctggccctgagagagttgcagcaagcggtccacgctggtttgccccag
caggcgaaaatcctgtttgatggtggttaacggcgggataatacagagctgtcttcggtatcg
tcgtatcccactaccgagatatccgcaccaacgcgcagcccggactcggtaatggcgcgcattg
cgcccagcgccatctgatcgttggcaaccagcatcgcagtgggaacgatgccctcattcagcat
ttgcatggtttgttgaaaaccggacatggcactccagtcgccttcccgttccgctatcggctga
atttgattgcgagtgagatatttatgccagccagccagacgcagacgcgccgagacagaactta
atgggcccgctaacagcgcgatttgctggtgacccaatgcgaccagatgctccacgccagtcg
cgtaccgtcttcatgggagaaaataatactgttgatgggtgtctggtcagagacatcaagaaat
aacgccggaacattagtgcaggcagcttccacagcaatggcatcctggtcatccagcggatagt
taatgatcagcccactgacgcgttgcgcgagaagattgtgcaccgccgctttacaggcttcgac
gccgcttcgttctaccatcgacaccaccacgctggcacccagttgatcggcgcgagatttaatc
gccgcgacaatttgcgacggcgcgtgcagggccagactggaggtggcaacgccaatcagcaacg
actgtttgcccgccagttgttgtgccacgcggttgggaatgtaattcagctccgccatcgccgc
ttccactttttcccgcgttttcgcagaaacgtggctggcctggttcaccacgcgggaaacggtc
tgataagagacaccggcatactctgcgacatcgtataacgttactggtttcacattcaccaccc
tgaattgactctcttccgggcgctatcatgccataccgcgaaaggttttgcgccattcgatggt
gtccgggatctcgacgctctcccttatgcgactcctgcattaggaagcagcccagtagtaggtt
gaggccgttgagcaccgccgccgcaaggaatggtgcatgcaaggagatggcgcccaacagtccc
ccggccacggggcctgccaccatacccacgcgaaacaagcgctcatgagcccgaagtggcgag
cccgatcttccccatcggtgatgtcggcgatataggcgccagcaaccgcacctgtggcgccggt
gatgccggccacgatgcgtccggcgtagaggatcgagatctcgatcccgcgaaattaatacgac
tcactatagggaattgtgagcggataacaattcccctctagaaataattttgtttaactttaa
gaaggagatatacatatgcgttgtagcgtgtccaccgaaaatgtgtctttcaccgaaactgaaa
ccgaagctcgtcgttctgcgaactacgaacctaacagctgggactatgattacctgctgtcctc
cgacacggacgagtccatcgaagtatacaaagacaaagcgaaaaagctggaagccgaagttcgt
cgcgagattaataacgaaaaagcagaatttctgaccctgctggaactgattgacaacgtccagc
gcctgggcctgggttaccgtttcgagtctgatatccgtggtgcgctggatcgcttcgtttcctc
cggcggcttcgatgcggtaaccaagacttccctgcacggtacggcactgtctttccgtctgctg

Figure 39C

Nucleotide sequence of MD09-161 (pET24a-P. alba FL(+)TEV)

```
cgtcaacacggttttgaggtttctcaggaagcgttcagcggcttcaaagaccaaaacggcaact
tcctggagaacctgaaggaagatatcaaagctatcctgagcctgtacgaggccagcttcctggc
tctggaaggcgaaaacatcctggacgaggcgaaggttttcgcaatctctcatctgaaagaactg
tctgaagaaaagatcggtaaagagctggcagaacaggtgaaccatgcactggaactgccactgc
atcgccgtactcagcgtctggaagcagtatggtctatcgaggcctaccgtaaaaaggaggacgc
gaatcaggttctgctggagctggcaattctggattacaacatgatccagtctgtataccagcgt
gatctgcgtgaaacgtcccgttggtggcgtcgtgggtctggcgaccaaactgcactttgctc
gtgaccgcctgattgagagcttctactgggccgtgggtgtagcattcgaaccgcaatactccga
ctgccgtaactccgtcgcaaaaatgttttctttcgtaaccattatcgacgatatctacgatgta
tacggcaccctggacgaactggagctgtttactgatgcagttgagcgttgggacgtaaacgcca
tcaacgactgccggattacatgaaactgtgctttctggctctgtataacactattaacgaaat
cgctacgacaacctgaaagataaaggtgagaacatcctgccgtatctgaccaaagcctgggct
gacctgtgcaacgctttcctgcaagaagccaagtggctgtacaacaaatctactccgacctttg
acgactacttcggcaacgcatggaaatcctcttctggcccgctgcaactggtgttcgcttactt
cgctgtcgtgcagaacattaaaaaggaagagatcgaaaacctgcaaaaataccatgacaccatc
tctcgtccttcccatatcttccgtctgtgcaatgacctggctagcgcgtctgcggaaattgcg
gtggtgaaaccgcaaatagcgtttcttgttacatgcgcactaaaggtatctccgaagaactggc
taccgaaagcgtgatgaatctgatcgatgaaacctggaaaagatgaacaaggaaaaactgggt
ggtagcctgttcgcgaaaccgttcgtggaaaccgcgatcaacctggcacgtcaatctcactgca
cttatcataacggcgacgcgcatacctctccggatgagctgacccgcaaacgcgttctgtctgt
aatcactgaaccgattctgccgtttgaacgcgaaaacctgtattttcagggctcgagcaccac
caccaccaccactgagatccggctgctaacaaagcccgaaggaagctgagttggctgctgcca
ccgctgagcaataactagcataaccccttggggcctctaaacgggtcttgaggggttttttgct
gaaaggaggaactatatccggat
```

Figure 51

Amino acid sequence of *P.alba* TRC (-3) (SEQ ID NO:136)

MTEARRSANYEPNSWDYDYLLSSDTDESIEVYKDKAKKLEAEVRREINNEKAEPLTLLELIDNV
QRLGLGYRFESDIRGALDRFVSSGGFDAVTKTSLHGTALSFRLLRQHGFEVSQEAFSGFKDQNG
NFLENLKEDIKAILSLYEASFLALEGENILDEAKVFAISHLKELSEEKIGKELAEQVNHALELP
LHRRTQRLEAVWSIEAYRKKEDANQVLLELAILDYNMIQSVYQRDLRETSRWWRRVGLATKLHF
ARDRLIESFYWAVGVAFEPQYSDCRNSVAKMFSFVTIIDDIYDVYGTLDELELFTDAVERWDVN
AINDLPDYMKLCFLALYNTINEIAYDNLKDKGENILPYLTKAWADLCNAFLQEAKWLYNKSTPT
FDDYFGNAWKSSSGPLQLVFAYFAVVQNIKKEEIENLQKYHDTISRPSHIFRLCNDLASASAEI
ARGETANSVSCYMRTKGISEELATESVMNLIDETWKKMNKEKLGGSLFAKPFVETAINLARQSH
CTYHNGDAHTSPDELTRKRVLSVITEPILPFER

Figure 52A

Nucleotide sequence of pDu47-3 (SEQ ID NO:137)

tggcgaatgggacgcgcctgtagcggcgcattaagcgcggcgggtgtggtggttacgcgcagc
gtgacgctacaattgccagcgccctagcgcccgtcctttcgcttctccttcctttctcg
ccacgttcgccggctttccccgtcaagctctaaatcgggggctcccttagggttccgatttag
tgctttacggcacctcgacccaaaaaacttgattaggtgatggttcacgtagtgggccatcg
ccctgatagacggttttcgcccttgacgttggagtccacgtttaatagtggactcttgt
tccaaactggaacaacactcaacctatctcggtctattcttttgatttataagggattttgcc
gatttcggcctattggttaaaaatgagctgatttaacaaaatttaacgcgaattttaacaaa
atattaacgtttacaatttcaggtggcacttttcgggaaatgtgcgcggaacccctatttgtt
tattttctaaatacattcaaatatgtatccgctcatgaattaattcttagaaaaactcatcga
gcatcaaatgaaactgcaattttattcatatcaggattatcaataccatattttgaaaaagccg
tttctgtaatgaaggagaaaactcaccgaggcagttccataggatggcaagatcctggtatcgg
tctgcgattccgactcgtccaacatcaatacaacctattaattttcccctcgtcaaaaataaggt
tatcaagtgagaaatcaccatgagtgacgactgaatccggtgagaatggcaaaagtttatgcat
ttctttccagacttgttcaacaggccagccattacgctcgtcatcaaaatcactcgcatcaacc
aaaccgttattcattcgtgattgcgcctgagcgagacgaaatacgcgatcgctgttaaaggac
aattacaaacaggaatcgaatgcaaccggcgcaggaacactgccagcgcatcaacaatattttc
acctgaatcaggatattcttctaataccggaatgctgttcccggggatcgcagtggtgagt
aaccatgcatcatcaggagtacggataaaatgcttgatggtcggaagaggcataaattccgtca
gccagtttagtctgaccatctcatctgtaacatcattggcaacgctaccttgccatgtttcag
aaacaactctggcgcatcgggcttccatacaatcgatagattgtcgcacctgattgcccgaca
ttatcgcgagcccatttatacccatataaatcagcatccatgttggaatttaatcgcggcctag
agcaagacgtttcccgttgaatatggctcataacaccccttgtattactgtttatgtaagcaga
cagttttattgttcatgaccaaaatcccttaacgtgagttttcgttccactgagcgtcagaccc
cgtagaaaagatcaaaggatcttcttgagatcctttttttctgcgcgtaatctgctgcttgcaa
acaaaaaaaccaccgctaccagcggtggtttgtttgccggatcaagagctaccaactctttttc
cgaaggtaactggcttcagcagagcgcagataccaaatactgtccttctagtgtagccgtagtt
aggccaccacttcaagaactctgtagcaccgcctacatacctcgctctgctaatcctgttacca
gtggctgctgccagtggcgataagtcgtgtcttaccgggttggactcaagacgatagttaccgg
ataaggcgcagcggtcgggctgaacggggggttcgtgcacacagcccagcttggagcgaacgac
ctacaccgaactgagatacctacagcgtgagctatgagaaagcgccacgcttcccgaagggaga
aaggcggacaggtatccggtaagcggcagggtcggaacaggagagcgcacgagggagcttccag
gggaaacgcctggtatctttatagtcctgtcgggtttcgccacctctgacttgagcgtcgatt
tttgtgatgctcgtcaggggggcggagcctatggaaaaacgccagcaacgcggcctttttacgg
ttcctggccttttgctggccttttgctcacatgttctttcctgcgttatccctgattctgtgg
ataaccgtattaccgcctttgagtgagctgataccgctcgccgcagccgaacgaccgagcgcag
cgagtcagtgagcgaggaagcggaagagcgcctgatgcggtattttctccttacgcatctgtgc
ggtatttcacaccgcatatggtgcactctcagtacaatctgctctgatgccgcatagttaag
ccagtatacactccgctatcgctacgtgactgggtcatggctgcgccccgacacccgccaacac
ccgctgacgcgccctgacgggcttgtctgctcccggcatccgcttacagacaagctgtgaccgt
ctccgggagctgcatgtgtcagaggttttcaccgtcatcaccgaaacgcgcgaggcagctgcgg
taaagctcatcagcgtggtcgtgaagcgattcacagatgtctgcctgttcatccgcgtccagct
cgttgagtttctccagaagcgttaatgtctggcttctgataaagcgggccatgttaagggcggt
ttttcctgtttggtcactgatgcctccgtgtaagggggattctgttcatgggggtaatgata

Figure 52B

Nucleotide sequence of pDu47-3

```
ccgatgaaacgagagaggatgctcacgatacgggttactgatgatgaacatgcccggttactgg
aacgttgtgagggtaaacaactggcggtatggatgcggcgggaccagagaaaaatcactcaggg
tcaatgccagcgcttcgttaatacagatgtaggtgttccacagggtagccagcagcatcctgcg
atgcagatccggaacataatggtgcaggcgctgacttccgcgtttccagactttacgaaacac
ggaaaccgaagaccattcatgttgttgctcaggtcgcagacgttttgcagcagcagtcgcttca
cgttcgctcgcgtatcggtgattcattctgctaaccagtaaggcaaccccgccagcctagccgg
gtcctcaacgacaggagcacgatcatgcgcaccgtggggccgccatgccggcgataatggcct
gcttctcgccgaaacgtttggtggcgggaccagtgacgaaggcttgagcgagggcgtgcaagat
tccgaataccgcaagcgacaggccgatcatcgtcgcgctccagcgaaagcggtcctcgccgaaa
atgacccagagcgctgccggcacctgtcctacgagttgcatgataaagaagacagtcataagtg
cggcgacgatagtcatgcccgcgccaccggaaggagctgactgggttgaaggctctcaaggg
catcggtcgagatcccggtgcctaatgagtgagctaacttacattaattgcgttgcgctcactg
cccgctttccagtcgggaaacctgtcgtgccagctgcattaatgaatcggccaacgcgcgggga
gaggcggtttgcgtattgggcgccagggtggttttttcttttcaccagtgagacgggcaacagct
gattgcccttcaccgcctggccctgagagagttgcagcaagcggtccacgctggtttgcccag
caggcgaaaatcctgtttgatggtggttaacggcgggatataacatgagctgtcttcggtatcg
tcgtatcccactaccgagatatccgcaccaacgcgcagcccggactcggtaatggcgcgcattg
cgcccagcgccatctgatcgttggcaaccagcatcgcagtgggaacgatgccctcattcagcat
ttgcatggtttgttgaaaacggacatggcactccagtcgccttccgttccgctatcggctga
atttgattgcgagtgagatatttatgccagccagccagacgcagacgcgccgagacagaactta
atgggcccgctaacagcgcgatttgctggtgacccaatgcgaccagatgctccacgccagtcg
cgtaccgtcttcatggagaaaataatactgttgatgggtgtctggtcagagacatcaagaaat
aacgccggaacattagtgcaggcagcttccacagcaatggcatcctggtcatccagcggatagt
taatgatcagcccactgacgcgttgcgcgagaagattgtgcaccgccgctttacaggcttcgac
gccgcttcgttctaccatcgacaccaccacgctggcacccagttgatcggcgcgagatttaatc
gccgcgacaatttgcgacggcgcgtgcagggccagactggaggtggcaacgccaatcagcaacg
actgtttgccgccagttgtgtgccacgcggtgggaatgtaattcagctccgccatcgccgc
ttccacttttccgcgttttcgcagaaacgtggctggcctggttcaccacgcgggaaacggtc
tgataagagacaccggcatactctgcgacatcgtataacgttactggtttcacattcaccaccc
tgaattgactctcttccgggcgctatcatgccataccgcgaaaggttttgcgccattcgatggt
gtccgggatctcgacgctctcccttatgcgactcctgcattaggaagcagcccagtagtaggtt
gaggccgttgagcaccgccgccgcaaggaatggtgcatgcaaggagatggcgccaacagtccc
ccggccacggggcctgccaccatacccacgccgaaacaagcgctcatgagcccgaagtggcgag
cccgatcttccccatcggtgatgtcggcgatataggcgccagcaacgcacctgtggcgccggt
gatgccggccacgatgcgtccggcgtagaggatcgagatctgatcccgcgaaattaatacgac
tcactatagggaattgtgagcggataacaattcccctctagaaataattttgtttaactttaa
gaaggagatatacatatgaccgaagctcgtcgtctgcgaactacgaacctaacagctgggact
atgattacctgctgtcctcgacacggacgagtccatcgaagtatacaaagacaaagcgaaaaa
gctggaagccgaagttcgtcgcgagattaataacgaaaagcagaatttctgaccctgctggaa
ctgattgacaacgtccagcgcctgggcctgggttaccgtttcgagtctgatatccgtggtgcgc
tggatcgcttcgtttcctccggcggcttcgatgcggtaaccaagacttccctgcacggtacggc
actgtctttccgtctgctgcgtcaacacggttttgaggttctcaggaagcgttcagcggcttc
aaagaccaaaacggcaacttcctggagaacctgaaggaagatatcaaagctatcctgagcctgt
```

Figure 52C

Nucleotide sequence of pDu47-3 acgaggccagcttcctggctctggaaggcgaaaacatcctggacgaggcgaaggttttcgcaat
ctctcatctgaaagaactgtctgaagaaaagatcggtaaagagctggcagaacaggtgaaccat
gcactggaactgccactgcatcgccgtactcagcgtctggaagcagtatggtctatcgaggcct
accgtaaaaggaggacgcgaatcaggttctgctggagctggcaattctggattacaacatgat
ccagtctgtataccagcgtgatctgcgtgaaacgtcccgttggtggcgtcgtgtgggtctggcg
accaaactgcactttgctcgtgaccgcctgattgagagcttctactgggccgtgggtgtagcat
tcgaaccgcaatactccgactgccgtaactccgtcgcaaaaatgttttctttcgtaaccattat
cgacgatatctacgatgtatacggcaccctggacgaactggagctgtttactgatgcagttgag
cgttgggacgtaaacgccatcaacgacctgccggattacatgaaactgtgctttctggctctgt
ataacactattaacgaaatcgcctacgacaacctgaaagataaaggtgagaacatcctgccgta
tctgaccaaagcctgggctgacctgtgcaacgcttcctgcaagaagccaagtggctgtacaac
aaatctactccgacctttgacgactacttcggcaacgcatggaaatcctcttctggcccgctgc
aactggtgttcgcttacttcgctgtcgtgcagaacattaaaaaggaagagatcgaaaacctgca
aaataccatgacaccatctctcgtccttcccatatcttccgtctgtgcaatgacctggctagc
gcgtctgcggaaattgcgcgtggtgaaaccgcaaatagcgtttcttgttacatgcgcactaaag
gtatctccgaagaactggctaccgaaagcgtgatgaatctgatcgatgaaacctggaaaagat
gaacaaggaaaaactgggtggtagcctgttcgcgaaaccgttcgtggaaaccgcgatcaacctg
gcacgtcaatctcactgcacttatcataacggcgacgcgcatacctctccggatgagctgaccc
gcaaacgcgttctgtctgtaatcactgaaccgattctgccgtttgaacgctaaggatccgaatt
cgagctccgtcgacaagcttgcggccgcactcgagcaccaccaccaccaccactgagatccggc
tgctaacaaagcccgaaaggaagctgagttggctgctgccaccgctgagcaataactagcataa
cccttggggcctctaaacgggtcttgaggggttttttgctgaaaggaggaactatatccggat

Figure 53

Amino acid sequence of *P. alba* TRC (-4) (SEQ ID NO:138)

METEARRSANYEPNSWDYDYLLSSDTDESIEVYKDKAKKLEAEVRREINNEKAEFLTLLELIDN
VQRLGLGYRFESDIRGALDRFVSSGGFDAVTKTSLHGTALSFRLLRQHGFEVSQEAFSGFKDQN
GNFLENLKEDIKAILSLYEASFLALEGENILDEAKVFAISHLKELSEEKIGKELAEQVNHALEL
PLHRRTQRLEAVWSIEAYRKKEDANQVLLELAILDYNMIQSVYQRDLRETSRWWRRVGLATKLH
FARDRLIESFYWAVGVAFEPQYSDCRNSVAKMFSFVTIIDDIYDVYGTLDELELFTDAVERWDV
NAINDLPDYMKLCFLALYNTINEIAYDNLKDKGENILPYLTKAWADLCNAFLQEAKWLYNKSTP
TFDDYFGNAWKSSSGPLQLVFAYFAVVQNIKKEEIENLQKYHDTISRPSHIFRLCNDLASASAE
IARGETANSVSCYMRTKGISEELATESVMNLIDETWKKMNKEKLGGSLFAKPFVETAINLARQS
HCTYHNGDAHTSPDELTRKRVLSVITEPILPFER

Figure 54A

Nucleotide sequence of pDu47-4 (SEQ ID NO:139)

tggcgaatgggacgcgccctgtagcggcgcattaagcgcggcgggtgtggtggttacgcgcagc
gtgaccgctacacttgccagcgccctagcgcccgtcctttcgctttcttcccttcctttctcg
ccacgttcgccggctttccccgtcaagctctaaatcgggggctcccttagggttccgatttag
tgctttacggcacctcgaccccaaaaaacttgattagggtgatggttcacgtagtgggccatcg
ccctgatagacggttttcgccctttgacgttggagtccacgttctttaatagtggactcttgt
tccaaactggaacaacactcaaccctatctcggtctattctttgatttataagggattttgcc
gatttcggcctattggttaaaaaatgagctgatttaacaaaatttaacgcgaattttaacaaa
atattaacgtttacaatttcaggtggcacttttcggggaaatgtgcgcggaacccctatttgtt
tatttttctaaatacattcaaatatgtatccgctcatgaattaattcttagaaaaactcatcga
gcatcaaatgaaactgcaattttattcatatcaggattatcaataccatattttgaaaaagccg
tttctgtaatgaaggagaaaactcaccgaggcagttccataggatggcaagatcctggtatcgg
tctgcgattccgactcgtccaacatcaatacaacctattaatttcccctcgtcaaaaataaggt
tatcaagtgagaaatcaccatgagtgacgactgaatccggtgagaatggcaaaagtttatgcat
ttctttccagacttgttcaacaggccagccattacgctcgtcatcaaaatcactcgcatcaacc
aaaccgttattcattcgtgattgcgcctgagcgagacgaaatacgcgatcgctgttaaaaggac
aattacaaacaggaatcgaatgcaaccggcgcaggaacactgccagcgcatcaacaatatttc
acctgaatcaggatattcttctaatacctggaatgctgttttcccggggatcgcagtggtgagt
aaccatgcatcatcaggagtacggataaaatgcttgatggtcggaagaggcataaattccgtca
gccagtttagtctgaccatctcatctgtaacatcattggcaacgctacctttgccatgtttcag
aaacaactctggcgcatcgggcttcccatacaatcgatagattgtcgcacctgattgcccgaca
ttatcgcgagcccatttatacccatataaatcagcatccatgttggaatttaatcgcggcctag
agcaagacgtttcccgttgaatatggctcataacaccccttgtattactgtttatgtaagcaga
cagttttattgttcatgaccaaaatcccttaacgtgagttttcgttccactgagcgtcagaccc
cgtagaaaagatcaaaggatcttcttgagatccttttttttctgcgcgtaatctgctgcttgcaa
acaaaaaaaccaccgctaccagcggtggtttgtttgccggatcaagagctaccaactctttttc
cgaaggtaactggcttcagcagagcgcagataccaaatactgtccttctagtgtagccgtagtt
aggccaccacttcaagaactctgtagcaccgcctacatacctcgctctgctaatcctgttacca
gtggctgctgccagtggcgataagtcgtgtcttaccgggttggactcaagacgatagttaccgg
ataaggcgcagcggtcgggctgaacggggggttcgtgcacacagcccagcttggagcgaacgac
ctacaccgaactgagatacctacagcgtgagctatgagaaagcgccacgcttcccgaagggaga
aaggcggacaggtatccggtaagcggcagggtcggaacaggagagcgcacgagggagcttccag
ggggaaacgcctggtatctttatagtcctgtcgggtttcgccacctctgacttgagcgtcgatt
tttgtgatgctcgtcaggggggcggagcctatggaaaaacgccagcaacgcggcctttttacgg
ttcctggccttttgctggccttttgctcacatgttctttcctgcgttatcccctgattctgtgg
ataaccgtattaccgcctttgagtgagctgataccgctcgccgcagccgaacgaccgagcgcag
cgagtcagtgagcgaggaagcggaagagcgcctgatgcggtattttctccttacgcatctgtgc
ggtatttcacaccgcatatatggtgcactctcagtacaatctgctctgatgccgcatagttaag
ccagtatacactccgctatcgctacgtgactgggtcatggctgcgccccgacacccgccaacac
ccgctgacgcgccctgacggcttgtctgctcccggcatccgcttacagacaagctgtgaccgt
ctccgggagctgcatgtgtcagaggttttcaccgtcatcaccgaaacgcgcgaggcagctgcgg
taaagctcatcagcgtggtcgtgaagcgattcacagatgtctgcctgttcatccgcgtccagct
cgttgagtttctccagaagcgttaatgtctggcttctgataaagcgggccatgttaagggcggt
ttttcctgtttggtcactgatgcctccgtgtaagggggatttctgttcatgggggtaatgata

Figure 54B

Nucleotide sequence of pDu47-4 ccgatgaaacgagagaggatgctcacgatacgggttactgatgatgaacatgcccggttactgg
aacgttgtgagggtaaacaactggcggtatggatgcggcgggaccagagaaaaatcactcaggg
tcaatgccagcgcttcgttaatacagatgtaggtgttccacagggtagccagcagcatcctgcg
atgcagatccggaacataatggtgcagggcgctgacttccgcgtttccagacttacgaaacac
ggaaaccgaagaccattcatgttgttgctcaggtcgcagacgttttgcagcagcagtcgcttca
cgttcgctcgcgtatcggtgattcattctgctaaccagtaaggcaacccgccagcctagccgg
gtcctcaacgacaggagcacgatcatgcgcacccgtggggccgccatgccggcgataatggcct
gcttctcgccgaaacgtttggtggcgggaccagtgacgaaggcttgagcgagggcgtgcaagat
tccgaataccgaagcgacaggccgatcatcgtcgcgctccagcgaaagcggtcctcgccgaaa
atgacccagagcgctgccggcacctgtcctacgagttgcatgataaagaagacagtcataagtg
cggcgacgatagtcatgcccgcgcccaccggaaggagctgactgggttgaaggctctcaaggg
catcggtcgagatcccggtgcctaatgagtgagctaacttacattaattgcgttgcgctcactg
cccgctttccagtcgggaaacctgtcgtgccagctgcattaatgaatcggccaacgcgcggga
gaggcggtttgcgtattgggcgccagggtggttttcttttcaccagtgagacgggcaacagct
gattgcccttcacgcgctggccctgagagagttgcagcaagcggtccacgctggtttgccccag
caggcgaaaatcctgtttgatggtggttaacggcgggatataacatgagctgtcttcggtatcg
tcgtatcccactaccgagatatccgcaccaacgcgcagcccggactcggtaatggcgcattg
cgccagcgccatctgatcgttggcaaccagcatcgcagtgggaacgatgccctcattcagcat
ttgcatggtttgttgaaaacggacatggcactccagtcgccttcccgttccgctatcggctga
atttgattgcgagtgagatatttatgccagccagccagacgcagacgcgccgagacagaactta
atgggcccgctaacagcgcgatttgctggtgacccaatgcgaccagatgctccacgcccagtcg
cgtaccgtcttcatgggagaaaataatactgttgatgggtgtctggtcagagacatcaagaaat
aacgccggaacattagtgcaggcagcttccacagcaatggcatcctggtcatccagcggatagt
taatgatcagcccactgacgcgttgcgcgagaagattgtgcaccgccgcttacaggcttcgac
gccgcttcgttctaccatcgacaccaccacgctggcacccagttgatcggcgcgagatttaatc
gccgcgacaatttgcgacggcgcgtgcagggccagactggaggtggcaacgccaatcagcaacg
actgtttgcccgccagttgttgtgccacgcggttgggaatgtaattcagctccgccatcgccgc
ttccacttttttccgcgttttcgcagaaacgtggctggcctggttcaccacgcgggaaacggtc
tgataagagacaccggcatactctgcgacatcgtataacgttactggtttcacattcaccaccc
tgaattgactctcttccgggcgctatcatgccataccgcgaaaggttttgcgccattcgatggt
gtccgggatctcgacgctctcccttatgcgactcctgcattaggaagcagcccagtagtaggtt
gaggccgttgagcaccgccgccgcaaggaatggtgcatgcaaggagatggcgcccaacagtccc
ccggccacggggcctgccaccatacccacgccgaaacaagcgctcatgagcccgaagtggcgag
cccgatcttccccatcggtgatgtcggcgatataggcgccagcaaccgcacctgtggcgccggt
gatgccggccacgatgcgtccggcgtagaggatcgagatctcgatcccgcgaaattaatacgac
tcactatagggaattgtgagcggataacaattcccctctagaaataattttgtttaactttaa
gaaggagatatacatatggaaaccgaagctcgtcgttctgcgaactacgaacctaacagctggg
actatgattacctgctgtcctccgacacggacgagtccatcgaagtatacaaagacaaagcgaa
aaagctggaagccgaagttcgtcgcgagattaataacgaaaagcagaatttctgaccctgctg
gaactgattgacaacgtccagcgcctgggcctgggttaccgtttcgagtctgatatccgtggtg
cgctggatcgcttcgtttcctccgcgcttcgatgcggtaaccaagacttccctgcacggtac
ggcactgtctttccgtctgctgcgtcaacacggttttgaggtttctcaggaagcgttcagcggc
ttcaaagaccaaaacggcaacttcctggagaacctgaaggaagatatcaaagctatcctgagcc Figure S4C Nucleotide sequence of pDu47-4 tgtacgaggccagcttcctggctctggaaggcgaaaacatcctggacgaggcgaaggttttcgc
aatctctcatctgaaagaactgtctgaagaaaagatcggtaaagagctggcagaacaggtgaac
catgcactggaactgccactgcatcgccgtactcagcgtctggaagcagtatggtctatcgagg
cctaccgtaaaaaggaggacgcgaatcaggttctgctggagctggcaattctggattacaacat
gatccagtctgtataccagcgtgatctgcgtgaaacgtcccgttggtggcgtcgtgtgggtctg
gcgaccaaactgcactttgctcgtgaccgcctgattgagagcttctactgggccgtgggtgtag
cattcgaaccgcaatactccgactgccgtaactccgtcgcaaaaatgttttctttcgtaaccat
tatcgacgatatctacgatgtatacggcaccctggacgaactggagctgtttactgatgcagtt
gagcgttgggacgtaaacgccatcaacgacctgccggattacatgaaactgtgctttctggctc
tgtataacactattaacgaaatcgcctacgacaacctgaaagataaaggtgagaacatcctgcc
gtatctgaccaaagcctgggctgacctgtgcaacgcttcctgcaagaagccaagtggctgtac
aacaaatctactccgacctttgacgactacttcggcaacgcatggaaatcctcttctggcccgc
tgcaactggtgttcgcttacttcgctgtcgtgcagaacattaaaaaggaagagatcgaaaacct
gcaaaaataccatgacaccatctctcgtccttcccatatcttccgtctgtgcaatgacctggct
agcgcgtctgcggaaattgcgcgtggtgaaaccgcaaatagcgtttcttgttacatgcgcacta
aaggtatctccgaagaactggctaccgaaagcgtgatgaatctgatcgatgaaacctggaaaaa
gatgaacaaggaaaaactgggtggtagcctgttcgcgaaaccgttcgtggaaaccgcgatcaac
ctggcacgtcaatctcactgcacttatcataacggcgacgcgcataccctccggatgagctga
cccgcaaacgcgttctgtctgtaatcactgaaccgattctgccgtttgaacgctaaggatccga
attcgagctccgtcgacaagcttgcggccgcactcgagcaccaccaccaccaccactgagatcc
ggctgctaacaaagcccgaaaggaagctgagttggctgctgccaccgctgagcaataactagca
taaccccttggggcctctaaacgggtcttgaggggttttttgctgaaaggaggaactatatccg
gat

Figure 55

Amino acid sequence of P.alba TRC (-5) (SEQ ID NO:140)

MTETEARRSANYEPNSWDYDYLLSSDTDESIEVYKDKAKKLEAEVRREINNEKAEFLTLLELID
NVQRLGLGYRFESDIRGALDRFVSSGGFDAVTKTSLHGTALSFRLLRQHGFEVSQEAFSGFKDQ
NGNFLENLKEDIKAILSLYEASFLALEGENILDEAKVPAISHLKELSEEKIGKELAEQVNHALE
LPLHRRTQRLEAVWSIEAYRKKEDANQVLLELAILDYNMIQSVYQRDLRETSRWWRRVGLATKL
HFARDRLIESFYWAVGVAFEPQYSDCRNSVAKMFSFVTIIDDIYDVYGTLDELELFTDAVERWD
VNAINDLPDYMKLCFLALYNTINEIAYDNLKDKGENILPYLTKAWADLCNAFLQEAKWLYNKST
PTFDDYFGNAWKSSSGPLQLVFAYFAVVQNIKKEEIENLQKYHDTISRPSHIFRLCNDLASASA
EIARGETANSVSCYMRTKGISEELATESVMNLIDETWKKMNKEKLGGSLFAKPFVETAINLARQ
SHCTYHNGDAHTSPDELTRKRVLSVITEPILPFER

Figure 56A

Nucleotide sequence of pDu47-5 (SEQ ID NO:141)

tggcgaatgggacgcgccctgtagcggcgcattaagcgcggcgggtgtggtggttacgcgcagc
gtgaccgctacacttgccagcgccctagcgcccgctcctttcgctttcttcccttcctttctcg
ccacgttcgccggctttccccgtcaagctctaaatcggggggctcccttagggttccgatttag
tgctttacggcacctcgaccccaaaaaacttgattagggtgatggttcacgtagtgggccatcg
ccctgatagacggttttcgccctttgacgttggagtccacgttctttaatagtggactcttgt
tccaaactggaacaacactcaaccctatctcggtctattcttttgatttataagggatttgcc
gatttcggcctattggttaaaaaatgagctgatttaacaaaaatttaacgcgaattttaacaaa
atattaacgtttacaatttcaggtggcacttttcggggaaatgtgcgcggaaccctatttgtt
tatttttctaaatacattcaaatatgtatccgctcatgaattaattcttagaaaaactcatcga
gcatcaaatgaaactgcaatttattcatatcaggattatcaataccatattttgaaaaagccg
tttctgtaatgaaggagaaaactcaccgaggcagttccataggatggcaagatcctggtatcgg
tctgcgattccgactcgtccaacatcaatacaacctattaatttccctcgtcaaaaataaggt
tatcaagtgagaaatcaccatgagtgacgactgaatccggtgagaatggcaaaagtttatgcat
ttctttccagacttgttcaacaggccagccattacgctcgtcatcaaaatcactcgcatcaacc
aaaccgttattcattcgtgattgcgcctgagcgagacgaaatacgcgatcgctgttaaaggac
aattacaaacaggaatcgaatgcaaccggcgcaggaacactgccagcgcatcaacaatatttc
acctgaatcaggatattcttctaatacctggaatgctgttttcccggggatcgcagtggtgagt
aaccatgcatcatcaggagtacggataaaatgcttgatggtcggaagaggcataaattccgtca
gccagtttagtctgaccatctcatctgtaacatcattggcaacgctacctttgccatgtttcag
aaacaactctggcgcatcgggcttcccatacaatcgatagattgtcgcacctgattgcccgaca
ttatcgcgagcccatttatacccatataaatcagcatccatgttggaatttaatcgcggcctag
agcaagacgtttcccgttgaatatggctcataacaccccttgtattactgtttatgtaagcaga
cagttttattgttcatgaccaaaatcccttaacgtgagttttcgttccactgagcgtcagaccc
cgtagaaaagatcaaaggatcttcttgagatcctttttttctgcgcgtaatctgctgcttgcaa
acaaaaaaaccaccgctaccagcggtggtttgtttgccggatcaagagctaccaactctttttc
cgaaggtaactggcttcagcagagcgcagataccaaatactgtccttctagtgtagccgtagtt
aggccaccacttcaagaactctgtagcaccgcctacatacctcgctctgctaatcctgttacca
gtggctgctgccagtggcgataagtcgtgtcttaccgggttggactcaagacgatagttaccgg
ataaggcgcagcggtcgggctgaacggggggttcgtgcacacagcccagcttggagcgaacgac
ctacaccgaactgagatacctacagcgtgagctatgagaaagcgccacgcttcccgaagggaga
aaggcggacaggtatccggtaagcggcagggtcggaacaggagagcgcacgagggagcttccag
gggaaacgcctggtatctttatagtcctgtcgggtttcgccacctctgacttgagcgtcgatt
tttgtgatgctcgtcaggggggcggagcctatggaaaaacgccagcaacgcggcctttttacgg
ttcctggccttttgctggccttttgctcacatgttctttcctgcgttatcccctgattctgtgg
ataaccgtattaccgcctttgagtgagctgataccgctcgccgcagccgaacgaccgagcgcag
cgagtcagtgagcgaggaagcggaagagcgcctgatgcggtattttctccttacgcatctgtgc
ggtatttcacaccgcatatatggtgcactctcagtacaatctgctctgatgccgcatagttaag
ccagtatacactccgctatcgctacgtgactgggtcatggctgcgccccgacacccgccaacac
ccgctgacgcgccctgacgggcttgtctgctcccggcatccgcttacagacaagctgtgaccgt
ctccgggagctgcatgtgtcagaggttttcaccgtcatcaccgaaacgcgcgaggcagctgcgg
taaagctcatcagcgtggtcgtgaagcgattcacagatgtctgcctgttcatccgcgtccagct
cgttgagtttctccagaagcgttaatgtctggcttctgataaagcgggccatgttaagggcggt
tttttcctgtttggtcactgatgcctccgtgtaaggggattctgttcatgggggtaatgata

Figure 56B

Nucleotide sequence of pDu47-5

```
ccgatgaaacgagagaggatgctcacgatacgggttactgatgatgaacatgcccggttactgg
aacgttgtgagggtaaacaactggcggtatggatgcggcgggaccagagaaaaatcactcaggg
tcaatgccagcgcttcgttaatacagatgtaggtgttccacagggtagccagcagcatcctgcg
atgcagatccggaacataatggtgcaggcgctgacttccgcgtttccagactttacgaaacac
ggaaaccgaagaccattcatgttgttgctcaggtcgcagacgtttgcagcagcagtcgcttca
cgttcgctcgcgtatcggtgattcattctgctaaccagtaaggcaacccgccagcctagccgg
gtcctcaacgacaggagcacgatcatgcgcacccgtggggccgccatgccggcgataatggcct
gcttctcgccgaaacgtttggtggcgggaccagtgacgaaggcttgagcgagggcgtgcaagat
tccgaataccgcaagcgacaggccgatcatcgtcgcgctccagcgaaagcggtcctcgccgaaa
atgacccagagcgctgccggcacctgtcctacgagttgcatgataaagaagacagtcataagtg
cggcgacgatagtcatgcccgcgccaccggaaggagctgactgggttgaaggctctcaaggg
catcggtcgagatcccggtgcctaatgagtgagctaacttacattaattgcgttgcgctcactg
cccgctttccagtcgggaaacctgtcgtgccagctgcattaatgaatcggccaacgcgcggga
gaggcggtttgcgtattgggcgccagggtggttttcttttcaccagtgagacgggcaacagct
gattgcccttcaccgcctggccctgagagagttgcagcaagcggtccacgctggtttgccccag
caggcgaaaatcctgtttgatggtggttaacggcgggatataacatgagctgtcttcggtatcg
tcgtatcccactaccgagatatccgcaccaacgcgcagcccggactcggtaatggcgcgcattg
cgcccagcgccatctgatcgttggcaaccagcatcgcagtgggaacgatgccctcattcagcat
ttgcatggtttgttgaaaacggacatggcactccagtcgccttcccgttccgctatcggctga
atttgattgcgagtgagatatttatgccagccagccagacgcagacgcgccgagacagaactta
atgggcccgctaacagcgcgatttgctggtgacccaatgcgaccagatgctccacgccagtcg
cgtaccgtcttcatgggagaaaataatactgttgatgggtgtctggtcagagacatcaagaaat
aacgccggaacattagtgcaggcagcttccacagcaatggcatcctggtcatccagcggatagt
taatgatcagcccactgacgcgttgcgcgagaagattgtgcaccgccgctttacaggcttcgac
gccgcttcgttctaccatcgacaccaccacgctggcacccagttgatcggcgcgagatttaatc
gccgcgacaatttgcgacggcgcgtgcagggccagactggaggtggcaacgccaatcagcaacg
actgtttgccgccagttgttgtgccacgcggttgggaatgtaattcagctccgccatcgccgc
ttccacttttccgcgttttcgcagaaacgtggctggcctggttcaccacgcgggaaacggtc
tgataagagacaccggcatactctgcgacatcgtataacgttactggtttcacattcaccacc
tgaattgactctcttccgggcgctatcatgccataccgcgaaaggttttgcgccattcgatggt
gtccgggatctcgacgctctcccttatgcgactcctgcattaggaagcagcccagtagtaggtt
gaggccgttgagcaccgccgccgcaaggaatggtgcatgcaaggagatggcgcccaacagtccc
ccggccacggggcctgccaccataccacgcgaaacaagcgctcatgagcccgaagtggcgag
cccgatcttcccatcggtgatgtcggcgatataggcgccagcaaccgcacctgtggcgccggt
gatgccggccacgatgcgtccggcgtagaggatcgagatctgatcccgcgaaattaatacgac
tcactatagggaattgtgagcggataacaattcccctctagaaataattttgtttaactttaa
gaaggagatatacatatgactgaaaccgaagctcgtcgttctgcgaactacgaacctaacagct
gggactatgattacctgctgtcctcgacacggacgagtccatcgaagtatacaaagacaaagc
gaaaagctggaagccgaagttcgtcgcgagattaataacgaaaaagcagaatttctgacccctg
ctggaactgattgacaacgtccagcgcctggcctgggttaccgtttcgagtctgatatccgtg
gtgcgctggatcgcttcgtttcctccggcggcttcgatgcggtaaccaagacttcctgcacgg
tacggcactgtctttccgtctgctgcgtcaacacggttttgaggtttctcaggaagcgttcagc
ggcttcaaagaccaaaacggcaacttcctggagaacctgaaggaagatatcaaagctatcctga
```

Figure 56C

Nucleotide sequence of pDu47-5 gcctgtacgaggccagcttcctggctctggaaggcgaaaacatcctggacgaggcgaaggtttt
cgcaatctctcatctgaaagaactgtctgaagaaagatcggtaaagagctggcagaacaggtg
aaccatgcactggaactgccactgcatcgccgtactcagcgtctggaagcagtatggtctatcg
aggcctaccgtaaaaaggaggacgcgaatcaggttctgctggagctggcaattctggattacaa
catgatccagtctgtataccagcgtgatctgcgtgaaacgtccgttggtggcgtcgtgtgggt
ctggcgaccaaactgcactttgctcgtgaccgcctgattgagagcttctactgggccgtgggtg
tagcattcgaaccgcaatactccgactgccgtaactccgtcgcaaaaatgtttctttcgtaac
cattatcgacgatatctacgatgtatacggcaccctggacgaactggagctgttactgatgca
gttgagcgttggacgtaaacgccatcaacgacctgccggattacatgaaactgtgctttctgg
ctctgtataacactattaacgaaatcgcctacgacaacctgaaagataaaggtgagaacatcct
gccgtatctgaccaaagcctgggctgacctgtgcaacgctttcctgcaagaagccaagtggctg
tacaacaaatctactccgacctttgacgactactcggcaacgcatggaaatcctcttctggcc
cgctgcaactggtgttcgcttacttcgctgtcgtgcagaacattaaaaaggaagagatcgaaaa
cctgcaaaaataccatgacaccatctctcgtccttcccatatcttccgtctgtgcaatgacctg
gctagcgcgtctgcggaaattgcgcgtggtgaaaccgcaaatagcgtttcttgttacatgcgca
ctaaaggtatctccgaagaactggctaccgaaagcgtgatgaatctgatcgatgaaacctggaa
aaagatgaacaaggaaaaactgggtggtagcctgttcgcgaaaccgttcgtggaaaccgcgatc
aacctggcacgtcaatctcactgcacttatcataacggcgacgcgcatacctctccggatgagc
tgacccgcaaacgcgttctgtctgtaatcactgaaccgattctgcgtttgaacgctaaggatc
cgaattcgagctccgtcgacaagcttgcggccgcactcgagcaccaccaccaccaccactgaga
tccggctgctaacaaagcccgaaaggaagctgagttggctgctgccaccgctgagcaataacta
gcataacccttggggcctctaaacgggtcttgaggggttttttgctgaaaggaggaactatat
ccggat

Figure 57

Amino acid sequence of *P.alba* TRC (-6) (SEQ ID NO:142)

METETEARRSANYEPNSWDYDYLLSSDTDESIEVYKDKAKKLEAEVRREINNEKAEPLTLLELI
DNVQRLGLGYRFESDIRGALDRFVSSGGFDAVTKTSLHGTALSFRLLRQHGFEVSQEAFSGFKD
QNGNFLENLKEDIKAILSLYEASFLALEGENILDEAKVFAISHLKELSEEKIGKELAEQVNHAL
ELPLHRRTQRLEAVWSIEAYRKKEDANQVLLELAILDYNMIQSVYQRDLRETSRWWRRVGLATK
LHFARDRLIESFYWAVGVAFEPQYSDCRNSVAKMFSFVTPIIDDIYDVYGTLDELELFTDAVERW
DVNAINDLPDYMKLCPLALYNTINEIAYDNLKDKGENILPYLTKAWADLCNAFLQEAKWLYNKS
TPTFDDYPGNAWKSSSGPLQLVFAYFAVVQNIKKEEIENLQKYHDTISRPSHIPRLCNDLASAS
AEIARGETANSVSCYMRTKGISEELATESVMNLIDETWKKMNKEKLGGSLFAKPFVETAINLAR
QSHCTYHNGDAHTSPDELTRKRVLSVITEPILPFER

Figure 58A

Nucleotide sequence of pDu47-6 (SEQ ID NO:143)

```
tggcgaatgggacgcgcctgtagcggcgcattaagcgcggcgggtgtggtggttacgcgcagc
gtgaccgctacacttgccagcgccctagcgcccgctcctttcgctttcttcccttcctttctcg
ccacgttcgccggctttccccgtcaagctctaaatcgggggctccctttagggttccgatttag
tgctttacggcacctcgaccccaaaaaacttgattagggtgatggttcacgtagtgggccatcg
ccctgatagacggtttttcgcccttttgacgttggagtccacgttctttaatagtggactcttgt
tccaaactggaacaacactcaaccctatctcggtctattcttttgatttataagggatttttgcc
gatttcggcctattggttaaaaaatgagctgatttaacaaaaatttaacgcgaattttaacaaa
atattaacgtttacaatttcaggtggcacttttcggggaaatgtgcgcggaacccctatttgtt
tatttttctaaatacattcaaatatgtatccgctcatgaattaattcttagaaaaactcatcga
gcatcaaatgaaactgcaatttattcatatcaggattatcaataccatattttgaaaaagccg
tttctgtaatgaaggagaaaactcaccgaggcagttccataggatggcaagatcctggtatcgg
tctgcgattccgactcgtccaacatcaatacaacctattaatttcccctcgtcaaaaataaggt
tatcaagtgagaaatcaccatgagtgacgactgaatccggtgagaatggcaaaagtttatgcat
ttctttccagacttgttcaacaggccagccattacgctcgtcatcaaaatcactcgcatcaacc
aaaccgttattcattcgtgattgcgcctgagcgagacgaaatacgcgatcgctgttaaaaggac
aattacaaacaggaatcgaatgcaaccggcgcaggaacactgccagcgcatcaacaatatttc
acctgaatcaggatattcttctaatacctggaatgctgttttccggggatcgcagtggtgagt
aaccatgcatcatcaggagtacggataaaatgcttgatggtcggaagaggcataaattccgtca
gccagtttagtctgaccatctcatctgtaacatcattggcaacgctacctttgccatgtttcag
aaacaactctggcgcatcgggcttcccatacaatcgatagattgtcgcacctgattgcccgaca
ttatcgcgagcccatttataccatataaatcagcatccatgttggaatttaatcgcggcctag
agcaagacgtttcccgttgaatatggctcataacaccccttgtattactgtttatgtaagcaga
cagttttattgttcatgaccaaaatcccttaacgtgagttttcgttccactgagcgtcagaccc
cgtagaaaagatcaaaggatcttcttgagatcctttttttctgcgcgtaatctgctgcttgcaa
acaaaaaaaccaccgctaccagcggtggtttgtttgccggatcaagagctaccaactctttttc
cgaaggtaactggcttcagcagagcgcagataccaaatactgtccttctagtgtagccgtagtt
aggccaccacttcaagaactctgtagcaccgcctacatacctcgctctgctaatcctgttacca
gtggctgctgccagtggcgataagtcgtgtcttaccgggttggactcaagacgatagttaccgg
ataaggcgcagcggtcgggctgaacggggggttcgtgcacacagcccagcttggagcgaacgac
ctacaccgaactgagatacctacagcgtgagctatgagaaagcgccacgcttcccgaagggaga
aaggcggacaggtatccggtaagcggcagggtcggaacaggagagcgcacgagggagcttccag
ggggaaacgcctggtatctttatagtcctgtcgggtttcgccacctctgacttgagcgtcgatt
tttgtgatgctcgtcaggggggcggagcctatggaaaaacgccagcaacgcggccttttacgg
ttcctggccttttgctggccttttgctcacatgttctttcctgcgttatccctgattctgtgg
ataaccgtattaccgcctttgagtgagctgataccgctcgccgcagccgaacgaccgagcgcag
cgagtcagtgagcgaggaagcggaagagcgcctgatgcggtattttctccttacgcatctgtgc
ggtatttcacaccgcatatatggtgcactctcagtacaatctgctctgatgccgcatagttaag
ccagtatacactccgctatcgctacgtgactgggtcatggctgcgccccgacacccgccaacac
ccgctgacgcgccctgacgggcttgtctgctcccggcatccgcttacagacaagctgtgaccgt
ctccgggagctgcatgtgtcagaggttttcaccgtcatcaccgaaacgcgcgaggcagctgcgg
taaagctcatcagcgtggtcgtgaagcgattcacagatgtctgcctgttcatccgcgtccagct
cgttgagtttctccagaagcgttaatgtctggcttctgataaagcgggccatgttaagggcggt
ttttcctgtttggtcactgatgcctccgtgtaaggggattctgttcatggggtaatgata
```

Figure 58B

Nucleotide sequence of pDu47-6 ccgatgaaacgagagaggatgctcacgatacgggttactgatgatgaacatgcccggttactgg
aacgttgtgagggtaaacaactggcggtatggatgcggcgggaccagagaaaaatcactcaggg
tcaatgccagcgcttcgttaatacagatgtaggtgttccacagggtagccagcagcatcctgcg
atgcagatccggaacataatggtgcagggcgctgacttccgcgtttccagactttacgaaacac
ggaaaccgaagaccattcatgttgttgctcaggtcgcagacgttttgcagcagcagtcgcttca
cgttcgctcgcgtatcggtgattcattctgctaaccagtaaggcaacccgccagcctagccgg
gtcctcaacgacaggagcacgatcatcgcacccgtggggccgccatgccggcgataatggcct
gcttctcgccgaaacgtttggtggcgggaccagtgacgaaggcttgagcgagggcgtgcaagat
tccgaataccgcaagcgacaggccgatcatcgtcgcgctccagcgaaagcggtcctcgccgaaa
atgacccagagcgctgccggcacctgtcctacgagttgcatgataaagaagacagtcataagtg
cggcgacgatagtcatgccccgcgcccaccggaaggagctgactgggttgaaggctctcaaggg
catcggtcgagatcccggtgcctaatgagtgagctaacttacattaattgcgttgcgctcactg
cccgctttccagtcgggaaacctgtcgtgccagctgcattaatgaatcggccaacgcgcggga
gaggcggtttgcgtattgggcgccagggtggttttcttttcaccagtgagacgggcaacagct
gattgcccttcaccgcctggccctgagagagttgcagcaagcggtccacgctggtttgccccag
caggcgaaaatcctgtttgatggtggttaacggcgggatataacatgagctgtcttcggtatcg
tcgtatcccactaccgagatatccgcaccaacgcgcagcccggactcggtaatggcgcgcattg
cgcccagcgccatctgatcgttggcaaccagcatcgcagtgggaacgatgccctcattcagcat
ttgcatggtttgttgaaaaccggacatggcactccagtcgccttcccgttccgctatcggctga
atttgattgcgagtgagatatttatgccagccagccagacgcagacgcgcgagacagaactta
atgggcccgctaacagcgcgatttgctggtgacccaatgcgaccagatgctccacgccagtcg
cgtaccgtcttcatgggagaaaataatactgttgatgggtgtctggtcagagacatcaagaaat
aacgccggaacattagtgcaggcagcttccacagcaatggcatcctggtcatccagcggatagt
taatgatcagcccactgacgcgttgcgcgagaagattgtgcaccgccgctttacaggcttcgac
gcggcttcgttctaccatcgacaccaccacgctggcacccagttgatcggcgcgagatttaatc
gccgcgacaatttgcgacggcgcgtgcagggccagactggaggtggcaacgccaatcagcaacg
actgtttgcccgccagttgttgtgccacgcggttgggaatgtaattcagctccgccatcgccgc
ttccacttttttcccgcgttttcgcagaaacgtggctggcctggttcaccacgcgggaaacggtc
tgataagagacaccggcatactctgcgacatcgtataacgttactggtttcacattcaccaccc
tgaattgactctcttccgggcgctatcatgccataccgcgaaaggttttgcgccattcgatggt
gtccgggatctcgacgctctcccttatgcgactcctgcattaggaagcagcccagtagtaggtt
gaggccgttgagcaccgccgccgcaaggaatggtgcatgcaaggagatggcgcccaacagtccc
ccggccacgggcctgccaccatacccacgcgaaacaagcgctcatgagcccgaagtggcgag
cccgatcttccccatcggtgatgtcggcgatataggcgccagcaaccgcacctgtggcgccggt
gatgccggccacgatgcgtccggcgtagaggatcgagatctcgatcccgcgaaattaatacgac
tcactatagggaattgtgagcggataacaattcccctctagaaataattttgtttaactttaa
gaaggagatatacatatggaaactgaaacgaagctcgtcgttctgcgaactacgaacctaaca
gctggactatgattacctgctgtcctccgacacggacgagtccatcgaagtatacaaagacaa
agcgaaaaagctggaagccgaagttcgtcgcgagattaataacgaaaagcagaatttctgacc
ctgctggaactgattgacaacgtccagcgcctgggcctgggttaccgtttcgagtctgatatcc
gtggtgcgctggatcgcttcgtttcctccggcggcttcgatgcggtaaccaagacttcctgca
cggtacggcactgtctttccgtctgctgcgtcaacacggttttgaggtttctcaggaagcgttc
agcggcttcaaagaccaaaacggcaacttcctggagaacctgaaggaagatatcaaagctatcc

Figure 58C

Nucleotide sequence of pDu47-6 tgagcctgtacgaggccagcttcctggctctggaaggcgaaaacatcctggacgaggcgaaggt
tttcgcaatctctcatctgaaagaactgtctgaagaaaagatcggtaaagagctggcagaacag
gtgaaccatgcactggaactgccactgcatcgccgtactcagcgtctggaagcagtatggtcta
tcgaggcctaccgtaaaaaggaggacgcgaatcaggttctgctggagctggcaattctggatta
caacatgatccagtctgtataccagcgtgatctgcgtgaaacgtcccgttggtggcgtcgtgtg
ggtctggcgaccaaactgcactttgctcgtgaccgcctgattgagagcttctactgggccgtgg
gtgtagcattcgaaccgcaatactccgactgccgtaactccgtcgcaaaaatgttttctttcgt
aaccattatcgacgatatctacgatgtatacggcaccctggacgaactggagctgtttactgat
gcagttgagcgttgggacgtaaacgccatcaacgacctgccggattacatgaaactgtgctttc
tggctctgtataacactattaacgaaatcgcctacgacaacctgaaagataaaggtgagaacat
cctgccgtatctgaccaaagcctgggctgacctgtgcaacgcttcctgcaagaagccaagtgg
ctgtacaacaaatctactccgacctttgacgactacttcggcaacgcatggaaatcctcttctg
gcccgctgcaactggtgttcgcttacttcgctgtcgtgcagaacattaaaaaggaagagatcga
aaacctgcaaaaataccatgacaccatctctcgtccttcccatatcttccgtctgtgcaatgac
ctggctagcgcgtctgcggaaattgcgcgtggtgaaaccgcaaatagcgtttcttgttacatgc
gcactaaaggtatctccgaagaactggctaccgaaagcgtgatgaatctgatcgatgaaacctg
gaaaaagatgaacaaggaaaaactgggtggtagcctgttcgcgaaaccgttcgtggaaaccgcg
atcaacctggcacgtcaatctcactgcacttatcataacggcgacgcgcatacctctccggatg
agctgaccgcaaacgcgttctgtctgtaatcactgaaccgattctgccgtttgaacgctaagg
atccgaattcgagctccgtcgacaagcttgcggccgcactcgagcaccaccaccaccaccactg
agatccggctgctaacaaagcccgaaaggaagctgagttggctgctgccaccgctgagcaataa
ctagcataaccccttggggcctctaaacgggtcttgaggggttttttgctgaaaggaggaacta
tatccggat

Figure 59

Amino acid sequence of *P.alba* TRC (-7) (SEQ ID NO:144)

MTETETEARRSANYEPNSWDYDYLLSSDTDESIEVYKDKAKKLEAEVRREINNEKAEFLTLLEL
IDNVQRLGLGYRFESDIRGALDRFVSSGGFDAVTKTSLHGTALSFRLLRQHGFEVSQEAFSGFK
DQNGNFLENLKEDIKAILSLYEASFLALEGENILDEAKVFAISHLKELSEEKIGKELAEQVNHA
LELFLHRRTQRLEAVWSIEAYRKKEDANQVLLELAILDYNMIQSVYQRDLRETSRWWRRVGLAT
KLHFARDRLIESFYWAVGVAFEPQYSDCRNSVAKMFSFVTIIDDIYDVYGTLDELELFTDAVER
WDVNAINDLPDYMKLCFLALYNTINEIAYDNLKDKGENILPYLTKAWADLCNAFLQEAKWLYNK
STPTFDDYFGNAWKSSSGPLQLVFAYFAVVQNIKKEEIENLQKYHDTISRPSHIFRLCNDLASA
SAEIARGETANSVSCYMRTKGISEELATESVMNLIDETWKKMNKEKLGGSLFAKFFVETAINLA
RQSHCTYHNGDAHTSPDELTRKRVLSVITEPILPFER

Figure 60A

Nucleotide sequence of pDu47-7 (SEQ ID NO:145)

tggcgaatgggacgcgcctgtagcggcgcattaagcgcggcgggtgtggtggttacgcgcagc
gtgaccgctacacttgccagcgccctagcgcccgctcctttcgctttcttcccttcctttctcg
ccacgttcgccggctttccccgtcaagctctaaatcgggggctccctttagggttccgatttag
tgctttacggcacctcgaccccaaaaaacttgattagggtgatggttcacgtagtgggccatcg
ccctgatagacggttttttcgccctttgacgttggagtccacgttctttaatagtggactcttgt
tccaaactggaacaacactcaaccctatctcggtctattcttttgatttataagggatttttgcc
gatttcggcctattggttaaaaaatgagctgatttaacaaaatttaacgcgaattttaacaaa
atattaacgtttacaattcaggtggcacttttcggggaaatgtgcgcggaacccctatttgtt
tatttttctaaatacattcaaatatgtatccgctcatgaattaattcttagaaaaactcatcga
gcatcaaatgaaactgcaatttattcatatcaggattatcaataccatattttgaaaaagccg
tttctgtaatgaaggagaaaactcaccgaggcagttccataggatggcaagatcctggtatcgg
tctgcgattccgactcgtccaacatcaatacaacctattaatttcccctcgtcaaaaataaggt
tatcaagtgagaaatcaccatgagtgacgactgaatccggtgagaatggcaaaagtttatgcat
ttctttccagacttgttcaacaggccagccattacgctcgtcatcaaaatcactcgcatcaacc
aaaccgttattcattcgtgattgcgcctgagcgagacgaaatacgcgatcgctgttaaaaggac
aattacaaacaggaatcgaatgcaaccggcgcaggaacactgccagcgcatcaacaatatttc
acctgaatcaggatattcttctaatacctggaatgctgttttcccggggatcgcagtggtgagt
aaccatgcatcatcaggagtacggataaaatgcttgatggtcggaagaggcataaattccgtca
gccagtttagtctgaccatctcatctgtaacatcattggcaacgctacctttgccatgtttcag
aaacaactctggcgcatcgggcttcccatacaatcgatagattgtcgcacctgattgcccgaca
ttatcgcgagcccatttataccatataaatcagcatccatgttggaatttaatcgcggcctag
agcaagacgtttcccgttgaatatggctcataacaccccttgtattactgtttatgtaagcaga
cagttttattgttcatgaccaaaatcccttaacgtgagttttcgttccactgagcgtcagaccc
cgtagaaaagatcaaaggatcttcttgagatcctttttttctgcgcgtaatctgctgcttgcaa
acaaaaaaaccaccgctaccagcggtggtttgtttgccggatcaagagctaccaactctttttc
cgaaggtaactggcttcagcagagcgcagataccaaatactgtccttctagtgtagccgtagtt
aggccaccacttcaagaactctgtagcaccgcctacatacctcgctctgctaatcctgttacca
gtggctgctgccagtggcgataagtcgtgtcttaccgggttggactcaagacgatagttaccgg
ataaggcgcagcggtcgggctgaacggggggttcgtgcacacagcccagcttggagcgaacgac
ctacaccgaactgagatacctacagcgtgagctatgagaaagcgccacgcttcccgaagggaga
aaggcggacaggtatccggtaagcggcagggtcggaacaggagagcgcacgagggagcttccag
ggggaaacgcctggtatctttatagtcctgtcgggtttcgccacctctgacttgagcgtcgatt
tttgtgatgctcgtcaggggggcggagcctatggaaaaacgccagcaacgcggcctttttacgg
ttcctggccttttgctggccttttgctcacatgttctttcctgcgttatcccctgattctgtgg
ataacgtattaccgcctttgagtgagctgataccgctcgccgcagccgaacgaccgagcgcag
cgagtcagtgagcgaggaagcggaagagcgcctgatgcggtatttctccttacgcatctgtgc
ggtatttcacaccgcatatatggtgcactctcagtacaatctgctctgatgccgcatagttaag
ccagtatacactccgctatcgctacgtgactgggtcatggctgcgccccgacacccgccaacac
ccgctgacgcgccctgacggcttgtctgctcccggcatccgcttacagacaagctgtgaccgt
ctccgggagctgcatgtgtcagaggttttcaccgtcatcaccgaaacgcgcgaggcagctgcgg
taaagctcatcagcgtggtcgtgaagcgattcacagatgtctgcctgttcatccgcgtccagct
cgttgagtttctccagaagcgttaatgtctggcttctgataaagcgggccatgttaagggcggt
ttttcctgtttggtcactgatgcctccgtgtaaggggattctgttcatgggggtaatgata

Figure 60B

Nucleotide sequence of pDu47-7 ccgatgaaacgagagaggatgctcacgatacgggttactgatgatgaacatgcccggttactgg
aacgttgtgagggtaaacaactggcggtatggatgcggcgggaccagagaaaaatcactcaggg
tcaatgccagcgcttcgttaatacagatgtaggtgttccacagggtagccagcagcatcctgcg
atgcagatccggaacataatggtgcagggcgctgacttccgcgtttccagactttacgaaacac
ggaaaccgaagaccattcatgttgttgctcaggtcgcagacgttttgcagcagcagtcgcttca
cgttcgctcgcgtatcggtgattcattctgctaaccagtaaggcaacccgccagcctagccgg
gtcctcaacgacaggagcacgatcatgcgcacccgtggggccgccatgccggcgataatggcct
gcttctcgccgaaacgtttggtggcgggaccagtgacgaaggcttgagcgagggcgtgcaagat
tccgaataccgcaagcgacaggccgatcatcgtcgcgctccagcgaaagcggtcctcgccgaaa
atgacccagagcgctgccggcacctgtcctacgagttgcatgataaagaagacagtcataagtg
cggcgacgatagtcatgcccgcgccaccggaaggagctgactgggttgaaggctctcaaggg
catcggtcgagatcccggtgcctaatgagtgagctaacttacattaattgcgttgcgctcactg
cccgctttccagtcgggaaacctgtcgtgccagctgcattaatgaatcggccaacgcgcggga
gaggcggtttgcgtattgggcgccagggtggtttttcttttcaccagtgagacgggcaacagct
gattgcccttcaccgcctggccctgagagagttgcagcaagcggtccacgctggtttgcccag
caggcgaaaatcctgtttgatggtggttaacgcgggatataacatgagctgtcttcggtatcg
tcgtatcccactaccgagatatccgcaccaacgcgcagcccggactcgtaatggcgcgcattg
cgcccagcgccatctgatcgttggcaaccagcatcgcagtgggaacgatgccctcattcagcat
ttgcatggtttgttgaaaaccggacatggcactccagtcgccttcccgttccgctatcggctga
atttgattgcgagtgagatatttatgccagccagccagacgcagacgcgccgagacagaactta
atgggcccgctaacagcgcgatttgctggtgacccaatgcgaccagatgctccacgcccagtcg
cgtaccgtcttcatgggagaaaataatactgttgatgggtgtctggtcagagacatcaagaaat
aacgccggaacattagtgcaggcagcttccacagcaatggcatcctggtcatccagcggatagt
taatgatcagcccactgacgcgttgcgcgagaagattgtgcaccgccgctttacaggcttcgac
gccgcttcgttctaccatcgacaccaccacgctggcacccagttgatcggcgcgagatttaatc
gccgcgacaatttgcgacggcgcgtgcagggccagactggaggtggcaacgccaatcagcaacg
actgtttgccgccagttgttgtgccacgcggttgggaatgtaattcagctccgccatcgccgc
ttccactttttcccgcgttttcgcagaaacgtggctggcctggttcaccacgcgggaaacggtc
tgataagagacaccggcatactctgcgacatcgtataacgttactggtttcacattcaccacc
tgaattgactctcttccgggcgctatcatgccataccgcgaaaggttttgcgccattcgatggt
gtccgggatctcgacgctctcccttatgcgactctgcattaggaagcagcccagtagtaggtt
gaggccgttgagcaccgccgccgcaaggaatggtgcatgcaaggagatggcgcccaacagtccc
ccggccacggggcctgccaccatacccacgccgaaacaagcgctcatgagcccgaagtggcgag
cccgatcttccccatcggtgatgtcggcgatataggcgccagcaaccgcacctgtggcgccggt
gatgccggccacgatgcgtccggcgtagaggatcgagatctcgatcccgcgaaattaatacgac
tcactataggggaattgtgagcggataacaattcccctctagaaataattttgtttaactttaa
gaaggagatatacatatgaccgaaactgaaaccgaagctcgtcgttctgcgaactacgaaccta
acagctgggactatgattacctgctgtcctccgacacggacgagtccatcgaagtatacaaaga
caaagcgaaaaagctggaagccgaagttcgtcgcgagattaataacgaaaagcagaatttctg
accctgctggaactgattgacaacgtccagcgcctgggcctgggttaccgtttcgagtctgata
tccgtggtgcgctggatcgcttcgtttcctccggcggcttcgatgcggtaaccaagacttcct
gcacggtacggcactgtctttccgtctgctgcgtcaacacggttttgaggtttctcaggaagcg
ttcagcggcttcaaagaccaaaacggcaacttcctggagaacctgaaggaagatatcaaagcta

Figure 60C

Nucleotide sequence of pDu47-7 tcctgagcctgtacgaggccagcttcctggctctggaaggcgaaaacatcctggacgaggcgaa
ggttttcgcaatctctcatctgaaagaactgtctgaagaaaagatcggtaaagagctggcagaa
caggtgaaccatgcactggaactgccactgcatcgccgtactcagcgtctggaagcagtatggt
ctatcgaggcctaccgtaaaaaggaggacgcgaatcaggttctgctggagctggcaattctgga
ttacaacatgatccagtctgtataccagcgtgatctgcgtgaaacgtcccgttggtggcgtcgt
gtgggtctggcgaccaaactgcactttgctcgtgaccgcctgattgagagcttctactgggccg
tgggtgtagcattcgaaccgcaatactccgactgccgtaactccgtcgcaaaatgttttctt
cgtaaccattatcgacgatatctacgatgtatacggcaccctggacgaactggagctgtttact
gatgcagttgagcgttgggacgtaaacgccatcaacgacctgccggattacatgaaactgtgct
tctggctctgtataacactattaacgaaatcgcctacgacaacctgaaagataaaggtgagaa
catcctgcgtatctgaccaaagcctggctgacctgtgcaacgcttcctgcaagaagccaag
tggctgtacaacaaatctactccgacctttgacgactacttcggcaacgcatggaaatcctctt
ctggcccgctgcaactggtgttcgcttacttcgctgtcgtgcagaacattaaaaaggaagagat
cgaaaacctgcaaaaataccatgacaccatctctcgtccttccatatcttccgtctgtgcaat
gacctggctagcgcgtctgcggaaattgcgcgtggtgaaacgcaaatagcgtttcttgttaca
tgcgcactaaaggtatctccgaagaactggctaccgaaagcgtgatgaatctgatcgatgaaac
ctggaaaagatgaacaaggaaaaactgggtggtagcctgttcgcgaaaccgttcgtggaaacc
gcgatcaacctggcacgtcaatctcactgcacttatcataacggcgacgcgcataccctctccgg
atgagctgaccgcaaacgcgttctgtctgtaatcactgaaccgattctgccgtttgaacgcta
aggatccgaattcgagctccgtcgacaagcttgggccgcactcgagcaccaccaccaccacca
ctgagatccggctgctaacaaagcccgaaggaagctgagttggctgctgccaccgctgagcaa
taactagcataaccccttggggcctctaaacgggtcttgaggggttttttgctgaaaggaggaa
ctatatccggat

Figure 61

Amino acid sequence of *P. tremu* TRC (MET) (SEQ ID NO:146)

METRRSANYEPNSWDYDYLLSSDTDESIEVHKDKAKKLEAEVRREINNEKAEFLTLLELIDNVQ
RLGLGYRFESDIRRALDRFVSSGGFDGVTKTSLHGTALSFRLLRQHGFEVSQEAFSGFKDQNGN
FLENLKEDIKAILSLYEASFLALEGENILDEAKVFAISHLKELSEEKIGKELAEQVSHALELPL
HRETQRLEAVWSIEAYRKKEDANQVLLELAILDYNMIQSVYQRDLRETSRWWRRVGLATKLHFA
RDRLIESFYWAVGVAFEPQYSDCRNSVAKMFSFVTIIDDIYDVYGTLDELELFTDAVERWDVNA
INDLPDYMKLCFLALYNTINEIAYDNLKDKGENILPYLTKAWADLCNAFLQEAKWLYNKSTPTF
DDYFGNAWKSSSGPLQLIFAYFAVVQNIKKEEIENLQKYHDIISRPSHIFRLCNDLASASAEIA
RGETANSVSCYMRTKGISEELATESVMNLIDETWKKMNKEKLGGSLFAKPFVETAINLARQSHC
TYHNGDAHTSPDELTRKRVLSVITEPILPFER

Figure 62A

Nucleotide sequence of pDu48 (SEQ ID NO:147)

tggcgaatgggacgcgcctgtagcggcgcattaagcgcggcgggtgtggtggttacgcgcagc
gtgaccgctacacttgccagcgccctagcgcccgtcctttcgctttcttcccttcctttctcg
ccacgttcgccggctttccccgtcaagctctaaatcgggggctccctttagggttccgatttag
tgctttacggcacctcgaccccaaaaaacttgattagggtgatggttcacgtagtgggccatcg
ccctgatagacggttttcgccctttgacgttggagtccacgttctttaatagtggactcttgt
tccaaactggaacaacactcaaccctatctcggtctattcttttgatttataagggattttgcc
gatttcggcctattggttaaaaatgagctgatttaacaaaatttaacgcgaattttaacaaa
atattaacgtttacaatttcaggtggcacttttcggggaaatgtgcgcggaacccctatttgtt
tattttctaaatacattcaaatatgtatccgctcatgaattaattcttagaaaaactcatcga
gcatcaaatgaaactgcaatttattcatatcaggattatcaataccatattttgaaaaagccg
tttctgtaatgaaggagaaaactcaccgaggcagttccataggatggcaagatcctggtatcgg
tctgcgattccgactcgtccaacatcaatacaacctattaatttcccctcgtcaaaaataaggt
tatcaagtgagaaatcaccatgagtgacgactgaatccggtgagaatggcaaaagtttatgcat
ttctttccagacttgttcaacaggccagccattacgctcgtcatcaaaatcactcgcatcaacc
aaacgttattcattcgtgattgcgcctgagcgagacgaaatacgcgatcgctgttaaaaggac
aattacaaacaggaatcgaatgcaaccggcgcaggaacactgccagcgcatcaacaatatttc
acctgaatcaggatattcttctaatacctggaatgctgtttttcccggggatcgcagtggtgagt
aaccatgcatcatcaggagtacggataaaatgcttgatggtcggaagaggcataaattccgtca
gccagtttagtctgaccatctcatctgtaacatcattggcaacgctacctttgccatgtttcag
aaacaactctggcgcatcgggcttcccatacaatcgatagattgtcgcacctgattgcccgaca
ttatcgcgagcccatttatacccatataaatcagcatccatgttggaatttaatcgcggcctag
agcaagacgtttcccgttgaatatggctcataacaccccttgtattactgtttatgtaagcaga
cagttttattgttcatgaccaaaatcccttaacgtgagttttcgttccactgagcgtcagaccc
cgtagaaaagatcaaaggatcttcttgagatcctttttttctgcgcgtaatctgctgcttgcaa
acaaaaaaaccaccgctaccagcggtggtttgtttgccggatcaagagctaccaactctttttc
cgaaggtaactggcttcagcagagcgcagataccaaatactgtccttctagtgtagccgtagtt
aggccaccacttcaagaactctgtagcaccgcctacatacctcgctctgctaatcctgttacca
gtggctgctgccagtggcgataagtcgtgtcttaccgggttggactcaagacgatagttaccgg
ataaggcgcagcggtcgggctgaacggggggttcgtgcacacagcccagcttggagcgaacgac
ctacaccgaactgagatacctacagcgtgagctatgagaaagcgccacgcttcccgaagggaga
aaggcggacaggtatccggtaagcggcagggtcggaacaggagagcgcacgagggagcttccag
gggaaacgcctggtatctttatagtcctgtcgggtttcgccacctctgacttgagcgtcgatt
tttgtgatgctcgtcaggggggcggagcctatggaaaaacgccagcaacgcggcctttttacgg
ttcctggccttttgctggccttttgctcacatgttctttcctgcgttatccctgattctgtgg
ataaccgtattaccgcctttgagtgagctgataccgctcgccgcagccgaacgaccgagcgcag
cgagtcagtgagcgaggaagcggaagagcgcctgatgcggtattttctccttacgcatctgtgc
ggtatttcacaccgcatatatggtgcactctcagtacaatctgctctgatgccgcatagttaag
ccagtatacactccgctatcgctacgtgactggtcatggctgcgccccgacacccgccaacac
ccgctgacgcgccctgacggcttgtctgctcccggcatccgcttacagacaagctgtgaccgt
ctccgggagctgcatgtgtcagaggttttcaccgtcatcaccgaaacgcgcgaggcagctgcgg
taaagctcatcagcgtggtcgtgaagcgattcacagatgtctgcctgttcatccgcgtccagct
cgttgagtttctccagaagcgttaatgtctggcttctgataaagcgggccatgttaagggcggt
ttttcctgtttggtcactgatgcctccgtgtaaggggattctgttcatggggtaatgata

Figure 62B

Nucleotide sequence of pDu48 ccgatgaaacgagagaggatgctcacgatacgggttactgatgatgaacatgcccggttactgg
aacgttgtgagggtaaacaactggcggtatggatgcggcgggaccagagaaaaatcactcaggg
tcaatgccagcgcttcgttaatacagatgtaggtgttccacagggtagccagcagcatcctgcg
atgcagatccggaacataatggtgcagggcgctgacttccgcgtttccagactttacgaaacac
ggaaaccgaagaccattcatgttgttgctcaggtcgcagacgtttgcagcagcagtcgcttca
cgttcgctcgcgtatcggtgattcattctgctaaccagtaaggcaacccgccagcctagccgg
gtcctcaacgacaggagcacgatcatgcgcacccgtggggcgccatgccggcgataatggcct
gcttctcgccgaaacgtttggtggcgggaccagtgacgaaggcttgagcgagggcgtgcaagat
tccgaataccgcaagcgacaggccgatcatcgtcgcgctccagcgaaagcggtcctcgccgaaa
atgacccagagcgctgccggcacctgtcctacgagttgcatgataaagaagacagtcataagtg
cggcgacgatagtcatgccccgcgcccaccggaaggagctgactgggttgaaggctctcaaggg
catcggtcgagatcccggtgcctaatgagtgagctaacttacattaattgcgttgcgctcactg
cccgctttccagtcgggaaacctgtcgtgccagctgcattaatgaatcggccaacgcgcgggga
gaggcggtttgcgtattgggcgccagggtggttttcttttcaccagtgagacgggcaacagct
gattgcccttcaccgcctggccctgagagagttgcagcaagcggtccacgctggtttgccccag
caggcgaaaatcctgtttgatggtggttaacggcgggataacatgagctgtcttcggtatcg
tcgtatcccactaccgagatatccgcaccaacgcgcagcccggactcggtaatggcgcgcattg
cgcccagcgccatctgatcgttggcaaccagcatcgcagtgggaacgatgccctcattcagcat
ttgcatggtttgttgaaaaccggacatggcactccagtcgccttcccgttccgctatcggctga
atttgattgcgagtgagatatttatgccagccagccagacgcagacgcgcgagacagaactta
atgggcccgctaacagcgcgatttgctggtgacccaatgcgaccagatgctccacgccagtcg
cgtaccgtcttcatgggagaaaataatactgttgatgggtgtctggtcagagacatcaagaaat
aacgccggaacattagtgcaggcagcttccacagcaatggcatcctggtcatccagcggatagt
taatgatcagcccactgacgcgttgcgcgagaagattgtgcaccgccgctttacaggcttcgac
gccgcttcgttctaccatcgacaccaccacgctggcacccagttgatcggcgcgagatttaatc
gccgcgacaatttgcgacggcgcgtgcagggccagactggaggtggcaacgccaatcagcaacg
actgtttgcccgccagttgttgtgccacgcggttgggaatgtaattcagctccgccatcgccgc
ttccacttttttcccgcgttttcgcagaaacgtggctggcctggttcaccacgcgggaaacggtc
tgataagagacaccggcatactctgcgacatcgtataacgttactggtttcacattcaccaccc
tgaattgactctcttccgggcgctatcatgccataccgcgaaaggttttgcgccattcgatggt
gtccgggatctcgacgctctcccttatgcgactcctgcattaggaagcagcccagtagtaggtt
gaggccgttgagcaccgccgccgcaaggaatggtgcatgcaaggagatggcgccaacagtccc
ccggccacggggcctgcaccatacccacgcgaaacaagcgctcatgagcccgaagtggcgag
cccgatcttcccatcggtgatgtcggcgatataggcgccagcaaccgcacctgtggcgccggt
gatgccggccacgatgcgtccggcgtagaggatcgagatctgatcccgcgaaattaatacgac
tcactatagggaattgtgagcggataacaattcccctctagaaataattttgtttaactttaa
gaaggagatatacatatggaaacgcgtcgttctgcgaactacgaacctaacagctgggactatg
attacctgctgtcctccgacacggacgagtccatcgaagtacacaaagacaaagcgaaaaagct
ggaagccgaagttcgtcgcgagattaataacgaaaagcagaattctgaccctgctggaactg
attgacaacgtccagcgcctgggcctgggttacgtttcgagtctgatatccgtcgtgcgctgg
atcgcttcgtttcctcggcggcttcgatggcgtaaccaagacttccctgcacggtacggcact
gtctttccgtctgctgcgtcaacacggttttgaggtttctcaggaagcgttcagcggcttcaaa
gaccaaaacggcaacttcctggagaacctgaaggaagatatcaaagctatcctgagcctgtacg

Figure 62C

Nucleotide sequence of pDu48 aggccagcttcctggctctggaaggcgaaaacatcctggacgaggcgaaggttttcgcaatctc
tcatctgaaagaactgtctgaagaaaagatcggtaaagagctggcagaacaggtgtcccatgca
ctggaactgccactgcatcgccgtactcagcgtctggaagcagtatggtctatcgaggcctacc
gtaaaaaggaggacgcgaaccaggttctgctggagctggcaattctggattacaacatgatcca
gtctgtataccagcgtgatctgcgtgaaacgtcccgttggtggcgtcgtgggtctggcgacc
aaactgcactttgctcgtgaccgcctgattgagagcttctactgggccgtgggtgtagcattcg
aaccgcaatactccgactgccgtaactccgtcgcaaaaatgtttctttcgtaaccattatcga
cgatatctacgatgtatacggcaccctggacgaactggagctgttactgatgcagttgagcgt
tgggacgtaaacgccatcaacgacctgccggattacatgaaactgtgctttctggctctgtata
acactattaacgaaatcgcctacgacaacctgaaagataaaggtgagaacatcctgccgtatct
gaccaaagcctgggctgacctgtgcaacgcttcctgcaagaagccaagtggctgtacaacaaa
tctactccgacctttgacgactacttcggcaacgcatggaaatcctcttctggccgctgcaac
tgatcttcgcttacttcgctgtcgtgcagaacattaaaaaggaagagatcgaaaacctgcaaaa
ataccatgacatcatctctcgtccttcccatatcttccgtctgtgcaatgacctggctagcgcg
tctgcggaaattgcgcgtggtgaaaccgcaaatagcgtttcttgttacatgcgcactaaaggta
tctccgaagaactggctaccgaaagcgtgatgaatctgatcgatgaaacctggaaaagatgaa
caaggaaaaactgggtggtagcctgttcgcgaaaccgttcgtggaaaccgcgatcaacctggca
cgtcaatctcactgcacttatcataacggcgacgcgcatacctctccggatgagctgacccgca
aacgcgttctgtctgtaatcactgaaccgattctgcgtttgaacgctaaggatccgaattcga
gctccgtcgacaagcttgcggccgcactcgagcaccaccaccaccaccactgagatccggctgc
taacaaagcccgaaaggaagctgagttggctgctgccaccgctgagcaataactagcataacc
cttggggcctctaaacgggtcttgaggggttttttgctgaaaggaggaactatatccggat

Figure 63

Amino acid sequence of *P. tricho* (TRC) (SEQ ID NO:148)

```
METRRSANYEPNSWDYDYLLSSDTDESIEVYKDKAKKLEAEVRREINNEKAEFLTLLELIDNVQ
RLGLGYRFESDIRRALDRFVSSGGFDAVTKTSLHATALSFRLLRQHGFEVSQEAFSGFKDQNGN
FLENLKEDIKAILSLYEASFLALEGENILDEAKVFAISHLKELSEEKIGKDLAEQVNHALELPL
HRRTQRLEAVLSIEAYRKKEDADQVLLELAILDYNMIQSVYQRDLRETSRWWRRVGLATKLHFA
RDRLIESFYWAVGVAPEPQYSDCRNSVAKMFSFVTIIDDIYDVYGTLDELELFTNAVERWDVNA
IDDLPDYMKLCFLALYNTINEIAYDNLKEKGENILPYLTKAWADLCNAFLQEAKWLYNKSTPTF
DEYFGNAWKSSSGPLQLVFAYFAVVQNIKKEEIENLQKYHDIISRPSHIFRLCNDLASASAEIA
RGETANSVSCYMRTKGISEELATESVMNLIDETWKKMNKEKLGGSLFAKPFVETAINLARQSHC
TYHNGDAHTSPDELTRKRVLSVITEPILPFER
```

Figure 64A

Nucleotide sequence of pDu49 (SEQ ID NO:149)

tggcgaatgggacgcgccctgtagcggcgcattaagcgcggcgggtgtggtggttacgcgcagc
gtgaccgctacacttgccagcgccctagcgcccgctcctttcgctttcttcccttcctttctcg
ccacgttcgccggctttccccgtcaagctctaaatcgggggctccctttagggttccgatttag
tgctttacggcacctcgaccccaaaaaacttgattagggtgatggttcacgtagtgggccatcg
ccctgatagacggttttcgccctttgacgttggagtccacgttctttaatagtggactcttgt
tccaaactggaacaacactcaaccctatctcggtctattcttttgatttataagggattttgcc
gatttcggcctattggttaaaaatgagctgatttaacaaaatttaacgcgaatttaacaaa
atattaacgtttacaatttcaggtggcacttttcggggaaatgtgcgcggaacccctatttgtt
tatttttctaaatacattcaaatatgtatccgctcatgaattaattcttagaaaaactcatcga
gcatcaaatgaaactgcaatttattcatatcaggattatcaataccatattttgaaaaagccg
tttctgtaatgaaggagaaaactcaccgaggcagttccataggatggcaagatcctggtatcgg
tctgcgattccgactcgtccaacatcaatacaacctattaatttccctcgtcaaaaataaggt
tatcaagtgagaaatcaccatgagtgacgactgaatccgtgagaatggcaaaagtttatgcat
ttctttccagacttgttcaacaggccagccattacgctcgtcatcaaaatcactcgcatcaacc
aaacgttattcattcgtgattgcgcctgagcgagacgaaatacgcgatcgctgttaaaaggac
aattacaaacaggaatcgaatgcaaccggcgcaggaacactgccagcgcatcaacaatatttc
acctgaatcaggatattcttctaatacctggaatgctgttttcccggggatcgcagtggtgagt
aaccatgcatcatcaggagtacggataaaatgcttgatggtcggaagaggcataaattccgtca
gccagtttagtctgaccatctcatctgtaacatcattggcaacgctacctttgccatgtttcag
aaacaactctggcgcatcgggcttcccatacaatcgatagattgtcgcacctgattgcccgaca
ttatcgcgagcccatttatacccatataaatcagcatccatgttggaatttaatcgcggctag
agcaagacgtttcccgttgaatatggctcataacaccccttgtattactgtttatgtaagcaga
cagttttattgttcatgaccaaaatcccttaacgtgagttttcgttccactgagcgtcagaccc
cgtagaaaagatcaaaggatcttcttgagatcctttttttctgcgcgtaatctgctgcttgcaa
acaaaaaaaccaccgctaccagcggtggtttgtttgccggatcaagagctaccaactctttttc
cgaaggtaactggcttcagcagagcgcagataccaaatactgtccttctagtgtagccgtagtt
aggccaccacttcaagaactctgtagcaccgcctacatacctcgctctgctaatcctgttacca
gtggctgctgccagtggcgataagtcgtgtcttaccgggttggactcaagacgatagttaccgg
ataaggcgcagcggtcgggctgaacggggggttcgtgcacacagcccagcttggagcgaacgac
ctacaccgaactgagataccctacagcgtgagctatgagaaagcgccacgcttcccgaagggaga
aaggcggacaggtatccggtaagcggcagggtcggaacaggagagcgcacgagggagcttccag
ggggaaacgcctggtatctttatagtcctgtcgggtttcgccacctctgacttgagcgtcgatt
tttgtgatgctcgtcaggggggcggagcctatggaaaaacgccagcaacgcggcctttttacgg
ttcctggccttttgctggccttttgctcacatgttctttcctgcgttatcccctgattctgtgg
ataaccgtattaccgcctttgagtgagctgataccgctcgccgcagccgaacgaccgagcgcag
cgagtcagtgagcgaggaagcggaagagcgcctgatgcggtatttctccttacgcatctgtgc
ggtatttcacaccgcatatatggtgcactctcagtacaatctgctctgatgccgcatagttaag
ccagtatacactccgctatcgctacgtgactgggtcatggctgcgccccgacacccgccaacac
ccgctgacgcgccctgacgggcttgtctgctcccggcatccgcttacagacaagctgtgaccgt
ctccgggagctgcatgtgtcagaggttttcaccgtcatcaccgaaacgcgcgaggcagctgcgg
taaagctcatcagcgtggtcgtgaagcgattcacagatgtctgcctgttcatccgcgtccagct
cgttgagtttctccagaagcgttaatgtctggcttctgataaagcgggccatgttaagggcggt
tttttcctgtttggtcactgatgcctccgtgtaagggggatttctgttcatgggggtaatgata

Figure 64B

Nucleotide sequence of pDu49 ccgatgaaacgagagaggatgctcacgatacgggttactgatgatgaacatgcccggttactgg
aacgttgtgagggtaaacaactggcggtatggatgcggcgggaccagagaaaaatcactcaggg
tcaatgccagcgcttcgttaatacagatgtaggtgttccacagggtagccagcagcatcctgcg
atgcagatccggaacataatggtgcaggcgctgacttccgcgtttccagactttacgaaacac
ggaaaccgaagaccattcatgttgttgctcaggtcgcagacgttttgcagcagcagtcgcttca
cgttcgctcgcgtatcggtgattcattctgctaaccagtaaggcaaccccgccagcctagccgg
gtcctcaacgacaggagcacgatcatgcgcacccgtggggccgccatgccggcgataatggcct
gcttctcgccgaaacgtttggtggcgggaccagtgacgaaggcttgagcgagggcgtgcaagat
tccgaataccgcaagcgacaggccgatcatcgtcgcgctccagcgaaagcggtcctcgccgaaa
atgacccagagcgctgccggcacctgtcctacgagttgcatgataaagaagacagtcataagtg
cggcgacgatagtcatgccccgcgccaccgaaggagctgactggttgaaggctctcaaggg
catcggtcgagatcccggtgcctaatgagtgagctaacttacattaattgcgttgcgctcactg
cccgctttccagtcgggaaacctgtcgtgccagctgcattaatgaatcggccaacgcgcgggga
gaggcggtttgcgtattgggcgccagggtggttttcttttcaccagtgagacgggcaacagct
gattgcccttcaccgcctggccctgagagagttgcagcaagcggtccacgctggtttgcccag
caggcgaaaatcctgtttgatggtggttaacggcgggatataacatgagctgtcttcggtatcg
tcgtatcccactaccgagatatccgcaccaacgcgcagcccggactcggtaatggcgcgcattg
cgcccagcgccatctgatcgttggcaaccagcatcgcagtgggaacgatgccctcattcagcat
ttgcatggtttgttgaaaaccggacatggcactccagtcgccttcccgttccgctatcggctga
atttgattgcgagtgagatatttatgccagccagccagacgcagacgcgccgagacagaactta
atgggcccgctaacagcgcgatttgctggtgacccaatgcgaccagatgctccacgccagtcg
cgtaccgtcttcatgggagaaaataatactgttgatggtgtctggtcagagacatcaagaaat
aacgccggaacattagtgcaggcagcttccacagcaatggcatcctggtcatccagcggatagt
taatgatcagcccactgacgcgttgcgcgagaagattgtgcaccgccgctttacaggcttcgac
gccgcttcgttctaccatcgacaccaccacgctggcacccagttgatcggcgcgagatttaatc
gccgcgacaatttgcgacggcgcgtgcagggccagactggaggtggcaacgccaatcagcaacg
actgtttgcccgccagttgttgtgccacgcggttgggaatgtaattcagctccgccatcgccgc
ttccactttttcccgcgttttcgcagaaacgtggctggcctggttcaccacgcgggaaacggtc
tgataagagacaccggcatactctgcgacatcgtataacgttactggtttcacattcaccaccc
tgaattgactctcttccgggcgctatcatgccataccgcgaaaggttttgcgccattcgatggt
gtccgggatctcgacgctctcccttatgcgactcctgcattaggaagcagcccagtagtaggtt
gaggccgttgagcaccgccgccgcaaggaatggtgcatgcaaggagatggcgccaacagtccc
ccggccacggggcctgccaccatacccacgccgaaacaagcgctcatgagcccgaagtggcgag
cccgatcttccccatcggtgatgtcggcgatataggcgccagcaacgcacctgtggcgccggt
gatgccggccacgatgcgtccggcgtagaggatcgagatctcgatcccgcgaaattaatacgac
tcactataggggaattgtgagcggataacaattcccctctagaaataattttgtttaactttaa
gaaggagatatacatatggaaacgcgtcgttctgcgaactacgaacctaacagctgggactatg
attacctgctgtcctccgacacggacgagtccatcgaagtatacaaagacaaagcgaaaaagct
ggaagccgaagttcgtcgcgagattaataacgaaaagcagaatttctgaccctgctggaactg
attgacaacgtccagcgcctgggcctgggttaccgtttcgagtctgatatccgtcgtgcgctgg
atcgcttcgtttcctcggcggcttcgatgcggtaaccaagacttccctgcacgcgacggcact
gtctttccgtctgctgcgtcaacacggttttgaggtttctcaggaagcgttcagcggcttcaaa
gaccaaaacggcaacttcctggagaacctgaaggaagatatcaaagctatcctgagcctgtacg

Figure 64C

Nucleotide sequence of pDu49 aggccagcttcctggctctggaaggcgaaaacatcctggacgaggcgaaggttttcgcaatctc
tcatctgaaagaactgtctgaagaaaagatcggtaaagatctggcagaacaggtgaaccatgca
ctggaactgccactgcatcgccgtactcagcgtctggaagcagtactgtctatcgaggcctacc
gtaaaaaggaggacgcggatcaggttctgctggagctggcaattctggattacaacatgatcca
gtctgtataccagcgtgatctgcgtgaaacgtccgttggtggcgtcgtgtgggtctggcgacc
aaactgcactttctcgtgaccgcctgattgagagcttctactgggccgtgggtgtagcattcg
aaccgcaatactccgactgccgtaactccgtcgcaaaaatgttttctttcgtaaccattatcga
cgatatctacgatgtatacggcaccctggacgaactggagctgtttactaacgcagttgagcgt
tgggacgtaaacgccatcgacgatctgccggattacatgaaactgtgctttctggctctgtata
acactattaacgaaatcgcctacgacaacctgaaagaaaaaggtgagaacatcctgccgtatct
gaccaaagcctgggctgacctgtgcaacgctttcctgcaagaagccaagtggctgtacaacaaa
tctactccgacctttgacgaatacttcggcaacgcatggaaatcctcttctggcccgctgcaac
tggtgttcgcttacttcgctgtcgtgcagaacattaaaaaggaagagatcgaaaacctgcaaaa
ataccatgacatcatctctcgtccttcccatatcttccgtctgtgcaatgacctggctagcgcg
tctgcggaaattgcgcgtggtgaaaccgcaaatagcgtttcttgttacatgcgcactaaaggta
tctccgaagaactggctaccgaaagcgtgatgaatctgatcgatgaaacctggaaaaagatgaa
caaggaaaaactgggtggtagcctgttcgcgaaaccgttcgtggaaccgcgatcaacctggca
cgtcaatctcactgcacttatcataacggcgacgcgcatacctctccggatgagctgaccgca
aacgcgttctgtctgtaatcactgaaccgattctgccgtttgaacgctaaggatccgaattcga
gctccgtcgacaagcttgcggccgcactcgagcaccaccaccaccaccactgagatccggctgc
taacaaagcccgaaaggaagctgagttggctgctgccaccgctgagcaataactagcataaccc
cttggggcctctaaacgggtcttgaggggttttttgctgaaaggaggaactatatccggat

Figure 65

Amino acid sequence of kudzu TRC (MEA) (SEQ ID NO:150)

MEARRSANYQPNLWNFEFLQSLENDLKVEKLEEKATKLEEEVRCMINRVDTQPLSLLELIDDVQ
RLGLTYKFEKDIIKALENIVLLDENKKNKSDLHATALSFRLLRQHGFEVSQDVFERFKDKEGGP
SGELKGDVQGLLSLYEASYLGFEGENLLEEARTFSITHLKNNLKEGINTKVAEQVSHALELPYH
QRLHRLEARWFLDKYEPKEPHHQLLLELAKLDFNMVQTLHQKELQDLSRWWTEMGLASKLDFVR
DRLMEVYFWALGMAPDPQPGECRKAVTKMFGLVTIIDDVYDVYGTLDELQLPTDAVERWDVNAI
NTLPDYMKLCFLALYNTVNDTSYSILKEKGHNNLSYLTKSWRELCKAFLQEAKWSNNKIIPAFS
KYLENASVSSSGVALLAPSYFSVCQQQEDISDHALRSLTDFHGLVRSSCVIFRLCNDLATSAAE
LERGETTNSIISYMHENDGTSEEQAREELRKLIDAEWKKMNRERVSDSTLLPKAFMEIAVNMAR
VSHCTYQYGDGLGRPDYATENRIKLLLIDPFPINQLMYV

Figure 66A

Nucleotide sequence of pDu50 (SEQ ID NO:151)

tcgagcaccaccaccaccaccactgagatccggctgctaacaaagcccgaaaggaagctgagtt
ggctgctgccaccgctgagcaataactagcataaccccttggggcctctaaacgggtcttgagg
ggttttttgctgaaaggaggaactatatccggattggcgaatgggacgcgccctgtagcggcgc
attaagcgcggcgggtgtggtggttacgcgcagcgtgaccgctacacttgccagcgccctagcg
cccgctcctttcgctttcttcccttcctttctcgccacgttcgccggctttccccgtcaagctc
taaatcgggggctccctttagggttccgatttagtgctttacggcacctcgaccccaaaaaact
tgattagggtgatggttcacgtagtgggccatcgccctgatagacggtttttcgccctttgacg
ttggagtccacgttctttaatagtggactcttgttccaaactggaacaacactcaaccctatct
cggtctattcttttgatttataaggattttgccgatttcggcctattggttaaaaaatgagct
gatttaacaaaaatttaacgcgaattttaacaaaatattaacgtttacaatttcaggtggcact
tttcggggaaatgtgcgcggaacccctatttgtttatttttctaaatacattcaaatatgtatc
cgctcatgaattaattcttagaaaaactcatcgagcatcaaatgaaactgcaatttattcatat
caggattatcaataccatattttgaaaaagccgtttctgtaatgaaggagaaaactcaccgag
gcagttccataggatggcaagatcctggtatcggtctgcgattccgactcgtccaacatcaata
caaccatattaatttcccctcgtcaaaaataaggttatcaagtgagaaatcaccatgagtgacga
ctgaatccggtgagaatggcaaaagtttatgcatttctttccagacttgttcaacaggccagcc
attacgctcgtcatcaaaatcactcgcatcaaccaaacgttattcattcgtgattgcgcctga
gcgagacgaaatacgcgatcgctgttaaaggacaattacaaacaggaatcgaatgcaaccggc
gcaggaacactgccagcgcatcaacaatatttcacctgaatcaggatattcttctaatacctg
gaatgctgttttcccggggatcgcagtggtgagtaaccatgcatcatcaggagtacggataaaa
tgcttgatggtcggaagaggcataaattccgtcagccagtttagtctgaccatctcatctgtaa
catcattggcaacgctacctttgccatgtttcagaaacaactctggcgcatcgggcttcccata
caatcgatagattgtcgcacctgattgcccgacattatcgcgagcccatttatacccatataaa
tcagcatccatgttggaatttaatcgcggcctagagcaagacgtttcccgttgaatatggctca
taacaccccttgtattactgtttatgtaagcagacagttttattgttcatgaccaaaatccctt
aacgtgagttttcgttccactgagcgtcagaccccgtagaaaagatcaaaggatcttcttgaga
tccttttttctgcgcgtaatctgctgcttgcaaacaaaaaaaccaccgctaccagcggtggtt
tgtttgccggatcaagagctaccaactctttttccgaaggtaactggcttcagcagagcgcaga
taccaaatactgtccttctagtgtagccgtagttaggccaccacttcaagaactctgtagcacc
gcctacatacctcgctctgctaatcctgttaccagtggctgctgccagtggcgataagtcgtgt
cttaccgggttggactcaagacgatagttaccggataaggcgcagcggtcgggctgaacgggg
ggttcgtgcacacagcccagcttggagcgaacgacctacaccgaactgagatacctacagcgtga
gctatgagaaagcgccacgcttcccgaagggagaaaggcggacaggtatccggtaagcggcagg
gtcggaacaggagagcgcacgagggagcttccaggggggaaacgcctggtatctttatagtcctg
tcgggtttcgccacctctgacttgagcgtcgatttttgtgatgctcgtcaggggggcggagcct
atggaaaaacgccagcaacgcggcctttttacggttcctggccttttgctggccttttgctcac
atgttctttcctgcgttatcccctgattctgtggataaccgtattaccgcctttgagtgagctg
ataccgctcgccgcagccgaacgaccgagcgcagcgagtcagtgagcgaggaagcggaagagcg
cctgatgcggtattttctccttacgcatctgtgcggtatttcacaccgcatatatggtgcactc
tcagtacaatctgctctgatgccgcatagttaagccagtatacactccgctatcgctacgtgac
tgggtcatggctgcgccccgacaacccgccaacacccgctgacgcgccctgacgggcttgtctgc
tcccggcatccgcttacagacaagctgtgaccgtctccgggagctgcatgtgtcagaggttttc
accgtcatcaccgaaacgcgcgaggcagctgcggtaaagctcatcagcgtggtcgtgaagcgat

Figure 66B

Nucleotide sequence of pDu50

```
tcacagatgtctgcctgttcatccgcgtccagctcgttgagtttctccagaagcgttaatgtct
ggcttctgataaagcgggccatgttaagggcggttttttcctgtttggtcactgatgctccgt
gtaaggggatttctgttcatgggggtaatgataccgatgaaacgagagaggatgctcacgata
cgggttactgatgatgaacatgcccggttactggaacgttgtgagggtaaacaactggcggtat
ggatgcggcgggaccagagaaaatcactcagggtcaatgccagcgcttcgttaatacagatgt
aggtgttccacagggtagccagcagcatcctgcgatgcagatccggaacataatggtgcaggc
gctgacttccgcgtttccagactttacgaaacacggaaacgaagaccattcatgttgttgctc
aggtcgcagacgttttgcagcagcagtcgcttcacgttcgctcgcgtatcggtgattcattctg
ctaaccagtaaggcaaccccgccagcctagccgggtcctcaacgacaggagcacgatcatgcgc
acccgtggggccgccatgccggcgataatggcctgcttctcgccgaaacgtttggtggcgggac
cagtgacgaaggcttgagcgagggcgtgcaagattccgaataccgcaagcgacaggccgatcat
cgtcgcgctccagcgaaagcggtcctcgccgaaaatgacccagagcgctgccggcacctgtcct
acgagttgcatgataaagaagacagtcataagtgcggcgacgatagtcatgcccgcgccacc
ggaaggagctgactgggttgaaggctctcaagggcatcggtcgagatcccggtgcctaatgagt
gagctaacttacattaattgcgttgcgctcactgcccgctttccagtcgggaaacctgtcgtgc
cagctgcattaatgaatcggccaacgcgcggggagaggcggtttgcgtattgggcgccagggtg
gtttttcttttcaccagtgagacgggcaacagctgattgcccttcaccgcctggccctgagaga
gttgcagcaagcggtccacgctggtttgccccagcaggcgaaaatcctgtttgatggtggttaa
cggcgggataaacatgagctgtcttcggtatcgtcgtatcccactaccgagatatccgcacca
acgcgcagcccggactcggtaatggcgcgcattgcgcccagcgccatctgatcgttggcaacca
gcatgcagtgggaacgatgccctcattcagcatttgcatggtttgttgaaaaccggacatggc
actccagtcgccttccgttccgctatcggctgaatttgattgcgagtgagatatttatgccag
ccagccagacgcagacgcgccgagacagaacttaatgggcccgctaacagcgcgatttgctggt
gacccaatgcgaccagatgctccacgcccagtcgcgtaccgtcttcatgggagaaaataatact
gttgatgggtgtctggtcagagacatcaagaaataacgccggaacattagtgcaggcagcttcc
acagcaatggcatcctggtcatccagcggatagttaatgatcagcccactgacgcgttgcgcga
gaagattgtgcaccgccgctttacaggcttcgacgccgcttcgttctaccatcgacaccaccac
gctggcacccagttgatcggcgcgagatttaatcgccgcgacaatttgcgacggcgcgtgcagg
gccagactggaggtggcaacgccaatcagcaacgactgtttgcccgccagttgttgtgccacgc
ggttgggaatgtaattcagctccgccatcgccgcttccactttttcccgcgttttcgcagaaac
gtggctggcctggttcaccacgcgggaaacggtctgataagagacaccggcatactctgcgaca
tcgtataacgttactggtttcacattcaccaccctgaattgactctcttccgggcgctatcatg
ccataccgcgaaaggttttgcgccattcgatggtgtccgggatctcgacgctctcccttatgcg
actcctgcattaggaagcagcccagtagtaggttgaggccgttgagcaccgccgccgcaaggaa
tggtgcatgcaaggagatggcgcccaacagtccccggccacggggcctgccaccatacccacg
ccgaaacaagcgctcatgagcccgaagtggcgagccgatcttccccatcggtgatgtcggcga
tataggcgccagcaaccgcacctgtggcgccggtgatgccggccacgatgcgtccggcgtagag
gatcgagatctcgatcccgcgaaattaatacgactcactatagggaattgtgagcggataaca
attcccctctagaaataattttgtttaactttaagaaggagatataccatggaagctcgtcgtt
ccgcaaactatcagccaaacctgtggaatttcgaattcctgcaatccctggagaacgacctgaa
agtggaaaagctggaggagaaagcgaccaaactggaggaagaagttcgctgcatgatcaaccgt
gtagacacccagccgctgtccctgctggagctgatcgacgatgtgcagcgcctgggtctgacct
acaaatttgaaaagacatcattaaagccctggaaaacatcgtactgctggacgaaaacaaaaa
```

Figure 66C

Nucleotide sequence of pDu50 gaacaaatctgacctgcacgcaaccgctctgtctttccgtctgctgcgtcagcacggtttcgag
gtttctcaggatgttttgagcgtttcaaggataaagaaggtggtttcagcggtgaactgaaag
gtgacgtccaaggcctgctgagcctgtatgaagcgtcttacctgggtttcgagggtgagaacct
gctggaggaggcgcgtacctttccatcacccacctgaagaacaacctgaaagaaggcattaat
accaaggttgcagaacaagtgagccacgccctggaactgccatatcaccagcgtctgcaccgtc
tggaggcacgttggttcctggataaatacgaaccgaaagaaccgcatcaccagctgctgctgga
gctggcgaagctggattttaacatggtacagaccctgcaccagaaagagctgcaagatctgtcc
cgctggtggaccgagatgggcctggctagcaaactggattttgtacgcgaccgcctgatggaag
tttatttctgggcactgggtatggcgccagacccgcagtttggtgaatgtcgcaaagctgttac
taaaatgtttggtctggtgacgatcatcgatgacgtgtatgacgtttatggcactctggacgaa
ctgcaactgttcaccgatgctgtagagcgctgggacgttaacgctattaacaccctgccggact
atatgaaactgtgtttcctggcactgtacaacaccgttaacgacacgtcctattctattctgaa
agagaaaggtcataacaacctgtcctatctgacgaaaagctggcgtgaactgtgcaaagccttt
ctgcaagaggcgaaatggtccaacaacaaaattatcccggctttctccaagtacctggaaaacg
ccagcgtttcctcctccggtgtagcgctgctggcgcgtcttacttttccgtatgccagcagca
ggaagacatctccgaccacgcgctgcgttccctgaccgacttccatggtctggtgcgttctagc
tgcgttatcttccgcctgtgcaacgatctggccacctctgcggcggagctggaacgtggcgaga
ctaccaattctatcattagctacatgcacgaaaacgatggtaccagcgaggaacaggcccgcga
agaactgcgtaaactgatcgacgccgaatggaaaaagatgaatcgtgaacgcgttagcgactcc
accctgctgcctaaagcgttcatggaaatcgcagttaacatggcacgtgtttccactgcacct
accagtatggcgatggtctgggtcgcccagactacgcgactgaaaaccgcatcaaactgctgct
gattgacccttttccgattaaccagctgatgtatgtctaactgcagggatccgaattcgagctc
cgtcgacaagcttgcggccgcac

Figure 67

Amino acid sequence of kudzu TRC (-4) (SEQ ID NO:152)

```
MEHNSRRSANYQPNLWNFEFLQSLENDLKVEKLEEKATKLEEEVRCMINRVDTQPLSLLELIDD
VQRLGLTYKFEKDIIKALENIVLLDENKKNKSDLHATALSFRLLRQHGFEVSQDVFERFKDKEG
GFSGELKGDVQGLLSLYEASYLGFEGENLLEEARTFSITHLKNNLKEGINTKVAEQVSHALELP
YHQRLHRLSARWFLDKYEPKEPHHQLLLELAKLDFNMVQTLHQKELQDLSRWWTEMGLASKLDF
VRDRLMEVYFWALGMAPDPQFGECRKAVTKMFGLVTIIDDVYDVYGTLDELQLFTDAVERWDVN
AINTLPDYMKLCFLALYNTVNDTSYSILKEKGHNNLSYLTKSWRELCKAFLQEAKWSNNKIIPA
FSKYLENASVSSSGVALLAPSYFSVCQQQEDISDHALRSLTDFHGLVRSSCVIPRLCNDLATSA
AELERGETTNSIISYMHENDGTSEEQAREELRKLIDAEWKKMNRERVSDSTLLPKAFMEIAVNM
ARVSHCTYQYGDGLGRPDYATENRIKLLLIDPFPINQLMYV
```

Figure 68A

Nucleotide sequence of pDu50-4 (SEQ ID NO:153)

tcgagcaccaccaccaccaccactgagatccggctgctaacaaagcccgaaaggaagctgagtt
ggctgctgccaccgctgagcaataactagcataaccccttggggcctctaaacgggtcttgagg
ggttttttgctgaaaggaggaactatatccggattggcgaatgggacgcgccctgtagcggcgc
attaagcgcggcgggtgtggtggttacgcgcagcgtgaccgctacacttgccagcgccctagcg
cccgctcctttcgctttcttcccttcctttctcgccacgttcgccggctttccccgtcaagctc
taaatcggggctccctttagggttccgatttagtgctttacggcacctcgaccccaaaaaact
tgattagggtgatggttcacgtagtgggccatcgccctgatagacggttttcgccctttgacg
ttggagtccacgttctttaatagtggactcttgttccaaactggaacaacactcaaccctatct
cggtctattcttttgatttataagggattttgccgatttcggcctattggttaaaaaatgagct
gatttaacaaaatttaacgcgaattttaacaaatattaacgtttacaatttcaggtggcact
tttcggggaaatgtgcgcggaacccctatttgtttatttttctaaatacattcaaatatgtatc
cgctcatgaattaattcttagaaaaactcatcgagcatcaaatgaaactgcaatttattcatat
caggattatcaataccatattttgaaaaagccgtttctgtaatgaaggagaaaactcaccgag
gcagttccataggatggcaagatcctggtatcggtctgcgattccgactcgtccaacatcaata
caaccattaatttcccctcgtcaaaaataaggttatcaagtgagaaatcaccatgagtgacga
ctgaatccggtgagaatggcaaaagtttatgcatttctttccagacttgttcaacaggccagcc
attacgctcgtcatcaaaatcactcgcatcaaccaaaccgttattcattcgtgattgcgcctga
gcgagacgaaatacgcgatcgctgttaaaaggacaattacaaacaggaatcgaatgcaaccggc
gcaggaacactgccagcgcatcaacaatatttcacctgaatcaggatattcttctaatacctg
gaatgctgttttcccggggatcgcagtggtgagtaaccatgcatcatcaggagtacggataaaa
tgcttgatggtcggaagaggcataaattccgtcagccagtttagtctgaccatctcatctgtaa
catcattggcaacgctacctttgccatgtttcagaaacaactctggcgcatcgggcttcccata
caatcgatagattgtcgcacctgattgcccgacattatcgcgagcccatttatacccatataaa
tcagcatccatgttggaatttaatcgcggcctagagcaagacgtttcccgttgaatatggctca
taacaccccttgtattactgtttatgtaagcagacagttttattgttcatgaccaaaatccctt
aacgtgagttttcgttccactgagcgtcagaccccgtagaaaagatcaaaggatcttcttgaga
tccttttttctgcgcgtaatctgctgcttgcaaacaaaaaaaccaccgctaccagcggtggtt
tgtttgccggatcaagagctaccaactctttttccgaaggtaactggcttcagcagagcgcaga
taccaaatactgtccttctagtgtagccgtagttaggccaccacttcaagaactctgtagcacc
gcctacatacctcgctctgctaatcctgttaccagtggctgctgccagtggcgataagtcgtgt
cttaccgggttggactcaagacgatagttaccggataaggcgcagcggtcgggctgaacggggg
gttcgtgcacacagcccagcttggagcgaacgacctacaccgaactgagatacctacagcgtga
gctatgagaaagcgccacgcttcccgaagggagaaaggcggacaggtatccggtaagcggcagg
gtcggaacaggagagcgcacgagggagcttccagggggaaacgcctggtatctttatagtcctg
tcgggtttcgccacctctgacttgagcgtcgatttttgtgatgctcgtcaggggggcggagcct
atggaaaaacgccagcaacgcggcctttttacggttcctggccttttgctggccttttgctcac
atgttctttcctgcgttatcccctgattctgtggataaccgtattaccgcctttgagtgagctg
ataccgctcgccgcagccgaacgaccgagcgcagcgagtcagtgagcgaggaagcggaagagcg
cctgatgcggtattttctccttacgcatctgtgcggtatttcacaccgcatatatggtgcactc
tcagtacaatctgctctgatgccgcatagttaagccagtatacactccgctatcgctacgtgac
tgggtcatggctgcgccccgacacccgccaacacccgctgacgcgccctgacgggcttgtctgc
tcccggcatccgcttacagacaagctgtgaccgtctccgggagctgcatgtgtcagaggttttc
accgtcatcaccgaaacgcgcgaggcagctgcggtaaagctcatcagcgtggtcgtgaagcgat

Figure 68B

Nucleotide sequence of pDu50-4

```
tcacagatgtctgcctgttcatccgcgtccagctcgttgagtttctccagaagcgttaatgtct
ggcttctgataaagcgggccatgttaagggcggttttttcctgtttggtcactgatgcctccgt
gtaaggggatttctgttcatggggtaatgataccgatgaaacgagagaggatgctcacgata
cgggttactgatgatgaacatgcccggttactggaacgttgtgagggtaaacaactggcggtat
ggatgcggcgggaccagagaaaaatcactcagggtcaatgccagcgcttcgttaatacagatgt
aggtgttccacagggtagccagcagcatcctgcgatgcagatccggaacataatggtgcagggc
gctgacttccgcgtttccagactttacgaaacacggaaaccgaagaccattcatgttgttgctc
aggtcgcagacgttttgcagcagcagtcgcttcacgttcgctcgcgtatcggtgattcattctg
ctaaccagtaaggcaaccccgccagcctagccgggtcctcaacgacaggagcacgatcatgcgc
acccgtggggccgccatgccggcgataatggcctgcttctcgccgaaacgtttggtggcgggac
cagtgacgaaggcttgagcgagggcgtgcaagattccgaataccgcaagcgacaggccgatcat
cgtcgcgctccagcgaaagcggtcctcgccgaaaatgacccagagcgctgccggcacctgtcct
acgagttgcatgataaagaagacagtcataagtgcggcgacgatagtcatgccccgcgccacc
ggaaggagctgactgggttgaaggctctcaagggcatcggtcgagatcccggtgcctaatgagt
gagctaacttacattaattgcgttgcgctcactgcccgctttccagtcgggaaacctgtcgtgc
cagctgcattaatgaatcggccaacgcgcggggagaggcggtttgcgtattgggcgccaggtg
gttttcttttcaccagtgagacgggcaacagctgattgcccttcaccgcctggccctgagaga
gttgcagcaagcggtccacgctggtttgccccagcaggcgaaaatcctgtttgatggtggttaa
cggcgggatataacatgagctgtcttcggtatcgtcgtatcccactaccgagatatccgcacca
acgcgcagcccggactcggtaatggcgcgcattgcgcccagcgccatctgatcgttggcaacca
gcatcgcagtgggaacgatgccctcattcagcatttgcatggtttgttgaaaaccggacatggc
actccagtcgccttcccgttccgctatcggctgaatttgattgcgagtgagatatttatgccag
ccagccagacgcagacgcgccgagacagaacttaatgggcccgctaacagcgcgatttgctggt
gacccaatgcgaccagatgctccacgcccagtcgcgtaccgtcttcatgggagaaaataatact
gttgatgggtgtctggtcagagacatcaagaaataacgccggaacattagtgcaggcagcttcc
acagcaatggcatcctggtcatccagcggatagttaatgatcagcccactgacgcgttgcgcga
gaagattgtgcaccgccgctttacaggcttcgacgccgcttcgttctaccatcgacaccaccac
gctggcacccagttgatcggcgcgagatttaatcgccgcgacaatttgcgacggcgcgtgcagg
gccagactggaggtggcaacgccaatcagcaacgactgtttgcccgccagttgttgtgccacgc
ggttgggaatgtaattcagctccgccatcgccgcttccactttttcccgcgttttcgcagaaac
gtggctggctggttcaccacgcgggaaacggtctgataagagacaccggcatactctgcgaca
tcgtataacgttactggtttcacattcaccaccctgaattgactctcttccgggcgctatcatg
ccataccgcgaaaggttttgcgccattcgatggtgtccgggatctcgacgctctccttatgcg
actcctgcattaggaagcagcccagtagtaggttgaggccgttgagcaccgccgccgcaaggaa
tggtgcatgcaaggagatggcgccaacagtccccggccacggggcctgccaccatacccacg
ccgaaacaagcgctcatgagcccgaagtggcgagccgatcttcccatcggtgatgtcggcga
tataggcgccagcaaccgcacctgtggcgccggtgatgccggccacgatgcgtccggcgtagag
gatcgagatctcgatccgcgaaattaatacgactcactatagggaattgtgagcggataaca
attccctctagaaataattttgtttaactttaagaaggagatataccatggagcataattccc
gtcgttccgcaaactatcagccaaacctgtggaattcgaattcctgcaatccctggagaacga
cctgaaagtggaaagctggaggagaaagcgaccaaactggaggaagaagttcgctgcatgatc
aaccgtgtagacacccagccgctgtccctgctggagctgatcgacgatgtgcagcgcctgggtc
tgacctacaaatttgaaaagacatcattaaagccctggaaaacatcgtactgctggacgaaaa
```

Figure 68C

Nucleotide sequence of pDu50-4 caaaaagaacaaatctgacctgcacgcaaccgctctgtctttccgtctgctgcgtcagcacggt
ttcgaggtttctcaggatgtttttgagcgtttcaaggataaagaaggtggtttcagcggtgaac
tgaaaggtgacgtccaaggcctgctgagcctgtatgaagcgtcttacctgggtttcgagggtga
gaacctgctggaggaggcgcgtacctttccatcacccacctgaagaacaacctgaaagaaggc
attaataccaaggttgcagaacaagtgagccacgccctggaactgccatatcaccagcgtctgc
accgtctggaggcacgttggttcctggataaatacgaaccgaaagaaccgcatcaccagctgct
gctggagctggcgaagctggattttaacatggtacagaccctgcaccagaaagagctgcaagat
ctgtcccgctggtggaccgagatgggcctggctagcaaactggattttgtacgcgaccgcctga
tggaagtttattctgggcactgggtatggcgccagacccgcagtttggtgaatgtcgcaaagc
tgttactaaaatgtttggtctggtgacgatcatcgatgacgtgtatgacgtttatggcactctg
gacgaactgcaactgttcaccgatgctgtagagcgctgggacgttaacgctattaacaccctgc
cggactatatgaaactgtgtttcctggcactgtacaacaccgttaacgacacgtcctattctat
tctgaaagagaaaggtcataacaacctgtcctatctgacgaaaagctggcgtgaactgtgcaaa
gcctttctgcaagaggcgaaatggtccaacaacaaaattatcccggcttctccaagtacctgg
aaaacgccagcgtttcctcctccggtgtagcgctgctggcgccgtcttacttttccgtatgcca
gcagcaggaagacatctccgaccacgcgctgcgttccctgaccgacttccatggtctggtgcgt
tctagctgcgttatcttccgcctgtcaacgatctggccacctctgcggcggagctggaacgtg
gcgagactaccaattctatcattagctacatgcacgaaaacgatggtaccagcgaggaacaggc
ccgcgaagaactgcgtaaactgatcgacgcgaatggaaaaagatgaatcgtgaacgcgttagc
gactccaccctgctgcctaaagcgttcatggaaatcgcagttaacatggcacgtgtttcccact
gcacctaccagtatggcgatggtctggtcgcccagactacgcgactgaaaaccgcatcaaact
gctgctgattgacccttttccgattaaccagctgatgtatgtctaactgcagggatccgaattc
gagctccgtcgacaagcttgcggccgcac Figure 69
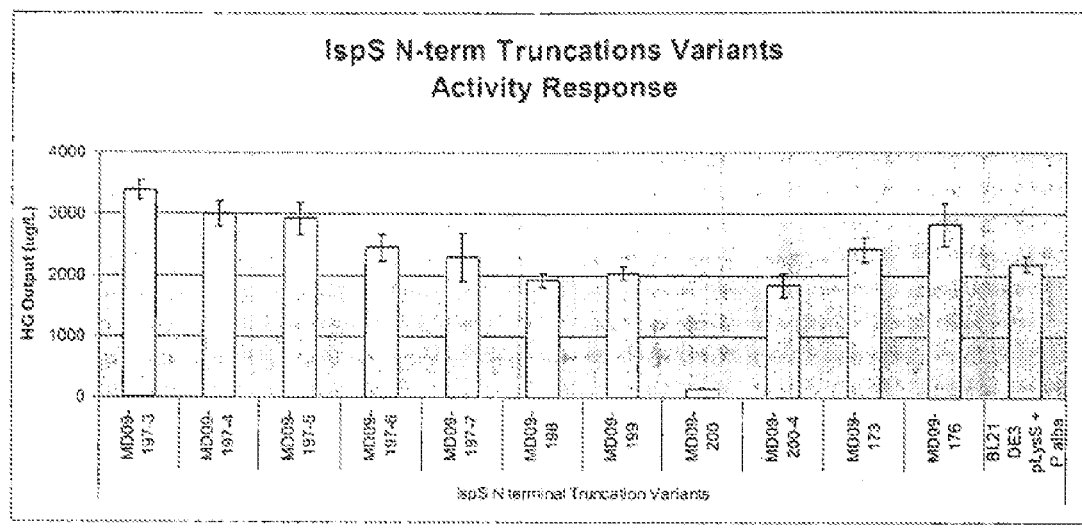
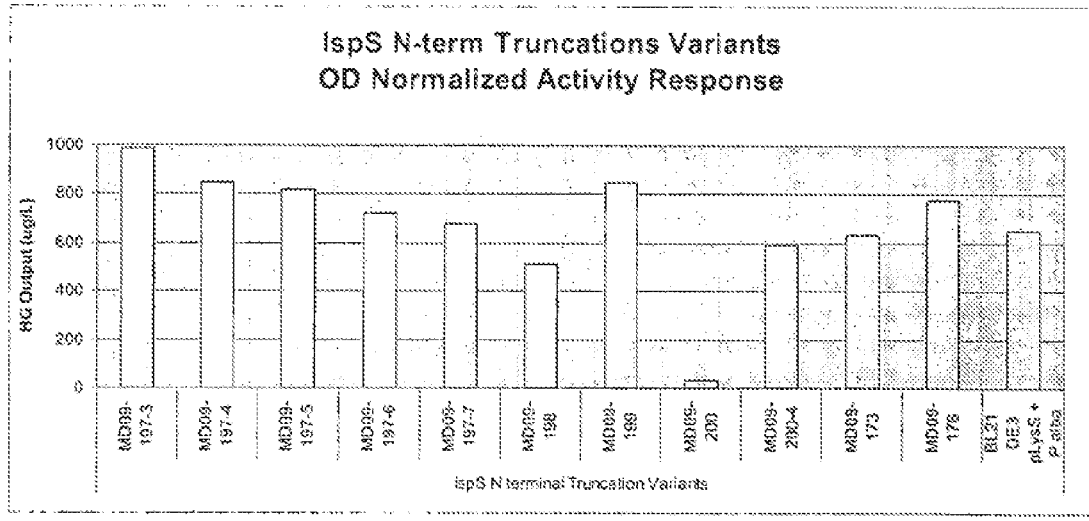

Figure 72A

Nucleotide sequence of p9795 (SEQ ID NO:154)

tagaaaaactcatcgagcatcaaatgaaactgcaatttattcatatcaggattatcaat
accatattttgaaaaagccgtttctgtaatgaaggagaaaactcaccgaggcagttcc
ataggatggcaagatcctggtatcggtctgcgattccgactcgtccaacatcaatacaa
cctattaatttcccctcgtcaaaaataaggttatcaagtgagaaatcaccatgagtgac
gactgaatccggtgagaatggcaaaagtttatgcattctttccagacttgttcaacag
gccagccattacgctcgtcatcaaaatcactcgcatcaaccaaaccgttattcattcgt
gattgcgcctgagcgaggcgaaatacgcgatcgctgttaaaaggacaattacaaacagg
aatcgagtgcaaccggcgcaggaacactgccagcgcatcaacaatatttcacctgaat
caggatattcttctaatacctggaacgctgttttccggggatcgcagtggtgagtaac
catgcatcatcaggagtacggataaaatgcttgatggtcggaagtggcataaattcgt
cagccagtttagtctgaccatctcatcbgtaacatcattggcaacgctacctttgccat
gtttcagaaacaactctggcgcatcgggcttcccatacaagcgatagattgtcgcacct
gattgcccgacattatcgcgagcccatttatacccatataaatcagcatccatgttgga
atttaatcgcggcctcgacgtttcccgttgaatatggctcatattcttccttttcaat
attattgaagcatttatcagggttattgtctcatgagcggatacatatttgaatgtatt
tagaaaaataaacaaataggggtcagtgttacaaccaattaaccaattctgaacattat
cgcgagcccatttatacctgaatatggctcataacaccccttgtttgcctggcggcagt
agcgcggtggtcccacctgacccatgccgaactcagaagtgaaacgccgtagcgccga
tggtagtgtggggactccccatgcgagagtagggaactgccaggcatcaaataaaacga
aaggctcagtcgaaagactgggcctttcgcccgggctaattagggggtgtcgcccttc
gattgacgctgcagttagacatacatcagctggttaatcgggaaagggtcaatcagcag
cagtttgatgcggttttcagtcgcgtagtctgggcgacccagaccatcgccatactggt
aggtgcagtgggaaacacgtgccatgttaactgcgattccatgaacgctttaggcagc
agggtggagtcgctaacgcgttcacgattcatcttttccattcggcgtcgatcagttt
acgcagttcttcgcgggctgttcctcgctggtaccatcgttttcgtgcatgtagctaa
tgatagaattggtagtctcgccacgttccagctccgccgcagaggtggccagatcgttg
cacaggcggaagataacgcagctagaacgcaccagaccatggaagtcggtcagggaacg
cagcgcgtggtcggagatgtcttcctgctgctggcatacggaaaagtaagacggcgcca
gcagcgctacaccggaggaggaaacgctggcgttttccaggtacttggagaaagccggg
ataattttgttgttggaccatttcgcctcttgcagaaaggctttgcacagttcacgcca
gcttttcgtcagataggacaggttgttatgacctttctctttcagaatagaataggacg
tgtcgttaacggtgttgtacagtgccaggaaacacagtttcatatagtccggcagggtg
ttaatagcgttaacgtcccagcgctctacagcatcggtgaacagttgcagttcgtccag
agtgccataaacgtcatacacgtcatcgatgatcgtcaccagaccaaacatttagtaa
cagctttgcgacattcaccaaactgcgggtctggcgccatacccagtgcccagaaataa
acttccatcaggcggtcgcgtacaaaatccagtttgctagccaggccatctcggtcca
ccagcgggacagatcttgcagctctttctggtgcagggtctgtaccatgttaaaatcca
gcttcgccagctccagcagcagctggtgatgcggttcttcggttcgtatttatccagg
aaccaacgtgcctccagacggtgcagacgctggtgatatggcagttccagggcgtggct
cacttgttctgcaaccttggtattaatgccttctttcaggttgttcttcaggtgggtga
tggaaaaggtacgcgcctcctccagcaggttctcaccctcgaaacccaggtaagacgct
tcatacaggctcagcaggccttggacgtcacctttcagttcaccgctgaaaccaccttc
tttatccttgaaacgctcaaaaacatcctgagaaacctcgaaaccgtgctgacgcagca

Figure 72B

Nucleotide sequence of p9795

```
gacggaaagacagagcggttgcgtgcaggtcagatttgttcttttgttttcgtccagc
agtacgatgttttccagggctttaatgatgtcttttcaaatttgtaggtcagaccag
gcgctgcacatcgtcgatcagctccagcagggacagcggctgggtgtctacacggtta
tcatgcagcgaacttcttcctccagtttggtcgctttctcctccagcttttccactttc
aggtcgttctccagggattgcaggaattcgaaattccacaggtttggctgatagtttgc
ggaacgacgggaattatgctcggtaatctgagtaaattgagaagaggtcgcacacatgt
tcagcgacaagggcgacacaaaatttattctaaatgcataataaatactgataacatct
tatagtttgtattatattttgtattatcgttgacatgtataattttgatatcaaaact
gatttccctttattattttcgagatttatttcttaattctctttaacaaactagaaa
tattgtatatacaaaaatcataataatagatgaatagtttaattataggtgttcatc
aatcgaaaagcaacgtatcttatttaaagtgcgttgcttttttctcatttataaggtt
aaataattctcatatatcaagcaaagtgacaggcgcccttaaatattctgacaaatgct
ctttccctaaactcccccataaaaaaaccgccgaagcgggttttacgttatttgcg
gattaacgattactcgttatcagaaccgcccaggggggcccgagcttaagactggccgtc
gttttacaacacagaaagagtttgtagaaacgcaaaaaggccatccgtcagggccttc
tgcttagtttgatgcctggcagttccctactctcgccttccgcttcctcgctcactgac
tcgctgcgctcggtcgttcggctgcggcgagcggtatcagctcactcaaaggcggtaat
acggttatccacagaatcaggggataacgcaggaaagaacatgtgagcaaaaggccagc
aaaaggccaggaaccgtaaaaaggccgcgttgctggcgtttttccataggctccgccc
cctgacgagcatcacaaaaatcgacgctcaagtcagaggtggcgaaacccgacaggact
ataaagataccaggcgtttccccctggaagctccctcgtgcgctctcctgttccgaccc
tgccgcttaccggatacctgtccgcctttctcccttcgggaagcgtggcgctttctcat
agctcacgctgtaggtatctcagttcggtgtaggtcgttcgctccaagctgggctgtgt
gcacgaaccccccgttcagcccgaccgctgcgccttatccggtaactatcgtcttgagt
ccaacccggtaagacacgacttatcgccactggcagcagccactggtaacaggattagc
agagcgaggtatgtaggcggtgctacagagttcttgaagtggtgggctaactacggcta
cactagaagaacagtatttggtatctgcgctctgctgaagccagttaccttcggaaaaa
gagttggtagctcttgatccggcaaacaaaccaccgctggtagcggtggtttttttgtt
tgcaagcagcagattacgcgcagaaaaaaggatctcaagaagatcctttgatcttttc
tacggggtctgacgctcagtggaacgacgcgcgcgtaactcacgttaagggatttggt
catgagcttgcgccgtccgtcaagtcagcgtaatgctctgcttt
```

Figure 74A

Nucleotide sequence of pTrcKudzu (SEQ ID NO:155)

```
gtttgacagcttatcatcgactgcacggtgcaccaatgcttctggcgtcaggcagccat
cggaagctgtggtatggctgtgcaggtcgtaaatcactgcataattcgtgtcgctcaag
gcgcactcccgttctggataatgttttttgcgccgacatcataacggttctggcaaata
ttctgaaatgagctgttgacaattaatcatccggctcgtataatgtgtggaattgtgag
cggataacaatttcacacaggaaacagcgccgctgagaaaaagcgaagcggcactgctc
tttaacaatttatcagacaatctgtgtgggcactcgaccggaattatcgattaacttta
ttattaaaaattaaagaggtatatattaatgtatcgattaaataaggaggaataaacca
tgtgtgcgacctcttctcaattactcagattaccgagcataattcccgtcgttccgca
aactatcagccaaacctgtggaatttcgaattcctgcaatccctggagaacgacctgaa
agtggaaaagctggaggagaaagcgaccaaactggaggaagaagttcgctgcatgatca
accgtgtagacacccagccgctgtccctgctggagctgatcgacgatgtgcagcgcctg
ggtctgacctacaaatttgaaaagacatcattaaagccctggaaaacatcgtactgct
ggacgaaaacaaaagaacaaatctgacctgcacgcaaccgctctgtctttccgtctgc
tgcgtcagcacggtttcgaggtttctcaggatgttttgagcgtttcaaggataaagaa
ggtggtttcagcggtgaactgaaaggtgacgtccaaggcctgctgagcctgtatgaagc
gtcttacctgggtttcgaggtgagaacctgctggaggaggcgcgtaccttttccatca
cccacctgaagaacaacctgaaagaaggcattaataccaaggttgcagaacaagtgagc
cacgccctggaactgccatatcaccagcgtctgcaccgtctggaggcacgttggttcct
ggataaatacgaaccgaaagaaccgcatcaccagctgctgctggagctggcgaagctgg
attttaacatggtacagaccctgcaccagaaagagctgcaagatctgtcccgctggtgg
accgagatgggcctggctagcaaactggattttgtacgcgaccgcctgatggaagttta
tttctgggcactgggtatggcgccagacccgcagtttggtgaatgtcgcaaagctgtta
ctaaaatgtttggtctggtgacgatcatcgatgacgtgtatgacgtttatggcactctg
gacgaactgcaactgttcaccgatgctgtagagcgctgggacgttaacgctattaacac
cctgccggactatatgaaactgtgtttcctggcactgtacaacaccgttaacgacacgt
cctattctattctgaaagagaaaggtcataacaacctgtcctatctgacgaaaagctgg
cgtgaactgtgcaaagcctttctgcaagaggcgaaatggtccaacaacaaaattatccc
ggctttctccaagtacctggaaaacgccagcgtttcctcctccggtgtagcgctgctgg
cgccgtcttactttccgtatgccagcagcaggaagacatctccgaccacgcgctgcgt
tccctgaccgacttccatggtctggtgcgttctagctgcgttatcttccgcctgtgcaa
cgatctggccacctctgcggcggagctggaacgtggcgagactaccaattctatcatta
gctacatgcacgaaaacgatggtaccagcgaggaacaggcccgcgaagaactgcgtaaa
ctgatcgacgccgaatggaaaaagatgaatcgtgaacgcgttagcgactccaccctgct
gcctaaagcgttcatggaaatcgcagttaacatggcacgtgtttcccactgcacctacc
agtatggcgatggtctgggtcgcccagactacgcgactgaaaaccgcatcaaactgctg
ctgattgacccttttccgattaaccagctgatgtatgtctaactgcagctggtaccata
tgggaattcgaagctttctagaacaaaaactcatctcagaagaggatctgaatagcgcc
gtcgaccatcatcatcatcatcattgagtttaaacggtctccagcttggctgttttggc
ggatgagagaagattttcagcctgatacagattaaatcagaacgcagaagcggtctgat
aaaacagaatttgcctggcggcagtagcgcggtggtcccacctgacccatgccgaact
cagaagtgaaacgccgtagcgccgatggtagtgtggggtctccccatgcgagagtaggg
aactgccaggcatcaaataaaacgaaaggctcagtcgaaagactgggcctttcgtttta
tctgttgtttgtcggtgaacgctctcctgagtaggacaaatccgccgggagcggatttg
```

Figure 74B

Nucleotide sequence of pTrcKudzu

```
aacgttgcgaagcaacggcccggagggtggcgggcaggacgccgccataaactgccag
gcatcaaattaagcagaaggccatcctgacggatggcctttttgcgtttctacaaactc
ttttgtttattttctaaatacattcaaatatgtatccgctcatgagacaataaccct
gataaatgcttcaataatattgaaaaaggaagagtatgagtattcaacatttccgtgtc
gcccttattcctttttgcggcattttgccttcctgtttttgctcacccagaaacgct
ggtgaaagtaaaagatgctgaagatcagttgggtgcacgagtgggttacatcgaactgg
atctcaacagcggtaagatccttgagagttttcgccccgaagaacgttttccaatgatg
agcactttaaagttctgctatgtggcgcggtattatcccgtgttgacgccgggcaaga
gcaactcggtcgccgcatacactattctcagaatgacttggttgagtactcaccagtca
cagaaaagcatcttacggatggcatgacagtaagagaattatgcagtgctgccataacc
atgagtgataacactgcggccaacttacttctgacaacgatcggaggaccgaaggagct
aaccgcttttttgcacaacatggggatcatgtaactcgccttgatcgttgggaaccgg
agctgaatgaagccataccaaacgacgagcgtgacaccacgatgcctgtagcaatggca
acaacgttgcgcaaactattaactggcgaactacttactctagcttcccggcaacaatt
aatagactggatggaggcggataaagttgcaggaccacttctgcgctcggcccttccgg
ctggctggtttattgctgataaatctggagccggtgagcgtgggtctcgcggtatcatt
gcagcactggggccagatggtaagccctcccgtatcgtagttatctacacgacggggag
tcaggcaactatggatgaacgaaatagacagatcgctgagataggtgcctcactgatta
agcattggtaactgtcagaccaagtttactcatatactttagattgatttaaaactt
cattttaatttaaaaggatctaggtgaagatcctttttgataatctcatgaccaaaat
cccttaacgtgagttttcgttccactgagcgtcagaccccgtagaaaagatcaaaggat
cttcttgagatcctttttttctgcgcgtaatctgctgcttgcaaacaaaaaaaccaccg
ctaccagcggtggtttgtttgccggatcaagagctaccaactctttttccgaaggtaac
tggcttcagcagagcgcagataccaaatactgtccttctagtgtagccgtagttaggcc
accacttcaagaactctgtagcaccgcctacatacctcgctctgctaatcctgttacca
gtggctgctgccagtggcgataagtcgtgtcttaccgggttggactcaagacgatagtt
accggataaggcgcagcggtcgggctgaacggggggttcgtgcacacagcccagcttgg
agcgaacgacctacaccgaactgagatacctacagcgtgagctatgagaaagcgccacg
cttcccgaagggagaaaggcggacaggtatccggtaagcggcagggtcggaacaggaga
gcgcacgagggagcttccaggggaaacgcctggtatctttatagtcctgtcgggtttc
gccacctctgacttgagcgtcgatttttgtgatgctcgtcaggggggcggagcctatgg
aaaaacgccagcaacgcggcctttttacggttcctggccttttgctggccttttgctca
catgttctttcctgcgttatccctgattctgtggataaccgtattaccgcctttgagt
gagctgataccgctcgccgcagccgaacgaccgagcgcagcgagtcagtgagcgaggaa
gcggaagagcgcctgatgcggtattttctccttacgcatctgtgcggtatttcacaccg
catatggtgcactctcagtacaatctgctctgatgccgcatagttaagccagtatacac
tccgctatcgctacgtgactgggtcatggctgcgccccgacacccgccaacacccgctg
acgcgccctgacgggcttgtctgctcccggcatccgcttacagacaagctgtgaccgtc
tccggagctgcatgtgtcagaggttttcaccgtcatcaccgaaacgcgcgaggcagca
gatcaattcgcgcgcgaaggcgaagcggcatgcatttacgttgacaccatcgaatggtg
caaaacctttcgcggtatggcatgatagcgcccggaagagagtcaattcagggtggtga
atgtgaaaccagtaacgttatacgatgtcgcagagtatgccggtgtctcttatcagacc
gtttcccgcgtggtgaaccaggccagccacgtttctgcgaaaacgcgggaaaaagtgga
```

Figure 74C

Nucleotide sequence of pTrcKudzu agcggcgatggcggagctgaattacattcccaaccgcgtggcacaacaactggcgggca
aacagtcgttgctgattggcgttgccacctccagtctggccctgcacgcgccgtcgcaa
attgtcgcggcgattaaatctcgcgccgatcaactgggtgccagcgtggtggtgtcgat
ggtagaacgaagcggcgtcgaagcctgtaaagcggcggtgcacaatcttctcgcgcaac
gcgtcagtgggctgatcattaactatccgctggatgaccaggatgccattgctgtggaa
gctgcctgcactaatgttccggcgttatttcttgatgtctctgaccagacacccatcaa
cagtattatttctcccatgaagacggtacgcgactgggcgtggagcatctggtcgcat
tgggtcaccagcaaatcgcgctgttagcgggcccattaagttctgtctcggcgcgtctg
cgtctggctggctggcataaatatctcactcgcaatcaaattcagccgatagcggaacg
ggaaggcgactggagtgccatgtccggttttcaacaaaccatgcaaatgctgaatgagg
gcatcgttcccactgcgatgctggttgccaacgatcagatggcgctgggcgcaatgcgc
gccattaccgagtccggctgcgcgttggtgcggatatctcggtagtgggatacgacga
taccgaagacagctcatgttatatcccgccgtcaaccaccatcaaacaggatttttcgcc
tgctggggcaaaccagcgtggaccgcttgctgcaactctctcagggccaggcggtgaag
ggcaatcagctgttgcccgtctcactggtgaaaagaaaaaccaccctggcgcccaatac
gcaaaccgcctctccccgcgcgttggccgattcattaatgcagctggcacgacaggttt
cccgactggaaagcgggcagtgagcgcaacgcaattaatgtgagttagcgcgaattgat
ctg

Figure 76A

Nucleotide sequence of pMAL-C4X (SEQ ID NO:156)

```
ccgacaccatcgaatggtgcaaaacctttcgcggtatggcatgatagcgcccggaagag
agtcaattcagggtggtgaatgtgaaaccagtaacgttatacgatgtcgcagagtatgc
cggtgtctcttatcagaccgtttcccgcgtggtgaaccaggccagccacgtttctgcga
aaacgcgggaaaaagtggaagcggcgatggcggagctgaattacattcccaaccgcgtg
gcacaacaactggcgggcaaacagtcgttgctgattggcgttgccacctccagtctggc
cctgcacgcgccgtcgcaaattgtcgcggcgattaaatctcgcgccgatcaactgggtg
ccagcgtggtggtgtcgatggtagaacgaagcggcgtcgaagcctgtaaagcggcggtg
cacaatcttctcgcgcaacgcgtcagtggctgatcattaactatccgctggatgacca
ggatgccattgctgtggaagctgcctgcactaatgttccggcgttatttcttgatgtct
ctgaccagacacccatcaacagtattatttctcccatgaagacggtacgcgactgggc
gtggagcatctggtcgcattgggtcaccagcaaatcgcgctgttagcgggcccattaag
ttctgtctcggcgcgtctgcgtctggctggctggcataaatatctcactcgcaatcaaa
ttcagccgatagcggaacgggaaggcgactggagtgccatgtccggttttcaacaaacc
atgcaaatgctgaatgagggcatcgttcccactgcgatgctggttgccaacgatcagat
ggcgctgggcgcaatgcgcgccattaccgagtccgggctgcgcgttggtgcggatatct
cggtagtgggatacgacgataccgaagacagctcatgttatatcccgcgttaaccacc
atcaaacaggattttcgcctgctggggcaaaccagcgtggaccgcttgctgcaactctc
tcagggccaggcggtgaagggcaatcagctgttgcccgtctcactggtgaaagaaaaa
ccacccctggcgcccaatacgcaaaccgcctctcccgcgcgttggccgattcattaatg
cagctggcacgacaggtttcccgactggaaagcgggcagtgagcgcaacgcaattaatg
taagttagctcactcattaggcacaattctcatgtttgacagcttatcatcgactgcac
ggtgcaccaatgcttctggcgtcaggcagccatcggaagctgtggtatggctgtgcagg
tcgtaaatcactgcataattcgtgtcgctcaaggcgcactcccgttctggataatgttt
tttgcgccgacatcataacggttctggcaaatattctgaaatgagctgttgacaattaa
tcatcggctcgtataatgtgtggaattgtgagcggataacaatttcacacaggaaacag
ccagtccgtttaggtgttttcacgagcacttcaccaacaaggaccatagcatatgaaaa
tcgaagaaggtaaactggtaatctggattaacggcgataaaggctataacggtctcgct
gaagtcggtaagaaattcgagaaagataccggaattaaagtcaccgttgagcatccgga
taaactggaagagaaattcccacaggttgcggcaactggcgatggccctgacattatct
tctgggcacacgaccgctttggtggctacgctcaatctggcctgttggctgaaatcacc
ccggacaaagcgttccaggacaagctgtatccgtttacctgggatgccgtacgttacaa
cggcaagctgattgcttacccgatcgctgttgaagcgttatcgctgatttataacaaag
atctgctgccgaacccgccaaaaacctgggaagagatcccggcgctggataaagaactg
aaagcgaaaggtaagagcgcgctgatgttcaacctgcaagaacgtacttcacctggcc
gctgattgctgtgacggggttatgcgttcaagtatgaaaacggcaagtacgacatta
aagacgtggcgtggataacgctggcgaaagcgggtctgaccttcctggttgacctg
attaaaaacaaacacatgaatgcagacaccgattactccatcgcagaagctgcctttaa
taaaggcgaaacagcgatgaccatcaacggcccgtgggcatggtccaacatcgacacca
gcaaagtgaattatggtgtaacggtactgccgaccttcaagggtcaaccatccaaaccg
ttcgttggcgtgctgagcgcaggtattaacgccgccagtccgaacaaagagctggcaaa
agagttcctcgaaaactatctgctgactgatgaaggtctggaagcggttaataaagaca
aaccgctgggtgccgtagcgctgaagtcttacgaggaagagttggtgaaagatccgcgg
attgccgccactatggaaaacgcccagaaaggtgaaatcatgccgaacatcccgcagat
```

Figure 76B

Nucleotide sequence of pMAL-C4X

```
gtccgctttctggtatgccgtgcgtactgcggtgatcaacgccgccagcggtcgtcaga
ctgtcgatgaagccctgaaagacgcgcagactaattcgagctcgaacaacaacaacaat
aacaataacaacaacctcgggatcgagggaaggatttcagaattcggatcctctagagt
cgacctgcaggcaagcttggcactggccgtcgttttacaacgtcgtgactgggaaaacc
ctggcgttacccaacttaatcgccttgcagcacatccccctttcgccagctggcgtaat
agcgaagaggcccgcaccgatcgcccttcccaacagttgcgcagcctgaatggcgaatg
gcagcttggctgttttggcggatgagataagattttcagcctgatacagattaaatcag
aacgcagaagcggtctgataaaacagaatttgcctggcggcagtagcgcggtggtccca
cctgacccatgccgaactcagaagtgaaacgccgtagcgccgatggtagtgtggggtc
tccccatgcgagagtagggaactgccaggcatcaataaaacgaaaggctcagtcgaaa
gactgggcctttcgttttatctgttgtttgtcggtgaacgctctcctgagtaggacaaa
tccgccgggagcggatttgaacgttgcgaagcaacggcccggagggtggcgggcaggac
gcccgccataaactgccaggcatcaattaagcagaaggccatcctgacggatggcctt
tttgcgtttctacaaactcttttgtttatttttctaaatacattcaaatatgtatccg
ctcatgagacaataaccctgataaatgcttcaataatattgaaaaaggaagagtatgag
tattcaacatttccgtgtcgcccttattcccttttttgcggcattttgccttcctgttt
ttgctcacccagaaacgctggtgaaagtaaaagatgctgaagatcagttgggtgcacga
gtgggttacatcgaactggatctcaacagcggtaagatccttgagagttttcgccccga
agaacgttctccaatgatgagcacttttaaagttctgctatgtggcgcggtattatccc
gtgttgacgccgggcaagagcaactcggtcgccgcatacactattctcagaatgacttg
gttgagtactcaccagtcacagaaaagcatcttacggatggcatgacagtaagagaatt
atgcagtgctgccataaccatgagtgataacactgcggccaacttacttctgacaacga
tcggaggaccgaaggagctaaccgcttttttgcacaacatggggatcatgtaactcgc
cttgatcgttgggaaccggagctgaatgaagccataccaaacgacgagcgtgacaccac
gatgcctgtagcaatggcaacaacgttgcgcaaactattaactggcgaactacttactc
tagcttcccggcaacaattaatagactggatggaggcggataaagttgcaggaccactt
ctgcgctcggcccttccggctggctggtttattgctgataaatctggagccggtgagcg
tgggtctcgcggtatcattgcagcactggggccagatggtaagccctcccgtatcgtag
ttatctacacgacggggagtcaggcaactatggatgaacgaaatagacagatcgctgag
ataggtgcctcactgattaagcattggtaactgtcagaccaagtttactcatatatact
ttagattgatttaccccggttgataatcagaaaagccccaaaaacaggaagattgtata
agcaaatatttaaattgtaaacgttaatattttgttaaaattcgcgttaaattttgtt
aaatcagctcattttttaaccaataggccgaaatcggcaaaatcccttataaatcaaaa
gaatagaccgagatagggttgagtgttgttccagtttggaacaagagtccactattaaa
gaacgtggactccaacgtcaaagggcgaaaaaccgtctatcagggcgatggcccactac
gtgaaccatcacccaaatcaagttttttggggtcgaggtgccgtaaagcactaaatcgg
aaccctaaagggagcccccgatttagagcttgacggggaaagccggcgaacgtggcgag
aaaggaagggaagaaagcgaaaggagcgggcgctagggcgctggcaagtgtagcggtca
cgctgcgcgtaaccaccacacccgccgcgcttaatgcgccgctacagggcgcgtaaaag
gatctaggtgaagatcctttttgataatctcatgaccaaaatcccttaacgtgagttt
cgttccactgagcgtcagaccccgtagaaaagatcaaaggatcttcttgagatcctttt
tttctgcgcgtaatctgctgcttgcaaacaaaaaaaccaccgctaccagcggtggtttg
tttgccggatcaagagctaccaactcttttccgaaggtaactggcttcagcagagcgc
```

Figure 76C

Nucleotide sequence of pMAL-C4X agataccaaatactgtccttctagtgtagccgtagttaggccaccacttcaagaactct
gtagcaccgcctacatacctcgctctgctaatcctgttaccagtggctgctgccagtgg
cgataagtcgtgtcttaccgggttggactcaagacgatagttaccggataaggcgcagc
ggtcgggctgaacggggggttcgtgcacacagcccagcttggagcgaacgacctacacc
gaactgagatacctacagcgtgagctatgagaaagcgccacgcttcccgaagggagaaa
ggcggacaggtatccggtaagcggcagggtcggaacaggagagcgcacgagggagcttc
caggggaaacgcctggtatctttatagtcctgtcgggtttcgccacctctgacttgag
cgtcgattttgtgatgctcgtcaggggggcggagcctatggaaaaacgccagcaacgc
ggccttttacggttcctggccttttgctggccttttgctcacatgttctttcctgcgt
tatcccctgattctgtggataaccgtattaccgcctttgagtgagctgataccgctcgc
cgcagccgaacgaccgagcgcagcgagtcagtgagcgaggaagcggaagagcgcctgat
gcggtattttctccttacgcatctgtgcggtatttcacaccgcatatatggtgcactct
cagtacaatctgctctgatgccgcatagttaagccagtatacactccgctatcgctacg
tgactgggtcatggctgcgccccgacacccgccaacacccgctgacgcgccctgacggg
cttgtctgctcccggcatccgcttacagacaagctgtgaccgtctccgggagctgcatg
tgtcagaggttttcaccgtcatcaccgaaacgcgcgaggcagctgcggtaaagctcatc
agcgtggtcgtgcagcgattcacagatgtctgcctgttcatccgcgtccagctcgttga
gtttctccagaagcgttaatgtctggcttctgataaagcgggccatgttaagggcggtt
ttttcctgtttggtcactgatgcctccgtgaagggggatttctgttcatggggtaat
gataccgatgaaacgagagaggatgctcacgatacgggttactgatgatgaacatgccc
ggttactggaacgttgtgagggtaaacaactggcggtatggatgcggcgggaccagaga
aaaatcactcagggtcaatgccagcgcttcgttaatacagatgtaggtgttccacaggg
tagccagcagcatcctgcgatgcagatccggaacataatggtgcagggcgctgacttcc
gcgtttcagactttacgaaacacggaaaccgaagaccattcatgttgttgctcaggtc
gcagacgttttgcagcagcagtcgcttcacgttcgctcgcgtatcggtgattcattctg
ctaaccagtaaggcaacccgccagcctagccgggtcctcaacgacaggagcacgatca
tgcgcacccgtggccaggacccaacgctgcccgaaatt

Figure 78A

Nucleotide sequence of pMAL-C4X Kudzu (SEQ ID NO:157)

```
ccgacaccatcgaatggtgcaaaacctttcgcggtatggcatgatagcgcccggaagag
agtcaattcagggtggtgaatgtgaaaccagtaacgttatacgatgtcgcagagtatgc
cggtgtctcttatcagaccgtttcccgcgtggtgaaccaggccagccacgtttctgcga
aaacgcgggaaaaagtggaagcggcgatggcggagctgaattacattcccaaccgcgtg
gcacaacaactggcgggcaaacagtcgttgctgattggcgttgccacctccagtctggc
cctgcacgcgccgtcgcaaattgtcgcggcgattaaatctcgcgccgatcaactgggtg
ccagcgtggtggtgtcgatggtagaacgaagcggcgtcgaagcctgtaaagcggcggtg
cacaatcttctcgcgcaacgcgtcagtgggctgatcattaactatccgctggatgacca
ggatgccattgctgtggaagctgcctgcactaatgttccggcgttatttcttgatgtct
ctgaccagacaccatcaacagtattatttctcccatgaagacggtacgcgactgggc
gtggagcatctggtcgcattgggtcaccagcaaatcgcgctgttagcgggcccattaag
ttctgtctcggcgcgtctgcgtctggctggctggcataaatatctcactcgcaatcaaa
ttcagccgatagcggaacgggaaggcgactggagtgccatgtccggttttcaacaaacc
atgcaaatgctgaatgagggcatcgttcccactgcgatgctggttgccaacgatcagat
ggcgctggcgcaatgcgcgccattaccgagtccgggctgcgcgttggtgcggatatct
cggtagtgggatacgacgataccgaagacagctcatgttatatcccgccgttaaccacc
atcaaacaggatttccgcctgctgggcaaaccagcgtggaccgcttgctgcaactctc
tcagggccaggcggtgaaggcaatcagctgttgcccgtctcactggtgaaaagaaaaa
ccaccctggcgccaatacgcaaaccgcctctccccgcgcgttggccgattcattaatg
cagctggcacgacaggtttccgactggaaagcgggcagtgagcgcaacgcaattaatg
taagttagctcactcattaggcacaattctcatgtttgacagcttatcatcgactgcac
ggtgcaccaatgcttctggcgtcaggcagccatcggaagctgtggtatggctgtgcagg
tcgtaaatcactgcataattcgtgtcgctcaaggcgcactcccgttctggataatgttt
tttgcgccgacatcataacggttctggcaaatattctgaaatgagctgttgacaattaa
tcatcggctcgtataatgtgtggaattgtgagcggataacaatttcacacaggaaacag
ccagtccgtttaggtgttttcacgagcacttcaccaacaaggaccatagcatatgaaaa
tcgaagaaggtaaactggtaatctggattaacggcgataaaggctataacggtctcgct
gaagtcggtaagaaattcgagaaagataccggaattaaagtcaccgttgagcatccgga
taaactggaagagaaattcccacaggttgcggcaactggcgatggccctgacattatct
tctgggcacacgaccgctttggtggctacgctcaatctggctgttggctgaaatcacc
ccggacaaagcgttccaggacaagctgtatccgtttacctgggatgccgtacgttacaa
cggcaagctgattgcttacccgatcgctgttgaagcgttatcgctgatttataacaaag
atctgctgccgaaccgccaaaaacctgggaagagatcccggcgctggataaagaactg
aaagcgaaaggtaagagcgcgctgatgttcaacctgcaagaaccgtacttcacctggcc
gctgattgctgctgacgggggttatgcgttcaagtatgaaaacggcaagtacgacatta
aagacgtgggcgtggataacgctggcgcgaaagcgggtctgacctcctggttgacctg
attaaaaacaaacacatgaatgcagacaccgattactccatcgcagaagctgcctttaa
taaaggcgaaacagcgatgaccatcaacggcccgtgggcatggtccaacatcgacacca
gcaaagtgaattatggtgtaacggtactgccgaccttcaagggtcaaccatccaaaccg
ttcgttggcgtgctgagcgcaggtattaacgccgcagtccgaacaaagagctggcaaa
agagttcctcgaaaactatctgctgactgatgaaggtctggaagcggttaataaagaca
aaccgctgggtgccgtagcgctgaagtcttacgaggaagagttggtgaaagatccgcgg
attgccgccactatggaaaacgcccagaaaggtgaaatcatgccgaacatcccgcagat
```

Figure 78B

Nucleotide sequence of pMAL-C4X Kudzu

```
gtccgctttctggtatgccgtgcgtactgcggtgatcaacgccgccagcggtcgtcaga
ctgtcgatgaagccctgaaagacgcgcagactaattcgagctcgaacaacaacaacaat
aacaataacaacaacctcgggatcgagggaaggatttcagaattctgtgcgacctcttc
tcaatttactcagattaccgagcataattcccgtcgttccgcaaactatcagccaaacc
tgtggaatttcgaattcctgcaatccctggagaacgacctgaaagtggaaaagctggag
gagaaagcgaccaaactggaggaagaagttcgctgcatgatcaaccgtgtagacaccca
gccgctgtccctgctggagctgatcgacgatgtgcagcgcctgggtctgacctacaaat
tgaaaaagacatcattaaagccctggaaaacatcgtactgctggacgaaaacaaaaag
aacaaatctgacctgcacgcaaccgctctgtctttccgtctgctgcgtcagcacggttt
cgaggtttctcaggatgttttgagcgtttcaaggataaagaaggtggtttcagcggtg
aactgaaaggtgacgtccaaggcctgctgagcctgtatgaagcgtcttacctgggtttc
gagggtgagaacctgctggaggaggcgcgtacctttccatcacccacctgaagaacaa
cctgaaagaaggcattaataccaaggttgcagaacaagtgagccacgccctggaactgc
catatcaccagcgtctgcaccgtctggaggcacgttggttcctggataaatacgaaccg
aaagaaccgcatcaccagctgctgctggagctggcgaagctggattttaacatggtaca
gaccctgcaccagaaagagctgcaagatctgtcccgctggtggaccgagatgggcctgg
ctagcaaactggattttgtacgcgaccgcctgatggaagtttatttctgggcactgggt
atggcgccagacccgcagtttggtgaatgtcgcaaagctgttactaaaatgtttggtct
ggtgacgatcatcgatgacgtgtatgacgtttatggcactctggacgaactgcaactgt
tcaccgatgctgtagagcgctgggacgttaacgctattaacaccctgccggactatatg
aaactgtgttcctggcactgtacaacaccgttaacgacacgtcctattctattctgaa
agagaaaggtcataacaacctgtcctatctgacgaaaagctggcgtgaactgtgcaaag
cctttctgcaagaggcgaaatggtccaacaacaaaattatcccggctttctccaagtac
ctggaaaacgccagcgttcctcctccggtgtagcgctgctggcgccgtcttactttc
cgtatgccagcagcaggaagacatctccgaccacgcgctgcgttcctgaccgacttcc
atggtctggtgcgttctagctgcgttatcttccgcctgtgcaacgatctggccacctct
gcggcggagctggaacgtggcgagactaccaattctatcattagctacatgcacgaaaa
cgatggtaccagcgaggaacaggcccgcgaagaactgcgtaaactgatcgacgccgaat
ggaaaagatgaatcgtgaacgcgttagcgactccaccctgctgcctaaagcgttcatg
gaaatcgcagttaacatggcacgtgtttcccactgcacctaccagtatggcgatggtct
gggtcgcccagactacgcgactgaaaaccgcatcaaactgctgctgattgacccttcc
cgattaaccagctgatgtatgtctaagcttggcactggccgtcgtttacaacgtcgtg
actgggaaaaccctggcgttacccaacttaatcgccttgcagcacatccccctttcgcc
agctggcgtaatagcgaagaggcccgcaccgatcgcccttcccaacagttgcgcagcct
gaatggcgaatggcagcttggctgtttggcggatgagataagatttcagcctgatac
agattaaatcagaacgcagaagcggtctgataaaacagaatttgcctggcggcagtagc
gcggtggtcccacctgaccccatgccgaactcagaagtgaaacgccgtagcgccgatgg
tagtgtggggtctccccatgcgagagtagggaactgccaggcatcaaataaaacgaaag
gctcagtcgaaagactgggcctttcgttttatctgttgtttgtcggtgaacgctctcct
gagtaggacaaatccgccgggagcggatttgaacgttgcgaagcaacggcccggagggt
ggcgggcaggacgcccgccataaactgccaggcatcaaattaagcagaaggccatcctg
acggatggcctttttgcgtttctacaaactcttttgtttatttttctaaatacattca
aatatgtatccgctcatgagacaataaccctgataaatgcttcaataatattgaaaag
```

Figure 78C

Nucleotide sequence of pMAL-C4X Kudzu gaagagtatgagtattcaacatttccgtgtcgcccttattccttttttgcggcatttt
gccttcctgttttttgctcacccagaaacgctggtgaaagtaaaagatgctgaagatcag
ttgggtgcacgagtgggttacatcgaactggatctcaacagcggtaagatccttgagag
ttttcgccccgaagaacgttctccaatgatgagcacttttaaagttctgctatgtggcg
cggtattatcccgtgttgacgccgggcaagagcaactcggtcgccgcatacactattct
cagaatgacttggttgagtactcaccagtcacagaaaagcatcttacggatggcatgac
agtaagagaattatgcagtgctgccataaccatgagtgataacactgcggccaacttac
ttctgacaacgatcggaggaccgaaggagctaaccgcttttttgcacaacatggggat
catgtaactcgccttgatcgttgggaaccggagctgaatgaagccataccaaacgacga
gcgtgacaccacgatgcctgtagcaatggcaacaacgttgcgcaaactattaactggcg
aactacttactctagcttcccggcaacaattaatagactggatggaggcggataaagtt
gcaggaccacttctgcgctcggcccttccggctggctggtttattgctgataaatctgg
agccggtgagcgtgggtctcgcggtatcattgcagcactggggccagatggtaagccct
cccgtatcgtagttatctacacgacggggagtcaggcaactatggatgaacgaaataga
cagatcgctgagataggtgcctcactgattaagcattggtaactgtcagaccaagttta
ctcatatactttagattgatttaccccggttgataatcagaaaagcccaaaaacag
gaagattgtataagcaaatatttaaattgtaaacgttaatattttgttaaaattcgcgt
taaattttgttaaatcagctcattttttaaccaataggccgaaatcggcaaaatccct
tataaatcaaaagaatagaccgagatagggttgagtgttgttccagtttggaacaagag
tccactattaaagaacgtggactccaacgtcaaagggcgaaaaaccgtctatcagggcg
atggcccactacgtgaaccatcacccaaatcaagttttttggggtcgaggtgccgtaaa
gcactaaatcggaaccctaaagggagccccgatttagagcttgacggggaaagccggc
gaacgtggcgagaaaggaagggaagaaagcgaaaggagcgggcgctagggcgctggcaa
gtgtagcggtcacgctgcgcgtaaccaccacccgccgcgcttaatgcgccgctacag
ggcgcgtaaaaggatctaggtgaagatcctttttgataatctcatgaccaaaatccctt
aacgtgagttttcgttccactgagcgtcagacccgtagaaaagatcaaaggatcttct
tgagatcctttttttctgcgcgtaatctgctgcttgcaaacaaaaaaaccaccgctacc
agcggtggtttgtttgccggatcaagagctaccaactctttttccgaaggtaactggct
tcagcagagcgcagataccaaatactgtccttctagtgtagccgtagttaggccaccac
ttcaagaactctgtagcaccgcctacatacctcgctctgctaatcctgttaccagtggc
tgctgccagtggcgataagtcgtgtcttaccgggttggactcaagacgatagttaccgg
ataaggcgcagcggtcgggctgaacggggggttcgtgcacacagcccagcttggagcga
acgacctacaccgaactgagatacctacagcgtgagctatgagaaagcgccacgcttcc
cgaagggagaaaggcggacaggtatccggtaagcggcagggtcggaacaggagagcgca
cgagggagcttccaggggaaacgcctggtatctttatagtcctgtcgggtttcgccac
ctctgacttgagcgtcgatttttgtgatgctcgtcaggggggcggagcctatggaaaaa
cgccagcaacgcggcctttttacggttcctggccttttgctggccttttgctcacatgt
tctttcctgcgttatcccctgattctgtggataaccgtattaccgcctttgagtgagct
gataccgctcgccgcagccgaacgaccgagcgcagcgagtcagtgagcgaggaagcgga
agagcgcctgatgcggtattttctccttacgcatctgtgcggtatttcacaccgcatat
atggtgcactctcagtacaatctgctctgatgccgcatagttaagccagtatacactcc
gctatcgctacgtgactgggtcatggctgcgccccgacacccgccaacacccgctgacg
cgccctgacgggcttgtctgctcccggcatccgcttacagacaagctgtgaccgtctcc

Figure 78D

Nucleotide sequence of pMAL-C4X Kudzu gggagctgcatgtgtcagaggttttcaccgtcatcaccgaaacgcgcgaggcagctgcg
gtaaagctcatcagcgtggtcgtgcagcgattcacagatgtctgcctgttcatccgcgt
ccagctcgttgagtttctccagaagcgttaatgtctggcttctgataaagcgggccatg
ttaagggcggttttttcctgtttggtcactgatgcctccgtgtaagggggatttctgtt
catggggtaatgataccgatgaaacgagagaggatgctcacgatacgggttactgatg
atgaacatgcccggttactggaacgttgtgagggtaaacaactggcggtatggatgcgg
cgggaccagagaaaaatcactcagggtcaatgccagcgcttcgttaatacagatgtagg
tgttccacagggtagccagcagcatcctgcgatgcagatccggaacataatggtgcagg
gcgctgacttccgcgtttccagactttacgaaacacggaaaccgaagaccattcatgtt
gttgctcaggtcgcagacgttttgcagcagcagtcgcttcacgttcgctcgcgtatcgg
tgattcattctgctaaccagtaaggcaaccccgccagcctagccgggtcctcaacgaca
ggagcacgatcatgcgcacccgtggccaggacccaacgctgcccgaatt

Figure 80

Amino acid sequence of *P. tremuloides* IspS (SEQ ID NO:158)

```
MRCSVSTENVSFSETETETRRSANYEPNSWDYDYLLSSDTDESIEVHKDKAKKLEAEVR
REINNEKAEFLTLLELIDNVQRLGLGYRFESDIRRALDRFVSSGGFDGVTKTSLHGTAL
SPRLLRQHGFEVSQEAFSGFKDQNGNFLENLKEDIKAILSLYEASFLALEGENILDEAK
VFAISHLKELSEEKIGKELAEQVSHALELPLHRRTQRLEAVWSIEAYRKKEDANQVLLE
LAILDYNMIQSVYQRDLRETSRWWRRVGLATKLHFARDRLIESFYWAVGVAFEPQYSDC
RNSVAKMFSFVTIIDDIYDVYGTLDELELFTDAVERWDVNAINDLPDYMKLCFLALYNT
INEIAYDNLKDKGENILPYLTKAWADLCNAFLQEAKWLYNKSTPTFDDYFGNAWKSSSG
PLQLIFAYFAVVQNIKKEEIENLQKYHDIISRPSHIFRLCNDLASASAEIARGETANSV
SCYMRTKGISEELATESVMNLIDETWKKMNKEKLGGSLFAKPFVETAINLARQSHCTYH
NGDAHTSPDELTRKRVLSVITEPILPFER
```

Figure 81A

Nucleotide sequence of P. tremuloides pET24a (SEQ ID NO:159)

```
tggcgaatgggacgcgccctgtagcggcgcattaagcgcggcgggtgtggtggttacgc
gcagcgtgaccgctacacttgccagcgccctagcgcccgctcctttcgctttcttccct
tcctttctcgccacgttcgccggctttccccgtcaagctctaaatcgggggctccctt
agggttccgatttagtgctttacggcacctcgaccccaaaaaacttgattagggtgatg
gttcacgtagtgggccatcgccctgatagacggttttcgcccttgacgttggagtcc
acgttctttaatagtggactcttgttccaaactggaacaacactcaacccatctcggt
ctattcttttgatttataagggattttgccgatttcggcctattggttaaaaatgagc
tgatttaacaaaatttaacgcgaattttaacaaaatattaacgtttacaatttcaggt
ggcacttttcggggaaatgtgcgcggaacccctatttgtttatttttctaaatacattc
aaatatgtatccgctcatgaattaattcttagaaaaactcatcgagcatcaaatgaaac
tgcaatttattcatatcaggattatcaataccatattttgaaaaagccgtttctgtaa
tgaaggagaaaactcaccgaggcagttccataggatggcaagatcctggtatcggtctg
cgattccgactcgtccaacatcaatacaacctattaatttcccctcgtcaaaaataagg
ttatcaagtgagaaatcaccatgagtgacgactgaatccggtgagaatggcaaaagttt
atgcatttcttttccagacttgttcaacaggccagccattacgctcgtcatcaaaatcac
tcgcatcaaccaaaccgttattcattcgtgattgcgcctgagcgagacgaaatacgcga
tcgctgttaaaaggacaattacaaacaggaatcgaatgcaaccggcgcaggaacactgc
cagcgcatcaacaatatttcacctgaatcaggatattcttctaatacctggaatgctg
ttttcccggggatcgcagtggtgagtaaccatgcatcatcaggagtacggataaaatgc
ttgatggtcggaagaggcataaattccgtcagccagtttagtctgaccatctcatctgt
aacatcattggcaacgctacctttgccatgtttcagaaacaactctggcgcatcgggct
tcccatacaatcgatagattgtcgcacctgattgcccgacattatcgcgagcccatta
tacccatataaatcagcatccatgttggaatttaatcgcggcctagagcaagacgtttc
ccgttgaatatggctcataacacccttgtattactgtttatgtaagcagacagtttta
ttgttcatgaccaaaatcccttaacgtgagttttcgttccactgagcgtcagacccgt
agaaaagatcaaaggatcttcttgagatcctttttttctgcgcgtaatctgctgcttgc
aaacaaaaaaaccaccgctaccagcggtggtttgtttgccggatcaagagctaccaact
cttttccgaaggtaactggcttcagcagagcgcagataccaaatactgtccttctagt
gtagccgtagttaggccaccacttcaagaactctgtagcaccgcctacatacctcgctc
tgctaatcctgttaccagtggctgctgccagtggcgataagtcgtgtcttaccggttg
gactcaagacgatagttaccggataaggcgcagcggtcgggctgaacggggggttcgtg
cacacagcccagcttggagcgaacgacctacaccgaactgagatacctacagcgtgagc
tatgagaaagcgccacgcttcccgaagggagaaaggcggacaggtatccggtaagcggc
agggtcggaacaggagagcgcacgagggagcttccagggggaaacgcctggtatcttta
tagtcctgtcgggtttcgccacctctgacttgagcgtcgatttttgtgatgctcgtcag
gggggcggagcctatggaaaaacgccagcaacgcggcctttttacggttcctggccttt
tgctggccttttgctcacatgttctttcctgcgttatcccctgattctgtggataaccg
tattaccgcctttgagtgagctgataccgctcgccgcagccgaacgaccgagcgcagcg
agtcagtgagcgaggaagcggaagagcgcctgatgcggtattttctccttacgcatctg
tgcggtatttcacaccgcatatatggtgcactctcagtacaatctgctctgatgccgca
tagttaagccagtatacactccgctatcgctacgtgactgggtcatggctgcgcccga
cacccgccaacacccgctgacgcgccctgacggcttgtctgctcccggcatccgctta
cagacaagctgtgaccgtctccgggagctgcatgtgtcagaggttttcaccgtcatcac
```

Figure 81B

Nucleotide sequence of P. tremuloides pET24a cgaaacgcgcgaggcagctgcggtaaagctcatcagcgtggtcgtgaagcgattcacag
atgtctgcctgttcatccgcgtccagctcgttgagtttctccagaagcgttaatgtctg
gcttctgataaagcgggccatgttaagggcggttttttcctgtttggtcactgatgcct
ccgtgtaaggggatttctgttcatgggggtaatgataccgatgaaacgagagaggatg
ctcacgatacgggttactgatgatgaacatgcccggttactggaacgttgtgagggtaa
acaactggcggtatggatgcggcgggaccagagaaaaatcactcagggtcaatgccagc
gcttcgttaatacagatgtaggtgttccacagggtagccagcagcatcctgcgatgcag
atccggaacataatggtgcagggcgctgacttccgcgtttccagactttacgaaacacg
gaaacgaagaccattcatgttgttgctcaggtcgcagacgtttgcagcagcagtcgc
ttcacgttcgctcgcgtatcggtgattcattctgctaaccagtaaggcaacccgccag
cctagccgggtcctcaacgacaggagcacgatcatgcgcaccgtggggccgccatgcc
ggcgataatggcctgcttctcgccgaaacgtttggtggcgggaccagtgacgaaggctt
gagcgagggcgtgcaagattccgaataccgcaagcgacaggcgatcatcgtcgcgctc
cagcgaaagcggtcctcgccgaaaatgacccagagcgctgccggcacctgtcctacgag
ttgcatgataaagaagacagtcataagtgcggcgacgatagtcatgcccgcgccacc
ggaaggagctgactgggttgaaggctctcaagggcatcggtcgagatcccggtgcctaa
tgagtgagctaacttacattaattgcgttgcgctcactgcccgctttccagtcgggaaa
cctgtcgtgccagctgcattaatgaatcggccaacgcgcggggagaggcggtttgcgta
ttgggcgccagggtggtttttcttttcaccagtgagacgggcaacagctgattgcctt
caccgcctggccctgagagagttgcagcaagcggtccacgctggtttgcccagcaggc
gaaaatcctgtttgatggtggttaacggcgggatataacatgagctgtcttcggtatcg
tcgtatcccactaccgagatatccgcaccaacgcgcagcccggactcggtaatggcgcg
cattgcgcccagcgccatctgatcgttggcaaccagcatcgcagtgggaacgatgccct
cattcagcatttgcatggtttgttgaaaaccggacatggcactccagtcgccttcccgt
tccgctatcggctgaatttgattgcgagtgagatatttatgccagccagccagacgcag
acgcgccgagacagaacttaatgggcccgctaacagcgcgatttgctggtgacccaatg
cgaccagatgctccacgccagtcgcgtaccgtcttcatgggagaaaataatactgttg
atgggtgtctggtcagagacatcaagaaataacgccggaacattagtgcaggcagcttc
cacagcaatggcatcctggtcatccagcggatagttaatgatcagcccactgacgcgtt
gcgcgagaagattgtgcaccgccgctttacaggcttcgacgccgcttcgttctaccatc
gacaccaccacgctggcacccagttgatcggcgcgagatttaatcgccgcgacaatttg
cgacggcgcgtgcagggccagactggaggtggcaacgccaatcagcaacgactgtttgc
ccgccagttgttgtgccacgcggttgggaatgtaattcagctccgccatcgccgcttcc
acttttcccgcgttttcgcagaaacgtggctggcctggttcaccacgcgggaaacggt
ctgataagagacaccggcatactctgcgacatcgtataacgttactggtttcacattca
ccaccctgaattgactctcttccgggcgctatcatgccataccgcgaaaggttttgcgc
cattcgatggtgtccgggatctcgacgctctcccttatgcgactcctgcattaggaagc
agcccagtagtaggttgaggccgttgagcaccgccgccgcaaggaatggtgcatgcaag
gagatggcgcccaacagtcccccggccacggggcctgccaccatacccacgccgaaaca
agcgctcatgagcccgaagtggcgagcccgatcttccccatcggtgatgtcggcgatat
aggcgccagcaaccgcacctgtggcgccggtgatgccggccacgatgcgtccggcgtag
aggatcgagatctcgatcccgcgaaattaatacgactcactatagggaattgtgagcg
gataacaattcccctctagaaataattttgtttaactttaagaaggagatatacatatg

Figure 81C

Nucleotide sequence of P. tremuloides pET24a cgttgtagcgtgtccaccgaaaatgtgtctttctctgaaactgaaaccgaaacgcgtcg
ttctgcgaactacgaacctaacagctgggactatgattacctgctgtcctccgacacgg
acgagtccatcgaagtacacaaagacaaagcgaaaaagctggaagccgaagttcgtcgc
gagattaataacgaaaaagcagaatttctgaccctgctggaactgattgacaacgtcca
gcgcctgggcctgggttaccgtttcgagtctgatatccgtcgtgcgctggatcgcttcg
ttcctccggcggcttcgatggcgtaaccaagacttccctgcacggtacggcactgtct
ttcgtctgctgcgtcaacacggttttgaggtttctcaggaagcgttcagcggcttcaa
agaccaaaacggcaacttcctggagaacctgaaggaagatatcaaagctatcctgagcc
tgtacgaggccagcttcctggctctggaaggcgaaaacatcctggacgaggcgaaggtt
ttcgcaatctctcatctgaaagaactgtctgaagaaagatcggtaaagagctggcaga
acaggtgtcccatgcactggaactgccactgcatcgccgtactcagcgtctggaagcag
tatggtctatcgaggcctaccgtaaaaaggaggacgcgaaccaggttctgctggagctg
gcaattctggattacaacatgatccagtctgtataccagcgtgatctgcgtgaaacgtc
ccgttggtggcgtcgtgtgggtctggcgaccaaactgcactttgctcgtgaccgcctga
ttgagcttctactgggccgtgggtgagcattcgaaccgcaatactccgactgccgt
aactccgtcgcaaaaatgttttctttcgtaaccattatcgacgatatctacgatgtata
cggcaccctggacgaactggagctgtttactgatgcagttgagcgttgggacgtaaacg
ccatcaacgacctgccggattacatgaaactgtgctttctggctctgtataacactatt
aacgaaatcgcctacgacaacctgaaagataaggtgagaacatcctgccgtatctgac
caaagcctgggctgacctgtcaacgcttcctgcaagaagccaagtggctgtacaaca
aatctactccgacctttgacgactacttcggcaacgcatggaaatcctcttctggcccg
ctgcaactgatcttcgcttacttcgctgtcgtgcagaacattaaaaaggaagagatcga
aaacctgcaaaaataccatgacatcatctctcgtccttccatatcttccgtctgtgca
atgacctggctagcgcgtctgcggaaattgcgcgtggtgaaaccgcaaatagcgtttct
tgttacatgcgcactaaaggtatctccgaagaactggctaccgaaagcgtgatgaatct
gatcgatgaaacctggaaaaagatgaacaaggaaaaactgggtggtagcctgttcgcga
aaccgttcgtggaaaccgcgatcaacctggcacgtcaatctcactgcacttatcataac
ggcgacgcgatacctctccggatgagctgacccgcaaacgcgttctgtctgtaatcac
tgaaccgattctgccgtttgaacgctaaggatccgaattcgagctccgtcgacaagctt
gcggccgcactcgagcaccaccaccaccaccactgagatccggctgctaacaaagcccg
aaaggaagctgagttggctgctgccaccgctgagcaataactagcataaccccttgggg
cctctaaacgggtcttgaggggttttttgctgaaaggaggaactatatccggat

Figure 82

Amino acid sequence of *P. trichocharpa* IspS (SEQ ID NO:160)

```
MRCSVSTENVSFTETETETRRSANYEPNSWDYDYLLSSDTDESIEVYKDKAKKLEAEVR
REINNEKAEFLTLLELIDNVQRLGLGYRFESDIRRALDRFVSSGGFDAVTKTSLHATAL
SFRLLRQHGFEVSQEAFSGFKDQNGNFLENLKEDIKAILSLYEASFLALEGENILDEAK
VFAISHLKELSEEKIGKDLAEQVNHALELPLHRRTQRLEAVLSIEAYRKKEDADQVLLE
LAILDYNMIQSVYQRDLRETSRWWRRVGLATKLHFARDRLIESFYWAVGVAFEPQYSDC
RNSVAKMPSFVTIIDDIYDVYGTLDELELFTNAVERWDVNAIDDLPDYMKLCFLALYNT
INEIAYDNLKEKGENILPYLTKAWADLCNAFLQEAKWLYNKSTPTFDEYFGNAWKSSSG
PLQLVPAYFAVVQNIKKEEIENLQKYHDIISRPSHIFRLCNDLASASAEIARGETANSV
SCYMRTKGISEELATESVMNLIDETWKKMNKEKLGGSLFAKPFVETAINLARQSHCTYH
NGDAHTSPDELTRKRVLSVITEPILPFER
```

Figure 83A

Nucleotide sequence of P. trichocharpa pET24a (SEQ ID NO:161)

```
tggcgaatgggacgcgcctgtagcggcgcattaagcgcggcgggtgtggtggttacgc
gcagcgtgaccgctacacttgccagcgccctagcgcccgctcctttcgctttcttccct
tcctttctcgccacgttcgccggctttccccgtcaagctctaaatcggggggctccctt
agggttccgatttagtgctttacggcacctcgaccccaaaaaacttgattagggtgatg
gttcacgtagtgggccatcgccctgatagacggtttttcgccctttgacgttggagtcc
acgttctttaatagtggactcttgttccaactggaacaacactcaaccctatctcggt
ctattcttttgatttataagggattttgccgatttcggcctattggttaaaaaatgagc
tgatttaacaaaatttaacgcgaattttaacaaatattaacgtttacaatttcaggt
ggcacttttcggggaaatgtgcgcggaacccctatttgtttatttttctaaatacattc
aaatatgtatccgctcatgaattaattcttagaaaaactcatcgagcatcaaatgaaac
tgcaatttattcatatcaggattatcaataccatattttgaaaaagccgtttctgtaa
tgaaggagaaaactcaccgaggcagttccataggatggcaagatcctggtatcggtctg
cgattccgactcgtccaacatcaatacaacctattaatttcccctcgtcaaaaataagg
ttatcaagtgagaaatcaccatgagtgacgactgaatccggtgagaatggcaaaagttt
atgcattctttccagacttgttcaacaggccagccattacgctcgtcatcaaaatcac
tcgcatcaaccaaaccgttattcattcgtgattgcgcctgagcgagacgaaatacgcga
tcgctgttaaaaggacaattacaaacaggaatcgaatgcaaccggcgcaggaacactgc
cagcgcatcaacaatattttcacctgaatcaggatattcttctaatacctggaatgctg
ttttcccggggatcgcagtggtgagtaaccatgcatcatcaggagtacggataaaatgc
ttgatggtcggaagaggcataaattccgtcagccagtttagtctgaccatctcatctgt
aacatcattggcaacgctacctttgccatgtttcagaaacaactctggcgcatcgggct
tccatacaatcgatagattgtcgcacctgattgcccgacattatcgcgagcccattta
tacccatataaatcagcatccatgttggaatttaatcgcggcctagagcaagacgtttc
ccgttgaatatggctcataacaccccttgtattactgtttatgtaagcagacagtttta
ttgttcatgaccaaaatcccttaacgtgagttttcgttccactgagcgtcagacccgt
agaaaagatcaaaggatcttcttgagatcctttttttctgcgcgtaatctgctgcttgc
aaacaaaaaaaccaccgctaccagcggtggtttgtttgccggatcaagagctaccaact
ctttttccgaaggtaactggcttcagcagagcgcagataccaaatactgtccttctagt
gtagccgtagttaggccaccacttcaagaactctgtagcaccgcctacatacctcgctc
tgctaatcctgttaccagtggctgctgccagtggcgataagtcgtgtcttaccggttg
gactcaagacgatagttaccggataaggcgcagcggtcgggctgaacggggggttcgtg
cacacagcccagcttggagcgaacgacctacaccgaactgagatacctacagcgtgagc
tatgagaaagcgccacgcttcccgaagggagaaaggcggacaggtatccggtaagcggc
agggtcggaacaggagagcgcacgagggagcttccagggggaaacgcctggtatcttta
tagtcctgtcgggtttcgccacctctgacttgagcgtcgatttttgtgatgctcgtcag
ggggcggagcctatggaaaaacgccagcaacgcggcctttttacggttcctggcctt
tgctggccttttgctcacatgttctttcctgcgttatcccctgattctgtggataaccg
tattaccgcctttgagtgagctgataccgctcgccgcagccgaacgaccgagcgcagc
gagtcagtgagcgaggaagcggaagagcgcctgatgcggtattttctccttacgcatctg
tgcggtatttcacaccgcatatatggtgcactctcagtacaatctgctctgatgccgca
tagttaagccagtatacactccgctatcgctacgtgactgggtcatggctgcgcccga
cacccgccaacacccgctgacgcgccctgacgggcttgtctgctcccggcatccgctta
cagacaagctgtgaccgtctccgggagctgcatgtgtcagaggttttcaccgtcatcac
```

Figure 83B

Nucleotide sequence of P. trichocharpa pET24a cgaaacgcgcgaggcagctgcggtaaagctcatcagcgtggtcgtgaagcgattcacag
atgtctgcctgttcatccgcgtccagctcgttgagtttctccagaagcgttaatgtctg
gcttctgataaagcgggccatgttaagggcggttttttcctgtttggtcactgatgcct
ccgtgtaaggggatttctgttcatggggtaatgataccgatgaaacgagagaggatg
ctcacgatacgggttactgatgatgaacatgcccggttactggaacgttgtgagggtaa
acaactggcggtatggatgcggcgggaccagagaaaatcactcagggtcaatgccagc
gcttcgttaatacagatgtaggtgttccacagggtagccagcagcatcctgcgatgcag
atccggaacataatggtgcagggcgctgacttccgcgtttccagactttacgaaacacg
gaaaccgaagaccattcatgttgttgctcaggtcgcagacgttttgcagcagcagtcgc
ttcacgttcgctcgcgtatcggtgattcattctgctaaccagtaaggcaacccgccag
cctagccgggtcctcaacgacaggagcacgatcatgcgcacccgtggggccgccatgcc
ggcgataatggcctgcttctcgccgaaacgtttggtggcgggaccagtgacgaaggctt
gagcgagggcgtgcaagattccgaataccgcaagcgacaggcgatcatcgtcgcgctc
cagcgaaagcggtcctcgccgaaaatgacccagagcgctgccggcacctgtcctacgag
ttgcatgataaagaagacagtcataagtgcggcgacgatagtcatgcccgcgcccacc
ggaaggagctgactgggttgaaggctctcagggcatcggtcgagatcccggtgcctaa
tgagtgagctaacttacattaattgcgttgcgctcactgcccgctttccagtcgggaaa
cctgtcgtgccagctgcattaatgaatcggccaacgcgcggggagaggcggtttgcgta
ttgggcgccagggtggttttttcttttcaccagtgagacgggcaacagctgattgcctt
cacgcctggccctgagagagttgcagcaagcggtccacgctggtttgcccagcaggc
gaaaatcctgtttgatggtggttaacggcgggatataacatgagctgtcttcggtatcg
tcgtatcccactaccgagatatccgcaccaacgcgcagccggactcggtaatggcgcg
cattgcgcccagcgccatctgatcgttggcaaccagcatcgcagtgggaacgatgccct
cattcagcatttgcatggtttgttgaaaaccggacatggcactccagtcgccttcccgt
tccgctatcggctgaatttgattgcgagtgagatatttatgccagccagccagacgcag
acgcgccgagacagaacttaatgggcccgctaacagcgcgatttgctggtgacccaatg
cgaccagatgctccacgcccagtcgcgtaccgtcttcatgggagaaaataatactgttg
atgggtgtctggtcagagacatcaagaaataacgccggaacattagtgcaggcagcttc
cacagcaatggcatcctggtcatccagcggatagttaatgatcagcccactgacgcgtt
gcgcgagaagattgtgcaccgccgctttacaggcttcgacgccgcttcgttctaccatc
gacaccaccacgctggcacccagttgatcggcgcgagatttaatcgccgcgacaatttg
cgacggcgcgtgcagggccagactggaggtggcaacgccaatcagcaacgactgtttgc
ccgccagttgttgtgccacgcggttgggaatgtaattcagctccgccatcgccgcttcc
acttttcccgcgttttcgcagaaacgtggctggcctggttcaccacgcgggaaacggt
ctgataagagacaccggcatactctgcgacatcgtataacgttactggtttcacattca
ccaccctgaattgactctcttccgggcgctatcatgccataccgcgaaaggttttcgc
cattcgatggtgtccgggatctcgacgctctcccttatgcgactcctgcattaggaagc
agcccagtagtaggttgaggccgttgagcaccgccgcgcaaggaatggtgcatgcaag
gagatggcgcccaacagtccccggccacgggcctgccaccatacccacgccgaaaca
agcgctcatgagcccgaagtggcgagcccgatcttccccatcggtgatgtcggcgatat
aggcgccagcaaccgcacctgtggcgccggtgatgccggccacgatgcgtccggcgtag
aggatcgagatctcgatcccgcgaaattaatacgactcactatagggaattgtgagcg
gataacaattcccctctagaaataattttgtttaactttaagaaggagatatacatatg

Figure 83C

Nucleotide sequence of P. trichocharpa pET24a

```
catatgcgttgtagcgtgtccaccgaaaatgtgtctttcaccgaaactgaaaccgaaac
gcgtcgttctgcgaactacgaacctaacagctgggactatgattacctgctgtcctccg
acacggacgagtccatcgaagtatacaaagacaaagcgaaaaagctggaagccgaagtt
cgtcgcgagattaataacgaaaaagcagaatttctgaccctgctggaactgattgacaa
cgtccagcgcctgggcctgggttaccgtttcgagtctgatatccgtcgtgcgctggatc
gcttcgtttctccggcggcttcgatgcggtaaccaagacttcctgcacgcgacggca
ctgtcttccgtctgctgcgtcaacacggttttgaggtttctcaggaagcgttcagcgg
cttcaaagaccaaaacggcaacttcctggagaacctgaaggaagatatcaaagctatcc
tgagcctgtacgaggccagcttcctggctctggaaggcgaaaacatcctggacgaggcg
aaggttttcgcaatctctcatctgaaagaactgtctgaagaaaagatcggtaaagatct
ggcagaacaggtgaaccatgcactggaactgccactgcatcgccgtactcagcgtctgg
aagcagtactgtctatcgaggcctaccgtaaaaaggaggacgcggatcaggttctgctg
gagctggcaattctggattacaacatgatccagtctgtataccagcgtgatctgcgtga
aacgtccgttggtggcgtcgtgtgggtctggcgaccaaactgcactttgctcgtgacc
gcctgattgagagcttctactgggccgtgggtgtagcattcgaaccgcaatactccgac
tgccgtaactccgtcgcaaaaatgttttctttcgtaaccattatcgacgatatctacga
tgtatacggcaccctggacgaactggagctgttactaacgcagttgagcgttgggacg
taaacgccatcgacgatctgccggattacatgaaactgtgtctctggctctgtataac
actattaacgaaatcgcctacgacaacctgaaagaaaaggtgagaacatcctgccgta
tctgaccaaagcctgggctgacctgtgcaacgcttcctgcaagaagccaagtggctgt
acaacaaatctactccgacctttgacgaatacttcggcaacgcatggaaatcctcttct
ggcccgctgcaactggtgttcgcttacttcgctgtcgtgcagaacattaaaaaggaaga
gatcgaaaacctgcaaaaataccatgacatcatctctcgtccttcccatatcttccgtc
tgtgcaatgacctggctagcgcgtctgcggaaattgcgcgtggtgaaaccgcaaatagc
gtttcttgttacatgcgcactaaaggtatctccgaagaactggctaccgaaagcgtgat
gaatctgatcgatgaaacctggaaaaagatgaacaaggaaaaactgggtggtagcctgt
tcgcgaaaccgttcgtggaaaccgcgatcaacctggcacgtcaatctcactgcacttat
cataacggcgacgcgcataccctctccggatgagctgaccgcaaacgcgttctgtctgt
aatcactgaaccgattctgccgtttgaacgctaaggatccgaattcgagctccgtcgac
aagcttgcggccgcactcgagcaccaccaccaccaccactgagatccggctgctaacaa
agcccgaaaggaagctgagttggctgctgccaccgctgagcaataactagcataacccc
ttggggcctctaaacgggtcttgagggttttttgctgaaaggaggaactatatccgga
t
```

Amino acid sequence of IspS variant P. albaTRC-pET200 (SEQ ID NO:162)

MRGSHHHHHHGMASMTGGQQMGRDLYDDDDKDHPFTMRRSANYEPNSWDYDYLLSSDTD
ESIEVYKDKAKKLEAEVRREINNEKAEFLTLLELIDNVQRLGLGYRFESDIRGALDRFV
SSGGFDAVTKTSLHGTALSFRLLRQHGFEVSQEAFSGFKDQNGNFLENLKEDIKAILSL
YEASFLALEGENILDEAKVFAISHLKELSEEKIGKELAEQVNHALELPLHRRTQRLEAV
WSIEAYRKKEDANQVLLELAILDYNMIQSVYQRDLRETSRWWRRVGLATKLHFARDRLI
ESPYWAVGVAFEPQYSDCRNSVAKMFSFVTIIDDIYDVYGTLDELELFTDAVERWDVNA
INDLPDYMKLCFLALYNTINEIAYDNLKDKGENILPYLTKAWADLCNAFLQEAKWLYNK
STPTFDDYFGNAWKSSSGPLQLVFAYFAVVQNIKKEEIENLQKYHDTISRPSHIFRLCN
DLASASAEIARGETANSVSCYMRTKGISEELATESVMNLIDETWKKMNKEKLGGSLFAK
PFVETAINLARQSHCTYHNGDAHTSPDELTRKRVLSVITEPILPFER

Figure 86A

Nucleotide Sequence of pDu30 (SEQ ID NO:163)

```
aagggcgagctcaacgatccggctgctaacaaagcccgaaaggaagctgagttggctgc
tgccaccgctgagcaataactagcataaccccttggggcctctaaacgggtcttgagga
gttttttgctgaaaggaggaactatatccggatatcccgcaagaggcccggcagtaccg
gcataaccaagcctatgcctacagcatccagggtgacggtgccgaggatgacgatgagc
gcattgttagatttcatacacggtgcctgactgcgttagcaatttaactgtgataaact
accgcattaaagcttatcgatgataagctgtcaaacatgagaattaattcttgaagacg
aaagggcctcgtgatacgcctatttttataggttaatgtcatgataataatggtttctt
agacgtcaggtggcacttttcggggaaatgtgcgcggaacccctatttgtttatttttc
taaatacattcaaatatgtatccgctcatgagacaataaccctgataaatgcttcaata
atattgaaaaaggaagagtatgattgaacaagatggattgcacgcaggttctccggcc
cttggtggagaggctattcggctatgactgggcacaactgacaatcggctgctctgat
gccgcgtgttccggctgtcagcgcaggggcgcccgttcttttgtcaagaccgacct
gtccggtgccctgaatgaactgcaggacgaggcagcgcggctatcgtggctggccacga
cgggcgttccttgcgcagctgtgctcgacgttgtcactgaagcgggaagggactggctg
ctattggcgaagtgccggggcaggatctcctgtcatctcaccttgctcctgccgagaa
agtatccatcatggctgatgcaatgcggcggctgcatacgcttgatccggctacctgcc
cattcgaccaccaagcgaaacatcgcatcgagcgggcacgtactcggatggaagccggt
cttgtcgatcaggatgatctggacgaagagcatcaggggctcgcgccagccgaactgtt
cgccaggctcaaggcgcgcatgcccgacggcgaggatctcgtcgtgacacatggcgatg
cctgcttgccgaatatcatggtggaaaatggccgcttttctggattcatcgactgtggc
cggctgggtgtggcggaccgctatcaggacatagcgttggctacccgtgatattgctga
agagcttggcggcgaatgggctgaccgcttcctcgtgctttacggtatcgccgctcccg
attcgcagcgcatcgccttctatcgccttcttgacgagttcttctgagcgggactctgg
ggttcgaaatgaccgaccaagcgacgcctaactgtcagaccaagtttactcatatatac
tttagattgatttaaaacttcatttttaatttaaaaggatctaggtgaagatcctttt
gataatctcatgaccaaaatcccttaacgtgagttttcgttccactgagcgtcagaccc
cgtagaaaagatcaaaggatcttcttgagatccttttttctgcgcgtaatctgctgct
tgcaaacaaaaaaaccaccgctaccagcggtggtttgtttgccggatcaagagctacca
actctttttccgaaggtaactggcttcagcagagcgcagataccaaatactgtccttct
agtgtagccgtagttaggccaccacttcaagaactctgtagcaccgcctacataccctcg
ctctgctaatcctgttaccagtggctgctgccagtggcgataagtcgtgtcttaccggg
ttggactcaagacgatagttaccggataaggcgcagcggtcgggctgaacggggggttc
gtgcacacagcccagcttggagcgaacgacctacaccgaactgagatacctacagcgtg
agctatgagaaagcgccacgcttcccgaagggagaaaggcggacaggtatccggtaagc
ggcagggtcggaacaggagagcgcacgagggagcttccagggggaaacgcctggtatct
ttatagtcctgtcgggtttcgccacctctgacttgagcgtcgatttttgtgatgctcgt
caggggggcggagcctatggaaaaacgccagcaacgcggcctttttacggttcctggcc
ttttgctggccttttgctcacatgttctttcctgcgttatcccctgattctgtggataa
ccgtattaccgcctttgagtgagctgataccgctcgccgcagccgaacgaccgagcgca
gcgagtcagtgagcgaggaagcggaagagcgcctgatgcggtattttctccttacgcat
ctgtgcggtatttcacaccgcaatggtgcactctcagtacaatctgctctgatgccgca
tagttaagccagtatacactccgctatcgctacgtgactgggtcatggctgcgccccga
cacccgccaacacccgctgacgcgccctgacgggcttgtctgctcccggcatccgctta
```

Figure 86B

Nucleotide Sequence of pDu30

```
cagacaagctgtgaccgtctccgggagctgcatgtgtcagaggttttcaccgtcatcac
cgaaacgcgcgaggcagctgcggtaaagctcatcagcgtggtcgtgaagcgattcacag
atgtctgctgttcatccgcgtccagctcgttgagtttctccagaagcgttaatgtctg
gcttctgataaagcgggccatgttaagggcggttttttcctgtttggtcactgatgcct
ccgtgtaaggggatttctgttcatggggtaatgataccgatgaaacgagagaggatg
ctcacgatacgggttactgatgatgaacatgcccggttactggaacgttgtgagggtaa
acaactggcggtatggatgcggcgggaccagagaaaaatcactcagggtcaatgccagc
gcttcgttaatacagatgtaggtgttccacagggtagccagcagcatcctgcgatgcag
atccggaacataatggtgcagggcgctgacttccgcgtttccagactttacgaaacacg
gaaaccgaagaccattcatgttgttgctcaggtcgcagacgttttgcagcagcagtcgc
ttcacgttcgctcgcgtatcggtgattcattctgctaaccagtaaggcaaccccgccag
cctagccgggtcctcaacgacaggagcacgatcatgcgcacccgtggccaggacccaac
gctgcccgagatgcgccgcgtgcggctgctggagatggcggacgcgatggatatgttct
gccaagggttggtttgcgcattcacagttctccgcaagaattgattggctccaattctt
ggagtggtgaatccgttagcgaggtgcgccggcttccattcaggtcgaggtggcccgg
ctccatgcaccgcgacgcaacgcggggaggcagacaaggtatagggcggcgcctacaat
ccatgccaacccgttccatgtgctcgccgaggcggcataaatcgccgtgacgatcagcg
gtccaatgatcgaagttaggctggtaagagccgcgagcgatccttgaagctgtccctga
tggtcgtcatctacctgcctggacagcatggcctgcaacgcgggcatcccgatgccgcc
ggaagcgagaagaatcataatggggaaggccatccagcctcgcgtcgcgaacgccagca
agacgtagcccagcgcgtcggccgccatgccggcgataatggcctgcttctcgccgaaa
cgtttggtggcgggaccagtgacgaaggcttgagcgagggcgtgcaagattccgaatac
cgcaagcgacaggccgatcatcgtcgcgctccagcgaaagcggtcctcgccgaaaatga
cccagagcgctgccggcacctgtcctacgagttgcatgataaagaagacagtcataagt
gcggcgacgatagtcatgccccgcgcccaccggaaggagctgactgggttgaaggctct
caagggcatcggtcgagatcccggtgcctaatgagtgagctaacttacattaattgcgt
tgcgctcactgcccgctttccagtcgggaaacctgtcgtgccagctgcattaatgaatc
ggccaacgcgcggggagaggcggtttgcgtattgggcgccagggtggttttttcttttca
ccagtgagacgggcaacagctgattgcccttcaccgcctggccctgagagagttgcagc
aagcggtccacgctggtttgccccagcaggcgaaaatcctgtttgatggtggttaacgg
cgggatataacatgagctgtcttcggtatcgtcgtatcccactaccgagatatccgcac
caacgcgcagcccggactcggtaatggcgcgcattgcgcccagcgccatctgatcgttg
gcaaccagcatcgcagtgggaacgatgccctcattcagcatttgcatggtttgttgaaa
accggacatggcactccagtcgccttcccgttccgctatcggctgaatttgattgcgag
tgagatatttatgccagccagccagacgcagacgcgccgagacagaacttaatgggccc
gctaacagcgcgatttgctggtgacccaatgcgaccagatgctccacgcccagtcgcgt
accgtcttcatgggagaaaataatactgttgatgggtgtctggtcagagacatcaagaa
ataacgccggaacattagtgcaggcagcttccacagcaatggcatcctggtcatccagc
ggatagttaatgatcagcccactgacgcgttgcgcgagaagattgtgcaccgccgcttt
acaggcttcgacgccgcttcgttctaccatcgacaccaccacgctggcacccagttgat
cggcgcgagatttaatcgccgcgacaatttgcgacggcgcgtgcagggccagactggag
gtggcaacgccaatcagcaacgactgtttgccgccagttgttgtgccacgcggttggg
aatgtaattcagctccgccatcgccgcttccactttttccgcgttttcgcagaaacgt
```

Figure 86C

Nucleotide Sequence of pDu30

```
ggctggcctggttcaccacgcgggaaacggtctgataagagacaccggcatactctgcg
acatcgtataacgttactggtttcacattcaccaccctgaattgactctcttccgggcg
ctatcatgccataccgcgaaaggttttgcgccattcgatggtgtccgggatctcgacgc
tctcccttatgcgactcctgcattaggaagcagcccagtagtaggttgaggccgttgag
caccgccgccgcaaggaatggtgcatgcaaggagatggcgccaacagtccccggcca
cggggcctgccaccatacccacgccgaaacaagcgctcatgagcccgaagtggcgagcc
cgatcttccccatcggtgatgtcggcgatataggcgccagcaaccgcacctgtggcgcc
ggtgatgccggccacgatgcgtccggcgtagaggatcgagatcgatcccgcgaatt
aatacgactcactatagggaattgtgagcggataacaattcccctctagaaataattt
tgtttaactttaagaaggagatatacatatgcggggttctcatcatcatcatcatg
gtatggctagcatgactggtggacagcaaatgggtcgggatctgtacgacgatgacgat
aaggatcatcccttcaccatgcgtcgttctgcgaactacgaacctaacagctgggacta
tgattacctgctgtcctccgacacggacgagtccatcgaagtatacaaagacaaagcga
aaagctggaagccgaagttcgtcgcgagattaataacgaaaagcagaattctgacc
ctgctggaactgattgacaacgtccagcgcctgggcctgggttaccgtttcgagtctga
tatccgtggtgcgctggatcgcttcgtttcctccggcggcttcgatgcggtaaccaaga
cttccctgcacggtacggcactgtctttccgtctgctgcgtcaacacggttttgaggtt
tctcaggaagcgttcagcggcttcaaagaccaaaacggcaacttcctggagaacctgaa
ggaagatatcaaagctatcctgagcctgtacgaggccagcttcctggctctggaaggcg
aaaacatcctggacgaggcgaaggttttcgcaatctctcatctgaaagaactgtctgaa
gaaaagatcggtaaagagctggcagaacaggtgaaccatgcactggaactgccactgca
tcgccgtactcagcgtctggaagcagtatggtctatcgaggcctaccgtaaaaaggagg
acgcgaatcaggttctgctggagctggcaattctggattacaacatgatccagtctgta
taccagcgtgatctgcgtgaaacgtcccgttggtggcgtcgtgtgggtctggcgaccaa
actgcactttgctcgtgaccgcctgattgagagcttctactgggccgtgggtgtagcat
tcgaaccgcaatactccgactgccgtaactccgtcgcaaaaatgttttctttcgtaacc
attatcgacgatatctacgatgtatacggcaccctggacgaactggagctgtttactga
tgcagttgagcgttgggacgtaaacgccatcaacgacctgccggattacatgaaactgt
gctttctggctctgtataacactattaacgaaatcgcctacgacaacctgaaagataaa
ggtgagaacatcctgccgtatctgaccaaagcctgggctgacctgtgcaacgctttcct
gcaagaagccaagtggctgtacaacaaatctactccgacctttgacgactacttcggca
acgcatggaaatcctcttctggcccgctgcaactggtgttcgcttacttcgctgtcgtg
cagaacattaaaaaggaagagatcgaaaacctgcaaaaataccatgacaccatctctcg
tccttcccatatcttccgtctgtgcaatgacctggctagcgcgtctgcggaaattgcg
gtggtgaaaccgcaaatagcgtttcttgttacatgcgcactaaaggtatctccgaagaa
ctggctaccgaaagcgtgatgaatctgatcgatgaaacctggaaaaagatgaacaagga
aaaactgggtggtagcctgttcgcgaaaccgttcgtggaaaccgcgatcaacctggcac
gtcaatctcactgcacttatcataacggcgacgcgcatacctctccggatgagctgacc
cgcaaacgcgttctgtctgtaatcactgaaccgattctgccgtttgaacgctaa
```

Figure 87

Amino acid sequence of IspS variant P.frem TRC-pET200 (SEQ ID NO:164)

MRGSHHHHHHGMASMTGGQQMGRDLYDDDDKDHPFTMRRSANYEPNSWDYDYLLSSDTD
ESIEVHKDKAKKLEAEVRREINNEKAEFLTLLELIDNVQRLGLGYRFESDIRRALDRFV
SSGGFDGVTKTSLHGTALSFRLLRQHGFEVSQEAFSGFKDQNGNFLENLKEDIKAILSL
YEASPLALEGENILDEAKVFAISHLKELSEEKIGKELAEQVSHALELPLHRRTQRLEAV
WSIEAYRKKEDANQVLLELAILDYNMIQSVYQRDLRETSRWWRRVGLATKLHFARDRLI
ESFYWAVGVAFEPQYSDCRNSVAKMFSFVTIIDDIYDVYGTLDELELPTDAVERWDVNA
INDLPDYMKLCFLALYNTINEIAYDNLKDKGENILPYLTKAWADLCNAFLQEAKWLYNK
STPTFDDYFGNAWKSSSGPLQLIFAYFAVVQNIKKEEIENLQKYHDIISRPSHIFRLCN
DLASASAEIARGETANSVSCYMRTKGISEELATESVMNLIDETWKKMNKEKLGGSLFAK
PFVETAINLARQSHCTYHNGDAHTSPDELTRKRVLSVITEPILPFER

Figure 88A

Nucleotide sequence of pDu31 (SEQ ID NO:165)

```
cgtcgttctgcgaactacgaacctaacagctgggactatgattacctgctgtcctccga
cacggacgagtccatcgaagtacacaaagacaaagcgaaaaagctggaagccgaagttc
gtcgcgagattaataacgaaaaagcagaatttctgaccctgctggaactgattgacaac
gtccagcgcctgggcctgggttaccgtttcgagtctgatatccgtcgtgcgctggatcg
cttcgtttcctccggcggcttcgatggcgtaaccaagacttccctgcacggtacggcac
tgtctttccgtctgctgcgtcaacacggttttgaggtttctcaggaagcgttcagcggc
ttcaaagaccaaaacggcaacttcctggagaacctgaaggaagatatcaaagctatcct
gagcctgtacgaggccagcttcctggctctggaaggcgaaaacatcctggacgaggcga
aggttttcgcaatctctcatctgaagaactgtctgaagaaaagatcggtaaagagctg
gcagaacaggtgtcccatgcactggaactgccactgcatcgccgtactcagcgtctgga
agcagtatggtctatcgaggcctaccgaaaaaggaggacgcgaaccaggttctgctgg
agctggcaattctggattacaacatgatccagtctgtataccagcgtgatctgcgtgaa
acgtcccgttggtggcgtcgtgtgggtctggcgaccaaactgcactttgctcgtgaccg
cctgattgagagcttctactgggccgtgggtgtagcattcgaaccgcaatactccgact
gccgtaactccgtcgcaaaaatgttttcttcgtaaccattatcgacgatatctacgat
gtatacggcaccctggacgaactggagctgtttactgatgcagttgagcgttgggacgt
aaacgccatcaacgacctgccggattacatgaaactgtgcttctggctctgtataaca
ctattaacgaaatcgcctacgacaacctgaaagataaaggtgagaacatcctgccgtat
ctgaccaaagcctgggctgacctgtgcaacgcttcctgcaagaagccaagtggctgta
caacaaatctactccgacctttgacgactacttcggcaacgcatggaaatcctcttctg
gcccgctgcaactgatcttcgcttacttcgctgtcgtgcagaacattaaaaaggaagag
atcgaaaacctgcaaaaataccatgacatcatctctcgtccttcccatatcttccgtct
gtgcaatgacctggctagcgcgtctgcggaaattgcgcgtggtgaaaccgcaaatagcg
tttcttgttacatgcgcactaaaggtatctccgaagaactggctaccgaaagcgtgatg
aatctgatcgatgaaacctggaaaagatgaacaaggaaaaactgggtggtagcctgtt
cgcgaaaccgttcgtggaaaccgcgatcaacctggcacgtcaatctcactgcacttatc
ataacggcgacgcgcataccctctccggatgagctgacccgcaaacgcgttctgtctgta
atcactgaaccgattctgccgtttgaacgctaaaagggcgagctcaacgatccggctgc
taacaaagcccgaaggaagctgagttggctgctgccaccgctgagcaataactagcat
aacccttggggcctctaaacgggtcttgaggagttttttgctgaaaggaggaactata
tccggatatcccgcaagaggcccggcagtaccggcataaccaagcctatgcctacagca
tccagggtgacggtgccgaggatgacgatgagcgcattgttagatttcatacacggtgc
ctgactgcgttagcaatttaactgtgataaactaccgcattaaagcttatcgatgataa
gctgtcaaacatgagaattaattcttgaagacgaaagggcctcgtgatacgcctatttt
tataggttaatgtcatgataataatggttcttagacgtcaggtggcacttttcgggga
aatgtgcgcggaacccctatttgtttattttctaaatacattcaaatatgtatccgct
catgagacaataaccctgataaatgcttcaataatattgaaaaggaagagtatgattg
aacaagatggattgcacgcaggttctccggccgcttgggtggagaggctattcggctat
gactgggcacaactgacaatcggctgctctgatgccgccgtgttccggctgtcagcgca
ggggcgcccggttcttttgtcaagaccgacctgtccggtgccctgaatgaactgcagg
acgaggcagcgcggctatcgtggctggccacgacgggcgttccttgcgcagctgtgctc
gacgttgtcactgaagcgggaagggactggctgctattgggcgaagtgccggggcagga
tctcctgtcatctcaccttgctcctgccgagaaagtatccatcatggctgatgcaatgc
```

Figure 88B

Nucleotide sequence of pDu31

```
ggcggctgcatacgcttgatccggctacctgcccattcgaccaccaagcgaaacatcgc
atcgagcgggcacgtactcggatggaagccggtcttgtcgatcaggatgatctggacga
agagcatcagggctcgcgccagccgaactgttcgccaggctcaaggcgcgcatgcccg
acggcgaggatctcgtcgtgacacatggcgatgcctgcttgccgaatatcatggtggaa
aatggccgcttttctggattcatcgactgtggccggctgggtgtggcggaccgctatca
ggacatagcgttggctacccgtgatattgctgaagagcttggcggcgaatgggctgacc
gcttcctcgtgctttacggtatcgccgctcccattcgcagcgcatcgccttctatcgc
cttcttgacgagttcttctgagcgggactctggggttcgaaatgaccgaccaagcgacg
cctaactgtcagaccaagtttactcatatactttagattgatttaaaacttcatttt
taatttaaaaggatctaggtgaagatcctttttgataatctcatgaccaaaatcctta
acgtgagttttcgttccactgagcgtcagaccccgtagaaaagatcaaaggatcttctt
gagatccttttttctgcgcgtaatctgctgcttgcaaacaaaaaaaccaccgctacca
gcggtggtttgtttgccggatcaagagctaccaactctttttccgaaggtaactggctt
cagcagagcgcagataccaaatactgtccttctagtgtagccgtagttaggccaccact
tcaagaactctgtagcaccgcctacatacctcgctctgctaatcctgttaccagtggct
gctgccagtggcgataagtcgtgtcttaccgggttggactcaagacgatagttaccgga
taaggcgcagcggtcgggctgaacggggggttcgtgcacacagcccagcttggagcgaa
cgacctacaccgaactgagataccctacagcgtgagctatgagaaagcgccacgcttcc
gaagggagaaaggcggacaggtatccggtaagcggcagggtcggaacaggagagcgcac
gagggagcttccaggggaaacgcctggtatctttatagtcctgtcgggtttcgccacc
tctgacttgagcgtcgatttttgtgatgctcgtcaggggggcggagcctatggaaaaac
gccagcaacgcggcctttttacggttcctggccttttgctggccttttgctcacatgtt
ctttcctgcgttatcccctgattctgtggataaccgtattaccgcctttgagtgagctg
ataccgctcgccgcagccgaacgaccgagcgcagcgagtcagtgagcgaggaagcggaa
gagcgcctgatgcggtattttctccttacgcatctgtgcggtatttcacaccgcaatgg
tgcactctcagtacaatctgctctgatgccgcatagttaagccagtatacactccgcta
tcgctacgtgactgggtcatggctgcgccccgacacccgccaacacccgctgacgcgcc
ctgacggcttgtctgctcccggcatccgcttacagacaagctgtgaccgtctccgga
gctgcatgtgtcagaggttttcaccgtcatcaccgaaacgcgcgaggcagctgcggtaa
agctcatcagcgtggtcgtgaagcgattcacagatgtctgcctgttcatccgcgtccag
ctcgttgagttctccagaagcgttaatgtctggcttctgataaagcgggccatgttaa
gggcggttttttcctgtttggtcactgatgcctccgtgtaagggggatttctgttcatg
ggggtaatgataccgatgaaacgagagaggatgctcacgatacgggttactgatgatga
acatgcccggttactggaacgttgtgagggtaaacaactggcggtatggatgcggcggg
accagagaaaaatcactcagggtcaatgccagcgcttcgttaatacagatgtaggtgtt
ccacagggtagccagcagcatcctgcgatgcagatccggaacataatggtgcagggcgc
tgacttccgcgtttccagactttacgaaacacggaaaccgaagaccattcatgttgttg
ctcaggtcgcagacgttttgcagcagcagtcgcttcacgttcgctcgcgtatcggtgat
tcattctgctaaccagtaaggcaacccgccagcctagccggtcctcaacgacaggag
cacgatcatgcgcacccgtggccaggacccaacgctgcccgagatgcgccgcgtgcgg
ctggagatggcggacgcgatggatatgttctgccaaggggttggtttgcgcattcaca
gttctccgcaagaattgattggctccaattcttggagtggtgaatccgttagcgaggtg
ccgccggcttccattcaggtcgaggtggcccggctccatgcaccgcgacgcaacgcggg
```

Figure 88C

Nucleotide sequence of pDu31

```
gaggcagacaaggtataggcggcgcctacaatccatgccaacccgttccatgtgctcg
ccgaggcggcataaatcgccgtgacgatcagcggtccaatgatcgaagttaggctggta
agagccgcgagcgatccttgaagctgtccctgatggtcgtcatctacctgcctggacag
catggcctgcaacgcgggcatcccgatgccgccggaagcgagaagaatcataatgggga
aggccatccagcctcgcgtcgcgaacgccagcaagacgtagcccagcgcgtcggccgcc
atgccggcgataatggcctgcttctcgccgaaacgtttggtggcgggaccagtgacgaa
ggcttgagcgagggcgtgcaagattccgaataccgaagcgacaggccgatcatcgtcg
cgctccagcgaaagcggtcctcgccgaaaatgacccagagcgctgccggcacctgtcct
acgagttgcatgataaagaagacagtcataagtgcggcgacgatagtcatgcccgcgc
ccaccggaaggagctgactgggttgaaggctctcaagggcatcggtcgagatcccggtg
cctaatgagtgagctaacttacattaattgcgttgcgctcactgcccgctttccagtcg
ggaaacctgtcgtgccagctgcattaatgaatcggccaacgcgcggggagaggcggttt
gcgtattgggcgccagggtggttttcttttcaccagtgagacgggcaacagctgattg
ccttcaccgcctggccctgagagagttgcagcaagcggtccacgctggtttgccccag
caggcgaaaatcctgtttgatggtggttaacggcgggataacatgagctgtcttcgg
tatcgtcgtatcccactaccgagatatccgccaccaacgcgcagcccggactcggtaatg
gcgcgcattgcgcccagcgccatctgatcgttggcaaccagcatcgcagtgggaacgat
gccctcattcagcatttgcatggtttgttgaaaaccggacatggcactccagtcgcctt
cccgttccgctatcggctgaatttgattgcgagtgagatatttatgccagccagccaga
cgcagacgcgccgagacagaacttaatgggccgctaacagcgcgatttgctggtgacc
caatgcgaccagatgctccacgcccagtcgcgtaccgtcttcatgggagaaaataatac
tgttgatgggtgtctggtcagagacatcaagaaataacgccggaacattagtgcaggca
gcttccacagcaatggcatcctggtcatccagcggatagttaatgatcagcccactgac
gcgttgcgcgagaagattgtgcaccgccgctttacaggcttcgacgccgcttcgttcta
ccatcgacaccaccacgctggcacccagttgatcggcgcgagatttaatcgccgcgaca
atttgcgacggcgcgtgcagggccagactggaggtggcaacgccaatcagcaacgactg
tttgccgccagttgttgtgccacgcggttgggaatgtaattcagctccgccatcgccg
cttccactttttcccgcgtttcgcagaaacgtggctggcctggttcaccacgcgggaa
acggtctgataagagacaccggcatactctgcgacatcgtataacgttactggtttcac
attcaccacctgaattgactctcttccgggcgctatcatgccataccgcgaaaggttt
tgcgccattcgatggtgtccgggatctcgacgctctcccttatgcgactcctgcattag
gaagcagccagtagtaggttgaggccgttgagcaccgccgcgcaaggaatggtgcat
gcaaggagatggcgcccaacagtccccggccacggggcctgccaccatacccacgccg
aaacaagcgctcatgagcccgaagtggcgagcccgatcttcccatcggtgatgtcggc
gatataggcgccagcaaccgcacctgtggcgccggtgatgccggccacgatgcgtccgg
cgtagaggatcgagatctcgatcccgcgaattaatacgactcactatagggaattgt
gagcggataacaattcccctctagaaataattttgtttaactttaagaaggagatatac
atatgcggggttctcatcatcatcatcatcatggtatgctagcatgactggtggacag
caaatgggtcgggatctgtacgacgatgacgataaggatcatcccttcaccatg
```

Figure 89

Amino acid sequence of IspS variant P.trichTRC-pET200 (SEQ ID NO:166)

MRGSHHHHHHGMASMTGGQQMGRDLYDDDDKDHPFTMRRSANYEPNSWDYDYLLSSDTD
ESIEVYKDKAKKLEAEVRREINNEKAEFLTLLELIDNVQRLGLGYRFESDIRRALDRFV
SSGGFDAVTKTSLHATALSFRLLRQHGFEVSQEAFSGFKDQNGNFLENLKEDIKAILSL
YEASFLALEGENILDEAKVPAISHLKELSEEKIGKDLAEQVNHALELPLHRRTQRLEAV
LSIEAYRKKEDADQVLLELAILDYNMIQSVYQRDLRETSRWWRRVGLATKLHPARDRLI
ESFYWAVGVAFEPQYSDCRNSVAKMPSFVTIIDDIYDVYGTLDELELFTNAVERWDVNA
IDDLPDYMKLCFLALYNTINEIAYDNLKEKGENILPYLTKAWADLCNAFLQEAKWLYNK
STPTFDEYFGNAWKSSSGPLQLVFAYFAVVQNIKKEEIENLQKYHDIISRPSHIFRLCN
DLASASAEIARGETANSVSCYMRTKGISEELATESVMNLIDETWKKMNKEKLGGSLFAK
PFVETAINLARQSHCTYHNGDAHTSPDELTRKRVLSVITEPILPFER

Figure 90A

Nucleotide Sequence of pDu32 (SEQ ID NO:167)

```
cgtcgttctgcgaactacgaacctaacagctgggactatgattacctgctgtcctccga
cacggacgagtccatcgaagtatacaaagacaaagcgaaaaagctggaagccgaagttc
gtcgcgagattaataacgaaaaagcagaatttctgaccctgctggaactgattgacaac
gtccagcgcctgggcctgggttaccgtttcgagtctgtatatccgtcgtgcgctggatcg
cttcgtttcctccggcggcttcgatgcggtaaccaagacttccctgcacgcgacggcac
tgtctttccgtctgctgcgtcaacacggttttgaggtttctcaggaagcgttcagcggc
ttcaaagaccaaaacggcaacttcctggagaacctgaaggaagatatcaaagctatcct
gagcctgtacgaggccagcttcctggctctggaaggcgaaaacatcctggacgaggcga
aggttttcgcaatctctcatctgaaagaactgtctgaagaaaagatcggtaaagatctg
gcagaacaggtgaaccatgcactggaactgccactgcatcgccgtactcagcgtctgga
agcagtactgtctatcgaggcctaccgtaaaaaggaggacgcggatcaggttctgctgg
agctggcaattctggattacaacatgatccagtctgtataccagcgtgatctgcgtgaa
acgtcccgttggtggcgtcgtgtgggtctggcgaccaaactgcactttgctcgtgaccg
cctgattgagagcttctactgggccgtggtgtagcattcgaaccgcaatactccgact
gccgtaactccgtcgcaaaaatgttttctttcgtaaccattatcgacgatatctacgat
gtatacggcaccctggacgaactggagctgtttactaacgcagttgagcgttgggacgt
aaacgccatcgacgatctgccggattacatgaaactgtgctttctggctctgtataaca
ctattaacgaaatcgcctacgacaacctgaaagaaaaggtgagaacatcctgccgtat
ctgaccaaagcctgggctgacctgtgcaacgctttcctgcaagaagccaagtggctgta
caacaaatctactccgaccttTgacgaatacttcggcaacgcatggaaatcctcttctg
gcccgctgcaactggtgttcgcttacttcgctgtcgtgcagaacattaaaaaggaagag
atcgaaaacctgcaaaaataccatgacatcatctctcgtccttcccatatcttccgtct
gtgcaatgacctggctagcgcgtctgcggaaattgcgcgtggtgaaaccgcaaatagcg
tttcttgttacatgcgcactaaaggtatctccgaagaactggctaccgaaagcgtgatg
aatctgatcgatgaaacctggaaaaagatgaacaaggaaaaactgggtggtagcctgtt
cgcgaaaccgttcgtggaaccgcgatcaacctggcacgtcaatctcactgcacttatc
ataacggcgacgcgcataccctcccggatgagctgacccgcaaacgcgttctgtctgta
atcactgaaccgattctgccgtttgaacgctaaaagggcgagctcaacgatccggctgc
taacaaagcccgaaaggaagctgagttggctgctgccaccgctgagcaataactagcat
aacccccttggggcctctaaacgggtcttgaggagttttttgctgaaaggaggaactata
tccggatatcccgcaagaggcccggcagtaccggcataaccaagcctatgcctacagca
tccagggtgacggtgccgaggatgacgatgagcgcattgttagatttcatacacggtgc
ctgactgcgttagcaatttaactgtgataaactaccgcattaaagcttatcgatgataa
gctgtcaaacatgagaattaattcttgaagacgaaagggcctcgtgatacgcctatttt
tataggttaatgtcatgataataatggtttcttagacgtcaggtggcacttttcgggga
aatgtgcgcggaaccccatttgtttattttctaaatacattcaaatatgtatccgct
catgagacaataaccctgataaatgcttcaataatattgaaaaaggaagagtatgattg
aacaagatggattgcacgcaggttctccggccgcttgggtggagaggctattcggctat
gactgggcacaactgacaatcggctgctctgatgccgccgtgttccggctgtcagcgca
gggcgcccggttcttttgtcaagaccgacctgtccggtgccctgaatgaactgcagg
acgaggcagcgcggctatcgtggctggccacgacgggcgttccttgcgcagctgtgctc
gacgttgtcactgaagcgggaagggactggctgctattgggcgaagtgccggggcagga
tctcctgtcatctcaccttgctcctgccgagaaagtatccatcatggctgatgcaatgc
```

Figure 90B

Nucleotide Sequence of pDu32 ggcggctgcatacgcttgatccggctacctgcccattcgaccaccaagcgaaacatcgc
atcgagcgggcacgtactcggatggaagccggtcttgtcgatcaggatgatctggacga
agagcatcaggggctcgcgccagccgaactgttcgccaggctcaaggcgcgcatgcccg
acggcgaggatctcgtcgtgacacatggcgatgcctgcttgccgaatatcatggtggaa
aatggccgcttttctggattcatcgactgtggccggctgggtgtggcggaccgctatca
ggacatagcgttggctaccgtgatattgctgaagagcttggcggcgaatgggctgacc
gcttcctcgtgctttacggtatcgccgctcccgattcgcagcgcatcgccttctatcgc
cttcttgacgagttcttctgagcgggactctggggttcgaaatgaccgaccaagcgacg
cctaactgtcagaccaagttactcatatactttagattgatttaaaacttcatttt
taatttaaaaggatctaggtgaagatcctttttgataatctcatgaccaaaatcccta
acgtgagttttcgttccactgagcgtcagaccccgtagaaaagatcaaaggatcttctt
gagatcctttttttctgcgcgtaatctgctgcttgcaaacaaaaaaaccaccgctacca
gcggtggtttgtttgccggatcaagagctaccaactctttttccgaaggtaactggctt
cagcagagcgcagataccaaatactgtccttctagtgtagccgtagttaggccaccact
tcaagaactctgtagcaccgcctacatacctcgctctgctaatcctgttaccagtgct
gctgccagtggcgataagtcgtgtcttaccgggttggactcaagacgatagttaccgga
taaggcgcagcggtcgggctgaacggggggttcgtgcacacagcccagcttggagcgaa
cgacctacaccgaactgagataccctacagcgtgagctatgagaaagcgccacgcttcc
gaagggagaaaggcggacaggtatccggtaagcggcagggtcggaacaggagagcgcac
gagggagcttccaggggggaaacgcctggtatctttatagtcctgtcgggtttcgccacc
tctgacttgagcgtcgatttttgtgatgctcgtcaggggcggagcctatggaaaaac
gccagcaacgcggcctttttacggttcctggccttttgctggccttttgctcacatgtt
ctttcctgcgttatcccctgattctgtggataaccgtattaccgcctttgagtgagctg
ataccgctcgccgcagccgaacgaccgagcgcagcgagtcagtgagcgaggaagcggaa
gagcgcctgatgcggtattttctccttacgcatctgtgcggtatttcacaccgcaatgg
tgcactctcagtacaatctgctctgatgccgcatagttaagccagtatacactccgcta
tgctacgtgactgggtcatggctgcgccccgacacccgccaacacccgctgacgcgcc
ctgacgggcttgtctgctcccggcatccgcttacagacaagctgtgaccgtctccgga
gctgcatgtgtcagaggttttcaccgtcatcaccgaaacgcgcgaggcagctgcggtaa
agctcatcagcgtggtcgtgaagcgattcacagatgtctgcctgttcatccgcgtccag
ctcgttgagtttctccagaagcgttaatgtctggcttctgataaagcgggccatgttaa
gggcggttttttcctgtttggtcactgatgcctccgtgtaaggggggatttctgttcatg
ggggtaatgataccgatgaaacgagagaggatgctcacgatacgggttactgatgatga
acatgcccggttactggaacgttgtgagggtaaacaactggcggtatggatgcggcggg
accagagaaaaatcactcagggtcaatgccagcgcttcgttaatacagatgtaggtgtt
ccacagggtagccagcagcatcctgcgatgcagatccggaacataatggtgcagggcgc
tgacttccgcgtttccagactttacgaaacacggaaaccgaagaccattcatgttgttg
ctcaggtcgcagacgttttgcagcagcagtcgcttcacgttcgctcgcgtatcggtgat
tcattctgctaaccagtaaggcaacccgccagcctagccgggtcctcaacgacaggag
cacgatcatgcgcacccgtggccaggacccaacgctgcccgagatgcgccgcgtgcggc
tgctggagatggcggacgcgatggatatgttctgccaagggttggtttgcgcattcaca
gttctccgcaagaattgattggctccaattcttggagtggtgaatccgttagcgaggtg
ccgccggcttccattcaggtcgaggtggcccggctccatgcaccgcgacgcaacgcggg

Figure 90C

Nucleotide Sequence of pDu32

```
gaggcagacaaggtataggcggcgcctacaatccatgccaacccgttccatgtgctcg
ccgaggcggcataaatcgccgtgacgatcagcggtccaatgatcgaagttaggctggta
agagccgcgagcgatccttgaagctgtccctgatggtcgtcatctacctgcctggacag
catggcctgcaacgcgggcatcccgatgccgccggaagcgagaagaatcataatgggga
aggccatccagcctcgcgtcgcgaacgccagcaagacgtagcccagcgcgtcggccgcc
atgccggcgataatggcctgcttctcgccgaaacgttggtggcgggaccagtgacgaa
ggcttgagcgagggcgtgcaagattccgaataccgcaagcgacaggcgatcatcgtcg
cgctccagcgaaagcggtcctcgccgaaaatgacccagagcgctgccggcacctgtcct
acgagttgcatgataaagaagacagtcataagtgcggcgacgatagtcatgccccgcgc
ccacggaaggagctgactggggttgaaggctctcaagggcatcggtcgagatcccggtg
cctaatgagtgagctaacttacattaattgcgttgcgctcactgcccgctttccagtcg
ggaaacctgtcgtgccagctgcattaatgaatcggccaacgcgcggggagaggcggttt
gcgtattgggcgccagggtggttttctttccaccagtgagacgggcaacagctgattg
ccctccaccgcctggccctgagagagttgcagcaagcggtccacgctggtttgccccag
caggcgaaaatctgtttgatggtggttaacggcgggataacatgagctgtcttcgg
tatcgtcgtatcccactaccgagatatccgcaccaacgcgcagcccggactcggtaatg
gcgcgcattgcgcccagcgccatctgatcgttggcaaccagcatcgcagtgggaacgat
gccctcattcagcatttgcatggtttgttgaaaaccggacatggcactccagtcgcctt
cccgttccgctatcggctgaatttgattgcgagtgagatattatgccagccagccaga
cgcagacgcgccgagacagaacttaatgggccgctaacagcgcgatttgctggtgacc
caatgcgaccagatgctccacgcccagtcgcgtaccgtcttcatgggagaaaataatac
tgttgatgggtgtctggtcagagacatcaagaaataacgccggaacattagtgcaggca
gcttccacagcaatggcatcctggtcatccagcggatagttaatgatcagccactgac
gcgttgcgcgagaagattgtgcaccgccgctttacaggcttcgacgccgcttcgttcta
ccatcgacaccaccacgctggcaccagttgatcggcgcgagatttaatcgccgcgaca
atttgcgacggcgcgtgcagggccagactggaggtggcaacgccaatcagcaacgactg
tttgccgccagttgttgtgccacgcggttgggaatgtaattcagctccgccatcgccg
cttccacttttcccgcgttttcgcagaaacgtggctggcctggttcaccacgcgggaa
acggtctgataagagacaccggcatactctgcgacatcgtataacgttactggtttcac
attcaccaccctgaattgactctcttccgggcgctatcatgccataccgcgaaaggttt
tgcgccattcgatggtgtccgggatctcgacgctctcccttatgcgactcctgcattag
gaagcagcccagtagtaggttgaggccgttgagcaccgccgcgcaaggaatggtgcat
gcaaggagatggcgccaacagtccccggccacggggcctgccaccataccacgccg
aaacaagcgctcatgagcccgaagtggcgagcccgatcttccccatcggtgatgtcggc
gatataggcgccagcaaccgcacctgtggcgccggtgatgccggccacgatgcgtccgg
cgtagaggatcgagatctcgatccgcgaaattaatacgactcactatagggaattgt
gagcggataacaattcccctctagaaataattttgtttaactttaagaaggagatatac
atatgcggggttctcatcatcatcatcatcatggtatggctagcatgactggtggacag
caaatgggtcgggatctgtacgacgatgacgataaggatcatcccttcaccatg
```

Figure 96
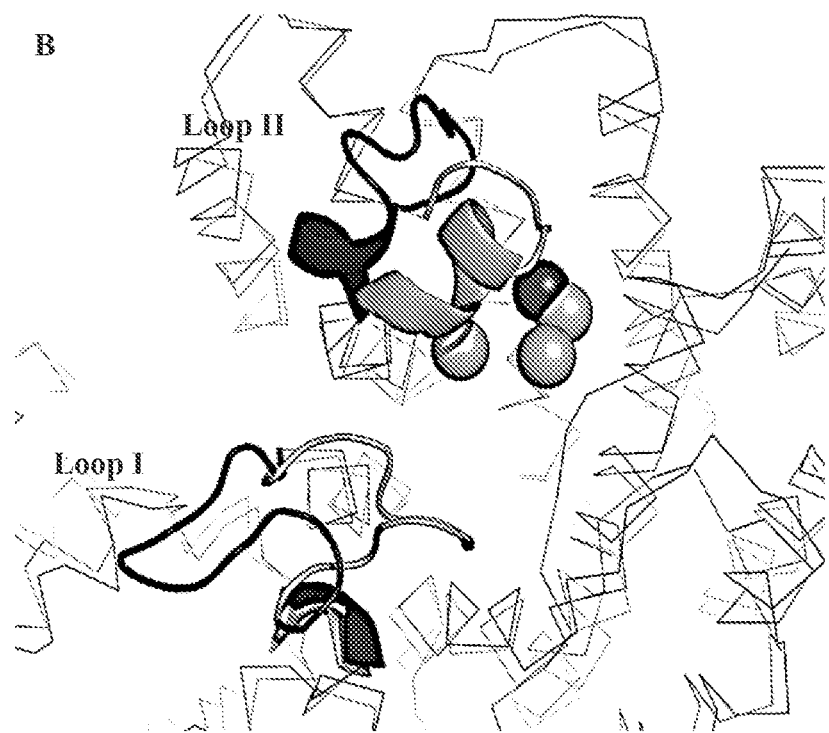

ISOPRENE SYNTHASE VARIANTS FOR IMPROVED MICROBIAL PRODUCTION OF ISOPRENE

CROSS-REFERENCE TO RELATED APPLICATIONS

This application is a continuation of U.S. patent application Ser. No. 12/429,143 filed Apr. 23, 2009, which is now U.S. Pat. No. 8,173,410, which claims the benefit of U.S. provisional application Ser. No. 61/125,336 filed Apr. 23, 2008, which are hereby incorporated by reference in their entirety.

FIELD OF THE INVENTION

The present invention provides methods and compositions comprising at least one isoprene synthase enzyme with improved catalytic activity and/or solubility. In particular, the present invention provides variant plant isoprene synthases for increased isoprene production in microbial host cells. Biosynthetically produced isoprene of the present invention finds use in the manufacture of rubber and elastomers.

BACKGROUND OF THE INVENTION

Isoprenoids are isoprene polymers that find use in pharmaceuticals, neutraceuticals, flavors, fragrances, and rubber products. Natural isoprenoid supplies, however, are limited due to ecological concerns. For this reason, and to provide isoprenoid compositions having fewer impurities and greater uniformity, isoprenoids such as rubber are often produced synthetically.

Isoprene (2-methyl-1,3-butadiene) is a volatile hydrocarbon that is insoluble in water and soluble in alcohol. Commercially viable quantities of isoprene can be obtained by direct isolation from petroleum C5 cracking fractions or by dehydration of C5 isoalkanes or isoalkenes (Weissermel and Arpe, Industrial Organic Chemistry, 4$^{th}$ ed., Wiley-VCH, pp. 117-122, 2003). The C5 skeleton can also be synthesized from smaller subunits. It would be desirable, however, to have a commercially viable method of producing isoprene that was independent of nonrenewable resources.

Biosynthetic production of isoprene occurs by two distinct metabolic pathways (Julsing et al., Appl Microbiol Biotechnol, 75:1377-1384, 2007). In eukaryotes and archae, isoprene is formed via the mevalonate (MVA) pathway, while some eubacteria and higher plants produce isoprene via the methylerythritol phosphate (MEP) pathway. Isoprene emissions from plants are light and temperature-dependent with increases linked to leaf development. An isoprene-producing enzyme, isoprene synthase, has been identified in Aspen trees (Silver and Fall, Plant Physiol, 97:1588-1591, 1991; and Silver and Fall, J Biol Chem, 270:13010-13016, 1995) and is believed to be responsible for the in vivo production of isoprene from whole leaves. Bacterial production of isoprene has also been described (Kuzma et al., Curr Microbiol, 30:97-103, 1995; and Wilkins, Chemosphere, 32:1427-1434, 1996), and varies in amount with the phase of bacterial growth and the nutrient content of the culture medium (U.S. Pat. No. 5,849,970 to Fall et al.; and Wagner et al., J Bacteriol, 181: 4700-4703, 1999, both herein incorporated by reference in their entirety). The levels of isoprene obtainable through bacterial systems of the prior art, however, are insufficient for commercial uses.

Thus what the art needs is an efficient, large scale, bacterial isoprene production process to provide feedstock for the manufacture of isoprenoids.

All patents, patent applications, articles and publications mentioned herein are hereby expressly incorporated herein by reference.

SUMMARY OF THE INVENTION

The present invention provides methods and compositions comprising at least one isoprene synthase enzyme with improved catalytic activity and/or solubility. In particular, the present invention provides variant plant isoprene synthases for increased isoprene production in microbial host cells. Biosynthetically produced isoprene of the present invention finds use in the manufacture of rubber and elastomers.

Specifically, the present invention provides isolated isoprene synthase variants, wherein the variant comprises a substitution at a position corresponding to one or more residues (one, two, three, four, five, six, seven, eight, nine or ten) of a kudzu isoprene synthase comprising the amino acid sequence set forth in SEQ ID NO: 2. In some embodiments, the isoprene synthase variant is a kudzu (*Pueraria* sp.) isoprene synthase variant or a poplar (*Populus* sp.) isoprene synthase variant. In some embodiments, the one or more residues are selected from but not limited to the group consisting of L26, E30, F31, Q33, L35, E36, N37, L39, K40, V41, K43, L44, R61, V62, D63, Q65, K87, E94, N95, L99, D100, N105, K137, E138, G143, E144, N182, L184, K185, G187, N189, T190, P225, H226, K247, T257, E258, M259, D266, N334, D353, S357, I358I, E361, N389, I392, I393, K398, E401, C421, Q423, Q424, E425, D426, H430, L432, R433, S434, D437, R443, L462, E463, H476, N478, D479, Q485, D508, P513, A515, Q532, Y533, L537, G538, R539, Y542, A543, and P557. In some embodiments, the one or more residues are selected from but not limited to the group consisting of P24, N25, Y309, D310, L377, F381, E384, Y399, N402, A403, S406, S407, G409, A411, L413, F449, A456, T457, S458, A459, A460, E461, L462, E463, R464, G465, E466, T467, T468, N469, M523, S527, and Y531. In some embodiments, the one or more residues are selected from but not limited to the group consisting of A20, N21, Y22, Q23, R271, W278, F299, V302, and S408. The present invention also provides an isolated isoprene synthase variant having an A20G substitution in a kudzu isoprene synthase having the amino acid sequence set forth in SEQ ID NO: 2. In a subset of these embodiments, the variant comprises at least two substitutions (two, three, four, five, six, seven, eight, nine or ten), wherein one of the substitutions is an A20G substitution in a kudzu isoprene synthase having the amino acid sequence set forth in SEQ ID NO: 2. The present invention also provides an isolated isoprene synthase variant having an S408D substitution in a kudzu isoprene synthase having the amino acid sequence set forth in SEQ ID NO: 2. In a subset of these embodiments, the variant comprises at least two substitutions (two, three, four, five, six, seven, eight, nine or ten), wherein one of the substitutions is an S408D substitution in a kudzu isoprene synthase having the amino acid sequence set forth in SEQ ID NO: 2. In some preferred embodiments, the isoprene synthase variant has at least one improved property as compared to wild-type isoprene synthase. In some particularly preferred embodiments, the at least one improved property is selected from but not limited to the group consisting of specific activity (production of isoprene from dimethylallyl diphosphate), and solubility.

In addition, the present invention further provides a polynucleotide sequence encoding the isoprene synthase variant.

Also provided is an expression vector comprising a polynucleotide sequence encoding the isoprene synthase variant in operable combination with a promoter. In further embodiments, the present invention provides a host cell comprising the expression vector. Also provided is a lysate of the host cell, wherein the lysate further comprises lysozyme. In some embodiments, the lysate has a neutral pH (6.5 to 7.5), while in other embodiments the lysate has a basic pH (above 7.5 and below 9.5). The present invention also provides methods of producing isoprene, comprising: (a) providing host cells comprising the expression vector; and (b) culturing the host cells under conditions suitable for producing isoprene. In some embodiments, the methods further comprise (c) recovering the isoprene. In still further embodiments, the methods further comprise (d) polymerizing the isoprene. The present invention further provides methods of detecting isoprene synthase activity, comprising: (a) culturing host cells comprising the expression vector under conditions suitable for producing the isoprene synthase variant; (b) lysing the host cells with a lysis buffer comprising lysozyme to produce a cell lysate; and (c) detecting isoprene synthase activity in the cell lysate by measuring isoprene production from dimethylallyl diphosphate (DMAPP). In some embodiments, the host is selected from but not limited to the group consisting of gram-positive bacterial cells, gram-negative bacterial cells, filamentous fungal cells, and yeast cells. In some preferred embodiments, the host is selected from but not limited to the group consisting of *Escherichia* sp. (*E. coli*), *Panteoa* sp. (*P. citrea*), *Bacillus* sp. (*B. subtilis*), *Yarrowia* sp. (*Y. lipolytica*), and *Trichoderma* (*T. reesei*). In some embodiments, the host cells are cultured in a medium that includes a carbon source selected from but not limited to the group consisting of glucose, glycerol, glycerine, dihydroxyacetone, yeast extract, biomass, molasses, sucrose, and oil.

Moreover, the present invention provides methods of detecting isoprene in a plurality of samples (high-throughput screening), comprising: (a) providing: i) a plurality of samples each comprising isoprene synthase; ii) a glass plate comprising a plurality of wells; and iii) a seal for the glass plate; (b) placing the plurality of samples in the plurality of wells of the glass plate; (c) sealing the glass plate with the seal to produce a sealed glass plate having a headspace associated with the sample in each of the plurality of wells; (d) incubating the glass plate under conditions in which the isoprene synthase is active; and (e) detecting isoprene in the headspace. In some embodiments, the isoprene is detected by gas chromatography-mass spectrometry (GC-MS). In some embodiments, the plurality of samples comprise host cells comprising an expression vector comprising a polynucleotide sequence encoding an isoprene synthase variant in operable combination with a promoter. In some embodiments, the plurality of samples comprise a lysate of the host cells, lysozyme, and dimethylallyl diphosphate (DMAPP). In some preferred embodiments, the glass plate is a deep-well glass block. In some preferred embodiments, the plurality of wells comprises at least 24 wells (preferably at least 48 wells, more preferably at least 96 wells, still more preferably at least 192 wells, and most preferably at least 384 wells). In particularly preferred embodiments, the plurality of wells each comprise a volume of 2 ml or less (preferably 2 ml to 0.2 ml).

Additionally the present invention provides a host cell comprising a heterologous polynucleotide sequence encoding an isoprene synthase variant in operable combination with a promoter, wherein the isoprene synthase variant comprises a substitution at a position corresponding to one or more residues (one, two, three, four, five, six, seven, eight, nine or ten) of a kudzu isoprene synthase comprising the amino acid sequence set forth in SEQ ID NO: 2. In some embodiments, the one or more residues are selected from but not limited to the group consisting of L26, E30, F31, Q33, L35, E36, N37, L39, K40, V41, K43, L44, R61, V62, D63, Q65, K87, E94, N95, L99, D100, N105, K137, E138, G143, E144, N182, L184, K185, G187, N189, T190, P225, H226, K247, T257, E258, M259, D266, N334, D353, S357, I358I, E361, N389, I392, I393, K398, E401, C421, Q423, Q424, E425, D426, H430, L432, R433, S434, D437, R443, L462, E463, H476, N478, D479, Q485, D508, P513, A515, Q532, Y533, L537, G538, R539, Y542, A543, and P557. In some embodiments, the one or more residues are selected from but not limited to the group consisting of P24, N25, Y309, D310, L377, F381, E384, Y399, N402, A403, S406, S407, G409, A411, L413, F449, A456, T457, 5458, A459, A460, E461, L462, E463, R464, G465, E466, T467, T468, N469, M523, S527, and Y531. In some embodiments, the one or more residues are selected from but not limited to the group consisting of A20, N21, Y22, Q23, R271, W278, F299, V302, and S408. The present invention also provides an isolated isoprene synthase variant having an A20G substitution and/or an S408D substitution in a kudzu isoprene synthase having the amino acid sequence set forth in SEQ ID NO: 2. In some preferred embodiments, the isoprene synthase variant has at least one improved property as compared to wild-type isoprene synthase. In some particularly preferred embodiments, the at least one improved property is selected from but not limited to the group consisting of specific activity (production of isoprene from dimethylallyl diphosphate), and solubility. In some preferred embodiments, the polynucleotide sequence is contained within a plasmid. In other preferred embodiments, the polynucleotide sequence is integrated into a chromosome of the host cell. In some embodiments, the host is selected from but not limited to the group consisting of gram-positive bacterial cells, gram-negative bacterial cells, filamentous fungal cells, and yeast cells. In some preferred embodiments, the host is selected from but not limited to the group consisting of *Escherichia* sp. (*E. coli*), *Panteoa* sp. (*P. citrea*), *Bacillus* sp. (*B. subtilis*), *Yarrowia* sp. (*Y. lipolytica*), and *Trichoderma* (*T. reesei*). In some embodiments, the host cells are cultured in a medium that includes a carbon source selected from but not limited to the group consisting of glucose, glycerol, glycerine, dihydroxyacetone, yeast extract, biomass, molasses, sucrose, and oil. In some embodiments, the host cell further comprises a heterologous or native nucleic acid encoding an IDI polypeptide and/or a heterologous or native nucleic acid encoding a DXS polypeptide, sometimes in combination with the native DXP pathway (for example, expression of dxs and idi in *E. coli* in addition to the native DXP pathway). Alternatively the entire DXP pathway (FIG. 15) maybe expressed on a plasmid or integrated on the chromosome as an operon, with a single promoter controlling expression, or promoters of varying strengths (example GI 1.20, GI 1.5, or GI 1.6) controlling one or more of the individual genes. In some embodiments, the host cell further comprises one or more nucleic acids encoding an IDI polypeptide and a DXS polypeptide, while in some preferred embodiments, one vector encodes the isoprene synthase variant, the IDI polypeptide, and the DXS polypeptide. In some embodiments, the host cell further comprises a heterologous nucleic acid encoding an MVA pathway polypeptide (e.g., an MVA pathway polypeptide from *Saccharomyces cerevisia* or *Enterococcus faecalis*). In some embodiments, the host cell further comprises one or more nucleic acids encoding an MVA pathway polypeptide and a DXS polypeptide, while in some preferred embodiments, one vector encodes the isoprene synthase variant, the MVA pathway polypeptide, and the DXS polypeptide. In some preferred embodiments, the host cell further comprises one or more nucleic acids encoding a DXS polypeptide, an IDI polypeptide, or one or more of the rest of the DXP pathway polypeptides, and a MVA pathway polypeptide. In some embodiments, the vector further comprises a selectable marker (e.g., antibiotic resistance nucleic acid). Also provided are methods of producing isoprene, comprising: (a) culturing the host cells under suitable culture conditions for production of isoprene; and (b) producing the isoprene. In some embodiments, the methods further comprise (c) recovering the isoprene. In some preferred embodiments, the methods further comprise (d) polymerizing isoprene. The present invention also provides methods of producing isoprene synthase, comprising: (a) providing: (i) a host cell; and (ii) a nucleic acid encoding an isoprene synthase variant in operable combination with a promoter, wherein the isoprene synthase variant comprises a substitution at a position corresponding to one or more residues (one, two, three, four, five, six, seven, eight, nine or ten) of a kudzu isoprene synthase comprising the amino acid sequence set forth in SEQ ID NO: 2; (b) contacting the host cell with the nucleic acid to produce a transformed host cell; and (c) culturing the transformed host cells under suitable culture conditions for production of isoprene synthase.

In another aspect, the invention provides for isolated poplar isoprene synthase variants. In one embodiment, the variant comprises a truncation in the N-terminal portion of isoprene synthase. In another embodiment, the isoprene synthase variant has an increased specific activity compared to a full length isoprene synthase. In another embodiment, the isoprene synthase is *P. alba* isoprene synthase of SEQ ID NO:120. In another embodiment, wherein the variant is selected from the group consisting of: an MEA variant (SEQ ID NO:122), an MSV variant (SEQ ID NO:124), an MVS variant (SEQ ID NO:126), an MTE variant (SEQ ID NO:128), an MNV variant (SEQ ID NO:130). In another embodiment, the variant is an MEA variant (SEQ ID NO:122). In another embodiment, the variant is selected from the group consisting of: a TRC (−3) variant (SEQ ID NO:136), a TRC (−4) variant (SEQ ID NO:138), a TRC (−5) variant (SEQ ID NO:140), a TRC (−6) variant (SEQ ID NO:142) and a TRC (−7) variant (SEQ ID NO:144). In another embodiment, the variant is a MET variant of *P. tremuloides* isoprene synthase (SEQ ID NO:146). In another embodiment, the variant is a MET variant of *P. trichocharpa* isoprene synthase (SEQ ID NO:148).

In another aspect, the invention provides for isolated poplar isoprene synthase variants, wherein the variant comprises a substitution of one or more amino acid residues of a wild type isoprene synthase; and wherein the isoprene synthase variant has increased isoprene synthase activity compared to a wild type isoprene synthase. In one embodiment, the increased isoprene synthase activity is indicated by a host cell comprising the isoprene variant growing at a faster rate in the presence of dimethylallyl pyrophosphate (DMAPP) compared to a host cell comprising a parent isoprene synthase. In another embodiment, the isoprene synthase is the *P. alba* isoprene synthase of SEQ ID NO:120. In another embodiment, the variant comprises one of more amino acid substitutions selected from the group consisting of V10M, F12S, T15A, E18G, V58I, V58F, L70Q, L70V, L70T, T71P, V79L, E89D, G94A, S119F, F120L, G127R, E175V, T212I, S257A, R262G, A266G, F280L, N297K, F305L, L319M, E323K, A328T, D342E, A359T, K366N, E368D, L374M, S396T, V418S, K438N, H440R, T442I, T442A, I449V, A469S, K500R, K505Q, G507S, S509N, F511Y, and N532K. In another embodiment, at least one amino acid substitution is a L70R substitution. In another embodiment, the variant comprises one of more amino acid substitutions selected from the group consisting of G127R/F511Y, L70Q/G94A/R262G/F305L, F12S/T15A/E18G/N297K, S396T/T442I, V10M/E323K, F120L/A266G, K438N/K500R, V79L/S509N, E175V/S257A/E368D/A469S, T71P/L374M, F280L/H440R, E89D/H440R, V58F/A328T/N532K, S119F/D342E/I449V, and K366N/G507S.

In another aspect, the invention provides for a crystalline form of a polypeptide comprising the amino acid residues of SEQ ID NO:120 (FIG. 19).

In another aspect, the invention provides for methods of producing isoprene, comprising: (a) providing a host cell comprising an expression vector comprising a polynucleotide sequence encoding an isoprene synthase variant; and (b) culturing the host cell under conditions suitable for producing isoprene. In one embodiment, the method further comprises (c) recovering the isoprene. In another embodiment, the method further comprises (d) polymerizing the isoprene.

In another aspect, the invention provides for methods of detecting isoprene synthase activity, comprising: (a) culturing a host cell comprising the expression vector under conditions suitable for producing an isoprene synthase variant; (b) lysing the host cells with a lysis buffer comprising lysozyme to produce a cell lysate; and (c) detecting isoprene synthase activity in the cell lysate by measuring isoprene production from dimethylallyl diphosphate (DMAPP). In one embodiment, the host cell is selected from the group consisting of gram-positive bacterial cells, gram-negative bacterial cells, filamentous fungal cells, and yeast cells. In another embodiment, the host cell is selected from the group consisting of *Escherichia* sp. (*E. coli*), *Panteoa* sp. (*P. citrea*), *Bacillus* sp. (*B. subtilis*), *Yarrowia* sp. (*Y. lipolytica*), and *Trichoderma* (*T. reesei*). In another embodiment, the host cell is cultured in a medium that includes a carbon source selected from the group consisting of glucose, glycerol, glycerine, dihydroxyacetone, yeast extract, biomass, molasses, sucrose, and oil.

In another aspect, the invention provides for host cells comprising a heterologous polynucleotide sequence encoding an isoprene synthase variant in operable combination with a promoter, wherein the isoprene synthase variant comprises a substitution at a position corresponding to one or more residues (one, two, three, four, five, six, seven, eight, nine or ten) of a poplar isoprene synthase. In one embodiment, the isoprene synthase is the *P. alba* isoprene synthase of SEQ ID NO:120. In another embodiment, the variant is selected from the group consisting of: an MEA variant (SEQ ID NO:122), an MSV variant (SEQ ID NO:124), an MVS variant (SEQ ID NO:126), an MTE variant (SEQ ID NO:128), an MNV variant (SEQ ID NO:130). In another embodiment, the variant is selected from the group consisting of: a TRC (−3) variant (SEQ ID NO:136), a TRC (−4) variant (SEQ ID NO:138), a TRC (−5) variant (SEQ ID NO:140), a TRC (−6) variant (SEQ ID NO:142) and a TRC (−7) variant (SEQ ID NO:144). In another embodiment, the variant is a MET variant of *P. tremuloides* isoprene synthase (SEQ ID NO:146). In another embodiment, the variant is a MET variant of *P. trichocharpa* isoprene synthase (SEQ ID NO:148). In another embodiment, the variant comprises one of more amino acid substitutions selected from the group consisting of V10M, F12S, T15A, E18G, V58I, V58F, L70Q, L70V, L70T, T71P, V79L, E89D, G94A, S119F, F120L, G127R, E175V, T212I, S257A, R262G, A266G, F280L, N297K, F305L, L319M, E323K, A328T, D342E, A359T, K366N, E368D, L374M, S396T, V418S, K438N, H440R, T442I, T442A, I449V, A469S, K500R, K505Q, G507S, S509N, F511Y, and N532K. In another embodiment, at least one amino acid substitution is a L70R substitution. In another embodiment, the variant comprises one of more amino acid substitutions selected from the group consisting of G127R/F511Y, L70Q/G94A/R262G/F305L, F12S/T15A/E18G/N297K, S396T/T442I, V10M/E323K, F120L/A266G, K438N/K500R, V79L/S509N, E175V/S257A/E368D/A469S, T71P/L374M, F280L/H440R, E89D/H440R, V58F/A328T/N532K, S119F/D342E/I449V, and K366N/G507S. In another embodiment, the polynucleotide sequence is contained within a plasmid. In another embodiment, the polynucleotide sequence is integrated into a chromosome of the host cell. In another embodiment, the host is selected from the group consisting of gram-positive bacterial cells, gram-negative bacterial cells, filamentous fungal cells, and yeast cells. In another embodiment, the host is selected from the group consisting of *Escherichia* sp. (*E. coli*), *Panteoa* sp. (*P. citrea*), *Bacillus* sp. (*B. subtilis*), *Yarrowia* sp. (*Y. lipolytica*), and *Trichoderma* (*T. reesei*). In another embodiment, the host cell is cultured in a medium comprising a carbon source selected from the group consisting of glucose, glycerol, glycerine, dihydroxyacetone, yeast extract, biomass, molasses, sucrose, and oil. In another embodiment, the host cell further comprises a heterologous or native nucleic acid encoding an IDI polypeptide and/or a heterologous or native nucleic acid encoding a DXS polypeptide, optionally in combination with the native DXP pathway. In another embodiment, the host cell further comprises one or more nucleic acids encoding an IDI polypeptide and a DXS polypeptide. In another embodiment, the host cell comprises one vector encoding the isoprene synthase variant, the IDI polypeptide, and the DXS polypeptide. In another embodiment, the host cell further comprises a heterologous nucleic acid encoding an MVA pathway polypeptide selected from the group consisting of an MVA pathway polypeptide from *Saccharomyces cerevisia* and *Enterococcus faecalis*. In another embodiment, the host cell further comprises one or more nucleic acids encoding an MVA pathway polypeptide and a DXS polypeptide and wherein one vector encodes the isoprene synthase variant, the MVA pathway polypeptide, and the DXS polypeptide. In another embodiment, the host cell further comprises one or more nucleic acids encoding a DXS polypeptide, an IDI polypeptide, or one or more of the rest of the DXP pathway polypeptides, and a MVA pathway polypeptide.

In another aspect, the invention provides for methods of producing isoprene, comprising: (a) culturing the host cells comprising a heterologous polynucleotide sequence encoding an isoprene synthase variant in operable combination with a promoter, wherein the isoprene synthase variant comprises a substitution at a position corresponding to one or more residues (one, two, three, four, five, six, seven, eight, nine or ten) of a poplar isoprene synthase under suitable culture conditions for production of isoprene; and (b) producing the isoprene. In one embodiment, the method further comprises (c) recovering the isoprene. In another embodiment, the method further comprises (d) polymerizing isoprene.

In another aspect, the invention provides for methods of producing isoprene synthase, comprising: (a) providing: (i) a host cell; and (ii) a nucleic acid encoding an isoprene synthase variant in operable combination with a promoter, wherein the isoprene synthase variant comprises a substitution at a position corresponding to one or more residues (one, two, three, four, five, six, seven, eight, nine or ten) of a *P. alba* isoprene synthase of SEQ ID NO:120; (b) contacting the host cell with the nucleic acid to produce a transformed host cell; and (c) culturing the transformed host cells under suitable culture conditions for production of isoprene synthase.

BRIEF DESCRIPTION OF THE DRAWINGS

FIG. 1 provides the coding sequence (SEQ ID NO:1) of kudzu (*Pueraria montana*) isoprene synthase, codon-optimized for expression in *Escherichia coli*.

FIG. 2 provides the amino acid sequence (SEQ ID NO:2) of kudzu isoprene synthase.

FIG. 3 provides the coding sequence (SEQ ID NO:6) of poplar (*Populus alba* x *tremula*) isoprene synthase, codon-optimized for expression in *Escherichia coli*.

FIG. 4 provides the amino acid sequence (SEQ ID NO:7) of poplar (*Populus alba* x *tremula*) isoprene synthase.

FIG. 10 provides the nucleotide sequence of plasmid MCM93 (SEQ ID NO:22).

FIG. 12 provides the nucleotide sequence of pET24D-Kudzu (SEQ ID NO:23).

FIG. 17 provides the amino acid sequence (SEQ ID NO:118) of 6Xhis N-terminally tagged *P. alba* IspS in pDu27.

FIG. 18 provides the nucleotide sequence (SEQ ID NO:119) of plasmid pDu27.

FIG. 19 provides the amino acid sequence (SEQ ID NO:120) of full length *P. alba* IspS in pET24a. Underlined residues indicate the locations of N-terminal truncations in IspS in plasmids pDu39 through pDu43.

FIG. 20 provides the nucleotide sequence (SEQ ID NO:121) of plasmid *P. alba* pET24a.

FIG. 25 provides the amino acid sequence (SEQ ID NO:122) of truncated "MEA" variant of *P. alba* IspS in pDu39.

FIG. 26 provides the nucleotide sequence (SEQ ID NO:123) of plasmid pDu39.

FIG. 27 provides the amino acid sequence (SEQ ID NO:124) of truncated "MSV" variant *P. alba* IspS in pDu41.

FIG. 28 provides the nucleotide sequence (SEQ ID NO:125) of plasmid pDu41 (pET24a-*P.alba* (MSV) Untagged).

FIG. 29 provides the amino acid sequence (SEQ ID NO:126) of truncated "MVS" variant *P. alba* IspS in pDu43.

FIG. 30 provides the nucleotide sequence (SEQ ID NO:127) of plasmid pDu43 (pET24a-*P.alba* (MVS) Untagged).

FIG. 31 provides the amino acid sequence (SEQ ID NO:128) of truncated "MTE" variant of *P. alba* IspS in pDu42.

FIG. 32 provides the nucleotide sequence (SEQ ID NO:129) of plasmid pDu42 (pET24a-*P.alba* (MTE) Untagged).

FIG. 33 provides the amino acid sequence (SEQ ID NO:130) of truncated "MNV" *P. alba* IspS in pDu40.

FIG. 34 provides the nucleotide sequence (SEQ ID NO:131) of plasmid pDu40 (pET24a-*P.alba* (MNV) Untagged).

FIG. 36 provides the amino acid sequence (SEQ ID NO:132) of *P. alba* MEA(+)TEV in MD09-163.

FIG. 37 provides the nucleotide sequence (SEQ ID NO:133) of plasmid MD09-163 (pET24a-*P.alba* MEA(+) TEV. CDS is underlined, TEV protease site is bold.

FIG. 38 provides the amino acid sequence (SEQ ID NO:134) of *P. alba* FL(+)TEV in MD09-161.

FIG. 39 provides the nucleotide sequence (SEQ ID NO:135) of plasmid MD09-161 (pET24a-*P.alba* FL(+)TEV. CDS is underlined, TEV protease site is bold.

FIG. 51 provides the amino acid sequence (SEQ ID NO:136) of *P. alba* TRC (−3) in pDu47-3.

FIG. 52 provides the nucleotide sequence (SEQ ID NO:137) of plasmid pDu47-3.

FIG. 53 provides the amino acid sequence (SEQ ID NO:138) of *P. alba* TRC (−4) in pDu47-4.

FIG. 54 provides the nucleotide sequence (SEQ ID NO:139) of plasmid pDu47-4.

FIG. 55 provides the amino acid sequence (SEQ ID NO:140) of *P. alba* TRC (−5) in pDu47-5.

FIG. 56 provides the nucleotide sequence (SEQ ID NO:141) of plasmid pDu47-5.

FIG. 57 provides the amino acid sequence (SEQ ID NO:142) of *P. alba* TRC (−6) in pDu47-6.

FIG. 58 provides the nucleotide sequence (SEQ ID NO:143) of plasmid pDu47-6.

FIG. 59 provides the amino acid sequence (SEQ ID NO:144) of *P. alba* TRC (−7) in pDu47-7.

FIG. 60 provides the nucleotide sequence (SEQ ID NO:145) of plasmid pDu47-7.

FIG. 61 provides the amino acid sequence (SEQ ID NO:146) of *P. tremuloides* TRC (MET) in pDu48.

FIG. 62 provides the nucleotide sequence (SEQ ID NO:147) of plasmid pDu48.

FIG. 63 provides the amino acid sequence (SEQ ID NO:148) of *P. trichocarpa* (TRC) in pDu49.

FIG. 64 provides the nucleotide sequence (SEQ ID NO:149) of plasmid pDu49.

FIG. 65 provides the amino acid sequence (SEQ ID NO:150) of Kudzu TRC (MEA) in pDu50.

FIG. 66 provides the nucleotide sequence (SEQ ID NO:151) of plasmid pDu50.

FIG. 67 provides the amino acid sequence (SEQ ID NO:152) of KudzuTRC (−4) in pDu50-4.

FIG. 68 provides the nucleotide sequence (SEQ ID NO:153) of plasmid pDu50-4.

FIG. 69 shows graphs demonstrating raw and OD-normalized data from DMAPP assay of truncated variants of IspS.

FIG. 72 provides the nucleotide sequence of plasmid p9795 (SEQ ID NO:154).

FIG. 74 provides the nucleotide sequence (SEQ ID NO:155) of plasmid pTrcKudzu.

FIG. 76 provides the nucleotide sequence (SEQ ID NO:156) of plasmid pMAL-C4X.

FIG. 78 provides the nucleotide sequence (SEQ ID NO:157) of plasmid pMAL-C4X-Kudzu.

FIG. 79 provides maps of plasmids pET24 *P. tremuloides* pET24a and *P. trichocarpa* pET24a.

FIG. 80 provides the amino acid sequence (SEQ ID NO:158) of *P. tremuloides* IspS in *P. trichocharpa* pET24a.

FIG. 81 provides the nucleotide sequence (SEQ ID NO:159) of plasmid *P. tremuloides* pET24a.

FIG. 82 provides the amino acid sequence (SEQ ID NO:160) of *P. trichocharpa* IspS in *P. trichocharpa* pET24a.

FIG. 83 provides the nucleotide sequence (SEQ ID NO:161) of plasmid *P. trichocharpa* pET24a.

FIG. 85 provides the amino acid sequence (SEQ ID NO:162) of IspS variant *P.alba*TRC-pET200 in pDu30.

FIG. 86 provides the nucleotide sequence (SEQ ID NO:163) of pDu30.

FIG. 87 provides the amino acid sequence (SEQ ID NO:164) of IspS variant P.tremTRC-pET200 in pDu31.

FIG. 88 provides the nucleotide sequence (SEQ ID NO:165) of pDu31.

FIG. 89 provides the amino acid sequence (SEQ ID NO:166) of IspS variant P.trichTRC-pET200 in pDu32.

FIG. 90 provides the nucleotide sequence (SEQ ID NO:167) of pDu32.

FIG. 96 shows the N-terminal loop of LS (light gray) and poplar IspS (dark gray) are structurally divergent. Panel A shows the N-terminal loop and panel B shows Loop I and Loop II.

GENERAL DESCRIPTION OF THE INVENTION

Figure 5:
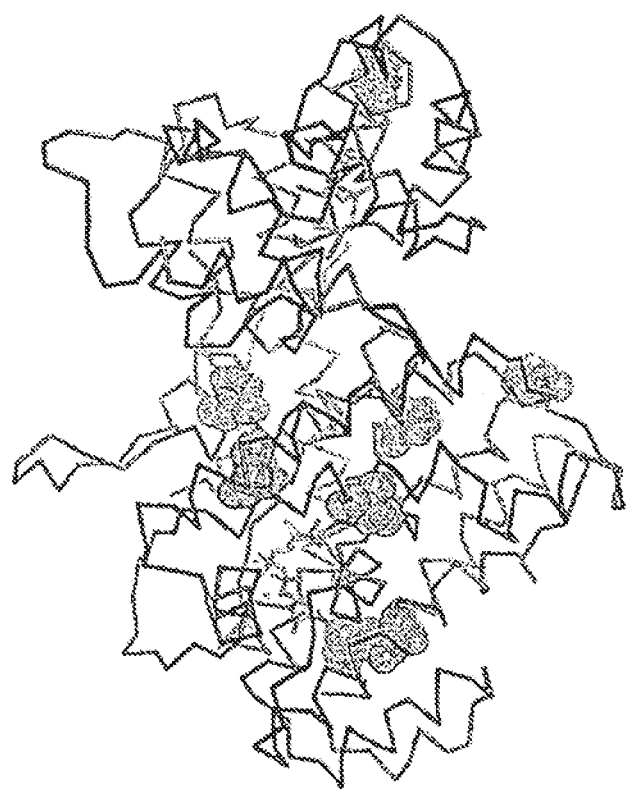
FIG. 5 provides a kudzu isoprene synthase homology model with the cysteine residues highlighted as space filling molecules.

The present invention provides methods and compositions comprising at least one isoprene synthase enzyme with improved catalytic activity and/or solubility. In particular, the present invention provides variant plant isoprene synthases for increased isoprene production in microbial host cells. Biosynthetically produced isoprene of the present invention finds use in the manufacture of rubber and elastomers.

Unless otherwise indicated, the practice of the present invention involves conventional techniques commonly used in molecular biology, microbiology, and recombinant DNA, which are within the skill of the art. Such techniques are known to those of skill in the art and are described in numerous texts and reference works (See e.g., Sambrook et al., "Molecular Cloning: A Laboratory Manual," Second Edition, Cold Spring Harbor, 1989; and Ausubel et al., "Current Protocols in Molecular Biology," 1987).

Unless defined otherwise herein, all technical and scientific terms used herein have the same meaning as commonly understood by one of ordinary skill in the art to which this invention pertains. For example, Singleton and Sainsbury, Dictionary of Microbiology and Molecular Biology, 2d Ed., John Wiley and Sons, NY (1994); and Hale and Marham, The Harper Collins Dictionary of Biology, Harper Perennial, NY (1991) provide those of skill in the art with a general dictionaries of many of the terms used in the invention. Although any methods and materials similar or equivalent to those described herein find use in the practice of the present invention, the preferred methods and materials are described herein. Accordingly, the terms defined immediately below are more fully described by reference to the Specification as a whole.

Furthermore, the headings provided herein are not limitations of the various aspects or embodiments of the invention, which can be had by reference to the specification as a whole. Accordingly, the terms defined immediately below are more fully defined by reference to the specification as a whole. Nonetheless, in order to facilitate understanding of the invention, a number of terms are defined below.

Definitions

Unless defined otherwise herein, all technical and scientific terms used herein have the same meaning as commonly understood by one of ordinary skill in the art to which this invention pertains. Although any methods and materials similar or equivalent to those described herein find use in the practice of the present invention, the preferred methods and materials are described herein. Accordingly, the terms defined immediately below are more fully described by reference to the Specification as a whole.

As used herein, the singular terms "a," "an," and "the" include the plural reference unless the context clearly indicates otherwise. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All documents cited are, in relevant part, incorporated herein by reference. However, the citation of any document is not to be construed as an admission that it is prior art with respect to the present invention.

As used herein, the term 2-methyl-1,3-butadiene (CAS#78-79-5) ("isoprene") refers to the direct and final volatile C5 hydrocarbon product from the elimination of pyrophosphate from 3,3-dimethylallyl pyrophosphate (DMAPP), and does not involve the linking or polymerization of [an] IPP molecule(s) to [a] DMAPP molecule(s). As used herein, the terms "isoprene synthase," and "IspS," refer to the enzymes that catalyze the elimination or pyrophosphate from diemethylallyl diphosphate (DMAPP) to form isoprene. In some preferred embodiments, the IspS is an enzyme obtained from plants such as kudzu, poplar or red oak. In some embodiments, the term "IspS" refers to a naturally occurring mature enzyme or portion thereof.

Related (and derivative) proteins comprise "variant proteins." In some preferred embodiments, variant proteins differ from a parent protein (e.g., kudzu IspS set forth as SEQ ID NO:2 or poplar IspS) and one another by a small number of amino acid residues. The number of differing amino acid residues may be one or more, preferably 1, 2, 3, 4, 5, 10, 15, 20, 30, 40, 50, or more amino acid residues. In some preferred embodiments, the number of different amino acids between variants is between 1 and 10. In some particularly preferred embodiments, related proteins and particularly variant proteins comprise at least 35%, 40%, 45%, 50%, 55%, 60%, 65%, 70%, 75%, 80%, 85%, 90%, 95%, 97%, 98%, or 99% amino acid sequence identity. Additionally, a related protein or a variant protein as used herein refers to a protein that differs from another related protein or a parent protein in the number of prominent regions. For example, in some embodiments, variant proteins have 1, 2, 3, 4, 5, or 10 corresponding prominent regions that differ from the parent protein.

Several methods are known in the art that are suitable for generating variants of the enzymes of the present invention, including but not limited to site-saturation mutagenesis, scanning mutagenesis, insertional mutagenesis, random mutagenesis, site-directed mutagenesis, and directed-evolution, as well as various other recombinatorial approaches.

Characterization of wild-type and mutant proteins is accomplished via any means or "test" suitable and is preferably based on the assessment of properties of interest. For example one or more of the following properties are assessed in some embodiments of the present invention: pH stability; temperature stability; oxidative stability; proteolytic stability; solubility; Km and/or specific activity of the conversion of DMAPP to isoprene in vitro; Km and/or specific activity of the conversion of DMAPP to isoprene in vivo in the context of a host organism (e.g., E. coli); and expression of enzyme(s) of the DXP pathway and/or the MVA pathway. Indeed, it is contemplated that enzymes having various degrees of stability, solubility, activity, and/or expression level in one or more of test conditions will find use in the present invention.

As used herein the term "gene" refers to a polynucleotide (e.g., a DNA segment) that encodes a polypeptide and includes regions preceding and following the coding regions as well as intervening sequences (introns) between individual coding segments (exons).

As used herein, "homologous genes" refers to a pair of genes from different, but usually related species, which correspond to each other and which are identical or very similar to each other. The term encompasses genes that are separated by speciation (i.e., the development of new species) (e.g., orthologous genes), as well as genes that have been separated by genetic duplication (e.g., paralogous genes).

As used herein, "ortholog" and "orthologous genes" refer to genes in different species that have evolved from a common ancestral gene (i.e., a homologous gene) by speciation. Typically, orthologs retain the same function during the course of evolution. Identification of orthologs finds use in the reliable prediction of gene function in newly sequenced genomes.

As used herein, "paralog" and "paralogous genes" refer to genes that are related by duplication within a genome. While orthologs retain the same function through the course of evolution, paralogs evolve new functions, even though some functions are often related to the original one.

As used herein, "homology" refers to sequence similarity or identity, with identity being preferred. This homology is determined using standard techniques known in the art (See e.g., Smith and Waterman, Adv Appl Math, 2:482, 1981; Needleman and Wunsch, J Mol Biol, 48:443, 1970; Pearson and Lipman, Proc Natl Acad Sci USA, 85:2444, 1988; programs such as GAP, BESTFIT, FASTA, and TFASTA in the Wisconsin Genetics Software Package, Genetics Computer Group, Madison, Wis.; and Devereux et al., Nucl Acid Res, 12:387-395, 1984).

As used herein, an "analogous sequence" is one wherein the function of the gene is essentially the same as the gene based on the kudzu isoprene synthase (IspS) or poplar IspS (IspS). Additionally, analogous genes include at least 45%, 50%, 55%, 60%, 65%, 70%, 75%, 80%, 85%, 90%, 95%, 97%, 98%, 99% or 100% sequence identity with the sequence of the kudzu isoprene synthase. In additional embodiments more than one of the above properties applies to the sequence. Analogous sequences are determined by known methods of sequence alignment. A commonly used alignment method is BLAST, although as indicated above and below, there are other methods that also find use in aligning sequences.

One example of a useful algorithm is PILEUP. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle (Feng and Doolittle, J Mol Evol, 35:351-360, 1987). The method is similar to that described by Higgins and Sharp (Higgins and Sharp, CABIOS 5:151-153, 1989). Useful PILEUP parameters including a default gap weight of 3.00, a default gap length weight of 0.10, and weighted end gaps.

Another example of a useful algorithm is the BLAST algorithm, described by Altschul et al., (Altschul et al., J Mol Biol, 215:403-410, 1990; and Karlin et al., Proc Natl Acad Sci USA, 90:5873-5787, 1993). A particularly useful BLAST program is the WU-BLAST-2 program (See, Altschul et al., Meth Enzymol, 266:460-480, 1996). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. However, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

Thus, "percent (%) nucleic acid sequence identity" is defined as the percentage of nucleotide residues in a candidate sequence that are identical to the nucleotide residues of the starting sequence (i.e., the sequence of interest). A preferred method utilizes the BLASTN module of WU-BLAST-2 set to the default parameters, with overlap span and overlap fraction set to 1 and 0.125, respectively.

As used herein, the term "hybridization" refers to the process by which a strand of nucleic acid joins with a complementary strand through base pairing, as known in the art.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm-5° C. (5° below the Tm of the probe); "high stringency" at about 5-10° C. below the Tm; "intermediate stringency" at about 10-20° C. below the Tm of the probe; and "low stringency" at about 20-25° C. below the Tm. Functionally, maximum stringency conditions may be used to identify sequences having strict identity or near-strict identity with the hybridization probe; while intermediate or low stringency hybridization can be used to identify or detect polynucleotide sequence homologs.

Moderate and high stringency hybridization conditions are well known in the art. An example of high stringency conditions includes hybridization at about 42° C. in 50% formamide, 5× SSC, 5× Denhardt's solution, 0.5% SDS and 100 μg/ml denatured carrier DNA followed by washing two times in 2× SSC and 0.5% SDS at room temperature and two additional times in 0.1× SSC and 0.5% SDS at 42° C. An example of moderate stringent conditions include an overnight incubation at 37° C. in a solution comprising 20% formamide, 5×SSC (150 mM NaCl, 15 mM trisodium citrate), 50 mM sodium phosphate (pH 7.6), 5×Denhardt's solution, 10% dextran sulfate and 20 mg/ml denatured sheared salmon sperm DNA, followed by washing the filters in 1× SSC at about 37-50° C. Those of skill in the art know how to adjust the temperature, ionic strength, etc. as necessary to accommodate factors such as probe length and the like.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. "Recombination," "recombining," and generating a "recombined" nucleic acid are generally the assembly of two or more nucleic acid fragments wherein the assembly gives rise to a chimeric gene.

In a preferred embodiment, mutant DNA sequences are generated with site saturation mutagenesis in at least one codon. In another preferred embodiment, site saturation mutagenesis is performed for two or more codons. In a further embodiment, mutant DNA sequences have more than 50%, more than 55%, more than 60%, more than 65%, more than 70%, more than 75%, more than 80%, more than 85%, more than 90%, more than 95%, or more than 98% homology with the wild-type sequence. In alternative embodiments, mutant DNA is generated in vivo using any known mutagenic procedure such as, for example, radiation, nitrosoguanidine and the like. The desired DNA sequence is then isolated and used in the methods provided herein.

As used herein, the term "target sequence" refers to a DNA sequence in the host cell that encodes the sequence where it is desired for the incoming sequence to be inserted into the host cell genome. In some embodiments, the target sequence encodes a functional wild-type gene or operon, while in other embodiments the target sequence encodes a functional mutant gene or operon, or a non-functional gene or operon.

As used herein, a "flanking sequence" refers to any sequence that is either upstream or downstream of the sequence being discussed (e.g., for genes A-B-C, gene B is flanked by the A and C gene sequences). In a preferred embodiment, the incoming sequence is flanked by a homology box on each side. In another embodiment, the incoming sequence and the homology boxes comprise a unit that is flanked by stuffer sequence on each side. In some embodiments, a flanking sequence is present on only a single side (either 3' or 5'), but in preferred embodiments, it is on each side of the sequence being flanked. In some embodiments, a flanking sequence is present on only a single side (either 3' or 5'), while in preferred embodiments, it is present on each side of the sequence being flanked.

As used herein, the term "stuffer sequence" refers to any extra DNA that flanks homology boxes (typically vector sequences). However, the term encompasses any non-homologous DNA sequence. Not to be limited by any theory, a stuffer sequence provides a noncritical target for a cell to initiate DNA uptake.

As used herein, the terms "amplification" and "gene amplification" refer to a process by which specific DNA sequences are disproportionately replicated such that the amplified gene becomes present in a higher copy number than was initially present in the genome. In some embodiments, selection of cells by growth in the presence of a drug (e.g., an inhibitor of an inhibitable enzyme) results in the amplification of either the endogenous gene encoding the gene product required for growth in the presence of the drug or by amplification of exogenous (i.e., input) sequences encoding this gene product, or both.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

As used herein, the term "co-amplification" refers to the introduction into a single cell of an amplifiable marker in conjunction with other gene sequences (i.e., comprising one or more non-selectable genes such as those contained within an expression vector) and the application of appropriate selective pressure such that the cell amplifies both the amplifiable marker and the other, non-selectable gene sequences. The amplifiable marker may be physically linked to the other gene sequences or alternatively two separate pieces of DNA, one containing the amplifiable marker and the other containing the non-selectable marker, may be introduced into the same cell.

As used herein, the terms "amplifiable marker," "amplifiable gene," and "amplification vector" refer to a gene or a vector encoding a gene, which permits the amplification of that gene under appropriate growth conditions.

"Template specificity" is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (See e.g., Kacian et al., Proc Natl Acad Sci USA 69:3038, 1972) and other nucleic acids are not replicated by this amplification enzyme. Similarly, in the case of T7 RNA polymerase, this amplification enzyme has a stringent specificity for its own promoters (See, Chamberlin et al., Nature 228:227, 1970). In the case of T4 DNA ligase, the enzyme will not ligate the two oligonucleotides or polynucleotides, where there is a mismatch between the oligonucleotide or polynucleotide substrate and the template at the ligation junction (See, Wu and Wallace, Genomics 4:560, 1989). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences.

As used herein, the term "amplifiable nucleic acid" refers to nucleic acids, which may be amplified by any amplification method. It is contemplated that "amplifiable nucleic acid" will usually comprise "sample template."

As used herein, the term "sample template" refers to nucleic acid originating from a sample, which is analyzed for the presence of "target" (defined below). In contrast, "background template" is used in reference to nucleic acid other than sample template, which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, in one embodiment, the term "polymerase chain reaction" ("PCR") refers to the methods of U.S. Pat. Nos. 4,683,195 4,683,202, and 4,965,188, hereby incorporated by reference, which include methods for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "RT-PCR" refers to the replication and amplification of RNA sequences. In this method, reverse transcription is coupled to PCR, most often using a one enzyme procedure in which a thermostable polymerase is employed, as described in U.S. Pat. No. 5,322,770, herein incorporated by reference. In RT-PCR, the RNA template is converted to cDNA due to the reverse transcriptase activity of the polymerase, and then amplified using the polymerizing activity of the polymerase (i.e., as in other PCR methods).

As used herein, the terms "restriction endonucleases" and "restriction enzymes" refer to bacterial enzymes, each of which cut double-stranded DNA at or near a specific nucleotide sequence.

A "restriction site" refers to a nucleotide sequence recognized and cleaved by a given restriction endonuclease and is frequently the site for insertion of DNA fragments. In certain embodiments of the invention restriction sites are engineered into the selective marker and into 5' and 3' ends of the DNA construct.

As used herein, the term "chromosomal integration" refers to the process whereby an incoming sequence is introduced into the chromosome of a host cell. The homologous regions of the transforming DNA align with homologous regions of the chromosome. Subsequently, the sequence between the homology boxes is replaced by the incoming sequence in a double crossover (i.e., homologous recombination). In some embodiments of the present invention, homologous sections of an inactivating chromosomal segment of a DNA construct align with the flanking homologous regions of the indigenous chromosomal region of the *Escherichia* chromosome. Subsequently, the indigenous chromosomal region is deleted by the DNA construct in a double crossover (i.e., homologous recombination).

"Homologous recombination" means the exchange of DNA fragments between two DNA molecules or paired chromosomes at the site of identical or nearly identical nucleotide sequences. In a preferred embodiment, chromosomal integration is homologous recombination.

"Homologous sequences" as used herein means a nucleic acid or polypeptide sequence having 100%, 99%, 98%, 97%, 96%, 95%, 94%, 93%, 92%, 91%, 90%, 88%, 85%, 80%, 75%, or 70% sequence identity to another nucleic acid or polypeptide sequence when optimally aligned for comparison. In some embodiments, homologous sequences have between 85% and 100% sequence identity, while in other embodiments there is between 90% and 100% sequence identity, and in more preferred embodiments, there is 95% and 100% sequence identity.

As used herein "amino acid" refers to peptide or protein sequences or portions thereof. The terms "protein," "peptide," and "polypeptide" are used interchangeably.

As used herein, the term "heterologous protein" refers to a protein or polypeptide that does not naturally occur in the host cell. Examples of heterologous proteins include enzymes such as isoprene synthases. In some embodiments, the genes encoding the proteins are naturally occurring genes, while in other embodiments mutated and/or synthetic genes are used.

As used herein, "homologous protein" refers to a protein or polypeptide native or naturally occurring in a cell. In preferred embodiments, the cell is a Gram-negative cell, while in particularly preferred embodiments the cell is an *Escherichia* host cell.

An enzyme is "overexpressed" in a host cell if the enzyme is expressed in the cell at a higher level that the level at which it is expressed in a corresponding wild-type cell.

The terms "protein" and "polypeptide" are used interchangeability herein. The 3-letter code for amino acids as defined in conformity with the IUPAC-IUB Joint Commission on Biochemical Nomenclature (JCBN) is used through out this disclosure. It is also understood that a polypeptide may be coded for by more than one nucleotide sequence due to the degeneracy of the genetic code.

The term "mature" form of a protein or peptide refers to the final functional form of the protein or peptide. To exemplify, a mature form of kudzu isoprene synthase includes the amino acid sequence of SEQ ID NO:2.

The term "precursor" form of a protein or peptide refers to a mature form of the protein having a prosequence operably linked to the amino or carbonyl terminus of the protein. The precursor may also have a "signal" sequence operably linked, to the amino terminus of the prosequence. The precursor may also have additional polynucleotides that are involved in post-translational activity (e.g., polynucleotides cleaved therefrom to leave the mature form of a protein or peptide).

"Naturally occurring enzyme" refers to an enzyme having the unmodified amino acid sequence identical to that found in nature. Naturally occurring enzymes include native enzymes, those enzymes naturally expressed or found in the particular microorganism.

The term "identical" in the context of two nucleic acids or polypeptide sequences refers to the residues in the two sequences that are the same when aligned for maximum correspondence, as measured using one of the following sequence comparison or analysis algorithms.

The term "optimal alignment" refers to the alignment giving the highest percent identity score.

"Percent sequence identity," "percent amino acid sequence identity," "percent gene sequence identity," and/or "percent nucleic acid/polynucloetide sequence identity," with respect to two amino acid, polynucleotide and/or gene sequences (as appropriate), refer to the percentage of residues that are identical in the two sequences when the sequences are optimally aligned. Thus, 80% amino acid sequence identity means that 80% of the amino acids in two optimally aligned polypeptide sequences are identical.

The phrase "substantially identical" in the context of two nucleic acids or polypeptides thus refers to a polynucleotide or polypeptide that comprising at least 70% sequence identity, preferably at least 75%, preferably at least 80%, preferably at least 85%, preferably at least 90%, preferably at least 95%, preferably at least 97%, preferably at least 98% and preferably at least 99% sequence identity as compared to a reference sequence using the programs or algorithms (e.g., BLAST, ALIGN, CLUSTAL) using standard parameters. One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

The term "isolated" or "purified" refers to a material that is removed from its original environment (e.g., the natural environment if it is naturally occurring). For example, the material is said to be "purified" when it is present in a particular composition in a higher or lower concentration than exists in a naturally occurring or wild type organism (e.g., kudzu) or in combination with components not normally present upon expression from a naturally occurring or wild type organism. For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector, and/or such polynucleotides or polypeptides could be part of a composition, and still be isolated in that such vector or composition is not part of its natural environment. In preferred embodiments, a nucleic acid or protein is said to be purified, for example, if it gives rise to essentially one band in an electrophoretic gel or blot.

The term "isolated", when used in reference to a DNA sequence, refers to a DNA sequence that has been removed from its natural genetic milieu and is thus free of other extraneous or unwanted coding sequences, and is in a form suitable for use within genetically engineered protein production systems. Similarly, the term "isolated", when used in reference to a recombinant DNA sequence, refers to a DNA sequence that has been removed from the genetic milieu of the host organism and is thus free of other extraneous or unwanted coding sequences (e.g., kudzu IspS expression vector propagated in E. coli). Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (See e.g., Dynan and Tijan, Nature 316:774-78, 1985). The term "an isolated DNA sequence" is alternatively referred to as "a cloned DNA sequence".

The term "isolated," when used in reference to a protein, refers to a protein that is found in a condition other than its native environment. In a preferred form, the isolated protein is substantially free of other proteins, particularly other homologous proteins. Similarly, the term "isolated", when used in reference to a recombinantly produced protein, refers to a protein that has been removed from the proteinaceous milieu of the host organism and is thus free of other extraneous or unwanted proteins (e.g., recombinant kudzu IspS produced in E. coli). An isolated protein is more than 10% pure, preferably more than 20% pure, and even more preferably more than 30% pure, as determined by SDS-PAGE. Further aspects of the invention encompass the protein in a highly purified form (i.e., more than 40% pure, more than 60% pure, more than 80% pure, more than 90% pure, more than 95% pure, more than 97% pure, and even more than 99% pure), as determined by SDS-PAGE.

The following cassette mutagenesis method may be used to facilitate the construction of the enzyme variants of the present invention, although other methods may be used. First, as described herein, a naturally-occurring gene encoding the enzyme is obtained and sequenced in whole or in part. Then, the sequence is scanned for a point at which it is desired to make a mutation (deletion, insertion or substitution) of one or more amino acids in the encoded enzyme. The sequences flanking this point are evaluated for the presence of restriction sites for replacing a short segment of the gene with an oligonucleotide pool which when expressed will encode various mutants. Such restriction sites are preferably unique sites within the protein gene so as to facilitate the replacement of the gene segment. However, any convenient restriction site that is not overly redundant in the enzyme gene may be used, provided the gene fragments generated by restriction digestion can be reassembled in proper sequence. If restriction sites are not present at locations within a convenient distance from the selected point (from 10 to 15 nucleotides), such sites are generated by substituting nucleotides in the gene in such a fashion that neither the reading frame nor the amino acids encoded are changed in the final construction. Mutation of the gene in order to change its sequence to conform to the desired sequence is accomplished by M13 primer extension in accord with generally known methods. The task of locating suitable flanking regions and evaluating the needed changes to arrive at two convenient restriction site sequences is made routine by the redundancy of the genetic code, a restriction enzyme map of the gene and the large number of different restriction enzymes. Note that if a convenient flanking restriction site is available, the above method need be used only in connection with the flanking region that does not contain a site.

Once the naturally-occurring DNA and/or synthetic DNA is cloned, the restriction sites flanking the positions to be mutated are digested with the cognate restriction enzymes and a plurality of end termini-complementary oligonucleotide cassettes are ligated into the gene. The mutagenesis is simplified by this method because all of the oligonucleotides can be synthesized so as to have the same restriction sites, and no synthetic linkers are necessary to create the restriction sites.

As used herein, "corresponding to," refers to a residue at the enumerated position in a protein or peptide, or a residue that is analogous, homologous, or equivalent to an enumerated residue in a protein or peptide. As used herein, "corresponding region," generally refers to an analogous position along related proteins or a parent protein.

As used herein, the term, "combinatorial mutagenesis" refers to methods in which libraries of variants of a starting sequence are generated. In these libraries, the variants contain one or several mutations chosen from a predefined set of mutations. In addition, the methods provide means to introduce random mutations, which were not members of the predefined set of mutations. In some embodiments, the methods include those set forth in U.S. application Ser. No. 09/699,250, hereby incorporated by reference. In alternative embodiments, combinatorial mutagenesis methods encompass commercially available kits (e.g., QUIKCHANGE Multisite mutagenesis kit, Stratagene, San Diego, Calif.).

As used herein, the term "library of mutants" refers to a population of cells which are identical in most of their genome but include different homologues of one or more genes. Such libraries can be used, for example, to identify genes or operons with improved traits.

As used herein, the terms "starting gene" and "parent gene" refer to a gene of interest that encodes a protein of interest that is to be improved and/or changed using the present invention.

As used herein, the terms "multiple sequence alignment" and "MSA" refer to the sequences of multiple homologs of a starting gene that are aligned using an algorithm (e.g., Clustal W).

As used herein, the terms "consensus sequence" and "canonical sequence" refer to an archetypical amino acid sequence against which all variants of a particular protein or sequence of interest are compared. The terms also refer to a sequence that sets forth the nucleotides that are most often present in a DNA sequence of interest. For each position of a gene, the consensus sequence gives the amino acid that is most abundant in that position in the MSA.

As used herein, the term "consensus mutation" refers to a difference in the sequence of a starting gene and a consensus sequence. Consensus mutations are identified by comparing the sequences of the starting gene and the consensus sequence obtained from a MSA. In some embodiments, consensus mutations are introduced into the starting gene such that it becomes more similar to the consensus sequence. Consensus mutations also include amino acid changes that change an amino acid in a starting gene to an amino acid that is more frequently found in an MSA at that position relative to the frequency of that amino acid in the starting gene. Thus, the term consensus mutation comprises all single amino acid changes that replace an amino acid of the starting gene with an amino acid that is more abundant than the amino acid in the MSA.

The terms "modified sequence" and "modified genes" are used interchangeably herein to refer to a sequence that includes a deletion, insertion or interruption of naturally occurring nucleic acid sequence. In some preferred embodiments, the expression product of the modified sequence is a truncated protein (e.g., if the modification is a deletion or interruption of the sequence). In some particularly preferred embodiments, the truncated protein retains biological activity. In alternative embodiments, the expression product of the modified sequence is an elongated protein (e.g., modifications comprising an insertion into the nucleic acid sequence). In some embodiments, an insertion leads to a truncated protein (e.g., when the insertion results in the formation of a stop codon). Thus, an insertion may result in either a truncated protein or an elongated protein as an expression product.

As used herein, the terms "mutant sequence" and "mutant gene" are used interchangeably and refer to a sequence that has an alteration in at least one codon occurring in a host cell's wild-type sequence. The expression product of the mutant sequence is a protein with an altered amino acid sequence relative to the wild-type. The expression product may have an altered functional capacity (e.g., enhanced enzymatic activity).

The terms "mutagenic primer" or "mutagenic oligonucleotide" (used interchangeably herein) are intended to refer to oligonucleotide compositions which correspond to a portion of the template sequence and which are capable of hybridizing thereto. With respect to mutagenic primers, the primer will not precisely match the template nucleic acid, the mismatch or mismatches in the primer being used to introduce the desired mutation into the nucleic acid library. As used herein, "non-mutagenic primer" or "non-mutagenic oligonucleotide" refers to oligonucleotide compositions that match precisely to the template nucleic acid. In one embodiment of the invention, only mutagenic primers are used. In another preferred embodiment of the invention, the primers are designed so that for at least one region at which a mutagenic primer has been included, there is also non-mutagenic primer included in the oligonucleotide mixture. By adding a mixture of mutagenic primers and non-mutagenic primers corresponding to at least one of the mutagenic primers, it is possible to produce a resulting nucleic acid library in which a variety of combinatorial mutational patterns are presented. For example, if it is desired that some of the members of the mutant nucleic acid library retain their parent sequence at certain positions while other members are mutant at such sites, the non-mutagenic primers provide the ability to obtain a specific level of non-mutant members within the nucleic acid library for a given residue. The methods of the invention employ mutagenic and non-mutagenic oligonucleotides which are generally between 10-50 bases in length, more preferably about 15-45 bases in length. However, it may be necessary to use primers that are either shorter than 10 bases or longer than 50 bases to obtain the mutagenesis result desired. With respect to corresponding mutagenic and non-mutagenic primers, it is not necessary that the corresponding oligonucleotides be of identical length, but only that there is overlap in the region corresponding to the mutation to be added.

Primers may be added in a pre-defined ratio according to the present invention. For example, if it is desired that the resulting library have a significant level of a certain specific mutation and a lesser amount of a different mutation at the same or different site, by adjusting the amount of primer added, it is possible to produce the desired biased library. Alternatively, by adding lesser or greater amounts of non-mutagenic primers, it is possible to adjust the frequency with which the corresponding mutation(s) are produced in the mutant nucleic acid library.

The terms "wild-type sequence" or "wild-type gene" are used interchangeably herein, to refer to a sequence that is native or naturally occurring in a host cell. In some embodiments, the wild-type sequence refers to a sequence of interest that is the starting point of a protein-engineering project. The wild-type sequence may encode either a homologous or heterologous protein. A homologous protein is one the host cell would produce without intervention. A heterologous protein is one that the host cell would not produce but for the intervention.

As used herein the term "lysate" refers to a solution containing the contents of lysed cells. In some embodiments, the lysate is a bacterial cell lysate (e.g., *E. coli* cells lysed using READYLYSE™ lysozyme solution from Epicentre; or *E. coli* cells lysed using a French Pressure cell).

As used herein the term "lysozyme" refers to a glycosidase that hydrolyzes the bond between N-acetyl muramic acid and N-acetul glucosamine, thus cleaving an important polymer in the cell wall of many bacteria. Suitable lysozymes for use with the present invention include but are not limited to hen egg white lysozyme (Sigma), T4 lysozyme, recombinant non-mammalian, non-avian lysozyme (READYLYSE™), or a fungal lysozyme.

As used herein, the term "headspace" refers to the vapor/air mixture trapped above a solid or liquid sample in a sealed vessel.

As used herein, the terms "high throughput screening" and "HTS" refer to measuring isoprene in at least 96 samples in 4 hours or less. In preferred embodiments, the sample volume is less than 2 mL.

Unless otherwise noted, all component or composition levels are in reference to the active level of that component or composition, and are exclusive of impurities, for example, residual solvents or by-products, which may be present in commercially available sources.

Enzyme components weights are based on total active protein. All percentages and ratios are calculated by weight unless otherwise indicated. All percentages and ratios are calculated based on the total composition unless otherwise.

DETAILED DESCRIPTION OF THE INVENTION

Isoprene monomer is employed in the manufacture of polyisoprene and various copolymers (with isobutylene, butadiene, styrene, or other monomers). To build a strain (prokaryotic or eukaryotic) capable of producing commercially viable levels of isoprene requires optimization of the entire pathway, either MVA to isoprene or DXP to isoprene. A key enzyme in the pathway is isoprene synthase (IspS), which converts the precursor DMAPP to isoprene. The only isoprene synthases (IspS) identified to date are those from plants such as poplar, English oak and kudzu vine. Although some bacteria, such as *Bacillus subtilis*, also produce isoprene, a prokaryotic IspS has yet to be identified and the native IspS activity in *Bacillus* is not sufficient for a commercial process. The plant IspS enzymes identified to date have been partially characterized in part by expression in *E. coli* and some of the kinetic parameters of these enzymes have been determined in vitro with purified protein. However, the kinetic parameters (Km, rate etc) of the native IspS enzymes are insufficient for commercial production of isoprene in a biological host.

To solve this problem as described herein, a plant IspS is expressed in a bacterial host. In addition the IspS is engineered for a change in a property of interest. Characterization of wild-type and mutant IspS is accomplished via any means or "test" suitable and is preferably based on the assessment of properties of interest. Properties of interest include but are not limited to: pH optima, temperature stability (e.g., $T_m$ value), intracellular and extracellular solubility, $K_m$ value, $k_{cat}$ value, or specific activity, as well as sensitivity to potential inhibitors including substrate or product inhibition. Oxidative and proteolytic stability are also of interest. Furthermore, activation or inhibition due to metal ion effects and ionic strength is of interest. These properties and parameters can be assessed by the conversion of DMAPP to isoprene in vitro with purified or partially purified isoprene synthase or in vivo in the context of a host organism such as *E. coli* expressing the DXP pathway, the MVA pathway, or both. It is contemplated that enzymes having various degrees of stability, solubility, activity, and/or expression level in one or more of test conditions will find use in the present invention for the production of isoprene in a diversity of hosts. High throughput methods such as those described in Example 10 are required to investigate these properties in an economical manner.

The invention features compositions and methods for the production of isoprene. In particular, these compositions and methods increase the rate of isoprene production and increase the total amount of isoprene that is produced. The biosynthetic processes for isoprene production described herein are a desirable alternative to using natural rubber. As discussed further below, the amount of isoprene produced by cells can be greatly increased by introducing a heterologous nucleic acid encoding an isoprene synthase (IspS) polypeptide into the cells. Isoprene synthase polypeptides convert dimethylallyl diphosphate (DMAPP) into isoprene. As shown in the examples, a heterologous *Pueraria montana* (kudzu) isoprene synthase polypeptide and variants thereof was expressed in Gram-negative bacterial cells (e.g., *Escherichia coli*). Also shown in the examples and contemplated within the scope of the invention are poplar isoprene synthase polypeptide and variants thereof was expressed in Gram-negative bacterial cells (e.g., *Escherichia coli*).

Heterologous expression of a plant IspS in bacterial host cells resulted in the production of more isoprene than the corresponding cells lacking the plant IspS.

It has been shown that mutating amino-acid residues on the surface of protease enzymes can improve their activity, expression, and stability (WO2008/153925, WO2008/153934, WO2008/153935). Surprisingly, we have found that mutating amino-acid residues on the surface of a completely different enzyme, isoprene synthase, can enhance its expression, solubility, and activity. L70R is an example of such a beneficial surface mutation.

Elucidation of the three-dimensional structure of an enzyme is essential for accurately identifying amino-acid residues on its surface. Homology modeling using structures with sequences approximately 40% identical to isoprene synthase (e.g., bornyl synthase and limonene synthase, the enzymes of known structure with closest identity to isoprene synthase) can reveal gross aspects of the modeled enzyme structure, but is insufficient to precisely identify surface-exposed residues and quantify their degree of surface exposure. Surface exposure of an amino-acid residue is quantified by the percentage of solvent-accessible surface area of its side chain.

The following classes of mutations in isoprene synthase may improve solubility of the enzyme by targeting amino-acid residues that are >50% solvent-exposed, preferably >65% solvent-exposed, and most preferably >85% solvent-exposed:

Hydrophobic→positively charged, and vice versa
Hydrophobic→negatively charged, and vice versa
Hydrophobic→neutral polar, and vice versa
Neutral polar→positively charged, and vice versa
Neutral polar→negatively charged, and vice versa
Positively charged→negatively charged, and vice versa Additionally isoprene production by cells containing a heterologous isoprene synthase nucleic acid can be enhanced by increasing the amount of a 1-deoxy-D-xylulose-5-phosphate synthase (DXS) polypeptide, and/or an isopentenyl diphosphate isomerase (IDI) polypeptide, expressed by the cells. For example, a DXS nucleic acid and/or an IDI nucleic acid can be introduced into the cells. The DXS nucleic acid may be a heterologous nucleic acid or a duplicate copy of an endogenous nucleic acid. Similarly, the IDI nucleic acid may be a heterologous nucleic acid or a duplicate copy of an endogenous nucleic acid. In some embodiments, the amount of DXS and/or IDI polypeptide is increased by replacing the endogenous DXS and/or IDI promoters or regulatory regions with other promoters and/or regulatory regions that result in greater transcription of the DXS and/or IDI nucleic acids. In some embodiments, the cells contain both a heterologous nucleic acid encoding an isoprene synthase polypeptide (e.g., a plant isoprene synthase nucleic acid) and a duplicate copy of an endogenous nucleic acid encoding an isoprene synthase polypeptide.

Figure 15:
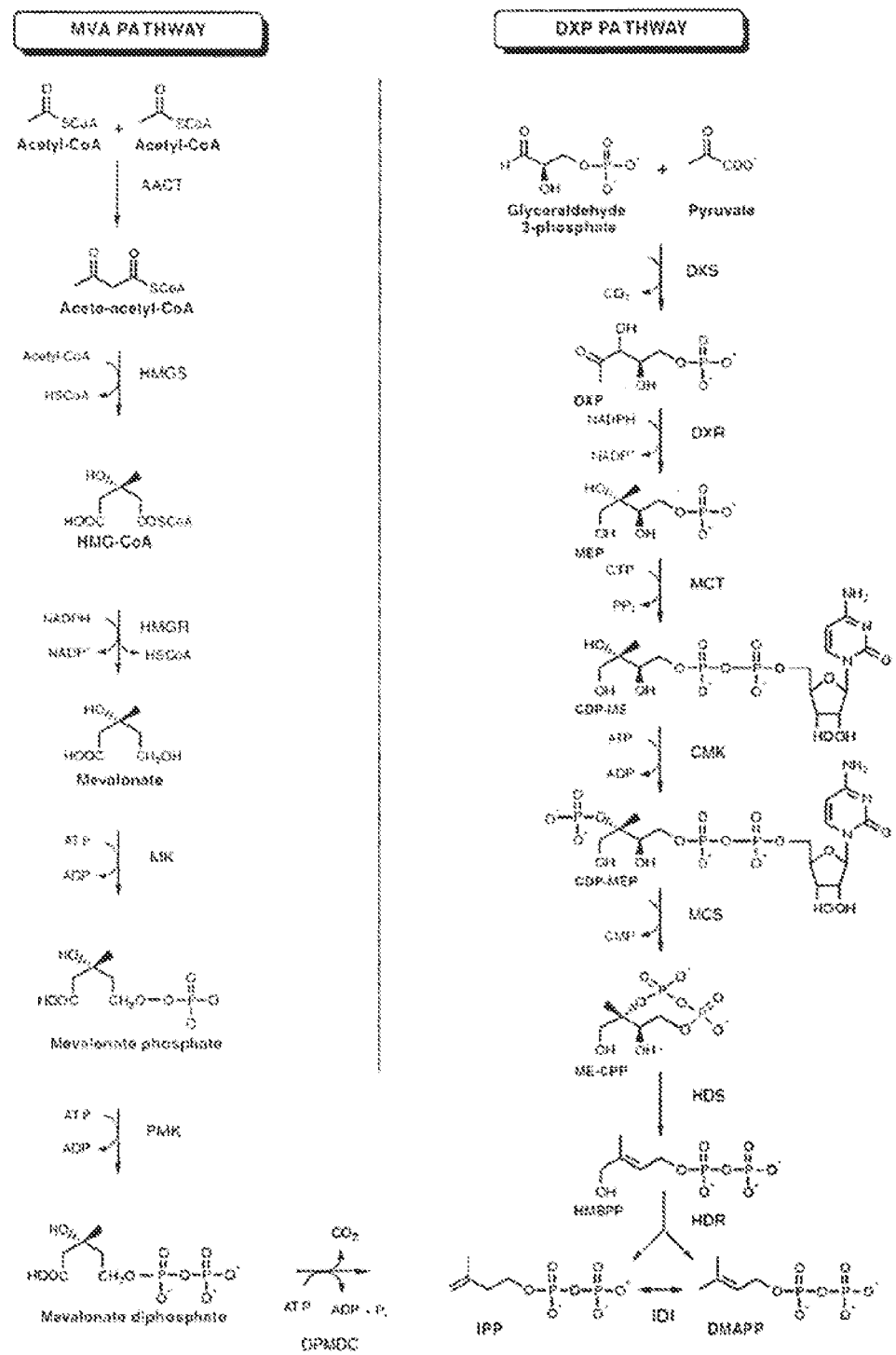
FIG. 15 shows the MVA and DXP metabolic pathways for isoprene (based on F. Bouvier et al., Progress in Lipid Res. 44: 357-429, 2005). The following description includes alternative names for each polypeptide in the pathways and a reference that discloses an assay for measuring the activity of the indicated polypeptide (each of these references are each hereby incorporated by reference in their entireties, particularly with respect to assays for polypeptide activity for polypeptides in the MVA and DXP pathways). Mevalonate Pathway: AACT; Acetyl-CoA acetyltransferase, MvaE, EC 2.3.1.9. Assay: J. Bacteriol., 184: 2116-2122, 2002; HMGS; Hydroxymethylglutaryl-CoA synthase, MvaS, EC 2.3.3.10. Assay: J. Bacteriol., 184: 4065-4070, 2002; HMGR; 3-Hydroxy-3-methylglutaryl-CoA reductase, MvaE, EC 1.1.1.34. Assay: J. Bacteriol., 184: 2116-2122, 2002; MVK; Mevalonate kinase, ERG12, EC 2.7.1.36. Assay: Curr Genet. 19:9-14, 1991. PMK; Phosphomevalonate kinase, ERG8, EC 2.7.4.2, Assay: Mol Cell Biol., 11:620-631, 1991; DPMDC; Diphosphomevalonate decarboxylase, MVD1, EC 4.1.1.33. Assay: Biochemistry, 33:13355-13362, 1994; IDI; Isopentenyl-diphosphate delta-isomerase, IDI1, EC 5.3.3.2. Assay: J. Biol. Chem. 264:19169-19175, 1989. DXP Pathway: DXS; 1-Deoxyxylulose-5-phosphate synthase, dxs, EC 2.2.1.7. Assay: PNAS, 94:12857-62, 1997; DXR; 1-Deoxy-D-xylulose 5-phosphate reductoisomerase, dxr, EC 2.2.1.7. Assay: Eur. J. Biochem. 269:4446-4457, 2002; MCT; 4-Diphosphocytidyl-2C-methyl-D-erythritol synthase, IspD, EC 2.7.7.60. Assay: PNAS, 97: 6451-6456, 2000; CMK; 4-Diphosphocytidyl-2-C-methyl-D-erythritol kinase, IspE, EC 2.7.1.148. Assay: PNAS, 97:1062-1067, 2000; MCS; 2C-Methyl-D-erythritol 2,4-cyclodiphosphate synthase, IspF, EC 4.6.1.12. Assay: PNAS, 96:11758-11763, 1999; HDS; 1-Hydroxy-2-methyl-2-(E)-butenyl 4-diphosphate synthase, ispG, EC 1.17.4.3. Assay: J. Org. Chem., 70:9168-9174, 2005; HDR; 1-Hydroxy-2-methyl-2-(E)-butenyl 4-diphosphate reductase, IspH, EC 1.17.1.2. Assay: JACS, 126:12847-12855, 2004.

The encoded DXS and IDI polypeptides are part of the DXP pathway for the biosynthesis of isoprene (FIG. 15). DXS polypeptides convert pyruvate and D-glyceraldehyde-3-phosphate into 1-deoxy-D-xylulose-5-phosphate. While not intending to be bound by any particular theory, it is believed that increasing the amount of DXS polypeptide increases the flow of carbon through the DXP pathway, leading to greater isoprene production. IDI polypeptides catalyze the interconversion of isopentenyl diphosphate (IPP) and dimethylallyl diphosphate (DMAPP). While not intending to be bound by any particular theory, it is believed that increasing the amount of IDI polypeptide in cells increases the amount of IPP that is converted into DMAPP, which in turn is converted into isoprene.

In some embodiments the production of isoprene by cells containing a heterologous isoprene synthase nucleic acid can be augmented by increasing expression of a MVA polypeptide in the cells (FIG. 15). Exemplary MVA pathways polypeptides include any of the following polypeptides: acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonte decarboxylase (MVD) polypeptides, IDI polypeptides, and polypeptides (e.g., fusion polypeptides) having an activity of two or more MVA pathway polypeptides. For example, one or more MVA pathway nucleic acids can be introduced into the cells. In some embodiments, the cells contain the upper MVA pathway, which includes AA-CoA thiolase, HMG-CoA synthase, and HMG-CoA reductase nucleic acids. In some embodiments, the cells contain the lower MVA pathway, which includes MVK, PMK, MVD, and IDI nucleic acids. In some embodiments, the cells contain the entire MVA pathway, which includes AA-CoA thiolase, HMG-CoA synthase, HMG-CoA reductase, MVK, PMK, MVD, and IDI nucleic acids. The MVA pathway nucleic acids may be heterologous nucleic acids or duplicate copies of endogenous nucleic acids. In some embodiments, the amount of one or more MVA pathway polypeptides is increased by replacing the endogenous promoters or regulatory regions for the MVA pathway nucleic acids with other promoters and/or regulatory regions that result in greater transcription of the MVA pathway nucleic acids. In some embodiments, the cells contain both a heterologous nucleic acid encoding an isoprene synthase polypeptide (e.g., a plant isoprene synthase nucleic acid) and a duplicate copy of an endogenous nucleic acid encoding an isoprene synthase polypeptide.

In some embodiments, at least a portion of the cells maintain the heterologous isoprene synthase, DXS, IDI, and/or MVA pathway nucleic acid for at least about 5, 10, 20, 50, 75, 100, 200, 300, or more cell divisions in a continuous culture (such as a continuous culture without dilution). In some embodiments of any of the aspects of the invention, the nucleic acid comprising the heterologous or duplicate copy of an endogenous isoprene synthase, DXS, IDI, and/or MVA pathway nucleic acid also comprises a selective marker, such as a kanamycin, ampicillin, carbenicillin, gentamicin, hygromycin, phleomycin, bleomycin, neomycin, or chloramphenicol antibiotic resistance nucleic acid.

I. Exemplary Polypeptides and Nucleic Acids

Various isoprene synthase, DXS, IDI, and/or MVA pathway polypeptides and nucleic acids can be used in the compositions and methods of the invention.

As used herein, "polypeptides" includes polypeptides, proteins, peptides, fragments of polypeptides, and fusion polypeptides that include part or all of a first polypeptide (e.g., an isoprene synthase, DXS, IDI, or MVA pathway polypeptide) and part or all of a second polypeptide (e.g., a peptide that facilitates purification or detection of the fusion polypeptide, such as a His-tag). In some embodiments, the fusion polypeptide has an activity of two or more MVA pathway polypeptides (such as AA-CoA thiolase and HMG-CoA reductase polypeptides). In some embodiments, the polypeptide is a naturally-occurring polypeptide (such as the polypeptide encoded by an *Enterococcus faecalis* mvaE nucleic acid) that has an activity of two or more MVA pathway polypeptides.

In various embodiments, a polypeptide has at least or about 50, 100, 150, 175, 200, 250, 300, 350, 400, or more amino acids. In some embodiments, the polypeptide fragment contains at least or about 25, 50, 75, 100, 150, 200, 300, or more contiguous amino acids from a full-length polypeptide and has at least or about 5%, 10%, 20%, 30%, 40%, 50%, 60%, 70%, 80%, 90%, 95%, or 100% of an activity of a corresponding full-length polypeptide. In particular embodiments the polypeptide includes a segment of or the entire amino acid sequence of any naturally-occurring isoprene synthase, DXS, IDI, or MVA pathway polypeptide. In some embodiments, the polypeptide has one or more mutations compared to the sequence of a wild-type (i.e., a sequence occurring in nature) isoprene synthase, DXS, IDI, or MVA pathway polypeptide.

In some embodiments, the polypeptide is an isolated polypeptide. As used herein, an "isolated polypeptide" is not part of a library of polypeptides, such as a library of 2, 5, 10, 20, 50 or more different polypeptides and is separated from at least one component with which it occurs in nature. An isolated polypeptide can be obtained, for example, by expression of a recombinant nucleic acid encoding the polypeptide.

In some embodiments, the polypeptide is a heterologous polypeptide. By "heterologous polypeptide" is meant a polypeptide whose amino acid sequence is not identical to that of another polypeptide naturally expressed in the same host cell.

As used herein, a "nucleic acid" refers to two or more deoxyribonucleotides and/or ribonucleotides in either single or double-stranded form. In some embodiments, the nucleic acid is a recombinant nucleic acid. By "recombinant nucleic acid" means a nucleic acid of interest that is free of one or more nucleic acids (e.g., genes), which in the genome occurring in nature of the organism from which the nucleic acid of interest is derived, flank the nucleic acid of interest. The term therefore includes, for example, a recombinant DNA which is incorporated into a vector, into an autonomously replicating plasmid or virus, or into the genomic DNA of a prokaryote or eukaryote, or which exists as a separate molecule (e.g., a cDNA, a genomic DNA fragment, or a cDNA fragment produced by PCR or restriction endonuclease digestion) independent of other sequences.

In various embodiments, the nucleic acid is a recombinant nucleic acid. For instance, in some embodiments, an isoprene synthase, DXS, IDI, or MVA pathway nucleic acid is operably linked to another nucleic acid encoding all or a portion of another polypeptide such that the recombinant nucleic acid encodes a fusion polypeptide that includes an isoprene synthase, DXS, IDI, or MVA pathway polypeptide and all or part of another polypeptide (e.g., a peptide that facilitates purification or detection of the fusion polypeptide, such as a His-tag). In some embodiments, part or all of a recombinant nucleic acid is chemically synthesized. In some embodiments, the nucleic acid is a heterologous nucleic acid. By "heterologous nucleic acid" is meant a nucleic acid whose nucleic acid sequence is not identical to that of another nucleic acid naturally found in the same host cell.

In particular embodiments the nucleic acid includes a segment of or the entire nucleic acid sequence of any naturally-occurring isoprene synthase, DXS, IDI, or MVA pathway nucleic acid. In some embodiments, the nucleic acid includes at least or about 50, 100, 150, 200, 300, 400, 500, 600, 700, 800, or more contiguous nucleotides from a naturally-occurring isoprene synthase nucleic acid DXS, IDI, or MVA pathway nucleic acid. In some embodiments, the nucleic acid has one or more mutations compared to the sequence of a wild-type (i.e., a sequence occurring in nature) isoprene synthase, DXS, IDI, or MVA pathway nucleic acid. In some embodiments, the nucleic acid has one or more mutations (e.g., a silent mutation) that increase the transcription or translation of isoprene synthase, DXS, IDI, or MVA pathway nucleic acid. In some embodiments, the nucleic acid is a degenerate variant of any nucleic acid encoding an isoprene synthase, DXS, IDI, or MVA pathway polypeptide.

"Codon degeneracy" refers to divergence in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a nucleic acid for improved expression in a host cell, it is desirable in some embodiments to design the nucleic acid such that its frequency of codon usage approaches the frequency of preferred codon usage of the host cell.

The accession numbers of exemplary isoprene synthase, DXS, IDI, and/or MVA pathway polypeptides and nucleic acids are listed in Appendix 1 of U.S. Application No. 61/013,574, herein incorporated by reference in its entirety, particularly with respect to the amino acid and nucleic acid sequences of isoprene synthase, DXS, IDI, and/or MVA pathway polypeptides and nucleic acids). The Kegg database also contains the amino acid and nucleic acid sequences of numerous exemplary isoprene synthase, DXS, IDI, and/or MVA pathway polypeptides and nucleic acids (See, e.g., the worldwide web at "genome.jp/kegg/pathway/map/map00100.html" and the sequences therein, which are each hereby incorporated by reference in their entireties, particularly with respect to the amino acid and nucleic acid sequences of isoprene synthase, DXS, IDI, and/or MVA pathway polypeptides and nucleic acids). In some embodiments, one or more of the isoprene synthase, DXS, IDI, and/or MVA pathway polypeptides and/or nucleic acids have a sequence identical to a sequence publicly available on Dec. 12, 2007, such as any of the sequences that correspond to any of the accession numbers in Appendix 1 of U.S. Application No. 61/013,574, or any of the sequences present in the Kegg database as of the date of this filing. Additional exemplary isoprene synthase, DXS, IDI, and/or MVA pathway polypeptides and nucleic acids are described further below.

Exemplary Isoprene Synthase Polypeptides and Nucleic Acids

As noted above, isoprene synthase polypeptides convert dimethylallyl diphosphate (DMAPP) into isoprene. Exemplary isoprene synthase polypeptides include polypeptides, fragments of polypeptides, peptides, and fusions polypeptides that have at least one activity of an isoprene synthase polypeptide. Standard methods can be used to determine whether a polypeptide has isoprene synthase polypeptide activity by measuring the ability of the polypeptide to convert DMAPP into isoprene in vitro, in a cell extract, or in vivo. Isoprene synthase polypeptide activity in the cell extract can be measured, for example, as described in Silver et al., J. Biol. Chem. 270:13010-13016, 1995 and references therein, which are each hereby incorporated by reference in their entireties, particularly with respect to assays for isoprene synthase polypeptide activity. DMAPP (Sigma) is evaporated to dryness under a stream of nitrogen and rehydrated to a concentration of 100 mM in 100 mM potassium phosphate buffer pH 8.2 and stored at −20° C. To perform the assay, a solution of 5 µl of 1M $MgCl_2$, 1 mM (250 µg/ml) DMAPP, 65 µl of Plant Extract Buffer (PEB) (50 mM Tris-HCl, pH 8.0, 20 mM $MgCl_2$, 5% glycerol, and 2 mM DTT) is added to 25 µl of cell extract in a 20 ml Headspace vial with a metal screw cap and teflon coated silicon septum (Agilent Technologies) and cultured at 37° C. for 15 minutes with shaking. The reaction is quenched by adding 200 µl of 250 mM EDTA or by heat inactivation, and isoprene is quantified by GC/MS.

Exemplary isoprene synthase nucleic acids include nucleic acids that encode a polypeptide, fragment of a polypeptide, peptide, or fusion polypeptide that has at least one activity of an isoprene synthase polypeptide. Exemplary isoprene synthase polypeptides and nucleic acids include naturally-occurring polypeptides and nucleic acids from any of the source organisms described herein as well as mutant polypeptides and nucleic acids derived from any of the source organisms described herein.

In some embodiments, the isoprene synthase polypeptide or nucleic acid is from the family Fabaceae, the family Salicaceae, or the family Fagaceae. In some embodiments, the isoprene synthase polypeptide or nucleic acid is a naturally-occurring polypeptide or nucleic acid from *Pueraria montana* (kudzu) (Sharkey et al., Plant Physiology 137: 700-712, 2005), poplar (such as *Populus alba* x *tremula* CAC35696) Miller et al., Planta 213: 483-487, 2001) aspen (such as *Populus tremuloides*) Silver et al., JBC 270(22): 13010-1316, 1995), or English Oak (*Quercus robur*) (Zimmer et al., WO 98/02550), which are each hereby incorporated by reference in their entireties, particularly with respect to isoprene synthase nucleic acids and the expression of isoprene synthase polypeptides. Suitable isoprene synthases include, but are not limited to, those identified by GenBank Accession Nos. AY341431, AY316691, AY279379, AJ457070, and AY182241, which are each hereby incorporated by reference in their entireties, particularly with respect to sequences of isoprene synthase nucleic acids and polypeptides. In some embodiments, the isoprene synthase polypeptide or nucleic acid is not a naturally-occurring polypeptide or nucleic acid from *Quercus robur* (i.e., the isoprene synthase polypeptide or nucleic acid is an isoprene synthase polypeptide or nucleic acid other than a naturally-occurring polypeptide or nucleic acid from *Quercus robur*). In some embodiments, the isoprene synthase nucleic acid or polypeptide is not a naturally-occurring polypeptide or nucleic acid from poplar (such as *Populus alba* x *tremula* CAC35696).

Exemplary DXS Polypeptides and Nucleic Acids

As noted above, 1-deoxy-D-xylulose-5-phosphate synthase (DXS) polypeptides convert pyruvate and D-glyceraldehyde-3-phosphate into 1-deoxy-D-xylulose-5-phosphate. Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde-3-phosphate into 1-deoxy-D-xylulose-5-phosphate in vitro, in a cell extract, or in vivo. Exemplary DXS nucleic acids include nucleic acids that encode a polypeptide, fragment of a polypeptide, peptide, or fusion polypeptide that has at least one activity of a DXS polypeptide. Exemplary DXS polypeptides and nucleic acids include naturally-occurring polypeptides and nucleic acids from any of the source organisms described herein as well as mutant polypeptides and nucleic acids derived from any of the source organisms described herein.

Exemplary IDI Polypeptides and Nucleic Acids

Isopentenyl diphosphate isomerase polypeptides (isopentenyl-diphosphate delta-isomerase or IDI) catalzyes the interconversion of isopentenyl diphosphate (IPP) and dimethylallyl diphosphate (DMAPP) (e.g., converting IPP into DMAPP and/or converting DMAPP into IPP). Exemplary IDI polypeptides include polypeptides, fragments of polypeptides, peptides, and fusions polypeptides that have at least one activity of an IDI polypeptide. Standard methods (such as those described herein) can be used to determine whether a polypeptide has IDI polypeptide activity by measuring the ability of the polypeptide to interconvert IPP and DMAPP in vitro, in a cell extract, or in vivo. Exemplary IDI nucleic acids include nucleic acids that encode a polypeptide, fragment of a polypeptide, peptide, or fusion polypeptide that has at least one activity of an IDI polypeptide. Exemplary IDI polypeptides and nucleic acids include naturally-occurring polypeptides and nucleic acids from any of the source organisms described herein as well as mutant polypeptides and nucleic acids derived from any of the source organisms described herein.

Exemplary MVA Pathway Polypeptides and Nucleic Acids

Exemplary MVA pathway polypeptides include acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonte decarboxylase (MVD) polypeptides, IDI polypeptides, and polypeptides (e.g., fusion polypeptides) having an activity of two or more MVA pathway polypeptides. In particular, MVA pathway polypeptides include polypeptides, fragments of polypeptides, peptides, and fusions polypeptides that have at least one activity of an MVA pathway polypeptide. Exemplary MVA pathway nucleic acids include nucleic acids that encode a polypeptide, fragment of a polypeptide, peptide, or fusion polypeptide that has at least one activity of an MVA pathway polypeptide. Exemplary MVA pathway polypeptides and nucleic acids include naturally-occurring polypeptides and nucleic acids from any of the source organisms described herein as well as mutant polypeptides and nucleic acids derived from any of the source organisms described herein.

In particular, acetyl-CoA acetyltransferase polypeptides (AA-CoA thiolase or AACT) convert two molecules of acetyl-CoA into acetoacetyl-CoA. Standard methods (such as those described herein) can be used to determine whether a polypeptide has AA-CoA thiolase polypeptide activity by measuring the ability of the polypeptide to convert two molecules of acetyl-CoA into acetoacetyl-CoA in vitro, in a cell extract, or in vivo.

3-hydroxy-3-methylglutaryl-CoA synthase (HMG-CoA synthase or HMGS) polypeptides convert acetoacetyl-CoA into 3-hydroxy-3-methylglutaryl-CoA. Standard methods (such as those described herein) can be used to determine whether a polypeptide has HMG-CoA synthase polypeptide activity by measuring the ability of the polypeptide to convert acetoacetyl-CoA into 3-hydroxy-3-methylglutaryl-CoA in vitro, in a cell extract, or in vivo.

3-hydroxy-3-methylglutaryl-CoA reductase (HMG-CoA reductase or HMGR) polypeptides convert 3-hydroxy-3-methylglutaryl-CoA into mevalonate. Standard methods (such as those described herein) can be used to determine whether a polypeptide has HMG-CoA reductase polypeptide activity by measuring the ability of the polypeptide to convert 3-hydroxy-3-methylglutaryl-CoA into mevalonate in vitro, in a cell extract, or in vivo.

Mevalonate kinase (MVK) polypeptides phosphorylates mevalonate to form mevalonate-5-phosphate. Standard methods (such as those described herein) can be used to determine whether a polypeptide has MVK polypeptide activity by measuring the ability of the polypeptide to convert mevalonate into mevalonate-5-phosphate in vitro, in a cell extract, or in vivo.

Phosphomevalonate kinase (PMK) polypeptides phosphorylates mevalonate-5-phosphate to form mevalonate-5-diphosphate. Standard methods (such as those described herein) can be used to determine whether a polypeptide has PMK polypeptide activity by measuring the ability of the polypeptide to convert mevalonate-5-phosphate into mevalonate-5-diphosphate in vitro, in a cell extract, or in vivo.

Diphosphomevalonte decarboxylase (MVD or DPMDC) polypeptides convert mevalonate-5-diphosphate into isopentenyl diphosphate polypeptides (IPP). Standard methods (such as those described herein) can be used to determine whether a polypeptide has MVD polypeptide activity by measuring the ability of the polypeptide to convert mevalonate-5-diphosphate into IPP in vitro, in a cell extract, or in vivo.

Exemplary Methods for Isolating Nucleic Acids

Isoprene synthase, DXS, IDI, and/or MVA pathway nucleic acids can be isolated using standard methods. Methods of obtaining desired nucleic acids from a source organism of interest (such as a bacterial genome) are common and well known in the art of molecular biology (see, for example, WO 2004/033646 and references cited therein, which are each hereby incorporated by reference in their entireties, particularly with respect to the isolation of nucleic acids of interest). For example, if the sequence of the nucleic acid is known (such as any of the known nucleic acids described herein), suitable genomic libraries may be created by restriction endonuclease digestion and may be screened with probes complementary to the desired nucleic acid sequence. Once the sequence is isolated, the DNA may be amplified using standard primer directed amplification methods such as polymerase chain reaction (PCR) (U.S. Pat. No. 4,683,202, which is incorporated by reference in its entirety, particularly with respect to PCR methods) to obtain amounts of DNA suitable for transformation using appropriate vectors. Alternatively, isoprene synthase, DXS, IDI, and/or MVA pathway nucleic acids (such as any isoprene synthase, DXS, IDI, and/or MVA pathway nucleic acids with a known nucleic acid sequence) can be chemically synthesized using standard methods.

Additional isoprene synthase, DXS, IDI, or MVA pathway polypeptides and nucleic acids that may be suitable for use in the compositions and methods described herein can be identified using standard methods. For example, cosmid libraries of the chromosomal DNA of organisms known to produce isoprene naturally can be constructed in organisms such as E. coli, and then screened for isoprene production. Additional methods for obtaining isoprene synthase, DXS, IDI, and/or MVA pathway nucleic acids include screening a metagenomic library by assay (such as the headspace assay described herein) or by PCR using primers directed against nucleotides encoding for a length of conserved amino acids (for example, at least 3 conserved amino acids). Conserved amino acids can be identified by aligning amino acid sequences of known isoprene synthase, DXS, IDI, and/or MVA pathway polypeptides. Conserved amino acids for isoprene synthase polypeptides can be identified based on aligned sequences of known isoprene synthase polypeptides. An organism found to produce isoprene naturally can be subjected to standard protein purification methods (which are well known in the art) and the resulting purified polypeptide can be sequenced using standard methods. Other methods are found in the literature (See, e.g., Julsing et al., Applied. Microbiol. Biotechnol. 75: 1377-84, 2007; and Withers et al., Appl Environ Microbiol. 73:6277-83, 2007, which are each hereby incorporated by reference in their entireties, particularly with respect to identification of nucleic acids involved in the synthesis of isoprene).

Additionally, standard sequence alignment and/or structure prediction programs can be used to identify additional DXS, IDI, or MVA pathway polypeptides and nucleic acids based on the similarity of their primary and/or predicted polypeptide secondary structure with that of known DXS, IDI, or MVA pathway polypeptides and nucleic acids. Standard databases such as the swissprot-trembl database (world-wide web at "expasy.org", Swiss Institute of Bioinformatics Swiss-Prot group CMU—1 rue Michel Servet CH-1211 Geneva 4, Switzerland) can also be used to identify isoprene synthase, DXS, IDI, or MVA pathway polypeptides and nucleic acids. The secondary and/or tertiary structure of an isoprene synthase, DXS, IDI, or MVA pathway polypeptide can be predicted using the default settings of standard structure prediction programs, such as PredictProtein (Rost et al., The PredictProtein Server. Nucleic Acids Research 32(Web Server issue):W321-W326, 2004). Alternatively, the actual secondary and/or tertiary structure of an isoprene synthase, DXS, IDI, or MVA pathway polypeptide can be determined using standard methods. Additional isoprene synthase, DXS, IDI, or MVA pathway nucleic acids can also be identified by hybridization to probes generated from known isoprene synthase, DXS, IDI, or MVA pathway nucleic acids.

Exemplary Promoters and Vectors

Any of the isoprene synthase, DXS, IDI, or MVA pathway nucleic acid described herein can be included in one or more vectors. Accordingly, the invention also features vectors with one more nucleic acids encoding any of the isoprene synthase, DXS, IDI, or MVA pathway polypeptides that are described herein. As used herein, a "vector" means a construct that is capable of delivering, and desirably expressing one or more nucleic acids of interest in a host cell. Examples of vectors include, but are not limited to, plasmids, viral vectors, DNA or RNA expression vectors, cosmids, and phage vectors. In some embodiments, the vector contains a nucleic acid under the control of an expression control sequence.

As used herein, an "expression control sequence" means a nucleic acid sequence that directs transcription of a nucleic acid of interest. An expression control sequence can be a promoter, such as a constitutive or an inducible promoter, or an enhancer. An "inducible promoter" is a promoter that is active under environmental or developmental regulation. The expression control sequence is operably linked to the nucleic acid segment to be transcribed.

In some embodiments, the vector contains a selective marker. The term "selective marker" refers to a nucleic acid capable of expression in a host cell that allows for ease of selection of those host cells containing an introduced nucleic acid or vector. Examples of selectable markers include, but are not limited to, antibiotic resistance nucleic acids (e.g., kanamycin, ampicillin, carbenicillin, gentamicin, hygromycin, phleomycin, bleomycin, neomycin, or chloramphenicol) and/or nucleic acids that confer a metabolic advantage, such as a nutritional advantage on the host cell. In some embodiments, an isoprene synthase, DXS, IDI, or MVA pathway nucleic acid integrates into a chromosome of the cells without a selective marker.

Suitable vectors are those that are compatible with the host cell employed. Suitable vectors can be derived, for example, from a bacterium, a virus (such as bacteriophage T7 or a M-13 derived phage), a cosmid, a yeast, or a plant. Protocols for obtaining and using such vectors are known in the art (See, e.g., Sambrook et al., Molecular Cloning: A Laboratory Manual, $2^{nd}$ ed., Cold Spring Harbor, 1989, which is hereby incorporated by reference in its entirety, particularly with respect to the use of vectors).

Promoters are well known in the art. Any promoter that functions in the host cell can be used for expression of an isoprene synthase, DXS, IDI, or MVA pathway nucleic acid in the host cell. Initiation control regions or promoters, which are useful to drive expression of isoprene synthase, DXS, IDI, or MVA pathway nucleic acids in various host cells are numerous and familiar to those skilled in the art (see, for example, WO 2004/033646 and references cited therein, which are each hereby incorporated by reference in their entireties, particularly with respect to vectors for the expression of nucleic acids of interest). Virtually any promoter capable of driving these nucleic acids is suitable for the present invention including, but not limited to lac, trp, $\lambda P_L$, $\lambda P_R$, T7, tac, and trc (useful for expression in E. coli).

In some embodiments, a glucose isomerase promoter is used (see, for example, U.S. Pat. No. 7,132,527 and references cited therein, which are each hereby incorporated by reference in their entireties, particularly with respect promoters and plasmid systems for expressing polypeptides of interest). Reported glucose isomerase promoter mutants can be used to vary the level of expression of the polypeptide encoded by a nucleic acid operably linked to the glucose isomerase promoter (U.S. Pat. No. 7,132,527). In various embodiments, the glucose isomerase promoter is contained in a low, medium, or high copy plasmid (U.S. Pat. No. 7,132, 527).

In various embodiments, an isoprene synthase, DXS, IDI, and/or MVA pathway nucleic acid is contained in a low copy plasmid (e.g., a plasmid that is maintained at about 1 to about 4 copies per cell), medium copy plasmid (e.g., a plasmid that is maintained at about 10 to about 15 copies per cell), or high copy plasmid (e.g., a plasmid that is maintained at about 50 or more copies per cell). In some embodiments, the heterologous or extra endogenous isoprene synthase, DXS, IDI, or MVA pathway nucleic acid is operably linked to a T7 promoter. In some embodiments, the heterologous or extra endogenous isoprene synthase, DXS, IDI, or MVA pathway nucleic acid operably linked to a T7 promoter is contained in a medium or high copy plasmid. In some embodiments, the heterologous or extra endogenous isoprene synthase, DXS, IDI, or MVA pathway nucleic acid is operably linked to a Trc promoter. In some embodiments, the heterologous or extra endogenous isoprene synthase, DXS, IDI, or MVA pathway nucleic acid operably linked to a Trc promoter is contained in a medium or high copy plasmid. In some embodiments, the heterologous or extra endogenous isoprene synthase, DXS, IDI, or MVA pathway nucleic acid is operably linked to a Lac promoter. In some embodiments, the heterologous or extra endogenous isoprene synthase, DXS, IDI, or MVA pathway nucleic acid operably linked to a Lac promoter is contained in a low copy plasmid. In some embodiments, the heterologous or extra endogenous isoprene synthase, DXS, IDI, or MVA pathway nucleic acid is operably linked to an endogenous promoter, such as an endogenous *Escherichia, Panteoa, Bacillus, Yarrowia, Streptomyces*, or *Trichoderma* promoter or an endogenous alkaline serine protease, isoprene synthase, DXS, IDI, or MVA pathway promoter. In some embodiments, the heterologous or extra endogenous isoprene synthase, DXS, IDI, or MVA pathway nucleic acid operably linked to an endogenous promoter is contained in a high copy plasmid. In some embodiments, the vector is a replicating plasmid that does not integrate into a chromosome in the cells. In some embodiments part or all of the vector integrates into a chromosome in the cells.

In some embodiments, the expression vector also includes a termination sequence. Termination control regions may also be derived from various genes native to the host cell. In some embodiments, the termination sequence and the promoter sequence are derived from the same source. In another embodiment, the termination sequence is endogenous to the host cell.

In some embodiments, the promoter, coding, region, and terminator all originate from the isoprene synthase, DXS, IDI, or MVA pathway nucleic acid to be expressed. In some embodiments, the coding region for an isoprene synthase, DXS, IDI, or MVA pathway nucleic acid is inserted into a general-purpose expression vector such that it is under the transcriptional control of the expression construct promoter and terminator sequences. In some embodiments, genes or part thereof are inserted downstream of the strong cbh1 promoter.

An isoprene synthase, DXS, IDI, or MVA pathway nucleic acid can be incorporated into a vector, such as an expression vector, using standard techniques (Sambrook et al., Molecular Cloning: A Laboratory Manual, Cold Spring Harbor, 1982, which is hereby incorporated by reference in its entirety, particularly with respect to the screening of appropriate DNA sequences and the construction of vectors). Methods used to ligate the DNA construct comprising a nucleic acid of interest (such as an isoprene synthase, DXS, IDI, or MVA pathway nucleic acid), a promoter, a terminator, and other sequences and to insert them into a suitable vector are well known in the art. For example, restriction enzymes can be used to cleave the isoprene synthase, DXS, IDI, or MVA pathway nucleic acid and the vector. Then, the compatible ends of the cleaved isoprene synthase, DXS, IDI, or MVA pathway nucleic acid and the cleaved vector can be ligated. Linking is generally accomplished by ligation at convenient restriction sites. If such sites do not exist, the synthetic oligonucleotide linkers are used in accordance with conventional practice (see, Sambrook et al., Molecular Cloning: A Laboratory Manual, $2^{nd}$ ed., Cold Spring Harbor, 1989, and Bennett and Lasure, More Gene Manipulations in Fungi, Academic Press, San Diego, pp 70-76, 1991, which are each hereby incorporated by reference in their entireties, particularly with respect to oligonucleotide linkers). Additionally, vectors can be constructed using known recombination techniques (e.g., Invitrogen Life Technologies, Gateway Technology).

In some embodiments, it may be desirable to over-express isoprene synthase, DXS, IDI, or MVA pathway nucleic acids at levels far higher than currently found in naturally-occurring cells. This result may be accomplished by the selective cloning of the nucleic acids encoding those polypeptides into multicopy plasmids or placing those nucleic acids under a strong inducible or constitutive promoter. Methods for over-expressing desired polypeptides are common and well known in the art of molecular biology and examples may be found in Sambrook et al., Molecular Cloning: A Laboratory Manual, $2^{nd}$ ed., Cold Spring Harbor, 1989, which is hereby incorporated by reference in its entirety, particularly with respect to cloning techniques.

The following resources include descriptions of additional general methodology useful in accordance with the invention: Kreigler, Gene Transfer and Expression; A Laboratory Manual, 1990; and Ausubel et al., Eds. Current Protocols in Molecular Biology, 1994, which are each hereby incorporated by reference in their entireties, particularly with respect to molecular biology and cloning techniques.

Exemplary Source Organisms

Isoprene synthase, DXS, IDI, or MVA pathway nucleic acids (and their encoded polypeptides) can be obtained from any organism that naturally contains isoprene synthase, DXS, IDI, and/or MVA pathway nucleic acids. As noted above, isoprene is formed naturally by a variety of organisms, such as bacteria, yeast, plants, and animals. Organisms contain the MVA pathway, DXP pathway, or both the MVA and DXP pathways for producing isoprene (FIG. 15). Thus, DXS nucleic acids can be obtained, e.g., from any organism that contains the DXP pathway or contains both the MVA and DXP pathways. IDI and isoprene synthase nucleic acids can be obtained, e.g., from any organism that contains the MVA pathway, DXP pathway, or both the MVA and DXP pathways. MVA pathway nucleic acids can be obtained, e.g., from any organism that contains the MVA pathway or contains both the MVA and DXP pathways.

In some embodiments, the nucleic acid sequence of the isoprene synthase, DXS, IDI, or MVA pathway nucleic is identical to the sequence of a nucleic acid that is produced by any of the following organisms in nature. In some embodiments, the amino acid sequence of the isoprene synthase, DXS, IDI, or MVA pathway polypeptide is identical to the sequence of a polypeptide that is produced by any of the following organisms in nature. In some embodiments, the isoprene synthase, DXS, IDI, or MVA pathway nucleic acid or polypeptide is a mutant nucleic acid or polypeptide derived from any of the organisms described herein. As used herein, "derived from" refers to the source of the nucleic acid or polypeptide into which one or more mutations is introduced. For example, a polypeptide that is "derived from a plant polypeptide" refers to polypeptide of interest that results from introducing one or more mutations into the sequence of a wild-type (i.e., a sequence occurring in nature) plant polypeptide.

In some embodiments, the source organism is a bacterium, such as strains of *Escherichia* (e.g., *E. coli*), or strains of *Bacillus* (e.g., *B. subtilis*).

As used herein, "the genus *Escherichia*" includes all species within the genus "*Escherichia*," as known to those of skill in the art, including but not limited to *E. coli, E. adecarboxylata, E. albertii, E. blattae, E. fergusonii, E. hermannii, E. senegalensis*, and *E. vulneris*. The genus "*Escherichia*" is defined as Gram-negative, non-spore forming, facultatively anaerobic, rod-shaped bacteria are classified as members of the Family Enterobacteriaceae, Order Enterobacteriales, Class Gamma Proteobacteria.

As used herein, "the genus *Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus*, and *Virgibacillus*.

Exemplary Host Cells

A variety of host cells can be used to express isoprene synthase, DXS, IDI, and/or MVA pathway polypeptides and to produce isoprene in the methods of the claimed invention. Exemplary host cells include cells from any of the organisms listed in the prior section under the heading "Exemplary Source Organisms." The host cell may be a cell that naturally produces isoprene or a cell that does not naturally produce isoprene. In some embodiments, the host cell naturally produces isoprene using the DXP pathway, and an isoprene synthase, DXS, and/or IDI nucleic acid is added to enhance production of isoprene using this pathway. In some embodiments, the host cell naturally produces isoprene using the MVA pathway, and an isoprene synthase and/or one or more MVA pathway nucleic acids are added to enhance production of isoprene using this pathway. In some embodiments, the host cell naturally produces isoprene using the DXP pathway and one or more MVA pathway nucleic acids are added to produce isoprene using part or all of the MVA pathway as well as the DXP pathway. In some embodiments, the host cell naturally produces isoprene using both the DXP and MVA pathways and one or more isoprene synthase, DXS, IDI, or MVA pathway nucleic acids are added to enhance production of isoprene by one or both of these pathways.

Exemplary Transformation Methods

Isoprene synthase, DXS, IDI, and/or MVA pathway nucleic acids or vectors containing them can be inserted into a host cell (e.g., a bacterial cell) using standard techniques for expression of the encoded isoprene synthase, DXS, IDI, and/or MVA pathway polypeptide. Introduction of a DNA construct or vector into a host cell can be performed using techniques such as transformation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion. General transformation techniques are known in the art (see, e.g., Current Protocols in Molecular Biology (F. M. Ausubel et al. (eds) Chapter 9, 1987; Sambrook et al., Molecular Cloning: A Laboratory Manual, $2^{nd}$ ed., Cold Spring Harbor, 1989; and Campbell et al., *Curr Genet*, 16:53-56, 1989, which are each hereby incorporated by reference in their entireties, particularly with respect to transformation methods). The introduced nucleic acids may be integrated into chromosomal DNA or maintained as extrachromosomal replicating sequences.

Exemplary Cell Culture Media

The invention also includes a cell or a population of cells in culture that produce isoprene. By "cells in culture" is meant two or more cells in a solution (e.g., a cell medium) that allows the cells to undergo one or more cell divisions. "Cells in culture" do not include plant cells that are part of a living, multicellular plant containing cells that have differentiated into plant tissues. In various embodiments, the cell culture includes at least or about 10, 20, 50, 100, 200, 500, 1,000, 5,000, 10,000 or more cells.

Any carbon source can be used to cultivate the host cells. The term "carbon source" refers to one or more carbon-containing compounds capable of being metabolized by a host cell or organism. For example, the cell medium used to cultivate the host cells may include any carbon source suitable for maintaining the viability or growing the host cells.

In some embodiments, the carbon source is a carbohydrate (such as monosaccharide, disaccharide, oligosaccharide, or polysaccharides), invert sugar (e.g., enzymatically treated sucrose syrup), glycerol, glycerine (e.g., a glycerine byproduct of a biodiesel or soap-making process), dihydroxyacetone, one-carbon source, fatty acid (e.g., a saturated fatty acid, unsaturated fatty acid, or polyunsaturated fatty acid), lipid, phospholipid, glycerolipid, monoglyceride, diglyceride, triglyceride, polypeptide (e.g., a microbial or plant protein or peptide), renewable carbon source (e.g., a biomass carbon source such as a hydrolyzed biomass carbon source; beet sugar or cane sugar molasses), yeast extract, component from a yeast extract, polymer, acid, alcohol, aldehyde, ketone, amino acid, succinate, lactate, acetate, ethanol, or any combination of two or more of the foregoing. In some embodiments, the carbon source is a product of photosynthesis, including, but not limited to, glucose.

Exemplary monosaccharides include glucose and fructose; exemplary oligosaccharides include lactose and sucrose, and exemplary polysaccharides include starch and cellulose. Exemplary carbohydrates include C6 sugars (e.g., fructose, mannose, galactose, or glucose) and C5 sugars (e.g., xylose or arabinose). In some embodiments, the cell medium includes a carbohydrate as well as a carbon source other than a carbohydrate (e.g., glycerol, glycerine, dihydroxyacetone, one-carbon source, fatty acid, lipid, phospholipid, glycerolipid, monoglyceride, diglyceride, triglyceride, renewable carbon source, or a component from a yeast extract). In some embodiments, the cell medium includes a carbohydrate as well as a polypeptide (e.g., a microbial or plant protein or peptide). In some embodiments, the microbial polypeptide is a polypeptide from yeast or bacteria. In some embodiments, the plant polypeptide is a polypeptide from soy, corn, canola, jatropha, palm, peanut, sunflower, coconut, mustard, rapeseed, cottonseed, palm kernel, olive, safflower, sesame, or linseed.

In some embodiments, the concentration of the carbohydrate is at least or about 5 grams per liter of broth (g/L, wherein the volume of broth includes both the volume of the cell medium and the volume of the cells), such as at least or about 10, 15, 20, 30, 40, 50, 60, 80, 100, 150, 200, 300, 400, or more g/L. In some embodiments, the concentration of the carbohydrate is between about 50 and about 400 g/L, such as between about 100 and about 360 g/L, between about 120 and about 360 g/L, or between about 200 and about 300 g/L. In some embodiments, this concentration of carbohydrate includes the total amount of carbohydrate that is added before and/or during the culturing of the host cells.

Exemplary lipids are any substance containing one or more fatty acids that are C4 and above fatty acids that are saturated, unsaturated, or branched.

Exemplary fatty acids include compounds of the formula R—COOH, where "R" is a hydrocarbon. Exemplary unsaturated fatty acids include compounds where "R" includes at least one carbon-carbon double bond. Exemplary unsaturated fatty acids include, but are not limited to, oleic acid, vaccenic acid, linoleic acid, palmitelaidic acid, and arachidonic acid. Exemplary polyunsaturated fatty acids include compounds where "R" includes a plurality of carbon-carbon double bonds. Exemplary saturated fatty acids include compounds where "R" is a saturated aliphatic group. In some embodiments, the carbon source includes one or more $C_{12}$-$C_{22}$ fatty acids, such as a $C_{12}$ saturated fatty acid, a $C_{14}$ saturated fatty acid, a $C_{16}$ saturated fatty acid, a $C_{18}$ saturated fatty acid, a $C_{20}$ saturated fatty acid, or a $C_{22}$ saturated fatty acid. In an exemplary embodiment, the fatty acid is palmitic acid. In some embodiments, the carbon source is a salt of a fatty acid (e.g., an unsaturated fatty acid), a derivative of a fatty acid (e.g., an unsaturated fatty acid), or a salt of a derivative of fatty acid (e.g., an unsaturated fatty acid). Suitable salts include, but are not limited to, lithium salts, potassium salts, sodium salts, and the like. Di- and triglycerols are fatty acid esters of glycerol.

In some embodiments, the concentration of the lipid, fatty acid, monoglyceride, diglyceride, or triglyceride is at least or about 1 gram per liter of broth (g/L, wherein the volume of broth includes both the volume of the cell medium and the volume of the cells), such as at least or about 5, 10, 15, 20, 30, 40, 50, 60, 80, 100, 150, 200, 300, 400, or more g/L. In some embodiments, the concentration of the lipid, fatty acid, monoglyceride, diglyceride, or triglyceride is between about 10 and about 400 g/L, such as between about 25 and about 300 g/L, between about 60 and about 180 g/L, or between about 75 and about 150 g/L. In some embodiments, the concentration includes the total amount of the lipid, fatty acid, monoglyceride, diglyceride, or triglyceride that is added before and/or during the culturing of the host cells. In some embodiments, the carbon source includes both (i) a lipid, fatty acid, monoglyceride, diglyceride, or triglyceride and (ii) a carbohydrate, such as glucose. In some embodiments, the ratio of the lipid, fatty acid, monoglyceride, diglyceride, or triglyceride to the carbohydrate is about 1:1 on a carbon basis (i.e., one carbon in the lipid, fatty acid, monoglyceride, diglyceride, or triglyceride per carbohydrate carbon). In particular embodiments, the amount of the lipid, fatty acid, monoglyceride, diglyceride, or triglyceride is between about 60 and 180 g/L, and the amount of the carbohydrate is between about 120 and 360 g/L.

Exemplary microbial polypeptide carbon sources include one or more polypeptides from yeast or bacteria. Exemplary plant polypeptide carbon sources include one or more polypeptides from soy, corn, canola, jatropha, palm, peanut, sunflower, coconut, mustard, rapeseed, cottonseed, palm kernel, olive, safflower, sesame, or linseed.

Exemplary renewable carbon sources include cheese whey permeate, cornsteep liquor, sugar beet molasses, barley malt, and components from any of the foregoing. Exemplary renewable carbon sources also include glucose, hexose, pentose and xylose present in biomass, such as corn, switchgrass, sugar cane, cell waste of fermentation processes, and protein by-product from the milling of soy, corn, or wheat. In some embodiments, the biomass carbon source is a lignocellulosic, hemicellulosic, or cellulosic material such as, but are not limited to, a grass, wheat, wheat straw, bagasse, sugar cane bagasse, soft wood pulp, corn, corn cob or husk, corn kernel, fiber from corn kernels, corn stover, switch grass, rice hull product, or a by-product from wet or dry milling of grains (e.g., corn, sorghum, rye, triticate, barley, wheat, and/or distillers grains). Exemplary cellulosic materials include wood, paper and pulp waste, herbaceous plants, and fruit pulp. In some embodiments, the carbon source includes any plant part, such as stems, grains, roots, or tubers. In some embodiments, all or part of any of the following plants are used as a carbon source: corn, wheat, rye, sorghum, triticate, rice, millet, barley, cassaya, legumes, such as beans and peas, potatoes, sweet potatoes, bananas, sugarcane, and/or tapioca. In some embodiments, the carbon source is a biomass hydrolysate, such as a biomass hydrolysate that includes both xylose and glucose or that includes both sucrose and glucose.

In some embodiments, the renewable carbon source (such as biomass) is pretreated before it is added to the cell culture medium. In some embodiments, the pretreatment includes enzymatic pretreatment, chemical pretreatment, or a combination of both enzymatic and chemical pretreatment (see, for example, Farzaneh et al., *Bioresource Technology* 96 (18): 2014-2018, 2005; U.S. Pat. No. 6,176,176; U.S. Pat. No. 6,106,888; which are each hereby incorporated by reference in their entireties, particularly with respect to the pretreatment of renewable carbon sources). In some embodiments, the renewable carbon source is partially or completely hydrolyzed before it is added to the cell culture medium.

In some embodiments, the renewable carbon source (such as corn stover) undergoes ammonia fiber expansion (AFEX) pretreatment before it is added to the cell culture medium (see, for example, Farzaneh et al., *Bioresource Technology* 96 (18): 2014-2018, 2005). During AFEX pretreatment, a renewable carbon source is treated with liquid anhydrous ammonia at moderate temperatures (such as about 60 to about 100° C.) and high pressure (such as about 250 to about 300 psi) for about 5 minutes. Then, the pressure is rapidly released. In this process, the combined chemical and physical effects of lignin solubilization, hemicellulose hydrolysis, cellulose decrystallization, and increased surface area enables near complete enzymatic conversion of cellulose and hemicellulose to fermentable sugars. AFEX pretreatment has the advantage that nearly all of the ammonia can be recovered and reused, while the remaining serves as nitrogen source for microbes in downstream processes. Also, a wash stream is not required for AFEX pretreatment. Thus, dry matter recovery following the AFEX treatment is essentially 100%. AFEX is basically a dry-to-dry process. The treated renewable carbon source is stable for long periods and can be fed at very high solid loadings in enzymatic hydrolysis or fermentation processes. Cellulose and hemicellulose are well preserved in the AFEX process, with little or no degradation. There is no need for neutralization prior to the enzymatic hydrolysis of a renewable carbon source that has undergone AFEX pretreatment. Enzymatic hydrolysis of AFEX-treated carbon sources produces clean sugar streams for subsequent fermentation use.

In some embodiments, the concentration of the carbon source (e.g., a renewable carbon source) is equivalent to at least or about 0.1, 0.5, 1, 1.5 2, 3, 4, 5, 10, 15, 20, 30, 40, or 50% glucose (w/v). The equivalent amount of glucose can be determined by using standard HPLC methods with glucose as a reference to measure the amount of glucose generated from the carbon source. In some embodiments, the concentration of the carbon source (e.g., a renewable carbon source) is equivalent to between about 0.1 and about 20% glucose, such as between about 0.1 and about 10% glucose, between about 0.5 and about 10% glucose, between about 1 and about 10% glucose, between about 1 and about 5% glucose, or between about 1 and about 2% glucose.

In some embodiments, the carbon source includes yeast extract or one or more components of yeast extract. In some embodiments, the concentration of yeast extract is at least 1 gram of yeast extract per liter of broth (g/L, wherein the volume of broth includes both the volume of the cell medium and the volume of the cells), such at least or about 5, 10, 15, 20, 30, 40, 50, 60, 80, 100, 150, 200, 300, or more g/L. In some embodiments, the concentration of yeast extract is between about 1 and about 300 g/L, such as between about 1 and about 200 g/L, between about 5 and about 200 g/L, between about 5 and about 100 g/L, or between about 5 and about 60 g/L. In some embodiments, the concentration includes the total amount of yeast extract that is added before and/or during the culturing of the host cells. In some embodiments, the carbon source includes both yeast extract (or one or more components thereof) and another carbon source, such as glucose. In some embodiments, the ratio of yeast extract to the other carbon source is about 1:5, about 1:10, or about 1:20 (w/w).

Additionally the carbon source may also be one-carbon substrates such as carbon dioxide, or methanol. Glycerol production from single carbon sources (e.g., methanol, formaldehyde, or formate) has been reported in methylotrophic yeasts (Yamada et al., *Agric. Biol. Chem.,* 53(2) 541-543, 1989, which is hereby incorporated by reference in its entirety, particularly with respect to carbon sources) and in bacteria (Hunter et. al., Biochemistry, 24, 4148-4155, 1985, which is hereby incorporated by reference in its entirety, particularly with respect to carbon sources). These organisms can assimilate single carbon compounds, ranging in oxidation state from methane to formate, and produce glycerol. The pathway of carbon assimilation can be through ribulose monophosphate, through serine, or through xylulose-monophosphate (Gottschalk, *Bacterial Metabolism,* Second Edition, Springer-Verlag: New York, 1986, which is hereby incorporated by reference in its entirety, particularly with respect to carbon sources). The ribulose monophosphate pathway involves the condensation of formate with ribulose-5-phosphate to form a six carbon sugar that becomes fructose and eventually the three carbon product glyceraldehyde-3-phosphate Likewise, the serine pathway assimilates the one-carbon compound into the glycolytic pathway via methylenetetrahydrofolate.

In addition to one and two carbon substrates, methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth Cl Compd.,* [Int. Symp.], $7^{th}$ ed., 415-32. Editors: Murrell et al., Publisher: Intercept, Andover, UK, 1993, which is hereby incorporated by reference in its entirety, particularly with respect to carbon sources). Similarly, various species of *Candida* metabolize alanine or oleic acid (Sulter et al., *Arch. Microbiol.* 153(5), 485-9, 1990, which is hereby incorporated by reference in its entirety, particularly with respect to carbon sources).

In some embodiments, cells are cultured in a standard medium containing physiological salts and nutrients (see, e.g., Pourquie, J. et al., Biochemistry and Genetics of Cellulose Degradation, eds. Aubert et al., Academic Press, pp. 71-86, 1988; and Ilmen et al., *Appl. Environ. Microbiol.* 63:1298-1306, 1997, hereby incorporated by reference, particularly with respect to cell media). Exemplary growth media are common commercially prepared media such as Luria Bertani (LB) broth, Sabouraud Dextrose (SD) broth, or Yeast medium (YM) broth. Other defined or synthetic growth media may also be used, and the appropriate medium for growth of particular host cells are known by someone skilled in the art of microbiology or fermentation science.

In addition to an appropriate carbon source, the cell medium desirably contains suitable minerals, salts, cofactors, buffers, and other components known to those skilled in the art suitable for the growth of the cultures or the enhancement of isoprene production (see, for example, WO 2004/033646 and references cited therein and WO 96/35796 and references cited therein, which are each hereby incorporated by reference in their entireties, particularly with respect cell medias and cell culture conditions). In some embodiments where an isoprene synthase, DXS, IDI, and/or MVA pathway nucleic acid is under the control of an inducible promoter, the inducing agent (e.g., a sugar, metal salt or antimicrobial), is desirably added to the medium at a concentration effective to induce expression of an isoprene synthase, DXS, IDI, and/or MVA pathway polypeptide. In some embodiments, cell medium has an antibiotic (such as kanamycin) that corresponds to the antibiotic resistance nucleic acid (such as a kanamycin resistance nucleic acid) on a vector that has one or more DXS, IDI, or MVA pathway nucleic acids.

Exemplary Production of Isoprene

In some embodiments, the cells are cultured in a culture medium under conditions permitting the production of isoprene by the cells. In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, or more nmole of isoprene/gram of cells for the wet weight of the cells/hour (nmole/$g_{wcm}$/hr). In some embodiments, the amount of isoprene is between about 2 to about 5,000 nmole/$g_{wcm}$/hr, such as between about 2 to about 100 nmole/$g_{wcm}$/hr, about 100 to about 500 nmole/$g_{wcm}$/hr, about 150 to about 500 nmole/$g_{wcm}$/hr, about 500 to about 1,000 nmole/$g_{wcm}$/hr, about 1,000 to about 2,000 nmole/$g_{wcm}$/hr, or about 2,000 to about 5,000 nmole/$g_{wcm}$/hr. The amount of isoprene in units of nmole/$g_{wcm}$/hr can be measured as disclosed in U.S. Pat. No. 5,849,970, which is hereby incorporated by reference in its entirety, particularly with respect to the measurement of isoprene production. For example, two mL of headspace (e.g., headspace from a culture such as 2 mL of culture cultured in sealed vials at 32° C. with shaking at 200 rpm for approximately 3 hours) are analyzed for isoprene using a standard gas chromatography system, such as a system operated isothermally (85° C.) with an n-octane/porasil C column (Alltech Associates, Inc., Deerfield, Ill.) and coupled to a RGD2 mercuric oxide reduction gas detector (Trace Analytical, Menlo Park, Calif.) (see, for example, Greenberg et al, *Atmos. Environ.* 27A: 2689-2692, 1993; Silver et al., *Plant Physiol.* 97:1588-1591, 1991, which are each hereby incorporated by reference in their entireties, particularly with respect to the measurement of isoprene production). The gas chromatography area units are converted to nmol isoprene via a standard isoprene concentration calibration curve. In some embodiments, the value for the grams of cells for the wet weight of the cells is calculated by obtaining the $A_{600}$ value for a sample of the cell culture, and then converting the $A_{600}$ value to grams of cells based on a calibration curve of wet weights for cell cultures with a known $A_{600}$ value. In some embodiments, the grams of the cells is estimated by assuming that one liter of broth (including cell medium and cells) with an $A_{600}$ value of 1 has a wet cell weight of 1 gram. The value is also divided by the number of hours the culture has been incubating for, such as three hours.

In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/$g_{wcm}$/h). In some embodiments, the amount of isoprene is between about 2 to about 5,000 ng/$g_{wcm}$/h, such as between about 2 to about 100 ng/$g_{wcm}$/h, about 100 to about 500 ng/$g_{wcm}$/h, about 500 to about 1,000 ng/$g_{wcm}$/h, about 1,000 to about 2,000 ng/$g_{wcm}$/h, or about 2,000 to about 5,000 ng/$g_{wcm}$/h. The amount of isoprene in ng/$g_{wcm}$/h can be calculated by multiplying the value for isoprene production in the units of nmole/$g_{wcm}$/hr discussed above by 68.1 (as described in Equation 5 below).

In some embodiments, the cells in culture produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium). In some embodiments, the amount of isoprene is between about 2 to about 5,000 mg/$L_{broth}$, such as between about 2 to about 100 mg/$L_{broth}$, about 100 to about 500 mg/$L_{broth}$, about 500 to about 1,000 mg/$L_{broth}$, about 1,000 to about 2,000 mg/$L_{broth}$, or about 2,000 to about 5,000 mg/$L_{broth}$. The specific productivity of isoprene in mg of isoprene/L of headspace from shake flask or similar cultures can be measured by taking a 1 ml sample from the cell culture at an $OD_{600}$ value of approximately 1.0, putting it in a 20 mL vial, incubating for 30 minutes, and then measuring the amount of isoprene in the headspace. If the $OD_{600}$ value is not 1.0, then the measurement can be normalized to an $OD_{600}$ value of 1.0 by dividing by the $OD_{600}$ value. The value of mg isoprene/L headspace can be converted to mg/$L_{broth}$/hr/$OD_{600}$ of culture broth by multiplying by a factor of 38. The value in units of mg/$L_{broth}$/hr/$OD_{600}$ can be multiplied by the number of hours and the $OD_{600}$ value to obtain the cumulative titer in units of mg of isoprene/L of broth.

The instantaneous isoprene production rate in mg/$L_{broth}$/hr in a fermentor can be measured by taking a sample of the fermentor off-gas, analyzing it for the amount of isoprene (in units such as mg of isoprene per $L_{gas}$), and multiplying this value by the rate at which off-gas is passed though each liter of broth (e.g., at 1 vvm (volume of air/volume of broth/minute) this is 60 $L_{gas}$ per hour). Thus, an off-gas level of 1 mg/$L_{gas}$ corresponds to an instantaneous production rate of 60 mg/$L_{broth}$/hr at air flow of 1 vvm. If desired, the value in the units mg/$L_{broth}$/hr can be divided by the $OD_{600}$ value to obtain the specific rate in units of mg/$L_{broth}$/hr/OD. The average value of mg isoprene/$L_{gas}$ can be converted to the total product productivity (grams of isoprene per liter of fermentation broth, mg/$L_{broth}$) by multiplying this average off-gas isoprene concentration by the total amount of off-gas sparged per liter of fermentation broth during the fermentation. Thus, an average off-gas isoprene concentration of 0.5 mg/$L_{broth}$/hr over 10 hours at 1 vvm corresponds to a total product concentration of 300 mg isoprene/$L_{broth}$.

In some embodiments, the cells in culture convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, or 1.6% of the carbon in the cell culture medium into isoprene. In some embodiments, the percent conversion of carbon into isoprene is between about 0.002 to about 1.6%, such as about 0.002 to about 0.005%, about 0.005 to about 0.01%, about 0.01 to about 0.05%, about 0.05 to about 0.15%, 0.15 to about 0.2%, about 0.2 to about 0.3%, about 0.3 to about 0.5%, about 0.5 to about 0.8%, about 0.8 to about 1.0%, or about 1.0 to about 1.6%. The percent conversion of carbon into isoprene (also referred to as "% carbon yield") can be measured by dividing the moles carbon in the isoprene produced by the moles carbon in the carbon source (such as the moles of carbon in batched and fed glucose and yeast extract). This number is multiplied by 100% to give a percentage value (as indicated in Equation 1).

$$\% \text{ Carbon Yield} = \text{(moles carbon in isoprene produced)} / \text{(moles carbon in carbon source)} * 100 \quad \text{Equation 1}$$

For this calculation, yeast extract can be assumed to contain 50% w/w carbon.

$$\% \text{ Carbon Yield} = (39.1 \text{ g isoprene} * 1/68.1 \text{ mol/g} * 5 \text{ C/mol})/[181221 \text{ g glucose} * 1/180 \text{ mol/g} * 6 \text{ C/mol}) + (17780 \text{ g yeast extract} * 0.5 * 1/12 \text{ mol/g})] * 100 = 0.042\% \quad \text{Equation 2}$$

One skilled in the art can readily convert the rates of isoprene production or amount of isoprene produced into any other units. Exemplary equations are listed below for interconverting between units.

Units for Rate of Isoprene Production (Total and Specific)

$$1 \text{ g isoprene}/L_{broth}/\text{hr} = 14.7 \text{ mmol isoprene}/L_{broth}/\text{hr} \text{ (total volumetric rate)} \quad \text{Equation 3}$$

$$1 \text{ nmol isoprene}/g_{wcm}/\text{hr} = 1 \text{ nmol isoprene}/L_{broth}/\text{hr}/OD_{600} \text{ (This conversion assumes that one liter of broth with an } OD_{600} \text{ value of 1 has a wet cell weight of 1 gram.)} \quad \text{Equation 4}$$

$$1 \text{ nmol isoprene}/g_{wcm}/\text{hr} = 68.1 \text{ ng isoprene}/g_{wcm}/\text{hr} \text{ (given the molecular weight of isoprene)} \quad \text{Equation 5}$$

$$1 \text{ nmol isoprene}/L_{gas} \, O_2/\text{hr} = 90 \text{ nmol isoprene}/L_{broth}/\text{hr (at an } O_2 \text{ flow rate of 90 L/hr per L of culture broth)} \quad \text{Equation 6}$$

$$1 \text{ µg isoprene}/L_{gas} \text{ isoprene in off-gas} = 60 \text{ µg isoprene}/L_{broth}/\text{hr at a flow rate of 60 } L_{gas} \text{ per } L_{broth} \text{ (1 vvm)} \quad \text{Equation 7}$$

Units for Titer (Total and Specific)

$$1 \text{ nmol isoprene/mg cell protein} = 150 \text{ nmol isoprene}/L_{broth}/OD_{600} \text{ (This conversion assumes that one liter of broth with an } OD_{600} \text{ value of 1 has a total cell protein of approximately 150 mg) (specific productivity)} \quad \text{Equation 8}$$

$$1 \text{ g isoprene}/L_{broth} = 14.7 \text{ mmol isoprene}/L_{broth} \text{ (total titer)} \quad \text{Equation 9}$$

If desired, Equation 10 can be used to convert any of the units that include the wet weight of the cells into the corresponding units that include the dry weight of the cells.

$$\text{Dry weight of cells} = \text{(wet weight of cells)}/3.3 \quad \text{Equation 10}$$

In some embodiments encompassed by the invention, a cell comprising a heterologous nucleic acid encoding an isoprene synthase polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acid encoding the isoprene synthase polypeptide.

In some embodiments encompassed by the invention, a cell comprising a heterologous nucleic acid encoding an isoprene synthase polypeptide and one or more heterologous nucleic acids encoding a DXS, IDI, and/or MVA pathway polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acids.

Exemplary Isoprene Purification Methods

In some embodiments, any of the methods described herein further include recovering the isoprene. For example, the isoprene produced using the compositions and methods of the invention can be recovered using standard techniques. such as gas stripping, fractionation, adsorption/desorption, pervaporation, thermal or vacuum desorption of isoprene from a solid phase, or extraction of isoprene immobilized or absorbed to a solid phase with a solvent (see, for example, U.S. Pat. Nos. 4,703,007 and 4,570,029, which are each hereby incorporated by reference in their entireties, particularly with respect to isoprene recovery and purification methods). In some embodiments, the recovery of isoprene involves the isolation of isoprene in a liquid form (such as a neat solution of isoprene or a solution of isoprene in a solvent). Gas stripping involves the removal of isoprene vapor from the fermentation off-gas stream in a continuous manner. Such removal can be achieved in several different ways including, but not limited to, adsorption to a solid phase, partition into a liquid phase, or direct condensation. In some embodiments, membrane enrichment of a dilute isoprene vapor stream above the dew point of the vapor resulting in the condensation of liquid isoprene.

The recovery of isoprene may involve one step or multiple steps. In some embodiments, the removal of isoprene vapor from the fermentation off-gas and the conversion of isoprene to a liquid phase are performed simultaneously. For example, isoprene can be directly condensed from the off-gas stream to form a liquid. In some embodiments, the removal of isoprene vapor from the fermentation off-gas and the conversion of isoprene to a liquid phase are performed sequentially. For example, isoprene may be adsorbed to a solid phase and then extracted from the solid phase with a solvent.

In some embodiments, any of the methods described herein further include purifying the isoprene. For example, the isoprene produced using the compositions and methods of the invention can be purified using standard techniques. Purification refers to a process through which isoprene is separated from one or more components that are present when the isoprene is produced. In some embodiments, the isoprene is obtained as a substantially pure liquid. Examples of purification methods include (i) distillation from a solution in a liquid extractant and (ii) chromatography. As used herein, "purified isoprene" means isoprene that has been separated from one or more components that are present when the isoprene is produced. In some embodiments, the isoprene is at least about 20%, by weight, free from other components that are present when the isoprene is produced. In various embodiments, the isoprene is at least or about 25%, 30%, 40%, 50%, 60%, 70%, 75%, 80%, 90%, 95%, or 99%, by weight, pure. Purity can be assayed by any appropriate method, e.g., by column chromatography, HPLC analysis, or GC-MS analysis.

Crystal Structure of Isoprene Synthase

The invention also contemplates crystalline forms of plant isoprene synthase (e.g., poplar and kudzu) and its variants as described supra and in the Examples. In one embodiment, the invention comprises any polypeptide which has the crystal structure of poplar isoprene synthase as disclosed in Table 16-7.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: ° C. (degrees Centigrade); rpm (revolutions per minute); $H_2O$ (water); $diH_2O$ (deionized water); aa and AA (amino acid); by (base pair); kb (kilobase pair); kD (kilodaltons); gm (grams); μg and ug (micrograms); mg (milligrams); ng (nanograms); μl and ul (microliters); ml (milliliters); mm (millimeters); qs (quantity sufficient); nm (nanometers); μm and um (micrometer); M (molar); mM (millimolar); μM and uM (micromolar); pM (picomolar); U (units); MW (molecular weight); sec (seconds); min (minute/minutes); hr (hour/hours); $OD_{600}$ (optical density at 600 nm); BSA (bovine serum albumin); DMAPP (dimethylallyl diphosphate); DTT (dithiothreitol); EtOH (ethanol); IPTG (isopropyl-beta-D-thiogalactopyranoside); isoprene (2-methyl-1,3-butadiene); IspS (isoprene synthase); PAGE (polyacrylamide gel electrophoresis); PBS (phosphate buffered saline [150 mM NaCl, 10 mM sodium phosphate buffer, pH 7.2]); and SDS (sodium dodecyl sulfate).

The following abbreviations apply to companies whose products or services may have been referred to in the experimental examples: Agilent (Agilent Technologies, Santa Clara, Calif.); Becton Coulter (Becton Coulter, Inc., Fullerton, Calif.); Bio-Rad (Bio-Rad Laboratories, Hercules, Calif.); Cayman Chemical (Cayman Chemical Co., Ann Arbor, Mich.); CTC Analytics (CTC Analytics A.G., Zwingen, Switzerland); EMS (Electron Microscopy Supply, Hatfield, Pa.); Epicentre (Epicentre Biotechnologies, Madison, Wis.); Integrated DNA Technologies (Integrated DNA Technologies, Coralville, Iowa); Invitrogen (Invitrogen Corp., Carlsbad, Calif.); Molecular Dynamics (Molecular Dynamics, Sunnyvale, Calif.); Novagen (Novagen, Inc., Madison, Wis.); Perkin Elmer (Perkin Elmer, Waltham, Mass.); Roche (Roche Applied Science, Indianapolis, Ind.); Sigma (Sigma-Aldrich, St. Louis, Mo.); Stratagene (Stratagene Cloning Systems, La Jolla, Calif.); Qiagen (Qiagen, Inc., Valencia, Calif.); Takara (Takara Bio USA, Madison, Wis.); Thomson Instrument (Thomson Instrument Co., Oceanside, Calif.); V&P Scientific (V&P Scientific, Inc., San Diego, Calif.); and Zinsser (Zinsser North America, Northridge, Calif.).

EXAMPLE 1

Cloning of Kudzu Isoprene Synthase for Expression in Recombinant Bacteria

In this example, methods used to produce kudzu isoprene synthase (IspS) in *E. coli* are described. The protein sequence for the kudzu (*Pueraria montana*) isoprene synthase gene (IspS) was obtained from GenBank (AAQ84170). A kudzu isoprene synthase gene, optimized for *E. coli* codon usage, was purchased from DNA2.0 (Menlo Park, Calif.), and is set forth as SEQ ID NO:1 (FIG. 1). The isoprene synthase gene was removed from the supplied plasmid by restriction endonuclease digestion with BspLU11I/PstI gel-purified, and ligated into pTrcHis2B (Invitrogen) that had been digested with NcoI/PstI. The construct was designed such that the stop codon in the isoprene synthase gene was 5' to the PstI site. As a result, when the construct was expressed the His-Tag is not attached to the isoprene synthase protein. The resulting plasmid, pTrcKudzu, was verified by sequencing.

The isoprene synthase gene was also cloned into pET16b (Novagen). In this case, the isoprene synthase gene was inserted into pET16b such that the recombinant isoprene synthase protein contained the N-terminal His tag. The isoprene synthase gene was amplified from pTrcKudzu by PCR using the primer set pET-His-Kudzu-2F: 5'-CGTGAGATCA TATGTGTGCG ACCTCTTCTC AATTTAC (SEQ ID NO:3) and pET-His-Kudzu-R: 5'-CGGTCGACGG ATCCCTGCAG TTAGACATAC ATCAGCTG (SEQ ID NO:4). These primers added an NdeI site at the 5'-end and a BamH1 site at the 3' end of the gene respectively. The plasmid pTrcKudzu, described above, was used as template DNA, HERCULASE DNA polymerase (Stratagene) was used according to manufacturer's directions, and primers were added at a concentration of 10 pM. The PCR was carried out in a total volume of 25 µl. The PCR product was digested with NdeI/BamH1 and cloned into pET16b digested with the same enzymes. The ligation mix was transformed into *E. coli* Top10 (Invitrogen) and the correct clone selected by sequencing. The resulting plasmid designated pETNHisKudzu is then transformed into BL21(λDE3)pLysS (Novagen) cells for expression from the T7 promoter.

The kudzu isoprene synthase gene was also cloned into the low copy number plasmid pCL1920 (Lerner and Inouye, Nucl Acids Res, 18:4631, 1990). Primers were used to amplify the kudzu isoprene synthase gene from pTrcKudzu described above. The forward primer added a HindIII site and an *E. coli* consensus RBS to the 5' end. The PstI cloning site was already present in pTrcKudzu just 3' of the stop codon so the reverse primer was constructed such that the final PCR product includes the PstI site. The sequences of the primers were: HindIII-rbs-Kudzu F: 5'-CATATGAAAG CTTG-TATCGA TTAAATAAGG AGGAATAAAC C (SEQ ID NO:5) and BamH1-Kudzu R: 5'-CGGTCGACGG ATCCCT-GCAG TTAGACATAC ATCAGCTG (SEQ ID NO:4). The PCR product was amplified using HERCULASE DNA polymerase (Stratagene) with primers at a concentration of 10 pM and with 1 ng of template DNA (pTrcKudzu). The amplification protocol included 30 cycles of (95° C. for 1 minute, 60° C. for 1 minute, 72° C. for 2 minutes). The product was digested with HindIII and PstI and ligated into pCL1920, which had also been digested with HindIII and PstI. The ligation mix was transformed into *E. coli* Top 10. Several transformants were verified by sequence analysis. The resulting plasmid was designated pCL-lac-Kudzu.

In order to remove the beta-lactamase gene, pTrcKudzu was digested with BspHI, treated with shrimp alkaline phosphatase (SAP), incubated at 65° C. for 10 min to heat kill the SAP, then end-filled by incubating with 2 units of Klenow fragment (New England BioLabs) and dNTPS. The 5 kb fragment was purified from an agarose gel and ligated to the Kan(R) gene. The Kan(R) gene was prepared by PCR amplification from pCR-Blunt-II-TOPO (Invitrogen) using primers MCM22 and MCM23 and Taq DNA polymerase according to the Manufacturer's instructions. The PCR fragment was digested with HindIII and PvuI, and end-filled using Klenow Fragment and dNTPs. The ligation mixture was transformed into *E. coli* Top 10 chemically competent cells and a transformant carrying a plasmid conferring kanamycin resistance, pTrcKudzu(kan), was selected on Luria Agar containing kanamycin (50 µg/ml). The sequences of the primers were: MCM22 5'-gatcaagctt AACCGGAATTGCCAGCTG (SEQ ID NO:15); and MCM23 5'-gatccgatcgTCAGAA-GAACTCGTCAAGAAGGC (SEQ ID NO:16).

EXAMPLE 2

Cloning of Poplar Isoprene Synthase for Expression in Recombinant Bacteria

In this example, methods used to produce poplar isoprene synthase (IspS) in *E. coli* are described. The protein sequence for the poplar (*Populus alba* x *Populus tremula*) isoprene synthase (Schnitzler et al., Planta 222:777-786, 2005) was obtained from GenBank (CAC35696). A gene, codon optimized for *E. coli*, was purchased from DNA2.0 and is set forth as SEQ ID NO:6 (FIG. 3). The isoprene synthase gene was removed from the supplied plasmid (p9796-poplar) by restriction endonuclease digestion with BspLU11I/PstI, gel-purified, and ligated into pTrcHis2B that had been digested with NcoI/PstI. The construct is cloned such that the stop codon in the insert is before the PstI site, which results in a construct in which the His-Tag is not attached to the isoprene synthase protein. The resulting plasmid, pTrcPoplar, was verified by sequencing using commercially available primers that hybridize within the vector sequence (Forward and Reverse), as well as the primer Poplar InSeq 5'-GAGAAAATCG GTAAGGAACT GG (SEQ ID NO:8).

EXAMPLE 3

Isoprene Production in Recombinant Bacteria

In this example, methods used to produce and measure isoprene in recombinant *E. coli* are described.

I. Determination of Isoprene Production

For the shake flask cultures, one ml of a culture was transferred from shake flasks to 20 ml CTC headspace vials (Agilent vial Catalog No. 5188 2753, and cap Catalog No. 5188 2759). The cap was screwed on tightly and the vials incubated at the equivalent temperature with shaking at 250 rpm. After 30 minutes, the vials were removed from the incubator and analyzed as described below. In cases where isoprene production in fermentors was determined, samples were taken from the off-gas of the fermentor and analyzed directly.

The analysis was performed using an Agilent 6890 GC/MS system interfaced with a CTC Analytics CombiPAL autosampler operating in headspace mode. An Agilent HP-5MS GC/MS column (30 m×0.25 mm; 0.25 µm film thickness) was used for separation of analytes. The sampler was set up to inject 500 µL of headspace gas. The GC/MS method utilized helium as the carrier gas at a flow of 1 ml/min. The injection port was held at 250° C. with a split ratio of 50:1. The oven temperature was held at 37° C. for the 2 min duration of the analysis. The Agilent 5793N mass selective detector was run in single ion monitoring (SIM) mode on m/z 67. The detector was switched off from 1.4 to 1.7 minutes to allow the elution of permanent gases. Under these conditions, isoprene (2-methyl-1,3-butadiene) was observed to elute at 1.78 minutes. A calibration table was used to quantify the absolute amount of isoprene and was found to be linear from 1 µg/L to 200 µg/L. The limit of detection was estimated to be 50 to 100 ng/L using this method.

II. Production of Isoprene in Shake Flasks

The vectors described above were introduced into *E. coli* strain BL21(λDE3)pLysS (Novagen) to produce strains BL21/ptrcKudzu, BL21/pCL-lac-Kudzu and BL21/pETHis-Kudzu. The strains were spread for isolation onto LA (Luria agar) containing the appropriate antibiotic (50 µg/ml carbenicillin for BL21/ptrcKudzu and BL21/pETHisKudzu or 50 µg/ml spectinomycin for BL21/pCL-lac-Kudzu) and incubated overnight at 37° C. Single colonies were inoculated into 250 ml baffled shake flasks containing 20 ml Luria Bertani broth (LB) and the appropriate antibiotic. Cultures were grown overnight at 20° C. with shaking at 200 rpm. The $OD_{600}$ of the overnight cultures was measured and the cultures were diluted into a 250 ml baffled shake flask containing 30 ml MAGICMEDIA expression medium (Invitrogen) containing the appropriate antibiotic to an $OD_{600}$~0.05. The culture was incubated at 30° C. with shaking at 200 rpm. When the $OD_{600}$~0.5-0.8, 400 µM IPTG was added and the cells were incubated for a further 6 hours at 30° C. with shaking at 200 rpm. At 0, 2, 4 and 6 hours after induction with IPTG, 1 ml aliquots of the cultures were collected, the $OD_{600}$ was determined and the amount of isoprene produced was measured as described above.

III. Production of Isoprene from BL21/ptrcKudzu in 14 Liter Fermentation

Large-scale production of isoprene from *E. coli* containing the recombinant kudzu isoprene synthase gene was determined from a fed-batch culture. The recipe for the fermentation media (TM2) per liter of fermentation medium was as follows: $K_2HPO_4$ 13.6 g, $KH_2PO_4$ 13.6 g, $MgSO_4*7H_2O$ 2 g, citric acid monohydrate 2 g, ferric ammonium citrate 0.3 g, $(NH_4)_2SO_4$ 3.2 g, yeast extract 5 g, 1000× Modified Trace Metal Solution 1 ml. All of the components were added together and dissolved in $diH_2O$. The pH was adjusted to 6.8 with potassium hydroxide (KOH) and qs to volume. The final product was filter sterilized with 0.22 µM filter, but not autoclaved. The recipe for 1000× Modified Trace Metal Solution was as follows: Citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO*7H_2O$ 1 g, $CuSO_4*5H_2O$ 100 mg, $H_3BO_3$ 100 mg, $NaMoO_4*2H_2O$ 100 mg. Each component was dissolved one at a time in $diH_2O$, the pH was adjusted to 3.0 with HCl/NaOH, then qs to volume and filter sterilized with a 0.22µ filter.

This experiment was carried out in 14 L bioreactor to monitor isoprene formation from glucose at the desired fermentation, pH 6.7 and temperature 34° C. An inoculum of *E. coli* strain BL21/ptrcKudzu taken from a frozen vial was prepared in soytone-yeast extract-glucose medium in two 600 ml flasks. After the inoculum grew to $OD_{550}=0.6$, two 600 ml flasks were centrifuged and the contents resuspended in 70 ml supernatant to transfer the cell pellet (70 ml of OD 3.1 material) to the bioreactor. At various times after inoculation, samples were removed and the amount of isoprene produced was determined as described above.

EXAMPLE 4

Selection of Sites for Improvement of Plant Isoprene Synthases

The isoprene synthases of plants were expected to be homologous to the terpene synthases. The three-dimensional structures of two homologous terpene synthases have been determined from bornyl diphosphate synthase (pdb entry 1N1B) and 5-epi-aristolochene synthase (pdb entry 5EAU). These enzymes share only 32% homology but their tertiary structure is conserved. In addition, the structures of intermediate complexes with both enzymes have shown that not only tertiary folding, but also detailed interactions in the active sites of these enzymes are highly conserved.

The kudzu and poplar isoprene synthases have higher sequence identity than was seen between the bornyl diphosphate synthase and the 5-epi-aristolochene synthase as shown in Table 4-1 below.

TABLE 4-1

Percent Identity of Various Enzymes

|  | BDP-synthase | 5EA-synthase | Kudzu IspS |
|---|---|---|---|
| Poplar IspS | 40.1 | 32.9 | 54.4 |
| Kudzu IspS | 40.7 | 33.8 |  |
| 5ES synthase | 31.9 |  |  |

A homology model of the poplar isoprene synthase has been made based on the bornyl diphosphate synthase (BDP-synthase) pdb entry 1N24 (~40% sequence identity). The homology model appears to be plausible based on the close similarity of 10 trial models created using the program MOE written and supported by The Chemical Computing Group, Inc. The plausibility is based on the conservation of common amino acid residues at sites found to be involved in catalysis in the BDP-synthase structure.

A comparison of the active site from the structure of BDP-synthase and the homology model of poplar IspS indicates that the active site involved in metal ion binding and phosphate recognition is conserved. In particular, Lys 272, Asp 309, Asp 313, Glu 387, Arg 450 and Asn 453 of poplar IspS were observed to overlap equivalent residues in BDP-synthase. In this example, amino acid residue positions for poplar IspS are derived from SEQ ID NO:7. The positioning of an intermediate of the BDP-synthase was also compared with the poplar IspS homology model. Based on this, it was possible to identify the analogous binding region and the approach direction that isopentenyl diphosphate would require in order to bind and react with the poplar IspS enzyme.

A homology model of the kudzu isoprene synthase has been made based on bornyl diphosphate synthase pdb entry 1N24 having (~40% sequence identity). A comparison of the active site from the structure of BDP-synthase with the homology model of kudzu IspS indicates that numerous active site residues involved in metal ion binding and phosphate recognition are conserved. In particular, Arg 269, Asp 306, Asp 310, Glu 384, Arg 450 and Asn 453 of kudzu IspS were observed to overlap equivalent residues in BDP-synthase.

A comparison of the active site residues identified in the homology models of poplar and kudzu IspS revealed that residues from one homology model are also quite homologous with similar residues, appearing with only minor shifts in the relative position numbers for some of the residues, in the other homology model. Based on the homology models, sites in poplar and kudzu IspS were identified as candidates for mutagenesis to produce variant IspS enzymes with improved performance. Briefly, sites were selected in the IspS that might alter the interaction of the metal binding, the diphosphate recognition, the IPP chain binding and/or the approach to the active site.

I. Diphosphate/Metal Binding Sites

The side chains of amino acid residues in the poplar IspS that are found in proximity to the metal and diphosphate (DPP) binding side chains were identified. These residues include Phe 384, Tyr 402, Ala 406, Ser 409, Ala 460 and Asn 469. The inventors note that Lys 272 is incorrect based on homology to other known poplar IspS sequences, which have an Arg at this position.

II. Substrate Access Loop

The substrate access loop of poplar IspS is in a region that deviates from the BDP-synthase structure. In the BDP-synthase structure the residues form a segment that creates a cover. Without being bound by theory, the inventors expect that this segment in the actual three-dimensional structure of poplar IspS will form a similar structure. As such the residues in this loop, including residues 455-466, will be in a position to alter the activity of the poplar IspS enzyme. In the poplar IspS enzyme residues 454-466 have the following sequence:

(SEQ ID NO: 9)
LASASAEIARGET.

III. Isoprenyl Binding Site

The complex of BDP-synthase and the product of the reaction, bornyl diphosphate (pdb entry 1N24), was used to identify residues in the poplar model that may modulate substrate specificity and/or reaction rate (altered on and off rates of substrate and product). These residues include Arg 274, Trp 281 Phe 302, Val 305, Ser 411, Gln 415, Phe 449, Ser 537 and Glu 540.

TABLE 4-2

Candidate Mutagenesis Sites

| | Poplar Amino Acid | Kudzu Amino Acid/codon |
|---|---|---|
| DPP/metal sites | Phe 384 | Phe 381/1141-1143 |
| | Tyr 402 | Tyr 399/1195-1197 |
| | Ala 406 | Ala 403/1207-1209 |
| | Ser 409 | Ser 406/1216-1218 |
| | Asn 469 | Asn 469/1405-1407 |
| Extra DPP sites | Tyr 312 | Tyr 309/925-927 |
| | Asp 313 | Asp 310/928-930 |
| | Leu 380 | Leu 377/1129-1131 |
| | Glu 387 | Glu 384/1150-1152 |
| | Asn 404 | Asn 402/1204-1206 |
| | Ser 410 | Ser 407/1219-1221 |
| N_terminal access segment | 22 | 20/58-60 |
| | 23 | 21/61-63 |
| | 24 | 22/64-66 |
| | 25 | 23/67-69 |
| | 26 | 24/70-72 |
| | 27 | 25/73-75 |
| Substrate access loop | Leu 454 | Ala 456/4102-4104 |
| | Ala 455 | Thr 457/4105-4107 |
| | Ser 456 | Ser 458/4108-4110 |
| | Ala 457 | Ala 459/4111-4113 |
| | Ser 458 | Ala 460/4114-4116 |
| | Ala 459 | Glu 461/4117-4119 |
| | Glu 460 | Leu 462/4120-4122 |
| | Ile 461 | Glu 463/4123-4125 |
| | Ala 462 | |
| | Arg 463 | Arg 464/4126-4128 |
| | Gly 464 | Gly 465/4129-4131 |
| | Glu 465 | Glu 466/4132-4134 |
| | Thr 466 | Thr 467/4135-4137 |
| | | Thr 468/4138-4140 |
| Isoprenyl binding site | Arg 274 | Arg 271/811-813 |
| | Trp 281 | Trp 278/832-834 |
| | Phe 302 | Phe 299/895-897 |
| | Val 305 | Val 302/904-906 |
| | Ser 411 | Ser 408/1222-1224 |
| | Gln 415 | |
| | Phe 449 | Phe 449/1345-1347 |
| | Ser 537 | Ser 458/1372-1374 |
| | Glu 540 | Tyr 531/1591-1593 |
| Extra Isoprenyl sites | Gly 412 | Gly 409/1225-1227 |
| | Leu 414 | Ala 411/1231-1233 |
| | Leu 416 | Leu 413/1237-1239 |
| | Leu 521 | Met 523/1567-1569 |
| | Ser 525 | Ser 527/1579-1581 |

EXAMPLE 5

Mutation of Non-Conserved Cysteines in Kudzu Isoprene Synthase

Figure 6:
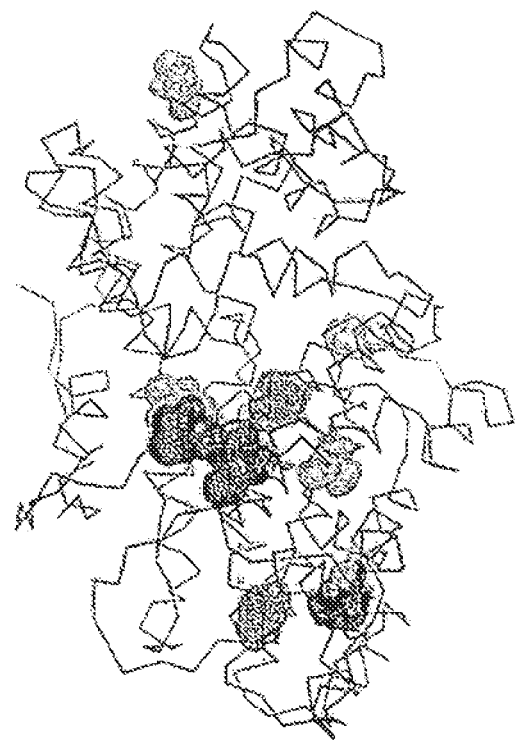
FIG. 6 provides a poplar isoprene synthase homology model with the cysteine residues highlighted as space filling molecules (dark grey). In addition, the cysteine residues from the kudzu model of FIG. 5 are superimposed on the poplar model as space filling molecules (light grey).

The kudzu and poplar isoprene synthase (IspS) homology models, based on the bornyl diphosphate synthase crystal structure, were compared with respect to the positions of the cysteine residues. Cysteines have the potential to form disulfide bonds and stabilize structures. The non-conserved cysteines, contemplated to affect solubility and/or activity, were altered by site-directed mutagenesis. The kudzu IspS amino acid sequence used for the modeling is shown in FIG. 2 (SEQ ID NO:2). There are eight cysteines in kudzu IspS at positions 57, 291, 343, 378, 421, 446, 451 and 529 (relative to the mature form of the protein) as shown in the homology model of FIG. 5. In contrast, there are five cysteines in poplar IspS amino acid sequence has five cysteines, as shown in the homology model of FIG. 6 upon which the kudzu cysteines are superimposed. Several of the cysteines are apparently conserved between the poplar and kudzu IspS sequences indicating that these positions are important in stabilizing the structure, activity and/or other protein function. The remaining cysteines (nonconserved residues 57, 291, 421 and 446) in kudzu were mutated to serine as described herein.

I. Mutagenesis

The QUIKCHANGE® Multi-Site Directed Mutagenesis Kit (Stratagene) was used as per the manufacturer's directions. The following primers were utilized for mutagenesis:

```
C57S-F
                                     (SEQ ID NO: 10)
5'-CTGGAGGAAGAAGTTCGC TCC

ATGATCAACCGTGTAGAC;

C291S-F
                                     (SEQ ID NO: 11)
5'-CGCCAGACCCGCAGTTTGGTGAA TCT

CGCAAAGCTGTTACTAAAATG;

C421S-F
                                     (SEQ ID NO: 12)
5'-CGCCGTCTTACTTTTCCGTA TCC

CAGCAGCAGGAAGACATC;

C446S-F
                                     (SEQ ID NO: 13)
5'-CATGGTCTGGTGCGTTCTAGC TCC

GTTATCTTCCGCCTGTGC;
and

C421S-R
                                     (SEQ ID NO: 14)
5'-GATGTCTTCCTGCTGCTG GGA

TACGGAAAAGTAAGACGGCG.
```

The plasmid pTrcKudzu(kan) described in Example 1 was used as template DNA. The primers C57S-F, C291S-F, C421S-F, and C446-F were combined in a single reaction (100 pmol). Template DNA was added (~200 nanograms) and 0.5 µl of Quiksolution was added to the recommended volumes of enzyme and buffer. The PCR reaction was carried out in an Eppendorf PCR machine using an annealing temperature of 55° C. and an extension time of 12 minutes for 30 cycles. Other parameters of the cycle were as indicated in the instructions. The PCR mix was treated with DpnI for 4 hours at 37° C. (2×1 µl for 2 h each) and then 5 µl of the reaction were transformed into E. coli Top10 (Invitrogen) chemically competent cells and plated on Luria agar containing kanamycin (50 µg/ml). After overnight incubation at 37° C., several colonies were picked and inoculated into 5 ml of Luria Broth containing kanamycin (50 µg/ml). The plasmids were isolated using the QIAprep Spin Miniprep kit (Qiagen), and the IspS genes were sequenced in their entirety. Various single and combinations of mutations were made as indicated in the Table 5-1 below.

TABLE 5-1

BL21(λDE3) Cells Transformed with Mutated pTrcKudzu Plasmids*

| Strain* | C57S | C291S | C421S | C446S |
|---|---|---|---|---|
| C1 | + | + | | |
| C2 | | + | | + |
| C4 | + | + | | + |

TABLE 5-1-continued

BL21(λDE3) Cells Transformed with Mutated pTrcKudzu Plasmids*

| Strain* | C57S | C291S | C421S | C446S |
|---------|------|-------|-------|-------|
| C6      | +    |       |       | +     |
| C11     |      |       |       | +     |
| C20     |      |       | +     |       |
| C6-4    | +    |       | +     | +     |

All the variant plasmids were transformed into chemically competent BL21(λDE3) cells (Novagen). In a second reaction pTrcKudzu(kan) and plasmid DNA isolated from C6 were used as templates in a QUIKCHANGE® site directed mutagenesis kit (Stratagene) single site reaction with C421S-F and C421S-R primers. After confirmation by sequencing, two additional strains were obtained.

II. Cell Growth and Isoprene Production

Figure 7:
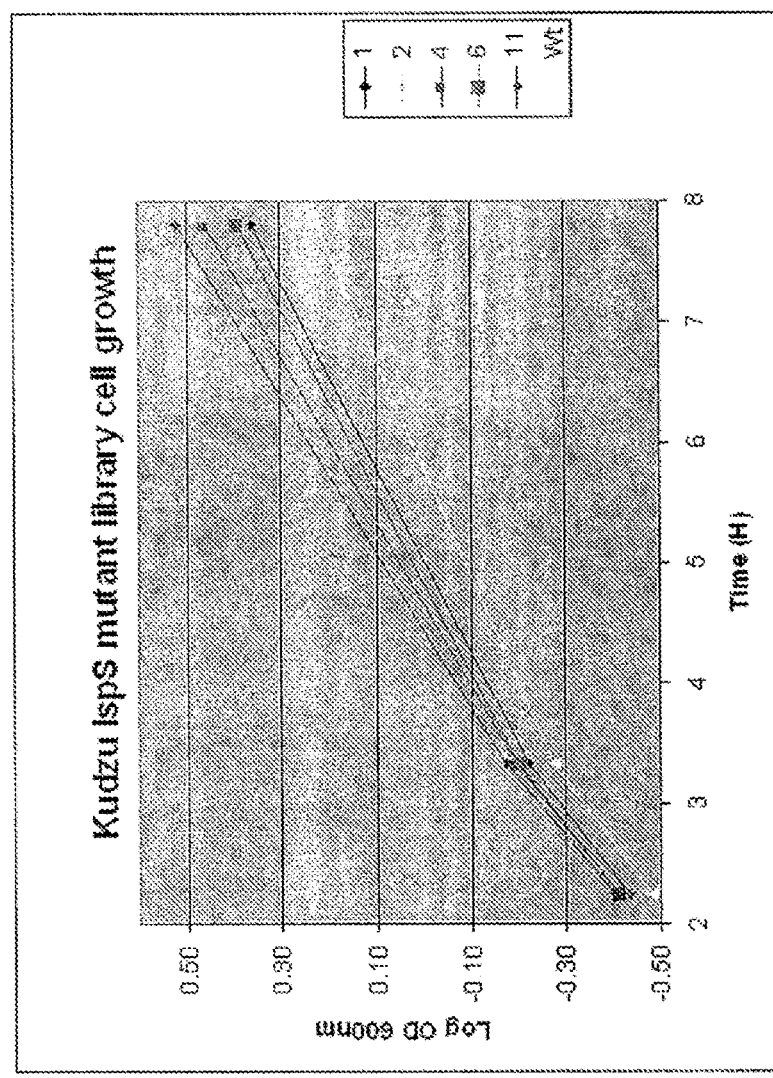
FIG. 7 provides a graph showing the growth curves of the kudzu IspS cysteine mutants of Example 5.

Cells were grown in 5 ml tubes containing Luria Broth supplemented with 50 mg/L kanamycin at 30° C. overnight with agitation. These cultures were diluted into TM3 broth supplemented with 10 g/L glucose and 50 mg/L kanamycin. The culture volume was 25 ml in a 250 ml baffled Bellco Delong flask in which cells were grown at 30° C. with agitation (225 rpm). Samples were taken aseptically, as indicated, for optical density measurements at $A_{600}$. The results are shown in FIG. 7. The cultures were induced at 3.33 hrs with 200 µM IPTG and allowed to continue growth until harvest at 7.8 hr. The cultures were centrifuged at 10,000×g for 10 min, the supernatants decanted and the cell pellets frozen at −80° C. overnight.

Figure 8:
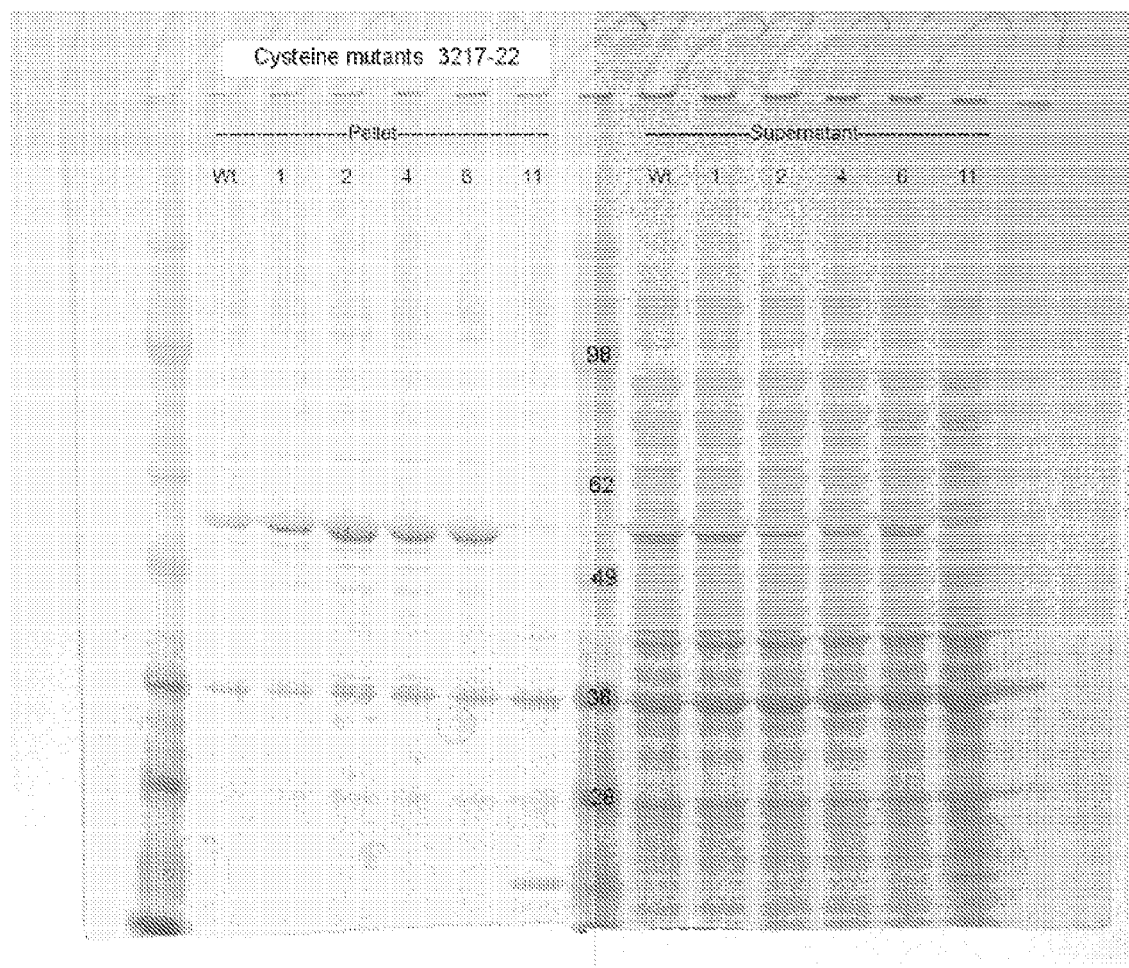
FIG. 8 shows an SDS-PAGE analysis of kudzu IspS cysteine mutants from lysed cells. Pellet and supernatant fractions were prepared by centrifugation.

Frozen cell pellets were thawed and resuspended in 2 ml PEB (50 mM Tris-HCl, pH 8.0, 20 mM MgCl, 2 mM dithiothreitol, and 50% [v/v] glycerol). Cells were lysed by French pressure cell disruption, one pass, at 20,000 psi. The lysate was centrifuged for 15 min at 10,000×g. The supernatants were decanted and the pellets resuspended in 2 ml PEB. The pellets and supernatants were analyzed by SDS-PAGE, 4-12% NuPage gels (Invitrogen), run in MES buffer under reducing conditions. The molecular weight standard was See-Blue2 (Invitrogen). The results are shown in FIG. 8. The IspS protein concentrations were estimated using the BCA assay (Pierce) using BSA as standard (Table 5-2).

III. Assays for Isoprene Synthase Activity and Solubility

Briefly the activity of the supernatants was measured by reaction with DMAPP, and the isoprene evolved was quantified by GC/MS.

Headspace Assay. A sample of 200 µl of the desired culture is inoculated into 2 ml CTC headspace vials (Agilent vial Catalog No. 5188 2753, and cap Catalog No. 5188 2759). The cap was screwed on tightly and the vials were incubated at 37° C. with shaking at 250 rpm. After 30 minutes the vials were removed from the incubator and cooled briefly with ambient tap water. The vials were placed into the CombiPal Headspace auto sampler for analysis by GC-MS. The analysis was performed using an Agilent 6890 GC/MS system interfaced with a CTC Analytics CombiPAL autosampler operating in headspace mode. An Agilent HP-5MS GC/MS column (30 m×0.25 mm; 0.25 µm film thickness) was used for separation of analytes. The sampler was set up to inject 500 µL of headspace gas. The GC/MS method utilized helium as the carrier gas at a flow of 1 ml/min. The injection port was held at 250° C. with a split ratio of 50:1. The oven temperature was held at 37° C. for the 2 min duration of the analysis. The Agilent 5793N mass selective detector was run in single ion monitoring (SIM) mode on m/z 67. The detector was switched off from 1.4 to 1.7 minutes to allow the elution of permanent gases. Under these conditions isoprene (2-methyl-1,3-butadiene) was observed to elute at 1.78 minutes. A calibration table was used to quantify the absolute amount of isoprene and was found to be linear from 1 µg/L to 200 µg/L. The limit of detection was estimated to be 50-100 ng/L using this method.

DMAPP Assay. An aliquot of 95 µl of the supernatant fraction from the centrifuged French Pressure cell lysate was added to the headspace vials. A 5 µL aliquot of 8 mM DMAPP in 100 mM potassium phosphate buffer, pH 8.2 was added, the vials sealed and allowed to incubate at room temperature for 30 min. The amount of isoprene produced was measured by GC/MS as described above and reported in Table 5-2.

TABLE 5-2

Isoprene Synthase Activity from Crude Extracts of Cysteine Mutants

| Supernatant | Activity (mU/ml) | Protein (mg/ml) | Specific Activity (mU/mgP) |
|-------------|------------------|-----------------|----------------------------|
| Wt          | 59.0             | 2.48            | 23.79                      |
| C1          | 5.3              | 2.64            | 2.01                       |
| C2          | 0.2              | 3.52            | 0.06                       |
| C4          | 0.5              | 3.22            | 0.16                       |
| C6          | 9.0              | 3.32            | 2.71                       |
| C11         | 0.1              | 4.26            | 0.03                       |

The values shown in Table 5-2 are averages of reactions with two different concentrations of extract. All proteins containing any of the cysteine mutations resulted in severe diminution of enzyme activity and an apparent decrease of soluble protein as judged by a relative increase in the proportion of protein in the insoluble (pellet) fraction.

EXAMPLE 6

Mutation of Residues in Poplar Isoprene Synthase

Alignment of the amino acid sequences of kudzu and poplar isoprene synthases with other synthases was done using Vector Nti (Invitrogen). The aligned sequences included: beta-ocimene synthase *Lotus corniculatus* (AAT86042); putative terpene synthetase *Medficago trunculata* (AAV36465); hypothetical protein *Vitis vinifera* (can65805); hypothetical protein *Vitis vinifera* (CAN62729); pinene synthase *Quercus ilex* (CAK55186); IspS *Pueraria montana* (kudzu) Sharkey (AAQ84170); monoterpene synthase *Eucaliptus globulus* (BAF02832); IspS *Populus nigra* Fortunati (CAL69918); IspS *Populus tremuloides* Sharkey (AAQ16588); IspS *Populus alba* (BAD98243); and IspS *Populus alba* x *tremula* Zimmer (CAC35696). The sequence from the database of *Populus alba* x *tremula* (CAC35696) exhibited different amino acids at positions 272 and 497 that were otherwise highly conserved. Additionally based on analysis of the homology model of poplar IspS, position 453 was identified as a third candidate for mutagenesis.

I. Mutagenesis

The QUIKCHANGE® Multi-Site Directed Mutagenesis kit (Stratagene) was used as per the manufacturer's directions to introduce the following mutations singly and in combination into the *Populus alba* x *tremula* IspS sequence (SEQ ID NO:7): K272R; C497W; and N453D. The following primers were utilized for mutagenesis:

Poplar K272R (SEQ ID NO: 17)
5'-ccaaactgcacttcg ctcgtgaccgcctgattgag;

Poplar N453D (SEQ ID NO: 18)
5'-atctttcgcctgtgcgacgacctggcaagc;
and

Poplar C497W (SEQ ID NO: 19)
5'-tgaatctgatcgacgaaacctggaagaaaatgaacaaagaaaaac.

The following primer, Poplar InSeq, 5'-gagaaaatcggtaag-gaactgg (SEQ ID NO:8) was used for sequencing.

Mutagenesis was done according to the manufacturer's directions, with all three mutagenesis primers being added to a single reaction mix (100 ng each) with pTrcPoplar as the template DNA (100 ng). Addition of 0.5 µl of Quik Solution aided the mutagenesis reaction. The suggested PCR cycle was run with an annealing temperature of 55° C. and an extension time of 12 min. Other parameters were as indicated in the instructions. The PCR mix was digested with DpnI for 4 hrs at 37° C. (1 µl each×2 h) and then 5 µl of the reaction was transformed into E. coli Top 10 chemically competent cells (Invitrogen). Several colonies were selected and grown up in 5 ml of Luria Broth (LB) containing carbenicillin (50 µg/ml). Plasmids were isolated using the Qiagen QIAprep spin miniprep kit and sent for sequencing using forward and reverse primers that hybridized to the vector, as well as the Poplar InSeq primer.

The resulting variants of pTrcPoplar were obtained: pTrcPoplar K272R, pTrcPoplar K272R/N453D; pTrcPoplar K272R/N453D/C497W; and pTrcPoplar 272R/497W. These plasmids were transformed into BL21(λDE3)pLysS chemically competent cells (Novagen) for analysis. The variants were analyzed for headspace activity (production of isoprene from whole cells), solubility, and specific activity.

II. Cell Growth and Isoprene Production

The variants, the parent Poplar strain, and the strain containing pTrcKudzu were grown overnight at 37° C. in 5 ml of Luria Bertani medium containing either carbenicillin (50 µg/ml-Poplar strains) or kanamycin (50 µg/ml-Kudzu strain). These cultures were diluted into TM3 broth to an $OD_{600}$ of 0.05, supplemented with 10 g/L glucose and either 50 µg/ml carbenicillin (Poplar mutants and wild type) or 50 mg/L kanamycin (BL21/pTrcKudzu). The recipe for TM3 broth is as follows: $K_2HPO_4$ (13.6 g/l) $KH_2PO_4$ (13.6 g/l), $MgSO_4*7H_2O$ (2 g/l) Citric Acid Monohydrate (2 g/L) Ferric Ammonium Citrate (0.3 g/L) $(NH_4)_2SO_4$ (3.2 g/L) yeast extract (0.2 g/L) 1 ml of 1000× Trace Elements solution, pH adjusted to 6.8 with ammonium hydroxide qs to volume with sterile $diH_2O$ and filter sterilized with a 0.22 micron filter. The recipe for 1000× Trace Elements solution is as follows: Citric Acids*$H_2O$ (40 g/L), $MnSO_4*H_2O$ (30 g/L), NaCl (10 g/L), $FeSO_4*7H_2O$ (1 g/L), $CoCl_2*6H_2O$ (1 g/L), $ZnSO*7H_2O$ (1 g/L), $CuSO_4*5H_2O$ (100 mg/L), $H_3BO_3$ (100 mg/L), $NaMoO_4*2H_2O$ (100 mg/L). Each component was dissolved one at a time in $diH_2O$, pH adjusted to 3.0 with HCl/NaOH, qs to volume and filter sterilized with a 0.22 micron filter.

The diluted culture volume was 25 ml in a 250 ml baffled Bellco Delong flask for growth at 30° C. with agitation (225 rpm). Samples were taken aseptically, as indicated, for optical density measurements at $A_{600}$. Two sets of cultures were set up, one for induction with 0.2 mM IPTG and one that remained un-induced. After 3 hours of growth at 30° C. with shaking at 200 rpm ($OD_{600}$~0.5), one set of the cultures was induced with 0.2 mM IPTG and incubated for a further 3 h at 30° C. with shaking at 200 rpm, the un-induced set was further incubated for the same amount of time. The $OD_{600}$ was determined for all cultures prior to the induction time (3 h post inoculation) and at the time of the measurement of isoprene by the Headspace assay (3 h post-induction, total of 6 h of growth). The cell cultures were centrifuged at 7000×g for 15 minutes in a Sorvall superspeed centrifuge to pellet the cells. The supernatant was removed and the cell pellet frozen for use in an in vitro assay for isoprene synthase activity. Results of the growth and headspace assays are shown in the following tables.

TABLE 6-1

Growth of E. coli Strains Expressing Poplar IspS Variants ($OD_{600}$ values)

| Strain | Pre-induction (after 3 h growth) | Post-induction (3 h with IPTG) | Non-induced (after 6 h growth) |
|---|---|---|---|
| pTrcPoplar K272R | 0.49 | 3.3 | 4.7 |
| pTrcPoplar K272R/N453D | 0.48 | 3.7 | 4.8 |
| pTrcPoplar K272R/N453D/C497W | 0.41 | 3.1 | 5.1 |
| pTrcPoplar K272R/497W H2 | 0.45 | 0.8 | 0.97 |
| pTrcPoplar WT | 0.49 | 3.5 | 4.7 |
| pTrcKudzu WT | 0.44 | 3.3 | 4.2 |

TABLE 6-2

Production of Isoprene by E. coli Strains Expressing Poplar IspS Variants (µg/L)

| Strain | Pre-induction (after 3 h growth) | Post-induction (3 h with IPTG) | Non-induced (after 6 h growth) |
|---|---|---|---|
| pTrcPoplar K272R | n/a | 0 | 0 |
| pTrcPoplar K272R/N453D | n/a | 0 | 0 |
| pTrcPoplar K272R/N453D/C497W | n/a | 0 | 0 |
| pTrcPoplar K272R/497W H2 | n/a | 0 | 0 |
| pTrcPoplar WT | n/a | 0 | 0 |
| pTrcKudzu WT | n/a | 1.3 | 0.29 |

Surprisingly, the strain expressing the kudzu IspS demonstrated any measurable isoprene production. This is unexpected given that kinetic properties of the poplar enzymes were reported in the literature to be superior to those of kudzu enzymes. In particular, the prior art describes the specific activity (U/mg) and $K_m$ (µM) of recombinant kudzu IspS to be 0.075 and 7,700 respectively, native aspen IspS to be 0.5 and 8,000 respectively, and recombinant poplar IspS to be 0.16 and 9,000 respectively (Silver and Fall, J Biol Chem, 270: 13010-1316, 1995; Miller et al., Planta, 213:483-487, 2001; and Sharkey et al., Plant Physiology, 137:700-712, 2005). The published $K_m$ values for the three enzymes are all quite high and within range of each other, but the specific activity for kudzu isoprene synthase is significantly worse than that of the other two isoprene synthases.

III. Assays for Isoprene Synthase Activity and Solubility

By using the DMAPP assay, the activity of isoprene synthase can be measured directly as DMAPP is the direct substrate for the enzyme. The cell pellets of the poplar parent and mutant strains, as well as the wild type kudzu were thawed and resuspended in 2 ml PEB (50 mM Tris-HCl, pH 8.0, 20 mM MgCl, 2 mM dithiothreitol, and 50% [v/v] glycerol). Cells were lysed by French pressure cell disruption, one pass, at 20,000 psi. The lysate (1 ml) was then centrifuged in a microfuge for 20 min at 20,000 rpm at 4° C. The supernatant was removed and the pellet resuspended in 1 ml of PEB. The supernatant and pellet samples were analyzed by SDS-PAGE, and DMAPP assay, while the total protein content was determined by BCA.

TABLE 6-3

DMAPP Assay of Isoprene Production from the Supernatant of the Centrifuged Cell Lysate

| Strain | OD600 (prior to lysis) | Total Protein (mg/ml) | Isoprene/ Total Protein |
|---|---|---|---|
| Induced | | | |
| pTrcPoplar K272R | 3.3 | 1.70 | 0.03 |
| pTrcPoplar K272R/N453D | 3.6 | 1.3 | 0.08 |
| pTrcPoplar K272R/N453D/C497W | 3.1 | 1.10 | 0.08 |
| pTrcPoplar K272R/497W H2 | 0.803 | 0.80 | 0.11 |
| pTrcPoplar WT | 3.5 | 1.30 | 0.06 |
| pTrcKudzu WT | 3.3 | 1.50 | 11.15 |
| Uninduced | | | |
| pTrcPoplar K272R | 4.7 | 1.7 | 0.26 |
| pTrcPoplar K272R/N453D | 4.8 | 1.8 | 0.07 |
| pTrcPoplar K272R/N453D/C497W | 5.2 | 1.9 | 0.02 |
| pTrcPoplar K272R/497W H2 | 0.969 | 1.0 | 0.17 |
| pTrcPoplar WT | 4.6 | 1.7 | 0.05 |
| pTrcKudzu WT | 4.2 | 1.9 | 1.62 |

Production was normalized to total cell lysate supernatant protein.

TABLE 6-4

DMAPP Assay of Isoprene Production from the Pellet of the Centrifuged Cell Lysate

| Strain | OD600 (prior to lysis) | Total Protein (mg/ml) | Isoprene/ Total Protein |
|---|---|---|---|
| Induced | | | |
| pTrcPoplar K272R | 3.3 | 1.02 | 0.118 |
| pTrcPoplar K272R/N453D | 3.6 | 1.36 | 0.000 |
| pTrcPoplar K272R/N453D/C497W | 3.1 | 1.49 | 0.040 |
| pTrcPoplar K272R/C497W H2 | 0.80 | 1.38 | 0.043 |
| pTrcPoplar WT | 3.5 | 1.57 | 0.050 |
| pTrcKudzu WT | 3.3 | 1.47 | 0.040 |
| Uninduced | | | |
| pTrcPoplar K272R | 4.7 | 1.40 | 0.170 |
| pTrcPoplar K272R/N453D | 4.8 | 1.53 | 0.120 |
| pTrcPoplar K272R/N453D/C497W | 5.2 | 1.42 | 0.131 |
| pTrcPoplar K272R/C497W H2 | 0.97 | 1.55 | 0.080 |
| pTrcPoplar WT | 4.6 | 1.38 | 0.120 |
| pTrcKudzu WT | 4.2 | 1.55 | 0.120 |

Production was normalized to total cell lysate pellet protein.

The poplar variant K272R/C497W showed a 1.8× increase in activity as compared to the wild type in the supernatant fraction of the induced cultures. Likewise, the poplar variants K272R and K272R/C497W showed a 5.2× and 3.4× increase in activity as compared to the wild type in the supernatant fraction of the uninduced cultures. Moreover the poplar variant K272R showed a 2× increase in activity as compared to wild type in the pellet of the induced cultures. However, the most striking result was that the kudzu IspS is more active than the poplar IspS employed herein (185×). In the above tables, H2 is the name of the clone designated pTrcPoplar K272R/C497W H2.

EXAMPLE 7

Subcloning of Kudzu Isoprene Synthase

Figure 9:
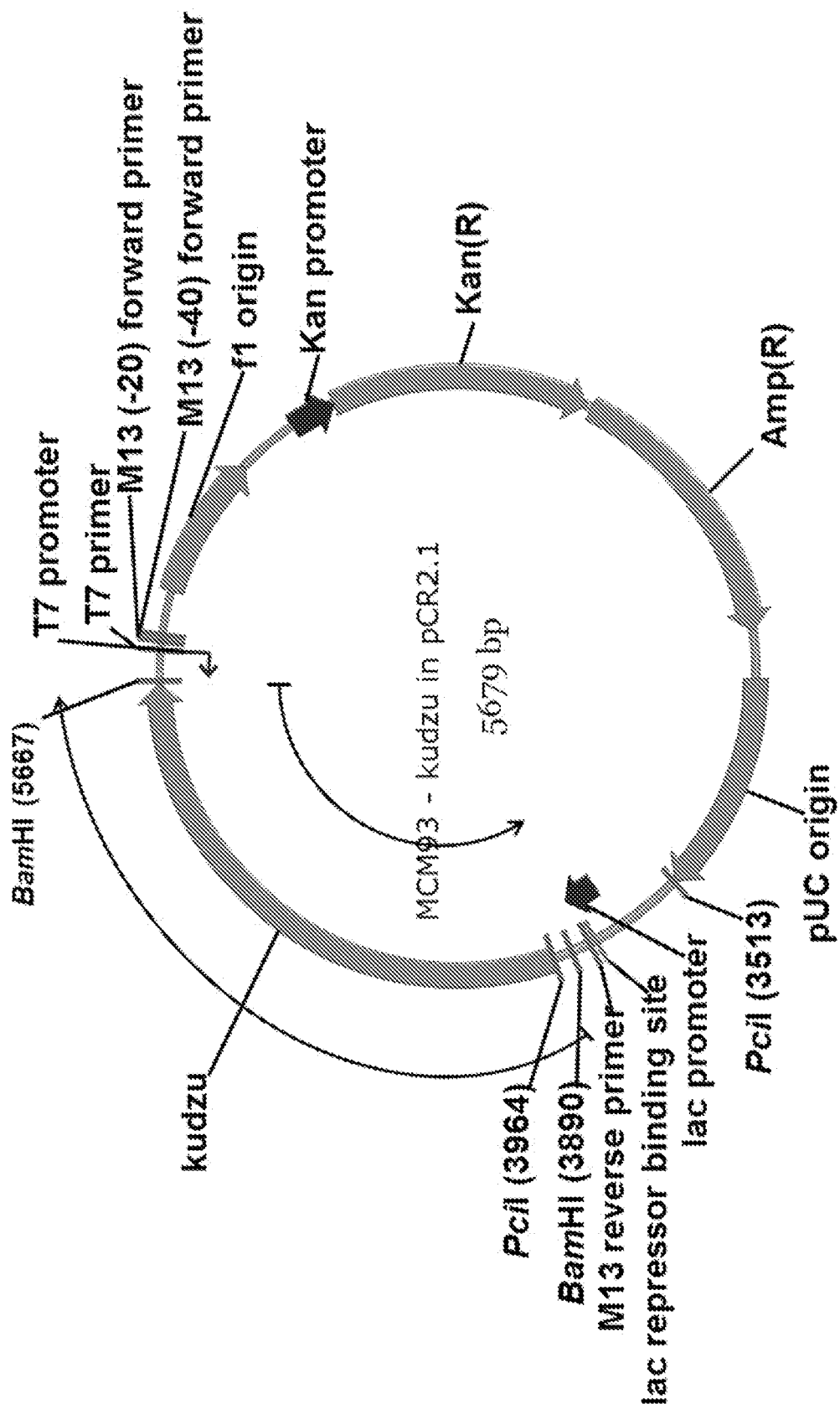
FIG. 9 provides a map of plasmid MCM93 (pCR2.1-Kudzu).

In this Example, methods used in the construction of kudzu isoprene synthase (IspS) SELs are described. To create an expression vector for construction of site evaluation libraries (SEL), the kudzu isoprene synthase gene was subcloned into the pET24d vector (Novagen) from the pCR2.1 vector (Invitrogen). The kudzu IspS gene was amplified from pTrcKudzu template DNA using primers MCM50 5'-GATCATGCAT TCGCCCTTAG GAGGTAAAAA AACATGTGTG CGACCTCTTC TCAATTTACT (SEQ ID NO:20); and MCM53 5'-CGGTCGACGG ATCCCTGCAG TTAGACATAC ATCAGCTG (SEQ ID NO:21). PCR reactions were carried out using Taq DNA Polymerase (Invitrogen), and the resulting PCR product was cloned into pCR2.1-TOPO TA cloning vector (Invitrogen), and transformed into E. coli Top10 chemically competent cells (Invitrogen). Transformants were plated on L agar containing carbenicillin (50 μg/ml) and incubated overnight at 37° C. Five ml Luria Broth cultures containing carbenicillin 50 μg/ml were inoculated with single transformants and grown overnight at 37° C. Five colonies were screened for the correct insert by sequencing of plasmid DNA isolated from 1 ml of liquid culture (Luria Broth) and purified using the QIAprep Spin Mini-prep Kit (Qiagen). The resulting plasmid, designated MCM93, contains the kudzu IspS coding sequence in a pCR2.1 backbone (FIG. 9). The sequence of MCM93 (SEQ ID NO:22) is shown in FIG. 10.

The kudzu coding sequence was removed by restriction endonuclease digestion with PciI and BamH1 (Roche) and gel purified using the QIAquick Gel Extraction kit (Qiagen).

Figure 11:
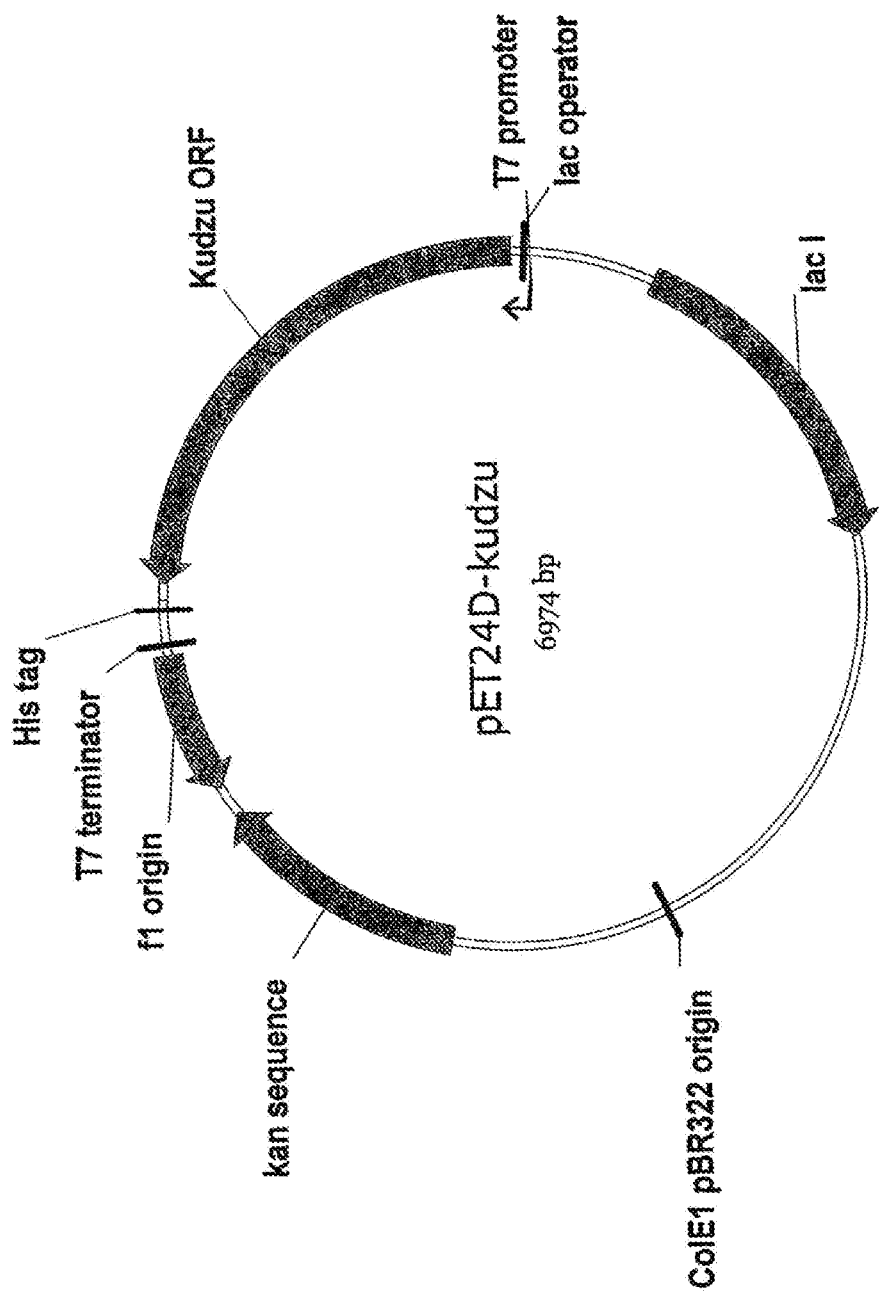
FIG. 11 provides a map of pET24D-Kudzu.

The pET24d vector DNA was digested with NcoI and BamHI (Roche), treated with shrimp alkaline phosphatase (Roche), and purified using the QIAprep Spin Mini-prep Kit (Qiagen). The kudzu IspS fragment was ligated to the NcoI/BamH1 digested pET24d using the Rapid DNA Ligation Kit (Roche) at a 5:1 fragment to vector ratio in a total volume of 20 µl. A portion of the ligation mixture (5 µl) was transformed into E. coli Top 10 chemically competent cells and plated on L agar containing kanamycin (50 µg/ml). The correct transformant was confirmed by sequencing and transformed into chemically competent BL21(λDE3)pLysS cells (Novagen). A single colony was selected after overnight growth at 37° C. on L agar containing kanamycin (50 µg/ml). A map of the resulting plasmid designated as pET24D-Kudzu is shown in FIG. 11. The sequence of pET24D-Kudzu (SEQ ID NO:23) is shown in FIG. 12. IspS Activity was confirmed using the headspace assay as described in Example 5).

EXAMPLE 8

Construction of Isoprene Synthase Site Evaluation Libraries (SELs)

In order to improve the kinetic parameters of a plant IspS SELs are prepared at sites selected from homology models of both the kudzu and the poplar IspS enzymes. While it is predicted from the homology models that engineering at the indicated sites would improve both enzymes, in this embodiment, kudzu SELs are described. Kudzu IspS surface sites of interest include but are not limited to: 26 L, 30 E, 31 F, 33 Q, 35 L, 36 E, 37 N, 39 L, 40 K, 41 V, 43 K, 44 L, 61 R, 62 V, 63 D, 65 Q, 87 K, 94 E, 95 N, 99 L, 100 D, 105 N, 137 K, 138 E, 143 G, 144 E, 182 N, 184 L, 185 K, 187 G, 189 N, 190 T, 225 P, 226 H, 247 K, 257 T, 258 E, 259 M, 266 D, 334 N, 353 D, 357 S, 358 I, 361 E, 389 N, 392 I, 393 I, 398 K, 401 E, 421 C, 423 Q, 424 Q, 425 E, 426 D, 430 H, 432 L, 433 R, 434 S, 437 D, 443 R, 462 L, 463 E, 476 H, 478 N, 479 D, 485 Q, 508 D, 513 P, 515 A, 532 Q, 533 Y, 537 L, 538 G, 539 R, 542 Y, 543 A, and 557 P. Kudzu IspS active site positions of interest include but are not limited to: 24 P, 25 N, 309 Y, 310 D, 377 L, 381 F, 384 E, 399 Y, 402 N, 403 A, 406 S, 407 S, 409 G, 411 A, 413 L, 449 F, 456 A, 457 T, 458 S, 458 S, 459 A, 460 A, 461 E, 462 L, 463 E, 464 R, 465 G, 466 E, 467 T, 468 T, 469 N, 523 M, 527 S, and 531 Y. Additional kudzu IspS active site positions of interest include but are not limited to: 20 A, 21 N, 22 Y, 23 Q, 271 R, 278 W, 299 F, 302 V, and 408 S. Each library SEL contains clones, maximally including 20 different variants. For example, kudzu isoprene synthase SEL 531 contains variants in which the DNA triplet coding for tyrosine at position 531 of the mature kudzu enzyme is replaced by another DNA triplet encoding: alanine, aspartic acid, cysteine, glutamic acid, phenylalanine, glycine, histidine, isoleucine, lysine, leucine, methionine, asparagine, proline, glutamine, arginine, serine, threonine, valine, or tryptophan. Briefly, DNA triplets of specific positions in the DNA coding strand of the mature IspS are replaced. The mutated IspS nucleic acids are subsequently ligated to a suitable expression vector and used to transform suitable host cells.

Site evaluation libraries are created either by ordering synthetic constructs (e.g., DNA2.0) or by ordering primers with the "nns" sequence in place of the codon to be mutated. The primers are then be used to mutate the gene to produce an SEL at the indicated site using commercially available mutagenesis kits (e.g., Stratagene) as has been described (e.g., WO0507682A2). The mutated codons are identified by sequence analysis. The site libraries are arrayed in 96 well master plates, and frozen for later use. Cultures are grown from the master plates and prepared for screening.

The desired end products are IspS enzymes that function optimally in a host metabolically engineered to maximize carbon flow through IspS. To this end several stages of screening are used to ensure that correct parameters are being addressed. Exemplary screens include but are not limited to: expression, DMAPP feeding for production of HG, microreactor, protein determination, and headspace assays. Expression screen: One example of a method to analyze the level of protein expression is as follows. Soluble and insoluble fractions of cell lysates (obtained from lysed cell cultures) are prepared by centrifugation. The resulting supernatants and pellets are analyzed by SDS-PAGE. The percent soluble protein is determined by densitometry analysis of the protein present in the supernatant versus the pellet.

In an exemplary embodiment, kudzu site evaluation libraries are constructed in the pET24D expression vector. The pET24D-Kudzu vector, containing the kudzu isoprene synthase gene, serves as the template DNA.

Materials:
pET24D-Kudzu vector (~50 ng/µl)
Kudzu IS site-directed mutagenic primers (Integrated DNA Technologies)
QUIKCHANGE® Multi Site-Directed Mutagenesis Kit (Stratagene)
MJ Research PTC-200 Peltier Thermal Cylcer (Bio-Rad Laboratories)
One Shot TOP10 competent cells (Invitrogen)
QIAprep Spin Miniprep Kit (Qiagen)
BL21(λDE3) pLysS competent cells (Invitrogen)
Luria Broth (LB) agar plates Methods:
The method of mutagenesis was based on the codon-specific mutation approach, in which the creation of all possible mutations in a specific DNA triplet was performed using a single forward primer with a length of 25 to 45 nucleotides, enclosing a specific designed triple DNA sequence NNS (N=A, C, T or G and S=C or G) corresponding with the sequence of the codon to be mutated. This method results in the random incorporation of nucleotides at a specific pET24D-kudzu codon of interest. Table 8-1 lists the oligonucleotide primers used for mutagenesis, with the number in the primer name corresponding with the codon position in the mature kudzu isoprene synthase enzyme sequence. All oligonucleotide primers were synthesized (Integrated DNA Technologies) on a 100 nmole scale and PAGE purified.

TABLE 8-1

| Kudzu IspS Codon-Specific Mutation Primers | | |
|---|---|---|
| Name | SEQ ID | Primer Sequence |
| IS_A20 | NO: 24 | CATAATTCCCGTCGTTCCNNSAACTATCAGCCAAACCTG |
| IS_N21 | NO: 25 | CATAATTCCCGTCGTTCCGCANNSTATCAGCCAAACCTGTG |
| IS_Y22 | NO: 26 | CCCGTCGTTCCGCAAACNNSCAGCCAAACCTGTGGAATTTC |
| IS_Q23 | NO: 27 | GTCGTTCCGCAAACTATNNSCCAAACCTGTGGAATTTC |
| IS_R271 | NO: 28 | CTGGATTTTGTACGCGACNNSCTGATGGAAGTTTATTTC |

TABLE 8-1 -continued

Kudzu IspS Codon-Specific Mutation Primers

| Name | SEQ ID NO: | Primer Sequence |
|---|---|---|
| IS_W278 | 29 | CTGATGGAAGTTTATTTCNNSGCACTGGGTATGGCGCC |
| IS_F299 | 30 | CAAAGCTGTTACTAAAATGNNSGGTCTGGTGACGATCATC |
| IS_V302 | 31 | CTAAAATGTTTGGTCTGNNSACGATCATCGATGACGTG |
| IS_S408 | 32 | GAAAACGCCAGCGTTTCCTCCNNSGGTGTAGCGCTGCTGGC |

A PCR reaction was set up in a 0.5 ml thin-walled PCR tube following the manufacturer's protocol for the QUIKCHANGE® Multi Site-Directed Mutagenesis Kit (Stratagene): 1 µl pET24 Kudzu vector (50 ng/µl); 1 µl Kudzu IS site-directed forward mutagenic primer (10 µM); 2.5 µl 10× QUIKCHANGE® Multi Reaction buffer; 1 µl dNTP Mix, 1 µl QUIKCHANGE® Multi enzyme blend (2.5 U/µl); and 18.5 µl distilled autoclaved water to provide a 25 µl total reaction mix. The pET24 Kudzu SELs were amplified using the following conditions: 95° C., for 1 min ($1^{st}$ cycle only), followed by 95° C. for 1 min, 55° C. for 1 min, 65° C. for 12 min, and repeat cycling 29 times. Then the reaction mixture was subjected to DpnI digestion (supplied with QUIKCHANGE® Multi Site-Directed Mutagenesis Kit) by addition of 1.5 µl DpnI restriction enzyme to each tube, and incubated at 37° C. for 2 hours to digest the parental pET24D-kudzu vector. The DpnI-treated PCR reaction was then transformed into One Shot TOP10 competent cells (Invitrogen), plated onto LB agar plates containing 50 µg/ml kanamycin, and incubated overnight at 37° C. The next day, 96 random colonies were picked and sequenced to identify a minimum of 15 of the possible 19 amino acid variants. Upon identification of the site-directed variants, each variant clone was then inoculated in a 5 ml tube of LB+50 µg/ml kanamycin and grown overnight at 37° C. with shaking (250 rpm). The following day plasmid DNA was purified using the QIAprep Spin Miniprep Kit (Qiagen). The variants were then transformed into One Shot BL21(λDE3) pLysS competent cells (Invitrogen) for protein expression screening, plated on LB agar plates containing 50 µg/ml kanamycin and 30 µg/ml chloramphenicol and incubated overnight at 37° C.

An alternative method for producing pET24D-Kudzu SELs in E. coli BL21(λDE3) pLysS cells was also successfully employed. The TOP10 competent cell transformants obtained from the DpnI-treated PCR reaction described above were harvested by applying 3 ml of LB media to the top of the agar and resuspending the cells by scraping with a sterile plate spreader. The 3 ml of pooled, resuspended cells were then used to inoculate a 25 ml shake flask containing LB+50 µg/ml kanamycin. The pooled culture was then grown overnight at 37° C. with shaking (250 rpm). The following day plasmid DNA was purified from the pooled cultures using the QIAprep Spin Miniprep Kit (Qiagen). The pooled plasmid DNA was then transformed into One Shot BL21(λDE3) pLysS competent cells for protein expression screening as described above.

To make a master plate, the correct constructs are arrayed in quadruplicate in 96 well plates. One colony of the correct sequence is used to inoculate 4 wells and the plates are grown for several hours to overnight at 37° C. in LB containing 50 µg/ml kanamycin with shaking (200 rpm). Sterile glycerol is added to the cultures to a final concentration of 15% (for a final total volume of 150-200 µl/well). The plates are then sealed using BREATHE-EASIER (EMS Catalog No. 70536-20) membranes and stored at −80° C.

EXAMPLE 9

Production and Purification of Isoprene Synthase Inclusion Bodies

Figure 13:
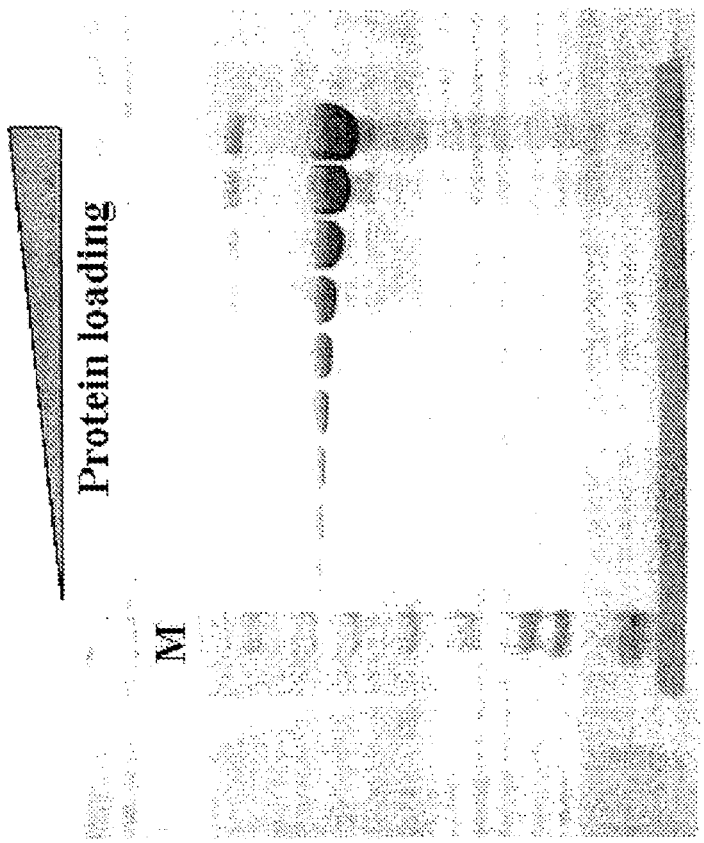
FIG. 13 shows an SDS-PAGE analysis of kudzu isoprene synthase-containing inclusion bodies. Lane M contains molecular weight markers, while the other lanes contain increasing amounts of the purified inclusion body preparation. The kudzu isoprene synthase was estimated to have a purity of >90%.

Inclusion bodies containing kudzu isoprene synthase were formed when the enzyme is overexpressed in the presence of the chaperone GroELS in the strain BL21(λDE3). Briefly pETNHisKudzu (U.S. Application No. 61/013,574, herein incorporated by reference) was subcloned into pGro7 (Takara Catalog No. 3340) according to the manufacturer's instructions. A 500 mL of culture was grown essentially as described (Whittington et al., Proc Natl Acad Sci USA, 99:15375-15380, 2002). Despite the presence of chaperone and low temperature of cultivation the culture yielded predominantly inclusion bodies and only low levels of soluble active protein. The inclusion bodies were harvested using the IFOLD Protein Refolding System (Novagen Catalog No. 71552-3) according to the manufacturer's instructions. This procedure led to a high yield (>50 mg) of recombinant kudzu isoprene synthase. The purity of the inclusion body is shown in FIG. 13. This preparation was used for the production of rabbit polyclonal anti-isoprene synthase antisera (Invitrogen).

EXAMPLE 10

High Throughput Biochemical Screen of Isoprene Synthase Variants

This example describes high throughput methods for the determination of isoprene synthase activity. Libraries of BL21(λDE3)pLysS E. coli host cells capable of expressing isoprene synthase variants are arrayed in 96-well plates and stored frozen at −80° C. as 15% glycerol stocks as described above in Example 8. To analyze a plate of up to 96 variants, a replica stamp of the glycerol stock master plate is made with a 96-pin MULTI-BLOT floating pin tool (V&P Scientific Catalog No. VP 408AF) onto Luria broth agar containing appropriate antibiotic(s) (e.g., 30 µg/mL chloramphenicol, 50 µg/mL kanamycin). The replica plate is incubated over night at 30° C. to allow growth of bacterial patches. Using the same floating pin replicator a 96-square deep well plate containing 250 µL of TM3 medium supplemented with 0.08% Biospringer yeast extract and 1% glucose plus antibiotics (30 µg/mL chloramphenicol, 50 µg/mL kanamycin) is inoculated from the agar plate and incubated overnight at 30° C. The recipe for TM3 broth is as follows: $K_2HPO_4$ (13.6 g/l) $KH_2PO_4$ (13.6 g/l), $MgSO_4*7H_2O$ (2 g/l) Citric Acid Monohydrate (2 g/L) Ferric Ammonium Citrate (0.3 g/L) $(NH_4)_2SO_4$ (3.2 g/L) yeast extract (0.2 g/L) 1 ml of 1000× Trace Elements solution, pH adjusted to 6.8 with ammonium hydroxide qs to volume with sterile $diH_2O$ and filter sterilized with a 0.22 micron filter. The recipe for 1000× Trace Elements solution is as follows: Citric Acids*$H_2O$ (40 g/L), $MnSO_4*H_2O$ (30 g/L), NaCl (10 g/L), $FeSO_4*7H_2O$ (1 g/L), $CoCl_2*6H_2O$ (1 g/L), $ZnSO*7H_2O$ (1 g/L), $CuSO_4*5H_2O$ (100 mg/L), $H_3BO_3$ (100 mg/L), $NaMoO_4*2H_2O$ (100 mg/L). Each component was dissolved one at a time in $diH_2O$, pH adjusted to 3.0 with HCl/NaOH, qs to volume and filter sterilized with a 0.22 micron filter. The overnight cultures are diluted with the same medium to an $OD_{600}$ of 0.05 and grown in another 96-square deep well plate (Thomson Instrument, Catalog No. 951652C), with each well containing 600 µL of the dilution. The dilutions are grown at 30° C. with shaking to an $OD_{600}$ of 0.8 and are then induced with IPTG added to a concentration of 400 µM. The plate is grown for 5 hours and $OD_{600}$ is determined for quality control and normalization.

A volume of 400 µL of culture is transferred into a new 96-well plate (Perkin Elmer, Catalog No. 6008290) and cells are harvested by centrifugation in a Beckman Coulter Allegra 6R centrifuge at 2500×g. The pellet is resuspended in 200 µL of hypotonic buffer (5 mM $MgCL_2$, 5 mM Tris HCl, 5 mM DTT pH 8.0) and the plate is frozen at −80° C. for a minimum time of 60 min. Cell lysate is prepared by thawing the plate and adding 32 µL of isoprene synthase DMAPP assay buffer (57 mM Tris HCl, 19 mM $MgCl_2$, 74 µg/mL DNase I (Sigma Catalog No. DN-25), $2.63 \times 10^5$ U/mL of READYLYSE lysozyme solution (Epicentre Catalog No. R1802M), and 5 mg/mL of molecular biology grade BSA. The plate is incubated with shaking at 25° C. for 30 min and then placed on ice. For isoprene production, an 80 µL aliquot of lysate is transferred to a 96-deep well glass plate (Zinsser Catalog No. 3600600) and 20 µL of a 10 mM DMAPP solution in 100 mM $KHPO_4$, pH 8.2 (Cayman Chemical Catalog No. 63180) is added. The plate is sealed with an aluminum plate seal (Beckman Coultor Catalog No. 538619) and incubated with shaking at 30° C. of 60 minutes. The enzymatic reactions are terminated by heating the glass block (70° C. for 5 min). The headspace of each well is quantitatively analyzed as described in Example 5.

Figure 14A:
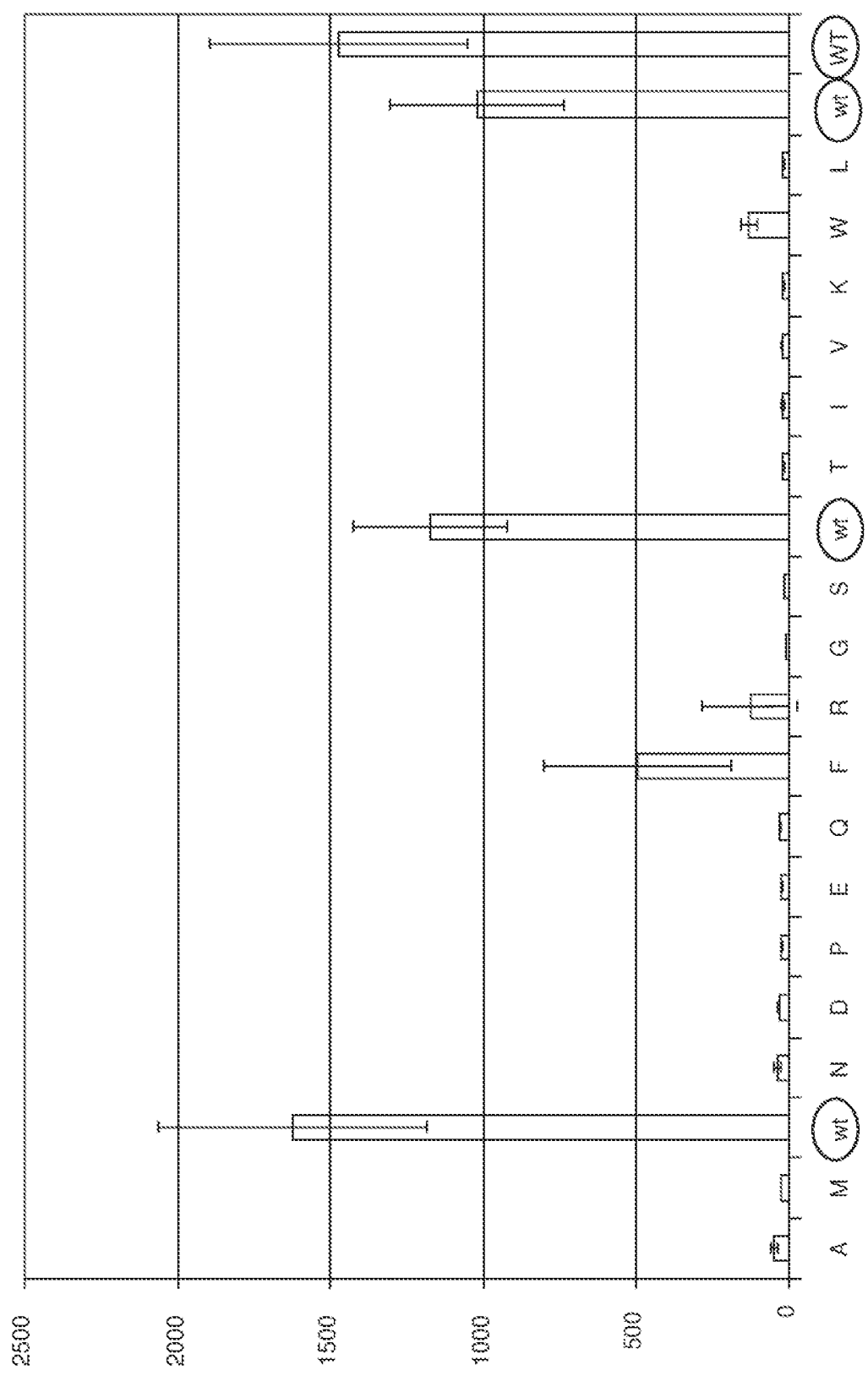
FIG. 14 provides graphs showing isoprene synthase activity of kudzu site evaluation library (SEL) members for positions Y22, A20 and S408. Most members show highly decreased activity, while conservative substitutions show a lesser decrease in activity. Panel A shows assay results for the Y22 library members in comparison with independent wild type samples (circled WT). Panel B shows assay results for the A20 library members in comparison to wild type samples (circled WT). Panel C shows assay results for the S408 library members, indicating that member S408D has 1.5 to 2-fold higher activity than the average of the wild type controls.
Figure 14B:
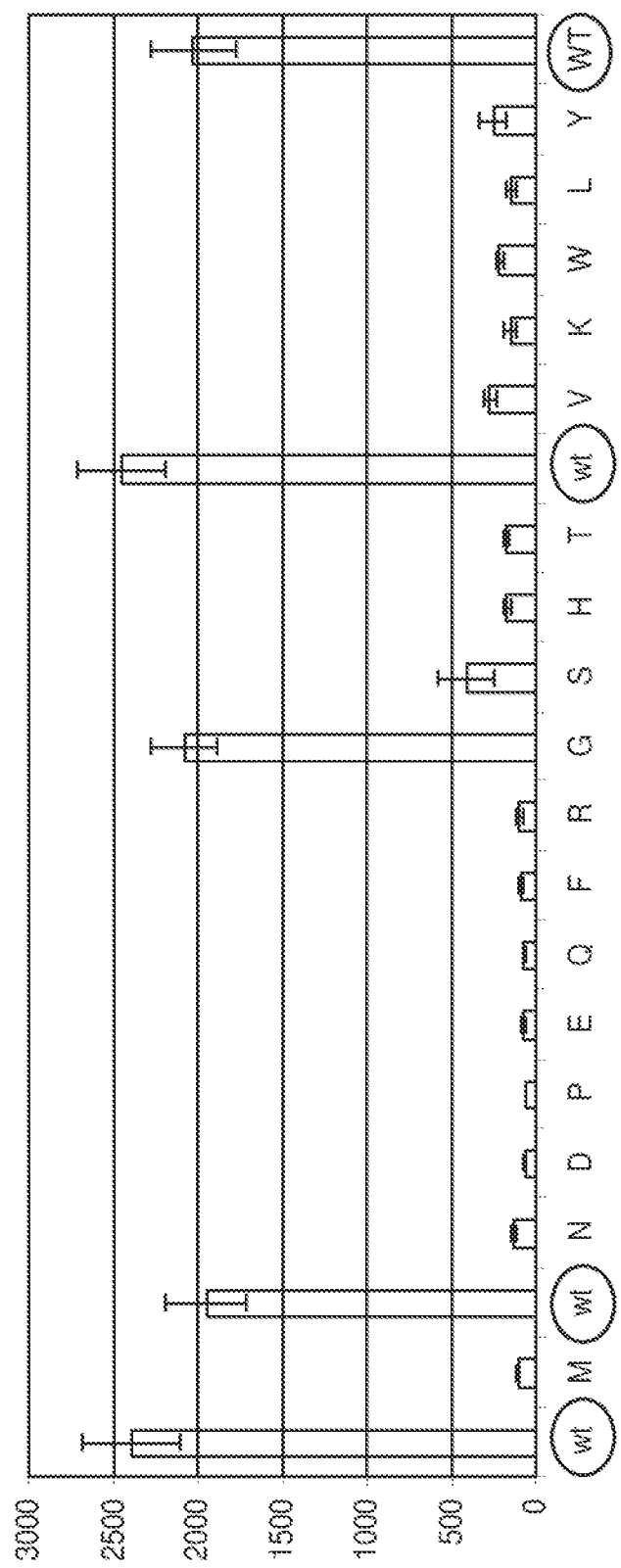

To determine protein concentration 5 µL or more of lysate is run on precast gels (Invitrogen Catalog No. NP0301BOX) for western blot analysis after transfer to a nitrocellulose membrane (Invitrogen Catalog No. LC2000). The primary antibody employed is an anti-isoprene synthase antibody of Example 9. Primary antibody binding is followed by development with a secondary antibody labeled with Alexa Fluor 488 (Invitrogen Catalog No. A-11008) to permit quantitative signal determination. The western blot procedure was carried out as described by Invitrogen. The fluorescence signal was recorded with a Molecular Dynamics STORM instrument using the blue filter setting and quantitatively analyzed with the Molecular Dynamics IMAGEQUANT image analysis software package. Specific activity of the library members was calculated from the ratio of the amount of isoprene produced divided by either the $A_{600}$ of the induction cultures or the isoprene synthase protein concentration determined by western blot. Isoprene synthase protein standard was calibrated by standard gel densitometry with BSA stained with Coomassie brilliant blue R250 serving as primary standard. Increased, decreased, or no change in specific activity of the entire library was tabulated for further analysis. FIG. 14 provides graphs showing isoprene synthase activity of kudzu site evaluation library (SEL) members for positions Y22, A20, and S408. Most members show highly decreased activity relative to wild type, while conservative substitutions show a lesser decrease in activity. Activity of variant A20G approximates that of the wild type kudzu enzyme, indicating that it is a candidate partner for a combinatorial mutant. Interestingly, variant S408D of library S408 showed an increase in activity compared to wild type thus providing another candidate partner for a combinatorial mutant.

EXAMPLE 11

Isoprene Synthase Truncations

Figure 21:
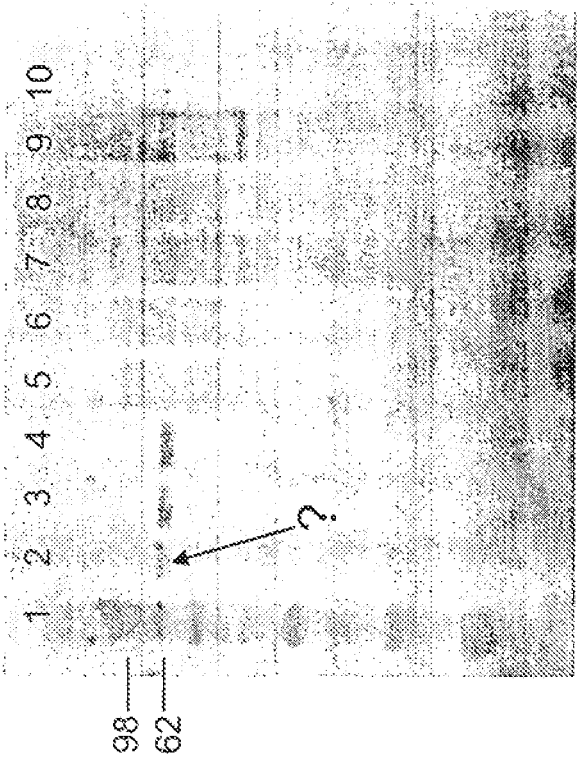
FIG. 21 shows purified IspS displays a lower molecular weight "doublet" by SDS-PAGE analysis.

This example describes the identification of the amino acid sequence of the protein in the lower band of the doublet seen in purified poplar IspS preparations (see FIG. 21). A series of N-terminally truncated IspS molecules based on putative cleavage sites identified by mass spectrometry was also generated. A shorter N-terminal truncation of IspS (the "MEA" truncation in pDu39, see below) was also generated, to examine the effect of further truncation on IspS activity (Williams D C, McGarvey D J, Katahira E J, Croteau R (1998) Biochemistry 37:12213-12220).

Figure 16:
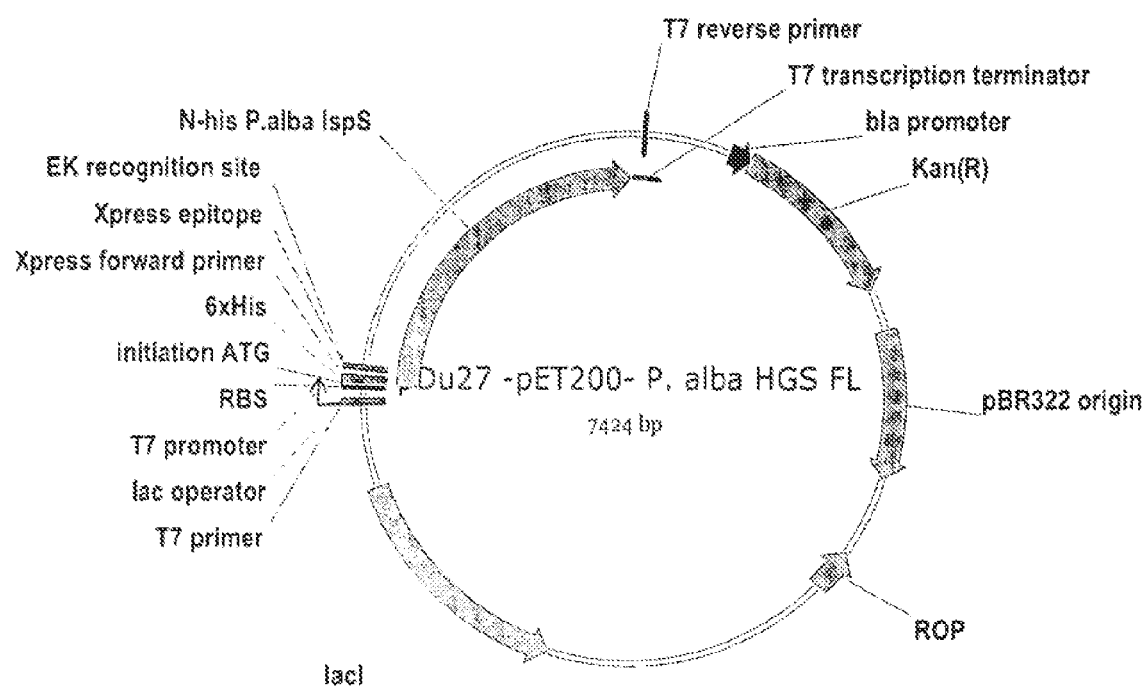
FIG. 16 provides a map of pDu27.

I. Construction of an N-Terminally 6×His-tagged IspS (in pDu27) for protein purification:

The full length *P. alba* IspS from the template *P. alba* pET24a (FIGS. 19 and 20) was prepared by PCR. The following PCR reaction was prepared: 1 µl (Template)-*P. alba* pET24a, 5 µl 10× PfuUltraII Fusion buffer, 1 µl dNTP's (10 mM), 1 µl primer (50 µM) primer F-(MCM219), 1 µl primer (50 µM) primer R-(MCM182), 41 µl $diH_2O$ and 1 µl of PfuUltra II Fusion DNA Polymerase (Stratagene). PCR cycling parameters were as follows: 95° C. 1 min., 95° C. 1 min, 55° C. 20 sec., 72° C. 27 sec. for 29 cycles followed by 72° C. 3 min and 4° C. until cool, using an Eppendorf Mastercycler. The PCR product was gel extracted and purified, using 0.8% E-gel (Invitrogen) and Qiagen QIAquick Gel Extraction and QIAprep Spin Miniprep kits, according to the manufacturer's recommended protocol. A 3 µl aliquot of purified product was ligated to the pET200D/TOPO vector (Invitrogen), according to the manufacturer's protocol. The reaction was incubated for 5 minutes at room temperature, and the 6 µl topoisomerase mixture was then transformed into *E. coli* Top10 chemically competent cells (Invitrogen) according to the manufacturer's protocol. Transformants were selected for on LB plates containing kanamycin (50 µg/ml) (Kan50), and incubated at 37° C. overnight. Five colonies were picked and screened using PuReTaq Ready-To-Go PCR Beads (Amersham) using the T7 Forward and MCM182 primers. Clones harboring inserts of the correct size were further verified by sequencing using the T7 Forward and T7 Reverse primers (Quintara Biosciences). One construct, pDu27 (FIGS. 16-18), was chosen for further study. A 1 µl aliquot of the plasmid preparation was transformed into BL21(λDE3) pLysS (Invitrogen) according to the manufacturer's protocol. Transformants were selected for on LB plates containing Kan50+ and chloramphenicol (35 µg/ml) (Cm35) and incubated at 37° C. overnight. The resulting strain was used for expression and purification of N-terminally 6×His-tagged *P. alba* IspS.

II. Purification of 6×His-tagged IspS
Expression of 6×His-tagged IspS

N-terminally 6×His-tagged IspS was expressed and purified from strain MD08-99. The growth procedure is suitable for histidine tagged enzymes expressed in BL21(λDE3) pLysS cells. A 10 ml of overnight culture was prepared for each 1L of planned growth. The appropriate antibiotics (50 mg/ml kanamycin, 50 mg/ml chloramphenicol, and/or 50 mg/ml Carbenecillin) was added to 10 ml of LB medium in a 25 ml flask and was inoculated with 1 colony from a fresh plate of cells or directly from glycerol frozen cell stock. Cultures were grown at 30° C. overnight with shaking at ~220 rpm. Day cultures were prepared in 1 liter of LB medium with appropriate antibiotics for each culture. Each 1L day culture was inoculated with 10 ml of overnight culture and grown at 30-37° C. with shaking at ~220 rpm until the $OD_{600}$ reached ~0.4-0.6. Day cultures were then induced with 400 µM IPTG and allowed to continue growing at 30° C. with shaking at 220 rpm for ~5-6 hours. Cells were then harvested by centrifugation at 10,000×g for 10 min, 4° C. Following Harvest, cells were used directly or stored at −80° C. until ready to process.

Purification of 6×His-Tagged IspS

For purification of histidine tagged enzymes from BL21 (λDE3)pLysS cells, cells were gently resuspended in fresh Lysis buffer (Lysis buffer: Ni wash buffer+0.5 mM PMSF, 0.01% Tween-20, 1 mg/ml lysozyme, 0.2 mg/ml DNaseI; Ni wash buffer: 50 mM $NaH_2PO_4$, 300 mM NaCl, 20 mM Imidazole, pH 8.0). Approximately 40-50 ml of lysis buffer was used per 1L of cell pellet. Cells were then incubated on ice for approximately 30 min. The cell suspension was then lysed fully by passing 2-3 times through a french pressure cell (large french press cell at 1200 psi/High setting) until lysate started to look clear. A sample of the lysate was saved for activity assay and gel analysis (~100 µl). The lysate was then clarified by centrifuging the lysate at 30,000×g for 30 min, 4° C. in a Sorvall Discovery 90SE ultracentrifuge. The supernatant was removed and retained. A sample of the "clarified lysate" was saved for activity assay and gel analysis (~100 µl).

The clarified lysate was run over HisTrap HP columns (GE Healthcare) using a gradient from 0-100% Ni buffer B. Samples were then analyzed by SDS-PAGE gel (4-12% gel NUPAGE, Invitrogen) according to manufacturer's directions. Desired fractions were concentrated on spin filters (Vivaspin-20, Sartoris,) and then desalted over a HiPrep 26/10 Desalting column (GE heathcare) packed with Sephadex G25 resin. The G-25 buffer consisted of 50 mM HEPES, 50 mM NaCl, and 1 mM DTT, pH 7.4. The desired sample was then purified over a HiTrap Q HP column (GE) using a gradient elution from 0% Q seph buffer A to 100% Q seph buffer B (Q seph buffer A: 50 mM Tris, 0.05 M NaCl, 1 mM DTT, pH 7.6 and Q seph buffer B: 50 mM Tris, 1.0 M NaCl, 1 mM DTT, pH 7.6). Fractions containing the desired protein were analyzed and concentrated. Sample buffer was then exchanged into 50 mM HEPES, 50 mM NaCL, pH 7.4 with 1 mM DTT by passing the sample over a Hi Prep 26/10 Desalting column (GE heathcare) packed with Sephadex G25 resin. A final polishing step of Gel filtration was used when necessary. The sample was passed through a Hi Load 26/60 Superdex 200 prep grade (GE) in gel fitration buffer: (50 mM HEPES, 150 mM NaCl, 1 mM DTT, pH 7.4). Fractions were then analyzed and concentrated. The samples were then stored at −80° C. For preparation for analysis of the band, the sample is run on an SDS-PAGE gel (4-12% NUPAGE gel, Invitrogen), stained and the desired band excised and processed as described below.

III. Mass Spectrometry of Isoprene Synthase

Sample Preparation

An In-Gel Digestion and LCQ-Deca Mass Spectrometry Procedure was utilized (Modified Rosenfeld in-gel Digest Protocol) (Rosenfeld et al, Anal. Biochem. (1992) 203, 173-179; Hellman et al, Anal Biochem, (1995) 224, 451-455). The purified sample of Isoprene synthase was run on a 4-12% SDS-PAGE (NUPAGE, Invitrogen) and stained with Coomassie Brilliant Blue R-250 (Thermo Scientific) or SimplyBlue Safe Stain (Invitrogen). Band(s) of interest were excised from the gel and destained. Each gel slice was diced into small pieces ~1 mm×1 mm and placed into 0.65 mL "slick" (siliconized) tubes from PGC Scientific. Approximately 100 µL of 25 mM $NH_4HCO_3$/50% $ACN/H_2O$ was added to each tube and vortexed for 10 min. Supernatants were extracted and discarded. These steps were repeated twice. Then gel pieces were then run in a Savant SpeedVac to dryness (~20 to 30 min).

Samples were then reduced and alkylated. For reduction, 25 µL (or enough to cover) of 10 mM DTT in 25 mM $NH_4HCO_3$ (prepared fresh) were added to dried gels. Tubes were then vortexed and spun briefly. Reactions were incubated at 50° C. for 1 hour. For alkylation, supernatants were removed and 25 µL or more of 55 mM iodoacetamide (IAA) in 25 mM $NH_4HCO_3$ were added to the gel. Reaction tubes were vortexed and spun briefly again. Reactions were allowed in dark for 1 hour at room temperature. Supernatants were removed and gels were washed with ~100 µL of 25 mM $NH_4HCO_3$/50% $ACN/H_2O$, by vortexing for 10 min and briefly spinning. Supernatant were removed and the wash step was repeated once. Gel pieces were then dried in a SpeedVac (~15-30 min).

Digestion buffer was prepared by adding 400 µL of 0.1% n-octyl B-D-glucopyranosidase water to 100 uL of 8M Urea. 400 uL of this digestion buffer was added to 20 ug of freshly prepared Trypsin. 0.05 µg/µL of sequencing-grade Trypsin was prepared from one vial of 20 µg sequencing grade trypsin (Promega) that was dissolved into 400 uL of 1.6 M Urea solution. Trypsin enzyme solution was added enough to cover gel pieces. Tubes were covered with parafilm and incubated at 37° C. overnight (16-20 hrs). It was ensured that there is a little extra buffer above the gel.

Peptides were extracted from gels by briefly vortexing and spinning the digest. The digest solution was transferred with gel loading tips into a 0.65 mL siliconized tube. 50 µL (enough to cover) of 50% $ACN/0.1\%$ $FA/H_2O$ were added to the gel pieces and samples were vortexed for 10 min, spun, and then sonicated for five min. Extracted peptides were pooled together in one tube. Extraction steps were repeated two to three more times until the gel pieces became white in appearance and shrank in size. Extracted digests were vortexed, spun and dried in a SpeedVac to a volume of 55 µL. In cases where the volume was less than 55 µL, enough 0.1% FA was added to make up a final volume of 55 µL.

Mass Spectrometry

The sample was injected onto a Thermofinnigan (San Jose, Calif.) LCQ-Deca electrospray ionization (ESI) ion-trap mass spectrometer. A Vydac C18 column (5µ, 300A, 0.2×150 mm, Michrom Bioresources, Auburn, Calif.) was used with a flow rate of 200 µL/min. The injection volume was 50 uL, and was filtered through an on-line trapping cartridge (Peptide CapTrap, Michrom Bioresources, Auburn, Calif.) before loading onto the column. Separation of the in-gel digest was performed with the following gradient (Solvent A: 0.1% trifluoroacetic acid in H2O (J. T. Baker, Phillipsburg, N.J.), Solvent B: 0.08% trifluoroacetic acid in acetonitrile (J. T. Baker, Phillipsburg, N.J.)):

TABLE 11-1

Gradient Table

| | min | A % | B % |
|---|---|---|---|
| 0 | 0.00 | 100 | 0 |
| 1 | 10.00 | 86 | 14 |
| 2 | 16.00 | 81 | 19 |
| 3 | 20.00 | 78 | 22 |
| 4 | 21.00 | 77 | 23 |
| 5 | 22.00 | 75 | 25 |
| 6 | 24.00 | 73 | 27 |
| 7 | 32.00 | 69 | 31 |
| 8 | 34.00 | 66 | 34 |
| 9 | 37.00 | 64 | 36 |
| 10 | 47.00 | 60 | 40 |
| 11 | 50.00 | 30 | 70 |
| 12 | 55.00 | 100 | 0 |
| 13 | 60.00 | 100 | 0 |
| 14 | 65.00 | 100 | 0 |
| 15 | | 100 | 0 |

Mass Spectrometry Results

Figure 22:
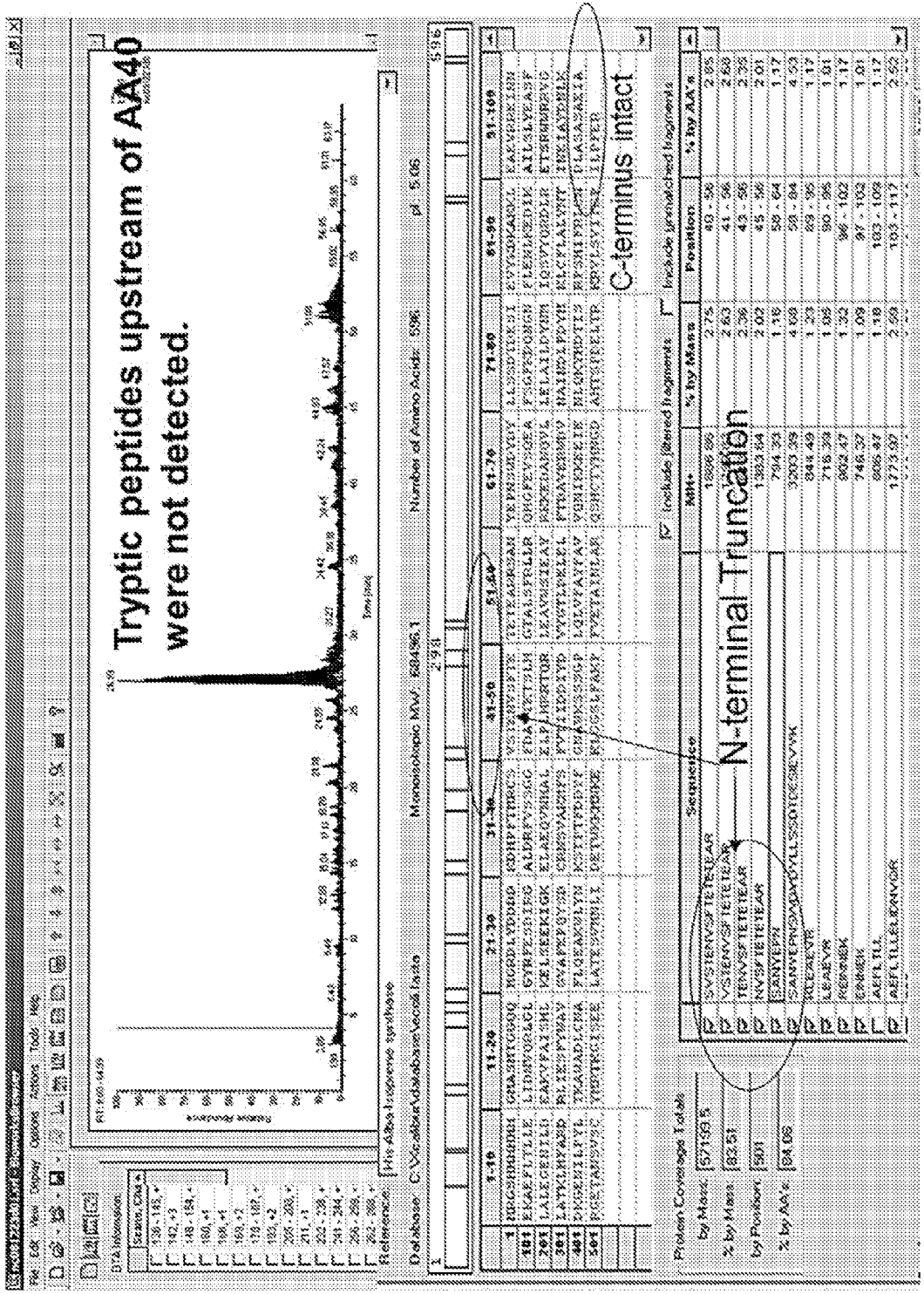
FIG. 22 shows tryptic peptides identified by mass spectrometry.
Figure 23:
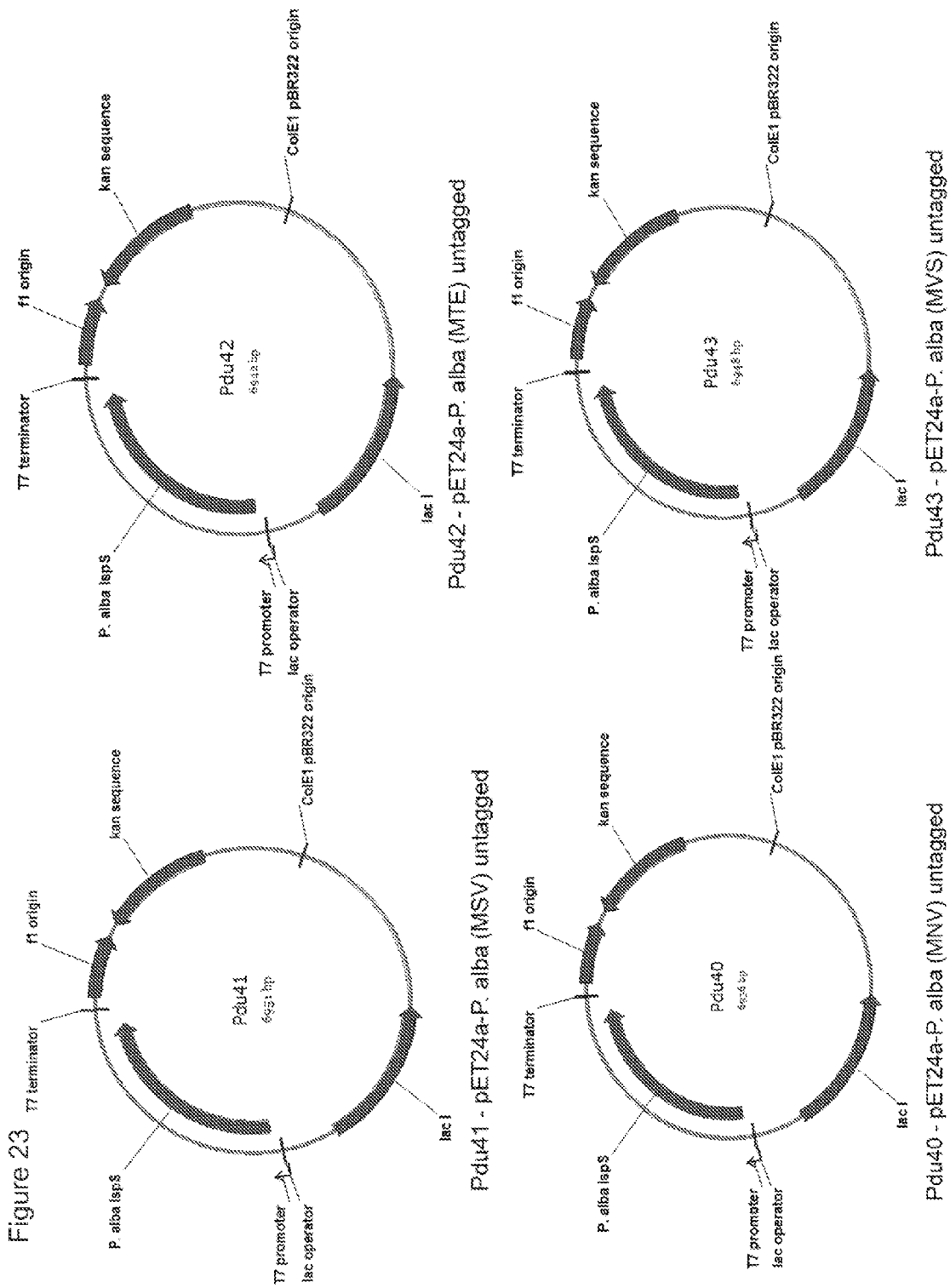
FIG. 23 provides maps of pDu40, pDu41, pDu42 and pDu43 harboring N-terminal truncations of *P. alba* IspS.
Figure 24:
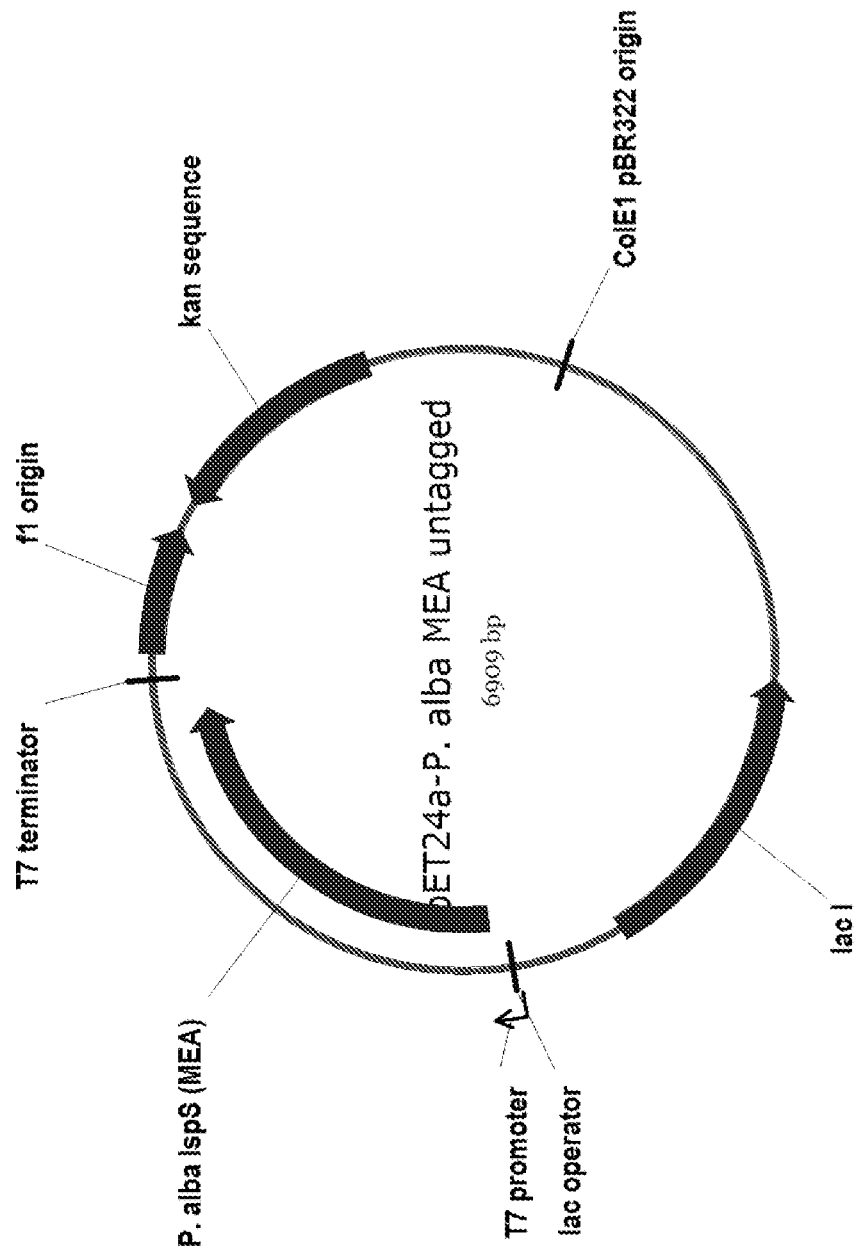
FIG. 24 provides a map of Pdu39 which is pET24a-*P. alba* MEA untagged (in strain MD09-173).
Figure 35:
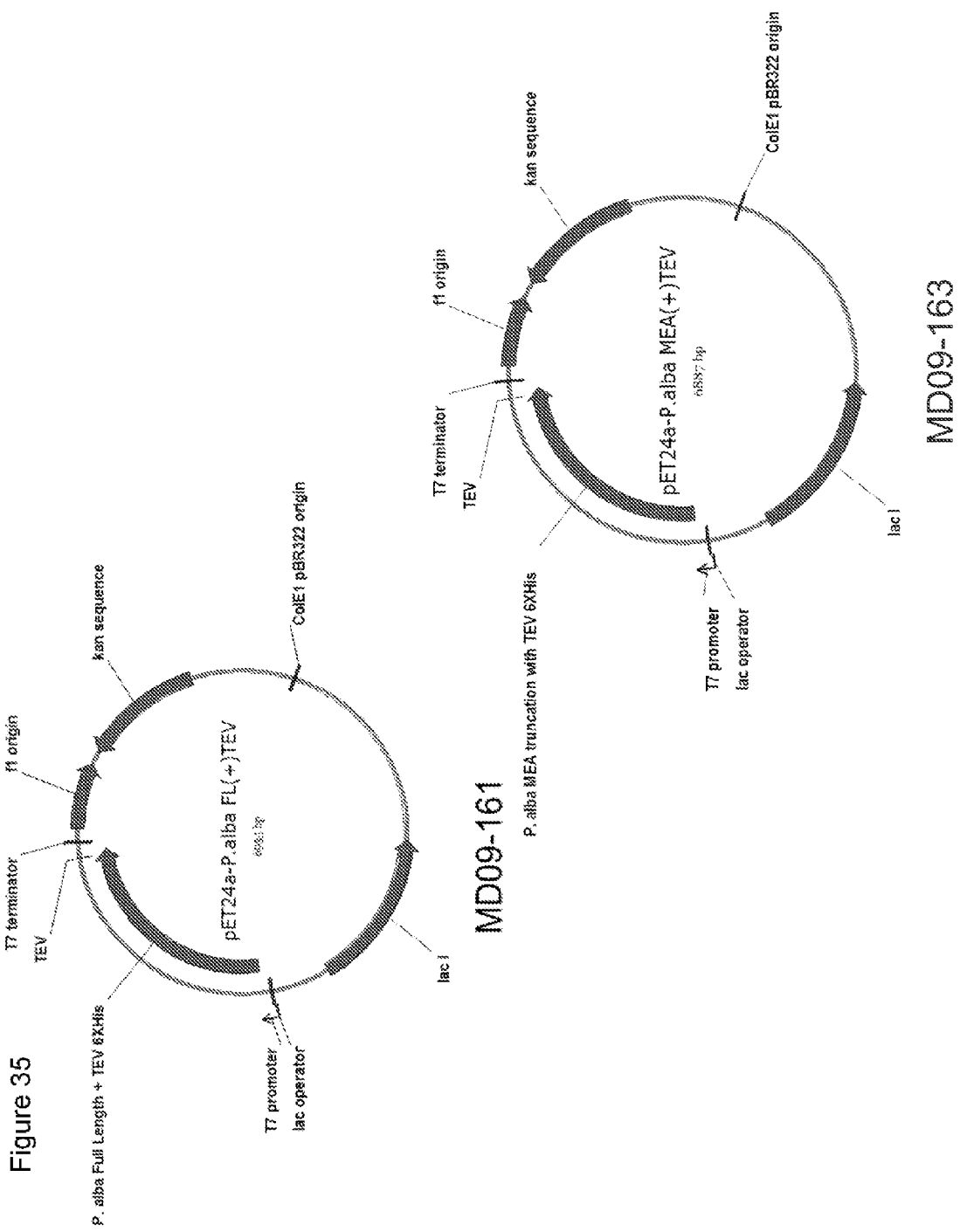
FIG. 35 provides maps of MD09-161 and MD09-163, C-terminally TEV, 6xHis-tagged IspS variants.

An aliquot of 6.4 μg of protein was loaded into 5 lanes on a 4-12% bis-tris NUPAGE gel (Invitrogen), MOPS buffer, 50 min run. As described above, the gel was stained for 2 minutes, and then de-stained for 15 minutes. The gel was washed in H$_2$O, then all bands were excised, cut into small pieces, and destained. Gel pieces were reduced and alkyated with DTT/IAA for 1 hour each at 52° C. and RT, respectively. Trypsin was added for an overnight digestion. Extracted peptides were run on the LCQ-Deca. FIGS. 21 and 22 show the results for the mass spectrometry analysis. The lower doublet band (in FIG. 21) is identified as IspS.

FIG. 22 shows that N-terminal truncations were observed after amino acids 39, 40, 42, and 44 (according to the peptide sequence of the N-terminally His-tagged IspS protein in pDu27). The C-terminus of IspS is intact.

IV. Construction of N-Terminally Truncated IspS Variants:

All truncated constructs without affinity tags were generated using the QuickChange Site-directed Mutagenesis kit (Stratagene) using the template *P. alba* pET24a for PCR amplification. Approximately 50 ng of template DNA was used for amplification (with an Eppendorf Mastercycler Gradient PCR Machine) of the mutagenized PCR product with the Forward (For) and Reverse (Rev) primer pairs that correspond to each relevant truncation (QC MSV For and QC MSV Rev, for example, see Table 11-2). The following PCR reaction mixtures were used: 1 μl *P. alba* pET24a, 5 μl 10× PfuUltra HF buffer, 1 μl dNTP's, 1 ul (50 μM) primer-For (e.g. QC MSV For), 1 μl (50 μM) primer-Rev (e.g. QC MSV Rev), 2 μl DMSO, 39 μl diH$_2$O, 1 μl PfuUltra HF Polymerase (Stratagene). The following PCR cycling parameters were used: 95° C. 1 min, 95° C. 30 sec., 55° C. 1 min., 68° C. 7.3 min. for one cycle followed by 95° C. 30 sec., 55° C. 1 min., 68° C. 7.3 min for a total of 18 cycles and then followed by 4° C.

The PCR products were treated with 1-2 μl of DpnI (Roche) for 1-3 hour at 37° C. A 5 μl aliquot of the DpnI treated products was visualized on a 0.8% E-gel (Invitrogen). A 1 μl aliquot of each product was transformed into chemically competent *E. coli* Top10 cells (Invitrogen) according to the manufacturer's protocol. Transformants were selected on LB medium containing kanamycin at a concentration of 50 μg/ml (Kan50), and incubated overnight at 37° C. Five colonies of each transformation were selected and grown to stationary phase in 3 ml liquid LB Kan50. Plasmids were purified using a Qiagen miniprep kit according to the manufacturer's recommended protocol. Purified plasmids were sequenced (by Quintara Biosciences) with T7 Forward and Reverse primers, and confirmed for their respective truncation. The resulting plasmids (pDU39 through pDU43, see Table 11-4, FIGS. 23-34) were transformed into chemically competent *E. coli* BL21(λDE3)pLysS (Invitrogen) according to the manufacturer's recommended protocol. Table X describes the strains used for expression of truncated IspS enzymes.

Constructs with affinity (6×His) and proteolysis (TEV, Tobacco Etch Virus) tags were generated using *P. alba* pET24a as a template for PCR reactions. PCR reaction mixtures were prepared as follows: 1 ul (*P. alba* pET24a), 5 ul 10× PfuUltraII Fusion buffer, 1 ul dNTP's (10 mM), 1 ul primer (50 μM) Alba FL-NdeI-For or Alba TRC (MEA)-NdeI-F, 1 ul primer (50 uM) Alba FLTRC (+) TEV-R, 41 ul diH$_2$O and 1 ul of PfuUltra II Fusion DNA Polymerase from Stratagene. PCR cycling parameters were as follows: 95° C. 1 min., 95° C. 30 sec., 55° C. 20 sec., 72° C. 25 sec. for one cycle and then repeating 95° C. 30 sec., 55° C. 20 sec., 72° C. 25 sec. for an additional 28 cycles, followed by 72° C. 3 min and then 4° C. After amplification and verification of the correct molecular weight of the product by visualization on 0.8% E-gel (Invitrogen), PCR products were digested with restriction enzymes NdeI and XhoI (Roche) for 2 hours at 37° C., and then gel purified using the Qiaquick Gel Purification system (Qiagen) according to the manufacturer's recommended protocol. 3 μl of purified product was ligated to pET-24a (Invitrogen) that was digested with NdeI and XhoI (Roche), gel purified and dephosphorylated (using SAP, shrimp alkaline phosphatase) (Promega) according to the manufacturer's recommended protocols. T4 ligase (NEB) was used for the ligation reaction, which was incubated overnight at 16° C. The ligation reaction was dialyzed into water for 30 min., and 2 μl of the reaction were used to electroporate MCM331 (see below) competent cells. Cells were allowed to recover at 30° C. for 2 hours, and then selected on Kan50 with 5 mM (R)-(−)-Mevalonolactone (MVA) (Sigma) spread onto the plate. Positive transformants were inoculated into 3 ml of liquid LB Kan50, and plasmids were isolated using the QIAPrep Spin miniprep kit (Qiagen). Inserts were verified by restriction digestion using NdeI and XhoI (Roche) and positive clones were sequenced (Quintara Biosciences) with T7 promoter and T7 terminator sequencing primers. 1 μl of each plasmid (see Table 11-4 for plasmid description and FIGS. 35-39) was transformed into chemically competent *E. coli* BL21(λDE3) pLysS (Invitrogen) according to the manufacturer's recommended protocol. Transformants were selected on LB Kan50+Cm35 (Chloramphenicol 35 ug/ml) plates and incubated at 37° C. See Table 11-5 for a description of all expression strains.

Strain MCM331 was prepared as follows. A synthetic operon containing mevalonate kinase, mevalonate phosphate kinase, mevalonate pyrophosphate decarboxylase, and the IPP isomerase was integrated into the chromosome of *E. coli*. If desired, expression may be altered by integrating different promoters 5' of the operon.

i) Target Vector Construction

The attTn7 site was selected for integration. Regions of homology upstream (attTn7 up) (primers MCM78 and MCM79) and downstream (attTn7 down) (primers MCM88 and MCM89) were amplified by PCR from MG1655 cells. A 50 μL reaction with 1 μL 10 μM primers, 3 μL ddH$_2$O, 45 μL Invitrogen Platinum PCR Supermix High Fidelity, and a scraped colony of MG1655 was denatured for 2:00 at 94° C., cycled 25 times (2:00 at 94° C., 0:30 at 50° C., and 1:00 at 68° C.), extended for 7:00 at 72° C., and cooled to 4° C. This resulting DNA was cloned into pCR2.1 (Invitrogen) according to the manufacturer's instructions, resulting in plasmids MCM278 (attTn7 up) and MCM252 (attTn7 down). The 832 bp ApaI-PvuI fragment digested and gel purified from MCM252 was cloned into ApaI-PvuI digested and gel purified plasmid pR6K, creating plasmid MCM276. The 825 bp PstI-NotI fragment digested and gel purified from MCM278 was cloned into PstI-NotI digested and gel purified MCM276, creating plasmid MCM281.

ii) Cloning of Lower Pathway and Promoter

MVK-PMK-MVD-IDI genes were amplified from pTrcK-KDyIkIS with primers MCM104 and MCM105 using Roche Expand Long PCR System according to the manufacturer's instructions. This product was digested with NotI and ApaI and cloned into MCM281 which had been digested with NotI and ApaI and gel purified. Primers MCM120 and MCM127 were used to amplify CMR cassette from the GeneBridges FRT-gb2-Cm-FRT template DNA using Stratagene Pfu Ultra II. A PCR program of denaturing at 95° C. for 4:00, 5 cycles of 95° C. for 0:20, 55° C. for 0:20, 72° C. for 2:00, 25 cycles of 95° C. for 0:20, 58° C. for 0:20, 72° C. for 2:00, 72° C. for 10:00, and then cooling to 4° C. was used with four 50 uL PCR reactions containing 1 uL~10 ng/μL template, 1 μL each primer, 1.25 μL 10 mM dNTPs, 5 μL 10× buffer, 1 μL enzyme, and 39.75 μL ddH$_2$O. Reactions were pooled, purified on a Qiagen PCR cleanup column, and used to electroporate water-washed Pir1 cells containing plasmid MCM296. Electroporation was carried out in 2 mM cuvettes at 2.5V and 200 ohms. Electroporation reactions were recovered in LB for 3 hr at 30° C. Transformant MCM330 was selected on LA with CMPS, Kan50.

iii) Integration into *E. coli* Chromosome

Miniprepped DNA (Qiaquick Spin kit) from MCM330 was digested with SnaBI and used to electroporate BL21(DE3) (Novagen) or MG1655 containing GeneBridges plasmid pRedET Carb. Cells were grown at 30° C. to ~OD1 then induced with 0.4% L-arabinose at 37° C. for 1.5 hours. These cells were washed three times in 4 C ddH$_2$O before electroporation with 2 μL of DNA. Integrants were selected on L agar with containing chloramphenicol (5 μg/ml) and subsequently confirmed to not grow on L agar+Kanamycin (50 μg/ml). BL21 integrant MCM331 and MG1655 integrant MCM333 were frozen.

TABLE 11-2

| | Primers | |
|---|---|---|
| MCM219 | caccatgcgttgtagcgtgtcca (SEQ ID NO: 33) | |
| MCM182 | gggcccgtttaaactttaactagactctgcagttagcgttcaaacggcagaa (SEQ ID NO: 34) | |
| QC MSV For | gaaggagatatacatatgagcgtgtccaccgaaaatg (SEQ ID NO: 35) | |
| QC MSV Rev | cattttcggtggacacgctcatatgtatatctccttc (SEQ ID NO: 36) | |
| QC MVS For | gaaggagatatacatatggtgtccaccgaaaatgtgtc (SEQ ID NO: 37) | |
| QC MVS Rev | gacacattttcggtggacaccatatgtatatctccttc (SEQ ID NO: 38) | |
| QC MTE For | gaaggagatatacatatgaccgaaaatgtgtctttcac (SEQ ID NO: 39) | |
| QC MTE Rev | gtgaaagacacattttcggtcatatgtatatctccttc (SEQ ID NO: 40) | |
| QC MNV For | gaaggagatatacatatgaatgtgtctttcaccgaaac (SEQ ID NO: 41) | |
| QC MNV Rev | gtttcggtgaaagacacattcatatgtatatctccttc (SEQ ID NO: 42) | |
| QC MEA For | gaaggagatatacatatggaagctcgtcgttctgcg (SEQ ID NO: 43) | |
| QC MEA Rev | cgcagaacgacgagcttccatatgtatatctccttc (SEQ ID NO: 44) | |
| Alba FL-NdeI-For | gaaggagatatacatatgcgttgtagcgtg (SEQ ID NO: 45) | |
| Alba FLTRC (+) TEV-R | cccgcgcttactcgaggccctgaaaatacaggttttcgcg ttcaaacggcagaatcggtt (SEQ ID NO: 46) | |
| Alba TRC (MEA)- NdeI-F | gaaactgaaacccatatggaagctcgtcgttctgc (SEQ ID NO: 47) | |

TABLE 11-3

| | Primers for construction of strain MCM331 | |
|---|---|---|
| MCM78 | attTn7 up rev for integration construct | gcatgctcgagcggccgcTTTTAATCAAACATCCTGCCAACTC (SEQ ID NO: 48) |
| MCM79 | attTn7 down rev for integration construct | gatcgaagggcgatcgTGTCACAGTCTGGCGAAACCG (SEQ ID NO: 49) |
| MCM88 | attTn7 up forw for integration construct | ctgaattctgcagatatcTGTTTTTCCACTCTTCGTTCACTTT (SEQ ID NO: 50) |
| MCM89 | attTn7 down forw for integration construct | tctagagggcccAAGAAAAATGCCCCGCTTACG (SEQ ID NO: 51) |
| MCM104 | GI1.2 promoter - MVK | Gatcgcggccgcgcccttgacgatgccacatcctgagcaa Ataattcaaccactaattgtgagcggataacacaaggagg Aaacagctatgtcattaccgttcttaacttc (SEQ ID NO: 52) |
| MCM105 | aspA terminator - yIDI | Gatcgggccccaagaaaaaaggcacgtcatctgacgtgcc Tttttttatttgtagacgcgttgttatagcattcta (SEQ ID NO: 53) |

TABLE 11-3 -continued

Primers for construction of strain MCM331

| MCM120 | Forward of attTn7: attTn7 homology, GB marker homology | aaagtagccgaagatgacggtttgtcacatggagtt ggcaggatgtttgattaaaagcAATTAACCCTCACTA AAGGGCGG (SEQ ID NO: 54) |
|---|---|---|
| MCM127 | Rev complement of 1.2 GI: GB marker homology (extra long), promoter, RBS, ATG | AGAGTGTTCACCAAAAATAATAACCTTTCCCGGTGCAgaa Gttaagaacggtaatgacatagctgtttcctccttgtgtt Atccgctcacaattagtggttgaattatttgctcaggatg tggcatcgtcaagggcTAATACGACTCACTATAGGGCTCG (SEQ ID NO: 55) |

TABLE 11-4

Plasmids for expression of IspS variants

| MD09-161 | pET24a-*P. alba* FL C-Term (+) TEV, His tag/MCM331 |
|---|---|
| MD09-163 | pET24a-*P. alba* TRC (MEA) C-Term (+) TEV, His tag/MCM331 |
| pDu27 | Alba-FL-pET200/D-TOPO |
| pDu39 | Mtg pET24a-*P. alba*-MEA/Top10 (Untagged) |
| pDu40 | Mtg pET24a-*P. alba*-MNV/Top10 (Untagged) |
| pDu41 | Mtg pET24a-*P. alba*-MSV/Top10 (Untagged) |
| pDu42 | Mtg pET24a-*P. alba*-MTE/Top10 (Untagged) |
| pDu43 | Mtg pET24a-*P. alba*-MVS/Top10 (Untagged) |

TABLE 11-5

Strains for expression of IspS variants

| MD08-99 | Alba-FL-pET200/D-TOPO (pDu27) in BL21 (λDE3) pLysS |
|---|---|
| MD09-165 | BL21(λDE3)pLysS, pET24a-*P. alba* FL C-Term (+) TEV, His tag |
| MD09-167 | BL21(λDE3) pLysS, pET24a-*P. alba* TRC (MEA) C-Term (+) TEV, His tag |
| MD09-173 | BL21(λDE3)pLysS, pET24a-*P. alba* (MEA) Untagged (pDu39) |
| MD09-174 | BL21(λDE3)pLysS, pET24a-*P. alba* (MNV) Untagged (pDu40) |
| MD09-175 | BL21(λDE3)pLysS, pET24a-*P. alba* (MSV) Untagged (pDu41) |
| MD09-176 | BL21(λDE3)pLysS, pET24a-*P. alba* (MTE) Untagged (pDu42) |
| MD09-177 | BL21(λDE3)pLysS, pET24a-*P. alba* (MVS) Untagged (pDu43) |

V. Biochemical Analysis of IspS Truncations

The relative activity of the various N-terminally truncated IspS enzymes was determined by DMAPP assay. The strains described above were analyzed via DMAPP assay in a 96-well plate. All strains were assayed in quadruplicate. The "Full Length" variant refers to the IspS enzyme expressed in BL21(λDE3) pLysS (Invitrogen) from the *P. alba* pET24a plasmid.

TABLE 11-6

DMAPP Assay of N-terminal Truncations

| | Activity Data | | | Avg | OD |
|---|---|---|---|---|---|
| Variant | Average | Std Dev | % CV | $OD_{600}$ | Normalized |
| MD09-173 | 1125.6 | 93.7 | 8.3 | 5.2 | 217.6 |
| MD09-174 | 118.6 | 8.0 | 6.7 | 5.2 | 22.8 |
| MD09-175 | 1064.6 | 71.7 | 6.7 | 4.9 | 219.0 |
| MD09-176 | 1179.1 | 64.7 | 5.5 | 4.9 | 238.7 |

TABLE 11-6-continued

DMAPP Assay of N-terminal Truncations

| | Activity Data | | | Avg | OD |
|---|---|---|---|---|---|
| Variant | Average | Std Dev | % CV | $OD_{600}$ | Normalized |
| MD09-177 | 831.7 | 89.6 | 10.8 | 4.9 | 168.2 |
| Full Length | 805.8 | 65.1 | 8.1 | 5.0 | 161.3 |

Results:

Table X shows that when normalized for $OD_{600}$, strains MD09-173 (with plasmid pDu39), MD09-175 (pDu41), MD09-176 (pDu42), and MD09-177 (pDu43) all displayed higher DMAPP activity than the "Full Length" wild type IspS enzyme (in strain BL21(λDE3) pLysS with *P. alba* pET24a).

VI. Detailed Kinetic Analysis of the "MEA" Truncation in IspS

The relative specific activity was determined and the kinetics of "N-terminally truncated" *P. alba* isoprene synthases were examined compared to "Full length" *P. alba* isoprene synthases. Four strains expressing four different constructs were used in this analysis: BL21(λDE3) pLysS with *P. alba* pET24a; MD09-173; MD09-165; and MD09-167 (Strains described above in detail). These strains express "full length" *P. alba* IspS, "truncated" *P. alba* IspS (the MEA truncation), "full length" C-terminally TEV and His-tagged *P. alba* IspS, and "truncated" C-terminally TEV and His-tagged *P. alba* IspS, respectively. In the experiments described below, "truncated" refers specifically to the MEA variant of *P. alba* IspS.

All strains were inoculated into LB containing 30 mg/L chloramphenicol(Cm) and 50 mg/L kanamycin and grown overnight in 2 mL culture tubes at 37° C. The overnight cultures were diluted 1:100 in 25 mL of LB broth containing 30 mg/L chloramphenicol(Cm) and 50 mg/L kanamycin the following morning and grown at 37° C. until OD~0.5. Each strain was grown in triplicate. The cultures were then induced with 400 uM IPTG and incubated at 30° C. for 4 hours. 20 mL of each culture were centrifuged at 3000×g for 20 min. and the supernatant was discarded. The pellets were frozen at −80° C. overnight. Pellets were resuspended in 2 mL of a buffer containing 100 mM Tris, 100 mM NaCl, 0.25 mg/mL lysozyme and 0.25 mg/mL DNAase, pH 8. Cell suspensions were french pressed at 20,000 psi twice and the lysate was then centrifuged at 14000×g for 20 minutes to yield cell free extract that was used for kinetic studies and protein concentration determination.

To measure specific activity, 5 μL of cell free extract from each strain was incubated with 5 mM DMAPP, 50 mM $MgCl_2$ in a buffer containing 100 mM Tris and 100 mM NaCl (pH 8) to a final volume of 100 μL for 15 min. at 30° C. in gas tight 2 mL vials. Reactions were terminated with the addition of 100 μL of 500 uM EDTA, pH 8. Samples were analyzed by GC-MS to determine the concentration of isoprene in the headspace of the vials.

To determine $k_{cat}$ and $K_M$, 5 uL of cell free extract from each strain was incubated with DMAPP at concentrations ranging from 0.625 to 40 mM DMAPP in a buffer containing 100 mM Tris, 50 mM MgCl$_2$ and 100 mM NaCl (pH 8) to a final volume of 100 μL for 15 min. at 30° C. in gas tight 2 mL vials. Reactions were terminated with the addition of 100 μL of 500 mM EDTA, pH 8. Samples were analyzed by GC-MS to determine the concentration of isoprene in the headspace of the vials. Data were analyzed using Kaleidagraph and fit to following equation for uncompetitive substrate inhibition: rate/E=$k_{cat}$*S/($K_M$+S*(1+S/$K_i$)). All data were run in triplicate with the exception of MD09-167 with 2.5 mM DMAPP which was run in duplicate.

Cell free extract was run on a Caliper microfluidic electrophoresis instrument (Caliper Life Sciences, Hopkinton, Mass., USA) in order to quantify the amount of isoprene synthase in each sample. The microfluidic chip and protein samples were prepared according to the manufacturer's instructions (LabChip® HT Protein Express, P/N 760301). Culture lysates were prepared in 96-well mictrotiter plates by adding 50 mM Tris pH 8.0 containing 0.1% Tween 20, 0.1 mg/ml lysozyme, 1.0 ug/ml DNAse at room temperature for 30 minutes, followed by centrifugation. Supernatants were then transferred to another 96 well plate and stored at –20° C. until use, when they were thawed at room temperature for 30 minutes. After shaking briefly, the 2 μl of each culture sample was transferred to a 96-well PCR plate (Bio-Rad, Hercules, Calif., USA) containing 7 μl samples buffer (Caliper) followed by heating the plate to 90° C. for 5 minutes on a thermostatically controlled plate heater. The plate was allowed to cool before adding 35 μl water to each sample. The plate was then placed in the instrument along with a protein standard supplied and calibrated by the manufacturer. The instrument functions by mixing the sample with a fluorescent dye that attaches non-covalently to the proteins, followed by electrophoresis through a gel matrix. As the proteins move past a focal point in the chip, the fluorescence signal is recorded and the protein concentration is determined by quantitating the signal relative to the signal generated by a calibrated set of protein standards.

TABLE 11-7

$k_{cat}$ and $K_M$ and specific activity values for isoprene synthases

| Isoprene Synthase | $k_{cat}$ ± S.D. (s$^{-1}$) | $K_M$ ± S.D. (mM) | $K_i$ ± S.D. (mM) | S.A. (nmol/mg/min) |
|---|---|---|---|---|
| Full Length | 0.72 ± 0.09 | 2.4 ± 0.3 | 15.7 ± 0.2 | 420 ± 60 |
| Truncated | 1.5 ± 0.2 | 1.8 ± 0.2 | 9.8 ± 0.9 | 800 ± 100 |
| MD09-165 | 0.8 ± 0.1 | 2.4 ± 0.5 | 19 ± 4 | 440 ± 80 |
| MD09-167 | 1.1 ± 0.3 | 2 ± 1 | 8.7 ± 0.9 | 610 ± 60 |

Parameters were determined by fitting the following uncompetitive substrate inhibition equation to data obtained for rate/[E] vs. [DMAPP]:

$$\frac{rate}{[E]} = \frac{k_{cat}*[S]}{K_M + [S]*\left(\left(1+\frac{[S]}{K_i}\right)\right)}$$

The specific activities (S.A.) were calculated for reactions containing 5 mM DMAPP, 50 mM MgCl$_2$, 100 mM Tris, 100 mM NaCl, and 2.5-4.5 μg isoprene synthase from the supernatant of whole cell lysate. Reactions were performed at 30° C. for 15 minutes in triplicate using independently grown cultures.

Figure 40:
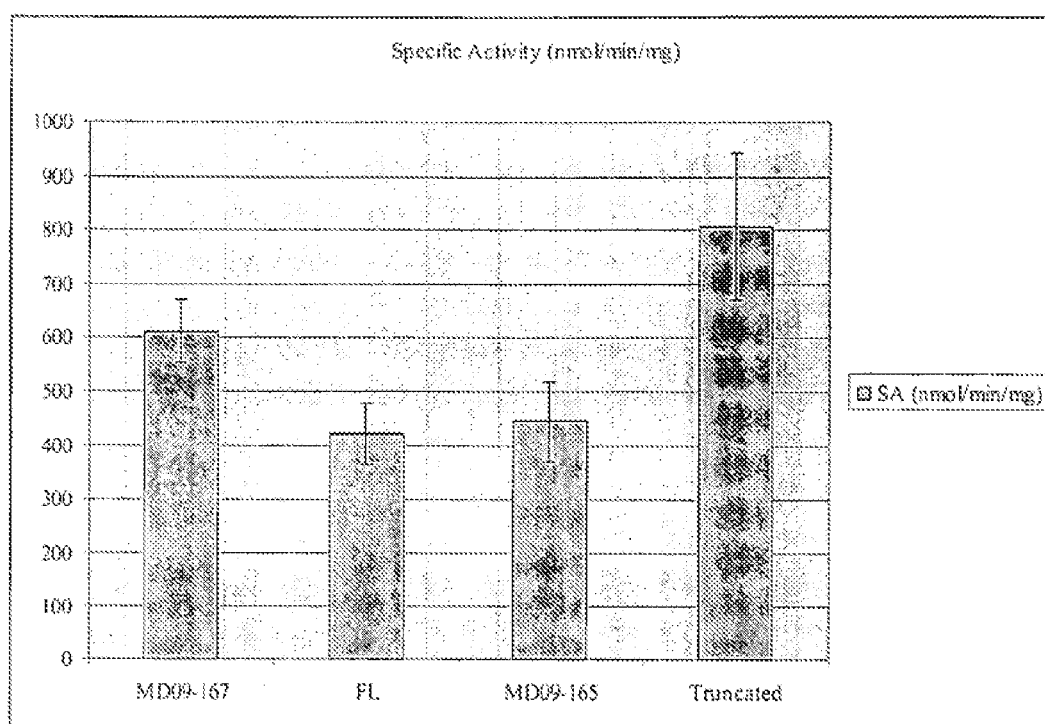
FIG. 40 shows a graph representing specific activities of MD09-167, Full length (FL), MD09-165, and Truncated isoprene synthase (MD09-173). Reactions were run at 30° C. for 15 minutes in a solution containing 100 mM Tris, 100 mM NaCl, 50 mM $MgCl_2$, 5 mM DMAPP, and 2.5-4.5 µg isoprene synthase in the supernatant of whole cell lysate.

Results/Discussion:

The specific activity of each protein was determined (FIG. 40 and Table 11-7). The specific activity of truncated isoprene synthase was approximately 2-fold greater than the specific activity of full length isoprene synthase. The C-terminally His-tagged full length isoprene synthase yielded approximately the same specific activity as the full length isoprene synthase. The C-terminally His-tagged truncated isoprene synthase gave a specific activity that was less than the non-tagged truncated isoprene synthase, but greater than the specific activity of both full length isoprene synthases.

Figure 41:
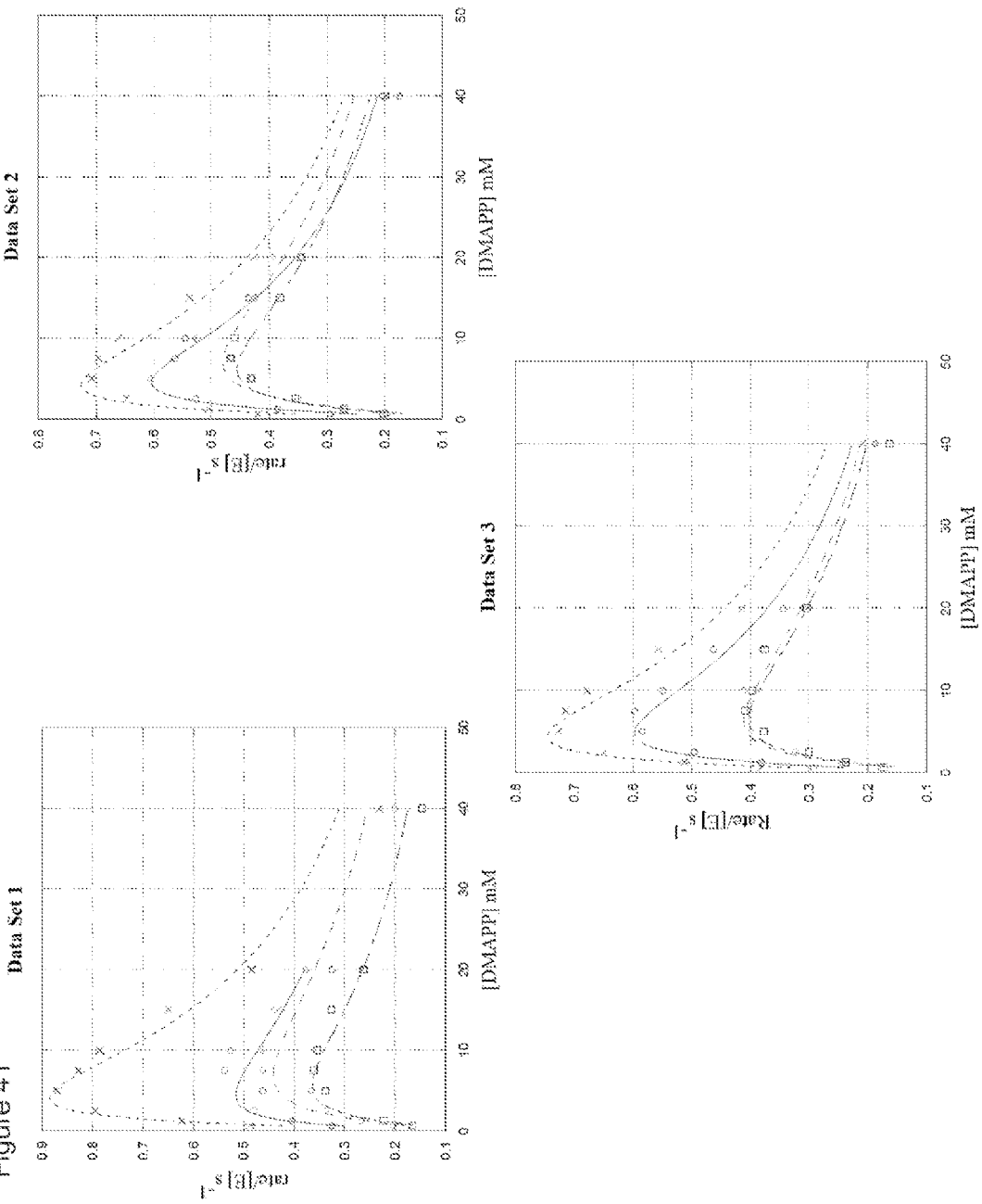
FIG. 41 shows graphs demonstrating Rate/[E] vs. [DMAPP]. X's represent MD09-173, circles represent MD09-167, diamonds represent MD09-165 and squares represent full length IspS.
Figure 42:
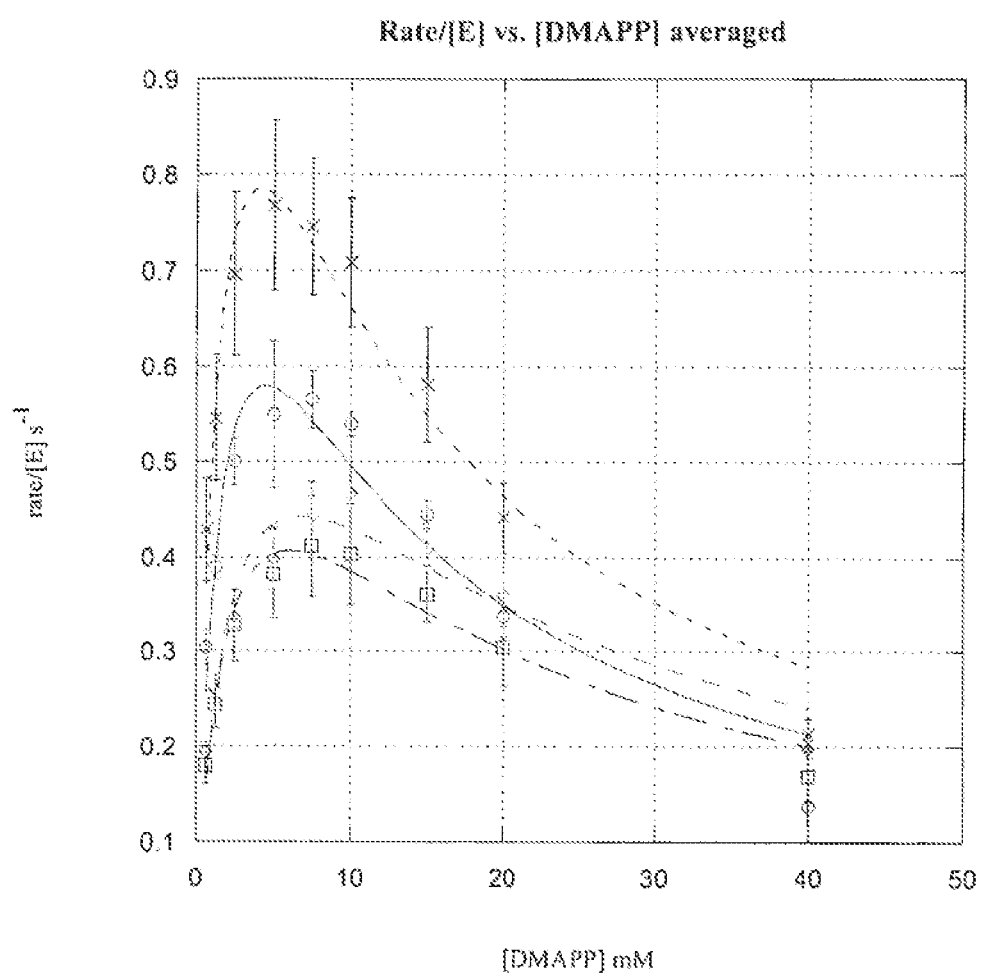
FIG. 42 shows a graph showing Isoprene synthase activity vs. [DMAPP]. X's represent data generated with MD09-173 truncated isoprene synthase. Circles represent data generated with MD09-167 isoprene synthase. Diamonds represent data generated with MD09-165 isoprene synthase. Squares represent data generated with full length isoprene synthase. Each data set was run in triplicate from independently grown cultures.
Figure 43:
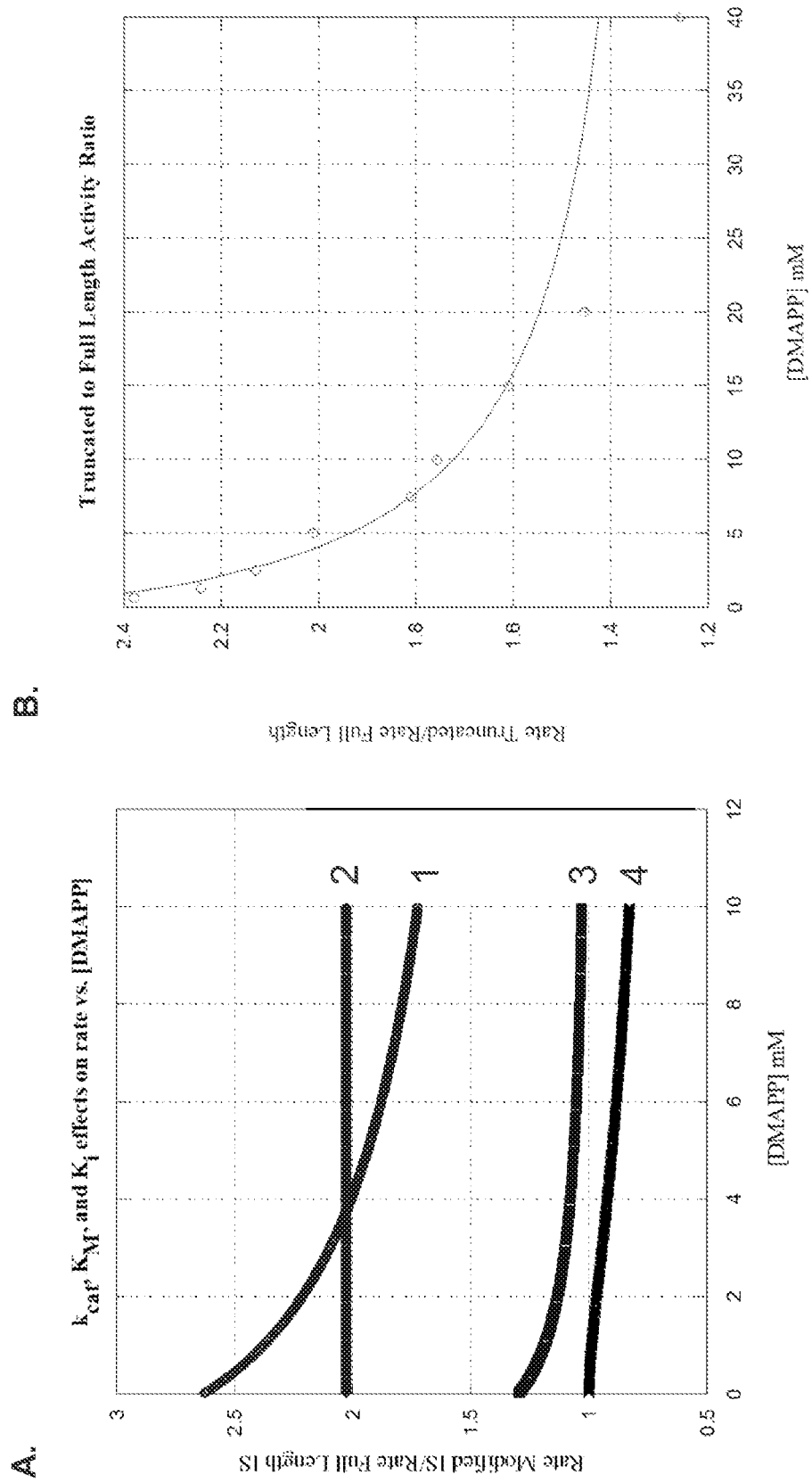
FIG. 43 shows graphs demonstrating the effects of varying $k_{cat}$ and $K_M$ and $K_i$ on reaction rate. In panel A, line 1 represents the rate equation of truncated isoprene synthase activity divided by the rate equation of full length isoprene synthase plotted at varying DMAPP concentrations. Line 2 represents the rate equation of full length isoprene synthase in which the $k_{cat}$ has been substituted by the $k_{cat}$ of the truncated isoprene synthase divided by the rate equation of the full length isoprene synthase. Line 3 represents the rate equation of full length isoprene synthase in which the $K_M$ has been substituted by the $K_M$ of the truncated isoprene synthase divided by the rate equation of the full length isoprene synthase. Line 4 represents the rate equation of full length isoprene synthase in which the $K_i$ has been substituted by the $K_i$ of the truncated isoprene synthase divided by the rate equation of the full length isoprene synthase. Panel B shows a graph demonstrating data fit to the ratio of the rate equation of truncated isoprene synthase to full length isoprene synthase vs. [DMAPP].

The rate of conversion of DMAPP to isoprene was analyzed over a range of DMAPP concentrations in order to determine the $k_{cat}$ and $K_M$ parameters of the enzymes (FIGS. 41 and 42 and Table 11-7). The enzymes all exhibited rate profiles consistent with uncompetitive substrate inhibition by DMAPP. The $K_i$ for the full length constructs was greater than the $K_i$ for truncated constructs as determined by altering $K_i$ and observing the best fit (R-value) to the data (data not shown). All data has been fit to a $K_i$ of 10 mM in the figures in this document. The $K_M$s of truncated isoprene synthase decreased relative to the full length isoprene synthases. Therefore, as the substrate concentration decreases the ratio between the isoprene synthase activity of the truncated isoprene synthase to the full length isoprene synthase will increase (FIG. 43). The $k_{cat}$s of truncated isoprene synthases increased relative to the full length isoprene synthases. This results in greater isoprene synthase activity for the truncated isoprene synthases than the full length isoprene synthases at all substrate concentrations (FIG. 43). The ratio of the isoprene synthase activity of the truncated isoprene synthase to the full length isoprene synthase at varying DMAPP levels was determined (FIG. 43).

Conclusions: "Truncated" isoprene synthases exhibit increased $k_{cat}$ values and decreased $K_M$ values with respect to the catalysis of the conversion of DMAPP to isoprene compared to "full length" isoprene synthases. The specific activity of "truncated" isoprene synthases is increased relative to the specific activity of "full length" isoprene synthases. The most active isoprene synthase was non-tagged truncated isoprene synthase "MEA" variant (in strain MD09-173). The truncated isoprene synthase may increase the isoprene synthase activity in organisms used for production of isoprene compared to the full length isoprene synthase.

EXAMPLE 12

Isoprene Synthase Enrichment-Relief of DMAPP Toxicity

This example identifies residue changes within IspS that confer better activity to the enzyme through kinetic improvement, increased expression, increased solubility, or any other means by which DMAPP is more effectively converted to isoprene by Isoprene Synthase. This procedure allows for the relief of cytotoxic intracellular levels of DMAPP by expression of improved IspS variants. In a population of cells expressing a heterogeneous mixture of IspS variants, the best enzymes should allow for better growth of their host strain, and should be enriched in the mixed population.

I. Strain Construction

Construction of Strains MCM518-521 and 528-531 in which Lambda promoters drive integrated mKKDyI was as follows. Primers MCM120 and MCM224 (Table 12-1) were used to amplify the resistance cassette from the GeneBridges FRT-gb2-Cm-FRT template using Stratagene Herculase II Fusion kit according to the manufacturer's protocol. Four 50

μL reactions were cycled as follows: 95° C., 2 min; (95° C., 20 sec, 55° C., 20 sec, 72° C., 1 min) for 30 cycles; 72° C., 3 min; and 4° C. until cool. The four reactions were pooled and purified on a Qiagen PCR column according to the manufacturer's protocol and eluted with 60 μL EB at 55° C.

Plasmid pRedET-carb (GeneBridges) was electroporated into MCM446. Transformants were recovered by shaking for one hour in SOC (Invitrogen) at 30° C. and then selected on LB containing carbenicillin (50 μg/ml) (carb50) plates at 30° C. overnight. A carbenicillin resistant colony was frozen as MCM508 (Table 12-2).

Strain MCM508 was grown from a fresh streak in 5 mL LB/carb50 at 30° C. to an $OD_{600}$ of ~0.5. 40 mM L-arabinose was added and culture was incubated at 37° C. for 1.5 hrs. Cells were harvested and electroporated with 3 μL of purified amplicons as previously, and then recovered in 500 μL SOC at 37° C. for 1.5-3 hrs. Transformants were selected on LB/kan10 plates at 37° C.

Recombination of the amplicon at the target locus was confirmed by PCR with primers GB-DW and MCM208. The resulting amplicons were sequenced to identify four clones with the sequences below. Carbenicillin-sensitive clones were frozen as strains MCM518-521.

MCM518-521 were restreaked on LB kan10 plates and grown overnight at 37° C.

Strains MCM518-521 were cultured in LB/kan10 at 37° C. and then electrotransformed with plasmid pCP20 (Datsenko K A, Wanner B L. One-step inactivation of chromosomal genes in *Escherichia coli* K-12 using PCR products. Proc Natl Acad Sci USA. 2000 Jun. 6; 97(12):6640-5). Cells were recovered in 500 μL SOC, shaking at 30° C. for 1 hour. Transformants were selected on LB/carb50 plates at 30° C. overnight. The following morning a colony from each transformation was grown at 30° C. in liquid LB/carb50 until visibly turbid. The culture was then shifted to 37° C. for at least 3 hrs. Cells were streaked from this culture onto LB plates and grown overnight at 37° C.

The following day colonies were patched to LB, LB/carb50 and LB/kan10. Clones that grew on neither carb50 nor kan10 and were cultured in liquid LB from the patch on LB and frozen as MCM528-531.

DNA Sequences

These assemblies include the new promoters inserted on the chromosome in strains MCM518-521, as well as the very beginning of the mMVK ORF. Upstream of these assemblies is sequence from the GeneBridges FRT-gb2-Cm-FRT cassette. Downstream is the remainder of the mMVK ORF and then the rest of the lower MVA pathway integron from strain MCM508.

MCM518

(SEQ ID NO: 56)

```
aaagaccgaccaagcgacgtctgagagctccctggcgaattcggtaccaataaaagagctttat tttcatgatctgtgtgttggttttgtgtgcggcgcggaagttcctattctctagaaagtatag gaacttcctcgagccctatagtgagtcgtattaaattcatataaaaaacatacagataaccatc tgcggtgataaattatctctggcggtgttgacataaataccactggcggtgatactgagcacat cagcaggacgcactgaccaccatgaaggtgcaaaggaggtaaaaaaacatggtatcctgttctg cgccgggtaagatttacctgttcggtgaacacgccgtagtttatggcgaaactgcaattgcgtg tgcggtggaactgcgtacccgtgttcgcgcggaactcaatgactctatcactattcagagc
```

MCM519

(SEQ ID NO: 57)

```
aaagaccgaccaagcgacgtctgagagctccctggcgaattcggtaccaataaaagagctttat tttcatgatctgtgtgttggttttgtgtgcggcgcggaagttcctattctctagaaagtatag gaacttcctcgagccctatagtgagtcgtattaaattcatataaaaaacatacagataaccatc tgcggtgataaattatctctggcggtgttgacctaaataccactggcggtgatactgagcacat cagcaggacgcactgaccaccatgaaggtgcaaaggaggtaaaaaaacatggtatcctgttctg cgccgggtaagatttacctgttcggtgaacacgccgtagtttatggcgaaactgcaattgcgtg tgcggtggaactgcgtacccgtgttcgcgcggaactcaatgactctatcactattcagagc
```

MCM520

(SEQ ID NO: 58)

```
aaagaccgaccaagcgacgtctgagagctccctggcgaattcggtaccaataaaagagctttat tttcatgatctgtgtgttggttttgtgtgcggcgcggaagttcctattctctagaaagtatag gaacttcctcgagccctatagtgagtcgtattaaattcatataaaaaacatacagataaccatc tgcggtgataaattatctctggcggtgttgacctaaataccactggcggtgatactgagcacat cagcaggacgcactgaccaccatgaaggtgcaaaggtaaaaaaacatggtatcctgttctgcgc cgggtaagatttacctgttcggtgaacacgccgtagtttatggcgaaactgcaattgcgtgtgc ggtggaactgcgtacccgtgttcgcgcggaactcaatgactctatcactattcagagc
```

-continued

MCM521 (in strains MCM531 and MD09-171)
(SEQ ID NO: 59)
aaagaccgaccaagcgacgtctgagagctccctggcgaattcggtaccaataaaagagctttat tttcatgatctgtgtgttggttttttgtgtgcggcgcggaagttcctattctctagaaagtatag gaacttcctcgagccctatagtgagtcgtattaaattcatataaaaaacatacagataaccatc tgcggtgataaattatctctggcggtgttgacgtaaataccactggcggtgatactgagcacat cagcaggacgcactgaccaccatgaaggtgcaaggaggtaaaaaaacatggtatcctgttctg cgccgggtaagatttacctgttcggtgaacacgccgtagtttatggcgaaactgcaattgcgtg tgcggtggaactgcgtacccgtgttcgcgcggaactcaatgactctatcactattcagagc The neo-PL.2-mKKDyI (from MCM521) was transduced into BL21(λDE3) to generate strain MD09-171. A P1 lysate of MCM521 was made and transduced into BL21(λDE3) according to standard molecular biology techniques (Miller, A Short Course in Bacterial Genetics). Transductants were selected on Kan20 LB medium plates. Positive colonies were further verified by PCR to confirm the presence of PL.2-mKKDyI in the BL21(λDE3) strain. 1 µl of pCP20 plasmid was then transformed into this strain and selected for on LB+Carb50 and incubated at 30° C. Positive transformants were subsequently streaked on an LB plate and incubated at 37° C. for loss of the pCP20 plasmid. To confirm the loss of the neomycin (kanamycin) resistance marker, colonies that grew at 37° C. were patched onto LB Kan20, LB Carb50, and plain LB plates. The strains with integrated PL.2 mKKDyI without the kanamycin resistance marker that have lost pCP20 should be sensitive to kanamycin and carbenicillin. 4 KanS CarbS were used to check by PCR for the presence of mKKDyI in BL21(λDE3) with the parental BL21(λDE3) strain as a control. Once PCR confirmed the presence of mKKDyI, the resulting strain was transformed with 1 µl of the pLysS plasmid (Invitrogen). The resulting strain, MD09-171, was used for the enrichment experiments described below.

TABLE 12-1

Primers used for strain construction

| MCM120 | aaagtagccgaagatgacggtttgtcacatggagttggcag gatgtttgattaaaagcaattaaccctcactaaagggcgg (SEQ ID NO: 60) |
|---|---|
| MCM208 | gctctgaatagtgatagagtca (SEQ ID NO: 61) |
| MCM224 | taaatcttaccccggcgcagaacaggataccatgttttttta cctcctttgcaccttcatggtggtcagtgcgtcctgctgat gtgctcagtatcaccgccagtggtatttangtcaacaccgc cagagataatttatcaccgcagatggttatctgtatgtttt ttatatgaatttaatacgactcactatagggctcg (SEQ ID NO: 62) |
| GB-DW | aaagaccgaccaagcgacgtctga (SEQ ID NO: 63) |
| MCM161 | caccatggtatcctgttctgcg (SEQ ID NO: 64) |
| MCM162 | ttaatctactttcagaccttgc (SEQ ID NO: 65) |
| MCM143 | aggaggtggtctcaaatgactgccgacaacaatagta (SEQ ID NO: 66) |
| MCM144 | aggaggtggtctcagcgctctgcagttatagcattctatga atttgcctg (SEQ ID NO: 67) |

TABLE 12-2

Strains

| Strain | Description | Parent |
|---|---|---|
| MCM508 | BL21 gi1.6-mKKDyI + predet.-carb | MCM446 |
| MCM518 | BL21 neo-PL.6-mKKDyI, clone10 | MCM508 |
| MCM519 | BL21 neo-PL.0-mKKDyI, clone11 | MCM508 |
| MCM520 | BL21 neo-PL.0-mKKDyI (bad RBS in front of mMVK), clone13 | MCM508 |
| MCM521 | BL21 neo-PL.2-mKKDyI, clone15 | MCM508 |
| MCM528 | BL21 PL.6-mKKDyI, loopedout | MCM518 |
| MCM529 | BL21 PL.0-mKKDyI, loopedout | MCM519 |
| MCM530 | BL21 PL.0-mKKDyI (bad RBS in front of mMVK), loopedout | MCM520 |
| MCM531 | BL21 PL.2-mKKDyI, loopedout | MCM521 |
| MD09-171 | BL21 (λDE3) PL.2-mKKDyI, loopedout + pLysS | MCM521 |

II. Growth Inhibition of MCM531 by Mevalonic Acid

Figure 44:
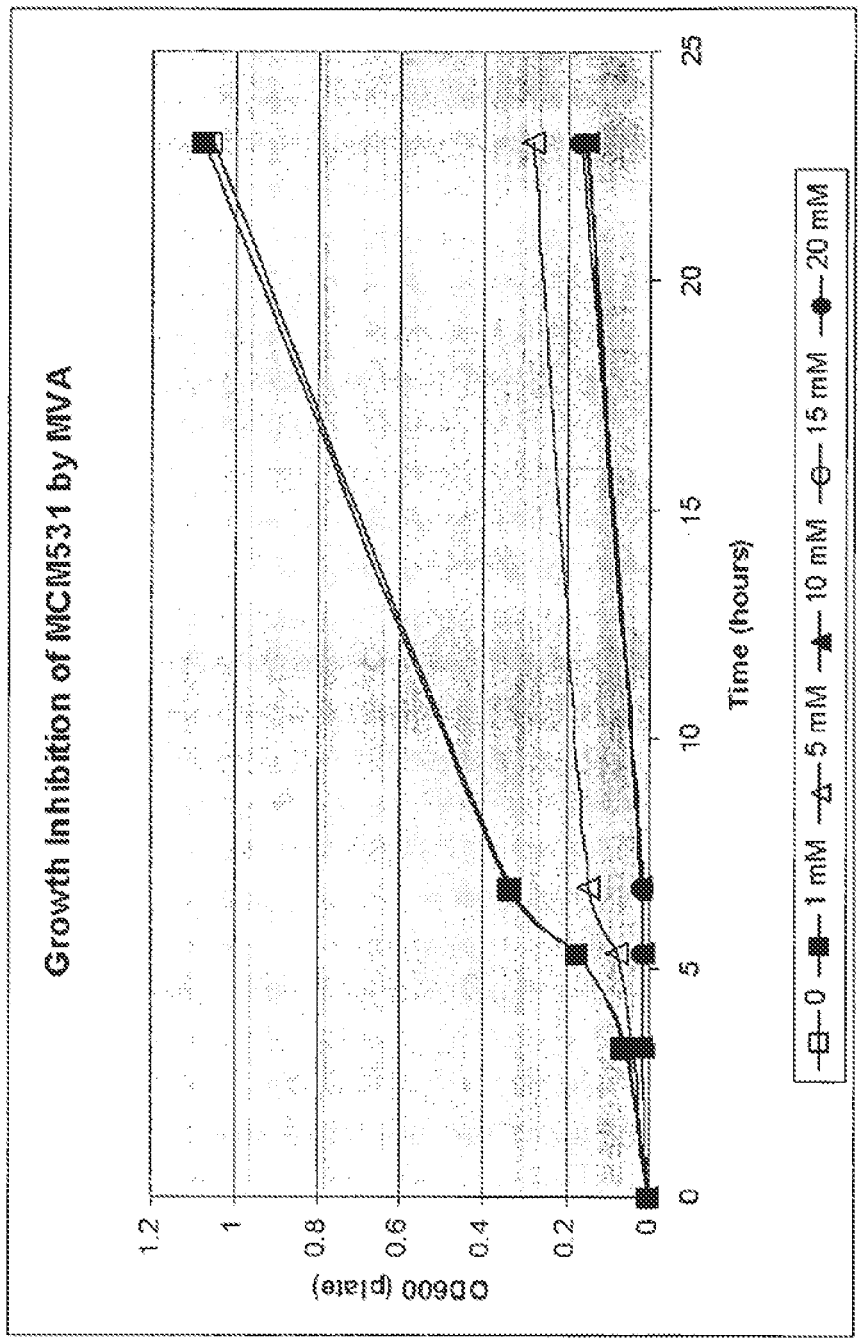
FIG. 44 shows a graph demonstrating growth inhibition of MCM531 by Mevalonic Acid (MVA). Cells were grown in TM3 medium in a microtiter plate with different concentrations of MVA. $OD_{600}$ of quadruplicate wells was measured at the indicated times.

An overnight culture of MCM531 (see strain description) was back-diluted to an $OD_{600}$ of 0.05 (this corresponds to an $OD_{600}$ of approx 0.005 in a 96-well plate reader) (SpectraMax M2, Molecular Devices). The diluted culture was then aliquotted into separate wells in a 96-well deep-well plate into standard TM3 medium (13.6 g $K_2PO_4$, 13.6 g $KH_2PO_4$, 2.0 g $MgSO_4*7H_2O$) supplemented with 1% glucose and 0.8 g/L Biospringer yeast extract (1% Yeast extract final)) with 0, 1, 5, 10, 15 or 20 mM MVA added. FIG. 44 shows the growth curve of MCM531 in the various concentrations of MVA. Each MVA concentration was assayed in quadruplicate, error bars were negligible. FIG. 44 shows that MCM531 was severely inhibited for growth at concentrations of 5 mM MVA and higher.

III. Mutagenesis of IspS and Selection/Enrichment Assay

To generate a randomly mutagenized IspS open reading frame, the GeneMorph II EZ Clone domain mutagenesis kit (Stratagene) was used according to the manufacturer's recommended protocol. Specific primers to amplify the template (Pdu39 (pET24a-P. alba (MEA))) are described below (Table 12-3, pET24 Megaprime Forward and Reverse). To achieve the desired mutation frequency, the protocol outlined in the GeneMorph II kit was followed. To generate 2 to 3 residue changes per molecule, approximately 150 ng of starting template DNA was used for the initial PCR reaction. More or less template was used to generate IspS enzymes with either fewer or more residue changes, respectively. The resulting mutant "megaprimers" were then used to amplify the rest of the plasmid according to the manufacturer's recommended protocol.

The final PCR product from the GeneMorph II kit was treated with DpnI according to the manufacturer's recommended protocol. Prior to transformation into E. coli, it was necessary to desalt the PCR reaction by microdialysis. Typically, approximately 20 µl of the PCR reaction was subjected to microdialysis and used for electroporation into strain MD09-171 (Table 12-2) by standard molecular biology procedures. After electroporation, cells were recovered for 2 hours at 30° C., and then plated onto LB medium Kan50 Cm35. The entire transformation volume was plated to recover all mutations generated by the mutagenesis procedure.

For enrichment, all transformants were scraped and pooled together. An aliquot from each pool was frozen for storage in the −80. Prior to the enrichment, strains (control or experimental pools) were inoculated directly into LB with Kan50 and grown for a few hours, to minimize the loss of pool heterogeneity. After this recovery period, cells were diluted into liquid TM3 medium (described above) with Kan50, 5 mM MVA, and 200 µM IPTG. (The exact dilution was determined empirically for each pool/source of medium/control reaction). Cultures were then placed in the shaking incubator at 34° C. until an $OD_{600}$ of no more than 5. At this point, plasmids were purified from 1 ml of the "enriched" culture via miniprep protocol (Qiagen). This plasmid preparation was then transformed into electrocompetent MD09-171 cells as described above. The transformed cells were recovered for 2 hours in LB medium without antibiotics, and then subjected to a subsequent round of enrichment by dilution into TM3 with Kan50, 5 mM MVA and 200 µM IPTG as described above. This culture was placed into the shaking incubator at 34° C. until it reached an $OD_{600}$ of no more than 5, as described above. Plasmids were then purified, retransformed and subjected to further rounds of "enrichment." The enrichment process continued for 5 or 6 rounds of selection, plasmid purification, and retransformation. The process continued until the culture was homogeneous, i.e. contained only one variant of IspS by sequencing analysis.

After the last round of enrichment, the plasmid pool was transformed into chemically competent *E. coli* Top10 cells (Invitrogen) per the manufacturer's recommended protocol, recovered, plated onto LB medium with Kan50, and sent for complete sequencing (Quintara Biosciences) for comparison to the wild type sequence of *P. alba* IspS. Primers used for sequencing are described below.

TABLE 12-3

| Primers used for IspS mutagenesis and sequencing | |
|---|---|
| pET24 Megaprime Forward | gtttaactttaagaaggagatatacat |
| pET24 Megaprime Reverse | gagctcgaattcggatcctta |
| alba sequencing reverse | ctcgtacaggctcaggatag |
| alba sequencing reverse2 | ttacgtcccaacgctcaact |
| EWL1000 | gcactgtctttccgtctgctgc |
| QB1493 | cttcggcaacgcatggaaat |

IV. Individual Residue Changes Identified by Enrichment/DMAPP Toxicity Relief:

Plasmids isolated from selection/enrichment were fully sequenced. The following residue changes were confirmed by sequencing (Quintara Biosciences). The residue numbering corresponds to the *P. alba* "Full Length" sequence (in *P. alba* pET24a; SEQ ID NO:120), where the starting methionine is amino acid number 1. Identified residue changes included: V10M, F12S, T15A, E18G, V58I, V58F, L70Q, L70V, L70T, T71P, V79L, E89D, G94A, S119F, F120L, G127R, E175V, T2121, S257A, R262G, A266G, F280L, N297K, F305L, L319M, E323K, A328T, D342E, A359T, K366N, E368D, L374M, S396T, V418S, K438N, H440R, T442I, T442A, I449V, A469S, K500R, K505Q, G507S, S509N, F511Y, and N532K.

Combinations of Residue Changes (in a single IspS enzyme) Identified by Enrichment/DMAPP Toxicity Relief: G127R/F511Y, L70Q/G94A/R262G/F305L, F12S/T15A/E18G/N297K, S396T/T442I, V10M/E323K, F120L/A266G, K438N/K500R, V79L/S509N, E175V/S257A/E368D/A469S, T71P/L374M, F280L/H440R, E89D/H440R, V58F/A328T/N532K, S119F/D342E/I449V, and K366N/G507S.

EXAMPLE 13

Construction of Site Saturation Libraries (SSLs) and Biochemical Analysis of the L70R Variant This example includes an examination of possible amino acid substitutions at sites identified by the selection/enrichment procedure described above and other sites of potential interest (active site, conserved between Poplar species) for their effect on solubility, expression, and activity of IspS.
I. Strain Construction Residues identified by the selection/enrichment procedure (L70, G94, R262, F305) described above were chosen for analysis. In addition, residues that are putatively involved in substrate binding (F303, V3065, F385, S412, Q416, F450), and residues that are different between the various Poplar species (e.g. V418, T442) were chosen for further analysis (numbering corresponds to the "full length" amino acid sequence of *P. alba* IspS). To generate a randomized pool of amino acid substitutions (the Site Saturation Library, SSL), pDu39 (see description above) was subjected to Quick-Change (Stratagene) mutagenesis with the QC primers indicated below (Table 13-1), according to the manufacturer's recommended protocol. The PCR Reaction was prepared as follows:

1 µl pDu39, 5 µl 10× PfuUltra HF buffer, 1 µl dNTP's, 1 µl (50 µM) primer-For (e.g. QC L69 F), 1 µl (50 uM) primer-Rev (e.g. QC L69 R), 2 µl DMSO, 39 µl diH2O, and 1 µl PfuUltra HF Polymerase (Stratagene). The PCR cycling parameters for QuickChange were as follows: 95° C. 1 min, 95° C. 30 sec., 55° C. 1 min., 68° C. 7.3 min. for one cycle followed by 95° C. 30 sec., 55° C. 1 min., 68° C. 7.3 min for 17 more cycles. The temperature was then reduced to 4° C. Incorporation of the bases NNK at the codon for the residues described above allows for the insertion of codons that represent all 20 possible amino acids at the given site. 1 µl of the resulting pools of mutagenized PCR products was DpnI treated (described above), and transformed into chemically competent *E. coli* Top10 cells (Invitrogen) according to the manufacturer's recommended protocol. Entire transformation reactions were recovered in 1 ml LB medium without antibiotics at 37° C. for 1 hour and plated onto LB Kan50. The next day, all transformants were scraped off of the LB plates, mixed thoroughly, and plasmids were purified via miniprep (Qiagen). Pools of plasmids were then transformed into chemically competent BL21(λDE3)pLysS cells (Invitrogen) according to the manufacturer's protocol. The transformation reactions were recovered in 1 ml LB medium at 37° C. for 1 hour and then plated onto LB Kan50 Cm35 at dilutions sufficient to generate separation of positive colonies. After overnight incubation at 37° C., individual colonies were inoculated into individual wells in a 96-well deep-well microtiter plate (VWR) containing 500 ul of liquid LB Kan50 Cm35 each. In eight wells (typically column 12, A through H) strain MD09-173 (see above) or BL21(λDE3)pLysS with *P. alba* pET24a (Full Length) was inoculated as a control for the DMAPP assay. The microtiter plates were then sealed with a semi-permeable membrane (Breathe-Easier, Diversified Biotech), and incubated overnight at 30° C. in a shaking incubator (Vertiga). The next day, 100 μl samples from each well within a 96-well plate were mixed with 50 μl of 50% glycerol in a new 200 ul 96-well plate, and frozen at −80° C. until further analysis. This plate was then used for the DMAPP assay described below.

tivity, when subjected to DMAPP analysis, were isolated from their original SSL plates stored at −80° C. (described above), and re-arrayed onto a new "winner" plate for secondary screening. Two wells containing MD09-173 were included as controls. All variants were sequenced (Quintara Biosciences) and subjected to the DMAPP assay as described above. See Table 13-2 for sequencing results. For the DMAPP assay, a single growth of each variant was assayed, and therefore a single lysate generated, but in quadruplicate to generate statistically significant data. Samples were assayed at the $OD_{600}$ indicated in Table 13-2. Protein analysis was per-

TABLE 13-1

Primers used for mutagenesis

| | | |
|---|---|---|
| QC L70 F | gaaaaagcagaatttnnkaccctgctggaactg | (SEQ ID NO: 68) |
| QC L70 R | cagttccagcagggtmnnaaattctgcttttc | (SEQ ID NO: 69) |
| QC G94 F | gagtctgatatccgtnnkgcgctggatcgcttc | (SEQ ID NO: 70) |
| QC G94 R | gaagcgatccagcgcmnnacggatatcagactc | (SEQ ID NO: 71) |
| QC R262 F | tcccgttggtggcgtnnkgtgggtctggcgacc | (SEQ ID NO: 72) |
| QC R262 R | ggtcgccagacccacmnnacgccaccaacggga | (SEQ ID NO: 73) |
| QC F303 F | tccgtcgcaaaaatgnnktctttcgtaaccatt | (SEQ ID NO: 74) |
| QC F303 R | aatggttacgaaagamnncattttgcgacgga | (SEQ ID NO: 75) |
| QC F305 F | gcaaaaatgttttctnnkgtaaccattatcgac | (SEQ ID NO: 76) |
| QC F305 R | gtcgataatggttacmnnagaaaacattttgc | (SEQ ID NO: 77) |
| QC V306 F | aaaatgttttctttcnnkaccattatcgacgat | (SEQ ID NO: 78) |
| QC V306 R | atcgtcgataatggtmnngaaagaaaacatttt | (SEQ ID NO: 79) |
| QC F385 F | gacctgtgcaacgctnnkctgcaagaagccaag | (SEQ ID NO: 80) |
| QC F385 R | cttggcttcttgcagmnnagcgttgcacaggtc | (SEQ ID NO: 81) |
| QC S412 F | gcatggaaatcctctnnkggcccgctgcaactg | (SEQ ID NO: 82) |
| QC S412 R | cagttgcagcgggccmnnagaggatttccatgc | (SEQ ID NO: 83) |
| QC Q416 F | tcttctggcccgctgnnkctggtgttcgcttac | (SEQ ID NO: 84) |
| QC Q416 R | gtaagcgaacaccagmnncagcgggccagaaga | (SEQ ID NO: 85) |
| QC V418 F | ggcccgctgcaactgnnkttcgcttacttcgct | (SEQ ID NO: 86) |
| QC V418 R | agcgaagtaagcgaamnncagttgcagcgggcc | (SEQ ID NO: 87) |
| QC T442 F | caaaaataccatgacnnkatctctcgtccttcc | (SEQ ID NO: 88) |
| QC T442 R | ggaaggacgagagatmnngtcatggtatttttg | (SEQ ID NO: 89) |
| QC F450 F | cgtccttcccatatcnnkcgtctgtgcaatgac | (SEQ ID NO: 90) |
| QC F450 R | gtcattgcacagacgmnngatatgggaaggacg | (SEQ ID NO: 91) |

Figure 45:
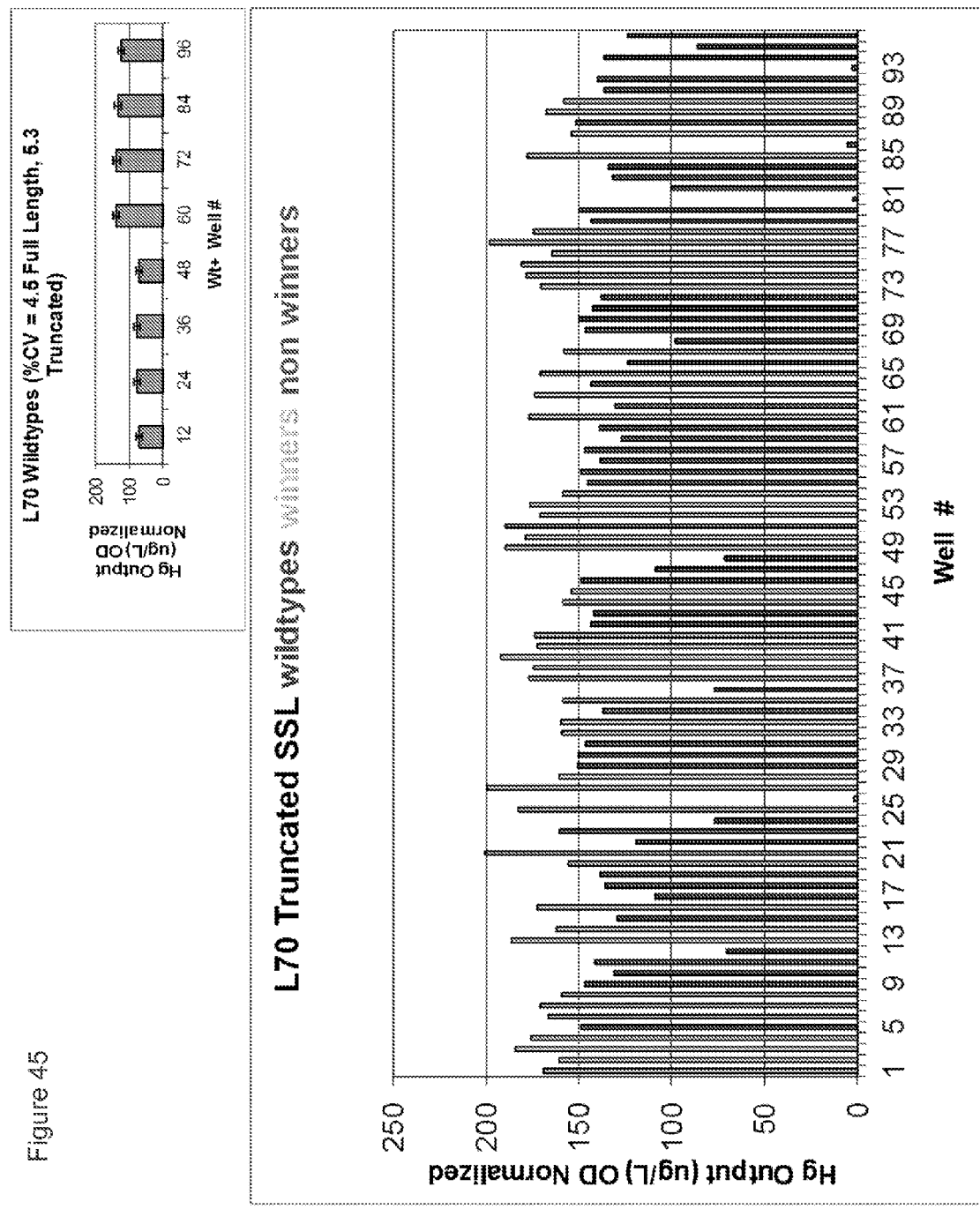
FIG. 45 shows graphs demonstrating DMAPP assays of L70 SSL plate. Dark bars represent either the full length (*P. alba* pET24a) or pDU39 (truncated) controls. The variants in wells C3 (27), D3 (39), or E3 (51) were chosen for further analysis.

II. Generation of a "Winner" Plate for Secondary Assay and Identification of L70R as a Variant with Increased Specific Activity Variants that displayed increased specific isoprene production when compared to wild type were chosen for further analysis. FIG. 45 shows a typical data set of an SSL plate for an individual residue, in this case L70. From this particular plate, the samples in wells C3 (27), D3 (39), and E3 (51) were chosen for further analysis. Other variants at different residues (listed above) that showed increased isoprene producformed on all lysates using the Western Breeze Western blot kit (Invitrogen) followed by fluorescence detection on a Storm860 (see below)

III. DMAPP Assay—Growth, Lysis and Isoprene Measurement

A patch plate was prepared from a glycerol stock plate using a VP-Scientific Replication Tool patch LB Agar CM35/Kan50 large patch plate from overnight glycerol stock Plate. Cultures were incubated at 30° C. overnight (20 to 24 hr). Plates were stored at 4° C. for up to a week.

An overnight growth plate was prepared from 500 mL of LB CM35/Kan50 media. 300 μL/well of LB CM35/Kan50 media were dispensed into deep 96 well plate. Using the V&S Replication Tool, the patch inoculum was transferred to a deep 96 well plate. Media was inoculated by dipping the tool then shaking the pin within the well. The overnight growth plate was sealed with a Breathe-Easier Sealing Membrane. The plate was incubated at 30° C. overnight in a Vertiga Shaking Incubator at 800 rpm for 16 to 18 hours.

A deep 96 well day growth plate was prepared by dispensing 588 μL/well of LB CM35/Kan50 media. The overnight growth plate was removed from the incubator and cultures were diluted 50-fold. 12 μL of overnight culture was transferred to a day growth plate containing 588 μL/well of supplemented LB media. The overnight growth plate was sealed with a new Breathe-Easier Sealing Membrane and was incubated at 34° C. and 800 rpm for 2.25 hr in the Vertiga Shaking Incubator.

To induce the expression of IspS, thawed 12 mM IPTG was poured into 50 mL or 100 mL sterile reservoir and dispensed 20 μL/well into each 600 μL/well culture. Overnight growth plate was resealed with Breathe-Easier Sealing Membrane and incubated at 34° C. and 800 rpm for 4 hours in the Vertiga Shaking Incubator.

To harvest cell, 200 μL of induced culture was transferred to 450 μL Nunc storage plate. The plate was centrifuged at 3300 rpm for 20 min at 4° C. in a low speed benchtop centrifuge. 180 μL supernatant was removed with a pipettor and discarded. The plate was sealed with an aluminum foil membrane, covered with a plastic plate lid and stored frozen at −80° C.

The $OD_{600}$ of the plates were read. 150 μL 1×PBS was dispensed into a 96 well Costar Read Plate (#9017). 50 μL of culture sample was then transferred to the read plate. The $OD_{600}$ reading was then taked with a Spectramax Plate Reader.

Lysis: The harvest plate was defrosted in a room temperature water bath for 4 min and then incubated in Thermomixer at 25° C. at 1200 rpm for 1 min. Lysis buffer was dispensed at 80 μL/well to 20 μL/well of harvest cells. 1.25× Lysis Working Stock buffer was prepared from 6.25 ml 1M Tris pH 8, 625 μl 10% Tween 20, 312.5 μl 0.2 M PMSF, 462.5 μl 10 mg/ml DNAse I (Sigma), 1.25 ml 1 M $MgCl_2$, 132.5 μl 25000 U/μl Lysozyme (Epicentre Technologies) and 40.968 ml $dIH_2O$. Plates were incubated on a Thermomixer at 25° C. and 1200 rpm for 30 min. 1× Lysis Buffer stock was prepared by diluting 19 ml of 1.25× Lysis Working stock with 4.75 ml $dIH_2O$.

DMAPP Working Stock was prepared as follows.

transferring the Glass Block to a 70° C. water bath and incubating for 6 min. GC Analysis was performed as previously described.

IV. Western Blot of Isoprene Synthase with Fluorescence Labeled Secondary Antibody.

Samples were prepared and run on NativePAGE™ Novex® Bis-Tris Gels (Invitrogen) according to the manufacturer's protocol. After completion of the run the gels were immediately transferred to Nitrocellulose membranes using the XCell II™ Blot Module (Invitrogen) according to the manufacturer's recommended protocol. After transfer, the membrane was placed in 15 ml of the appropriate Blocking Solution (Ultra filtered Water 31.5 ml, Blocker/Diluent (Part A) 9 ml, Blocker/Diluent (Part B) 4.5 ml) in the covered, plastic dish provided in the kit and incubated for 30 minutes on a rotary shaker set at 1 revolution/sec. The Blocking Solution was decanted and the membrane rinsed 2 times with 20 ml of water for 5 minutes. The membrane was incubated with 15 ml of Primary Antibody (Ab) Solution (24 μl of primary Ab in 15 ml Blocking solution) for 1 hour, followed by washing 3 times 5 minutes with 20 ml of 1× Antibody Wash Solution. The membrane was then incubated in 15 ml of SecondaryAntibody Solution (15 ul secondary Ab (Alexa Fluor 488 goat anti-rabbit IgG (H+L, Invitrogen)) in 15 of blocking solution) for 30 minutes. The membrane was washed 3 times at 5 minutes with 20 ml of Antibody Wash, and rinsed two times 2 minutes with 20 ml of water. The membrane was dried between paper towels and stored at room temperature for further detection. The fluorescent bands were detected and quantified using the Storm 860 Molecular Imager (GMI, Inc).

Figure 46:
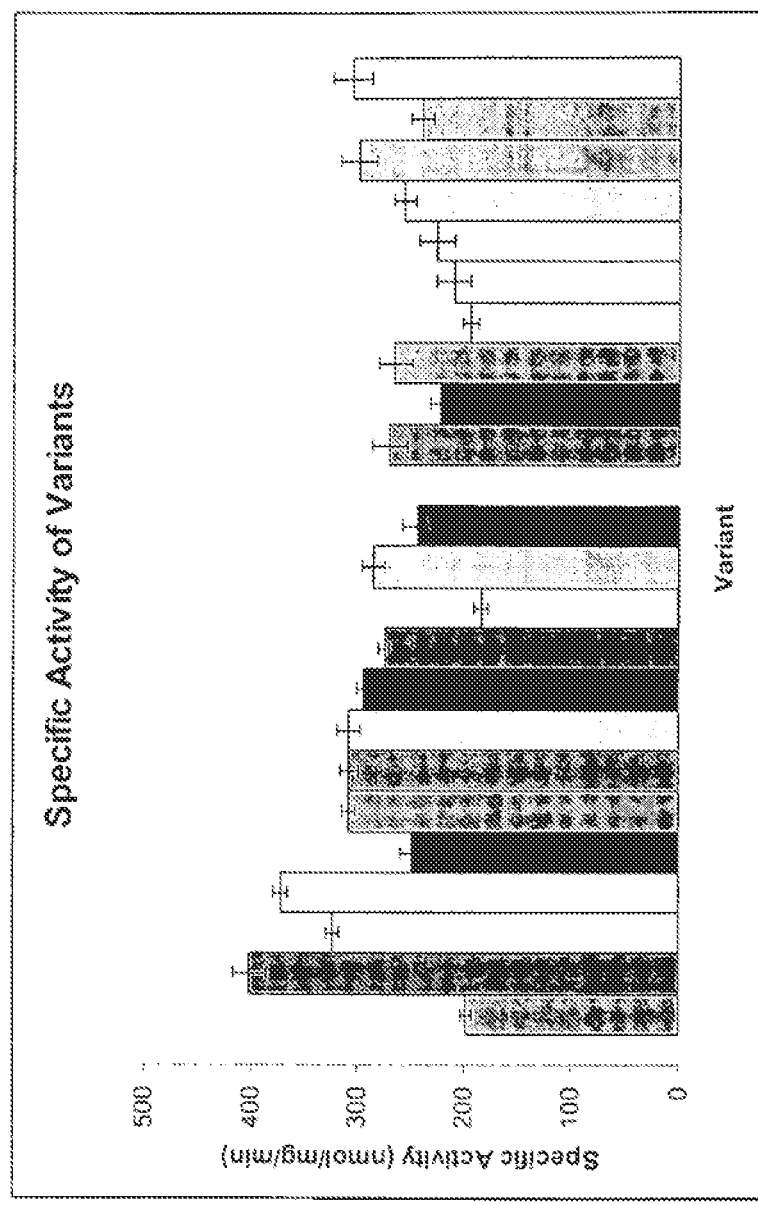
FIG. 46 shows a graph demonstrating the average specific activity of all variants selected for DMAPP assay with protein determination. Error bars show one standard deviation. All 3 L70R variants display higher activity than the control (WT).

V. Results:

Table 13-2 shows all of the relevant data for each variant assayed: sequencing results, residue change, average isoprene production, protein concentration, and average specific activity (of all 4 replicates). FIG. 46 shows the graphical representation of the data shown in Table 13-2. Specific activity was calculated by multiplying the isoprene produced (μg/l) by 0.0414 and then dividing by protein concentration (mg/ml). This conversion factor (0.0414) accounts for the total headspace volume in a sealed 2 ml GC vial (1.9 ml), the lysate volume (15 ul), the duration of the DMAPP assay (45 min), and the molecular weight of isoprene. Thus, specific activity values are given in nmol isoprene/mg Isps/min.

The data in Table 13-2 and the graph in FIG. 46 show that of all variants analyzed, all three L70R variants displayed higher specific activity than wild type. To analyze the L70R variants further, the specific activity values for all 3 isolates (4 replicates of each) were averaged and compared to the controls (2 isolates, 4 replicates each). Therefore, there were 12

| Dimethylallyl Pyrophosphate (triammonium salt) 25 mg (Cayman Chemicals, Cat No. 63180) | | | | | | | | |
|---|---|---|---|---|---|---|---|---|
| final | total vol | diluent | stock vol | stock | dilution | Reagent | Units | Plate(s) |
| 30 | 840 | 840 | solid | 25000 | 1 | DMAPP | mg/mL | 1 |
| 3 | 2500 | 2250 | 250 | 30 | 10 | DMAPP | mg/mL | 1 |

The Diluent was 0.1 M Potassium Phosphate. 200 uL/well was dispensed for transfer to sample wells and was stored on ice.

Figure 47:
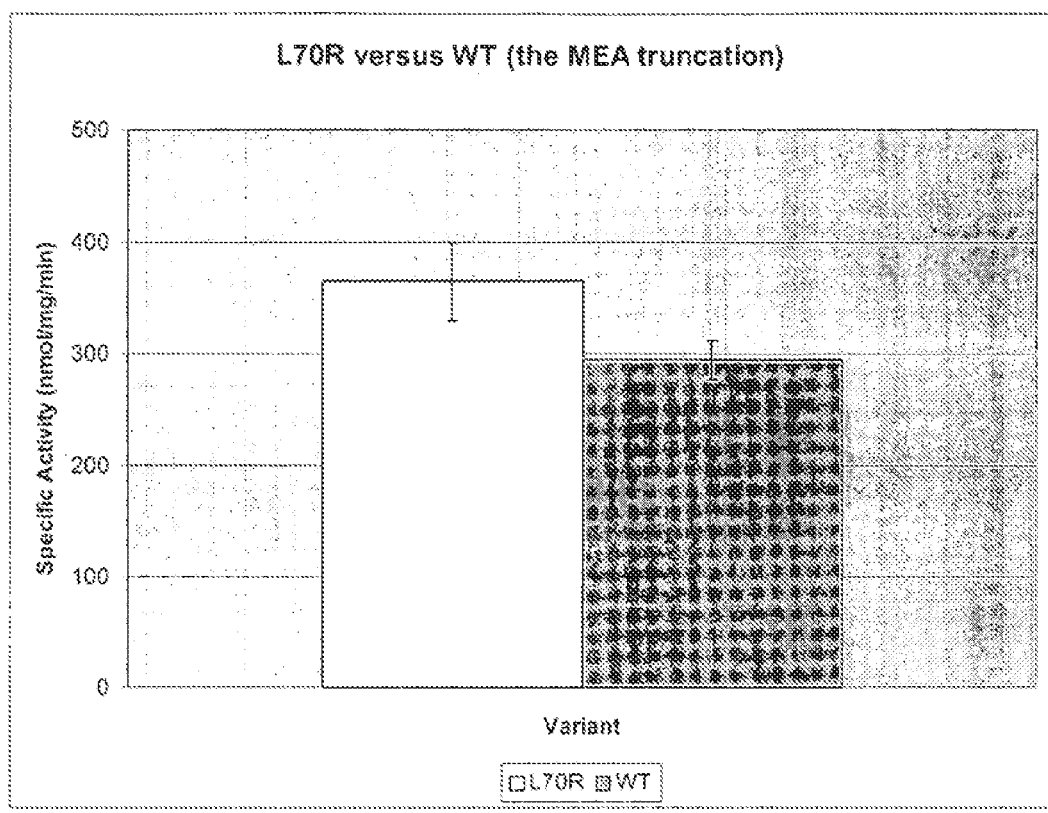
FIG. 47 shows a graph demonstrating the average specific activity of all 3 L70R variants compared to the "MEA" truncated *P. alba* IspS enzyme. Error bars show one standard deviation.
Figure 48:
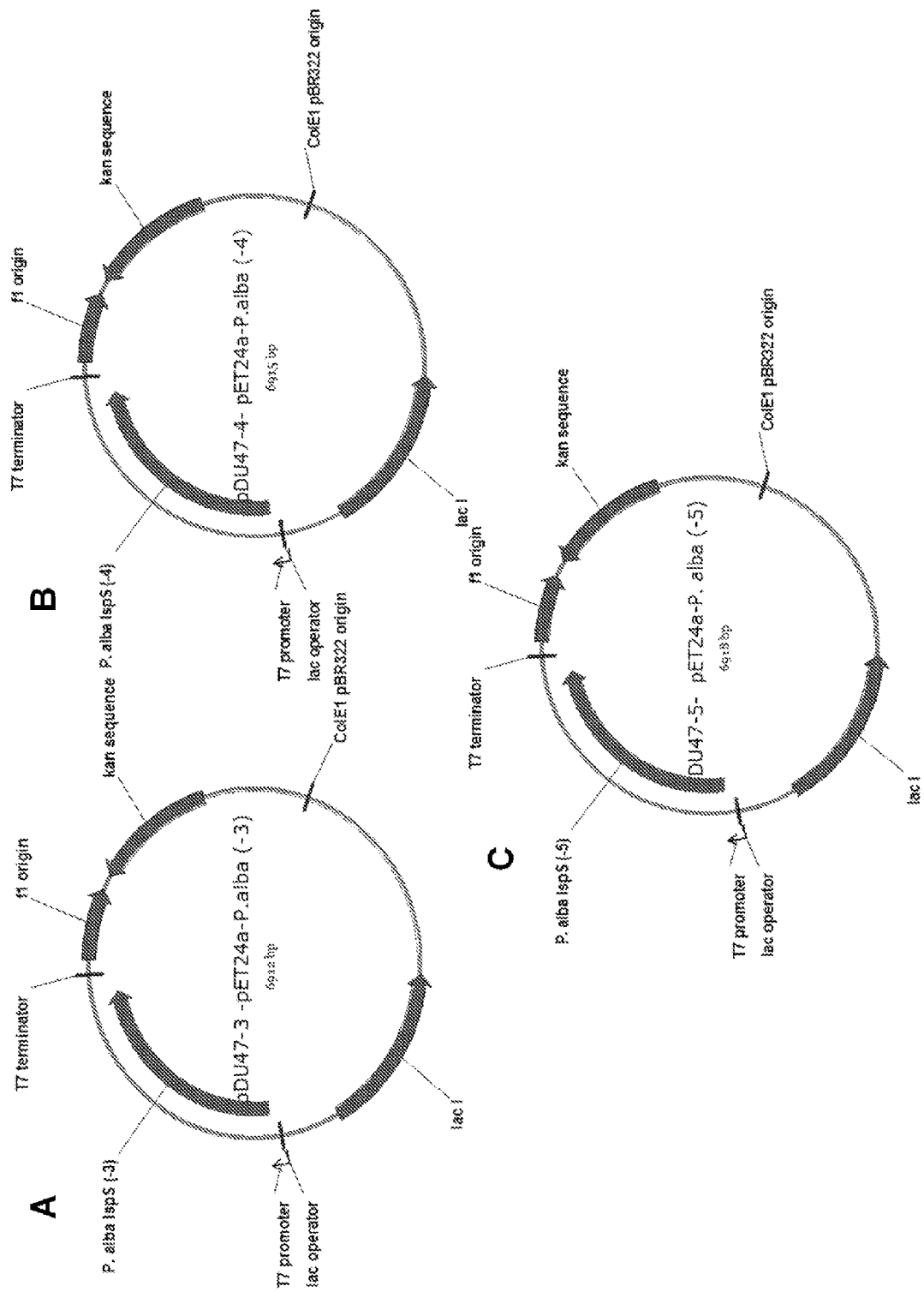
FIG. 48 provides maps of plasmids pDu47-3, pDu47-4, and pDu47-5.

DMAPP Reaction: 1× Lysis Buffer was dispensed at 65 μL/well. 15 μL/well of lysate was transferred to the respective sample wells in a 96 Deep well Zinsser Glass Block. DMAPP reagent was dispensed at 20 μL/well. The glass block was sealed with an aluminum foil membrane and incubated at 25° C. at 450 rpm for 45 min. The reaction was stopped by measurements for the L70R variant, and 8 for wild type. These data are shown below in Table 13-3. When corrected for protein, the L70R variants displayed a 25% increase in activity over MD09-173 (the MEA truncation). FIG. 47 shows the average specific activity for all L70R variants compared to MEA. Error bars show one standard deviation. The two data sets for L70R and the MEA control were subjected to a Student's T-Test for statistical analysis, which yielded a P-value of $6.0011 \times 10^{-5}$.

TABLE 13-2

Sequencing Results, Isoprene Production, Protein concentration, and Specific Activity for all residues in the Winner Plate

| Residue | WT codon | Mutant codon | Amino acid change | OD600 | Avg. Isoprene produced (4 replicates) | Std. Dev. (isoprene) | Protein concentration (mg/ml) | Avg. Specific Activity (4 replicates) | Std. Dev. (Specific Activity) |
|---|---|---|---|---|---|---|---|---|---|
| L70 | CTG | TGG | W | 2.6488 | 663.00 | 18.64 | 0.139 | 198.020 | 5.566 |
| L70 | CTG | CGG | R | 3.4944 | 1235.72 | 48.82 | 0.127 | 401.451 | 15.860 |
| L70 | CTG | CGT | R | 3.32416 | 944.77 | 19.15 | 0.121 | 322.523 | 6.539 |
| L70 | CTG | CGT | R | 3.37232 | 947.11 | 17.74 | 0.106 | 371.375 | 6.957 |
| L70 | CTG | TGG | W | 2.83584 | 774.49 | 32.60 | 0.129 | 248.925 | 10.477 |
| G94 | GGT | GAG | E | 3.304 | 1070.41 | 20.52 | 0.144 | 307.731 | 5.898 |
| G94 | GGT | GGG | G | 3.40816 | 982.64 | 27.37 | 0.133 | 306.891 | 8.549 |
| R262 | CGT | CGT | R | 3.01616 | 861.08 | 29.13 | 0.116 | 307.227 | 10.395 |
| R262 | CGT | CGG | R | 3.31744 | 965.44 | 19.25 | 0.136 | 294.311 | 5.868 |
| F305 | TTC | TTT | F | 2.90864 | 788.46 | 15.15 | 0.119 | 274.297 | 5.270 |
| F305 | TTC | CTG | L | 2.7776 | 626.70 | 22.91 | 0.141 | 183.823 | 6.719 |
| WT1 | | | | 3.71392 | 991.65 | 35.78 | 0.144 | 285.216 | 10.292 |
| F305 | TTC | TTC | F | 2.604 | 694.03 | 35.93 | 0.118 | 244.488 | 12.658 |
| V306 | GTA | GTA | V | 3.33648 | 912.56 | 38.76 | nd | nd | nd |
| V306 | GTA | GTA | V | 3.17632 | 892.97 | 56.10 | 0.137 | 269.415 | 16.927 |
| F385 | TTC | TTC | F | 2.89184 | 721.24 | 29.36 | 0.134 | 223.380 | 9.094 |
| Q416 | CAA | CAG | Q | 3.00272 | 953.07 | 57.38 | 0.149 | 264.718 | 15.938 |
| V418 | GTG | ATG | M | 2.14144 | 767.25 | 27.94 | 0.164 | 194.099 | 7.067 |
| V418 | GTG | ACG | T | 3.24688 | 973.57 | 75.08 | 0.192 | 209.801 | 16.179 |
| V418 | GTG | ACG | T | 3.13264 | 936.98 | 68.50 | 0.171 | 226.197 | 16.536 |
| T442 | ACC | GTA | V | 3.07552 | 951.64 | 38.06 | 0.154 | 255.496 | 10.217 |
| F450 | TTC | TTC | F | 2.93328 | 911.44 | 50.88 | 0.126 | 299.018 | 16.691 |
| V418 | GTG | ACG | T | 3.08896 | 1057.71 | 46.28 | 0.183 | 238.887 | 10.454 |
| WT2 | | | | 3.37568 | 960.25 | 58.16 | 0.131 | 304.346 | 18.434 |

Note that sequence of all plasmids is identical to Pdu39 (see above) with the exception of the indicated codon. The L70R variants are highlighted in gray.

TABLE 13-3

Average Specific Activity of all L70R variants relative to the MEA control.

| Variant Average | Specific Activity | Standard Deviation |
|---|---|---|
| L70R | 365.116 | 35.31977 |
| WT (the MEA control) | 294.7809 | 17.19228 |

See FIG. 47 for bar graph.

EXAMPLE 14

Truncations of P. alba, P. tremuloides, P. trichocharpa, and Kudzu Isoprene Synthases This example describes the generation of a series of truncations in the IspS enzymes of P. alba, P. tremuloides, P. trichocharpa, and Kudzu and to determine their effect on activity.

I. Strain Construction

Figure 49:
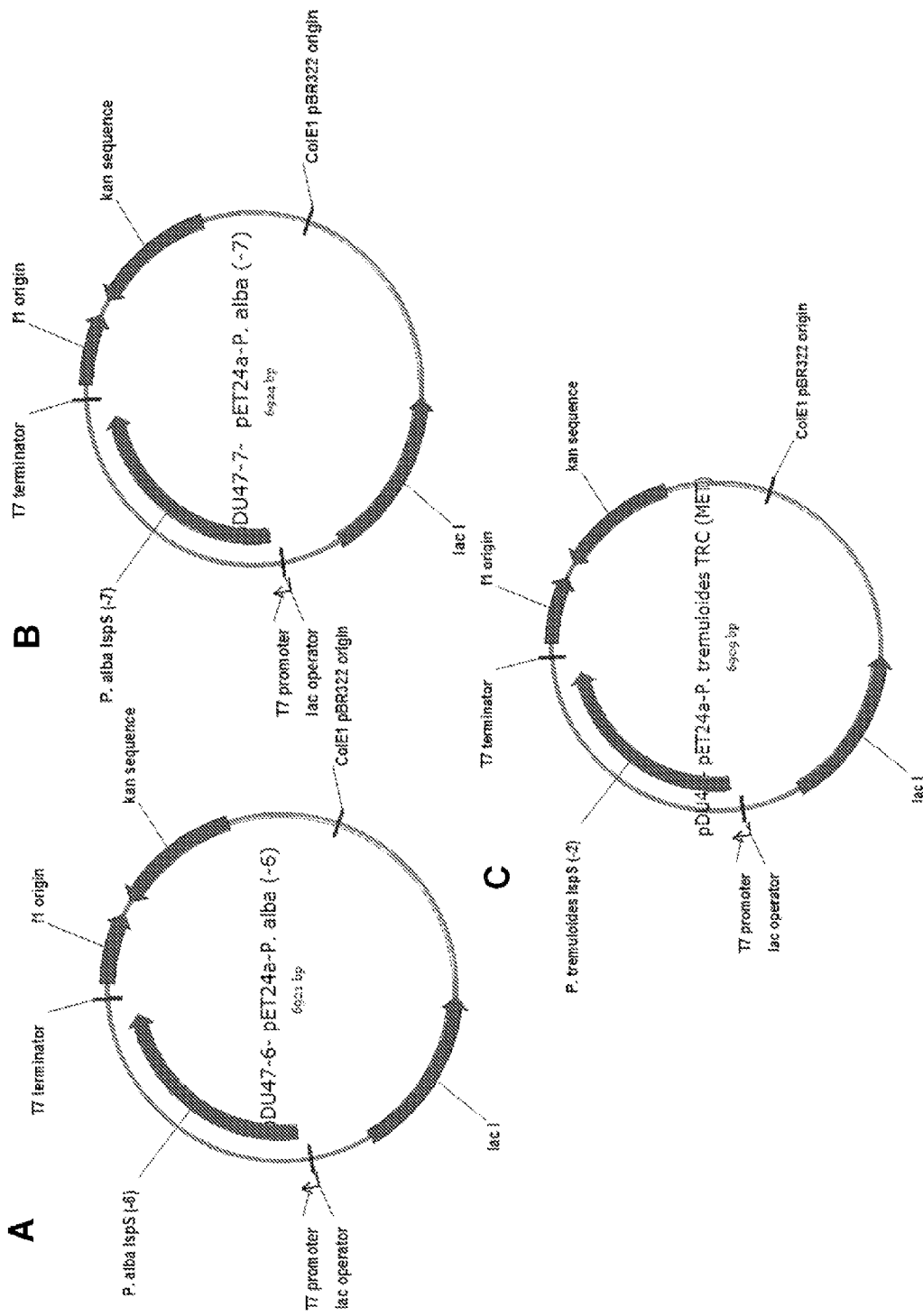
FIG. 49 provides maps of plasmids pDu47-6, pDu47-7, and pDu48.
Figure 50:
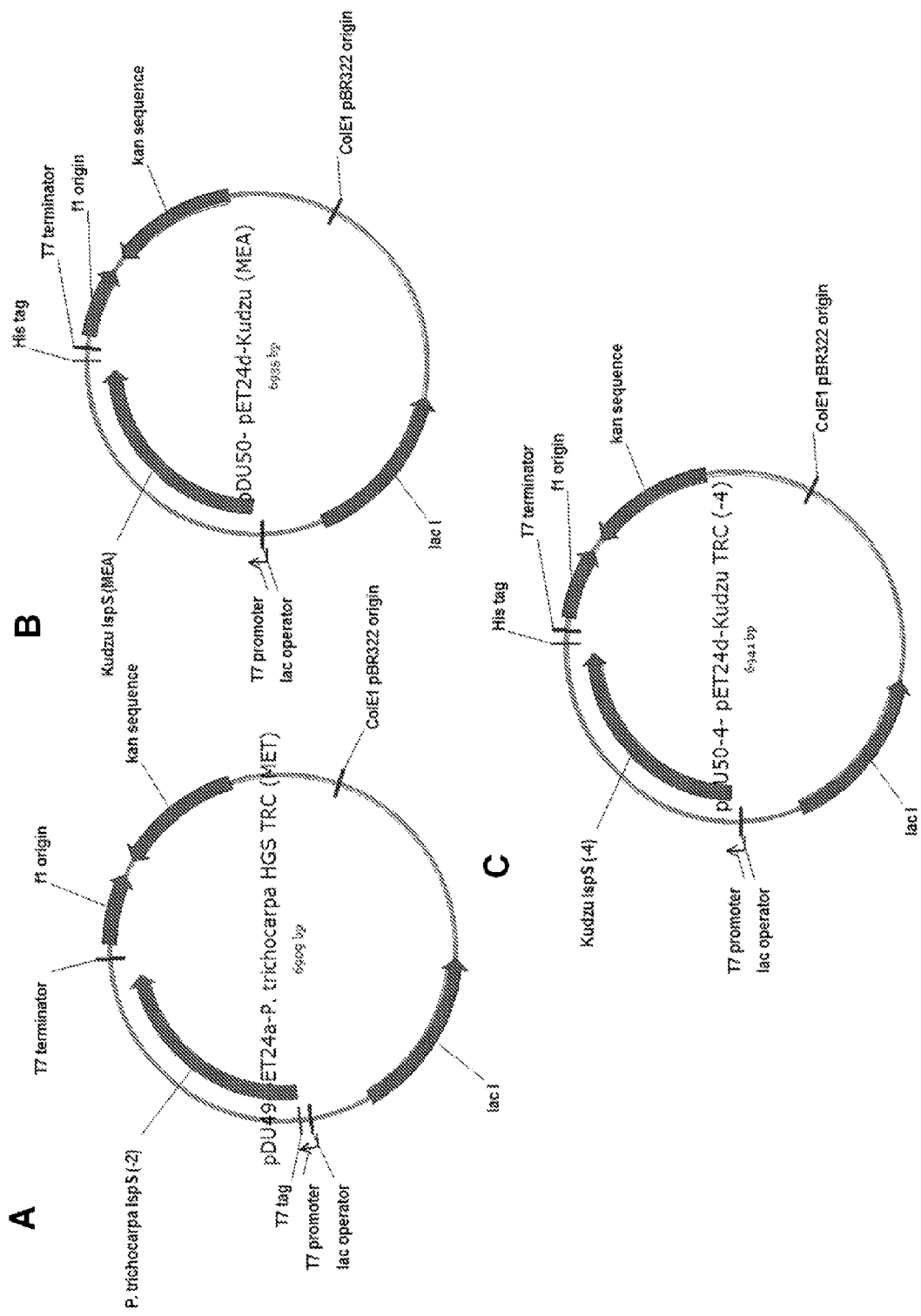
FIG. 50 provides maps of plasmids pDu49, pDu50 and pDu50-4.

All isoprene synthase genes were codon optimized for E. coli, synthesized, and cloned into pET24a by DNA2.0 (Menlo Park, Calif.). All truncated constructs were generated using the QuickChange Site-Directed Mutagensis kit (Stratagene) using the previously described templates P. alba pET24a (for plasmids pDu47-3 through -7, FIGS. 48, 49, 51-60), P. tremuloides pET24a (plasmid pDu48, FIGS. 49C, 61 and 62), P. trichocharpa pET24a (pDu49, FIGS. 50A, 63, 64), or pET24d-Kudzu (pDu50 and 50-4, FIGS. 50B, 50C, 65-68) for PCR amplification. Approximately 50 ng of template DNA was used for amplification (with an Eppendorf Mastercycler Gradient PCR Machine) of the PCR product with the Forward (For) and Reverse (Rev) primer pairs that correspond to each relevant truncation (QC Trunc −3 F and QC Trunc −3 R, for example, see Table 14-1). PCR reactions mixtures were as follows: 1 µl P. alba pET24a (or other template), 5 µl 10× PfuUltra HF buffer, 1 µl dNTP's (10 mM), 1 µl (50 uM) primer-For, 1 µl (50 µM) primer-Rev, 1.5 µl DMSO, 39.5 µl diH$_2$O and 1 µl PfuUltra HF Polymerase. PCR cycle parameters were as follows: (95° C. 1 min., 95° C. 1 min., 55° C. 1 min., 68° C. 7.30 min.) for 18 cycles then 4° C. until cool using an Eppendorf Mastercycler Gradient Machine. The PCR products were treated with 1-2 µl of DpnI (Roche) for 1-3 hour at 37° C. 5 µl of the DpnI treated products were visualized on a 0.8% E-gel (Invitrogen). 1 µl of each product was transformed into chemically competent E. coli Top10 cells (Invitrogen) (according to the manufacturer's protocol). Transformants were selected for on LB medium containing kanamycin at a concentration of 50 µg/ml (Kan50), and incubated overnight at 37° C. Five colonies of each transformation were selected and grown to stationary phase in 3 ml liquid LB Kan50. Plasmids were purified using a QIAPrep Spin miniprep kit (Qiagen) according to the manufacturer's recommended protocol. Purified plasmids were sequenced (by Quintara Biosciences) with T7 Forward and Reverse primers, compared to the parental sequence, and confirmed for their respective truncation. The resulting plasmids (pDu47-3 through pDu50-4, see Table 14-2) were transformed into chemically competent *E. coli* BL21(DE3) pLysS (Invitrogen) according to the manufacturer's recommended protocol. Table 14-3 describes the strains used for expression of truncated IspS enzymes.

After overnight incubation at 37° C., individual colonies were inoculated into individual wells in a 96-well deep-well microtiter plate (VWR) containing 500 µl of liquid LB Kan50 CM35 each. Microtiter plates were then sealed with a semi-permeable membrane (Breathe-Easier, Diversified Biotech), and incubated overnight at 30° C. in a shaking incubator (Vertiga). The next day, 100 µl samples from each well within a 96-well plate were mixed with 50 µl of 50% glycerol in a new 200 µl 96-well plate, and frozen at −80° C. until further analysis. This plate was then used for the DMAPP assay as described in Example 13. Table 14-4 shows the average specific productivity of all samples, and FIG. 69 shows the graphical representation of the same data.

DMAPP activity and protein quantitation was determined as described in Example 13.

Specific activity was calculated by multiplying the isoprene produced (µg/1) by 0.00776 and then dividing by protein concentration (mg/ml). This conversion factor (0.00776) accounts for the total headspace volume in a sealed 2 ml GC vial (1.9 ml), the lysate volume (80 µl), the duration of the DMAPP assay (45 min), and the molecular weight of isoprene. Thus, specific activity values are given in nmol isoprene/mg IspS/min.

TABLE 14-2

| Plasmids | |
|---|---|
| pDu47-3 | Mtg pET24a-*P.alba* TRC (-3) |
| pDu47-4 | Mtg pET24a-*P.alba* TRC (-4) |
| pDu47-5 | Mtg pET24a-*P.alba* TRC (-5) |
| pDu47-6 | Mtg pET24a-*P.alba* TRC (-6) |
| pDu47-7 | Mtg pET24a-*P.alba* TRC (-7) |
| pDu48 | Mtg pET24a-*P.tremu* TRC (MET) |
| pDu49 | Mtg pET24a-*P.tricho* TRC (MET) |
| pDu50 | Mtg pET24d-Kudzu TRC (MEA) |
| pDu50-4 | Mtg pET24d-Kudzu TRC (-4) |

TABLE 14-3

| Strains | |
|---|---|
| MD09-197-3 | BL21(DE3)pLysS, pDu47-3 |
| MD09-197-4 | BL21(DE3)pLysS, pDu47-4 |
| MD09-197-5 | BL21(DE3)pLysS, pDu47-5 |
| MD09-197-6 | BL21(DE3)pLysS, pDu47-6 |
| MD09-197-7 | BL21(DE3)pLysS, pDu47-7 |
| MD09-198 | BL21(DE3)pLysS, pDu48 |
| MD09-199 | BL21(DE3)pLysS, pDu49 |
| MD09-200 | BL21(DE3)pLysS, pDu50 |
| MD09-200-4 | BL21(DE3)pLysS, pDu50-4 |

TABLE 14-1

| Primers | | |
|---|---|---|
| QC Trunc-3 F | gaaggagatatacatatgaccgaagctcgtcgt | (SEQ ID NO: 92) |
| QC Trunc-3 R | acgacgagcttcggtcatatgtatatctccttc | (SEQ ID NO: 93) |
| QC Trunc-4 F | gaaggagatatacatatggaaaccgaagctcgt | (SEQ ID NO: 94) |
| QC Trunc-4 R | acgagcttcggtttccatatgtatatctccttc | (SEQ ID NO: 95) |
| QC Trunc-5 F | gaaggagatatacatatgactgaaaccgaagct | (SEQ ID NO: 96) |
| QC Trunc-5 R | agcttcggtttcagtcatatgtatatctccttc | (SEQ ID NO: 97) |
| QC Trunc-6 F | gaaggagatatacatatggaaactgaaaccgaa | (SEQ ID NO: 98) |
| QC Trunc-6 R | ttcggtttcagtttccatatgtatatctccttc | (SEQ ID NO: 99) |
| QC Trunc-7 F | gaaggagatatacatatgaccgaaactgaaacc | (SEQ ID NO: 100) |
| QC Trunc-7 F | ggtttcagtttcggtcatatgtatatctccttc | (SEQ ID NO: 101) |
| QC Kudzu MEA F | agaaggagatataccatggaagctcgtcgttccgcaaac | (SEQ ID NO: 102) |
| QC Kudzu MEA R | gtttgcggaacgacgagcttccatggtatatctccttct | (SEQ ID NO: 103) |
| QC Kudzu-4 F | agaaggagatataccatggagcataattcccgt | (SEQ ID NO: 104) |
| QC Kudzu-4 R | acgggaattatgctccatggtatatctccttct | (SEQ ID NO: 105) |
| QC Trem/Trich-2 F | gaaggagatatacatatggaaacgcgtcgttct | (SEQ ID NO: 106) |
| QC Trem/Trich-2 R | agaacgacgcgtttccatatgtatatctccttc | (SEQ ID NO: 107) |

TABLE 14-4

Specific Productivity of Variants listed above

| Sample | Sample | Isoprene Produced (µg/l) | | | OD$_{600}$ | | OD |
| --- | --- | --- | --- | --- | --- | --- | --- |
| | | Average | Std Dev | % CV | Raw | xDF xCF | Norm |
| IspS N | MD09-197-3 | 3381 | 154 | 5 | 0.3060 | 3.4 | 986.6 |
| terminal | MD09-197-4 | 3000 | 206 | 7 | 0.3160 | 3.5 | 847.7 |
| Truncation | MD09-197-5 | 2932 | 266 | 9 | 0.3200 | 3.6 | 818.2 |
| Variants | MD09-197-6 | 2450 | 217 | 9 | 0.3040 | 3.4 | 719.4 |
| | MD09-197-7 | 2285 | 397 | 17 | 0.3020 | 3.4 | 675.5 |
| | MD09-198 | 1916 | 106 | 6 | 0.3330 | 3.7 | 513.6 |
| | MD09-199 | 2031 | 108 | 5 | 0.2140 | 2.4 | 847.6 |
| | MD09-200 | 141 | 8 | 6 | 0.3700 | 4.1 | 34.0 |
| | MD09-200-4 | 1829 | 197 | 11 | 0.2760 | 3.1 | 591.5 |
| | MD09-173 | 2414 | 201 | 8 | 0.3400 | 3.8 | 633.9 |
| | MD09-176 | 2826 | 354 | 13 | 0.3260 | 3.7 | 773.9 |
| | BL21 DE3 pLysS + P alba pET24a | 2175 | 117 | 5 | 0.2990 | 3.3 | 649.6 |

A second experiment was conducted with the strains outlined in Table 14-5. Control was BL21 DE3 pLysS with *P. alba* pET24a (full length *P. alba* IspS).

TABLE 14-5

Strains

| | |
| --- | --- |
| MD09-197-3 | BL21(DE3)pLysS, pDu47-3 |
| MD09-197-4 | BL21(DE3)pLysS, pDu47-4 |
| MD09-197-5 | BL21(DE3)pLysS, pDu47-5 |
| MD09-197-6 | BL21(DE3)pLysS, pDu47-6 |
| MD09-197-7 | BL21(DE3)pLysS, pDu47-7 |
| MD09-198 | BL21(DE3)pLysS, pDu48 |
| MD09-199 | BL21(DE3)pLysS, pDu49 |
| MD09-173 | BL21(DE3)pLysS, pET24a-*P.alba* (MEA) Untagged (pDu39) |
| MD09-174 | BL21(DE3)pLysS, pET24a-*P.alba* (MNV) Untagged (pDu40) |
| MD09-175 | BL21(DE3)pLysS, pET24a-*P.alba* (MSV) Untagged (pDu41) |
| MD09-176 | BL21(DE3)pLysS, pET24a-*P.alba* (MTE) Untagged (pDu42) |
| MD09-177 | BL21(DE3)pLysS, pET24a-*P.alba* (MVS) Untagged (pDu43) |
| MD09-197-3 | BL21(DE3)pLysS, pDu47-3 |
| MD09-197-4 | BL21(DE3)pLysS, pDu47-4 |

Results

Figure 70:
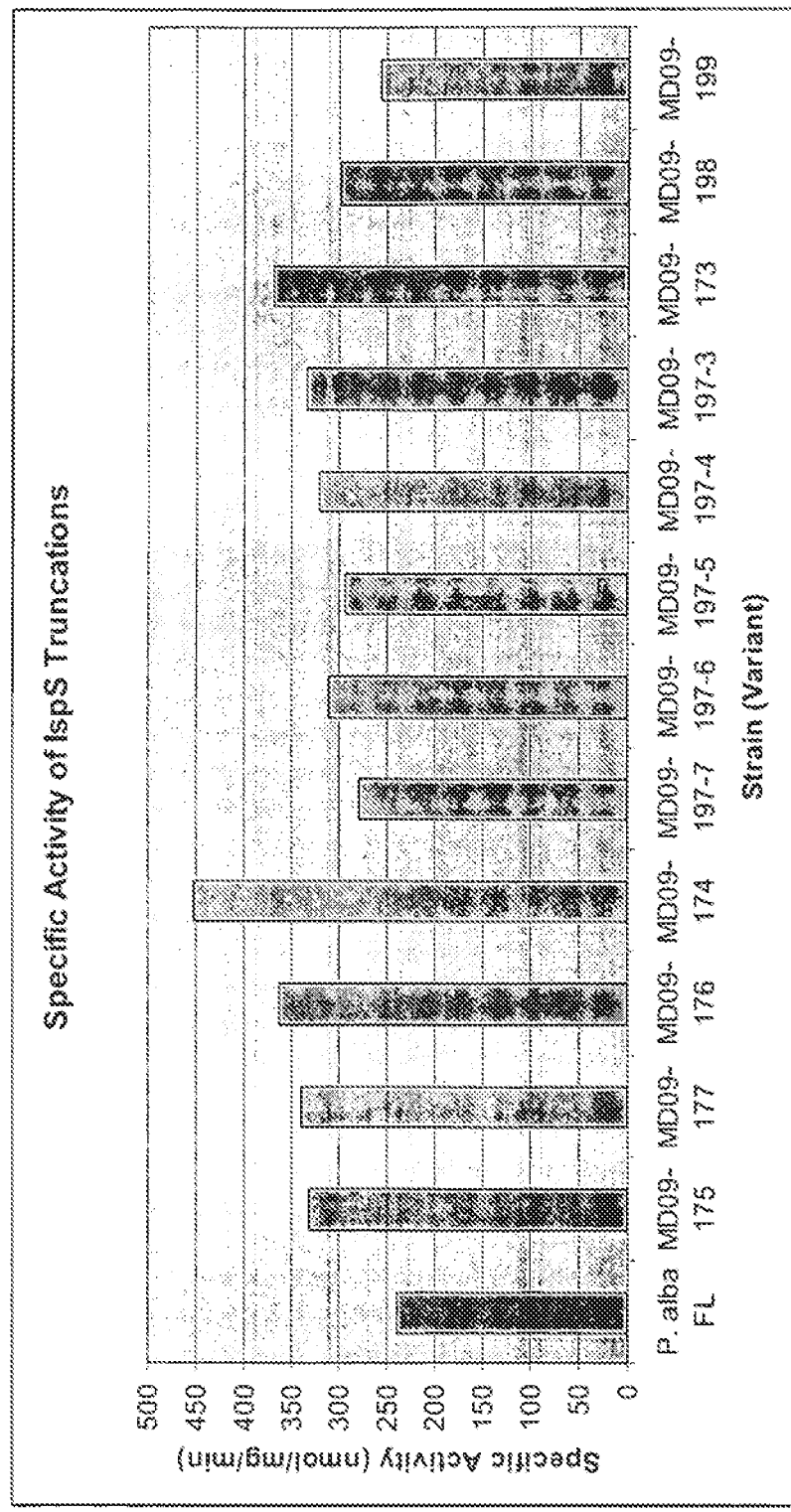
FIG. 70 shows a graph representing the specific activity of IspS truncations. *P. alba, P. tremuloides* and *P. trichocarpa* truncations were compared for specific activity relative to the *P. alba* "full length" variant.

All truncations of *P. alba* IspS and two from *P. tremuloides* and *P. trichocharpa* were assayed in parallel to compare their relevant specific activities via DMAPP assay and quantitative Western blot. At least two samples per variant were assayed for isoprene production and amount of IspS in mg/ml. Variant MD09-174 produced little isoprene and expressed little protein, yet displayed high specific activity. High specific activities were also displayed by MD09-173, MD09-176, and MD09-197-3 (see Table 14-6 and FIG. 70). The highest levels of protein (µg) in 3 µg total protein were displayed by MD09-176 and MD09-197-3, indicating that these variants are more effectively expressed in the *E. coli* BL21 DE3 host strain.

TABLE 14-6

Specific Activity of truncations.

| Strain | Average Specific Activity | Standard Deviation | Average µg IspS/ 3 µg total protein |
| --- | --- | --- | --- |
| *P. alba* FL | 240.16239 | 31.0423851 | 0.198 |
| MD09-175 | 331.8755329 | 8.958408319 | 0.188 |
| MD09-177 | 340.1959506 | 39.72104203 | 0.150 |

TABLE 14-6-continued

Specific Activity of truncations.

| Strain | Average Specific Activity | Standard Deviation | Average µg IspS/ 3 µg total protein |
| --- | --- | --- | --- |
| MD09-176 | 363.516921 | 3.376026129 | 0.202 |
| MD09-174 | 452.7792122 | 27.71567075 | 0.018 |
| MD09-197-7 | 279.2042431 | 23.82331163 | 0.158 |
| MD09-197-6 | 309.8357305 | 7.903564316 | 0.164 |
| MD09-197-5 | 293.22592 | 20.97161876 | 0.165 |
| MD09-197-4 | 321.3926574 | 56.13760028 | 0.186 |
| MD09-197-3 | 333.0604155 | 45.92710529 | 0.207 |
| MD09-173 | 368.4597405 | 37.80631246 | 0.159 |
| MD09-198 | 297.6476631 | 56.81405985 | 0.154 |
| MD09-199 | 256.7342861 | 8.239697653 | 0.216 |

EXAMPLE 15

Constructs for Three-Dimensional Structure Determination

I. Construction of pMAL-C4X Kudzu

Figure 71:
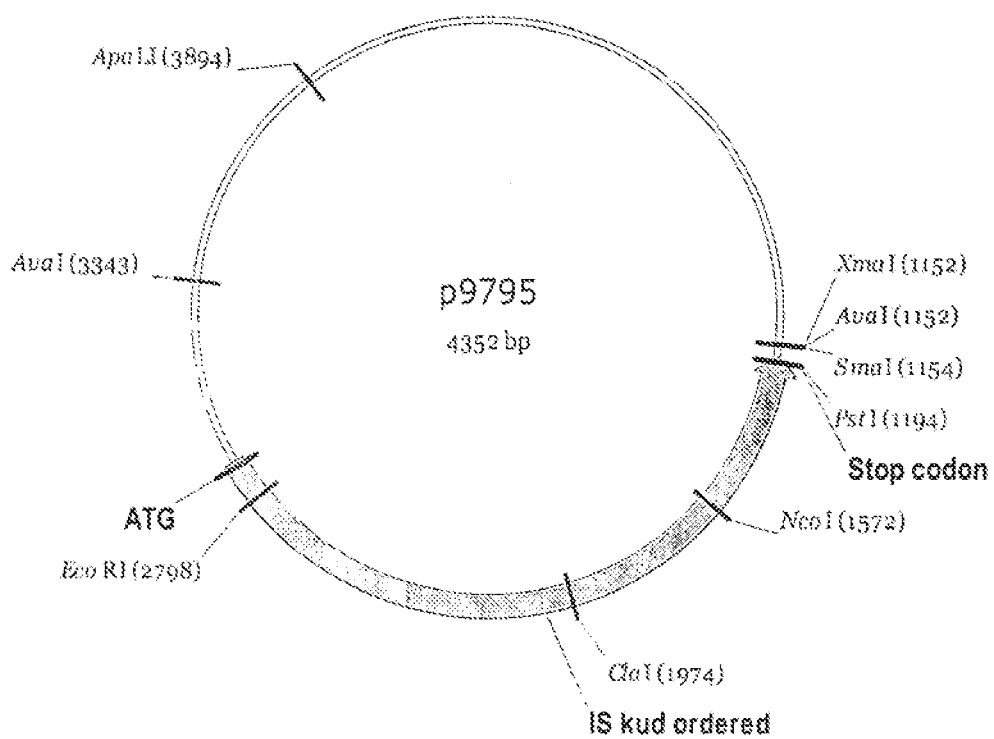
FIG. 71 provides a map of plasmid p9795.
Figure 73:
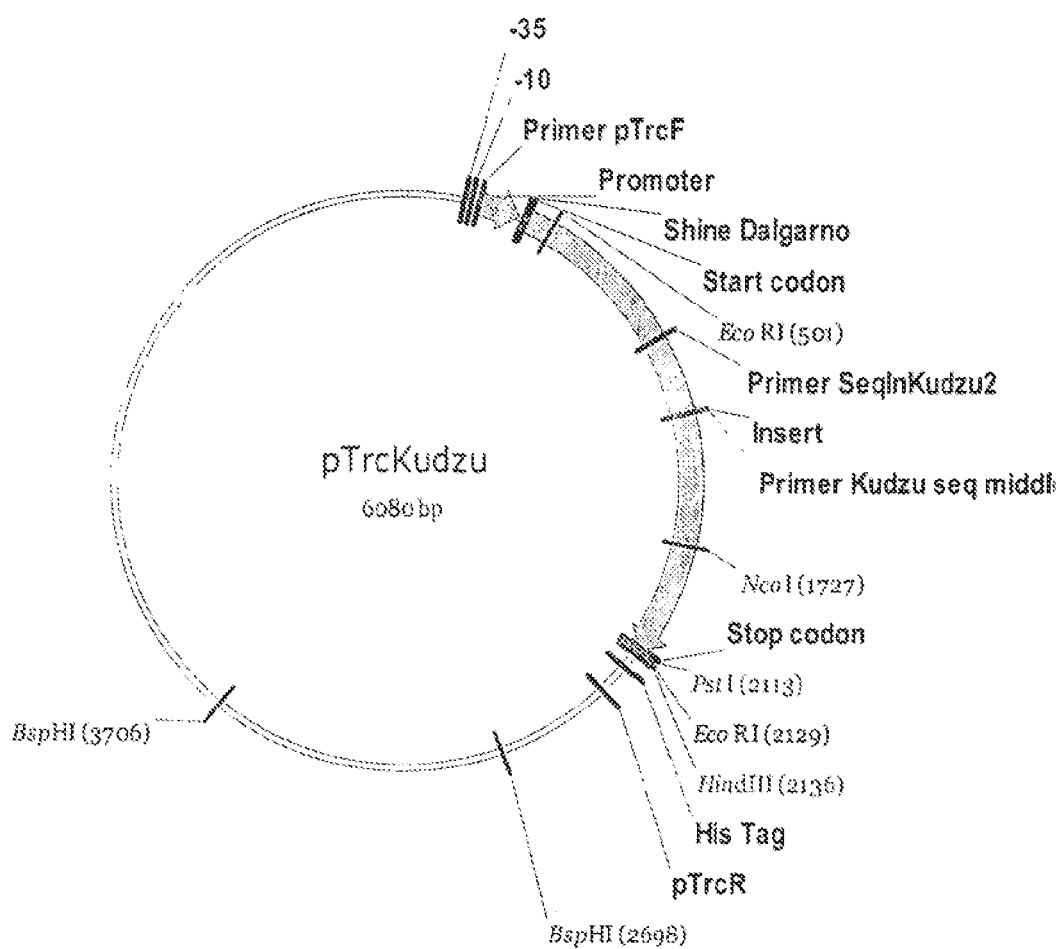
FIG. 73 provides a map of plasmid pTrcKudzu.

A synthetic gene, coding for isoprene synthase (IspS) of the Kudzu vine (*Pueraria lobata*) and codon-optimized for *E. coli*, was purchased from DNA2.0 (Menlo Park, Calif.) and provided as plasmid p9795 (FIGS. 71 and 72). The insert was removed by digestion with BspLU11I/PstI, gel-purified, and religated into NcoI/PstI-digested pTrcHis2B (Invitrogen, Carlsbad, Calif.). The resulting plasmid was named pTrcKudzu (FIG. 73: map of pTrcKudzu). The stop codon in the insert is before the PstI site, which results in a construct in which the His-Tag is not attached to the IspS protein.

A PCR reaction was performed to amplify the *E. coli* codon-optimized Kudzu gene using plasmid pTrcKudzu as the DNA template, primers EL-959 and EL-960, 10 mM dNTP (Roche, Indianapolis, Ind.), and Pfu Ultra II Fusion DNA polymerase (Stratagene, La Jolla, Calif.) according to manufacturer's protocol. PCR conditions were as follows: 95° C. for 2 min (first cycle only), 95° C. for 25 sec, 60° C. for 25 sec, 72° C. for 30 sec, repeat for 28 cycles, with final extension at 72° C. for 1 min. The PCR product was then purified using the QIAquick PCR Purification Kit (Qiagen Inc, Valencia, Calif.).

Figure 75:
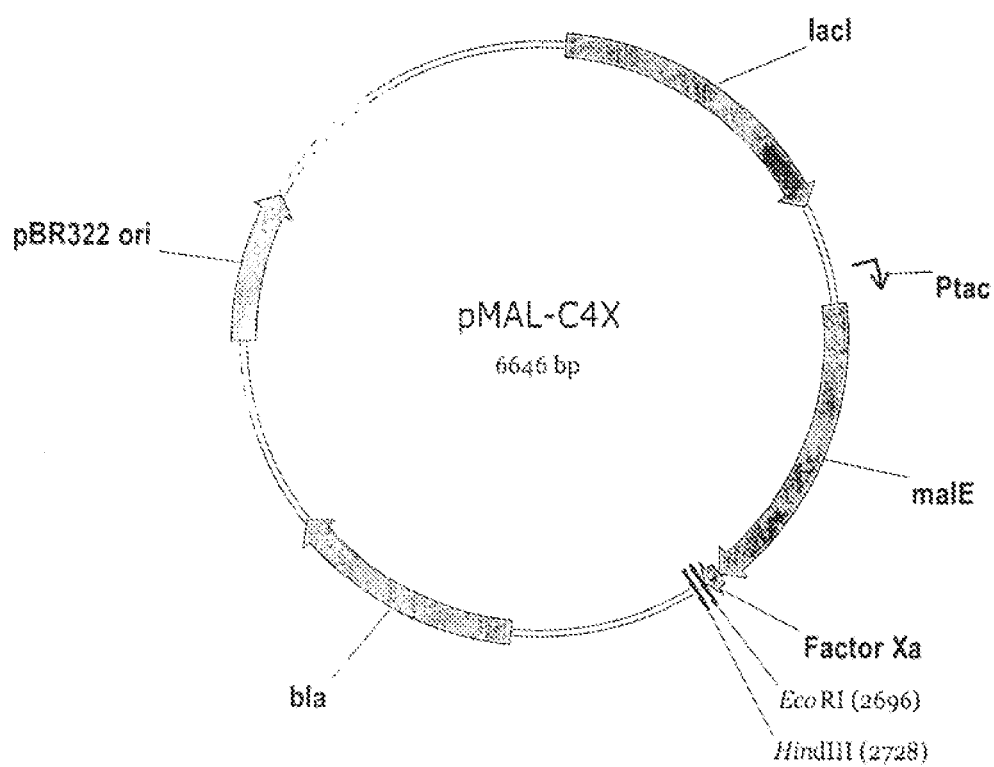
FIG. 75 provides a map of plasmid pMAL-C4X.

The Kudzu PCR product (1 µg) was digested using EcoRI and HindIII restriction endonucleases (Roche) according to manufacturer's protocol. The digest was incubated 37° C. for 30 minutes to minimize digestion of the internal EcoRI site that is present in the Kudzu gene. The digested PCR fragment was then purified using the QIAquick PCR Purification Kit. The vector pMAL-C4X (0.5 μg) (New England Biolabs, Ipswich, Mass.; FIGS. 75 and 76) was digested using EcoRI and HindIII restriction endonucleases (Roche) according to manufacturer's protocol. The digested vector was then gel purified using the QIAquick Gel Extraction Kit (Qiagen Inc). A DNA ligation reaction was performed using T4 DNA ligase (New England Biolabs) with a 5:1 ratio of digested Kudzu PCR product to digested pMAL-C4X vector according to manufacturer's protocol. An aliquot of the ligation reaction was then transformed into TOP10 chemically competent cells (Invitrogen Corp). Transformants were selected on LA+50 μg/μl carbenicillin plates.

Figure 77:
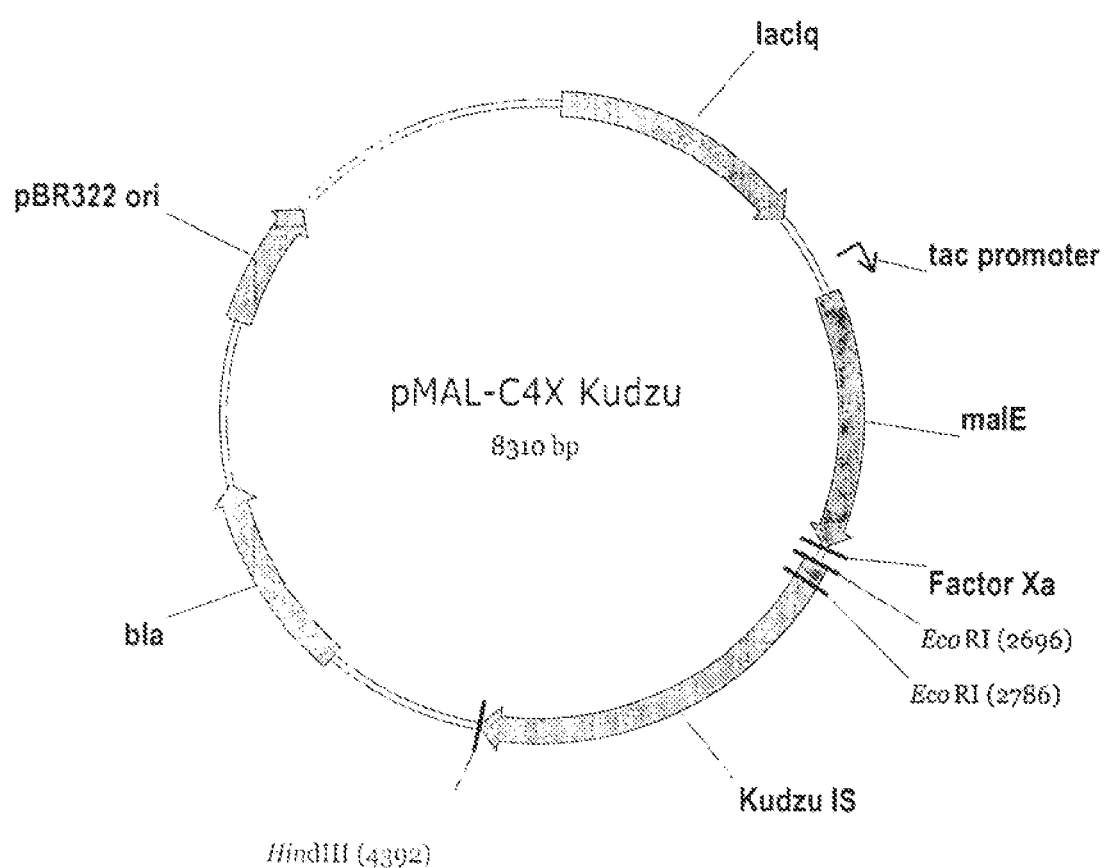
FIG. 77 provides a map of plasmid pMAL-C4X-Kudzu.
Figure 79:
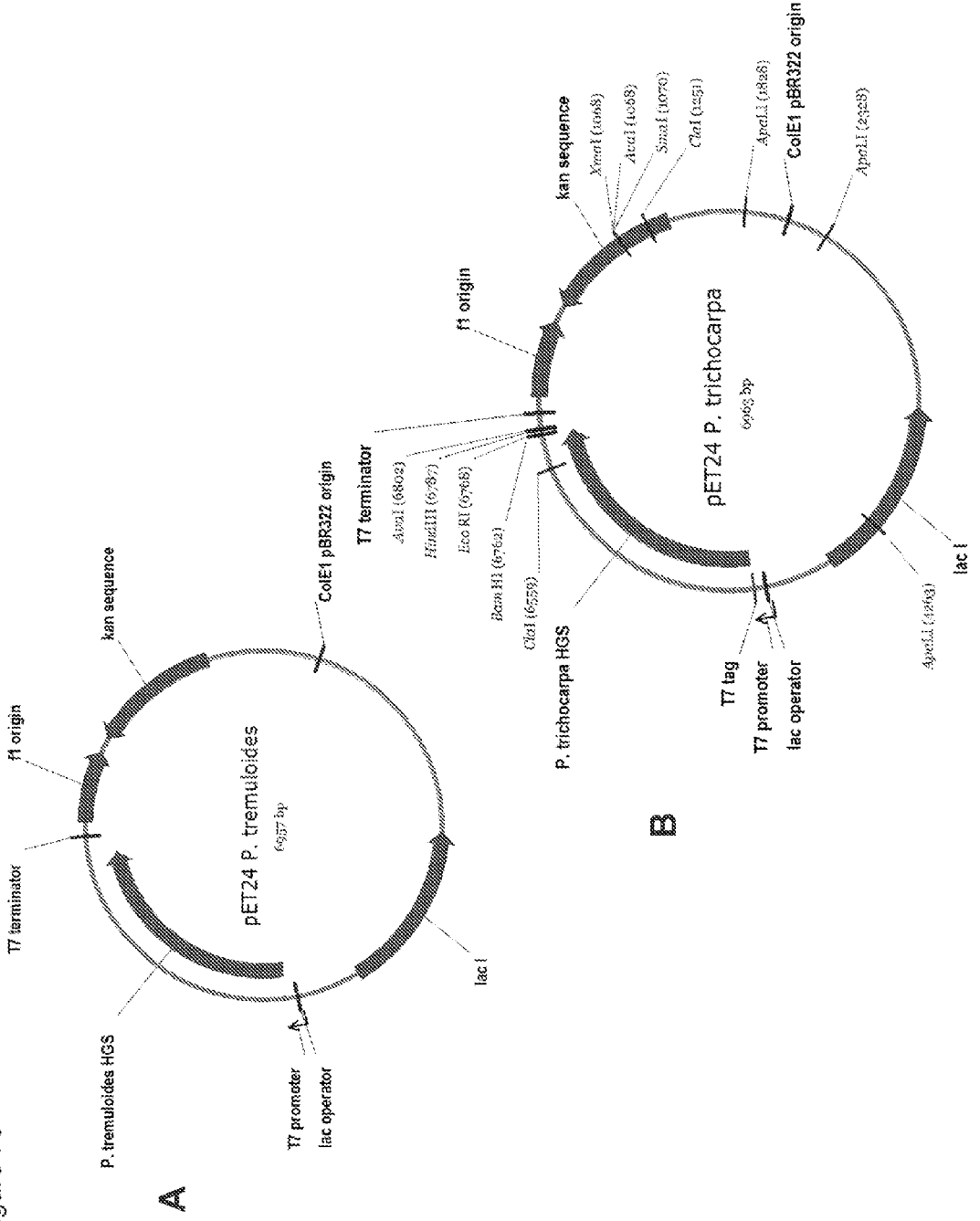
Figure 84:
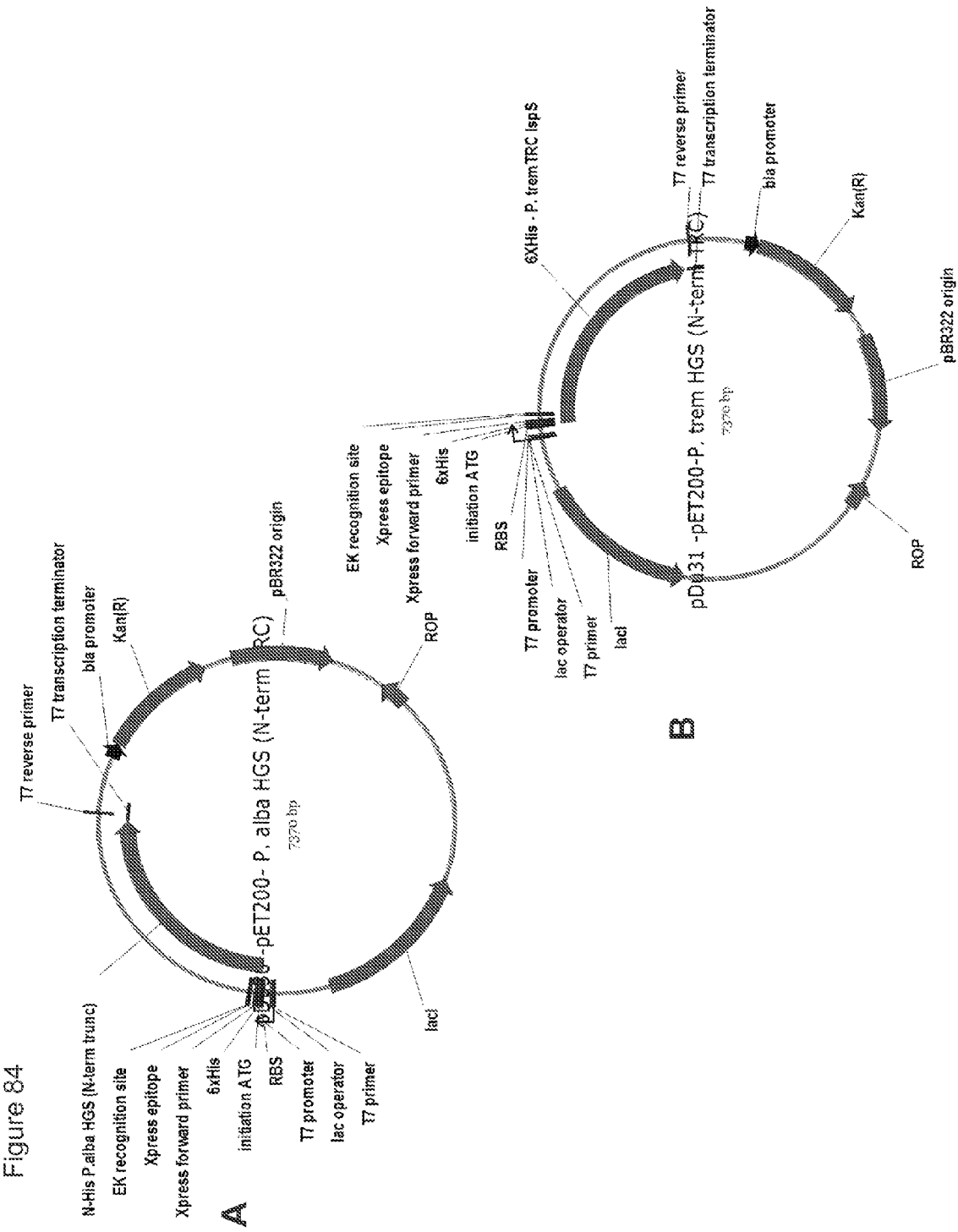
FIG. 84 provides maps of plasmids pDu30, pDu31, and pDu32.
Figure 84:
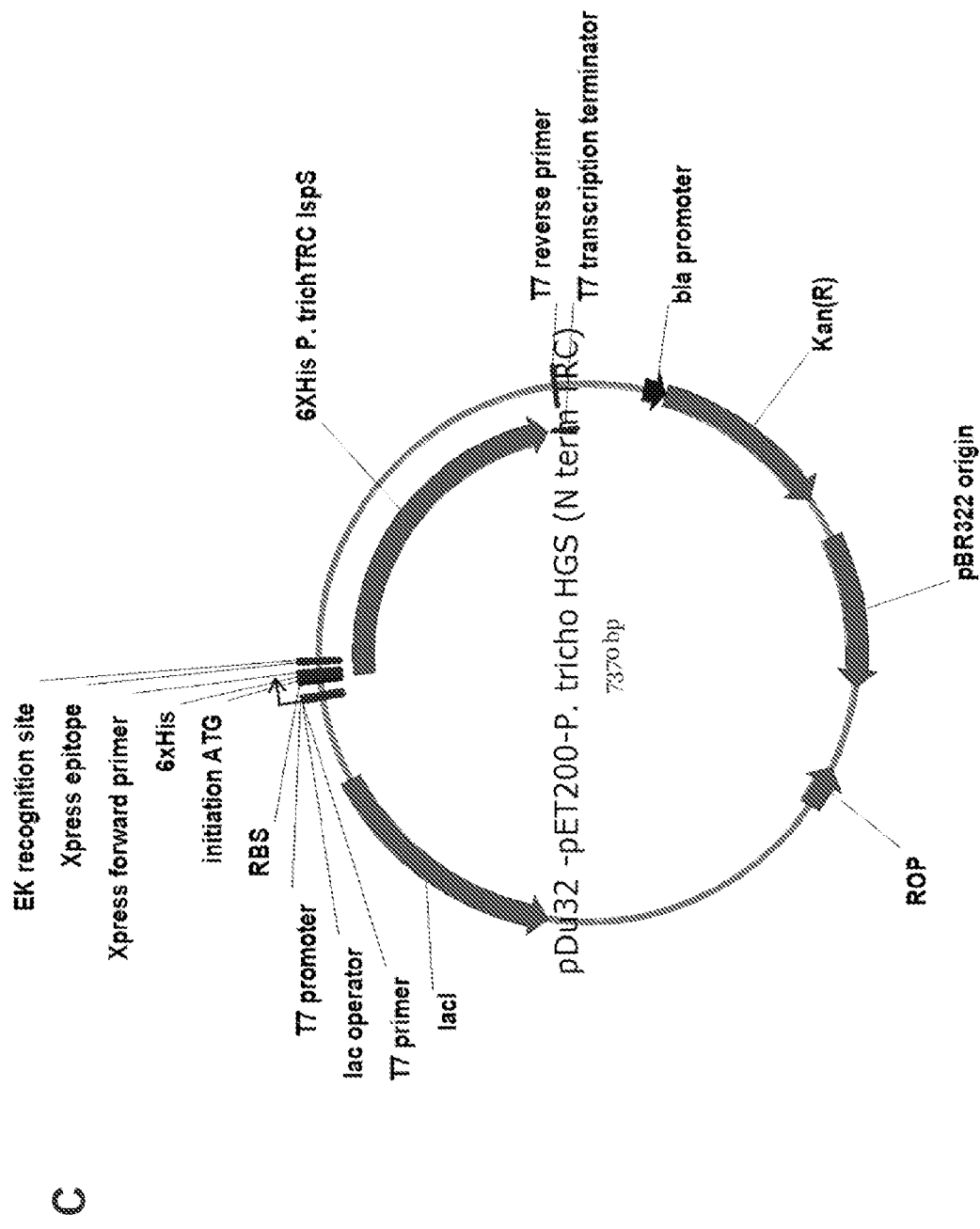

Screening of transformants containing the Kudzu gene was performed by picking colonies and performing PCR with primers EL-957 and EL-966 using PuReTaq Ready-To-Go PCR beads (GE Healthcare, Piscataway, N.J.) according to manufacturer's protocol. PCR conditions were as follows: 95° C. for 2 min (first cycle only), 95° C. for 30 sec, 50° C. for 30 sec, 72° C. for 40 sec, repeat for 28 cycles, with final extension at 72° C. for 1 min. PCR products were analyzed on a 2% E-gel (Invitrogen Corp) looking for a 600 bp fragment. Colonies containing the correct sized PCR product insert were submitted for DNA sequencing using primers EL-950, EL-951, EL-953, and EL-957. DNA sequencing confirmed the construction of plasmid pMAL-C4X Kudzu (FIGS. 77-79).

TABLE 15-1

Primer sequences

| Primer name | Primer sequence |
|---|---|
| EL-950 | CGGTGAACTGAAAGGTGACGTCC (SEQ ID NO: 108) |
| EL-951 | GGACGTTAACGCTATTAACACCCTG (SEQ ID NO: 109) |
| EL-953 | CACATCGTCGATCAGCTCCAGC (SEQ ID NO: 110) |
| EL-957 | GGTCGTCAGACTGTCGATGAAGCC (SEQ ID NO: 111) |
| EL-959 | GCTTATGAATTCTGTGCGACCTCTTCTCAATTTACTCAG (SEQ ID NO: 112) |
| EL-960 | GCTTATAAGCTTAGACATACATCAGCTGGTTAATCGGG (SEQ ID NO: 113) |
| EL-966 | CTCCTCCAGCAGGTTCTCACC (SEQ ID NO: 114) |

Plasmid pMAL-C4X Kudzu was transformed into One-Shot BL21(λDE3) chemically competent cells (Invitrogen Corp). Expression strain transformants were selected on LA+50 mg/ml carbenicillin plates.

II. IspS Variants for Crystal Structure Trials

This example describes methods to generate affinity tagged isoprene synthase (IspS) enzymes for expression, purification and crystallization.

Strain Construction

For constructs in the pET200D-TOPO vector (Invitrogen), PCR products of the IspS enzymes from *P. alba*, *P. tremuloides*, and *P. trichocharpa* were gel extracted and purified (Qiagen), using 0.8% E-gel (Invitrogen), according to the manufacturer's recommended protocol. PCR reactions for pET200 constructs are as follows: Reaction mixture was 1 μl (Templates)-pET24a-*P.alba*, 5 μl 10× PfuUltraII Fusion buffer, 1 μl dNTP's (10 mM), 1 μl primer (50 uM) primer F-(MCM219 or 218), 1 μl primer (50 uM) primer R-(MCM182), 41 μl diH2O and 1 μl of PfuUltra II Fusion DNA Polymerase from Stratagene; Cycle Parameter were 95° C. 1 min., 95° C. 1 min, 55° C. 20 sec., 72° C. 27 sec. for 29 cycles followed by 72° C. for 3 min and then 4° C. until cool, using an Eppendorf Mastercycler. Similar reactions were performed for *P. tremuloides*, *P. trichocarpa*, and Kudzu. 3 μl of purified product was then ligated to the pET200D/TOPO vector (Invitrogen), according to the manufacturer's protocol. The reaction was incubated for 5 minutes at room temperature, and the 6 μl topoisomerase mixture was then transformed into *E. coli* Top10 chemically competent cells (Invitrogen) according to the manufacturer's protocol. Transformants were selected for on LB Kan50, and incubated at 37° C. overnight. Five colonies per construct were chosen and screened using PuReTaq Ready-To-Go PCR Beads (Amersham) using the T7 Forward and MCM182 primers (Table 15-2). Clones harboring inserts of the correct size were further verified by plasmid miniprep using the QIAPrep Spin Miniprep kit (Qiagen) followed by sequencing using the T7 Forward and T7 Reverse primers (Quintara Biosciences). One fully sequenced construct for each IspS variant (see below for details and sequence/FIGS. 79-90), was chosen for further study. 1 μl of each plasmid was transformed into BL21(λDE3) pLysS (Invitrogen) according to the manufacturer's protocol. Transformants were selected for on LB medium with Kan50+Cm35 and incubated at 37° C. overnight. The resulting strains were used for expression and purification of various IspS enzymes for crystallography studies.

Construction of N-terminally 6His-tagged IspS plasmids, strains and purification is described in Example 11.

TABLE 15-2

Primers

| MCM219 | caccatgcgttgtagcgtgtcca (SEQ ID NO: 114) |
|---|---|
| MCM182 | gggcccgtttaaactttaactagactctgcagttagcgttc aaacggcagaa (SEQ ID NO: 115) |
| MCM218 | caccatgcgtcgttctgcgaactac (SEQ ID NO: 116) |

TABLE 15-3

| | Plasmids |
|---|---|
| *P. alba* pET24a | pET24a with "full length" IspS from *P. alba* |
| *P. trichocharpa* pET24a | pET24a with "full length" IspS from *P. trichocharpa* |
| *P. tremuloides* pET24a | pET24a with "full length" IspS from *P. tremuloides* |
| MBP-Kudzu | |
| pDu27 | P. albaFL-pET200/Top 10 |
| pDu30 | P. albaTRC-pET200/Top10 |
| pDu31 | P. tremTRC-pET200/Top 10 |
| pDu32 | P. trichTRC-pET200/Top10 |
| MD09-161 | pET24a-*P.alba* FL C-Term (+) TEV, His tag/MCM331 |
| MD09-163 | pET24a-*P.alba* TRC (MEA) C-Term (+) TEV, His tag/MCM331 |

TABLE 15-4

Strains

MBP-Kudzu

| | |
|---|---|
| MD08-99 | BL21 DE3 pLys + pDu27 |
| MD08-100 | BL21 DE3 pLys + pDu30 |
| MD08-102 | BL21 DE3 pLys + pDu31 |
| MD08-104 | BL21 DE3 pLys + pDu32 |
| MD09-165 | BL21(DE3)pLysS, pET24a-P.alba FL C-Term (+) TEV, His tag |
| MD09-167 | BL21(DE3) pLysS, pET24a-P.alba TRC (MEA) C-Term (+) TEV, His tag |

III. Digestion of TEV (Tobacco Etch Virus) or EK (Enterokinase)-Tagged Enzymes

TEV Cleavage (IspS from Strains MD09-165 and MD09-167)

Strains MD09-165 and MD09-167 are described in Example 11. For digestion, enzymes were purified through a Ni charged sepharose (GE Healthcare) and desalted into 50 mM HEPES, 50 mM NaCl pH 7.4 buffer containing 1 mM DTT. Digestion was performed with TurboTEV Protease from Eton Bioscience Inc. One unit of TurboTEV per 10 μg of purified protein was used. The digest was performed at 4° C. overnight. Samples were passed through another Ni column equilibrated in the Ni buffer to remove uncleaved enzyme, tag, TurboTEV protease (that is also tagged) and impurities. The Ni column pass though and washes were analyzed using SDS-PAGE gel (NUPAGE, Invitrogen) and DMAPP activity assays. Samples containing pure enzyme were pooled and desalted into 50 mM NaCl pH 7.4 buffer containing 1 mM DTT and stored at –80° C.

EK Cleavage (IspS from Strains MD08-102 and MD08-104)

For digestion enzymes were purified through a Ni charged sepharose (GE Healthcare) and desalted into 50 mM HEPES, 50 mM NaCl pH 7.4 buffer containing 1 mM DTT.

Digestion was performed with EKMax (E180-02) (Invitrogen) using 1 unit of EKMax per 20 μg of purified protein at 4° C. overnight. Samples were passed over EK Away resin (Invitrogen) to remove excess enterokinase. Samples were batched onto Ni charged sepharose resin (equilibrated in the Ni wash buffer) and incubated for 30 min at 4° C., with occasional inverting. This removed uncleaved enzyme, tag, and impurities. The Ni column pass through and washes were analyzed using SDS-PAGE gel (4-12% NUPAGE, Invitrogen) and DMAPP activity assays. Samples containing pure enzyme were pooled and desalted into 50 mM HEPES, 50 mM NaCl pH 7.4 buffer containing 1 mM DTT and stored at –80° C.

IV. Purification of MBP-IspS

Construction of pMAL-C4X Kudzu for the expression of MBP-Kudzu isoprene synthase is described above. MBP-Kudzu isoprene synthase production from E. coli grown in batch culture at the 15-L scale.

Medium Recipe (Per Liter Fermentation Medium)

$K_2HPO_4$ 7.5 g, $MgSO_4*7H_2O$ 2 g, citric acid monohydrate 2 g, ferric ammonium citrate 0.3 g, yeast extract 0.5 g, 1000× Modified Trace Metal Solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution

Citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO*7H_2O$ 1 g, $CuSO_4*5H_2O$ 100 mg, $H_3BO_3$ 100 mg, $NaMoO_4*2H_2O$ 100 mg. Each component is dissolved one at a time in $diH_2O$, pH to 3.0 with HCl/NaOH, then q.s. to volume and filter sterilized with 0.22 micron filter.

Fermentation was performed in a 15-L bioreactor with BL21 (DE3) E. coli cells containing the pMAL-C4X plasmid expressing a maltose binding protein (MBP)-Kudzu isoprene synthase fusion molecule. This experiment was carried out to produce isoprene synthase at the desired fermentation pH 7.0 and temperature 30° C. A frozen vial of the E. coli strain was thawed and inoculated into tryptone-yeast extract medium. After the inoculum grew to OD 1.0, measured at 550 nm ($OD_{550}$), 120 mL was used to inoculate a 15-L bioreactor bringing the initial volume to 9-L.

Expression of the desired molecule was achieved by adding isopropyl-beta-D-1-thiogalactopyranoside (IPTG). The IPTG concentration was brought to 1 mM when the $OD_{550}$ reached a value of 10. Cells containing the desired product were harvested 3 hrs after IPTG addition.

MBP-IspS Purification

The broth was centrifuged for 15 min at 10000×g. The pellet was collected and frozen at –80° C. until further purification. Cells were resuspended in MBP-Bind Buffer (5% glycerol, 20 mM Tris pH 7.4, 200 mM NaCl, 2 mM DTT, 1 mg/ml lysozyme) and passed through the french press three times at 20000 psi. The lysate was then ultracentrifuged at 100000×g for 1 hour to yield a relatively clear solution. The supernatant was pipetted from the top of the tube without disturbing the gelatinous material on the bottom of the centrifuge tube. Gel filtration was performed on the supernatant using a Superdex-200 26/60 column (GE healthcare). The column was developed using MBP-Bind buffer at a flow rate of 3 mL/min at 23° C. Fractions were tested for DMAPP activity as described below. Active fractions were pooled and loaded onto 25 mL amylose resin (New England Biolabs). The column was washed with 10 column volumes MBP-Bind buffer and the protein was then eluted with 2 column volumes of MBP-Bind buffer containing 10 mM maltose to yield >90% pure MBP-IspS.

V. DMAPP Assay

The following reaction mixture was used for the DMAPP assay: 25 μL lysate mixture, 5 μL $MgCl_2$ (1 M), 5 μL DMAPP (100 mM), and 65 μL 100 mM Tris pH 8, 100 mM NaCl for a total volume of 100 μL. The reaction is performed at 30° C. for 15 minutes in a gas tight 1.8 mL GC tube. Reactions are terminated by the addition of 100 μL 500 mM EDTA (pH 8). The amount of isoprene produced was measured by GC/MS as described above.

EXAMPLE 16

Three-Dimensional Structure of IspS

Seven constructs of plant isoprene synthase (IspS) were prepared to generate crystals suitable for x-ray diffraction. These were: a construct containing N-terminal histidine-tagged maltose binding protein and kudzu IspS (MBP-kudzu), full-length P. alba IspS with N-terminal histidine-tag (MD08-99), P. alba IspS with the first nineteen N-terminal residues removed (MD08-100), this construct also had the N-terminal his-tag removed after purification. Full-length, untagged P. alba IspS (strain RM11608-2). A truncated P. alba IspS construct featuring two additional residues before the twin-arginine motif was generated (MD09-167). P. tricharpa IspS was generated, which contains both an N-terminal his-tag and N-terminal truncation (MD08-104), and another construct composed of IspS from P. tremuloides was generated with an N-terminal his-tag and N-terminal truncation (MD08-102). Construction of strains expressing various isoprene synthases are described above.

Each construct was purified and a concentrated protein solution was then prepared for surveying possible crystallization conditions. Each construct was purified independently and surveyed as described below. All in-house crystallization screens were set up using the hanging drop vapor diffusion method. At a minimum, each construct was surveyed using the following commercial screens: the Crystal Screen from Hampton Research (Aliso Viejo, Calif.) and the JCSG+Suite from Qiagen (Valencia, Calif.).

Purified MBP-kudzu using was set up using the following commercial screens: the Crystal Screen from Hampton Research and the JCSG+Suite from. Additionally, purified MBP-kudzu was sent to the Hauptman-Woodward Institute (Buffalo, N.Y.) for high-throughput screening, where no fewer than 1536 conditions were surveyed. The purified MBP-kudzu fusion precipitated out of solution in the majority of conditions, and no protein crystals were observed.

The next construct used for crystallization screening was MD08-99 (full-length P. alba IspS with N-terminal histidine-tag). MD08-99 was purified and the histidine-tag was removed. The same three initial crystallization screens were performed as for MBP-kudzu. The Hampton Research Crystal Screen and Qiagen JCSG+Suite were each performed at multiple protein concentrations. Small needle-like crystals were observed in some Hampton Research Crystal Screen conditions. Further attempts to improve the crystals involved co-crystallization with the IspS inhibitor sodium ibandronate (Sigma-Aldrich, St Louis, Mo.). Taken together, an additional 288 crystallization conditions were attempted with variations of pH, concentration, and crystallization reagents. The nine best crystals were then prepared for data collection and tested in-house on a Rigaku RU200 rotating anode generator and R-AXIS IV++, and they either did not diffract x-rays or were salt crystals.

The first nineteen N-terminal residues of P. alba IspS were removed to produce construct MD08-100. This construct had the N-terminal histidine-tag removed after purification. In house crystallization screens were performed using the Hampton Research Crystal Screen and Qiagen JCSG+Suite, each with multiple protein concentrations. Initial crystal hits included hexagonal plates that diffracted to 16 Å resolution, and small rods that diffracted to 5 Å resolution using the in-house x-ray generator. In an attempt to improve the crystals, MD08-100 was co-crystallized with either sodium ibandronate or sodium pyrophosphate (Sigma-Aldrich, St Louis, Mo.), both of which are inhibitors of the IspS activity. Neither inhibitor resulted in improved crystals or improved diffraction. An additional 168 crystallization conditions were attempted with variations of pH, concentration, and crystallization reagents. The twenty-one most promising MD08-100 crystals were screened for diffraction, with the best resolution obtained being 5 Å.

Full-length, untagged P. alba IspS (strain RM11608-2) from a fermentation run was purified. An initial screen was set up using the Hampton Research Crystal Screen, and crystals were observed in four different conditions. All four crystals were tested for diffraction in-house, with three being salt crystals and one not diffracting.

A truncated P. alba IspS construct featuring two additional residues before the twin-arginine motif was generated (MD09-167). This construct contains a C-terminal histidine-tag, and crystallization experiments were set up with the tag either cleaved or not cleaved, at varying protein concentrations, and with or without sodium pyrophosphate. Initial crystallization screens were done as per MBP-kudzu. Crystals from this construct were observed in numerous conditions; optimization included 528 variations of pH, precipitating agents, concentrations, and inhibitors. From the optimization experiments, fifteen different MD09-167 crystals were screened in-house for diffraction. In an effort to improve the resolution, various crystal freezing conditions were tested, with the effect of improving the diffraction limits from 10 Å to 6.5 Å.

A new construct containing P. tricharpa IspS was generated, which contains both an N-terminal histidine-tag and an N-terminal truncation (MD08-104). Purified MD08-104 with cleaved histidine-tag was surveyed using the Hampton Research Crystal Screen and the Qiagen JCSG+suite. This construct generated heavier precipitate than the P. alba IspS constructs. Very small needles were observed, with none of the crystals being suitable for diffraction.

Another construct composed of IspS from P. tremuloides was generated with an N-terminal histidine-tag and an N-terminal truncation (MD08-102). Purified MD08-102 with and without cleaved histidine-tag was set up using the Hampton Research Crystal Screen and the Qiagen JCSG+Suite at varying protein concentrations. Rod and plate-like crystals were observed in some conditions and an additional 120 experiments were performed to improve the crystals by varying pH, concentration, and crystallization reagents. From the optimization experiments, ten crystals were tested in-house, with the initial best diffraction reaching 5 Å. Upon further modification of the freezing conditions of the crystals, a crystal was found that diffracted to 3.3 Å from the non-cleaved histidine-tagged protein. This crystal was grown by mixing 2 µL of protein (10 mg/ml, with 30 mM $MgCl_2$) with 2 µL of precipitant solution [10% (wt/vol) polyethylene glycol 8000, 0.1 M HEPES, pH 7.5, 8% ethylene glycol] and equilibrated against 500 µL of precipitant. A cluster of rod-shaped crystals appeared after three weeks. The crystals belong to the tetragonal space group P43212, and have unit cell dimensions a=154.2, b=154.2, c=142.7.

In-house x-ray diffraction data were collected under a nitrogen stream at 100 K using a Rigaku RU200 generator and R-AXIS IV++ detector. Before flash-freezing the crystal in liquid nitrogen, it was cryoprotected by swiping it through a solution containing 10% (wt/vol) polyethylene glycol 8000, 0.1 M HEPES, pH 7.5, and 25% ethylene glycol. Data were integrated using Mosflm (Leslie, A. (1998) J. of Appl. Crystallography 30, 1036-1040) and scaled using SCALA (Collaborative Computational Project, N. (1994) Acta Crystallographica Section D 50, 760-763). The data were then phased by molecular replacement using MrBUMP (Keegan, R. M., and Winn, M. D. (2007) Acta Crystallographica Section D 63, 447-457; Vagin, A., and Teplyakov, A. (1997) J. of Appl. Crystallography 30, 1022-1025), with a monomer of limonene synthase (Protein Data Bank ID 2ONH)(Berman, H., et al. (2007) Nucl. Acids Res. 35, D301-303) as the starting model. The crystal contains one dimer in the asymmetric unit with a solvent content of 66%.

A 3.05 Å data set from the same crystal was then collected using beamline 11-1 of the Stanford Synchrotron Radiation Laboratory. These data were also processed using Mosflm and SCALA. Data collection and refinement statistics are given in Table 16-1.

Refinement with Refmac5 (Collaborative Computational Project, N. (1994) Acta Crystallographica Section D 50, 760-763) was used with iterative manual rebuilding steps using the visualization program Coot (Emsley, P., and Cowtan, K. (2004) Acta Crystallographica Section D 60, 2126-2132). During refinement, the geometry of the protein was checked using Molprobity (Davis, I. W., et al. (2007) Nucl. Acids Res., gkm216).

The fold of poplar IspS is similar to bornyl diphosphate synthase (Whittington, D. A., et al. (2002) Proc. Natl. Acad. Sci. USA 99, 15375-15380), limonene synthase (Hyatt, D. C., et al. (2007) Proc. Natl. Acad. Sci. USA 104, 5360-5365), and tobacco 5-epi-aristolochene synthase (Starks, C. M., et al.

Figure 91:
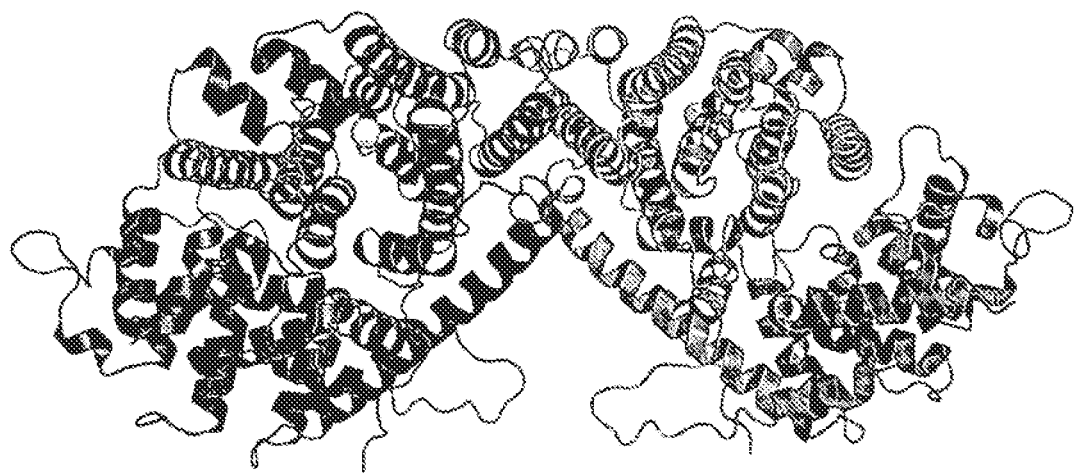
FIG. 91 provides the three-dimensional structure of *P. tremuloides* IspS shown as a dimer. Chain A is in dark gray, chain B is in medium gray and the single magnesium ion found in each active site is light gray.
Figure 92:
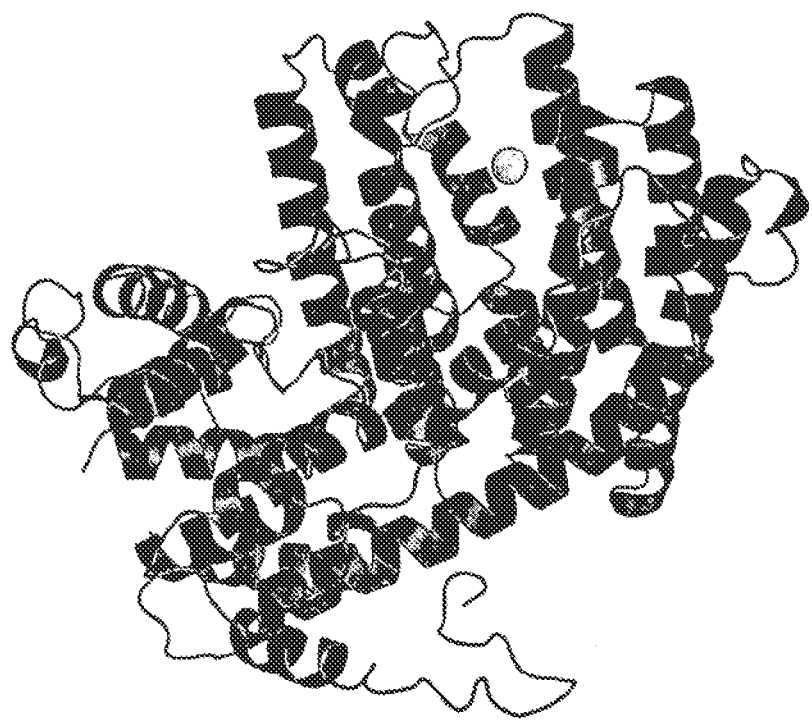
FIG. 92 provides a monomer view of the structure of *P. tremuloides* IspS. The magnesium is shown as a light gray sphere and the N- and C-terminals are indicated.
Figure 93:
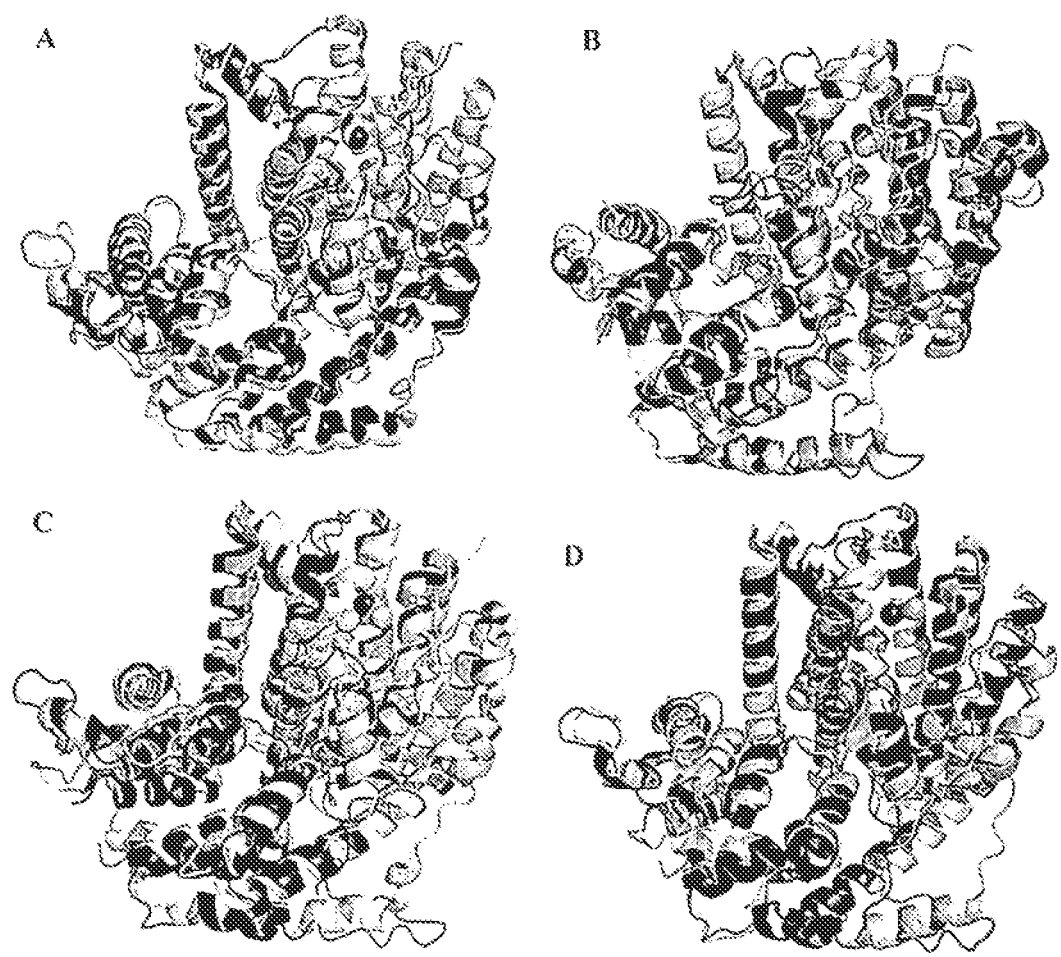
FIG. 93 shows the structural alignments between (A) BdpS and LS, (B) BdpS and poplar IspS, (C) LS and poplar IspS, and (D) TEAS and poplar IspS. In each case the first structure is in light gray and the second is in dark gray. Divalent cations are shown as spheres.

(1997) Science 277, 1815-1820). The structure consists of two helical domains, a C-terminal domain containing the active site and N-terminal domain (FIGS. 90 and 91). Coordinates are provided in Table 16-7.

TABLE 16-1

Data Collection and Refinement Statistics

| Data Collection | |
| --- | --- |
| Space Group | P4$_3$2$_1$2 |
| Cell dimensions | |
| a, b, c (Å) | 154.2, 154.2, 142.7 |
| α, β, γ, (°) | 90.0, 90.0, 90.0 |
| Resolution (Å) | 37.8-3.05 |
| R$_{merge}$ | 16.4 (72.9)$^a$ |
| <I/σI> | 10.3 (2.6) |
| Completeness (%) | 99.8 (100) |
| Redundancy | 7.3 (7.4) |
| Refinement | |
| Resolution (Å) | 37.8-3.05 |
| No. measured reflections | 248741 |
| No. Unique reflections | 34201 |
| R$_{work}$ | 21.1 |
| R$_{free}$ | 27.1 |
| rmsd bonds, (Å) | 0.011 |
| rmsd angles, (°) | 1.28 |
| No. of Atoms | |
| Protein, ions$^b$ | 8331 |
| Water | 18 |

Flexible Loops

Figure 94:
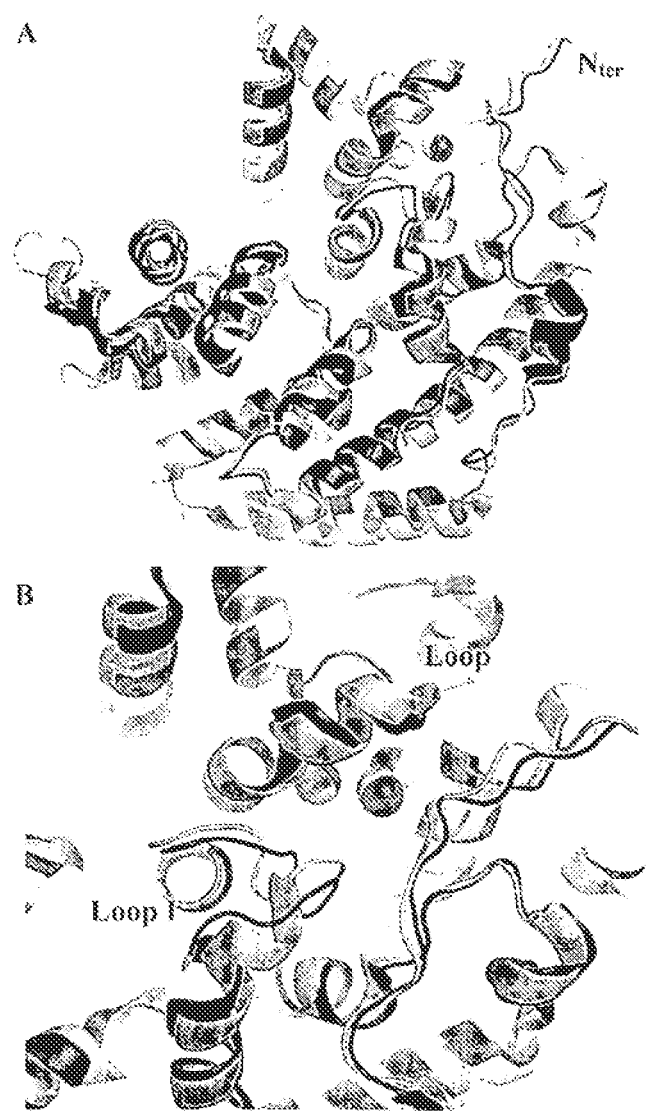
FIG. 94 shows the three dimensional structure of loops in BdpS and LS. Panel A shows the N-terminal loop of Ls in light gray and the N-terminal loop of BdpS in dark gray. Panel B shows that Loop I and Loop II are structurally homologous.
Figure 95:
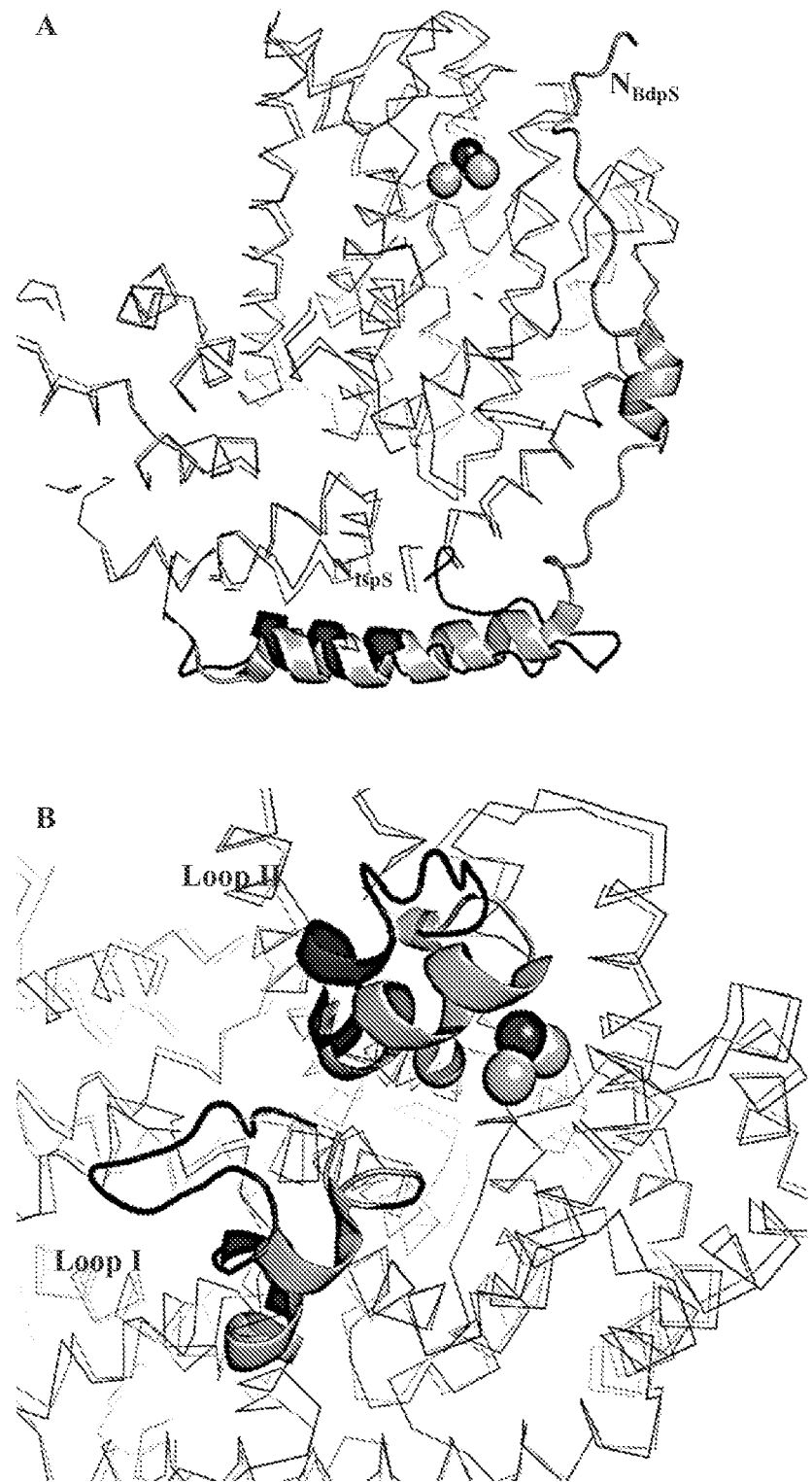
FIG. 95 shows the N-terminal loop of BdpS (dark gray) and poplar IspS (light gray) are structurally divergent. Panel A shows the N-terminal loop and panel B shows Loop I and Loop II.
Figure 97:
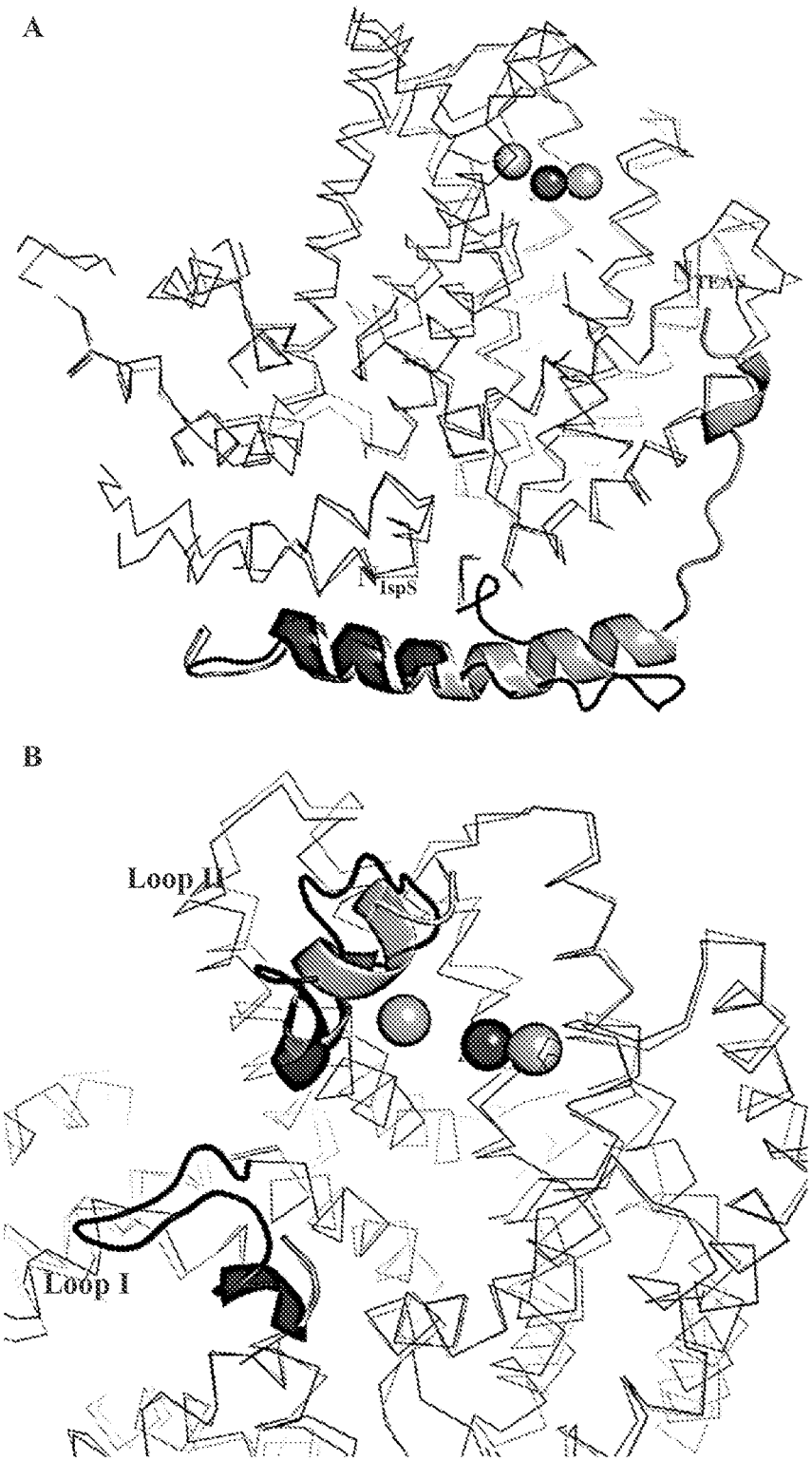
FIG. 97 shows the N-terminal loop of TEAS (light gray) and poplar IspS (dark gray) are structurally divergent. Panel A shows the N-terminal loop and panel B shows Loop I and Loop II. Loop I is disordered in TEAS.

The unique and unexpected discovery coming from the determination of the three dimensional structure of isoprene synthase is that several crucial loops forming the active site are flexible. The discovery can be immediately seen when the known structure of other terpene synthases are compared with the structure of isoprene synthase (FIG. 94). Overall, the structures are highly conserved in the conformation of secondary structure and connectivity loops. (In this example of the *Poplar tremuloides* IspS from construct P.tremTRC-pET200, the numbering convention is such that the first number of the complete sequence containing the tag is −35, with the first residue of IspS being 1.) However, three segments, forming a considerable portion of the substrate binding pocket, notably the truncated N-terminus, along with two loops comprised of residues 438-453 (Loop I) and residues 512-527 (Loop II) are seen to diverge (FIGS. 95 to 97). This has been attributed to the absence of substrate complexed with the enzyme in our structure determination.

In comparing the enzyme with BdpS, for example, we find that the loops corresponding to residues 498-513 and 573-587 are composed of the same number of residues and have a homologous, but not identical amino sequence in these regions. We expect that the related terpene synthases will be found to display similar flexibility in the segments as these structure become more thoroughly studied. The residues in terpene synthases corresponding to these variable loop regions are enumerated in Table 16-2.

TABLE 16-2

Residues corresponding to variable loops in terpene synthases

| | Poplar IspS | LS | BdpS | TEAS |
| --- | --- | --- | --- | --- |
| N-term I | Met 1 | Met 57 | Ile 54 | Val 14 |
| | Arg 2 | Arg 58 | Arg 55 | Arg 15 |
| | Arg 3 | Arg 59 | Arg 56 | Pro 16 |
| | Ser 4 | Ser 60 | Ser 57 | Val 17 |
| | Ala 5 | Gly 61 | Gly 58 | Ala 18 |

TABLE 16-2-continued

Residues corresponding to variable loops in terpene synthases

| | Poplar IspS | LS | BdpS | TEAS |
| --- | --- | --- | --- | --- |
| | Asn 6 | Asn 62 | Asn 59 | Asp 19 |
| | Tyr 7 | Tyr 63 | Tyr 60 | Phe 20 |
| | Glu 8 | Asn 64 | Gln 61 | Ser 21 |
| | Pro 9 | Pro 65 | Pro 62 | Pro 22 |
| | Asn 10 | Ser 66 | Ala 63 | Ser 23 |
| | Ser 11 | Arg 67 | Leu 64 | Leu 24 |
| | Trp 12 | Trp 68 | Trp 65 | Trp 25 |
| | Asp 13 | Asp 69 | Asp 66 | Gly 26 |
| | Tyr 14 | Val 70 | Ser 67 | Asp 27 |
| | Asp 15 | Asn 71 | Asn 68 | Gln 28 |
| | Tyr 16 | Phe 72 | Tyr 69 | Phe 29 |
| N-term II | Leu 17 | Ile 73 | Ile 70 | Leu 30 |
| | Leu 18 | Gln 74 | Gln 71 | Ser 31 |
| | Ser 19 | Ser 75 | Ser 72 | Phe 32 |
| | Ser 20 | Leu 76 | Leu 73 | Ser 34 |
| | Asp 21 | Leu 77 | Asn 74 | Ile 35 |
| | Thr 22 | Ser 78 | Thr 75 | Asp 36 |
| | Asp 23 | Asp 79 | Pro 76 | Asn 37 |
| | Glu 24 | Tyr 80 | Tyr 77 | Gln 38 |
| | Ser 25 | Lys 81 | Thr 78 | Val 39 |
| | Ile 26 | Glu 82 | Glu 79 | Ala 40 |
| | Glu 27 | Asp 83 | Glu 80 | Glu 41 |
| | Val 28 | Lys 84 | Arg 81 | Lys 42 |
| Loop I | Leu 438 | Leu 498 | Leu 498 | Thr 446 |
| | Ala 439 | Gly 499 | Gly 499 | Ala 447 |
| | Ser 440 | Thr 500 | Thr 500 | The 448 |
| | Ala 441 | Ser 501 | Ser 502 | Tyr 449 |
| | Ser 442 | Val 502 | Tyr 503 | Glu 450 |
| | Ala 443 | Glu 503 | Phe 504 | Val 451 |
| | Glu 444 | Glu 504 | Glu 505 | Glu 452 |
| | Ile 445 | Val 505 | Leu 506 | Lys 453 |
| | Ala 446 | Ser 506 | Ala 507 | Ser 454 |
| | Arg 447 | Arg 507 | Arg 508 | Arg 455 |
| | Gly 448 | Gly 508 | Gly 509 | Gly 456 |
| | Glu 449 | Asp 509 | Asp 510 | Gln 457 |
| | Thr 450 | Val 510 | Val 511 | Ile 458 |
| | Ala 451 | Pro 511 | Pro 512 | Ala 459 |
| | Asn 452 | Lys 512 | Lys 513 | Thr 460 |
| | Ser 453 | Ser 513 | Thr 514 | Gly 461 |
| Loop II | Tyr 512 | Tyr 576 | Tyr 573 | Tyr 520 |
| | | | | Ile 521 |
| | His 513 | His 577 | Leu 574 | His 522 |
| | Asn 514 | Asn 578 | His 575 | Asn 523 |
| | Gly 515 | Gly 579 | Gly 576 | Leu 524 |
| | Asp 516 | Asp 580 | Asp 577 | Asp 525 |
| | Ala 517 | Gly 581 | Gly 578 | Gly 526 |
| | His 518 | His 582 | Phe 579 | Tyr 527 |
| | Thr 519 | Gly 583 | Gly 580 | The 528 |
| | Ser 520 | Thr 584 | Val 581 | His 529 |
| | Pro 521 | Gln 585 | Gln 582 | Pro 530 |
| | Asp 522 | His 585 | His 583 | Glu 531 |
| | Glu 523 | Pro 586 | Ser 584 | Lys 532 |
| | Leu 524 | Ile 587 | Lys 585 | Val 533 |
| | Thr 525 | Ile 588 | Thr 586 | Lue 534 |
| | Arg 526 | His 589 | Tyr 587 | Lys 535 |

This important finding can be exploited for the engineering of improved isoprene synthase in a straightforward manner. It would be desirable to exploit the flexibility to enhance enzyme performance by making substitutions in the amino aids forming these segments to facilitate the transitions the enzyme must undergo in the steps of binding substrate and allowing rearrangement of substrate in different kinetic steps that are postulated to occur during enzymatic de-phosphorylation and for electron transfer to convert DMAPP to isoprene.

The structure provides the new insight that these loops can be present in at least two conformations: the "open" form in the absence of substrate, as we have see in the uncomplexed structure of the isoprene synthase, and a "closed," or active form when the substrate is bound. It would therefore also be beneficial to modify residues coming in contact with the loops in the active form as described in Table 16-3.

TABLE 16-3

Residues coming within 5 angstroms of flexible elements

|  | P trem IspS | 1N1B | 2ONG | 5EAS[e] |
|---|---|---|---|---|
| N-term neigbors | L17, L18, S19, S20, S239, R243, F253, A254, R255, D256, R257, I259, E260, D293, Y295, D296, V297, Y298, G299, T300, E303, Y325, L374, Y375, elements of loop I, elements of loop II, V529, L530, T534 | 70I, 71Q, 72S, 73L, 298S, 302S, 312F, 313V, 314R, 315D, 316R, 318V, 319E, 352D, 354Y, 355D, 356V, 357Y, 358G, 359T, 362E, 384Y, 433Y, 434H, elements of loop I, elements of loop II, 589I, 590A, 594F | I73, Q74, S75, L76, F299, R303, F313, A314, R315, A316, R317, V319, E320, D353, Y355, D356, V357, Y358, G359, T360, E363, Y385, F434, Y435, elements of loop I, elements of loop II, M590, T591, F595 | L30, S31, F32, S33, S248, K252, Y262, A263, R264, D265, R266, V268, E269, D302, F304, D305, A306, Y307, G308, T309, E312, Y334, F383, I384, elements of loop I, elements of loop II, I538, I538, V543 |
| Loop I neighbors | Elements of N-term, D293, Y295, V297, E370, A371, W373, L374, S378, T379, P380, F382, Y385, F386, R433, L434 C435, N436, D437, V454, S455, C456, Y457, M458, T469, V472, I476, Y512, elements of loop II | Elements of N-term, 352D, 354Y, 356V, 429E, 430A, 432W, 433Y, 437Y, 438T, 439P, 441L, 444Y, 445L, 493R, 494L, 495P, 496D, 497D, 514I, 515Q, 516C, 517Y, 518M, 529V, 532V, 536I, 572Y, elements of loop II | Elements of N-term, D353, Y355, V357, E430, A431, W433, F434, H438, K439, P440, L442, Y445, L446, R493, L494, A495, D496, D497, L514, Q515, C516, Y517, M518, R529, V532, I536, Y573, elements of loop II | Elements of N-term, D304, F304, A306, E379, S380, W382, F383, Y387, T388, P389, V391, Y394, L395, R441, V442, I443, D444, D445, I462, E463, C464, C465, M466, M477, F480, A484, Y520, elements of loop II |
| Loop II neighbors | Elements of N-terminus, E187, L188, R255, R257, F270, E271, Q273, Y274, F285, V288, A439, S440, S442, S508, H509, C510, T511, Y512, R528, V529, L530, S531, V532 | Elements of N-terminus, 246D, 247L, 314R, 316R, 329E, 330S, 332F, 333W, 344I, 348I, 499G, 500T, 503Y, 568A, 569Q, 570F, 571I, 572Y, 588H, 589I, 590A, 591G, 592L | Elements of N-terminus, D247, I248, R315, R317, E330, P331, Q333, H334, N345, I347, G499, T500, V502, A569, Q570, L571, M572, Y573, Q589, M590, T591, R592, T593 | Elements of N-terminus, E195, Q196, R264, R266, F279, E280, Q282, Y283, I294, I297, A447, T448, E450, V516, E517, V518, T519, Y520, H537, I538, I539, N540, L541 |

Selection of Sites for Improvement of Plant Isoprene Synthase

The isoprene synthases of plants were expected to be homologous to the terpene synthases. The three-dimensional structures of three homologous terpene synthases have been determined: *Salvia officinalis* bornyl diphosphate synthase (BdpS; pdb entry 1N1B), *Mentha spicata* limonene synthase (LS; pdb entry 2ONG), and tobacco 5-epi-aristolochene synthase (TEAS; pdb entry 5EAS). These enzymes share only 33% homology but their tertiary structure is conserved. Sequence identity is shown in Table 16-4, and structural homology between the structures is shown in Table 16-5. In addition, the structures of intermediate complexes with all three related enzymes have shown that not only tertiary folding, but also detailed interactions in the active sites of these enzymes are highly conserved.

TABLE 16-4

Percent Identity of Terpene Cyclases.

|  | P trem IspS | 1N1B | 2ONG | 5EAS[e] |
|---|---|---|---|---|
| P alba IspS[a] | 98.6 | 40.7 | 41.3 | 33.2 |
| P trem IspS[b] |  | 41.0 | 41.4 | 33.2 |
| 1N1B[c] |  |  | 51.4 | 33.8 |
| 2ONG[d] |  |  |  | 33.3 |

[a]Polar alba isoprene synthase
[b]Polar tremuloides isoprene synthase
[c]bornyl diphosphate synthase
[d]limonene synthase
[e]5-epi-aristolochene synthase

TABLE 16-5

Structural Alignment of Terpene Synthases

|  | 1N1B[b] | 2ONG[c] | 5EAS[d] |
|---|---|---|---|
| P trem IspS[a] | 1.40 (465)[e] | 1.29 (468) | 1.62 (458) |
| 1N1B |  | 1.27 (520) | 1.97 (476) |
| 2ONG |  |  | 1.83 (477) |

[a]Polar tremuloides isoprene synthase
[b]bornyl diphosphate synthase
[c]limonene synthase
[d]5-epi-aristolochene synthase
[e]Root mean square deviation in Å for Cα atoms, with the number of aligned residues in parenthesis In this example of the *Poplar tremuloides* IspS from construct P.tremTRC-pET200, the numbering convention is such that the first number of the complete sequence containing the tag is −35, with the first residue of IspS being 1.

A comparison of the active site from the structure of BdpS and the structure of poplar IspS indicates that the active site involved in metal ion binding and phosphate recognition is conserved. In particular, Arg 255, Asp 292, Asp 296, Glu 370, Arg 433 and Asn 436 of poplar IspS were observed to overlap equivalent residues in BdpS. The positioning of an intermediate of the BdpS was also compared with the poplar IspS structure. Based on this it was possible to identify the analogous binding region and the approach direction that dimethylallyl pyrophosphate would require in order to bind and react with the poplar IspS enzyme.

Based on the structure of poplar IspS, sites in the poplar IspS were identified as candidates for mutagenesis to produce variant IspS enzymes with improved performance. Briefly, sites were selected in the IspS that might alter the interaction of the metal binding, diphosphate recognition, DMAPP chain binding and/or the approach to the active site.

I. Diphosphate/Metal Binding Sites

The side chains of amino acid residues in the poplar IspS that are found in proximity to the metal and diphosphate binding side chains were identified. These residues include Asp 293, Tyr 385, Ser 392, and Asp 437. Engineering of these sites may result in increased enzyme activity.

II. Substrate Access Loops

The substrate access loops of poplar IspS are in regions that deviate from the BdpS structure. In the BdpS structure the residues create a cover over the active site. It is likely that upon substrate binding the structure of poplar IspS will form a similar structure. As such the residues in these loops, including residues 440-453 and 512-524, may be in a position to alter the activity of the poplar IspS. In the poplar IspS enzyme, residues 440-453 have the sequence SASAEIARGETANS and residues 512-526 have the sequence YHNGDAHTSPDEL.

III. Isoprenyl Binding Site

The complex of BdpS and the product of the reaction, bornyl diphosphate (PDB entry 1N24), was used to identify residues in the poplar IspS structure that with protein engineering may be used modulate substrate specificity and/or reaction rate (altered on and off rates of substrate and product). These residues include Ser 261, Trp 264, Phe 285, Thr 289, Ser 393, Ser 394, Phe 432, and Try 512.

TABLE 16-6

Candidate mutagenesis sites.

| | Poplar IspS |
|---|---|
| DPP/Metal Binding Sites | Asp 293 |
| | Tyr 385 |
| | Ser 392 |
| | Asp 437 |
| Substrate Access Loop I | Ser 440 |
| | Ala 441 |
| | Ser 442 |
| | Ala 443 |
| | Glu 444 |
| | Ile 445 |
| | Ala 446 |
| | Arg 447 |
| | Gly 448 |
| | Glu 449 |
| | Thr 450 |
| | Ala 451 |
| | Asn 452 |
| | Ser 453 |
| Substate Access Loop II | Tyr 512 |
| | His 513 |
| | Asn 514 |
| | Gly 515 |
| | Asp 516 |
| | Ala 517 |
| | His 518 |
| | Thr 519 |
| | Ser 520 |
| | Pro 521 |
| | Asp 522 |
| | Glu 523 |
| | Leu 524 |
| Isoprenyl Binding Site | Ser 261 |
| | Trp 264 |
| | Phe 285 |
| | Thr 289 |
| | Ser 393 |
| | Ser 394 |
| | Phe 432 |
| | Tyr 512 |

TABLE 16-7

Coordinates of *P. tremuloides* IspS

```
HEADER    ----              XX-XXX-XX    xxxx
COMPND    ---
REMARK  3
REMARK  3   REFINEMENT.
REMARK  3     PROGRAM    : REFMAC 5.5.0088
REMARK  3     AUTHORS    : MURSHUDOV, VAGIN, DODSON
REMARK  3
REMARK  3     REFINEMENT TARGET: MAXIMUM LIKELIHOOD
REMARK  3
REMARK  3   DATA USED IN REFINEMENT.
REMARK  3     RESOLUTION RANGE HIGH (ANGSTROMS):   3.05
REMARK  3     RESOLUTION RANGE LOW  (ANGSTROMS): 110.17
REMARK  3     DATA CUTOFF       (SIGMA(F)): NONE
REMARK  3     COMPLETENESS FOR RANGE     (%): 99.67
REMARK  3     NUMBER OF REFLECTIONS        : 32446
REMARK  3
REMARK  3   FIT TO DATA USED IN REFINEMENT.
REMARK  3     CROSS-VALIDATION METHOD      : THROUGHOUT
REMARK  3     FREE R VALUE TEST SET SELECTION: RANDOM
REMARK  3     R VALUE    (WORKING + TEST SET): .21396
REMARK  3     R VALUE       (WORKING SET): .21092
REMARK  3     FREE R VALUE             : .27112
REMARK  3     FREE R VALUE TEST SET SIZE (%): 5.1
REMARK  3     FREE R VALUE TEST SET COUNT   : 1727
REMARK  3
REMARK  3   FIT IN THE HIGHEST RESOLUTION BIN.
REMARK  3     TOTAL NUMBER OF BINS USED    :      20
REMARK  3     BIN RESOLUTION RANGE HIGH    :   3.050
REMARK  3     BIN RESOLUTION RANGE LOW     :   3.129
REMARK  3     REFLECTION IN BIN (WORKING SET):     2359
REMARK  3     BIN COMPLETENESS (WORKING + TEST) (%):  100.00
REMARK  3     BIN R VALUE (WORKING SET): .288
REMARK  3     BIN FREE R VALUE SET COUNT    :    127
```

TABLE 16-7-continued

Coordinates of *P. tremuloides* IspS

```
REMARK  3    BIN FREE R VALUE            :   .352
REMARK  3
REMARK  3    NUMBER OF NON-HYDROGEN ATOMS USED IN REFINEMENT.
REMARK  3     ALL ATOMS            :    8349
REMARK  3
REMARK  3    B VALUES.
REMARK  3     FROM WILSON PLOT      (A**2): NULL
REMARK  3     MEAN B VALUE     (OVERALL, A**2): 24.592
REMARK  3     OVERALL ANISOTROPIC B VALUE.
REMARK  3      B11 (A**2):    .41
REMARK  3      B22 (A**2):    .41
REMARK  3      B33 (A**2):   -.81
REMARK  3      B12 (A**2):    .00
REMARK  3      B13 (A**2):    .00
REMARK  3      B23 (A**2):    .00
REMARK  3
REMARK  3    ESTIMATED OVERALL COORDINATE ERROR.
REMARK  3     ESU BASED ON R VALUE       (A): NULL
REMARK  3     ESU BASED ON FREE R VALUE     (A):  .427
REMARK  3     ESU BASED ON MAXIMUM LIKELIHOOD      (A):  .327
REMARK  3     ESU FOR B VALUES BASED ON MAXIMUM LIKELIHOOD (A**2): 39.836
REMARK  3
REMARK  3    CORRELATION COEFFICIENTS.
REMARK  3     CORRELATION COEFFICIENT FO-FC      :   .916
REMARK  3     CORRELATION COEFFICIENT FO-FC FREE:    .868
REMARK  3
REMARK  3    RMS DEVIATIONS FROM IDEAL VALUES     COUNT    RMS     WEIGHT
REMARK  3     BOND LENGTHS REFINED ATOMS       (A): 8495; .011; .022
REMARK  3     BOND LENGTHS OTHERS       (A): 5804; .001; .020
REMARK  3     BOND ANGLES REFINED ATOMS (DEGREES): 11476; 1.279; 1.953
REMARK  3     BOND ANGLES OTHERS       (DEGREES): 14093; .882; 3.000
REMARK  3     TORSION ANGLES, PERIOD 1    (DEGREES): 1020; 7.002; 5.000
REMARK  3     TORSION ANGLES, PERIOD 2   (DEGREES):   435; 35.412; 24.299
REMARK  3     TORSION ANGLES, PERIOD 3   (DEGREES):   1525; 18.250; 15.000
REMARK  3     TORSION ANGLES, PERIOD 4   (DEGREES):    58; 16.811; 15.000
REMARK  3     CHIRAL-CENTER RESTRAINTS       (A**3): 1266; .070; .200
REMARK  3     GENERAL PLANES REFINED ATOMS     (A): 9416; .005; .020
REMARK  3     GENERAL PLANES OTHERS      (A): 1780; .001; .020
REMARK  3
REMARK  3    ISOTROPIC THERMAL FACTOR RESTRAINTS.    COUNT   RMS    WEIGHT
REMARK  3     MAIN-CHAIN BOND REFINED ATOMS   (A**2): 5104; .514; 1.500
REMARK  3     MAIN-CHAIN BOND OTHER ATOMS   (A**2): 2068; .059; 1.500
REMARK  3     MAIN-CHAIN ANGLE REFINED ATOMS (A**2): 8204; 1.000; 2.000
REMARK  3     SIDE-CHAIN BOND REFINED ATOMS (A**2): 3391; 1.218; 3.000
REMARK  3     SIDE-CHAIN ANGLE REFINED ATOMS (A**2): 3272; 2.157; 4.500
REMARK  3
REMARK  3    NCS RESTRAINTS STATISTICS
REMARK  3     NUMBER OF DIFFERENT NCS GROUPS:  1
REMARK  3
REMARK  3    NCS GROUP NUMBER         : 1
REMARK  3      CHAIN NAMES          : A B
REMARK  3     NUMBER OF COMPONENTS NCS GROUP: 1
REMARK  3       COMPONENT C SSSEQI TO C   SSSEQI CODE
REMARK  3        1    A    17   A    541    6
REMARK  3        1    B    17   B    541    6
REMARK  3          GROUP CHAIN     COUNT   RMS    WEIGHT
REMARK  3    LOOSE POSITIONAL 1  1     (A):  7038; .37; 5.00
REMARK  3    LOOSE THERMAL    1  1 (A**2):   7038; 1.09; 10.00
REMARK  3
REMARK  3    TWIN DETAILS
REMARK  3    NUMBER OF TWIN DOMAINS: NULL
REMARK  3
REMARK  3
REMARK  3    TLS DETAILS
REMARK  3     NUMBER OF TLS GROUPS:  8
REMARK  3     ATOM RECORD CONTAINS RESIDUAL B FACTORS ONLY
REMARK  3
REMARK  3    TLS GROUP:  1
REMARK  3     NUMBER OF COMPONENTS GROUP:   1
REMARK  3     COMPONENTS    C SSSEQI   TO C SSSEQI
REMARK  3     RESIDUE RANGE:   A    17    A    219
REMARK  3     ORIGIN FOR THE GROUP (A): -64.7667 37.6643  -.0896
REMARK  3     T TENSOR
REMARK  3      T11:   .0648 T22:    .0357
REMARK  3      T33:   .0787 T12:    .0200
REMARK  3      T13:   .0129 T23:   -.0089
REMARK  3     L TENSOR
REMARK  3      L11:  3.7204 L22:   1.5111
```

TABLE 16-7-continued

Coordinates of *P. tremuloides* IspS

```
REMARK  3       L33:    2.6701 L12:      .5715
REMARK  3       L13:     .6692 L23:    -.9699
REMARK  3       S TENSOR
REMARK  3       S11:     .0562 S12:     .0478 S13:  -.1976
REMARK  3       S21:    -.1702 S22:    -.0055 S23:   .1376
REMARK  3       S31:     .0900 S32:    -.2188 S33:  -.0507
REMARK  3
REMARK  3    TLS GROUP:  2
REMARK  3     NUMBER OF COMPONENTS GROUP:   1
REMARK  3     COMPONENTS      C SSSEQI   TO C SSSEQI
REMARK  3     RESIDUE RANGE:  A    220    A    287
REMARK  3     ORIGIN FOR THE GROUP (A): -59.5787 8.4529 -.7693
REMARK  3       T TENSOR
REMARK  3       T11:    .1615 T22:     .0645
REMARK  3       T33:    .1539 T12:    -.0314
REMARK  3       T13:   -.0461 T23:     .0198
REMARK  3       L TENSOR
REMARK  3       L11:    2.4192 L22:    4.6709
REMARK  3       L33:     .7709 L12:   -3.2943
REMARK  3       L13:    -.1814 L23:    -.0705
REMARK  3       S TENSOR
REMARK  3       S11:     .0055 S12:   -.0699 S13:  -.2073
REMARK  3       S21:    -.1805 S22:    .0996 S23:   .3781
REMARK  3       S31:     .2596 S32:    .0887 S33:  -.1051
REMARK  3
REMARK  3    TLS GROUP:   3
REMARK  3     NUMBER OF COMPONENTS GROUP:   1
REMARK  3     COMPONENTS      C SSSEQI   TO C SSSEQI
REMARK  3     RESIDUE RANGE: A    288    A    374
REMARK  3     ORIGIN FOR THE GROUP (A): -40.1866 1.6932  .5805
REMARK  3       T TENSOR
REMARK  3       T11:    .1149 T22:     .1003
REMARK  3       T33:    .1629 T12:     .0153
REMARK  3       T13:    .0224 T23:     .0164
REMARK  3       L TENSOR
REMARK  3       L11:    .2271 L22:     .7399
REMARK  3       L33:   4.8529 L12:     .3413
REMARK  3       L13:    .4755 L23:    -.1746
REMARK  3       S TENSOR
REMARK  3       S11:   -.0449 S12:   -.0288 S13:  -.1131
REMARK  3       S21:   -.1346 S22:   -.0665 S23:  -.2749
REMARK  3       S31:   -.0040 S32:    .1558 S33:   .1114
REMARK  3
REMARK  3    TLS GROUP:  4
REMARK  3     NUMBER OF COMPONENTS GROUP:   1
REMARK  3     COMPONENTS      C SSSEQI TO C SSSEQI
REMARK  3     RESIDUE RANGE: A    375    A    541
REMARK  3     ORIGIN FOR THE GROUP (A): -47.2220 21.5399 6.9217
REMARK  3       T TENSOR
REMARK  3       T11:    .1551 T22:     .1194
REMARK  3       T33:    .1485 T12:    -.0666
REMARK  3       T13:    .0275 T23:     .0272
REMARK  3       L TENSOR
REMARK  3       L11:   2.2352 L22:    2.1698
REMARK  3       L33:   2.3370 L12:    -.4501
REMARK  3       L13:   2.2662 L23:    -.1852
REMARK  3       S TENSOR
REMARK  3       S11:    .0233 S12:   -.3041 S13:  -.0323
REMARK  3       S21:    .3375 S22:    .0236 S23:   .0121
REMARK  3       S31:    .0592 S32:   -.2979 S33:  -.0469
REMARK  3
REMARK  3    TLS GROUP:   5
REMARK  3     NUMBER OF COMPONENTS GROUP:   1
REMARK  3     COMPONENTS      C SSSEQI   TO C SSSEQI
REMARK  3     RESIDUE RANGE: B     17    B    219
REMARK  3     ORIGIN FOR THE GROUP (A): -73.9834 -39.9016 -18.5783
REMARK  3       T TENSOR
REMARK  3       T11:    .0658 T22:     .1153
REMARK  3       T33:    .1251 T12:    -.0621
REMARK  3       T13:   -.0164 T23:    -.0098
REMARK  3       L TENSOR
REMARK  3       L11:   4.6230 L22:    1.7260
REMARK  3       L33:   3.8816 L12:    -.4202
REMARK  3       L13:  -1.8646 L23:    -.9046
REMARK  3       S TENSOR
REMARK  3       S11:   -.0685 S12:    .0375 S13:  -.0003
REMARK  3       S21:    .1931 S22:    .0510 S23:  -.0097
REMARK  3       S31:    .0317 S32:   -.2047 S33:   .0175
```

TABLE 16-7-continued

Coordinates of *P. tremuloides* IspS

| REMARK | 3 | | | | | | | | | |
|---|---|---|---|---|---|---|---|---|---|---|
| REMARK | 3 | TLS GROUP: | 6 | | | | | | | |
| REMARK | 3 | NUMBER OF COMPONENTS GROUP: | 1 | | | | | | | |
| REMARK | 3 | COMPONENTS | C SSSEQI TO C SSSEQI | | | | | | | |
| REMARK | 3 | RESIDUE RANGE: B | 220 | B | 287 | | | | | |
| REMARK | 3 | ORIGIN FOR THE GROUP (A): −62.1586 −12.7634 −18.1912 | | | | | | | | |
| REMARK | 3 | T TENSOR | | | | | | | | |
| REMARK | 3 | T11: | .1825 T22: | .0804 | | | | | | |
| REMARK | 3 | T33: | .1512 T12: | .0549 | | | | | | |
| REMARK | 3 | T13: | .0773 T23: | .0208 | | | | | | |
| REMARK | 3 | L TENSOR | | | | | | | | |
| REMARK | 3 | L11: | 5.4421 L22: | 4.0606 | | | | | | |
| REMARK | 3 | L33: | 1.5369 L12: | 4.6706 | | | | | | |
| REMARK | 3 | L13: | −2.0058 L23: | −1.5537 | | | | | | |
| REMARK | 3 | S TENSOR | | | | | | | | |
| REMARK | 3 | S11: | .1622 S12: | .0431 S13: | .3257 | | | | | |
| REMARK | 3 | S21: | .1755 S22: | .0292 S23: | .2977 | | | | | |
| REMARK | 3 | S31: | −.1910 S32: | −.0506 S33: | −.1914 | | | | | |
| REMARK | 3 | | | | | | | | | |
| REMARK | 3 | TLS GROUP: | 7 | | | | | | | |
| REMARK | 3 | NUMBER OF COMPONENTS GROUP: | 1 | | | | | | | |
| REMARK | 3 | COMPONENTS | C SSSEQI TO C SSSEQI | | | | | | | |
| REMARK | 3 | RESIDUE RANGE: B | 288 | B | 374 | | | | | |
| REMARK | 3 | ORIGIN FOR THE GROUP (A): −41.6930 −10.8250 −19.6636 | | | | | | | | |
| REMARK | 3 | T TENSOR | | | | | | | | |
| REMARK | 3 | T11: | .1424 T22: | .0604 | | | | | | |
| REMARK | 3 | T33: | .1153 T12: | .0184 | | | | | | |
| REMARK | 3 | T13: | .0146 T23: | .0276 | | | | | | |
| REMARK | 3 | L TENSOR | | | | | | | | |
| REMARK | 3 | L11: | .6426 L22: | .8163 | | | | | | |
| REMARK | 3 | L33: | 2.3437 L12: | −.1831 | | | | | | |
| REMARK | 3 | L13: | −.5246 L23: | .4917 | | | | | | |
| REMARK | 3 | S TENSOR | | | | | | | | |
| REMARK | 3 | S11: | .0592 S12: | −.0206 S13: | .0071 | | | | | |
| REMARK | 3 | S21: | .0906 S22: | −.0229 S23: | −.1585 | | | | | |
| REMARK | 3 | S31: | −.0355 S32: | .0262 S33: | −.0363 | | | | | |
| REMARK | 3 | | | | | | | | | |
| REMARK | 3 | TLS GROUP: | 8 | | | | | | | |
| REMARK | 3 | NUMBER OF COMPONENTS GROUP: | 1 | | | | | | | |
| REMARK | 3 | OMPONENTS | C SSSEQI TO C SSSEQI | | | | | | | |
| REMARK | 3 | RESIDUE RANGE: B | 375 | B | 541 | | | | | |
| REMARK | 3 | ORIGIN FOR THE GROUP (A): −53.4886 −28.3212 −26.0670 | | | | | | | | |
| REMARK | 3 | T TENSOR | | | | | | | | |
| REMARK | 3 | T11: | .1107 T22: | .1220 | | | | | | |
| REMARK | 3 | T33: | .1514 T12: | .0692 | | | | | | |
| REMARK | 3 | T13: | −.0073 T23: | .0518 | | | | | | |
| REMARK | 3 | L TENSOR | | | | | | | | |
| REMARK | 3 | L11: | 2.6766 L22: | 1.8433 | | | | | | |
| REMARK | 3 | L33: | 2.6389 L12: | .1130 | | | | | | |
| REMARK | 3 | L13: | −2.4696 L23: | .6986 | | | | | | |
| REMARK | 3 | S TENSOR | | | | | | | | |
| REMARK | 3 | S11: | .1115 S12: | .3882 S13: | .0569 | | | | | |
| REMARK | 3 | S21: | −.0725 S22: | −.0724 S23: | .1450 | | | | | |
| REMARK | 3 | S31: | −.1453 S32: | −.4044 S33: | −.0392 | | | | | |
| REMARK | 3 | | | | | | | | | |
| REMARK | 3 | | | | | | | | | |
| REMARK | 3 | BULK SOLVENT MODELLING. | | | | | | | | |
| REMARK | 3 | METHOD USED: MASK | | | | | | | | |
| REMARK | 3 | PARAMETERS FOR MASK CALCULATION | | | | | | | | |
| REMARK | 3 | VDW PROBE RADIUS : 1.40 | | | | | | | | |
| REMARK | 3 | ION PROBE RADIUS : .80 | | | | | | | | |
| REMARK | 3 | SHRINKAGE RADIUS : .80 | | | | | | | | |
| REMARK | 3 | | | | | | | | | |
| REMARK | 3 | OTHER REFINEMENT REMARKS: | | | | | | | | |
| REMARK | 3 | HYDROGENS HAVE BEEN ADDED IN THE RIDING POSITIONS | | | | | | | | |
| REMARK | 3 | U VALUES : RESIDUAL ONLY | | | | | | | | |
| REMARK | 3 | | | | | | | | | |
| CISPEP | 1 | ALA A 446 | ARG A 447 | .00 | | | | | | |
| CISPEP | 2 | GLY A 515 | ASP A 516 | .00 | | | | | | |
| CISPEP | 3 | THR B 22 | ASP B 23 | .00 | | | | | | |
| CISPEP | 4 | ALA B 446 | ARG B 447 | .00 | | | | | | |
| CISPEP | 5 | GLY B 515 | ASP B 516 | .00 | | | | | | |
| CRYST1 | 155.800 155.800 143.690 90.00 90.00 90.00 P 43 21 2 | | | | | | | | | |
| SCALE1 | .006418 .000000 .000000 | | .00000 | | | | | | | |
| SCALE2 | .000000 .006418 .000000 | | .00000 | | | | | | | |
| SCALE3 | .000000 .000000 .006959 | | .00000 | | | | | | | |
| ATOM | 1 | N | LEU | A | 17 | −63.930 | 24.416 | −19.202 | 1.00 | 30.90 N |
| ATOM | 2 | CA | LEU | A | 17 | −64.132 | 23.019 | −19.731 | 1.00 | 31.43 C |

TABLE 16-7-continued

Coordinates of *P. tremuloides* IspS

| ATOM | 4 | CB | LEU | A | 17 | −63.308 | 22.800 | −21.021 | 1.00 | 31.35 | C |
|---|---|---|---|---|---|---|---|---|---|---|---|
| ATOM | 7 | CG | LEU | A | 17 | −64.002 | 23.016 | −22.386 | 1.00 | 31.95 | C |
| ATOM | 9 | CD1 | LEU | A | 17 | −62.989 | 23.068 | −23.550 | 1.00 | 31.88 | C |
| ATOM | 13 | CD2 | LEU | A | 17 | −65.052 | 21.915 | −22.676 | 1.00 | 31.95 | C |
| ATOM | 17 | C | LEU | A | 17 | −63.783 | 21.952 | −18.660 | 1.00 | 31.39 | C |
| ATOM | 18 | O | LEU | A | 17 | −63.142 | 22.291 | −17.651 | 1.00 | 31.61 | O |
| ATOM | 22 | N | LEU | A | 18 | −64.216 | 20.693 | −18.877 | 1.00 | 31.11 | N |
| ATOM | 23 | CA | LEU | A | 18 | −63.986 | 19.529 | −17.957 | 1.00 | 30.78 | C |
| ATOM | 25 | CB | LEU | A | 18 | −62.503 | 19.072 | −17.935 | 1.00 | 30.97 | C |
| ATOM | 28 | CG | LEU | A | 18 | −61.303 | 19.949 | −17.496 | 1.00 | 31.10 | C |
| ATOM | 30 | CD1 | LEU | A | 18 | −61.406 | 20.430 | −16.064 | 1.00 | 30.71 | C |
| ATOM | 34 | CD2 | LEU | A | 18 | −59.977 | 19.173 | −17.703 | 1.00 | 31.87 | C |
| ATOM | 38 | C | LEU | A | 18 | −64.531 | 19.665 | −16.522 | 1.00 | 30.38 | C |
| ATOM | 39 | O | LEU | A | 18 | −64.837 | 18.667 | −15.883 | 1.00 | 29.86 | O |
| ATOM | 41 | N | SER | A | 19 | −64.587 | 20.900 | −16.023 | 1.00 | 30.45 | N |
| ATOM | 42 | CA | SER | A | 19 | −65.335 | 21.276 | −14.815 | 1.00 | 30.37 | C |
| ATOM | 44 | CB | SER | A | 19 | −64.604 | 22.417 | −14.026 | 1.00 | 30.02 | C |
| ATOM | 47 | OG | SER | A | 19 | −64.881 | 23.741 | −14.489 | 1.00 | 28.00 | O |
| ATOM | 49 | C | SER | A | 19 | −66.784 | 21.654 | −15.218 | 1.00 | 31.03 | C |
| ATOM | 50 | O | SER | A | 19 | −67.666 | 21.711 | −14.367 | 1.00 | 30.95 | O |
| ATOM | 52 | N | SER | A | 20 | −67.023 | 21.880 | −16.519 | 1.00 | 31.85 | N |
| ATOM | 53 | CA | SER | A | 20 | −68.355 | 22.247 | −17.051 | 1.00 | 32.37 | C |
| ATOM | 55 | CB | SER | A | 20 | −68.291 | 22.507 | −18.579 | 1.00 | 32.39 | C |
| ATOM | 58 | OG | SER | A | 20 | −67.387 | 23.542 | −18.931 | 1.00 | 31.77 | O |
| ATOM | 60 | C | SER | A | 20 | −69.357 | 21.124 | −16.744 | 1.00 | 33.04 | C |
| ATOM | 61 | O | SER | A | 20 | −69.076 | 20.254 | −15.922 | 1.00 | 33.08 | O |
| ATOM | 63 | N | ASP | A | 21 | −70.522 | 21.136 | −17.393 | 1.00 | 33.88 | N |
| ATOM | 64 | CA | ASP | A | 21 | −71.512 | 20.069 | −17.206 | 1.00 | 34.48 | C |
| ATOM | 66 | CB | ASP | A | 21 | −72.907 | 20.655 | −17.127 | 1.00 | 34.59 | C |
| ATOM | 69 | CG | ASP | A | 21 | −73.022 | 21.661 | −16.006 | 1.00 | 35.54 | C |
| ATOM | 70 | OD1 | ASP | A | 21 | −72.041 | 21.836 | −15.251 | 1.00 | 35.31 | O |
| ATOM | 71 | OD2 | ASP | A | 21 | −74.082 | 22.289 | −15.870 | 1.00 | 38.72 | O |
| ATOM | 72 | C | ASP | A | 21 | −71.409 | 18.975 | −18.260 | 1.00 | 34.94 | C |
| ATOM | 73 | O | ASP | A | 21 | −72.134 | 18.947 | −19.269 | 1.00 | 34.58 | O |
| ATOM | 75 | N | THR | A | 22 | −70.457 | 18.086 | −17.989 | 1.00 | 35.66 | N |
| ATOM | 76 | CA | THR | A | 22 | −70.340 | 16.799 | −18.657 | 1.00 | 36.27 | C |
| ATOM | 78 | CB | THR | A | 22 | −68.895 | 16.576 | −19.168 | 1.00 | 36.30 | C |
| ATOM | 80 | OG1 | THR | A | 22 | −67.968 | 17.278 | −18.322 | 1.00 | 36.04 | O |
| ATOM | 82 | CG2 | THR | A | 22 | −68.755 | 17.088 | −20.604 | 1.00 | 36.11 | C |
| ATOM | 86 | C | THR | A | 22 | −70.792 | 15.714 | −17.648 | 1.00 | 36.83 | C |
| ATOM | 87 | O | THR | A | 22 | −69.968 | 15.022 | −17.035 | 1.00 | 37.05 | O |
| ATOM | 89 | N | ASP | A | 23 | −72.121 | 15.599 | −17.494 | 1.00 | 37.27 | N |
| ATOM | 90 | CA | ASP | A | 23 | −72.790 | 14.802 | −16.441 | 1.00 | 37.25 | C |
| ATOM | 92 | CB | ASP | A | 23 | −72.962 | 15.659 | −15.167 | 1.00 | 37.17 | C |
| ATOM | 95 | CG | ASP | A | 23 | −71.625 | 16.081 | −14.549 | 1.00 | 37.74 | C |
| ATOM | 96 | OD1 | ASP | A | 23 | −70.714 | 15.241 | −14.436 | 1.00 | 38.88 | O |
| ATOM | 97 | OD2 | ASP | A | 23 | −71.472 | 17.256 | −14.164 | 1.00 | 38.91 | O |
| ATOM | 98 | C | ASP | A | 23 | −74.172 | 14.351 | −16.956 | 1.00 | 37.18 | C |
| ATOM | 99 | O | ASP | A | 23 | −75.137 | 15.112 | −16.846 | 1.00 | 37.10 | O |
| ATOM | 101 | N | GLU | A | 24 | −74.280 | 13.134 | −17.501 | 1.00 | 37.23 | N |
| ATOM | 102 | CA | GLU | A | 24 | −75.406 | 12.815 | −18.410 | 1.00 | 37.58 | C |
| ATOM | 104 | CB | GLU | A | 24 | −74.941 | 13.007 | −19.865 | 1.00 | 37.77 | C |
| ATOM | 107 | CG | GLU | A | 24 | −74.424 | 14.417 | −20.239 | 1.00 | 37.98 | C |
| ATOM | 110 | CD | GLU | A | 24 | −74.121 | 14.556 | −21.746 | 1.00 | 38.35 | C |
| ATOM | 111 | OE1 | GLU | A | 24 | −74.284 | 13.564 | −22.503 | 1.00 | 38.12 | O |
| ATOM | 112 | OE2 | GLU | A | 24 | −73.721 | 15.661 | −22.174 | 1.00 | 38.18 | O |
| ATOM | 113 | C | GLU | A | 24 | −76.139 | 11.440 | −18.323 | 1.00 | 37.79 | C |
| ATOM | 114 | O | GLU | A | 24 | −77.323 | 11.397 | −17.960 | 1.00 | 37.90 | O |
| ATOM | 116 | N | SER | A | 25 | −75.462 | 10.345 | −18.696 | 1.00 | 37.92 | N |
| ATOM | 117 | CA | SER | A | 25 | −76.140 | 9.070 | −19.048 | 1.00 | 38.09 | C |
| ATOM | 119 | CB | SER | A | 25 | −75.167 | 8.076 | −19.723 | 1.00 | 38.11 | C |
| ATOM | 122 | OG | SER | A | 25 | −74.503 | 7.239 | −18.787 | 1.00 | 38.02 | O |
| ATOM | 124 | C | SER | A | 25 | −76.917 | 8.374 | −17.907 | 1.00 | 38.42 | C |
| ATOM | 125 | O | SER | A | 25 | −76.635 | 8.581 | −16.724 | 1.00 | 38.15 | O |
| ATOM | 127 | N | ILE | A | 26 | −77.861 | 7.511 | −18.312 | 1.00 | 39.00 | N |
| ATOM | 128 | CA | ILE | A | 26 | −78.993 | 7.042 | −17.476 | 1.00 | 39.30 | C |
| ATOM | 130 | CB | ILE | A | 26 | −78.594 | 5.965 | −16.429 | 1.00 | 39.34 | C |
| ATOM | 132 | CG1 | ILE | A | 26 | −77.892 | 4.791 | −17.120 | 1.00 | 39.37 | C |
| ATOM | 135 | CD1 | ILE | A | 26 | −77.766 | 3.531 | −16.253 | 1.00 | 39.46 | C |
| ATOM | 139 | CG2 | ILE | A | 26 | −79.836 | 5.423 | −15.714 | 1.00 | 39.29 | C |
| ATOM | 143 | C | ILE | A | 26 | −79.716 | 8.260 | −16.852 | 1.00 | 39.66 | C |
| ATOM | 144 | O | ILE | A | 26 | −79.274 | 8.831 | −15.838 | 1.00 | 39.49 | O |
| ATOM | 146 | N | GLU | A | 27 | −80.837 | 8.623 | −17.486 | 1.00 | 39.99 | N |
| ATOM | 147 | CA | GLU | A | 27 | −81.450 | 9.965 | −17.383 | 1.00 | 40.11 | C |
| ATOM | 149 | CB | GLU | A | 27 | −82.395 | 10.183 | −18.587 | 1.00 | 40.19 | C |
| ATOM | 152 | CG | GLU | A | 27 | −81.632 | 10.311 | −19.904 | 1.00 | 40.60 | C |
| ATOM | 155 | CD | GLU | A | 27 | −82.528 | 10.434 | −21.116 | 1.00 | 41.06 | C |
| ATOM | 156 | OE1 | GLU | A | 27 | −83.328 | 9.502 | −21.367 | 1.00 | 41.10 | O |

TABLE 16-7-continued

Coordinates of *P. tremuloides* IspS

| ATOM | 157 | OE2 | GLU | A | 27 | −82.409 | 11.458 | −21.830 | 1.00 | 41.36 | O |
|---|---|---|---|---|---|---|---|---|---|---|---|
| ATOM | 158 | C | GLU | A | 27 | −82.144 | 10.264 | −16.042 | 1.00 | 40.02 | C |
| ATOM | 159 | O | GLU | A | 27 | −81.977 | 9.518 | −15.071 | 1.00 | 40.01 | O |
| ATOM | 161 | N | VAL | A | 28 | −82.899 | 11.370 | −16.005 | 1.00 | 39.84 | N |
| ATOM | 162 | CA | VAL | A | 28 | −83.463 | 11.960 | −14.779 | 1.00 | 39.65 | C |
| ATOM | 164 | CB | VAL | A | 28 | −83.884 | 10.905 | −13.694 | 1.00 | 39.78 | C |
| ATOM | 166 | CG1 | VAL | A | 28 | −84.472 | 11.596 | −12.456 | 1.00 | 39.87 | C |
| ATOM | 170 | CG2 | VAL | A | 28 | −84.887 | 9.880 | −14.274 | 1.00 | 39.49 | C |
| ATOM | 174 | C | VAL | A | 28 | −82.469 | 12.980 | −14.206 | 1.00 | 39.46 | C |
| ATOM | 175 | O | VAL | A | 28 | −82.798 | 13.717 | −13.270 | 1.00 | 39.38 | O |
| ATOM | 177 | N | HIS | A | 29 | −81.264 | 13.025 | −14.786 | 1.00 | 39.30 | N |
| ATOM | 178 | CA | HIS | A | 29 | −80.236 | 14.006 | −14.412 | 1.00 | 39.23 | C |
| ATOM | 180 | CB | HIS | A | 29 | −78.866 | 13.344 | −14.186 | 1.00 | 39.45 | C |
| ATOM | 183 | CG | HIS | A | 29 | −78.910 | 12.139 | −13.296 | 1.00 | 41.29 | C |
| ATOM | 184 | ND1 | HIS | A | 29 | −78.407 | 12.140 | −12.007 | 1.00 | 42.51 | N |
| ATOM | 186 | CE1 | HIS | A | 29 | −78.585 | 10.942 | −11.472 | 1.00 | 43.37 | C |
| ATOM | 188 | NE2 | HIS | A | 29 | −79.181 | 10.164 | −12.365 | 1.00 | 43.18 | N |
| ATOM | 190 | CD2 | HIS | A | 29 | −79.393 | 10.888 | −13.515 | 1.00 | 42.55 | C |
| ATOM | 192 | C | HIS | A | 29 | −80.090 | 15.110 | −15.464 | 1.00 | 38.60 | C |
| ATOM | 193 | O | HIS | A | 29 | −79.049 | 15.774 | −15.499 | 1.00 | 38.61 | O |
| ATOM | 195 | N | LYS | A | 30 | −81.110 | 15.320 | −16.311 | 1.00 | 37.87 | N |
| ATOM | 196 | CA | LYS | A | 30 | −81.265 | 16.610 | −17.001 | 1.00 | 37.22 | C |
| ATOM | 198 | CB | LYS | A | 30 | −82.283 | 16.542 | −18.140 | 1.00 | 37.09 | C |
| ATOM | 201 | CG | LYS | A | 30 | −81.764 | 15.794 | −19.360 | 1.00 | 37.00 | C |
| ATOM | 204 | CD | LYS | A | 30 | −82.831 | 15.653 | −20.457 | 1.00 | 36.89 | C |
| ATOM | 207 | CE | LYS | A | 30 | −82.413 | 14.637 | −21.531 | 1.00 | 36.48 | C |
| ATOM | 210 | NZ | LYS | A | 30 | −83.422 | 14.458 | −22.611 | 1.00 | 35.46 | N |
| ATOM | 214 | C | LYS | A | 30 | −81.648 | 17.649 | −15.938 | 1.00 | 36.88 | C |
| ATOM | 215 | O | LYS | A | 30 | −82.516 | 18.499 | −16.136 | 1.00 | 36.71 | O |
| ATOM | 217 | N | ASP | A | 31 | −80.982 | 17.506 | −14.788 | 1.00 | 36.58 | N |
| ATOM | 218 | CA | ASP | A | 31 | −80.895 | 18.476 | −13.720 | 1.00 | 36.18 | C |
| ATOM | 220 | CB | ASP | A | 31 | −80.518 | 17.751 | −12.396 | 1.00 | 36.20 | C |
| ATOM | 223 | CG | ASP | A | 31 | −79.863 | 18.669 | −11.342 | 1.00 | 36.65 | C |
| ATOM | 224 | OD1 | ASP | A | 31 | −80.055 | 19.901 | −11.390 | 1.00 | 38.17 | O |
| ATOM | 225 | OD2 | ASP | A | 31 | −79.147 | 18.150 | −10.449 | 1.00 | 35.46 | O |
| ATOM | 226 | C | ASP | A | 31 | −79.811 | 19.426 | −14.226 | 1.00 | 35.74 | C |
| ATOM | 227 | O | ASP | A | 31 | −78.628 | 19.279 | −13.918 | 1.00 | 35.44 | O |
| ATOM | 229 | N | LYS | A | 32 | −80.220 | 20.343 | −15.096 | 1.00 | 35.30 | N |
| ATOM | 230 | CA | LYS | A | 32 | −79.360 | 21.449 | −15.507 | 1.00 | 34.69 | C |
| ATOM | 232 | CB | LYS | A | 32 | −78.698 | 21.188 | −16.849 | 1.00 | 34.63 | C |
| ATOM | 235 | CG | LYS | A | 32 | −77.699 | 20.042 | −16.765 | 1.00 | 34.51 | C |
| ATOM | 238 | CD | LYS | A | 32 | −76.953 | 19.853 | −18.078 | 1.00 | 34.48 | C |
| ATOM | 241 | CE | LYS | A | 32 | −76.859 | 18.387 | −18.503 | 1.00 | 33.77 | C |
| ATOM | 244 | NZ | LYS | A | 32 | −77.002 | 18.244 | −19.985 | 1.00 | 32.92 | N |
| ATOM | 248 | C | LYS | A | 32 | −80.162 | 22.745 | −15.459 | 1.00 | 34.01 | C |
| ATOM | 249 | O | LYS | A | 32 | −80.468 | 23.380 | −16.473 | 1.00 | 33.41 | O |
| ATOM | 251 | N | ALA | A | 33 | −80.540 | 23.051 | −14.219 | 1.00 | 33.21 | N |
| ATOM | 252 | CA | ALA | A | 33 | −80.785 | 24.381 | −13.766 | 1.00 | 32.60 | C |
| ATOM | 254 | CB | ALA | A | 33 | −81.619 | 24.347 | −12.484 | 1.00 | 32.28 | C |
| ATOM | 258 | C | ALA | A | 33 | −79.411 | 25.031 | −13.524 | 1.00 | 32.31 | C |
| ATOM | 259 | O | ALA | A | 33 | −79.335 | 26.081 | −12.901 | 1.00 | 32.80 | O |
| ATOM | 261 | N | LYS | A | 34 | −78.323 | 24.389 | −13.968 | 1.00 | 31.70 | N |
| ATOM | 262 | CA | LYS | A | 34 | −77.035 | 25.071 | −14.186 | 1.00 | 31.12 | C |
| ATOM | 264 | CB | LYS | A | 34 | −75.863 | 24.089 | −14.128 | 1.00 | 31.23 | C |
| ATOM | 267 | CG | LYS | A | 34 | −75.118 | 24.077 | −12.791 | 1.00 | 31.76 | C |
| ATOM | 270 | CD | LYS | A | 34 | −73.584 | 24.412 | −12.921 | 1.00 | 31.49 | C |
| ATOM | 273 | CE | LYS | A | 34 | −72.685 | 23.269 | −12.506 | 1.00 | 30.50 | C |
| ATOM | 276 | NZ | LYS | A | 34 | −72.951 | 22.090 | −13.348 | 1.00 | 29.53 | N |
| ATOM | 280 | C | LYS | A | 34 | −77.024 | 25.884 | −15.518 | 1.00 | 30.50 | C |
| ATOM | 281 | O | LYS | A | 34 | −76.977 | 25.353 | −16.625 | 1.00 | 29.82 | O |
| ATOM | 283 | N | LYS | A | 35 | −76.927 | 27.191 | −15.337 | 1.00 | 29.97 | N |
| ATOM | 284 | CA | LYS | A | 35 | −77.632 | 28.233 | −16.098 | 1.00 | 29.41 | C |
| ATOM | 286 | CB | LYS | A | 35 | −78.852 | 27.704 | −16.867 | 1.00 | 29.53 | C |
| ATOM | 289 | CG | LYS | A | 35 | −80.166 | 27.594 | −16.077 | 1.00 | 30.18 | C |
| ATOM | 292 | CD | LYS | A | 35 | −81.030 | 28.858 | −16.203 | 1.00 | 31.25 | C |
| ATOM | 295 | CE | LYS | A | 35 | −82.375 | 28.721 | −15.486 | 1.00 | 31.85 | C |
| ATOM | 298 | NZ | LYS | A | 35 | −83.298 | 29.865 | −15.783 | 1.00 | 31.73 | N |
| ATOM | 302 | C | LYS | A | 35 | −78.053 | 29.277 | −15.026 | 1.00 | 28.53 | C |
| ATOM | 303 | O | LYS | A | 35 | −78.246 | 30.460 | −15.307 | 1.00 | 28.53 | O |
| ATOM | 305 | N | LEU | A | 36 | −78.225 | 28.791 | −13.796 | 1.00 | 27.29 | N |
| ATOM | 306 | CA | LEU | A | 36 | −77.998 | 29.576 | −12.594 | 1.00 | 26.21 | C |
| ATOM | 308 | CB | LEU | A | 36 | −78.088 | 28.679 | −11.364 | 1.00 | 25.76 | C |
| ATOM | 311 | CG | LEU | A | 36 | −79.468 | 28.350 | −10.832 | 1.00 | 24.08 | C |
| ATOM | 313 | CD1 | LEU | A | 36 | −79.376 | 27.233 | −9.836 | 1.00 | 22.16 | C |
| ATOM | 317 | CD2 | LEU | A | 36 | −80.051 | 29.586 | −10.213 | 1.00 | 23.45 | C |
| ATOM | 321 | C | LEU | A | 36 | −76.587 | 30.137 | −12.665 | 1.00 | 25.93 | C |
| ATOM | 322 | O | LEU | A | 36 | −76.290 | 31.221 | −12.137 | 1.00 | 26.11 | O |
| ATOM | 324 | N | GLU | A | 37 | −75.714 | 29.332 | −13.260 | 1.00 | 25.24 | N |

TABLE 16-7-continued

Coordinates of *P. tremuloides* IspS

| ATOM | 325 | CA | GLU | A | 37 | −74.381 | 29.739 | −13.650 | 1.00 | 24.85 | C |
|---|---|---|---|---|---|---|---|---|---|---|---|
| ATOM | 327 | CB | GLU | A | 37 | −73.678 | 28.566 | −14.313 | 1.00 | 24.74 | C |
| ATOM | 330 | CG | GLU | A | 37 | −72.182 | 28.667 | −14.285 | 1.00 | 23.93 | C |
| ATOM | 333 | CD | GLU | A | 37 | −71.519 | 27.490 | −14.937 | 1.00 | 22.32 | C |
| ATOM | 334 | OE1 | GLU | A | 37 | −72.203 | 26.738 | −15.657 | 1.00 | 20.57 | O |
| ATOM | 335 | OE2 | GLU | A | 37 | −70.303 | 27.322 | −14.728 | 1.00 | 22.27 | O |
| ATOM | 336 | C | GLU | A | 37 | −74.391 | 30.927 | −14.600 | 1.00 | 24.69 | C |
| ATOM | 337 | O | GLU | A | 37 | −73.666 | 31.891 | −14.389 | 1.00 | 24.49 | O |
| ATOM | 339 | N | ALA | A | 38 | −75.203 | 30.850 | −15.650 | 1.00 | 24.68 | N |
| ATOM | 340 | CA | ALA | A | 38 | −75.352 | 31.960 | −16.599 | 1.00 | 24.87 | C |
| ATOM | 342 | CB | ALA | A | 38 | −76.453 | 31.656 | −17.609 | 1.00 | 24.53 | C |
| ATOM | 346 | C | ALA | A | 38 | −75.643 | 33.278 | −15.880 | 1.00 | 25.08 | C |
| ATOM | 347 | O | ALA | A | 38 | −75.009 | 34.295 | −16.135 | 1.00 | 25.21 | O |
| ATOM | 349 | N | GLU | A | 39 | −76.591 | 33.228 | −14.956 | 1.00 | 25.35 | N |
| ATOM | 350 | CA | GLU | A | 39 | −77.050 | 34.400 | −14.219 | 1.00 | 25.51 | C |
| ATOM | 352 | CB | GLU | A | 39 | −78.283 | 34.014 | −13.396 | 1.00 | 25.95 | C |
| ATOM | 355 | CG | GLU | A | 39 | −79.302 | 35.119 | −13.136 | 1.00 | 27.03 | C |
| ATOM | 358 | CD | GLU | A | 39 | −80.715 | 34.557 | −12.906 | 1.00 | 28.70 | C |
| ATOM | 359 | OE1 | GLU | A | 39 | −81.006 | 33.416 | −13.346 | 1.00 | 27.40 | O |
| ATOM | 360 | OE2 | GLU | A | 39 | −81.540 | 35.266 | −12.289 | 1.00 | 31.12 | O |
| ATOM | 361 | C | GLU | A | 39 | −75.970 | 34.966 | −13.306 | 1.00 | 25.11 | C |
| ATOM | 362 | O | GLU | A | 39 | −75.870 | 36.167 | −13.164 | 1.00 | 25.28 | O |
| ATOM | 364 | N | VAL | A | 40 | −75.182 | 34.107 | −12.672 | 1.00 | 24.86 | N |
| ATOM | 365 | CA | VAL | A | 40 | −74.079 | 34.568 | −11.824 | 1.00 | 24.69 | C |
| ATOM | 367 | CB | VAL | A | 40 | −73.511 | 33.420 | −10.952 | 1.00 | 24.56 | C |
| ATOM | 369 | CG1 | VAL | A | 40 | −72.239 | 33.857 | −10.240 | 1.00 | 23.69 | C |
| ATOM | 373 | CG2 | VAL | A | 40 | −74.553 | 32.955 | −9.955 | 1.00 | 24.68 | C |
| ATOM | 377 | C | VAL | A | 40 | −72.971 | 35.148 | −12.698 | 1.00 | 24.76 | C |
| ATOM | 378 | O | VAL | A | 40 | −72.337 | 36.139 | −12.362 | 1.00 | 24.16 | O |
| ATOM | 380 | N | ARG | A | 41 | −72.744 | 34.506 | −13.831 | 1.00 | 25.25 | N |
| ATOM | 381 | CA | ARG | A | 41 | −71.727 | 34.948 | −14.769 | 1.00 | 25.66 | C |
| ATOM | 383 | CB | ARG | A | 41 | −71.576 | 33.927 | −15.896 | 1.00 | 25.88 | C |
| ATOM | 386 | CG | ARG | A | 41 | −70.726 | 34.385 | −17.062 | 1.00 | 27.04 | C |
| ATOM | 389 | CD | ARG | A | 41 | −71.519 | 35.178 | −18.095 | 1.00 | 27.90 | C |
| ATOM | 392 | NE | ARG | A | 41 | −70.653 | 35.635 | −19.180 | 1.00 | 29.20 | N |
| ATOM | 394 | CZ | ARG | A | 41 | −70.946 | 36.615 | −20.034 | 1.00 | 29.94 | C |
| ATOM | 395 | NH1 | ARG | A | 41 | −70.077 | 36.945 | −20.980 | 1.00 | 29.86 | N |
| ATOM | 398 | NH2 | ARG | A | 41 | −72.096 | 37.273 | −19.957 | 1.00 | 30.54 | N |
| ATOM | 401 | C | ARG | A | 41 | −72.104 | 36.301 | −15.335 | 1.00 | 25.60 | C |
| ATOM | 402 | O | ARG | A | 41 | −71.237 | 37.113 | −15.612 | 1.00 | 25.77 | O |
| ATOM | 404 | N | ARG | A | 42 | −73.400 | 36.521 | −15.537 | 1.00 | 25.50 | N |
| ATOM | 405 | CA | ARG | A | 42 | −73.900 | 37.810 | −15.979 | 1.00 | 25.39 | C |
| ATOM | 407 | CB | ARG | A | 42 | −75.389 | 37.723 | −16.313 | 1.00 | 25.09 | C |
| ATOM | 410 | CG | ARG | A | 42 | −76.077 | 39.062 | −16.445 | 1.00 | 23.84 | C |
| ATOM | 413 | CD | ARG | A | 42 | −77.459 | 38.906 | −16.980 | 1.00 | 22.37 | C |
| ATOM | 416 | NE | ARG | A | 42 | −78.448 | 38.554 | −15.965 | 1.00 | 21.69 | N |
| ATOM | 418 | CZ | ARG | A | 42 | −79.705 | 38.206 | −16.248 | 1.00 | 22.99 | C |
| ATOM | 419 | NH1 | ARG | A | 42 | −80.122 | 38.146 | −17.517 | 1.00 | 24.16 | N |
| ATOM | 422 | NH2 | ARG | A | 42 | −80.557 | 37.900 | −15.275 | 1.00 | 22.94 | N |
| ATOM | 425 | C | ARG | A | 42 | −73.666 | 38.889 | −14.925 | 1.00 | 26.00 | C |
| ATOM | 426 | O | ARG | A | 42 | −73.173 | 39.959 | −15.244 | 1.00 | 26.17 | O |
| ATOM | 428 | N | GLU | A | 43 | −74.014 | 38.621 | −13.673 | 1.00 | 26.66 | N |
| ATOM | 429 | CA | GLU | A | 43 | −73.930 | 39.662 | −12.650 | 1.00 | 27.47 | C |
| ATOM | 431 | CB | GLU | A | 43 | −74.749 | 39.304 | −11.401 | 1.00 | 27.97 | C |
| ATOM | 434 | CG | GLU | A | 43 | −76.274 | 39.266 | −11.661 | 1.00 | 31.05 | C |
| ATOM | 437 | CD | GLU | A | 43 | −76.869 | 40.636 | −12.063 | 1.00 | 34.68 | C |
| ATOM | 438 | OE1 | GLU | A | 43 | −76.804 | 41.571 | −11.222 | 1.00 | 37.63 | O |
| ATOM | 439 | OE2 | GLU | A | 43 | −77.398 | 40.773 | −13.205 | 1.00 | 34.52 | O |
| ATOM | 440 | C | GLU | A | 43 | −72.494 | 40.035 | −12.275 | 1.00 | 27.15 | C |
| ATOM | 441 | O | GLU | A | 43 | −72.292 | 41.118 | −11.716 | 1.00 | 27.49 | O |
| ATOM | 443 | N | ILE | A | 44 | −71.517 | 39.166 | −12.588 | 1.00 | 26.57 | N |
| ATOM | 444 | CA | ILE | A | 44 | −70.090 | 39.456 | −12.334 | 1.00 | 25.80 | C |
| ATOM | 446 | CB | ILE | A | 44 | −69.206 | 38.187 | −12.187 | 1.00 | 25.52 | C |
| ATOM | 448 | CG1 | ILE | A | 44 | −69.624 | 37.320 | −11.010 | 1.00 | 24.69 | C |
| ATOM | 451 | CD1 | ILE | A | 44 | −68.828 | 36.061 | −10.899 | 1.00 | 23.08 | C |
| ATOM | 455 | CG2 | ILE | A | 44 | −67.790 | 38.581 | −11.916 | 1.00 | 25.73 | C |
| ATOM | 459 | C | ILE | A | 44 | −69.522 | 40.286 | −13.472 | 1.00 | 25.40 | C |
| ATOM | 460 | O | ILE | A | 44 | −68.745 | 41.211 | −13.236 | 1.00 | 25.26 | O |
| ATOM | 462 | N | ASN | A | 45 | −69.912 | 39.945 | −14.700 | 1.00 | 25.14 | N |
| ATOM | 463 | CA | ASN | A | 45 | −69.480 | 40.669 | −15.906 | 1.00 | 25.02 | C |
| ATOM | 465 | CB | ASN | A | 45 | −69.696 | 39.813 | −17.151 | 1.00 | 24.69 | C |
| ATOM | 468 | CG | ASN | A | 45 | −68.662 | 38.735 | −17.302 | 1.00 | 24.01 | C |
| ATOM | 469 | OD1 | ASN | A | 45 | −67.470 | 39.013 | −17.395 | 1.00 | 23.81 | O |
| ATOM | 470 | ND2 | ASN | A | 45 | −69.111 | 37.490 | −17.344 | 1.00 | 23.28 | N |
| ATOM | 473 | C | ASN | A | 45 | −70.177 | 42.014 | −16.114 | 1.00 | 25.52 | C |
| ATOM | 474 | O | ASN | A | 45 | −69.704 | 42.836 | −16.890 | 1.00 | 25.40 | O |
| ATOM | 476 | N | ASN | A | 46 | −71.308 | 42.210 | −15.437 | 1.00 | 26.33 | N |
| ATOM | 477 | CA | ASN | A | 46 | −72.085 | 43.453 | −15.468 | 1.00 | 26.72 | C |

TABLE 16-7-continued

Coordinates of *P. tremuloides* IspS

| | | | | | | | | | | |
|---|---|---|---|---|---|---|---|---|---|---|
| ATOM | 479 | CB | ASN | A | 46 | −73.102 | 43.404 | −14.322 | 1.00 | 26.31 C |
| ATOM | 482 | CG | ASN | A | 46 | −73.935 | 44.641 | −14.209 | 1.00 | 24.24 C |
| ATOM | 483 | OD1 | ASN | A | 46 | −73.948 | 45.472 | −15.091 | 1.00 | 22.38 O |
| ATOM | 484 | ND2 | ASN | A | 46 | −74.645 | 44.766 | −13.106 | 1.00 | 21.64 N |
| ATOM | 487 | C | ASN | A | 46 | −71.185 | 44.680 | −15.349 | 1.00 | 28.11 C |
| ATOM | 488 | O | ASN | A | 46 | −70.603 | 44.933 | −14.304 | 1.00 | 28.16 O |
| ATOM | 490 | N | GLU | A | 47 | −71.084 | 45.441 | −16.433 | 1.00 | 29.93 N |
| ATOM | 491 | CA | GLU | A | 47 | −70.128 | 46.558 | −16.544 | 1.00 | 31.30 C |
| ATOM | 493 | CB | GLU | A | 47 | −69.933 | 46.969 | −18.013 | 1.00 | 31.28 C |
| ATOM | 496 | CG | GLU | A | 47 | −69.737 | 45.795 | −19.020 | 1.00 | 32.37 C |
| ATOM | 499 | CD | GLU | A | 47 | −71.060 | 45.127 | −19.545 | 1.00 | 32.69 C |
| ATOM | 500 | OE1 | GLU | A | 47 | −72.055 | 45.833 | −19.816 | 1.00 | 32.16 O |
| ATOM | 501 | OE2 | GLU | A | 47 | −71.087 | 43.880 | −19.699 | 1.00 | 32.41 O |
| ATOM | 502 | C | GLU | A | 47 | −70.582 | 47.774 | −15.729 | 1.00 | 32.47 C |
| ATOM | 503 | O | GLU | A | 47 | −69.760 | 48.525 | −15.230 | 1.00 | 32.86 O |
| ATOM | 505 | N | LYS | A | 48 | −71.898 | 47.945 | −15.585 | 1.00 | 33.93 N |
| ATOM | 506 | CA | LYS | A | 48 | −72.491 | 49.075 | −14.861 | 1.00 | 34.85 C |
| ATOM | 508 | CB | LYS | A | 48 | −73.660 | 49.672 | −15.684 | 1.00 | 35.08 C |
| ATOM | 511 | CG | LYS | A | 48 | −73.221 | 50.119 | −17.126 | 1.00 | 36.58 C |
| ATOM | 514 | CD | LYS | A | 48 | −74.035 | 51.277 | −17.751 | 1.00 | 37.93 C |
| ATOM | 517 | CE | LYS | A | 48 | −75.353 | 50.799 | −18.415 | 1.00 | 39.02 C |
| ATOM | 520 | NZ | LYS | A | 48 | −75.159 | 49.990 | −19.669 | 1.00 | 39.11 N |
| ATOM | 524 | C | LYS | A | 48 | −72.926 | 48.632 | −13.465 | 1.00 | 35.26 C |
| ATOM | 525 | O | LYS | A | 48 | −74.011 | 48.954 | −13.015 | 1.00 | 35.04 O |
| ATOM | 527 | N | ALA | A | 49 | −72.051 | 47.890 | −12.790 | 1.00 | 36.29 N |
| ATOM | 528 | CA | ALA | A | 49 | −72.321 | 47.348 | −11.456 | 1.00 | 37.18 C |
| ATOM | 530 | CB | ALA | A | 49 | −71.828 | 45.923 | −11.353 | 1.00 | 37.20 C |
| ATOM | 534 | C | ALA | A | 49 | −71.618 | 48.191 | −10.418 | 1.00 | 37.88 C |
| ATOM | 535 | O | ALA | A | 49 | −70.480 | 48.610 | −10.638 | 1.00 | 38.17 O |
| ATOM | 537 | N | GLU | A | 50 | −72.278 | 48.404 | −9.280 | 1.00 | 38.53 N |
| ATOM | 538 | CA | GLU | A | 50 | −71.730 | 49.242 | −8.213 | 1.00 | 39.08 C |
| ATOM | 540 | CB | GLU | A | 50 | −72.790 | 49.545 | −7.146 | 1.00 | 39.43 C |
| ATOM | 543 | CG | GLU | A | 50 | −72.708 | 50.953 | −6.600 | 1.00 | 40.86 C |
| ATOM | 546 | CD | GLU | A | 50 | −73.089 | 52.010 | −7.639 | 1.00 | 42.77 C |
| ATOM | 547 | OE1 | GLU | A | 50 | −74.225 | 52.530 | −7.570 | 1.00 | 45.07 O |
| ATOM | 548 | OE2 | GLU | A | 50 | −72.265 | 52.320 | −8.530 | 1.00 | 43.35 O |
| ATOM | 549 | C | GLU | A | 50 | −70.560 | 48.521 | −7.600 | 1.00 | 38.89 C |
| ATOM | 550 | O | GLU | A | 50 | −70.699 | 47.378 | −7.201 | 1.00 | 39.05 O |
| ATOM | 552 | N | PHE | A | 51 | −69.411 | 49.181 | −7.536 | 1.00 | 38.99 N |
| ATOM | 553 | CA | PHE | A | 51 | −68.161 | 48.502 | −7.196 | 1.00 | 39.52 C |
| ATOM | 555 | CB | PHE | A | 51 | −67.000 | 49.494 | −7.098 | 1.00 | 40.05 C |
| ATOM | 558 | CG | PHE | A | 51 | −66.460 | 49.948 | −8.431 | 1.00 | 42.80 C |
| ATOM | 559 | CD1 | PHE | A | 51 | −66.135 | 49.014 | −9.435 | 1.00 | 45.21 C |
| ATOM | 561 | CE1 | PHE | A | 51 | −65.612 | 49.425 | −10.675 | 1.00 | 46.12 C |
| ATOM | 563 | CZ | PHE | A | 51 | −65.403 | 50.790 | −10.917 | 1.00 | 47.21 C |
| ATOM | 565 | CE2 | PHE | A | 51 | −65.726 | 51.741 | −9.913 | 1.00 | 46.72 C |
| ATOM | 567 | CD2 | PHE | A | 51 | −66.247 | 51.310 | −8.679 | 1.00 | 45.05 C |
| ATOM | 569 | C | PHE | A | 51 | −68.223 | 47.687 | −5.905 | 1.00 | 39.05 C |
| ATOM | 570 | O | PHE | A | 51 | −67.897 | 46.506 | −5.900 | 1.00 | 39.28 O |
| ATOM | 572 | N | LEU | A | 52 | −68.648 | 48.307 | −4.813 | 1.00 | 38.42 N |
| ATOM | 573 | CA | LEU | A | 52 | −68.709 | 47.610 | −3.528 | 1.00 | 37.94 C |
| ATOM | 575 | CB | LEU | A | 52 | −69.084 | 48.594 | −2.413 | 1.00 | 38.53 C |
| ATOM | 578 | CG | LEU | A | 52 | −68.057 | 49.726 | −2.181 | 1.00 | 40.46 C |
| ATOM | 580 | CD1 | LEU | A | 52 | −68.691 | 51.101 | −1.787 | 1.00 | 41.88 C |
| ATOM | 584 | CD2 | LEU | A | 52 | −67.020 | 49.274 | −1.141 | 1.00 | 41.83 C |
| ATOM | 588 | C | LEU | A | 52 | −69.667 | 46.406 | −3.532 | 1.00 | 36.72 C |
| ATOM | 589 | O | LEU | A | 52 | −69.517 | 45.494 | −2.724 | 1.00 | 36.84 O |
| ATOM | 591 | N | THR | A | 53 | −70.649 | 46.398 | −4.431 | 1.00 | 35.37 N |
| ATOM | 592 | CA | THR | A | 53 | −71.545 | 45.247 | −4.569 | 1.00 | 34.11 C |
| ATOM | 594 | CB | THR | A | 53 | −72.867 | 45.594 | −5.277 | 1.00 | 33.87 C |
| ATOM | 596 | OG1 | THR | A | 53 | −73.339 | 46.863 | −4.828 | 1.00 | 33.49 O |
| ATOM | 598 | CG2 | THR | A | 53 | −73.917 | 44.535 | −4.983 | 1.00 | 33.70 C |
| ATOM | 602 | C | THR | A | 53 | −70.853 | 44.148 | −5.359 | 1.00 | 33.04 C |
| ATOM | 603 | O | THR | A | 53 | −70.893 | 42.977 | −4.973 | 1.00 | 32.90 O |
| ATOM | 605 | N | LEU | A | 54 | −70.228 | 44.528 | −6.467 | 1.00 | 31.76 N |
| ATOM | 606 | CA | LEU | A | 54 | −69.469 | 43.578 | −7.286 | 1.00 | 31.13 C |
| ATOM | 608 | CB | LEU | A | 54 | −68.721 | 44.308 | −8.392 | 1.00 | 30.92 C |
| ATOM | 611 | CG | LEU | A | 54 | −68.028 | 43.437 | −9.424 | 1.00 | 30.27 C |
| ATOM | 613 | CD1 | LEU | A | 54 | −69.034 | 42.769 | −10.310 | 1.00 | 29.56 C |
| ATOM | 617 | CD2 | LEU | A | 54 | −67.108 | 44.306 | −10.242 | 1.00 | 31.15 C |
| ATOM | 621 | C | LEU | A | 54 | −68.466 | 42.808 | −6.443 | 1.00 | 30.60 C |
| ATOM | 622 | O | LEU | A | 54 | −68.378 | 41.587 | −6.543 | 1.00 | 30.30 O |
| ATOM | 624 | N | LEU | A | 55 | −67.725 | 43.551 | −5.618 | 1.00 | 30.09 N |
| ATOM | 625 | CA | LEU | A | 55 | −66.730 | 43.000 | −4.695 | 1.00 | 29.47 C |
| ATOM | 627 | CB | LEU | A | 55 | −66.006 | 44.126 | −3.944 | 1.00 | 29.44 C |
| ATOM | 630 | CG | LEU | A | 55 | −65.069 | 45.017 | −4.781 | 1.00 | 29.74 C |
| ATOM | 632 | CD1 | LEU | A | 55 | −64.609 | 46.255 | −4.003 | 1.00 | 29.43 C |
| ATOM | 636 | CD2 | LEU | A | 55 | −63.859 | 44.234 | −5.286 | 1.00 | 29.64 C |

TABLE 16-7-continued

Coordinates of *P. tremuloides* IspS

| ATOM | 640 | C | LEU | A | 55 | −67.340 | 42.024 | −3.696 | 1.00 | 28.87 | C |
|---|---|---|---|---|---|---|---|---|---|---|---|
| ATOM | 641 | O | LEU | A | 55 | −66.746 | 40.991 | −3.383 | 1.00 | 28.98 | O |
| ATOM | 643 | N | GLU | A | 56 | −68.525 | 42.330 | −3.198 | 1.00 | 28.01 | N |
| ATOM | 644 | CA | GLU | A | 56 | −69.160 | 41.419 | −2.256 | 1.00 | 27.64 | C |
| ATOM | 646 | CB | GLU | A | 56 | −70.172 | 42.173 | −1.395 | 1.00 | 28.19 | C |
| ATOM | 649 | CG | GLU | A | 56 | −69.497 | 43.167 | −.459 | 1.00 | 29.75 | C |
| ATOM | 652 | CD | GLU | A | 56 | −70.457 | 43.858 | .478 | 1.00 | 33.04 | C |
| ATOM | 653 | OE1 | GLU | A | 56 | −71.667 | 43.538 | .481 | 1.00 | 34.46 | O |
| ATOM | 654 | OE2 | GLU | A | 56 | −69.988 | 44.737 | 1.226 | 1.00 | 36.78 | O |
| ATOM | 655 | C | GLU | A | 56 | −69.776 | 40.200 | −2.945 | 1.00 | 26.37 | C |
| ATOM | 656 | O | GLU | A | 56 | −69.914 | 39.146 | −2.333 | 1.00 | 26.02 | O |
| ATOM | 658 | N | LEU | A | 57 | −70.134 | 40.347 | −4.218 | 1.00 | 25.30 | N |
| ATOM | 659 | CA | LEU | A | 57 | −70.569 | 39.212 | −5.036 | 1.00 | 24.17 | C |
| ATOM | 661 | CB | LEU | A | 57 | −71.125 | 39.680 | −6.382 | 1.00 | 23.71 | C |
| ATOM | 664 | CG | LEU | A | 57 | −71.417 | 38.568 | −7.390 | 1.00 | 22.27 | C |
| ATOM | 666 | CD1 | LEU | A | 57 | −72.515 | 37.675 | −6.858 | 1.00 | 19.31 | C |
| ATOM | 670 | CD2 | LEU | A | 57 | −71.752 | 39.167 | −8.768 | 1.00 | 20.30 | C |
| ATOM | 674 | C | LEU | A | 57 | −69.404 | 38.267 | −5.284 | 1.00 | 23.69 | C |
| ATOM | 675 | O | LEU | A | 57 | −69.547 | 37.051 | −5.136 | 1.00 | 23.83 | O |
| ATOM | 677 | N | ILE | A | 58 | −68.261 | 38.822 | −5.682 | 1.00 | 22.82 | N |
| ATOM | 678 | CA | ILE | A | 58 | −67.070 | 38.019 | −5.925 | 1.00 | 22.39 | C |
| ATOM | 680 | CB | ILE | A | 58 | −65.884 | 38.899 | −6.355 | 1.00 | 22.21 | C |
| ATOM | 682 | CG1 | ILE | A | 58 | −66.088 | 39.386 | −7.792 | 1.00 | 21.83 | C |
| ATOM | 685 | CD1 | ILE | A | 58 | −65.002 | 40.314 | −8.320 | 1.00 | 20.43 | C |
| ATOM | 689 | CG2 | ILE | A | 58 | −64.565 | 38.131 | −6.245 | 1.00 | 22.64 | C |
| ATOM | 693 | C | ILE | A | 58 | −66.719 | 37.227 | −4.662 | 1.00 | 22.35 | C |
| ATOM | 694 | O | ILE | A | 58 | −66.520 | 36.002 | −4.706 | 1.00 | 21.95 | O |
| ATOM | 696 | N | ASP | A | 59 | −66.676 | 37.951 | −3.543 | 1.00 | 22.32 | N |
| ATOM | 697 | CA | ASP | A | 59 | −66.396 | 37.396 | −2.215 | 1.00 | 22.26 | C |
| ATOM | 699 | CB | ASP | A | 59 | −66.570 | 38.500 | −1.171 | 1.00 | 22.67 | C |
| ATOM | 702 | CG | ASP | A | 59 | −66.126 | 38.092 | .213 | 1.00 | 23.91 | C |
| ATOM | 703 | OD1 | ASP | A | 59 | −65.271 | 37.182 | .338 | 1.00 | 23.77 | O |
| ATOM | 704 | OD2 | ASP | A | 59 | −66.641 | 38.718 | 1.178 | 1.00 | 27.12 | O |
| ATOM | 705 | C | ASP | A | 59 | −67.304 | 36.216 | −1.901 | 1.00 | 21.79 | C |
| ATOM | 706 | O | ASP | A | 59 | −66.828 | 35.102 | −1.668 | 1.00 | 21.71 | O |
| ATOM | 708 | N | ASN | A | 60 | −68.610 | 36.466 | −1.926 | 1.00 | 21.51 | N |
| ATOM | 709 | CA | ASN | A | 60 | −69.619 | 35.418 | −1.759 | 1.00 | 21.28 | C |
| ATOM | 711 | CB | ASN | A | 60 | −71.012 | 36.006 | −1.958 | 1.00 | 21.25 | C |
| ATOM | 714 | CG | ASN | A | 60 | −71.476 | 36.827 | −.776 | 1.00 | 21.82 | C |
| ATOM | 715 | OD1 | ASN | A | 60 | −71.067 | 36.598 | .364 | 1.00 | 20.81 | O |
| ATOM | 716 | ND2 | ASN | A | 60 | −72.361 | 37.783 | −1.043 | 1.00 | 23.63 | N |
| ATOM | 719 | C | ASN | A | 60 | −69.445 | 34.240 | −2.725 | 1.00 | 21.22 | C |
| ATOM | 720 | O | ASN | A | 60 | −69.444 | 33.053 | −2.303 | 1.00 | 20.95 | O |
| ATOM | 722 | N | VAL | A | 61 | −69.308 | 34.566 | −4.018 | 1.00 | 20.83 | N |
| ATOM | 723 | CA | VAL | A | 61 | −69.147 | 33.536 | −5.043 | 1.00 | 20.57 | C |
| ATOM | 725 | CB | VAL | A | 61 | −68.915 | 34.122 | −6.466 | 1.00 | 20.53 | C |
| ATOM | 727 | CG1 | VAL | A | 61 | −68.382 | 33.042 | −7.430 | 1.00 | 19.44 | C |
| ATOM | 731 | CG2 | VAL | A | 61 | −70.190 | 34.758 | −7.006 | 1.00 | 19.75 | C |
| ATOM | 735 | C | VAL | A | 61 | −67.981 | 32.646 | −4.644 | 1.00 | 20.62 | C |
| ATOM | 736 | O | VAL | A | 61 | −68.080 | 31.431 | −4.699 | 1.00 | 20.56 | O |
| ATOM | 738 | N | GLN | A | 62 | −66.888 | 33.255 | −4.209 | 1.00 | 20.76 | N |
| ATOM | 739 | CA | GLN | A | 62 | −65.703 | 32.481 | −3.898 | 1.00 | 21.18 | C |
| ATOM | 741 | CB | GLN | A | 62 | −64.461 | 33.379 | −3.824 | 1.00 | 21.39 | C |
| ATOM | 744 | CG | GLN | A | 62 | −64.007 | 33.920 | −5.165 | 1.00 | 21.64 | C |
| ATOM | 747 | CD | GLN | A | 62 | −62.608 | 34.512 | −5.135 | 1.00 | 22.04 | C |
| ATOM | 748 | OE1 | GLN | A | 62 | −61.890 | 34.483 | −6.145 | 1.00 | 23.18 | O |
| ATOM | 749 | NE2 | GLN | A | 62 | −62.217 | 35.062 | −3.989 | 1.00 | 20.39 | N |
| ATOM | 752 | C | GLN | A | 62 | −65.891 | 31.681 | −2.607 | 1.00 | 21.09 | C |
| ATOM | 753 | O | GLN | A | 62 | −65.544 | 30.485 | −2.554 | 1.00 | 21.30 | O |
| ATOM | 755 | N | ARG | A | 63 | −66.448 | 32.325 | −1.583 | 1.00 | 20.63 | N |
| ATOM | 756 | CA | ARG | A | 63 | −66.590 | 31.677 | −.273 | 1.00 | 20.54 | C |
| ATOM | 758 | CB | ARG | A | 63 | −67.025 | 32.686 | .786 | 1.00 | 20.57 | C |
| ATOM | 761 | CG | ARG | A | 63 | −66.031 | 33.823 | .930 | 1.00 | 22.55 | C |
| ATOM | 764 | CD | ARG | A | 63 | −66.214 | 34.632 | 2.179 | 1.00 | 24.93 | C |
| ATOM | 767 | NE | ARG | A | 63 | −66.123 | 33.781 | 3.355 | 1.00 | 27.75 | N |
| ATOM | 769 | CZ | ARG | A | 63 | −66.496 | 34.151 | 4.573 | 1.00 | 30.24 | C |
| ATOM | 770 | NH1 | ARG | A | 63 | −66.971 | 35.385 | 4.782 | 1.00 | 31.79 | N |
| ATOM | 773 | NH2 | ARG | A | 63 | −66.399 | 33.285 | 5.581 | 1.00 | 30.07 | N |
| ATOM | 776 | C | ARG | A | 63 | −67.557 | 30.499 | −.338 | 1.00 | 19.81 | C |
| ATOM | 777 | O | ARG | A | 63 | −67.283 | 29.431 | .209 | 1.00 | 19.67 | O |
| ATOM | 779 | N | LEU | A | 64 | −68.661 | 30.684 | −1.057 | 1.00 | 19.04 | N |
| ATOM | 780 | CA | LEU | A | 64 | −69.636 | 29.617 | −1.246 | 1.00 | 18.44 | C |
| ATOM | 782 | CB | LEU | A | 64 | −70.865 | 30.167 | −1.954 | 1.00 | 18.59 | C |
| ATOM | 785 | CG | LEU | A | 64 | −71.662 | 31.170 | −1.140 | 1.00 | 18.32 | C |
| ATOM | 787 | CD1 | LEU | A | 64 | −72.669 | 31.852 | −2.034 | 1.00 | 18.10 | C |
| ATOM | 791 | CD2 | LEU | A | 64 | −72.334 | 30.444 | .004 | 1.00 | 18.29 | C |
| ATOM | 795 | C | LEU | A | 64 | −69.089 | 28.436 | −2.037 | 1.00 | 17.80 | C |
| ATOM | 796 | O | LEU | A | 64 | −69.802 | 27.453 | −2.252 | 1.00 | 17.79 | O |

TABLE 16-7-continued

Coordinates of *P. tremuloides* IspS

| ATOM | 798 | N | GLY | A | 65 | −67.850 | 28.573 | −2.515 | 1.00 | 17.07 | N |
|---|---|---|---|---|---|---|---|---|---|---|---|
| ATOM | 799 | CA | GLY | A | 65 | −67.084 | 27.480 | −3.081 | 1.00 | 16.27 | C |
| ATOM | 802 | C | GLY | A | 65 | −67.137 | 27.406 | −4.588 | 1.00 | 15.77 | C |
| ATOM | 803 | O | GLY | A | 65 | −66.893 | 26.347 | −5.154 | 1.00 | 15.78 | O |
| ATOM | 805 | N | LEU | A | 66 | −67.439 | 28.521 | −5.246 | 1.00 | 15.24 | N |
| ATOM | 806 | CA | LEU | A | 66 | −67.621 | 28.537 | −6.701 | 1.00 | 14.93 | C |
| ATOM | 808 | CB | LEU | A | 66 | −68.977 | 29.146 | −7.021 | 1.00 | 14.84 | C |
| ATOM | 811 | CG | LEU | A | 66 | −70.204 | 28.334 | −6.619 | 1.00 | 13.97 | C |
| ATOM | 813 | CD1 | LEU | A | 66 | −71.391 | 29.260 | −6.650 | 1.00 | 13.74 | C |
| ATOM | 817 | CD2 | LEU | A | 66 | −70.415 | 27.125 | −7.534 | 1.00 | 11.22 | C |
| ATOM | 821 | C | LEU | A | 66 | −66.533 | 29.314 | −7.454 | 1.00 | 15.09 | C |
| ATOM | 822 | O | LEU | A | 66 | −66.621 | 29.497 | −8.678 | 1.00 | 14.81 | O |
| ATOM | 824 | N | GLY | A | 67 | −65.510 | 29.758 | −6.720 | 1.00 | 15.21 | N |
| ATOM | 825 | CA | GLY | A | 67 | −64.404 | 30.526 | −7.280 | 1.00 | 14.98 | C |
| ATOM | 828 | C | GLY | A | 67 | −63.873 | 29.952 | −8.569 | 1.00 | 14.60 | C |
| ATOM | 829 | O | GLY | A | 67 | −63.891 | 30.619 | −9.579 | 1.00 | 14.63 | O |
| ATOM | 831 | N | TYR | A | 68 | −63.419 | 28.706 | −8.523 | 1.00 | 14.57 | N |
| ATOM | 832 | CA | TYR | A | 68 | −62.831 | 28.029 | −9.688 | 1.00 | 14.72 | C |
| ATOM | 834 | CB | TYR | A | 68 | −62.608 | 26.539 | −9.372 | 1.00 | 14.73 | C |
| ATOM | 837 | CG | TYR | A | 68 | −63.858 | 25.689 | −9.330 | 1.00 | 12.47 | C |
| ATOM | 838 | CD1 | TYR | A | 68 | −64.163 | 24.826 | −10.366 | 1.00 | 10.68 | C |
| ATOM | 840 | CE1 | TYR | A | 68 | −65.310 | 24.043 | −10.340 | 1.00 | 10.55 | C |
| ATOM | 842 | CZ | TYR | A | 68 | −66.163 | 24.119 | −9.258 | 1.00 | 10.41 | C |
| ATOM | 843 | OH | TYR | A | 68 | −67.311 | 23.349 | −9.212 | 1.00 | 6.97 | O |
| ATOM | 845 | CE2 | TYR | A | 68 | −65.864 | 24.979 | −8.210 | 1.00 | 11.44 | C |
| ATOM | 847 | CD2 | TYR | A | 68 | −64.722 | 25.750 | −8.252 | 1.00 | 11.29 | C |
| ATOM | 849 | C | TYR | A | 68 | −63.648 | 28.141 | −10.980 | 1.00 | 15.31 | C |
| ATOM | 850 | O | TYR | A | 68 | −63.106 | 28.230 | −12.083 | 1.00 | 15.01 | O |
| ATOM | 852 | N | ARG | A | 69 | −64.959 | 28.136 | −10.816 | 1.00 | 16.03 | N |
| ATOM | 853 | CA | ARG | A | 69 | −65.884 | 28.083 | −11.922 | 1.00 | 16.67 | C |
| ATOM | 855 | CB | ARG | A | 69 | −67.224 | 27.649 | −11.348 | 1.00 | 16.58 | C |
| ATOM | 858 | CG | ARG | A | 69 | −68.332 | 27.445 | −12.335 | 1.00 | 16.07 | C |
| ATOM | 861 | CD | ARG | A | 69 | −69.378 | 26.578 | −11.701 | 1.00 | 14.26 | C |
| ATOM | 864 | NE | ARG | A | 69 | −68.915 | 25.205 | −11.677 | 1.00 | 12.82 | N |
| ATOM | 866 | CZ | ARG | A | 69 | −69.063 | 24.346 | −12.676 | 1.00 | 12.42 | C |
| ATOM | 867 | NH1 | ARG | A | 69 | −69.676 | 24.694 | −13.792 | 1.00 | 12.27 | N |
| ATOM | 870 | NH2 | ARG | A | 69 | −68.601 | 23.119 | −12.553 | 1.00 | 13.23 | N |
| ATOM | 873 | C | ARG | A | 69 | −66.010 | 29.409 | −12.692 | 1.00 | 17.62 | C |
| ATOM | 874 | O | ARG | A | 69 | −66.281 | 29.401 | −13.892 | 1.00 | 17.10 | O |
| ATOM | 876 | N | PHE | A | 70 | −65.811 | 30.529 | −11.985 | 1.00 | 19.11 | N |
| ATOM | 877 | CA | PHE | A | 70 | −65.936 | 31.891 | −12.530 | 1.00 | 19.96 | C |
| ATOM | 879 | CB | PHE | A | 70 | −67.024 | 32.666 | −11.763 | 1.00 | 19.89 | C |
| ATOM | 882 | CG | PHE | A | 70 | −68.365 | 32.010 | −11.784 | 1.00 | 18.68 | C |
| ATOM | 883 | CD1 | PHE | A | 70 | −69.158 | 32.082 | −12.903 | 1.00 | 18.05 | C |
| ATOM | 885 | CE1 | PHE | A | 70 | −70.376 | 31.452 | −12.938 | 1.00 | 18.03 | C |
| ATOM | 887 | CZ | PHE | A | 70 | −70.825 | 30.754 | −11.851 | 1.00 | 17.26 | C |
| ATOM | 889 | CE2 | PHE | A | 70 | −70.051 | 30.672 | −10.736 | 1.00 | 17.60 | C |
| ATOM | 891 | CD2 | PHE | A | 70 | −68.822 | 31.300 | −10.700 | 1.00 | 17.86 | C |
| ATOM | 893 | C | PHE | A | 70 | −64.627 | 32.661 | −12.400 | 1.00 | 21.34 | C |
| ATOM | 894 | O | PHE | A | 70 | −64.629 | 33.862 | −12.171 | 1.00 | 21.25 | O |
| ATOM | 896 | N | GLU | A | 71 | −63.501 | 31.977 | −12.541 | 1.00 | 23.19 | N |
| ATOM | 897 | CA | GLU | A | 71 | −62.211 | 32.591 | −12.214 | 1.00 | 24.60 | C |
| ATOM | 899 | CB | GLU | A | 71 | −61.127 | 31.524 | −12.073 | 1.00 | 25.03 | C |
| ATOM | 902 | CG | GLU | A | 71 | −59.717 | 32.059 | −11.861 | 1.00 | 27.10 | C |
| ATOM | 905 | CD | GLU | A | 71 | −58.712 | 30.949 | −11.549 | 1.00 | 30.10 | C |
| ATOM | 906 | OE1 | GLU | A | 71 | −59.084 | 30.007 | −10.796 | 1.00 | 32.05 | O |
| ATOM | 907 | OE2 | GLU | A | 71 | −57.558 | 31.027 | −12.051 | 1.00 | 30.50 | O |
| ATOM | 908 | C | GLU | A | 71 | −61.809 | 33.644 | −13.241 | 1.00 | 25.23 | C |
| ATOM | 909 | O | GLU | A | 71 | −61.362 | 34.717 | −12.862 | 1.00 | 25.54 | O |
| ATOM | 911 | N | SER | A | 72 | −61.979 | 33.345 | −14.530 | 1.00 | 25.91 | N |
| ATOM | 912 | CA | SER | A | 72 | −61.641 | 34.294 | −15.588 | 1.00 | 26.37 | C |
| ATOM | 914 | CB | SER | A | 72 | −61.656 | 33.606 | −16.941 | 1.00 | 26.32 | C |
| ATOM | 917 | OG | SER | A | 72 | −62.985 | 33.278 | −17.291 | 1.00 | 27.28 | O |
| ATOM | 919 | C | SER | A | 72 | −62.609 | 35.476 | −15.608 | 1.00 | 26.84 | C |
| ATOM | 920 | O | SER | A | 72 | −62.197 | 36.601 | −15.852 | 1.00 | 27.02 | O |
| ATOM | 922 | N | ASP | A | 73 | −63.893 | 35.214 | −15.361 | 1.00 | 27.45 | N |
| ATOM | 923 | CA | ASP | A | 73 | −64.895 | 36.277 | −15.246 | 1.00 | 27.87 | C |
| ATOM | 925 | CB | ASP | A | 73 | −66.289 | 35.705 | −14.968 | 1.00 | 27.99 | C |
| ATOM | 928 | CG | ASP | A | 73 | −66.842 | 34.913 | −16.140 | 1.00 | 29.49 | C |
| ATOM | 929 | OD1 | ASP | A | 73 | −67.215 | 35.530 | −17.155 | 1.00 | 30.90 | O |
| ATOM | 930 | OD2 | ASP | A | 73 | −66.916 | 33.667 | −16.054 | 1.00 | 31.85 | O |
| ATOM | 931 | C | ASP | A | 73 | −64.518 | 37.221 | −14.121 | 1.00 | 27.86 | C |
| ATOM | 932 | O | ASP | A | 73 | −64.598 | 38.435 | −14.286 | 1.00 | 28.05 | O |
| ATOM | 934 | N | ILE | A | 74 | −64.118 | 36.652 | −12.985 | 1.00 | 27.88 | N |
| ATOM | 935 | CA | ILE | A | 74 | −63.698 | 37.422 | −11.821 | 1.00 | 27.98 | C |
| ATOM | 937 | CB | ILE | A | 74 | −63.348 | 36.521 | −10.637 | 1.00 | 27.71 | C |
| ATOM | 939 | CG1 | ILE | A | 74 | −64.607 | 36.007 | −9.960 | 1.00 | 27.60 | C |
| ATOM | 942 | CD1 | ILE | A | 74 | −64.355 | 34.846 | −9.023 | 1.00 | 27.67 | C |

TABLE 16-7-continued

Coordinates of *P. tremuloides* IspS

| ATOM | 946 | CG2 | ILE | A | 74 | −62.551 | 37.272 | −9.621 | 1.00 | 26.82 C |
|---|---|---|---|---|---|---|---|---|---|---|
| ATOM | 950 | C | ILE | A | 74 | −62.472 | 38.252 | −12.133 | 1.00 | 28.80 C |
| ATOM | 951 | O | ILE | A | 74 | −62.475 | 39.453 | −11.917 | 1.00 | 29.00 O |
| ATOM | 953 | N | ARG | A | 75 | −61.415 | 37.616 | −12.628 | 1.00 | 29.80 N |
| ATOM | 954 | CA | ARG | A | 75 | −60.197 | 38.341 | −12.968 | 1.00 | 30.79 C |
| ATOM | 956 | CB | ARG | A | 75 | −59.286 | 37.507 | −13.841 | 1.00 | 31.33 C |
| ATOM | 959 | CG | ARG | A | 75 | −58.506 | 36.441 | −13.115 | 1.00 | 34.25 C |
| ATOM | 962 | CD | ARG | A | 75 | −57.286 | 36.009 | −13.929 | 1.00 | 37.53 C |
| ATOM | 965 | NE | ARG | A | 75 | −56.238 | 37.019 | −13.799 | 1.00 | 40.89 N |
| ATOM | 967 | CZ | ARG | A | 75 | −54.934 | 36.807 | −13.967 | 1.00 | 44.24 C |
| ATOM | 968 | NH1 | ARG | A | 75 | −54.459 | 35.602 | −14.294 | 1.00 | 45.02 N |
| ATOM | 971 | NH2 | ARG | A | 75 | −54.089 | 37.821 | −13.796 | 1.00 | 45.88 N |
| ATOM | 974 | C | ARG | A | 75 | −60.548 | 39.596 | −13.727 | 1.00 | 30.95 C |
| ATOM | 975 | O | ARG | A | 75 | −60.163 | 40.685 | −13.336 | 1.00 | 31.27 O |
| ATOM | 977 | N | ARG | A | 76 | −61.293 | 39.435 | −14.815 | 1.00 | 31.31 N |
| ATOM | 978 | CA | ARG | A | 76 | −61.712 | 40.567 | −15.638 | 1.00 | 31.62 C |
| ATOM | 980 | CB | ARG | A | 76 | −62.593 | 40.106 | −16.794 | 1.00 | 31.97 C |
| ATOM | 983 | CG | ARG | A | 76 | −61.833 | 39.392 | −17.895 | 1.00 | 32.91 C |
| ATOM | 986 | CD | ARG | A | 76 | −62.615 | 39.453 | −19.205 | 1.00 | 34.43 C |
| ATOM | 989 | NE | ARG | A | 76 | −63.925 | 38.803 | −19.128 | 1.00 | 35.66 N |
| ATOM | 991 | CZ | ARG | A | 76 | −64.115 | 37.480 | −19.106 | 1.00 | 37.15 C |
| ATOM | 992 | NH1 | ARG | A | 76 | −63.085 | 36.632 | −19.129 | 1.00 | 37.93 N |
| ATOM | 995 | NH2 | ARG | A | 76 | −65.347 | 36.992 | −19.048 | 1.00 | 37.64 N |
| ATOM | 998 | C | ARG | A | 76 | −62.453 | 41.629 | −14.849 | 1.00 | 31.41 C |
| ATOM | 999 | O | ARG | A | 76 | −62.144 | 42.798 | −14.966 | 1.00 | 31.35 O |
| ATOM | 1001 | N | ALA | A | 77 | −63.437 | 41.230 | −14.058 | 1.00 | 31.53 N |
| ATOM | 1002 | CA | ALA | A | 77 | −64.136 | 42.177 | −13.211 | 1.00 | 31.73 C |
| ATOM | 1004 | CB | ALA | A | 77 | −65.074 | 41.468 | −12.275 | 1.00 | 31.69 C |
| ATOM | 1008 | C | ALA | A | 77 | −63.107 | 42.950 | −12.423 | 1.00 | 32.23 C |
| ATOM | 1009 | O | ALA | A | 77 | −63.116 | 44.176 | −12.411 | 1.00 | 32.42 O |
| ATOM | 1011 | N | LEU | A | 78 | −62.198 | 42.223 | −11.786 | 1.00 | 32.95 N |
| ATOM | 1012 | CA | LEU | A | 78 | −61.168 | 42.838 | −10.963 | 1.00 | 33.51 C |
| ATOM | 1014 | CB | LEU | A | 78 | −60.319 | 41.775 | −10.265 | 1.00 | 33.10 C |
| ATOM | 1017 | CG | LEU | A | 78 | −60.959 | 41.077 | −9.081 | 1.00 | 32.30 C |
| ATOM | 1019 | CD1 | LEU | A | 78 | −59.960 | 40.104 | −8.472 | 1.00 | 30.80 C |
| ATOM | 1023 | CD2 | LEU | A | 78 | −61.438 | 42.117 | −8.056 | 1.00 | 31.89 C |
| ATOM | 1027 | C | LEU | A | 78 | −60.249 | 43.752 | −11.753 | 1.00 | 34.70 C |
| ATOM | 1028 | O | LEU | A | 78 | −59.790 | 44.753 | −11.214 | 1.00 | 35.18 O |
| ATOM | 1030 | N | ASP | A | 79 | −59.955 | 43.404 | −13.007 | 1.00 | 35.91 N |
| ATOM | 1031 | CA | ASP | A | 79 | −59.054 | 44.205 | −13.828 | 1.00 | 36.89 C |
| ATOM | 1033 | CB | ASP | A | 79 | −58.637 | 43.452 | −15.083 | 1.00 | 37.06 C |
| ATOM | 1036 | CG | ASP | A | 79 | −57.518 | 44.150 | −15.821 | 1.00 | 38.41 C |
| ATOM | 1037 | OD1 | ASP | A | 79 | −57.800 | 45.080 | −16.615 | 1.00 | 39.85 O |
| ATOM | 1038 | OD2 | ASP | A | 79 | −56.347 | 43.775 | −15.592 | 1.00 | 40.78 O |
| ATOM | 1039 | C | ASP | A | 79 | −59.721 | 45.505 | −14.220 | 1.00 | 37.75 C |
| ATOM | 1040 | O | ASP | A | 79 | −59.105 | 46.568 | −14.177 | 1.00 | 37.82 O |
| ATOM | 1042 | N | ARG | A | 80 | −60.984 | 45.401 | −14.615 | 1.00 | 38.99 N |
| ATOM | 1043 | CA | ARG | A | 80 | −61.814 | 46.558 | −14.923 | 1.00 | 39.88 C |
| ATOM | 1045 | CB | ARG | A | 80 | −63.191 | 46.106 | −15.427 | 1.00 | 40.41 C |
| ATOM | 1048 | CG | ARG | A | 80 | −64.025 | 47.183 | −16.122 | 1.00 | 42.77 C |
| ATOM | 1051 | CD | ARG | A | 80 | −65.347 | 46.624 | −16.718 | 1.00 | 45.79 C |
| ATOM | 1054 | NE | ARG | A | 80 | −66.107 | 45.799 | −15.765 | 1.00 | 48.55 N |
| ATOM | 1056 | CZ | ARG | A | 80 | −66.136 | 44.457 | −15.742 | 1.00 | 50.37 C |
| ATOM | 1057 | NH1 | ARG | A | 80 | −65.450 | 43.724 | −16.636 | 1.00 | 49.78 N |
| ATOM | 1060 | NH2 | ARG | A | 80 | −66.868 | 43.835 | −14.805 | 1.00 | 50.77 N |
| ATOM | 1063 | C | ARG | A | 80 | −61.946 | 47.409 | −13.668 | 1.00 | 39.80 C |
| ATOM | 1064 | O | ARG | A | 80 | −61.840 | 48.630 | −13.742 | 1.00 | 40.37 O |
| ATOM | 1066 | N | PHE | A | 81 | −62.136 | 46.771 | −12.516 | 1.00 | 39.62 N |
| ATOM | 1067 | CA | PHE | A | 81 | −62.216 | 47.505 | −11.245 | 1.00 | 39.61 C |
| ATOM | 1069 | CB | PHE | A | 81 | −62.392 | 46.561 | −10.053 | 1.00 | 39.74 C |
| ATOM | 1072 | CG | PHE | A | 81 | −62.282 | 47.247 | −8.712 | 1.00 | 38.81 C |
| ATOM | 1073 | CD1 | PHE | A | 81 | −63.238 | 48.153 | −8.315 | 1.00 | 39.03 C |
| ATOM | 1075 | CE1 | PHE | A | 81 | −63.153 | 48.787 | −7.100 | 1.00 | 39.69 C |
| ATOM | 1077 | CZ | PHE | A | 81 | −62.095 | 48.515 | −6.261 | 1.00 | 39.54 C |
| ATOM | 1079 | CE2 | PHE | A | 81 | −61.134 | 47.608 | −6.647 | 1.00 | 38.66 C |
| ATOM | 1081 | CD2 | PHE | A | 81 | −61.228 | 46.986 | −7.865 | 1.00 | 38.27 C |
| ATOM | 1083 | C | PHE | A | 81 | −61.006 | 48.378 | −10.970 | 1.00 | 39.58 C |
| ATOM | 1084 | O | PHE | A | 81 | −61.165 | 49.535 | −10.581 | 1.00 | 39.76 O |
| ATOM | 1086 | N | VAL | A | 82 | −59.810 | 47.817 | −11.142 | 1.00 | 39.50 N |
| ATOM | 1087 | CA | VAL | A | 82 | −58.575 | 48.562 | −10.892 | 1.00 | 39.47 C |
| ATOM | 1089 | CB | VAL | A | 82 | −57.314 | 47.659 | −10.977 | 1.00 | 39.37 C |
| ATOM | 1091 | CG1 | VAL | A | 82 | −56.108 | 48.426 | −11.521 | 1.00 | 39.06 C |
| ATOM | 1095 | CG2 | VAL | A | 82 | −57.009 | 47.079 | −9.614 | 1.00 | 39.23 C |
| ATOM | 1099 | C | VAL | A | 82 | −58.457 | 49.755 | −11.833 | 1.00 | 39.54 C |
| ATOM | 1100 | O | VAL | A | 82 | −58.222 | 50.884 | −11.378 | 1.00 | 39.45 O |
| ATOM | 1102 | N | SER | A | 83 | −58.678 | 49.513 | −13.126 | 1.00 | 39.65 N |
| ATOM | 1103 | CA | SER | A | 83 | −58.469 | 50.535 | −14.157 | 1.00 | 39.82 C |
| ATOM | 1105 | CB | SER | A | 83 | −58.196 | 49.880 | −15.526 | 1.00 | 39.84 C |

TABLE 16-7-continued

Coordinates of *P. tremuloides* IspS

| ATOM | 1108 | OG | SER | A | 83 | −59.138 | 48.870 | −15.829 | 1.00 | 40.00 | O |
|---|---|---|---|---|---|---|---|---|---|---|---|
| ATOM | 1110 | C | SER | A | 83 | −59.617 | 51.561 | −14.219 | 1.00 | 39.62 | C |
| ATOM | 1111 | O | SER | A | 83 | −60.149 | 51.853 | −15.286 | 1.00 | 39.59 | O |
| ATOM | 1113 | N | SER | A | 84 | −59.957 | 52.108 | −13.052 | 1.00 | 39.44 | N |
| ATOM | 1114 | CA | SER | A | 84 | −60.926 | 53.197 | −12.910 | 1.00 | 39.13 | C |
| ATOM | 1116 | CB | SER | A | 84 | −62.238 | 52.834 | −13.618 | 1.00 | 39.03 | C |
| ATOM | 1119 | OG | SER | A | 84 | −62.620 | 51.505 | −13.325 | 1.00 | 37.97 | O |
| ATOM | 1121 | C | SER | A | 84 | −61.243 | 53.580 | −11.446 | 1.00 | 39.17 | C |
| ATOM | 1122 | O | SER | A | 84 | −62.189 | 54.341 | −11.230 | 1.00 | 39.58 | O |
| ATOM | 1124 | N | GLY | A | 85 | −60.482 | 53.077 | −10.457 | 1.00 | 38.74 | N |
| ATOM | 1125 | CA | GLY | A | 85 | −60.795 | 53.282 | −9.024 | 1.00 | 38.26 | C |
| ATOM | 1128 | C | GLY | A | 85 | −61.724 | 52.238 | −8.413 | 1.00 | 37.79 | C |
| ATOM | 1129 | O | GLY | A | 85 | −61.529 | 51.799 | −7.273 | 1.00 | 36.84 | O |
| ATOM | 1131 | N | SER | A | 94 | −63.557 | 54.187 | 1.994 | 1.00 | 28.27 | N |
| ATOM | 1132 | CA | SER | A | 94 | −64.069 | 52.892 | 2.476 | 1.00 | 28.03 | C |
| ATOM | 1134 | CB | SER | A | 94 | −64.856 | 52.225 | 1.359 | 1.00 | 27.84 | C |
| ATOM | 1137 | OG | SER | A | 94 | −65.234 | 50.921 | 1.743 | 1.00 | 28.20 | O |
| ATOM | 1139 | C | SER | A | 94 | −62.992 | 51.910 | 2.934 | 1.00 | 27.83 | C |
| ATOM | 1140 | O | SER | A | 94 | −62.339 | 51.325 | 2.090 | 1.00 | 28.15 | O |
| ATOM | 1142 | N | LEU | A | 95 | −62.815 | 51.705 | 4.245 | 1.00 | 27.70 | N |
| ATOM | 1143 | CA | LEU | A | 95 | −61.813 | 50.728 | 4.751 | 1.00 | 27.59 | C |
| ATOM | 1145 | CB | LEU | A | 95 | −61.692 | 50.747 | 6.282 | 1.00 | 27.49 | C |
| ATOM | 1148 | CG | LEU | A | 95 | −60.871 | 49.596 | 6.909 | 1.00 | 27.47 | C |
| ATOM | 1150 | CD1 | LEU | A | 95 | −59.400 | 49.900 | 6.902 | 1.00 | 27.70 | C |
| ATOM | 1154 | CD2 | LEU | A | 95 | −61.292 | 49.274 | 8.329 | 1.00 | 27.50 | C |
| ATOM | 1158 | C | LEU | A | 95 | −62.173 | 49.314 | 4.318 | 1.00 | 27.71 | C |
| ATOM | 1159 | O | LEU | A | 95 | −61.303 | 48.537 | 3.914 | 1.00 | 27.73 | O |
| ATOM | 1161 | N | HIS | A | 96 | −63.461 | 48.989 | 4.437 | 1.00 | 27.74 | N |
| ATOM | 1162 | CA | HIS | A | 96 | −64.003 | 47.715 | 3.977 | 1.00 | 27.54 | C |
| ATOM | 1164 | CB | HIS | A | 96 | −65.497 | 47.680 | 4.230 | 1.00 | 27.57 | C |
| ATOM | 1167 | CG | HIS | A | 96 | −66.161 | 46.482 | 3.654 | 1.00 | 28.65 | C |
| ATOM | 1168 | ND1 | HIS | A | 96 | −65.790 | 45.201 | 3.988 | 1.00 | 30.59 | N |
| ATOM | 1170 | CE1 | HIS | A | 96 | −66.540 | 44.341 | 3.325 | 1.00 | 31.88 | C |
| ATOM | 1172 | NE2 | HIS | A | 96 | −67.384 | 45.021 | 2.570 | 1.00 | 32.06 | N |
| ATOM | 1174 | CD2 | HIS | A | 96 | −67.166 | 46.364 | 2.758 | 1.00 | 30.47 | C |
| ATOM | 1176 | C | HIS | A | 96 | −63.705 | 47.450 | 2.492 | 1.00 | 27.09 | C |
| ATOM | 1177 | O | HIS | A | 96 | −63.128 | 46.425 | 2.150 | 1.00 | 27.18 | O |
| ATOM | 1179 | N | GLY | A | 97 | −64.079 | 48.386 | 1.625 | 1.00 | 26.55 | N |
| ATOM | 1180 | CA | GLY | A | 97 | −63.760 | 48.300 | .205 | 1.00 | 26.26 | C |
| ATOM | 1183 | C | GLY | A | 97 | −62.277 | 48.112 | −.088 | 1.00 | 26.23 | C |
| ATOM | 1184 | O | GLY | A | 97 | −61.918 | 47.334 | −.974 | 1.00 | 26.39 | O |
| ATOM | 1186 | N | THR | A | 98 | −61.415 | 48.815 | .653 | 1.00 | 25.83 | N |
| ATOM | 1187 | CA | THR | A | 98 | −59.967 | 48.755 | .435 | 1.00 | 25.36 | C |
| ATOM | 1189 | CB | THR | A | 98 | −59.204 | 49.847 | 1.215 | 1.00 | 25.07 | C |
| ATOM | 1191 | OG1 | THR | A | 98 | −59.796 | 51.123 | .980 | 1.00 | 23.62 | O |
| ATOM | 1193 | CG2 | THR | A | 98 | −57.755 | 49.905 | .780 | 1.00 | 24.88 | C |
| ATOM | 1197 | C | THR | A | 98 | −59.416 | 47.389 | .845 | 1.00 | 25.69 | C |
| ATOM | 1198 | O | THR | A | 98 | −58.622 | 46.802 | .111 | 1.00 | 25.66 | O |
| ATOM | 1200 | N | ALA | A | 99 | −59.847 | 46.890 | 2.008 | 1.00 | 25.95 | N |
| ATOM | 1201 | CA | ALA | A | 99 | −59.468 | 45.540 | 2.495 | 1.00 | 25.93 | C |
| ATOM | 1203 | CB | ALA | A | 99 | −59.945 | 45.330 | 3.929 | 1.00 | 25.82 | C |
| ATOM | 1207 | C | ALA | A | 99 | −59.984 | 44.404 | 1.595 | 1.00 | 25.64 | C |
| ATOM | 1208 | O | ALA | A | 99 | −59.204 | 43.599 | 1.102 | 1.00 | 25.38 | O |
| ATOM | 1210 | N | LEU | A | 100 | −61.290 | 44.348 | 1.371 | 1.00 | 25.46 | N |
| ATOM | 1211 | CA | LEU | A | 100 | −61.856 | 43.335 | .474 | 1.00 | 25.55 | C |
| ATOM | 1213 | CB | LEU | A | 100 | −63.361 | 43.540 | .326 | 1.00 | 25.37 | C |
| ATOM | 1216 | CG | LEU | A | 100 | −64.118 | 42.464 | −.443 | 1.00 | 25.41 | C |
| ATOM | 1218 | CD1 | LEU | A | 100 | −64.038 | 41.115 | .281 | 1.00 | 26.01 | C |
| ATOM | 1222 | CD2 | LEU | A | 100 | −65.555 | 42.893 | −.639 | 1.00 | 25.19 | C |
| ATOM | 1226 | C | LEU | A | 100 | −61.196 | 43.353 | −.919 | 1.00 | 25.70 | C |
| ATOM | 1227 | O | LEU | A | 100 | −60.819 | 42.301 | −1.469 | 1.00 | 25.36 | O |
| ATOM | 1229 | N | SER | A | 101 | −61.064 | 44.550 | −1.489 | 1.00 | 25.77 | N |
| ATOM | 1230 | CA | SER | A | 101 | −60.434 | 44.688 | −2.805 | 1.00 | 25.67 | C |
| ATOM | 1232 | CB | SER | A | 101 | −60.629 | 46.098 | −3.375 | 1.00 | 25.83 | C |
| ATOM | 1235 | OG | SER | A | 101 | −59.840 | 47.064 | −2.688 | 1.00 | 26.98 | O |
| ATOM | 1237 | C | SER | A | 101 | −58.947 | 44.336 | −2.756 | 1.00 | 25.01 | C |
| ATOM | 1238 | O | SER | A | 101 | −58.427 | 43.705 | −3.672 | 1.00 | 24.94 | O |
| ATOM | 1240 | N | PHE | A | 102 | −58.270 | 44.737 | −1.687 | 1.00 | 24.30 | N |
| ATOM | 1241 | CA | PHE | A | 102 | −56.852 | 44.436 | −1.560 | 1.00 | 23.99 | C |
| ATOM | 1243 | CB | PHE | A | 102 | −56.295 | 44.963 | −.229 | 1.00 | 23.84 | C |
| ATOM | 1246 | CG | PHE | A | 102 | −54.860 | 44.606 | .027 | 1.00 | 23.24 | C |
| ATOM | 1247 | CD1 | PHE | A | 102 | −53.849 | 45.504 | −.259 | 1.00 | 23.56 | C |
| ATOM | 1249 | CE1 | PHE | A | 102 | −52.507 | 45.182 | −.007 | 1.00 | 24.50 | C |
| ATOM | 1251 | CZ | PHE | A | 102 | −52.175 | 43.941 | .540 | 1.00 | 24.27 | C |
| ATOM | 1253 | CE2 | PHE | A | 102 | −53.180 | 43.042 | .834 | 1.00 | 23.95 | C |
| ATOM | 1255 | CD2 | PHE | A | 102 | −54.520 | 43.376 | .576 | 1.00 | 23.45 | C |
| ATOM | 1257 | C | PHE | A | 102 | −56.673 | 42.928 | −1.679 | 1.00 | 23.65 | C |
| ATOM | 1258 | O | PHE | A | 102 | −55.890 | 42.442 | −2.501 | 1.00 | 23.55 | O |

TABLE 16-7-continued

Coordinates of *P. tremuloides* IspS

| ATOM | 1260 | N | ARG | A | 103 | −57.443 | 42.202 | −.880 | 1.00 | 23.20 | N |
|---|---|---|---|---|---|---|---|---|---|---|---|
| ATOM | 1261 | CA | ARG | A | 103 | −57.298 | 40.765 | −.764 | 1.00 | 22.84 | C |
| ATOM | 1263 | CB | ARG | A | 103 | −58.250 | 40.231 | .291 | 1.00 | 23.01 | C |
| ATOM | 1266 | CG | ARG | A | 103 | −58.054 | 38.774 | .597 | 1.00 | 23.93 | C |
| ATOM | 1269 | CD | ARG | A | 103 | −58.703 | 38.376 | 1.937 | 1.00 | 23.84 | C |
| ATOM | 1272 | NE | ARG | A | 103 | −60.150 | 38.538 | 1.919 | 1.00 | 22.36 | N |
| ATOM | 1274 | CZ | ARG | A | 103 | −60.982 | 37.763 | 1.240 | 1.00 | 20.62 | C |
| ATOM | 1275 | NH1 | ARG | A | 103 | −60.512 | 36.773 | .490 | 1.00 | 20.19 | N |
| ATOM | 1278 | NH2 | ARG | A | 103 | −62.288 | 38.003 | 1.293 | 1.00 | 20.32 | N |
| ATOM | 1281 | C | ARG | A | 103 | −57.602 | 40.117 | −2.082 | 1.00 | 22.34 | C |
| ATOM | 1282 | O | ARG | A | 103 | −56.826 | 39.303 | −2.576 | 1.00 | 22.37 | O |
| ATOM | 1284 | N | LEU | A | 104 | −58.729 | 40.496 | −2.667 | 1.00 | 21.98 | N |
| ATOM | 1285 | CA | LEU | A | 104 | −59.129 | 39.926 | −3.951 | 1.00 | 21.60 | C |
| ATOM | 1287 | CB | LEU | A | 104 | −60.503 | 40.442 | −4.378 | 1.00 | 21.23 | C |
| ATOM | 1290 | CG | LEU | A | 104 | −61.590 | 39.832 | −3.522 | 1.00 | 20.30 | C |
| ATOM | 1292 | CD1 | LEU | A | 104 | −62.949 | 40.401 | −3.856 | 1.00 | 19.53 | C |
| ATOM | 1296 | CD2 | LEU | A | 104 | −61.554 | 38.344 | −3.725 | 1.00 | 19.71 | C |
| ATOM | 1300 | C | LEU | A | 104 | −58.101 | 40.198 | −5.040 | 1.00 | 21.48 | C |
| ATOM | 1301 | O | LEU | A | 104 | −57.743 | 39.294 | −5.780 | 1.00 | 21.62 | O |
| ATOM | 1303 | N | LEU | A | 105 | −57.623 | 41.432 | −5.139 | 1.00 | 21.14 | N |
| ATOM | 1304 | CA | LEU | A | 105 | −56.655 | 41.747 | −6.173 | 1.00 | 21.05 | C |
| ATOM | 1306 | CB | LEU | A | 105 | −56.352 | 43.248 | −6.205 | 1.00 | 20.94 | C |
| ATOM | 1309 | CG | LEU | A | 105 | −57.465 | 44.165 | −6.732 | 1.00 | 20.06 | C |
| ATOM | 1311 | CD1 | LEU | A | 105 | −57.060 | 45.617 | −6.580 | 1.00 | 17.92 | C |
| ATOM | 1315 | CD2 | LEU | A | 105 | −57.804 | 43.857 | −8.174 | 1.00 | 19.18 | C |
| ATOM | 1319 | C | LEU | A | 105 | −55.372 | 40.908 | −5.997 | 1.00 | 21.32 | C |
| ATOM | 1320 | O | LEU | A | 105 | −54.840 | 40.357 | −6.976 | 1.00 | 21.37 | O |
| ATOM | 1322 | N | ARG | A | 106 | −54.893 | 40.777 | −4.763 | 1.00 | 21.25 | N |
| ATOM | 1323 | CA | ARG | A | 106 | −53.678 | 40.003 | −4.528 | 1.00 | 21.33 | C |
| ATOM | 1325 | CB | ARG | A | 106 | −53.151 | 40.211 | −3.117 | 1.00 | 21.53 | C |
| ATOM | 1328 | CG | ARG | A | 106 | −51.772 | 39.588 | −2.917 | 1.00 | 22.60 | C |
| ATOM | 1331 | CD | ARG | A | 106 | −51.098 | 40.091 | −1.666 | 1.00 | 23.60 | C |
| ATOM | 1334 | NE | ARG | A | 106 | −50.374 | 41.330 | −1.897 | 1.00 | 24.60 | N |
| ATOM | 1336 | CZ | ARG | A | 106 | −49.606 | 41.916 | −.989 | 1.00 | 26.54 | C |
| ATOM | 1337 | NH1 | ARG | A | 106 | −49.469 | 41.380 | .225 | 1.00 | 26.98 | N |
| ATOM | 1340 | NH2 | ARG | A | 106 | −48.967 | 43.041 | −1.295 | 1.00 | 27.19 | N |
| ATOM | 1343 | C | ARG | A | 106 | −53.888 | 38.517 | −4.767 | 1.00 | 21.19 | C |
| ATOM | 1344 | O | ARG | A | 106 | −52.998 | 37.821 | −5.278 | 1.00 | 21.18 | O |
| ATOM | 1346 | N | GLN | A | 107 | −55.061 | 38.028 | −4.378 | 1.00 | 21.09 | N |
| ATOM | 1347 | CA | GLN | A | 107 | −55.425 | 36.635 | −4.618 | 1.00 | 20.76 | C |
| ATOM | 1349 | CB | GLN | A | 107 | −56.861 | 36.378 | −4.168 | 1.00 | 20.51 | C |
| ATOM | 1352 | CG | GLN | A | 107 | −57.329 | 34.941 | −4.327 | 1.00 | 19.68 | C |
| ATOM | 1355 | CD | GLN | A | 107 | −58.790 | 34.772 | −4.010 | 1.00 | 18.26 | C |
| ATOM | 1356 | OE1 | GLN | A | 107 | −59.395 | 35.591 | −3.334 | 1.00 | 17.44 | O |
| ATOM | 1357 | NE2 | GLN | A | 107 | −59.366 | 33.698 | −4.497 | 1.00 | 18.48 | N |
| ATOM | 1360 | C | GLN | A | 107 | −55.304 | 36.306 | −6.094 | 1.00 | 20.93 | C |
| ATOM | 1361 | O | GLN | A | 107 | −54.917 | 35.212 | −6.447 | 1.00 | 21.45 | O |
| ATOM | 1363 | N | HIS | A | 108 | −55.642 | 37.260 | −6.951 | 1.00 | 21.09 | N |
| ATOM | 1364 | CA | HIS | A | 108 | −55.686 | 37.030 | −8.379 | 1.00 | 21.28 | C |
| ATOM | 1366 | CB | HIS | A | 108 | −57.024 | 37.541 | −8.913 | 1.00 | 21.02 | C |
| ATOM | 1369 | CG | HIS | A | 108 | −58.182 | 36.706 | −8.478 | 1.00 | 19.70 | C |
| ATOM | 1370 | ND1 | HIS | A | 108 | −58.637 | 35.632 | −9.210 | 1.00 | 19.91 | N |
| ATOM | 1372 | CE1 | HIS | A | 108 | −59.641 | 35.060 | −8.571 | 1.00 | 19.27 | C |
| ATOM | 1374 | NE2 | HIS | A | 108 | −59.851 | 35.720 | −7.449 | 1.00 | 18.10 | N |
| ATOM | 1376 | CD2 | HIS | A | 108 | −58.950 | 36.753 | −7.367 | 1.00 | 18.98 | C |
| ATOM | 1378 | C | HIS | A | 108 | −54.456 | 37.621 | −9.108 | 1.00 | 22.21 | C |
| ATOM | 1379 | O | HIS | A | 108 | −54.505 | 37.980 | −10.304 | 1.00 | 21.80 | O |
| ATOM | 1381 | N | GLY | A | 109 | −53.345 | 37.686 | −8.375 | 1.00 | 23.19 | N |
| ATOM | 1382 | CA | GLY | A | 109 | −52.055 | 38.007 | −8.956 | 1.00 | 24.17 | C |
| ATOM | 1385 | C | GLY | A | 109 | −51.813 | 39.470 | −9.275 | 1.00 | 25.25 | C |
| ATOM | 1386 | O | GLY | A | 109 | −50.767 | 39.802 | −9.845 | 1.00 | 25.26 | O |
| ATOM | 1388 | N | PHE | A | 110 | −52.755 | 40.349 | −8.917 | 1.00 | 26.42 | N |
| ATOM | 1389 | CA | PHE | A | 110 | −52.575 | 41.783 | −9.154 | 1.00 | 27.33 | C |
| ATOM | 1391 | CB | PHE | A | 110 | −53.895 | 42.546 | −9.067 | 1.00 | 27.36 | C |
| ATOM | 1394 | CG | PHE | A | 110 | −54.838 | 42.250 | −10.193 | 1.00 | 27.83 | C |
| ATOM | 1395 | CD1 | PHE | A | 110 | −54.633 | 42.801 | −11.439 | 1.00 | 28.69 | C |
| ATOM | 1397 | CE1 | PHE | A | 110 | −55.490 | 42.529 | −12.488 | 1.00 | 28.91 | C |
| ATOM | 1399 | CZ | PHE | A | 110 | −56.568 | 41.702 | −12.295 | 1.00 | 28.85 | C |
| ATOM | 1401 | CE2 | PHE | A | 110 | −56.787 | 41.146 | −11.060 | 1.00 | 28.67 | C |
| ATOM | 1403 | CD2 | PHE | A | 110 | −55.923 | 41.418 | −10.013 | 1.00 | 28.39 | C |
| ATOM | 1405 | C | PHE | A | 110 | −51.582 | 42.369 | −8.163 | 1.00 | 28.25 | C |
| ATOM | 1406 | O | PHE | A | 110 | −51.449 | 41.890 | −7.024 | 1.00 | 28.71 | O |
| ATOM | 1408 | N | GLU | A | 111 | −50.886 | 43.411 | −8.607 | 1.00 | 29.05 | N |
| ATOM | 1409 | CA | GLU | A | 111 | −49.951 | 44.142 | −7.760 | 1.00 | 29.66 | C |
| ATOM | 1411 | CB | GLU | A | 111 | −48.902 | 44.803 | −8.648 | 1.00 | 30.37 | C |
| ATOM | 1414 | CG | GLU | A | 111 | −47.750 | 45.509 | −7.947 | 1.00 | 33.30 | C |
| ATOM | 1417 | CD | GLU | A | 111 | −46.916 | 46.342 | −8.946 | 1.00 | 38.00 | C |
| ATOM | 1418 | OE1 | GLU | A | 111 | −46.312 | 45.750 | −9.885 | 1.00 | 39.60 | O |

TABLE 16-7-continued

Coordinates of *P. tremuloides* IspS

| | | | | | | | | | | |
|---|---|---|---|---|---|---|---|---|---|---|
| ATOM | 1419 | OE2 | GLU | A | 111 | −46.886 | 47.594 | −8.802 | 1.00 | 40.87 O |
| ATOM | 1420 | C | GLU | A | 111 | −50.724 | 45.184 | −6.935 | 1.00 | 28.98 C |
| ATOM | 1421 | O | GLU | A | 111 | −51.293 | 46.123 | −7.495 | 1.00 | 28.45 O |
| ATOM | 1423 | N | VAL | A | 112 | −50.787 | 44.961 | −5.618 | 1.00 | 28.47 N |
| ATOM | 1424 | CA | VAL | A | 112 | −51.284 | 45.950 | −4.655 | 1.00 | 28.09 C |
| ATOM | 1426 | CB | VAL | A | 112 | −52.564 | 45.501 | −3.908 | 1.00 | 27.76 C |
| ATOM | 1428 | CG1 | VAL | A | 112 | −53.745 | 45.466 | −4.836 | 1.00 | 27.38 C |
| ATOM | 1432 | CG2 | VAL | A | 112 | −52.360 | 44.167 | −3.252 | 1.00 | 27.80 C |
| ATOM | 1436 | C | VAL | A | 112 | −50.193 | 46.199 | −3.631 | 1.00 | 28.15 C |
| ATOM | 1437 | O | VAL | A | 112 | −49.339 | 45.354 | −3.436 | 1.00 | 27.90 O |
| ATOM | 1439 | N | SER | A | 113 | −50.241 | 47.354 | −2.974 | 1.00 | 28.54 N |
| ATOM | 1440 | CA | SER | A | 113 | −49.194 | 47.782 | −2.047 | 1.00 | 28.93 C |
| ATOM | 1442 | CB | SER | A | 113 | −48.563 | 49.064 | −2.564 | 1.00 | 29.12 C |
| ATOM | 1445 | OG | SER | A | 113 | −47.692 | 49.644 | −1.619 | 1.00 | 29.57 O |
| ATOM | 1447 | C | SER | A | 113 | −49.780 | 48.041 | −.685 | 1.00 | 29.13 C |
| ATOM | 1448 | O | SER | A | 113 | −50.937 | 48.426 | −.581 | 1.00 | 28.90 O |
| ATOM | 1450 | N | GLN | A | 114 | −48.985 | 47.857 | .367 | 1.00 | 29.84 N |
| ATOM | 1451 | CA | GLN | A | 114 | −49.524 | 48.019 | 1.736 | 1.00 | 30.40 C |
| ATOM | 1453 | CB | GLN | A | 114 | −48.568 | 47.507 | 2.830 | 1.00 | 30.34 C |
| ATOM | 1456 | CG | GLN | A | 114 | −47.199 | 48.159 | 2.844 | 1.00 | 30.61 C |
| ATOM | 1459 | CD | GLN | A | 114 | −46.456 | 47.928 | 4.147 | 1.00 | 30.77 C |
| ATOM | 1460 | OE1 | GLN | A | 114 | −46.876 | 47.129 | 4.982 | 1.00 | 31.92 O |
| ATOM | 1461 | NE2 | GLN | A | 114 | −45.341 | 48.624 | 4.324 | 1.00 | 30.02 N |
| ATOM | 1464 | C | GLN | A | 114 | −49.939 | 49.440 | 2.068 | 1.00 | 30.62 C |
| ATOM | 1465 | O | GLN | A | 114 | −50.573 | 49.644 | 3.094 | 1.00 | 30.73 O |
| ATOM | 1467 | N | GLU | A | 115 | −49.592 | 50.407 | 1.216 | 1.00 | 30.94 N |
| ATOM | 1468 | CA | GLU | A | 115 | −49.963 | 51.794 | 1.458 | 1.00 | 31.45 C |
| ATOM | 1470 | CB | GLU | A | 115 | −48.881 | 52.777 | .975 | 1.00 | 31.86 C |
| ATOM | 1473 | CG | GLU | A | 115 | −48.489 | 52.723 | −.509 | 1.00 | 33.48 C |
| ATOM | 1476 | CD | GLU | A | 115 | −47.006 | 53.100 | −.759 | 1.00 | 36.13 C |
| ATOM | 1477 | OE1 | GLU | A | 115 | −46.106 | 52.668 | .022 | 1.00 | 38.72 O |
| ATOM | 1478 | OE2 | GLU | A | 115 | −46.741 | 53.811 | −1.754 | 1.00 | 35.70 O |
| ATOM | 1479 | C | GLU | A | 115 | −51.338 | 52.125 | .895 | 1.00 | 31.45 C |
| ATOM | 1480 | O | GLU | A | 115 | −51.716 | 53.283 | .808 | 1.00 | 31.80 O |
| ATOM | 1482 | N | ALA | A | 116 | −52.108 | 51.105 | .549 | 1.00 | 31.58 N |
| ATOM | 1483 | CA | ALA | A | 116 | −53.524 | 51.286 | .284 | 1.00 | 31.67 C |
| ATOM | 1485 | CB | ALA | A | 116 | −54.071 | 50.092 | −.461 | 1.00 | 31.62 C |
| ATOM | 1489 | C | ALA | A | 116 | −54.273 | 51.473 | 1.596 | 1.00 | 31.88 C |
| ATOM | 1490 | O | ALA | A | 116 | −55.428 | 51.874 | 1.604 | 1.00 | 31.82 O |
| ATOM | 1492 | N | PHE | A | 117 | −53.608 | 51.161 | 2.702 | 1.00 | 32.39 N |
| ATOM | 1493 | CA | PHE | A | 117 | −54.193 | 51.271 | 4.030 | 1.00 | 32.87 C |
| ATOM | 1495 | CB | PHE | A | 117 | −53.884 | 50.003 | 4.856 | 1.00 | 32.79 C |
| ATOM | 1498 | CG | PHE | A | 117 | −54.539 | 48.758 | 4.323 | 1.00 | 31.03 C |
| ATOM | 1499 | CD1 | PHE | A | 117 | −53.782 | 47.749 | 3.760 | 1.00 | 28.79 C |
| ATOM | 1501 | CE1 | PHE | A | 117 | −54.379 | 46.620 | 3.265 | 1.00 | 28.36 C |
| ATOM | 1503 | CZ | PHE | A | 117 | −55.754 | 46.489 | 3.316 | 1.00 | 29.50 C |
| ATOM | 1505 | CE2 | PHE | A | 117 | −56.527 | 47.493 | 3.872 | 1.00 | 29.91 C |
| ATOM | 1507 | CD2 | PHE | A | 117 | −55.917 | 48.613 | 4.375 | 1.00 | 30.09 C |
| ATOM | 1509 | C | PHE | A | 117 | −53.683 | 52.493 | 4.773 | 1.00 | 33.71 C |
| ATOM | 1510 | O | PHE | A | 117 | −54.012 | 52.678 | 5.937 | 1.00 | 33.61 O |
| ATOM | 1512 | N | SER | A | 118 | −52.886 | 53.325 | 4.107 | 1.00 | 35.09 N |
| ATOM | 1513 | CA | SER | A | 118 | −52.186 | 54.429 | 4.779 | 1.00 | 36.12 C |
| ATOM | 1515 | CB | SER | A | 118 | −51.073 | 54.990 | 3.895 | 1.00 | 36.09 C |
| ATOM | 1518 | OG | SER | A | 118 | −51.607 | 55.747 | 2.820 | 1.00 | 35.96 O |
| ATOM | 1520 | C | SER | A | 118 | −53.134 | 55.552 | 5.184 | 1.00 | 37.17 C |
| ATOM | 1521 | O | SER | A | 118 | −52.873 | 56.255 | 6.166 | 1.00 | 37.22 O |
| ATOM | 1523 | N | GLY | A | 119 | −54.231 | 55.705 | 4.436 | 1.00 | 38.40 N |
| ATOM | 1524 | CA | GLY | A | 119 | −55.227 | 56.735 | 4.708 | 1.00 | 39.47 C |
| ATOM | 1527 | C | GLY | A | 119 | −56.255 | 56.398 | 5.778 | 1.00 | 40.62 C |
| ATOM | 1528 | O | GLY | A | 119 | −57.259 | 57.086 | 5.877 | 1.00 | 40.74 O |
| ATOM | 1530 | N | PHE | A | 120 | −56.024 | 55.344 | 6.563 | 1.00 | 42.13 N |
| ATOM | 1531 | CA | PHE | A | 120 | −56.906 | 54.971 | 7.684 | 1.00 | 43.27 C |
| ATOM | 1533 | CB | PHE | A | 120 | −57.510 | 53.586 | 7.455 | 1.00 | 43.21 C |
| ATOM | 1536 | CG | PHE | A | 120 | −58.176 | 53.439 | 6.134 | 1.00 | 42.36 C |
| ATOM | 1537 | CD1 | PHE | A | 120 | −59.418 | 54.006 | 5.911 | 1.00 | 41.23 C |
| ATOM | 1539 | CE1 | PHE | A | 120 | −60.035 | 53.880 | 4.691 | 1.00 | 40.87 C |
| ATOM | 1541 | CZ | PHE | A | 120 | −59.414 | 53.182 | 3.675 | 1.00 | 41.03 C |
| ATOM | 1543 | CE2 | PHE | A | 120 | −58.167 | 52.618 | 3.883 | 1.00 | 40.92 C |
| ATOM | 1545 | CD2 | PHE | A | 120 | −57.556 | 52.746 | 5.106 | 1.00 | 41.30 C |
| ATOM | 1547 | C | PHE | A | 120 | −56.179 | 54.952 | 9.019 | 1.00 | 44.71 C |
| ATOM | 1548 | O | PHE | A | 120 | −56.732 | 54.489 | 10.025 | 1.00 | 44.80 O |
| ATOM | 1550 | N | LYS | A | 121 | −54.939 | 55.430 | 9.021 | 1.00 | 46.38 N |
| ATOM | 1551 | CA | LYS | A | 121 | −54.153 | 55.519 | 10.235 | 1.00 | 47.81 C |
| ATOM | 1553 | CB | LYS | A | 121 | −52.722 | 55.050 | 9.957 | 1.00 | 47.86 C |
| ATOM | 1556 | CG | LYS | A | 121 | −52.648 | 53.537 | 9.648 | 1.00 | 48.24 C |
| ATOM | 1559 | CD | LYS | A | 121 | −51.417 | 53.119 | 8.823 | 1.00 | 49.41 C |
| ATOM | 1562 | CE | LYS | A | 121 | −50.095 | 53.142 | 9.621 | 1.00 | 49.88 C |
| ATOM | 1565 | NZ | LYS | A | 121 | −49.944 | 52.005 | 10.584 | 1.00 | 49.89 N |

TABLE 16-7-continued

Coordinates of *P. tremuloides* IspS

| | | | | | | | | | | | |
|---|---|---|---|---|---|---|---|---|---|---|---|
| ATOM | 1569 | C | LYS | A | 121 | −54.257 | 56.964 | 10.735 | 1.00 | 49.00 | C |
| ATOM | 1570 | O | LYS | A | 121 | −54.712 | 57.839 | 10.000 | 1.00 | 49.11 | O |
| ATOM | 1572 | N | ASP | A | 122 | −53.899 | 57.206 | 11.995 | 1.00 | 50.51 | N |
| ATOM | 1573 | CA | ASP | A | 122 | −54.078 | 58.537 | 12.596 | 1.00 | 51.46 | C |
| ATOM | 1575 | CB | ASP | A | 122 | −54.604 | 58.443 | 14.050 | 1.00 | 51.29 | C |
| ATOM | 1578 | CG | ASP | A | 122 | −53.570 | 57.919 | 15.036 | 1.00 | 50.73 | C |
| ATOM | 1579 | OD1 | ASP | A | 122 | −52.353 | 58.025 | 14.777 | 1.00 | 49.90 | O |
| ATOM | 1580 | OD2 | ASP | A | 122 | −53.988 | 57.398 | 16.088 | 1.00 | 49.66 | O |
| ATOM | 1581 | C | ASP | A | 122 | −52.792 | 59.358 | 12.502 | 1.00 | 52.60 | C |
| ATOM | 1582 | O | ASP | A | 122 | −51.830 | 58.953 | 11.835 | 1.00 | 52.65 | O |
| ATOM | 1584 | N | GLN | A | 123 | −52.802 | 60.512 | 13.172 | 1.00 | 53.88 | N |
| ATOM | 1585 | CA | GLN | A | 123 | −51.680 | 61.456 | 13.195 | 1.00 | 54.66 | C |
| ATOM | 1587 | CB | GLN | A | 123 | −51.993 | 62.594 | 14.178 | 1.00 | 55.01 | C |
| ATOM | 1590 | CG | GLN | A | 123 | −53.249 | 63.442 | 13.831 | 1.00 | 56.15 | C |
| ATOM | 1593 | CD | GLN | A | 123 | −52.943 | 64.736 | 13.064 | 1.00 | 57.64 | C |
| ATOM | 1594 | OE1 | GLN | A | 123 | −51.779 | 65.102 | 12.859 | 1.00 | 59.10 | O |
| ATOM | 1595 | NE2 | GLN | A | 123 | −54.001 | 65.438 | 12.652 | 1.00 | 57.63 | N |
| ATOM | 1598 | C | GLN | A | 123 | −50.365 | 60.772 | 13.591 | 1.00 | 54.87 | C |
| ATOM | 1599 | O | GLN | A | 123 | −49.309 | 61.078 | 13.034 | 1.00 | 54.67 | O |
| ATOM | 1601 | N | ASN | A | 124 | −50.458 | 59.834 | 14.538 | 1.00 | 55.21 | N |
| ATOM | 1602 | CA | ASN | A | 124 | −49.300 | 59.137 | 15.109 | 1.00 | 55.39 | C |
| ATOM | 1604 | CB | ASN | A | 124 | −49.421 | 59.122 | 16.637 | 1.00 | 55.52 | C |
| ATOM | 1607 | CG | ASN | A | 124 | −49.833 | 60.478 | 17.202 | 1.00 | 55.98 | C |
| ATOM | 1608 | OD1 | ASN | A | 124 | −49.093 | 61.460 | 17.091 | 1.00 | 56.93 | O |
| ATOM | 1609 | ND2 | ASN | A | 124 | −51.026 | 60.540 | 17.797 | 1.00 | 55.99 | N |
| ATOM | 1612 | C | ASN | A | 124 | −49.116 | 57.705 | 14.589 | 1.00 | 55.27 | C |
| ATOM | 1613 | O | ASN | A | 124 | −48.530 | 56.864 | 15.271 | 1.00 | 55.18 | O |
| ATOM | 1615 | N | GLY | A | 125 | −49.626 | 57.430 | 13.391 | 1.00 | 55.18 | N |
| ATOM | 1616 | CA | GLY | A | 125 | −49.311 | 56.190 | 12.672 | 1.00 | 55.08 | C |
| ATOM | 1619 | C | GLY | A | 125 | −49.994 | 54.897 | 13.119 | 1.00 | 54.90 | C |
| ATOM | 1620 | O | GLY | A | 125 | −49.543 | 53.806 | 12.750 | 1.00 | 55.24 | O |
| ATOM | 1622 | N | ASN | A | 126 | −51.072 | 55.008 | 13.900 | 1.00 | 54.23 | N |
| ATOM | 1623 | CA | ASN | A | 126 | −51.871 | 53.853 | 14.329 | 1.00 | 53.39 | C |
| ATOM | 1625 | CB | ASN | A | 126 | −51.927 | 53.782 | 15.852 | 1.00 | 53.27 | C |
| ATOM | 1628 | CG | ASN | A | 126 | −50.596 | 53.425 | 16.466 | 1.00 | 52.81 | C |
| ATOM | 1629 | OD1 | ASN | A | 126 | −49.636 | 53.113 | 15.764 | 1.00 | 52.29 | O |
| ATOM | 1630 | ND2 | ASN | A | 126 | −50.532 | 53.460 | 17.789 | 1.00 | 52.53 | N |
| ATOM | 1633 | C | ASN | A | 126 | −53.274 | 53.978 | 13.771 | 1.00 | 52.82 | C |
| ATOM | 1634 | O | ASN | A | 126 | −53.724 | 55.081 | 13.494 | 1.00 | 52.69 | O |
| ATOM | 1636 | N | PHE | A | 127 | −53.968 | 52.857 | 13.607 | 1.00 | 52.17 | N |
| ATOM | 1637 | CA | PHE | A | 127 | −55.287 | 52.875 | 12.962 | 1.00 | 51.56 | C |
| ATOM | 1639 | CB | PHE | A | 127 | −55.805 | 51.451 | 12.721 | 1.00 | 51.35 | C |
| ATOM | 1642 | CG | PHE | A | 127 | −55.119 | 50.730 | 11.587 | 1.00 | 50.06 | C |
| ATOM | 1643 | CD1 | PHE | A | 127 | −54.068 | 49.856 | 11.831 | 1.00 | 48.90 | C |
| ATOM | 1645 | CE1 | PHE | A | 127 | −53.437 | 49.187 | 10.789 | 1.00 | 47.59 | C |
| ATOM | 1647 | CZ | PHE | A | 127 | −53.857 | 49.383 | 9.495 | 1.00 | 47.40 | C |
| ATOM | 1649 | CE2 | PHE | A | 127 | −54.906 | 50.244 | 9.234 | 1.00 | 47.96 | C |
| ATOM | 1651 | CD2 | PHE | A | 127 | −55.533 | 50.915 | 10.276 | 1.00 | 48.85 | C |
| ATOM | 1653 | C | PHE | A | 127 | −56.303 | 53.690 | 13.776 | 1.00 | 51.35 | C |
| ATOM | 1654 | O | PHE | A | 127 | −56.347 | 53.594 | 15.002 | 1.00 | 51.09 | O |
| ATOM | 1656 | N | LEU | A | 128 | −57.100 | 54.500 | 13.083 | 1.00 | 51.15 | N |
| ATOM | 1657 | CA | LEU | A | 128 | −58.143 | 55.280 | 13.727 | 1.00 | 51.09 | C |
| ATOM | 1659 | CB | LEU | A | 128 | −59.039 | 55.979 | 12.694 | 1.00 | 51.17 | C |
| ATOM | 1662 | CG | LEU | A | 128 | −58.463 | 57.046 | 11.746 | 1.00 | 51.31 | C |
| ATOM | 1664 | CD1 | LEU | A | 128 | −59.571 | 57.628 | 10.855 | 1.00 | 50.76 | C |
| ATOM | 1668 | CD2 | LEU | A | 128 | −57.762 | 58.157 | 12.508 | 1.00 | 50.98 | C |
| ATOM | 1672 | C | LEU | A | 128 | −58.996 | 54.353 | 14.581 | 1.00 | 51.06 | C |
| ATOM | 1673 | O | LEU | A | 128 | −59.573 | 53.393 | 14.078 | 1.00 | 50.94 | O |
| ATOM | 1675 | N | GLU | A | 129 | −59.053 | 54.637 | 15.879 | 1.00 | 51.12 | N |
| ATOM | 1676 | CA | GLU | A | 129 | −59.916 | 53.913 | 16.808 | 1.00 | 50.99 | C |
| ATOM | 1678 | CB | GLU | A | 129 | −60.019 | 54.665 | 18.132 | 1.00 | 51.14 | C |
| ATOM | 1681 | CG | GLU | A | 129 | −58.850 | 54.431 | 19.049 | 1.00 | 52.04 | C |
| ATOM | 1684 | CD | GLU | A | 129 | −58.903 | 53.069 | 19.697 | 1.00 | 53.22 | C |
| ATOM | 1685 | OE1 | GLU | A | 129 | −58.040 | 52.219 | 19.376 | 1.00 | 54.19 | O |
| ATOM | 1686 | OE2 | GLU | A | 129 | −59.823 | 52.848 | 20.516 | 1.00 | 53.51 | O |
| ATOM | 1687 | C | GLU | A | 129 | −61.314 | 53.712 | 16.260 | 1.00 | 50.66 | C |
| ATOM | 1688 | O | GLU | A | 129 | −61.791 | 52.587 | 16.200 | 1.00 | 50.83 | O |
| ATOM | 1690 | N | ASN | A | 130 | −61.960 | 54.799 | 15.839 | 1.00 | 50.28 | N |
| ATOM | 1691 | CA | ASN | A | 130 | −63.389 | 54.765 | 15.486 | 1.00 | 50.03 | C |
| ATOM | 1693 | CB | ASN | A | 130 | −63.910 | 56.182 | 15.193 | 1.00 | 50.09 | C |
| ATOM | 1696 | CG | ASN | A | 130 | −63.286 | 56.805 | 13.960 | 1.00 | 50.37 | C |
| ATOM | 1697 | OD1 | ASN | A | 130 | −62.504 | 56.177 | 13.249 | 1.00 | 51.44 | O |
| ATOM | 1698 | ND2 | ASN | A | 130 | −63.634 | 58.056 | 13.701 | 1.00 | 50.27 | N |
| ATOM | 1701 | C | ASN | A | 130 | −63.804 | 53.782 | 14.369 | 1.00 | 49.56 | C |
| ATOM | 1702 | O | ASN | A | 130 | −64.993 | 53.581 | 14.131 | 1.00 | 49.44 | O |
| ATOM | 1704 | N | LEU | A | 131 | −62.828 | 53.175 | 13.699 | 1.00 | 49.21 | N |
| ATOM | 1705 | CA | LEU | A | 131 | −63.087 | 52.103 | 12.729 | 1.00 | 48.78 | C |
| ATOM | 1707 | CB | LEU | A | 131 | −61.846 | 51.832 | 11.875 | 1.00 | 48.64 | C |

TABLE 16-7-continued

Coordinates of *P. tremuloides* IspS

| ATOM | 1710 | CG | LEU | A | 131 | −61.445 | 52.939 | 10.898 | 1.00 | 48.26 | C |
|------|------|-----|-----|---|-----|---------|--------|--------|------|-------|---|
| ATOM | 1712 | CD1 | LEU | A | 131 | −60.029 | 52.709 | 10.375 | 1.00 | 47.76 | C |
| ATOM | 1716 | CD2 | LEU | A | 131 | −62.441 | 53.039 | 9.754 | 1.00 | 47.32 | C |
| ATOM | 1720 | C | LEU | A | 131 | −63.516 | 50.798 | 13.394 | 1.00 | 48.58 | C |
| ATOM | 1721 | O | LEU | A | 131 | −64.093 | 49.939 | 12.731 | 1.00 | 48.64 | O |
| ATOM | 1723 | N | LYS | A | 132 | −63.225 | 50.645 | 14.689 | 1.00 | 48.23 | N |
| ATOM | 1724 | CA | LYS | A | 132 | −63.650 | 49.474 | 15.465 | 1.00 | 47.80 | C |
| ATOM | 1726 | CB | LYS | A | 132 | −63.156 | 49.587 | 16.913 | 1.00 | 47.71 | C |
| ATOM | 1729 | CG | LYS | A | 132 | −63.930 | 50.615 | 17.728 | 1.00 | 47.80 | C |
| ATOM | 1732 | CD | LYS | A | 132 | −63.430 | 50.779 | 19.153 | 1.00 | 47.75 | C |
| ATOM | 1735 | CE | LYS | A | 132 | −64.438 | 51.577 | 19.982 | 1.00 | 47.22 | C |
| ATOM | 1738 | NZ | LYS | A | 132 | −63.769 | 52.364 | 21.033 | 1.00 | 46.65 | N |
| ATOM | 1742 | C | LYS | A | 132 | −65.182 | 49.308 | 15.446 | 1.00 | 47.56 | C |
| ATOM | 1743 | O | LYS | A | 132 | −65.696 | 48.204 | 15.616 | 1.00 | 47.76 | O |
| ATOM | 1745 | N | GLU | A | 133 | −65.901 | 50.413 | 15.249 | 1.00 | 47.18 | N |
| ATOM | 1746 | CA | GLU | A | 133 | −67.371 | 50.412 | 15.191 | 1.00 | 46.79 | C |
| ATOM | 1748 | CB | GLU | A | 133 | −67.898 | 51.850 | 15.337 | 1.00 | 46.95 | C |
| ATOM | 1751 | CG | GLU | A | 133 | −67.840 | 52.376 | 16.776 | 1.00 | 47.56 | C |
| ATOM | 1754 | CD | GLU | A | 133 | −67.613 | 53.886 | 16.863 | 1.00 | 48.41 | C |
| ATOM | 1755 | OE1 | GLU | A | 133 | −68.247 | 54.648 | 16.093 | 1.00 | 47.67 | O |
| ATOM | 1756 | OE2 | GLU | A | 133 | −66.798 | 54.304 | 17.721 | 1.00 | 48.92 | O |
| ATOM | 1757 | C | GLU | A | 133 | −67.949 | 49.770 | 13.918 | 1.00 | 46.10 | C |
| ATOM | 1758 | O | GLU | A | 133 | −69.140 | 49.446 | 13.874 | 1.00 | 46.11 | O |
| ATOM | 1760 | N | ASP | A | 134 | −67.103 | 49.601 | 12.896 | 1.00 | 45.11 | N |
| ATOM | 1761 | CA | ASP | A | 134 | −67.477 | 48.995 | 11.608 | 1.00 | 44.06 | C |
| ATOM | 1763 | CB | ASP | A | 134 | −66.934 | 49.868 | 10.474 | 1.00 | 43.97 | C |
| ATOM | 1766 | CG | ASP | A | 134 | −67.380 | 49.411 | 9.104 | 1.00 | 44.08 | C |
| ATOM | 1767 | OD1 | ASP | A | 134 | −68.072 | 48.373 | 8.972 | 1.00 | 43.42 | O |
| ATOM | 1768 | OD2 | ASP | A | 134 | −67.020 | 50.116 | 8.141 | 1.00 | 44.84 | O |
| ATOM | 1769 | C | ASP | A | 134 | −66.910 | 47.570 | 11.526 | 1.00 | 43.12 | C |
| ATOM | 1770 | O | ASP | A | 134 | −65.788 | 47.357 | 11.080 | 1.00 | 43.19 | O |
| ATOM | 1772 | N | ILE | A | 135 | −67.708 | 46.594 | 11.944 | 1.00 | 41.85 | N |
| ATOM | 1773 | CA | ILE | A | 135 | −67.216 | 45.247 | 12.216 | 1.00 | 40.75 | C |
| ATOM | 1775 | CB | ILE | A | 135 | −68.183 | 44.507 | 13.170 | 1.00 | 40.80 | C |
| ATOM | 1777 | CG1 | ILE | A | 135 | −68.227 | 45.226 | 14.524 | 1.00 | 41.21 | C |
| ATOM | 1780 | CD1 | ILE | A | 135 | −69.353 | 46.283 | 14.633 | 1.00 | 42.86 | C |
| ATOM | 1784 | CG2 | ILE | A | 135 | −67.776 | 43.063 | 13.373 | 1.00 | 40.88 | C |
| ATOM | 1788 | C | ILE | A | 135 | −66.980 | 44.457 | 10.933 | 1.00 | 39.67 | C |
| ATOM | 1789 | O | ILE | A | 135 | −66.166 | 43.537 | 10.901 | 1.00 | 39.37 | O |
| ATOM | 1791 | N | LYS | A | 136 | −67.690 | 44.828 | 9.877 | 1.00 | 38.62 | N |
| ATOM | 1792 | CA | LYS | A | 136 | −67.465 | 44.256 | 8.554 | 1.00 | 37.88 | C |
| ATOM | 1794 | CB | LYS | A | 136 | −68.525 | 44.749 | 7.561 | 1.00 | 38.33 | C |
| ATOM | 1797 | CG | LYS | A | 136 | −69.955 | 44.342 | 7.879 | 1.00 | 40.17 | C |
| ATOM | 1800 | CD | LYS | A | 136 | −70.486 | 43.262 | 6.911 | 1.00 | 42.97 | C |
| ATOM | 1803 | CE | LYS | A | 136 | −71.624 | 42.389 | 7.536 | 1.00 | 44.00 | C |
| ATOM | 1806 | NZ | LYS | A | 136 | −72.950 | 43.086 | 7.726 | 1.00 | 43.82 | N |
| ATOM | 1810 | C | LYS | A | 136 | −66.097 | 44.687 | 8.047 | 1.00 | 36.38 | C |
| ATOM | 1811 | O | LYS | A | 136 | −65.399 | 43.914 | 7.388 | 1.00 | 36.24 | O |
| ATOM | 1813 | N | ALA | A | 137 | −65.728 | 45.931 | 8.341 | 1.00 | 34.51 | N |
| ATOM | 1814 | CA | ALA | A | 137 | −64.463 | 46.474 | 7.876 | 1.00 | 33.41 | C |
| ATOM | 1816 | CB | ALA | A | 137 | −64.432 | 47.981 | 8.058 | 1.00 | 33.43 | C |
| ATOM | 1820 | C | ALA | A | 137 | −63.291 | 45.827 | 8.600 | 1.00 | 32.30 | C |
| ATOM | 1821 | O | ALA | A | 137 | −62.288 | 45.481 | 7.995 | 1.00 | 31.89 | O |
| ATOM | 1823 | N | ILE | A | 138 | −63.437 | 45.662 | 9.905 | 1.00 | 31.41 | N |
| ATOM | 1824 | CA | ILE | A | 138 | −62.395 | 45.074 | 10.737 | 1.00 | 30.60 | C |
| ATOM | 1826 | CB | ILE | A | 138 | −62.770 | 45.131 | 12.238 | 1.00 | 30.20 | C |
| ATOM | 1828 | CG1 | ILE | A | 138 | −62.914 | 46.576 | 12.689 | 1.00 | 29.92 | C |
| ATOM | 1831 | CD1 | ILE | A | 138 | −61.681 | 47.414 | 12.417 | 1.00 | 30.50 | C |
| ATOM | 1835 | CG2 | ILE | A | 138 | −61.706 | 44.470 | 13.085 | 1.00 | 29.73 | C |
| ATOM | 1839 | C | ILE | A | 138 | −62.140 | 43.631 | 10.320 | 1.00 | 30.34 | C |
| ATOM | 1840 | O | ILE | A | 138 | −60.972 | 43.203 | 10.212 | 1.00 | 30.65 | O |
| ATOM | 1842 | N | LEU | A | 139 | −63.227 | 42.884 | 10.098 | 1.00 | 29.69 | N |
| ATOM | 1843 | CA | LEU | A | 139 | −63.134 | 41.523 | 9.562 | 1.00 | 29.23 | C |
| ATOM | 1845 | CB | LEU | A | 139 | −64.517 | 40.917 | 9.332 | 1.00 | 28.92 | C |
| ATOM | 1848 | CG | LEU | A | 139 | −65.066 | 40.185 | 10.545 | 1.00 | 29.06 | C |
| ATOM | 1850 | CD1 | LEU | A | 139 | −66.541 | 39.875 | 10.352 | 1.00 | 28.20 | C |
| ATOM | 1854 | CD2 | LEU | A | 139 | −64.250 | 38.922 | 10.813 | 1.00 | 28.59 | C |
| ATOM | 1858 | C | LEU | A | 139 | −62.382 | 41.546 | 8.247 | 1.00 | 29.00 | C |
| ATOM | 1859 | O | LEU | A | 139 | −61.444 | 40.773 | 8.035 | 1.00 | 29.50 | O |
| ATOM | 1861 | N | SER | A | 140 | −62.790 | 42.458 | 7.372 | 1.00 | 28.14 | N |
| ATOM | 1862 | CA | SER | A | 140 | −62.222 | 42.526 | 6.054 | 1.00 | 27.40 | C |
| ATOM | 1864 | CB | SER | A | 140 | −62.912 | 43.619 | 5.260 | 1.00 | 27.35 | C |
| ATOM | 1867 | OG | SER | A | 140 | −63.310 | 43.103 | 4.015 | 1.00 | 28.43 | O |
| ATOM | 1869 | C | SER | A | 140 | −60.720 | 42.777 | 6.123 | 1.00 | 26.77 | C |
| ATOM | 1870 | O | SER | A | 140 | −59.975 | 42.269 | 5.298 | 1.00 | 27.29 | O |
| ATOM | 1872 | N | LEU | A | 141 | −60.285 | 43.563 | 7.105 | 1.00 | 25.89 | N |
| ATOM | 1873 | CA | LEU | A | 141 | −58.872 | 43.897 | 7.283 | 1.00 | 25.20 | C |
| ATOM | 1875 | CB | LEU | A | 141 | −58.717 | 45.164 | 8.155 | 1.00 | 25.00 | C |

TABLE 16-7-continued

Coordinates of *P. tremuloides* IspS

| ATOM | 1878 | CG | LEU | A | 141 | −57.298 | 45.670 | 8.489 | 1.00 | 24.35 | C |
| ATOM | 1880 | CD1 | LEU | A | 141 | −56.497 | 45.974 | 7.232 | 1.00 | 22.75 | C |
| ATOM | 1884 | CD2 | LEU | A | 141 | −57.329 | 46.893 | 9.385 | 1.00 | 22.81 | C |
| ATOM | 1888 | C | LEU | A | 141 | −58.140 | 42.721 | 7.920 | 1.00 | 24.92 | C |
| ATOM | 1889 | O | LEU | A | 141 | −57.034 | 42.380 | 7.521 | 1.00 | 24.77 | O |
| ATOM | 1891 | N | TYR | A | 142 | −58.751 | 42.101 | 8.921 | 1.00 | 24.51 | N |
| ATOM | 1892 | CA | TYR | A | 142 | −58.163 | 40.913 | 9.514 | 1.00 | 24.36 | C |
| ATOM | 1894 | CB | TYR | A | 142 | −59.120 | 40.325 | 10.538 | 1.00 | 24.18 | C |
| ATOM | 1897 | CG | TYR | A | 142 | −58.774 | 38.941 | 11.046 | 1.00 | 23.72 | C |
| ATOM | 1898 | CD1 | TYR | A | 142 | −57.878 | 38.763 | 12.091 | 1.00 | 22.97 | C |
| ATOM | 1900 | CE1 | TYR | A | 142 | −57.593 | 37.500 | 12.582 | 1.00 | 24.25 | C |
| ATOM | 1902 | CZ | TYR | A | 142 | −58.229 | 36.386 | 12.030 | 1.00 | 25.75 | C |
| ATOM | 1903 | OH | TYR | A | 142 | −57.967 | 35.100 | 12.500 | 1.00 | 26.97 | O |
| ATOM | 1905 | CE2 | TYR | A | 142 | −59.120 | 36.551 | 10.988 | 1.00 | 25.02 | C |
| ATOM | 1907 | CD2 | TYR | A | 142 | −59.390 | 37.820 | 10.511 | 1.00 | 24.01 | C |
| ATOM | 1909 | C | TYR | A | 142 | −57.877 | 39.896 | 8.423 | 1.00 | 24.39 | C |
| ATOM | 1910 | O | TYR | A | 142 | −56.822 | 39.276 | 8.380 | 1.00 | 24.19 | O |
| ATOM | 1912 | N | GLU | A | 143 | −58.841 | 39.760 | 7.527 | 1.00 | 24.59 | N |
| ATOM | 1913 | CA | GLU | A | 143 | −58.820 | 38.728 | 6.521 | 1.00 | 24.70 | C |
| ATOM | 1915 | CB | GLU | A | 143 | −60.194 | 38.636 | 5.853 | 1.00 | 24.69 | C |
| ATOM | 1918 | CG | GLU | A | 143 | −60.651 | 37.219 | 5.547 | 1.00 | 27.21 | C |
| ATOM | 1921 | CD | GLU | A | 143 | −61.127 | 36.426 | 6.774 | 1.00 | 30.20 | C |
| ATOM | 1922 | OE1 | GLU | A | 143 | −60.261 | 35.776 | 7.393 | 1.00 | 33.40 | O |
| ATOM | 1923 | OE2 | GLU | A | 143 | −62.351 | 36.421 | 7.097 | 1.00 | 30.50 | O |
| ATOM | 1924 | C | GLU | A | 143 | −57.701 | 39.010 | 5.518 | 1.00 | 24.08 | C |
| ATOM | 1925 | O | GLU | A | 143 | −56.984 | 38.090 | 5.126 | 1.00 | 24.53 | O |
| ATOM | 1927 | N | ALA | A | 144 | −57.537 | 40.281 | 5.147 | 1.00 | 23.30 | N |
| ATOM | 1928 | CA | ALA | A | 144 | −56.515 | 40.715 | 4.173 | 1.00 | 22.79 | C |
| ATOM | 1930 | CB | ALA | A | 144 | −56.787 | 42.154 | 3.740 | 1.00 | 22.49 | C |
| ATOM | 1934 | C | ALA | A | 144 | −55.073 | 40.598 | 4.701 | 1.00 | 22.42 | C |
| ATOM | 1935 | O | ALA | A | 144 | −54.128 | 40.380 | 3.935 | 1.00 | 22.36 | O |
| ATOM | 1937 | N | SER | A | 145 | −54.909 | 40.713 | 6.012 | 1.00 | 21.80 | N |
| ATOM | 1938 | CA | SER | A | 145 | −53.593 | 40.822 | 6.600 | 1.00 | 21.36 | C |
| ATOM | 1940 | CB | SER | A | 145 | −53.726 | 41.170 | 8.066 | 1.00 | 21.21 | C |
| ATOM | 1943 | OG | SER | A | 145 | −54.337 | 40.100 | 8.753 | 1.00 | 21.59 | O |
| ATOM | 1945 | C | SER | A | 145 | −52.797 | 39.537 | 6.476 | 1.00 | 21.30 | C |
| ATOM | 1946 | O | SER | A | 145 | −51.571 | 39.533 | 6.701 | 1.00 | 21.50 | O |
| ATOM | 1948 | N | PHE | A | 146 | −53.488 | 38.439 | 6.154 | 1.00 | 21.00 | N |
| ATOM | 1949 | CA | PHE | A | 146 | −52.827 | 37.127 | 6.030 | 1.00 | 20.41 | C |
| ATOM | 1951 | CB | PHE | A | 146 | −53.796 | 35.979 | 6.338 | 1.00 | 20.20 | C |
| ATOM | 1954 | CG | PHE | A | 146 | −54.130 | 35.873 | 7.798 | 1.00 | 19.91 | C |
| ATOM | 1955 | CD1 | PHE | A | 146 | −53.382 | 35.087 | 8.637 | 1.00 | 20.48 | C |
| ATOM | 1957 | CE1 | PHE | A | 146 | −53.679 | 35.012 | 9.992 | 1.00 | 20.59 | C |
| ATOM | 1959 | CZ | PHE | A | 146 | −54.731 | 35.740 | 10.508 | 1.00 | 19.15 | C |
| ATOM | 1961 | CE2 | PHE | A | 146 | −55.464 | 36.536 | 9.691 | 1.00 | 19.10 | C |
| ATOM | 1963 | CD2 | PHE | A | 146 | −55.155 | 36.615 | 8.343 | 1.00 | 20.16 | C |
| ATOM | 1965 | C | PHE | A | 146 | −52.174 | 36.964 | 4.680 | 1.00 | 19.76 | C |
| ATOM | 1966 | O | PHE | A | 146 | −51.305 | 36.116 | 4.523 | 1.00 | 19.46 | O |
| ATOM | 1968 | N | LEU | A | 147 | −52.550 | 37.819 | 3.729 | 1.00 | 19.34 | N |
| ATOM | 1969 | CA | LEU | A | 147 | −51.933 | 37.804 | 2.402 | 1.00 | 19.13 | C |
| ATOM | 1971 | CB | LEU | A | 147 | −52.905 | 38.367 | 1.347 | 1.00 | 18.67 | C |
| ATOM | 1974 | CG | LEU | A | 147 | −53.964 | 37.334 | .919 | 1.00 | 18.11 | C |
| ATOM | 1976 | CD1 | LEU | A | 147 | −55.090 | 37.248 | 1.961 | 1.00 | 15.10 | C |
| ATOM | 1980 | CD2 | LEU | A | 147 | −54.494 | 37.609 | −.499 | 1.00 | 16.50 | C |
| ATOM | 1984 | C | LEU | A | 147 | −50.582 | 38.525 | 2.369 | 1.00 | 19.10 | C |
| ATOM | 1985 | O | LEU | A | 147 | −49.992 | 38.715 | 1.311 | 1.00 | 19.44 | O |
| ATOM | 1987 | N | ALA | A | 148 | −50.075 | 38.882 | 3.542 | 1.00 | 19.13 | N |
| ATOM | 1988 | CA | ALA | A | 148 | −48.967 | 39.806 | 3.664 | 1.00 | 18.84 | C |
| ATOM | 1990 | CB | ALA | A | 148 | −48.762 | 40.167 | 5.117 | 1.00 | 18.78 | C |
| ATOM | 1994 | C | ALA | A | 148 | −47.723 | 39.184 | 3.113 | 1.00 | 18.85 | C |
| ATOM | 1995 | O | ALA | A | 148 | −47.548 | 37.975 | 3.206 | 1.00 | 18.80 | O |
| ATOM | 1997 | N | LEU | A | 149 | −46.869 | 40.013 | 2.523 | 1.00 | 19.08 | N |
| ATOM | 1998 | CA | LEU | A | 149 | −45.507 | 39.601 | 2.215 | 1.00 | 19.32 | C |
| ATOM | 2000 | CB | LEU | A | 149 | −45.056 | 40.145 | .863 | 1.00 | 19.14 | C |
| ATOM | 2003 | CG | LEU | A | 149 | −45.819 | 39.650 | −.364 | 1.00 | 19.16 | C |
| ATOM | 2005 | CD1 | LEU | A | 149 | −45.036 | 39.929 | −1.645 | 1.00 | 18.43 | C |
| ATOM | 2009 | CD2 | LEU | A | 149 | −46.089 | 38.175 | −.259 | 1.00 | 20.09 | C |
| ATOM | 2013 | C | LEU | A | 149 | −44.527 | 40.029 | 3.304 | 1.00 | 19.60 | C |
| ATOM | 2014 | O | LEU | A | 149 | −44.797 | 40.916 | 4.113 | 1.00 | 19.20 | O |
| ATOM | 2016 | N | GLU | A | 150 | −43.384 | 39.361 | 3.309 | 1.00 | 20.42 | N |
| ATOM | 2017 | CA | GLU | A | 150 | −42.286 | 39.674 | 4.215 | 1.00 | 21.03 | C |
| ATOM | 2019 | CB | GLU | A | 150 | −41.098 | 38.741 | 3.948 | 1.00 | 21.03 | C |
| ATOM | 2022 | CG | GLU | A | 150 | −40.491 | 38.176 | 5.205 | 1.00 | 22.23 | C |
| ATOM | 2025 | CD | GLU | A | 150 | −39.433 | 37.117 | 4.941 | 1.00 | 24.34 | C |
| ATOM | 2026 | OE1 | GLU | A | 150 | −39.189 | 36.786 | 3.753 | 1.00 | 24.53 | O |
| ATOM | 2027 | OE2 | GLU | A | 150 | −38.843 | 36.625 | 5.940 | 1.00 | 25.82 | O |
| ATOM | 2028 | C | GLU | A | 150 | −41.887 | 41.130 | 4.011 | 1.00 | 21.29 | C |
| ATOM | 2029 | O | GLU | A | 150 | −41.619 | 41.544 | 2.885 | 1.00 | 21.13 | O |

TABLE 16-7-continued

Coordinates of *P. tremuloides* IspS

| ATOM | 2031 | N | GLY | A | 151 | −41.893 | 41.903 | 5.094 | 1.00 | 21.89 | N |
|---|---|---|---|---|---|---|---|---|---|---|---|
| ATOM | 2032 | CA | GLY | A | 151 | −41.636 | 43.341 | 5.030 | 1.00 | 22.25 | C |
| ATOM | 2035 | C | GLY | A | 151 | −42.871 | 44.221 | 5.152 | 1.00 | 22.67 | C |
| ATOM | 2036 | O | GLY | A | 151 | −42.757 | 45.397 | 5.462 | 1.00 | 22.84 | O |
| ATOM | 2038 | N | GLU | A | 152 | −44.055 | 43.669 | 4.918 | 1.00 | 23.19 | N |
| ATOM | 2039 | CA | GLU | A | 152 | −45.263 | 44.474 | 4.937 | 1.00 | 23.76 | C |
| ATOM | 2041 | CB | GLU | A | 152 | −46.350 | 43.813 | 4.100 | 1.00 | 23.79 | C |
| ATOM | 2044 | CG | GLU | A | 152 | −46.037 | 43.890 | 2.615 | 1.00 | 23.98 | C |
| ATOM | 2047 | CD | GLU | A | 152 | −47.147 | 43.368 | 1.749 | 1.00 | 23.72 | C |
| ATOM | 2048 | OE1 | GLU | A | 152 | −47.226 | 43.771 | .574 | 1.00 | 22.11 | O |
| ATOM | 2049 | OE2 | GLU | A | 152 | −47.939 | 42.542 | 2.241 | 1.00 | 25.41 | O |
| ATOM | 2050 | C | GLU | A | 152 | −45.722 | 44.719 | 6.365 | 1.00 | 24.47 | C |
| ATOM | 2051 | O | GLU | A | 152 | −46.586 | 44.006 | 6.906 | 1.00 | 24.70 | O |
| ATOM | 2053 | N | ASN | A | 153 | −45.134 | 45.744 | 6.969 | 1.00 | 25.00 | N |
| ATOM | 2054 | CA | ASN | A | 153 | −45.287 | 45.978 | 8.404 | 1.00 | 25.59 | C |
| ATOM | 2056 | CB | ASN | A | 153 | −44.221 | 46.957 | 8.902 | 1.00 | 25.55 | C |
| ATOM | 2059 | CG | ASN | A | 153 | −44.386 | 48.331 | 8.308 | 1.00 | 25.57 | C |
| ATOM | 2060 | OD1 | ASN | A | 153 | −44.114 | 48.557 | 7.128 | 1.00 | 24.52 | O |
| ATOM | 2061 | ND2 | ASN | A | 153 | −44.867 | 49.256 | 9.117 | 1.00 | 27.05 | N |
| ATOM | 2064 | C | ASN | A | 153 | −46.679 | 46.486 | 8.772 | 1.00 | 25.92 | C |
| ATOM | 2065 | O | ASN | A | 153 | −47.172 | 46.238 | 9.872 | 1.00 | 26.02 | O |
| ATOM | 2067 | N | ILE | A | 154 | −47.310 | 47.197 | 7.847 | 1.00 | 26.35 | N |
| ATOM | 2068 | CA | ILE | A | 154 | −48.638 | 47.751 | 8.082 | 1.00 | 26.57 | C |
| ATOM | 2070 | CB | ILE | A | 154 | −49.013 | 48.779 | 7.007 | 1.00 | 26.45 | C |
| ATOM | 2072 | CG1 | ILE | A | 154 | −48.159 | 50.023 | 7.164 | 1.00 | 26.36 | C |
| ATOM | 2075 | CD1 | ILE | A | 154 | −48.060 | 50.790 | 5.883 | 1.00 | 27.92 | C |
| ATOM | 2079 | CG2 | ILE | A | 154 | −50.467 | 49.152 | 7.089 | 1.00 | 26.25 | C |
| ATOM | 2083 | C | ILE | A | 154 | −49.674 | 46.643 | 8.111 | 1.00 | 26.96 | C |
| ATOM | 2084 | O | ILE | A | 154 | −50.650 | 46.741 | 8.851 | 1.00 | 27.12 | O |
| ATOM | 2086 | N | LEU | A | 155 | −49.467 | 45.588 | 7.320 | 1.00 | 27.35 | N |
| ATOM | 2087 | CA | LEU | A | 155 | −50.422 | 44.475 | 7.304 | 1.00 | 27.76 | C |
| ATOM | 2089 | CB | LEU | A | 155 | −50.238 | 43.594 | 6.067 | 1.00 | 27.73 | C |
| ATOM | 2092 | CG | LEU | A | 155 | −51.090 | 43.990 | 4.875 | 1.00 | 27.31 | C |
| ATOM | 2094 | CD1 | LEU | A | 155 | −50.980 | 45.456 | 4.683 | 1.00 | 28.13 | C |
| ATOM | 2098 | CD2 | LEU | A | 155 | −50.633 | 43.262 | 3.623 | 1.00 | 27.79 | C |
| ATOM | 2102 | C | LEU | A | 155 | −50.340 | 43.642 | 8.582 | 1.00 | 28.22 | C |
| ATOM | 2103 | O | LEU | A | 155 | −51.361 | 43.237 | 9.112 | 1.00 | 27.95 | O |
| ATOM | 2105 | N | ASP | A | 156 | −49.128 | 43.395 | 9.068 | 1.00 | 28.95 | N |
| ATOM | 2106 | CA | ASP | A | 156 | −48.944 | 42.723 | 10.348 | 1.00 | 29.71 | C |
| ATOM | 2108 | CB | ASP | A | 156 | −47.450 | 42.461 | 10.639 | 1.00 | 30.23 | C |
| ATOM | 2111 | CG | ASP | A | 156 | −46.938 | 41.125 | 10.027 | 1.00 | 32.82 | C |
| ATOM | 2112 | OD1 | ASP | A | 156 | −47.765 | 40.240 | 9.658 | 1.00 | 36.27 | O |
| ATOM | 2113 | OD2 | ASP | A | 156 | −45.700 | 40.961 | 9.923 | 1.00 | 34.48 | O |
| ATOM | 2114 | C | ASP | A | 156 | −49.570 | 43.539 | 11.469 | 1.00 | 29.66 | C |
| ATOM | 2115 | O | ASP | A | 156 | −50.109 | 42.969 | 12.425 | 1.00 | 29.81 | O |
| ATOM | 2117 | N | GLU | A | 157 | −49.514 | 44.866 | 11.345 | 1.00 | 29.69 | N |
| ATOM | 2118 | CA | GLU | A | 157 | −50.129 | 45.768 | 12.329 | 1.00 | 29.57 | C |
| ATOM | 2120 | CB | GLU | A | 157 | −49.581 | 47.186 | 12.178 | 1.00 | 29.71 | C |
| ATOM | 2123 | CG | GLU | A | 157 | −48.164 | 47.326 | 12.712 | 1.00 | 30.53 | C |
| ATOM | 2126 | CD | GLU | A | 157 | −47.455 | 48.544 | 12.169 | 1.00 | 31.96 | C |
| ATOM | 2127 | OE1 | GLU | A | 157 | −48.167 | 49.491 | 11.741 | 1.00 | 33.56 | O |
| ATOM | 2128 | OE2 | GLU | A | 157 | −46.195 | 48.546 | 12.166 | 1.00 | 31.54 | O |
| ATOM | 2129 | C | GLU | A | 157 | −51.649 | 45.771 | 12.230 | 1.00 | 29.16 | C |
| ATOM | 2130 | O | GLU | A | 157 | −52.330 | 45.819 | 13.241 | 1.00 | 29.00 | O |
| ATOM | 2132 | N | ALA | A | 158 | −52.172 | 45.716 | 11.010 | 1.00 | 28.86 | N |
| ATOM | 2133 | CA | ALA | A | 158 | −53.606 | 45.570 | 10.792 | 1.00 | 28.79 | C |
| ATOM | 2135 | CB | ALA | A | 158 | −53.893 | 45.456 | 9.301 | 1.00 | 28.44 | C |
| ATOM | 2139 | C | ALA | A | 158 | −54.171 | 44.352 | 11.536 | 1.00 | 28.93 | C |
| ATOM | 2140 | O | ALA | A | 158 | −55.265 | 44.402 | 12.098 | 1.00 | 28.77 | O |
| ATOM | 2142 | N | LYS | A | 159 | −53.416 | 43.260 | 11.528 | 1.00 | 29.19 | N |
| ATOM | 2143 | CA | LYS | A | 159 | −53.849 | 42.022 | 12.143 | 1.00 | 29.57 | C |
| ATOM | 2145 | CB | LYS | A | 159 | −52.929 | 40.880 | 11.710 | 1.00 | 29.62 | C |
| ATOM | 2148 | CG | LYS | A | 159 | −53.297 | 39.513 | 12.258 | 1.00 | 30.27 | C |
| ATOM | 2151 | CD | LYS | A | 159 | −52.765 | 38.365 | 11.387 | 1.00 | 31.78 | C |
| ATOM | 2154 | CE | LYS | A | 159 | −51.259 | 38.132 | 11.525 | 1.00 | 33.15 | C |
| ATOM | 2157 | NZ | LYS | A | 159 | −50.911 | 36.696 | 11.248 | 1.00 | 33.88 | N |
| ATOM | 2161 | C | LYS | A | 159 | −53.866 | 42.160 | 13.670 | 1.00 | 29.99 | C |
| ATOM | 2162 | O | LYS | A | 159 | −54.767 | 41.642 | 14.332 | 1.00 | 30.29 | O |
| ATOM | 2164 | N | VAL | A | 160 | −52.886 | 42.862 | 14.236 | 1.00 | 30.07 | N |
| ATOM | 2165 | CA | VAL | A | 160 | −52.840 | 43.047 | 15.696 | 1.00 | 30.03 | C |
| ATOM | 2167 | CB | VAL | A | 160 | −51.520 | 43.691 | 16.162 | 1.00 | 29.88 | C |
| ATOM | 2169 | CG1 | VAL | A | 160 | −51.515 | 43.863 | 17.671 | 1.00 | 28.94 | C |
| ATOM | 2173 | CG2 | VAL | A | 160 | −50.341 | 42.848 | 15.707 | 1.00 | 30.23 | C |
| ATOM | 2177 | C | VAL | A | 160 | −53.996 | 43.925 | 16.149 | 1.00 | 30.05 | C |
| ATOM | 2178 | O | VAL | A | 160 | −54.544 | 43.752 | 17.234 | 1.00 | 30.31 | O |
| ATOM | 2180 | N | PHE | A | 161 | −54.355 | 44.862 | 15.290 | 1.00 | 30.08 | N |
| ATOM | 2181 | CA | PHE | A | 161 | −55.407 | 45.808 | 15.558 | 1.00 | 30.09 | C |
| ATOM | 2183 | CB | PHE | A | 161 | −55.255 | 46.993 | 14.598 | 1.00 | 29.92 | C |

TABLE 16-7-continued

Coordinates of *P. tremuloides* IspS

| ATOM | 2186 | CG | PHE | A | 161 | −56.370 | 47.974 | 14.654 | 1.00 | 28.52 | C |
|---|---|---|---|---|---|---|---|---|---|---|---|
| ATOM | 2187 | CD1 | PHE | A | 161 | −56.347 | 49.005 | 15.554 | 1.00 | 27.92 | C |
| ATOM | 2189 | CE1 | PHE | A | 161 | −57.361 | 49.903 | 15.600 | 1.00 | 28.06 | C |
| ATOM | 2191 | CZ | PHE | A | 161 | −58.411 | 49.783 | 14.733 | 1.00 | 28.76 | C |
| ATOM | 2193 | CE2 | PHE | A | 161 | −58.441 | 48.757 | 13.826 | 1.00 | 28.31 | C |
| ATOM | 2195 | CD2 | PHE | A | 161 | −57.429 | 47.869 | 13.789 | 1.00 | 28.16 | C |
| ATOM | 2197 | C | PHE | A | 161 | −56.746 | 45.123 | 15.388 | 1.00 | 30.55 | C |
| ATOM | 2198 | O | PHE | A | 161 | −57.598 | 45.203 | 16.258 | 1.00 | 30.53 | O |
| ATOM | 2200 | N | ALA | A | 162 | −56.930 | 44.438 | 14.271 | 1.00 | 31.34 | N |
| ATOM | 2201 | CA | ALA | A | 162 | −58.193 | 43.770 | 14.023 | 1.00 | 32.26 | C |
| ATOM | 2203 | CB | ALA | A | 162 | −58.217 | 43.139 | 12.643 | 1.00 | 32.31 | C |
| ATOM | 2207 | C | ALA | A | 162 | −58.500 | 42.734 | 15.118 | 1.00 | 33.09 | C |
| ATOM | 2208 | O | ALA | A | 162 | −59.557 | 42.814 | 15.735 | 1.00 | 33.83 | O |
| ATOM | 2210 | N | ILE | A | 163 | −57.587 | 41.799 | 15.393 | 1.00 | 33.59 | N |
| ATOM | 2211 | CA | ILE | A | 163 | −57.826 | 40.799 | 16.438 | 1.00 | 34.02 | C |
| ATOM | 2213 | CB | ILE | A | 163 | −56.597 | 39.907 | 16.745 | 1.00 | 33.98 | C |
| ATOM | 2215 | CG1 | ILE | A | 163 | −56.235 | 39.008 | 15.566 | 1.00 | 34.37 | C |
| ATOM | 2218 | CD1 | ILE | A | 163 | −54.878 | 38.317 | 15.722 | 1.00 | 34.38 | C |
| ATOM | 2222 | CG2 | ILE | A | 163 | −56.883 | 38.995 | 17.919 | 1.00 | 33.38 | C |
| ATOM | 2226 | C | ILE | A | 163 | −58.225 | 41.472 | 17.744 | 1.00 | 34.75 | C |
| ATOM | 2227 | O | ILE | A | 163 | −59.189 | 41.064 | 18.373 | 1.00 | 35.03 | O |
| ATOM | 2229 | N | SER | A | 164 | −57.501 | 42.504 | 18.156 | 1.00 | 35.76 | N |
| ATOM | 2230 | CA | SER | A | 164 | −57.763 | 43.117 | 19.463 | 1.00 | 36.59 | C |
| ATOM | 2232 | CB | SER | A | 164 | −56.828 | 44.293 | 19.735 | 1.00 | 36.59 | C |
| ATOM | 2235 | OG | SER | A | 164 | −57.350 | 45.485 | 19.164 | 1.00 | 36.46 | O |
| ATOM | 2237 | C | SER | A | 164 | −59.196 | 43.611 | 19.556 | 1.00 | 37.42 | C |
| ATOM | 2238 | O | SER | A | 164 | −59.860 | 43.420 | 20.571 | 1.00 | 37.38 | O |
| ATOM | 2240 | N | HIS | A | 165 | −59.661 | 44.251 | 18.486 | 1.00 | 38.51 | N |
| ATOM | 2241 | CA | HIS | A | 165 | −60.990 | 44.851 | 18.467 | 1.00 | 39.40 | C |
| ATOM | 2243 | CB | HIS | A | 165 | −61.008 | 46.097 | 17.574 | 1.00 | 39.76 | C |
| ATOM | 2246 | CG | HIS | A | 165 | −60.467 | 47.323 | 18.251 | 1.00 | 42.06 | C |
| ATOM | 2247 | ND1 | HIS | A | 165 | −59.205 | 47.821 | 18.000 | 1.00 | 44.21 | N |
| ATOM | 2249 | CE1 | HIS | A | 165 | −58.998 | 48.893 | 18.748 | 1.00 | 45.04 | C |
| ATOM | 2251 | NE2 | HIS | A | 165 | −60.080 | 49.106 | 19.478 | 1.00 | 44.99 | N |
| ATOM | 2253 | CD2 | HIS | A | 165 | −61.011 | 48.135 | 19.192 | 1.00 | 43.76 | C |
| ATOM | 2255 | C | HIS | A | 165 | −62.078 | 43.872 | 18.060 | 1.00 | 39.38 | C |
| ATOM | 2256 | O | HIS | A | 165 | −63.248 | 44.244 | 18.067 | 1.00 | 39.43 | O |
| ATOM | 2258 | N | LEU | A | 166 | −61.683 | 42.632 | 17.745 | 1.00 | 39.54 | N |
| ATOM | 2259 | CA | LEU | A | 166 | −62.589 | 41.550 | 17.326 | 1.00 | 39.55 | C |
| ATOM | 2261 | CB | LEU | A | 166 | −62.001 | 40.766 | 16.154 | 1.00 | 39.28 | C |
| ATOM | 2264 | CG | LEU | A | 166 | −62.156 | 41.339 | 14.752 | 1.00 | 38.23 | C |
| ATOM | 2266 | CD1 | LEU | A | 166 | −61.361 | 40.501 | 13.805 | 1.00 | 37.53 | C |
| ATOM | 2270 | CD2 | LEU | A | 166 | −63.594 | 41.367 | 14.332 | 1.00 | 37.21 | C |
| ATOM | 2274 | C | LEU | A | 166 | −62.842 | 40.555 | 18.438 | 1.00 | 40.08 | C |
| ATOM | 2275 | O | LEU | A | 166 | −63.991 | 40.220 | 18.733 | 1.00 | 40.42 | O |
| ATOM | 2277 | N | LYS | A | 167 | −61.766 | 40.074 | 19.052 | 1.00 | 40.58 | N |
| ATOM | 2278 | CA | LYS | A | 167 | −61.875 | 39.090 | 20.133 | 1.00 | 41.09 | C |
| ATOM | 2280 | CB | LYS | A | 167 | −60.491 | 38.632 | 20.595 | 1.00 | 41.13 | C |
| ATOM | 2283 | CG | LYS | A | 167 | −59.897 | 39.399 | 21.768 | 1.00 | 42.16 | C |
| ATOM | 2286 | CD | LYS | A | 167 | −58.421 | 39.035 | 22.013 | 1.00 | 44.45 | C |
| ATOM | 2289 | CE | LYS | A | 167 | −58.070 | 37.561 | 21.654 | 1.00 | 45.56 | C |
| ATOM | 2292 | NZ | LYS | A | 167 | −56.610 | 37.237 | 21.798 | 1.00 | 46.20 | N |
| ATOM | 2296 | C | LYS | A | 167 | −62.678 | 39.584 | 21.337 | 1.00 | 41.23 | C |
| ATOM | 2297 | O | LYS | A | 167 | −62.994 | 38.793 | 22.215 | 1.00 | 41.47 | O |
| ATOM | 2299 | N | GLU | A | 168 | −62.995 | 40.884 | 21.352 | 1.00 | 41.49 | N |
| ATOM | 2300 | CA | GLU | A | 168 | −63.704 | 41.583 | 22.437 | 1.00 | 41.42 | C |
| ATOM | 2302 | CB | GLU | A | 168 | −65.201 | 41.730 | 22.100 | 1.00 | 41.27 | C |
| ATOM | 2305 | CG | GLU | A | 168 | −65.995 | 40.424 | 22.016 | 1.00 | 41.01 | C |
| ATOM | 2308 | CD | GLU | A | 168 | −66.928 | 40.328 | 20.787 | 1.00 | 40.84 | C |
| ATOM | 2309 | OE1 | GLU | A | 168 | −66.701 | 41.040 | 19.770 | 1.00 | 39.82 | O |
| ATOM | 2310 | OE2 | GLU | A | 168 | −67.884 | 39.509 | 20.845 | 1.00 | 39.04 | O |
| ATOM | 2311 | C | GLU | A | 168 | −63.484 | 41.004 | 23.843 | 1.00 | 41.66 | C |
| ATOM | 2312 | O | GLU | A | 168 | −62.435 | 41.231 | 24.469 | 1.00 | 41.46 | O |
| ATOM | 2314 | N | GLU | A | 172 | −71.668 | 38.961 | 21.192 | 1.00 | 55.65 | N |
| ATOM | 2315 | CA | GLU | A | 172 | −73.052 | 39.153 | 20.721 | 1.00 | 56.00 | C |
| ATOM | 2317 | CB | GLU | A | 172 | −73.876 | 37.880 | 20.937 | 1.00 | 56.27 | C |
| ATOM | 2320 | CG | GLU | A | 172 | −73.198 | 36.620 | 20.390 | 1.00 | 57.12 | C |
| ATOM | 2323 | CD | GLU | A | 172 | −74.056 | 35.363 | 20.516 | 1.00 | 58.18 | C |
| ATOM | 2324 | OE1 | GLU | A | 172 | −75.300 | 35.480 | 20.622 | 1.00 | 58.84 | O |
| ATOM | 2325 | OE2 | GLU | A | 172 | −73.480 | 34.249 | 20.498 | 1.00 | 58.98 | O |
| ATOM | 2326 | C | GLU | A | 172 | −73.766 | 40.386 | 21.334 | 1.00 | 55.70 | C |
| ATOM | 2327 | O | GLU | A | 172 | −74.956 | 40.347 | 21.688 | 1.00 | 54.95 | O |
| ATOM | 2329 | N | LYS | A | 173 | −72.987 | 41.458 | 21.486 | 1.00 | 55.58 | N |
| ATOM | 2330 | CA | LYS | A | 173 | −73.496 | 42.831 | 21.466 | 1.00 | 55.43 | C |
| ATOM | 2332 | CB | LYS | A | 173 | −72.649 | 43.741 | 22.357 | 1.00 | 55.51 | C |
| ATOM | 2335 | CG | LYS | A | 173 | −72.527 | 43.223 | 23.793 | 1.00 | 56.07 | C |
| ATOM | 2338 | CD | LYS | A | 173 | −72.803 | 44.291 | 24.868 | 1.00 | 55.87 | C |
| ATOM | 2341 | CE | LYS | A | 173 | −73.111 | 43.642 | 26.221 | 1.00 | 55.20 | C |

TABLE 16-7-continued

Coordinates of *P. tremuloides* IspS

| ATOM | 2344 | NZ | LYS | A | 173 | −72.893 | 44.576 | 27.348 | 1.00 | 54.63 | N |
| --- | --- | --- | --- | --- | --- | --- | --- | --- | --- | --- | --- |
| ATOM | 2348 | C | LYS | A | 173 | −73.449 | 43.297 | 20.009 | 1.00 | 55.01 | C |
| ATOM | 2349 | O | LYS | A | 173 | −74.091 | 44.274 | 19.625 | 1.00 | 54.97 | O |
| ATOM | 2351 | N | ILE | A | 174 | −72.647 | 42.581 | 19.223 | 1.00 | 54.57 | N |
| ATOM | 2352 | CA | ILE | A | 174 | −72.713 | 42.550 | 17.767 | 1.00 | 54.22 | C |
| ATOM | 2354 | CB | ILE | A | 174 | −71.429 | 41.845 | 17.227 | 1.00 | 54.21 | C |
| ATOM | 2356 | CG1 | ILE | A | 174 | −70.196 | 42.724 | 17.474 | 1.00 | 54.73 | C |
| ATOM | 2359 | CD1 | ILE | A | 174 | −68.858 | 41.949 | 17.553 | 1.00 | 55.78 | C |
| ATOM | 2363 | CG2 | ILE | A | 174 | −71.532 | 41.504 | 15.759 | 1.00 | 54.06 | C |
| ATOM | 2367 | C | ILE | A | 174 | −73.957 | 41.744 | 17.384 | 1.00 | 53.88 | C |
| ATOM | 2368 | O | ILE | A | 174 | −74.587 | 41.134 | 18.250 | 1.00 | 53.83 | O |
| ATOM | 2370 | N | GLY | A | 175 | −74.332 | 41.747 | 16.107 | 1.00 | 53.59 | N |
| ATOM | 2371 | CA | GLY | A | 175 | −75.351 | 40.817 | 15.613 | 1.00 | 53.51 | C |
| ATOM | 2374 | C | GLY | A | 175 | −75.130 | 39.395 | 16.126 | 1.00 | 53.43 | C |
| ATOM | 2375 | O | GLY | A | 175 | −74.119 | 39.105 | 16.760 | 1.00 | 53.80 | O |
| ATOM | 2377 | N | LYS | A | 176 | −76.070 | 38.495 | 15.861 | 1.00 | 53.10 | N |
| ATOM | 2378 | CA | LYS | A | 176 | −75.926 | 37.098 | 16.286 | 1.00 | 52.68 | C |
| ATOM | 2380 | CB | LYS | A | 176 | −77.291 | 36.522 | 16.677 | 1.00 | 52.99 | C |
| ATOM | 2383 | CG | LYS | A | 176 | −78.003 | 37.387 | 17.746 | 1.00 | 54.12 | C |
| ATOM | 2386 | CD | LYS | A | 176 | −79.201 | 36.697 | 18.436 | 1.00 | 54.57 | C |
| ATOM | 2389 | CE | LYS | A | 176 | −79.503 | 37.369 | 19.792 | 1.00 | 54.79 | C |
| ATOM | 2392 | NZ | LYS | A | 176 | −80.458 | 36.598 | 20.653 | 1.00 | 55.20 | N |
| ATOM | 2396 | C | LYS | A | 176 | −75.246 | 36.267 | 15.196 | 1.00 | 51.83 | C |
| ATOM | 2397 | O | LYS | A | 176 | −74.393 | 35.433 | 15.486 | 1.00 | 51.69 | O |
| ATOM | 2399 | N | GLU | A | 177 | −75.609 | 36.520 | 13.940 | 1.00 | 50.90 | N |
| ATOM | 2400 | CA | GLU | A | 177 | −74.975 | 35.854 | 12.800 | 1.00 | 50.19 | C |
| ATOM | 2402 | CB | GLU | A | 177 | −75.792 | 36.062 | 11.507 | 1.00 | 50.41 | C |
| ATOM | 2405 | CG | GLU | A | 177 | −75.506 | 37.368 | 10.735 | 1.00 | 51.03 | C |
| ATOM | 2408 | CD | GLU | A | 177 | −76.403 | 37.572 | 9.507 | 1.00 | 52.17 | C |
| ATOM | 2409 | OE1 | GLU | A | 177 | −75.955 | 38.276 | 8.569 | 1.00 | 52.63 | O |
| ATOM | 2410 | OE2 | GLU | A | 177 | −77.546 | 37.048 | 9.479 | 1.00 | 52.03 | O |
| ATOM | 2411 | C | GLU | A | 177 | −73.549 | 36.369 | 12.607 | 1.00 | 49.10 | C |
| ATOM | 2412 | O | GLU | A | 177 | −72.626 | 35.597 | 12.321 | 1.00 | 49.53 | O |
| ATOM | 2414 | N | LEU | A | 178 | −73.388 | 37.681 | 12.770 | 1.00 | 47.39 | N |
| ATOM | 2415 | CA | LEU | A | 178 | −72.110 | 38.371 | 12.575 | 1.00 | 45.63 | C |
| ATOM | 2417 | CB | LEU | A | 178 | −72.352 | 39.877 | 12.615 | 1.00 | 45.59 | C |
| ATOM | 2420 | CG | LEU | A | 178 | −71.280 | 40.809 | 12.085 | 1.00 | 45.45 | C |
| ATOM | 2422 | CD1 | LEU | A | 178 | −70.969 | 40.515 | 10.620 | 1.00 | 45.45 | C |
| ATOM | 2426 | CD2 | LEU | A | 178 | −71.765 | 42.233 | 12.279 | 1.00 | 44.63 | C |
| ATOM | 2430 | C | LEU | A | 178 | −71.095 | 37.979 | 13.634 | 1.00 | 44.06 | C |
| ATOM | 2431 | O | LEU | A | 178 | −69.902 | 38.012 | 13.387 | 1.00 | 43.70 | O |
| ATOM | 2433 | N | ALA | A | 179 | −71.586 | 37.611 | 14.810 | 1.00 | 42.54 | N |
| ATOM | 2434 | CA | ALA | A | 179 | −70.753 | 37.041 | 15.847 | 1.00 | 41.66 | C |
| ATOM | 2436 | CB | ALA | A | 179 | −71.545 | 36.884 | 17.122 | 1.00 | 41.69 | C |
| ATOM | 2440 | C | ALA | A | 179 | −70.193 | 35.695 | 15.416 | 1.00 | 40.75 | C |
| ATOM | 2441 | O | ALA | A | 179 | −69.078 | 35.351 | 15.769 | 1.00 | 40.61 | O |
| ATOM | 2443 | N | GLU | A | 180 | −70.974 | 34.931 | 14.664 | 1.00 | 39.88 | N |
| ATOM | 2444 | CA | GLU | A | 180 | −70.518 | 33.639 | 14.143 | 1.00 | 39.40 | C |
| ATOM | 2446 | CB | GLU | A | 180 | −71.710 | 32.781 | 13.718 | 1.00 | 39.74 | C |
| ATOM | 2449 | CG | GLU | A | 180 | −72.650 | 32.415 | 14.865 | 1.00 | 40.88 | C |
| ATOM | 2452 | CD | GLU | A | 180 | −73.913 | 31.710 | 14.398 | 1.00 | 42.02 | C |
| ATOM | 2453 | OE1 | GLU | A | 180 | −74.380 | 32.022 | 13.271 | 1.00 | 43.05 | O |
| ATOM | 2454 | OE2 | GLU | A | 180 | −74.437 | 30.857 | 15.166 | 1.00 | 41.93 | O |
| ATOM | 2455 | C | GLU | A | 180 | −69.565 | 33.805 | 12.960 | 1.00 | 38.29 | C |
| ATOM | 2456 | O | GLU | A | 180 | −68.739 | 32.940 | 12.699 | 1.00 | 38.23 | O |
| ATOM | 2458 | N | GLN | A | 181 | −69.704 | 34.911 | 12.240 | 1.00 | 36.92 | N |
| ATOM | 2459 | CA | GLN | A | 181 | −68.748 | 35.299 | 11.223 | 1.00 | 35.74 | C |
| ATOM | 2461 | CB | GLN | A | 181 | −69.272 | 36.516 | 10.463 | 1.00 | 35.94 | C |
| ATOM | 2464 | CG | GLN | A | 181 | −68.931 | 36.537 | 8.975 | 1.00 | 36.93 | C |
| ATOM | 2467 | CD | GLN | A | 181 | −69.693 | 35.492 | 8.176 | 1.00 | 37.72 | C |
| ATOM | 2468 | OE1 | GLN | A | 181 | −70.769 | 35.067 | 8.567 | 1.00 | 38.78 | O |
| ATOM | 2469 | NE2 | GLN | A | 181 | −69.139 | 35.083 | 7.050 | 1.00 | 38.11 | N |
| ATOM | 2472 | C | GLN | A | 181 | −67.406 | 35.632 | 11.881 | 1.00 | 34.64 | C |
| ATOM | 2473 | O | GLN | A | 181 | −66.348 | 35.411 | 11.294 | 1.00 | 34.73 | O |
| ATOM | 2475 | N | VAL | A | 182 | −67.448 | 36.158 | 13.102 | 1.00 | 33.29 | N |
| ATOM | 2476 | CA | VAL | A | 182 | −66.224 | 36.488 | 13.842 | 1.00 | 32.28 | C |
| ATOM | 2478 | CB | VAL | A | 182 | −66.433 | 37.653 | 14.855 | 1.00 | 32.10 | C |
| ATOM | 2480 | CG1 | VAL | A | 182 | −66.328 | 38.991 | 14.166 | 1.00 | 31.51 | C |
| ATOM | 2484 | CG2 | VAL | A | 182 | −65.420 | 37.594 | 15.957 | 1.00 | 31.69 | C |
| ATOM | 2488 | C | VAL | A | 182 | −65.613 | 35.298 | 14.575 | 1.00 | 31.49 | C |
| ATOM | 2489 | O | VAL | A | 182 | −64.396 | 35.230 | 14.668 | 1.00 | 31.43 | O |
| ATOM | 2491 | N | SER | A | 183 | −66.422 | 34.378 | 15.106 | 1.00 | 30.56 | N |
| ATOM | 2492 | CA | SER | A | 183 | −65.860 | 33.174 | 15.744 | 1.00 | 30.16 | C |
| ATOM | 2494 | CB | SER | A | 183 | −66.926 | 32.253 | 16.327 | 1.00 | 30.29 | C |
| ATOM | 2497 | OG | SER | A | 183 | −67.796 | 32.934 | 17.214 | 1.00 | 32.35 | O |
| ATOM | 2499 | C | SER | A | 183 | −65.111 | 32.403 | 14.692 | 1.00 | 29.30 | C |
| ATOM | 2500 | O | SER | A | 183 | −63.974 | 31.981 | 14.903 | 1.00 | 29.32 | O |
| ATOM | 2502 | N | HIS | A | 184 | −65.768 | 32.252 | 13.546 | 1.00 | 28.24 | N |

TABLE 16-7-continued

Coordinates of *P. tremuloides* IspS

| ATOM | 2503 | CA | HIS | A | 184 | −65.215 | 31.578 | 12.379 | 1.00 | 27.36 | C |
| ATOM | 2505 | CB | HIS | A | 184 | −66.245 | 31.653 | 11.254 | 1.00 | 27.41 | C |
| ATOM | 2508 | CG | HIS | A | 184 | −65.930 | 30.807 | 10.064 | 1.00 | 26.90 | C |
| ATOM | 2509 | ND1 | HIS | A | 184 | −65.484 | 29.511 | 10.166 | 1.00 | 27.76 | N |
| ATOM | 2511 | CE1 | HIS | A | 184 | −65.321 | 29.009 | 8.955 | 1.00 | 27.47 | C |
| ATOM | 2513 | NE2 | HIS | A | 184 | −65.661 | 29.929 | 8.075 | 1.00 | 26.52 | N |
| ATOM | 2515 | CD2 | HIS | A | 184 | −66.059 | 31.058 | 8.742 | 1.00 | 26.61 | C |
| ATOM | 2517 | C | HIS | A | 184 | −63.898 | 32.200 | 11.940 | 1.00 | 26.69 | C |
| ATOM | 2518 | O | HIS | A | 184 | −62.881 | 31.525 | 11.862 | 1.00 | 26.44 | O |
| ATOM | 2520 | N | ALA | A | 185 | −63.909 | 33.498 | 11.675 | 1.00 | 26.11 | N |
| ATOM | 2521 | CA | ALA | A | 185 | −62.711 | 34.176 | 11.205 | 1.00 | 25.63 | C |
| ATOM | 2523 | CB | ALA | A | 185 | −62.970 | 35.627 | 11.109 | 1.00 | 25.74 | C |
| ATOM | 2527 | C | ALA | A | 185 | −61.552 | 33.917 | 12.153 | 1.00 | 25.33 | C |
| ATOM | 2528 | O | ALA | A | 185 | −60.451 | 33.572 | 11.725 | 1.00 | 25.79 | O |
| ATOM | 2530 | N | LEU | A | 186 | −61.814 | 34.066 | 13.450 | 1.00 | 24.77 | N |
| ATOM | 2531 | CA | LEU | A | 186 | −60.776 | 33.940 | 14.470 | 1.00 | 24.05 | C |
| ATOM | 2533 | CB | LEU | A | 186 | −61.256 | 34.498 | 15.814 | 1.00 | 23.63 | C |
| ATOM | 2536 | CG | LEU | A | 186 | −61.516 | 36.012 | 15.903 | 1.00 | 22.51 | C |
| ATOM | 2538 | CD1 | LEU | A | 186 | −62.057 | 36.399 | 17.266 | 1.00 | 20.79 | C |
| ATOM | 2542 | CD2 | LEU | A | 186 | −60.273 | 36.793 | 15.613 | 1.00 | 21.13 | C |
| ATOM | 2546 | C | LEU | A | 186 | −60.316 | 32.497 | 14.613 | 1.00 | 24.02 | C |
| ATOM | 2547 | O | LEU | A | 186 | −59.169 | 32.250 | 14.943 | 1.00 | 24.27 | O |
| ATOM | 2549 | N | GLU | A | 187 | −61.201 | 31.543 | 14.347 | 1.00 | 23.88 | N |
| ATOM | 2550 | CA | GLU | A | 187 | −60.836 | 30.117 | 14.348 | 1.00 | 23.53 | C |
| ATOM | 2552 | CB | GLU | A | 187 | −62.029 | 29.270 | 13.919 | 1.00 | 23.66 | C |
| ATOM | 2555 | CG | GLU | A | 187 | −61.945 | 27.828 | 14.316 | 1.00 | 25.26 | C |
| ATOM | 2558 | CD | GLU | A | 187 | −63.049 | 26.971 | 13.693 | 1.00 | 28.04 | C |
| ATOM | 2559 | OE1 | GLU | A | 187 | −63.672 | 27.393 | 12.681 | 1.00 | 28.67 | O |
| ATOM | 2560 | OE2 | GLU | A | 187 | −63.288 | 25.858 | 14.225 | 1.00 | 29.72 | O |
| ATOM | 2561 | C | GLU | A | 187 | −59.686 | 29.838 | 13.395 | 1.00 | 22.92 | C |
| ATOM | 2562 | O | GLU | A | 187 | −58.765 | 29.091 | 13.729 | 1.00 | 22.53 | O |
| ATOM | 2564 | N | LEU | A | 188 | −59.763 | 30.446 | 12.209 | 1.00 | 22.46 | N |
| ATOM | 2565 | CA | LEU | A | 188 | −58.799 | 30.246 | 11.121 | 1.00 | 22.07 | C |
| ATOM | 2567 | CB | LEU | A | 188 | −58.802 | 28.794 | 10.635 | 1.00 | 22.11 | C |
| ATOM | 2570 | CG | LEU | A | 188 | −57.876 | 28.362 | 9.493 | 1.00 | 22.17 | C |
| ATOM | 2572 | CD1 | LEU | A | 188 | −56.456 | 28.051 | 9.961 | 1.00 | 21.62 | C |
| ATOM | 2576 | CD2 | LEU | A | 188 | −58.464 | 27.134 | 8.822 | 1.00 | 22.40 | C |
| ATOM | 2580 | C | LEU | A | 188 | −59.237 | 31.137 | 9.985 | 1.00 | 21.69 | C |
| ATOM | 2581 | O | LEU | A | 188 | −60.380 | 31.075 | 9.563 | 1.00 | 21.53 | O |
| ATOM | 2583 | N | PRO | A | 189 | −58.333 | 31.973 | 9.474 | 1.00 | 21.46 | N |
| ATOM | 2584 | CA | PRO | A | 189 | −58.745 | 32.935 | 8.472 | 1.00 | 21.18 | C |
| ATOM | 2586 | CB | PRO | A | 189 | −57.592 | 33.936 | 8.486 | 1.00 | 21.03 | C |
| ATOM | 2589 | CG | PRO | A | 189 | −56.423 | 33.118 | 8.757 | 1.00 | 21.21 | C |
| ATOM | 2592 | CD | PRO | A | 189 | −56.873 | 31.992 | 9.668 | 1.00 | 21.61 | C |
| ATOM | 2595 | C | PRO | A | 189 | −58.946 | 32.314 | 7.076 | 1.00 | 20.96 | C |
| ATOM | 2596 | O | PRO | A | 189 | −58.418 | 31.247 | 6.793 | 1.00 | 21.02 | O |
| ATOM | 2597 | N | LEU | A | 190 | −59.714 | 32.994 | 6.226 | 1.00 | 20.89 | N |
| ATOM | 2598 | CA | LEU | A | 190 | −60.018 | 32.533 | 4.867 | 1.00 | 20.74 | C |
| ATOM | 2600 | CB | LEU | A | 190 | −60.597 | 33.690 | 4.053 | 1.00 | 20.76 | C |
| ATOM | 2603 | CG | LEU | A | 190 | −62.090 | 33.924 | 4.259 | 1.00 | 21.35 | C |
| ATOM | 2605 | CD1 | LEU | A | 190 | −62.537 | 35.196 | 3.578 | 1.00 | 20.54 | C |
| ATOM | 2609 | CD2 | LEU | A | 190 | −62.889 | 32.712 | 3.720 | 1.00 | 23.39 | C |
| ATOM | 2613 | C | LEU | A | 190 | −58.814 | 31.971 | 4.112 | 1.00 | 20.35 | C |
| ATOM | 2614 | O | LEU | A | 190 | −58.859 | 30.871 | 3.546 | 1.00 | 20.08 | O |
| ATOM | 2616 | N | HIS | A | 191 | −57.734 | 32.746 | 4.132 | 1.00 | 19.81 | N |
| ATOM | 2617 | CA | HIS | A | 191 | −56.537 | 32.448 | 3.364 | 1.00 | 18.89 | C |
| ATOM | 2619 | CB | HIS | A | 191 | −55.548 | 33.592 | 3.536 | 1.00 | 18.92 | C |
| ATOM | 2622 | CG | HIS | A | 191 | −54.372 | 33.520 | 2.623 | 1.00 | 18.51 | C |
| ATOM | 2623 | ND1 | HIS | A | 191 | −54.482 | 33.647 | 1.258 | 1.00 | 18.08 | N |
| ATOM | 2625 | CE1 | HIS | A | 191 | −53.281 | 33.544 | .718 | 1.00 | 18.96 | C |
| ATOM | 2627 | NE2 | HIS | A | 191 | −52.397 | 33.371 | 1.684 | 1.00 | 17.01 | N |
| ATOM | 2629 | CD2 | HIS | A | 191 | −53.054 | 33.355 | 2.884 | 1.00 | 17.94 | C |
| ATOM | 2631 | C | HIS | A | 191 | −55.889 | 31.142 | 3.759 | 1.00 | 18.32 | C |
| ATOM | 2632 | O | HIS | A | 191 | −55.217 | 30.531 | 2.942 | 1.00 | 17.98 | O |
| ATOM | 2634 | N | ARG | A | 192 | −56.093 | 30.719 | 5.006 | 1.00 | 18.06 | N |
| ATOM | 2635 | CA | ARG | A | 192 | −55.502 | 29.480 | 5.523 | 1.00 | 17.99 | C |
| ATOM | 2637 | CB | ARG | A | 192 | −54.940 | 29.722 | 6.909 | 1.00 | 17.77 | C |
| ATOM | 2640 | CG | ARG | A | 192 | −53.822 | 30.683 | 6.881 | 1.00 | 18.47 | C |
| ATOM | 2643 | CD | ARG | A | 192 | −53.082 | 30.748 | 8.196 | 1.00 | 19.80 | C |
| ATOM | 2646 | NE | ARG | A | 192 | −52.174 | 31.900 | 8.224 | 1.00 | 20.33 | N |
| ATOM | 2648 | CZ | ARG | A | 192 | −51.176 | 32.048 | 9.077 | 1.00 | 20.10 | C |
| ATOM | 2649 | NH1 | ARG | A | 192 | −50.928 | 31.113 | 9.972 | 1.00 | 21.72 | N |
| ATOM | 2652 | NH2 | ARG | A | 192 | −50.407 | 33.119 | 9.019 | 1.00 | 20.79 | N |
| ATOM | 2655 | C | ARG | A | 192 | −56.477 | 28.311 | 5.590 | 1.00 | 18.00 | C |
| ATOM | 2656 | O | ARG | A | 192 | −56.067 | 27.170 | 5.871 | 1.00 | 18.21 | O |
| ATOM | 2658 | N | ARG | A | 193 | −57.758 | 28.588 | 5.335 | 1.00 | 17.59 | N |
| ATOM | 2659 | CA | ARG | A | 193 | −58.779 | 27.563 | 5.382 | 1.00 | 17.16 | C |
| ATOM | 2661 | CB | ARG | A | 193 | −60.141 | 28.164 | 5.741 | 1.00 | 17.45 | C |

TABLE 16-7-continued

Coordinates of *P. tremuloides* IspS

| ATOM | 2664 | CG | ARG | A | 193 | −61.109 | 27.132 | 6.322 | 1.00 | 18.70 | C |
|---|---|---|---|---|---|---|---|---|---|---|---|
| ATOM | 2667 | CD | ARG | A | 193 | −62.479 | 27.682 | 6.686 | 1.00 | 20.20 | C |
| ATOM | 2670 | NE | ARG | A | 193 | −62.423 | 28.682 | 7.751 | 1.00 | 22.59 | N |
| ATOM | 2672 | CZ | ARG | A | 193 | −62.386 | 28.435 | 9.067 | 1.00 | 24.12 | C |
| ATOM | 2673 | NH1 | ARG | A | 193 | −62.395 | 27.198 | 9.575 | 1.00 | 22.66 | N |
| ATOM | 2676 | NH2 | ARG | A | 193 | −62.348 | 29.469 | 9.898 | 1.00 | 26.36 | N |
| ATOM | 2679 | C | ARG | A | 193 | −58.871 | 26.842 | 4.058 | 1.00 | 16.63 | C |
| ATOM | 2680 | O | ARG | A | 193 | −58.861 | 27.461 | 3.005 | 1.00 | 15.93 | O |
| ATOM | 2682 | N | THR | A | 194 | −58.955 | 25.518 | 4.149 | 1.00 | 16.72 | N |
| ATOM | 2683 | CA | THR | A | 194 | −59.332 | 24.638 | 3.051 | 1.00 | 16.88 | C |
| ATOM | 2685 | CB | THR | A | 194 | −59.520 | 23.250 | 3.592 | 1.00 | 16.43 | C |
| ATOM | 2687 | OG1 | THR | A | 194 | −58.252 | 22.605 | 3.583 | 1.00 | 17.74 | O |
| ATOM | 2689 | CG2 | THR | A | 194 | −60.454 | 22.441 | 2.754 | 1.00 | 18.43 | C |
| ATOM | 2693 | C | THR | A | 194 | −60.607 | 25.112 | 2.384 | 1.00 | 17.28 | C |
| ATOM | 2694 | O | THR | A | 194 | −61.441 | 25.734 | 3.022 | 1.00 | 17.44 | O |
| ATOM | 2696 | N | GLN | A | 195 | −60.765 | 24.855 | 1.091 | 1.00 | 18.05 | N |
| ATOM | 2697 | CA | GLN | A | 195 | −61.925 | 25.402 | .397 | 1.00 | 18.76 | C |
| ATOM | 2699 | CB | GLN | A | 195 | −61.768 | 25.381 | −1.114 | 1.00 | 18.87 | C |
| ATOM | 2702 | CG | GLN | A | 195 | −63.145 | 25.523 | −1.761 | 1.00 | 20.75 | C |
| ATOM | 2705 | CD | GLN | A | 195 | −63.095 | 25.922 | −3.179 | 1.00 | 23.41 | C |
| ATOM | 2706 | OE1 | GLN | A | 195 | −62.031 | 26.088 | −3.733 | 1.00 | 27.07 | O |
| ATOM | 2707 | NE2 | GLN | A | 195 | −64.248 | 26.090 | −3.791 | 1.00 | 25.02 | N |
| ATOM | 2710 | C | GLN | A | 195 | −63.243 | 24.704 | .765 | 1.00 | 18.93 | C |
| ATOM | 2711 | O | GLN | A | 195 | −64.169 | 25.333 | 1.291 | 1.00 | 19.42 | O |
| ATOM | 2713 | N | ARG | A | 196 | −63.345 | 23.418 | .443 | 1.00 | 18.90 | N |
| ATOM | 2714 | CA | ARG | A | 196 | −64.577 | 22.685 | .663 | 1.00 | 18.68 | C |
| ATOM | 2716 | CB | ARG | A | 196 | −64.356 | 21.186 | .454 | 1.00 | 18.53 | C |
| ATOM | 2719 | CG | ARG | A | 196 | −64.851 | 20.644 | −.888 | 1.00 | 18.31 | C |
| ATOM | 2722 | CD | ARG | A | 196 | −64.705 | 21.622 | −2.037 | 1.00 | 17.93 | C |
| ATOM | 2725 | NE | ARG | A | 196 | −65.930 | 21.720 | −2.834 | 1.00 | 18.52 | N |
| ATOM | 2727 | CZ | ARG | A | 196 | −66.480 | 22.857 | −3.256 | 1.00 | 18.63 | C |
| ATOM | 2728 | NH1 | ARG | A | 196 | −65.938 | 24.014 | −2.937 | 1.00 | 19.84 | N |
| ATOM | 2731 | NH2 | ARG | A | 196 | −67.582 | 22.844 | −3.999 | 1.00 | 18.53 | N |
| ATOM | 2734 | C | ARG | A | 196 | −65.070 | 22.982 | 2.061 | 1.00 | 19.02 | C |
| ATOM | 2735 | O | ARG | A | 196 | −66.276 | 23.085 | 2.284 | 1.00 | 19.30 | O |
| ATOM | 2737 | N | LEU | A | 197 | −64.127 | 23.152 | 2.990 | 1.00 | 19.09 | N |
| ATOM | 2738 | CA | LEU | A | 197 | −64.444 | 23.432 | 4.379 | 1.00 | 19.19 | C |
| ATOM | 2740 | CB | LEU | A | 197 | −63.203 | 23.346 | 5.262 | 1.00 | 19.14 | C |
| ATOM | 2743 | CG | LEU | A | 197 | −63.135 | 22.097 | 6.130 | 1.00 | 19.99 | C |
| ATOM | 2745 | CD1 | LEU | A | 197 | −64.476 | 21.899 | 6.811 | 1.00 | 21.56 | C |
| ATOM | 2749 | CD2 | LEU | A | 197 | −62.016 | 22.198 | 7.161 | 1.00 | 20.06 | C |
| ATOM | 2753 | C | LEU | A | 197 | −65.071 | 24.781 | 4.553 | 1.00 | 19.52 | C |
| ATOM | 2754 | O | LEU | A | 197 | −66.052 | 24.902 | 5.252 | 1.00 | 19.85 | O |
| ATOM | 2756 | N | GLU | A | 198 | −64.488 | 25.803 | 3.941 | 1.00 | 20.11 | N |
| ATOM | 2757 | CA | GLU | A | 198 | −65.051 | 27.147 | 3.986 | 1.00 | 20.47 | C |
| ATOM | 2759 | CB | GLU | A | 198 | −64.079 | 28.156 | 3.385 | 1.00 | 20.84 | C |
| ATOM | 2762 | CG | GLU | A | 198 | −64.659 | 29.539 | 3.069 | 1.00 | 22.30 | C |
| ATOM | 2765 | CD | GLU | A | 198 | −65.206 | 30.260 | 4.283 | 1.00 | 24.40 | C |
| ATOM | 2766 | OE1 | GLU | A | 198 | −64.852 | 29.894 | 5.418 | 1.00 | 25.34 | O |
| ATOM | 2767 | OE2 | GLU | A | 198 | −65.991 | 31.217 | 4.106 | 1.00 | 26.83 | O |
| ATOM | 2768 | C | GLU | A | 198 | −66.360 | 27.186 | 3.226 | 1.00 | 20.57 | C |
| ATOM | 2769 | O | GLU | A | 198 | −67.212 | 28.009 | 3.529 | 1.00 | 20.65 | O |
| ATOM | 2771 | N | ALA | A | 199 | −66.519 | 26.298 | 2.240 | 1.00 | 20.76 | N |
| ATOM | 2772 | CA | ALA | A | 199 | −67.751 | 26.229 | 1.452 | 1.00 | 20.52 | C |
| ATOM | 2774 | CB | ALA | A | 199 | −67.521 | 25.492 | .166 | 1.00 | 20.44 | C |
| ATOM | 2778 | C | ALA | A | 199 | −68.907 | 25.611 | 2.232 | 1.00 | 20.55 | C |
| ATOM | 2779 | O | ALA | A | 199 | −69.988 | 26.158 | 2.202 | 1.00 | 20.17 | O |
| ATOM | 2781 | N | VAL | A | 200 | −68.701 | 24.493 | 2.933 | 1.00 | 21.10 | N |
| ATOM | 2782 | CA | VAL | A | 200 | −69.791 | 23.935 | 3.774 | 1.00 | 21.51 | C |
| ATOM | 2784 | CB | VAL | A | 200 | −69.509 | 22.576 | 4.485 | 1.00 | 21.18 | C |
| ATOM | 2786 | CG1 | VAL | A | 200 | −69.618 | 21.460 | 3.525 | 1.00 | 21.27 | C |
| ATOM | 2790 | CG2 | VAL | A | 200 | −68.161 | 22.569 | 5.200 | 1.00 | 21.23 | C |
| ATOM | 2794 | C | VAL | A | 200 | −70.170 | 24.905 | 4.860 | 1.00 | 21.99 | C |
| ATOM | 2795 | O | VAL | A | 200 | −71.338 | 25.022 | 5.186 | 1.00 | 22.99 | O |
| ATOM | 2797 | N | TRP | A | 201 | −69.204 | 25.590 | 5.440 | 1.00 | 22.10 | N |
| ATOM | 2798 | CA | TRP | A | 201 | −69.551 | 26.565 | 6.433 | 1.00 | 22.58 | C |
| ATOM | 2800 | CB | TRP | A | 201 | −68.315 | 27.144 | 7.121 | 1.00 | 22.92 | C |
| ATOM | 2803 | CG | TRP | A | 201 | −68.667 | 27.957 | 8.310 | 1.00 | 23.65 | C |
| ATOM | 2804 | CD1 | TRP | A | 201 | −68.758 | 27.520 | 9.588 | 1.00 | 25.08 | C |
| ATOM | 2806 | NE1 | TRP | A | 201 | −69.127 | 28.549 | 10.417 | 1.00 | 26.35 | N |
| ATOM | 2808 | CE2 | TRP | A | 201 | −69.290 | 29.683 | 9.669 | 1.00 | 25.48 | C |
| ATOM | 2809 | CD2 | TRP | A | 201 | −69.010 | 29.344 | 8.332 | 1.00 | 24.77 | C |
| ATOM | 2810 | CE3 | TRP | A | 201 | −69.095 | 30.336 | 7.355 | 1.00 | 24.92 | C |
| ATOM | 2812 | CZ3 | TRP | A | 201 | −69.450 | 31.616 | 7.739 | 1.00 | 24.96 | C |
| ATOM | 2814 | CH2 | TRP | A | 201 | −69.720 | 31.918 | 9.078 | 1.00 | 25.08 | C |
| ATOM | 2816 | CZ2 | TRP | A | 201 | −69.648 | 30.968 | 10.056 | 1.00 | 24.68 | C |
| ATOM | 2818 | C | TRP | A | 201 | −70.351 | 27.662 | 5.758 | 1.00 | 22.71 | C |
| ATOM | 2819 | O | TRP | A | 201 | −71.482 | 27.921 | 6.140 | 1.00 | 22.76 | O |

TABLE 16-7-continued

Coordinates of *P. tremuloides* IspS

| ATOM | 2821 | N | SER | A | 202 | −69.776 | 28.272 | 4.727 | 1.00 | 23.04 | N |
| --- | --- | --- | --- | --- | --- | --- | --- | --- | --- | --- | --- |
| ATOM | 2822 | CA | SER | A | 202 | −70.335 | 29.500 | 4.165 | 1.00 | 23.29 | C |
| ATOM | 2824 | CB | SER | A | 202 | −69.304 | 30.205 | 3.290 | 1.00 | 23.20 | C |
| ATOM | 2827 | OG | SER | A | 202 | −68.306 | 30.807 | 4.111 | 1.00 | 23.07 | O |
| ATOM | 2829 | C | SER | A | 202 | −71.666 | 29.341 | 3.432 | 1.00 | 23.66 | C |
| ATOM | 2830 | O | SER | A | 202 | −72.392 | 30.310 | 3.265 | 1.00 | 23.38 | O |
| ATOM | 2832 | N | ILE | A | 203 | −71.996 | 28.124 | 3.016 | 1.00 | 24.49 | N |
| ATOM | 2833 | CA | ILE | A | 203 | −73.321 | 27.859 | 2.460 | 1.00 | 25.07 | C |
| ATOM | 2835 | CB | ILE | A | 203 | −73.391 | 26.530 | 1.653 | 1.00 | 24.74 | C |
| ATOM | 2837 | CG1 | ILE | A | 203 | −72.494 | 26.587 | .423 | 1.00 | 24.36 | C |
| ATOM | 2840 | CD1 | ILE | A | 203 | −72.344 | 25.255 | −.281 | 1.00 | 23.81 | C |
| ATOM | 2844 | CG2 | ILE | A | 203 | −74.795 | 26.292 | 1.156 | 1.00 | 24.45 | C |
| ATOM | 2848 | C | ILE | A | 203 | −74.338 | 27.858 | 3.607 | 1.00 | 25.91 | C |
| ATOM | 2849 | O | ILE | A | 203 | −75.350 | 28.554 | 3.546 | 1.00 | 26.26 | O |
| ATOM | 2851 | N | GLU | A | 204 | −74.051 | 27.104 | 4.662 | 1.00 | 26.69 | N |
| ATOM | 2852 | CA | GLU | A | 204 | −74.929 | 27.053 | 5.824 | 1.00 | 27.40 | C |
| ATOM | 2854 | CB | GLU | A | 204 | −74.286 | 26.217 | 6.931 | 1.00 | 27.65 | C |
| ATOM | 2857 | CG | GLU | A | 204 | −75.132 | 26.032 | 8.183 | 1.00 | 29.02 | C |
| ATOM | 2860 | CD | GLU | A | 204 | −76.530 | 25.491 | 7.903 | 1.00 | 30.44 | C |
| ATOM | 2861 | OE1 | GLU | A | 204 | −76.746 | 24.858 | 6.844 | 1.00 | 31.22 | O |
| ATOM | 2862 | OE2 | GLU | A | 204 | −77.417 | 25.703 | 8.753 | 1.00 | 31.96 | O |
| ATOM | 2863 | C | GLU | A | 204 | −75.258 | 28.451 | 6.342 | 1.00 | 27.61 | C |
| ATOM | 2864 | O | GLU | A | 204 | −76.409 | 28.778 | 6.526 | 1.00 | 27.78 | O |
| ATOM | 2866 | N | ALA | A | 205 | −74.240 | 29.274 | 6.547 | 1.00 | 28.15 | N |
| ATOM | 2867 | CA | ALA | A | 205 | −74.416 | 30.637 | 7.050 | 1.00 | 28.41 | C |
| ATOM | 2869 | CB | ALA | A | 205 | −73.062 | 31.285 | 7.274 | 1.00 | 28.41 | C |
| ATOM | 2873 | C | ALA | A | 205 | −75.234 | 31.520 | 6.136 | 1.00 | 28.84 | C |
| ATOM | 2874 | O | ALA | A | 205 | −76.050 | 32.302 | 6.610 | 1.00 | 28.54 | O |
| ATOM | 2876 | N | TYR | A | 206 | −74.978 | 31.408 | 4.832 | 1.00 | 29.84 | N |
| ATOM | 2877 | CA | TYR | A | 206 | −75.581 | 32.281 | 3.805 | 1.00 | 30.41 | C |
| ATOM | 2879 | CB | TYR | A | 206 | −74.801 | 32.170 | 2.493 | 1.00 | 30.20 | C |
| ATOM | 2882 | CG | TYR | A | 206 | −75.180 | 33.173 | 1.425 | 1.00 | 29.62 | C |
| ATOM | 2883 | CD1 | TYR | A | 206 | −74.721 | 34.482 | 1.484 | 1.00 | 30.32 | C |
| ATOM | 2885 | CE1 | TYR | A | 206 | −75.047 | 35.412 | .489 | 1.00 | 29.70 | C |
| ATOM | 2887 | CZ | TYR | A | 206 | −75.830 | 35.028 | −.578 | 1.00 | 28.41 | C |
| ATOM | 2888 | OH | TYR | A | 206 | −76.155 | 35.956 | −1.548 | 1.00 | 26.74 | O |
| ATOM | 2890 | CE2 | TYR | A | 206 | −76.291 | 33.724 | −.659 | 1.00 | 28.16 | C |
| ATOM | 2892 | CD2 | TYR | A | 206 | −75.958 | 32.806 | .335 | 1.00 | 28.39 | C |
| ATOM | 2894 | C | TYR | A | 206 | −77.038 | 31.918 | 3.561 | 1.00 | 31.15 | C |
| ATOM | 2895 | O | TYR | A | 206 | −77.858 | 32.781 | 3.268 | 1.00 | 31.30 | O |
| ATOM | 2897 | N | ARG | A | 207 | −77.341 | 30.631 | 3.676 | 1.00 | 32.05 | N |
| ATOM | 2898 | CA | ARG | A | 207 | −78.691 | 30.128 | 3.555 | 1.00 | 32.81 | C |
| ATOM | 2900 | CB | ARG | A | 207 | −78.684 | 28.623 | 3.813 | 1.00 | 32.86 | C |
| ATOM | 2903 | CG | ARG | A | 207 | −80.028 | 27.941 | 3.673 | 1.00 | 34.01 | C |
| ATOM | 2906 | CD | ARG | A | 207 | −80.066 | 26.632 | 4.450 | 1.00 | 35.11 | C |
| ATOM | 2909 | NE | ARG | A | 207 | −79.096 | 25.669 | 3.939 | 1.00 | 35.35 | N |
| ATOM | 2911 | CZ | ARG | A | 207 | −79.353 | 24.737 | 3.022 | 1.00 | 36.00 | C |
| ATOM | 2912 | NH1 | ARG | A | 207 | −80.562 | 24.611 | 2.478 | 1.00 | 35.55 | N |
| ATOM | 2915 | NH2 | ARG | A | 207 | −78.381 | 23.918 | 2.640 | 1.00 | 37.05 | N |
| ATOM | 2918 | C | ARG | A | 207 | −79.609 | 30.826 | 4.550 | 1.00 | 33.57 | C |
| ATOM | 2919 | O | ARG | A | 207 | −80.783 | 31.003 | 4.263 | 1.00 | 33.82 | O |
| ATOM | 2921 | N | LYS | A | 208 | −79.064 | 31.223 | 5.707 | 1.00 | 34.58 | N |
| ATOM | 2922 | CA | LYS | A | 208 | −79.835 | 31.830 | 6.812 | 1.00 | 35.21 | C |
| ATOM | 2924 | CB | LYS | A | 208 | −79.137 | 31.599 | 8.159 | 1.00 | 35.05 | C |
| ATOM | 2927 | CG | LYS | A | 208 | −78.847 | 30.147 | 8.496 | 1.00 | 34.78 | C |
| ATOM | 2930 | CD | LYS | A | 208 | −78.583 | 29.974 | 9.980 | 1.00 | 34.44 | C |
| ATOM | 2933 | CE | LYS | A | 208 | −77.992 | 28.619 | 10.309 | 1.00 | 34.16 | C |
| ATOM | 2936 | NZ | LYS | A | 208 | −76.540 | 28.693 | 10.572 | 1.00 | 33.81 | N |
| ATOM | 2940 | C | LYS | A | 208 | −80.075 | 33.333 | 6.663 | 1.00 | 36.06 | C |
| ATOM | 2941 | O | LYS | A | 208 | −81.032 | 33.857 | 7.226 | 1.00 | 36.19 | O |
| ATOM | 2943 | N | LYS | A | 209 | −79.197 | 34.032 | 5.946 | 1.00 | 36.93 | N |
| ATOM | 2944 | CA | LYS | A | 209 | −79.412 | 35.445 | 5.652 | 1.00 | 37.77 | C |
| ATOM | 2946 | CB | LYS | A | 209 | −78.284 | 35.998 | 4.779 | 1.00 | 38.18 | C |
| ATOM | 2949 | CG | LYS | A | 209 | −76.928 | 36.134 | 5.458 | 1.00 | 39.90 | C |
| ATOM | 2952 | CD | LYS | A | 209 | −75.982 | 37.023 | 4.621 | 1.00 | 42.39 | C |
| ATOM | 2955 | CE | LYS | A | 209 | −74.531 | 37.016 | 5.169 | 1.00 | 44.21 | C |
| ATOM | 2958 | NZ | LYS | A | 209 | −74.350 | 37.688 | 6.509 | 1.00 | 44.75 | N |
| ATOM | 2962 | C | LYS | A | 209 | −80.738 | 35.600 | 4.911 | 1.00 | 37.89 | C |
| ATOM | 2963 | O | LYS | A | 209 | −81.049 | 34.785 | 4.036 | 1.00 | 38.20 | O |
| ATOM | 2965 | N | GLU | A | 210 | −81.518 | 36.632 | 5.243 | 1.00 | 37.87 | N |
| ATOM | 2966 | CA | GLU | A | 210 | −82.847 | 36.797 | 4.630 | 1.00 | 37.72 | C |
| ATOM | 2968 | CB | GLU | A | 210 | −83.821 | 37.578 | 5.549 | 1.00 | 38.19 | C |
| ATOM | 2971 | CG | GLU | A | 210 | −83.850 | 39.130 | 5.404 | 1.00 | 39.68 | C |
| ATOM | 2974 | CD | GLU | A | 210 | −85.270 | 39.736 | 5.534 | 1.00 | 41.27 | C |
| ATOM | 2975 | OE1 | GLU | A | 210 | −86.172 | 39.100 | 6.136 | 1.00 | 41.67 | O |
| ATOM | 2976 | OE2 | GLU | A | 210 | −85.482 | 40.859 | 5.019 | 1.00 | 42.17 | O |
| ATOM | 2977 | C | GLU | A | 210 | −82.760 | 37.394 | 3.219 | 1.00 | 36.68 | C |
| ATOM | 2978 | O | GLU | A | 210 | −83.605 | 37.103 | 2.371 | 1.00 | 36.39 | O |

TABLE 16-7-continued

Coordinates of *P. tremuloides* IspS

| ATOM | 2980 | N | ASP | A | 211 | −81.725 | 38.198 | 2.969 | 1.00 | 35.65 | N |
|---|---|---|---|---|---|---|---|---|---|---|---|
| ATOM | 2981 | CA | ASP | A | 211 | −81.481 | 38.777 | 1.632 | 1.00 | 34.94 | C |
| ATOM | 2983 | CB | ASP | A | 211 | −81.064 | 40.257 | 1.740 | 1.00 | 35.22 | C |
| ATOM | 2986 | CG | ASP | A | 211 | −79.811 | 40.477 | 2.599 | 1.00 | 35.84 | C |
| ATOM | 2987 | OD1 | ASP | A | 211 | −79.379 | 39.557 | 3.341 | 1.00 | 35.60 | O |
| ATOM | 2988 | OD2 | ASP | A | 211 | −79.276 | 41.606 | 2.536 | 1.00 | 36.73 | O |
| ATOM | 2989 | C | ASP | A | 211 | −80.451 | 37.989 | .811 | 1.00 | 33.73 | C |
| ATOM | 2990 | O | ASP | A | 211 | −79.753 | 38.556 | −.021 | 1.00 | 33.40 | O |
| ATOM | 2992 | N | ALA | A | 212 | −80.366 | 36.682 | 1.057 | 1.00 | 32.53 | N |
| ATOM | 2993 | CA | ALA | A | 212 | −79.506 | 35.783 | .293 | 1.00 | 31.40 | C |
| ATOM | 2995 | CB | ALA | A | 212 | −79.569 | 34.382 | .889 | 1.00 | 30.79 | C |
| ATOM | 2999 | C | ALA | A | 212 | −79.940 | 35.762 | −1.176 | 1.00 | 30.60 | C |
| ATOM | 3000 | O | ALA | A | 212 | −81.124 | 35.594 | −1.467 | 1.00 | 30.37 | O |
| ATOM | 3002 | N | ASN | A | 213 | −79.000 | 35.967 | −2.097 | 1.00 | 29.71 | N |
| ATOM | 3003 | CA | ASN | A | 213 | −79.304 | 35.809 | −3.520 | 1.00 | 29.27 | C |
| ATOM | 3005 | CB | ASN | A | 213 | −78.144 | 36.315 | −4.402 | 1.00 | 29.30 | C |
| ATOM | 3008 | CG | ASN | A | 213 | −78.442 | 36.217 | −5.911 | 1.00 | 29.07 | C |
| ATOM | 3009 | OD1 | ASN | A | 213 | −78.437 | 37.215 | −6.624 | 1.00 | 29.38 | O |
| ATOM | 3010 | ND2 | ASN | A | 213 | −78.691 | 35.015 | −6.389 | 1.00 | 28.37 | N |
| ATOM | 3013 | C | ASN | A | 213 | −79.634 | 34.328 | −3.785 | 1.00 | 28.81 | C |
| ATOM | 3014 | O | ASN | A | 213 | −78.784 | 33.455 | −3.658 | 1.00 | 29.04 | O |
| ATOM | 3016 | N | GLN | A | 214 | −80.880 | 34.053 | −4.145 | 1.00 | 28.04 | N |
| ATOM | 3017 | CA | GLN | A | 214 | −81.376 | 32.692 | −4.191 | 1.00 | 27.32 | C |
| ATOM | 3019 | CB | GLN | A | 214 | −82.906 | 32.700 | −4.178 | 1.00 | 27.47 | C |
| ATOM | 3022 | CG | GLN | A | 214 | −83.505 | 33.269 | −2.889 | 1.00 | 27.68 | C |
| ATOM | 3025 | CD | GLN | A | 214 | −83.294 | 32.359 | −1.688 | 1.00 | 27.54 | C |
| ATOM | 3026 | OE1 | GLN | A | 214 | −83.940 | 31.320 | −1.571 | 1.00 | 28.19 | O |
| ATOM | 3027 | NE2 | GLN | A | 214 | −82.392 | 32.748 | −.790 | 1.00 | 26.90 | N |
| ATOM | 3030 | C | GLN | A | 214 | −80.858 | 31.902 | −5.385 | 1.00 | 26.71 | C |
| ATOM | 3031 | O | GLN | A | 214 | −80.863 | 30.668 | −5.355 | 1.00 | 26.91 | O |
| ATOM | 3033 | N | VAL | A | 215 | −80.439 | 32.600 | −6.442 | 1.00 | 25.81 | N |
| ATOM | 3034 | CA | VAL | A | 215 | −79.789 | 31.947 | −7.588 | 1.00 | 24.88 | C |
| ATOM | 3036 | CB | VAL | A | 215 | −79.651 | 32.894 | −8.808 | 1.00 | 24.81 | C |
| ATOM | 3038 | CG1 | VAL | A | 215 | −78.459 | 32.483 | −9.680 | 1.00 | 24.94 | C |
| ATOM | 3042 | CG2 | VAL | A | 215 | −80.935 | 32.907 | −9.620 | 1.00 | 23.74 | C |
| ATOM | 3046 | C | VAL | A | 215 | −78.415 | 31.427 | −7.176 | 1.00 | 24.18 | C |
| ATOM | 3047 | O | VAL | A | 215 | −78.073 | 30.282 | −7.430 | 1.00 | 23.74 | O |
| ATOM | 3049 | N | LEU | A | 216 | −77.650 | 32.283 | −6.510 | 1.00 | 23.78 | N |
| ATOM | 3050 | CA | LEU | A | 216 | −76.299 | 31.961 | −6.036 | 1.00 | 23.33 | C |
| ATOM | 3052 | CB | LEU | A | 216 | −75.680 | 33.195 | −5.373 | 1.00 | 23.10 | C |
| ATOM | 3055 | CG | LEU | A | 216 | −74.194 | 33.192 | −5.059 | 1.00 | 22.91 | C |
| ATOM | 3057 | CD1 | LEU | A | 216 | −73.383 | 32.962 | −6.312 | 1.00 | 22.88 | C |
| ATOM | 3061 | CD2 | LEU | A | 216 | −73.826 | 34.518 | −4.424 | 1.00 | 22.03 | C |
| ATOM | 3065 | C | LEU | A | 216 | −76.333 | 30.797 | −5.050 | 1.00 | 22.92 | C |
| ATOM | 3066 | O | LEU | A | 216 | −75.598 | 29.826 | −5.201 | 1.00 | 23.38 | O |
| ATOM | 3068 | N | LEU | A | 217 | −77.214 | 30.890 | −4.060 | 1.00 | 22.09 | N |
| ATOM | 3069 | CA | LEU | A | 217 | −77.367 | 29.851 | −3.054 | 1.00 | 21.14 | C |
| ATOM | 3071 | CB | LEU | A | 217 | −78.488 | 30.225 | −2.090 | 1.00 | 21.11 | C |
| ATOM | 3074 | CG | LEU | A | 217 | −78.782 | 29.236 | −.961 | 1.00 | 21.08 | C |
| ATOM | 3076 | CD1 | LEU | A | 217 | −77.703 | 29.267 | .101 | 1.00 | 19.87 | C |
| ATOM | 3080 | CD2 | LEU | A | 217 | −80.146 | 29.535 | −.360 | 1.00 | 21.46 | C |
| ATOM | 3084 | C | LEU | A | 217 | −77.682 | 28.517 | −3.685 | 1.00 | 20.38 | C |
| ATOM | 3085 | O | LEU | A | 217 | −77.133 | 27.508 | −3.286 | 1.00 | 20.04 | O |
| ATOM | 3087 | N | GLU | A | 218 | −78.579 | 28.512 | −4.661 | 1.00 | 19.97 | N |
| ATOM | 3088 | CA | GLU | A | 218 | −79.027 | 27.260 | −5.273 | 1.00 | 19.72 | C |
| ATOM | 3090 | CB | GLU | A | 218 | −80.220 | 27.499 | −6.212 | 1.00 | 19.87 | C |
| ATOM | 3093 | CG | GLU | A | 218 | −81.005 | 26.228 | −6.627 | 1.00 | 21.03 | C |
| ATOM | 3096 | CD | GLU | A | 218 | −82.303 | 26.535 | −7.424 | 1.00 | 22.59 | C |
| ATOM | 3097 | OE1 | GLU | A | 218 | −82.643 | 27.730 | −7.619 | 1.00 | 23.61 | O |
| ATOM | 3098 | OE2 | GLU | A | 218 | −82.983 | 25.578 | −7.863 | 1.00 | 22.31 | O |
| ATOM | 3099 | C | GLU | A | 218 | −77.854 | 26.613 | −6.009 | 1.00 | 19.03 | C |
| ATOM | 3100 | O | GLU | A | 218 | −77.522 | 25.452 | −5.764 | 1.00 | 18.97 | O |
| ATOM | 3102 | N | LEU | A | 219 | −77.203 | 27.381 | −6.878 | 1.00 | 18.06 | N |
| ATOM | 3103 | CA | LEU | A | 219 | −76.012 | 26.907 | −7.573 | 1.00 | 17.15 | C |
| ATOM | 3105 | CB | LEU | A | 219 | −75.439 | 28.029 | −8.418 | 1.00 | 16.75 | C |
| ATOM | 3108 | CG | LEU | A | 219 | −74.196 | 27.717 | −9.231 | 1.00 | 16.01 | C |
| ATOM | 3110 | CD1 | LEU | A | 219 | −74.511 | 26.832 | −10.404 | 1.00 | 12.99 | C |
| ATOM | 3114 | CD2 | LEU | A | 219 | −73.577 | 29.028 | −9.675 | 1.00 | 16.20 | C |
| ATOM | 3118 | C | LEU | A | 219 | −74.973 | 26.409 | −6.570 | 1.00 | 16.75 | C |
| ATOM | 3119 | O | LEU | A | 219 | −74.377 | 25.355 | −6.757 | 1.00 | 16.47 | O |
| ATOM | 3121 | N | ALA | A | 220 | −74.786 | 27.169 | −5.496 | 1.00 | 16.40 | N |
| ATOM | 3122 | CA | ALA | A | 220 | −73.858 | 26.808 | −4.422 | 1.00 | 16.15 | C |
| ATOM | 3124 | CB | ALA | A | 220 | −73.906 | 27.830 | −3.302 | 1.00 | 16.13 | C |
| ATOM | 3128 | C | ALA | A | 220 | −74.137 | 25.436 | −3.862 | 1.00 | 16.03 | C |
| ATOM | 3129 | O | ALA | A | 220 | −73.253 | 24.603 | −3.799 | 1.00 | 16.30 | O |
| ATOM | 3131 | N | ILE | A | 221 | −75.371 | 25.201 | −3.447 | 1.00 | 16.24 | N |
| ATOM | 3132 | CA | ILE | A | 221 | −75.731 | 23.916 | −2.857 | 1.00 | 16.33 | C |
| ATOM | 3134 | CB | ILE | A | 221 | −77.203 | 23.895 | −2.352 | 1.00 | 15.94 | C |

TABLE 16-7-continued

Coordinates of *P. tremuloides* IspS

| ATOM | 3136 | CG1 | ILE | A | 221 | −77.410 | 24.879 | −1.203 | 1.00 | 15.36 | C |
|---|---|---|---|---|---|---|---|---|---|---|---|
| ATOM | 3139 | CD1 | ILE | A | 221 | −78.842 | 25.234 | −.962 | 1.00 | 14.49 | C |
| ATOM | 3143 | CG2 | ILE | A | 221 | −77.571 | 22.537 | −1.836 | 1.00 | 15.18 | C |
| ATOM | 3147 | C | ILE | A | 221 | −75.509 | 22.841 | −3.911 | 1.00 | 17.06 | C |
| ATOM | 3148 | O | ILE | A | 221 | −74.899 | 21.819 | −3.653 | 1.00 | 16.51 | O |
| ATOM | 3150 | N | LEU | A | 222 | −75.981 | 23.138 | −5.117 | 1.00 | 18.53 | N |
| ATOM | 3151 | CA | LEU | A | 222 | −76.006 | 22.207 | −6.243 | 1.00 | 19.25 | C |
| ATOM | 3153 | CB | LEU | A | 222 | −76.657 | 22.891 | −7.445 | 1.00 | 19.18 | C |
| ATOM | 3156 | CG | LEU | A | 222 | −77.037 | 21.972 | −8.597 | 1.00 | 19.65 | C |
| ATOM | 3158 | CD1 | LEU | A | 222 | −78.318 | 22.489 | −9.268 | 1.00 | 19.24 | C |
| ATOM | 3162 | CD2 | LEU | A | 222 | −75.869 | 21.788 | −9.597 | 1.00 | 18.75 | C |
| ATOM | 3166 | C | LEU | A | 222 | −74.618 | 21.751 | −6.630 | 1.00 | 20.07 | C |
| ATOM | 3167 | O | LEU | A | 222 | −74.381 | 20.558 | −6.778 | 1.00 | 20.55 | O |
| ATOM | 3169 | N | ASP | A | 223 | −73.710 | 22.711 | −6.797 | 1.00 | 20.92 | N |
| ATOM | 3170 | CA | ASP | A | 223 | −72.330 | 22.427 | −7.189 | 1.00 | 21.43 | C |
| ATOM | 3172 | CB | ASP | A | 223 | −71.621 | 23.723 | −7.585 | 1.00 | 21.63 | C |
| ATOM | 3175 | CG | ASP | A | 223 | −70.202 | 23.495 | −8.070 | 1.00 | 22.51 | C |
| ATOM | 3176 | OD1 | ASP | A | 223 | −69.296 | 23.282 | −7.225 | 1.00 | 24.67 | O |
| ATOM | 3177 | OD2 | ASP | A | 223 | −69.990 | 23.544 | −9.296 | 1.00 | 22.73 | O |
| ATOM | 3178 | C | ASP | A | 223 | −71.573 | 21.722 | −6.060 | 1.00 | 21.79 | C |
| ATOM | 3179 | O | ASP | A | 223 | −70.843 | 20.764 | −6.313 | 1.00 | 21.73 | O |
| ATOM | 3181 | N | TYR | A | 224 | −71.755 | 22.182 | −4.820 | 1.00 | 22.14 | N |
| ATOM | 3182 | CA | TYR | A | 224 | −71.120 | 21.529 | −3.686 | 1.00 | 22.22 | C |
| ATOM | 3184 | CB | TYR | A | 224 | −71.462 | 22.190 | −2.355 | 1.00 | 22.38 | C |
| ATOM | 3187 | CG | TYR | A | 224 | −70.673 | 21.542 | −1.249 | 1.00 | 22.65 | C |
| ATOM | 3188 | CD1 | TYR | A | 224 | −69.356 | 21.864 | −1.053 | 1.00 | 22.59 | C |
| ATOM | 3190 | CE1 | TYR | A | 224 | −68.622 | 21.258 | −.098 | 1.00 | 23.38 | C |
| ATOM | 3192 | CZ | TYR | A | 224 | −69.177 | 20.288 | .670 | 1.00 | 23.22 | C |
| ATOM | 3193 | OH | TYR | A | 224 | −68.402 | 19.684 | 1.620 | 1.00 | 23.93 | O |
| ATOM | 3195 | CE2 | TYR | A | 224 | −70.483 | 19.931 | .500 | 1.00 | 23.36 | C |
| ATOM | 3197 | CD2 | TYR | A | 224 | −71.221 | 20.547 | −.464 | 1.00 | 23.41 | C |
| ATOM | 3199 | C | TYR | A | 224 | −71.485 | 20.065 | −3.605 | 1.00 | 22.52 | C |
| ATOM | 3200 | O | TYR | A | 224 | −70.641 | 19.233 | −3.311 | 1.00 | 22.93 | O |
| ATOM | 3202 | N | ASN | A | 225 | −72.742 | 19.749 | −3.856 | 1.00 | 22.94 | N |
| ATOM | 3203 | CA | ASN | A | 225 | −73.187 | 18.374 | −3.801 | 1.00 | 23.44 | C |
| ATOM | 3205 | CB | ASN | A | 225 | −74.706 | 18.310 | −3.729 | 1.00 | 23.34 | C |
| ATOM | 3208 | CG | ASN | A | 225 | −75.210 | 18.579 | −2.352 | 1.00 | 22.62 | C |
| ATOM | 3209 | OD1 | ASN | A | 225 | −74.749 | 17.977 | −1.407 | 1.00 | 23.33 | O |
| ATOM | 3210 | ND2 | ASN | A | 225 | −76.146 | 19.494 | −2.223 | 1.00 | 22.52 | N |
| ATOM | 3213 | C | ASN | A | 225 | −72.694 | 17.523 | −4.959 | 1.00 | 24.26 | C |
| ATOM | 3214 | O | ASN | A | 225 | −72.408 | 16.328 | −4.767 | 1.00 | 24.88 | O |
| ATOM | 3216 | N | MET | A | 226 | −72.607 | 18.119 | −6.150 | 1.00 | 24.67 | N |
| ATOM | 3217 | CA | MET | A | 226 | −72.167 | 17.395 | −7.349 | 1.00 | 24.95 | C |
| ATOM | 3219 | CB | MET | A | 226 | −72.421 | 18.237 | −8.594 | 1.00 | 25.37 | C |
| ATOM | 3222 | CG | MET | A | 226 | −71.785 | 17.713 | −9.873 | 1.00 | 27.23 | C |
| ATOM | 3225 | SD | MET | A | 226 | −70.837 | 19.010 | −10.708 | 1.00 | 31.73 | S |
| ATOM | 3226 | CE | MET | A | 226 | −72.185 | 20.000 | −11.367 | 1.00 | 31.30 | C |
| ATOM | 3230 | C | MET | A | 226 | −70.688 | 17.045 | −7.247 | 1.00 | 24.70 | C |
| ATOM | 3231 | O | MET | A | 226 | −70.291 | 15.929 | −7.568 | 1.00 | 24.91 | O |
| ATOM | 3233 | N | ILE | A | 227 | −69.873 | 17.995 | −6.799 | 1.00 | 24.43 | N |
| ATOM | 3234 | CA | ILE | A | 227 | −68.456 | 17.726 | −6.598 | 1.00 | 24.18 | C |
| ATOM | 3236 | CB | ILE | A | 227 | −67.656 | 18.971 | −6.154 | 1.00 | 24.15 | C |
| ATOM | 3238 | CG1 | ILE | A | 227 | −67.628 | 20.021 | −7.253 | 1.00 | 23.64 | C |
| ATOM | 3241 | CD1 | ILE | A | 227 | −66.853 | 21.246 | −6.880 | 1.00 | 23.11 | C |
| ATOM | 3245 | CG2 | ILE | A | 227 | −66.229 | 18.603 | −5.827 | 1.00 | 24.36 | C |
| ATOM | 3249 | C | ILE | A | 227 | −68.329 | 16.645 | −5.546 | 1.00 | 23.98 | C |
| ATOM | 3250 | O | ILE | A | 227 | −67.609 | 15.689 | −5.747 | 1.00 | 24.35 | O |
| ATOM | 3252 | N | GLN | A | 228 | −69.048 | 16.779 | −4.439 | 1.00 | 23.79 | N |
| ATOM | 3253 | CA | GLN | A | 228 | −69.020 | 15.754 | −3.382 | 1.00 | 23.66 | C |
| ATOM | 3255 | CB | GLN | A | 228 | −70.077 | 16.010 | −2.305 | 1.00 | 23.64 | C |
| ATOM | 3258 | CG | GLN | A | 228 | −69.972 | 15.049 | −1.145 | 1.00 | 22.91 | C |
| ATOM | 3261 | CD | GLN | A | 228 | −70.891 | 15.417 | −.033 | 1.00 | 23.26 | C |
| ATOM | 3262 | OE1 | GLN | A | 228 | −72.082 | 15.098 | −.069 | 1.00 | 25.64 | O |
| ATOM | 3263 | NE2 | GLN | A | 228 | −70.357 | 16.083 | .978 | 1.00 | 21.77 | N |
| ATOM | 3266 | C | GLN | A | 228 | −69.243 | 14.349 | −3.893 | 1.00 | 23.54 | C |
| ATOM | 3267 | O | GLN | A | 228 | −68.664 | 13.412 | −3.357 | 1.00 | 23.59 | O |
| ATOM | 3269 | N | SER | A | 229 | −70.105 | 14.194 | −4.893 | 1.00 | 23.27 | N |
| ATOM | 3270 | CA | SER | A | 229 | −70.394 | 12.868 | −5.406 | 1.00 | 23.35 | C |
| ATOM | 3272 | CB | SER | A | 229 | −71.753 | 12.812 | −6.095 | 1.00 | 23.31 | C |
| ATOM | 3275 | OG | SER | A | 229 | −71.836 | 13.823 | −7.060 | 1.00 | 24.31 | O |
| ATOM | 3277 | C | SER | A | 229 | −69.287 | 12.394 | −6.331 | 1.00 | 23.19 | C |
| ATOM | 3278 | O | SER | A | 229 | −69.130 | 11.194 | −6.512 | 1.00 | 23.44 | O |
| ATOM | 3280 | N | VAL | A | 230 | −68.512 | 13.306 | −6.914 | 1.00 | 23.14 | N |
| ATOM | 3281 | CA | VAL | A | 230 | −67.269 | 12.874 | −7.552 | 1.00 | 23.00 | C |
| ATOM | 3283 | CB | VAL | A | 230 | −66.469 | 13.998 | −8.253 | 1.00 | 22.75 | C |
| ATOM | 3285 | CG1 | VAL | A | 230 | −65.091 | 13.470 | −8.667 | 1.00 | 21.87 | C |
| ATOM | 3289 | CG2 | VAL | A | 230 | −67.222 | 14.539 | −9.459 | 1.00 | 21.74 | C |
| ATOM | 3293 | C | VAL | A | 230 | −66.417 | 12.268 | −6.452 | 1.00 | 23.35 | C |

TABLE 16-7-continued

Coordinates of *P. tremuloides* IspS

| ATOM | 3294 | O | VAL | A | 230 | −65.917 | 11.173 | −6.589 | 1.00 | 23.68 | O |
|---|---|---|---|---|---|---|---|---|---|---|---|
| ATOM | 3296 | N | TYR | A | 231 | −66.284 | 12.968 | −5.340 | 1.00 | 23.96 | N |
| ATOM | 3297 | CA | TYR | A | 231 | −65.414 | 12.509 | −4.274 | 1.00 | 24.60 | C |
| ATOM | 3299 | CB | TYR | A | 231 | −65.486 | 13.426 | −3.051 | 1.00 | 24.69 | C |
| ATOM | 3302 | CG | TYR | A | 231 | −64.963 | 14.837 | −3.211 | 1.00 | 24.11 | C |
| ATOM | 3303 | CD1 | TYR | A | 231 | −64.071 | 15.190 | −4.214 | 1.00 | 24.31 | C |
| ATOM | 3305 | CE1 | TYR | A | 231 | −63.592 | 16.491 | −4.322 | 1.00 | 24.63 | C |
| ATOM | 3307 | CZ | TYR | A | 231 | −63.994 | 17.441 | −3.406 | 1.00 | 25.13 | C |
| ATOM | 3308 | OH | TYR | A | 231 | −63.554 | 18.754 | −3.456 | 1.00 | 24.64 | O |
| ATOM | 3310 | CE2 | TYR | A | 231 | −64.863 | 17.086 | −2.402 | 1.00 | 25.76 | C |
| ATOM | 3312 | CD2 | TYR | A | 231 | −65.329 | 15.800 | −2.308 | 1.00 | 24.28 | C |
| ATOM | 3314 | C | TYR | A | 231 | −65.785 | 11.111 | −3.833 | 1.00 | 25.26 | C |
| ATOM | 3315 | O | TYR | A | 231 | −64.917 | 10.315 | −3.488 | 1.00 | 25.44 | O |
| ATOM | 3317 | N | GLN | A | 232 | −67.079 | 10.819 | −3.833 | 1.00 | 26.04 | N |
| ATOM | 3318 | CA | GLN | A | 232 | −67.566 | 9.532 | −3.362 | 1.00 | 26.57 | C |
| ATOM | 3320 | CB | GLN | A | 232 | −69.060 | 9.621 | −3.057 | 1.00 | 26.44 | C |
| ATOM | 3323 | CG | GLN | A | 232 | −69.339 | 10.397 | −1.778 | 1.00 | 26.25 | C |
| ATOM | 3326 | CD | GLN | A | 232 | −70.786 | 10.819 | −1.630 | 1.00 | 26.53 | C |
| ATOM | 3327 | OE1 | GLN | A | 232 | −71.667 | 10.305 | −2.318 | 1.00 | 27.77 | O |
| ATOM | 3328 | NE2 | GLN | A | 232 | −71.040 | 11.759 | −.723 | 1.00 | 25.51 | N |
| ATOM | 3331 | C | GLN | A | 232 | −67.238 | 8.414 | −4.351 | 1.00 | 27.44 | C |
| ATOM | 3332 | O | GLN | A | 232 | −66.852 | 7.319 | −3.935 | 1.00 | 27.33 | O |
| ATOM | 3334 | N | ARG | A | 233 | −67.373 | 8.691 | −5.649 | 1.00 | 28.66 | N |
| ATOM | 3335 | CA | ARG | A | 233 | −66.905 | 7.768 | −6.685 | 1.00 | 29.86 | C |
| ATOM | 3337 | CB | ARG | A | 233 | −67.212 | 8.292 | −8.090 | 1.00 | 30.08 | C |
| ATOM | 3340 | CG | ARG | A | 233 | −66.378 | 7.634 | −9.179 | 1.00 | 32.80 | C |
| ATOM | 3343 | CD | ARG | A | 233 | −66.913 | 7.923 | −10.572 | 1.00 | 36.74 | C |
| ATOM | 3346 | NE | ARG | A | 233 | −66.962 | 9.363 | −10.860 | 1.00 | 40.33 | N |
| ATOM | 3348 | CZ | ARG | A | 233 | −68.069 | 10.119 | −10.891 | 1.00 | 43.12 | C |
| ATOM | 3349 | NH1 | ARG | A | 233 | −69.276 | 9.600 | −10.655 | 1.00 | 44.55 | N |
| ATOM | 3352 | NH2 | ARG | A | 233 | −67.971 | 11.418 | −11.169 | 1.00 | 43.38 | N |
| ATOM | 3355 | C | ARG | A | 233 | −65.401 | 7.518 | −6.514 | 1.00 | 30.34 | C |
| ATOM | 3356 | O | ARG | A | 233 | −64.962 | 6.374 | −6.412 | 1.00 | 30.55 | O |
| ATOM | 3358 | N | ASP | A | 234 | −64.621 | 8.591 | −6.461 | 1.00 | 31.00 | N |
| ATOM | 3359 | CA | ASP | A | 234 | −63.187 | 8.487 | −6.205 | 1.00 | 31.48 | C |
| ATOM | 3361 | CB | ASP | A | 234 | −62.594 | 9.870 | −5.942 | 1.00 | 31.56 | C |
| ATOM | 3364 | CG | ASP | A | 234 | −62.573 | 10.741 | −7.167 | 1.00 | 32.78 | C |
| ATOM | 3365 | OD1 | ASP | A | 234 | −62.911 | 10.249 | −8.276 | 1.00 | 34.25 | O |
| ATOM | 3366 | OD2 | ASP | A | 234 | −62.215 | 11.930 | −7.011 | 1.00 | 34.81 | O |
| ATOM | 3367 | C | ASP | A | 234 | −62.885 | 7.596 | −5.010 | 1.00 | 31.70 | C |
| ATOM | 3368 | O | ASP | A | 234 | −61.985 | 6.780 | −5.053 | 1.00 | 31.56 | O |
| ATOM | 3370 | N | LEU | A | 235 | −63.647 | 7.766 | −3.943 | 1.00 | 32.43 | N |
| ATOM | 3371 | CA | LEU | A | 235 | −63.366 | 7.102 | −2.685 | 1.00 | 33.04 | C |
| ATOM | 3373 | CB | LEU | A | 235 | −64.072 | 7.833 | −1.553 | 1.00 | 32.57 | C |
| ATOM | 3376 | CG | LEU | A | 235 | −63.884 | 7.252 | −.167 | 1.00 | 30.85 | C |
| ATOM | 3378 | CD1 | LEU | A | 235 | −62.428 | 7.261 | .174 | 1.00 | 28.78 | C |
| ATOM | 3382 | CD2 | LEU | A | 235 | −64.703 | 8.050 | .823 | 1.00 | 29.93 | C |
| ATOM | 3386 | C | LEU | A | 235 | −63.789 | 5.637 | −2.686 | 1.00 | 34.69 | C |
| ATOM | 3387 | O | LEU | A | 235 | −63.123 | 4.812 | −2.065 | 1.00 | 35.29 | O |
| ATOM | 3389 | N | ARG | A | 236 | −64.893 | 5.299 | −3.354 | 1.00 | 36.09 | N |
| ATOM | 3390 | CA | ARG | A | 236 | −65.290 | 3.893 | −3.458 | 1.00 | 37.26 | C |
| ATOM | 3392 | CB | ARG | A | 236 | −66.672 | 3.736 | −4.103 | 1.00 | 37.64 | C |
| ATOM | 3395 | CG | ARG | A | 236 | −67.839 | 4.000 | −3.157 | 1.00 | 39.15 | C |
| ATOM | 3398 | CD | ARG | A | 236 | −69.162 | 3.528 | −3.741 | 1.00 | 40.25 | C |
| ATOM | 3401 | NE | ARG | A | 236 | −69.385 | 4.046 | −5.095 | 1.00 | 41.64 | N |
| ATOM | 3403 | CZ | ARG | A | 236 | −69.837 | 5.269 | −5.392 | 1.00 | 42.54 | C |
| ATOM | 3404 | NH1 | ARG | A | 236 | −70.115 | 6.147 | −4.430 | 1.00 | 42.18 | N |
| ATOM | 3407 | NH2 | ARG | A | 236 | −70.012 | 5.621 | −6.668 | 1.00 | 43.04 | N |
| ATOM | 3410 | C | ARG | A | 236 | −64.266 | 3.108 | −4.262 | 1.00 | 37.81 | C |
| ATOM | 3411 | O | ARG | A | 236 | −64.104 | 1.912 | −4.060 | 1.00 | 38.07 | O |
| ATOM | 3413 | N | GLU | A | 237 | −63.584 | 3.801 | −5.168 | 1.00 | 38.69 | N |
| ATOM | 3414 | CA | GLU | A | 237 | −62.639 | 3.189 | −6.102 | 1.00 | 39.45 | C |
| ATOM | 3416 | CB | GLU | A | 237 | −62.452 | 4.108 | −7.338 | 1.00 | 40.25 | C |
| ATOM | 3419 | CG | GLU | A | 237 | −62.268 | 3.387 | −8.710 | 1.00 | 43.02 | C |
| ATOM | 3422 | CD | GLU | A | 237 | −60.835 | 3.458 | −9.287 | 1.00 | 46.64 | C |
| ATOM | 3423 | OE1 | GLU | A | 237 | −60.093 | 4.440 | −8.997 | 1.00 | 48.03 | O |
| ATOM | 3424 | OE2 | GLU | A | 237 | −60.466 | 2.519 | −10.047 | 1.00 | 48.35 | O |
| ATOM | 3425 | C | GLU | A | 237 | −61.310 | 2.905 | −5.408 | 1.00 | 38.70 | C |
| ATOM | 3426 | O | GLU | A | 237 | −60.832 | 1.782 | −5.440 | 1.00 | 38.33 | O |
| ATOM | 3428 | N | THR | A | 238 | −60.726 | 3.908 | −4.764 | 1.00 | 38.40 | N |
| ATOM | 3429 | CA | THR | A | 238 | −59.504 | 3.669 | −4.009 | 1.00 | 38.74 | C |
| ATOM | 3431 | CB | THR | A | 238 | −58.710 | 4.965 | −3.593 | 1.00 | 38.78 | C |
| ATOM | 3433 | OG1 | THR | A | 238 | −59.294 | 5.583 | −2.444 | 1.00 | 38.38 | O |
| ATOM | 3435 | CG2 | THR | A | 238 | −58.612 | 5.963 | −4.743 | 1.00 | 38.94 | C |
| ATOM | 3439 | C | THR | A | 238 | −59.802 | 2.834 | −2.773 | 1.00 | 39.05 | C |
| ATOM | 3440 | O | THR | A | 238 | −58.886 | 2.294 | −2.153 | 1.00 | 39.17 | O |
| ATOM | 3442 | N | SER | A | 239 | −61.076 | 2.717 | −2.408 | 1.00 | 39.34 | N |
| ATOM | 3443 | CA | SER | A | 239 | −61.443 | 1.841 | −1.304 | 1.00 | 39.47 | C |

TABLE 16-7-continued

Coordinates of *P. tremuloides* IspS

| ATOM | 3445 | CB | SER | A | 239 | −62.844 | 2.149 | −.792 | 1.00 | 39.34 | C |
|---|---|---|---|---|---|---|---|---|---|---|---|
| ATOM | 3448 | OG | SER | A | 239 | −63.087 | 1.428 | .396 | 1.00 | 39.94 | O |
| ATOM | 3450 | C | SER | A | 239 | −61.313 | .367 | −1.699 | 1.00 | 39.53 | C |
| ATOM | 3451 | O | SER | A | 239 | −60.834 | −.439 | −.900 | 1.00 | 39.53 | O |
| ATOM | 3453 | N | ARG | A | 240 | −61.728 | .021 | −2.921 | 1.00 | 39.69 | N |
| ATOM | 3454 | CA | ARG | A | 240 | −61.559 | −1.341 | −3.439 | 1.00 | 39.79 | C |
| ATOM | 3456 | CB | ARG | A | 240 | −62.105 | −1.492 | −4.867 | 1.00 | 40.34 | C |
| ATOM | 3459 | CG | ARG | A | 240 | −63.624 | −1.715 | −4.947 | 1.00 | 43.03 | C |
| ATOM | 3462 | CD | ARG | A | 240 | −64.104 | −2.125 | −6.364 | 1.00 | 46.66 | C |
| ATOM | 3465 | NE | ARG | A | 240 | −63.780 | −1.136 | −7.416 | 1.00 | 50.46 | N |
| ATOM | 3467 | CZ | ARG | A | 240 | −64.535 | −.082 | −7.775 | 1.00 | 53.13 | C |
| ATOM | 3468 | NH1 | ARG | A | 240 | −64.112 | .732 | −8.749 | 1.00 | 53.13 | N |
| ATOM | 3471 | NH2 | ARG | A | 240 | −65.707 | .178 | −7.178 | 1.00 | 54.02 | N |
| ATOM | 3474 | C | ARG | A | 240 | −60.089 | −1.704 | −3.414 | 1.00 | 38.94 | C |
| ATOM | 3475 | O | ARG | A | 240 | −59.732 | −2.795 | −2.978 | 1.00 | 39.09 | O |
| ATOM | 3477 | N | TRP | A | 241 | −59.246 | −.775 | −3.862 | 1.00 | 37.92 | N |
| ATOM | 3478 | CA | TRP | A | 241 | −57.787 | −.947 | −3.842 | 1.00 | 36.93 | C |
| ATOM | 3480 | CB | TRP | A | 241 | −57.099 | .318 | −4.388 | 1.00 | 36.57 | C |
| ATOM | 3483 | CG | TRP | A | 241 | −55.624 | .333 | −4.209 | 1.00 | 34.71 | C |
| ATOM | 3484 | CD1 | TRP | A | 241 | −54.702 | −.312 | −4.969 | 1.00 | 33.50 | C |
| ATOM | 3486 | NE1 | TRP | A | 241 | −53.441 | −.068 | −4.482 | 1.00 | 32.62 | N |
| ATOM | 3488 | CE2 | TRP | A | 241 | −53.538 | .747 | −3.392 | 1.00 | 31.16 | C |
| ATOM | 3489 | CD2 | TRP | A | 241 | −54.896 | 1.022 | −3.191 | 1.00 | 32.61 | C |
| ATOM | 3490 | CE3 | TRP | A | 241 | −55.268 | 1.837 | −2.117 | 1.00 | 32.63 | C |
| ATOM | 3492 | CZ3 | TRP | A | 241 | −54.293 | 2.345 | −1.307 | 1.00 | 31.31 | C |
| ATOM | 3494 | CH2 | TRP | A | 241 | −52.956 | 2.053 | −1.537 | 1.00 | 31.81 | C |
| ATOM | 3496 | CZ2 | TRP | A | 241 | −52.560 | 1.252 | −2.577 | 1.00 | 31.18 | C |
| ATOM | 3498 | C | TRP | A | 241 | −57.263 | −1.274 | −2.444 | 1.00 | 36.67 | C |
| ATOM | 3499 | O | TRP | A | 241 | −56.540 | −2.247 | −2.252 | 1.00 | 36.32 | O |
| ATOM | 3501 | N | TRP | A | 242 | −57.647 | −.460 | −1.471 | 1.00 | 36.59 | N |
| ATOM | 3502 | CA | TRP | A | 242 | −57.150 | −.593 | −.100 | 1.00 | 36.80 | C |
| ATOM | 3504 | CB | TRP | A | 242 | −57.694 | .582 | .734 | 1.00 | 36.47 | C |
| ATOM | 3507 | CG | TRP | A | 242 | −57.113 | .754 | 2.107 | 1.00 | 35.59 | C |
| ATOM | 3508 | CD1 | TRP | A | 242 | −57.806 | .831 | 3.270 | 1.00 | 35.14 | C |
| ATOM | 3510 | NE1 | TRP | A | 242 | −56.950 | .999 | 4.328 | 1.00 | 34.47 | N |
| ATOM | 3512 | CE2 | TRP | A | 242 | −55.667 | 1.032 | 3.859 | 1.00 | 34.64 | C |
| ATOM | 3513 | CD2 | TRP | A | 242 | −55.728 | .884 | 2.461 | 1.00 | 35.26 | C |
| ATOM | 3514 | CE3 | TRP | A | 242 | −54.531 | .882 | 1.732 | 1.00 | 35.22 | C |
| ATOM | 3516 | CZ3 | TRP | A | 242 | −53.342 | 1.024 | 2.409 | 1.00 | 34.30 | C |
| ATOM | 3518 | CH2 | TRP | A | 242 | −53.318 | 1.169 | 3.799 | 1.00 | 34.70 | C |
| ATOM | 3520 | CZ2 | TRP | A | 242 | −54.467 | 1.173 | 4.542 | 1.00 | 34.63 | C |
| ATOM | 3522 | C | TRP | A | 242 | −57.482 | −1.975 | .524 | 1.00 | 37.34 | C |
| ATOM | 3523 | O | TRP | A | 242 | −56.628 | −2.623 | 1.126 | 1.00 | 36.53 | O |
| ATOM | 3525 | N | ARG | A | 243 | −58.720 | −2.421 | .348 | 1.00 | 38.54 | N |
| ATOM | 3526 | CA | ARG | A | 243 | −59.149 | −3.734 | .822 | 1.00 | 39.71 | C |
| ATOM | 3528 | CB | ARG | A | 243 | −60.669 | −3.896 | .687 | 1.00 | 40.10 | C |
| ATOM | 3531 | CG | ARG | A | 243 | −61.495 | −3.134 | 1.747 | 1.00 | 42.18 | C |
| ATOM | 3534 | CD | ARG | A | 243 | −62.826 | −2.623 | 1.169 | 1.00 | 45.18 | C |
| ATOM | 3537 | NE | ARG | A | 243 | −63.506 | −3.656 | .369 | 1.00 | 48.22 | N |
| ATOM | 3539 | CZ | ARG | A | 243 | −64.374 | −3.431 | −.629 | 1.00 | 49.95 | C |
| ATOM | 3540 | NH1 | ARG | A | 243 | −64.717 | −2.182 | −.991 | 1.00 | 50.13 | N |
| ATOM | 3543 | NH2 | ARG | A | 243 | −64.911 | −4.477 | −1.273 | 1.00 | 49.77 | N |
| ATOM | 3546 | C | ARG | A | 243 | −58.438 | −4.852 | .068 | 1.00 | 40.08 | C |
| ATOM | 3547 | O | ARG | A | 243 | −58.084 | −5.870 | .665 | 1.00 | 40.45 | O |
| ATOM | 3549 | N | ARG | A | 244 | −58.236 | −4.663 | −1.236 | 1.00 | 40.42 | N |
| ATOM | 3550 | CA | ARG | A | 244 | −57.499 | −5.621 | −2.063 | 1.00 | 40.65 | C |
| ATOM | 3552 | CB | ARG | A | 244 | −57.370 | −5.100 | −3.503 | 1.00 | 41.29 | C |
| ATOM | 3555 | CG | ARG | A | 244 | −56.939 | −6.126 | −4.560 | 1.00 | 43.27 | C |
| ATOM | 3558 | CD | ARG | A | 244 | −58.090 | −7.062 | −4.952 | 1.00 | 46.01 | C |
| ATOM | 3561 | NE | ARG | A | 244 | −57.595 | −8.337 | −5.485 | 1.00 | 48.77 | N |
| ATOM | 3563 | CZ | ARG | A | 244 | −57.075 | −9.332 | −4.752 | 1.00 | 51.17 | C |
| ATOM | 3564 | NH1 | ARG | A | 244 | −56.968 | −9.234 | −3.422 | 1.00 | 51.63 | N |
| ATOM | 3567 | NH2 | ARG | A | 244 | −56.656 | −10.448 | −5.353 | 1.00 | 52.11 | N |
| ATOM | 3570 | C | ARG | A | 244 | −56.120 | −5.861 | −1.465 | 1.00 | 40.12 | C |
| ATOM | 3571 | O | ARG | A | 244 | −55.728 | −7.000 | −1.235 | 1.00 | 39.96 | O |
| ATOM | 3573 | N | VAL | A | 245 | −55.399 | −4.778 | −1.201 | 1.00 | 39.78 | N |
| ATOM | 3574 | CA | VAL | A | 245 | −54.099 | −4.858 | −.543 | 1.00 | 39.68 | C |
| ATOM | 3576 | CB | VAL | A | 245 | −53.430 | −3.458 | −.437 | 1.00 | 39.70 | C |
| ATOM | 3578 | CG1 | VAL | A | 245 | −53.133 | −2.914 | −1.824 | 1.00 | 39.54 | C |
| ATOM | 3582 | CG2 | VAL | A | 245 | −52.145 | −3.507 | .395 | 1.00 | 39.41 | C |
| ATOM | 3586 | C | VAL | A | 245 | −54.262 | −5.472 | .841 | 1.00 | 39.73 | C |
| ATOM | 3587 | O | VAL | A | 245 | −53.455 | −6.291 | 1.253 | 1.00 | 39.53 | O |
| ATOM | 3589 | N | GLY | A | 246 | −55.312 | −5.051 | 1.544 | 1.00 | 40.11 | N |
| ATOM | 3590 | CA | GLY | A | 246 | −55.705 | −5.617 | 2.839 | 1.00 | 40.35 | C |
| ATOM | 3593 | C | GLY | A | 246 | −54.621 | −5.648 | 3.894 | 1.00 | 40.58 | C |
| ATOM | 3594 | O | GLY | A | 246 | −54.396 | −6.676 | 4.510 | 1.00 | 40.68 | O |
| ATOM | 3596 | N | LEU | A | 247 | −53.963 | −4.522 | 4.129 | 1.00 | 41.15 | N |
| ATOM | 3597 | CA | LEU | A | 247 | −52.778 | −4.519 | 4.982 | 1.00 | 41.71 | C |

TABLE 16-7-continued

Coordinates of *P. tremuloides* IspS

| ATOM | 3599 | CB | LEU | A | 247 | −51.808 | −3.422 | 4.537 | 1.00 | 41.60 | C |
|---|---|---|---|---|---|---|---|---|---|---|---|
| ATOM | 3602 | CG | LEU | A | 247 | −50.334 | −3.815 | 4.441 | 1.00 | 40.83 | C |
| ATOM | 3604 | CD1 | LEU | A | 247 | −50.158 | −5.014 | 3.539 | 1.00 | 40.54 | C |
| ATOM | 3608 | CD2 | LEU | A | 247 | −49.534 | −2.644 | 3.918 | 1.00 | 39.92 | C |
| ATOM | 3612 | C | LEU | A | 247 | −53.136 | −4.385 | 6.471 | 1.00 | 42.60 | C |
| ATOM | 3613 | O | LEU | A | 247 | −52.588 | −5.111 | 7.313 | 1.00 | 42.06 | O |
| ATOM | 3615 | N | ALA | A | 248 | −54.064 | −3.475 | 6.788 | 1.00 | 43.75 | N |
| ATOM | 3616 | CA | ALA | A | 248 | −54.603 | −3.352 | 8.162 | 1.00 | 44.52 | C |
| ATOM | 3618 | CB | ALA | A | 248 | −55.712 | −2.296 | 8.210 | 1.00 | 44.31 | C |
| ATOM | 3622 | C | ALA | A | 248 | −55.129 | −4.706 | 8.695 | 1.00 | 45.10 | C |
| ATOM | 3623 | O | ALA | A | 248 | −54.969 | −5.041 | 9.875 | 1.00 | 44.96 | O |
| ATOM | 3625 | N | THR | A | 249 | −55.742 | −5.477 | 7.802 | 1.00 | 45.91 | N |
| ATOM | 3626 | CA | THR | A | 249 | −56.328 | −6.768 | 8.154 | 1.00 | 46.50 | C |
| ATOM | 3628 | CB | THR | A | 249 | −57.303 | −7.277 | 7.041 | 1.00 | 46.48 | C |
| ATOM | 3630 | OG1 | THR | A | 249 | −56.583 | −8.039 | 6.063 | 1.00 | 46.20 | O |
| ATOM | 3632 | CG2 | THR | A | 249 | −58.033 | −6.102 | 6.350 | 1.00 | 46.70 | C |
| ATOM | 3636 | C | THR | A | 249 | −55.257 | −7.840 | 8.447 | 1.00 | 47.06 | C |
| ATOM | 3637 | O | THR | A | 249 | −55.531 | −8.813 | 9.159 | 1.00 | 47.22 | O |
| ATOM | 3639 | N | LYS | A | 250 | −54.049 | −7.661 | 7.905 | 1.00 | 47.52 | N |
| ATOM | 3640 | CA | LYS | A | 250 | −52.952 | −8.620 | 8.096 | 1.00 | 47.91 | C |
| ATOM | 3642 | CB | LYS | A | 250 | −52.319 | −8.976 | 6.744 | 1.00 | 48.09 | C |
| ATOM | 3645 | CG | LYS | A | 250 | −52.911 | −10.229 | 6.088 | 1.00 | 48.91 | C |
| ATOM | 3648 | CD | LYS | A | 250 | −52.210 | −11.510 | 6.585 | 1.00 | 49.88 | C |
| ATOM | 3651 | CE | LYS | A | 250 | −53.066 | −12.760 | 6.349 | 1.00 | 50.12 | C |
| ATOM | 3654 | NZ | LYS | A | 250 | −52.385 | −14.011 | 6.791 | 1.00 | 49.99 | N |
| ATOM | 3658 | C | LYS | A | 250 | −51.880 | −8.129 | 9.078 | 1.00 | 48.13 | C |
| ATOM | 3659 | O | LYS | A | 250 | −51.252 | −8.939 | 9.759 | 1.00 | 47.89 | O |
| ATOM | 3661 | N | LEU | A | 251 | −51.667 | −6.812 | 9.134 | 1.00 | 48.63 | N |
| ATOM | 3662 | CA | LEU | A | 251 | −50.758 | −6.187 | 10.114 | 1.00 | 48.83 | C |
| ATOM | 3664 | CB | LEU | A | 251 | −49.981 | −5.020 | 9.485 | 1.00 | 48.74 | C |
| ATOM | 3667 | CG | LEU | A | 251 | −48.569 | −5.296 | 8.960 | 1.00 | 48.51 | C |
| ATOM | 3669 | CD1 | LEU | A | 251 | −48.472 | −6.594 | 8.174 | 1.00 | 47.96 | C |
| ATOM | 3673 | CD2 | LEU | A | 251 | −48.102 | −4.115 | 8.116 | 1.00 | 48.76 | C |
| ATOM | 3677 | C | LEU | A | 251 | −51.559 | −5.703 | 11.324 | 1.00 | 49.17 | C |
| ATOM | 3678 | O | LEU | A | 251 | −52.176 | −4.632 | 11.304 | 1.00 | 49.28 | O |
| ATOM | 3680 | N | HIS | A | 252 | −51.521 | −6.486 | 12.393 | 1.00 | 49.53 | N |
| ATOM | 3681 | CA | HIS | A | 252 | −52.470 | −6.322 | 13.494 | 1.00 | 50.02 | C |
| ATOM | 3683 | CB | HIS | A | 252 | −52.598 | −7.647 | 14.266 | 1.00 | 50.42 | C |
| ATOM | 3686 | CG | HIS | A | 252 | −52.860 | −8.834 | 13.380 | 1.00 | 52.23 | C |
| ATOM | 3687 | ND1 | HIS | A | 252 | −54.032 | −8.989 | 12.667 | 1.00 | 53.75 | N |
| ATOM | 3689 | CE1 | HIS | A | 252 | −53.978 | −10.113 | 11.973 | 1.00 | 54.43 | C |
| ATOM | 3691 | NE2 | HIS | A | 252 | −52.810 | −10.689 | 12.201 | 1.00 | 54.52 | N |
| ATOM | 3693 | CD2 | HIS | A | 252 | −52.090 | −9.910 | 13.077 | 1.00 | 53.70 | C |
| ATOM | 3695 | C | HIS | A | 252 | −52.161 | −5.147 | 14.441 | 1.00 | 49.64 | C |
| ATOM | 3696 | O | HIS | A | 252 | −52.951 | −4.849 | 15.336 | 1.00 | 49.61 | O |
| ATOM | 3698 | N | PHE | A | 253 | −51.027 | −4.483 | 14.229 | 1.00 | 49.37 | N |
| ATOM | 3699 | CA | PHE | A | 253 | −50.652 | −3.273 | 14.973 | 1.00 | 49.15 | C |
| ATOM | 3701 | CB | PHE | A | 253 | −49.144 | −3.273 | 15.260 | 1.00 | 49.07 | C |
| ATOM | 3704 | CG | PHE | A | 253 | −48.307 | −3.112 | 14.025 | 1.00 | 48.30 | C |
| ATOM | 3705 | CD1 | PHE | A | 253 | −48.028 | −1.851 | 13.518 | 1.00 | 48.10 | C |
| ATOM | 3707 | CE1 | PHE | A | 253 | −47.290 | −1.702 | 12.349 | 1.00 | 48.21 | C |
| ATOM | 3709 | CZ | PHE | A | 253 | −46.825 | −2.825 | 11.675 | 1.00 | 47.88 | C |
| ATOM | 3711 | CE2 | PHE | A | 253 | −47.101 | −4.090 | 12.175 | 1.00 | 47.66 | C |
| ATOM | 3713 | CD2 | PHE | A | 253 | −47.842 | −4.226 | 13.338 | 1.00 | 47.74 | C |
| ATOM | 3715 | C | PHE | A | 253 | −50.974 | −2.006 | 14.176 | 1.00 | 49.31 | C |
| ATOM | 3716 | O | PHE | A | 253 | −50.846 | −.893 | 14.702 | 1.00 | 49.01 | O |
| ATOM | 3718 | N | ALA | A | 254 | −51.365 | −2.185 | 12.910 | 1.00 | 49.48 | N |
| ATOM | 3719 | CA | ALA | A | 254 | −51.412 | −1.095 | 11.931 | 1.00 | 49.63 | C |
| ATOM | 3721 | CB | ALA | A | 254 | −51.344 | −1.663 | 10.524 | 1.00 | 49.64 | C |
| ATOM | 3725 | C | ALA | A | 254 | −52.650 | −.224 | 12.061 | 1.00 | 49.77 | C |
| ATOM | 3726 | O | ALA | A | 254 | −53.761 | −.735 | 12.219 | 1.00 | 49.86 | O |
| ATOM | 3728 | N | ARG | A | 255 | −52.452 | 1.090 | 11.975 | 1.00 | 49.93 | N |
| ATOM | 3729 | CA | ARG | A | 255 | −53.562 | 2.042 | 11.908 | 1.00 | 50.27 | C |
| ATOM | 3731 | CB | ARG | A | 255 | −53.094 | 3.468 | 12.237 | 1.00 | 50.43 | C |
| ATOM | 3734 | CG | ARG | A | 255 | −52.678 | 3.736 | 13.696 | 1.00 | 50.82 | C |
| ATOM | 3737 | CD | ARG | A | 255 | −52.242 | 5.211 | 13.887 | 1.00 | 51.32 | C |
| ATOM | 3740 | NE | ARG | A | 255 | −51.003 | 5.522 | 13.155 | 1.00 | 51.81 | N |
| ATOM | 3742 | CZ | ARG | A | 255 | −50.571 | 6.746 | 12.829 | 1.00 | 51.67 | C |
| ATOM | 3743 | NH1 | ARG | A | 255 | −51.264 | 7.839 | 13.146 | 1.00 | 51.63 | N |
| ATOM | 3746 | NH2 | ARG | A | 255 | −49.427 | 6.877 | 12.162 | 1.00 | 51.52 | N |
| ATOM | 3749 | C | ARG | A | 255 | −54.160 | 2.040 | 10.497 | 1.00 | 50.32 | C |
| ATOM | 3750 | O | ARG | A | 255 | −53.416 | 2.081 | 9.504 | 1.00 | 50.35 | O |
| ATOM | 3752 | N | ASP | A | 256 | −55.492 | 2.005 | 10.412 | 1.00 | 50.17 | N |
| ATOM | 3753 | CA | ASP | A | 256 | −56.190 | 2.090 | 9.128 | 1.00 | 50.18 | C |
| ATOM | 3755 | CB | ASP | A | 256 | −57.259 | 1.009 | 9.037 | 1.00 | 50.37 | C |
| ATOM | 3758 | CG | ASP | A | 256 | −58.095 | 1.130 | 7.780 | 1.00 | 50.96 | C |
| ATOM | 3759 | OD1 | ASP | A | 256 | −59.252 | 1.601 | 7.881 | 1.00 | 52.00 | O |
| ATOM | 3760 | OD2 | ASP | A | 256 | −57.581 | .787 | 6.693 | 1.00 | 50.94 | O |

TABLE 16-7-continued

Coordinates of *P. tremuloides* IspS

| ATOM | 3761 | C | ASP | A | 256 | −56.838 | 3.470 | 8.945 | 1.00 | 49.85 | C |
| --- | --- | --- | --- | --- | --- | --- | --- | --- | --- | --- | --- |
| ATOM | 3762 | O | ASP | A | 256 | −57.812 | 3.804 | 9.624 | 1.00 | 50.13 | O |
| ATOM | 3764 | N | ARG | A | 257 | −56.315 | 4.263 | 8.013 | 1.00 | 49.11 | N |
| ATOM | 3765 | CA | ARG | A | 257 | −56.712 | 5.665 | 7.913 | 1.00 | 48.59 | C |
| ATOM | 3767 | CB | ARG | A | 257 | −55.622 | 6.553 | 8.529 | 1.00 | 48.79 | C |
| ATOM | 3770 | CG | ARG | A | 257 | −55.318 | 6.275 | 10.006 | 1.00 | 49.85 | C |
| ATOM | 3773 | CD | ARG | A | 257 | −56.538 | 6.480 | 10.908 | 1.00 | 51.01 | C |
| ATOM | 3776 | NE | ARG | A | 257 | −56.198 | 7.274 | 12.089 | 1.00 | 51.80 | N |
| ATOM | 3778 | CZ | ARG | A | 257 | −55.779 | 6.791 | 13.260 | 1.00 | 52.00 | C |
| ATOM | 3779 | NH1 | ARG | A | 257 | −55.643 | 5.486 | 13.468 | 1.00 | 51.64 | N |
| ATOM | 3782 | NH2 | ARG | A | 257 | −55.501 | 7.638 | 14.245 | 1.00 | 52.62 | N |
| ATOM | 3785 | C | ARG | A | 257 | −56.988 | 6.112 | 6.477 | 1.00 | 47.58 | C |
| ATOM | 3786 | O | ARG | A | 257 | −56.476 | 7.144 | 6.031 | 1.00 | 47.40 | O |
| ATOM | 3788 | N | LEU | A | 258 | −57.814 | 5.352 | 5.761 | 1.00 | 46.18 | N |
| ATOM | 3789 | CA | LEU | A | 258 | −58.094 | 5.672 | 4.358 | 1.00 | 44.78 | C |
| ATOM | 3791 | CB | LEU | A | 258 | −58.777 | 4.508 | 3.629 | 1.00 | 44.57 | C |
| ATOM | 3794 | CG | LEU | A | 258 | −58.917 | 4.731 | 2.121 | 1.00 | 43.79 | C |
| ATOM | 3796 | CD1 | LEU | A | 258 | −57.557 | 4.661 | 1.478 | 1.00 | 43.89 | C |
| ATOM | 3800 | CD2 | LEU | A | 258 | −59.850 | 3.733 | 1.492 | 1.00 | 42.88 | C |
| ATOM | 3804 | C | LEU | A | 258 | −58.970 | 6.907 | 4.259 | 1.00 | 43.52 | C |
| ATOM | 3805 | O | LEU | A | 258 | −58.643 | 7.849 | 3.545 | 1.00 | 43.42 | O |
| ATOM | 3807 | N | ILE | A | 259 | −60.080 | 6.895 | 4.983 | 1.00 | 41.98 | N |
| ATOM | 3808 | CA | ILE | A | 259 | −61.072 | 7.948 | 4.843 | 1.00 | 40.89 | C |
| ATOM | 3810 | CB | ILE | A | 259 | −62.349 | 7.703 | 5.693 | 1.00 | 41.02 | C |
| ATOM | 3812 | CG1 | ILE | A | 259 | −62.846 | 6.248 | 5.570 | 1.00 | 41.82 | C |
| ATOM | 3815 | CD1 | ILE | A | 259 | −64.029 | 5.872 | 6.508 | 1.00 | 42.29 | C |
| ATOM | 3819 | CG2 | ILE | A | 259 | −63.446 | 8.662 | 5.262 | 1.00 | 40.47 | C |
| ATOM | 3823 | C | ILE | A | 259 | −60.424 | 9.253 | 5.273 | 1.00 | 39.74 | C |
| ATOM | 3824 | O | ILE | A | 259 | −60.607 | 10.291 | 4.635 | 1.00 | 39.25 | O |
| ATOM | 3826 | N | GLU | A | 260 | −59.650 | 9.191 | 6.355 | 1.00 | 38.46 | N |
| ATOM | 3827 | CA | GLU | A | 260 | −58.951 | 10.366 | 6.846 | 1.00 | 37.44 | C |
| ATOM | 3829 | CB | GLU | A | 260 | −58.183 | 10.072 | 8.140 | 1.00 | 37.74 | C |
| ATOM | 3832 | CG | GLU | A | 260 | −59.041 | 9.934 | 9.393 | 1.00 | 38.71 | C |
| ATOM | 3835 | CD | GLU | A | 260 | −59.469 | 8.501 | 9.693 | 1.00 | 41.00 | C |
| ATOM | 3836 | OE1 | GLU | A | 260 | −59.273 | 7.594 | 8.842 | 1.00 | 42.70 | O |
| ATOM | 3837 | OE2 | GLU | A | 260 | −60.012 | 8.281 | 10.800 | 1.00 | 42.43 | O |
| ATOM | 3838 | C | GLU | A | 260 | −57.995 | 10.841 | 5.764 | 1.00 | 35.94 | C |
| ATOM | 3839 | O | GLU | A | 260 | −57.981 | 12.020 | 5.418 | 1.00 | 36.10 | O |
| ATOM | 3841 | N | SER | A | 261 | −57.222 | 9.908 | 5.212 | 1.00 | 34.02 | N |
| ATOM | 3842 | CA | SER | A | 261 | −56.263 | 10.229 | 4.152 | 1.00 | 32.47 | C |
| ATOM | 3844 | CB | SER | A | 261 | −55.407 | 9.015 | 3.774 | 1.00 | 32.51 | C |
| ATOM | 3847 | OG | SER | A | 261 | −54.253 | 8.940 | 4.584 | 1.00 | 33.14 | O |
| ATOM | 3849 | C | SER | A | 261 | −56.894 | 10.764 | 2.889 | 1.00 | 30.82 | C |
| ATOM | 3850 | O | SER | A | 261 | −56.199 | 11.306 | 2.062 | 1.00 | 30.79 | O |
| ATOM | 3852 | N | PHE | A | 262 | −58.194 | 10.589 | 2.713 | 1.00 | 29.25 | N |
| ATOM | 3853 | CA | PHE | A | 262 | −58.861 | 11.091 | 1.514 | 1.00 | 27.98 | C |
| ATOM | 3855 | CB | PHE | A | 262 | −60.011 | 10.185 | 1.119 | 1.00 | 27.57 | C |
| ATOM | 3858 | CG | PHE | A | 262 | −60.473 | 10.423 | −.251 | 1.00 | 26.11 | C |
| ATOM | 3859 | CD1 | PHE | A | 262 | −59.763 | 9.914 | −1.318 | 1.00 | 25.14 | C |
| ATOM | 3861 | CE1 | PHE | A | 262 | −60.169 | 10.147 | −2.605 | 1.00 | 24.32 | C |
| ATOM | 3863 | CZ | PHE | A | 262 | −61.284 | 10.917 | −2.840 | 1.00 | 24.36 | C |
| ATOM | 3865 | CE2 | PHE | A | 262 | −61.987 | 11.445 | −1.785 | 1.00 | 25.23 | C |
| ATOM | 3867 | CD2 | PHE | A | 262 | −61.575 | 11.201 | −.492 | 1.00 | 25.61 | C |
| ATOM | 3869 | C | PHE | A | 262 | −59.394 | 12.507 | 1.707 | 1.00 | 27.29 | C |
| ATOM | 3870 | O | PHE | A | 262 | −59.275 | 13.359 | .821 | 1.00 | 27.39 | O |
| ATOM | 3872 | N | TYR | A | 263 | −60.025 | 12.723 | 2.856 | 1.00 | 26.19 | N |
| ATOM | 3873 | CA | TYR | A | 263 | −60.415 | 14.052 | 3.310 | 1.00 | 25.22 | C |
| ATOM | 3875 | CB | TYR | A | 263 | −60.975 | 13.942 | 4.735 | 1.00 | 25.21 | C |
| ATOM | 3878 | CG | TYR | A | 263 | −61.037 | 15.199 | 5.578 | 1.00 | 25.37 | C |
| ATOM | 3879 | CD1 | TYR | A | 263 | −62.020 | 16.152 | 5.385 | 1.00 | 24.95 | C |
| ATOM | 3881 | CE1 | TYR | A | 263 | −62.084 | 17.282 | 6.197 | 1.00 | 26.54 | C |
| ATOM | 3883 | CZ | TYR | A | 263 | −61.158 | 17.455 | 7.229 | 1.00 | 27.44 | C |
| ATOM | 3884 | OH | TYR | A | 263 | −61.186 | 18.567 | 8.059 | 1.00 | 28.97 | O |
| ATOM | 3886 | CE2 | TYR | A | 263 | −60.185 | 16.512 | 7.438 | 1.00 | 27.10 | C |
| ATOM | 3888 | CD2 | TYR | A | 263 | −60.136 | 15.390 | 6.626 | 1.00 | 26.91 | C |
| ATOM | 3890 | C | TYR | A | 263 | −59.190 | 14.946 | 3.238 | 1.00 | 24.29 | C |
| ATOM | 3891 | O | TYR | A | 263 | −59.267 | 16.077 | 2.757 | 1.00 | 24.13 | O |
| ATOM | 3893 | N | TRP | A | 264 | −58.055 | 14.415 | 3.682 | 1.00 | 23.01 | N |
| ATOM | 3894 | CA | TRP | A | 264 | −56.789 | 15.121 | 3.567 | 1.00 | 22.32 | C |
| ATOM | 3896 | CB | TRP | A | 264 | −55.642 | 14.261 | 4.119 | 1.00 | 22.26 | C |
| ATOM | 3899 | CG | TRP | A | 264 | −54.326 | 14.874 | 3.860 | 1.00 | 22.16 | C |
| ATOM | 3900 | CD1 | TRP | A | 264 | −53.614 | 14.821 | 2.699 | 1.00 | 22.68 | C |
| ATOM | 3902 | NE1 | TRP | A | 264 | −52.456 | 15.538 | 2.818 | 1.00 | 23.08 | N |
| ATOM | 3904 | CE2 | TRP | A | 264 | −52.407 | 16.083 | 4.072 | 1.00 | 23.07 | C |
| ATOM | 3905 | CD2 | TRP | A | 264 | −53.579 | 15.686 | 4.753 | 1.00 | 22.18 | C |
| ATOM | 3906 | CE3 | TRP | A | 264 | −53.782 | 16.119 | 6.066 | 1.00 | 22.57 | C |
| ATOM | 3908 | CZ3 | TRP | A | 264 | −52.824 | 16.925 | 6.657 | 1.00 | 23.43 | C |
| ATOM | 3910 | CH2 | TRP | A | 264 | −51.656 | 17.297 | 5.955 | 1.00 | 24.14 | C |

TABLE 16-7-continued

Coordinates of *P. tremuloides* IspS

| ATOM | 3912 | CZ2 | TRP | A | 264 | −51.433 | 16.886 | 4.663 | 1.00 | 23.64 | C |
|---|---|---|---|---|---|---|---|---|---|---|---|
| ATOM | 3914 | C | TRP | A | 264 | −56.485 | 15.523 | 2.112 | 1.00 | 21.50 | C |
| ATOM | 3915 | O | TRP | A | 264 | −56.179 | 16.682 | 1.820 | 1.00 | 21.29 | O |
| ATOM | 3917 | N | ALA | A | 265 | −56.561 | 14.547 | 1.213 | 1.00 | 20.41 | N |
| ATOM | 3918 | CA | ALA | A | 265 | −56.242 | 14.760 | −.187 | 1.00 | 19.63 | C |
| ATOM | 3920 | CB | ALA | A | 265 | −56.298 | 13.437 | −.953 | 1.00 | 19.39 | C |
| ATOM | 3924 | C | ALA | A | 265 | −57.176 | 15.792 | −.798 | 1.00 | 19.07 | C |
| ATOM | 3925 | O | ALA | A | 265 | −56.760 | 16.573 | −1.633 | 1.00 | 18.99 | O |
| ATOM | 3927 | N | VAL | A | 266 | −58.431 | 15.814 | −.359 | 1.00 | 18.78 | N |
| ATOM | 3928 | CA | VAL | A | 266 | −59.396 | 16.828 | −.818 | 1.00 | 18.56 | C |
| ATOM | 3930 | CB | VAL | A | 266 | −60.839 | 16.541 | −.278 | 1.00 | 18.41 | C |
| ATOM | 3932 | CG1 | VAL | A | 266 | −61.405 | 15.298 | −.935 | 1.00 | 18.88 | C |
| ATOM | 3936 | CG2 | VAL | A | 266 | −61.780 | 17.709 | −.505 | 1.00 | 17.21 | C |
| ATOM | 3940 | C | VAL | A | 266 | −58.947 | 18.257 | −.450 | 1.00 | 18.43 | C |
| ATOM | 3941 | O | VAL | A | 266 | −59.250 | 19.200 | −1.171 | 1.00 | 18.83 | O |
| ATOM | 3943 | N | GLY | A | 267 | −58.230 | 18.411 | .663 | 1.00 | 17.96 | N |
| ATOM | 3944 | CA | GLY | A | 267 | −57.714 | 19.712 | 1.067 | 1.00 | 17.45 | C |
| ATOM | 3947 | C | GLY | A | 267 | −56.687 | 20.180 | .070 | 1.00 | 17.20 | C |
| ATOM | 3948 | O | GLY | A | 267 | −56.574 | 21.365 | −.215 | 1.00 | 17.41 | O |
| ATOM | 3950 | N | VAL | A | 268 | −55.959 | 19.219 | −.480 | 1.00 | 16.88 | N |
| ATOM | 3951 | CA | VAL | A | 268 | −54.822 | 19.487 | −1.319 | 1.00 | 16.62 | C |
| ATOM | 3953 | CB | VAL | A | 268 | −53.833 | 18.300 | −1.290 | 1.00 | 16.19 | C |
| ATOM | 3955 | CG1 | VAL | A | 268 | −52.691 | 18.536 | −2.240 | 1.00 | 15.50 | C |
| ATOM | 3959 | CG2 | VAL | A | 268 | −53.310 | 18.121 | .103 | 1.00 | 15.30 | C |
| ATOM | 3963 | C | VAL | A | 268 | −55.262 | 19.788 | −2.736 | 1.00 | 17.15 | C |
| ATOM | 3964 | O | VAL | A | 268 | −54.748 | 20.710 | −3.350 | 1.00 | 17.12 | O |
| ATOM | 3966 | N | ALA | A | 269 | −56.217 | 19.014 | −3.243 | 1.00 | 17.99 | N |
| ATOM | 3967 | CA | ALA | A | 269 | −56.688 | 19.158 | −4.622 | 1.00 | 18.79 | C |
| ATOM | 3969 | CB | ALA | A | 269 | −55.958 | 18.183 | −5.551 | 1.00 | 18.26 | C |
| ATOM | 3973 | C | ALA | A | 269 | −58.196 | 18.938 | −4.672 | 1.00 | 19.70 | C |
| ATOM | 3974 | O | ALA | A | 269 | −58.665 | 17.834 | −4.958 | 1.00 | 19.50 | O |
| ATOM | 3976 | N | PHE | A | 270 | −58.945 | 20.011 | −4.417 | 1.00 | 21.09 | N |
| ATOM | 3977 | CA | PHE | A | 270 | −60.393 | 19.910 | −4.211 | 1.00 | 22.32 | C |
| ATOM | 3979 | CB | PHE | A | 270 | −60.925 | 21.108 | −3.404 | 1.00 | 22.49 | C |
| ATOM | 3982 | CG | PHE | A | 270 | −61.193 | 22.321 | −4.246 | 1.00 | 23.31 | C |
| ATOM | 3983 | CD1 | PHE | A | 270 | −62.423 | 22.483 | −4.883 | 1.00 | 24.16 | C |
| ATOM | 3985 | CE1 | PHE | A | 270 | −62.662 | 23.569 | −5.683 | 1.00 | 23.84 | C |
| ATOM | 3987 | CZ | PHE | A | 270 | −61.675 | 24.497 | −5.871 | 1.00 | 23.93 | C |
| ATOM | 3989 | CE2 | PHE | A | 270 | −60.448 | 24.349 | −5.242 | 1.00 | 23.33 | C |
| ATOM | 3991 | CD2 | PHE | A | 270 | −60.213 | 23.268 | −4.443 | 1.00 | 23.11 | C |
| ATOM | 3993 | C | PHE | A | 270 | −61.173 | 19.820 | −5.515 | 1.00 | 23.21 | C |
| ATOM | 3994 | O | PHE | A | 270 | −62.142 | 19.069 | −5.599 | 1.00 | 23.48 | O |
| ATOM | 3996 | N | GLU | A | 271 | −60.771 | 20.599 | −6.522 | 1.00 | 24.16 | N |
| ATOM | 3997 | CA | GLU | A | 271 | −61.595 | 20.744 | −7.741 | 1.00 | 25.01 | C |
| ATOM | 3999 | CB | GLU | A | 271 | −61.065 | 21.863 | −8.655 | 1.00 | 25.19 | C |
| ATOM | 4002 | CG | GLU | A | 271 | −59.563 | 21.909 | −8.794 | 1.00 | 27.45 | C |
| ATOM | 4005 | CD | GLU | A | 271 | −58.857 | 22.910 | −7.857 | 1.00 | 30.03 | C |
| ATOM | 4006 | OE1 | GLU | A | 271 | −58.905 | 24.145 | −8.147 | 1.00 | 29.41 | O |
| ATOM | 4007 | OE2 | GLU | A | 271 | −58.227 | 22.431 | −6.865 | 1.00 | 30.71 | O |
| ATOM | 4008 | C | GLU | A | 271 | −61.799 | 19.391 | −8.484 | 1.00 | 24.95 | C |
| ATOM | 4009 | O | GLU | A | 271 | −60.972 | 18.480 | −8.352 | 1.00 | 25.70 | O |
| ATOM | 4011 | N | PRO | A | 272 | −62.918 | 19.242 | −9.224 | 1.00 | 24.59 | N |
| ATOM | 4012 | CA | PRO | A | 272 | −63.399 | 17.915 | −9.656 | 1.00 | 24.38 | C |
| ATOM | 4014 | CB | PRO | A | 272 | −64.675 | 18.243 | −10.430 | 1.00 | 24.25 | C |
| ATOM | 4017 | CG | PRO | A | 272 | −65.105 | 19.536 | −9.869 | 1.00 | 24.53 | C |
| ATOM | 4020 | CD | PRO | A | 272 | −63.855 | 20.295 | −9.639 | 1.00 | 24.42 | C |
| ATOM | 4023 | C | PRO | A | 272 | −62.475 | 17.111 | −10.549 | 1.00 | 24.29 | C |
| ATOM | 4024 | O | PRO | A | 272 | −62.406 | 15.886 | −10.410 | 1.00 | 24.45 | O |
| ATOM | 4025 | N | GLN | A | 273 | −61.777 | 17.781 | −11.462 | 1.00 | 24.13 | N |
| ATOM | 4026 | CA | GLN | A | 273 | −60.998 | 17.064 | −12.461 | 1.00 | 24.13 | C |
| ATOM | 4028 | CB | GLN | A | 273 | −60.523 | 17.983 | −13.567 | 1.00 | 23.84 | C |
| ATOM | 4031 | CG | GLN | A | 273 | −59.556 | 19.041 | −13.117 | 1.00 | 24.37 | C |
| ATOM | 4034 | CD | GLN | A | 273 | −60.222 | 20.360 | −12.775 | 1.00 | 25.22 | C |
| ATOM | 4035 | OE1 | GLN | A | 273 | −61.392 | 20.412 | −12.367 | 1.00 | 25.71 | O |
| ATOM | 4036 | NE2 | GLN | A | 273 | −59.468 | 21.441 | −12.932 | 1.00 | 24.95 | N |
| ATOM | 4039 | C | GLN | A | 273 | −59.808 | 16.327 | −11.877 | 1.00 | 24.33 | C |
| ATOM | 4040 | O | GLN | A | 273 | −59.224 | 15.486 | −12.555 | 1.00 | 24.91 | O |
| ATOM | 4042 | N | TYR | A | 274 | −59.462 | 16.607 | −10.626 | 1.00 | 24.27 | N |
| ATOM | 4043 | CA | TYR | A | 274 | −58.211 | 16.119 | −10.067 | 1.00 | 24.38 | C |
| ATOM | 4045 | CB | TYR | A | 274 | −57.639 | 17.180 | −9.138 | 1.00 | 24.36 | C |
| ATOM | 4048 | CG | TYR | A | 274 | −57.066 | 18.398 | −9.819 | 1.00 | 24.35 | C |
| ATOM | 4049 | CD1 | TYR | A | 274 | −56.249 | 18.291 | −10.935 | 1.00 | 24.13 | C |
| ATOM | 4051 | CE1 | TYR | A | 274 | −55.716 | 19.409 | −11.542 | 1.00 | 23.75 | C |
| ATOM | 4053 | CZ | TYR | A | 274 | −55.968 | 20.646 | −11.019 | 1.00 | 24.14 | C |
| ATOM | 4054 | OH | TYR | A | 274 | −55.431 | 21.762 | −11.597 | 1.00 | 24.45 | O |
| ATOM | 4056 | CE2 | TYR | A | 274 | −56.755 | 20.780 | −9.903 | 1.00 | 24.92 | C |
| ATOM | 4058 | CD2 | TYR | A | 274 | −57.297 | 19.658 | −9.308 | 1.00 | 24.74 | C |
| ATOM | 4060 | C | TYR | A | 274 | −58.319 | 14.796 | −9.310 | 1.00 | 24.63 | C |

TABLE 16-7-continued

Coordinates of *P. tremuloides* IspS

| ATOM | 4061 | O | TYR | A | 274 | −57.681 | 14.613 | −8.276 | 1.00 | 24.47 | O |
|---|---|---|---|---|---|---|---|---|---|---|---|
| ATOM | 4063 | N | SER | A | 275 | −59.097 | 13.852 | −9.821 | 1.00 | 25.00 | N |
| ATOM | 4064 | CA | SER | A | 275 | −59.254 | 12.575 | −9.116 | 1.00 | 25.11 | C |
| ATOM | 4066 | CB | SER | A | 275 | −60.244 | 11.664 | −9.842 | 1.00 | 25.14 | C |
| ATOM | 4069 | OG | SER | A | 275 | −61.537 | 12.252 | −9.852 | 1.00 | 25.96 | O |
| ATOM | 4071 | C | SER | A | 275 | −57.907 | 11.885 | −8.963 | 1.00 | 24.94 | C |
| ATOM | 4072 | O | SER | A | 275 | −57.544 | 11.439 | −7.877 | 1.00 | 24.57 | O |
| ATOM | 4074 | N | ASP | A | 276 | −57.149 | 11.822 | −10.052 | 1.00 | 25.01 | N |
| ATOM | 4075 | CA | ASP | A | 276 | −55.840 | 11.187 | −9.990 | 1.00 | 24.92 | C |
| ATOM | 4077 | CB | ASP | A | 276 | −55.102 | 11.257 | −11.324 | 1.00 | 25.02 | C |
| ATOM | 4080 | CG | ASP | A | 276 | −55.827 | 10.495 | −12.407 | 1.00 | 26.27 | C |
| ATOM | 4081 | OD1 | ASP | A | 276 | −56.372 | 9.411 | −12.080 | 1.00 | 26.65 | O |
| ATOM | 4082 | OD2 | ASP | A | 276 | −55.880 | 10.991 | −13.563 | 1.00 | 28.21 | O |
| ATOM | 4083 | C | ASP | A | 276 | −55.026 | 11.798 | −8.881 | 1.00 | 24.30 | C |
| ATOM | 4084 | O | ASP | A | 276 | −54.454 | 11.064 | −8.099 | 1.00 | 24.64 | O |
| ATOM | 4086 | N | CYS | A | 277 | −55.005 | 13.124 | −8.772 | 1.00 | 23.61 | N |
| ATOM | 4087 | CA | CYS | A | 277 | −54.210 | 13.746 | −7.715 | 1.00 | 22.91 | C |
| ATOM | 4089 | CB | CYS | A | 277 | −54.262 | 15.268 | −7.748 | 1.00 | 22.83 | C |
| ATOM | 4092 | SG | CYS | A | 277 | −53.048 | 15.994 | −6.615 | 1.00 | 22.43 | S |
| ATOM | 4094 | C | CYS | A | 277 | −54.653 | 13.251 | −6.357 | 1.00 | 22.39 | C |
| ATOM | 4095 | O | CYS | A | 277 | −53.822 | 12.833 | −5.559 | 1.00 | 22.23 | O |
| ATOM | 4097 | N | ARG | A | 278 | −55.962 | 13.262 | −6.115 | 1.00 | 22.01 | N |
| ATOM | 4098 | CA | ARG | A | 278 | −56.519 | 12.813 | −4.829 | 1.00 | 21.40 | C |
| ATOM | 4100 | CB | ARG | A | 278 | −58.021 | 13.053 | −4.753 | 1.00 | 21.07 | C |
| ATOM | 4103 | CG | ARG | A | 278 | −58.382 | 14.509 | −4.754 | 1.00 | 20.39 | C |
| ATOM | 4106 | CD | ARG | A | 278 | −59.852 | 14.698 | −4.527 | 1.00 | 20.05 | C |
| ATOM | 4109 | NE | ARG | A | 278 | −60.683 | 14.331 | −5.675 | 1.00 | 18.86 | N |
| ATOM | 4111 | CZ | ARG | A | 278 | −60.993 | 15.144 | −6.679 | 1.00 | 18.58 | C |
| ATOM | 4112 | NH1 | ARG | A | 278 | −60.530 | 16.391 | −6.730 | 1.00 | 18.45 | N |
| ATOM | 4115 | NH2 | ARG | A | 278 | −61.775 | 14.702 | −7.647 | 1.00 | 19.04 | N |
| ATOM | 4118 | C | ARG | A | 278 | −56.224 | 11.358 | −4.530 | 1.00 | 21.12 | C |
| ATOM | 4119 | O | ARG | A | 278 | −55.804 | 11.050 | −3.434 | 1.00 | 21.59 | O |
| ATOM | 4121 | N | ASN | A | 279 | −56.412 | 10.467 | −5.493 | 1.00 | 20.94 | N |
| ATOM | 4122 | CA | ASN | A | 279 | −56.168 | 9.044 | −5.243 | 1.00 | 21.08 | C |
| ATOM | 4124 | CB | ASN | A | 279 | −56.672 | 8.182 | −6.401 | 1.00 | 21.54 | C |
| ATOM | 4127 | CG | ASN | A | 279 | −58.199 | 8.346 | −6.642 | 1.00 | 23.94 | C |
| ATOM | 4128 | OD1 | ASN | A | 279 | −58.920 | 8.941 | −5.823 | 1.00 | 26.47 | O |
| ATOM | 4129 | ND2 | ASN | A | 279 | −58.685 | 7.825 | −7.769 | 1.00 | 25.52 | N |
| ATOM | 4132 | C | ASN | A | 279 | −54.699 | 8.798 | −4.972 | 1.00 | 20.30 | C |
| ATOM | 4133 | O | ASN | A | 279 | −54.337 | 8.200 | −3.977 | 1.00 | 19.95 | O |
| ATOM | 4135 | N | SER | A | 280 | −53.851 | 9.297 | −5.856 | 1.00 | 20.02 | N |
| ATOM | 4136 | CA | SER | A | 280 | −52.409 | 9.335 | −5.612 | 1.00 | 19.32 | C |
| ATOM | 4138 | CB | SER | A | 280 | −51.725 | 10.304 | −6.580 | 1.00 | 19.35 | C |
| ATOM | 4141 | OG | SER | A | 280 | −50.624 | 9.705 | −7.212 | 1.00 | 19.77 | O |
| ATOM | 4143 | C | SER | A | 280 | −52.122 | 9.745 | −4.166 | 1.00 | 18.55 | C |
| ATOM | 4144 | O | SER | A | 280 | −51.514 | 8.976 | −3.436 | 1.00 | 18.98 | O |
| ATOM | 4146 | N | VAL | A | 281 | −52.580 | 10.923 | −3.743 | 1.00 | 17.45 | N |
| ATOM | 4147 | CA | VAL | A | 281 | −52.235 | 11.444 | −2.416 | 1.00 | 17.01 | C |
| ATOM | 4149 | CB | VAL | A | 281 | −52.650 | 12.934 | −2.235 | 1.00 | 17.20 | C |
| ATOM | 4151 | CG1 | VAL | A | 281 | −52.492 | 13.376 | −.787 | 1.00 | 16.76 | C |
| ATOM | 4155 | CG2 | VAL | A | 281 | −51.826 | 13.847 | −3.128 | 1.00 | 17.13 | C |
| ATOM | 4159 | C | VAL | A | 281 | −52.861 | 10.607 | −1.301 | 1.00 | 16.82 | C |
| ATOM | 4160 | O | VAL | A | 281 | −52.217 | 10.314 | −.289 | 1.00 | 16.81 | O |
| ATOM | 4162 | N | ALA | A | 282 | −54.118 | 10.225 | −1.481 | 1.00 | 16.55 | N |
| ATOM | 4163 | CA | ALA | A | 282 | −54.774 | 9.304 | −.559 | 1.00 | 16.31 | C |
| ATOM | 4165 | CB | ALA | A | 282 | −56.174 | 8.951 | −1.060 | 1.00 | 16.08 | C |
| ATOM | 4169 | C | ALA | A | 282 | −53.946 | 8.036 | −.355 | 1.00 | 16.31 | C |
| ATOM | 4170 | O | ALA | A | 282 | −53.671 | 7.653 | .762 | 1.00 | 16.16 | O |
| ATOM | 4172 | N | LYS | A | 283 | −53.539 | 7.395 | −1.443 | 1.00 | 16.92 | N |
| ATOM | 4173 | CA | LYS | A | 283 | −52.773 | 6.139 | −1.368 | 1.00 | 17.39 | C |
| ATOM | 4175 | CB | LYS | A | 283 | −52.454 | 5.596 | −2.773 | 1.00 | 17.31 | C |
| ATOM | 4178 | CG | LYS | A | 283 | −53.680 | 5.066 | −3.519 | 1.00 | 17.85 | C |
| ATOM | 4181 | CD | LYS | A | 283 | −53.389 | 4.527 | −4.941 | 1.00 | 18.98 | C |
| ATOM | 4184 | CE | LYS | A | 283 | −54.709 | 4.275 | −5.718 | 1.00 | 19.79 | C |
| ATOM | 4187 | NZ | LYS | A | 283 | −54.695 | 3.091 | −6.625 | 1.00 | 20.11 | N |
| ATOM | 4191 | C | LYS | A | 283 | −51.483 | 6.338 | −.591 | 1.00 | 17.82 | C |
| ATOM | 4192 | O | LYS | A | 283 | −51.170 | 5.577 | .331 | 1.00 | 17.37 | O |
| ATOM | 4194 | N | MET | A | 284 | −50.744 | 7.381 | −.964 | 1.00 | 18.49 | N |
| ATOM | 4195 | CA | MET | A | 284 | −49.434 | 7.622 | −.373 | 1.00 | 18.82 | C |
| ATOM | 4197 | CB | MET | A | 284 | −48.688 | 8.795 | −1.047 | 1.00 | 18.84 | C |
| ATOM | 4200 | CG | MET | A | 284 | −48.118 | 8.506 | −2.444 | 1.00 | 18.47 | C |
| ATOM | 4203 | SD | MET | A | 284 | −47.540 | 6.819 | −2.718 | 1.00 | 19.50 | S |
| ATOM | 4204 | CE | MET | A | 284 | −49.088 | 5.982 | −3.094 | 1.00 | 19.36 | C |
| ATOM | 4208 | C | MET | A | 284 | −49.575 | 7.848 | 1.115 | 1.00 | 18.95 | C |
| ATOM | 4209 | O | MET | A | 284 | −48.901 | 7.166 | 1.892 | 1.00 | 19.29 | O |
| ATOM | 4211 | N | PHE | A | 285 | −50.465 | 8.762 | 1.507 | 1.00 | 18.94 | N |
| ATOM | 4212 | CA | PHE | A | 285 | −50.671 | 9.082 | 2.930 | 1.00 | 19.26 | C |
| ATOM | 4214 | CB | PHE | A | 285 | −51.714 | 10.185 | 3.073 | 1.00 | 19.72 | C |

TABLE 16-7-continued

Coordinates of *P. tremuloides* IspS

| | | | | | | | | | | |
|---|---|---|---|---|---|---|---|---|---|---|
| ATOM | 4217 | CG | PHE | A | 285 | −51.575 | 11.016 | 4.328 | 1.00 | 21.97 C |
| ATOM | 4218 | CD1 | PHE | A | 285 | −50.335 | 11.202 | 4.954 | 1.00 | 24.49 C |
| ATOM | 4220 | CE1 | PHE | A | 285 | −50.209 | 11.996 | 6.086 | 1.00 | 25.11 C |
| ATOM | 4222 | CZ | PHE | A | 285 | −51.321 | 12.634 | 6.597 | 1.00 | 26.40 C |
| ATOM | 4224 | CE2 | PHE | A | 285 | −52.566 | 12.470 | 5.977 | 1.00 | 26.44 C |
| ATOM | 4226 | CD2 | PHE | A | 285 | −52.678 | 11.670 | 4.846 | 1.00 | 24.55 C |
| ATOM | 4228 | C | PHE | A | 285 | −51.097 | 7.879 | 3.770 | 1.00 | 18.74 C |
| ATOM | 4229 | O | PHE | A | 285 | −50.700 | 7.729 | 4.924 | 1.00 | 18.31 O |
| ATOM | 4231 | N | SER | A | 286 | −51.903 | 7.019 | 3.169 | 1.00 | 18.49 N |
| ATOM | 4232 | CA | SER | A | 286 | −52.281 | 5.772 | 3.791 | 1.00 | 18.38 C |
| ATOM | 4234 | CB | SER | A | 286 | −53.302 | 5.065 | 2.926 | 1.00 | 18.45 C |
| ATOM | 4237 | OG | SER | A | 286 | −54.389 | 5.949 | 2.687 | 1.00 | 19.82 O |
| ATOM | 4239 | C | SER | A | 286 | −51.070 | 4.888 | 4.048 | 1.00 | 18.08 C |
| ATOM | 4240 | O | SER | A | 286 | −50.931 | 4.376 | 5.146 | 1.00 | 18.18 O |
| ATOM | 4242 | N | PHE | A | 287 | −50.195 | 4.714 | 3.054 | 1.00 | 17.72 N |
| ATOM | 4243 | CA | PHE | A | 287 | −48.911 | 4.024 | 3.279 | 1.00 | 17.23 C |
| ATOM | 4245 | CB | PHE | A | 287 | −48.133 | 3.801 | 1.977 | 1.00 | 17.09 C |
| ATOM | 4248 | CG | PHE | A | 287 | −48.513 | 2.555 | 1.258 | 1.00 | 17.26 C |
| ATOM | 4249 | CD1 | PHE | A | 287 | −48.220 | 1.315 | 1.802 | 1.00 | 18.31 C |
| ATOM | 4251 | CE1 | PHE | A | 287 | −48.583 | .129 | 1.131 | 1.00 | 18.47 C |
| ATOM | 4253 | CZ | PHE | A | 287 | −49.237 | .198 | −.091 | 1.00 | 17.88 C |
| ATOM | 4255 | CE2 | PHE | A | 287 | −49.530 | 1.441 | −.642 | 1.00 | 17.57 C |
| ATOM | 4257 | CD2 | PHE | A | 287 | −49.168 | 2.608 | .031 | 1.00 | 17.79 C |
| ATOM | 4259 | C | PHE | A | 287 | −48.022 | 4.787 | 4.277 | 1.00 | 16.92 C |
| ATOM | 4260 | O | PHE | A | 287 | −47.369 | 4.173 | 5.143 | 1.00 | 17.18 O |
| ATOM | 4262 | N | VAL | A | 288 | −47.989 | 6.113 | 4.174 | 1.00 | 16.00 N |
| ATOM | 4263 | CA | VAL | A | 288 | −47.148 | 6.883 | 5.080 | 1.00 | 15.45 C |
| ATOM | 4265 | CB | VAL | A | 288 | −47.289 | 8.399 | 4.863 | 1.00 | 15.21 C |
| ATOM | 4267 | CG1 | VAL | A | 288 | −46.433 | 9.162 | 5.852 | 1.00 | 14.24 C |
| ATOM | 4271 | CG2 | VAL | A | 288 | −46.898 | 8.757 | 3.450 | 1.00 | 14.46 C |
| ATOM | 4275 | C | VAL | A | 288 | −47.479 | 6.499 | 6.527 | 1.00 | 15.46 C |
| ATOM | 4276 | O | VAL | A | 288 | −46.590 | 6.160 | 7.299 | 1.00 | 14.79 O |
| ATOM | 4278 | N | THR | A | 289 | −48.759 | 6.494 | 6.880 | 1.00 | 15.62 N |
| ATOM | 4279 | CA | THR | A | 289 | −49.110 | 6.272 | 8.274 | 1.00 | 16.09 C |
| ATOM | 4281 | CB | THR | A | 289 | −50.602 | 6.557 | 8.588 | 1.00 | 15.72 C |
| ATOM | 4283 | OG1 | THR | A | 289 | −51.422 | 5.827 | 7.708 | 1.00 | 16.52 O |
| ATOM | 4285 | CG2 | THR | A | 289 | −50.927 | 8.007 | 8.371 | 1.00 | 16.56 C |
| ATOM | 4289 | C | THR | A | 289 | −48.677 | 4.879 | 8.727 | 1.00 | 16.34 C |
| ATOM | 4290 | O | THR | A | 289 | −48.234 | 4.707 | 9.881 | 1.00 | 16.68 O |
| ATOM | 4292 | N | ILE | A | 290 | −48.737 | 3.904 | 7.820 | 1.00 | 16.29 N |
| ATOM | 4293 | CA | ILE | A | 290 | −48.347 | 2.538 | 8.166 | 1.00 | 16.56 C |
| ATOM | 4295 | CB | ILE | A | 290 | −48.734 | 1.516 | 7.096 | 1.00 | 16.48 C |
| ATOM | 4297 | CG1 | ILE | A | 290 | −50.247 | 1.440 | 6.944 | 1.00 | 16.91 C |
| ATOM | 4300 | CD1 | ILE | A | 290 | −50.677 | .564 | 5.811 | 1.00 | 16.52 C |
| ATOM | 4304 | CG2 | ILE | A | 290 | −48.262 | .145 | 7.488 | 1.00 | 16.52 C |
| ATOM | 4308 | C | ILE | A | 290 | −46.842 | 2.456 | 8.402 | 1.00 | 16.94 C |
| ATOM | 4309 | O | ILE | A | 290 | −46.404 | 1.968 | 9.443 | 1.00 | 17.06 O |
| ATOM | 4311 | N | ILE | A | 291 | −46.048 | 2.942 | 7.451 | 1.00 | 17.22 N |
| ATOM | 4312 | CA | ILE | A | 291 | −44.595 | 2.969 | 7.640 | 1.00 | 17.20 C |
| ATOM | 4314 | CB | ILE | A | 291 | −43.842 | 3.534 | 6.405 | 1.00 | 17.32 C |
| ATOM | 4316 | CG1 | ILE | A | 291 | −44.172 | 2.744 | 5.125 | 1.00 | 17.61 C |
| ATOM | 4319 | CD1 | ILE | A | 291 | −44.004 | 1.265 | 5.250 | 1.00 | 18.21 C |
| ATOM | 4323 | CG2 | ILE | A | 291 | −42.336 | 3.550 | 6.637 | 1.00 | 16.64 C |
| ATOM | 4327 | C | ILE | A | 291 | −44.262 | 3.794 | 8.886 | 1.00 | 17.36 C |
| ATOM | 4328 | O | ILE | A | 291 | −43.420 | 3.413 | 9.670 | 1.00 | 17.06 O |
| ATOM | 4330 | N | ASP | A | 292 | −44.950 | 4.906 | 9.093 | 1.00 | 18.12 N |
| ATOM | 4331 | CA | ASP | A | 292 | −44.627 | 5.755 | 10.227 | 1.00 | 18.83 C |
| ATOM | 4333 | CB | ASP | A | 292 | −45.511 | 7.017 | 10.285 | 1.00 | 19.22 C |
| ATOM | 4336 | CG | ASP | A | 292 | −45.185 | 7.920 | 11.485 | 1.00 | 19.93 C |
| ATOM | 4337 | OD1 | ASP | A | 292 | −44.062 | 8.460 | 11.544 | 1.00 | 21.80 O |
| ATOM | 4338 | OD2 | ASP | A | 292 | −46.048 | 8.080 | 12.375 | 1.00 | 20.46 O |
| ATOM | 4339 | C | ASP | A | 292 | −44.745 | 4.947 | 11.509 | 1.00 | 18.96 C |
| ATOM | 4340 | O | ASP | A | 292 | −43.902 | 5.094 | 12.394 | 1.00 | 19.05 O |
| ATOM | 4342 | N | ASP | A | 293 | −45.774 | 4.097 | 11.610 | 1.00 | 19.05 N |
| ATOM | 4343 | CA | ASP | A | 293 | −45.951 | 3.273 | 12.817 | 1.00 | 18.99 C |
| ATOM | 4345 | CB | ASP | A | 293 | −47.237 | 2.443 | 12.790 | 1.00 | 18.95 C |
| ATOM | 4348 | CG | ASP | A | 293 | −48.496 | 3.272 | 12.921 | 1.00 | 19.27 C |
| ATOM | 4349 | OD1 | ASP | A | 293 | −48.483 | 4.361 | 13.523 | 1.00 | 21.51 O |
| ATOM | 4350 | OD2 | ASP | A | 293 | −49.536 | 2.812 | 12.421 | 1.00 | 19.61 O |
| ATOM | 4351 | C | ASP | A | 293 | −44.783 | 2.322 | 12.935 | 1.00 | 19.07 C |
| ATOM | 4352 | O | ASP | A | 293 | −44.244 | 2.135 | 14.024 | 1.00 | 19.35 O |
| ATOM | 4354 | N | ILE | A | 294 | −44.390 | 1.730 | 11.805 | 1.00 | 19.10 N |
| ATOM | 4355 | CA | ILE | A | 294 | −43.320 | .727 | 11.786 | 1.00 | 19.04 C |
| ATOM | 4357 | CB | ILE | A | 294 | −43.137 | .109 | 10.386 | 1.00 | 18.49 C |
| ATOM | 4359 | CG1 | ILE | A | 294 | −44.343 | −.754 | 10.038 | 1.00 | 17.60 C |
| ATOM | 4362 | CD1 | ILE | A | 294 | −44.204 | −1.504 | 8.752 | 1.00 | 16.77 C |
| ATOM | 4366 | CG2 | ILE | A | 294 | −41.895 | −.745 | 10.348 | 1.00 | 18.77 C |
| ATOM | 4370 | C | ILE | A | 294 | −41.974 | 1.273 | 12.298 | 1.00 | 19.55 C |

TABLE 16-7-continued

Coordinates of *P. tremuloides* IspS

| ATOM | 4371 | O | ILE | A | 294 | −41.234 | .550 | 12.974 | 1.00 | 19.75 | O |
| ATOM | 4373 | N | TYR | A | 295 | −41.649 | 2.525 | 11.983 | 1.00 | 19.75 | N |
| ATOM | 4374 | CA | TYR | A | 295 | −40.411 | 3.103 | 12.476 | 1.00 | 19.91 | C |
| ATOM | 4376 | CB | TYR | A | 295 | −39.856 | 4.178 | 11.542 | 1.00 | 19.66 | C |
| ATOM | 4379 | CG | TYR | A | 295 | −39.206 | 3.695 | 10.245 | 1.00 | 18.19 | C |
| ATOM | 4380 | CD1 | TYR | A | 295 | −37.821 | 3.727 | 10.075 | 1.00 | 16.19 | C |
| ATOM | 4382 | CE1 | TYR | A | 295 | −37.222 | 3.331 | 8.882 | 1.00 | 14.68 | C |
| ATOM | 4384 | CZ | TYR | A | 295 | −38.004 | 2.906 | 7.828 | 1.00 | 15.04 | C |
| ATOM | 4385 | OH | TYR | A | 295 | −37.428 | 2.485 | 6.631 | 1.00 | 12.25 | O |
| ATOM | 4387 | CE2 | TYR | A | 295 | −39.383 | 2.871 | 7.975 | 1.00 | 16.48 | C |
| ATOM | 4389 | CD2 | TYR | A | 295 | −39.975 | 3.271 | 9.172 | 1.00 | 17.01 | C |
| ATOM | 4391 | C | TYR | A | 295 | −40.647 | 3.677 | 13.858 | 1.00 | 20.73 | C |
| ATOM | 4392 | O | TYR | A | 295 | −39.749 | 3.635 | 14.717 | 1.00 | 21.64 | O |
| ATOM | 4394 | N | ASP | A | 296 | −41.843 | 4.200 | 14.103 | 1.00 | 21.38 | N |
| ATOM | 4395 | CA | ASP | A | 296 | −42.100 | 4.865 | 15.391 | 1.00 | 22.20 | C |
| ATOM | 4397 | CB | ASP | A | 296 | −43.421 | 5.644 | 15.391 | 1.00 | 22.69 | C |
| ATOM | 4400 | CG | ASP | A | 296 | −43.567 | 6.548 | 16.607 | 1.00 | 23.85 | C |
| ATOM | 4401 | OD1 | ASP | A | 296 | −42.568 | 7.179 | 17.014 | 1.00 | 25.49 | O |
| ATOM | 4402 | OD2 | ASP | A | 296 | −44.689 | 6.648 | 17.145 | 1.00 | 26.12 | O |
| ATOM | 4403 | C | ASP | A | 296 | −42.106 | 3.890 | 16.549 | 1.00 | 22.10 | C |
| ATOM | 4404 | O | ASP | A | 296 | −41.376 | 4.082 | 17.506 | 1.00 | 22.14 | O |
| ATOM | 4406 | N | VAL | A | 297 | −42.900 | 2.828 | 16.435 | 1.00 | 22.25 | N |
| ATOM | 4407 | CA | VAL | A | 297 | −43.163 | 1.937 | 17.570 | 1.00 | 22.22 | C |
| ATOM | 4409 | CB | VAL | A | 297 | −44.635 | 2.116 | 18.057 | 1.00 | 22.07 | C |
| ATOM | 4411 | CG1 | VAL | A | 297 | −44.958 | 3.587 | 18.215 | 1.00 | 21.63 | C |
| ATOM | 4415 | CG2 | VAL | A | 297 | −45.618 | 1.459 | 17.099 | 1.00 | 20.76 | C |
| ATOM | 4419 | C | VAL | A | 297 | −42.861 | .422 | 17.373 | 1.00 | 22.49 | C |
| ATOM | 4420 | O | VAL | A | 297 | −42.517 | −.255 | 18.343 | 1.00 | 22.40 | O |
| ATOM | 4422 | N | TYR | A | 298 | −42.990 | −.117 | 16.157 | 1.00 | 22.69 | N |
| ATOM | 4423 | CA | TYR | A | 298 | −43.065 | −1.579 | 15.993 | 1.00 | 22.90 | C |
| ATOM | 4425 | CB | TYR | A | 298 | −44.089 | −1.974 | 14.934 | 1.00 | 22.77 | C |
| ATOM | 4428 | CG | TYR | A | 298 | −44.341 | −3.469 | 14.932 | 1.00 | 23.74 | C |
| ATOM | 4429 | CD1 | TYR | A | 298 | −45.249 | −4.043 | 15.819 | 1.00 | 25.72 | C |
| ATOM | 4431 | CE1 | TYR | A | 298 | −45.484 | −5.435 | 15.833 | 1.00 | 26.12 | C |
| ATOM | 4433 | CZ | TYR | A | 298 | −44.798 | −6.247 | 14.954 | 1.00 | 25.59 | C |
| ATOM | 4434 | OH | TYR | A | 298 | −45.027 | −7.593 | 14.970 | 1.00 | 25.33 | O |
| ATOM | 4436 | CE2 | TYR | A | 298 | −43.890 | −5.702 | 14.062 | 1.00 | 24.79 | C |
| ATOM | 4438 | CD2 | TYR | A | 298 | −43.661 | −4.317 | 14.061 | 1.00 | 24.20 | C |
| ATOM | 4440 | C | TYR | A | 298 | −41.750 | −2.258 | 15.649 | 1.00 | 23.02 | C |
| ATOM | 4441 | O | TYR | A | 298 | −41.387 | −3.257 | 16.256 | 1.00 | 22.80 | O |
| ATOM | 4443 | N | GLY | A | 299 | −41.069 | −1.747 | 14.634 | 1.00 | 23.47 | N |
| ATOM | 4444 | CA | GLY | A | 299 | −39.839 | −2.361 | 14.149 | 1.00 | 23.36 | C |
| ATOM | 4447 | C | GLY | A | 299 | −38.631 | −1.978 | 14.984 | 1.00 | 23.27 | C |
| ATOM | 4448 | O | GLY | A | 299 | −38.532 | −.858 | 15.501 | 1.00 | 23.35 | O |
| ATOM | 4450 | N | THR | A | 300 | −37.702 | −2.918 | 15.098 | 1.00 | 23.11 | N |
| ATOM | 4451 | CA | THR | A | 300 | −36.459 | −2.682 | 15.797 | 1.00 | 22.90 | C |
| ATOM | 4453 | CB | THR | A | 300 | −35.869 | −3.957 | 16.386 | 1.00 | 22.83 | C |
| ATOM | 4455 | OG1 | THR | A | 300 | −35.328 | −4.756 | 15.328 | 1.00 | 22.61 | O |
| ATOM | 4457 | CG2 | THR | A | 300 | −36.928 | −4.732 | 17.162 | 1.00 | 22.18 | C |
| ATOM | 4461 | C | THR | A | 300 | −35.482 | −2.120 | 14.796 | 1.00 | 23.00 | C |
| ATOM | 4462 | O | THR | A | 300 | −35.606 | −2.364 | 13.602 | 1.00 | 23.13 | O |
| ATOM | 4464 | N | LEU | A | 301 | −34.496 | −1.394 | 15.309 | 1.00 | 23.07 | N |
| ATOM | 4465 | CA | LEU | A | 301 | −33.596 | −.572 | 14.498 | 1.00 | 22.84 | C |
| ATOM | 4467 | CB | LEU | A | 301 | −32.515 | .007 | 15.403 | 1.00 | 22.80 | C |
| ATOM | 4470 | CG | LEU | A | 301 | −31.965 | 1.412 | 15.182 | 1.00 | 22.39 | C |
| ATOM | 4472 | CD1 | LEU | A | 301 | −32.983 | 2.365 | 14.587 | 1.00 | 22.44 | C |
| ATOM | 4476 | CD2 | LEU | A | 301 | −31.482 | 1.919 | 16.536 | 1.00 | 22.19 | C |
| ATOM | 4480 | C | LEU | A | 301 | −32.964 | −1.358 | 13.361 | 1.00 | 22.95 | C |
| ATOM | 4481 | O | LEU | A | 301 | −32.910 | −.888 | 12.232 | 1.00 | 22.50 | O |
| ATOM | 4483 | N | ASP | A | 302 | −32.511 | −2.569 | 13.673 | 1.00 | 23.35 | N |
| ATOM | 4484 | CA | ASP | A | 302 | −31.929 | −3.469 | 12.670 | 1.00 | 23.65 | C |
| ATOM | 4486 | CB | ASP | A | 302 | −31.332 | −4.747 | 13.328 | 1.00 | 24.12 | C |
| ATOM | 4489 | CG | ASP | A | 302 | −29.984 | −4.498 | 14.057 | 1.00 | 25.23 | C |
| ATOM | 4490 | OD1 | ASP | A | 302 | −29.003 | −4.051 | 13.409 | 1.00 | 26.43 | O |
| ATOM | 4491 | OD2 | ASP | A | 302 | −29.896 | −4.780 | 15.277 | 1.00 | 26.92 | O |
| ATOM | 4492 | C | ASP | A | 302 | −32.945 | −3.859 | 11.581 | 1.00 | 23.11 | C |
| ATOM | 4493 | O | ASP | A | 302 | −32.544 | −4.086 | 10.445 | 1.00 | 23.05 | O |
| ATOM | 4495 | N | GLU | A | 303 | −34.235 | −3.965 | 11.927 | 1.00 | 22.63 | N |
| ATOM | 4496 | CA | GLU | A | 303 | −35.295 | −4.248 | 10.931 | 1.00 | 22.40 | C |
| ATOM | 4498 | CB | GLU | A | 303 | −36.625 | −4.675 | 11.589 | 1.00 | 22.20 | C |
| ATOM | 4501 | CG | GLU | A | 303 | −36.537 | −5.956 | 12.426 | 1.00 | 22.66 | C |
| ATOM | 4504 | CD | GLU | A | 303 | −37.832 | −6.341 | 13.159 | 1.00 | 22.69 | C |
| ATOM | 4505 | OE1 | GLU | A | 303 | −38.614 | −5.449 | 13.568 | 1.00 | 22.23 | O |
| ATOM | 4506 | OE2 | GLU | A | 303 | −38.051 | −7.558 | 13.338 | 1.00 | 21.64 | O |
| ATOM | 4507 | C | GLU | A | 303 | −35.533 | −3.017 | 10.067 | 1.00 | 22.35 | C |
| ATOM | 4508 | O | GLU | A | 303 | −35.658 | −3.105 | 8.841 | 1.00 | 22.27 | O |
| ATOM | 4510 | N | LEU | A | 304 | −35.597 | −1.866 | 10.724 | 1.00 | 22.34 | N |
| ATOM | 4511 | CA | LEU | A | 304 | −35.776 | −.607 | 10.040 | 1.00 | 22.26 | C |

TABLE 16-7-continued

Coordinates of *P. tremuloides* IspS

| ATOM | 4513 | CB | LEU | A | 304 | −35.861 | .537 | 11.052 | 1.00 | 22.49 | C |
|---|---|---|---|---|---|---|---|---|---|---|---|
| ATOM | 4516 | CG | LEU | A | 304 | −37.089 | .517 | 11.973 | 1.00 | 23.05 | C |
| ATOM | 4518 | CD1 | LEU | A | 304 | −37.109 | 1.708 | 12.932 | 1.00 | 23.46 | C |
| ATOM | 4522 | CD2 | LEU | A | 304 | −38.353 | .511 | 11.142 | 1.00 | 23.96 | C |
| ATOM | 4526 | C | LEU | A | 304 | −34.634 | −.383 | 9.063 | 1.00 | 22.09 | C |
| ATOM | 4527 | O | LEU | A | 304 | −34.873 | .094 | 7.969 | 1.00 | 22.32 | O |
| ATOM | 4529 | N | GLU | A | 305 | −33.408 | −.740 | 9.450 | 1.00 | 21.91 | N |
| ATOM | 4530 | CA | GLU | A | 305 | −32.259 | −.685 | 8.541 | 1.00 | 21.93 | C |
| ATOM | 4532 | CB | GLU | A | 305 | −30.988 | −1.194 | 9.219 | 1.00 | 22.35 | C |
| ATOM | 4535 | CG | GLU | A | 305 | −30.363 | −.258 | 10.249 | 1.00 | 24.12 | C |
| ATOM | 4538 | CD | GLU | A | 305 | −29.751 | 1.002 | 9.649 | 1.00 | 26.11 | C |
| ATOM | 4539 | OE1 | GLU | A | 305 | −29.275 | 1.846 | 10.454 | 1.00 | 25.68 | O |
| ATOM | 4540 | OE2 | GLU | A | 305 | −29.756 | 1.146 | 8.391 | 1.00 | 27.67 | O |
| ATOM | 4541 | C | GLU | A | 305 | −32.475 | −1.524 | 7.295 | 1.00 | 21.54 | C |
| ATOM | 4542 | O | GLU | A | 305 | −32.010 | −1.162 | 6.220 | 1.00 | 21.75 | O |
| ATOM | 4544 | N | LEU | A | 306 | −33.155 | −2.660 | 7.448 | 1.00 | 21.21 | N |
| ATOM | 4545 | CA | LEU | A | 306 | −33.459 | −3.557 | 6.316 | 1.00 | 20.66 | C |
| ATOM | 4547 | CB | LEU | A | 306 | −33.880 | −4.956 | 6.795 | 1.00 | 20.26 | C |
| ATOM | 4550 | CG | LEU | A | 306 | −32.725 | −5.854 | 7.220 | 1.00 | 19.57 | C |
| ATOM | 4552 | CD1 | LEU | A | 306 | −33.261 | −7.150 | 7.777 | 1.00 | 20.18 | C |
| ATOM | 4556 | CD2 | LEU | A | 306 | −31.791 | −6.120 | 6.061 | 1.00 | 18.29 | C |
| ATOM | 4560 | C | LEU | A | 306 | −34.535 | −2.967 | 5.416 | 1.00 | 20.23 | C |
| ATOM | 4561 | O | LEU | A | 306 | −34.412 | −2.966 | 4.197 | 1.00 | 19.97 | O |
| ATOM | 4563 | N | PHE | A | 307 | −35.588 | −2.457 | 6.023 | 1.00 | 19.99 | N |
| ATOM | 4564 | CA | PHE | A | 307 | −36.635 | −1.861 | 5.237 | 1.00 | 20.00 | C |
| ATOM | 4566 | CB | PHE | A | 307 | −37.771 | −1.388 | 6.118 | 1.00 | 20.08 | C |
| ATOM | 4569 | CG | PHE | A | 307 | −39.011 | −1.115 | 5.370 | 1.00 | 19.05 | C |
| ATOM | 4570 | CD1 | PHE | A | 307 | −39.895 | −2.118 | 5.119 | 1.00 | 18.77 | C |
| ATOM | 4572 | CE1 | PHE | A | 307 | −41.037 | −1.873 | 4.421 | 1.00 | 20.07 | C |
| ATOM | 4574 | CZ | PHE | A | 307 | −41.296 | −.621 | 3.959 | 1.00 | 19.63 | C |
| ATOM | 4576 | CE2 | PHE | A | 307 | −40.411 | .391 | 4.199 | 1.00 | 19.27 | C |
| ATOM | 4578 | CD2 | PHE | A | 307 | −39.278 | .142 | 4.900 | 1.00 | 19.17 | C |
| ATOM | 4580 | C | PHE | A | 307 | −36.087 | −.695 | 4.447 | 1.00 | 20.25 | C |
| ATOM | 4581 | O | PHE | A | 307 | −36.356 | −.589 | 3.242 | 1.00 | 20.08 | O |
| ATOM | 4583 | N | THR | A | 308 | −35.325 | .167 | 5.137 | 1.00 | 20.51 | N |
| ATOM | 4584 | CA | THR | A | 308 | −34.737 | 1.379 | 4.538 | 1.00 | 20.60 | C |
| ATOM | 4586 | CB | THR | A | 308 | −33.860 | 2.177 | 5.541 | 1.00 | 20.41 | C |
| ATOM | 4588 | OG1 | THR | A | 308 | −34.672 | 2.661 | 6.611 | 1.00 | 20.05 | O |
| ATOM | 4590 | CG2 | THR | A | 308 | −33.198 | 3.376 | 4.864 | 1.00 | 20.38 | C |
| ATOM | 4594 | C | THR | A | 308 | −33.895 | 1.009 | 3.331 | 1.00 | 20.82 | C |
| ATOM | 4595 | O | THR | A | 308 | −34.057 | 1.571 | 2.243 | 1.00 | 20.45 | O |
| ATOM | 4597 | N | ASP | A | 309 | −33.020 | .031 | 3.522 | 1.00 | 21.32 | N |
| ATOM | 4598 | CA | ASP | A | 309 | −32.138 | −.399 | 2.449 | 1.00 | 21.88 | C |
| ATOM | 4600 | CB | ASP | A | 309 | −31.042 | −1.324 | 2.971 | 1.00 | 22.44 | C |
| ATOM | 4603 | CG | ASP | A | 309 | −30.164 | −1.847 | 1.857 | 1.00 | 25.69 | C |
| ATOM | 4604 | OD1 | ASP | A | 309 | −29.599 | −1.010 | 1.089 | 1.00 | 28.02 | O |
| ATOM | 4605 | OD2 | ASP | A | 309 | −30.076 | −3.100 | 1.730 | 1.00 | 30.59 | O |
| ATOM | 4606 | C | ASP | A | 309 | −32.928 | −1.085 | 1.357 | 1.00 | 21.17 | C |
| ATOM | 4607 | O | ASP | A | 309 | −32.601 | −.948 | .188 | 1.00 | 20.95 | O |
| ATOM | 4609 | N | ALA | A | 310 | −33.965 | −1.818 | 1.757 | 1.00 | 20.99 | N |
| ATOM | 4610 | CA | ALA | A | 310 | −34.885 | −2.474 | .828 | 1.00 | 20.91 | C |
| ATOM | 4612 | CB | ALA | A | 310 | −35.931 | −3.244 | 1.591 | 1.00 | 20.77 | C |
| ATOM | 4616 | C | ALA | A | 310 | −35.567 | −1.501 | −.123 | 1.00 | 21.08 | C |
| ATOM | 4617 | O | ALA | A | 310 | −35.745 | −1.816 | −1.305 | 1.00 | 20.76 | O |
| ATOM | 4619 | N | VAL | A | 311 | −35.958 | −.334 | .402 | 1.00 | 21.51 | N |
| ATOM | 4620 | CA | VAL | A | 311 | −36.594 | .719 | −.396 | 1.00 | 21.50 | C |
| ATOM | 4622 | CB | VAL | A | 311 | −37.424 | 1.715 | .477 | 1.00 | 21.73 | C |
| ATOM | 4624 | CG1 | VAL | A | 311 | −38.724 | 1.076 | .941 | 1.00 | 21.01 | C |
| ATOM | 4628 | CG2 | VAL | A | 311 | −37.765 | 2.993 | −.292 | 1.00 | 21.88 | C |
| ATOM | 4632 | C | VAL | A | 311 | −35.553 | 1.445 | −1.230 | 1.00 | 21.67 | C |
| ATOM | 4633 | O | VAL | A | 311 | −35.811 | 1.728 | −2.389 | 1.00 | 21.71 | O |
| ATOM | 4635 | N | GLU | A | 312 | −34.381 | 1.724 | −.663 | 1.00 | 22.25 | N |
| ATOM | 4636 | CA | GLU | A | 312 | −33.248 | 2.284 | −1.443 | 1.00 | 23.00 | C |
| ATOM | 4638 | CB | GLU | A | 312 | −31.951 | 2.331 | −.608 | 1.00 | 23.36 | C |
| ATOM | 4641 | CG | GLU | A | 312 | −31.897 | 3.383 | .511 | 1.00 | 24.72 | C |
| ATOM | 4644 | CD | GLU | A | 312 | −30.526 | 3.469 | 1.189 | 1.00 | 27.09 | C |
| ATOM | 4645 | OE1 | GLU | A | 312 | −30.083 | 4.608 | 1.458 | 1.00 | 30.07 | O |
| ATOM | 4646 | OE2 | GLU | A | 312 | −29.885 | 2.418 | 1.454 | 1.00 | 27.86 | O |
| ATOM | 4647 | C | GLU | A | 312 | −32.954 | 1.498 | −2.731 | 1.00 | 23.13 | C |
| ATOM | 4648 | O | GLU | A | 312 | −32.851 | 2.064 | −3.803 | 1.00 | 22.88 | O |
| ATOM | 4650 | N | ARG | A | 313 | −32.819 | .188 | −2.615 | 1.00 | 23.74 | N |
| ATOM | 4651 | CA | ARG | A | 313 | −32.400 | −.628 | −3.743 | 1.00 | 24.46 | C |
| ATOM | 4653 | CB | ARG | A | 313 | −31.758 | −1.916 | −3.232 | 1.00 | 25.01 | C |
| ATOM | 4656 | CG | ARG | A | 313 | −30.421 | −1.667 | −2.481 | 1.00 | 27.74 | C |
| ATOM | 4659 | CD | ARG | A | 313 | −29.715 | −2.963 | −2.072 | 1.00 | 31.41 | C |
| ATOM | 4662 | NE | ARG | A | 313 | −30.675 | −3.921 | −1.499 | 1.00 | 34.94 | N |
| ATOM | 4664 | CZ | ARG | A | 313 | −31.203 | −4.974 | −2.138 | 1.00 | 37.87 | C |
| ATOM | 4665 | NH1 | ARG | A | 313 | −30.861 | −5.282 | −3.402 | 1.00 | 38.35 | N |

TABLE 16-7-continued

Coordinates of *P. tremuloides* IspS

| ATOM | 4668 | NH2 | ARG | A | 313 | −32.079 | −5.746 | −1.495 | 1.00 | 38.82 | N |
|---|---|---|---|---|---|---|---|---|---|---|---|
| ATOM | 4671 | C | ARG | A | 313 | −33.523 | −.914 | −4.739 | 1.00 | 24.27 | C |
| ATOM | 4672 | O | ARG | A | 313 | −33.257 | −1.178 | −5.898 | 1.00 | 24.17 | O |
| ATOM | 4674 | N | TRP | A | 314 | −34.770 | −.873 | −4.282 | 1.00 | 24.59 | N |
| ATOM | 4675 | CA | TRP | A | 314 | −35.939 | −1.042 | −5.142 | 1.00 | 24.66 | C |
| ATOM | 4677 | CB | TRP | A | 314 | −36.175 | .234 | −5.961 | 1.00 | 24.39 | C |
| ATOM | 4680 | CG | TRP | A | 314 | −37.575 | .382 | −6.386 | 1.00 | 22.61 | C |
| ATOM | 4681 | CD1 | TRP | A | 314 | −38.073 | .204 | −7.635 | 1.00 | 21.66 | C |
| ATOM | 4683 | NE1 | TRP | A | 314 | −39.429 | .403 | −7.634 | 1.00 | 21.42 | N |
| ATOM | 4685 | CE2 | TRP | A | 314 | −39.829 | .707 | −6.360 | 1.00 | 20.99 | C |
| ATOM | 4686 | CD2 | TRP | A | 314 | −38.683 | .701 | −5.550 | 1.00 | 21.41 | C |
| ATOM | 4687 | CE3 | TRP | A | 314 | −38.817 | .991 | −4.191 | 1.00 | 21.48 | C |
| ATOM | 4689 | CZ3 | TRP | A | 314 | −40.080 | 1.277 | −3.693 | 1.00 | 21.38 | C |
| ATOM | 4691 | CH2 | TRP | A | 314 | −41.204 | 1.269 | −4.523 | 1.00 | 20.84 | C |
| ATOM | 4693 | CZ2 | TRP | A | 314 | −41.099 | .985 | −5.857 | 1.00 | 20.87 | C |
| ATOM | 4695 | C | TRP | A | 314 | −35.831 | −2.286 | −6.038 | 1.00 | 25.65 | C |
| ATOM | 4696 | O | TRP | A | 314 | −36.069 | −2.238 | −7.259 | 1.00 | 25.69 | O |
| ATOM | 4698 | N | ASP | A | 315 | −35.480 | −3.400 | −5.404 | 1.00 | 26.79 | N |
| ATOM | 4699 | CA | ASP | A | 315 | −35.253 | −4.667 | −6.087 | 1.00 | 28.01 | C |
| ATOM | 4701 | CB | ASP | A | 315 | −33.801 | −5.097 | −5.890 | 1.00 | 28.07 | C |
| ATOM | 4704 | CG | ASP | A | 315 | −33.553 | −6.536 | −6.296 | 1.00 | 29.92 | C |
| ATOM | 4705 | OD1 | ASP | A | 315 | −34.262 | −7.026 | −7.197 | 1.00 | 32.58 | O |
| ATOM | 4706 | OD2 | ASP | A | 315 | −32.648 | −7.194 | −5.722 | 1.00 | 32.73 | O |
| ATOM | 4707 | C | ASP | A | 315 | −36.202 | −5.710 | −5.518 | 1.00 | 28.91 | C |
| ATOM | 4708 | O | ASP | A | 315 | −36.019 | −6.163 | −4.399 | 1.00 | 29.17 | O |
| ATOM | 4710 | N | VAL | A | 316 | −37.218 | −6.091 | −6.283 | 1.00 | 30.25 | N |
| ATOM | 4711 | CA | VAL | A | 316 | −38.233 | −7.012 | −5.778 | 1.00 | 31.47 | C |
| ATOM | 4713 | CB | VAL | A | 316 | −39.396 | −7.156 | −6.755 | 1.00 | 31.56 | C |
| ATOM | 4715 | CG1 | VAL | A | 316 | −40.668 | −7.590 | −6.027 | 1.00 | 30.99 | C |
| ATOM | 4719 | CG2 | VAL | A | 316 | −39.033 | −8.141 | −7.862 | 1.00 | 31.84 | C |
| ATOM | 4723 | C | VAL | A | 316 | −37.663 | −8.405 | −5.540 | 1.00 | 32.86 | C |
| ATOM | 4724 | O | VAL | A | 316 | −38.170 | −9.153 | −4.708 | 1.00 | 32.99 | O |
| ATOM | 4726 | N | ASN | A | 317 | −36.607 | −8.750 | −6.278 | 1.00 | 34.55 | N |
| ATOM | 4727 | CA | ASN | A | 317 | −35.940 | −10.060 | −6.160 | 1.00 | 35.53 | C |
| ATOM | 4729 | CB | ASN | A | 317 | −35.013 | −10.298 | −7.367 | 1.00 | 35.68 | C |
| ATOM | 4732 | CG | ASN | A | 317 | −35.752 | −10.264 | −8.713 | 1.00 | 35.92 | C |
| ATOM | 4733 | OD1 | ASN | A | 317 | −36.634 | −11.092 | −8.971 | 1.00 | 36.95 | O |
| ATOM | 4734 | ND2 | ASN | A | 317 | −35.368 | −9.323 | −9.585 | 1.00 | 34.17 | N |
| ATOM | 4737 | C | ASN | A | 317 | −35.126 | −10.225 | −4.871 | 1.00 | 36.40 | C |
| ATOM | 4738 | O | ASN | A | 317 | −34.385 | −11.195 | −4.747 | 1.00 | 36.47 | O |
| ATOM | 4740 | N | ALA | A | 318 | −35.239 | −9.265 | −3.944 | 1.00 | 37.52 | N |
| ATOM | 4741 | CA | ALA | A | 318 | −34.614 | −9.335 | −2.613 | 1.00 | 38.45 | C |
| ATOM | 4743 | CB | ALA | A | 318 | −33.371 | −8.465 | −2.557 | 1.00 | 38.43 | C |
| ATOM | 4747 | C | ALA | A | 318 | −35.631 | −8.902 | −1.554 | 1.00 | 39.28 | C |
| ATOM | 4748 | O | ALA | A | 318 | −35.361 | −8.094 | −.662 | 1.00 | 39.55 | O |
| ATOM | 4750 | N | ILE | A | 319 | −36.823 | −9.456 | −1.698 | 1.00 | 40.17 | N |
| ATOM | 4751 | CA | ILE | A | 319 | −37.905 | −9.310 | −.740 | 1.00 | 40.49 | C |
| ATOM | 4753 | CB | ILE | A | 319 | −39.275 | −9.588 | −1.469 | 1.00 | 40.64 | C |
| ATOM | 4755 | CG1 | ILE | A | 319 | −40.473 | −9.078 | −.683 | 1.00 | 40.88 | C |
| ATOM | 4758 | CD1 | ILE | A | 319 | −41.799 | −9.535 | −1.280 | 1.00 | 40.86 | C |
| ATOM | 4762 | CG2 | ILE | A | 319 | −39.460 | −11.082 | −1.801 | 1.00 | 40.50 | C |
| ATOM | 4766 | C | ILE | A | 319 | −37.656 | −10.319 | .393 | 1.00 | 40.69 | C |
| ATOM | 4767 | O | ILE | A | 319 | −38.136 | −10.138 | 1.504 | 1.00 | 40.88 | O |
| ATOM | 4769 | N | ASN | A | 320 | −36.886 | −11.374 | .104 | 1.00 | 40.79 | N |
| ATOM | 4770 | CA | ASN | A | 320 | −36.689 | −12.483 | 1.049 | 1.00 | 40.64 | C |
| ATOM | 4772 | CB | ASN | A | 320 | −36.240 | −13.761 | .314 | 1.00 | 40.73 | C |
| ATOM | 4775 | CG | ASN | A | 320 | −37.370 | −14.422 | −.468 | 1.00 | 40.98 | C |
| ATOM | 4776 | OD1 | ASN | A | 320 | −38.556 | −14.309 | −.119 | 1.00 | 40.77 | O |
| ATOM | 4777 | ND2 | ASN | A | 320 | −37.001 | −15.131 | −1.529 | 1.00 | 41.31 | N |
| ATOM | 4780 | C | ASN | A | 320 | −35.711 | −12.175 | 2.169 | 1.00 | 40.16 | C |
| ATOM | 4781 | O | ASN | A | 320 | −35.546 | −12.978 | 3.077 | 1.00 | 40.15 | O |
| ATOM | 4783 | N | ASP | A | 321 | −35.067 | −11.017 | 2.101 | 1.00 | 39.66 | N |
| ATOM | 4784 | CA | ASP | A | 321 | −34.111 | −10.615 | 3.126 | 1.00 | 39.51 | C |
| ATOM | 4786 | CB | ASP | A | 321 | −33.114 | −9.571 | 2.575 | 1.00 | 40.17 | C |
| ATOM | 4789 | CG | ASP | A | 321 | −32.595 | −9.904 | 1.152 | 1.00 | 42.12 | C |
| ATOM | 4790 | OD1 | ASP | A | 321 | −32.425 | −11.115 | .820 | 1.00 | 44.15 | O |
| ATOM | 4791 | OD2 | ASP | A | 321 | −32.354 | −8.934 | .375 | 1.00 | 43.28 | O |
| ATOM | 4792 | C | ASP | A | 321 | −34.851 | −10.030 | 4.337 | 1.00 | 38.27 | C |
| ATOM | 4793 | O | ASP | A | 321 | −34.304 | −9.987 | 5.443 | 1.00 | 38.15 | O |
| ATOM | 4795 | N | LEU | A | 322 | −36.089 | −9.583 | 4.108 | 1.00 | 36.72 | N |
| ATOM | 4796 | CA | LEU | A | 322 | −36.887 | −8.875 | 5.104 | 1.00 | 35.38 | C |
| ATOM | 4798 | CB | LEU | A | 322 | −37.894 | −7.942 | 4.422 | 1.00 | 35.15 | C |
| ATOM | 4801 | CG | LEU | A | 322 | −37.370 | −6.840 | 3.503 | 1.00 | 34.83 | C |
| ATOM | 4803 | CD1 | LEU | A | 322 | −38.479 | −6.286 | 2.626 | 1.00 | 34.45 | C |
| ATOM | 4807 | CD2 | LEU | A | 322 | −36.742 | −5.740 | 4.316 | 1.00 | 34.89 | C |
| ATOM | 4811 | C | LEU | A | 322 | −37.683 | −9.834 | 5.963 | 1.00 | 34.57 | C |
| ATOM | 4812 | O | LEU | A | 322 | −37.975 | −10.933 | 5.527 | 1.00 | 34.27 | O |
| ATOM | 4814 | N | PRO | A | 323 | −38.039 | −9.402 | 7.189 | 1.00 | 33.93 | N |

TABLE 16-7-continued

Coordinates of *P. tremuloides* IspS

| ATOM | 4815 | CA  | PRO | A | 323 | −39.070 | −9.917  | 8.067  | 1.00 | 33.49 | C |
|------|------|-----|-----|---|-----|---------|---------|--------|------|-------|---|
| ATOM | 4817 | CB  | PRO | A | 323 | −39.151 | −8.840  | 9.141  | 1.00 | 33.31 | C |
| ATOM | 4820 | CG  | PRO | A | 323 | −37.791 | −8.419  | 9.311  | 1.00 | 33.67 | C |
| ATOM | 4823 | CD  | PRO | A | 323 | −37.154 | −8.496  | 7.941  | 1.00 | 34.20 | C |
| ATOM | 4826 | C   | PRO | A | 323 | −40.429 | −10.036 | 7.425  | 1.00 | 33.33 | C |
| ATOM | 4827 | O   | PRO | A | 323 | −40.776 | −9.232  | 6.579  | 1.00 | 33.35 | O |
| ATOM | 4828 | N   | ASP | A | 324 | −41.209 | −11.005 | 7.891  | 1.00 | 33.37 | N |
| ATOM | 4829 | CA  | ASP | A | 324 | −42.511 | −11.329 | 7.313  | 1.00 | 33.36 | C |
| ATOM | 4831 | CB  | ASP | A | 324 | −43.137 | −12.542 | 8.037  | 1.00 | 33.59 | C |
| ATOM | 4834 | CG  | ASP | A | 324 | −42.496 | −13.881 | 7.619  | 1.00 | 34.18 | C |
| ATOM | 4835 | OD1 | ASP | A | 324 | −41.885 | −13.915 | 6.518  | 1.00 | 36.44 | O |
| ATOM | 4836 | OD2 | ASP | A | 324 | −42.607 | −14.887 | 8.371  | 1.00 | 32.19 | O |
| ATOM | 4837 | C   | ASP | A | 324 | −43.484 | −10.149 | 7.289  | 1.00 | 32.90 | C |
| ATOM | 4838 | O   | ASP | A | 324 | −44.108 | −9.885  | 6.255  | 1.00 | 33.36 | O |
| ATOM | 4840 | N   | TYR | A | 325 | −43.606 | −9.423  | 8.392  | 1.00 | 32.10 | N |
| ATOM | 4841 | CA  | TYR | A | 325 | −44.515 | −8.279  | 8.400  | 1.00 | 31.65 | C |
| ATOM | 4843 | CB  | TYR | A | 325 | −44.718 | −7.726  | 9.815  | 1.00 | 31.68 | C |
| ATOM | 4846 | CG  | TYR | A | 325 | −43.618 | −6.846  | 10.352 | 1.00 | 31.35 | C |
| ATOM | 4847 | CD1 | TYR | A | 325 | −42.507 | −7.389  | 10.992 | 1.00 | 31.31 | C |
| ATOM | 4849 | CE1 | TYR | A | 325 | −41.497 | −6.574  | 11.504 | 1.00 | 31.46 | C |
| ATOM | 4851 | CZ  | TYR | A | 325 | −41.613 | −5.192  | 11.392 | 1.00 | 32.41 | C |
| ATOM | 4852 | OH  | TYR | A | 325 | −40.637 | −4.336  | 11.893 | 1.00 | 32.78 | O |
| ATOM | 4854 | CE2 | TYR | A | 325 | −42.723 | −4.644  | 10.769 | 1.00 | 32.17 | C |
| ATOM | 4856 | CD2 | TYR | A | 325 | −43.713 | −5.470  | 10.261 | 1.00 | 31.47 | C |
| ATOM | 4858 | C   | TYR | A | 325 | −44.094 | −7.179  | 7.424  | 1.00 | 31.17 | C |
| ATOM | 4859 | O   | TYR | A | 325 | −44.947 | −6.458  | 6.920  | 1.00 | 31.09 | O |
| ATOM | 4861 | N   | MET | A | 326 | −42.796 | −7.068  | 7.145  | 1.00 | 30.73 | N |
| ATOM | 4862 | CA  | MET | A | 326 | −42.277 | −6.036  | 6.225  | 1.00 | 30.49 | C |
| ATOM | 4864 | CB  | MET | A | 326 | −40.832 | −5.702  | 6.565  | 1.00 | 30.16 | C |
| ATOM | 4867 | CG  | MET | A | 326 | −40.725 | −4.918  | 7.830  | 1.00 | 29.57 | C |
| ATOM | 4870 | SD  | MET | A | 326 | −39.057 | −4.376  | 8.166  | 1.00 | 28.39 | S |
| ATOM | 4871 | CE  | MET | A | 326 | −39.407 | −2.787  | 8.933  | 1.00 | 26.18 | C |
| ATOM | 4875 | C   | MET | A | 326 | −42.371 | −6.418  | 4.748  | 1.00 | 30.59 | C |
| ATOM | 4876 | O   | MET | A | 326 | −42.786 | −5.603  | 3.920  | 1.00 | 30.48 | O |
| ATOM | 4878 | N   | LYS | A | 327 | −41.936 | −7.643  | 4.438  | 1.00 | 30.68 | N |
| ATOM | 4879 | CA  | LYS | A | 327 | −42.170 | −8.299  | 3.143  | 1.00 | 30.56 | C |
| ATOM | 4881 | CB  | LYS | A | 327 | −42.267 | −9.830  | 3.326  | 1.00 | 30.84 | C |
| ATOM | 4884 | CG  | LYS | A | 327 | −41.052 | −10.607 | 2.844  | 1.00 | 32.35 | C |
| ATOM | 4887 | CD  | LYS | A | 327 | −40.990 | −12.019 | 3.412  | 1.00 | 34.43 | C |
| ATOM | 4890 | CE  | LYS | A | 327 | −40.221 | −12.941 | 2.462  | 1.00 | 35.77 | C |
| ATOM | 4893 | NZ  | LYS | A | 327 | −39.691 | −14.162 | 3.150  | 1.00 | 37.20 | N |
| ATOM | 4897 | C   | LYS | A | 327 | −43.453 | −7.811  | 2.515  | 1.00 | 29.89 | C |
| ATOM | 4898 | O   | LYS | A | 327 | −43.447 | −7.220  | 1.436  | 1.00 | 29.85 | O |
| ATOM | 4900 | N   | LEU | A | 328 | −44.544 | −8.046  | 3.230  | 1.00 | 29.10 | N |
| ATOM | 4901 | CA  | LEU | A | 328 | −45.871 | −7.781  | 2.730  | 1.00 | 28.77 | C |
| ATOM | 4903 | CB  | LEU | A | 328 | −46.899 | −8.336  | 3.709  | 1.00 | 28.81 | C |
| ATOM | 4906 | CG  | LEU | A | 328 | −48.349 | −8.364  | 3.257  | 1.00 | 28.82 | C |
| ATOM | 4908 | CD1 | LEU | A | 328 | −48.519 | −9.260  | 2.046  | 1.00 | 29.09 | C |
| ATOM | 4912 | CD2 | LEU | A | 328 | −49.202 | −8.845  | 4.411  | 1.00 | 29.16 | C |
| ATOM | 4916 | C   | LEU | A | 328 | −46.057 | −6.291  | 2.564  | 1.00 | 28.61 | C |
| ATOM | 4917 | O   | LEU | A | 328 | −46.582 | −5.828  | 1.554  | 1.00 | 29.00 | O |
| ATOM | 4919 | N   | CYS | A | 329 | −45.612 | −5.532  | 3.557  | 1.00 | 28.24 | N |
| ATOM | 4920 | CA  | CYS | A | 329 | −45.737 | −4.086  | 3.504  | 1.00 | 27.95 | C |
| ATOM | 4922 | CB  | CYS | A | 329 | −45.311 | −3.459  | 4.834  | 1.00 | 28.21 | C |
| ATOM | 4925 | SG  | CYS | A | 329 | −45.280 | −1.630  | 4.817  | 1.00 | 32.39 | S |
| ATOM | 4927 | C   | CYS | A | 329 | −44.921 | −3.541  | 2.327  | 1.00 | 26.34 | C |
| ATOM | 4928 | O   | CYS | A | 329 | −45.459 | −2.853  | 1.475  | 1.00 | 26.23 | O |
| ATOM | 4930 | N   | PHE | A | 330 | −43.642 | −3.882  | 2.269  | 1.00 | 24.82 | N |
| ATOM | 4931 | CA  | PHE | A | 330 | −42.790 | −3.514  | 1.130  | 1.00 | 23.82 | C |
| ATOM | 4933 | CB  | PHE | A | 330 | −41.397 | −4.137  | 1.283  | 1.00 | 23.64 | C |
| ATOM | 4936 | CG  | PHE | A | 330 | −40.492 | −3.873  | .117   | 1.00 | 22.63 | C |
| ATOM | 4937 | CD1 | PHE | A | 330 | −39.845 | −2.658  | −.008  | 1.00 | 21.68 | C |
| ATOM | 4939 | CE1 | PHE | A | 330 | −39.020 | −2.393  | −1.082 | 1.00 | 21.07 | C |
| ATOM | 4941 | CZ  | PHE | A | 330 | −38.829 | −3.343  | −2.046 | 1.00 | 22.00 | C |
| ATOM | 4943 | CE2 | PHE | A | 330 | −39.474 | −4.568  | −1.944 | 1.00 | 22.60 | C |
| ATOM | 4945 | CD2 | PHE | A | 330 | −40.309 | −4.824  | −.865  | 1.00 | 22.36 | C |
| ATOM | 4947 | C   | PHE | A | 330 | −43.348 | −3.863  | −.281  | 1.00 | 22.99 | C |
| ATOM | 4948 | O   | PHE | A | 330 | −43.350 | −3.012  | −1.182 | 1.00 | 22.98 | O |
| ATOM | 4950 | N   | LEU | A | 331 | −43.789 | −5.101  | −.492  | 1.00 | 21.65 | N |
| ATOM | 4951 | CA  | LEU | A | 331 | −44.306 | −5.484  | −1.816 | 1.00 | 20.74 | C |
| ATOM | 4953 | CB  | LEU | A | 331 | −44.573 | −6.990  | −1.912 | 1.00 | 20.57 | C |
| ATOM | 4956 | CG  | LEU | A | 331 | −44.959 | −7.575  | −3.277 | 1.00 | 19.82 | C |
| ATOM | 4958 | CD1 | LEU | A | 331 | −43.936 | −7.246  | −4.329 | 1.00 | 19.00 | C |
| ATOM | 4962 | CD2 | LEU | A | 331 | −45.128 | −9.092  | −3.165 | 1.00 | 19.11 | C |
| ATOM | 4966 | C   | LEU | A | 331 | −45.568 | −4.710  | −2.159 | 1.00 | 19.98 | C |
| ATOM | 4967 | O   | LEU | A | 331 | −45.753 | −4.324  | −3.300 | 1.00 | 20.15 | O |
| ATOM | 4969 | N   | ALA | A | 332 | −46.431 | −4.495  | −1.172 | 1.00 | 19.09 | N |
| ATOM | 4970 | CA  | ALA | A | 332 | −47.619 | −3.675  | −1.353 | 1.00 | 18.46 | C |

TABLE 16-7-continued

Coordinates of *P. tremuloides* IspS

| | | | | | | | | | | |
|---|---|---|---|---|---|---|---|---|---|---|
| ATOM | 4972 | CB | ALA | A | 332 | −48.406 | −3.587 | −.045 | 1.00 | 18.20 C |
| ATOM | 4976 | C | ALA | A | 332 | −47.248 | −2.279 | −1.856 | 1.00 | 17.91 C |
| ATOM | 4977 | O | ALA | A | 332 | −47.890 | −1.745 | −2.744 | 1.00 | 17.98 O |
| ATOM | 4979 | N | LEU | A | 333 | −46.197 | −1.706 | −1.295 | 1.00 | 17.62 N |
| ATOM | 4980 | CA | LEU | A | 333 | −45.753 | −.353 | −1.637 | 1.00 | 17.60 C |
| ATOM | 4982 | CB | LEU | A | 333 | −44.725 | .132 | −.598 | 1.00 | 17.59 C |
| ATOM | 4985 | CG | LEU | A | 333 | −44.122 | 1.533 | −.761 | 1.00 | 17.16 C |
| ATOM | 4987 | CD1 | LEU | A | 333 | −45.166 | 2.629 | −.554 | 1.00 | 16.99 C |
| ATOM | 4991 | CD2 | LEU | A | 333 | −42.979 | 1.704 | .200 | 1.00 | 15.89 C |
| ATOM | 4995 | C | LEU | A | 333 | −45.100 | −.320 | −3.005 | 1.00 | 17.70 C |
| ATOM | 4996 | O | LEU | A | 333 | −45.321 | .603 | −3.795 | 1.00 | 17.86 O |
| ATOM | 4998 | N | TYR | A | 334 | −44.248 | −1.319 | −3.234 | 1.00 | 17.63 N |
| ATOM | 4999 | CA | TYR | A | 334 | −43.542 | −1.531 | −4.489 | 1.00 | 17.44 C |
| ATOM | 5001 | CB | TYR | A | 334 | −42.893 | −2.908 | −4.444 | 1.00 | 17.50 C |
| ATOM | 5004 | CG | TYR | A | 334 | −41.897 | −3.169 | −5.523 | 1.00 | 18.03 C |
| ATOM | 5005 | CD1 | TYR | A | 334 | −40.698 | −2.473 | −5.569 | 1.00 | 18.83 C |
| ATOM | 5007 | CE1 | TYR | A | 334 | −39.764 | −2.725 | −6.542 | 1.00 | 18.13 C |
| ATOM | 5009 | CZ | TYR | A | 334 | −40.016 | −3.678 | −7.478 | 1.00 | 18.78 C |
| ATOM | 5010 | OH | TYR | A | 334 | −39.096 | −3.929 | −8.439 | 1.00 | 21.71 O |
| ATOM | 5012 | CE2 | TYR | A | 334 | −41.180 | −4.391 | −7.462 | 1.00 | 19.74 C |
| ATOM | 5014 | CD2 | TYR | A | 334 | −42.118 | −4.139 | −6.472 | 1.00 | 19.59 C |
| ATOM | 5016 | C | TYR | A | 334 | −44.500 | −1.497 | −5.649 | 1.00 | 17.43 C |
| ATOM | 5017 | O | TYR | A | 334 | −44.264 | −.803 | −6.636 | 1.00 | 17.64 O |
| ATOM | 5019 | N | ASN | A | 335 | −45.589 | −2.253 | −5.504 | 1.00 | 17.30 N |
| ATOM | 5020 | CA | ASN | A | 335 | −46.574 | −2.448 | −6.553 | 1.00 | 17.23 C |
| ATOM | 5022 | CB | ASN | A | 335 | −47.544 | −3.551 | −6.166 | 1.00 | 17.32 C |
| ATOM | 5025 | CG | ASN | A | 335 | −46.952 | −4.920 | −6.332 | 1.00 | 18.16 C |
| ATOM | 5026 | OD1 | ASN | A | 335 | −45.913 | −5.090 | −6.989 | 1.00 | 18.99 O |
| ATOM | 5027 | ND2 | ASN | A | 335 | −47.616 | −5.921 | −5.749 | 1.00 | 18.49 N |
| ATOM | 5030 | C | ASN | A | 335 | −47.365 | −1.218 | −6.812 | 1.00 | 17.12 C |
| ATOM | 5031 | O | ASN | A | 335 | −47.613 | −.852 | −7.965 | 1.00 | 17.36 O |
| ATOM | 5033 | N | THR | A | 336 | −47.789 | −.602 | −5.722 | 1.00 | 17.20 N |
| ATOM | 5034 | CA | THR | A | 336 | −48.601 | .593 | −5.779 | 1.00 | 17.36 C |
| ATOM | 5036 | CB | THR | A | 336 | −48.888 | 1.104 | −4.381 | 1.00 | 17.20 C |
| ATOM | 5038 | OG1 | THR | A | 336 | −49.611 | .103 | −3.657 | 1.00 | 16.26 O |
| ATOM | 5040 | CG2 | THR | A | 336 | −49.688 | 2.384 | −4.452 | 1.00 | 17.18 C |
| ATOM | 5044 | C | THR | A | 336 | −47.893 | 1.691 | −6.550 | 1.00 | 17.84 C |
| ATOM | 5045 | O | THR | A | 336 | −48.511 | 2.388 | −7.360 | 1.00 | 18.07 O |
| ATOM | 5047 | N | ILE | A | 337 | −46.595 | 1.831 | −6.298 | 1.00 | 18.14 N |
| ATOM | 5048 | CA | ILE | A | 337 | −45.817 | 2.904 | −6.895 | 1.00 | 18.50 C |
| ATOM | 5050 | CB | ILE | A | 337 | −44.584 | 3.209 | −6.066 | 1.00 | 18.31 C |
| ATOM | 5052 | CG1 | ILE | A | 337 | −45.014 | 3.997 | −4.837 | 1.00 | 18.58 C |
| ATOM | 5055 | CD1 | ILE | A | 337 | −44.043 | 3.866 | −3.735 | 1.00 | 20.66 C |
| ATOM | 5059 | CG2 | ILE | A | 337 | −43.570 | 3.988 | −6.867 | 1.00 | 16.98 C |
| ATOM | 5063 | C | ILE | A | 337 | −45.447 | 2.548 | −8.314 | 1.00 | 19.29 C |
| ATOM | 5064 | O | ILE | A | 337 | −45.556 | 3.387 | −9.214 | 1.00 | 19.17 O |
| ATOM | 5066 | N | ASN | A | 338 | −45.033 | 1.299 | −8.513 | 1.00 | 20.16 N |
| ATOM | 5067 | CA | ASN | A | 338 | −44.861 | .767 | −9.864 | 1.00 | 20.93 C |
| ATOM | 5069 | CB | ASN | A | 338 | −44.409 | −.695 | −9.830 | 1.00 | 21.07 C |
| ATOM | 5072 | CG | ASN | A | 338 | −42.953 | −.845 | −9.439 | 1.00 | 21.61 C |
| ATOM | 5073 | OD1 | ASN | A | 338 | −42.232 | .143 | −9.308 | 1.00 | 22.40 O |
| ATOM | 5074 | ND2 | ASN | A | 338 | −42.509 | −2.086 | −9.260 | 1.00 | 21.92 N |
| ATOM | 5077 | C | ASN | A | 338 | −46.123 | .914 | −10.719 | 1.00 | 21.44 C |
| ATOM | 5078 | O | ASN | A | 338 | −46.022 | 1.202 | −11.904 | 1.00 | 21.25 O |
| ATOM | 5080 | N | GLU | A | 339 | −47.303 | .747 | −10.128 | 1.00 | 22.21 N |
| ATOM | 5081 | CA | GLU | A | 339 | −48.532 | 1.000 | −10.880 | 1.00 | 23.31 C |
| ATOM | 5083 | CB | GLU | A | 339 | −49.768 | .464 | −10.164 | 1.00 | 24.13 C |
| ATOM | 5086 | CG | GLU | A | 339 | −50.146 | −.936 | −10.660 | 1.00 | 28.69 C |
| ATOM | 5089 | CD | GLU | A | 339 | −50.939 | −1.740 | −9.638 | 1.00 | 35.06 C |
| ATOM | 5090 | OE1 | GLU | A | 339 | −51.899 | −1.136 | −9.067 | 1.00 | 39.51 O |
| ATOM | 5091 | OE2 | GLU | A | 339 | −50.596 | −2.952 | −9.414 | 1.00 | 36.64 O |
| ATOM | 5092 | C | GLU | A | 339 | −48.725 | 2.463 | −11.269 | 1.00 | 22.71 C |
| ATOM | 5093 | O | GLU | A | 339 | −49.215 | 2.743 | −12.372 | 1.00 | 22.48 O |
| ATOM | 5095 | N | ILE | A | 340 | −48.339 | 3.390 | −10.390 | 1.00 | 22.19 N |
| ATOM | 5096 | CA | ILE | A | 340 | −48.406 | 4.813 | −10.734 | 1.00 | 21.64 C |
| ATOM | 5098 | CB | ILE | A | 340 | −48.135 | 5.739 | −9.538 | 1.00 | 21.33 C |
| ATOM | 5100 | CG1 | ILE | A | 340 | −49.229 | 5.596 | −8.482 | 1.00 | 21.29 C |
| ATOM | 5103 | CD1 | ILE | A | 340 | −48.925 | 6.306 | −7.150 | 1.00 | 20.00 C |
| ATOM | 5107 | CG2 | ILE | A | 340 | −48.091 | 7.177 | −9.982 | 1.00 | 20.28 C |
| ATOM | 5111 | C | ILE | A | 340 | −47.414 | 5.128 | −11.861 | 1.00 | 21.78 C |
| ATOM | 5112 | O | ILE | A | 340 | −47.786 | 5.826 | −12.818 | 1.00 | 22.13 O |
| ATOM | 5114 | N | ALA | A | 341 | −46.179 | 4.609 | −11.771 | 1.00 | 21.34 N |
| ATOM | 5115 | CA | ALA | A | 341 | −45.147 | 4.892 | −12.787 | 1.00 | 21.03 C |
| ATOM | 5117 | CB | ALA | A | 341 | −43.837 | 4.268 | −12.406 | 1.00 | 20.55 C |
| ATOM | 5121 | C | ALA | A | 341 | −45.592 | 4.426 | −14.183 | 1.00 | 21.32 C |
| ATOM | 5122 | O | ALA | A | 341 | −45.228 | 5.036 | −15.217 | 1.00 | 21.11 O |
| ATOM | 5124 | N | TYR | A | 342 | −46.393 | 3.355 | −14.196 | 1.00 | 21.45 N |
| ATOM | 5125 | CA | TYR | A | 342 | −47.008 | 2.861 | −15.414 | 1.00 | 21.41 C |

TABLE 16-7-continued

Coordinates of *P. tremuloides* IspS

| ATOM | 5127 | CB | TYR | A | 342 | −47.627 | 1.468 | −15.208 | 1.00 | 21.31 | C |
|---|---|---|---|---|---|---|---|---|---|---|---|
| ATOM | 5130 | CG | TYR | A | 342 | −48.336 | .957 | −16.450 | 1.00 | 19.60 | C |
| ATOM | 5131 | CD1 | TYR | A | 342 | −47.613 | .463 | −17.521 | 1.00 | 16.69 | C |
| ATOM | 5133 | CE1 | TYR | A | 342 | −48.231 | .032 | −18.643 | 1.00 | 15.50 | C |
| ATOM | 5135 | CZ | TYR | A | 342 | −49.595 | .085 | −18.728 | 1.00 | 15.88 | C |
| ATOM | 5136 | OH | TYR | A | 342 | −50.196 | −.352 | −19.877 | 1.00 | 16.46 | O |
| ATOM | 5138 | CE2 | TYR | A | 342 | −50.352 | .558 | −17.681 | 1.00 | 16.50 | C |
| ATOM | 5140 | CD2 | TYR | A | 342 | −49.725 | .997 | −16.556 | 1.00 | 18.17 | C |
| ATOM | 5142 | C | TYR | A | 342 | −48.064 | 3.830 | −15.899 | 1.00 | 22.08 | C |
| ATOM | 5143 | O | TYR | A | 342 | −48.094 | 4.169 | −17.048 | 1.00 | 22.07 | O |
| ATOM | 5145 | N | ASP | A | 343 | −48.942 | 4.283 | −15.032 | 1.00 | 23.41 | N |
| ATOM | 5146 | CA | ASP | A | 343 | −49.970 | 5.211 | −15.481 | 1.00 | 24.66 | C |
| ATOM | 5148 | CB | ASP | A | 343 | −50.851 | 5.674 | −14.318 | 1.00 | 25.10 | C |
| ATOM | 5151 | CG | ASP | A | 343 | −51.720 | 4.552 | −13.732 | 1.00 | 26.06 | C |
| ATOM | 5152 | OD1 | ASP | A | 343 | −52.107 | 3.613 | −14.477 | 1.00 | 26.39 | O |
| ATOM | 5153 | OD2 | ASP | A | 343 | −52.032 | 4.642 | −12.516 | 1.00 | 27.29 | O |
| ATOM | 5154 | C | ASP | A | 343 | −49.316 | 6.420 | −16.142 | 1.00 | 25.22 | C |
| ATOM | 5155 | O | ASP | A | 343 | −49.755 | 6.874 | −17.192 | 1.00 | 25.47 | O |
| ATOM | 5157 | N | ASN | A | 344 | −48.260 | 6.936 | −15.528 | 1.00 | 25.87 | N |
| ATOM | 5158 | CA | ASN | A | 344 | −47.508 | 8.042 | −16.127 | 1.00 | 26.41 | C |
| ATOM | 5160 | CB | ASN | A | 344 | −46.498 | 8.605 | −15.134 | 1.00 | 26.56 | C |
| ATOM | 5163 | CG | ASN | A | 344 | −47.152 | 9.407 | −14.073 | 1.00 | 26.95 | C |
| ATOM | 5164 | OD1 | ASN | A | 344 | −47.495 | 10.568 | −14.296 | 1.00 | 29.13 | O |
| ATOM | 5165 | ND2 | ASN | A | 344 | −47.367 | 8.799 | −12.916 | 1.00 | 26.36 | N |
| ATOM | 5168 | C | ASN | A | 344 | −46.785 | 7.674 | −17.416 | 1.00 | 26.53 | C |
| ATOM | 5169 | O | ASN | A | 344 | −46.658 | 8.508 | −18.304 | 1.00 | 26.74 | O |
| ATOM | 5171 | N | LEU | A | 345 | −46.280 | 6.448 | −17.510 | 1.00 | 26.56 | N |
| ATOM | 5172 | CA | LEU | A | 345 | −45.634 | 6.019 | −18.739 | 1.00 | 26.37 | C |
| ATOM | 5174 | CB | LEU | A | 345 | −44.890 | 4.693 | −18.550 | 1.00 | 26.32 | C |
| ATOM | 5177 | CG | LEU | A | 345 | −43.995 | 4.339 | −19.750 | 1.00 | 25.96 | C |
| ATOM | 5179 | CD1 | LEU | A | 345 | −42.706 | 5.133 | −19.665 | 1.00 | 25.07 | C |
| ATOM | 5183 | CD2 | LEU | A | 345 | −43.724 | 2.835 | −19.874 | 1.00 | 24.75 | C |
| ATOM | 5187 | C | LEU | A | 345 | −46.679 | 5.908 | −19.856 | 1.00 | 26.38 | C |
| ATOM | 5188 | O | LEU | A | 345 | −46.435 | 6.335 | −20.966 | 1.00 | 26.52 | O |
| ATOM | 5190 | N | LYS | A | 346 | −47.839 | 5.340 | −19.563 | 1.00 | 26.59 | N |
| ATOM | 5191 | CA | LYS | A | 346 | −48.880 | 5.176 | −20.572 | 1.00 | 26.89 | C |
| ATOM | 5193 | CB | LYS | A | 346 | −50.065 | 4.367 | −20.011 | 1.00 | 26.80 | C |
| ATOM | 5196 | CG | LYS | A | 346 | −51.073 | 3.931 | −21.062 | 1.00 | 26.26 | C |
| ATOM | 5199 | CD | LYS | A | 346 | −52.210 | 3.080 | −20.517 | 1.00 | 26.15 | C |
| ATOM | 5202 | CE | LYS | A | 346 | −53.227 | 3.849 | −19.689 | 1.00 | 26.40 | C |
| ATOM | 5205 | NZ | LYS | A | 346 | −53.136 | 3.506 | −18.223 | 1.00 | 27.67 | N |
| ATOM | 5209 | C | LYS | A | 346 | −49.372 | 6.537 | −21.071 | 1.00 | 27.52 | C |
| ATOM | 5210 | O | LYS | A | 346 | −49.562 | 6.742 | −22.272 | 1.00 | 27.57 | O |
| ATOM | 5212 | N | ASP | A | 347 | −49.567 | 7.472 | −20.148 | 1.00 | 28.10 | N |
| ATOM | 5213 | CA | ASP | A | 347 | −50.309 | 8.689 | −20.465 | 1.00 | 28.58 | C |
| ATOM | 5215 | CB | ASP | A | 347 | −51.305 | 9.017 | −19.329 | 1.00 | 28.85 | C |
| ATOM | 5218 | CG | ASP | A | 347 | −52.426 | 7.950 | −19.197 | 1.00 | 30.01 | C |
| ATOM | 5219 | OD1 | ASP | A | 347 | −52.827 | 7.349 | −20.223 | 1.00 | 30.51 | O |
| ATOM | 5220 | OD2 | ASP | A | 347 | −52.910 | 7.704 | −18.069 | 1.00 | 32.61 | O |
| ATOM | 5221 | C | ASP | A | 347 | −49.407 | 9.871 | −20.804 | 1.00 | 28.22 | C |
| ATOM | 5222 | O | ASP | A | 347 | −49.778 | 10.710 | −21.611 | 1.00 | 28.39 | O |
| ATOM | 5224 | N | LYS | A | 348 | −48.228 | 9.930 | −20.206 | 1.00 | 28.03 | N |
| ATOM | 5225 | CA | LYS | A | 348 | −47.301 | 11.021 | −20.467 | 1.00 | 28.01 | C |
| ATOM | 5227 | CB | LYS | A | 348 | −46.785 | 11.648 | −19.164 | 1.00 | 28.39 | C |
| ATOM | 5230 | CG | LYS | A | 348 | −47.834 | 12.305 | −18.257 | 1.00 | 30.18 | C |
| ATOM | 5233 | CD | LYS | A | 348 | −47.143 | 12.898 | −17.003 | 1.00 | 32.40 | C |
| ATOM | 5236 | CE | LYS | A | 348 | −48.124 | 13.121 | −15.874 | 1.00 | 33.59 | C |
| ATOM | 5239 | NZ | LYS | A | 348 | −49.319 | 13.878 | −16.341 | 1.00 | 35.48 | N |
| ATOM | 5243 | C | LYS | A | 348 | −46.107 | 10.551 | −21.260 | 1.00 | 27.25 | C |
| ATOM | 5244 | O | LYS | A | 348 | −45.241 | 11.345 | −21.566 | 1.00 | 27.60 | O |
| ATOM | 5246 | N | GLY | A | 349 | −46.036 | 9.271 | −21.583 | 1.00 | 26.47 | N |
| ATOM | 5247 | CA | GLY | A | 349 | −44.863 | 8.742 | −22.261 | 1.00 | 26.01 | C |
| ATOM | 5250 | C | GLY | A | 349 | −43.559 | 9.109 | −21.587 | 1.00 | 25.67 | C |
| ATOM | 5251 | O | GLY | A | 349 | −42.613 | 9.472 | −22.250 | 1.00 | 25.85 | O |
| ATOM | 5253 | N | GLU | A | 350 | −43.498 | 9.032 | −20.269 | 1.00 | 25.55 | N |
| ATOM | 5254 | CA | GLU | A | 350 | −42.272 | 9.374 | −19.555 | 1.00 | 25.76 | C |
| ATOM | 5256 | CB | GLU | A | 350 | −42.332 | 10.814 | −19.021 | 1.00 | 26.34 | C |
| ATOM | 5259 | CG | GLU | A | 350 | −42.179 | 11.928 | −20.106 | 1.00 | 29.04 | C |
| ATOM | 5262 | CD | GLU | A | 350 | −40.745 | 12.101 | −20.598 | 1.00 | 32.08 | C |
| ATOM | 5263 | OE1 | GLU | A | 350 | −39.853 | 12.170 | −19.716 | 1.00 | 35.46 | O |
| ATOM | 5264 | OE2 | GLU | A | 350 | −40.516 | 12.174 | −21.839 | 1.00 | 31.64 | O |
| ATOM | 5265 | C | GLU | A | 350 | −42.084 | 8.414 | −18.400 | 1.00 | 24.87 | C |
| ATOM | 5266 | O | GLU | A | 350 | −43.067 | 8.046 | −17.760 | 1.00 | 25.16 | O |
| ATOM | 5268 | N | ASN | A | 351 | −40.833 | 8.009 | −18.145 | 1.00 | 23.71 | N |
| ATOM | 5269 | CA | ASN | A | 351 | −40.494 | 7.189 | −16.980 | 1.00 | 22.88 | C |
| ATOM | 5271 | CB | ASN | A | 351 | −39.351 | 6.229 | −17.287 | 1.00 | 22.88 | C |
| ATOM | 5274 | CG | ASN | A | 351 | −39.141 | 5.215 | −16.184 | 1.00 | 22.98 | C |
| ATOM | 5275 | OD1 | ASN | A | 351 | −39.006 | 5.584 | −15.035 | 1.00 | 22.68 | O |

TABLE 16-7-continued

Coordinates of *P. tremuloides* IspS

| ATOM | 5276 | ND2 | ASN | A | 351 | −39.139 | 3.924 | −16.529 | 1.00 | 24.38 | N |
|------|------|-----|-----|---|-----|---------|-------|---------|------|-------|---|
| ATOM | 5279 | C | ASN | A | 351 | −40.126 | 8.058 | −15.786 | 1.00 | 22.40 | C |
| ATOM | 5280 | O | ASN | A | 351 | −39.097 | 8.741 | −15.785 | 1.00 | 22.66 | O |
| ATOM | 5282 | N | ILE | A | 352 | −40.965 | 8.021 | −14.760 | 1.00 | 21.55 | N |
| ATOM | 5283 | CA | ILE | A | 352 | −40.770 | 8.860 | −13.591 | 1.00 | 20.75 | C |
| ATOM | 5285 | CB | ILE | A | 352 | −42.002 | 9.788 | −13.360 | 1.00 | 20.95 | C |
| ATOM | 5287 | CG1 | ILE | A | 352 | −43.263 | 8.970 | −13.022 | 1.00 | 20.82 | C |
| ATOM | 5290 | CD1 | ILE | A | 352 | −44.237 | 9.698 | −12.122 | 1.00 | 20.21 | C |
| ATOM | 5294 | CG2 | ILE | A | 352 | −42.266 | 10.669 | −14.582 | 1.00 | 19.85 | C |
| ATOM | 5298 | C | ILE | A | 352 | −40.516 | 8.016 | −12.339 | 1.00 | 20.37 | C |
| ATOM | 5299 | O | ILE | A | 352 | −40.574 | 8.513 | −11.224 | 1.00 | 20.55 | O |
| ATOM | 5301 | N | LEU | A | 353 | −40.236 | 6.733 | −12.519 | 1.00 | 19.98 | N |
| ATOM | 5302 | CA | LEU | A | 353 | −40.061 | 5.828 | −11.387 | 1.00 | 19.42 | C |
| ATOM | 5304 | CB | LEU | A | 353 | −39.894 | 4.392 | −11.870 | 1.00 | 19.27 | C |
| ATOM | 5307 | CG | LEU | A | 353 | −39.989 | 3.318 | −10.799 | 1.00 | 19.01 | C |
| ATOM | 5309 | CD1 | LEU | A | 353 | −41.164 | 3.574 | −9.867 | 1.00 | 18.35 | C |
| ATOM | 5313 | CD2 | LEU | A | 353 | −40.085 | 1.938 | −11.468 | 1.00 | 18.74 | C |
| ATOM | 5317 | C | LEU | A | 353 | −38.890 | 6.240 | −10.523 | 1.00 | 19.11 | C |
| ATOM | 5318 | O | LEU | A | 353 | −39.022 | 6.319 | −9.314 | 1.00 | 18.96 | O |
| ATOM | 5320 | N | PRO | A | 354 | −37.746 | 6.549 | −11.142 | 1.00 | 19.06 | N |
| ATOM | 5321 | CA | PRO | A | 354 | −36.631 | 7.069 | −10.367 | 1.00 | 19.29 | C |
| ATOM | 5323 | CB | PRO | A | 354 | −35.749 | 7.717 | −11.438 | 1.00 | 19.25 | C |
| ATOM | 5326 | CG | PRO | A | 354 | −35.997 | 6.942 | −12.638 | 1.00 | 19.08 | C |
| ATOM | 5329 | CD | PRO | A | 354 | −37.409 | 6.472 | −12.572 | 1.00 | 19.00 | C |
| ATOM | 5332 | C | PRO | A | 354 | −37.024 | 8.122 | −9.328 | 1.00 | 19.33 | C |
| ATOM | 5333 | O | PRO | A | 354 | −36.534 | 8.057 | −8.193 | 1.00 | 19.73 | O |
| ATOM | 5334 | N | TYR | A | 355 | −37.891 | 9.063 | −9.721 | 1.00 | 18.83 | N |
| ATOM | 5335 | CA | TYR | A | 355 | −38.206 | 10.221 | −8.898 | 1.00 | 18.79 | C |
| ATOM | 5337 | CB | TYR | A | 355 | −38.836 | 11.359 | −9.707 | 1.00 | 19.10 | C |
| ATOM | 5340 | CG | TYR | A | 355 | −38.142 | 11.708 | −11.009 | 1.00 | 20.15 | C |
| ATOM | 5341 | CD1 | TYR | A | 355 | −36.940 | 12.403 | −11.027 | 1.00 | 20.78 | C |
| ATOM | 5343 | CE1 | TYR | A | 355 | −36.321 | 12.719 | −12.232 | 1.00 | 22.19 | C |
| ATOM | 5345 | CZ | TYR | A | 355 | −36.918 | 12.347 | −13.438 | 1.00 | 22.19 | C |
| ATOM | 5346 | OH | TYR | A | 355 | −36.341 | 12.660 | −14.657 | 1.00 | 23.29 | O |
| ATOM | 5348 | CE2 | TYR | A | 355 | −38.113 | 11.677 | −13.430 | 1.00 | 21.62 | C |
| ATOM | 5350 | CD2 | TYR | A | 355 | −38.720 | 11.371 | −12.227 | 1.00 | 21.05 | C |
| ATOM | 5352 | C | TYR | A | 355 | −39.155 | 9.864 | −7.777 | 1.00 | 18.43 | C |
| ATOM | 5353 | O | TYR | A | 355 | −39.081 | 10.460 | −6.709 | 1.00 | 18.61 | O |
| ATOM | 5355 | N | LEU | A | 356 | −40.058 | 8.917 | −8.023 | 1.00 | 17.92 | N |
| ATOM | 5356 | CA | LEU | A | 356 | −40.993 | 8.467 | −6.994 | 1.00 | 17.38 | C |
| ATOM | 5358 | CB | LEU | A | 356 | −42.136 | 7.658 | −7.597 | 1.00 | 17.17 | C |
| ATOM | 5361 | CG | LEU | A | 356 | −42.956 | 8.366 | −8.682 | 1.00 | 17.56 | C |
| ATOM | 5363 | CD1 | LEU | A | 356 | −43.933 | 7.419 | −9.371 | 1.00 | 17.47 | C |
| ATOM | 5367 | CD2 | LEU | A | 356 | −43.698 | 9.548 | −8.112 | 1.00 | 18.08 | C |
| ATOM | 5371 | C | LEU | A | 356 | −40.241 | 7.623 | −5.978 | 1.00 | 17.10 | C |
| ATOM | 5372 | O | LEU | A | 356 | −40.332 | 7.859 | −4.783 | 1.00 | 17.62 | O |
| ATOM | 5374 | N | THR | A | 357 | −39.464 | 6.656 | −6.442 | 1.00 | 16.64 | N |
| ATOM | 5375 | CA | THR | A | 357 | −38.775 | 5.769 | −5.513 | 1.00 | 16.18 | C |
| ATOM | 5377 | CB | THR | A | 357 | −38.104 | 4.554 | −6.213 | 1.00 | 16.04 | C |
| ATOM | 5379 | OG1 | THR | A | 357 | −37.092 | 4.996 | −7.123 | 1.00 | 15.93 | O |
| ATOM | 5381 | CG2 | THR | A | 357 | −39.142 | 3.732 | −6.962 | 1.00 | 14.99 | C |
| ATOM | 5385 | C | THR | A | 357 | −37.764 | 6.544 | −4.686 | 1.00 | 16.16 | C |
| ATOM | 5386 | O | THR | A | 357 | −37.599 | 6.278 | −3.506 | 1.00 | 16.07 | O |
| ATOM | 5388 | N | LYS | A | 358 | −37.107 | 7.524 | −5.291 | 1.00 | 16.20 | N |
| ATOM | 5389 | CA | LYS | A | 358 | −36.186 | 8.365 | −4.543 | 1.00 | 16.46 | C |
| ATOM | 5391 | CB | LYS | A | 358 | −35.518 | 9.386 | −5.453 | 1.00 | 16.80 | C |
| ATOM | 5394 | CG | LYS | A | 358 | −34.612 | 10.388 | −4.741 | 1.00 | 18.30 | C |
| ATOM | 5397 | CD | LYS | A | 358 | −33.352 | 9.738 | −4.168 | 1.00 | 20.21 | C |
| ATOM | 5400 | CE | LYS | A | 358 | −32.335 | 10.811 | −3.768 | 1.00 | 21.96 | C |
| ATOM | 5403 | NZ | LYS | A | 358 | −31.163 | 10.275 | −3.019 | 1.00 | 22.95 | N |
| ATOM | 5407 | C | LYS | A | 358 | −36.936 | 9.083 | −3.440 | 1.00 | 16.26 | C |
| ATOM | 5408 | O | LYS | A | 358 | −36.448 | 9.161 | −2.320 | 1.00 | 16.15 | O |
| ATOM | 5410 | N | ALA | A | 359 | −38.126 | 9.593 | −3.763 | 1.00 | 16.11 | N |
| ATOM | 5411 | CA | ALA | A | 359 | −38.937 | 10.332 | −2.798 | 1.00 | 16.10 | C |
| ATOM | 5413 | CB | ALA | A | 359 | −40.221 | 10.768 | −3.406 | 1.00 | 15.71 | C |
| ATOM | 5417 | C | ALA | A | 359 | −39.215 | 9.476 | −1.588 | 1.00 | 16.52 | C |
| ATOM | 5418 | O | ALA | A | 359 | −39.247 | 9.970 | −.442 | 1.00 | 16.82 | O |
| ATOM | 5420 | N | TRP | A | 360 | −39.398 | 8.187 | −1.843 | 1.00 | 16.79 | N |
| ATOM | 5421 | CA | TRP | A | 360 | −39.704 | 7.247 | −.780 | 1.00 | 17.25 | C |
| ATOM | 5423 | CB | TRP | A | 360 | −40.390 | 6.006 | −1.352 | 1.00 | 17.41 | C |
| ATOM | 5426 | CG | TRP | A | 360 | −41.852 | 6.129 | −1.318 | 1.00 | 17.06 | C |
| ATOM | 5427 | CD1 | TRP | A | 360 | −42.664 | 6.451 | −2.346 | 1.00 | 17.94 | C |
| ATOM | 5429 | NE1 | TRP | A | 360 | −43.967 | 6.489 | −1.926 | 1.00 | 18.03 | N |
| ATOM | 5431 | CE2 | TRP | A | 360 | −44.002 | 6.193 | −.592 | 1.00 | 17.72 | C |
| ATOM | 5432 | CD2 | TRP | A | 360 | −42.684 | 5.965 | −.179 | 1.00 | 16.60 | C |
| ATOM | 5433 | CE3 | TRP | A | 360 | −42.441 | 5.654 | 1.155 | 1.00 | 16.65 | C |
| ATOM | 5435 | CZ3 | TRP | A | 360 | −43.508 | 5.573 | 2.022 | 1.00 | 16.91 | C |
| ATOM | 5437 | CH2 | TRP | A | 360 | −44.811 | 5.807 | 1.586 | 1.00 | 17.82 | C |

TABLE 16-7-continued

Coordinates of *P. tremuloides* IspS

| ATOM | 5439 | CZ2 | TRP | A | 360 | −45.080 | 6.114 | .282 | 1.00 | 18.49 | C |
| ATOM | 5441 | C | TRP | A | 360 | −38.490 | 6.865 | .073 | 1.00 | 17.52 | C |
| ATOM | 5442 | O | TRP | A | 360 | −38.603 | 6.767 | 1.297 | 1.00 | 17.38 | O |
| ATOM | 5444 | N | ALA | A | 361 | −37.344 | 6.651 | −.568 | 1.00 | 17.82 | N |
| ATOM | 5445 | CA | ALA | A | 361 | −36.122 | 6.336 | .157 | 1.00 | 18.11 | C |
| ATOM | 5447 | CB | ALA | A | 361 | −34.982 | 6.050 | −.805 | 1.00 | 17.92 | C |
| ATOM | 5451 | C | ALA | A | 361 | −35.781 | 7.507 | 1.063 | 1.00 | 18.52 | C |
| ATOM | 5452 | O | ALA | A | 361 | −35.434 | 7.327 | 2.229 | 1.00 | 18.48 | O |
| ATOM | 5454 | N | ASP | A | 362 | −35.911 | 8.711 | .521 | 1.00 | 19.16 | N |
| ATOM | 5455 | CA | ASP | A | 362 | −35.627 | 9.925 | 1.276 | 1.00 | 19.90 | C |
| ATOM | 5457 | CB | ASP | A | 362 | −35.797 | 11.167 | .387 | 1.00 | 20.39 | C |
| ATOM | 5460 | CG | ASP | A | 362 | −34.596 | 11.424 | −.530 | 1.00 | 21.84 | C |
| ATOM | 5461 | OD1 | ASP | A | 362 | −33.630 | 10.625 | −.561 | 1.00 | 22.88 | O |
| ATOM | 5462 | OD2 | ASP | A | 362 | −34.630 | 12.453 | −1.231 | 1.00 | 24.83 | O |
| ATOM | 5463 | C | ASP | A | 362 | −36.532 | 10.039 | 2.510 | 1.00 | 19.91 | C |
| ATOM | 5464 | O | ASP | A | 362 | −36.074 | 10.427 | 3.591 | 1.00 | 19.76 | O |
| ATOM | 5466 | N | LEU | A | 363 | −37.813 | 9.707 | 2.346 | 1.00 | 19.95 | N |
| ATOM | 5467 | CA | LEU | A | 363 | −38.747 | 9.688 | 3.478 | 1.00 | 19.85 | C |
| ATOM | 5469 | CB | LEU | A | 363 | −40.175 | 9.415 | 3.006 | 1.00 | 19.70 | C |
| ATOM | 5472 | CG | LEU | A | 363 | −41.219 | 9.293 | 4.123 | 1.00 | 18.58 | C |
| ATOM | 5474 | CD1 | LEU | A | 363 | −41.189 | 10.551 | 4.965 | 1.00 | 18.37 | C |
| ATOM | 5478 | CD2 | LEU | A | 363 | −42.597 | 9.073 | 3.551 | 1.00 | 16.43 | C |
| ATOM | 5482 | C | LEU | A | 363 | −38.368 | 8.613 | 4.488 | 1.00 | 20.24 | C |
| ATOM | 5483 | O | LEU | A | 363 | −38.314 | 8.875 | 5.691 | 1.00 | 20.52 | O |
| ATOM | 5485 | N | CYS | A | 364 | −38.129 | 7.397 | 3.997 | 1.00 | 20.29 | N |
| ATOM | 5486 | CA | CYS | A | 364 | −37.741 | 6.308 | 4.874 | 1.00 | 20.39 | C |
| ATOM | 5488 | CB | CYS | A | 364 | −37.595 | 4.985 | 4.111 | 1.00 | 20.37 | C |
| ATOM | 5491 | SG | CYS | A | 364 | −39.208 | 4.201 | 3.666 | 1.00 | 20.69 | S |
| ATOM | 5493 | C | CYS | A | 364 | −36.467 | 6.683 | 5.646 | 1.00 | 20.59 | C |
| ATOM | 5494 | O | CYS | A | 364 | −36.386 | 6.445 | 6.863 | 1.00 | 20.82 | O |
| ATOM | 5496 | N | ASN | A | 365 | −35.495 | 7.314 | 4.980 | 1.00 | 20.35 | N |
| ATOM | 5497 | CA | ASN | A | 365 | −34.282 | 7.716 | 5.697 | 1.00 | 20.14 | C |
| ATOM | 5499 | CB | ASN | A | 365 | −33.188 | 8.203 | 4.754 | 1.00 | 20.18 | C |
| ATOM | 5502 | CG | ASN | A | 365 | −32.359 | 7.064 | 4.184 | 1.00 | 20.55 | C |
| ATOM | 5503 | OD1 | ASN | A | 365 | −31.706 | 6.316 | 4.925 | 1.00 | 20.40 | O |
| ATOM | 5504 | ND2 | ASN | A | 365 | −32.365 | 6.938 | 2.854 | 1.00 | 21.25 | N |
| ATOM | 5507 | C | ASN | A | 365 | −34.590 | 8.746 | 6.779 | 1.00 | 19.92 | C |
| ATOM | 5508 | O | ASN | A | 365 | −33.997 | 8.685 | 7.857 | 1.00 | 19.94 | O |
| ATOM | 5510 | N | ALA | A | 366 | −35.531 | 9.658 | 6.507 | 1.00 | 19.58 | N |
| ATOM | 5511 | CA | ALA | A | 366 | −36.036 | 10.578 | 7.537 | 1.00 | 19.39 | C |
| ATOM | 5513 | CB | ALA | A | 366 | −37.083 | 11.507 | 6.971 | 1.00 | 18.79 | C |
| ATOM | 5517 | C | ALA | A | 366 | −36.597 | 9.784 | 8.730 | 1.00 | 19.75 | C |
| ATOM | 5518 | O | ALA | A | 366 | −36.215 | 10.049 | 9.891 | 1.00 | 19.53 | O |
| ATOM | 5520 | N | PHE | A | 367 | −37.460 | 8.797 | 8.447 | 1.00 | 19.69 | N |
| ATOM | 5521 | CA | PHE | A | 367 | −37.985 | 7.925 | 9.502 | 1.00 | 20.11 | C |
| ATOM | 5523 | CB | PHE | A | 367 | −38.952 | 6.857 | 8.967 | 1.00 | 20.47 | C |
| ATOM | 5526 | CG | PHE | A | 367 | −40.293 | 7.370 | 8.494 | 1.00 | 21.35 | C |
| ATOM | 5527 | CD1 | PHE | A | 367 | −40.985 | 8.347 | 9.180 | 1.00 | 21.54 | C |
| ATOM | 5529 | CE1 | PHE | A | 367 | −42.224 | 8.775 | 8.732 | 1.00 | 21.47 | C |
| ATOM | 5531 | CZ | PHE | A | 367 | −42.798 | 8.213 | 7.612 | 1.00 | 21.87 | C |
| ATOM | 5533 | CE2 | PHE | A | 367 | −42.135 | 7.230 | 6.924 | 1.00 | 22.60 | C |
| ATOM | 5535 | CD2 | PHE | A | 367 | −40.894 | 6.798 | 7.373 | 1.00 | 22.90 | C |
| ATOM | 5537 | C | PHE | A | 367 | −36.871 | 7.179 | 10.252 | 1.00 | 20.12 | C |
| ATOM | 5538 | O | PHE | A | 367 | −36.940 | 7.009 | 11.476 | 1.00 | 19.88 | O |
| ATOM | 5540 | N | LEU | A | 368 | −35.868 | 6.696 | 9.516 | 1.00 | 20.30 | N |
| ATOM | 5541 | CA | LEU | A | 368 | −34.775 | 5.931 | 10.133 | 1.00 | 20.19 | C |
| ATOM | 5543 | CB | LEU | A | 368 | −33.783 | 5.413 | 9.085 | 1.00 | 20.08 | C |
| ATOM | 5546 | CG | LEU | A | 368 | −32.743 | 4.363 | 9.514 | 1.00 | 19.30 | C |
| ATOM | 5548 | CD1 | LEU | A | 368 | −33.384 | 3.227 | 10.260 | 1.00 | 18.66 | C |
| ATOM | 5552 | CD2 | LEU | A | 368 | −31.968 | 3.807 | 8.319 | 1.00 | 18.16 | C |
| ATOM | 5556 | C | LEU | A | 368 | −34.063 | 6.812 | 11.128 | 1.00 | 20.41 | C |
| ATOM | 5557 | O | LEU | A | 368 | −33.842 | 6.407 | 12.257 | 1.00 | 20.01 | O |
| ATOM | 5559 | N | GLN | A | 369 | −33.751 | 8.036 | 10.711 | 1.00 | 20.89 | N |
| ATOM | 5560 | CA | GLN | A | 369 | −33.037 | 8.970 | 11.564 | 1.00 | 21.49 | C |
| ATOM | 5562 | CB | GLN | A | 369 | −32.782 | 10.280 | 10.832 | 1.00 | 21.58 | C |
| ATOM | 5565 | CG | GLN | A | 369 | −32.071 | 11.359 | 11.677 | 1.00 | 21.20 | C |
| ATOM | 5568 | CD | GLN | A | 369 | −30.639 | 11.006 | 11.976 | 1.00 | 20.04 | C |
| ATOM | 5569 | OE1 | GLN | A | 369 | −30.282 | 10.650 | 13.108 | 1.00 | 19.10 | O |
| ATOM | 5570 | NE2 | GLN | A | 369 | −29.803 | 11.095 | 10.956 | 1.00 | 18.75 | N |
| ATOM | 5573 | C | GLN | A | 369 | −33.763 | 9.265 | 12.870 | 1.00 | 22.21 | C |
| ATOM | 5574 | O | GLN | A | 369 | −33.122 | 9.343 | 13.909 | 1.00 | 22.41 | O |
| ATOM | 5576 | N | GLU | A | 370 | −35.080 | 9.455 | 12.822 | 1.00 | 23.05 | N |
| ATOM | 5577 | CA | GLU | A | 370 | −35.856 | 9.718 | 14.046 | 1.00 | 23.71 | C |
| ATOM | 5579 | CB | GLU | A | 370 | −37.329 | 10.041 | 13.726 | 1.00 | 24.04 | C |
| ATOM | 5582 | CG | GLU | A | 370 | −37.484 | 11.293 | 12.862 | 1.00 | 26.84 | C |
| ATOM | 5585 | CD | GLU | A | 370 | −38.897 | 11.910 | 12.834 | 1.00 | 30.36 | C |
| ATOM | 5586 | OE1 | GLU | A | 370 | −39.886 | 11.161 | 12.586 | 1.00 | 31.90 | O |
| ATOM | 5587 | OE2 | GLU | A | 370 | −38.992 | 13.164 | 13.014 | 1.00 | 31.62 | O |

TABLE 16-7-continued

Coordinates of *P. tremuloides* IspS

| ATOM | 5588 | C | GLU | A | 370 | −35.755 | 8.523 | 14.994 | 1.00 | 23.60 | C |
| ATOM | 5589 | O | GLU | A | 370 | −35.534 | 8.689 | 16.199 | 1.00 | 23.33 | O |
| ATOM | 5591 | N | ALA | A | 371 | −35.904 | 7.322 | 14.435 | 1.00 | 23.72 | N |
| ATOM | 5592 | CA | ALA | A | 371 | −35.771 | 6.091 | 15.201 | 1.00 | 23.91 | C |
| ATOM | 5594 | CB | ALA | A | 371 | −35.991 | 4.868 | 14.312 | 1.00 | 23.76 | C |
| ATOM | 5598 | C | ALA | A | 371 | −34.392 | 6.051 | 15.840 | 1.00 | 24.20 | C |
| ATOM | 5599 | O | ALA | A | 371 | −34.277 | 5.804 | 17.035 | 1.00 | 24.54 | O |
| ATOM | 5601 | N | LYS | A | 372 | −33.355 | 6.333 | 15.049 | 1.00 | 24.38 | N |
| ATOM | 5602 | CA | LYS | A | 372 | −31.979 | 6.273 | 15.530 | 1.00 | 24.39 | C |
| ATOM | 5604 | CB | LYS | A | 372 | −30.970 | 6.466 | 14.393 | 1.00 | 24.43 | C |
| ATOM | 5607 | CG | LYS | A | 372 | −30.623 | 5.164 | 13.645 | 1.00 | 25.20 | C |
| ATOM | 5610 | CD | LYS | A | 372 | −29.188 | 5.149 | 13.069 | 1.00 | 26.09 | C |
| ATOM | 5613 | CE | LYS | A | 372 | −29.114 | 5.437 | 11.557 | 1.00 | 27.01 | C |
| ATOM | 5616 | NZ | LYS | A | 372 | −29.002 | 4.200 | 10.709 | 1.00 | 26.82 | N |
| ATOM | 5620 | C | LYS | A | 372 | −31.717 | 7.268 | 16.645 | 1.00 | 24.59 | C |
| ATOM | 5621 | O | LYS | A | 372 | −31.096 | 6.908 | 17.627 | 1.00 | 25.13 | O |
| ATOM | 5623 | N | TRP | A | 373 | −32.181 | 8.507 | 16.520 | 1.00 | 24.78 | N |
| ATOM | 5624 | CA | TRP | A | 373 | −32.006 | 9.473 | 17.610 | 1.00 | 24.90 | C |
| ATOM | 5626 | CB | TRP | A | 373 | −32.565 | 10.863 | 17.266 | 1.00 | 24.75 | C |
| ATOM | 5629 | CG | TRP | A | 373 | −31.701 | 11.677 | 16.338 | 1.00 | 23.59 | C |
| ATOM | 5630 | CD1 | TRP | A | 373 | −30.344 | 11.663 | 16.259 | 1.00 | 22.38 | C |
| ATOM | 5632 | NE1 | TRP | A | 373 | −29.915 | 12.539 | 15.298 | 1.00 | 21.59 | N |
| ATOM | 5634 | CE2 | TRP | A | 373 | −30.999 | 13.162 | 14.744 | 1.00 | 21.69 | C |
| ATOM | 5635 | CD2 | TRP | A | 373 | −32.147 | 12.644 | 15.376 | 1.00 | 22.41 | C |
| ATOM | 5636 | CE3 | TRP | A | 373 | −33.409 | 13.110 | 14.976 | 1.00 | 21.98 | C |
| ATOM | 5638 | CZ3 | TRP | A | 373 | −33.480 | 14.072 | 13.979 | 1.00 | 22.08 | C |
| ATOM | 5640 | CH2 | TRP | A | 373 | −32.313 | 14.567 | 13.366 | 1.00 | 22.31 | C |
| ATOM | 5642 | CZ2 | TRP | A | 373 | −31.067 | 14.124 | 13.736 | 1.00 | 21.87 | C |
| ATOM | 5644 | C | TRP | A | 373 | −32.678 | 8.970 | 18.881 | 1.00 | 25.53 | C |
| ATOM | 5645 | O | TRP | A | 373 | −32.101 | 9.072 | 19.972 | 1.00 | 25.99 | O |
| ATOM | 5647 | N | LEU | A | 374 | −33.881 | 8.420 | 18.739 | 1.00 | 25.84 | N |
| ATOM | 5648 | CA | LEU | A | 374 | −34.667 | 7.980 | 19.893 | 1.00 | 26.29 | C |
| ATOM | 5650 | CB | LEU | A | 374 | −36.070 | 7.562 | 19.443 | 1.00 | 26.32 | C |
| ATOM | 5653 | CG | LEU | A | 374 | −37.227 | 7.646 | 20.444 | 1.00 | 26.39 | C |
| ATOM | 5655 | CD1 | LEU | A | 374 | −38.456 | 8.286 | 19.761 | 1.00 | 26.95 | C |
| ATOM | 5659 | CD2 | LEU | A | 374 | −37.583 | 6.281 | 21.050 | 1.00 | 26.24 | C |
| ATOM | 5663 | C | LEU | A | 374 | −33.982 | 6.824 | 20.623 | 1.00 | 26.77 | C |
| ATOM | 5664 | O | LEU | A | 374 | −33.995 | 6.758 | 21.860 | 1.00 | 26.95 | O |
| ATOM | 5666 | N | TYR | A | 375 | −33.383 | 5.919 | 19.854 | 1.00 | 27.23 | N |
| ATOM | 5667 | CA | TYR | A | 375 | −32.706 | 4.761 | 20.425 | 1.00 | 27.74 | C |
| ATOM | 5669 | CB | TYR | A | 375 | −32.195 | 3.814 | 19.328 | 1.00 | 27.78 | C |
| ATOM | 5672 | CG | TYR | A | 375 | −31.526 | 2.556 | 19.848 | 1.00 | 28.74 | C |
| ATOM | 5673 | CD1 | TYR | A | 375 | −32.264 | 1.394 | 20.090 | 1.00 | 29.61 | C |
| ATOM | 5675 | CE1 | TYR | A | 375 | −31.652 | .232 | 20.573 | 1.00 | 29.89 | C |
| ATOM | 5677 | CZ | TYR | A | 375 | −30.287 | .226 | 20.817 | 1.00 | 30.15 | C |
| ATOM | 5678 | OH | TYR | A | 375 | −29.676 | −.917 | 21.286 | 1.00 | 30.57 | O |
| ATOM | 5680 | CE2 | TYR | A | 375 | −29.530 | 1.367 | 20.579 | 1.00 | 30.05 | C |
| ATOM | 5682 | CD2 | TYR | A | 375 | −30.152 | 2.522 | 20.096 | 1.00 | 29.74 | C |
| ATOM | 5684 | C | TYR | A | 375 | −31.553 | 5.248 | 21.275 | 1.00 | 27.97 | C |
| ATOM | 5685 | O | TYR | A | 375 | −31.404 | 4.837 | 22.422 | 1.00 | 28.00 | O |
| ATOM | 5687 | N | ASN | A | 376 | −30.763 | 6.158 | 20.719 | 1.00 | 28.32 | N |
| ATOM | 5688 | CA | ASN | A | 376 | −29.531 | 6.590 | 21.368 | 1.00 | 28.71 | C |
| ATOM | 5690 | CB | ASN | A | 376 | −28.569 | 7.161 | 20.329 | 1.00 | 28.60 | C |
| ATOM | 5693 | CG | ASN | A | 376 | −28.215 | 6.159 | 19.255 | 1.00 | 28.32 | C |
| ATOM | 5694 | OD1 | ASN | A | 376 | −27.961 | 4.977 | 19.527 | 1.00 | 25.72 | O |
| ATOM | 5695 | ND2 | ASN | A | 376 | −28.195 | 6.631 | 18.015 | 1.00 | 29.29 | N |
| ATOM | 5698 | C | ASN | A | 376 | −29.728 | 7.617 | 22.484 | 1.00 | 29.05 | C |
| ATOM | 5699 | O | ASN | A | 376 | −28.752 | 8.021 | 23.136 | 1.00 | 29.03 | O |
| ATOM | 5701 | N | LYS | A | 377 | −30.977 | 8.021 | 22.716 | 1.00 | 29.16 | N |
| ATOM | 5702 | CA | LYS | A | 377 | −31.254 | 9.178 | 23.549 | 1.00 | 29.27 | C |
| ATOM | 5704 | CB | LYS | A | 377 | −31.051 | 8.879 | 25.050 | 1.00 | 29.52 | C |
| ATOM | 5707 | CG | LYS | A | 377 | −32.202 | 8.112 | 25.723 | 1.00 | 30.36 | C |
| ATOM | 5710 | CD | LYS | A | 377 | −32.202 | 6.638 | 25.340 | 1.00 | 31.54 | C |
| ATOM | 5713 | CE | LYS | A | 377 | −33.322 | 5.862 | 26.031 | 1.00 | 32.30 | C |
| ATOM | 5716 | NZ | LYS | A | 377 | −33.559 | 4.509 | 25.411 | 1.00 | 32.13 | N |
| ATOM | 5720 | C | LYS | A | 377 | −30.337 | 10.299 | 23.080 | 1.00 | 28.92 | C |
| ATOM | 5721 | O | LYS | A | 377 | −29.590 | 10.867 | 23.875 | 1.00 | 28.94 | O |
| ATOM | 5723 | N | SER | A | 378 | −30.377 | 10.575 | 21.776 | 1.00 | 28.52 | N |
| ATOM | 5724 | CA | SER | A | 378 | −29.652 | 11.700 | 21.201 | 1.00 | 28.30 | C |
| ATOM | 5726 | CB | SER | A | 378 | −29.623 | 11.620 | 19.678 | 1.00 | 28.33 | C |
| ATOM | 5729 | OG | SER | A | 378 | −28.919 | 10.482 | 19.237 | 1.00 | 29.36 | O |
| ATOM | 5731 | C | SER | A | 378 | −30.355 | 12.977 | 21.594 | 1.00 | 27.97 | C |
| ATOM | 5732 | O | SER | A | 378 | −31.483 | 12.947 | 22.108 | 1.00 | 27.91 | O |
| ATOM | 5734 | N | THR | A | 379 | −29.684 | 14.098 | 21.344 | 1.00 | 27.60 | N |
| ATOM | 5735 | CA | THR | A | 379 | −30.257 | 15.422 | 21.581 | 1.00 | 27.24 | C |
| ATOM | 5737 | CB | THR | A | 379 | −29.929 | 15.950 | 23.002 | 1.00 | 27.23 | C |
| ATOM | 5739 | OG1 | THR | A | 379 | −28.512 | 16.102 | 23.158 | 1.00 | 26.85 | O |
| ATOM | 5741 | CG2 | THR | A | 379 | −30.467 | 15.007 | 24.067 | 1.00 | 27.48 | C |

TABLE 16-7-continued

Coordinates of *P. tremuloides* IspS

| ATOM | 5745 | C | THR | A | 379 | −29.738 | 16.414 | 20.548 | 1.00 | 26.83 | C |
| --- | --- | --- | --- | --- | --- | --- | --- | --- | --- | --- | --- |
| ATOM | 5746 | O | THR | A | 379 | −28.834 | 17.190 | 20.844 | 1.00 | 26.69 | O |
| ATOM | 5748 | N | PRO | A | 380 | −30.305 | 16.390 | 19.331 | 1.00 | 26.56 | N |
| ATOM | 5749 | CA | PRO | A | 380 | −29.884 | 17.315 | 18.278 | 1.00 | 26.52 | C |
| ATOM | 5751 | CB | PRO | A | 380 | −30.380 | 16.648 | 16.992 | 1.00 | 26.46 | C |
| ATOM | 5754 | CG | PRO | A | 380 | −31.281 | 15.533 | 17.408 | 1.00 | 26.41 | C |
| ATOM | 5757 | CD | PRO | A | 380 | −31.395 | 15.508 | 18.887 | 1.00 | 26.53 | C |
| ATOM | 5760 | C | PRO | A | 380 | −30.469 | 18.728 | 18.386 | 1.00 | 26.55 | C |
| ATOM | 5761 | O | PRO | A | 380 | −31.472 | 18.966 | 19.063 | 1.00 | 26.69 | O |
| ATOM | 5762 | N | THR | A | 381 | −29.840 | 19.661 | 17.692 | 1.00 | 26.51 | N |
| ATOM | 5763 | CA | THR | A | 381 | −30.299 | 21.034 | 17.699 | 1.00 | 26.51 | C |
| ATOM | 5765 | CB | THR | A | 381 | −29.261 | 21.955 | 17.033 | 1.00 | 26.99 | C |
| ATOM | 5767 | OG1 | THR | A | 381 | −28.919 | 21.431 | 15.732 | 1.00 | 27.65 | O |
| ATOM | 5769 | CG2 | THR | A | 381 | −28.003 | 22.082 | 17.930 | 1.00 | 26.41 | C |
| ATOM | 5773 | C | THR | A | 381 | −31.635 | 21.167 | 16.970 | 1.00 | 26.06 | C |
| ATOM | 5774 | O | THR | A | 381 | −31.972 | 20.347 | 16.112 | 1.00 | 26.03 | O |
| ATOM | 5776 | N | PHE | A | 382 | −32.386 | 22.218 | 17.294 | 1.00 | 25.52 | N |
| ATOM | 5777 | CA | PHE | A | 382 | −33.681 | 22.436 | 16.654 | 1.00 | 24.83 | C |
| ATOM | 5779 | CB | PHE | A | 382 | −34.284 | 23.793 | 17.011 | 1.00 | 24.53 | C |
| ATOM | 5782 | CG | PHE | A | 382 | −35.495 | 24.113 | 16.211 | 1.00 | 23.77 | C |
| ATOM | 5783 | CD1 | PHE | A | 382 | −36.745 | 23.715 | 16.637 | 1.00 | 24.50 | C |
| ATOM | 5785 | CE1 | PHE | A | 382 | −37.873 | 23.977 | 15.878 | 1.00 | 24.49 | C |
| ATOM | 5787 | CZ | PHE | A | 382 | −37.744 | 24.630 | 14.673 | 1.00 | 24.41 | C |
| ATOM | 5789 | CE2 | PHE | A | 382 | −36.490 | 25.014 | 14.235 | 1.00 | 23.88 | C |
| ATOM | 5791 | CD2 | PHE | A | 382 | −35.381 | 24.752 | 14.999 | 1.00 | 23.29 | C |
| ATOM | 5793 | C | PHE | A | 382 | −33.542 | 22.342 | 15.150 | 1.00 | 24.49 | C |
| ATOM | 5794 | O | PHE | A | 382 | −34.361 | 21.731 | 14.485 | 1.00 | 24.32 | O |
| ATOM | 5796 | N | ASP | A | 383 | −32.498 | 22.969 | 14.627 | 1.00 | 24.42 | N |
| ATOM | 5797 | CA | ASP | A | 383 | −32.257 | 23.005 | 13.190 | 1.00 | 24.19 | C |
| ATOM | 5799 | CB | ASP | A | 383 | −31.101 | 23.966 | 12.867 | 1.00 | 24.21 | C |
| ATOM | 5802 | CG | ASP | A | 383 | −31.473 | 25.423 | 13.050 | 1.00 | 23.72 | C |
| ATOM | 5803 | OD1 | ASP | A | 383 | −32.634 | 25.794 | 12.837 | 1.00 | 25.60 | O |
| ATOM | 5804 | OD2 | ASP | A | 383 | −30.594 | 26.220 | 13.383 | 1.00 | 24.03 | O |
| ATOM | 5805 | C | ASP | A | 383 | −31.982 | 21.612 | 12.599 | 1.00 | 24.06 | C |
| ATOM | 5806 | O | ASP | A | 383 | −32.393 | 21.342 | 11.473 | 1.00 | 24.00 | O |
| ATOM | 5808 | N | ASP | A | 384 | −31.298 | 20.739 | 13.336 | 1.00 | 23.78 | N |
| ATOM | 5809 | CA | ASP | A | 384 | −31.078 | 19.379 | 12.848 | 1.00 | 24.11 | C |
| ATOM | 5811 | CB | ASP | A | 384 | −29.981 | 18.651 | 13.632 | 1.00 | 24.54 | C |
| ATOM | 5814 | CG | ASP | A | 384 | −28.573 | 19.009 | 13.159 | 1.00 | 26.32 | C |
| ATOM | 5815 | OD1 | ASP | A | 384 | −28.441 | 19.852 | 12.232 | 1.00 | 28.55 | O |
| ATOM | 5816 | OD2 | ASP | A | 384 | −27.599 | 18.451 | 13.728 | 1.00 | 27.18 | O |
| ATOM | 5817 | C | ASP | A | 384 | −32.351 | 18.550 | 12.905 | 1.00 | 23.83 | C |
| ATOM | 5818 | O | ASP | A | 384 | −32.670 | 17.825 | 11.955 | 1.00 | 24.24 | O |
| ATOM | 5820 | N | TYR | A | 385 | −33.070 | 18.637 | 14.017 | 1.00 | 23.31 | N |
| ATOM | 5821 | CA | TYR | A | 385 | −34.294 | 17.861 | 14.179 | 1.00 | 22.89 | C |
| ATOM | 5823 | CB | TYR | A | 385 | −34.833 | 17.979 | 15.608 | 1.00 | 22.86 | C |
| ATOM | 5826 | CG | TYR | A | 385 | −36.144 | 17.245 | 15.807 | 1.00 | 22.65 | C |
| ATOM | 5827 | CD1 | TYR | A | 385 | −36.163 | 15.868 | 16.030 | 1.00 | 22.36 | C |
| ATOM | 5829 | CE1 | TYR | A | 385 | −37.351 | 15.189 | 16.206 | 1.00 | 22.77 | C |
| ATOM | 5831 | CZ | TYR | A | 385 | −38.545 | 15.887 | 16.146 | 1.00 | 23.54 | C |
| ATOM | 5832 | OH | TYR | A | 385 | −39.733 | 15.212 | 16.309 | 1.00 | 24.38 | O |
| ATOM | 5834 | CE2 | TYR | A | 385 | −38.554 | 17.258 | 15.913 | 1.00 | 22.76 | C |
| ATOM | 5836 | CD2 | TYR | A | 385 | −37.360 | 17.923 | 15.744 | 1.00 | 22.12 | C |
| ATOM | 5838 | C | TYR | A | 385 | −35.375 | 18.299 | 13.190 | 1.00 | 22.55 | C |
| ATOM | 5839 | O | TYR | A | 385 | −36.050 | 17.467 | 12.584 | 1.00 | 22.85 | O |
| ATOM | 5841 | N | PHE | A | 386 | −35.537 | 19.609 | 13.042 | 1.00 | 22.08 | N |
| ATOM | 5842 | CA | PHE | A | 386 | −36.626 | 20.155 | 12.248 | 1.00 | 21.62 | C |
| ATOM | 5844 | CB | PHE | A | 386 | −36.857 | 21.628 | 12.568 | 1.00 | 21.73 | C |
| ATOM | 5847 | CG | PHE | A | 386 | −38.033 | 22.209 | 11.851 | 1.00 | 21.54 | C |
| ATOM | 5848 | CD1 | PHE | A | 386 | −39.311 | 21.933 | 12.273 | 1.00 | 21.29 | C |
| ATOM | 5850 | CE1 | PHE | A | 386 | −40.380 | 22.444 | 11.623 | 1.00 | 22.11 | C |
| ATOM | 5852 | CZ | PHE | A | 386 | −40.193 | 23.240 | 10.517 | 1.00 | 23.28 | C |
| ATOM | 5854 | CE2 | PHE | A | 386 | −38.920 | 23.502 | 10.069 | 1.00 | 23.10 | C |
| ATOM | 5856 | CD2 | PHE | A | 386 | −37.853 | 22.989 | 10.737 | 1.00 | 22.15 | C |
| ATOM | 5858 | C | PHE | A | 386 | −36.369 | 19.987 | 10.769 | 1.00 | 21.09 | C |
| ATOM | 5859 | O | PHE | A | 386 | −37.278 | 19.700 | 10.006 | 1.00 | 20.91 | O |
| ATOM | 5861 | N | GLY | A | 387 | −35.127 | 20.177 | 10.362 | 1.00 | 20.68 | N |
| ATOM | 5862 | CA | GLY | A | 387 | −34.747 | 19.917 | 8.985 | 1.00 | 20.43 | C |
| ATOM | 5865 | C | GLY | A | 387 | −35.151 | 18.521 | 8.544 | 1.00 | 19.95 | C |
| ATOM | 5866 | O | GLY | A | 387 | −35.553 | 18.327 | 7.398 | 1.00 | 20.24 | O |
| ATOM | 5868 | N | ASN | A | 388 | −35.032 | 17.554 | 9.451 | 1.00 | 19.12 | N |
| ATOM | 5869 | CA | ASN | A | 388 | −35.451 | 16.182 | 9.202 | 1.00 | 18.73 | C |
| ATOM | 5871 | CB | ASN | A | 388 | −34.744 | 15.272 | 10.205 | 1.00 | 18.90 | C |
| ATOM | 5874 | CG | ASN | A | 388 | −34.863 | 13.795 | 9.871 | 1.00 | 18.35 | C |
| ATOM | 5875 | OD1 | ASN | A | 388 | −34.163 | 13.284 | 8.993 | 1.00 | 17.24 | O |
| ATOM | 5876 | ND2 | ASN | A | 388 | −35.714 | 13.092 | 10.614 | 1.00 | 17.01 | N |
| ATOM | 5879 | C | ASN | A | 388 | −36.968 | 16.033 | 9.350 | 1.00 | 18.65 | C |
| ATOM | 5880 | O | ASN | A | 388 | −37.624 | 15.370 | 8.551 | 1.00 | 18.82 | O |

TABLE 16-7-continued

Coordinates of *P. tremuloides* IspS

| ATOM | 5882 | N | ALA | A | 389 | −37.527 | 16.670 | 10.371 | 1.00 | 18.38 | N |
|---|---|---|---|---|---|---|---|---|---|---|---|
| ATOM | 5883 | CA | ALA | A | 389 | −38.926 | 16.477 | 10.728 | 1.00 | 18.02 | C |
| ATOM | 5885 | CB | ALA | A | 389 | −39.203 | 17.107 | 12.084 | 1.00 | 17.83 | C |
| ATOM | 5889 | C | ALA | A | 389 | −39.949 | 16.966 | 9.700 | 1.00 | 17.90 | C |
| ATOM | 5890 | O | ALA | A | 389 | −41.095 | 16.544 | 9.760 | 1.00 | 17.74 | O |
| ATOM | 5892 | N | TRP | A | 390 | −39.585 | 17.860 | 8.783 | 1.00 | 18.11 | N |
| ATOM | 5893 | CA | TRP | A | 390 | −40.543 | 18.254 | 7.731 | 1.00 | 18.46 | C |
| ATOM | 5895 | CB | TRP | A | 390 | −40.459 | 19.737 | 7.329 | 1.00 | 18.59 | C |
| ATOM | 5898 | CG | TRP | A | 390 | −39.143 | 20.224 | 6.821 | 1.00 | 19.26 | C |
| ATOM | 5899 | CD1 | TRP | A | 390 | −38.224 | 20.947 | 7.519 | 1.00 | 20.64 | C |
| ATOM | 5901 | NE1 | TRP | A | 390 | −37.138 | 21.224 | 6.729 | 1.00 | 20.62 | N |
| ATOM | 5903 | CE2 | TRP | A | 390 | −37.352 | 20.694 | 5.485 | 1.00 | 19.57 | C |
| ATOM | 5904 | CD2 | TRP | A | 390 | −38.607 | 20.066 | 5.504 | 1.00 | 19.15 | C |
| ATOM | 5905 | CE3 | TRP | A | 390 | −39.060 | 19.448 | 4.344 | 1.00 | 20.13 | C |
| ATOM | 5907 | CZ3 | TRP | A | 390 | −38.254 | 19.477 | 3.224 | 1.00 | 20.27 | C |
| ATOM | 5909 | CH2 | TRP | A | 390 | −37.017 | 20.110 | 3.239 | 1.00 | 19.38 | C |
| ATOM | 5911 | CZ2 | TRP | A | 390 | −36.549 | 20.724 | 4.356 | 1.00 | 19.49 | C |
| ATOM | 5913 | C | TRP | A | 390 | −40.407 | 17.343 | 6.527 | 1.00 | 18.73 | C |
| ATOM | 5914 | O | TRP | A | 390 | −41.369 | 17.143 | 5.788 | 1.00 | 18.32 | O |
| ATOM | 5916 | N | LYS | A | 391 | −39.200 | 16.806 | 6.336 | 1.00 | 19.30 | N |
| ATOM | 5917 | CA | LYS | A | 391 | −38.969 | 15.692 | 5.404 | 1.00 | 19.70 | C |
| ATOM | 5919 | CB | LYS | A | 391 | −37.459 | 15.392 | 5.244 | 1.00 | 19.92 | C |
| ATOM | 5922 | CG | LYS | A | 391 | −36.812 | 15.953 | 3.935 | 1.00 | 22.08 | C |
| ATOM | 5925 | CD | LYS | A | 391 | −35.257 | 16.217 | 4.040 | 1.00 | 23.92 | C |
| ATOM | 5928 | CE | LYS | A | 391 | −34.918 | 17.698 | 4.426 | 1.00 | 24.43 | C |
| ATOM | 5931 | NZ | LYS | A | 391 | −33.699 | 17.901 | 5.307 | 1.00 | 23.23 | N |
| ATOM | 5935 | C | LYS | A | 391 | −39.731 | 14.441 | 5.861 | 1.00 | 19.46 | C |
| ATOM | 5936 | O | LYS | A | 391 | −40.284 | 13.709 | 5.032 | 1.00 | 20.07 | O |
| ATOM | 5938 | N | SER | A | 392 | −39.793 | 14.202 | 7.170 | 1.00 | 18.95 | N |
| ATOM | 5939 | CA | SER | A | 392 | −40.455 | 12.998 | 7.666 | 1.00 | 18.63 | C |
| ATOM | 5941 | CB | SER | A | 392 | −39.850 | 12.508 | 9.000 | 1.00 | 18.75 | C |
| ATOM | 5944 | OG | SER | A | 392 | −40.314 | 13.230 | 10.126 | 1.00 | 18.94 | O |
| ATOM | 5946 | C | SER | A | 392 | −41.964 | 13.152 | 7.771 | 1.00 | 18.20 | C |
| ATOM | 5947 | O | SER | A | 392 | −42.654 | 12.182 | 8.031 | 1.00 | 18.12 | O |
| ATOM | 5949 | N | SER | A | 393 | −42.477 | 14.360 | 7.567 | 1.00 | 18.07 | N |
| ATOM | 5950 | CA | SER | A | 393 | −43.929 | 14.591 | 7.556 | 1.00 | 18.02 | C |
| ATOM | 5952 | CB | SER | A | 393 | −44.229 | 16.078 | 7.504 | 1.00 | 18.08 | C |
| ATOM | 5955 | OG | SER | A | 393 | −43.995 | 16.558 | 6.192 | 1.00 | 18.01 | O |
| ATOM | 5957 | C | SER | A | 393 | −44.594 | 13.971 | 6.340 | 1.00 | 17.87 | C |
| ATOM | 5958 | O | SER | A | 393 | −45.778 | 13.661 | 6.372 | 1.00 | 18.03 | O |
| ATOM | 5960 | N | SER | A | 394 | −43.823 | 13.841 | 5.264 | 1.00 | 17.69 | N |
| ATOM | 5961 | CA | SER | A | 394 | −44.284 | 13.306 | 3.989 | 1.00 | 17.59 | C |
| ATOM | 5963 | CB | SER | A | 394 | −45.329 | 12.180 | 4.149 | 1.00 | 17.61 | C |
| ATOM | 5966 | OG | SER | A | 394 | −46.648 | 12.681 | 4.294 | 1.00 | 17.18 | O |
| ATOM | 5968 | C | SER | A | 394 | −44.828 | 14.415 | 3.115 | 1.00 | 17.42 | C |
| ATOM | 5969 | O | SER | A | 394 | −45.345 | 14.146 | 2.024 | 1.00 | 17.31 | O |
| ATOM | 5971 | N | GLY | A | 395 | −44.711 | 15.654 | 3.592 | 1.00 | 17.23 | N |
| ATOM | 5972 | CA | GLY | A | 395 | −45.088 | 16.827 | 2.807 | 1.00 | 17.26 | C |
| ATOM | 5975 | C | GLY | A | 395 | −44.478 | 16.749 | 1.415 | 1.00 | 17.29 | C |
| ATOM | 5976 | O | GLY | A | 395 | −45.203 | 16.653 | .413 | 1.00 | 18.06 | O |
| ATOM | 5978 | N | PRO | A | 396 | −43.145 | 16.754 | 1.331 | 1.00 | 16.72 | N |
| ATOM | 5979 | CA | PRO | A | 396 | −42.582 | 16.610 | .006 | 1.00 | 16.40 | C |
| ATOM | 5981 | CB | PRO | A | 396 | −41.080 | 16.549 | .259 | 1.00 | 16.62 | C |
| ATOM | 5984 | CG | PRO | A | 396 | −40.903 | 16.749 | 1.775 | 1.00 | 17.11 | C |
| ATOM | 5987 | CD | PRO | A | 396 | −42.157 | 17.252 | 2.296 | 1.00 | 16.87 | C |
| ATOM | 5990 | C | PRO | A | 396 | −43.053 | 15.374 | −.748 | 1.00 | 15.89 | C |
| ATOM | 5991 | O | PRO | A | 396 | −43.501 | 15.498 | −1.894 | 1.00 | 15.90 | O |
| ATOM | 5992 | N | LEU | A | 397 | −42.973 | 14.197 | −.135 | 1.00 | 15.27 | N |
| ATOM | 5993 | CA | LEU | A | 397 | −43.287 | 12.976 | −.886 | 1.00 | 14.57 | C |
| ATOM | 5995 | CB | LEU | A | 397 | −43.332 | 11.733 | −.008 | 1.00 | 14.36 | C |
| ATOM | 5998 | CG | LEU | A | 397 | −43.541 | 10.431 | −.781 | 1.00 | 14.02 | C |
| ATOM | 6000 | CD1 | LEU | A | 397 | −42.690 | 9.348 | −.206 | 1.00 | 15.04 | C |
| ATOM | 6004 | CD2 | LEU | A | 397 | −44.985 | 9.976 | −.805 | 1.00 | 13.75 | C |
| ATOM | 6008 | C | LEU | A | 397 | −44.618 | 13.182 | −1.542 | 1.00 | 14.39 | C |
| ATOM | 6009 | O | LEU | A | 397 | −44.736 | 12.999 | −2.745 | 1.00 | 14.57 | O |
| ATOM | 6011 | N | GLN | A | 398 | −45.604 | 13.607 | −.751 | 1.00 | 14.08 | N |
| ATOM | 6012 | CA | GLN | A | 398 | −46.962 | 13.828 | −1.245 | 1.00 | 13.91 | C |
| ATOM | 6014 | CB | GLN | A | 398 | −47.860 | 14.363 | −.136 | 1.00 | 13.99 | C |
| ATOM | 6017 | CG | GLN | A | 398 | −48.274 | 13.321 | .909 | 1.00 | 14.01 | C |
| ATOM | 6020 | CD | GLN | A | 398 | −49.189 | 13.902 | 1.983 | 1.00 | 13.41 | C |
| ATOM | 6021 | OE1 | GLN | A | 398 | −49.941 | 14.847 | 1.740 | 1.00 | 14.65 | O |
| ATOM | 6022 | NE2 | GLN | A | 398 | −49.122 | 13.344 | 3.168 | 1.00 | 12.17 | N |
| ATOM | 6025 | C | GLN | A | 398 | −47.015 | 14.800 | −2.403 | 1.00 | 13.84 | C |
| ATOM | 6026 | O | GLN | A | 398 | −47.677 | 14.547 | −3.396 | 1.00 | 13.46 | O |
| ATOM | 6028 | N | LEU | A | 399 | −46.319 | 15.922 | −2.272 | 1.00 | 14.11 | N |
| ATOM | 6029 | CA | LEU | A | 399 | −46.359 | 16.942 | −3.315 | 1.00 | 14.37 | C |
| ATOM | 6031 | CB | LEU | A | 399 | −45.900 | 18.282 | −2.756 | 1.00 | 14.26 | C |
| ATOM | 6034 | CG | LEU | A | 399 | −46.882 | 18.830 | −1.704 | 1.00 | 14.44 | C |

TABLE 16-7-continued

Coordinates of *P. tremuloides* IspS

| | | | | | | | | | |
|---|---|---|---|---|---|---|---|---|---|
| ATOM | 6036 | CD1 | LEU | A | 399 | −46.250 | 19.960 | −.919 | 1.00 | 16.43 C |
| ATOM | 6040 | CD2 | LEU | A | 399 | −48.191 | 19.304 | −2.317 | 1.00 | 12.20 C |
| ATOM | 6044 | C | LEU | A | 399 | −45.582 | 16.525 | −4.578 | 1.00 | 14.68 C |
| ATOM | 6045 | O | LEU | A | 399 | −46.043 | 16.784 | −5.687 | 1.00 | 14.70 O |
| ATOM | 6047 | N | ILE | A | 400 | −44.443 | 15.844 | −4.419 | 1.00 | 14.92 N |
| ATOM | 6048 | CA | ILE | A | 400 | −43.748 | 15.221 | −5.564 | 1.00 | 15.08 C |
| ATOM | 6050 | CB | ILE | A | 400 | −42.549 | 14.355 | −5.129 | 1.00 | 15.35 C |
| ATOM | 6052 | CG1 | ILE | A | 400 | −41.406 | 15.254 | −4.611 | 1.00 | 16.83 C |
| ATOM | 6055 | CD1 | ILE | A | 400 | −40.234 | 14.490 | −3.958 | 1.00 | 17.18 C |
| ATOM | 6059 | CG2 | ILE | A | 400 | −42.060 | 13.486 | −6.292 | 1.00 | 14.03 C |
| ATOM | 6063 | C | ILE | A | 400 | −44.682 | 14.329 | −6.358 | 1.00 | 15.08 C |
| ATOM | 6064 | O | ILE | A | 400 | −44.672 | 14.362 | −7.574 | 1.00 | 15.18 O |
| ATOM | 6066 | N | PHE | A | 401 | −45.474 | 13.524 | −5.650 | 1.00 | 15.16 N |
| ATOM | 6067 | CA | PHE | A | 401 | −46.501 | 12.674 | −6.258 | 1.00 | 14.90 C |
| ATOM | 6069 | CB | PHE | A | 401 | −47.052 | 11.663 | −5.240 | 1.00 | 14.51 C |
| ATOM | 6072 | CG | PHE | A | 401 | −46.294 | 10.378 | −5.201 | 1.00 | 12.92 C |
| ATOM | 6073 | CD1 | PHE | A | 401 | −46.727 | 9.282 | −5.931 | 1.00 | 11.98 C |
| ATOM | 6075 | CE1 | PHE | A | 401 | −46.032 | 8.093 | −5.917 | 1.00 | 11.20 C |
| ATOM | 6077 | CZ | PHE | A | 401 | −44.881 | 7.985 | −5.165 | 1.00 | 12.03 C |
| ATOM | 6079 | CE2 | PHE | A | 401 | −44.431 | 9.078 | −4.428 | 1.00 | 11.98 C |
| ATOM | 6081 | CD2 | PHE | A | 401 | −45.143 | 10.263 | −4.453 | 1.00 | 12.09 C |
| ATOM | 6083 | C | PHE | A | 401 | −47.641 | 13.509 | −6.806 | 1.00 | 15.39 C |
| ATOM | 6084 | O | PHE | A | 401 | −48.183 | 13.215 | −7.858 | 1.00 | 15.51 O |
| ATOM | 6086 | N | ALA | A | 402 | −48.022 | 14.545 | −6.080 | 1.00 | 16.15 N |
| ATOM | 6087 | CA | ALA | A | 402 | −49.110 | 15.393 | −6.525 | 1.00 | 16.90 C |
| ATOM | 6089 | CB | ALA | A | 402 | −49.391 | 16.473 | −5.505 | 1.00 | 16.99 C |
| ATOM | 6093 | C | ALA | A | 402 | −48.722 | 16.003 | −7.856 | 1.00 | 17.50 C |
| ATOM | 6094 | O | ALA | A | 402 | −49.549 | 16.100 | −8.770 | 1.00 | 17.48 O |
| ATOM | 6096 | N | TYR | A | 403 | −47.444 | 16.367 | −7.963 | 1.00 | 18.28 N |
| ATOM | 6097 | CA | TYR | A | 403 | −46.916 | 17.046 | −9.142 | 1.00 | 18.94 C |
| ATOM | 6099 | CB | TYR | A | 403 | −45.412 | 17.252 | −9.043 | 1.00 | 19.03 C |
| ATOM | 6102 | CG | TYR | A | 403 | −44.823 | 17.801 | −10.314 | 1.00 | 19.79 C |
| ATOM | 6103 | CD1 | TYR | A | 403 | −44.973 | 19.138 | −10.652 | 1.00 | 20.80 C |
| ATOM | 6105 | CE1 | TYR | A | 403 | −44.436 | 19.643 | −11.827 | 1.00 | 20.73 C |
| ATOM | 6107 | CZ | TYR | A | 403 | −43.759 | 18.804 | −12.674 | 1.00 | 21.16 C |
| ATOM | 6108 | OH | TYR | A | 403 | −43.231 | 19.283 | −13.836 | 1.00 | 22.98 O |
| ATOM | 6110 | CE2 | TYR | A | 403 | −43.608 | 17.476 | −12.370 | 1.00 | 21.23 C |
| ATOM | 6112 | CD2 | TYR | A | 403 | −44.137 | 16.980 | −11.195 | 1.00 | 20.93 C |
| ATOM | 6114 | C | TYR | A | 403 | −47.198 | 16.293 | −10.413 | 1.00 | 19.39 C |
| ATOM | 6115 | O | TYR | A | 403 | −47.567 | 16.904 | −11.422 | 1.00 | 19.57 O |
| ATOM | 6117 | N | PHE | A | 404 | −47.023 | 14.976 | −10.376 | 1.00 | 19.74 N |
| ATOM | 6118 | CA | PHE | A | 404 | −47.239 | 14.177 | −11.573 | 1.00 | 20.35 C |
| ATOM | 6120 | CB | PHE | A | 404 | −46.533 | 12.841 | −11.466 | 1.00 | 19.96 C |
| ATOM | 6123 | CG | PHE | A | 404 | −45.048 | 12.971 | −11.387 | 1.00 | 18.81 C |
| ATOM | 6124 | CD1 | PHE | A | 404 | −44.292 | 13.115 | −12.528 | 1.00 | 17.42 C |
| ATOM | 6126 | CE1 | PHE | A | 404 | −42.935 | 13.239 | −12.457 | 1.00 | 17.24 C |
| ATOM | 6128 | CZ | PHE | A | 404 | −42.312 | 13.237 | −11.237 | 1.00 | 17.40 C |
| ATOM | 6130 | CE2 | PHE | A | 404 | −43.056 | 13.106 | −10.093 | 1.00 | 17.72 C |
| ATOM | 6132 | CD2 | PHE | A | 404 | −44.413 | 12.975 | −10.170 | 1.00 | 17.93 C |
| ATOM | 6134 | C | PHE | A | 404 | −48.713 | 13.994 | −11.894 | 1.00 | 21.59 C |
| ATOM | 6135 | O | PHE | A | 404 | −49.072 | 13.717 | −13.046 | 1.00 | 21.71 O |
| ATOM | 6137 | N | ALA | A | 405 | −49.572 | 14.169 | −10.896 | 1.00 | 22.87 N |
| ATOM | 6138 | CA | ALA | A | 405 | −50.990 | 13.939 | −11.099 | 1.00 | 24.06 C |
| ATOM | 6140 | CB | ALA | A | 405 | −51.604 | 13.408 | −9.833 | 1.00 | 24.15 C |
| ATOM | 6144 | C | ALA | A | 405 | −51.724 | 15.192 | −11.556 | 1.00 | 25.21 C |
| ATOM | 6145 | O | ALA | A | 405 | −52.876 | 15.114 | −11.939 | 1.00 | 25.51 O |
| ATOM | 6147 | N | VAL | A | 406 | −51.056 | 16.336 | −11.530 | 1.00 | 26.52 N |
| ATOM | 6148 | CA | VAL | A | 406 | −51.713 | 17.617 | −11.759 | 1.00 | 27.68 C |
| ATOM | 6150 | CB | VAL | A | 406 | −51.694 | 18.406 | −10.434 | 1.00 | 27.60 C |
| ATOM | 6152 | CG1 | VAL | A | 406 | −51.654 | 19.913 | −10.663 | 1.00 | 28.07 C |
| ATOM | 6156 | CG2 | VAL | A | 406 | −52.883 | 18.009 | −9.596 | 1.00 | 27.41 C |
| ATOM | 6160 | C | VAL | A | 406 | −51.097 | 18.429 | −12.925 | 1.00 | 29.10 C |
| ATOM | 6161 | O | VAL | A | 406 | −51.810 | 19.104 | −13.678 | 1.00 | 28.53 O |
| ATOM | 6163 | N | VAL | A | 407 | −49.772 | 18.356 | −13.059 | 1.00 | 30.90 N |
| ATOM | 6164 | CA | VAL | A | 407 | −49.052 | 19.003 | −14.151 | 1.00 | 32.15 C |
| ATOM | 6166 | CB | VAL | A | 407 | −47.574 | 19.228 | −13.777 | 1.00 | 32.25 C |
| ATOM | 6168 | CG1 | VAL | A | 407 | −46.770 | 19.780 | −14.964 | 1.00 | 32.22 C |
| ATOM | 6172 | CG2 | VAL | A | 407 | −47.490 | 20.154 | −12.583 | 1.00 | 32.25 C |
| ATOM | 6176 | C | VAL | A | 407 | −49.134 | 18.160 | −15.421 | 1.00 | 33.36 C |
| ATOM | 6177 | O | VAL | A | 407 | −48.688 | 17.009 | −15.454 | 1.00 | 33.40 O |
| ATOM | 6179 | N | GLN | A | 408 | −49.693 | 18.767 | −16.463 | 1.00 | 34.93 N |
| ATOM | 6180 | CA | GLN | A | 408 | −49.930 | 18.102 | −17.749 | 1.00 | 36.16 C |
| ATOM | 6182 | CB | GLN | A | 408 | −50.779 | 19.016 | −18.638 | 1.00 | 36.63 C |
| ATOM | 6185 | CG | GLN | A | 408 | −51.625 | 18.270 | −19.672 | 1.00 | 38.95 C |
| ATOM | 6188 | CD | GLN | A | 408 | −52.991 | 18.930 | −19.887 | 1.00 | 41.80 C |
| ATOM | 6189 | OE1 | GLN | A | 408 | −53.739 | 19.150 | −18.921 | 1.00 | 43.40 O |
| ATOM | 6190 | NE2 | GLN | A | 408 | −53.323 | 19.244 | −21.151 | 1.00 | 41.68 N |
| ATOM | 6193 | C | GLN | A | 408 | −48.630 | 17.725 | −18.470 | 1.00 | 36.22 C |

TABLE 16-7-continued

Coordinates of *P. tremuloides* IspS

| ATOM | 6194 | O | GLN | A | 408 | −48.456 | 16.588 | −18.920 | 1.00 | 35.86 | O |
|---|---|---|---|---|---|---|---|---|---|---|---|
| ATOM | 6196 | N | ASN | A | 409 | −47.726 | 18.694 | −18.578 | 1.00 | 36.64 | N |
| ATOM | 6197 | CA | ASN | A | 409 | −46.400 | 18.441 | −19.136 | 1.00 | 36.85 | C |
| ATOM | 6199 | CB | ASN | A | 409 | −46.134 | 19.306 | −20.373 | 1.00 | 36.73 | C |
| ATOM | 6202 | CG | ASN | A | 409 | −46.808 | 18.752 | −21.604 | 1.00 | 36.19 | C |
| ATOM | 6203 | OD1 | ASN | A | 409 | −46.178 | 18.072 | −22.420 | 1.00 | 35.00 | O |
| ATOM | 6204 | ND2 | ASN | A | 409 | −48.110 | 18.994 | −21.720 | 1.00 | 34.99 | N |
| ATOM | 6207 | C | ASN | A | 409 | −45.312 | 18.613 | −18.095 | 1.00 | 36.96 | C |
| ATOM | 6208 | O | ASN | A | 409 | −45.032 | 19.720 | −17.618 | 1.00 | 36.81 | O |
| ATOM | 6210 | N | ILE | A | 410 | −44.713 | 17.488 | −17.734 | 1.00 | 37.10 | N |
| ATOM | 6211 | CA | ILE | A | 410 | −43.625 | 17.508 | −16.792 | 1.00 | 37.27 | C |
| ATOM | 6213 | CB | ILE | A | 410 | −43.265 | 16.092 | −16.295 | 1.00 | 37.38 | C |
| ATOM | 6215 | CG1 | ILE | A | 410 | −42.745 | 15.209 | −17.426 | 1.00 | 37.84 | C |
| ATOM | 6218 | CD1 | ILE | A | 410 | −42.416 | 13.824 | −16.985 | 1.00 | 38.96 | C |
| ATOM | 6222 | CG2 | ILE | A | 410 | −44.491 | 15.437 | −15.676 | 1.00 | 37.67 | C |
| ATOM | 6226 | C | ILE | A | 410 | −42.467 | 18.179 | −17.492 | 1.00 | 37.12 | C |
| ATOM | 6227 | O | ILE | A | 410 | −42.150 | 17.839 | −18.617 | 1.00 | 36.87 | O |
| ATOM | 6229 | N | LYS | A | 411 | −41.896 | 19.187 | −16.851 | 1.00 | 37.38 | N |
| ATOM | 6230 | CA | LYS | A | 411 | −40.680 | 19.813 | −17.332 | 1.00 | 37.73 | C |
| ATOM | 6232 | CB | LYS | A | 411 | −40.756 | 21.332 | −17.171 | 1.00 | 38.15 | C |
| ATOM | 6235 | CG | LYS | A | 411 | −41.979 | 21.962 | −17.837 | 1.00 | 39.89 | C |
| ATOM | 6238 | CD | LYS | A | 411 | −41.797 | 23.463 | −18.080 | 1.00 | 42.48 | C |
| ATOM | 6241 | CE | LYS | A | 411 | −43.029 | 24.069 | −18.795 | 1.00 | 44.22 | C |
| ATOM | 6244 | NZ | LYS | A | 411 | −42.977 | 25.576 | −18.904 | 1.00 | 45.31 | N |
| ATOM | 6248 | C | LYS | A | 411 | −39.562 | 19.244 | −16.489 | 1.00 | 37.38 | C |
| ATOM | 6249 | O | LYS | A | 411 | −39.721 | 19.112 | −15.281 | 1.00 | 37.28 | O |
| ATOM | 6251 | N | LYS | A | 412 | −38.445 | 18.886 | −17.122 | 1.00 | 37.24 | N |
| ATOM | 6252 | CA | LYS | A | 412 | −37.333 | 18.243 | −16.413 | 1.00 | 36.95 | C |
| ATOM | 6254 | CB | LYS | A | 412 | −36.286 | 17.701 | −17.384 | 1.00 | 37.14 | C |
| ATOM | 6257 | CG | LYS | A | 412 | −35.233 | 16.818 | −16.720 | 1.00 | 37.89 | C |
| ATOM | 6260 | CD | LYS | A | 412 | −34.334 | 16.125 | −17.757 | 1.00 | 39.54 | C |
| ATOM | 6263 | CE | LYS | A | 412 | −33.263 | 17.068 | −18.348 | 1.00 | 40.08 | C |
| ATOM | 6266 | NZ | LYS | A | 412 | −32.161 | 17.399 | −17.376 | 1.00 | 40.16 | N |
| ATOM | 6270 | C | LYS | A | 412 | −36.664 | 19.177 | −15.419 | 1.00 | 36.42 | C |
| ATOM | 6271 | O | LYS | A | 412 | −36.246 | 18.728 | −14.357 | 1.00 | 36.56 | O |
| ATOM | 6273 | N | GLU | A | 413 | −36.570 | 20.466 | −15.744 | 1.00 | 35.77 | N |
| ATOM | 6274 | CA | GLU | A | 413 | −35.948 | 21.423 | −14.820 | 1.00 | 35.38 | C |
| ATOM | 6276 | CB | GLU | A | 413 | −35.688 | 22.792 | −15.489 | 1.00 | 35.73 | C |
| ATOM | 6279 | CG | GLU | A | 413 | −36.510 | 24.013 | −14.973 | 1.00 | 37.10 | C |
| ATOM | 6282 | CD | GLU | A | 413 | −35.621 | 25.235 | −14.633 | 1.00 | 38.51 | C |
| ATOM | 6283 | OE1 | GLU | A | 413 | −34.778 | 25.125 | −13.714 | 1.00 | 39.24 | O |
| ATOM | 6284 | OE2 | GLU | A | 413 | −35.768 | 26.306 | −15.266 | 1.00 | 39.04 | O |
| ATOM | 6285 | C | GLU | A | 413 | −36.760 | 21.551 | −13.522 | 1.00 | 34.43 | C |
| ATOM | 6286 | O | GLU | A | 413 | −36.196 | 21.801 | −12.460 | 1.00 | 34.34 | O |
| ATOM | 6288 | N | GLU | A | 414 | −38.074 | 21.360 | −13.616 | 1.00 | 33.45 | N |
| ATOM | 6289 | CA | GLU | A | 414 | −38.956 | 21.407 | −12.452 | 1.00 | 32.80 | C |
| ATOM | 6291 | CB | GLU | A | 414 | −40.435 | 21.425 | −12.864 | 1.00 | 32.83 | C |
| ATOM | 6294 | CG | GLU | A | 414 | −40.923 | 22.736 | −13.478 | 1.00 | 33.15 | C |
| ATOM | 6297 | CD | GLU | A | 414 | −42.360 | 22.668 | −14.003 | 1.00 | 33.82 | C |
| ATOM | 6298 | OE1 | GLU | A | 414 | −42.876 | 21.560 | −14.231 | 1.00 | 35.31 | O |
| ATOM | 6299 | OE2 | GLU | A | 414 | −42.985 | 23.727 | −14.204 | 1.00 | 33.98 | O |
| ATOM | 6300 | C | GLU | A | 414 | −38.715 | 20.222 | −11.536 | 1.00 | 32.18 | C |
| ATOM | 6301 | O | GLU | A | 414 | −38.407 | 20.409 | −10.372 | 1.00 | 32.25 | O |
| ATOM | 6303 | N | ILE | A | 415 | −38.863 | 19.002 | −12.044 | 1.00 | 31.63 | N |
| ATOM | 6304 | CA | ILE | A | 415 | −38.725 | 17.819 | −11.181 | 1.00 | 31.28 | C |
| ATOM | 6306 | CB | ILE | A | 415 | −39.131 | 16.472 | −11.852 | 1.00 | 31.14 | C |
| ATOM | 6308 | CG1 | ILE | A | 415 | −38.349 | 16.204 | −13.133 | 1.00 | 31.13 | C |
| ATOM | 6311 | CD1 | ILE | A | 415 | −38.786 | 14.926 | −13.836 | 1.00 | 30.72 | C |
| ATOM | 6315 | CG2 | ILE | A | 415 | −40.611 | 16.454 | −12.160 | 1.00 | 31.12 | C |
| ATOM | 6319 | C | ILE | A | 415 | −37.316 | 17.705 | −10.636 | 1.00 | 31.08 | C |
| ATOM | 6320 | O | ILE | A | 415 | −37.105 | 17.188 | −9.539 | 1.00 | 31.22 | O |
| ATOM | 6322 | N | GLU | A | 416 | −36.345 | 18.208 | −11.381 | 1.00 | 30.67 | N |
| ATOM | 6323 | CA | GLU | A | 416 | −34.998 | 18.270 | −10.850 | 1.00 | 30.55 | C |
| ATOM | 6325 | CB | GLU | A | 416 | −34.011 | 18.654 | −11.955 | 1.00 | 30.91 | C |
| ATOM | 6328 | CG | GLU | A | 416 | −32.654 | 17.967 | −11.845 | 1.00 | 32.55 | C |
| ATOM | 6331 | CD | GLU | A | 416 | −31.802 | 18.130 | −13.109 | 1.00 | 34.91 | C |
| ATOM | 6332 | OE1 | GLU | A | 416 | −32.337 | 18.563 | −14.161 | 1.00 | 35.53 | O |
| ATOM | 6333 | OE2 | GLU | A | 416 | −30.590 | 17.816 | −13.052 | 1.00 | 36.45 | O |
| ATOM | 6334 | C | GLU | A | 416 | −34.962 | 19.249 | −9.650 | 1.00 | 29.74 | C |
| ATOM | 6335 | O | GLU | A | 416 | −34.143 | 19.097 | −8.738 | 1.00 | 29.73 | O |
| ATOM | 6337 | N | ASN | A | 417 | −35.864 | 20.234 | −9.652 | 1.00 | 28.69 | N |
| ATOM | 6338 | CA | ASN | A | 417 | −36.060 | 21.134 | −8.503 | 1.00 | 27.92 | C |
| ATOM | 6340 | CB | ASN | A | 417 | −36.632 | 22.477 | −8.963 | 1.00 | 27.75 | C |
| ATOM | 6343 | CG | ASN | A | 417 | −35.572 | 23.532 | −9.095 | 1.00 | 26.84 | C |
| ATOM | 6344 | OD1 | ASN | A | 417 | −35.160 | 24.132 | −8.105 | 1.00 | 24.88 | O |
| ATOM | 6345 | ND2 | ASN | A | 417 | −35.117 | 23.765 | −10.318 | 1.00 | 26.28 | N |
| ATOM | 6348 | C | ASN | A | 417 | −36.917 | 20.580 | −7.356 | 1.00 | 27.41 | C |
| ATOM | 6349 | O | ASN | A | 417 | −36.650 | 20.838 | −6.187 | 1.00 | 27.15 | O |

TABLE 16-7-continued

Coordinates of *P. tremuloides* IspS

| ATOM | 6351 | N | LEU | A | 418 | −37.955 | 19.834 | −7.675 | 1.00 | 27.09 | N |
| --- | --- | --- | --- | --- | --- | --- | --- | --- | --- | --- | --- |
| ATOM | 6352 | CA | LEU | A | 418 | −38.694 | 19.156 | −6.628 | 1.00 | 27.02 | C |
| ATOM | 6354 | CB | LEU | A | 418 | −39.921 | 18.423 | −7.200 | 1.00 | 26.95 | C |
| ATOM | 6357 | CG | LEU | A | 418 | −41.030 | 19.284 | −7.826 | 1.00 | 25.97 | C |
| ATOM | 6359 | CD1 | LEU | A | 418 | −42.127 | 18.429 | −8.447 | 1.00 | 24.88 | C |
| ATOM | 6363 | CD2 | LEU | A | 418 | −41.623 | 20.226 | −6.803 | 1.00 | 24.50 | C |
| ATOM | 6367 | C | LEU | A | 418 | −37.763 | 18.196 | −5.860 | 1.00 | 27.26 | C |
| ATOM | 6368 | O | LEU | A | 418 | −37.834 | 18.123 | −4.644 | 1.00 | 27.07 | O |
| ATOM | 6370 | N | GLN | A | 419 | −36.873 | 17.494 | −6.561 | 1.00 | 27.67 | N |
| ATOM | 6371 | CA | GLN | A | 419 | −35.924 | 16.575 | −5.909 | 1.00 | 28.28 | C |
| ATOM | 6373 | CB | GLN | A | 419 | −35.155 | 15.758 | −6.945 | 1.00 | 28.36 | C |
| ATOM | 6376 | CG | GLN | A | 419 | −35.747 | 14.375 | −7.146 | 1.00 | 29.43 | C |
| ATOM | 6379 | CD | GLN | A | 419 | −35.052 | 13.573 | −8.215 | 1.00 | 29.76 | C |
| ATOM | 6380 | OE1 | GLN | A | 419 | −34.355 | 14.112 | −9.066 | 1.00 | 29.93 | O |
| ATOM | 6381 | NE2 | GLN | A | 419 | −35.252 | 12.270 | −8.184 | 1.00 | 31.33 | N |
| ATOM | 6384 | C | GLN | A | 419 | −34.922 | 17.219 | −4.947 | 1.00 | 28.73 | C |
| ATOM | 6385 | O | GLN | A | 419 | −34.540 | 16.608 | −3.952 | 1.00 | 28.90 | O |
| ATOM | 6387 | N | LYS | A | 420 | −34.490 | 18.440 | −5.240 | 1.00 | 29.27 | N |
| ATOM | 6388 | CA | LYS | A | 420 | −33.608 | 19.166 | −4.335 | 1.00 | 29.81 | C |
| ATOM | 6390 | CB | LYS | A | 420 | −32.758 | 20.163 | −5.129 | 1.00 | 30.24 | C |
| ATOM | 6393 | CG | LYS | A | 420 | −31.592 | 19.513 | −5.867 | 1.00 | 31.75 | C |
| ATOM | 6396 | CD | LYS | A | 420 | −31.259 | 20.217 | −7.183 | 1.00 | 34.14 | C |
| ATOM | 6399 | CE | LYS | A | 420 | −30.140 | 19.463 | −7.953 | 1.00 | 36.21 | C |
| ATOM | 6402 | NZ | LYS | A | 420 | −30.073 | 19.759 | −9.439 | 1.00 | 36.76 | N |
| ATOM | 6406 | C | LYS | A | 420 | −34.375 | 19.872 | −3.204 | 1.00 | 29.98 | C |
| ATOM | 6407 | O | LYS | A | 420 | −33.759 | 20.547 | −2.384 | 1.00 | 30.44 | O |
| ATOM | 6409 | N | TYR | A | 421 | −35.706 | 19.694 | −3.162 | 1.00 | 30.07 | N |
| ATOM | 6410 | CA | TYR | A | 421 | −36.646 | 20.309 | −2.171 | 1.00 | 29.73 | C |
| ATOM | 6412 | CB | TYR | A | 421 | −36.298 | 19.949 | −.712 | 1.00 | 29.59 | C |
| ATOM | 6415 | CG | TYR | A | 421 | −36.386 | 18.468 | −.470 | 1.00 | 30.57 | C |
| ATOM | 6416 | CD1 | TYR | A | 421 | −37.582 | 17.785 | −.643 | 1.00 | 30.87 | C |
| ATOM | 6418 | CE1 | TYR | A | 421 | −37.665 | 16.414 | −.448 | 1.00 | 31.28 | C |
| ATOM | 6420 | CZ | TYR | A | 421 | −36.549 | 15.705 | −.068 | 1.00 | 31.90 | C |
| ATOM | 6421 | OH | TYR | A | 421 | −36.620 | 14.347 | .124 | 1.00 | 32.43 | O |
| ATOM | 6423 | CE2 | TYR | A | 421 | −35.355 | 16.354 | .119 | 1.00 | 32.68 | C |
| ATOM | 6425 | CD2 | TYR | A | 421 | −35.274 | 17.736 | −.095 | 1.00 | 32.42 | C |
| ATOM | 6427 | C | TYR | A | 421 | −36.850 | 21.816 | −2.347 | 1.00 | 29.24 | C |
| ATOM | 6428 | O | TYR | A | 421 | −36.709 | 22.590 | −1.401 | 1.00 | 29.26 | O |
| ATOM | 6430 | N | HIS | A | 422 | −37.219 | 22.214 | −3.563 | 1.00 | 28.65 | N |
| ATOM | 6431 | CA | HIS | A | 422 | −37.540 | 23.604 | −3.859 | 1.00 | 28.26 | C |
| ATOM | 6433 | CB | HIS | A | 422 | −38.150 | 23.715 | −5.256 | 1.00 | 28.33 | C |
| ATOM | 6436 | CG | HIS | A | 422 | −38.299 | 25.124 | −5.748 | 1.00 | 28.44 | C |
| ATOM | 6437 | ND1 | HIS | A | 422 | −37.225 | 25.904 | −6.106 | 1.00 | 28.97 | N |
| ATOM | 6439 | CE1 | HIS | A | 422 | −37.660 | 27.082 | −6.520 | 1.00 | 29.40 | C |
| ATOM | 6441 | NE2 | HIS | A | 422 | −38.977 | 27.090 | −6.443 | 1.00 | 28.14 | N |
| ATOM | 6443 | CD2 | HIS | A | 422 | −39.399 | 25.879 | −5.965 | 1.00 | 27.76 | C |
| ATOM | 6445 | C | HIS | A | 422 | −38.511 | 24.147 | −2.816 | 1.00 | 27.74 | C |
| ATOM | 6446 | O | HIS | A | 422 | −39.357 | 23.408 | −2.310 | 1.00 | 27.53 | O |
| ATOM | 6448 | N | ASP | A | 423 | −38.384 | 25.437 | −2.505 | 1.00 | 27.12 | N |
| ATOM | 6449 | CA | ASP | A | 423 | −39.186 | 26.072 | −1.454 | 1.00 | 26.63 | C |
| ATOM | 6451 | CB | ASP | A | 423 | −38.877 | 27.575 | −1.349 | 1.00 | 27.05 | C |
| ATOM | 6454 | CG | ASP | A | 423 | −37.456 | 27.875 | −.851 | 1.00 | 28.35 | C |
| ATOM | 6455 | OD1 | ASP | A | 423 | −36.951 | 27.121 | .018 | 1.00 | 30.99 | O |
| ATOM | 6456 | OD2 | ASP | A | 423 | −36.860 | 28.884 | −1.322 | 1.00 | 27.89 | O |
| ATOM | 6457 | C | ASP | A | 423 | −40.689 | 25.883 | −1.698 | 1.00 | 25.71 | C |
| ATOM | 6458 | O | ASP | A | 423 | −41.487 | 25.831 | −.749 | 1.00 | 26.26 | O |
| ATOM | 6460 | N | ILE | A | 424 | −41.075 | 25.781 | −2.966 | 1.00 | 24.01 | N |
| ATOM | 6461 | CA | ILE | A | 424 | −42.479 | 25.596 | −3.327 | 1.00 | 22.72 | C |
| ATOM | 6463 | CB | ILE | A | 424 | −42.639 | 25.391 | −4.843 | 1.00 | 22.40 | C |
| ATOM | 6465 | CG1 | ILE | A | 424 | −44.029 | 25.668 | −5.318 | 1.00 | 21.78 | C |
| ATOM | 6468 | CD1 | ILE | A | 424 | −44.086 | 25.499 | −6.793 | 1.00 | 22.22 | C |
| ATOM | 6472 | CG2 | ILE | A | 424 | −42.340 | 23.985 | −5.255 | 1.00 | 22.87 | C |
| ATOM | 6476 | C | ILE | A | 424 | −43.103 | 24.442 | −2.562 | 1.00 | 21.91 | C |
| ATOM | 6477 | O | ILE | A | 424 | −44.238 | 24.574 | −2.115 | 1.00 | 21.73 | O |
| ATOM | 6479 | N | ILE | A | 425 | −42.365 | 23.334 | −2.399 | 1.00 | 21.23 | N |
| ATOM | 6480 | CA | ILE | A | 425 | −42.853 | 22.173 | −1.634 | 1.00 | 20.73 | C |
| ATOM | 6482 | CB | ILE | A | 425 | −42.622 | 20.820 | −2.330 | 1.00 | 20.10 | C |
| ATOM | 6484 | CG1 | ILE | A | 425 | −41.158 | 20.409 | −2.290 | 1.00 | 18.72 | C |
| ATOM | 6487 | CD1 | ILE | A | 425 | −40.923 | 19.075 | −2.948 | 1.00 | 18.27 | C |
| ATOM | 6491 | CG2 | ILE | A | 425 | −43.146 | 20.840 | −3.741 | 1.00 | 19.57 | C |
| ATOM | 6495 | C | ILE | A | 425 | −42.252 | 22.060 | −.242 | 1.00 | 21.21 | C |
| ATOM | 6496 | O | ILE | A | 425 | −42.810 | 21.370 | .613 | 1.00 | 21.30 | O |
| ATOM | 6498 | N | SER | A | 426 | −41.129 | 22.721 | −.002 | 1.00 | 21.56 | N |
| ATOM | 6499 | CA | SER | A | 426 | −40.492 | 22.620 | 1.299 | 1.00 | 22.23 | C |
| ATOM | 6501 | CB | SER | A | 426 | −39.043 | 23.082 | 1.234 | 1.00 | 22.36 | C |
| ATOM | 6504 | OG | SER | A | 426 | −38.977 | 24.501 | 1.342 | 1.00 | 24.09 | O |
| ATOM | 6506 | C | SER | A | 426 | −41.242 | 23.460 | 2.334 | 1.00 | 22.39 | C |
| ATOM | 6507 | O | SER | A | 426 | −41.390 | 23.051 | 3.491 | 1.00 | 22.95 | O |

TABLE 16-7-continued

Coordinates of *P. tremuloides* IspS

| ATOM | 6509 | N | ARG | A | 427 | −41.701 | 24.643 | 1.937 | 1.00 | 22.08 | N |
|---|---|---|---|---|---|---|---|---|---|---|---|
| ATOM | 6510 | CA | ARG | A | 427 | −42.332 | 25.541 | 2.905 | 1.00 | 21.87 | C |
| ATOM | 6512 | CB | ARG | A | 427 | −42.466 | 26.955 | 2.345 | 1.00 | 21.99 | C |
| ATOM | 6515 | CG | ARG | A | 427 | −41.170 | 27.696 | 2.493 | 1.00 | 23.36 | C |
| ATOM | 6518 | CD | ARG | A | 427 | −40.954 | 28.727 | 1.433 | 1.00 | 26.07 | C |
| ATOM | 6521 | NE | ARG | A | 427 | −39.680 | 29.407 | 1.667 | 1.00 | 28.18 | N |
| ATOM | 6523 | CZ | ARG | A | 427 | −39.127 | 30.298 | .844 | 1.00 | 29.21 | C |
| ATOM | 6524 | NH1 | ARG | A | 427 | −39.723 | 30.633 | −.298 | 1.00 | 28.60 | N |
| ATOM | 6527 | NH2 | ARG | A | 427 | −37.962 | 30.854 | 1.173 | 1.00 | 30.48 | N |
| ATOM | 6530 | C | ARG | A | 427 | −43.651 | 25.003 | 3.434 | 1.00 | 21.21 | C |
| ATOM | 6531 | O | ARG | A | 427 | −43.817 | 24.891 | 4.645 | 1.00 | 21.11 | O |
| ATOM | 6533 | N | PRO | A | 428 | −44.573 | 24.622 | 2.541 | 1.00 | 20.52 | N |
| ATOM | 6534 | CA | PRO | A | 428 | −45.789 | 23.999 | 3.040 | 1.00 | 20.27 | C |
| ATOM | 6536 | CB | PRO | A | 428 | −46.410 | 23.369 | 1.791 | 1.00 | 20.44 | C |
| ATOM | 6539 | CG | PRO | A | 428 | −45.864 | 24.119 | .666 | 1.00 | 20.63 | C |
| ATOM | 6542 | CD | PRO | A | 428 | −44.521 | 24.644 | 1.074 | 1.00 | 20.54 | C |
| ATOM | 6545 | C | PRO | A | 428 | −45.450 | 22.917 | 4.050 | 1.00 | 19.75 | C |
| ATOM | 6546 | O | PRO | A | 428 | −46.089 | 22.834 | 5.095 | 1.00 | 19.77 | O |
| ATOM | 6547 | N | SER | A | 429 | −44.424 | 22.123 | 3.747 | 1.00 | 18.97 | N |
| ATOM | 6548 | CA | SER | A | 429 | −44.008 | 21.045 | 4.636 | 1.00 | 18.45 | C |
| ATOM | 6550 | CB | SER | A | 429 | −42.954 | 20.180 | 3.972 | 1.00 | 18.35 | C |
| ATOM | 6553 | OG | SER | A | 429 | −43.452 | 19.716 | 2.733 | 1.00 | 19.12 | O |
| ATOM | 6555 | C | SER | A | 429 | −43.519 | 21.525 | 5.985 | 1.00 | 17.97 | C |
| ATOM | 6556 | O | SER | A | 429 | −43.733 | 20.846 | 6.968 | 1.00 | 17.88 | O |
| ATOM | 6558 | N | HIS | A | 430 | −42.879 | 22.689 | 6.053 | 1.00 | 17.73 | N |
| ATOM | 6559 | CA | HIS | A | 430 | −42.593 | 23.289 | 7.359 | 1.00 | 17.71 | C |
| ATOM | 6561 | CB | HIS | A | 430 | −41.937 | 24.668 | 7.241 | 1.00 | 17.97 | C |
| ATOM | 6564 | CG | HIS | A | 430 | −40.558 | 24.663 | 6.651 | 1.00 | 18.87 | C |
| ATOM | 6565 | ND1 | HIS | A | 430 | −39.940 | 23.524 | 6.186 | 1.00 | 19.85 | N |
| ATOM | 6567 | CE1 | HIS | A | 430 | −38.746 | 23.836 | 5.709 | 1.00 | 19.43 | C |
| ATOM | 6569 | NE2 | HIS | A | 430 | −38.573 | 25.137 | 5.838 | 1.00 | 19.06 | N |
| ATOM | 6571 | CD2 | HIS | A | 430 | −39.693 | 25.681 | 6.418 | 1.00 | 19.32 | C |
| ATOM | 6573 | C | HIS | A | 430 | −43.914 | 23.444 | 8.131 | 1.00 | 17.31 | C |
| ATOM | 6574 | O | HIS | A | 430 | −44.023 | 23.013 | 9.287 | 1.00 | 17.06 | O |
| ATOM | 6576 | N | ILE | A | 431 | −44.913 | 24.050 | 7.475 | 1.00 | 16.74 | N |
| ATOM | 6577 | CA | ILE | A | 431 | −46.218 | 24.304 | 8.091 | 1.00 | 16.15 | C |
| ATOM | 6579 | CB | ILE | A | 431 | −47.174 | 25.057 | 7.174 | 1.00 | 16.18 | C |
| ATOM | 6581 | CG1 | ILE | A | 431 | −46.613 | 26.428 | 6.801 | 1.00 | 17.05 | C |
| ATOM | 6584 | CD1 | ILE | A | 431 | −46.441 | 27.352 | 7.994 | 1.00 | 18.34 | C |
| ATOM | 6588 | CG2 | ILE | A | 431 | −48.496 | 25.263 | 7.860 | 1.00 | 15.28 | C |
| ATOM | 6592 | C | ILE | A | 431 | −46.899 | 23.021 | 8.476 | 1.00 | 15.75 | C |
| ATOM | 6593 | O | ILE | A | 431 | −47.624 | 22.980 | 9.445 | 1.00 | 15.95 | O |
| ATOM | 6595 | N | PHE | A | 432 | −46.663 | 21.969 | 7.714 | 1.00 | 15.59 | N |
| ATOM | 6596 | CA | PHE | A | 432 | −47.192 | 20.652 | 8.041 | 1.00 | 15.52 | C |
| ATOM | 6598 | CB | PHE | A | 432 | −46.837 | 19.683 | 6.913 | 1.00 | 15.23 | C |
| ATOM | 6601 | CG | PHE | A | 432 | −47.451 | 18.318 | 7.031 | 1.00 | 15.98 | C |
| ATOM | 6602 | CD1 | PHE | A | 432 | −48.324 | 17.972 | 8.052 | 1.00 | 16.55 | C |
| ATOM | 6604 | CE1 | PHE | A | 432 | −48.867 | 16.700 | 8.102 | 1.00 | 16.04 | C |
| ATOM | 6606 | CZ | PHE | A | 432 | −48.559 | 15.774 | 7.130 | 1.00 | 15.29 | C |
| ATOM | 6608 | CE2 | PHE | A | 432 | −47.718 | 16.107 | 6.114 | 1.00 | 15.37 | C |
| ATOM | 6610 | CD2 | PHE | A | 432 | −47.172 | 17.364 | 6.061 | 1.00 | 16.74 | C |
| ATOM | 6612 | C | PHE | A | 432 | −46.640 | 20.191 | 9.392 | 1.00 | 15.54 | C |
| ATOM | 6613 | O | PHE | A | 432 | −47.383 | 20.006 | 10.343 | 1.00 | 15.37 | O |
| ATOM | 6615 | N | ARG | A | 433 | −45.328 | 20.041 | 9.483 | 1.00 | 15.98 | N |
| ATOM | 6616 | CA | ARG | A | 433 | −44.695 | 19.542 | 10.709 | 1.00 | 16.20 | C |
| ATOM | 6618 | CB | ARG | A | 433 | −43.176 | 19.476 | 10.526 | 1.00 | 15.85 | C |
| ATOM | 6621 | CG | ARG | A | 433 | −42.411 | 19.183 | 11.804 | 1.00 | 16.11 | C |
| ATOM | 6624 | CD | ARG | A | 433 | −42.848 | 17.890 | 12.489 | 1.00 | 15.70 | C |
| ATOM | 6627 | NE | ARG | A | 433 | −42.811 | 16.747 | 11.588 | 1.00 | 15.64 | N |
| ATOM | 6629 | CZ | ARG | A | 433 | −43.377 | 15.571 | 11.838 | 1.00 | 16.27 | C |
| ATOM | 6630 | NH1 | ARG | A | 433 | −44.029 | 15.359 | 12.965 | 1.00 | 16.82 | N |
| ATOM | 6633 | NH2 | ARG | A | 433 | −43.302 | 14.598 | 10.948 | 1.00 | 16.96 | N |
| ATOM | 6636 | C | ARG | A | 433 | −45.029 | 20.411 | 11.935 | 1.00 | 16.46 | C |
| ATOM | 6637 | O | ARG | A | 433 | −45.296 | 19.890 | 13.031 | 1.00 | 16.31 | O |
| ATOM | 6639 | N | LEU | A | 434 | −45.006 | 21.731 | 11.724 | 1.00 | 16.47 | N |
| ATOM | 6640 | CA | LEU | A | 434 | −45.123 | 22.701 | 12.800 | 1.00 | 15.98 | C |
| ATOM | 6642 | CB | LEU | A | 434 | −44.771 | 24.114 | 12.303 | 1.00 | 15.83 | C |
| ATOM | 6645 | CG | LEU | A | 434 | −43.287 | 24.486 | 12.218 | 1.00 | 14.95 | C |
| ATOM | 6647 | CD1 | LEU | A | 434 | −43.130 | 25.918 | 11.826 | 1.00 | 15.09 | C |
| ATOM | 6651 | CD2 | LEU | A | 434 | −42.600 | 24.281 | 13.536 | 1.00 | 14.37 | C |
| ATOM | 6655 | C | LEU | A | 434 | −46.517 | 22.660 | 13.387 | 1.00 | 16.19 | C |
| ATOM | 6656 | O | LEU | A | 434 | −46.669 | 22.564 | 14.604 | 1.00 | 15.92 | O |
| ATOM | 6658 | N | CYS | A | 435 | −47.529 | 22.715 | 12.520 | 1.00 | 16.78 | N |
| ATOM | 6659 | CA | CYS | A | 435 | −48.936 | 22.591 | 12.940 | 1.00 | 17.48 | C |
| ATOM | 6661 | CB | CYS | A | 435 | −49.870 | 22.617 | 11.726 | 1.00 | 17.54 | C |
| ATOM | 6664 | SG | CYS | A | 435 | −50.110 | 24.233 | 10.985 | 1.00 | 18.80 | S |
| ATOM | 6666 | C | CYS | A | 435 | −49.192 | 21.296 | 13.708 | 1.00 | 17.84 | C |
| ATOM | 6667 | O | CYS | A | 435 | −50.043 | 21.250 | 14.597 | 1.00 | 17.92 | O |

TABLE 16-7-continued

Coordinates of *P. tremuloides* IspS

| ATOM | 6669 | N | ASN | A | 436 | −48.446 | 20.257 | 13.333 | 1.00 | 18.24 | N |
|---|---|---|---|---|---|---|---|---|---|---|---|
| ATOM | 6670 | CA | ASN | A | 436 | −48.603 | 18.913 | 13.846 | 1.00 | 18.50 | C |
| ATOM | 6672 | CB | ASN | A | 436 | −47.936 | 17.949 | 12.867 | 1.00 | 18.63 | C |
| ATOM | 6675 | CG | ASN | A | 436 | −48.156 | 16.487 | 13.213 | 1.00 | 18.58 | C |
| ATOM | 6676 | OD1 | ASN | A | 436 | −48.810 | 16.129 | 14.185 | 1.00 | 18.80 | O |
| ATOM | 6677 | ND2 | ASN | A | 436 | −47.588 | 15.633 | 12.398 | 1.00 | 19.29 | N |
| ATOM | 6680 | C | ASN | A | 436 | −47.975 | 18.755 | 15.210 | 1.00 | 18.83 | C |
| ATOM | 6681 | O | ASN | A | 436 | −48.551 | 18.153 | 16.115 | 1.00 | 19.00 | O |
| ATOM | 6683 | N | ASP | A | 437 | −46.763 | 19.255 | 15.351 | 1.00 | 19.29 | N |
| ATOM | 6684 | CA | ASP | A | 437 | −46.097 | 19.179 | 16.634 | 1.00 | 19.62 | C |
| ATOM | 6686 | CB | ASP | A | 437 | −44.615 | 19.522 | 16.510 | 1.00 | 19.45 | C |
| ATOM | 6689 | CG | ASP | A | 437 | −43.849 | 18.480 | 15.734 | 1.00 | 19.36 | C |
| ATOM | 6690 | OD1 | ASP | A | 437 | −44.491 | 17.586 | 15.158 | 1.00 | 19.89 | O |
| ATOM | 6691 | OD2 | ASP | A | 437 | −42.608 | 18.543 | 15.699 | 1.00 | 19.86 | O |
| ATOM | 6692 | C | ASP | A | 437 | −46.799 | 20.106 | 17.597 | 1.00 | 20.01 | C |
| ATOM | 6693 | O | ASP | A | 437 | −46.916 | 19.790 | 18.779 | 1.00 | 20.30 | O |
| ATOM | 6695 | N | LEU | A | 438 | −47.288 | 21.233 | 17.092 | 1.00 | 20.40 | N |
| ATOM | 6696 | CA | LEU | A | 438 | −47.996 | 22.174 | 17.940 | 1.00 | 21.03 | C |
| ATOM | 6698 | CB | LEU | A | 438 | −48.510 | 23.363 | 17.126 | 1.00 | 21.01 | C |
| ATOM | 6701 | CG | LEU | A | 438 | −47.575 | 24.565 | 17.078 | 1.00 | 20.32 | C |
| ATOM | 6703 | CD1 | LEU | A | 438 | −47.938 | 25.524 | 15.952 | 1.00 | 19.14 | C |
| ATOM | 6707 | CD2 | LEU | A | 438 | −47.611 | 25.263 | 18.415 | 1.00 | 19.73 | C |
| ATOM | 6711 | C | LEU | A | 438 | −49.153 | 21.496 | 18.679 | 1.00 | 21.81 | C |
| ATOM | 6712 | O | LEU | A | 438 | −49.277 | 21.633 | 19.902 | 1.00 | 21.55 | O |
| ATOM | 6714 | N | ALA | A | 439 | −49.973 | 20.754 | 17.932 | 1.00 | 22.76 | N |
| ATOM | 6715 | CA | ALA | A | 439 | −51.138 | 20.055 | 18.486 | 1.00 | 23.58 | C |
| ATOM | 6717 | CB | ALA | A | 439 | −51.905 | 19.360 | 17.386 | 1.00 | 23.57 | C |
| ATOM | 6721 | C | ALA | A | 439 | −50.746 | 19.042 | 19.542 | 1.00 | 24.47 | C |
| ATOM | 6722 | O | ALA | A | 439 | −51.386 | 18.951 | 20.575 | 1.00 | 24.63 | O |
| ATOM | 6724 | N | SER | A | 440 | −49.685 | 18.291 | 19.276 | 1.00 | 25.78 | N |
| ATOM | 6725 | CA | SER | A | 440 | −49.242 | 17.227 | 20.168 | 1.00 | 26.84 | C |
| ATOM | 6727 | CB | SER | A | 440 | −48.566 | 16.130 | 19.353 | 1.00 | 26.92 | C |
| ATOM | 6730 | OG | SER | A | 440 | −47.321 | 16.582 | 18.859 | 1.00 | 27.46 | O |
| ATOM | 6732 | C | SER | A | 440 | −48.270 | 17.691 | 21.244 | 1.00 | 27.68 | C |
| ATOM | 6733 | O | SER | A | 440 | −47.934 | 16.923 | 22.132 | 1.00 | 28.00 | O |
| ATOM | 6735 | N | ALA | A | 441 | −47.822 | 18.935 | 21.174 | 1.00 | 28.83 | N |
| ATOM | 6736 | CA | ALA | A | 441 | −46.760 | 19.419 | 22.056 | 1.00 | 29.73 | C |
| ATOM | 6738 | CB | ALA | A | 441 | −46.529 | 20.910 | 21.841 | 1.00 | 29.84 | C |
| ATOM | 6742 | C | ALA | A | 441 | −46.982 | 19.132 | 23.539 | 1.00 | 30.57 | C |
| ATOM | 6743 | O | ALA | A | 441 | −46.306 | 18.274 | 24.093 | 1.00 | 30.50 | O |
| ATOM | 6745 | N | SER | A | 442 | −47.929 | 19.827 | 24.172 | 1.00 | 31.90 | N |
| ATOM | 6746 | CA | SER | A | 442 | −47.999 | 19.862 | 25.654 | 1.00 | 32.95 | C |
| ATOM | 6748 | CB | SER | A | 442 | −49.043 | 20.870 | 26.169 | 1.00 | 32.91 | C |
| ATOM | 6751 | OG | SER | A | 442 | −50.331 | 20.614 | 25.650 | 1.00 | 33.50 | O |
| ATOM | 6753 | C | SER | A | 442 | −48.219 | 18.497 | 26.289 | 1.00 | 33.69 | C |
| ATOM | 6754 | O | SER | A | 442 | −47.754 | 18.246 | 27.397 | 1.00 | 33.59 | O |
| ATOM | 6756 | N | ALA | A | 443 | −48.922 | 17.623 | 25.578 | 1.00 | 34.93 | N |
| ATOM | 6757 | CA | ALA | A | 443 | −49.050 | 16.231 | 25.980 | 1.00 | 35.81 | C |
| ATOM | 6759 | CB | ALA | A | 443 | −49.981 | 15.488 | 25.030 | 1.00 | 35.72 | C |
| ATOM | 6763 | C | ALA | A | 443 | −47.663 | 15.580 | 25.996 | 1.00 | 36.71 | C |
| ATOM | 6764 | O | ALA | A | 443 | −47.198 | 15.115 | 27.047 | 1.00 | 36.94 | O |
| ATOM | 6766 | N | GLU | A | 444 | −46.999 | 15.567 | 24.838 | 1.00 | 37.47 | N |
| ATOM | 6767 | CA | GLU | A | 444 | −45.688 | 14.930 | 24.718 | 1.00 | 37.93 | C |
| ATOM | 6769 | CB | GLU | A | 444 | −45.164 | 14.996 | 23.277 | 1.00 | 37.99 | C |
| ATOM | 6772 | CG | GLU | A | 444 | −45.952 | 14.100 | 22.326 | 1.00 | 39.24 | C |
| ATOM | 6775 | CD | GLU | A | 444 | −45.419 | 14.080 | 20.886 | 1.00 | 41.03 | C |
| ATOM | 6776 | OE1 | GLU | A | 444 | −44.612 | 14.958 | 20.510 | 1.00 | 42.16 | O |
| ATOM | 6777 | OE2 | GLU | A | 444 | −45.827 | 13.178 | 20.119 | 1.00 | 42.36 | O |
| ATOM | 6778 | C | GLU | A | 444 | −44.694 | 15.534 | 25.708 | 1.00 | 38.09 | C |
| ATOM | 6779 | O | GLU | A | 444 | −43.924 | 14.803 | 26.324 | 1.00 | 38.17 | O |
| ATOM | 6781 | N | ILE | A | 445 | −44.739 | 16.851 | 25.889 | 1.00 | 38.41 | N |
| ATOM | 6782 | CA | ILE | A | 445 | −43.829 | 17.530 | 26.814 | 1.00 | 38.75 | C |
| ATOM | 6784 | CB | ILE | A | 445 | −43.802 | 19.065 | 26.587 | 1.00 | 38.69 | C |
| ATOM | 6786 | CG1 | ILE | A | 445 | −43.314 | 19.396 | 25.170 | 1.00 | 38.18 | C |
| ATOM | 6789 | CD1 | ILE | A | 445 | −43.702 | 20.775 | 24.712 | 1.00 | 37.58 | C |
| ATOM | 6793 | CG2 | ILE | A | 445 | −42.909 | 19.753 | 27.617 | 1.00 | 38.26 | C |
| ATOM | 6797 | C | ILE | A | 445 | −44.243 | 17.194 | 28.246 | 1.00 | 39.35 | C |
| ATOM | 6798 | O | ILE | A | 445 | −45.039 | 17.901 | 28.870 | 1.00 | 39.44 | O |
| ATOM | 6800 | N | ALA | A | 446 | −43.696 | 16.092 | 28.750 | 1.00 | 40.02 | N |
| ATOM | 6801 | CA | ALA | A | 446 | −44.082 | 15.540 | 30.045 | 1.00 | 40.51 | C |
| ATOM | 6803 | CB | ALA | A | 446 | −43.815 | 16.552 | 31.170 | 1.00 | 40.55 | C |
| ATOM | 6807 | C | ALA | A | 446 | −45.559 | 15.130 | 30.029 | 1.00 | 40.86 | C |
| ATOM | 6808 | O | ALA | A | 446 | −46.407 | 16.021 | 30.121 | 1.00 | 40.77 | O |
| ATOM | 6810 | N | ARG | A | 447 | −45.925 | 13.842 | 29.899 | 1.00 | 41.31 | N |
| ATOM | 6811 | CA | ARG | A | 447 | −45.072 | 12.633 | 29.691 | 1.00 | 41.58 | C |
| ATOM | 6813 | CB | ARG | A | 447 | −45.272 | 12.092 | 28.258 | 1.00 | 41.84 | C |
| ATOM | 6816 | CG | ARG | A | 447 | −46.667 | 11.495 | 27.991 | 1.00 | 42.69 | C |
| ATOM | 6819 | CD | ARG | A | 447 | −46.778 | 10.901 | 26.582 | 1.00 | 43.92 | C |

TABLE 16-7-continued

Coordinates of *P. tremuloides* IspS

| ATOM | 6822 | NE | ARG | A | 447 | −47.764 | 11.589 | 25.744 | 1.00 | 45.34 | N |
|---|---|---|---|---|---|---|---|---|---|---|---|
| ATOM | 6824 | CZ | ARG | A | 447 | −47.887 | 11.435 | 24.420 | 1.00 | 46.56 | C |
| ATOM | 6825 | NH1 | ARG | A | 447 | −47.077 | 10.623 | 23.742 | 1.00 | 46.71 | N |
| ATOM | 6828 | NH2 | ARG | A | 447 | −48.828 | 12.107 | 23.757 | 1.00 | 46.97 | N |
| ATOM | 6831 | C | ARG | A | 447 | −43.581 | 12.728 | 30.054 | 1.00 | 41.38 | C |
| ATOM | 6832 | O | ARG | A | 447 | −43.231 | 12.747 | 31.238 | 1.00 | 41.92 | O |
| ATOM | 6834 | N | GLY | A | 448 | −42.710 | 12.736 | 29.051 | 1.00 | 40.88 | N |
| ATOM | 6835 | CA | GLY | A | 448 | −41.312 | 13.128 | 29.234 | 1.00 | 40.44 | C |
| ATOM | 6838 | C | GLY | A | 448 | −40.579 | 13.316 | 27.915 | 1.00 | 40.08 | C |
| ATOM | 6839 | O | GLY | A | 448 | −39.364 | 13.488 | 27.901 | 1.00 | 40.05 | O |
| ATOM | 6841 | N | GLU | A | 449 | −41.323 | 13.332 | 26.809 | 1.00 | 39.56 | N |
| ATOM | 6842 | CA | GLU | A | 449 | −40.750 | 13.132 | 25.486 | 1.00 | 39.19 | C |
| ATOM | 6844 | CB | GLU | A | 449 | −41.827 | 12.668 | 24.502 | 1.00 | 39.52 | C |
| ATOM | 6847 | CG | GLU | A | 449 | −42.403 | 11.290 | 24.810 | 1.00 | 40.61 | C |
| ATOM | 6850 | CD | GLU | A | 449 | −43.348 | 10.782 | 23.715 | 1.00 | 42.21 | C |
| ATOM | 6851 | OE1 | GLU | A | 449 | −43.068 | 11.019 | 22.503 | 1.00 | 41.83 | O |
| ATOM | 6852 | OE2 | GLU | A | 449 | −44.368 | 10.141 | 24.082 | 1.00 | 42.41 | O |
| ATOM | 6853 | C | GLU | A | 449 | −40.037 | 14.365 | 24.921 | 1.00 | 38.34 | C |
| ATOM | 6854 | O | GLU | A | 449 | −40.511 | 15.497 | 25.031 | 1.00 | 38.01 | O |
| ATOM | 6856 | N | THR | A | 450 | −38.904 | 14.106 | 24.279 | 1.00 | 37.37 | N |
| ATOM | 6857 | CA | THR | A | 450 | −38.047 | 15.138 | 23.726 | 1.00 | 36.37 | C |
| ATOM | 6859 | CB | THR | A | 450 | −36.607 | 14.985 | 24.285 | 1.00 | 36.39 | C |
| ATOM | 6861 | OG1 | THR | A | 450 | −35.846 | 16.153 | 23.982 | 1.00 | 36.63 | O |
| ATOM | 6863 | CG2 | THR | A | 450 | −35.888 | 13.749 | 23.706 | 1.00 | 36.52 | C |
| ATOM | 6867 | C | THR | A | 450 | −38.013 | 15.100 | 22.190 | 1.00 | 35.36 | C |
| ATOM | 6868 | O | THR | A | 450 | −37.175 | 15.764 | 21.583 | 1.00 | 35.43 | O |
| ATOM | 6870 | N | ALA | A | 451 | −38.917 | 14.338 | 21.563 | 1.00 | 33.98 | N |
| ATOM | 6871 | CA | ALA | A | 451 | −38.920 | 14.182 | 20.096 | 1.00 | 32.81 | C |
| ATOM | 6873 | CB | ALA | A | 451 | −39.030 | 12.708 | 19.708 | 1.00 | 32.99 | C |
| ATOM | 6877 | C | ALA | A | 451 | −40.043 | 14.987 | 19.459 | 1.00 | 31.46 | C |
| ATOM | 6878 | O | ALA | A | 451 | −41.050 | 14.432 | 18.996 | 1.00 | 31.06 | O |
| ATOM | 6880 | N | ASN | A | 452 | −39.848 | 16.302 | 19.432 | 1.00 | 29.88 | N |
| ATOM | 6881 | CA | ASN | A | 452 | −40.881 | 17.225 | 18.973 | 1.00 | 28.81 | C |
| ATOM | 6883 | CB | ASN | A | 452 | −41.957 | 17.329 | 20.051 | 1.00 | 28.57 | C |
| ATOM | 6886 | CG | ASN | A | 452 | −42.969 | 18.380 | 19.757 | 1.00 | 28.30 | C |
| ATOM | 6887 | OD1 | ASN | A | 452 | −42.622 | 19.517 | 19.468 | 1.00 | 29.35 | O |
| ATOM | 6888 | ND2 | ASN | A | 452 | −44.236 | 18.018 | 19.836 | 1.00 | 28.36 | N |
| ATOM | 6891 | C | ASN | A | 452 | −40.285 | 18.590 | 18.641 | 1.00 | 27.76 | C |
| ATOM | 6892 | O | ASN | A | 452 | −39.365 | 19.018 | 19.296 | 1.00 | 28.04 | O |
| ATOM | 6894 | N | SER | A | 453 | −40.807 | 19.269 | 17.630 | 1.00 | 26.77 | N |
| ATOM | 6895 | CA | SER | A | 453 | −40.226 | 20.533 | 17.182 | 1.00 | 26.38 | C |
| ATOM | 6897 | CB | SER | A | 453 | −40.912 | 21.015 | 15.903 | 1.00 | 26.40 | C |
| ATOM | 6900 | OG | SER | A | 453 | −40.796 | 20.044 | 14.876 | 1.00 | 25.79 | O |
| ATOM | 6902 | C | SER | A | 453 | −40.253 | 21.643 | 18.233 | 1.00 | 26.12 | C |
| ATOM | 6903 | O | SER | A | 453 | −39.280 | 22.361 | 18.385 | 1.00 | 25.97 | O |
| ATOM | 6905 | N | VAL | A | 454 | −41.368 | 21.784 | 18.942 | 1.00 | 26.15 | N |
| ATOM | 6906 | CA | VAL | A | 454 | −41.518 | 22.780 | 20.022 | 1.00 | 26.21 | C |
| ATOM | 6908 | CB | VAL | A | 454 | −42.975 | 22.818 | 20.532 | 1.00 | 26.04 | C |
| ATOM | 6910 | CG1 | VAL | A | 454 | −43.122 | 23.787 | 21.694 | 1.00 | 25.24 | C |
| ATOM | 6914 | CG2 | VAL | A | 454 | −43.913 | 23.190 | 19.401 | 1.00 | 26.32 | C |
| ATOM | 6918 | C | VAL | A | 454 | −40.617 | 22.451 | 21.211 | 1.00 | 26.63 | C |
| ATOM | 6919 | O | VAL | A | 454 | −40.173 | 23.328 | 21.959 | 1.00 | 26.53 | O |
| ATOM | 6921 | N | SER | A | 455 | −40.374 | 21.160 | 21.380 | 1.00 | 27.21 | N |
| ATOM | 6922 | CA | SER | A | 455 | −39.541 | 20.651 | 22.437 | 1.00 | 27.60 | C |
| ATOM | 6924 | CB | SER | A | 455 | −39.677 | 19.141 | 22.490 | 1.00 | 27.31 | C |
| ATOM | 6927 | OG | SER | A | 455 | −38.922 | 18.625 | 23.545 | 1.00 | 28.13 | O |
| ATOM | 6929 | C | SER | A | 455 | −38.096 | 21.045 | 22.181 | 1.00 | 28.29 | C |
| ATOM | 6930 | O | SER | A | 455 | −37.445 | 21.628 | 23.043 | 1.00 | 28.63 | O |
| ATOM | 6932 | N | CYS | A | 456 | −37.599 | 20.748 | 20.988 | 1.00 | 29.04 | N |
| ATOM | 6933 | CA | CYS | A | 456 | −36.219 | 21.082 | 20.640 | 1.00 | 29.65 | C |
| ATOM | 6935 | CB | CYS | A | 456 | −35.868 | 20.535 | 19.256 | 1.00 | 29.52 | C |
| ATOM | 6938 | SG | CYS | A | 456 | −35.959 | 18.734 | 19.163 | 1.00 | 29.71 | S |
| ATOM | 6940 | C | CYS | A | 456 | −35.955 | 22.589 | 20.710 | 1.00 | 30.26 | C |
| ATOM | 6941 | O | CYS | A | 456 | −34.887 | 23.007 | 21.162 | 1.00 | 30.49 | O |
| ATOM | 6943 | N | TYR | A | 457 | −36.924 | 23.399 | 20.283 | 1.00 | 30.88 | N |
| ATOM | 6944 | CA | TYR | A | 457 | −36.767 | 24.850 | 20.308 | 1.00 | 31.45 | C |
| ATOM | 6946 | CB | TYR | A | 457 | −37.967 | 25.557 | 19.648 | 1.00 | 31.55 | C |
| ATOM | 6949 | CG | TYR | A | 457 | −37.691 | 26.991 | 19.178 | 1.00 | 32.09 | C |
| ATOM | 6950 | CD1 | TYR | A | 457 | −37.378 | 27.269 | 17.843 | 1.00 | 31.69 | C |
| ATOM | 6952 | CE1 | TYR | A | 457 | −37.128 | 28.569 | 17.418 | 1.00 | 31.73 | C |
| ATOM | 6954 | CZ | TYR | A | 457 | −37.186 | 29.613 | 18.328 | 1.00 | 32.84 | C |
| ATOM | 6955 | OH | TYR | A | 457 | −36.945 | 30.917 | 17.927 | 1.00 | 33.81 | O |
| ATOM | 6957 | CE2 | TYR | A | 457 | −37.492 | 29.364 | 19.658 | 1.00 | 32.72 | C |
| ATOM | 6959 | CD2 | TYR | A | 457 | −37.746 | 28.064 | 20.074 | 1.00 | 32.44 | C |
| ATOM | 6961 | C | TYR | A | 457 | −36.571 | 25.295 | 21.758 | 1.00 | 31.99 | C |
| ATOM | 6962 | O | TYR | A | 457 | −35.648 | 26.053 | 22.052 | 1.00 | 31.98 | O |
| ATOM | 6964 | N | MET | A | 458 | −37.419 | 24.799 | 22.661 | 1.00 | 32.76 | N |
| ATOM | 6965 | CA | MET | A | 458 | −37.211 | 24.987 | 24.105 | 1.00 | 33.37 | C |

TABLE 16-7-continued

Coordinates of *P. tremuloides* IspS

| ATOM | 6967 | CB | MET | A | 458 | −38.151 | 24.097 | 24.921 | 1.00 | 33.43 | C |
| --- | --- | --- | --- | --- | --- | --- | --- | --- | --- | --- | --- |
| ATOM | 6970 | CG | MET | A | 458 | −39.570 | 24.593 | 25.059 | 1.00 | 33.70 | C |
| ATOM | 6973 | SD | MET | A | 458 | −40.641 | 23.312 | 25.737 | 1.00 | 34.59 | S |
| ATOM | 6974 | CE | MET | A | 458 | −39.709 | 22.763 | 27.179 | 1.00 | 34.71 | C |
| ATOM | 6978 | C | MET | A | 458 | −35.784 | 24.641 | 24.517 | 1.00 | 33.78 | C |
| ATOM | 6979 | O | MET | A | 458 | −35.101 | 25.437 | 25.151 | 1.00 | 33.73 | O |
| ATOM | 6981 | N | ARG | A | 459 | −35.347 | 23.445 | 24.145 | 1.00 | 34.46 | N |
| ATOM | 6982 | CA | ARG | A | 459 | −34.051 | 22.926 | 24.581 | 1.00 | 35.15 | C |
| ATOM | 6984 | CB | ARG | A | 459 | −33.876 | 21.447 | 24.171 | 1.00 | 35.68 | C |
| ATOM | 6987 | CG | ARG | A | 459 | −32.494 | 20.864 | 24.500 | 1.00 | 37.23 | C |
| ATOM | 6990 | CD | ARG | A | 459 | −32.491 | 19.345 | 24.752 | 1.00 | 39.80 | C |
| ATOM | 6993 | NE | ARG | A | 459 | −33.140 | 18.538 | 23.711 | 1.00 | 42.88 | N |
| ATOM | 6995 | CZ | ARG | A | 459 | −32.704 | 18.407 | 22.453 | 1.00 | 45.43 | C |
| ATOM | 6996 | NH1 | ARG | A | 459 | −31.615 | 19.062 | 22.035 | 1.00 | 47.50 | N |
| ATOM | 6999 | NH2 | ARG | A | 459 | −33.366 | 17.629 | 21.595 | 1.00 | 44.77 | N |
| ATOM | 7002 | C | ARG | A | 459 | −32.878 | 23.749 | 24.072 | 1.00 | 34.92 | C |
| ATOM | 7003 | O | ARG | A | 459 | −32.007 | 24.109 | 24.849 | 1.00 | 35.06 | O |
| ATOM | 7005 | N | THR | A | 460 | −32.854 | 24.047 | 22.778 | 1.00 | 34.96 | N |
| ATOM | 7006 | CA | THR | A | 460 | −31.674 | 24.678 | 22.163 | 1.00 | 34.91 | C |
| ATOM | 7008 | CB | THR | A | 460 | −31.494 | 24.263 | 20.680 | 1.00 | 34.88 | C |
| ATOM | 7010 | OG1 | THR | A | 460 | −32.330 | 25.067 | 19.841 | 1.00 | 34.39 | O |
| ATOM | 7012 | CG2 | THR | A | 460 | −31.825 | 22.776 | 20.488 | 1.00 | 35.44 | C |
| ATOM | 7016 | C | THR | A | 460 | −31.672 | 26.210 | 22.258 | 1.00 | 34.78 | C |
| ATOM | 7017 | O | THR | A | 460 | −30.673 | 26.837 | 21.911 | 1.00 | 34.92 | O |
| ATOM | 7019 | N | LYS | A | 461 | −32.781 | 26.806 | 22.701 | 1.00 | 34.41 | N |
| ATOM | 7020 | CA | LYS | A | 461 | −32.811 | 28.231 | 23.039 | 1.00 | 34.25 | C |
| ATOM | 7022 | CB | LYS | A | 461 | −33.921 | 28.947 | 22.265 | 1.00 | 34.56 | C |
| ATOM | 7025 | CG | LYS | A | 461 | −33.717 | 28.986 | 20.750 | 1.00 | 35.84 | C |
| ATOM | 7028 | CD | LYS | A | 461 | −32.519 | 29.859 | 20.347 | 1.00 | 37.64 | C |
| ATOM | 7031 | CE | LYS | A | 461 | −32.232 | 29.804 | 18.838 | 1.00 | 38.44 | C |
| ATOM | 7034 | NZ | LYS | A | 461 | −33.141 | 30.671 | 18.027 | 1.00 | 38.31 | N |
| ATOM | 7038 | C | LYS | A | 461 | −32.974 | 28.476 | 24.544 | 1.00 | 33.73 | C |
| ATOM | 7039 | O | LYS | A | 461 | −32.994 | 29.626 | 24.983 | 1.00 | 33.23 | O |
| ATOM | 7041 | N | GLY | A | 462 | −33.078 | 27.395 | 25.321 | 1.00 | 33.48 | N |
| ATOM | 7042 | CA | GLY | A | 462 | −33.173 | 27.464 | 26.784 | 1.00 | 33.23 | C |
| ATOM | 7045 | C | GLY | A | 462 | −34.332 | 28.320 | 27.239 | 1.00 | 32.95 | C |
| ATOM | 7046 | O | GLY | A | 462 | −34.144 | 29.258 | 28.004 | 1.00 | 33.17 | O |
| ATOM | 7048 | N | ILE | A | 463 | −35.528 | 28.000 | 26.757 | 1.00 | 32.52 | N |
| ATOM | 7049 | CA | ILE | A | 463 | −36.694 | 28.843 | 26.971 | 1.00 | 32.32 | C |
| ATOM | 7051 | CB | ILE | A | 463 | −37.006 | 29.724 | 25.734 | 1.00 | 32.47 | C |
| ATOM | 7053 | CG1 | ILE | A | 463 | −37.152 | 28.866 | 24.463 | 1.00 | 32.41 | C |
| ATOM | 7056 | CD1 | ILE | A | 463 | −37.359 | 29.675 | 23.191 | 1.00 | 32.02 | C |
| ATOM | 7060 | CG2 | ILE | A | 463 | −35.937 | 30.810 | 25.571 | 1.00 | 32.44 | C |
| ATOM | 7064 | C | ILE | A | 463 | −37.902 | 28.006 | 27.309 | 1.00 | 32.15 | C |
| ATOM | 7065 | O | ILE | A | 463 | −37.886 | 26.799 | 27.145 | 1.00 | 32.01 | O |
| ATOM | 7067 | N | SER | A | 464 | −38.950 | 28.670 | 27.780 | 1.00 | 32.27 | N |
| ATOM | 7068 | CA | SER | A | 464 | −40.163 | 28.006 | 28.239 | 1.00 | 32.52 | C |
| ATOM | 7070 | CB | SER | A | 464 | −40.964 | 28.974 | 29.110 | 1.00 | 32.65 | C |
| ATOM | 7073 | OG | SER | A | 464 | −41.112 | 30.224 | 28.457 | 1.00 | 32.69 | O |
| ATOM | 7075 | C | SER | A | 464 | −41.036 | 27.522 | 27.079 | 1.00 | 32.53 | C |
| ATOM | 7076 | O | SER | A | 464 | −40.968 | 28.069 | 25.986 | 1.00 | 32.62 | O |
| ATOM | 7078 | N | GLU | A | 465 | −41.857 | 26.500 | 27.332 | 1.00 | 32.47 | N |
| ATOM | 7079 | CA | GLU | A | 465 | −42.836 | 26.010 | 26.353 | 1.00 | 32.33 | C |
| ATOM | 7081 | CB | GLU | A | 465 | −43.689 | 24.868 | 26.935 | 1.00 | 32.34 | C |
| ATOM | 7084 | CG | GLU | A | 465 | −44.756 | 24.312 | 25.974 | 1.00 | 32.37 | C |
| ATOM | 7087 | CD | GLU | A | 465 | −45.675 | 23.279 | 26.611 | 1.00 | 32.47 | C |
| ATOM | 7088 | OE1 | GLU | A | 465 | −45.297 | 22.659 | 27.630 | 1.00 | 31.63 | O |
| ATOM | 7089 | OE2 | GLU | A | 465 | −46.785 | 23.086 | 26.074 | 1.00 | 32.77 | O |
| ATOM | 7090 | C | GLU | A | 465 | −43.758 | 27.124 | 25.864 | 1.00 | 32.33 | C |
| ATOM | 7091 | O | GLU | A | 465 | −44.078 | 27.183 | 24.676 | 1.00 | 32.60 | O |
| ATOM | 7093 | N | GLU | A | 466 | −44.196 | 28.001 | 26.767 | 1.00 | 32.08 | N |
| ATOM | 7094 | CA | GLU | A | 466 | −45.085 | 29.097 | 26.380 | 1.00 | 31.79 | C |
| ATOM | 7096 | CB | GLU | A | 466 | −45.606 | 29.832 | 27.624 | 1.00 | 31.91 | C |
| ATOM | 7099 | CG | GLU | A | 466 | −46.503 | 31.041 | 27.304 | 1.00 | 32.82 | C |
| ATOM | 7102 | CD | GLU | A | 466 | −47.426 | 31.472 | 28.452 | 1.00 | 33.67 | C |
| ATOM | 7103 | OE1 | GLU | A | 466 | −47.519 | 30.756 | 29.478 | 1.00 | 35.09 | O |
| ATOM | 7104 | OE2 | GLU | A | 466 | −48.077 | 32.533 | 28.312 | 1.00 | 33.12 | O |
| ATOM | 7105 | C | GLU | A | 466 | −44.392 | 30.052 | 25.386 | 1.00 | 31.13 | C |
| ATOM | 7106 | O | GLU | A | 466 | −45.032 | 30.603 | 24.492 | 1.00 | 30.87 | O |
| ATOM | 7108 | N | LEU | A | 467 | −43.077 | 30.194 | 25.531 | 1.00 | 30.57 | N |
| ATOM | 7109 | CA | LEU | A | 467 | −42.265 | 31.102 | 24.708 | 1.00 | 30.18 | C |
| ATOM | 7111 | CB | LEU | A | 467 | −41.055 | 31.604 | 25.524 | 1.00 | 30.38 | C |
| ATOM | 7114 | CG | LEU | A | 467 | −40.674 | 33.087 | 25.463 | 1.00 | 30.39 | C |
| ATOM | 7116 | CD1 | LEU | A | 467 | −41.608 | 33.900 | 26.362 | 1.00 | 30.23 | C |
| ATOM | 7120 | CD2 | LEU | A | 467 | −39.214 | 33.308 | 25.872 | 1.00 | 30.31 | C |
| ATOM | 7124 | C | LEU | A | 467 | −41.773 | 30.401 | 23.439 | 1.00 | 29.47 | C |
| ATOM | 7125 | O | LEU | A | 467 | −41.660 | 31.010 | 22.382 | 1.00 | 29.17 | O |
| ATOM | 7127 | N | ALA | A | 468 | −41.445 | 29.121 | 23.562 | 1.00 | 28.93 | N |

TABLE 16-7-continued

Coordinates of *P. tremuloides* IspS

| ATOM | 7128 | CA | ALA | A | 468 | −41.095 | 28.310 | 22.404 | 1.00 | 28.45 | C |
|---|---|---|---|---|---|---|---|---|---|---|---|
| ATOM | 7130 | CB | ALA | A | 468 | −40.613 | 26.935 | 22.830 | 1.00 | 28.10 | C |
| ATOM | 7134 | C | ALA | A | 468 | −42.306 | 28.193 | 21.494 | 1.00 | 28.08 | C |
| ATOM | 7135 | O | ALA | A | 468 | −42.179 | 28.321 | 20.285 | 1.00 | 28.24 | O |
| ATOM | 7137 | N | THR | A | 469 | −43.479 | 27.964 | 22.080 | 1.00 | 27.58 | N |
| ATOM | 7138 | CA | THR | A | 469 | −44.719 | 27.870 | 21.322 | 1.00 | 27.26 | C |
| ATOM | 7140 | CB | THR | A | 469 | −45.928 | 27.710 | 22.261 | 1.00 | 27.28 | C |
| ATOM | 7142 | OG1 | THR | A | 469 | −46.063 | 26.330 | 22.627 | 1.00 | 27.55 | O |
| ATOM | 7144 | CG2 | THR | A | 469 | −47.222 | 28.185 | 21.597 | 1.00 | 27.34 | C |
| ATOM | 7148 | C | THR | A | 469 | −44.916 | 29.099 | 20.449 | 1.00 | 27.10 | C |
| ATOM | 7149 | O | THR | A | 469 | −45.176 | 28.989 | 19.250 | 1.00 | 27.11 | O |
| ATOM | 7151 | N | GLU | A | 470 | −44.774 | 30.267 | 21.061 | 1.00 | 26.88 | N |
| ATOM | 7152 | CA | GLU | A | 470 | −44.944 | 31.542 | 20.376 | 1.00 | 26.84 | C |
| ATOM | 7154 | CB | GLU | A | 470 | −44.832 | 32.663 | 21.400 | 1.00 | 27.07 | C |
| ATOM | 7157 | CG | GLU | A | 470 | −45.357 | 34.003 | 20.958 | 1.00 | 28.47 | C |
| ATOM | 7160 | CD | GLU | A | 470 | −45.140 | 35.087 | 22.008 | 1.00 | 30.51 | C |
| ATOM | 7161 | OE1 | GLU | A | 470 | −45.029 | 34.775 | 23.221 | 1.00 | 31.53 | O |
| ATOM | 7162 | OE2 | GLU | A | 470 | −45.083 | 36.269 | 21.608 | 1.00 | 32.59 | O |
| ATOM | 7163 | C | GLU | A | 470 | −43.926 | 31.750 | 19.239 | 1.00 | 26.48 | C |
| ATOM | 7164 | O | GLU | A | 470 | −44.261 | 32.296 | 18.184 | 1.00 | 26.29 | O |
| ATOM | 7166 | N | SER | A | 471 | −42.686 | 31.316 | 19.452 | 1.00 | 26.12 | N |
| ATOM | 7167 | CA | SER | A | 471 | −41.660 | 31.386 | 18.408 | 1.00 | 25.85 | C |
| ATOM | 7169 | CB | SER | A | 471 | −40.296 | 30.933 | 18.941 | 1.00 | 25.96 | C |
| ATOM | 7172 | OG | SER | A | 471 | −39.656 | 31.939 | 19.711 | 1.00 | 26.53 | O |
| ATOM | 7174 | C | SER | A | 471 | −42.036 | 30.529 | 17.208 | 1.00 | 25.35 | C |
| ATOM | 7175 | O | SER | A | 471 | −41.761 | 30.899 | 16.067 | 1.00 | 25.43 | O |
| ATOM | 7177 | N | VAL | A | 472 | −42.653 | 29.381 | 17.482 | 1.00 | 24.95 | N |
| ATOM | 7178 | CA | VAL | A | 472 | −43.097 | 28.451 | 16.438 | 1.00 | 24.65 | C |
| ATOM | 7180 | CB | VAL | A | 472 | −43.485 | 27.055 | 17.024 | 1.00 | 24.57 | C |
| ATOM | 7182 | CG1 | VAL | A | 472 | −44.257 | 26.222 | 16.016 | 1.00 | 23.23 | C |
| ATOM | 7186 | CG2 | VAL | A | 472 | −42.232 | 26.309 | 17.494 | 1.00 | 23.83 | C |
| ATOM | 7190 | C | VAL | A | 472 | −44.252 | 29.039 | 15.631 | 1.00 | 24.71 | C |
| ATOM | 7191 | O | VAL | A | 472 | −44.369 | 28.776 | 14.440 | 1.00 | 24.63 | O |
| ATOM | 7193 | N | MET | A | 473 | −45.073 | 29.866 | 16.269 | 1.00 | 24.79 | N |
| ATOM | 7194 | CA | MET | A | 473 | −46.143 | 30.591 | 15.565 | 1.00 | 24.94 | C |
| ATOM | 7196 | CB | MET | A | 473 | −47.059 | 31.266 | 16.576 | 1.00 | 25.11 | C |
| ATOM | 7199 | CG | MET | A | 473 | −47.683 | 30.335 | 17.560 | 1.00 | 25.11 | C |
| ATOM | 7202 | SD | MET | A | 473 | −48.967 | 29.391 | 16.780 | 1.00 | 25.35 | S |
| ATOM | 7203 | CE | MET | A | 473 | −50.064 | 29.163 | 18.189 | 1.00 | 26.11 | C |
| ATOM | 7207 | C | MET | A | 473 | −45.613 | 31.672 | 14.605 | 1.00 | 24.86 | C |
| ATOM | 7208 | O | MET | A | 473 | −46.132 | 31.849 | 13.513 | 1.00 | 24.57 | O |
| ATOM | 7210 | N | ASN | A | 474 | −44.589 | 32.405 | 15.032 | 1.00 | 24.89 | N |
| ATOM | 7211 | CA | ASN | A | 474 | −43.951 | 33.383 | 14.166 | 1.00 | 25.00 | C |
| ATOM | 7213 | CB | ASN | A | 474 | −43.009 | 34.278 | 14.966 | 1.00 | 25.12 | C |
| ATOM | 7216 | CG | ASN | A | 474 | −43.700 | 34.966 | 16.127 | 1.00 | 25.77 | C |
| ATOM | 7217 | OD1 | ASN | A | 474 | −43.058 | 35.312 | 17.114 | 1.00 | 26.96 | O |
| ATOM | 7218 | ND2 | ASN | A | 474 | −45.015 | 35.163 | 16.021 | 1.00 | 26.31 | N |
| ATOM | 7221 | C | ASN | A | 474 | −43.195 | 32.707 | 13.024 | 1.00 | 24.84 | C |
| ATOM | 7222 | O | ASN | A | 474 | −42.979 | 33.313 | 11.973 | 1.00 | 25.07 | O |
| ATOM | 7224 | N | LEU | A | 475 | −42.792 | 31.455 | 13.227 | 1.00 | 24.46 | N |
| ATOM | 7225 | CA | LEU | A | 475 | −42.218 | 30.671 | 12.142 | 1.00 | 24.06 | C |
| ATOM | 7227 | CB | LEU | A | 475 | −41.596 | 29.367 | 12.653 | 1.00 | 24.27 | C |
| ATOM | 7230 | CG | LEU | A | 475 | −40.307 | 29.072 | 11.886 | 1.00 | 25.08 | C |
| ATOM | 7232 | CD1 | LEU | A | 475 | −39.207 | 30.000 | 12.419 | 1.00 | 25.89 | C |
| ATOM | 7236 | CD2 | LEU | A | 475 | −39.887 | 27.622 | 11.985 | 1.00 | 25.33 | C |
| ATOM | 7240 | C | LEU | A | 475 | −43.278 | 30.365 | 11.085 | 1.00 | 23.26 | C |
| ATOM | 7241 | O | LEU | A | 475 | −43.018 | 30.479 | 9.884 | 1.00 | 22.90 | O |
| ATOM | 7243 | N | ILE | A | 476 | −44.471 | 29.978 | 11.534 | 1.00 | 22.53 | N |
| ATOM | 7244 | CA | ILE | A | 476 | −45.544 | 29.632 | 10.606 | 1.00 | 21.93 | C |
| ATOM | 7246 | CB | ILE | A | 476 | −46.773 | 29.017 | 11.308 | 1.00 | 21.58 | C |
| ATOM | 7248 | CG1 | ILE | A | 476 | −46.499 | 27.550 | 11.664 | 1.00 | 21.32 | C |
| ATOM | 7251 | CD1 | ILE | A | 476 | −47.552 | 26.902 | 12.598 | 1.00 | 20.33 | C |
| ATOM | 7255 | CG2 | ILE | A | 476 | −47.994 | 29.104 | 10.428 | 1.00 | 20.46 | C |
| ATOM | 7259 | C | ILE | A | 476 | −45.926 | 30.887 | 9.853 | 1.00 | 22.07 | C |
| ATOM | 7260 | O | ILE | A | 476 | −46.007 | 30.869 | 8.626 | 1.00 | 22.47 | O |
| ATOM | 7262 | N | ASP | A | 477 | −46.122 | 31.982 | 10.584 | 1.00 | 21.81 | N |
| ATOM | 7263 | CA | ASP | A | 477 | −46.483 | 33.245 | 9.970 | 1.00 | 21.56 | C |
| ATOM | 7265 | CB | ASP | A | 477 | −46.643 | 34.337 | 11.032 | 1.00 | 21.89 | C |
| ATOM | 7268 | CG | ASP | A | 477 | −47.962 | 34.217 | 11.817 | 1.00 | 23.39 | C |
| ATOM | 7269 | OD1 | ASP | A | 477 | −48.854 | 33.441 | 11.375 | 1.00 | 24.41 | O |
| ATOM | 7270 | OD2 | ASP | A | 477 | −48.103 | 34.902 | 12.875 | 1.00 | 23.80 | O |
| ATOM | 7271 | C | ASP | A | 477 | −45.425 | 33.626 | 8.947 | 1.00 | 21.06 | C |
| ATOM | 7272 | O | ASP | A | 477 | −45.759 | 33.913 | 7.795 | 1.00 | 20.78 | O |
| ATOM | 7274 | N | GLU | A | 478 | −44.156 | 33.591 | 9.361 | 1.00 | 20.63 | N |
| ATOM | 7275 | CA | GLU | A | 478 | −43.027 | 33.919 | 8.467 | 1.00 | 20.45 | C |
| ATOM | 7277 | CB | GLU | A | 478 | −41.680 | 33.793 | 9.200 | 1.00 | 20.66 | C |
| ATOM | 7280 | CG | GLU | A | 478 | −40.422 | 34.044 | 8.339 | 1.00 | 22.27 | C |
| ATOM | 7283 | CD | GLU | A | 478 | −39.107 | 33.579 | 9.018 | 1.00 | 24.72 | C |

TABLE 16-7-continued

Coordinates of *P. tremuloides* IspS

| ATOM | 7284 | OE1 | GLU | A | 478 | −38.553 | 34.367 | 9.817 | 1.00 | 26.19 | O |
|---|---|---|---|---|---|---|---|---|---|---|---|
| ATOM | 7285 | OE2 | GLU | A | 478 | −38.619 | 32.442 | 8.745 | 1.00 | 25.66 | O |
| ATOM | 7286 | C | GLU | A | 478 | −43.041 | 33.042 | 7.217 | 1.00 | 19.54 | C |
| ATOM | 7287 | O | GLU | A | 478 | −42.879 | 33.544 | 6.102 | 1.00 | 19.02 | O |
| ATOM | 7289 | N | THR | A | 479 | −43.250 | 31.743 | 7.413 | 1.00 | 18.76 | N |
| ATOM | 7290 | CA | THR | A | 479 | −43.358 | 30.808 | 6.294 | 1.00 | 18.45 | C |
| ATOM | 7292 | CB | THR | A | 479 | −43.503 | 29.339 | 6.774 | 1.00 | 18.26 | C |
| ATOM | 7294 | OG1 | THR | A | 479 | −42.334 | 28.955 | 7.494 | 1.00 | 17.30 | O |
| ATOM | 7296 | CG2 | THR | A | 479 | −43.669 | 28.394 | 5.592 | 1.00 | 17.93 | C |
| ATOM | 7300 | C | THR | A | 479 | −44.504 | 31.173 | 5.314 | 1.00 | 18.39 | C |
| ATOM | 7301 | O | THR | A | 479 | −44.280 | 31.200 | 4.103 | 1.00 | 18.58 | O |
| ATOM | 7303 | N | TRP | A | 480 | −45.709 | 31.457 | 5.818 | 1.00 | 17.85 | N |
| ATOM | 7304 | CA | TRP | A | 480 | −46.801 | 31.909 | 4.942 | 1.00 | 17.44 | C |
| ATOM | 7306 | CB | TRP | A | 480 | −48.086 | 32.225 | 5.728 | 1.00 | 17.67 | C |
| ATOM | 7309 | CG | TRP | A | 480 | −48.969 | 31.042 | 5.888 | 1.00 | 17.09 | C |
| ATOM | 7310 | CD1 | TRP | A | 480 | −48.996 | 30.195 | 6.936 | 1.00 | 16.76 | C |
| ATOM | 7312 | NE1 | TRP | A | 480 | −49.914 | 29.216 | 6.724 | 1.00 | 17.08 | N |
| ATOM | 7314 | CE2 | TRP | A | 480 | −50.501 | 29.410 | 5.507 | 1.00 | 17.86 | C |
| ATOM | 7315 | CD2 | TRP | A | 480 | −49.930 | 30.559 | 4.954 | 1.00 | 17.15 | C |
| ATOM | 7316 | CE3 | TRP | A | 480 | −50.356 | 30.980 | 3.696 | 1.00 | 18.31 | C |
| ATOM | 7318 | CZ3 | TRP | A | 480 | −51.337 | 30.244 | 3.039 | 1.00 | 19.10 | C |
| ATOM | 7320 | CH2 | TRP | A | 480 | −51.897 | 29.107 | 3.622 | 1.00 | 18.83 | C |
| ATOM | 7322 | CZ2 | TRP | A | 480 | −51.493 | 28.673 | 4.855 | 1.00 | 18.86 | C |
| ATOM | 7324 | C | TRP | A | 480 | −46.426 | 33.124 | 4.097 | 1.00 | 17.10 | C |
| ATOM | 7325 | O | TRP | A | 480 | −46.824 | 33.215 | 2.943 | 1.00 | 17.22 | O |
| ATOM | 7327 | N | LYS | A | 481 | −45.675 | 34.062 | 4.659 | 1.00 | 16.60 | N |
| ATOM | 7328 | CA | LYS | A | 481 | −45.275 | 35.215 | 3.886 | 1.00 | 16.23 | C |
| ATOM | 7330 | CB | LYS | A | 481 | −44.566 | 36.243 | 4.747 | 1.00 | 16.42 | C |
| ATOM | 7333 | CG | LYS | A | 481 | −45.417 | 36.954 | 5.769 | 1.00 | 16.42 | C |
| ATOM | 7336 | CD | LYS | A | 481 | −44.555 | 37.979 | 6.505 | 1.00 | 16.40 | C |
| ATOM | 7339 | CE | LYS | A | 481 | −45.199 | 38.504 | 7.782 | 1.00 | 16.66 | C |
| ATOM | 7342 | NZ | LYS | A | 481 | −44.184 | 38.717 | 8.846 | 1.00 | 16.72 | N |
| ATOM | 7346 | C | LYS | A | 481 | −44.357 | 34.782 | 2.767 | 1.00 | 15.94 | C |
| ATOM | 7347 | O | LYS | A | 481 | −44.451 | 35.291 | 1.674 | 1.00 | 16.09 | O |
| ATOM | 7349 | N | LYS | A | 482 | −43.461 | 33.849 | 3.034 | 1.00 | 15.98 | N |
| ATOM | 7350 | CA | LYS | A | 482 | −42.559 | 33.369 | 1.996 | 1.00 | 16.30 | C |
| ATOM | 7352 | CB | LYS | A | 482 | −41.409 | 32.563 | 2.594 | 1.00 | 16.51 | C |
| ATOM | 7355 | CG | LYS | A | 482 | −40.354 | 33.445 | 3.286 | 1.00 | 17.46 | C |
| ATOM | 7358 | CD | LYS | A | 482 | −39.486 | 32.647 | 4.241 | 1.00 | 18.48 | C |
| ATOM | 7361 | CE | LYS | A | 482 | −38.625 | 33.548 | 5.096 | 1.00 | 18.94 | C |
| ATOM | 7364 | NZ | LYS | A | 482 | −37.865 | 32.773 | 6.129 | 1.00 | 20.40 | N |
| ATOM | 7368 | C | LYS | A | 482 | −43.296 | 32.561 | .938 | 1.00 | 16.40 | C |
| ATOM | 7369 | O | LYS | A | 482 | −42.941 | 32.614 | −.229 | 1.00 | 16.85 | O |
| ATOM | 7371 | N | MET | A | 483 | −44.328 | 31.824 | 1.332 | 1.00 | 16.57 | N |
| ATOM | 7372 | CA | MET | A | 483 | −45.149 | 31.100 | .366 | 1.00 | 16.67 | C |
| ATOM | 7374 | CB | MET | A | 483 | −46.128 | 30.156 | 1.057 | 1.00 | 16.55 | C |
| ATOM | 7377 | CG | MET | A | 483 | −45.496 | 28.923 | 1.675 | 1.00 | 16.50 | C |
| ATOM | 7380 | SD | MET | A | 483 | −46.715 | 27.684 | 2.194 | 1.00 | 17.39 | S |
| ATOM | 7381 | CE | MET | A | 483 | −47.937 | 28.704 | 3.025 | 1.00 | 17.27 | C |
| ATOM | 7385 | C | MET | A | 483 | −45.928 | 32.069 | −.495 | 1.00 | 17.06 | C |
| ATOM | 7386 | O | MET | A | 483 | −46.027 | 31.867 | −1.688 | 1.00 | 17.17 | O |
| ATOM | 7388 | N | ASN | A | 484 | −46.483 | 33.110 | .118 | 1.00 | 17.72 | N |
| ATOM | 7389 | CA | ASN | A | 484 | −47.305 | 34.093 | −.587 | 1.00 | 18.35 | C |
| ATOM | 7391 | CB | ASN | A | 484 | −47.861 | 35.129 | .397 | 1.00 | 18.26 | C |
| ATOM | 7394 | CG | ASN | A | 484 | −48.994 | 34.601 | 1.248 | 1.00 | 17.35 | C |
| ATOM | 7395 | OD1 | ASN | A | 484 | −49.597 | 33.577 | .934 | 1.00 | 17.54 | O |
| ATOM | 7396 | ND2 | ASN | A | 484 | −49.304 | 35.317 | 2.331 | 1.00 | 14.10 | N |
| ATOM | 7399 | C | ASN | A | 484 | −46.541 | 34.839 | −1.677 | 1.00 | 19.51 | C |
| ATOM | 7400 | O | ASN | A | 484 | −47.123 | 35.250 | −2.685 | 1.00 | 19.49 | O |
| ATOM | 7402 | N | LYS | A | 485 | −45.243 | 35.035 | −1.463 | 1.00 | 20.86 | N |
| ATOM | 7403 | CA | LYS | A | 485 | −44.394 | 35.681 | −2.456 | 1.00 | 22.12 | C |
| ATOM | 7405 | CB | LYS | A | 485 | −43.070 | 36.092 | −1.823 | 1.00 | 22.08 | C |
| ATOM | 7408 | CG | LYS | A | 485 | −42.229 | 37.060 | −2.641 | 1.00 | 23.09 | C |
| ATOM | 7411 | CD | LYS | A | 485 | −40.783 | 37.072 | −2.109 | 1.00 | 25.38 | C |
| ATOM | 7414 | CE | LYS | A | 485 | −40.098 | 38.460 | −2.135 | 1.00 | 26.12 | C |
| ATOM | 7417 | NZ | LYS | A | 485 | −38.943 | 38.555 | −3.086 | 1.00 | 26.61 | N |
| ATOM | 7421 | C | LYS | A | 485 | −44.164 | 34.743 | −3.656 | 1.00 | 23.36 | C |
| ATOM | 7422 | O | LYS | A | 485 | −44.120 | 35.191 | −4.802 | 1.00 | 23.00 | O |
| ATOM | 7424 | N | GLU | A | 486 | −44.027 | 33.442 | −3.400 | 1.00 | 24.99 | N |
| ATOM | 7425 | CA | GLU | A | 486 | −43.902 | 32.479 | −4.491 | 1.00 | 26.35 | C |
| ATOM | 7427 | CB | GLU | A | 486 | −43.627 | 31.061 | −3.978 | 1.00 | 26.55 | C |
| ATOM | 7430 | CG | GLU | A | 486 | −42.985 | 30.130 | −5.033 | 1.00 | 28.29 | C |
| ATOM | 7433 | CD | GLU | A | 486 | −41.466 | 30.324 | −5.191 | 1.00 | 31.11 | C |
| ATOM | 7434 | OE1 | GLU | A | 486 | −40.981 | 30.466 | −6.341 | 1.00 | 32.07 | O |
| ATOM | 7435 | OE2 | GLU | A | 486 | −40.744 | 30.335 | −4.159 | 1.00 | 33.04 | O |
| ATOM | 7436 | C | GLU | A | 486 | −45.157 | 32.501 | −5.362 | 1.00 | 27.13 | C |
| ATOM | 7437 | O | GLU | A | 486 | −45.064 | 32.618 | −6.583 | 1.00 | 27.57 | O |
| ATOM | 7439 | N | LYS | A | 487 | −46.325 | 32.422 | −4.739 | 1.00 | 28.12 | N |

TABLE 16-7-continued

Coordinates of P. tremuloides IspS

| ATOM | 7440 | CA | LYS | A | 487 | −47.582 | 32.378 | −5.485 | 1.00 | 29.12 | C |
| --- | --- | --- | --- | --- | --- | --- | --- | --- | --- | --- | --- |
| ATOM | 7442 | CB | LYS | A | 487 | −48.788 | 32.260 | −4.542 | 1.00 | 29.21 | C |
| ATOM | 7445 | CG | LYS | A | 487 | −50.167 | 32.296 | −5.235 | 1.00 | 28.57 | C |
| ATOM | 7448 | CD | LYS | A | 487 | −50.403 | 31.040 | −6.036 | 1.00 | 27.91 | C |
| ATOM | 7451 | CE | LYS | A | 487 | −51.615 | 31.141 | −6.936 | 1.00 | 28.38 | C |
| ATOM | 7454 | NZ | LYS | A | 487 | −52.874 | 31.460 | −6.211 | 1.00 | 28.03 | N |
| ATOM | 7458 | C | LYS | A | 487 | −47.756 | 33.603 | −6.352 | 1.00 | 30.18 | C |
| ATOM | 7459 | O | LYS | A | 487 | −48.308 | 33.514 | −7.446 | 1.00 | 30.21 | O |
| ATOM | 7461 | N | LEU | A | 488 | −47.295 | 34.743 | −5.844 | 1.00 | 31.64 | N |
| ATOM | 7462 | CA | LEU | A | 488 | −47.422 | 36.026 | −6.532 | 1.00 | 32.65 | C |
| ATOM | 7464 | CB | LEU | A | 488 | −47.426 | 37.144 | −5.494 | 1.00 | 32.43 | C |
| ATOM | 7467 | CG | LEU | A | 488 | −48.091 | 38.446 | −5.907 | 1.00 | 32.50 | C |
| ATOM | 7469 | CD1 | LEU | A | 488 | −49.593 | 38.288 | −5.943 | 1.00 | 32.66 | C |
| ATOM | 7473 | CD2 | LEU | A | 488 | −47.707 | 39.554 | −4.943 | 1.00 | 33.38 | C |
| ATOM | 7477 | C | LEU | A | 488 | −46.286 | 36.242 | −7.542 | 1.00 | 33.99 | C |
| ATOM | 7478 | O | LEU | A | 488 | −46.536 | 36.539 | −8.705 | 1.00 | 33.72 | O |
| ATOM | 7480 | N | GLY | A | 489 | −45.046 | 36.045 | −7.091 | 1.00 | 35.85 | N |
| ATOM | 7481 | CA | GLY | A | 489 | −43.845 | 36.361 | −7.874 | 1.00 | 37.37 | C |
| ATOM | 7484 | C | GLY | A | 489 | −43.278 | 35.221 | −8.709 | 1.00 | 38.76 | C |
| ATOM | 7485 | O | GLY | A | 489 | −42.414 | 34.467 | −8.250 | 1.00 | 39.06 | O |
| ATOM | 7487 | N | GLY | A | 490 | −43.760 | 35.119 | −9.947 | 1.00 | 40.26 | N |
| ATOM | 7488 | CA | GLY | A | 490 | −43.285 | 34.130 | −10.927 | 1.00 | 41.03 | C |
| ATOM | 7491 | C | GLY | A | 490 | −42.193 | 33.194 | −10.436 | 1.00 | 41.61 | C |
| ATOM | 7492 | O | GLY | A | 490 | −41.010 | 33.547 | −10.423 | 1.00 | 41.62 | O |
| ATOM | 7494 | N | SER | A | 491 | −42.590 | 31.996 | −10.023 | 1.00 | 42.17 | N |
| ATOM | 7495 | CA | SER | A | 491 | −41.619 | 30.962 | −9.662 | 1.00 | 42.54 | C |
| ATOM | 7497 | CB | SER | A | 491 | −42.279 | 29.909 | −8.741 | 1.00 | 42.63 | C |
| ATOM | 7500 | OG | SER | A | 491 | −43.451 | 29.345 | −9.294 | 1.00 | 42.44 | O |
| ATOM | 7502 | C | SER | A | 491 | −41.032 | 30.349 | −10.952 | 1.00 | 42.50 | C |
| ATOM | 7503 | O | SER | A | 491 | −41.117 | 30.961 | −12.030 | 1.00 | 42.57 | O |
| ATOM | 7505 | N | LEU | A | 492 | −40.405 | 29.177 | −10.843 | 1.00 | 42.18 | N |
| ATOM | 7506 | CA | LEU | A | 492 | −40.185 | 28.333 | −12.021 | 1.00 | 41.96 | C |
| ATOM | 7508 | CB | LEU | A | 492 | −39.110 | 27.270 | −11.782 | 1.00 | 42.39 | C |
| ATOM | 7511 | CG | LEU | A | 492 | −37.695 | 27.671 | −11.353 | 1.00 | 44.21 | C |
| ATOM | 7513 | CD1 | LEU | A | 492 | −36.783 | 26.438 | −11.498 | 1.00 | 45.26 | C |
| ATOM | 7517 | CD2 | LEU | A | 492 | −37.120 | 28.896 | −12.129 | 1.00 | 45.51 | C |
| ATOM | 7521 | C | LEU | A | 492 | −41.479 | 27.610 | −12.356 | 1.00 | 40.88 | C |
| ATOM | 7522 | O | LEU | A | 492 | −41.713 | 27.244 | −13.504 | 1.00 | 40.78 | O |
| ATOM | 7524 | N | PHE | A | 493 | −42.308 | 27.409 | −11.339 | 1.00 | 39.61 | N |
| ATOM | 7525 | CA | PHE | A | 493 | −43.500 | 26.595 | −11.460 | 1.00 | 38.85 | C |
| ATOM | 7527 | CB | PHE | A | 493 | −43.783 | 25.911 | −10.124 | 1.00 | 38.62 | C |
| ATOM | 7530 | CG | PHE | A | 493 | −42.725 | 24.937 | −9.713 | 1.00 | 37.16 | C |
| ATOM | 7531 | CD1 | PHE | A | 493 | −42.901 | 23.587 | −9.916 | 1.00 | 35.26 | C |
| ATOM | 7533 | CE1 | PHE | A | 493 | −41.934 | 22.698 | −9.546 | 1.00 | 34.86 | C |
| ATOM | 7535 | CZ | PHE | A | 493 | −40.769 | 23.143 | −8.966 | 1.00 | 35.09 | C |
| ATOM | 7537 | CE2 | PHE | A | 493 | −40.574 | 24.482 | −8.759 | 1.00 | 35.45 | C |
| ATOM | 7539 | CD2 | PHE | A | 493 | −41.549 | 25.374 | −9.130 | 1.00 | 36.36 | C |
| ATOM | 7541 | C | PHE | A | 493 | −44.714 | 27.412 | −11.890 | 1.00 | 38.62 | C |
| ATOM | 7542 | O | PHE | A | 493 | −44.756 | 28.621 | −11.702 | 1.00 | 38.86 | O |
| ATOM | 7544 | N | ALA | A | 494 | −45.698 | 26.731 | −12.469 | 1.00 | 38.32 | N |
| ATOM | 7545 | CA | ALA | A | 494 | −46.977 | 27.337 | −12.843 | 1.00 | 38.09 | C |
| ATOM | 7547 | CB | ALA | A | 494 | −47.658 | 26.486 | −13.906 | 1.00 | 38.17 | C |
| ATOM | 7551 | C | ALA | A | 494 | −47.891 | 27.479 | −11.623 | 1.00 | 37.76 | C |
| ATOM | 7552 | O | ALA | A | 494 | −48.039 | 26.541 | −10.845 | 1.00 | 38.15 | O |
| ATOM | 7554 | N | LYS | A | 495 | −48.541 | 28.629 | −11.484 | 1.00 | 37.15 | N |
| ATOM | 7555 | CA | LYS | A | 495 | −49.321 | 28.947 | −10.270 | 1.00 | 36.53 | C |
| ATOM | 7557 | CB | LYS | A | 495 | −50.116 | 30.258 | −10.477 | 1.00 | 36.90 | C |
| ATOM | 7560 | CG | LYS | A | 495 | −49.235 | 31.524 | −10.582 | 1.00 | 37.72 | C |
| ATOM | 7563 | CD | LYS | A | 495 | −50.061 | 32.826 | −10.585 | 1.00 | 38.87 | C |
| ATOM | 7566 | CE | LYS | A | 495 | −49.140 | 34.065 | −10.665 | 1.00 | 39.78 | C |
| ATOM | 7569 | NZ | LYS | A | 495 | −49.786 | 35.369 | −10.282 | 1.00 | 39.78 | N |
| ATOM | 7573 | C | LYS | A | 495 | −50.238 | 27.809 | −9.724 | 1.00 | 35.25 | C |
| ATOM | 7574 | O | LYS | A | 495 | −50.261 | 27.563 | −8.523 | 1.00 | 34.91 | O |
| ATOM | 7576 | N | PRO | A | 496 | −50.978 | 27.107 | −10.599 | 1.00 | 33.76 | N |
| ATOM | 7577 | CA | PRO | A | 496 | −51.846 | 26.015 | −10.162 | 1.00 | 32.74 | C |
| ATOM | 7579 | CB | PRO | A | 496 | −52.222 | 25.340 | −11.474 | 1.00 | 32.99 | C |
| ATOM | 7582 | CG | PRO | A | 496 | −52.337 | 26.470 | −12.385 | 1.00 | 33.75 | C |
| ATOM | 7585 | CD | PRO | A | 496 | −51.196 | 27.400 | −12.022 | 1.00 | 33.83 | C |
| ATOM | 7588 | C | PRO | A | 496 | −51.194 | 24.998 | −9.267 | 1.00 | 31.24 | C |
| ATOM | 7589 | O | PRO | A | 496 | −51.822 | 24.522 | −8.331 | 1.00 | 31.54 | O |
| ATOM | 7590 | N | PHE | A | 497 | −49.954 | 24.642 | −9.566 | 1.00 | 29.40 | N |
| ATOM | 7591 | CA | PHE | A | 497 | −49.229 | 23.726 | −8.708 | 1.00 | 27.76 | C |
| ATOM | 7593 | CB | PHE | A | 497 | −48.162 | 22.948 | −9.474 | 1.00 | 27.62 | C |
| ATOM | 7596 | CG | PHE | A | 497 | −47.351 | 22.040 | −8.597 | 1.00 | 26.33 | C |
| ATOM | 7597 | CD1 | PHE | A | 497 | −47.944 | 20.969 | −7.974 | 1.00 | 24.96 | C |
| ATOM | 7599 | CE1 | PHE | A | 497 | −47.218 | 20.151 | −7.156 | 1.00 | 25.04 | C |
| ATOM | 7601 | CZ | PHE | A | 497 | −45.875 | 20.396 | −6.940 | 1.00 | 24.79 | C |
| ATOM | 7603 | CE2 | PHE | A | 497 | −45.274 | 21.457 | −7.549 | 1.00 | 24.73 | C |

TABLE 16-7-continued

Coordinates of *P. tremuloides* IspS

| ATOM | 7605 | CD2 | PHE | A | 497 | −46.010 | 22.282 | −8.366 | 1.00 | 25.48 | C |
| ATOM | 7607 | C | PHE | A | 497 | −48.592 | 24.407 | −7.494 | 1.00 | 26.59 | C |
| ATOM | 7608 | O | PHE | A | 497 | −48.361 | 23.738 | −6.500 | 1.00 | 26.77 | O |
| ATOM | 7610 | N | VAL | A | 498 | −48.291 | 25.704 | −7.535 | 1.00 | 24.83 | N |
| ATOM | 7611 | CA | VAL | A | 498 | −47.869 | 26.338 | −6.289 | 1.00 | 23.86 | C |
| ATOM | 7613 | CB | VAL | A | 498 | −47.181 | 27.722 | −6.455 | 1.00 | 23.47 | C |
| ATOM | 7615 | CG1 | VAL | A | 498 | −48.163 | 28.755 | −6.759 | 1.00 | 24.57 | C |
| ATOM | 7619 | CG2 | VAL | A | 498 | −46.151 | 27.690 | −7.551 | 1.00 | 23.54 | C |
| ATOM | 7623 | C | VAL | A | 498 | −49.094 | 26.396 | −5.355 | 1.00 | 22.97 | C |
| ATOM | 7624 | O | VAL | A | 498 | −48.978 | 26.130 | −4.161 | 1.00 | 23.39 | O |
| ATOM | 7626 | N | GLU | A | 499 | −50.268 | 26.687 | −5.903 | 1.00 | 21.68 | N |
| ATOM | 7627 | CA | GLU | A | 499 | −51.473 | 26.719 | −5.106 | 1.00 | 20.84 | C |
| ATOM | 7629 | CB | GLU | A | 499 | −52.677 | 27.136 | −5.930 | 1.00 | 20.99 | C |
| ATOM | 7632 | CG | GLU | A | 499 | −53.957 | 27.352 | −5.099 | 1.00 | 21.25 | C |
| ATOM | 7635 | CD | GLU | A | 499 | −53.930 | 28.630 | −4.265 | 1.00 | 21.77 | C |
| ATOM | 7636 | OE1 | GLU | A | 499 | −52.982 | 29.448 | −4.383 | 1.00 | 20.74 | O |
| ATOM | 7637 | OE2 | GLU | A | 499 | −54.876 | 28.812 | −3.476 | 1.00 | 22.76 | O |
| ATOM | 7638 | C | GLU | A | 499 | −51.766 | 25.371 | −4.497 | 1.00 | 20.35 | C |
| ATOM | 7639 | O | GLU | A | 499 | −52.137 | 25.308 | −3.318 | 1.00 | 20.78 | O |
| ATOM | 7641 | N | THR | A | 500 | −51.629 | 24.286 | −5.264 | 1.00 | 19.40 | N |
| ATOM | 7642 | CA | THR | A | 500 | −51.894 | 22.970 | −4.667 | 1.00 | 18.94 | C |
| ATOM | 7644 | CB | THR | A | 500 | −51.993 | 21.782 | −5.683 | 1.00 | 18.96 | C |
| ATOM | 7646 | OG1 | THR | A | 500 | −50.708 | 21.475 | −6.202 | 1.00 | 19.44 | O |
| ATOM | 7648 | CG2 | THR | A | 500 | −52.991 | 22.071 | −6.835 | 1.00 | 18.75 | C |
| ATOM | 7652 | C | THR | A | 500 | −50.895 | 22.674 | −3.526 | 1.00 | 18.20 | C |
| ATOM | 7653 | O | THR | A | 500 | −51.280 | 22.100 | −2.519 | 1.00 | 17.68 | O |
| ATOM | 7655 | N | ALA | A | 501 | −49.646 | 23.119 | −3.666 | 1.00 | 17.49 | N |
| ATOM | 7656 | CA | ALA | A | 501 | −48.663 | 23.021 | −2.593 | 1.00 | 17.18 | C |
| ATOM | 7658 | CB | ALA | A | 501 | −47.348 | 23.563 | −3.051 | 1.00 | 16.98 | C |
| ATOM | 7662 | C | ALA | A | 501 | −49.120 | 23.770 | −1.338 | 1.00 | 17.38 | C |
| ATOM | 7663 | O | ALA | A | 501 | −49.098 | 23.219 | −.230 | 1.00 | 17.45 | O |
| ATOM | 7665 | N | ILE | A | 502 | −49.517 | 25.031 | −1.508 | 1.00 | 17.29 | N |
| ATOM | 7666 | CA | ILE | A | 502 | −49.971 | 25.857 | −.386 | 1.00 | 17.07 | C |
| ATOM | 7668 | CB | ILE | A | 502 | −50.353 | 27.304 | −.846 | 1.00 | 17.09 | C |
| ATOM | 7670 | CG1 | ILE | A | 502 | −49.092 | 28.069 | −1.286 | 1.00 | 17.17 | C |
| ATOM | 7673 | CD1 | ILE | A | 502 | −49.345 | 29.345 | −2.116 | 1.00 | 16.25 | C |
| ATOM | 7677 | CG2 | ILE | A | 502 | −51.110 | 28.076 | .265 | 1.00 | 16.14 | C |
| ATOM | 7681 | C | ILE | A | 502 | −51.155 | 25.168 | .285 | 1.00 | 17.24 | C |
| ATOM | 7682 | O | ILE | A | 502 | −51.265 | 25.163 | 1.516 | 1.00 | 17.03 | O |
| ATOM | 7684 | N | ASN | A | 503 | −52.022 | 24.559 | −.522 | 1.00 | 17.32 | N |
| ATOM | 7685 | CA | ASN | A | 503 | −53.167 | 23.823 | .022 | 1.00 | 17.75 | C |
| ATOM | 7687 | CB | ASN | A | 503 | −53.986 | 23.221 | −1.121 | 1.00 | 17.70 | C |
| ATOM | 7690 | CG | ASN | A | 503 | −54.760 | 24.261 | −1.888 | 1.00 | 18.41 | C |
| ATOM | 7691 | OD1 | ASN | A | 503 | −55.058 | 25.334 | −1.382 | 1.00 | 18.94 | O |
| ATOM | 7692 | ND2 | ASN | A | 503 | −55.107 | 23.939 | −3.119 | 1.00 | 20.42 | N |
| ATOM | 7695 | C | ASN | A | 503 | −52.803 | 22.727 | 1.075 | 1.00 | 17.74 | C |
| ATOM | 7696 | O | ASN | A | 503 | −53.619 | 22.387 | 1.949 | 1.00 | 17.96 | O |
| ATOM | 7698 | N | LEU | A | 504 | −51.589 | 22.185 | .993 | 1.00 | 17.23 | N |
| ATOM | 7699 | CA | LEU | A | 504 | −51.105 | 21.249 | 1.994 | 1.00 | 17.10 | C |
| ATOM | 7701 | CB | LEU | A | 504 | −49.745 | 20.686 | 1.583 | 1.00 | 17.28 | C |
| ATOM | 7704 | CG | LEU | A | 504 | −49.213 | 19.528 | 2.426 | 1.00 | 17.29 | C |
| ATOM | 7706 | CD1 | LEU | A | 504 | −49.570 | 18.196 | 1.762 | 1.00 | 17.22 | C |
| ATOM | 7710 | CD2 | LEU | A | 504 | −47.708 | 19.686 | 2.616 | 1.00 | 16.83 | C |
| ATOM | 7714 | C | LEU | A | 504 | −50.971 | 21.939 | 3.347 | 1.00 | 16.97 | C |
| ATOM | 7715 | O | LEU | A | 504 | −51.237 | 21.330 | 4.379 | 1.00 | 16.84 | O |
| ATOM | 7717 | N | ALA | A | 505 | −50.535 | 23.201 | 3.330 | 1.00 | 16.90 | N |
| ATOM | 7718 | CA | ALA | A | 505 | −50.433 | 24.015 | 4.540 | 1.00 | 16.68 | C |
| ATOM | 7720 | CB | ALA | A | 505 | −49.739 | 25.309 | 4.243 | 1.00 | 16.54 | C |
| ATOM | 7724 | C | ALA | A | 505 | −51.826 | 24.281 | 5.074 | 1.00 | 16.77 | C |
| ATOM | 7725 | O | ALA | A | 505 | −52.087 | 24.123 | 6.266 | 1.00 | 16.80 | O |
| ATOM | 7727 | N | ARG | A | 506 | −52.726 | 24.664 | 4.172 | 1.00 | 16.82 | N |
| ATOM | 7728 | CA | ARG | A | 506 | −54.128 | 24.875 | 4.521 | 1.00 | 16.84 | C |
| ATOM | 7730 | CB | ARG | A | 506 | −54.944 | 25.274 | 3.286 | 1.00 | 16.86 | C |
| ATOM | 7733 | CG | ARG | A | 506 | −54.649 | 26.661 | 2.795 | 1.00 | 16.27 | C |
| ATOM | 7736 | CD | ARG | A | 506 | −55.586 | 27.090 | 1.726 | 1.00 | 15.26 | C |
| ATOM | 7739 | NE | ARG | A | 506 | −55.240 | 28.436 | 1.273 | 1.00 | 15.31 | N |
| ATOM | 7741 | CZ | ARG | A | 506 | −54.744 | 28.758 | .082 | 1.00 | 14.28 | C |
| ATOM | 7742 | NH1 | ARG | A | 506 | −54.519 | 27.856 | −.856 | 1.00 | 14.12 | N |
| ATOM | 7745 | NH2 | ARG | A | 506 | −54.471 | 30.018 | −.176 | 1.00 | 15.94 | N |
| ATOM | 7748 | C | ARG | A | 506 | −54.732 | 23.631 | 5.122 | 1.00 | 16.96 | C |
| ATOM | 7749 | O | ARG | A | 506 | −55.480 | 23.707 | 6.089 | 1.00 | 16.71 | O |
| ATOM | 7751 | N | GLN | A | 507 | −54.415 | 22.481 | 4.542 | 1.00 | 17.37 | N |
| ATOM | 7752 | CA | GLN | A | 507 | −54.962 | 21.233 | 5.048 | 1.00 | 17.87 | C |
| ATOM | 7754 | CB | GLN | A | 507 | −54.712 | 20.075 | 4.087 | 1.00 | 17.80 | C |
| ATOM | 7757 | CG | GLN | A | 507 | −55.293 | 18.740 | 4.571 | 1.00 | 17.24 | C |
| ATOM | 7760 | CD | GLN | A | 507 | −56.777 | 18.805 | 4.860 | 1.00 | 16.23 | C |
| ATOM | 7761 | OE1 | GLN | A | 507 | −57.506 | 19.585 | 4.250 | 1.00 | 16.66 | O |
| ATOM | 7762 | NE2 | GLN | A | 507 | −57.233 | 17.980 | 5.790 | 1.00 | 14.96 | N |

TABLE 16-7-continued

Coordinates of *P. tremuloides* IspS

| ATOM | 7765 | C | GLN | A | 507 | −54.401 | 20.890 | 6.423 | 1.00 | 18.28 | C |
| ATOM | 7766 | O | GLN | A | 507 | −55.148 | 20.419 | 7.287 | 1.00 | 18.53 | O |
| ATOM | 7768 | N | SER | A | 508 | −53.096 | 21.113 | 6.609 | 1.00 | 18.50 | N |
| ATOM | 7769 | CA | SER | A | 508 | −52.435 | 20.924 | 7.908 | 1.00 | 18.54 | C |
| ATOM | 7771 | CB | SER | A | 508 | −50.979 | 21.385 | 7.856 | 1.00 | 18.40 | C |
| ATOM | 7774 | OG | SER | A | 508 | −50.259 | 20.694 | 6.857 | 1.00 | 18.51 | O |
| ATOM | 7776 | C | SER | A | 508 | −53.147 | 21.752 | 8.942 | 1.00 | 18.78 | C |
| ATOM | 7777 | O | SER | A | 508 | −53.535 | 21.278 | 10.006 | 1.00 | 18.33 | O |
| ATOM | 7779 | N | HIS | A | 509 | −53.324 | 23.014 | 8.599 | 1.00 | 19.37 | N |
| ATOM | 7780 | CA | HIS | A | 509 | −54.014 | 23.922 | 9.466 | 1.00 | 19.92 | C |
| ATOM | 7782 | CB | HIS | A | 509 | −54.126 | 25.295 | 8.818 | 1.00 | 20.07 | C |
| ATOM | 7785 | CG | HIS | A | 509 | −53.000 | 26.188 | 9.174 | 1.00 | 19.82 | C |
| ATOM | 7786 | ND1 | HIS | A | 509 | −52.079 | 26.631 | 8.255 | 1.00 | 19.73 | N |
| ATOM | 7788 | CE1 | HIS | A | 509 | −51.187 | 27.383 | 8.866 | 1.00 | 20.25 | C |
| ATOM | 7790 | NE2 | HIS | A | 509 | −51.485 | 27.426 | 10.149 | 1.00 | 21.66 | N |
| ATOM | 7792 | CD2 | HIS | A | 509 | −52.615 | 26.682 | 10.368 | 1.00 | 20.98 | C |
| ATOM | 7794 | C | HIS | A | 509 | −55.389 | 23.448 | 9.839 | 1.00 | 20.41 | C |
| ATOM | 7795 | O | HIS | A | 509 | −55.821 | 23.694 | 10.934 | 1.00 | 20.22 | O |
| ATOM | 7797 | N | CYS | A | 510 | −56.093 | 22.808 | 8.918 | 1.00 | 21.33 | N |
| ATOM | 7798 | CA | CYS | A | 510 | −57.470 | 22.396 | 9.189 | 1.00 | 22.03 | C |
| ATOM | 7800 | CB | CYS | A | 510 | −58.278 | 22.383 | 7.894 | 1.00 | 21.90 | C |
| ATOM | 7803 | SG | CYS | A | 510 | −58.522 | 24.055 | 7.270 | 1.00 | 21.93 | S |
| ATOM | 7805 | C | CYS | A | 510 | −57.527 | 21.054 | 9.908 | 1.00 | 22.60 | C |
| ATOM | 7806 | O | CYS | A | 510 | −58.423 | 20.822 | 10.706 | 1.00 | 22.23 | O |
| ATOM | 7808 | N | THR | A | 511 | −56.553 | 20.194 | 9.627 | 1.00 | 23.67 | N |
| ATOM | 7809 | CA | THR | A | 511 | −56.421 | 18.920 | 10.305 | 1.00 | 24.81 | C |
| ATOM | 7811 | CB | THR | A | 511 | −55.437 | 18.000 | 9.565 | 1.00 | 24.70 | C |
| ATOM | 7813 | OG1 | THR | A | 511 | −56.071 | 17.485 | 8.394 | 1.00 | 24.45 | O |
| ATOM | 7815 | CG2 | THR | A | 511 | −55.003 | 16.844 | 10.448 | 1.00 | 24.23 | C |
| ATOM | 7819 | C | THR | A | 511 | −55.965 | 19.086 | 11.756 | 1.00 | 26.22 | C |
| ATOM | 7820 | O | THR | A | 511 | −56.685 | 18.717 | 12.679 | 1.00 | 26.12 | O |
| ATOM | 7822 | N | TYR | A | 512 | −54.775 | 19.643 | 11.959 | 1.00 | 28.08 | N |
| ATOM | 7823 | CA | TYR | A | 512 | −54.177 | 19.657 | 13.298 | 1.00 | 29.63 | C |
| ATOM | 7825 | CB | TYR | A | 512 | −52.663 | 19.783 | 13.238 | 1.00 | 29.67 | C |
| ATOM | 7828 | CG | TYR | A | 512 | −52.117 | 18.579 | 12.560 | 1.00 | 29.56 | C |
| ATOM | 7829 | CD1 | TYR | A | 512 | −51.965 | 17.395 | 13.246 | 1.00 | 29.66 | C |
| ATOM | 7831 | CE1 | TYR | A | 512 | −51.507 | 16.273 | 12.614 | 1.00 | 30.94 | C |
| ATOM | 7833 | CZ | TYR | A | 512 | −51.217 | 16.326 | 11.263 | 1.00 | 32.04 | C |
| ATOM | 7834 | OH | TYR | A | 512 | −50.757 | 15.209 | 10.608 | 1.00 | 33.78 | O |
| ATOM | 7836 | CE2 | TYR | A | 512 | −51.390 | 17.492 | 10.557 | 1.00 | 31.29 | C |
| ATOM | 7838 | CD2 | TYR | A | 512 | −51.847 | 18.600 | 11.205 | 1.00 | 30.53 | C |
| ATOM | 7840 | C | TYR | A | 512 | −54.812 | 20.676 | 14.206 | 1.00 | 31.11 | C |
| ATOM | 7841 | O | TYR | A | 512 | −55.494 | 20.277 | 15.139 | 1.00 | 31.34 | O |
| ATOM | 7843 | N | HIS | A | 513 | −54.583 | 21.969 | 13.966 | 1.00 | 32.89 | N |
| ATOM | 7844 | CA | HIS | A | 513 | −55.505 | 23.023 | 14.442 | 1.00 | 34.48 | C |
| ATOM | 7846 | CB | HIS | A | 513 | −56.372 | 23.461 | 13.225 | 1.00 | 35.13 | C |
| ATOM | 7849 | CG | HIS | A | 513 | −57.704 | 24.108 | 13.529 | 1.00 | 37.10 | C |
| ATOM | 7850 | ND1 | HIS | A | 513 | −58.265 | 25.040 | 12.678 | 1.00 | 38.69 | N |
| ATOM | 7852 | CE1 | HIS | A | 513 | −59.442 | 25.416 | 13.151 | 1.00 | 39.23 | C |
| ATOM | 7854 | NE2 | HIS | A | 513 | −59.678 | 24.751 | 14.268 | 1.00 | 38.18 | N |
| ATOM | 7856 | CD2 | HIS | A | 513 | −58.615 | 23.915 | 14.519 | 1.00 | 38.17 | C |
| ATOM | 7858 | C | HIS | A | 513 | −56.337 | 22.503 | 15.610 | 1.00 | 35.00 | C |
| ATOM | 7859 | O | HIS | A | 513 | −56.302 | 23.074 | 16.712 | 1.00 | 35.48 | O |
| ATOM | 7861 | N | ASN | A | 514 | −57.079 | 21.419 | 15.351 | 1.00 | 35.23 | N |
| ATOM | 7862 | CA | ASN | A | 514 | −57.934 | 20.768 | 16.347 | 1.00 | 35.46 | C |
| ATOM | 7864 | CB | ASN | A | 514 | −58.342 | 19.343 | 15.903 | 1.00 | 35.39 | C |
| ATOM | 7867 | CG | ASN | A | 514 | −59.383 | 19.345 | 14.786 | 1.00 | 34.01 | C |
| ATOM | 7868 | OD1 | ASN | A | 514 | −59.336 | 20.185 | 13.896 | 1.00 | 33.36 | O |
| ATOM | 7869 | ND2 | ASN | A | 514 | −60.315 | 18.406 | 14.833 | 1.00 | 31.13 | N |
| ATOM | 7872 | C | ASN | A | 514 | −57.464 | 20.751 | 17.818 | 1.00 | 36.15 | C |
| ATOM | 7873 | O | ASN | A | 514 | −56.397 | 20.211 | 18.153 | 1.00 | 36.13 | O |
| ATOM | 7875 | N | GLY | A | 515 | −58.277 | 21.430 | 18.640 | 1.00 | 36.95 | N |
| ATOM | 7876 | CA | GLY | A | 515 | −58.427 | 21.235 | 20.079 | 1.00 | 37.43 | C |
| ATOM | 7879 | C | GLY | A | 515 | −59.724 | 20.470 | 20.381 | 1.00 | 38.18 | C |
| ATOM | 7880 | O | GLY | A | 515 | −59.636 | 19.418 | 21.021 | 1.00 | 38.57 | O |
| ATOM | 7882 | N | ASP | A | 516 | −60.930 | 20.921 | 19.969 | 1.00 | 38.73 | N |
| ATOM | 7883 | CA | ASP | A | 516 | −61.249 | 22.194 | 19.293 | 1.00 | 39.26 | C |
| ATOM | 7885 | CB | ASP | A | 516 | −61.607 | 21.904 | 17.845 | 1.00 | 39.51 | C |
| ATOM | 7888 | CG | ASP | A | 516 | −60.523 | 22.291 | 16.894 | 1.00 | 42.32 | C |
| ATOM | 7889 | OD1 | ASP | A | 516 | −59.613 | 23.084 | 17.286 | 1.00 | 45.56 | O |
| ATOM | 7890 | OD2 | ASP | A | 516 | −60.578 | 21.797 | 15.740 | 1.00 | 45.52 | O |
| ATOM | 7891 | C | ASP | A | 516 | −62.466 | 22.913 | 19.884 | 1.00 | 39.38 | C |
| ATOM | 7892 | O | ASP | A | 516 | −63.032 | 22.454 | 20.880 | 1.00 | 39.74 | O |
| ATOM | 7894 | N | ALA | A | 517 | −62.850 | 24.038 | 19.259 | 1.00 | 39.40 | N |
| ATOM | 7895 | CA | ALA | A | 517 | −64.140 | 24.752 | 19.481 | 1.00 | 39.50 | C |
| ATOM | 7897 | CB | ALA | A | 517 | −65.117 | 24.403 | 18.333 | 1.00 | 39.27 | C |
| ATOM | 7901 | C | ALA | A | 517 | −64.837 | 24.566 | 20.863 | 1.00 | 39.90 | C |
| ATOM | 7902 | O | ALA | A | 517 | −64.173 | 24.428 | 21.899 | 1.00 | 39.89 | O |

TABLE 16-7-continued

Coordinates of *P. tremuloides* IspS

| ATOM | 7904 | N | HIS | A | 518 | −66.175 | 24.617 | 20.876 | 1.00 | 40.33 N |
|---|---|---|---|---|---|---|---|---|---|---|
| ATOM | 7905 | CA | HIS | A | 518 | −66.973 | 24.112 | 22.016 | 1.00 | 40.73 C |
| ATOM | 7907 | CB | HIS | A | 518 | −68.091 | 25.092 | 22.396 | 1.00 | 41.22 C |
| ATOM | 7910 | CG | HIS | A | 518 | −67.578 | 26.419 | 22.866 | 1.00 | 43.58 C |
| ATOM | 7911 | ND1 | HIS | A | 518 | −67.426 | 26.725 | 24.207 | 1.00 | 45.88 N |
| ATOM | 7913 | CE1 | HIS | A | 518 | −66.938 | 27.950 | 24.320 | 1.00 | 46.42 C |
| ATOM | 7915 | NE2 | HIS | A | 518 | −66.760 | 28.446 | 23.102 | 1.00 | 46.25 N |
| ATOM | 7917 | CD2 | HIS | A | 518 | −67.145 | 27.506 | 22.174 | 1.00 | 45.24 C |
| ATOM | 7919 | C | HIS | A | 518 | −67.526 | 22.725 | 21.655 | 1.00 | 40.17 C |
| ATOM | 7920 | O | HIS | A | 518 | −68.738 | 22.501 | 21.571 | 1.00 | 40.02 O |
| ATOM | 7922 | N | THR | A | 519 | −66.581 | 21.812 | 21.448 | 1.00 | 39.64 N |
| ATOM | 7923 | CA | THR | A | 519 | −66.808 | 20.466 | 20.918 | 1.00 | 39.16 C |
| ATOM | 7925 | CB | THR | A | 519 | −67.414 | 20.469 | 19.453 | 1.00 | 39.16 C |
| ATOM | 7927 | OG1 | THR | A | 519 | −66.847 | 21.529 | 18.665 | 1.00 | 39.04 O |
| ATOM | 7929 | CG2 | THR | A | 519 | −68.942 | 20.633 | 19.480 | 1.00 | 38.82 C |
| ATOM | 7933 | C | THR | A | 519 | −65.428 | 19.771 | 20.978 | 1.00 | 38.85 C |
| ATOM | 7934 | O | THR | A | 519 | −64.391 | 20.433 | 20.878 | 1.00 | 38.66 O |
| ATOM | 7936 | N | SER | A | 520 | −65.407 | 18.455 | 21.170 | 1.00 | 38.37 N |
| ATOM | 7937 | CA | SER | A | 520 | −64.160 | 17.745 | 21.500 | 1.00 | 38.08 C |
| ATOM | 7939 | CB | SER | A | 520 | −64.514 | 16.320 | 21.931 | 1.00 | 38.06 C |
| ATOM | 7942 | OG | SER | A | 520 | −64.560 | 15.475 | 20.805 | 1.00 | 38.66 O |
| ATOM | 7944 | C | SER | A | 520 | −63.136 | 17.771 | 20.327 | 1.00 | 37.86 C |
| ATOM | 7945 | O | SER | A | 520 | −63.420 | 18.369 | 19.289 | 1.00 | 37.50 O |
| ATOM | 7947 | N | PRO | A | 521 | −61.948 | 17.122 | 20.482 | 1.00 | 37.98 N |
| ATOM | 7948 | CA | PRO | A | 521 | −60.944 | 17.170 | 19.379 | 1.00 | 37.92 C |
| ATOM | 7950 | CB | PRO | A | 521 | −59.674 | 16.527 | 19.987 | 1.00 | 37.87 C |
| ATOM | 7953 | CG | PRO | A | 521 | −60.091 | 15.919 | 21.330 | 1.00 | 38.28 C |
| ATOM | 7956 | CD | PRO | A | 521 | −61.577 | 16.137 | 21.526 | 1.00 | 38.13 C |
| ATOM | 7959 | C | PRO | A | 521 | −61.432 | 16.446 | 18.110 | 1.00 | 37.96 C |
| ATOM | 7960 | O | PRO | A | 521 | −61.769 | 17.118 | 17.140 | 1.00 | 38.09 O |
| ATOM | 7961 | N | ASP | A | 522 | −61.483 | 15.108 | 18.107 | 1.00 | 38.07 N |
| ATOM | 7962 | CA | ASP | A | 522 | −62.351 | 14.393 | 17.161 | 1.00 | 38.14 C |
| ATOM | 7964 | CB | ASP | A | 522 | −62.132 | 12.877 | 17.204 | 1.00 | 38.31 C |
| ATOM | 7967 | CG | ASP | A | 522 | −60.769 | 12.456 | 16.640 | 1.00 | 39.45 C |
| ATOM | 7968 | OD1 | ASP | A | 522 | −60.160 | 13.200 | 15.827 | 1.00 | 39.72 O |
| ATOM | 7969 | OD2 | ASP | A | 522 | −60.302 | 11.361 | 17.025 | 1.00 | 41.59 O |
| ATOM | 7970 | C | ASP | A | 522 | −63.760 | 14.780 | 17.591 | 1.00 | 37.92 C |
| ATOM | 7971 | O | ASP | A | 522 | −63.908 | 15.608 | 18.474 | 1.00 | 38.01 O |
| ATOM | 7973 | N | GLU | A | 523 | −64.799 | 14.239 | 16.974 | 1.00 | 37.79 N |
| ATOM | 7974 | CA | GLU | A | 523 | −66.150 | 14.818 | 17.121 | 1.00 | 37.83 C |
| ATOM | 7976 | CB | GLU | A | 523 | −66.618 | 14.919 | 18.591 | 1.00 | 37.85 C |
| ATOM | 7979 | CG | GLU | A | 523 | −66.346 | 13.678 | 19.483 | 1.00 | 39.40 C |
| ATOM | 7982 | CD | GLU | A | 523 | −66.916 | 13.802 | 20.931 | 1.00 | 41.49 C |
| ATOM | 7983 | OE1 | GLU | A | 523 | −67.714 | 14.737 | 21.207 | 1.00 | 42.81 O |
| ATOM | 7984 | OE2 | GLU | A | 523 | −66.566 | 12.957 | 21.800 | 1.00 | 42.04 O |
| ATOM | 7985 | C | GLU | A | 523 | −66.242 | 16.203 | 16.430 | 1.00 | 37.51 C |
| ATOM | 7986 | O | GLU | A | 523 | −67.338 | 16.751 | 16.283 | 1.00 | 37.70 O |
| ATOM | 7988 | N | LEU | A | 524 | −65.097 | 16.775 | 16.043 | 1.00 | 37.03 N |
| ATOM | 7989 | CA | LEU | A | 524 | −65.044 | 17.863 | 15.067 | 1.00 | 36.58 C |
| ATOM | 7991 | CB | LEU | A | 524 | −64.174 | 19.022 | 15.559 | 1.00 | 36.56 C |
| ATOM | 7994 | CG | LEU | A | 524 | −63.963 | 20.225 | 14.624 | 1.00 | 36.35 C |
| ATOM | 7996 | CD1 | LEU | A | 524 | −63.400 | 21.376 | 15.418 | 1.00 | 35.74 C |
| ATOM | 8000 | CD2 | LEU | A | 524 | −65.242 | 20.681 | 13.910 | 1.00 | 36.53 C |
| ATOM | 8004 | C | LEU | A | 524 | −64.478 | 17.287 | 13.782 | 1.00 | 36.20 C |
| ATOM | 8005 | O | LEU | A | 524 | −65.106 | 17.363 | 12.733 | 1.00 | 36.14 O |
| ATOM | 8007 | N | THR | A | 525 | −63.298 | 16.686 | 13.869 | 1.00 | 35.83 N |
| ATOM | 8008 | CA | THR | A | 525 | −62.756 | 15.935 | 12.748 | 1.00 | 35.66 C |
| ATOM | 8010 | CB | THR | A | 525 | −61.585 | 15.015 | 13.173 | 1.00 | 35.48 C |
| ATOM | 8012 | OG1 | THR | A | 525 | −60.776 | 15.678 | 14.152 | 1.00 | 35.55 O |
| ATOM | 8014 | CG2 | THR | A | 525 | −60.720 | 14.641 | 11.978 | 1.00 | 34.73 C |
| ATOM | 8018 | C | THR | A | 525 | −63.875 | 15.098 | 12.123 | 1.00 | 35.89 C |
| ATOM | 8019 | O | THR | A | 525 | −64.040 | 15.095 | 10.909 | 1.00 | 35.98 O |
| ATOM | 8021 | N | ARG | A | 526 | −64.667 | 14.420 | 12.954 | 1.00 | 36.06 N |
| ATOM | 8022 | CA | ARG | A | 526 | −65.739 | 13.574 | 12.448 | 1.00 | 36.18 C |
| ATOM | 8024 | CB | ARG | A | 526 | −66.340 | 12.718 | 13.555 | 1.00 | 36.56 C |
| ATOM | 8027 | CG | ARG | A | 526 | −67.416 | 11.754 | 13.054 | 1.00 | 38.35 C |
| ATOM | 8030 | CD | ARG | A | 526 | −67.781 | 10.702 | 14.092 | 1.00 | 41.00 C |
| ATOM | 8033 | NE | ARG | A | 526 | −67.740 | 11.207 | 15.470 | 1.00 | 43.08 N |
| ATOM | 8035 | CZ | ARG | A | 526 | −68.637 | 12.033 | 16.024 | 1.00 | 44.51 C |
| ATOM | 8036 | NH1 | ARG | A | 526 | −69.681 | 12.500 | 15.336 | 1.00 | 44.46 N |
| ATOM | 8039 | NH2 | ARG | A | 526 | −68.476 | 12.406 | 17.288 | 1.00 | 45.02 N |
| ATOM | 8042 | C | ARG | A | 526 | −66.834 | 14.384 | 11.774 | 1.00 | 35.68 C |
| ATOM | 8043 | O | ARG | A | 526 | −67.253 | 14.035 | 10.675 | 1.00 | 35.84 O |
| ATOM | 8045 | N | LYS | A | 527 | −67.309 | 15.447 | 12.424 | 1.00 | 35.06 N |
| ATOM | 8046 | CA | LYS | A | 527 | −68.285 | 16.343 | 11.780 | 1.00 | 34.61 C |
| ATOM | 8048 | CB | LYS | A | 527 | −68.680 | 17.528 | 12.683 | 1.00 | 34.74 C |
| ATOM | 8051 | CG | LYS | A | 527 | −69.818 | 17.225 | 13.651 | 1.00 | 35.40 C |
| ATOM | 8054 | CD | LYS | A | 527 | −70.301 | 18.452 | 14.441 | 1.00 | 35.99 C |

TABLE 16-7-continued

Coordinates of *P. tremuloides* IspS

| ATOM | 8057 | CE | LYS | A | 527 | −71.280 | 18.021 | 15.556 | 1.00 | 36.42 | C |
|---|---|---|---|---|---|---|---|---|---|---|---|
| ATOM | 8060 | NZ | LYS | A | 527 | −71.652 | 19.095 | 16.530 | 1.00 | 36.31 | N |
| ATOM | 8064 | C | LYS | A | 527 | −67.723 | 16.860 | 10.457 | 1.00 | 33.77 | C |
| ATOM | 8065 | O | LYS | A | 527 | −68.377 | 16.763 | 9.423 | 1.00 | 33.75 | O |
| ATOM | 8067 | N | ARG | A | 528 | −66.501 | 17.388 | 10.499 | 1.00 | 32.71 | N |
| ATOM | 8068 | CA | ARG | A | 528 | −65.840 | 17.929 | 9.310 | 1.00 | 31.79 | C |
| ATOM | 8070 | CB | ARG | A | 528 | −64.425 | 18.464 | 9.644 | 1.00 | 31.74 | C |
| ATOM | 8073 | CG | ARG | A | 528 | −64.419 | 19.844 | 10.330 | 1.00 | 30.90 | C |
| ATOM | 8076 | CD | ARG | A | 528 | −63.021 | 20.439 | 10.527 | 1.00 | 29.75 | C |
| ATOM | 8079 | NE | ARG | A | 528 | −63.098 | 21.745 | 11.190 | 1.00 | 29.55 | N |
| ATOM | 8081 | CZ | ARG | A | 528 | −62.056 | 22.513 | 11.528 | 1.00 | 29.96 | C |
| ATOM | 8082 | NH1 | ARG | A | 528 | −60.801 | 22.145 | 11.284 | 1.00 | 29.74 | N |
| ATOM | 8085 | NH2 | ARG | A | 528 | −62.269 | 23.677 | 12.130 | 1.00 | 30.71 | N |
| ATOM | 8088 | C | ARG | A | 528 | −65.796 | 16.904 | 8.172 | 1.00 | 30.99 | C |
| ATOM | 8089 | O | ARG | A | 528 | −66.226 | 17.206 | 7.068 | 1.00 | 30.97 | O |
| ATOM | 8091 | N | VAL | A | 529 | −65.313 | 15.694 | 8.450 | 1.00 | 30.12 | N |
| ATOM | 8092 | CA | VAL | A | 529 | −65.239 | 14.631 | 7.438 | 1.00 | 29.43 | C |
| ATOM | 8094 | CB | VAL | A | 529 | −64.557 | 13.354 | 7.972 | 1.00 | 29.39 | C |
| ATOM | 8096 | CG1 | VAL | A | 529 | −64.785 | 12.187 | 7.023 | 1.00 | 28.89 | C |
| ATOM | 8100 | CG2 | VAL | A | 529 | −63.062 | 13.589 | 8.186 | 1.00 | 29.44 | C |
| ATOM | 8104 | C | VAL | A | 529 | −66.609 | 14.243 | 6.887 | 1.00 | 28.95 | C |
| ATOM | 8105 | O | VAL | A | 529 | −66.755 | 14.016 | 5.690 | 1.00 | 29.09 | O |
| ATOM | 8107 | N | LEU | A | 530 | −67.615 | 14.153 | 7.744 | 1.00 | 28.18 | N |
| ATOM | 8108 | CA | LEU | A | 530 | −68.956 | 13.874 | 7.246 | 1.00 | 27.72 | C |
| ATOM | 8110 | CB | LEU | A | 530 | −69.971 | 13.715 | 8.395 | 1.00 | 27.75 | C |
| ATOM | 8113 | CG | LEU | A | 530 | −70.334 | 12.274 | 8.775 | 1.00 | 27.36 | C |
| ATOM | 8115 | CD1 | LEU | A | 530 | −69.096 | 11.415 | 9.050 | 1.00 | 26.86 | C |
| ATOM | 8119 | CD2 | LEU | A | 530 | −71.273 | 12.279 | 9.968 | 1.00 | 27.14 | C |
| ATOM | 8123 | C | LEU | A | 530 | −69.401 | 14.963 | 6.256 | 1.00 | 27.16 | C |
| ATOM | 8124 | O | LEU | A | 530 | −69.861 | 14.652 | 5.161 | 1.00 | 27.42 | O |
| ATOM | 8126 | N | SER | A | 531 | −69.230 | 16.229 | 6.635 | 1.00 | 26.21 | N |
| ATOM | 8127 | CA | SER | A | 531 | −69.730 | 17.359 | 5.853 | 1.00 | 25.12 | C |
| ATOM | 8129 | CB | SER | A | 531 | −69.519 | 18.657 | 6.618 | 1.00 | 25.01 | C |
| ATOM | 8132 | OG | SER | A | 531 | −68.167 | 18.791 | 6.985 | 1.00 | 23.94 | O |
| ATOM | 8134 | C | SER | A | 531 | −69.055 | 17.476 | 4.507 | 1.00 | 24.48 | C |
| ATOM | 8135 | O | SER | A | 531 | −69.687 | 17.886 | 3.538 | 1.00 | 24.14 | O |
| ATOM | 8137 | N | VAL | A | 532 | −67.774 | 17.115 | 4.461 | 1.00 | 23.89 | N |
| ATOM | 8138 | CA | VAL | A | 532 | −66.962 | 17.226 | 3.246 | 1.00 | 23.53 | C |
| ATOM | 8140 | CB | VAL | A | 532 | −65.470 | 17.437 | 3.575 | 1.00 | 23.09 | C |
| ATOM | 8142 | CG1 | VAL | A | 532 | −64.633 | 17.355 | 2.348 | 1.00 | 22.32 | C |
| ATOM | 8146 | CG2 | VAL | A | 532 | −65.268 | 18.773 | 4.198 | 1.00 | 23.07 | C |
| ATOM | 8150 | C | VAL | A | 532 | −67.100 | 16.028 | 2.316 | 1.00 | 23.67 | C |
| ATOM | 8151 | O | VAL | A | 532 | −67.137 | 16.209 | 1.099 | 1.00 | 23.58 | O |
| ATOM | 8153 | N | ILE | A | 533 | −67.187 | 14.824 | 2.886 | 1.00 | 23.85 | N |
| ATOM | 8154 | CA | ILE | A | 533 | −67.172 | 13.578 | 2.107 | 1.00 | 24.08 | C |
| ATOM | 8156 | CB | ILE | A | 533 | −66.172 | 12.555 | 2.691 | 1.00 | 24.10 | C |
| ATOM | 8158 | CG1 | ILE | A | 533 | −64.745 | 13.079 | 2.631 | 1.00 | 23.47 | C |
| ATOM | 8161 | CD1 | ILE | A | 533 | −64.178 | 13.083 | 1.255 | 1.00 | 23.42 | C |
| ATOM | 8165 | CG2 | ILE | A | 533 | −66.254 | 11.231 | 1.932 | 1.00 | 24.56 | C |
| ATOM | 8169 | C | ILE | A | 533 | −68.522 | 12.859 | 1.990 | 1.00 | 24.27 | C |
| ATOM | 8170 | O | ILE | A | 533 | −68.991 | 12.620 | .887 | 1.00 | 24.34 | O |
| ATOM | 8172 | N | THR | A | 534 | −69.133 | 12.487 | 3.111 | 1.00 | 24.57 | N |
| ATOM | 8173 | CA | THR | A | 534 | −70.279 | 11.564 | 3.072 | 1.00 | 24.92 | C |
| ATOM | 8175 | CB | THR | A | 534 | −70.200 | 10.522 | 4.207 | 1.00 | 24.93 | C |
| ATOM | 8177 | OG1 | THR | A | 534 | −70.491 | 11.149 | 5.458 | 1.00 | 25.28 | O |
| ATOM | 8179 | CG2 | THR | A | 534 | −68.804 | 9.885 | 4.257 | 1.00 | 24.75 | C |
| ATOM | 8183 | C | THR | A | 534 | −71.673 | 12.209 | 3.083 | 1.00 | 25.00 | C |
| ATOM | 8184 | O | THR | A | 534 | −72.601 | 11.646 | 2.522 | 1.00 | 24.94 | O |
| ATOM | 8186 | N | GLU | A | 535 | −71.821 | 13.374 | 3.708 | 1.00 | 25.26 | N |
| ATOM | 8187 | CA | GLU | A | 535 | −73.132 | 14.024 | 3.833 | 1.00 | 25.34 | C |
| ATOM | 8189 | CB | GLU | A | 535 | −73.333 | 14.523 | 5.255 | 1.00 | 25.44 | C |
| ATOM | 8192 | CG | GLU | A | 535 | −73.753 | 13.424 | 6.196 | 1.00 | 25.80 | C |
| ATOM | 8195 | CD | GLU | A | 535 | −74.307 | 13.963 | 7.468 | 1.00 | 25.72 | C |
| ATOM | 8196 | OE1 | GLU | A | 535 | −75.375 | 13.487 | 7.881 | 1.00 | 24.50 | O |
| ATOM | 8197 | OE2 | GLU | A | 535 | −73.678 | 14.877 | 8.039 | 1.00 | 27.03 | O |
| ATOM | 8198 | C | GLU | A | 535 | −73.363 | 15.179 | 2.859 | 1.00 | 25.26 | C |
| ATOM | 8199 | O | GLU | A | 535 | −72.686 | 16.206 | 2.939 | 1.00 | 25.02 | O |
| ATOM | 8201 | N | PRO | A | 536 | −74.351 | 15.030 | 1.959 | 1.00 | 25.25 | N |
| ATOM | 8202 | CA | PRO | A | 536 | −74.655 | 16.111 | 1.050 | 1.00 | 25.18 | C |
| ATOM | 8204 | CB | PRO | A | 536 | −75.661 | 15.484 | .076 | 1.00 | 25.15 | C |
| ATOM | 8207 | CG | PRO | A | 536 | −75.825 | 14.077 | .476 | 1.00 | 24.98 | C |
| ATOM | 8210 | CD | PRO | A | 536 | −75.363 | 13.965 | 1.868 | 1.00 | 25.26 | C |
| ATOM | 8213 | C | PRO | A | 536 | −75.289 | 17.265 | 1.801 | 1.00 | 25.30 | C |
| ATOM | 8214 | O | PRO | A | 536 | −75.826 | 17.070 | 2.883 | 1.00 | 25.57 | O |
| ATOM | 8215 | N | ILE | A | 537 | −75.213 | 18.458 | 1.230 | 1.00 | 25.36 | N |
| ATOM | 8216 | CA | ILE | A | 537 | −75.807 | 19.638 | 1.827 | 1.00 | 25.34 | C |
| ATOM | 8218 | CB | ILE | A | 537 | −75.201 | 20.918 | 1.221 | 1.00 | 25.14 | C |
| ATOM | 8220 | CG1 | ILE | A | 537 | −73.787 | 21.131 | 1.744 | 1.00 | 24.32 | C |

TABLE 16-7-continued

Coordinates of *P. tremuloides* IspS

| ATOM | 8223 | CD1 | ILE | A | 537 | −73.228 | 22.472 | 1.406 | 1.00 | 23.22 | C |
|---|---|---|---|---|---|---|---|---|---|---|---|
| ATOM | 8227 | CG2 | ILE | A | 537 | −76.030 | 22.131 | 1.569 | 1.00 | 25.54 | C |
| ATOM | 8231 | C | ILE | A | 537 | −77.313 | 19.603 | 1.611 | 1.00 | 25.67 | C |
| ATOM | 8232 | O | ILE | A | 537 | −77.786 | 19.132 | .579 | 1.00 | 25.47 | O |
| ATOM | 8234 | N | LEU | A | 538 | −78.071 | 20.088 | 2.586 | 1.00 | 26.22 | N |
| ATOM | 8235 | CA | LEU | A | 538 | −79.514 | 20.051 | 2.467 | 1.00 | 26.65 | C |
| ATOM | 8237 | CB | LEU | A | 538 | −80.213 | 20.525 | 3.749 | 1.00 | 26.78 | C |
| ATOM | 8240 | CG | LEU | A | 538 | −80.162 | 19.609 | 4.989 | 1.00 | 26.64 | C |
| ATOM | 8242 | CD1 | LEU | A | 538 | −81.218 | 20.033 | 6.007 | 1.00 | 26.16 | C |
| ATOM | 8246 | CD2 | LEU | A | 538 | −80.346 | 18.138 | 4.633 | 1.00 | 26.12 | C |
| ATOM | 8250 | C | LEU | A | 538 | −79.925 | 20.881 | 1.262 | 1.00 | 27.08 | C |
| ATOM | 8253 | N | PRO | A | 539 | −80.786 | 20.306 | .414 | 1.00 | 28.03 | N |
| ATOM | 8254 | CA | PRO | A | 539 | −81.117 | 20.855 | −.888 | 1.00 | 28.44 | C |
| ATOM | 8256 | CB | PRO | A | 539 | −82.093 | 19.828 | −1.449 | 1.00 | 28.40 | C |
| ATOM | 8259 | CG | PRO | A | 539 | −82.793 | 19.328 | −.253 | 1.00 | 28.30 | C |
| ATOM | 8262 | CD | PRO | A | 539 | −81.720 | 19.228 | .787 | 1.00 | 28.11 | C |
| ATOM | 8265 | C | PRO | A | 539 | −81.813 | 22.194 | −.804 | 1.00 | 28.89 | C |
| ATOM | 8266 | O | PRO | A | 539 | −82.396 | 22.535 | .226 | 1.00 | 28.97 | O |
| ATOM | 8267 | N | PHE | A | 540 | −81.774 | 22.932 | −1.906 | 1.00 | 29.32 | N |
| ATOM | 8268 | CA | PHE | A | 540 | −82.380 | 24.245 | −1.962 | 1.00 | 29.50 | C |
| ATOM | 8270 | CB | PHE | A | 540 | −82.146 | 24.874 | −3.326 | 1.00 | 29.56 | C |
| ATOM | 8273 | CG | PHE | A | 540 | −82.757 | 26.227 | −3.463 | 1.00 | 29.75 | C |
| ATOM | 8274 | CD1 | PHE | A | 540 | −83.874 | 26.429 | −4.255 | 1.00 | 29.47 | C |
| ATOM | 8276 | CE1 | PHE | A | 540 | −84.441 | 27.681 | −4.364 | 1.00 | 29.46 | C |
| ATOM | 8278 | CZ | PHE | A | 540 | −83.901 | 28.743 | −3.674 | 1.00 | 29.81 | C |
| ATOM | 8280 | CE2 | PHE | A | 540 | −82.791 | 28.553 | −2.877 | 1.00 | 30.21 | C |
| ATOM | 8282 | CD2 | PHE | A | 540 | −82.229 | 27.300 | −2.770 | 1.00 | 30.17 | C |
| ATOM | 8284 | C | PHE | A | 540 | −83.865 | 24.129 | −1.722 | 1.00 | 29.66 | C |
| ATOM | 8285 | O | PHE | A | 540 | −84.568 | 23.551 | −2.545 | 1.00 | 29.66 | O |
| ATOM | 8287 | N | GLU | A | 541 | −84.337 | 24.673 | −.601 | 1.00 | 29.90 | N |
| ATOM | 8288 | CA | GLU | A | 541 | −85.761 | 24.605 | −.233 | 1.00 | 30.06 | C |
| ATOM | 8290 | CB | GLU | A | 541 | −85.951 | 23.724 | 1.017 | 1.00 | 30.15 | C |
| ATOM | 8293 | CG | GLU | A | 541 | −87.411 | 23.361 | 1.367 | 1.00 | 30.64 | C |
| ATOM | 8296 | CD | GLU | A | 541 | −88.091 | 24.351 | 2.322 | 1.00 | 31.35 | C |
| ATOM | 8297 | OE1 | GLU | A | 541 | −87.468 | 25.370 | 2.680 | 1.00 | 32.67 | O |
| ATOM | 8298 | OE2 | GLU | A | 541 | −89.254 | 24.114 | 2.719 | 1.00 | 30.48 | O |
| ATOM | 8299 | C | GLU | A | 541 | −86.315 | 26.011 | −.010 | 1.00 | 29.89 | C |
| ATOM | 8300 | O | GLU | A | 541 | −86.835 | 26.636 | −.936 | 1.00 | 29.71 | O |
| ATOM | 8302 | N | LEU | B | 17 | −69.666 | −25.325 | 2.227 | 1.00 | 33.20 | N |
| ATOM | 8303 | CA | LEU | B | 17 | −69.356 | −25.417 | .755 | 1.00 | 33.49 | C |
| ATOM | 8305 | CB | LEU | B | 17 | −70.240 | −26.475 | .048 | 1.00 | 33.44 | C |
| ATOM | 8308 | CG | LEU | B | 17 | −70.077 | −27.986 | .328 | 1.00 | 33.60 | C |
| ATOM | 8310 | CD1 | LEU | B | 17 | −71.285 | −28.778 | −.217 | 1.00 | 32.76 | C |
| ATOM | 8314 | CD2 | LEU | B | 17 | −68.763 | −28.553 | −.230 | 1.00 | 33.21 | C |
| ATOM | 8318 | C | LEU | B | 17 | −69.513 | −24.044 | .055 | 1.00 | 33.54 | C |
| ATOM | 8319 | O | LEU | B | 17 | −70.550 | −23.380 | .195 | 1.00 | 33.77 | O |
| ATOM | 8323 | N | LEU | B | 18 | −68.481 | −23.637 | −.696 | 1.00 | 33.44 | N |
| ATOM | 8324 | CA | LEU | B | 18 | −68.476 | −22.362 | −1.454 | 1.00 | 33.07 | C |
| ATOM | 8326 | CB | LEU | B | 18 | −67.029 | −21.960 | −1.840 | 1.00 | 33.21 | C |
| ATOM | 8329 | CG | LEU | B | 18 | −66.065 | −21.488 | −.721 | 1.00 | 34.06 | C |
| ATOM | 8331 | CD1 | LEU | B | 18 | −64.607 | −21.351 | −1.235 | 1.00 | 34.51 | C |
| ATOM | 8335 | CD2 | LEU | B | 18 | −66.516 | −20.164 | −.061 | 1.00 | 33.43 | C |
| ATOM | 8339 | C | LEU | B | 18 | −69.379 | −22.400 | −2.714 | 1.00 | 32.37 | C |
| ATOM | 8340 | O | LEU | B | 18 | −69.710 | −21.355 | −3.274 | 1.00 | 32.29 | O |
| ATOM | 8342 | N | SER | B | 19 | −69.765 | −23.597 | −3.153 | 1.00 | 31.62 | N |
| ATOM | 8343 | CA | SER | B | 19 | −70.711 | −23.749 | −4.253 | 1.00 | 31.16 | C |
| ATOM | 8345 | CB | SER | B | 19 | −70.443 | −25.067 | −5.033 | 1.00 | 31.09 | C |
| ATOM | 8348 | OG | SER | B | 19 | −70.977 | −26.243 | −4.421 | 1.00 | 29.36 | O |
| ATOM | 8350 | C | SER | B | 19 | −72.168 | −23.663 | −3.759 | 1.00 | 31.45 | C |
| ATOM | 8351 | O | SER | B | 19 | −73.076 | −23.432 | −4.551 | 1.00 | 31.13 | O |
| ATOM | 8353 | N | SER | B | 20 | −72.386 | −23.824 | −2.451 | 1.00 | 31.91 | N |
| ATOM | 8354 | CA | SER | B | 20 | −73.749 | −23.900 | −1.879 | 1.00 | 32.34 | C |
| ATOM | 8356 | CB | SER | B | 20 | −73.706 | −24.122 | −.357 | 1.00 | 32.35 | C |
| ATOM | 8359 | OG | SER | B | 20 | −73.393 | −25.473 | −.055 | 1.00 | 32.34 | O |
| ATOM | 8361 | C | SER | B | 20 | −74.601 | −22.670 | −2.204 | 1.00 | 32.69 | C |
| ATOM | 8362 | O | SER | B | 20 | −74.072 | −21.600 | −2.487 | 1.00 | 32.89 | O |
| ATOM | 8364 | N | ASP | B | 21 | −75.921 | −22.831 | −2.119 | 1.00 | 33.13 | N |
| ATOM | 8365 | CA | ASP | B | 21 | −76.874 | −21.901 | −2.745 | 1.00 | 33.40 | C |
| ATOM | 8367 | CB | ASP | B | 21 | −78.179 | −22.628 | −3.045 | 1.00 | 33.64 | C |
| ATOM | 8370 | CG | ASP | B | 21 | −77.943 | −23.883 | −3.828 | 1.00 | 35.35 | C |
| ATOM | 8371 | OD1 | ASP | B | 21 | −77.031 | −23.866 | −4.684 | 1.00 | 38.26 | O |
| ATOM | 8372 | OD2 | ASP | B | 21 | −78.631 | −24.890 | −3.590 | 1.00 | 37.55 | O |
| ATOM | 8373 | C | ASP | B | 21 | −77.141 | −20.649 | −1.940 | 1.00 | 33.23 | C |
| ATOM | 8374 | O | ASP | B | 21 | −78.039 | −20.616 | −1.106 | 1.00 | 32.91 | O |
| ATOM | 8376 | N | THR | B | 22 | −76.348 | −19.621 | −2.229 | 1.00 | 33.46 | N |
| ATOM | 8377 | CA | THR | B | 22 | −76.443 | −18.307 | −1.593 | 1.00 | 33.79 | C |
| ATOM | 8379 | CB | THR | B | 22 | −76.460 | −18.378 | −.016 | 1.00 | 33.74 | C |
| ATOM | 8381 | OG1 | THR | B | 22 | −75.426 | −19.250 | .460 | 1.00 | 32.97 | O |

TABLE 16-7-continued

Coordinates of *P. tremuloides* IspS

| ATOM | 8383 | CG2 | THR | B | 22 | −77.805 | −18.838 | .535 | 1.00 | 33.55 | C |
|---|---|---|---|---|---|---|---|---|---|---|---|
| ATOM | 8387 | C | THR | B | 22 | −75.217 | −17.479 | −2.018 | 1.00 | 34.24 | C |
| ATOM | 8388 | O | THR | B | 22 | −74.102 | −17.988 | −1.892 | 1.00 | 33.95 | O |
| ATOM | 8390 | N | ASP | B | 23 | −75.361 | −16.248 | −2.543 | 1.00 | 34.99 | N |
| ATOM | 8391 | CA | ASP | B | 23 | −76.603 | −15.620 | −3.103 | 1.00 | 35.61 | C |
| ATOM | 8393 | CB | ASP | B | 23 | −77.242 | −16.538 | −4.170 | 1.00 | 35.51 | C |
| ATOM | 8396 | CG | ASP | B | 23 | −76.196 | −17.236 | −5.034 | 1.00 | 36.08 | C |
| ATOM | 8397 | OD1 | ASP | B | 23 | −75.084 | −16.685 | −5.194 | 1.00 | 35.58 | O |
| ATOM | 8398 | OD2 | ASP | B | 23 | −76.473 | −18.344 | −5.541 | 1.00 | 37.65 | O |
| ATOM | 8399 | C | ASP | B | 23 | −77.662 | −15.083 | −2.097 | 1.00 | 36.10 | C |
| ATOM | 8400 | O | ASP | B | 23 | −78.644 | −15.770 | −1.799 | 1.00 | 36.13 | O |
| ATOM | 8402 | N | GLU | B | 24 | −77.487 | −13.845 | −1.616 | 1.00 | 36.74 | N |
| ATOM | 8403 | CA | GLU | B | 24 | −78.358 | −13.316 | −.543 | 1.00 | 37.59 | C |
| ATOM | 8405 | CB | GLU | B | 24 | −77.765 | −13.666 | .838 | 1.00 | 37.88 | C |
| ATOM | 8408 | CG | GLU | B | 24 | −77.624 | −15.173 | 1.120 | 1.00 | 38.51 | C |
| ATOM | 8411 | CD | GLU | B | 24 | −77.314 | −15.510 | 2.588 | 1.00 | 39.48 | C |
| ATOM | 8412 | OE1 | GLU | B | 24 | −77.171 | −14.581 | 3.434 | 1.00 | 39.60 | O |
| ATOM | 8413 | OE2 | GLU | B | 24 | −77.221 | −16.725 | 2.884 | 1.00 | 39.51 | O |
| ATOM | 8414 | C | GLU | B | 24 | −78.730 | −11.809 | −.559 | 1.00 | 38.11 | C |
| ATOM | 8415 | O | GLU | B | 24 | −79.840 | −11.453 | −.972 | 1.00 | 38.20 | O |
| ATOM | 8417 | N | SER | B | 25 | −77.825 | −10.941 | −.089 | 1.00 | 38.70 | N |
| ATOM | 8418 | CA | SER | B | 25 | −78.192 | −9.560 | .312 | 1.00 | 39.21 | C |
| ATOM | 8420 | CB | SER | B | 25 | −76.995 | −8.783 | .916 | 1.00 | 39.29 | C |
| ATOM | 8423 | OG | SER | B | 25 | −76.267 | −8.037 | −.056 | 1.00 | 39.40 | O |
| ATOM | 8425 | C | SER | B | 25 | −78.853 | −8.738 | −.802 | 1.00 | 39.69 | C |
| ATOM | 8426 | O | SER | B | 25 | −78.707 | −9.050 | −1.995 | 1.00 | 39.75 | O |
| ATOM | 8428 | N | ILE | B | 26 | −79.544 | −7.670 | −.378 | 1.00 | 40.21 | N |
| ATOM | 8429 | CA | ILE | B | 26 | −80.554 | −6.962 | −1.189 | 1.00 | 40.55 | C |
| ATOM | 8431 | CB | ILE | B | 26 | −79.925 | −6.082 | −2.319 | 1.00 | 40.66 | C |
| ATOM | 8433 | CG1 | ILE | B | 26 | −79.083 | −4.951 | −1.700 | 1.00 | 40.73 | C |
| ATOM | 8436 | CD1 | ILE | B | 26 | −78.596 | −3.877 | −2.698 | 1.00 | 40.68 | C |
| ATOM | 8440 | CG2 | ILE | B | 26 | −81.018 | −5.475 | −3.203 | 1.00 | 40.88 | C |
| ATOM | 8444 | C | ILE | B | 26 | −81.575 | −7.999 | −1.714 | 1.00 | 40.72 | C |
| ATOM | 8445 | O | ILE | B | 26 | −81.311 | −8.710 | −2.690 | 1.00 | 40.80 | O |
| ATOM | 8447 | N | GLU | B | 27 | −82.729 | −8.070 | −1.037 | 1.00 | 40.86 | N |
| ATOM | 8448 | CA | GLU | B | 27 | −83.694 | −9.190 | −1.160 | 1.00 | 40.88 | C |
| ATOM | 8450 | CB | GLU | B | 27 | −84.782 | −9.060 | −.061 | 1.00 | 40.95 | C |
| ATOM | 8453 | CG | GLU | B | 27 | −84.235 | −9.257 | 1.379 | 1.00 | 41.28 | C |
| ATOM | 8456 | CD | GLU | B | 27 | −85.123 | −8.657 | 2.484 | 1.00 | 41.74 | C |
| ATOM | 8457 | OE1 | GLU | B | 27 | −85.593 | −7.504 | 2.344 | 1.00 | 41.14 | O |
| ATOM | 8458 | OE2 | GLU | B | 27 | −85.332 | −9.337 | 3.514 | 1.00 | 42.36 | O |
| ATOM | 8459 | C | GLU | B | 27 | −84.290 | −9.355 | −2.587 | 1.00 | 40.75 | C |
| ATOM | 8460 | O | GLU | B | 27 | −83.664 | −8.936 | −3.569 | 1.00 | 40.88 | O |
| ATOM | 8462 | N | VAL | B | 28 | −85.461 | −9.994 | −2.712 | 1.00 | 40.40 | N |
| ATOM | 8463 | CA | VAL | B | 28 | −86.033 | −10.361 | −4.027 | 1.00 | 39.97 | C |
| ATOM | 8465 | CB | VAL | B | 28 | −86.034 | −9.157 | −5.053 | 1.00 | 40.03 | C |
| ATOM | 8467 | CG1 | VAL | B | 28 | −86.494 | −9.600 | −6.444 | 1.00 | 39.63 | C |
| ATOM | 8471 | CG2 | VAL | B | 28 | −86.900 | −7.994 | −4.525 | 1.00 | 39.86 | C |
| ATOM | 8475 | C | VAL | B | 28 | −85.335 | −11.600 | −4.625 | 1.00 | 39.63 | C |
| ATOM | 8476 | O | VAL | B | 28 | −85.858 | −12.204 | −5.567 | 1.00 | 39.63 | O |
| ATOM | 8478 | N | HIS | B | 29 | −84.175 | −11.980 | −4.069 | 1.00 | 39.21 | N |
| ATOM | 8479 | CA | HIS | B | 29 | −83.431 | −13.177 | −4.504 | 1.00 | 38.81 | C |
| ATOM | 8481 | CB | HIS | B | 29 | −81.914 | −12.913 | −4.665 | 1.00 | 38.97 | C |
| ATOM | 8484 | CG | HIS | B | 29 | −81.571 | −11.721 | −5.512 | 1.00 | 39.99 | C |
| ATOM | 8485 | ND1 | HIS | B | 29 | −81.181 | −11.825 | −6.834 | 1.00 | 40.79 | N |
| ATOM | 8487 | CE1 | HIS | B | 29 | −80.931 | −10.615 | −7.312 | 1.00 | 40.76 | C |
| ATOM | 8489 | NE2 | HIS | B | 29 | −81.134 | −9.734 | −6.346 | 1.00 | 40.27 | N |
| ATOM | 8491 | CD2 | HIS | B | 29 | −81.525 | −10.400 | −5.209 | 1.00 | 40.17 | C |
| ATOM | 8493 | C | HIS | B | 29 | −83.611 | −14.340 | −3.523 | 1.00 | 38.05 | C |
| ATOM | 8494 | O | HIS | B | 29 | −82.782 | −15.259 | −3.526 | 1.00 | 38.02 | O |
| ATOM | 8496 | N | LYS | B | 30 | −84.667 | −14.321 | −2.694 | 1.00 | 37.06 | N |
| ATOM | 8497 | CA | LYS | B | 30 | −85.107 | −15.559 | −2.022 | 1.00 | 36.33 | C |
| ATOM | 8499 | CB | LYS | B | 30 | −86.056 | −15.286 | −.836 | 1.00 | 36.27 | C |
| ATOM | 8502 | CG | LYS | B | 30 | −85.352 | −14.818 | .461 | 1.00 | 36.09 | C |
| ATOM | 8505 | CD | LYS | B | 30 | −86.355 | −14.599 | 1.612 | 1.00 | 36.03 | C |
| ATOM | 8508 | CE | LYS | B | 30 | −85.811 | −13.659 | 2.701 | 1.00 | 36.24 | C |
| ATOM | 8511 | NZ | LYS | B | 30 | −86.802 | −13.356 | 3.789 | 1.00 | 35.65 | N |
| ATOM | 8515 | C | LYS | B | 30 | −85.710 | −16.510 | −3.094 | 1.00 | 35.69 | C |
| ATOM | 8516 | O | LYS | B | 30 | −86.706 | −17.205 | −2.879 | 1.00 | 35.35 | O |
| ATOM | 8518 | N | ASP | B | 31 | −85.075 | −16.484 | −4.268 | 1.00 | 35.13 | N |
| ATOM | 8519 | CA | ASP | B | 31 | −85.145 | −17.519 | −5.282 | 1.00 | 34.64 | C |
| ATOM | 8521 | CB | ASP | B | 31 | −84.592 | −16.962 | −6.623 | 1.00 | 34.60 | C |
| ATOM | 8524 | CG | ASP | B | 31 | −84.419 | −18.032 | −7.725 | 1.00 | 34.24 | C |
| ATOM | 8525 | OD1 | ASP | B | 31 | −84.914 | −19.165 | −7.570 | 1.00 | 34.58 | O |
| ATOM | 8526 | OD2 | ASP | B | 31 | −83.776 | −17.732 | −8.761 | 1.00 | 31.56 | O |
| ATOM | 8527 | C | ASP | B | 31 | −84.304 | −18.675 | −4.721 | 1.00 | 34.31 | C |
| ATOM | 8528 | O | ASP | B | 31 | −83.122 | −18.838 | −5.038 | 1.00 | 34.03 | O |
| ATOM | 8530 | N | LYS | B | 32 | −84.917 | −19.429 | −3.813 | 1.00 | 33.94 | N |

TABLE 16-7-continued

Coordinates of P. tremuloides IspS

| ATOM | 8531 | CA | LYS | B | 32 | −84.380 | −20.710 | −3.369 | 1.00 | 33.36 | C |
| --- | --- | --- | --- | --- | --- | --- | --- | --- | --- | --- | --- |
| ATOM | 8533 | CB | LYS | B | 32 | −83.772 | −20.607 | −1.973 | 1.00 | 33.45 | C |
| ATOM | 8536 | CG | LYS | B | 32 | −82.540 | −19.693 | −1.951 | 1.00 | 33.56 | C |
| ATOM | 8539 | CD | LYS | B | 32 | −82.025 | −19.455 | −.532 | 1.00 | 34.17 | C |
| ATOM | 8542 | CE | LYS | B | 32 | −81.671 | −17.987 | −.283 | 1.00 | 34.16 | C |
| ATOM | 8545 | NZ | LYS | B | 32 | −80.746 | −17.437 | −1.311 | 1.00 | 34.07 | N |
| ATOM | 8549 | C | LYS | B | 32 | −85.490 | −21.764 | −3.499 | 1.00 | 32.57 | C |
| ATOM | 8550 | O | LYS | B | 32 | −85.908 | −22.412 | −2.538 | 1.00 | 32.10 | O |
| ATOM | 8552 | N | ALA | B | 33 | −85.976 | −21.859 | −4.738 | 1.00 | 31.66 | N |
| ATOM | 8553 | CA | ALA | B | 33 | −86.576 | −23.055 | −5.259 | 1.00 | 30.94 | C |
| ATOM | 8555 | CB | ALA | B | 33 | −87.247 | −22.773 | −6.597 | 1.00 | 30.47 | C |
| ATOM | 8559 | C | ALA | B | 33 | −85.442 | −24.081 | −5.403 | 1.00 | 30.55 | C |
| ATOM | 8560 | O | ALA | B | 33 | −85.684 | −25.230 | −5.751 | 1.00 | 31.12 | O |
| ATOM | 8562 | N | LYS | B | 34 | −84.200 | −23.660 | −5.161 | 1.00 | 29.73 | N |
| ATOM | 8563 | CA | LYS | B | 34 | −83.107 | −24.585 | −4.839 | 1.00 | 29.09 | C |
| ATOM | 8565 | CB | LYS | B | 34 | −81.776 | −23.817 | −4.865 | 1.00 | 29.30 | C |
| ATOM | 8568 | CG | LYS | B | 34 | −80.678 | −24.474 | −5.726 | 1.00 | 29.76 | C |
| ATOM | 8571 | CD | LYS | B | 34 | −79.633 | −23.458 | −6.283 | 1.00 | 28.74 | C |
| ATOM | 8574 | CE | LYS | B | 34 | −78.417 | −24.186 | −6.890 | 1.00 | 27.56 | C |
| ATOM | 8577 | NZ | LYS | B | 34 | −78.745 | −25.174 | −7.935 | 1.00 | 26.16 | N |
| ATOM | 8581 | C | LYS | B | 34 | −83.376 | −25.320 | −3.472 | 1.00 | 28.37 | C |
| ATOM | 8582 | O | LYS | B | 34 | −83.254 | −24.755 | −2.374 | 1.00 | 27.82 | O |
| ATOM | 8584 | N | LYS | B | 35 | −83.635 | −26.620 | −3.604 | 1.00 | 27.53 | N |
| ATOM | 8585 | CA | LYS | B | 35 | −84.629 | −27.429 | −2.851 | 1.00 | 26.77 | C |
| ATOM | 8587 | CB | LYS | B | 35 | −85.729 | −26.602 | −2.170 | 1.00 | 26.81 | C |
| ATOM | 8590 | CG | LYS | B | 35 | −87.089 | −26.520 | −2.907 | 1.00 | 27.05 | C |
| ATOM | 8593 | CD | LYS | B | 35 | −88.096 | −27.604 | −2.452 | 1.00 | 27.41 | C |
| ATOM | 8596 | CE | LYS | B | 35 | −89.394 | −27.636 | −3.300 | 1.00 | 27.21 | C |
| ATOM | 8599 | NZ | LYS | B | 35 | −90.501 | −26.792 | −2.762 | 1.00 | 26.28 | N |
| ATOM | 8603 | C | LYS | B | 35 | −85.257 | −28.357 | −3.920 | 1.00 | 26.03 | C |
| ATOM | 8604 | O | LYS | B | 35 | −85.853 | −29.386 | −3.626 | 1.00 | 26.00 | O |
| ATOM | 8606 | N | LEU | B | 36 | −85.171 | −27.909 | −5.168 | 1.00 | 24.98 | N |
| ATOM | 8607 | CA | LEU | B | 36 | −85.095 | −28.783 | −6.319 | 1.00 | 24.02 | C |
| ATOM | 8609 | CB | LEU | B | 36 | −85.004 | −27.930 | −7.594 | 1.00 | 23.83 | C |
| ATOM | 8612 | CG | LEU | B | 36 | −86.208 | −27.103 | −8.062 | 1.00 | 22.23 | C |
| ATOM | 8614 | CD1 | LEU | B | 36 | −85.762 | −25.873 | −8.802 | 1.00 | 19.93 | C |
| ATOM | 8618 | CD2 | LEU | B | 36 | −87.092 | −27.930 | −8.951 | 1.00 | 22.11 | C |
| ATOM | 8622 | C | LEU | B | 36 | −83.834 | −29.659 | −6.185 | 1.00 | 23.58 | C |
| ATOM | 8623 | O | LEU | B | 36 | −83.840 | −30.842 | −6.508 | 1.00 | 23.38 | O |
| ATOM | 8625 | N | GLU | B | 37 | −82.742 | −29.046 | −5.739 | 1.00 | 23.18 | N |
| ATOM | 8626 | CA | GLU | B | 37 | −81.510 | −29.753 | −5.396 | 1.00 | 22.88 | C |
| ATOM | 8628 | CB | GLU | B | 37 | −80.466 | −28.766 | −4.855 | 1.00 | 22.76 | C |
| ATOM | 8631 | CG | GLU | B | 37 | −79.038 | −29.297 | −4.874 | 1.00 | 22.24 | C |
| ATOM | 8634 | CD | GLU | B | 37 | −78.085 | −28.505 | −4.009 | 1.00 | 21.06 | C |
| ATOM | 8635 | OE1 | GLU | B | 37 | −78.368 | −27.331 | −3.737 | 1.00 | 19.65 | O |
| ATOM | 8636 | OE2 | GLU | B | 37 | −77.037 | −29.059 | −3.615 | 1.00 | 20.62 | O |
| ATOM | 8637 | C | GLU | B | 37 | −81.748 | −30.856 | −4.364 | 1.00 | 22.95 | C |
| ATOM | 8638 | O | GLU | B | 37 | −81.164 | −31.933 | −4.458 | 1.00 | 22.99 | O |
| ATOM | 8640 | N | ALA | B | 38 | −82.591 | −30.575 | −3.372 | 1.00 | 23.02 | N |
| ATOM | 8641 | CA | ALA | B | 38 | −82.973 | −31.565 | −2.364 | 1.00 | 22.93 | C |
| ATOM | 8643 | CB | ALA | B | 38 | −83.966 | −30.959 | −1.374 | 1.00 | 22.73 | C |
| ATOM | 8647 | C | ALA | B | 38 | −83.580 | −32.778 | −3.044 | 1.00 | 23.05 | C |
| ATOM | 8648 | O | ALA | B | 38 | −83.170 | −33.909 | −2.813 | 1.00 | 22.52 | O |
| ATOM | 8650 | N | GLU | B | 39 | −84.546 | −32.506 | −3.912 | 1.00 | 23.66 | N |
| ATOM | 8651 | CA | GLU | B | 39 | −85.273 | −33.534 | −4.642 | 1.00 | 24.08 | C |
| ATOM | 8653 | CB | GLU | B | 39 | −86.403 | −32.891 | −5.453 | 1.00 | 24.28 | C |
| ATOM | 8656 | CG | GLU | B | 39 | −87.405 | −33.869 | −6.075 | 1.00 | 25.14 | C |
| ATOM | 8659 | CD | GLU | B | 39 | −88.773 | −33.227 | −6.341 | 1.00 | 26.43 | C |
| ATOM | 8660 | OE1 | GLU | B | 39 | −89.232 | −32.381 | −5.519 | 1.00 | 25.90 | O |
| ATOM | 8661 | OE2 | GLU | B | 39 | −89.387 | −33.584 | −7.375 | 1.00 | 26.99 | O |
| ATOM | 8662 | C | GLU | B | 39 | −84.362 | −34.359 | −5.545 | 1.00 | 24.18 | C |
| ATOM | 8663 | O | GLU | B | 39 | −84.483 | −35.579 | −5.575 | 1.00 | 24.32 | O |
| ATOM | 8665 | N | VAL | B | 40 | −83.450 | −33.710 | −6.269 | 1.00 | 24.43 | N |
| ATOM | 8666 | CA | VAL | B | 40 | −82.533 | −34.437 | −7.153 | 1.00 | 24.59 | C |
| ATOM | 8668 | CB | VAL | B | 40 | −81.734 | −33.496 | −8.087 | 1.00 | 24.65 | C |
| ATOM | 8670 | CG1 | VAL | B | 40 | −80.611 | −34.258 | −8.792 | 1.00 | 24.14 | C |
| ATOM | 8674 | CG2 | VAL | B | 40 | −82.662 | −32.852 | −9.106 | 1.00 | 23.89 | C |
| ATOM | 8678 | C | VAL | B | 40 | −81.592 | −35.304 | −6.328 | 1.00 | 24.99 | C |
| ATOM | 8679 | O | VAL | B | 40 | −81.265 | −36.407 | −6.717 | 1.00 | 24.77 | O |
| ATOM | 8681 | N | ARG | B | 41 | −81.184 | −34.811 | −5.171 | 1.00 | 25.79 | N |
| ATOM | 8682 | CA | ARG | B | 41 | −80.387 | −35.613 | −4.248 | 1.00 | 26.75 | C |
| ATOM | 8684 | CB | ARG | B | 41 | −80.032 | −34.823 | −2.998 | 1.00 | 27.38 | C |
| ATOM | 8687 | CG | ARG | B | 41 | −78.568 | −34.777 | −2.757 | 1.00 | 30.18 | C |
| ATOM | 8690 | CD | ARG | B | 41 | −78.281 | −34.610 | −1.273 | 1.00 | 34.43 | C |
| ATOM | 8693 | NE | ARG | B | 41 | −76.896 | −34.198 | −1.016 | 1.00 | 37.07 | N |
| ATOM | 8695 | CZ | ARG | B | 41 | −76.350 | −33.045 | −1.416 | 1.00 | 38.54 | C |
| ATOM | 8696 | NH1 | ARG | B | 41 | −75.083 | −32.797 | −1.112 | 1.00 | 40.04 | N |
| ATOM | 8699 | NH2 | ARG | B | 41 | −77.037 | −32.145 | −2.128 | 1.00 | 38.45 | N |

TABLE 16-7-continued

Coordinates of *P. tremuloides* IspS

| ATOM | 8702 | C | ARG | B | 41 | −81.081 | −36.860 | −3.762 | 1.00 | 26.60 | C |
| --- | --- | --- | --- | --- | --- | --- | --- | --- | --- | --- | --- |
| ATOM | 8703 | O | ARG | B | 41 | −80.446 | −37.894 | −3.627 | 1.00 | 26.89 | O |
| ATOM | 8705 | N | ARG | B | 42 | −82.363 | −36.733 | −3.423 | 1.00 | 26.41 | N |
| ATOM | 8706 | CA | ARG | B | 42 | −83.159 | −37.870 | −3.002 | 1.00 | 26.09 | C |
| ATOM | 8708 | CB | ARG | B | 42 | −84.588 | −37.452 | −2.674 | 1.00 | 25.99 | C |
| ATOM | 8711 | CG | ARG | B | 42 | −85.426 | −38.562 | −2.049 | 1.00 | 25.45 | C |
| ATOM | 8714 | CD | ARG | B | 42 | −86.783 | −38.078 | −1.645 | 1.00 | 24.26 | C |
| ATOM | 8717 | NE | ARG | B | 42 | −87.549 | −37.602 | −2.794 | 1.00 | 23.73 | N |
| ATOM | 8719 | CZ | ARG | B | 42 | −88.547 | −36.722 | −2.717 | 1.00 | 24.51 | C |
| ATOM | 8720 | NH1 | ARG | B | 42 | −88.912 | −36.195 | −1.545 | 1.00 | 24.99 | N |
| ATOM | 8723 | NH2 | ARG | B | 42 | −89.185 | −36.354 | −3.816 | 1.00 | 24.46 | N |
| ATOM | 8726 | C | ARG | B | 42 | −83.167 | −38.894 | −4.118 | 1.00 | 26.28 | C |
| ATOM | 8727 | O | ARG | B | 42 | −82.864 | −40.054 | −3.888 | 1.00 | 26.39 | O |
| ATOM | 8729 | N | GLU | B | 43 | −83.476 | −38.460 | −5.334 | 1.00 | 26.52 | N |
| ATOM | 8730 | CA | GLU | B | 43 | −83.476 | −39.370 | −6.479 | 1.00 | 27.00 | C |
| ATOM | 8732 | CB | GLU | B | 43 | −83.982 | −38.676 | −7.753 | 1.00 | 27.50 | C |
| ATOM | 8735 | CG | GLU | B | 43 | −85.469 | −38.275 | −7.699 | 1.00 | 29.78 | C |
| ATOM | 8738 | CD | GLU | B | 43 | −86.342 | −39.301 | −6.974 | 1.00 | 32.52 | C |
| ATOM | 8739 | OE1 | GLU | B | 43 | −86.388 | −40.455 | −7.445 | 1.00 | 35.06 | O |
| ATOM | 8740 | OE2 | GLU | B | 43 | −86.966 | −38.963 | −5.936 | 1.00 | 33.80 | O |
| ATOM | 8741 | C | GLU | B | 43 | −82.147 | −40.059 | −6.769 | 1.00 | 26.37 | C |
| ATOM | 8742 | O | GLU | B | 43 | −82.162 | −41.126 | −7.355 | 1.00 | 26.63 | O |
| ATOM | 8744 | N | ILE | B | 44 | −81.018 | −39.472 | −6.373 | 1.00 | 25.85 | N |
| ATOM | 8745 | CA | ILE | B | 44 | −79.717 | −40.126 | −6.555 | 1.00 | 25.55 | C |
| ATOM | 8747 | CB | ILE | B | 44 | −78.547 | −39.121 | −6.692 | 1.00 | 25.26 | C |
| ATOM | 8749 | CG1 | ILE | B | 44 | −78.706 | −38.273 | −7.953 | 1.00 | 24.47 | C |
| ATOM | 8752 | CD1 | ILE | B | 44 | −77.690 | −37.163 | −8.114 | 1.00 | 23.21 | C |
| ATOM | 8756 | CG2 | ILE | B | 44 | −77.207 | −39.863 | −6.778 | 1.00 | 25.35 | C |
| ATOM | 8760 | C | ILE | B | 44 | −79.404 | −41.109 | −5.428 | 1.00 | 25.84 | C |
| ATOM | 8761 | O | ILE | B | 44 | −78.925 | −42.208 | −5.698 | 1.00 | 25.97 | O |
| ATOM | 8763 | N | ASN | B | 45 | −79.663 | −40.708 | −4.177 | 1.00 | 26.25 | N |
| ATOM | 8764 | CA | ASN | B | 45 | −79.403 | −41.542 | −2.983 | 1.00 | 26.34 | C |
| ATOM | 8766 | CB | ASN | B | 45 | −79.284 | −40.681 | −1.719 | 1.00 | 26.01 | C |
| ATOM | 8769 | CG | ASN | B | 45 | −78.072 | −39.789 | −1.723 | 1.00 | 24.65 | C |
| ATOM | 8770 | OD1 | ASN | B | 45 | −76.957 | −40.226 | −1.434 | 1.00 | 22.47 | O |
| ATOM | 8771 | ND2 | ASN | B | 45 | −78.288 | −38.516 | −2.009 | 1.00 | 23.36 | N |
| ATOM | 8774 | C | ASN | B | 45 | −80.488 | −42.586 | −2.731 | 1.00 | 27.18 | C |
| ATOM | 8775 | O | ASN | B | 45 | −80.374 | −43.390 | −1.806 | 1.00 | 27.30 | O |
| ATOM | 8777 | N | ASN | B | 46 | −81.553 | −42.541 | −3.527 | 1.00 | 28.17 | N |
| ATOM | 8778 | CA | ASN | B | 46 | −82.619 | −43.536 | −3.489 | 1.00 | 29.02 | C |
| ATOM | 8780 | CB | ASN | B | 46 | −83.558 | −43.289 | −4.665 | 1.00 | 29.05 | C |
| ATOM | 8783 | CG | ASN | B | 46 | −84.615 | −44.345 | −4.806 | 1.00 | 28.82 | C |
| ATOM | 8784 | OD1 | ASN | B | 46 | −84.861 | −45.132 | −3.895 | 1.00 | 28.14 | O |
| ATOM | 8785 | ND2 | ASN | B | 46 | −85.255 | −44.369 | −5.968 | 1.00 | 29.67 | N |
| ATOM | 8788 | C | ASN | B | 46 | −82.076 | −44.958 | −3.549 | 1.00 | 30.14 | C |
| ATOM | 8789 | O | ASN | B | 46 | −81.566 | −45.408 | −4.581 | 1.00 | 30.30 | O |
| ATOM | 8791 | N | GLU | B | 47 | −82.218 | −45.674 | −2.446 | 1.00 | 31.36 | N |
| ATOM | 8792 | CA | GLU | B | 47 | −81.575 | −46.968 | −2.295 | 1.00 | 32.61 | C |
| ATOM | 8794 | CB | GLU | B | 47 | −81.617 | −47.430 | −.823 | 1.00 | 33.09 | C |
| ATOM | 8797 | CG | GLU | B | 47 | −80.974 | −46.466 | .218 | 1.00 | 34.19 | C |
| ATOM | 8800 | CD | GLU | B | 47 | −81.919 | −45.337 | .721 | 1.00 | 34.57 | C |
| ATOM | 8801 | OE1 | GLU | B | 47 | −82.911 | −45.012 | .029 | 1.00 | 34.53 | O |
| ATOM | 8802 | OE2 | GLU | B | 47 | −81.652 | −44.762 | 1.805 | 1.00 | 34.30 | O |
| ATOM | 8803 | C | GLU | B | 47 | −82.205 | −48.046 | −3.172 | 1.00 | 33.18 | C |
| ATOM | 8804 | O | GLU | B | 47 | −81.604 | −49.088 | −3.370 | 1.00 | 33.44 | O |
| ATOM | 8806 | N | LYS | B | 48 | −83.408 | −47.808 | −3.692 | 1.00 | 34.11 | N |
| ATOM | 8807 | CA | LYS | B | 48 | −84.164 | −48.853 | −4.396 | 1.00 | 34.85 | C |
| ATOM | 8809 | CB | LYS | B | 48 | −85.379 | −49.254 | −3.542 | 1.00 | 35.09 | C |
| ATOM | 8812 | CG | LYS | B | 48 | −85.003 | −49.723 | −2.127 | 1.00 | 36.00 | C |
| ATOM | 8815 | CD | LYS | B | 48 | −86.174 | −50.338 | −1.350 | 1.00 | 37.13 | C |
| ATOM | 8818 | CE | LYS | B | 48 | −87.312 | −49.340 | −1.094 | 1.00 | 37.90 | C |
| ATOM | 8821 | NZ | LYS | B | 48 | −86.908 | −48.161 | −.272 | 1.00 | 38.31 | N |
| ATOM | 8825 | C | LYS | B | 48 | −84.586 | −48.487 | −5.835 | 1.00 | 35.13 | C |
| ATOM | 8826 | O | LYS | B | 48 | −85.544 | −49.030 | −6.361 | 1.00 | 34.60 | O |
| ATOM | 8828 | N | ALA | B | 49 | −83.858 | −47.576 | −6.474 | 1.00 | 36.09 | N |
| ATOM | 8829 | CA | ALA | B | 49 | −84.093 | −47.261 | −7.886 | 1.00 | 36.87 | C |
| ATOM | 8831 | CB | ALA | B | 49 | −83.550 | −45.880 | −8.238 | 1.00 | 36.73 | C |
| ATOM | 8835 | C | ALA | B | 49 | −83.406 | −48.325 | −8.714 | 1.00 | 37.56 | C |
| ATOM | 8836 | O | ALA | B | 49 | −82.315 | −48.761 | −8.363 | 1.00 | 37.62 | O |
| ATOM | 8838 | N | GLU | B | 50 | −84.028 | −48.754 | −9.807 | 1.00 | 38.54 | N |
| ATOM | 8839 | CA | GLU | B | 50 | −83.399 | −49.772 | −10.652 | 1.00 | 39.40 | C |
| ATOM | 8841 | CB | GLU | B | 50 | −84.380 | −50.384 | −11.673 | 1.00 | 39.71 | C |
| ATOM | 8844 | CG | GLU | B | 50 | −83.959 | −51.808 | −12.179 | 1.00 | 41.33 | C |
| ATOM | 8847 | CD | GLU | B | 50 | −83.733 | −52.860 | −11.039 | 1.00 | 42.88 | C |
| ATOM | 8848 | OE1 | GLU | B | 50 | −84.683 | −53.628 | −10.718 | 1.00 | 42.94 | O |
| ATOM | 8849 | OE2 | GLU | B | 50 | −82.603 | −52.921 | −10.472 | 1.00 | 42.96 | O |
| ATOM | 8850 | C | GLU | B | 50 | −82.171 | −49.163 | −11.330 | 1.00 | 39.43 | C |
| ATOM | 8851 | O | GLU | B | 50 | −82.211 | −48.017 | −11.791 | 1.00 | 39.66 | O |

TABLE 16-7-continued

Coordinates of *P. tremuloides* IspS

| | | | | | | | | | | |
|---|---|---|---|---|---|---|---|---|---|---|
| ATOM | 8853 | N | PHE | B | 51 | −81.084 | −49.929 | −11.376 | 1.00 | 39.32 N |
| ATOM | 8854 | CA | PHE | B | 51 | −79.763 | −49.360 | −11.636 | 1.00 | 39.32 C |
| ATOM | 8856 | CB | PHE | B | 51 | −78.675 | −50.429 | −11.476 | 1.00 | 39.62 C |
| ATOM | 8859 | CG | PHE | B | 51 | −78.470 | −50.889 | −10.032 | 1.00 | 41.82 C |
| ATOM | 8860 | CD1 | PHE | B | 51 | −78.093 | −49.978 | −9.032 | 1.00 | 42.93 C |
| ATOM | 8862 | CE1 | PHE | B | 51 | −77.892 | −50.391 | −7.705 | 1.00 | 43.30 C |
| ATOM | 8864 | CZ | PHE | B | 51 | −78.059 | −51.729 | −7.359 | 1.00 | 44.33 C |
| ATOM | 8866 | CE2 | PHE | B | 51 | −78.430 | −52.659 | −8.341 | 1.00 | 44.75 C |
| ATOM | 8868 | CD2 | PHE | B | 51 | −78.633 | −52.234 | −9.677 | 1.00 | 44.06 C |
| ATOM | 8870 | C | PHE | B | 51 | −79.646 | −48.625 | −12.976 | 1.00 | 38.57 C |
| ATOM | 8871 | O | PHE | B | 51 | −79.045 | −47.564 | −13.046 | 1.00 | 38.50 O |
| ATOM | 8873 | N | LEU | B | 52 | −80.262 | −49.155 | −14.024 | 1.00 | 37.99 N |
| ATOM | 8874 | CA | LEU | B | 52 | −80.176 | −48.539 | −15.351 | 1.00 | 37.42 C |
| ATOM | 8876 | CB | LEU | B | 52 | −80.774 | −49.476 | −16.399 | 1.00 | 37.66 C |
| ATOM | 8879 | CG | LEU | B | 52 | −80.502 | −49.168 | −17.876 | 1.00 | 38.39 C |
| ATOM | 8881 | CD1 | LEU | B | 52 | −80.171 | −50.452 | −18.652 | 1.00 | 38.46 C |
| ATOM | 8885 | CD2 | LEU | B | 52 | −81.703 | −48.432 | −18.500 | 1.00 | 39.23 C |
| ATOM | 8889 | C | LEU | B | 52 | −80.824 | −47.143 | −15.431 | 1.00 | 36.69 C |
| ATOM | 8890 | O | LEU | B | 52 | −80.383 | −46.312 | −16.224 | 1.00 | 36.59 O |
| ATOM | 8892 | N | THR | B | 53 | −81.859 | −46.879 | −14.625 | 1.00 | 35.87 N |
| ATOM | 8893 | CA | THR | B | 53 | −82.409 | −45.510 | −14.513 | 1.00 | 34.91 C |
| ATOM | 8895 | CB | THR | B | 53 | −83.784 | −45.421 | −13.805 | 1.00 | 34.72 C |
| ATOM | 8897 | OG1 | THR | B | 53 | −84.724 | −46.269 | −14.455 | 1.00 | 34.04 O |
| ATOM | 8899 | CG2 | THR | B | 53 | −84.316 | −43.981 | −13.855 | 1.00 | 34.81 C |
| ATOM | 8903 | C | THR | B | 53 | −81.454 | −44.642 | −13.722 | 1.00 | 34.05 C |
| ATOM | 8904 | O | THR | B | 53 | −81.170 | −43.513 | −14.121 | 1.00 | 34.16 O |
| ATOM | 8906 | N | LEU | B | 54 | −80.987 | −45.167 | −12.593 | 1.00 | 32.84 N |
| ATOM | 8907 | CA | LEU | B | 54 | −80.027 | −44.461 | −11.772 | 1.00 | 32.16 C |
| ATOM | 8909 | CB | LEU | B | 54 | −79.506 | −45.354 | −10.662 | 1.00 | 32.27 C |
| ATOM | 8912 | CG | LEU | B | 54 | −78.521 | −44.702 | −9.698 | 1.00 | 32.56 C |
| ATOM | 8914 | CD1 | LEU | B | 54 | −79.275 | −43.760 | −8.769 | 1.00 | 32.38 C |
| ATOM | 8918 | CD2 | LEU | B | 54 | −77.755 | −45.789 | −8.917 | 1.00 | 33.29 C |
| ATOM | 8922 | C | LEU | B | 54 | −78.870 | −44.006 | −12.634 | 1.00 | 31.50 C |
| ATOM | 8923 | O | LEU | B | 54 | −78.509 | −42.840 | −12.607 | 1.00 | 31.98 O |
| ATOM | 8925 | N | LEU | B | 55 | −78.297 | −44.914 | −13.418 | 1.00 | 30.43 N |
| ATOM | 8926 | CA | LEU | B | 55 | −77.220 | −44.540 | −14.333 | 1.00 | 29.36 C |
| ATOM | 8928 | CB | LEU | B | 55 | −76.765 | −45.733 | −15.173 | 1.00 | 29.23 C |
| ATOM | 8931 | CG | LEU | B | 55 | −76.157 | −46.902 | −14.391 | 1.00 | 28.60 C |
| ATOM | 8933 | CD1 | LEU | B | 55 | −75.697 | −48.004 | −15.348 | 1.00 | 27.60 C |
| ATOM | 8937 | CD2 | LEU | B | 55 | −75.020 | −46.440 | −13.469 | 1.00 | 27.20 C |
| ATOM | 8941 | C | LEU | B | 55 | −77.678 | −43.406 | −15.230 | 1.00 | 28.60 C |
| ATOM | 8942 | O | LEU | B | 55 | −77.063 | −42.365 | −15.267 | 1.00 | 28.17 O |
| ATOM | 8944 | N | GLU | B | 56 | −78.786 | −43.594 | −15.919 | 1.00 | 28.23 N |
| ATOM | 8945 | CA | GLU | B | 56 | −79.326 | −42.530 | −16.759 | 1.00 | 28.64 C |
| ATOM | 8947 | CB | GLU | B | 56 | −80.567 | −43.031 | −17.524 | 1.00 | 29.27 C |
| ATOM | 8950 | CG | GLU | B | 56 | −80.229 | −43.783 | −18.829 | 1.00 | 31.73 C |
| ATOM | 8953 | CD | GLU | B | 56 | −81.265 | −44.860 | −19.206 | 1.00 | 35.52 C |
| ATOM | 8954 | OE1 | GLU | B | 56 | −82.474 | −44.693 | −18.889 | 1.00 | 36.97 O |
| ATOM | 8955 | OE2 | GLU | B | 56 | −80.856 | −45.877 | −19.825 | 1.00 | 37.55 O |
| ATOM | 8956 | C | GLU | B | 56 | −79.632 | −41.203 | −15.995 | 1.00 | 27.77 C |
| ATOM | 8957 | O | GLU | B | 56 | −79.561 | −40.103 | −16.582 | 1.00 | 27.84 O |
| ATOM | 8959 | N | LEU | B | 57 | −79.976 | −41.303 | −14.710 | 1.00 | 26.29 N |
| ATOM | 8960 | CA | LEU | B | 57 | −80.158 | −40.120 | −13.895 | 1.00 | 25.06 C |
| ATOM | 8962 | CB | LEU | B | 57 | −80.724 | −40.462 | −12.514 | 1.00 | 24.83 C |
| ATOM | 8965 | CG | LEU | B | 57 | −80.952 | −39.298 | −11.544 | 1.00 | 23.72 C |
| ATOM | 8967 | CD1 | LEU | B | 57 | −81.909 | −38.278 | −12.117 | 1.00 | 21.43 C |
| ATOM | 8971 | CD2 | LEU | B | 57 | −81.477 | −39.830 | −10.227 | 1.00 | 22.41 C |
| ATOM | 8975 | C | LEU | B | 57 | −78.801 | −39.459 | −13.780 | 1.00 | 24.40 C |
| ATOM | 8976 | O | LEU | B | 57 | −78.591 | −38.373 | −14.306 | 1.00 | 24.70 O |
| ATOM | 8978 | N | ILE | B | 58 | −77.855 | −40.133 | −13.144 | 1.00 | 23.56 N |
| ATOM | 8979 | CA | ILE | B | 58 | −76.509 | −39.574 | −12.991 | 1.00 | 22.91 C |
| ATOM | 8981 | CB | ILE | B | 58 | −75.454 | −40.635 | −12.599 | 1.00 | 22.49 C |
| ATOM | 8983 | CG1 | ILE | B | 58 | −75.753 | −41.251 | −11.235 | 1.00 | 22.09 C |
| ATOM | 8986 | CD1 | ILE | B | 58 | −74.936 | −42.464 | −10.926 | 1.00 | 20.88 C |
| ATOM | 8990 | CG2 | ILE | B | 58 | −74.103 | −39.992 | −12.534 | 1.00 | 22.63 C |
| ATOM | 8994 | C | ILE | B | 58 | −76.062 | −38.927 | −14.302 | 1.00 | 22.64 C |
| ATOM | 8995 | O | ILE | B | 58 | −75.603 | −37.796 | −14.315 | 1.00 | 22.38 O |
| ATOM | 8997 | N | ASP | B | 59 | −76.228 | −39.646 | −15.404 | 1.00 | 22.56 N |
| ATOM | 8998 | CA | ASP | B | 59 | −75.715 | −39.196 | −16.684 | 1.00 | 22.76 C |
| ATOM | 9000 | CB | ASP | B | 59 | −75.926 | −40.269 | −17.757 | 1.00 | 22.93 C |
| ATOM | 9003 | CG | ASP | B | 59 | −75.274 | −39.904 | −19.088 | 1.00 | 24.58 C |
| ATOM | 9004 | OD1 | ASP | B | 59 | −74.157 | −39.322 | −19.081 | 1.00 | 25.70 O |
| ATOM | 9005 | OD2 | ASP | B | 59 | −75.897 | −40.186 | −20.142 | 1.00 | 27.51 O |
| ATOM | 9006 | C | ASP | B | 59 | −76.343 | −37.863 | −17.104 | 1.00 | 22.40 C |
| ATOM | 9007 | O | ASP | B | 59 | −75.634 | −36.939 | −17.520 | 1.00 | 22.40 O |
| ATOM | 9009 | N | ASN | B | 60 | −77.662 | −37.767 | −16.991 | 1.00 | 21.91 N |
| ATOM | 9010 | CA | ASN | B | 60 | −78.349 | −36.500 | −17.217 | 1.00 | 21.70 C |
| ATOM | 9012 | CB | ASN | B | 60 | −79.867 | −36.674 | −17.088 | 1.00 | 22.12 C |

TABLE 16-7-continued

Coordinates of *P. tremuloides* IspS

| ATOM | 9015 | CG | ASN | B | 60 | −80.477 | −37.390 | −18.268 | 1.00 | 22.76 | C |
|---|---|---|---|---|---|---|---|---|---|---|---|
| ATOM | 9016 | OD1 | ASN | B | 60 | −80.027 | −37.233 | −19.393 | 1.00 | 24.28 | O |
| ATOM | 9017 | ND2 | ASN | B | 60 | −81.515 | −38.172 | −18.017 | 1.00 | 24.36 | N |
| ATOM | 9020 | C | ASN | B | 60 | −77.898 | −35.427 | −16.234 | 1.00 | 21.17 | C |
| ATOM | 9021 | O | ASN | B | 60 | −77.700 | −34.273 | −16.614 | 1.00 | 20.85 | O |
| ATOM | 9023 | N | VAL | B | 61 | −77.745 | −35.805 | −14.968 | 1.00 | 20.60 | N |
| ATOM | 9024 | CA | VAL | B | 61 | −77.382 | −34.841 | −13.942 | 1.00 | 20.48 | C |
| ATOM | 9026 | CB | VAL | B | 61 | −77.277 | −35.490 | −12.551 | 1.00 | 20.26 | C |
| ATOM | 9028 | CG1 | VAL | B | 61 | −76.585 | −34.562 | −11.565 | 1.00 | 19.92 | C |
| ATOM | 9032 | CG2 | VAL | B | 61 | −78.668 | −35.857 | −12.049 | 1.00 | 20.66 | C |
| ATOM | 9036 | C | VAL | B | 61 | −76.068 | −34.208 | −14.335 | 1.00 | 20.66 | C |
| ATOM | 9037 | O | VAL | B | 61 | −75.871 | −32.998 | −14.182 | 1.00 | 20.74 | O |
| ATOM | 9039 | N | GLN | B | 62 | −75.187 | −35.048 | −14.875 | 1.00 | 20.92 | N |
| ATOM | 9040 | CA | GLN | B | 62 | −73.854 | −34.636 | −15.285 | 1.00 | 20.69 | C |
| ATOM | 9042 | CB | GLN | B | 62 | −72.917 | −35.847 | −15.404 | 1.00 | 20.77 | C |
| ATOM | 9045 | CG | GLN | B | 62 | −72.456 | −36.369 | −14.035 | 1.00 | 20.91 | C |
| ATOM | 9048 | CD | GLN | B | 62 | −71.328 | −37.383 | −14.112 | 1.00 | 20.75 | C |
| ATOM | 9049 | OE1 | GLN | B | 62 | −70.512 | −37.498 | −13.192 | 1.00 | 20.93 | O |
| ATOM | 9050 | NE2 | GLN | B | 62 | −71.291 | −38.135 | −15.195 | 1.00 | 20.39 | N |
| ATOM | 9053 | C | GLN | B | 62 | −73.900 | −33.834 | −16.567 | 1.00 | 20.32 | C |
| ATOM | 9054 | O | GLN | B | 62 | −73.410 | −32.712 | −16.569 | 1.00 | 20.79 | O |
| ATOM | 9056 | N | ARG | B | 63 | −74.512 | −34.373 | −17.625 | 1.00 | 19.87 | N |
| ATOM | 9057 | CA | ARG | B | 63 | −74.520 | −33.696 | −18.940 | 1.00 | 19.81 | C |
| ATOM | 9059 | CB | ARG | B | 63 | −75.240 | −34.536 | −20.013 | 1.00 | 19.75 | C |
| ATOM | 9062 | CG | ARG | B | 63 | −74.492 | −35.846 | −20.345 | 1.00 | 21.69 | C |
| ATOM | 9065 | CD | ARG | B | 63 | −75.158 | −36.786 | −21.368 | 1.00 | 24.89 | C |
| ATOM | 9068 | NE | ARG | B | 63 | −74.674 | −36.558 | −22.741 | 1.00 | 29.32 | N |
| ATOM | 9070 | CZ | ARG | B | 63 | −75.323 | −35.878 | −23.702 | 1.00 | 33.71 | C |
| ATOM | 9071 | NH1 | ARG | B | 63 | −76.537 | −35.345 | −23.510 | 1.00 | 36.67 | N |
| ATOM | 9074 | NH2 | ARG | B | 63 | −74.761 | −35.736 | −24.894 | 1.00 | 34.58 | N |
| ATOM | 9077 | C | ARG | B | 63 | −75.099 | −32.276 | −18.822 | 1.00 | 19.39 | C |
| ATOM | 9078 | O | ARG | B | 63 | −74.553 | −31.310 | −19.395 | 1.00 | 19.63 | O |
| ATOM | 9080 | N | LEU | B | 64 | −76.155 | −32.148 | −18.017 | 1.00 | 18.62 | N |
| ATOM | 9081 | CA | LEU | B | 64 | −76.811 | −30.856 | −17.753 | 1.00 | 17.96 | C |
| ATOM | 9083 | CB | LEU | B | 64 | −78.136 | −31.077 | −17.008 | 1.00 | 17.97 | C |
| ATOM | 9086 | CG | LEU | B | 64 | −79.264 | −31.737 | −17.809 | 1.00 | 17.08 | C |
| ATOM | 9088 | CD1 | LEU | B | 64 | −80.276 | −32.354 | −16.879 | 1.00 | 15.15 | C |
| ATOM | 9092 | CD2 | LEU | B | 64 | −79.904 | −30.734 | −18.737 | 1.00 | 15.30 | C |
| ATOM | 9096 | C | LEU | B | 64 | −75.975 | −29.847 | −16.966 | 1.00 | 17.39 | C |
| ATOM | 9097 | O | LEU | B | 64 | −76.370 | −28.685 | −16.825 | 1.00 | 17.38 | O |
| ATOM | 9099 | N | GLY | B | 65 | −74.848 | −30.286 | −16.432 | 1.00 | 16.73 | N |
| ATOM | 9100 | CA | GLY | B | 65 | −73.917 | −29.374 | −15.818 | 1.00 | 16.65 | C |
| ATOM | 9103 | C | GLY | B | 65 | −74.077 | −29.249 | −14.319 | 1.00 | 16.68 | C |
| ATOM | 9104 | O | GLY | B | 65 | −73.565 | −28.302 | −13.718 | 1.00 | 16.79 | O |
| ATOM | 9106 | N | LEU | B | 66 | −74.758 | −30.209 | −13.702 | 1.00 | 16.60 | N |
| ATOM | 9107 | CA | LEU | B | 66 | −74.978 | −30.177 | −12.264 | 1.00 | 16.58 | C |
| ATOM | 9109 | CB | LEU | B | 66 | −76.465 | −30.389 | −11.957 | 1.00 | 16.35 | C |
| ATOM | 9112 | CG | LEU | B | 66 | −77.363 | −29.187 | −12.234 | 1.00 | 15.57 | C |
| ATOM | 9114 | CD1 | LEU | B | 66 | −78.828 | −29.602 | −12.163 | 1.00 | 15.26 | C |
| ATOM | 9118 | CD2 | LEU | B | 66 | −77.063 | −28.051 | −11.270 | 1.00 | 13.66 | C |
| ATOM | 9122 | C | LEU | B | 66 | −74.129 | −31.203 | −11.513 | 1.00 | 16.94 | C |
| ATOM | 9123 | O | LEU | B | 66 | −74.152 | −31.251 | −10.279 | 1.00 | 17.50 | O |
| ATOM | 9125 | N | GLY | B | 67 | −73.373 | −32.017 | −12.236 | 1.00 | 17.03 | N |
| ATOM | 9126 | CA | GLY | B | 67 | −72.541 | −33.036 | −11.602 | 1.00 | 17.13 | C |
| ATOM | 9129 | C | GLY | B | 67 | −71.642 | −32.557 | −10.461 | 1.00 | 17.08 | C |
| ATOM | 9130 | O | GLY | B | 67 | −71.378 | −33.317 | −9.522 | 1.00 | 17.33 | O |
| ATOM | 9132 | N | TYR | B | 68 | −71.159 | −31.316 | −10.541 | 1.00 | 16.83 | N |
| ATOM | 9133 | CA | TYR | B | 68 | −70.217 | −30.804 | −9.552 | 1.00 | 16.64 | C |
| ATOM | 9135 | CB | TYR | B | 68 | −69.654 | −29.437 | −9.951 | 1.00 | 16.25 | C |
| ATOM | 9138 | CG | TYR | B | 68 | −70.609 | −28.273 | −9.802 | 1.00 | 13.51 | C |
| ATOM | 9139 | CD1 | TYR | B | 68 | −70.521 | −27.411 | −8.738 | 1.00 | 10.49 | C |
| ATOM | 9141 | CE1 | TYR | B | 68 | −71.407 | −26.342 | −8.608 | 1.00 | 10.25 | C |
| ATOM | 9143 | CZ | TYR | B | 68 | −72.382 | −26.135 | −9.555 | 1.00 | 9.74 | C |
| ATOM | 9144 | OH | TYR | B | 68 | −73.253 | −25.086 | −9.450 | 1.00 | 7.62 | O |
| ATOM | 9146 | CE2 | TYR | B | 68 | −72.484 | −26.978 | −10.625 | 1.00 | 11.14 | C |
| ATOM | 9148 | CD2 | TYR | B | 68 | −71.603 | −28.037 | −10.748 | 1.00 | 12.56 | C |
| ATOM | 9150 | C | TYR | B | 68 | −70.828 | −30.700 | −8.172 | 1.00 | 17.79 | C |
| ATOM | 9151 | O | TYR | B | 68 | −70.107 | −30.811 | −7.182 | 1.00 | 18.00 | O |
| ATOM | 9153 | N | ARG | B | 69 | −72.146 | −30.485 | −8.090 | 1.00 | 18.85 | N |
| ATOM | 9154 | CA | ARG | B | 69 | −72.784 | −30.269 | −6.789 | 1.00 | 19.46 | C |
| ATOM | 9156 | CB | ARG | B | 69 | −73.708 | −29.047 | −6.819 | 1.00 | 19.23 | C |
| ATOM | 9159 | CG | ARG | B | 69 | −75.030 | −29.219 | −7.509 | 1.00 | 18.83 | C |
| ATOM | 9162 | CD | ARG | B | 69 | −76.053 | −28.192 | −6.985 | 1.00 | 17.73 | C |
| ATOM | 9165 | NE | ARG | B | 69 | −75.642 | −26.830 | −7.297 | 1.00 | 16.01 | N |
| ATOM | 9167 | CZ | ARG | B | 69 | −75.330 | −25.889 | −6.417 | 1.00 | 14.68 | C |
| ATOM | 9168 | NH1 | ARG | B | 69 | −75.400 | −26.093 | −5.112 | 1.00 | 14.99 | N |
| ATOM | 9171 | NH2 | ARG | B | 69 | −74.959 | −24.707 | −6.861 | 1.00 | 15.04 | N |
| ATOM | 9174 | C | ARG | B | 69 | −73.490 | −31.489 | −6.234 | 1.00 | 20.50 | C |

TABLE 16-7-continued

Coordinates of *P. tremuloides* IspS

| ATOM | 9175 | O | ARG | B | 69 | −74.084 | −31.418 | −5.163 | 1.00 | 20.67 | O |
|---|---|---|---|---|---|---|---|---|---|---|---|
| ATOM | 9177 | N | PHE | B | 70 | −73.416 | −32.607 | −6.959 | 1.00 | 22.04 | N |
| ATOM | 9178 | CA | PHE | B | 70 | −73.853 | −33.917 | −6.450 | 1.00 | 23.03 | C |
| ATOM | 9180 | CB | PHE | B | 70 | −75.081 | −34.428 | −7.211 | 1.00 | 22.94 | C |
| ATOM | 9183 | CG | PHE | B | 70 | −76.236 | −33.503 | −7.157 | 1.00 | 21.78 | C |
| ATOM | 9184 | CD1 | PHE | B | 70 | −77.024 | −33.441 | −6.028 | 1.00 | 20.54 | C |
| ATOM | 9186 | CE1 | PHE | B | 70 | −78.076 | −32.571 | −5.959 | 1.00 | 20.32 | C |
| ATOM | 9188 | CZ | PHE | B | 70 | −78.353 | −31.752 | −7.025 | 1.00 | 20.73 | C |
| ATOM | 9190 | CE2 | PHE | B | 70 | −77.564 | −31.796 | −8.160 | 1.00 | 21.24 | C |
| ATOM | 9192 | CD2 | PHE | B | 70 | −76.511 | −32.665 | −8.220 | 1.00 | 21.22 | C |
| ATOM | 9194 | C | PHE | B | 70 | −72.765 | −34.962 | −6.570 | 1.00 | 24.33 | C |
| ATOM | 9195 | O | PHE | B | 70 | −73.069 | −36.142 | −6.614 | 1.00 | 24.56 | O |
| ATOM | 9197 | N | GLU | B | 71 | −71.500 | −34.547 | −6.624 | 1.00 | 26.01 | N |
| ATOM | 9198 | CA | GLU | B | 71 | −70.413 | −35.506 | −6.804 | 1.00 | 27.04 | C |
| ATOM | 9200 | CB | GLU | B | 71 | −69.042 | −34.824 | −6.885 | 1.00 | 27.48 | C |
| ATOM | 9203 | CG | GLU | B | 71 | −67.851 | −35.816 | −6.794 | 1.00 | 28.94 | C |
| ATOM | 9206 | CD | GLU | B | 71 | −66.491 | −35.192 | −7.081 | 1.00 | 30.38 | C |
| ATOM | 9207 | OE1 | GLU | B | 71 | −66.398 | −34.192 | −7.835 | 1.00 | 30.52 | O |
| ATOM | 9208 | OE2 | GLU | B | 71 | −65.501 | −35.730 | −6.544 | 1.00 | 32.16 | O |
| ATOM | 9209 | C | GLU | B | 71 | −70.436 | −36.531 | −5.680 | 1.00 | 27.46 | C |
| ATOM | 9210 | O | GLU | B | 71 | −70.449 | −37.723 | −5.937 | 1.00 | 27.67 | O |
| ATOM | 9212 | N | SER | B | 72 | −70.464 | −36.087 | −4.435 | 1.00 | 28.04 | N |
| ATOM | 9213 | CA | SER | B | 72 | −70.381 | −37.044 | −3.348 | 1.00 | 28.86 | C |
| ATOM | 9215 | CB | SER | B | 72 | −70.388 | −36.340 | −1.983 | 1.00 | 29.09 | C |
| ATOM | 9218 | OG | SER | B | 72 | −71.649 | −35.751 | −1.687 | 1.00 | 30.21 | O |
| ATOM | 9220 | C | SER | B | 72 | −71.519 | −38.058 | −3.481 | 1.00 | 29.30 | C |
| ATOM | 9221 | O | SER | B | 72 | −71.304 | −39.265 | −3.384 | 1.00 | 29.24 | O |
| ATOM | 9223 | N | ASP | B | 73 | −72.719 | −37.560 | −3.756 | 1.00 | 30.03 | N |
| ATOM | 9224 | CA | ASP | B | 73 | −73.897 | −38.417 | −3.874 | 1.00 | 30.63 | C |
| ATOM | 9226 | CB | ASP | B | 73 | −75.184 | −37.598 | −4.116 | 1.00 | 30.74 | C |
| ATOM | 9229 | CG | ASP | B | 73 | −75.419 | −36.509 | −3.052 | 1.00 | 31.84 | C |
| ATOM | 9230 | OD1 | ASP | B | 73 | −75.562 | −36.830 | −1.841 | 1.00 | 31.70 | O |
| ATOM | 9231 | OD2 | ASP | B | 73 | −75.473 | −35.317 | −3.443 | 1.00 | 33.81 | O |
| ATOM | 9232 | C | ASP | B | 73 | −73.722 | −39.443 | −4.994 | 1.00 | 30.81 | C |
| ATOM | 9233 | O | ASP | B | 73 | −74.130 | −40.590 | −4.835 | 1.00 | 31.39 | O |
| ATOM | 9235 | N | ILE | B | 74 | −73.122 | −39.031 | −6.112 | 1.00 | 30.96 | N |
| ATOM | 9236 | CA | ILE | B | 74 | −72.917 | −39.912 | −7.282 | 1.00 | 31.04 | C |
| ATOM | 9238 | CB | ILE | B | 74 | −72.461 | −39.114 | −8.524 | 1.00 | 30.88 | C |
| ATOM | 9240 | CG1 | ILE | B | 74 | −73.585 | −38.213 | −9.018 | 1.00 | 30.99 | C |
| ATOM | 9243 | CD1 | ILE | B | 74 | −73.105 | −37.120 | −9.923 | 1.00 | 31.54 | C |
| ATOM | 9247 | CG2 | ILE | B | 74 | −72.052 | −40.035 | −9.642 | 1.00 | 29.85 | C |
| ATOM | 9251 | C | ILE | B | 74 | −71.885 | −41.005 | −6.999 | 1.00 | 31.45 | C |
| ATOM | 9252 | O | ILE | B | 74 | −72.098 | −42.165 | −7.347 | 1.00 | 31.31 | O |
| ATOM | 9254 | N | ARG | B | 75 | −70.768 | −40.628 | −6.380 | 1.00 | 31.93 | N |
| ATOM | 9255 | CA | ARG | B | 75 | −69.778 | −41.601 | −5.947 | 1.00 | 32.38 | C |
| ATOM | 9257 | CB | ARG | B | 75 | −68.629 | −40.959 | −5.137 | 1.00 | 32.87 | C |
| ATOM | 9260 | CG | ARG | B | 75 | −67.310 | −40.751 | −5.915 | 1.00 | 35.01 | C |
| ATOM | 9263 | CD | ARG | B | 75 | −66.089 | −40.489 | −5.003 | 1.00 | 37.62 | C |
| ATOM | 9266 | NE | ARG | B | 75 | −65.260 | −41.687 | −4.783 | 1.00 | 41.03 | N |
| ATOM | 9268 | CZ | ARG | B | 75 | −64.461 | −42.253 | −5.700 | 1.00 | 44.29 | C |
| ATOM | 9269 | NH1 | ARG | B | 75 | −64.385 | −41.751 | −6.931 | 1.00 | 46.22 | N |
| ATOM | 9272 | NH2 | ARG | B | 75 | −63.741 | −43.341 | −5.404 | 1.00 | 44.30 | N |
| ATOM | 9275 | C | ARG | B | 75 | −70.478 | −42.673 | −5.126 | 1.00 | 32.18 | C |
| ATOM | 9276 | O | ARG | B | 75 | −70.307 | −43.849 | −5.398 | 1.00 | 32.19 | O |
| ATOM | 9278 | N | ARG | B | 76 | −71.280 | −42.275 | −4.143 | 1.00 | 32.21 | N |
| ATOM | 9279 | CA | ARG | B | 76 | −71.975 | −43.256 | −3.307 | 1.00 | 32.61 | C |
| ATOM | 9281 | CB | ARG | B | 76 | −72.737 | −42.582 | −2.162 | 1.00 | 32.75 | C |
| ATOM | 9284 | CG | ARG | B | 76 | −71.880 | −42.320 | −.929 | 1.00 | 33.44 | C |
| ATOM | 9287 | CD | ARG | B | 76 | −72.720 | −42.046 | .334 | 1.00 | 34.16 | C |
| ATOM | 9290 | NE | ARG | B | 76 | −73.797 | −41.074 | .124 | 1.00 | 34.53 | N |
| ATOM | 9292 | CZ | ARG | B | 76 | −73.627 | −39.765 | −.063 | 1.00 | 34.38 | C |
| ATOM | 9293 | NH1 | ARG | B | 76 | −72.414 | −39.219 | −.092 | 1.00 | 34.34 | N |
| ATOM | 9296 | NH2 | ARG | B | 76 | −74.689 | −38.993 | −.241 | 1.00 | 34.71 | N |
| ATOM | 9299 | C | ARG | B | 76 | −72.918 | −44.159 | −4.112 | 1.00 | 32.81 | C |
| ATOM | 9300 | O | ARG | B | 76 | −72.863 | −45.379 | −3.995 | 1.00 | 32.86 | O |
| ATOM | 9302 | N | ALA | B | 77 | −73.780 | −43.559 | −4.923 | 1.00 | 33.10 | N |
| ATOM | 9303 | CA | ALA | B | 77 | −74.655 | −44.307 | −5.813 | 1.00 | 33.27 | C |
| ATOM | 9305 | CB | ALA | B | 77 | −75.321 | −43.366 | −6.770 | 1.00 | 33.26 | C |
| ATOM | 9309 | C | ALA | B | 77 | −73.884 | −45.370 | −6.578 | 1.00 | 33.80 | C |
| ATOM | 9310 | O | ALA | B | 77 | −74.235 | −46.542 | −6.559 | 1.00 | 33.75 | O |
| ATOM | 9312 | N | LEU | B | 78 | −72.816 | −44.952 | −7.242 | 1.00 | 34.77 | N |
| ATOM | 9313 | CA | LEU | B | 78 | −71.987 | −45.868 | −8.019 | 1.00 | 35.41 | C |
| ATOM | 9315 | CB | LEU | B | 78 | −70.845 | −45.109 | −8.702 | 1.00 | 35.01 | C |
| ATOM | 9318 | CG | LEU | B | 78 | −71.220 | −44.092 | −9.782 | 1.00 | 34.37 | C |
| ATOM | 9320 | CD1 | LEU | B | 78 | −69.945 | −43.502 | −10.381 | 1.00 | 33.93 | C |
| ATOM | 9324 | CD2 | LEU | B | 78 | −72.109 | −44.692 | −10.873 | 1.00 | 32.94 | C |
| ATOM | 9328 | C | LEU | B | 78 | −71.409 | −46.974 | −7.142 | 1.00 | 36.50 | C |
| ATOM | 9329 | O | LEU | B | 78 | −71.336 | −48.124 | −7.552 | 1.00 | 36.87 | O |

TABLE 16-7-continued

Coordinates of *P. tremuloides* IspS

| ATOM | 9331 | N | ASP | B | 79 | −71.005 | −46.619 | −5.931 | 1.00 | 37.74 | N |
|---|---|---|---|---|---|---|---|---|---|---|---|
| ATOM | 9332 | CA | ASP | B | 79 | −70.308 | −47.545 | −5.056 | 1.00 | 38.74 | C |
| ATOM | 9334 | CB | ASP | B | 79 | −69.787 | −46.810 | −3.819 | 1.00 | 38.99 | C |
| ATOM | 9337 | CG | ASP | B | 79 | −68.499 | −47.386 | −3.313 | 1.00 | 40.08 | C |
| ATOM | 9338 | OD1 | ASP | B | 79 | −68.494 | −48.591 | −2.976 | 1.00 | 42.32 | O |
| ATOM | 9339 | OD2 | ASP | B | 79 | −67.494 | −46.638 | −3.261 | 1.00 | 41.24 | O |
| ATOM | 9340 | C | ASP | B | 79 | −71.207 | −48.705 | −4.645 | 1.00 | 39.42 | C |
| ATOM | 9341 | O | ASP | B | 79 | −70.736 | −49.835 | −4.505 | 1.00 | 39.58 | O |
| ATOM | 9343 | N | ARG | B | 80 | −72.495 | −48.424 | −4.450 | 1.00 | 40.26 | N |
| ATOM | 9344 | CA | ARG | B | 80 | −73.471 | −49.470 | −4.143 | 1.00 | 40.92 | C |
| ATOM | 9346 | CB | ARG | B | 80 | −74.823 | −48.881 | −3.716 | 1.00 | 41.46 | C |
| ATOM | 9349 | CG | ARG | B | 80 | −74.871 | −48.247 | −2.308 | 1.00 | 42.87 | C |
| ATOM | 9352 | CD | ARG | B | 80 | −76.316 | −47.826 | −1.936 | 1.00 | 44.62 | C |
| ATOM | 9355 | NE | ARG | B | 80 | −76.946 | −46.968 | −2.949 | 1.00 | 45.87 | N |
| ATOM | 9357 | CZ | ARG | B | 80 | −76.741 | −45.651 | −3.089 | 1.00 | 46.82 | C |
| ATOM | 9358 | NH1 | ARG | B | 80 | −75.905 | −44.989 | −2.282 | 1.00 | 46.27 | N |
| ATOM | 9361 | NH2 | ARG | B | 80 | −77.378 | −44.988 | −4.059 | 1.00 | 47.22 | N |
| ATOM | 9364 | C | ARG | B | 80 | −73.667 | −50.341 | −5.371 | 1.00 | 40.77 | C |
| ATOM | 9365 | O | ARG | B | 80 | −73.642 | −51.563 | −5.275 | 1.00 | 41.06 | O |
| ATOM | 9367 | N | PHE | B | 81 | −73.863 | −49.705 | −6.520 | 1.00 | 40.56 | N |
| ATOM | 9368 | CA | PHE | B | 81 | −73.986 | −50.418 | −7.787 | 1.00 | 40.59 | C |
| ATOM | 9370 | CB | PHE | B | 81 | −73.984 | −49.426 | −8.956 | 1.00 | 40.73 | C |
| ATOM | 9373 | CG | PHE | B | 81 | −73.898 | −50.063 | −10.323 | 1.00 | 40.84 | C |
| ATOM | 9374 | CD1 | PHE | B | 81 | −75.000 | −50.668 | −10.893 | 1.00 | 41.39 | C |
| ATOM | 9376 | CE1 | PHE | B | 81 | −74.925 | −51.236 | −12.167 | 1.00 | 41.67 | C |
| ATOM | 9378 | CZ | PHE | B | 81 | −73.741 | −51.191 | −12.877 | 1.00 | 41.33 | C |
| ATOM | 9380 | CE2 | PHE | B | 81 | −72.638 | −50.580 | −12.326 | 1.00 | 41.19 | C |
| ATOM | 9382 | CD2 | PHE | B | 81 | −72.720 | −50.012 | −11.057 | 1.00 | 41.39 | C |
| ATOM | 9384 | C | PHE | B | 81 | −72.871 | −51.441 | −7.953 | 1.00 | 40.47 | C |
| ATOM | 9385 | O | PHE | B | 81 | −73.134 | −52.583 | −8.311 | 1.00 | 40.85 | O |
| ATOM | 9387 | N | VAL | B | 82 | −71.633 | −51.051 | −7.683 | 1.00 | 40.26 | N |
| ATOM | 9388 | CA | VAL | B | 82 | −70.522 | −51.986 | −7.821 | 1.00 | 40.24 | C |
| ATOM | 9390 | CB | VAL | B | 82 | −69.173 | −51.386 | −7.379 | 1.00 | 40.28 | C |
| ATOM | 9392 | CG1 | VAL | B | 82 | −68.164 | −52.493 | −7.063 | 1.00 | 39.98 | C |
| ATOM | 9396 | CG2 | VAL | B | 82 | −68.644 | −50.462 | −8.451 | 1.00 | 40.09 | C |
| ATOM | 9400 | C | VAL | B | 82 | −70.788 | −53.230 | −7.005 | 1.00 | 40.16 | C |
| ATOM | 9401 | O | VAL | B | 82 | −70.880 | −54.313 | −7.559 | 1.00 | 40.13 | O |
| ATOM | 9403 | N | SER | B | 83 | −70.953 | −53.056 | −5.698 | 1.00 | 40.26 | N |
| ATOM | 9404 | CA | SER | B | 83 | −71.070 | −54.174 | −4.749 | 1.00 | 40.43 | C |
| ATOM | 9406 | CB | SER | B | 83 | −70.797 | −53.666 | −3.331 | 1.00 | 40.54 | C |
| ATOM | 9409 | OG | SER | B | 83 | −71.256 | −52.330 | −3.191 | 1.00 | 40.89 | O |
| ATOM | 9411 | C | SER | B | 83 | −72.415 | −54.912 | −4.831 | 1.00 | 40.34 | C |
| ATOM | 9412 | O | SER | B | 83 | −73.137 | −55.046 | −3.845 | 1.00 | 39.99 | O |
| ATOM | 9414 | N | SER | B | 84 | −72.698 | −55.400 | −6.038 | 1.00 | 40.57 | N |
| ATOM | 9415 | CA | SER | B | 84 | −73.902 | −56.154 | −6.411 | 1.00 | 40.63 | C |
| ATOM | 9417 | CB | SER | B | 84 | −75.154 | −55.679 | −5.651 | 1.00 | 40.56 | C |
| ATOM | 9420 | OG | SER | B | 84 | −75.292 | −54.268 | −5.663 | 1.00 | 39.82 | O |
| ATOM | 9422 | C | SER | B | 84 | −74.104 | −56.026 | −7.940 | 1.00 | 40.85 | C |
| ATOM | 9423 | O | SER | B | 84 | −75.104 | −55.462 | −8.395 | 1.00 | 41.24 | O |
| ATOM | 9425 | N | GLY | B | 85 | −73.136 | −56.524 | −8.720 | 1.00 | 40.75 | N |
| ATOM | 9426 | CA | GLY | B | 85 | −73.201 | −56.506 | −10.191 | 1.00 | 40.64 | C |
| ATOM | 9429 | C | GLY | B | 85 | −73.225 | −55.120 | −10.815 | 1.00 | 40.64 | C |
| ATOM | 9430 | O | GLY | B | 85 | −74.133 | −54.794 | −11.590 | 1.00 | 40.32 | O |
| ATOM | 9432 | N | THR | B | 93 | −74.847 | −57.360 | −18.759 | 1.00 | 36.30 | N |
| ATOM | 9433 | CA | THR | B | 93 | −75.593 | −58.129 | −19.774 | 1.00 | 35.99 | C |
| ATOM | 9435 | CB | THR | B | 93 | −76.251 | −59.379 | −19.152 | 1.00 | 35.87 | C |
| ATOM | 9437 | OG1 | THR | B | 93 | −76.347 | −60.389 | −20.158 | 1.00 | 35.64 | O |
| ATOM | 9439 | CG2 | THR | B | 93 | −77.646 | −59.062 | −18.548 | 1.00 | 34.95 | C |
| ATOM | 9443 | C | THR | B | 93 | −76.625 | −57.274 | −20.583 | 1.00 | 35.90 | C |
| ATOM | 9444 | O | THR | B | 93 | −77.764 | −57.688 | −20.843 | 1.00 | 35.74 | O |
| ATOM | 9446 | N | SER | B | 94 | −76.175 | −56.076 | −20.963 | 1.00 | 35.58 | N |
| ATOM | 9447 | CA | SER | B | 94 | −76.874 | −55.150 | −21.866 | 1.00 | 34.97 | C |
| ATOM | 9449 | CB | SER | B | 94 | −78.074 | −54.472 | −21.190 | 1.00 | 35.06 | C |
| ATOM | 9452 | OG | SER | B | 94 | −77.702 | −53.260 | −20.541 | 1.00 | 34.37 | O |
| ATOM | 9454 | C | SER | B | 94 | −75.831 | −54.097 | −22.232 | 1.00 | 34.39 | C |
| ATOM | 9455 | O | SER | B | 94 | −75.212 | −53.518 | −21.341 | 1.00 | 34.11 | O |
| ATOM | 9457 | N | LEU | B | 95 | −75.619 | −53.864 | −23.522 | 1.00 | 33.77 | N |
| ATOM | 9458 | CA | LEU | B | 95 | −74.490 | −53.045 | −23.952 | 1.00 | 33.33 | C |
| ATOM | 9460 | CB | LEU | B | 95 | −74.373 | −53.010 | −25.475 | 1.00 | 33.30 | C |
| ATOM | 9463 | CG | LEU | B | 95 | −73.154 | −52.246 | −26.006 | 1.00 | 33.27 | C |
| ATOM | 9465 | CD1 | LEU | B | 95 | −71.909 | −52.455 | −25.137 | 1.00 | 32.89 | C |
| ATOM | 9469 | CD2 | LEU | B | 95 | −72.864 | −52.649 | −27.438 | 1.00 | 33.19 | C |
| ATOM | 9473 | C | LEU | B | 95 | −74.551 | −51.623 | −23.413 | 1.00 | 33.00 | C |
| ATOM | 9474 | O | LEU | B | 95 | −73.588 | −51.151 | −22.809 | 1.00 | 32.83 | O |
| ATOM | 9476 | N | HIS | B | 96 | −75.678 | −50.949 | −23.633 | 1.00 | 32.64 | N |
| ATOM | 9477 | CA | HIS | B | 96 | −75.853 | −49.576 | −23.171 | 1.00 | 32.39 | C |
| ATOM | 9479 | CB | HIS | B | 96 | −77.246 | −49.069 | −23.527 | 1.00 | 32.64 | C |
| ATOM | 9482 | CG | HIS | B | 96 | −77.528 | −47.689 | −23.025 | 1.00 | 34.16 | C |

TABLE 16-7-continued

Coordinates of *P. tremuloides* IspS

| ATOM | 9483 | ND1 | HIS | B | 96 | −76.565 | −46.703 | −22.981 | 1.00 | 36.21 | N |
| ATOM | 9485 | CE1 | HIS | B | 96 | −77.096 | −45.594 | −22.496 | 1.00 | 36.92 | C |
| ATOM | 9487 | NE2 | HIS | B | 96 | −78.371 | −45.827 | −22.227 | 1.00 | 37.06 | N |
| ATOM | 9489 | CD2 | HIS | B | 96 | −78.664 | −47.130 | −22.548 | 1.00 | 35.43 | C |
| ATOM | 9491 | C | HIS | B | 96 | −75.612 | −49.445 | −21.665 | 1.00 | 31.78 | C |
| ATOM | 9492 | O | HIS | B | 96 | −74.936 | −48.523 | −21.215 | 1.00 | 31.95 | O |
| ATOM | 9494 | N | GLY | B | 97 | −76.156 | −50.372 | −20.887 | 1.00 | 31.10 | N |
| ATOM | 9495 | CA | GLY | B | 97 | −75.907 | −50.396 | −19.446 | 1.00 | 30.52 | C |
| ATOM | 9498 | C | GLY | B | 97 | −74.434 | −50.532 | −19.085 | 1.00 | 29.95 | C |
| ATOM | 9499 | O | GLY | B | 97 | −73.936 | −49.797 | −18.241 | 1.00 | 30.21 | O |
| ATOM | 9501 | N | THR | B | 98 | −73.740 | −51.470 | −19.726 | 1.00 | 29.15 | N |
| ATOM | 9502 | CA | THR | B | 98 | −72.314 | −51.690 | −19.490 | 1.00 | 28.55 | C |
| ATOM | 9504 | CB | THR | B | 98 | −71.803 | −52.955 | −20.248 | 1.00 | 28.48 | C |
| ATOM | 9506 | OG1 | THR | B | 98 | −72.678 | −54.066 | −19.997 | 1.00 | 28.41 | O |
| ATOM | 9508 | CG2 | THR | B | 98 | −70.405 | −53.331 | −19.816 | 1.00 | 27.74 | C |
| ATOM | 9512 | C | THR | B | 98 | −71.492 | −50.452 | −19.894 | 1.00 | 28.31 | C |
| ATOM | 9513 | O | THR | B | 98 | −70.658 | −49.979 | −19.127 | 1.00 | 28.13 | O |
| ATOM | 9515 | N | ALA | B | 99 | −71.750 | −49.910 | −21.080 | 1.00 | 28.04 | N |
| ATOM | 9516 | CA | ALA | B | 99 | −70.984 | −48.758 | −21.578 | 1.00 | 27.88 | C |
| ATOM | 9518 | CB | ALA | B | 99 | −71.387 | −48.406 | −23.014 | 1.00 | 27.78 | C |
| ATOM | 9522 | C | ALA | B | 99 | −71.127 | −47.538 | −20.684 | 1.00 | 27.62 | C |
| ATOM | 9523 | O | ALA | B | 99 | −70.135 | −46.885 | −20.361 | 1.00 | 27.84 | O |
| ATOM | 9525 | N | LEU | B | 100 | −72.357 | −47.233 | −20.290 | 1.00 | 27.20 | N |
| ATOM | 9526 | CA | LEU | B | 100 | −72.613 | −46.088 | −19.422 | 1.00 | 27.08 | C |
| ATOM | 9528 | CB | LEU | B | 100 | −74.122 | −45.900 | −19.230 | 1.00 | 26.95 | C |
| ATOM | 9531 | CG | LEU | B | 100 | −74.560 | −44.715 | −18.367 | 1.00 | 26.27 | C |
| ATOM | 9533 | CD1 | LEU | B | 100 | −73.753 | −43.478 | −18.734 | 1.00 | 26.19 | C |
| ATOM | 9537 | CD2 | LEU | B | 100 | −76.052 | −44.445 | −18.504 | 1.00 | 25.20 | C |
| ATOM | 9541 | C | LEU | B | 100 | −71.928 | −46.221 | −18.046 | 1.00 | 27.23 | C |
| ATOM | 9542 | O | LEU | B | 100 | −71.368 | −45.243 | −17.523 | 1.00 | 27.16 | O |
| ATOM | 9544 | N | SER | B | 101 | −71.980 | −47.429 | −17.472 | 1.00 | 27.00 | N |
| ATOM | 9545 | CA | SER | B | 101 | −71.475 | −47.682 | −16.117 | 1.00 | 26.63 | C |
| ATOM | 9547 | CB | SER | B | 101 | −72.039 | −48.992 | −15.568 | 1.00 | 26.49 | C |
| ATOM | 9550 | OG | SER | B | 101 | −71.758 | −50.063 | −16.442 | 1.00 | 26.38 | O |
| ATOM | 9552 | C | SER | B | 101 | −69.956 | −47.740 | −16.090 | 1.00 | 26.47 | C |
| ATOM | 9553 | O | SER | B | 101 | −69.326 | −47.324 | −15.121 | 1.00 | 26.35 | O |
| ATOM | 9555 | N | PHE | B | 102 | −69.381 | −48.288 | −17.154 | 1.00 | 26.29 | N |
| ATOM | 9556 | CA | PHE | B | 102 | −67.934 | −48.332 | −17.322 | 1.00 | 25.91 | C |
| ATOM | 9558 | CB | PHE | B | 102 | −67.588 | −49.005 | −18.652 | 1.00 | 25.96 | C |
| ATOM | 9561 | CG | PHE | B | 102 | −66.133 | −49.020 | −18.958 | 1.00 | 25.81 | C |
| ATOM | 9562 | CD1 | PHE | B | 102 | −65.360 | −50.115 | −18.633 | 1.00 | 25.96 | C |
| ATOM | 9564 | CE1 | PHE | B | 102 | −63.999 | −50.122 | −18.909 | 1.00 | 26.94 | C |
| ATOM | 9566 | CZ | PHE | B | 102 | −63.403 | −49.026 | −19.519 | 1.00 | 26.27 | C |
| ATOM | 9568 | CE2 | PHE | B | 102 | −64.174 | −47.930 | −19.848 | 1.00 | 26.19 | C |
| ATOM | 9570 | CD2 | PHE | B | 102 | −65.531 | −47.933 | −19.573 | 1.00 | 26.04 | C |
| ATOM | 9572 | C | PHE | B | 102 | −67.416 | −46.911 | −17.315 | 1.00 | 25.56 | C |
| ATOM | 9573 | O | PHE | B | 102 | −66.486 | −46.564 | −16.568 | 1.00 | 25.37 | O |
| ATOM | 9575 | N | ARG | B | 103 | −68.050 | −46.095 | −18.152 | 1.00 | 25.20 | N |
| ATOM | 9576 | CA | ARG | B | 103 | −67.663 | −44.696 | −18.322 | 1.00 | 25.09 | C |
| ATOM | 9578 | CB | ARG | B | 103 | −68.510 | −44.026 | −19.400 | 1.00 | 25.12 | C |
| ATOM | 9581 | CG | ARG | B | 103 | −68.194 | −42.561 | −19.572 | 1.00 | 25.41 | C |
| ATOM | 9584 | CD | ARG | B | 103 | −68.744 | −42.035 | −20.889 | 1.00 | 26.68 | C |
| ATOM | 9587 | NE | ARG | B | 103 | −70.197 | −41.843 | −20.877 | 1.00 | 27.49 | N |
| ATOM | 9589 | CZ | ARG | B | 103 | −70.826 | −40.851 | −20.246 | 1.00 | 26.56 | C |
| ATOM | 9590 | NH1 | ARG | B | 103 | −70.139 | −39.963 | −19.531 | 1.00 | 27.11 | N |
| ATOM | 9593 | NH2 | ARG | B | 103 | −72.148 | −40.759 | −20.310 | 1.00 | 25.20 | N |
| ATOM | 9596 | C | ARG | B | 103 | −67.785 | −43.898 | −17.033 | 1.00 | 24.61 | C |
| ATOM | 9597 | O | ARG | B | 103 | −66.865 | −43.168 | −16.659 | 1.00 | 24.67 | O |
| ATOM | 9599 | N | LEU | B | 104 | −68.927 | −44.013 | −16.371 | 1.00 | 23.79 | N |
| ATOM | 9600 | CA | LEU | B | 104 | −69.125 | −43.263 | −15.148 | 1.00 | 23.23 | C |
| ATOM | 9602 | CB | LEU | B | 104 | −70.591 | −43.342 | −14.693 | 1.00 | 23.01 | C |
| ATOM | 9605 | CG | LEU | B | 104 | −71.607 | −42.620 | −15.584 | 1.00 | 21.36 | C |
| ATOM | 9607 | CD1 | LEU | B | 104 | −73.002 | −42.860 | −15.067 | 1.00 | 19.31 | C |
| ATOM | 9611 | CD2 | LEU | B | 104 | −71.310 | −41.157 | −15.633 | 1.00 | 19.57 | C |
| ATOM | 9615 | C | LEU | B | 104 | −68.156 | −43.781 | −14.071 | 1.00 | 23.15 | C |
| ATOM | 9616 | O | LEU | B | 104 | −67.445 | −43.007 | −13.423 | 1.00 | 23.40 | O |
| ATOM | 9618 | N | LEU | B | 105 | −68.106 | −45.091 | −13.894 | 1.00 | 22.79 | N |
| ATOM | 9619 | CA | LEU | B | 105 | −67.203 | −45.659 | −12.916 | 1.00 | 22.40 | C |
| ATOM | 9621 | CB | LEU | B | 105 | −67.303 | −47.178 | −12.912 | 1.00 | 22.42 | C |
| ATOM | 9624 | CG | LEU | B | 105 | −68.505 | −47.709 | −12.163 | 1.00 | 21.82 | C |
| ATOM | 9626 | CD1 | LEU | B | 105 | −68.810 | −49.120 | −12.591 | 1.00 | 21.95 | C |
| ATOM | 9630 | CD2 | LEU | B | 105 | −68.201 | −47.648 | −10.692 | 1.00 | 22.14 | C |
| ATOM | 9634 | C | LEU | B | 105 | −65.767 | −45.239 | −13.196 | 1.00 | 22.33 | C |
| ATOM | 9635 | O | LEU | B | 105 | −65.049 | −44.823 | −12.275 | 1.00 | 22.13 | O |
| ATOM | 9637 | N | ARG | B | 106 | −65.331 | −45.342 | −14.451 | 1.00 | 22.08 | N |
| ATOM | 9638 | CA | ARG | B | 106 | −63.953 | −44.973 | −14.730 | 1.00 | 22.20 | C |
| ATOM | 9640 | CB | ARG | B | 106 | −63.521 | −45.266 | −16.151 | 1.00 | 22.33 | C |
| ATOM | 9643 | CG | ARG | B | 106 | −62.075 | −44.827 | −16.329 | 1.00 | 23.60 | C |

TABLE 16-7-continued

Coordinates of *P. tremuloides* IspS

| ATOM | 9646 | CD | ARG | B | 106 | −61.383 | −45.445 | −17.513 | 1.00 | 24.71 | C |
| ATOM | 9649 | NE | ARG | B | 106 | −61.078 | −46.852 | −17.319 | 1.00 | 24.66 | N |
| ATOM | 9651 | CZ | ARG | B | 106 | −60.418 | −47.582 | −18.206 | 1.00 | 25.75 | C |
| ATOM | 9652 | NH1 | ARG | B | 106 | −59.995 | −47.028 | −19.337 | 1.00 | 26.41 | N |
| ATOM | 9655 | NH2 | ARG | B | 106 | −60.182 | −48.866 | −17.971 | 1.00 | 26.54 | N |
| ATOM | 9658 | C | ARG | B | 106 | −63.732 | −43.504 | −14.438 | 1.00 | 21.75 | C |
| ATOM | 9659 | O | ARG | B | 106 | −62.801 | −43.145 | −13.725 | 1.00 | 21.50 | O |
| ATOM | 9661 | N | GLN | B | 107 | −64.609 | −42.680 | −15.003 | 1.00 | 21.69 | N |
| ATOM | 9662 | CA | GLN | B | 107 | −64.630 | −41.239 | −14.794 | 1.00 | 21.64 | C |
| ATOM | 9664 | CB | GLN | B | 107 | −65.964 | −40.664 | −15.261 | 1.00 | 21.71 | C |
| ATOM | 9667 | CG | GLN | B | 107 | −66.169 | −39.178 | −14.929 | 1.00 | 21.97 | C |
| ATOM | 9670 | CD | GLN | B | 107 | −67.588 | −38.723 | −15.172 | 1.00 | 21.54 | C |
| ATOM | 9671 | OE1 | GLN | B | 107 | −68.355 | −39.365 | −15.906 | 1.00 | 20.08 | O |
| ATOM | 9672 | NE2 | GLN | B | 107 | −67.948 | −37.600 | −14.556 | 1.00 | 21.45 | N |
| ATOM | 9675 | C | GLN | B | 107 | −64.454 | −40.850 | −13.352 | 1.00 | 21.70 | C |
| ATOM | 9676 | O | GLN | B | 107 | −63.776 | −39.865 | −13.078 | 1.00 | 22.14 | O |
| ATOM | 9678 | N | HIS | B | 108 | −65.091 | −41.599 | −12.450 | 1.00 | 21.53 | N |
| ATOM | 9679 | CA | HIS | B | 108 | −65.049 | −41.326 | −11.019 | 1.00 | 21.63 | C |
| ATOM | 9681 | CB | HIS | B | 108 | −66.447 | −41.535 | −10.429 | 1.00 | 21.47 | C |
| ATOM | 9684 | CG | HIS | B | 108 | −67.416 | −40.445 | −10.752 | 1.00 | 20.91 | C |
| ATOM | 9685 | ND1 | HIS | B | 108 | −67.541 | −39.315 | −9.976 | 1.00 | 20.66 | N |
| ATOM | 9687 | CE1 | HIS | B | 108 | −68.476 | −38.535 | −10.490 | 1.00 | 20.90 | C |
| ATOM | 9689 | NE2 | HIS | B | 108 | −68.966 | −39.118 | −11.567 | 1.00 | 19.67 | N |
| ATOM | 9691 | CD2 | HIS | B | 108 | −68.326 | −40.320 | −11.747 | 1.00 | 20.76 | C |
| ATOM | 9693 | C | HIS | B | 108 | −64.024 | −42.209 | −10.269 | 1.00 | 22.22 | C |
| ATOM | 9694 | O | HIS | B | 108 | −64.220 | −42.553 | −9.104 | 1.00 | 22.17 | O |
| ATOM | 9696 | N | GLY | B | 109 | −62.950 | −42.613 | −10.933 | 1.00 | 22.91 | N |
| ATOM | 9697 | CA | GLY | B | 109 | −61.846 | −43.288 | −10.245 | 1.00 | 23.85 | C |
| ATOM | 9700 | C | GLY | B | 109 | −61.986 | −44.748 | −9.800 | 1.00 | 24.50 | C |
| ATOM | 9701 | O | GLY | B | 109 | −61.053 | −45.306 | −9.189 | 1.00 | 24.12 | O |
| ATOM | 9703 | N | PHE | B | 110 | −63.128 | −45.371 | −10.094 | 1.00 | 25.16 | N |
| ATOM | 9704 | CA | PHE | B | 110 | −63.309 | −46.791 | −9.800 | 1.00 | 25.67 | C |
| ATOM | 9706 | CB | PHE | B | 110 | −64.782 | −47.187 | −9.891 | 1.00 | 25.80 | C |
| ATOM | 9709 | CG | PHE | B | 110 | −65.625 | −46.656 | −8.772 | 1.00 | 26.12 | C |
| ATOM | 9710 | CD1 | PHE | B | 110 | −65.564 | −47.230 | −7.510 | 1.00 | 27.13 | C |
| ATOM | 9712 | CE1 | PHE | B | 110 | −66.353 | −46.751 | −6.468 | 1.00 | 27.42 | C |
| ATOM | 9714 | CZ | PHE | B | 110 | −67.215 | −45.691 | −6.692 | 1.00 | 26.93 | C |
| ATOM | 9716 | CE2 | PHE | B | 110 | −67.284 | −45.119 | −7.954 | 1.00 | 26.49 | C |
| ATOM | 9718 | CD2 | PHE | B | 110 | −66.494 | −45.601 | −8.981 | 1.00 | 25.96 | C |
| ATOM | 9720 | C | PHE | B | 110 | −62.505 | −47.615 | −10.793 | 1.00 | 25.92 | C |
| ATOM | 9721 | O | PHE | B | 110 | −62.232 | −47.157 | −11.898 | 1.00 | 26.41 | O |
| ATOM | 9723 | N | GLU | B | 111 | −62.134 | −48.832 | −10.406 | 1.00 | 26.06 | N |
| ATOM | 9724 | CA | GLU | B | 111 | −61.403 | −49.724 | −11.304 | 1.00 | 26.17 | C |
| ATOM | 9726 | CB | GLU | B | 111 | −60.444 | −50.609 | −10.511 | 1.00 | 26.50 | C |
| ATOM | 9729 | CG | GLU | B | 111 | −59.372 | −51.272 | −11.374 | 1.00 | 28.11 | C |
| ATOM | 9732 | CD | GLU | B | 111 | −58.607 | −52.377 | −10.646 | 1.00 | 30.70 | C |
| ATOM | 9733 | OE1 | GLU | B | 111 | −58.660 | −52.436 | −9.390 | 1.00 | 31.99 | O |
| ATOM | 9734 | OE2 | GLU | B | 111 | −57.948 | −53.190 | −11.338 | 1.00 | 32.09 | O |
| ATOM | 9735 | C | GLU | B | 111 | −62.355 | −50.598 | −12.130 | 1.00 | 25.60 | C |
| ATOM | 9736 | O | GLU | B | 111 | −63.116 | −51.388 | −11.585 | 1.00 | 25.48 | O |
| ATOM | 9738 | N | VAL | B | 112 | −62.314 | −50.439 | −13.447 | 1.00 | 25.24 | N |
| ATOM | 9739 | CA | VAL | B | 112 | −63.026 | −51.331 | −14.357 | 1.00 | 24.90 | C |
| ATOM | 9741 | CB | VAL | B | 112 | −64.308 | −50.712 | −14.908 | 1.00 | 24.92 | C |
| ATOM | 9743 | CG1 | VAL | B | 112 | −65.268 | −50.437 | −13.771 | 1.00 | 25.26 | C |
| ATOM | 9747 | CG2 | VAL | B | 112 | −63.999 | −49.450 | −15.706 | 1.00 | 24.77 | C |
| ATOM | 9751 | C | VAL | B | 112 | −62.144 | −51.701 | −15.522 | 1.00 | 24.66 | C |
| ATOM | 9752 | O | VAL | B | 112 | −61.217 | −50.964 | −15.862 | 1.00 | 23.80 | O |
| ATOM | 9754 | N | SER | B | 113 | −62.467 | −52.842 | −16.132 | 1.00 | 24.88 | N |
| ATOM | 9755 | CA | SER | B | 113 | −61.604 | −53.494 | −17.109 | 1.00 | 25.21 | C |
| ATOM | 9757 | CB | SER | B | 113 | −61.286 | −54.913 | −16.654 | 1.00 | 24.94 | C |
| ATOM | 9760 | OG | SER | B | 113 | −60.357 | −55.523 | −17.528 | 1.00 | 24.31 | O |
| ATOM | 9762 | C | SER | B | 113 | −62.233 | −53.532 | −18.492 | 1.00 | 25.88 | C |
| ATOM | 9763 | O | SER | B | 113 | −63.446 | −53.651 | −18.630 | 1.00 | 25.86 | O |
| ATOM | 9765 | N | GLN | B | 114 | −61.406 | −53.438 | −19.526 | 1.00 | 26.92 | N |
| ATOM | 9766 | CA | GLN | B | 114 | −61.928 | −53.491 | −20.880 | 1.00 | 27.83 | C |
| ATOM | 9768 | CB | GLN | B | 114 | −60.846 | −53.194 | −21.917 | 1.00 | 27.75 | C |
| ATOM | 9771 | CG | GLN | B | 114 | −59.559 | −53.952 | −21.726 | 1.00 | 28.05 | C |
| ATOM | 9774 | CD | GLN | B | 114 | −58.739 | −54.077 | −23.007 | 1.00 | 28.39 | C |
| ATOM | 9775 | OE1 | GLN | B | 114 | −59.086 | −53.515 | −24.051 | 1.00 | 29.05 | O |
| ATOM | 9776 | NE2 | GLN | B | 114 | −57.637 | −54.808 | −22.925 | 1.00 | 27.62 | N |
| ATOM | 9779 | C | GLN | B | 114 | −62.615 | −54.827 | −21.158 | 1.00 | 28.78 | C |
| ATOM | 9780 | O | GLN | B | 114 | −63.484 | −54.905 | −22.022 | 1.00 | 29.10 | O |
| ATOM | 9782 | N | GLU | B | 115 | −62.248 | −55.861 | −20.401 | 1.00 | 29.99 | N |
| ATOM | 9783 | CA | GLU | B | 115 | −62.888 | −57.181 | −20.505 | 1.00 | 30.89 | C |
| ATOM | 9785 | CB | GLU | B | 115 | −62.252 | −58.202 | −19.549 | 1.00 | 31.10 | C |
| ATOM | 9788 | CG | GLU | B | 115 | −60.740 | −58.394 | −19.697 | 1.00 | 32.35 | C |
| ATOM | 9791 | CD | GLU | B | 115 | −60.320 | −58.796 | −21.106 | 1.00 | 34.20 | C |
| ATOM | 9792 | OE1 | GLU | B | 115 | −60.965 | −59.699 | −21.688 | 1.00 | 34.94 | O |

TABLE 16-7-continued

Coordinates of *P. tremuloides* IspS

| ATOM | 9793 | OE2 | GLU | B | 115 | −59.348 | −58.201 | −21.634 | 1.00 | 35.60 | O |
|---|---|---|---|---|---|---|---|---|---|---|---|
| ATOM | 9794 | C | GLU | B | 115 | −64.380 | −57.120 | −20.224 | 1.00 | 31.26 | C |
| ATOM | 9795 | O | GLU | B | 115 | −65.125 | −57.971 | −20.691 | 1.00 | 31.54 | O |
| ATOM | 9797 | N | ALA | B | 116 | −64.825 | −56.127 | −19.465 | 1.00 | 31.91 | N |
| ATOM | 9798 | CA | ALA | B | 116 | −66.255 | −55.937 | −19.259 | 1.00 | 32.69 | C |
| ATOM | 9800 | CB | ALA | B | 116 | −66.521 | −54.648 | −18.513 | 1.00 | 32.62 | C |
| ATOM | 9804 | C | ALA | B | 116 | −66.999 | −55.950 | −20.597 | 1.00 | 33.33 | C |
| ATOM | 9805 | O | ALA | B | 116 | −68.156 | −56.364 | −20.668 | 1.00 | 33.26 | O |
| ATOM | 9807 | N | PHE | B | 117 | −66.316 | −55.521 | −21.655 | 1.00 | 34.16 | N |
| ATOM | 9808 | CA | PHE | B | 117 | −66.889 | −55.498 | −22.996 | 1.00 | 34.98 | C |
| ATOM | 9810 | CB | PHE | B | 117 | −66.310 | −54.314 | −23.766 | 1.00 | 35.02 | C |
| ATOM | 9813 | CG | PHE | B | 117 | −66.868 | −52.997 | −23.345 | 1.00 | 35.06 | C |
| ATOM | 9814 | CD1 | PHE | B | 117 | −66.061 | −52.046 | −22.729 | 1.00 | 35.33 | C |
| ATOM | 9816 | CE1 | PHE | B | 117 | −66.576 | −50.825 | −22.342 | 1.00 | 35.16 | C |
| ATOM | 9818 | CZ | PHE | B | 117 | −67.907 | −50.544 | −22.570 | 1.00 | 35.37 | C |
| ATOM | 9820 | CE2 | PHE | B | 117 | −68.723 | −51.488 | −23.187 | 1.00 | 35.28 | C |
| ATOM | 9822 | CD2 | PHE | B | 117 | −68.201 | −52.701 | −23.571 | 1.00 | 34.68 | C |
| ATOM | 9824 | C | PHE | B | 117 | −66.676 | −56.766 | −23.830 | 1.00 | 35.86 | C |
| ATOM | 9825 | O | PHE | B | 117 | −66.934 | −56.755 | −25.037 | 1.00 | 35.91 | O |
| ATOM | 9827 | N | SER | B | 118 | −66.215 | −57.853 | −23.212 | 1.00 | 36.98 | N |
| ATOM | 9828 | CA | SER | B | 118 | −65.924 | −59.086 | −23.960 | 1.00 | 37.76 | C |
| ATOM | 9830 | CB | SER | B | 118 | −64.836 | −59.907 | −23.262 | 1.00 | 37.73 | C |
| ATOM | 9833 | OG | SER | B | 118 | −65.272 | −60.346 | −21.987 | 1.00 | 37.77 | O |
| ATOM | 9835 | C | SER | B | 118 | −67.178 | −59.939 | −24.215 | 1.00 | 38.48 | C |
| ATOM | 9836 | O | SER | B | 118 | −67.207 | −60.724 | −25.157 | 1.00 | 38.42 | O |
| ATOM | 9838 | N | GLY | B | 119 | −68.221 | −59.765 | −23.407 | 1.00 | 39.51 | N |
| ATOM | 9839 | CA | GLY | B | 119 | −69.481 | −60.473 | −23.629 | 1.00 | 40.51 | C |
| ATOM | 9842 | C | GLY | B | 119 | −70.287 | −60.034 | −24.848 | 1.00 | 41.51 | C |
| ATOM | 9843 | O | GLY | B | 119 | −71.444 | −60.433 | −25.002 | 1.00 | 41.53 | O |
| ATOM | 9845 | N | PHE | B | 120 | −69.688 | −59.210 | −25.709 | 1.00 | 42.79 | N |
| ATOM | 9846 | CA | PHE | B | 120 | −70.382 | −58.621 | −26.864 | 1.00 | 43.81 | C |
| ATOM | 9848 | CB | PHE | B | 120 | −70.643 | −57.121 | −26.601 | 1.00 | 43.76 | C |
| ATOM | 9851 | CG | PHE | B | 120 | −71.367 | −56.853 | −25.293 | 1.00 | 43.65 | C |
| ATOM | 9852 | CD1 | PHE | B | 120 | −72.762 | −56.874 | −25.230 | 1.00 | 43.48 | C |
| ATOM | 9854 | CE1 | PHE | B | 120 | −73.437 | −56.650 | −24.023 | 1.00 | 43.03 | C |
| ATOM | 9856 | CZ | PHE | B | 120 | −72.717 | −56.413 | −22.865 | 1.00 | 43.09 | C |
| ATOM | 9858 | CE2 | PHE | B | 120 | −71.323 | −56.397 | −22.909 | 1.00 | 43.38 | C |
| ATOM | 9860 | CD2 | PHE | B | 120 | −70.655 | −56.619 | −24.120 | 1.00 | 43.41 | C |
| ATOM | 9862 | C | PHE | B | 120 | −69.607 | −58.832 | −28.175 | 1.00 | 44.81 | C |
| ATOM | 9863 | O | PHE | B | 120 | −69.930 | −58.238 | −29.205 | 1.00 | 44.65 | O |
| ATOM | 9865 | N | LYS | B | 121 | −68.602 | −59.705 | −28.126 | 1.00 | 46.19 | N |
| ATOM | 9866 | CA | LYS | B | 121 | −67.757 | −60.004 | −29.272 | 1.00 | 47.31 | C |
| ATOM | 9868 | CB | LYS | B | 121 | −66.275 | −59.928 | −28.870 | 1.00 | 47.47 | C |
| ATOM | 9871 | CG | LYS | B | 121 | −65.743 | −58.495 | −28.637 | 1.00 | 48.13 | C |
| ATOM | 9874 | CD | LYS | B | 121 | −64.532 | −58.439 | −27.675 | 1.00 | 48.89 | C |
| ATOM | 9877 | CE | LYS | B | 121 | −63.261 | −59.094 | −28.241 | 1.00 | 49.20 | C |
| ATOM | 9880 | NZ | LYS | B | 121 | −62.541 | −58.232 | −29.218 | 1.00 | 49.04 | N |
| ATOM | 9884 | C | LYS | B | 121 | −68.096 | −61.400 | −29.810 | 1.00 | 48.15 | C |
| ATOM | 9885 | O | LYS | B | 121 | −68.199 | −62.361 | −29.043 | 1.00 | 48.36 | O |
| ATOM | 9887 | N | ASP | B | 122 | −68.270 | −61.510 | −31.126 | 1.00 | 49.04 | N |
| ATOM | 9888 | CA | ASP | B | 122 | −68.611 | −62.788 | −31.754 | 1.00 | 49.60 | C |
| ATOM | 9890 | CB | ASP | B | 122 | −69.070 | −62.596 | −33.217 | 1.00 | 49.52 | C |
| ATOM | 9893 | CG | ASP | B | 122 | −67.989 | −62.015 | −34.126 | 1.00 | 49.18 | C |
| ATOM | 9894 | OD1 | ASP | B | 122 | −66.792 | −62.306 | −33.938 | 1.00 | 48.96 | O |
| ATOM | 9895 | OD2 | ASP | B | 122 | −68.351 | −61.268 | −35.057 | 1.00 | 48.82 | O |
| ATOM | 9896 | C | ASP | B | 122 | −67.455 | −63.785 | −31.651 | 1.00 | 50.31 | C |
| ATOM | 9897 | O | ASP | B | 122 | −66.369 | −63.441 | −31.171 | 1.00 | 50.33 | O |
| ATOM | 9899 | N | GLN | B | 123 | −67.705 | −65.014 | −32.098 | 1.00 | 51.05 | N |
| ATOM | 9900 | CA | GLN | B | 123 | −66.716 | −66.095 | −32.057 | 1.00 | 51.61 | C |
| ATOM | 9902 | CB | GLN | B | 123 | −67.263 | −67.330 | −32.785 | 1.00 | 51.82 | C |
| ATOM | 9905 | CG | GLN | B | 123 | −68.483 | −67.986 | −32.117 | 1.00 | 52.32 | C |
| ATOM | 9908 | CD | GLN | B | 123 | −68.117 | −69.137 | −31.184 | 1.00 | 52.64 | C |
| ATOM | 9909 | OE1 | GLN | B | 123 | −67.146 | −69.062 | −30.432 | 1.00 | 53.02 | O |
| ATOM | 9910 | NE2 | GLN | B | 123 | −68.904 | −70.207 | −31.230 | 1.00 | 52.04 | N |
| ATOM | 9913 | C | GLN | B | 123 | −65.358 | −65.694 | −32.659 | 1.00 | 51.78 | C |
| ATOM | 9914 | O | GLN | B | 123 | −64.309 | −66.000 | −32.090 | 1.00 | 51.67 | O |
| ATOM | 9916 | N | ASN | B | 124 | −65.388 | −65.004 | −33.799 | 1.00 | 52.05 | N |
| ATOM | 9917 | CA | ASN | B | 124 | −64.166 | −64.547 | −34.473 | 1.00 | 52.25 | C |
| ATOM | 9919 | CB | ASN | B | 124 | −64.486 | −64.042 | −35.884 | 1.00 | 52.25 | C |
| ATOM | 9922 | CG | ASN | B | 124 | −64.911 | −65.158 | −36.819 | 1.00 | 51.88 | C |
| ATOM | 9923 | OD1 | ASN | B | 124 | −65.918 | −65.825 | −36.592 | 1.00 | 51.43 | O |
| ATOM | 9924 | ND2 | ASN | B | 124 | −64.144 | −65.364 | −37.880 | 1.00 | 51.23 | N |
| ATOM | 9927 | C | ASN | B | 124 | −63.382 | −63.466 | −33.716 | 1.00 | 52.43 | C |
| ATOM | 9928 | O | ASN | B | 124 | −62.189 | −63.287 | −33.959 | 1.00 | 52.33 | O |
| ATOM | 9930 | N | GLY | B | 125 | −64.051 | −62.747 | −32.815 | 1.00 | 52.66 | N |
| ATOM | 9931 | CA | GLY | B | 125 | −63.396 | −61.745 | −31.968 | 1.00 | 52.68 | C |
| ATOM | 9934 | C | GLY | B | 125 | −63.916 | −60.329 | −32.135 | 1.00 | 52.63 | C |
| ATOM | 9935 | O | GLY | B | 125 | −63.539 | −59.447 | −31.367 | 1.00 | 52.57 | O |

TABLE 16-7-continued

Coordinates of *P. tremuloides* IspS

| ATOM | 9937 | N | ASN | B | 126 | −64.782 | −60.117 | −33.129 | 1.00 | 52.54 | N |
|---|---|---|---|---|---|---|---|---|---|---|---|
| ATOM | 9938 | CA | ASN | B | 126 | −65.343 | −58.793 | −33.443 | 1.00 | 52.41 | C |
| ATOM | 9940 | CB | ASN | B | 126 | −65.575 | −58.671 | −34.949 | 1.00 | 52.40 | C |
| ATOM | 9943 | CG | ASN | B | 126 | −64.322 | −58.951 | −35.751 | 1.00 | 52.64 | C |
| ATOM | 9944 | OD1 | ASN | B | 126 | −63.426 | −59.665 | −35.297 | 1.00 | 52.77 | O |
| ATOM | 9945 | ND2 | ASN | B | 126 | −64.249 | −58.390 | −36.952 | 1.00 | 53.00 | N |
| ATOM | 9948 | C | ASN | B | 126 | −66.656 | −58.524 | −32.712 | 1.00 | 52.10 | C |
| ATOM | 9949 | O | ASN | B | 126 | −67.253 | −59.432 | −32.153 | 1.00 | 52.27 | O |
| ATOM | 9951 | N | PHE | B | 127 | −67.111 | −57.279 | −32.724 | 1.00 | 51.61 | N |
| ATOM | 9952 | CA | PHE | B | 127 | −68.362 | −56.936 | −32.055 | 1.00 | 51.23 | C |
| ATOM | 9954 | CB | PHE | B | 127 | −68.506 | −55.416 | −31.905 | 1.00 | 51.21 | C |
| ATOM | 9957 | CG | PHE | B | 127 | −67.702 | −54.848 | −30.770 | 1.00 | 50.58 | C |
| ATOM | 9958 | CD1 | PHE | B | 127 | −66.513 | −54.192 | −31.003 | 1.00 | 50.15 | C |
| ATOM | 9960 | CE1 | PHE | B | 127 | −65.777 | −53.686 | −29.948 | 1.00 | 50.15 | C |
| ATOM | 9962 | CZ | PHE | B | 127 | −66.225 | −53.839 | −28.647 | 1.00 | 49.71 | C |
| ATOM | 9964 | CE2 | PHE | B | 127 | −67.399 | −54.496 | −28.405 | 1.00 | 49.50 | C |
| ATOM | 9966 | CD2 | PHE | B | 127 | −68.132 | −54.999 | −29.459 | 1.00 | 49.99 | C |
| ATOM | 9968 | C | PHE | B | 127 | −69.537 | −57.505 | −32.821 | 1.00 | 50.99 | C |
| ATOM | 9969 | O | PHE | B | 127 | −69.468 | −57.641 | −34.040 | 1.00 | 50.92 | O |
| ATOM | 9971 | N | LEU | B | 128 | −70.609 | −57.840 | −32.106 | 1.00 | 50.83 | N |
| ATOM | 9972 | CA | LEU | B | 128 | −71.799 | −58.422 | −32.731 | 1.00 | 50.76 | C |
| ATOM | 9974 | CB | LEU | B | 128 | −72.780 | −58.953 | −31.669 | 1.00 | 50.80 | C |
| ATOM | 9977 | CG | LEU | B | 128 | −72.341 | −60.098 | −30.734 | 1.00 | 50.91 | C |
| ATOM | 9979 | CD1 | LEU | B | 128 | −73.483 | −60.532 | −29.813 | 1.00 | 50.61 | C |
| ATOM | 9983 | CD2 | LEU | B | 128 | −71.818 | −61.303 | −31.497 | 1.00 | 50.79 | C |
| ATOM | 9987 | C | LEU | B | 128 | −72.500 | −57.407 | −33.646 | 1.00 | 50.55 | C |
| ATOM | 9988 | O | LEU | B | 128 | −73.105 | −56.455 | −33.171 | 1.00 | 50.34 | O |
| ATOM | 9990 | N | GLU | B | 129 | −72.402 | −57.628 | −34.957 | 1.00 | 50.50 | N |
| ATOM | 9991 | CA | GLU | B | 129 | −73.038 | −56.783 | −35.982 | 1.00 | 50.48 | C |
| ATOM | 9993 | CB | GLU | B | 129 | −73.150 | −57.551 | −37.310 | 1.00 | 50.68 | C |
| ATOM | 9996 | CG | GLU | B | 129 | −72.262 | −57.024 | −38.434 | 1.00 | 51.36 | C |
| ATOM | 9999 | CD | GLU | B | 129 | −72.799 | −55.745 | −39.060 | 1.00 | 51.88 | C |
| ATOM | 10000 | OE1 | GLU | B | 129 | −72.110 | −54.707 | −38.961 | 1.00 | 52.72 | O |
| ATOM | 10001 | OE2 | GLU | B | 129 | −73.906 | −55.773 | −39.643 | 1.00 | 51.58 | O |
| ATOM | 10002 | C | GLU | B | 129 | −74.428 | −56.264 | −35.629 | 1.00 | 50.25 | C |
| ATOM | 10003 | O | GLU | B | 129 | −74.737 | −55.110 | −35.899 | 1.00 | 50.18 | O |
| ATOM | 10005 | N | ASN | B | 130 | −75.263 | −57.125 | −35.047 | 1.00 | 50.06 | N |
| ATOM | 10006 | CA | ASN | B | 130 | −76.678 | −56.806 | −34.785 | 1.00 | 49.71 | C |
| ATOM | 10008 | CB | ASN | B | 130 | −77.477 | −58.100 | −34.550 | 1.00 | 49.69 | C |
| ATOM | 10011 | CG | ASN | B | 130 | −77.053 | −58.837 | −33.291 | 1.00 | 49.39 | C |
| ATOM | 10012 | OD1 | ASN | B | 130 | −76.357 | −59.848 | −33.361 | 1.00 | 48.74 | O |
| ATOM | 10013 | ND2 | ASN | B | 130 | −77.468 | −58.329 | −32.134 | 1.00 | 48.99 | N |
| ATOM | 10016 | C | ASN | B | 130 | −76.934 | −55.800 | −33.646 | 1.00 | 49.37 | C |
| ATOM | 10017 | O | ASN | B | 130 | −78.083 | −55.456 | −33.366 | 1.00 | 49.29 | O |
| ATOM | 10019 | N | LEU | B | 131 | −75.868 | −55.336 | −32.996 | 1.00 | 48.98 | N |
| ATOM | 10020 | CA | LEU | B | 131 | −75.957 | −54.279 | −31.988 | 1.00 | 48.56 | C |
| ATOM | 10022 | CB | LEU | B | 131 | −74.797 | −54.392 | −30.991 | 1.00 | 48.44 | C |
| ATOM | 10025 | CG | LEU | B | 131 | −74.759 | −55.671 | −30.148 | 1.00 | 48.19 | C |
| ATOM | 10027 | CD1 | LEU | B | 131 | −73.382 | −55.852 | −29.523 | 1.00 | 47.23 | C |
| ATOM | 10031 | CD2 | LEU | B | 131 | −75.861 | −55.670 | −29.083 | 1.00 | 47.77 | C |
| ATOM | 10035 | C | LEU | B | 131 | −75.968 | −52.875 | −32.604 | 1.00 | 48.29 | C |
| ATOM | 10036 | O | LEU | B | 131 | −76.022 | −51.895 | −31.874 | 1.00 | 48.44 | O |
| ATOM | 10038 | N | LYS | B | 132 | −75.927 | −52.771 | −33.934 | 1.00 | 47.95 | N |
| ATOM | 10039 | CA | LYS | B | 132 | −76.020 | −51.471 | −34.621 | 1.00 | 47.64 | C |
| ATOM | 10041 | CB | LYS | B | 132 | −75.548 | −51.590 | −36.080 | 1.00 | 47.63 | C |
| ATOM | 10044 | CG | LYS | B | 132 | −76.595 | −52.235 | −36.998 | 1.00 | 48.19 | C |
| ATOM | 10047 | CD | LYS | B | 132 | −76.111 | −52.483 | −38.429 | 1.00 | 48.16 | C |
| ATOM | 10050 | CE | LYS | B | 132 | −77.239 | −53.040 | −39.290 | 1.00 | 47.23 | C |
| ATOM | 10053 | NZ | LYS | B | 132 | −76.725 | −53.936 | −40.331 | 1.00 | 47.01 | N |
| ATOM | 10057 | C | LYS | B | 132 | −77.449 | −50.907 | −34.597 | 1.00 | 47.13 | C |
| ATOM | 10058 | O | LYS | B | 132 | −77.683 | −49.772 | −35.005 | 1.00 | 46.87 | O |
| ATOM | 10060 | N | GLU | B | 133 | −78.403 | −51.716 | −34.149 | 1.00 | 46.77 | N |
| ATOM | 10061 | CA | GLU | B | 133 | −79.806 | −51.315 | −34.107 | 1.00 | 46.49 | C |
| ATOM | 10063 | CB | GLU | B | 133 | −80.691 | −52.458 | −34.622 | 1.00 | 46.56 | C |
| ATOM | 10066 | CG | GLU | B | 133 | −80.732 | −52.515 | −36.155 | 1.00 | 47.01 | C |
| ATOM | 10069 | CD | GLU | B | 133 | −80.737 | −53.926 | −36.715 | 1.00 | 47.40 | C |
| ATOM | 10070 | OE1 | GLU | B | 133 | −81.500 | −54.775 | −36.206 | 1.00 | 47.97 | O |
| ATOM | 10071 | OE2 | GLU | B | 133 | −79.983 | −54.177 | −37.679 | 1.00 | 47.22 | O |
| ATOM | 10072 | C | GLU | B | 133 | −80.260 | −50.830 | −32.723 | 1.00 | 45.92 | C |
| ATOM | 10073 | O | GLU | B | 133 | −81.369 | −50.308 | −32.600 | 1.00 | 46.14 | O |
| ATOM | 10075 | N | ASP | B | 134 | −79.424 | −51.002 | −31.691 | 1.00 | 44.98 | N |
| ATOM | 10076 | CA | ASP | B | 134 | −79.611 | −50.277 | −30.428 | 1.00 | 44.14 | C |
| ATOM | 10078 | CB | ASP | B | 134 | −79.375 | −51.162 | −29.197 | 1.00 | 43.95 | C |
| ATOM | 10081 | CG | ASP | B | 134 | −79.646 | −50.419 | −27.883 | 1.00 | 43.57 | C |
| ATOM | 10082 | OD1 | ASP | B | 134 | −80.014 | −49.230 | −27.919 | 1.00 | 42.21 | O |
| ATOM | 10083 | OD2 | ASP | B | 134 | −79.488 | −51.011 | −26.802 | 1.00 | 43.69 | O |
| ATOM | 10084 | C | ASP | B | 134 | −78.662 | −49.073 | −30.426 | 1.00 | 43.47 | C |
| ATOM | 10085 | O | ASP | B | 134 | −77.478 | −49.196 | −30.104 | 1.00 | 43.55 | O |

TABLE 16-7-continued

Coordinates of *P. tremuloides* IspS

| ATOM | 10087 | N | ILE | B | 135 | −79.198 | −47.908 | −30.776 | 1.00 | 42.47 | N |
|---|---|---|---|---|---|---|---|---|---|---|---|
| ATOM | 10088 | CA | ILE | B | 135 | −78.375 | −46.739 | −31.033 | 1.00 | 41.65 | C |
| ATOM | 10090 | CB | ILE | B | 135 | −79.080 | −45.783 | −32.012 | 1.00 | 41.45 | C |
| ATOM | 10092 | CG1 | ILE | B | 135 | −78.877 | −46.313 | −33.434 | 1.00 | 41.74 | C |
| ATOM | 10095 | CD1 | ILE | B | 135 | −79.174 | −45.331 | −34.540 | 1.00 | 42.77 | C |
| ATOM | 10099 | CG2 | ILE | B | 135 | −78.533 | −44.391 | −31.905 | 1.00 | 41.68 | C |
| ATOM | 10103 | C | ILE | B | 135 | −77.901 | −46.059 | −29.746 | 1.00 | 41.14 | C |
| ATOM | 10104 | O | ILE | B | 135 | −76.752 | −45.624 | −29.676 | 1.00 | 41.11 | O |
| ATOM | 10106 | N | LYS | B | 136 | −78.742 | −45.998 | −28.714 | 1.00 | 40.53 | N |
| ATOM | 10107 | CA | LYS | B | 136 | −78.281 | −45.480 | −27.409 | 1.00 | 40.10 | C |
| ATOM | 10109 | CB | LYS | B | 136 | −79.431 | −45.361 | −26.375 | 1.00 | 40.40 | C |
| ATOM | 10112 | CG | LYS | B | 136 | −79.910 | −46.697 | −25.786 | 1.00 | 42.49 | C |
| ATOM | 10115 | CD | LYS | B | 136 | −81.002 | −46.574 | −24.698 | 1.00 | 44.79 | C |
| ATOM | 10118 | CE | LYS | B | 136 | −81.599 | −47.994 | −24.363 | 1.00 | 46.03 | C |
| ATOM | 10121 | NZ | LYS | B | 136 | −82.231 | −48.149 | −22.994 | 1.00 | 46.23 | N |
| ATOM | 10125 | C | LYS | B | 136 | −77.104 | −46.327 | −26.863 | 1.00 | 38.85 | C |
| ATOM | 10126 | O | LYS | B | 136 | −76.246 | −45.806 | −26.143 | 1.00 | 38.91 | O |
| ATOM | 10128 | N | ALA | B | 137 | −77.062 | −47.617 | −27.219 | 1.00 | 37.27 | N |
| ATOM | 10129 | CA | ALA | B | 137 | −75.935 | −48.486 | −26.864 | 1.00 | 35.88 | C |
| ATOM | 10131 | CB | ALA | B | 137 | −76.255 | −49.952 | −27.116 | 1.00 | 35.69 | C |
| ATOM | 10135 | C | ALA | B | 137 | −74.708 | −48.085 | −27.645 | 1.00 | 34.63 | C |
| ATOM | 10136 | O | ALA | B | 137 | −73.647 | −47.894 | −27.055 | 1.00 | 34.70 | O |
| ATOM | 10138 | N | ILE | B | 138 | −74.845 | −47.946 | −28.965 | 1.00 | 33.12 | N |
| ATOM | 10139 | CA | ILE | B | 138 | −73.693 | −47.597 | −29.805 | 1.00 | 31.97 | C |
| ATOM | 10141 | CB | ILE | B | 138 | −74.020 | −47.572 | −31.296 | 1.00 | 31.50 | C |
| ATOM | 10143 | CG1 | ILE | B | 138 | −74.433 | −48.955 | −31.774 | 1.00 | 31.28 | C |
| ATOM | 10146 | CD1 | ILE | B | 138 | −73.460 | −50.052 | −31.417 | 1.00 | 30.86 | C |
| ATOM | 10150 | CG2 | ILE | B | 138 | −72.819 | −47.138 | −32.073 | 1.00 | 30.61 | C |
| ATOM | 10154 | C | ILE | B | 138 | −73.124 | −46.245 | −29.413 | 1.00 | 31.57 | C |
| ATOM | 10155 | O | ILE | B | 138 | −71.909 | −46.090 | −29.305 | 1.00 | 31.77 | O |
| ATOM | 10157 | N | LEU | B | 139 | −73.997 | −45.268 | −29.192 | 1.00 | 30.92 | N |
| ATOM | 10158 | CA | LEU | B | 139 | −73.555 | −43.962 | −28.713 | 1.00 | 30.29 | C |
| ATOM | 10160 | CB | LEU | B | 139 | −74.732 | −43.000 | −28.530 | 1.00 | 30.13 | C |
| ATOM | 10163 | CG | LEU | B | 139 | −74.778 | −41.890 | −29.574 | 1.00 | 29.96 | C |
| ATOM | 10165 | CD1 | LEU | B | 139 | −73.496 | −41.060 | −29.508 | 1.00 | 28.26 | C |
| ATOM | 10169 | CD2 | LEU | B | 139 | −76.022 | −41.019 | −29.397 | 1.00 | 29.48 | C |
| ATOM | 10173 | C | LEU | B | 139 | −72.835 | −44.136 | −27.397 | 1.00 | 29.95 | C |
| ATOM | 10174 | O | LEU | B | 139 | −71.709 | −43.687 | −27.232 | 1.00 | 30.45 | O |
| ATOM | 10176 | N | SER | B | 140 | −73.492 | −44.807 | −26.463 | 1.00 | 29.33 | N |
| ATOM | 10177 | CA | SER | B | 140 | −72.916 | −45.061 | −25.150 | 1.00 | 28.84 | C |
| ATOM | 10179 | CB | SER | B | 140 | −73.900 | −45.878 | −24.298 | 1.00 | 28.93 | C |
| ATOM | 10182 | OG | SER | B | 140 | −73.527 | −45.870 | −22.930 | 1.00 | 30.33 | O |
| ATOM | 10184 | C | SER | B | 140 | −71.555 | −45.770 | −25.243 | 1.00 | 27.78 | C |
| ATOM | 10185 | O | SER | B | 140 | −70.637 | −45.454 | −24.489 | 1.00 | 27.46 | O |
| ATOM | 10187 | N | LEU | B | 141 | −71.432 | −46.719 | −26.167 | 1.00 | 26.82 | N |
| ATOM | 10188 | CA | LEU | B | 141 | −70.178 | −47.433 | −26.348 | 1.00 | 26.34 | C |
| ATOM | 10190 | CB | LEU | B | 141 | −70.366 | −48.658 | −27.256 | 1.00 | 26.16 | C |
| ATOM | 10193 | CG | LEU | B | 141 | −69.098 | −49.472 | −27.584 | 1.00 | 26.09 | C |
| ATOM | 10195 | CD1 | LEU | B | 141 | −68.355 | −49.960 | −26.330 | 1.00 | 24.64 | C |
| ATOM | 10199 | CD2 | LEU | B | 141 | −69.455 | −50.643 | −28.481 | 1.00 | 25.94 | C |
| ATOM | 10203 | C | LEU | B | 141 | −69.124 | −46.476 | −26.914 | 1.00 | 25.89 | C |
| ATOM | 10204 | O | LEU | B | 141 | −68.025 | −46.346 | −26.366 | 1.00 | 25.77 | O |
| ATOM | 10206 | N | TYR | B | 142 | −69.471 | −45.809 | −28.008 | 1.00 | 25.41 | N |
| ATOM | 10207 | CA | TYR | B | 142 | −68.609 | −44.804 | −28.610 | 1.00 | 25.03 | C |
| ATOM | 10209 | CB | TYR | B | 142 | −69.399 | −43.982 | −29.617 | 1.00 | 24.80 | C |
| ATOM | 10212 | CG | TYR | B | 142 | −68.736 | −42.695 | −30.043 | 1.00 | 24.47 | C |
| ATOM | 10213 | CD1 | TYR | B | 142 | −67.761 | −42.686 | −31.029 | 1.00 | 24.18 | C |
| ATOM | 10215 | CE1 | TYR | B | 142 | −67.166 | −41.516 | −31.438 | 1.00 | 24.70 | C |
| ATOM | 10217 | CZ | TYR | B | 142 | −67.548 | −40.315 | −30.871 | 1.00 | 25.80 | C |
| ATOM | 10218 | OH | TYR | B | 142 | −66.940 | −39.129 | −31.279 | 1.00 | 27.63 | O |
| ATOM | 10220 | CE2 | TYR | B | 142 | −68.522 | −40.299 | −29.890 | 1.00 | 25.57 | C |
| ATOM | 10222 | CD2 | TYR | B | 142 | −69.110 | −41.485 | −29.485 | 1.00 | 24.73 | C |
| ATOM | 10224 | C | TYR | B | 142 | −68.095 | −43.883 | −27.537 | 1.00 | 25.17 | C |
| ATOM | 10225 | O | TYR | B | 142 | −66.886 | −43.732 | −27.360 | 1.00 | 25.40 | O |
| ATOM | 10227 | N | GLU | B | 143 | −69.038 | −43.293 | −26.807 | 1.00 | 25.12 | N |
| ATOM | 10228 | CA | GLU | B | 143 | −68.744 | −42.256 | −25.828 | 1.00 | 25.10 | C |
| ATOM | 10230 | CB | GLU | B | 143 | −70.046 | −41.726 | −25.226 | 1.00 | 25.33 | C |
| ATOM | 10233 | CG | GLU | B | 143 | −70.006 | −40.244 | −24.849 | 1.00 | 27.57 | C |
| ATOM | 10236 | CD | GLU | B | 143 | −70.321 | −39.313 | −26.023 | 1.00 | 30.43 | C |
| ATOM | 10237 | OE1 | GLU | B | 143 | −69.343 | −38.764 | −26.583 | 1.00 | 32.89 | O |
| ATOM | 10238 | OE2 | GLU | B | 143 | −71.526 | −39.130 | −26.377 | 1.00 | 30.86 | O |
| ATOM | 10239 | C | GLU | B | 143 | −67.794 | −42.746 | −24.729 | 1.00 | 24.43 | C |
| ATOM | 10240 | O | GLU | B | 143 | −67.026 | −41.959 | −24.179 | 1.00 | 24.06 | O |
| ATOM | 10242 | N | ALA | B | 144 | −67.840 | −44.050 | −24.449 | 1.00 | 24.01 | N |
| ATOM | 10243 | CA | ALA | B | 144 | −67.033 | −44.681 | −23.399 | 1.00 | 23.74 | C |
| ATOM | 10245 | CB | ALA | B | 144 | −67.726 | −45.943 | −22.883 | 1.00 | 23.48 | C |
| ATOM | 10249 | C | ALA | B | 144 | −65.631 | −45.025 | −23.864 | 1.00 | 23.57 | C |
| ATOM | 10250 | O | ALA | B | 144 | −64.720 | −45.171 | −23.060 | 1.00 | 23.69 | O |

TABLE 16-7-continued

Coordinates of *P. tremuloides* IspS

| ATOM | 10252 | N | SER | B | 145 | −65.455 | −45.168 | −25.165 | 1.00 | 23.45 | N |
| ATOM | 10253 | CA | SER | B | 145 | −64.168 | −45.568 | −25.701 | 1.00 | 23.44 | C |
| ATOM | 10255 | CB | SER | B | 145 | −64.300 | −45.856 | −27.214 | 1.00 | 23.63 | C |
| ATOM | 10258 | OG | SER | B | 145 | −64.822 | −44.748 | −27.952 | 1.00 | 24.24 | O |
| ATOM | 10260 | C | SER | B | 145 | −63.065 | −44.520 | −25.416 | 1.00 | 23.24 | C |
| ATOM | 10261 | O | SER | B | 145 | −61.877 | −44.848 | −25.288 | 1.00 | 23.25 | O |
| ATOM | 10263 | N | PHE | B | 146 | −63.454 | −43.257 | −25.285 | 1.00 | 22.92 | N |
| ATOM | 10264 | CA | PHE | B | 146 | −62.464 | −42.189 | −25.170 | 1.00 | 22.35 | C |
| ATOM | 10266 | CB | PHE | B | 146 | −63.090 | −40.837 | −25.478 | 1.00 | 22.09 | C |
| ATOM | 10269 | CG | PHE | B | 146 | −63.505 | −40.717 | −26.911 | 1.00 | 22.40 | C |
| ATOM | 10270 | CD1 | PHE | B | 146 | −62.619 | −40.229 | −27.868 | 1.00 | 21.98 | C |
| ATOM | 10272 | CE1 | PHE | B | 146 | −62.985 | −40.156 | −29.201 | 1.00 | 21.80 | C |
| ATOM | 10274 | CZ | PHE | B | 146 | −64.241 | −40.579 | −29.594 | 1.00 | 21.91 | C |
| ATOM | 10276 | CE2 | PHE | B | 146 | −65.123 | −41.098 | −28.649 | 1.00 | 22.29 | C |
| ATOM | 10278 | CD2 | PHE | B | 146 | −64.751 | −41.170 | −27.323 | 1.00 | 22.34 | C |
| ATOM | 10280 | C | PHE | B | 146 | −61.762 | −42.208 | −23.837 | 1.00 | 21.91 | C |
| ATOM | 10281 | O | PHE | B | 146 | −60.669 | −41.683 | −23.733 | 1.00 | 22.30 | O |
| ATOM | 10283 | N | LEU | B | 147 | −62.361 | −42.864 | −22.841 | 1.00 | 21.27 | N |
| ATOM | 10284 | CA | LEU | B | 147 | −61.727 | −43.050 | −21.535 | 1.00 | 20.49 | C |
| ATOM | 10286 | CB | LEU | B | 147 | −62.791 | −43.333 | −20.478 | 1.00 | 20.14 | C |
| ATOM | 10289 | CG | LEU | B | 147 | −63.609 | −42.109 | −20.102 | 1.00 | 18.87 | C |
| ATOM | 10291 | CD1 | LEU | B | 147 | −64.813 | −42.020 | −20.959 | 1.00 | 15.94 | C |
| ATOM | 10295 | CD2 | LEU | B | 147 | −63.988 | −42.189 | −18.642 | 1.00 | 18.62 | C |
| ATOM | 10299 | C | LEU | B | 147 | −60.678 | −44.163 | −21.498 | 1.00 | 20.41 | C |
| ATOM | 10300 | O | LEU | B | 147 | −60.243 | −44.552 | −20.415 | 1.00 | 20.44 | O |
| ATOM | 10302 | N | ALA | B | 148 | −60.268 | −44.664 | −22.662 | 1.00 | 20.28 | N |
| ATOM | 10303 | CA | ALA | B | 148 | −59.330 | −45.784 | −22.745 | 1.00 | 20.33 | C |
| ATOM | 10305 | CB | ALA | B | 148 | −59.188 | −46.231 | −24.194 | 1.00 | 20.15 | C |
| ATOM | 10309 | C | ALA | B | 148 | −57.952 | −45.462 | −22.170 | 1.00 | 20.54 | C |
| ATOM | 10310 | O | ALA | B | 148 | −57.435 | −44.366 | −22.341 | 1.00 | 20.23 | O |
| ATOM | 10312 | N | LEU | B | 149 | −57.366 | −46.435 | −21.486 | 1.00 | 21.19 | N |
| ATOM | 10313 | CA | LEU | B | 149 | −55.969 | −46.354 | −21.067 | 1.00 | 22.02 | C |
| ATOM | 10315 | CB | LEU | B | 149 | −55.768 | −47.073 | −19.725 | 1.00 | 21.90 | C |
| ATOM | 10318 | CG | LEU | B | 149 | −56.541 | −46.496 | −18.523 | 1.00 | 21.50 | C |
| ATOM | 10320 | CD1 | LEU | B | 149 | −55.979 | −47.006 | −17.223 | 1.00 | 20.96 | C |
| ATOM | 10324 | CD2 | LEU | B | 149 | −56.520 | −44.974 | −18.505 | 1.00 | 20.95 | C |
| ATOM | 10328 | C | LEU | B | 149 | −55.054 | −46.930 | −22.159 | 1.00 | 22.84 | C |
| ATOM | 10329 | O | LEU | B | 149 | −55.507 | −47.678 | −23.017 | 1.00 | 22.91 | O |
| ATOM | 10331 | N | GLU | B | 150 | −53.781 | −46.550 | −22.163 | 1.00 | 23.93 | N |
| ATOM | 10332 | CA | GLU | B | 150 | −52.858 | −47.071 | −23.174 | 1.00 | 25.03 | C |
| ATOM | 10334 | CB | GLU | B | 150 | −51.472 | −46.431 | −23.012 | 1.00 | 25.41 | C |
| ATOM | 10337 | CG | GLU | B | 150 | −50.530 | −46.608 | −24.213 | 1.00 | 27.44 | C |
| ATOM | 10340 | CD | GLU | B | 150 | −49.132 | −45.987 | −23.992 | 1.00 | 30.04 | C |
| ATOM | 10341 | OE1 | GLU | B | 150 | −48.925 | −45.330 | −22.943 | 1.00 | 31.41 | O |
| ATOM | 10342 | OE2 | GLU | B | 150 | −48.242 | −46.161 | −24.867 | 1.00 | 30.34 | O |
| ATOM | 10343 | C | GLU | B | 150 | −52.787 | −48.600 | −23.024 | 1.00 | 25.36 | C |
| ATOM | 10344 | O | GLU | B | 150 | −52.613 | −49.098 | −21.911 | 1.00 | 25.58 | O |
| ATOM | 10346 | N | GLY | B | 151 | −52.968 | −49.337 | −24.122 | 1.00 | 25.79 | N |
| ATOM | 10347 | CA | GLY | B | 151 | −52.959 | −50.816 | −24.086 | 1.00 | 26.11 | C |
| ATOM | 10350 | C | GLY | B | 151 | −54.323 | −51.522 | −24.047 | 1.00 | 26.44 | C |
| ATOM | 10351 | O | GLY | B | 151 | −54.393 | −52.747 | −24.135 | 1.00 | 26.91 | O |
| ATOM | 10353 | N | GLU | B | 152 | −55.407 | −50.768 | −23.899 | 1.00 | 26.58 | N |
| ATOM | 10354 | CA | GLU | B | 152 | −56.757 | −51.319 | −23.971 | 1.00 | 26.57 | C |
| ATOM | 10356 | CB | GLU | B | 152 | −57.697 | −50.531 | −23.065 | 1.00 | 26.74 | C |
| ATOM | 10359 | CG | GLU | B | 152 | −57.291 | −50.595 | −21.596 | 1.00 | 27.63 | C |
| ATOM | 10362 | CD | GLU | B | 152 | −58.271 | −49.893 | −20.668 | 1.00 | 28.86 | C |
| ATOM | 10363 | OE1 | GLU | B | 152 | −58.239 | −50.192 | −19.449 | 1.00 | 28.80 | O |
| ATOM | 10364 | OE2 | GLU | B | 152 | −59.066 | −49.044 | −21.154 | 1.00 | 29.26 | O |
| ATOM | 10365 | C | GLU | B | 152 | −57.254 | −51.303 | −25.415 | 1.00 | 26.53 | C |
| ATOM | 10366 | O | GLU | B | 152 | −57.937 | −50.381 | −25.869 | 1.00 | 26.00 | O |
| ATOM | 10368 | N | ASN | B | 153 | −56.888 | −52.354 | −26.127 | 1.00 | 26.77 | N |
| ATOM | 10369 | CA | ASN | B | 153 | −57.189 | −52.498 | −27.545 | 1.00 | 27.05 | C |
| ATOM | 10371 | CB | ASN | B | 153 | −56.345 | −53.640 | −28.104 | 1.00 | 27.12 | C |
| ATOM | 10374 | CG | ASN | B | 153 | −56.770 | −54.992 | −27.549 | 1.00 | 27.81 | C |
| ATOM | 10375 | OD1 | ASN | B | 153 | −56.540 | −55.307 | −26.379 | 1.00 | 27.65 | O |
| ATOM | 10376 | ND2 | ASN | B | 153 | −57.426 | −55.782 | −28.382 | 1.00 | 29.43 | N |
| ATOM | 10379 | C | ASN | B | 153 | −58.659 | −52.788 | −27.873 | 1.00 | 27.09 | C |
| ATOM | 10380 | O | ASN | B | 153 | −59.053 | −52.658 | −29.029 | 1.00 | 27.11 | O |
| ATOM | 10382 | N | ILE | B | 154 | −59.448 | −53.223 | −26.884 | 1.00 | 27.17 | N |
| ATOM | 10383 | CA | ILE | B | 154 | −60.865 | −53.544 | −27.100 | 1.00 | 27.11 | C |
| ATOM | 10385 | CB | ILE | B | 154 | −61.454 | −54.369 | −25.956 | 1.00 | 26.99 | C |
| ATOM | 10387 | CG1 | ILE | B | 154 | −60.811 | −55.750 | −25.907 | 1.00 | 27.16 | C |
| ATOM | 10390 | CD1 | ILE | B | 154 | −61.309 | −56.622 | −24.746 | 1.00 | 27.41 | C |
| ATOM | 10394 | CG2 | ILE | B | 154 | −62.953 | −54.519 | −26.124 | 1.00 | 26.65 | C |
| ATOM | 10398 | C | ILE | B | 154 | −61.704 | −52.284 | −27.229 | 1.00 | 27.43 | C |
| ATOM | 10399 | O | ILE | B | 154 | −62.718 | −52.279 | −27.939 | 1.00 | 27.39 | O |
| ATOM | 10401 | N | LEU | B | 155 | −61.296 | −51.226 | −26.522 | 1.00 | 27.76 | N |
| ATOM | 10402 | CA | LEU | B | 155 | −61.964 | −49.918 | −26.609 | 1.00 | 27.75 | C |

TABLE 16-7-continued

Coordinates of *P. tremuloides* IspS

| ATOM | 10404 | CB | LEU | B | 155 | −61.578 | −49.024 | −25.430 | 1.00 | 27.31 | C |
| ATOM | 10407 | CG | LEU | B | 155 | −61.968 | −49.544 | −24.052 | 1.00 | 26.64 | C |
| ATOM | 10409 | CD1 | LEU | B | 155 | −61.444 | −48.631 | −22.981 | 1.00 | 25.82 | C |
| ATOM | 10413 | CD2 | LEU | B | 155 | −63.465 | −49.674 | −23.944 | 1.00 | 26.45 | C |
| ATOM | 10417 | C | LEU | B | 155 | −61.620 | −49.226 | −27.924 | 1.00 | 28.32 | C |
| ATOM | 10418 | O | LEU | B | 155 | −62.499 | −48.672 | −28.583 | 1.00 | 28.72 | O |
| ATOM | 10420 | N | ASP | B | 156 | −60.348 | −49.264 | −28.309 | 1.00 | 28.84 | N |
| ATOM | 10421 | CA | ASP | B | 156 | −59.934 | −48.737 | −29.601 | 1.00 | 29.43 | C |
| ATOM | 10423 | CB | ASP | B | 156 | −58.423 | −48.928 | −29.823 | 1.00 | 29.92 | C |
| ATOM | 10426 | CG | ASP | B | 156 | −57.566 | −47.912 | −29.045 | 1.00 | 31.35 | C |
| ATOM | 10427 | OD1 | ASP | B | 156 | −57.803 | −46.680 | −29.162 | 1.00 | 33.23 | O |
| ATOM | 10428 | OD2 | ASP | B | 156 | −56.640 | −48.351 | −28.324 | 1.00 | 33.08 | O |
| ATOM | 10429 | C | ASP | B | 156 | −60.719 | −49.411 | −30.717 | 1.00 | 29.36 | C |
| ATOM | 10430 | O | ASP | B | 156 | −61.075 | −48.768 | −31.697 | 1.00 | 29.33 | O |
| ATOM | 10432 | N | GLU | B | 157 | −60.981 | −50.705 | −30.558 | 1.00 | 29.63 | N |
| ATOM | 10433 | CA | GLU | B | 157 | −61.845 | −51.457 | −31.479 | 1.00 | 29.98 | C |
| ATOM | 10435 | CB | GLU | B | 157 | −61.729 | −52.971 | −31.234 | 1.00 | 30.30 | C |
| ATOM | 10438 | CG | GLU | B | 157 | −60.664 | −53.647 | −32.087 | 1.00 | 31.79 | C |
| ATOM | 10441 | CD | GLU | B | 157 | −60.075 | −54.901 | −31.439 | 1.00 | 33.87 | C |
| ATOM | 10442 | OE1 | GLU | B | 157 | −60.793 | −55.560 | −30.640 | 1.00 | 35.07 | O |
| ATOM | 10443 | OE2 | GLU | B | 157 | −58.894 | −55.223 | −31.743 | 1.00 | 33.70 | O |
| ATOM | 10444 | C | GLU | B | 157 | −63.304 | −51.030 | −31.349 | 1.00 | 29.53 | C |
| ATOM | 10445 | O | GLU | B | 157 | −63.999 | −50.878 | −32.351 | 1.00 | 29.53 | O |
| ATOM | 10447 | N | ALA | B | 158 | −63.758 | −50.853 | −30.112 | 1.00 | 29.11 | N |
| ATOM | 10448 | CA | ALA | B | 158 | −65.104 | −50.370 | −29.840 | 1.00 | 28.87 | C |
| ATOM | 10450 | CB | ALA | B | 158 | −65.307 | −50.195 | −28.351 | 1.00 | 28.82 | C |
| ATOM | 10454 | C | ALA | B | 158 | −65.383 | −49.065 | −30.567 | 1.00 | 28.73 | C |
| ATOM | 10455 | O | ALA | B | 158 | −66.485 | −48.857 | −31.065 | 1.00 | 28.80 | O |
| ATOM | 10457 | N | LYS | B | 159 | −64.385 | −48.197 | −30.642 | 1.00 | 28.65 | N |
| ATOM | 10458 | CA | LYS | B | 159 | −64.553 | −46.910 | −31.296 | 1.00 | 28.98 | C |
| ATOM | 10460 | CB | LYS | B | 159 | −63.439 | −45.950 | −30.857 | 1.00 | 29.16 | C |
| ATOM | 10463 | CG | LYS | B | 159 | −63.558 | −44.536 | −31.426 | 1.00 | 29.82 | C |
| ATOM | 10466 | CD | LYS | B | 159 | −62.812 | −43.493 | −30.592 | 1.00 | 30.96 | C |
| ATOM | 10469 | CE | LYS | B | 159 | −61.295 | −43.610 | −30.691 | 1.00 | 31.57 | C |
| ATOM | 10472 | NZ | LYS | B | 159 | −60.630 | −42.426 | −30.079 | 1.00 | 31.49 | N |
| ATOM | 10476 | C | LYS | B | 159 | −64.594 | −47.041 | −32.826 | 1.00 | 29.08 | C |
| ATOM | 10477 | O | LYS | B | 159 | −65.385 | −46.372 | −33.486 | 1.00 | 28.73 | O |
| ATOM | 10479 | N | VAL | B | 160 | −63.736 | −47.891 | −33.386 | 1.00 | 29.53 | N |
| ATOM | 10480 | CA | VAL | B | 160 | −63.686 | −48.087 | −34.836 | 1.00 | 29.89 | C |
| ATOM | 10482 | CB | VAL | B | 160 | −62.466 | −48.971 | −35.282 | 1.00 | 29.93 | C |
| ATOM | 10484 | CG1 | VAL | B | 160 | −62.576 | −49.375 | −36.756 | 1.00 | 29.58 | C |
| ATOM | 10488 | CG2 | VAL | B | 160 | −61.152 | −48.244 | −35.040 | 1.00 | 29.41 | C |
| ATOM | 10492 | C | VAL | B | 160 | −65.001 | −48.723 | −35.263 | 1.00 | 30.32 | C |
| ATOM | 10493 | O | VAL | B | 160 | −65.507 | −48.459 | −36.362 | 1.00 | 30.41 | O |
| ATOM | 10495 | N | PHE | B | 161 | −65.558 | −49.540 | −34.371 | 1.00 | 30.83 | N |
| ATOM | 10496 | CA | PHE | B | 161 | −66.854 | −50.178 | −34.599 | 1.00 | 31.34 | C |
| ATOM | 10498 | CB | PHE | B | 161 | −67.090 | −51.321 | −33.599 | 1.00 | 31.34 | C |
| ATOM | 10501 | CG | PHE | B | 161 | −68.492 | −51.834 | −33.603 | 1.00 | 31.09 | C |
| ATOM | 10502 | CD1 | PHE | B | 161 | −68.940 | −52.636 | −34.633 | 1.00 | 31.61 | C |
| ATOM | 10504 | CE1 | PHE | B | 161 | −70.249 | −53.098 | −34.649 | 1.00 | 31.48 | C |
| ATOM | 10506 | CZ | PHE | B | 161 | −71.114 | −52.748 | −33.628 | 1.00 | 30.76 | C |
| ATOM | 10508 | CE2 | PHE | B | 161 | −70.677 | −51.944 | −32.606 | 1.00 | 30.19 | C |
| ATOM | 10510 | CD2 | PHE | B | 161 | −69.378 | −51.486 | −32.597 | 1.00 | 30.70 | C |
| ATOM | 10512 | C | PHE | B | 161 | −67.992 | −49.173 | −34.504 | 1.00 | 31.65 | C |
| ATOM | 10513 | O | PHE | B | 161 | −68.785 | −49.038 | −35.432 | 1.00 | 31.62 | O |
| ATOM | 10515 | N | ALA | B | 162 | −68.068 | −48.483 | −33.373 | 1.00 | 32.26 | N |
| ATOM | 10516 | CA | ALA | B | 162 | −69.135 | −47.519 | −33.129 | 1.00 | 32.84 | C |
| ATOM | 10518 | CB | ALA | B | 162 | −68.948 | −46.854 | −31.778 | 1.00 | 32.66 | C |
| ATOM | 10522 | C | ALA | B | 162 | −69.224 | −46.474 | −34.245 | 1.00 | 33.40 | C |
| ATOM | 10523 | O | ALA | B | 162 | −70.229 | −46.408 | −34.937 | 1.00 | 33.45 | O |
| ATOM | 10525 | N | ILE | B | 163 | −68.164 | −45.697 | −34.444 | 1.00 | 34.38 | N |
| ATOM | 10526 | CA | ILE | B | 163 | −68.166 | −44.610 | −35.439 | 1.00 | 35.23 | C |
| ATOM | 10528 | CB | ILE | B | 163 | −66.734 | −44.062 | −35.733 | 1.00 | 35.18 | C |
| ATOM | 10530 | CG1 | ILE | B | 163 | −66.092 | −43.457 | −34.488 | 1.00 | 35.21 | C |
| ATOM | 10533 | CD1 | ILE | B | 163 | −64.620 | −43.171 | −34.663 | 1.00 | 35.96 | C |
| ATOM | 10537 | CG2 | ILE | B | 163 | −66.778 | −42.977 | −36.799 | 1.00 | 34.72 | C |
| ATOM | 10541 | C | ILE | B | 163 | −68.778 | −45.052 | −36.766 | 1.00 | 36.18 | C |
| ATOM | 10542 | O | ILE | B | 163 | −69.588 | −44.335 | −37.360 | 1.00 | 35.87 | O |
| ATOM | 10544 | N | SER | B | 164 | −68.379 | −46.240 | −37.217 | 1.00 | 37.67 | N |
| ATOM | 10545 | CA | SER | B | 164 | −68.761 | −46.752 | −38.539 | 1.00 | 38.74 | C |
| ATOM | 10547 | CB | SER | B | 164 | −68.104 | −48.117 | −38.815 | 1.00 | 38.80 | C |
| ATOM | 10550 | OG | SER | B | 164 | −68.733 | −49.158 | −38.077 | 1.00 | 39.07 | O |
| ATOM | 10552 | C | SER | B | 164 | −70.277 | −46.861 | −38.699 | 1.00 | 39.51 | C |
| ATOM | 10553 | O | SER | B | 164 | −70.820 | −46.494 | −39.737 | 1.00 | 39.96 | O |
| ATOM | 10555 | N | HIS | B | 165 | −70.962 | −47.363 | −37.680 | 1.00 | 40.28 | N |
| ATOM | 10556 | CA | HIS | B | 165 | −72.410 | −47.485 | −37.767 | 1.00 | 41.07 | C |
| ATOM | 10558 | CB | HIS | B | 165 | −72.911 | −48.686 | −36.957 | 1.00 | 41.38 | C |
| ATOM | 10561 | CG | HIS | B | 165 | −72.571 | −50.005 | −37.587 | 1.00 | 42.65 | C |

TABLE 16-7-continued

Coordinates of *P. tremuloides* IspS

| ATOM | 10562 | ND1 | HIS | B | 165 | −71.647 | −50.875 | −37.046 | 1.00 | 43.54 | N |
| ATOM | 10564 | CE1 | HIS | B | 165 | −71.535 | −51.938 | −37.825 | 1.00 | 43.54 | C |
| ATOM | 10566 | NE2 | HIS | B | 165 | −72.346 | −51.785 | −38.858 | 1.00 | 43.25 | N |
| ATOM | 10568 | CD2 | HIS | B | 165 | −73.001 | −50.582 | −38.737 | 1.00 | 43.31 | C |
| ATOM | 10570 | C | HIS | B | 165 | −73.125 | −46.193 | −37.380 | 1.00 | 41.21 | C |
| ATOM | 10571 | O | HIS | B | 165 | −74.257 | −45.980 | −37.805 | 1.00 | 41.53 | O |
| ATOM | 10573 | N | LEU | B | 166 | −72.459 | −45.326 | −36.614 | 1.00 | 41.32 | N |
| ATOM | 10574 | CA | LEU | B | 166 | −73.042 | −44.039 | −36.201 | 1.00 | 41.31 | C |
| ATOM | 10576 | CB | LEU | B | 166 | −72.317 | −43.460 | −34.973 | 1.00 | 41.14 | C |
| ATOM | 10579 | CG | LEU | B | 166 | −72.732 | −43.975 | −33.589 | 1.00 | 40.03 | C |
| ATOM | 10581 | CD1 | LEU | B | 166 | −71.673 | −43.634 | −32.579 | 1.00 | 38.86 | C |
| ATOM | 10585 | CD2 | LEU | B | 166 | −74.077 | −43.421 | −33.151 | 1.00 | 38.52 | C |
| ATOM | 10589 | C | LEU | B | 166 | −73.045 | −42.992 | −37.313 | 1.00 | 41.80 | C |
| ATOM | 10590 | O | LEU | B | 166 | −74.006 | −42.230 | −37.442 | 1.00 | 41.73 | O |
| ATOM | 10592 | N | LYS | B | 167 | −71.982 | −42.947 | −38.116 | 1.00 | 42.47 | N |
| ATOM | 10593 | CA | LYS | B | 167 | −71.847 | −41.891 | −39.137 | 1.00 | 43.00 | C |
| ATOM | 10595 | CB | LYS | B | 167 | −70.416 | −41.822 | −39.702 | 1.00 | 43.12 | C |
| ATOM | 10598 | CG | LYS | B | 167 | −69.937 | −43.068 | −40.450 | 1.00 | 44.12 | C |
| ATOM | 10601 | CD | LYS | B | 167 | −69.138 | −42.725 | −41.736 | 1.00 | 45.36 | C |
| ATOM | 10604 | CE | LYS | B | 167 | −67.898 | −41.842 | −41.483 | 1.00 | 45.65 | C |
| ATOM | 10607 | NZ | LYS | B | 167 | −67.267 | −41.400 | −42.762 | 1.00 | 44.94 | N |
| ATOM | 10611 | C | LYS | B | 167 | −72.873 | −41.950 | −40.283 | 1.00 | 42.99 | C |
| ATOM | 10612 | O | LYS | B | 167 | −72.826 | −41.124 | −41.182 | 1.00 | 42.95 | O |
| ATOM | 10614 | N | GLU | B | 168 | −73.791 | −42.912 | −40.244 | 1.00 | 43.23 | N |
| ATOM | 10615 | CA | GLU | B | 168 | −74.928 | −42.940 | −41.167 | 1.00 | 43.44 | C |
| ATOM | 10617 | CB | GLU | B | 168 | −74.652 | −43.969 | −42.272 | 1.00 | 43.58 | C |
| ATOM | 10620 | CG | GLU | B | 168 | −73.918 | −43.363 | −43.501 | 1.00 | 44.36 | C |
| ATOM | 10623 | CD | GLU | B | 168 | −72.618 | −44.082 | −43.895 | 1.00 | 44.53 | C |
| ATOM | 10624 | OE1 | GLU | B | 168 | −71.853 | −44.494 | −42.992 | 1.00 | 44.71 | O |
| ATOM | 10625 | OE2 | GLU | B | 168 | −72.351 | −44.197 | −45.115 | 1.00 | 43.31 | O |
| ATOM | 10626 | C | GLU | B | 168 | −76.263 | −43.214 | −40.442 | 1.00 | 43.24 | C |
| ATOM | 10627 | O | GLU | B | 168 | −76.932 | −42.291 | −39.942 | 1.00 | 42.54 | O |
| ATOM | 10629 | N | GLY | B | 175 | −83.548 | −42.037 | −36.239 | 1.00 | 49.43 | N |
| ATOM | 10630 | CA | GLY | B | 175 | −84.473 | −41.266 | −35.416 | 1.00 | 49.54 | C |
| ATOM | 10633 | C | GLY | B | 175 | −84.709 | −39.884 | −36.001 | 1.00 | 49.76 | C |
| ATOM | 10634 | O | GLY | B | 175 | −84.828 | −39.741 | −37.220 | 1.00 | 49.70 | O |
| ATOM | 10636 | N | LYS | B | 176 | −84.766 | −38.870 | −35.131 | 1.00 | 49.95 | N |
| ATOM | 10637 | CA | LYS | B | 176 | −85.014 | −37.468 | −35.534 | 1.00 | 50.05 | C |
| ATOM | 10639 | CB | LYS | B | 176 | −86.522 | −37.225 | −35.730 | 1.00 | 50.27 | C |
| ATOM | 10642 | CG | LYS | B | 176 | −87.301 | −36.813 | −34.460 | 1.00 | 51.33 | C |
| ATOM | 10645 | CD | LYS | B | 176 | −88.553 | −37.658 | −34.202 | 1.00 | 52.21 | C |
| ATOM | 10648 | CE | LYS | B | 176 | −88.841 | −37.754 | −32.695 | 1.00 | 52.36 | C |
| ATOM | 10651 | NZ | LYS | B | 176 | −90.029 | −38.607 | −32.422 | 1.00 | 52.15 | N |
| ATOM | 10655 | C | LYS | B | 176 | −84.427 | −36.432 | −34.554 | 1.00 | 49.75 | C |
| ATOM | 10656 | O | LYS | B | 176 | −83.990 | −35.370 | −34.972 | 1.00 | 49.88 | O |
| ATOM | 10658 | N | GLU | B | 177 | −84.473 | −36.729 | −33.254 | 1.00 | 49.46 | N |
| ATOM | 10659 | CA | GLU | B | 177 | −83.769 | −35.959 | −32.221 | 1.00 | 48.92 | C |
| ATOM | 10661 | CB | GLU | B | 177 | −84.628 | −35.813 | −30.946 | 1.00 | 49.03 | C |
| ATOM | 10664 | CG | GLU | B | 177 | −84.196 | −36.691 | −29.732 | 1.00 | 49.60 | C |
| ATOM | 10667 | CD | GLU | B | 177 | −85.278 | −36.871 | −28.662 | 1.00 | 50.10 | C |
| ATOM | 10668 | OE1 | GLU | B | 177 | −84.998 | −37.576 | −27.670 | 1.00 | 49.78 | O |
| ATOM | 10669 | OE2 | GLU | B | 177 | −86.401 | −36.336 | −28.808 | 1.00 | 50.78 | O |
| ATOM | 10670 | C | GLU | B | 177 | −82.469 | −36.703 | −31.924 | 1.00 | 48.19 | C |
| ATOM | 10671 | O | GLU | B | 177 | −81.421 | −36.085 | −31.721 | 1.00 | 48.68 | O |
| ATOM | 10673 | N | LEU | B | 178 | −82.557 | −38.037 | −31.900 | 1.00 | 46.98 | N |
| ATOM | 10674 | CA | LEU | B | 178 | −81.398 | −38.924 | −31.817 | 1.00 | 45.91 | C |
| ATOM | 10676 | CB | LEU | B | 178 | −81.838 | −40.387 | −31.945 | 1.00 | 45.70 | C |
| ATOM | 10679 | CG | LEU | B | 178 | −81.111 | −41.408 | −31.074 | 1.00 | 45.24 | C |
| ATOM | 10681 | CD1 | LEU | B | 178 | −81.498 | −41.225 | −29.609 | 1.00 | 44.88 | C |
| ATOM | 10685 | CD2 | LEU | B | 178 | −81.413 | −42.826 | −31.539 | 1.00 | 44.19 | C |
| ATOM | 10689 | C | LEU | B | 178 | −80.423 | −38.571 | −32.934 | 1.00 | 45.27 | C |
| ATOM | 10690 | O | LEU | B | 178 | −79.211 | −38.624 | −32.759 | 1.00 | 44.99 | O |
| ATOM | 10692 | N | ALA | B | 179 | −80.970 | −38.203 | −34.088 | 1.00 | 44.75 | N |
| ATOM | 10693 | CA | ALA | B | 179 | −80.174 | −37.661 | −35.181 | 1.00 | 44.24 | C |
| ATOM | 10695 | CB | ALA | B | 179 | −81.088 | −37.069 | −36.231 | 1.00 | 44.30 | C |
| ATOM | 10699 | C | ALA | B | 179 | −79.192 | −36.602 | −34.683 | 1.00 | 43.65 | C |
| ATOM | 10700 | O | ALA | B | 179 | −78.028 | −36.604 | −35.061 | 1.00 | 43.56 | O |
| ATOM | 10702 | N | GLU | B | 180 | −79.675 | −35.707 | −33.827 | 1.00 | 43.01 | N |
| ATOM | 10703 | CA | GLU | B | 180 | −78.863 | −34.610 | −33.311 | 1.00 | 42.49 | C |
| ATOM | 10705 | CB | GLU | B | 180 | −79.749 | −33.477 | −32.789 | 1.00 | 42.85 | C |
| ATOM | 10708 | CG | GLU | B | 180 | −80.574 | −32.800 | −33.881 | 1.00 | 44.23 | C |
| ATOM | 10711 | CD | GLU | B | 180 | −80.991 | −31.382 | −33.519 | 1.00 | 45.80 | C |
| ATOM | 10712 | OE1 | GLU | B | 180 | −80.098 | −30.580 | −33.156 | 1.00 | 46.69 | O |
| ATOM | 10713 | OE2 | GLU | B | 180 | −82.203 | −31.065 | −33.610 | 1.00 | 46.71 | O |
| ATOM | 10714 | C | GLU | B | 180 | −77.944 | −35.075 | −32.210 | 1.00 | 41.39 | C |
| ATOM | 10715 | O | GLU | B | 180 | −76.843 | −34.562 | −32.071 | 1.00 | 41.27 | O |
| ATOM | 10717 | N | GLN | B | 181 | −78.404 | −36.035 | −31.419 | 1.00 | 40.20 | N |
| ATOM | 10718 | CA | GLN | B | 181 | −77.570 | −36.632 | −30.394 | 1.00 | 39.45 | C |

TABLE 16-7-continued

Coordinates of *P. tremuloides* IspS

| ATOM | 10720 | CB | GLN | B | 181 | −78.280 | −37.809 | −29.736 | 1.00 | 39.88 | C |
|------|-------|-----|-----|---|-----|---------|---------|---------|------|-------|---|
| ATOM | 10723 | CG | GLN | B | 181 | −78.005 | −37.959 | −28.249 | 1.00 | 41.64 | C |
| ATOM | 10726 | CD | GLN | B | 181 | −78.873 | −37.036 | −27.404 | 1.00 | 44.00 | C |
| ATOM | 10727 | OE1 | GLN | B | 181 | −80.109 | −36.992 | −27.581 | 1.00 | 45.65 | O |
| ATOM | 10728 | NE2 | GLN | B | 181 | −78.235 | −36.291 | −26.474 | 1.00 | 43.41 | N |
| ATOM | 10731 | C | GLN | B | 181 | −76.270 | −37.120 | −31.003 | 1.00 | 38.28 | C |
| ATOM | 10732 | O | GLN | B | 181 | −75.203 | −36.767 | −30.523 | 1.00 | 38.27 | O |
| ATOM | 10734 | N | VAL | B | 182 | −76.358 | −37.911 | −32.072 | 1.00 | 37.05 | N |
| ATOM | 10735 | CA | VAL | B | 182 | −75.160 | −38.515 | −32.675 | 1.00 | 36.20 | C |
| ATOM | 10737 | CB | VAL | B | 182 | −75.486 | −39.661 | −33.681 | 1.00 | 36.11 | C |
| ATOM | 10739 | CG1 | VAL | B | 182 | −76.493 | −40.641 | −33.080 | 1.00 | 36.13 | C |
| ATOM | 10743 | CG2 | VAL | B | 182 | −75.977 | −39.106 | −35.004 | 1.00 | 36.06 | C |
| ATOM | 10747 | C | VAL | B | 182 | −74.238 | −37.495 | −33.364 | 1.00 | 35.44 | C |
| ATOM | 10748 | O | VAL | B | 182 | −73.012 | −37.682 | −33.375 | 1.00 | 35.19 | O |
| ATOM | 10750 | N | SER | B | 183 | −74.811 | −36.432 | −33.936 | 1.00 | 34.41 | N |
| ATOM | 10751 | CA | SER | B | 183 | −73.998 | −35.416 | −34.630 | 1.00 | 33.74 | C |
| ATOM | 10753 | CB | SER | B | 183 | −74.858 | −34.438 | −35.422 | 1.00 | 33.58 | C |
| ATOM | 10756 | OG | SER | B | 183 | −76.003 | −35.085 | −35.925 | 1.00 | 34.52 | O |
| ATOM | 10758 | C | SER | B | 183 | −73.184 | −34.644 | −33.625 | 1.00 | 32.88 | C |
| ATOM | 10759 | O | SER | B | 183 | −72.055 | −34.251 | −33.906 | 1.00 | 33.25 | O |
| ATOM | 10761 | N | HIS | B | 184 | −73.788 | −34.427 | −32.461 | 1.00 | 31.83 | N |
| ATOM | 10762 | CA | HIS | B | 184 | −73.150 | −33.787 | −31.326 | 1.00 | 30.98 | C |
| ATOM | 10764 | CB | HIS | B | 184 | −74.188 | −33.627 | −30.212 | 1.00 | 31.14 | C |
| ATOM | 10767 | CG | HIS | B | 184 | −73.710 | −32.849 | −29.030 | 1.00 | 31.91 | C |
| ATOM | 10768 | ND1 | HIS | B | 184 | −73.326 | −31.527 | −29.114 | 1.00 | 33.18 | N |
| ATOM | 10770 | CE1 | HIS | B | 184 | −72.960 | −31.107 | −27.914 | 1.00 | 33.10 | C |
| ATOM | 10772 | NE2 | HIS | B | 184 | −73.106 | −32.102 | −27.056 | 1.00 | 31.85 | N |
| ATOM | 10774 | CD2 | HIS | B | 184 | −73.583 | −33.200 | −27.727 | 1.00 | 31.86 | C |
| ATOM | 10776 | C | HIS | B | 184 | −71.968 | −34.632 | −30.865 | 1.00 | 30.13 | C |
| ATOM | 10777 | O | HIS | B | 184 | −70.863 | −34.122 | −30.709 | 1.00 | 29.95 | O |
| ATOM | 10779 | N | ALA | B | 185 | −72.194 | −35.931 | −30.683 | 1.00 | 29.27 | N |
| ATOM | 10780 | CA | ALA | B | 185 | −71.123 | −36.856 | −30.281 | 1.00 | 28.64 | C |
| ATOM | 10782 | CB | ALA | B | 185 | −71.689 | −38.233 | −29.986 | 1.00 | 28.44 | C |
| ATOM | 10786 | C | ALA | B | 185 | −70.017 | −36.965 | −31.330 | 1.00 | 28.08 | C |
| ATOM | 10787 | O | ALA | B | 185 | −68.839 | −37.043 | −30.992 | 1.00 | 28.26 | O |
| ATOM | 10789 | N | LEU | B | 186 | −70.394 | −36.984 | −32.602 | 1.00 | 27.40 | N |
| ATOM | 10790 | CA | LEU | B | 186 | −69.412 | −37.101 | −33.674 | 1.00 | 26.84 | C |
| ATOM | 10792 | CB | LEU | B | 186 | −70.088 | −37.481 | −35.000 | 1.00 | 26.75 | C |
| ATOM | 10795 | CG | LEU | B | 186 | −70.085 | −38.983 | −35.320 | 1.00 | 26.70 | C |
| ATOM | 10797 | CD1 | LEU | B | 186 | −70.214 | −39.868 | −34.075 | 1.00 | 27.07 | C |
| ATOM | 10801 | CD2 | LEU | B | 186 | −71.179 | −39.306 | −36.303 | 1.00 | 26.29 | C |
| ATOM | 10805 | C | LEU | B | 186 | −68.594 | −35.822 | −33.815 | 1.00 | 26.45 | C |
| ATOM | 10806 | O | LEU | B | 186 | −67.449 | −35.875 | −34.237 | 1.00 | 26.48 | O |
| ATOM | 10808 | N | GLU | B | 187 | −69.186 | −34.685 | −33.454 | 1.00 | 25.93 | N |
| ATOM | 10809 | CA | GLU | B | 187 | −68.479 | −33.406 | −33.403 | 1.00 | 25.57 | C |
| ATOM | 10811 | CB | GLU | B | 187 | −69.447 | −32.310 | −32.962 | 1.00 | 25.61 | C |
| ATOM | 10814 | CG | GLU | B | 187 | −69.035 | −30.899 | −33.325 | 1.00 | 26.29 | C |
| ATOM | 10817 | CD | GLU | B | 187 | −69.930 | −29.857 | −32.671 | 1.00 | 27.10 | C |
| ATOM | 10818 | OE1 | GLU | B | 187 | −70.312 | −30.057 | −31.487 | 1.00 | 26.51 | O |
| ATOM | 10819 | OE2 | GLU | B | 187 | −70.251 | −28.846 | −33.344 | 1.00 | 27.54 | O |
| ATOM | 10820 | C | GLU | B | 187 | −67.307 | −33.490 | −32.418 | 1.00 | 25.13 | C |
| ATOM | 10821 | O | GLU | B | 187 | −66.155 | −33.165 | −32.749 | 1.00 | 24.85 | O |
| ATOM | 10823 | N | LEU | B | 188 | −67.625 | −33.938 | −31.204 | 1.00 | 24.58 | N |
| ATOM | 10824 | CA | LEU | B | 188 | −66.644 | −34.137 | −30.148 | 1.00 | 24.06 | C |
| ATOM | 10826 | CB | LEU | B | 188 | −66.343 | −32.817 | −29.451 | 1.00 | 24.12 | C |
| ATOM | 10829 | CG | LEU | B | 188 | −65.042 | −32.714 | −28.670 | 1.00 | 23.61 | C |
| ATOM | 10831 | CD1 | LEU | B | 188 | −63.895 | −32.872 | −29.629 | 1.00 | 23.12 | C |
| ATOM | 10835 | CD2 | LEU | B | 188 | −64.976 | −31.368 | −27.964 | 1.00 | 23.18 | C |
| ATOM | 10839 | C | LEU | B | 188 | −67.248 | −35.087 | −29.140 | 1.00 | 23.70 | C |
| ATOM | 10840 | O | LEU | B | 188 | −68.392 | −34.901 | −28.743 | 1.00 | 23.68 | O |
| ATOM | 10842 | N | PRO | B | 189 | −66.493 | −36.106 | −28.713 | 1.00 | 23.34 | N |
| ATOM | 10843 | CA | PRO | B | 189 | −67.031 | −36.983 | −27.692 | 1.00 | 23.08 | C |
| ATOM | 10845 | CB | PRO | B | 189 | −66.018 | −38.115 | −27.638 | 1.00 | 22.96 | C |
| ATOM | 10848 | CG | PRO | B | 189 | −64.743 | −37.452 | −27.940 | 1.00 | 23.22 | C |
| ATOM | 10851 | CD | PRO | B | 189 | −65.059 | −36.350 | −28.929 | 1.00 | 23.54 | C |
| ATOM | 10854 | C | PRO | B | 189 | −67.053 | −36.229 | −26.387 | 1.00 | 22.86 | C |
| ATOM | 10855 | O | PRO | B | 189 | −66.284 | −35.285 | −26.215 | 1.00 | 23.03 | O |
| ATOM | 10856 | N | LEU | B | 190 | −67.912 | −36.628 | −25.465 | 1.00 | 22.56 | N |
| ATOM | 10857 | CA | LEU | B | 190 | −68.152 | −35.773 | −24.323 | 1.00 | 22.41 | C |
| ATOM | 10859 | CB | LEU | B | 190 | −69.567 | −35.970 | −23.766 | 1.00 | 23.04 | C |
| ATOM | 10862 | CG | LEU | B | 190 | −69.853 | −37.136 | −22.848 | 1.00 | 23.41 | C |
| ATOM | 10864 | CD1 | LEU | B | 190 | −69.303 | −36.733 | −21.481 | 1.00 | 25.02 | C |
| ATOM | 10868 | CD2 | LEU | B | 190 | −71.342 | −37.411 | −22.820 | 1.00 | 21.69 | C |
| ATOM | 10872 | C | LEU | B | 190 | −67.065 | −35.899 | −23.266 | 1.00 | 21.56 | C |
| ATOM | 10873 | O | LEU | B | 190 | −66.860 | −34.976 | −22.477 | 1.00 | 21.67 | O |
| ATOM | 10875 | N | HIS | B | 191 | −66.320 | −36.998 | −23.283 | 1.00 | 20.39 | N |
| ATOM | 10876 | CA | HIS | B | 191 | −65.089 | −37.037 | −22.490 | 1.00 | 19.40 | C |
| ATOM | 10878 | CB | HIS | B | 191 | −64.399 | −38.393 | −22.597 | 1.00 | 19.19 | C |

TABLE 16-7-continued

Coordinates of *P. tremuloides* IspS

| ATOM | 10881 | CG | HIS | B | 191 | −63.222 | −38.530 | −21.689 | 1.00 | 19.32 | C |
|---|---|---|---|---|---|---|---|---|---|---|---|
| ATOM | 10882 | ND1 | HIS | B | 191 | −63.347 | −38.562 | −20.317 | 1.00 | 20.95 | N |
| ATOM | 10884 | CE1 | HIS | B | 191 | −62.145 | −38.659 | −19.771 | 1.00 | 21.15 | C |
| ATOM | 10886 | NE2 | HIS | B | 191 | −61.245 | −38.689 | −20.741 | 1.00 | 19.36 | N |
| ATOM | 10888 | CD2 | HIS | B | 191 | −61.893 | −38.604 | −21.948 | 1.00 | 19.49 | C |
| ATOM | 10890 | C | HIS | B | 191 | −64.094 | −35.913 | −22.841 | 1.00 | 18.62 | C |
| ATOM | 10891 | O | HIS | B | 191 | −63.150 | −35.677 | −22.085 | 1.00 | 18.59 | O |
| ATOM | 10893 | N | ARG | B | 192 | −64.307 | −35.216 | −23.957 | 1.00 | 17.72 | N |
| ATOM | 10894 | CA | ARG | B | 192 | −63.394 | −34.150 | −24.394 | 1.00 | 17.57 | C |
| ATOM | 10896 | CB | ARG | B | 192 | −62.838 | −34.504 | −25.773 | 1.00 | 17.81 | C |
| ATOM | 10899 | CG | ARG | B | 192 | −61.971 | −35.736 | −25.781 | 1.00 | 18.59 | C |
| ATOM | 10902 | CD | ARG | B | 192 | −61.484 | −36.067 | −27.181 | 1.00 | 20.10 | C |
| ATOM | 10905 | NE | ARG | B | 192 | −60.462 | −37.116 | −27.165 | 1.00 | 21.62 | N |
| ATOM | 10907 | CZ | ARG | B | 192 | −59.919 | −37.648 | −28.254 | 1.00 | 22.77 | C |
| ATOM | 10908 | NH1 | ARG | B | 192 | −60.304 | −37.248 | −29.454 | 1.00 | 24.20 | N |
| ATOM | 10911 | NH2 | ARG | B | 192 | −58.987 | −38.581 | −28.149 | 1.00 | 23.37 | N |
| ATOM | 10914 | C | ARG | B | 192 | −63.983 | −32.726 | −24.440 | 1.00 | 17.01 | C |
| ATOM | 10915 | O | ARG | B | 192 | −63.242 | −31.739 | −24.526 | 1.00 | 15.78 | O |
| ATOM | 10917 | N | ARG | B | 193 | −65.309 | −32.634 | −24.392 | 1.00 | 17.01 | N |
| ATOM | 10918 | CA | ARG | B | 193 | −66.015 | −31.350 | −24.453 | 1.00 | 16.99 | C |
| ATOM | 10920 | CB | ARG | B | 193 | −67.476 | −31.582 | −24.892 | 1.00 | 17.29 | C |
| ATOM | 10923 | CG | ARG | B | 193 | −68.192 | −30.318 | −25.377 | 1.00 | 18.42 | C |
| ATOM | 10926 | CD | ARG | B | 193 | −69.664 | −30.559 | −25.646 | 1.00 | 19.63 | C |
| ATOM | 10929 | NE | ARG | B | 193 | −69.912 | −31.592 | −26.648 | 1.00 | 21.16 | N |
| ATOM | 10931 | CZ | ARG | B | 193 | −69.868 | −31.398 | −27.971 | 1.00 | 23.56 | C |
| ATOM | 10932 | NH1 | ARG | B | 193 | −69.575 | −30.210 | −28.496 | 1.00 | 23.37 | N |
| ATOM | 10935 | NH2 | ARG | B | 193 | −70.112 | −32.413 | −28.789 | 1.00 | 25.37 | N |
| ATOM | 10938 | C | ARG | B | 193 | −65.974 | −30.658 | −23.087 | 1.00 | 16.46 | C |
| ATOM | 10939 | O | ARG | B | 193 | −66.040 | −31.323 | −22.034 | 1.00 | 16.47 | O |
| ATOM | 10941 | N | THR | B | 194 | −65.864 | −29.335 | −23.078 | 1.00 | 15.84 | N |
| ATOM | 10942 | CA | THR | B | 194 | −65.886 | −28.629 | −21.799 | 1.00 | 15.67 | C |
| ATOM | 10944 | CB | THR | B | 194 | −65.354 | −27.199 | −21.884 | 1.00 | 15.48 | C |
| ATOM | 10946 | OG1 | THR | B | 194 | −66.077 | −26.478 | −22.882 | 1.00 | 15.55 | O |
| ATOM | 10948 | CG2 | THR | B | 194 | −63.877 | −27.189 | −22.211 | 1.00 | 14.65 | C |
| ATOM | 10952 | C | THR | B | 194 | −67.310 | −28.613 | −21.270 | 1.00 | 15.79 | C |
| ATOM | 10953 | O | THR | B | 194 | −68.264 | −28.652 | −22.030 | 1.00 | 15.73 | O |
| ATOM | 10955 | N | GLN | B | 195 | −67.444 | −28.557 | −19.957 | 1.00 | 16.20 | N |
| ATOM | 10956 | CA | GLN | B | 195 | −68.737 | −28.711 | −19.328 | 1.00 | 16.84 | C |
| ATOM | 10958 | CB | GLN | B | 195 | −68.601 | −28.781 | −17.816 | 1.00 | 17.07 | C |
| ATOM | 10961 | CG | GLN | B | 195 | −69.921 | −28.440 | −17.153 | 1.00 | 18.86 | C |
| ATOM | 10964 | CD | GLN | B | 195 | −69.999 | −28.875 | −15.746 | 1.00 | 20.95 | C |
| ATOM | 10965 | OE1 | GLN | B | 195 | −69.099 | −29.511 | −15.245 | 1.00 | 24.63 | O |
| ATOM | 10966 | NE2 | GLN | B | 195 | −71.071 | −28.529 | −15.082 | 1.00 | 22.36 | N |
| ATOM | 10969 | C | GLN | B | 195 | −69.757 | −27.623 | −19.669 | 1.00 | 16.93 | C |
| ATOM | 10970 | O | GLN | B | 195 | −70.858 | −27.931 | −20.136 | 1.00 | 16.98 | O |
| ATOM | 10972 | N | ARG | B | 196 | −69.430 | −26.366 | −19.386 | 1.00 | 16.92 | N |
| ATOM | 10973 | CA | ARG | B | 196 | −70.358 | −25.301 | −19.685 | 1.00 | 17.06 | C |
| ATOM | 10975 | CB | ARG | B | 196 | −69.719 | −23.932 | −19.459 | 1.00 | 17.00 | C |
| ATOM | 10978 | CG | ARG | B | 196 | −70.095 | −23.289 | −18.120 | 1.00 | 17.09 | C |
| ATOM | 10981 | CD | ARG | B | 196 | −70.283 | −24.320 | −16.995 | 1.00 | 17.56 | C |
| ATOM | 10984 | NE | ARG | B | 196 | −71.452 | −24.043 | −16.146 | 1.00 | 17.64 | N |
| ATOM | 10986 | CZ | ARG | B | 196 | −72.289 | −24.965 | −15.664 | 1.00 | 17.93 | C |
| ATOM | 10987 | NH1 | ARG | B | 196 | −72.136 | −26.244 | −15.966 | 1.00 | 17.72 | N |
| ATOM | 10990 | NH2 | ARG | B | 196 | −73.305 | −24.611 | −14.878 | 1.00 | 18.27 | N |
| ATOM | 10993 | C | ARG | B | 196 | −70.881 | −25.481 | −21.098 | 1.00 | 17.42 | C |
| ATOM | 10994 | O | ARG | B | 196 | −72.079 | −25.519 | −21.317 | 1.00 | 17.66 | O |
| ATOM | 10996 | N | LEU | B | 197 | −69.984 | −25.676 | −22.044 | 1.00 | 18.04 | N |
| ATOM | 10997 | CA | LEU | B | 197 | −70.379 | −25.925 | −23.425 | 1.00 | 18.51 | C |
| ATOM | 10999 | CB | LEU | B | 197 | −69.133 | −26.085 | −24.289 | 1.00 | 18.52 | C |
| ATOM | 11002 | CG | LEU | B | 197 | −68.998 | −25.185 | −25.508 | 1.00 | 18.06 | C |
| ATOM | 11004 | CD1 | LEU | B | 197 | −68.209 | −23.932 | −25.205 | 1.00 | 15.52 | C |
| ATOM | 11008 | CD2 | LEU | B | 197 | −68.293 | −26.002 | −26.574 | 1.00 | 20.21 | C |
| ATOM | 11012 | C | LEU | B | 197 | −71.290 | −27.163 | −23.580 | 1.00 | 19.14 | C |
| ATOM | 11013 | O | LEU | B | 197 | −72.226 | −27.150 | −24.372 | 1.00 | 19.52 | O |
| ATOM | 11015 | N | GLU | B | 198 | −71.030 | −28.235 | −22.842 | 1.00 | 19.72 | N |
| ATOM | 11016 | CA | GLU | B | 198 | −71.918 | −29.396 | −22.909 | 1.00 | 20.43 | C |
| ATOM | 11018 | CB | GLU | B | 198 | −71.272 | −30.631 | −22.270 | 1.00 | 20.65 | C |
| ATOM | 11021 | CG | GLU | B | 198 | −72.176 | −31.880 | −22.172 | 1.00 | 22.51 | C |
| ATOM | 11024 | CD | GLU | B | 198 | −72.635 | −32.460 | −23.522 | 1.00 | 25.57 | C |
| ATOM | 11025 | OE1 | GLU | B | 198 | −72.315 | −31.896 | −24.581 | 1.00 | 28.90 | O |
| ATOM | 11026 | OE2 | GLU | B | 198 | −73.326 | −33.506 | −23.540 | 1.00 | 28.09 | O |
| ATOM | 11027 | C | GLU | B | 198 | −73.271 | −29.101 | −22.259 | 1.00 | 20.72 | C |
| ATOM | 11028 | O | GLU | B | 198 | −74.281 | −29.693 | −22.644 | 1.00 | 20.82 | O |
| ATOM | 11030 | N | ALA | B | 199 | −73.282 | −28.199 | −21.270 | 1.00 | 20.86 | N |
| ATOM | 11031 | CA | ALA | B | 199 | −74.508 | −27.814 | −20.565 | 1.00 | 20.66 | C |
| ATOM | 11033 | CB | ALA | B | 199 | −74.176 | −27.013 | −19.326 | 1.00 | 20.36 | C |
| ATOM | 11037 | C | ALA | B | 199 | −75.472 | −27.033 | −21.461 | 1.00 | 20.84 | C |
| ATOM | 11038 | O | ALA | B | 199 | −76.644 | −27.404 | −21.590 | 1.00 | 20.84 | O |

TABLE 16-7-continued

Coordinates of *P. tremuloides* IspS

| ATOM | 11040 | N | VAL | B | 200 | −75.002 | −25.961 | −22.092 | 1.00 | 21.12 | N |
|---|---|---|---|---|---|---|---|---|---|---|---|
| ATOM | 11041 | CA | VAL | B | 200 | −75.903 | −25.177 | −22.942 | 1.00 | 21.60 | C |
| ATOM | 11043 | CB | VAL | B | 200 | −75.215 | −24.042 | −23.701 | 1.00 | 21.30 | C |
| ATOM | 11045 | CG1 | VAL | B | 200 | −74.660 | −23.055 | −22.738 | 1.00 | 21.26 | C |
| ATOM | 11049 | CG2 | VAL | B | 200 | −74.135 | −24.575 | −24.626 | 1.00 | 21.28 | C |
| ATOM | 11053 | C | VAL | B | 200 | −76.603 | −26.077 | −23.944 | 1.00 | 22.32 | C |
| ATOM | 11054 | O | VAL | B | 200 | −77.791 | −25.908 | −24.218 | 1.00 | 22.32 | O |
| ATOM | 11056 | N | TRP | B | 201 | −75.872 | −27.047 | −24.472 | 1.00 | 23.16 | N |
| ATOM | 11057 | CA | TRP | B | 201 | −76.441 | −27.946 | −25.454 | 1.00 | 24.02 | C |
| ATOM | 11059 | CB | TRP | B | 201 | −75.348 | −28.718 | −26.195 | 1.00 | 24.36 | C |
| ATOM | 11062 | CG | TRP | B | 201 | −75.898 | −29.510 | −27.331 | 1.00 | 24.84 | C |
| ATOM | 11063 | CD1 | TRP | B | 201 | −76.060 | −29.092 | −28.613 | 1.00 | 25.41 | C |
| ATOM | 11065 | NE1 | TRP | B | 201 | −76.599 | −30.094 | −29.374 | 1.00 | 25.61 | N |
| ATOM | 11067 | CE2 | TRP | B | 201 | −76.807 | −31.184 | −28.579 | 1.00 | 25.34 | C |
| ATOM | 11068 | CD2 | TRP | B | 201 | −76.374 | −30.847 | −27.279 | 1.00 | 25.56 | C |
| ATOM | 11069 | CE3 | TRP | B | 201 | −76.466 | −31.800 | −26.264 | 1.00 | 27.13 | C |
| ATOM | 11071 | CZ3 | TRP | B | 201 | −76.989 | −33.046 | −26.574 | 1.00 | 28.66 | C |
| ATOM | 11073 | CH2 | TRP | B | 201 | −77.419 | −33.347 | −27.885 | 1.00 | 28.01 | C |
| ATOM | 11075 | CZ2 | TRP | B | 201 | −77.332 | −32.425 | −28.894 | 1.00 | 26.09 | C |
| ATOM | 11077 | C | TRP | B | 201 | −77.411 | −28.938 | −24.833 | 1.00 | 24.22 | C |
| ATOM | 11078 | O | TRP | B | 201 | −78.473 | −29.172 | −25.383 | 1.00 | 24.83 | O |
| ATOM | 11080 | N | SER | B | 202 | −77.034 | −29.541 | −23.715 | 1.00 | 24.39 | N |
| ATOM | 11081 | CA | SER | B | 202 | −77.818 | −30.626 | −23.144 | 1.00 | 24.50 | C |
| ATOM | 11083 | CB | SER | B | 202 | −76.968 | −31.455 | −22.184 | 1.00 | 24.42 | C |
| ATOM | 11086 | OG | SER | B | 202 | −75.848 | −32.021 | −22.848 | 1.00 | 23.80 | O |
| ATOM | 11088 | C | SER | B | 202 | −79.067 | −30.099 | −22.441 | 1.00 | 24.98 | C |
| ATOM | 11089 | O | SER | B | 202 | −80.057 | −30.816 | −22.324 | 1.00 | 24.73 | O |
| ATOM | 11091 | N | ILE | B | 203 | −79.032 | −28.849 | −21.982 | 1.00 | 25.60 | N |
| ATOM | 11092 | CA | ILE | B | 203 | −80.219 | −28.255 | −21.372 | 1.00 | 25.98 | C |
| ATOM | 11094 | CB | ILE | B | 203 | −79.908 | −26.967 | −20.591 | 1.00 | 25.85 | C |
| ATOM | 11096 | CG1 | ILE | B | 203 | −79.086 | −27.326 | −19.348 | 1.00 | 25.76 | C |
| ATOM | 11099 | CD1 | ILE | B | 203 | −78.779 | −26.159 | −18.431 | 1.00 | 26.28 | C |
| ATOM | 11103 | CG2 | ILE | B | 203 | −81.212 | −26.253 | −20.206 | 1.00 | 24.51 | C |
| ATOM | 11107 | C | ILE | B | 203 | −81.280 | −28.016 | −22.443 | 1.00 | 26.67 | C |
| ATOM | 11108 | O | ILE | B | 203 | −82.428 | −28.398 | −22.260 | 1.00 | 26.96 | O |
| ATOM | 11110 | N | GLU | B | 204 | −80.879 | −27.412 | −23.563 | 1.00 | 27.30 | N |
| ATOM | 11111 | CA | GLU | B | 204 | −81.758 | −27.205 | −24.720 | 1.00 | 27.49 | C |
| ATOM | 11113 | CB | GLU | B | 204 | −81.036 | −26.384 | −25.804 | 1.00 | 27.67 | C |
| ATOM | 11116 | CG | GLU | B | 204 | −81.849 | −26.077 | −27.073 | 1.00 | 28.50 | C |
| ATOM | 11119 | CD | GLU | B | 204 | −82.987 | −25.072 | −26.855 | 1.00 | 29.81 | C |
| ATOM | 11120 | OE1 | GLU | B | 204 | −83.158 | −24.600 | −25.711 | 1.00 | 31.40 | O |
| ATOM | 11121 | OE2 | GLU | B | 204 | −83.710 | −24.750 | −27.832 | 1.00 | 29.57 | O |
| ATOM | 11122 | C | GLU | B | 204 | −82.201 | −28.542 | −25.287 | 1.00 | 27.52 | C |
| ATOM | 11123 | O | GLU | B | 204 | −83.321 | −28.667 | −25.738 | 1.00 | 27.67 | O |
| ATOM | 11125 | N | ALA | B | 205 | −81.326 | −29.539 | −25.266 | 1.00 | 27.74 | N |
| ATOM | 11126 | CA | ALA | B | 205 | −81.684 | −30.872 | −25.728 | 1.00 | 28.09 | C |
| ATOM | 11128 | CB | ALA | B | 205 | −80.472 | −31.789 | −25.726 | 1.00 | 27.75 | C |
| ATOM | 11132 | C | ALA | B | 205 | −82.771 | −31.448 | −24.839 | 1.00 | 28.81 | C |
| ATOM | 11133 | O | ALA | B | 205 | −83.811 | −31.877 | −25.325 | 1.00 | 28.90 | O |
| ATOM | 11135 | N | TYR | B | 206 | −82.517 | −31.433 | −23.531 | 1.00 | 29.72 | N |
| ATOM | 11136 | CA | TYR | B | 206 | −83.408 | −32.020 | −22.527 | 1.00 | 30.30 | C |
| ATOM | 11138 | CB | TYR | B | 206 | −82.760 | −31.915 | −21.149 | 1.00 | 30.24 | C |
| ATOM | 11141 | CG | TYR | B | 206 | −83.276 | −32.889 | −20.127 | 1.00 | 29.79 | C |
| ATOM | 11142 | CD1 | TYR | B | 206 | −83.055 | −34.245 | −20.286 | 1.00 | 30.71 | C |
| ATOM | 11144 | CE1 | TYR | B | 206 | −83.498 | −35.161 | −19.360 | 1.00 | 30.78 | C |
| ATOM | 11146 | CZ | TYR | B | 206 | −84.159 | −34.731 | −18.238 | 1.00 | 30.03 | C |
| ATOM | 11147 | OH | TYR | B | 206 | −84.582 | −35.684 | −17.343 | 1.00 | 30.51 | O |
| ATOM | 11149 | CE2 | TYR | B | 206 | −84.394 | −33.379 | −18.042 | 1.00 | 29.42 | C |
| ATOM | 11151 | CD2 | TYR | B | 206 | −83.945 | −32.463 | −18.989 | 1.00 | 29.05 | C |
| ATOM | 11153 | C | TYR | B | 206 | −84.744 | −31.308 | −22.467 | 1.00 | 31.19 | C |
| ATOM | 11154 | O | TYR | B | 206 | −85.790 | −31.930 | −22.311 | 1.00 | 31.44 | O |
| ATOM | 11156 | N | ARG | B | 207 | −84.683 | −29.988 | −22.558 | 1.00 | 32.21 | N |
| ATOM | 11157 | CA | ARG | B | 207 | −85.853 | −29.128 | −22.521 | 1.00 | 33.04 | C |
| ATOM | 11159 | CB | ARG | B | 207 | −85.394 | −27.700 | −22.843 | 1.00 | 32.86 | C |
| ATOM | 11162 | CG | ARG | B | 207 | −86.441 | −26.637 | −22.846 | 1.00 | 32.82 | C |
| ATOM | 11165 | CD | ARG | B | 207 | −85.905 | −25.360 | −23.462 | 1.00 | 32.76 | C |
| ATOM | 11168 | NE | ARG | B | 207 | −85.148 | −24.561 | −22.504 | 1.00 | 32.80 | N |
| ATOM | 11170 | CZ | ARG | B | 207 | −85.676 | −23.709 | −21.628 | 1.00 | 33.40 | C |
| ATOM | 11171 | NH1 | ARG | B | 207 | −86.989 | −23.526 | −21.555 | 1.00 | 34.29 | N |
| ATOM | 11174 | NH2 | ARG | B | 207 | −84.884 | −23.030 | −20.808 | 1.00 | 33.89 | N |
| ATOM | 11177 | C | ARG | B | 207 | −86.971 | −29.606 | −23.478 | 1.00 | 34.14 | C |
| ATOM | 11178 | O | ARG | B | 207 | −88.144 | −29.521 | −23.128 | 1.00 | 34.34 | O |
| ATOM | 11180 | N | LYS | B | 208 | −86.607 | −30.137 | −24.652 | 1.00 | 35.32 | N |
| ATOM | 11181 | CA | LYS | B | 208 | −87.581 | −30.535 | −25.688 | 1.00 | 36.16 | C |
| ATOM | 11183 | CB | LYS | B | 208 | −86.960 | −30.468 | −27.090 | 1.00 | 36.01 | C |
| ATOM | 11186 | CG | LYS | B | 208 | −86.126 | −29.234 | −27.368 | 1.00 | 35.85 | C |
| ATOM | 11189 | CD | LYS | B | 208 | −85.934 | −29.023 | −28.861 | 1.00 | 35.98 | C |
| ATOM | 11192 | CE | LYS | B | 208 | −84.774 | −28.086 | −29.186 | 1.00 | 35.63 | C |

TABLE 16-7-continued

Coordinates of *P. tremuloides* IspS

| ATOM | 11195 | NZ | LYS | B | 208 | −83.566 | −28.843 | −29.596 | 1.00 | 35.17 | N |
|------|-------|-----|-----|---|-----|---------|---------|---------|------|-------|---|
| ATOM | 11199 | C | LYS | B | 208 | −88.166 | −31.937 | −25.490 | 1.00 | 37.25 | C |
| ATOM | 11200 | O | LYS | B | 208 | −89.212 | −32.250 | −26.054 | 1.00 | 37.50 | O |
| ATOM | 11202 | N | LYS | B | 209 | −87.484 | −32.788 | −24.730 | 1.00 | 38.58 | N |
| ATOM | 11203 | CA | LYS | B | 209 | −88.026 | −34.106 | −24.383 | 1.00 | 39.89 | C |
| ATOM | 11205 | CB | LYS | B | 209 | −87.013 | −34.923 | −23.578 | 1.00 | 40.23 | C |
| ATOM | 11208 | CG | LYS | B | 209 | −85.914 | −35.604 | −24.373 | 1.00 | 41.47 | C |
| ATOM | 11211 | CD | LYS | B | 209 | −84.858 | −36.178 | −23.417 | 1.00 | 43.71 | C |
| ATOM | 11214 | CE | LYS | B | 209 | −84.448 | −37.612 | −23.764 | 1.00 | 45.15 | C |
| ATOM | 11217 | NZ | LYS | B | 209 | −85.390 | −38.621 | −23.163 | 1.00 | 45.73 | N |
| ATOM | 11221 | C | LYS | B | 209 | −89.288 | −33.950 | −23.530 | 1.00 | 40.51 | C |
| ATOM | 11222 | O | LYS | B | 209 | −89.230 | −33.367 | −22.441 | 1.00 | 40.84 | O |
| ATOM | 11224 | N | GLU | B | 210 | −90.418 | −34.477 | −24.000 | 1.00 | 40.92 | N |
| ATOM | 11225 | CA | GLU | B | 210 | −91.652 | −34.386 | −23.223 | 1.00 | 41.27 | C |
| ATOM | 11227 | CB | GLU | B | 210 | −92.855 | −34.935 | −23.998 | 1.00 | 41.77 | C |
| ATOM | 11230 | CG | GLU | B | 210 | −92.822 | −36.446 | −24.265 | 1.00 | 43.47 | C |
| ATOM | 11233 | CD | GLU | B | 210 | −94.049 | −36.922 | −25.032 | 1.00 | 45.23 | C |
| ATOM | 11234 | OE1 | GLU | B | 210 | −95.188 | −36.590 | −24.612 | 1.00 | 45.02 | O |
| ATOM | 11235 | OE2 | GLU | B | 210 | −93.863 | −37.629 | −26.053 | 1.00 | 46.74 | O |
| ATOM | 11236 | C | GLU | B | 210 | −91.494 | −35.121 | −21.895 | 1.00 | 40.71 | C |
| ATOM | 11237 | O | GLU | B | 210 | −91.996 | −34.667 | −20.864 | 1.00 | 40.99 | O |
| ATOM | 11239 | N | ASP | B | 211 | −90.773 | −36.240 | −21.924 | 1.00 | 39.76 | N |
| ATOM | 11240 | CA | ASP | B | 211 | −90.533 | −37.050 | −20.721 | 1.00 | 38.96 | C |
| ATOM | 11242 | CB | ASP | B | 211 | −90.151 | −38.476 | −21.123 | 1.00 | 39.10 | C |
| ATOM | 11245 | CG | ASP | B | 211 | −89.101 | −38.499 | −22.212 | 1.00 | 40.26 | C |
| ATOM | 11246 | OD1 | ASP | B | 211 | −89.327 | −37.827 | −23.254 | 1.00 | 41.25 | O |
| ATOM | 11247 | OD2 | ASP | B | 211 | −88.055 | −39.160 | −22.020 | 1.00 | 41.66 | O |
| ATOM | 11248 | C | ASP | B | 211 | −89.440 | −36.468 | −19.826 | 1.00 | 37.75 | C |
| ATOM | 11249 | O | ASP | B | 211 | −89.009 | −37.131 | −18.892 | 1.00 | 37.62 | O |
| ATOM | 11251 | N | ALA | B | 212 | −88.989 | −35.245 | −20.115 | 1.00 | 36.47 | N |
| ATOM | 11252 | CA | ALA | B | 212 | −87.941 | −34.587 | −19.335 | 1.00 | 35.36 | C |
| ATOM | 11254 | CB | ALA | B | 212 | −87.516 | −33.294 | −20.011 | 1.00 | 35.23 | C |
| ATOM | 11258 | C | ALA | B | 212 | −88.423 | −34.307 | −17.920 | 1.00 | 34.40 | C |
| ATOM | 11259 | O | ALA | B | 212 | −89.559 | −33.870 | −17.728 | 1.00 | 34.42 | O |
| ATOM | 11261 | N | ASN | B | 213 | −87.565 | −34.574 | −16.937 | 1.00 | 33.24 | N |
| ATOM | 11262 | CA | ASN | B | 213 | −87.890 | −34.333 | −15.533 | 1.00 | 32.67 | C |
| ATOM | 11264 | CB | ASN | B | 213 | −86.840 | −34.986 | −14.623 | 1.00 | 32.58 | C |
| ATOM | 11267 | CG | ASN | B | 213 | −87.204 | −34.912 | −13.152 | 1.00 | 32.67 | C |
| ATOM | 11268 | OD1 | ASN | B | 213 | −87.891 | −33.994 | −12.722 | 1.00 | 32.62 | O |
| ATOM | 11269 | ND2 | ASN | B | 213 | −86.734 | −35.882 | −12.371 | 1.00 | 33.18 | N |
| ATOM | 11272 | C | ASN | B | 213 | −87.990 | −32.825 | −15.266 | 1.00 | 32.19 | C |
| ATOM | 11273 | O | ASN | B | 213 | −87.010 | −32.092 | −15.376 | 1.00 | 32.38 | O |
| ATOM | 11275 | N | GLN | B | 214 | −89.182 | −32.356 | −14.923 | 1.00 | 31.48 | N |
| ATOM | 11276 | CA | GLN | B | 214 | −89.389 | −30.924 | −14.756 | 1.00 | 30.85 | C |
| ATOM | 11278 | CB | GLN | B | 214 | −90.889 | −30.581 | −14.693 | 1.00 | 30.82 | C |
| ATOM | 11281 | CG | GLN | B | 214 | −91.684 | −30.869 | −16.002 | 1.00 | 30.80 | C |
| ATOM | 11284 | CD | GLN | B | 214 | −90.990 | −30.378 | −17.291 | 1.00 | 29.69 | C |
| ATOM | 11285 | OE1 | GLN | B | 214 | −90.893 | −29.174 | −17.543 | 1.00 | 29.07 | O |
| ATOM | 11286 | NE2 | GLN | B | 214 | −90.526 | −31.321 | −18.113 | 1.00 | 27.71 | N |
| ATOM | 11289 | C | GLN | B | 214 | −88.638 | −30.369 | −13.543 | 1.00 | 30.37 | C |
| ATOM | 11290 | O | GLN | B | 214 | −88.263 | −29.200 | −13.533 | 1.00 | 30.80 | O |
| ATOM | 11292 | N | VAL | B | 215 | −88.393 | −31.200 | −12.532 | 1.00 | 29.54 | N |
| ATOM | 11293 | CA | VAL | B | 215 | −87.566 | −30.779 | −11.395 | 1.00 | 28.56 | C |
| ATOM | 11295 | CB | VAL | B | 215 | −87.564 | −31.818 | −10.260 | 1.00 | 28.64 | C |
| ATOM | 11297 | CG1 | VAL | B | 215 | −86.758 | −31.299 | −9.075 | 1.00 | 27.94 | C |
| ATOM | 11301 | CG2 | VAL | B | 215 | −88.999 | −32.167 | −9.856 | 1.00 | 28.26 | C |
| ATOM | 11305 | C | VAL | B | 215 | −86.124 | −30.545 | −11.845 | 1.00 | 27.63 | C |
| ATOM | 11306 | O | VAL | B | 215 | −85.566 | −29.472 | −11.615 | 1.00 | 27.58 | O |
| ATOM | 11308 | N | LEU | B | 216 | −85.546 | −31.548 | −12.504 | 1.00 | 26.37 | N |
| ATOM | 11309 | CA | LEU | B | 216 | −84.143 | −31.509 | −12.930 | 1.00 | 25.47 | C |
| ATOM | 11311 | CB | LEU | B | 216 | −83.714 | −32.866 | −13.490 | 1.00 | 25.46 | C |
| ATOM | 11314 | CG | LEU | B | 216 | −82.274 | −32.995 | −13.979 | 1.00 | 24.97 | C |
| ATOM | 11316 | CD1 | LEU | B | 216 | −81.289 | −32.640 | −12.883 | 1.00 | 24.62 | C |
| ATOM | 11320 | CD2 | LEU | B | 216 | −82.042 | −34.407 | −14.472 | 1.00 | 24.55 | C |
| ATOM | 11324 | C | LEU | B | 216 | −83.861 | −30.447 | −13.972 | 1.00 | 24.68 | C |
| ATOM | 11325 | O | LEU | B | 216 | −82.819 | −29.820 | −13.929 | 1.00 | 24.91 | O |
| ATOM | 11327 | N | LEU | B | 217 | −84.776 | −30.269 | −14.916 | 1.00 | 23.79 | N |
| ATOM | 11328 | CA | LEU | B | 217 | −84.625 | −29.260 | −15.960 | 1.00 | 23.13 | C |
| ATOM | 11330 | CB | LEU | B | 217 | −85.765 | −29.384 | −16.972 | 1.00 | 23.36 | C |
| ATOM | 11333 | CG | LEU | B | 217 | −85.808 | −28.374 | −18.123 | 1.00 | 23.18 | C |
| ATOM | 11335 | CD1 | LEU | B | 217 | −84.462 | −28.268 | −18.796 | 1.00 | 22.69 | C |
| ATOM | 11339 | CD2 | LEU | B | 217 | −86.861 | −28.786 | −19.126 | 1.00 | 23.38 | C |
| ATOM | 11343 | C | LEU | B | 217 | −84.631 | −27.853 | −15.383 | 1.00 | 22.51 | C |
| ATOM | 11344 | O | LEU | B | 217 | −83.903 | −26.973 | −15.855 | 1.00 | 22.08 | O |
| ATOM | 11346 | N | GLU | B | 218 | −85.481 | −27.647 | −14.375 | 1.00 | 21.84 | N |
| ATOM | 11347 | CA | GLU | B | 218 | −85.619 | −26.339 | −13.725 | 1.00 | 21.26 | C |
| ATOM | 11349 | CB | GLU | B | 218 | −86.813 | −26.341 | −12.768 | 1.00 | 21.27 | C |
| ATOM | 11352 | CG | GLU | B | 218 | −87.206 | −24.956 | −12.246 | 1.00 | 21.35 | C |

TABLE 16-7-continued

Coordinates of *P. tremuloides* IspS

| ATOM | 11355 | CD | GLU | B | 218 | −88.501 | −24.964 | −11.441 | 1.00 | 20.89 | C |
|---|---|---|---|---|---|---|---|---|---|---|---|
| ATOM | 11356 | OE1 | GLU | B | 218 | −89.097 | −26.052 | −11.263 | 1.00 | 20.47 | O |
| ATOM | 11357 | OE2 | GLU | B | 218 | −88.915 | −23.874 | −10.986 | 1.00 | 20.15 | O |
| ATOM | 11358 | C | GLU | B | 218 | −84.348 | −26.001 | −12.969 | 1.00 | 20.58 | C |
| ATOM | 11359 | O | GLU | B | 218 | −83.877 | −24.865 | −12.982 | 1.00 | 20.31 | O |
| ATOM | 11361 | N | LEU | B | 219 | −83.802 | −27.015 | −12.312 | 1.00 | 19.87 | N |
| ATOM | 11362 | CA | LEU | B | 219 | −82.559 | −26.885 | −11.592 | 1.00 | 19.12 | C |
| ATOM | 11364 | CB | LEU | B | 219 | −82.310 | −28.132 | −10.746 | 1.00 | 18.58 | C |
| ATOM | 11367 | CG | LEU | B | 219 | −81.159 | −28.054 | −9.762 | 1.00 | 17.07 | C |
| ATOM | 11369 | CD1 | LEU | B | 219 | −81.321 | −26.847 | −8.872 | 1.00 | 16.10 | C |
| ATOM | 11373 | CD2 | LEU | B | 219 | −81.107 | −29.311 | −8.954 | 1.00 | 15.22 | C |
| ATOM | 11377 | C | LEU | B | 219 | −81.443 | −26.675 | −12.599 | 1.00 | 19.16 | C |
| ATOM | 11378 | O | LEU | B | 219 | −80.684 | −25.721 | −12.478 | 1.00 | 19.42 | O |
| ATOM | 11380 | N | ALA | B | 220 | −81.368 | −27.546 | −13.606 | 1.00 | 19.04 | N |
| ATOM | 11381 | CA | ALA | B | 220 | −80.356 | −27.431 | −14.669 | 1.00 | 19.04 | C |
| ATOM | 11383 | CB | ALA | B | 220 | −80.648 | −28.398 | −15.817 | 1.00 | 18.64 | C |
| ATOM | 11387 | C | ALA | B | 220 | −80.257 | −26.004 | −15.196 | 1.00 | 19.06 | C |
| ATOM | 11388 | O | ALA | B | 220 | −79.159 | −25.472 | −15.321 | 1.00 | 19.08 | O |
| ATOM | 11390 | N | ILE | B | 221 | −81.410 | −25.393 | −15.475 | 1.00 | 19.19 | N |
| ATOM | 11391 | CA | ILE | B | 221 | −81.473 | −24.016 | −15.963 | 1.00 | 19.22 | C |
| ATOM | 11393 | CB | ILE | B | 221 | −82.898 | −23.638 | −16.423 | 1.00 | 19.03 | C |
| ATOM | 11395 | CG1 | ILE | B | 221 | −83.229 | −24.323 | −17.755 | 1.00 | 18.52 | C |
| ATOM | 11398 | CD1 | ILE | B | 221 | −84.687 | −24.645 | −17.928 | 1.00 | 17.52 | C |
| ATOM | 11402 | CG2 | ILE | B | 221 | −83.024 | −22.121 | −16.564 | 1.00 | 18.03 | C |
| ATOM | 11406 | C | ILE | B | 221 | −81.030 | −23.013 | −14.906 | 1.00 | 19.62 | C |
| ATOM | 11407 | O | ILE | B | 221 | −80.137 | −22.190 | −15.136 | 1.00 | 19.53 | O |
| ATOM | 11409 | N | LEU | B | 222 | −81.666 | −23.096 | −13.745 | 1.00 | 20.27 | N |
| ATOM | 11410 | CA | LEU | B | 222 | −81.412 | −22.161 | −12.654 | 1.00 | 20.63 | C |
| ATOM | 11412 | CB | LEU | B | 222 | −82.203 | −22.561 | −11.412 | 1.00 | 20.50 | C |
| ATOM | 11415 | CG | LEU | B | 222 | −82.195 | −21.523 | −10.296 | 1.00 | 20.76 | C |
| ATOM | 11417 | CD1 | LEU | B | 222 | −83.439 | −21.675 | −9.431 | 1.00 | 21.02 | C |
| ATOM | 11421 | CD2 | LEU | B | 222 | −80.924 | −21.625 | −9.453 | 1.00 | 20.21 | C |
| ATOM | 11425 | C | LEU | B | 222 | −79.925 | −22.089 | −12.341 | 1.00 | 20.98 | C |
| ATOM | 11426 | O | LEU | B | 222 | −79.337 | −21.011 | −12.381 | 1.00 | 21.40 | O |
| ATOM | 11428 | N | ASP | B | 223 | −79.319 | −23.240 | −12.064 | 1.00 | 21.24 | N |
| ATOM | 11429 | CA | ASP | B | 223 | −77.907 | −23.298 | −11.709 | 1.00 | 21.48 | C |
| ATOM | 11431 | CB | ASP | B | 223 | −77.509 | −24.724 | −11.314 | 1.00 | 21.66 | C |
| ATOM | 11434 | CG | ASP | B | 223 | −76.168 | −24.792 | −10.589 | 1.00 | 22.70 | C |
| ATOM | 11435 | OD1 | ASP | B | 223 | −75.095 | −24.775 | −11.244 | 1.00 | 24.25 | O |
| ATOM | 11436 | OD2 | ASP | B | 223 | −76.190 | −24.893 | −9.349 | 1.00 | 24.85 | O |
| ATOM | 11437 | C | ASP | B | 223 | −77.017 | −22.768 | −12.835 | 1.00 | 21.64 | C |
| ATOM | 11438 | O | ASP | B | 223 | −76.035 | −22.104 | −12.548 | 1.00 | 21.66 | O |
| ATOM | 11440 | N | TYR | B | 224 | −77.361 | −23.023 | −14.100 | 1.00 | 22.07 | N |
| ATOM | 11441 | CA | TYR | B | 224 | −76.517 | −22.561 | −15.218 | 1.00 | 22.47 | C |
| ATOM | 11443 | CB | TYR | B | 224 | −76.980 | −23.111 | −16.589 | 1.00 | 22.35 | C |
| ATOM | 11446 | CG | TYR | B | 224 | −76.032 | −22.733 | −17.724 | 1.00 | 22.25 | C |
| ATOM | 11447 | CD1 | TYR | B | 224 | −75.002 | −23.576 | −18.116 | 1.00 | 21.46 | C |
| ATOM | 11449 | CE1 | TYR | B | 224 | −74.126 | −23.216 | −19.135 | 1.00 | 21.43 | C |
| ATOM | 11451 | CZ | TYR | B | 224 | −74.260 | −21.991 | −19.761 | 1.00 | 21.62 | C |
| ATOM | 11452 | OH | TYR | B | 224 | −73.387 | −21.618 | −20.760 | 1.00 | 20.46 | O |
| ATOM | 11454 | CE2 | TYR | B | 224 | −75.270 | −21.132 | −19.387 | 1.00 | 22.04 | C |
| ATOM | 11456 | CD2 | TYR | B | 224 | −76.144 | −21.500 | −18.373 | 1.00 | 22.73 | C |
| ATOM | 11458 | C | TYR | B | 224 | −76.414 | −21.023 | −15.262 | 1.00 | 23.06 | C |
| ATOM | 11459 | O | TYR | B | 224 | −75.323 | −20.467 | −15.507 | 1.00 | 22.89 | O |
| ATOM | 11461 | N | ASN | B | 225 | −77.543 | −20.350 | −15.027 | 1.00 | 23.66 | N |
| ATOM | 11462 | CA | ASN | B | 225 | −77.593 | −18.884 | −15.072 | 1.00 | 24.16 | C |
| ATOM | 11464 | CB | ASN | B | 225 | −79.040 | −18.367 | −15.107 | 1.00 | 24.12 | C |
| ATOM | 11467 | CG | ASN | B | 225 | −79.778 | −18.761 | −16.365 | 1.00 | 23.89 | C |
| ATOM | 11468 | OD1 | ASN | B | 225 | −79.182 | −18.877 | −17.437 | 1.00 | 24.33 | O |
| ATOM | 11469 | ND2 | ASN | B | 225 | −81.088 | −18.965 | −16.244 | 1.00 | 22.05 | N |
| ATOM | 11472 | C | ASN | B | 225 | −76.880 | −18.265 | −13.881 | 1.00 | 24.73 | C |
| ATOM | 11473 | O | ASN | B | 225 | −76.195 | −17.247 | −14.027 | 1.00 | 25.09 | O |
| ATOM | 11475 | N | MET | B | 226 | −77.067 | −18.864 | −12.703 | 1.00 | 25.15 | N |
| ATOM | 11476 | CA | MET | B | 226 | −76.423 | −18.390 | −11.479 | 1.00 | 25.53 | C |
| ATOM | 11478 | CB | MET | B | 226 | −76.806 | −19.278 | −10.282 | 1.00 | 26.11 | C |
| ATOM | 11481 | CG | MET | B | 226 | −75.905 | −19.169 | −9.023 | 1.00 | 27.59 | C |
| ATOM | 11484 | SD | MET | B | 226 | −75.676 | −20.788 | −8.214 | 1.00 | 30.67 | S |
| ATOM | 11485 | CE | MET | B | 226 | −77.308 | −21.005 | −7.476 | 1.00 | 29.78 | C |
| ATOM | 11489 | C | MET | B | 226 | −74.920 | −18.380 | −11.692 | 1.00 | 25.16 | C |
| ATOM | 11490 | O | MET | B | 226 | −74.258 | −17.387 | −11.391 | 1.00 | 25.10 | O |
| ATOM | 11492 | N | ILE | B | 227 | −74.388 | −19.473 | −12.239 | 1.00 | 24.88 | N |
| ATOM | 11493 | CA | ILE | B | 227 | −72.944 | −19.564 | −12.501 | 1.00 | 24.70 | C |
| ATOM | 11495 | CB | ILE | B | 227 | −72.476 | −20.994 | −12.882 | 1.00 | 24.45 | C |
| ATOM | 11497 | CG1 | ILE | B | 227 | −72.656 | −21.947 | −11.695 | 1.00 | 23.80 | C |
| ATOM | 11500 | CD1 | ILE | B | 227 | −72.094 | −23.332 | −11.885 | 1.00 | 21.97 | C |
| ATOM | 11504 | CG2 | ILE | B | 227 | −71.030 | −20.969 | −13.266 | 1.00 | 24.90 | C |
| ATOM | 11508 | C | ILE | B | 227 | −72.529 | −18.550 | −13.566 | 1.00 | 24.45 | C |
| ATOM | 11509 | O | ILE | B | 227 | −71.578 | −17.810 | −13.373 | 1.00 | 24.42 | O |

TABLE 16-7-continued

Coordinates of *P. tremuloides* IspS

| ATOM | 11511 | N | GLN | B | 228 | −73.264 | −18.484 | −14.668 | 1.00 | 24.31 | N |
|---|---|---|---|---|---|---|---|---|---|---|---|
| ATOM | 11512 | CA | GLN | B | 228 | −73.038 | −17.414 | −15.639 | 1.00 | 24.19 | C |
| ATOM | 11514 | CB | GLN | B | 228 | −74.143 | −17.363 | −16.688 | 1.00 | 24.02 | C |
| ATOM | 11517 | CG | GLN | B | 228 | −73.788 | −16.488 | −17.864 | 1.00 | 23.42 | C |
| ATOM | 11520 | CD | GLN | B | 228 | −74.807 | −16.567 | −18.983 | 1.00 | 23.70 | C |
| ATOM | 11521 | OE1 | GLN | B | 228 | −75.790 | −15.813 | −19.015 | 1.00 | 24.07 | O |
| ATOM | 11522 | NE2 | GLN | B | 228 | −74.564 | −17.465 | −19.927 | 1.00 | 23.49 | N |
| ATOM | 11525 | C | GLN | B | 228 | −72.913 | −16.037 | −14.987 | 1.00 | 24.37 | C |
| ATOM | 11526 | O | GLN | B | 228 | −72.145 | −15.210 | −15.470 | 1.00 | 24.45 | O |
| ATOM | 11528 | N | SER | B | 229 | −73.653 | −15.776 | −13.909 | 1.00 | 24.45 | N |
| ATOM | 11529 | CA | SER | B | 229 | −73.578 | −14.459 | −13.264 | 1.00 | 24.76 | C |
| ATOM | 11531 | CB | SER | B | 229 | −74.815 | −14.163 | −12.397 | 1.00 | 24.84 | C |
| ATOM | 11534 | OG | SER | B | 229 | −74.711 | −14.718 | −11.096 | 1.00 | 25.81 | O |
| ATOM | 11536 | C | SER | B | 229 | −72.270 | −14.279 | −12.469 | 1.00 | 24.64 | C |
| ATOM | 11537 | O | SER | B | 229 | −71.726 | −13.172 | −12.408 | 1.00 | 24.95 | O |
| ATOM | 11539 | N | VAL | B | 230 | −71.751 | −15.350 | −11.878 | 1.00 | 24.20 | N |
| ATOM | 11540 | CA | VAL | B | 230 | −70.415 | −15.277 | −11.299 | 1.00 | 23.99 | C |
| ATOM | 11542 | CB | VAL | B | 230 | −70.006 | −16.581 | −10.574 | 1.00 | 23.92 | C |
| ATOM | 11544 | CG1 | VAL | B | 230 | −68.546 | −16.510 | −10.105 | 1.00 | 23.71 | C |
| ATOM | 11548 | CG2 | VAL | B | 230 | −70.923 | −16.853 | −9.409 | 1.00 | 23.52 | C |
| ATOM | 11552 | C | VAL | B | 230 | −69.386 | −14.966 | −12.400 | 1.00 | 24.12 | C |
| ATOM | 11553 | O | VAL | B | 230 | −68.397 | −14.291 | −12.136 | 1.00 | 24.01 | O |
| ATOM | 11555 | N | TYR | B | 231 | −69.612 | −15.461 | −13.621 | 1.00 | 24.30 | N |
| ATOM | 11556 | CA | TYR | B | 231 | −68.672 | −15.235 | −14.728 | 1.00 | 24.53 | C |
| ATOM | 11558 | CB | TYR | B | 231 | −68.997 | −16.104 | −15.946 | 1.00 | 24.08 | C |
| ATOM | 11561 | CG | TYR | B | 231 | −68.892 | −17.605 | −15.754 | 1.00 | 23.29 | C |
| ATOM | 11562 | CD1 | TYR | B | 231 | −68.173 | −18.168 | −14.706 | 1.00 | 23.08 | C |
| ATOM | 11564 | CE1 | TYR | B | 231 | −68.073 | −19.547 | −14.565 | 1.00 | 22.01 | C |
| ATOM | 11566 | CZ | TYR | B | 231 | −68.685 | −20.369 | −15.479 | 1.00 | 21.16 | C |
| ATOM | 11567 | OH | TYR | B | 231 | −68.607 | −21.746 | −15.353 | 1.00 | 20.18 | O |
| ATOM | 11569 | CE2 | TYR | B | 231 | −69.387 | −19.825 | −16.523 | 1.00 | 21.64 | C |
| ATOM | 11571 | CD2 | TYR | B | 231 | −69.476 | −18.464 | −16.662 | 1.00 | 22.15 | C |
| ATOM | 11573 | C | TYR | B | 231 | −68.658 | −13.772 | −15.166 | 1.00 | 25.37 | C |
| ATOM | 11574 | O | TYR | B | 231 | −67.602 | −13.221 | −15.528 | 1.00 | 25.25 | O |
| ATOM | 11576 | N | GLN | B | 232 | −69.832 | −13.148 | −15.129 | 1.00 | 26.11 | N |
| ATOM | 11577 | CA | GLN | B | 232 | −69.978 | −11.797 | −15.622 | 1.00 | 26.68 | C |
| ATOM | 11579 | CB | GLN | B | 232 | −71.430 | −11.541 | −15.995 | 1.00 | 26.45 | C |
| ATOM | 11582 | CG | GLN | B | 232 | −71.883 | −12.385 | −17.176 | 1.00 | 25.67 | C |
| ATOM | 11585 | CD | GLN | B | 232 | −73.388 | −12.394 | −17.381 | 1.00 | 24.91 | C |
| ATOM | 11586 | OE1 | GLN | B | 232 | −74.140 | −11.761 | −16.637 | 1.00 | 24.81 | O |
| ATOM | 11587 | NE2 | GLN | B | 232 | −73.834 | −13.113 | −18.407 | 1.00 | 23.39 | N |
| ATOM | 11590 | C | GLN | B | 232 | −69.445 | −10.802 | −14.593 | 1.00 | 27.90 | C |
| ATOM | 11591 | O | GLN | B | 232 | −68.909 | −9.752 | −14.958 | 1.00 | 27.96 | O |
| ATOM | 11593 | N | ARG | B | 233 | −69.572 | −11.145 | −13.312 | 1.00 | 29.35 | N |
| ATOM | 11594 | CA | ARG | B | 233 | −68.908 | −10.396 | −12.241 | 1.00 | 30.59 | C |
| ATOM | 11596 | CB | ARG | B | 233 | −69.490 | −10.775 | −10.867 | 1.00 | 30.99 | C |
| ATOM | 11599 | CG | ARG | B | 233 | −68.824 | −10.114 | −9.661 | 1.00 | 32.72 | C |
| ATOM | 11602 | CD | ARG | B | 233 | −69.695 | −10.210 | −8.391 | 1.00 | 35.70 | C |
| ATOM | 11605 | NE | ARG | B | 233 | −70.162 | −11.578 | −8.086 | 1.00 | 38.29 | N |
| ATOM | 11607 | CZ | ARG | B | 233 | −71.403 | −12.053 | −8.276 | 1.00 | 39.65 | C |
| ATOM | 11608 | NH1 | ARG | B | 233 | −72.367 | −11.287 | −8.787 | 1.00 | 40.23 | N |
| ATOM | 11611 | NH2 | ARG | B | 233 | −71.687 | −13.320 | −7.949 | 1.00 | 39.61 | N |
| ATOM | 11614 | C | ARG | B | 233 | −67.390 | −10.632 | −12.303 | 1.00 | 31.10 | C |
| ATOM | 11615 | O | ARG | B | 233 | −66.615 | −9.693 | −12.181 | 1.00 | 31.19 | O |
| ATOM | 11617 | N | ASP | B | 234 | −66.954 | −11.868 | −12.517 | 1.00 | 31.91 | N |
| ATOM | 11618 | CA | ASP | B | 234 | −65.530 | −12.102 | −12.750 | 1.00 | 32.63 | C |
| ATOM | 11620 | CB | ASP | B | 234 | −65.220 | −13.566 | −13.090 | 1.00 | 32.53 | C |
| ATOM | 11623 | CG | ASP | B | 234 | −65.336 | −14.493 | −11.894 | 1.00 | 32.90 | C |
| ATOM | 11624 | OD1 | ASP | B | 234 | −65.477 | −14.028 | −10.746 | 1.00 | 33.06 | O |
| ATOM | 11625 | OD2 | ASP | B | 234 | −65.293 | −15.713 | −12.107 | 1.00 | 34.22 | O |
| ATOM | 11626 | C | ASP | B | 234 | −65.058 | −11.206 | −13.886 | 1.00 | 33.10 | C |
| ATOM | 11627 | O | ASP | B | 234 | −64.097 | −10.458 | −13.723 | 1.00 | 33.55 | O |
| ATOM | 11629 | N | LEU | B | 235 | −65.753 | −11.256 | −15.017 | 1.00 | 33.49 | N |
| ATOM | 11630 | CA | LEU | B | 235 | −65.311 | −10.550 | −16.216 | 1.00 | 34.06 | C |
| ATOM | 11632 | CB | LEU | B | 235 | −66.139 | −10.996 | −17.422 | 1.00 | 33.80 | C |
| ATOM | 11635 | CG | LEU | B | 235 | −65.769 | −10.403 | −18.775 | 1.00 | 32.13 | C |
| ATOM | 11637 | CD1 | LEU | B | 235 | −64.303 | −10.679 | −19.050 | 1.00 | 30.94 | C |
| ATOM | 11641 | CD2 | LEU | B | 235 | −66.670 | −10.959 | −19.870 | 1.00 | 29.93 | C |
| ATOM | 11645 | C | LEU | B | 235 | −65.345 | −9.023 | −16.103 | 1.00 | 35.40 | C |
| ATOM | 11646 | O | LEU | B | 235 | −64.500 | −8.352 | −16.682 | 1.00 | 35.61 | O |
| ATOM | 11648 | N | ARG | B | 236 | −66.327 | −8.473 | −15.386 | 1.00 | 36.92 | N |
| ATOM | 11649 | CA | ARG | B | 236 | −66.380 | −7.019 | −15.137 | 1.00 | 38.06 | C |
| ATOM | 11651 | CB | ARG | B | 236 | −67.650 | −6.607 | −14.367 | 1.00 | 38.43 | C |
| ATOM | 11654 | CG | ARG | B | 236 | −68.882 | −6.321 | −15.230 | 1.00 | 39.58 | C |
| ATOM | 11657 | CD | ARG | B | 236 | −69.958 | −5.520 | −14.459 | 1.00 | 40.93 | C |
| ATOM | 11660 | NE | ARG | B | 236 | −70.383 | −6.149 | −13.199 | 1.00 | 41.74 | N |
| ATOM | 11662 | CZ | ARG | B | 236 | −71.208 | −7.195 | −13.095 | 1.00 | 42.20 | C |
| ATOM | 11663 | NH1 | ARG | B | 236 | −71.719 | −7.784 | −14.175 | 1.00 | 41.61 | N |

TABLE 16-7-continued

| | | | | | | | | | | |
|---|---|---|---|---|---|---|---|---|---|---|
| ATOM | 11666 | NH2 | ARG | B | 236 | −71.517 | −7.672 | −11.892 | 1.00 | 42.99 N |
| ATOM | 11669 | C | ARG | B | 236 | −65.170 | −6.550 | −14.343 | 1.00 | 38.57 C |
| ATOM | 11670 | O | ARG | B | 236 | −64.593 | −5.524 | −14.665 | 1.00 | 38.61 O |
| ATOM | 11672 | N | GLU | B | 237 | −64.822 | −7.292 | −13.291 | 1.00 | 39.42 N |
| ATOM | 11673 | CA | GLU | B | 237 | −63.625 | −7.017 | −12.480 | 1.00 | 40.18 C |
| ATOM | 11675 | CB | GLU | B | 237 | −63.471 | −8.033 | −11.317 | 1.00 | 40.67 C |
| ATOM | 11678 | CG | GLU | B | 237 | −64.336 | −7.750 | −10.057 | 1.00 | 42.61 C |
| ATOM | 11681 | CD | GLU | B | 237 | −64.258 | −8.858 | −8.961 | 1.00 | 45.07 C |
| ATOM | 11682 | OE1 | GLU | B | 237 | −64.051 | −10.066 | −9.282 | 1.00 | 46.74 O |
| ATOM | 11683 | OE2 | GLU | B | 237 | −64.436 | −8.511 | −7.764 | 1.00 | 45.87 O |
| ATOM | 11684 | C | GLU | B | 237 | −62.352 | −7.024 | −13.344 | 1.00 | 39.93 C |
| ATOM | 11685 | O | GLU | B | 237 | −61.593 | −6.050 | −13.332 | 1.00 | 39.96 O |
| ATOM | 11687 | N | THR | B | 238 | −62.123 | −8.104 | −14.095 | 1.00 | 39.56 N |
| ATOM | 11688 | CA | THR | B | 238 | −60.900 | −8.200 | −14.895 | 1.00 | 39.42 C |
| ATOM | 11690 | CB | THR | B | 238 | −60.492 | −9.666 | −15.268 | 1.00 | 39.39 C |
| ATOM | 11692 | OG1 | THR | B | 238 | −61.222 | −10.123 | −16.413 | 1.00 | 39.37 O |
| ATOM | 11694 | CG2 | THR | B | 238 | −60.683 | −10.612 | −14.095 | 1.00 | 38.73 C |
| ATOM | 11698 | C | THR | B | 238 | −60.961 | −7.326 | −16.156 | 1.00 | 39.48 C |
| ATOM | 11699 | O | THR | B | 238 | −59.930 | −7.062 | −16.761 | 1.00 | 39.48 O |
| ATOM | 11701 | N | SER | B | 239 | −62.149 | −6.871 | −16.549 | 1.00 | 39.62 N |
| ATOM | 11702 | CA | SER | B | 239 | −62.264 | −5.882 | −17.631 | 1.00 | 39.63 C |
| ATOM | 11704 | CB | SER | B | 239 | −63.689 | −5.810 | −18.172 | 1.00 | 39.56 C |
| ATOM | 11707 | OG | SER | B | 239 | −63.945 | −6.917 | −19.010 | 1.00 | 38.96 O |
| ATOM | 11709 | C | SER | B | 239 | −61.796 | −4.496 | −17.181 | 1.00 | 39.99 C |
| ATOM | 11710 | O | SER | B | 239 | −61.108 | −3.807 | −17.933 | 1.00 | 40.10 O |
| ATOM | 11712 | N | ARG | B | 240 | −62.168 | −4.088 | −15.965 | 1.00 | 40.35 N |
| ATOM | 11713 | CA | ARG | B | 240 | −61.624 | −2.864 | −15.363 | 1.00 | 40.68 C |
| ATOM | 11715 | CB | ARG | B | 240 | −62.025 | −2.712 | −13.881 | 1.00 | 41.26 C |
| ATOM | 11718 | CG | ARG | B | 240 | −63.231 | −1.782 | −13.621 | 1.00 | 43.86 C |
| ATOM | 11721 | CD | ARG | B | 240 | −63.334 | −1.375 | −12.130 | 1.00 | 47.07 C |
| ATOM | 11724 | NE | ARG | B | 240 | −63.365 | −2.537 | −11.222 | 1.00 | 50.14 N |
| ATOM | 11726 | CZ | ARG | B | 240 | −64.462 | −3.077 | −10.671 | 1.00 | 52.32 C |
| ATOM | 11727 | NH1 | ARG | B | 240 | −64.342 | −4.141 | −9.875 | 1.00 | 53.16 N |
| ATOM | 11730 | NH2 | ARG | B | 240 | −65.677 | −2.577 | −10.899 | 1.00 | 53.18 N |
| ATOM | 11733 | C | ARG | B | 240 | −60.113 | −2.914 | −15.464 | 1.00 | 39.91 C |
| ATOM | 11734 | O | ARG | B | 240 | −59.490 | −2.000 | −15.988 | 1.00 | 39.86 O |
| ATOM | 11736 | N | TRP | B | 241 | −59.541 | −4.002 | −14.962 | 1.00 | 39.14 N |
| ATOM | 11737 | CA | TRP | B | 241 | −58.105 | −4.217 | −15.004 | 1.00 | 38.37 C |
| ATOM | 11739 | CB | TRP | B | 241 | −57.773 | −5.635 | −14.521 | 1.00 | 38.17 C |
| ATOM | 11742 | CG | TRP | B | 241 | −56.373 | −6.005 | −14.773 | 1.00 | 36.58 C |
| ATOM | 11743 | CD1 | TRP | B | 241 | −55.290 | −5.668 | −14.022 | 1.00 | 36.32 C |
| ATOM | 11745 | NE1 | TRP | B | 241 | −54.152 | −6.176 | −14.587 | 1.00 | 35.63 N |
| ATOM | 11747 | CE2 | TRP | B | 241 | −54.494 | −6.846 | −15.731 | 1.00 | 34.31 C |
| ATOM | 11748 | CD2 | TRP | B | 241 | −55.883 | −6.757 | −15.874 | 1.00 | 33.99 C |
| ATOM | 11749 | CE3 | TRP | B | 241 | −56.484 | −7.357 | −16.977 | 1.00 | 33.28 C |
| ATOM | 11751 | CZ3 | TRP | B | 241 | −55.691 | −8.034 | −17.883 | 1.00 | 32.79 C |
| ATOM | 11753 | CH2 | TRP | B | 241 | −54.313 | −8.101 | −17.720 | 1.00 | 33.06 C |
| ATOM | 11755 | CZ2 | TRP | B | 241 | −53.697 | −7.515 | −16.648 | 1.00 | 34.16 C |
| ATOM | 11757 | C | TRP | B | 241 | −57.561 | −3.999 | −16.409 | 1.00 | 38.25 C |
| ATOM | 11758 | O | TRP | B | 241 | −56.607 | −3.252 | −16.603 | 1.00 | 38.13 O |
| ATOM | 11760 | N | TRP | B | 242 | −58.186 | −4.644 | −17.386 | 1.00 | 38.21 N |
| ATOM | 11761 | CA | TRP | B | 242 | −57.695 | −4.628 | −18.765 | 1.00 | 38.27 C |
| ATOM | 11763 | CB | TRP | B | 242 | −58.479 | −5.640 | −19.609 | 1.00 | 38.31 C |
| ATOM | 11766 | CG | TRP | B | 242 | −57.948 | −5.872 | −20.990 | 1.00 | 38.61 C |
| ATOM | 11767 | CD1 | TRP | B | 242 | −58.642 | −5.754 | −22.156 | 1.00 | 39.11 C |
| ATOM | 11769 | NE1 | TRP | B | 242 | −57.828 | −6.046 | −23.224 | 1.00 | 39.31 N |
| ATOM | 11771 | CE2 | TRP | B | 242 | −56.582 | −6.363 | −22.759 | 1.00 | 38.95 C |
| ATOM | 11772 | CD2 | TRP | B | 242 | −56.617 | −6.263 | −21.356 | 1.00 | 38.66 C |
| ATOM | 11773 | CE3 | TRP | B | 242 | −55.454 | −6.528 | −20.637 | 1.00 | 38.98 C |
| ATOM | 11775 | CZ3 | TRP | B | 242 | −54.314 | −6.886 | −21.326 | 1.00 | 39.20 C |
| ATOM | 11777 | CH2 | TRP | B | 242 | −54.313 | −6.985 | −22.716 | 1.00 | 39.12 C |
| ATOM | 11779 | CZ2 | TRP | B | 242 | −55.434 | −6.724 | −23.451 | 1.00 | 39.22 C |
| ATOM | 11781 | C | TRP | B | 242 | −57.739 | −3.241 | −19.400 | 1.00 | 38.27 C |
| ATOM | 11782 | O | TRP | B | 242 | −56.814 | −2.873 | −20.108 | 1.00 | 37.81 O |
| ATOM | 11784 | N | ARG | B | 243 | −58.809 | −2.489 | −19.140 | 1.00 | 38.79 N |
| ATOM | 11785 | CA | ARG | B | 243 | −58.936 | −1.097 | −19.607 | 1.00 | 39.37 C |
| ATOM | 11787 | CB | ARG | B | 243 | −60.351 | −.552 | −19.346 | 1.00 | 39.66 C |
| ATOM | 11790 | CG | ARG | B | 243 | −61.324 | −.792 | −20.520 | 1.00 | 41.96 C |
| ATOM | 11793 | CD | ARG | B | 243 | −62.687 | −1.338 | −20.085 | 1.00 | 44.82 C |
| ATOM | 11796 | NE | ARG | B | 243 | −63.461 | −.380 | −19.296 | 1.00 | 47.15 N |
| ATOM | 11798 | CZ | ARG | B | 243 | −64.389 | −.704 | −18.386 | 1.00 | 49.26 C |
| ATOM | 11799 | NH1 | ARG | B | 243 | −64.685 | −1.976 | −18.109 | 1.00 | 49.18 N |
| ATOM | 11802 | NH2 | ARG | B | 243 | −65.028 | .262 | −17.729 | 1.00 | 50.40 N |
| ATOM | 11805 | C | ARG | B | 243 | −57.890 | −.183 | −18.980 | 1.00 | 39.28 C |
| ATOM | 11806 | O | ARG | B | 243 | −57.246 | .577 | −19.681 | 1.00 | 39.40 O |
| ATOM | 11808 | N | ARG | B | 244 | −57.724 | −.282 | −17.665 | 1.00 | 39.52 N |
| ATOM | 11809 | CA | ARG | B | 244 | −56.734 | .489 | −16.888 | 1.00 | 39.61 C |
| ATOM | 11811 | CB | ARG | B | 244 | −56.774 | .041 | −15.409 | 1.00 | 40.25 C |

TABLE 16-7-continued

Coordinates of *P. tremuloides* IspS

| ATOM | 11814 | CG | ARG | B | 244 | −56.115 | .971 | −14.383 | 1.00 | 42.01 | C |
|---|---|---|---|---|---|---|---|---|---|---|---|
| ATOM | 11817 | CD | ARG | B | 244 | −57.029 | 2.154 | −14.017 | 1.00 | 44.39 | C |
| ATOM | 11820 | NE | ARG | B | 244 | −56.391 | 3.115 | −13.103 | 1.00 | 46.36 | N |
| ATOM | 11822 | CZ | ARG | B | 244 | −55.434 | 3.984 | −13.441 | 1.00 | 48.06 | C |
| ATOM | 11823 | NH1 | ARG | B | 244 | −54.951 | 4.043 | −14.686 | 1.00 | 48.90 | N |
| ATOM | 11826 | NH2 | ARG | B | 244 | −54.947 | 4.805 | −12.519 | 1.00 | 48.82 | N |
| ATOM | 11829 | C | ARG | B | 244 | −55.323 | .322 | −17.437 | 1.00 | 38.83 | C |
| ATOM | 11830 | O | ARG | B | 244 | −54.594 | 1.300 | −17.567 | 1.00 | 38.39 | O |
| ATOM | 11832 | N | VAL | B | 245 | −54.953 | −.922 | −17.738 | 1.00 | 38.52 | N |
| ATOM | 11833 | CA | VAL | B | 245 | −53.694 | −1.241 | −18.437 | 1.00 | 38.43 | C |
| ATOM | 11835 | CB | VAL | B | 245 | −53.491 | −2.760 | −18.614 | 1.00 | 38.31 | C |
| ATOM | 11837 | CG1 | VAL | B | 245 | −53.247 | −3.426 | −17.283 | 1.00 | 37.77 | C |
| ATOM | 11841 | CG2 | VAL | B | 245 | −52.344 | −3.036 | −19.561 | 1.00 | 37.66 | C |
| ATOM | 11845 | C | VAL | B | 245 | −53.650 | −.638 | −19.832 | 1.00 | 38.68 | C |
| ATOM | 11846 | O | VAL | B | 245 | −52.615 | −.153 | −20.247 | 1.00 | 38.57 | O |
| ATOM | 11848 | N | GLY | B | 246 | −54.765 | −.724 | −20.559 | 1.00 | 39.26 | N |
| ATOM | 11849 | CA | GLY | B | 246 | −54.974 | −.012 | −21.834 | 1.00 | 39.62 | C |
| ATOM | 11852 | C | GLY | B | 246 | −53.962 | −.262 | −22.942 | 1.00 | 40.08 | C |
| ATOM | 11853 | O | GLY | B | 246 | −53.617 | .650 | −23.700 | 1.00 | 39.89 | O |
| ATOM | 11855 | N | LEU | B | 247 | −53.502 | −1.500 | −23.062 | 1.00 | 40.75 | N |
| ATOM | 11856 | CA | LEU | B | 247 | −52.347 | −1.778 | −23.905 | 1.00 | 41.34 | C |
| ATOM | 11858 | CB | LEU | B | 247 | −51.655 | −3.065 | −23.459 | 1.00 | 41.15 | C |
| ATOM | 11861 | CG | LEU | B | 247 | −50.132 | −3.026 | −23.298 | 1.00 | 40.49 | C |
| ATOM | 11863 | CD1 | LEU | B | 247 | −49.622 | −1.769 | −22.605 | 1.00 | 39.50 | C |
| ATOM | 11867 | CD2 | LEU | B | 247 | −49.695 | −4.242 | −22.526 | 1.00 | 39.98 | C |
| ATOM | 11871 | C | LEU | B | 247 | −52.744 | −1.836 | −25.370 | 1.00 | 42.50 | C |
| ATOM | 11872 | O | LEU | B | 247 | −52.005 | −1.358 | −26.225 | 1.00 | 42.33 | O |
| ATOM | 11874 | N | ALA | B | 248 | −53.925 | −2.390 | −25.654 | 1.00 | 44.14 | N |
| ATOM | 11875 | CA | ALA | B | 248 | −54.439 | −2.494 | −27.041 | 1.00 | 45.16 | C |
| ATOM | 11877 | CB | ALA | B | 248 | −55.705 | −3.347 | −27.087 | 1.00 | 45.15 | C |
| ATOM | 11881 | C | ALA | B | 248 | −54.692 | −1.140 | −27.739 | 1.00 | 45.98 | C |
| ATOM | 11882 | O | ALA | B | 248 | −54.604 | −1.053 | −28.971 | 1.00 | 46.37 | O |
| ATOM | 11884 | N | THR | B | 249 | −55.004 | −.095 | −26.975 | 1.00 | 46.64 | N |
| ATOM | 11885 | CA | THR | B | 249 | −55.142 | 1.234 | −27.570 | 1.00 | 47.25 | C |
| ATOM | 11887 | CB | THR | B | 249 | −55.905 | 2.253 | −26.655 | 1.00 | 47.44 | C |
| ATOM | 11889 | OG1 | THR | B | 249 | −55.001 | 2.845 | −25.706 | 1.00 | 47.52 | O |
| ATOM | 11891 | CG2 | THR | B | 249 | −57.104 | 1.592 | −25.928 | 1.00 | 47.44 | C |
| ATOM | 11895 | C | THR | B | 249 | −53.756 | 1.793 | −27.931 | 1.00 | 47.59 | C |
| ATOM | 11896 | O | THR | B | 249 | −53.553 | 2.279 | −29.049 | 1.00 | 48.07 | O |
| ATOM | 11898 | N | LYS | B | 250 | −52.808 | 1.710 | −26.995 | 1.00 | 47.67 | N |
| ATOM | 11899 | CA | LYS | B | 250 | −51.469 | 2.299 | −27.185 | 1.00 | 47.68 | C |
| ATOM | 11901 | CB | LYS | B | 250 | −50.793 | 2.553 | −25.833 | 1.00 | 47.68 | C |
| ATOM | 11904 | CG | LYS | B | 250 | −51.428 | 3.673 | −24.999 | 1.00 | 47.77 | C |
| ATOM | 11907 | CD | LYS | B | 250 | −51.142 | 5.086 | −25.552 | 1.00 | 47.59 | C |
| ATOM | 11910 | CE | LYS | B | 250 | −49.676 | 5.496 | −25.441 | 1.00 | 46.75 | C |
| ATOM | 11913 | NZ | LYS | B | 250 | −49.479 | 6.878 | −25.948 | 1.00 | 46.49 | N |
| ATOM | 11917 | C | LYS | B | 250 | −50.541 | 1.465 | −28.082 | 1.00 | 47.72 | C |
| ATOM | 11918 | O | LYS | B | 250 | −49.591 | 1.988 | −28.663 | 1.00 | 47.54 | O |
| ATOM | 11920 | N | LEU | B | 251 | −50.804 | .169 | −28.184 | 1.00 | 47.82 | N |
| ATOM | 11921 | CA | LEU | B | 251 | −50.072 | −.675 | −29.118 | 1.00 | 47.96 | C |
| ATOM | 11923 | CB | LEU | B | 251 | −49.584 | −1.970 | −28.447 | 1.00 | 48.04 | C |
| ATOM | 11926 | CG | LEU | B | 251 | −48.109 | −2.064 | −28.033 | 1.00 | 47.39 | C |
| ATOM | 11928 | CD1 | LEU | B | 251 | −47.659 | −.881 | −27.186 | 1.00 | 46.47 | C |
| ATOM | 11932 | CD2 | LEU | B | 251 | −47.894 | −3.376 | −27.304 | 1.00 | 46.78 | C |
| ATOM | 11936 | C | LEU | B | 251 | −50.985 | −.964 | −30.306 | 1.00 | 48.19 | C |
| ATOM | 11937 | O | LEU | B | 251 | −51.975 | −1.693 | −30.194 | 1.00 | 48.38 | O |
| ATOM | 11939 | N | HIS | B | 252 | −50.627 | −.396 | −31.449 | 1.00 | 48.42 | N |
| ATOM | 11940 | CA | HIS | B | 252 | −51.521 | −.329 | −32.601 | 1.00 | 48.62 | C |
| ATOM | 11942 | CB | HIS | B | 252 | −51.110 | .850 | −33.492 | 1.00 | 48.99 | C |
| ATOM | 11945 | CG | HIS | B | 252 | −51.000 | 2.145 | −32.742 | 1.00 | 50.56 | C |
| ATOM | 11946 | ND1 | HIS | B | 252 | −52.095 | 2.935 | −32.453 | 1.00 | 52.11 | N |
| ATOM | 11948 | CE1 | HIS | B | 252 | −51.704 | 3.993 | −31.766 | 1.00 | 52.68 | C |
| ATOM | 11950 | NE2 | HIS | B | 252 | −50.397 | 3.912 | −31.585 | 1.00 | 52.86 | N |
| ATOM | 11952 | CD2 | HIS | B | 252 | −49.932 | 2.764 | −32.181 | 1.00 | 51.68 | C |
| ATOM | 11954 | C | HIS | B | 252 | −51.582 | −1.636 | −33.383 | 1.00 | 48.14 | C |
| ATOM | 11955 | O | HIS | B | 252 | −52.615 | −1.975 | −33.935 | 1.00 | 48.02 | O |
| ATOM | 11957 | N | PHE | B | 253 | −50.481 | −2.372 | −33.405 | 1.00 | 48.10 | N |
| ATOM | 11958 | CA | PHE | B | 253 | −50.422 | −3.702 | −34.044 | 1.00 | 48.18 | C |
| ATOM | 11960 | CB | PHE | B | 253 | −48.965 | −4.070 | −34.375 | 1.00 | 48.16 | C |
| ATOM | 11963 | CG | PHE | B | 253 | −48.119 | −4.311 | −33.163 | 1.00 | 47.85 | C |
| ATOM | 11964 | CD1 | PHE | B | 253 | −47.900 | −5.596 | −32.702 | 1.00 | 48.56 | C |
| ATOM | 11966 | CE1 | PHE | B | 253 | −47.140 | −5.812 | −31.576 | 1.00 | 48.98 | C |
| ATOM | 11968 | CZ | PHE | B | 253 | −46.602 | −4.729 | −30.895 | 1.00 | 48.50 | C |
| ATOM | 11970 | CE2 | PHE | B | 253 | −46.817 | −3.454 | −31.349 | 1.00 | 47.40 | C |
| ATOM | 11972 | CD2 | PHE | B | 253 | −47.569 | −3.249 | −32.465 | 1.00 | 47.22 | C |
| ATOM | 11974 | C | PHE | B | 253 | −51.038 | −4.819 | −33.185 | 1.00 | 48.30 | C |
| ATOM | 11975 | O | PHE | B | 253 | −51.344 | −5.903 | −33.691 | 1.00 | 47.63 | O |
| ATOM | 11977 | N | ALA | B | 254 | −51.204 | −4.541 | −31.888 | 1.00 | 48.86 | N |

TABLE 16-7-continued

Coordinates of *P. tremuloides* IspS

| ATOM | 11978 | CA | ALA | B | 254 | −51.653 | −5.531 | −30.903 | 1.00 | 49.13 | C |
|------|-------|-----|-----|---|-----|---------|--------|---------|------|-------|---|
| ATOM | 11980 | CB | ALA | B | 254 | −51.290 | −5.071 | −29.494 | 1.00 | 49.02 | C |
| ATOM | 11984 | C | ALA | B | 254 | −53.153 | −5.806 | −30.982 | 1.00 | 49.46 | C |
| ATOM | 11985 | O | ALA | B | 254 | −53.967 | −4.870 | −31.011 | 1.00 | 49.50 | O |
| ATOM | 11987 | N | ARG | B | 255 | −53.501 | −7.097 | −31.006 | 1.00 | 49.75 | N |
| ATOM | 11988 | CA | ARG | B | 255 | −54.896 | −7.549 | −30.918 | 1.00 | 49.89 | C |
| ATOM | 11990 | CB | ARG | B | 255 | −55.028 | −9.051 | −31.245 | 1.00 | 49.94 | C |
| ATOM | 11993 | CG | ARG | B | 255 | −54.839 | −9.439 | −32.724 | 1.00 | 49.93 | C |
| ATOM | 11996 | CD | ARG | B | 255 | −54.709 | −10.967 | −32.904 | 1.00 | 49.79 | C |
| ATOM | 11999 | NE | ARG | B | 255 | −53.527 | −11.505 | −32.219 | 1.00 | 50.11 | N |
| ATOM | 12001 | CZ | ARG | B | 255 | −53.276 | −12.801 | −32.010 | 1.00 | 50.54 | C |
| ATOM | 12002 | NH1 | ARG | B | 255 | −54.117 | −13.736 | −32.439 | 1.00 | 51.36 | N |
| ATOM | 12005 | NH2 | ARG | B | 255 | −52.175 | −13.172 | −31.360 | 1.00 | 50.21 | N |
| ATOM | 12008 | C | ARG | B | 255 | −55.425 | −7.308 | −29.511 | 1.00 | 49.83 | C |
| ATOM | 12009 | O | ARG | B | 255 | −54.666 | −6.975 | −28.599 | 1.00 | 49.95 | O |
| ATOM | 12011 | N | ASP | B | 256 | −56.736 | −7.463 | −29.350 | 1.00 | 49.72 | N |
| ATOM | 12012 | CA | ASP | B | 256 | −57.360 | −7.483 | −28.034 | 1.00 | 49.55 | C |
| ATOM | 12014 | CB | ASP | B | 256 | −58.183 | −6.222 | −27.812 | 1.00 | 49.52 | C |
| ATOM | 12017 | CG | ASP | B | 256 | −59.134 | −6.362 | −26.654 | 1.00 | 50.30 | C |
| ATOM | 12018 | OD1 | ASP | B | 256 | −60.310 | −5.944 | −26.780 | 1.00 | 50.45 | O |
| ATOM | 12019 | OD2 | ASP | B | 256 | −58.702 | −6.926 | −25.622 | 1.00 | 51.68 | O |
| ATOM | 12020 | C | ASP | B | 256 | −58.254 | −8.721 | −27.931 | 1.00 | 49.15 | C |
| ATOM | 12021 | O | ASP | B | 256 | −59.159 | −8.901 | −28.737 | 1.00 | 49.28 | O |
| ATOM | 12023 | N | ARG | B | 257 | −57.998 | −9.565 | −26.937 | 1.00 | 48.61 | N |
| ATOM | 12024 | CA | ARG | B | 257 | −58.743 | −10.809 | −26.765 | 1.00 | 48.20 | C |
| ATOM | 12026 | CB | ARG | B | 257 | −57.949 | −11.984 | −27.373 | 1.00 | 48.41 | C |
| ATOM | 12029 | CG | ARG | B | 257 | −57.505 | −11.799 | −28.821 | 1.00 | 49.37 | C |
| ATOM | 12032 | CD | ARG | B | 257 | −58.693 | −11.636 | −29.784 | 1.00 | 50.80 | C |
| ATOM | 12035 | NE | ARG | B | 257 | −58.908 | −12.814 | −30.627 | 1.00 | 52.11 | N |
| ATOM | 12037 | CZ | ARG | B | 257 | −58.678 | −12.876 | −31.944 | 1.00 | 52.99 | C |
| ATOM | 12038 | NH1 | ARG | B | 257 | −58.214 | −11.820 | −32.623 | 1.00 | 52.37 | N |
| ATOM | 12041 | NH2 | ARG | B | 257 | −58.918 | −14.016 | −32.596 | 1.00 | 52.97 | N |
| ATOM | 12044 | C | ARG | B | 257 | −59.032 | −11.089 | −25.280 | 1.00 | 47.32 | C |
| ATOM | 12045 | O | ARG | B | 257 | −58.579 | −12.101 | −24.735 | 1.00 | 47.46 | O |
| ATOM | 12047 | N | LEU | B | 258 | −59.770 | −10.201 | −24.616 | 1.00 | 45.94 | N |
| ATOM | 12048 | CA | LEU | B | 258 | −60.108 | −10.430 | −23.205 | 1.00 | 44.67 | C |
| ATOM | 12050 | CB | LEU | B | 258 | −60.332 | −9.130 | −22.438 | 1.00 | 44.61 | C |
| ATOM | 12053 | CG | LEU | B | 258 | −60.422 | −9.323 | −20.920 | 1.00 | 43.83 | C |
| ATOM | 12055 | CD1 | LEU | B | 258 | −59.045 | −9.552 | −20.339 | 1.00 | 43.48 | C |
| ATOM | 12059 | CD2 | LEU | B | 258 | −61.073 | −8.139 | −20.262 | 1.00 | 43.85 | C |
| ATOM | 12063 | C | LEU | B | 258 | −61.347 | −11.286 | −23.090 | 1.00 | 43.49 | C |
| ATOM | 12064 | O | LEU | B | 258 | −61.375 | −12.220 | −22.295 | 1.00 | 43.84 | O |
| ATOM | 12066 | N | ILE | B | 259 | −62.364 | −10.968 | −23.883 | 1.00 | 41.92 | N |
| ATOM | 12067 | CA | ILE | B | 259 | −63.617 | −11.711 | −23.841 | 1.00 | 40.80 | C |
| ATOM | 12069 | CB | ILE | B | 259 | −64.718 | −11.132 | −24.783 | 1.00 | 41.05 | C |
| ATOM | 12071 | CG1 | ILE | B | 259 | −64.852 | −9.598 | −24.653 | 1.00 | 41.61 | C |
| ATOM | 12074 | CD1 | ILE | B | 259 | −65.200 | −8.874 | −25.985 | 1.00 | 42.16 | C |
| ATOM | 12078 | CG2 | ILE | B | 259 | −66.065 | −11.816 | −24.496 | 1.00 | 40.46 | C |
| ATOM | 12082 | C | ILE | B | 259 | −63.319 | −13.151 | −24.250 | 1.00 | 39.50 | C |
| ATOM | 12083 | O | ILE | B | 259 | −63.782 | −14.082 | −23.598 | 1.00 | 39.30 | O |
| ATOM | 12085 | N | GLU | B | 260 | −62.524 | −13.318 | −25.316 | 1.00 | 37.99 | N |
| ATOM | 12086 | CA | GLU | B | 260 | −62.120 | −14.652 | −25.812 | 1.00 | 36.60 | C |
| ATOM | 12088 | CB | GLU | B | 260 | −61.329 | −14.574 | −27.142 | 1.00 | 36.75 | C |
| ATOM | 12091 | CG | GLU | B | 260 | −62.167 | −14.319 | −28.425 | 1.00 | 37.79 | C |
| ATOM | 12094 | CD | GLU | B | 260 | −62.134 | −12.851 | −28.905 | 1.00 | 39.47 | C |
| ATOM | 12095 | OE1 | GLU | B | 260 | −62.207 | −11.923 | −28.055 | 1.00 | 39.97 | O |
| ATOM | 12096 | OE2 | GLU | B | 260 | −62.033 | −12.628 | −30.139 | 1.00 | 40.31 | O |
| ATOM | 12097 | C | GLU | B | 260 | −61.282 | −15.381 | −24.770 | 1.00 | 34.83 | C |
| ATOM | 12098 | O | GLU | B | 260 | −61.465 | −16.568 | −24.544 | 1.00 | 34.69 | O |
| ATOM | 12100 | N | SER | B | 261 | −60.365 | −14.669 | −24.131 | 1.00 | 32.89 | N |
| ATOM | 12101 | CA | SER | B | 261 | −59.508 | −15.292 | −23.139 | 1.00 | 31.48 | C |
| ATOM | 12103 | CB | SER | B | 261 | −58.341 | −14.376 | −22.768 | 1.00 | 31.55 | C |
| ATOM | 12106 | OG | SER | B | 261 | −57.298 | −14.493 | −23.728 | 1.00 | 31.75 | O |
| ATOM | 12108 | C | SER | B | 261 | −60.294 | −15.716 | −21.900 | 1.00 | 30.04 | C |
| ATOM | 12109 | O | SER | B | 261 | −59.921 | −16.674 | −21.208 | 1.00 | 29.70 | O |
| ATOM | 12111 | N | PHE | B | 262 | −61.389 | −15.021 | −21.618 | 1.00 | 28.25 | N |
| ATOM | 12112 | CA | PHE | B | 262 | −62.203 | −15.404 | −20.480 | 1.00 | 26.75 | C |
| ATOM | 12114 | CB | PHE | B | 262 | −63.111 | −14.278 | −20.009 | 1.00 | 26.36 | C |
| ATOM | 12117 | CG | PHE | B | 262 | −63.532 | −14.453 | −18.603 | 1.00 | 24.33 | C |
| ATOM | 12118 | CD1 | PHE | B | 262 | −62.697 | −14.092 | −17.584 | 1.00 | 22.66 | C |
| ATOM | 12120 | CE1 | PHE | B | 262 | −63.047 | −14.283 | −16.301 | 1.00 | 22.65 | C |
| ATOM | 12122 | CZ | PHE | B | 262 | −64.245 | −14.873 | −16.007 | 1.00 | 23.93 | C |
| ATOM | 12124 | CE2 | PHE | B | 262 | −65.076 | −15.267 | −17.010 | 1.00 | 24.08 | C |
| ATOM | 12126 | CD2 | PHE | B | 262 | −64.711 | −15.067 | −18.304 | 1.00 | 23.96 | C |
| ATOM | 12128 | C | PHE | B | 262 | −63.017 | −16.660 | −20.751 | 1.00 | 26.02 | C |
| ATOM | 12129 | O | PHE | B | 262 | −63.074 | −17.546 | −19.909 | 1.00 | 26.32 | O |
| ATOM | 12131 | N | TYR | B | 263 | −63.652 | −16.732 | −21.915 | 1.00 | 24.98 | N |
| ATOM | 12132 | CA | TYR | B | 263 | −64.299 | −17.969 | −22.396 | 1.00 | 24.14 | C |

TABLE 16-7-continued

| | | | | | | | | | | |
|---|---|---|---|---|---|---|---|---|---|---|
| ATOM | 12134 | CB | TYR | B | 263 | −64.701 | −17.756 | −23.853 | 1.00 | 24.00 C |
| ATOM | 12137 | CG | TYR | B | 263 | −65.080 | −18.961 | −24.667 | 1.00 | 24.32 C |
| ATOM | 12138 | CD1 | TYR | B | 263 | −66.302 | −19.604 | −24.489 | 1.00 | 25.03 C |
| ATOM | 12140 | CE1 | TYR | B | 263 | −66.666 | −20.694 | −25.285 | 1.00 | 25.81 C |
| ATOM | 12142 | CZ | TYR | B | 263 | −65.798 | −21.132 | −26.287 | 1.00 | 27.06 C |
| ATOM | 12143 | OH | TYR | B | 263 | −66.106 | −22.191 | −27.123 | 1.00 | 27.14 O |
| ATOM | 12145 | CE2 | TYR | B | 263 | −64.590 | −20.489 | −26.479 | 1.00 | 26.80 C |
| ATOM | 12147 | CD2 | TYR | B | 263 | −64.250 | −19.404 | −25.680 | 1.00 | 25.65 C |
| ATOM | 12149 | C | TYR | B | 263 | −63.351 | −19.162 | −22.256 | 1.00 | 23.35 C |
| ATOM | 12150 | O | TYR | B | 263 | −63.712 | −20.219 | −21.740 | 1.00 | 22.80 O |
| ATOM | 12152 | N | TRP | B | 264 | −62.119 | −18.955 | −22.702 | 1.00 | 22.64 N |
| ATOM | 12153 | CA | TRP | B | 264 | −61.047 | −19.918 | −22.523 | 1.00 | 21.95 C |
| ATOM | 12155 | CB | TRP | B | 264 | −59.737 | −19.334 | −23.061 | 1.00 | 21.84 C |
| ATOM | 12158 | CG | TRP | B | 264 | −58.603 | −20.278 | −22.964 | 1.00 | 22.90 C |
| ATOM | 12159 | CD1 | TRP | B | 264 | −57.700 | −20.387 | −21.943 | 1.00 | 23.98 C |
| ATOM | 12161 | NE1 | TRP | B | 264 | −56.800 | −21.386 | −22.214 | 1.00 | 23.95 N |
| ATOM | 12163 | CE2 | TRP | B | 264 | −57.124 | −21.949 | −23.417 | 1.00 | 23.51 C |
| ATOM | 12164 | CD2 | TRP | B | 264 | −58.252 | −21.273 | −23.915 | 1.00 | 23.40 C |
| ATOM | 12165 | CE3 | TRP | B | 264 | −58.776 | −21.652 | −25.147 | 1.00 | 23.68 C |
| ATOM | 12167 | CZ3 | TRP | B | 264 | −58.178 | −22.669 | −25.826 | 1.00 | 24.44 C |
| ATOM | 12169 | CH2 | TRP | B | 264 | −57.060 | −23.324 | −25.310 | 1.00 | 24.97 C |
| ATOM | 12171 | CZ2 | TRP | B | 264 | −56.521 | −22.978 | −24.103 | 1.00 | 24.44 C |
| ATOM | 12173 | C | TRP | B | 264 | −60.897 | −20.326 | −21.050 | 1.00 | 21.11 C |
| ATOM | 12174 | O | TRP | B | 264 | −60.768 | −21.511 | −20.748 | 1.00 | 20.98 O |
| ATOM | 12176 | N | ALA | B | 265 | −60.916 | −19.344 | −20.147 | 1.00 | 20.17 N |
| ATOM | 12177 | CA | ALA | B | 265 | −60.774 | −19.602 | −18.712 | 1.00 | 19.36 C |
| ATOM | 12179 | CB | ALA | B | 265 | −60.621 | −18.305 | −17.944 | 1.00 | 19.30 C |
| ATOM | 12183 | C | ALA | B | 265 | −61.947 | −20.397 | −18.171 | 1.00 | 18.63 C |
| ATOM | 12184 | O | ALA | B | 265 | −61.763 | −21.349 | −17.434 | 1.00 | 18.64 O |
| ATOM | 12186 | N | VAL | B | 266 | −63.159 | −20.034 | −18.557 | 1.00 | 18.11 N |
| ATOM | 12187 | CA | VAL | B | 266 | −64.335 | −20.758 | −18.075 | 1.00 | 17.60 C |
| ATOM | 12189 | CB | VAL | B | 266 | −65.652 | −20.221 | −18.675 | 1.00 | 17.38 C |
| ATOM | 12191 | CG1 | VAL | B | 266 | −65.902 | −18.803 | −18.199 | 1.00 | 17.09 C |
| ATOM | 12195 | CG2 | VAL | B | 266 | −66.817 | −21.120 | −18.312 | 1.00 | 15.40 C |
| ATOM | 12199 | C | VAL | B | 266 | −64.221 | −22.246 | −18.376 | 1.00 | 17.67 C |
| ATOM | 12200 | O | VAL | B | 266 | −64.766 | −23.058 | −17.647 | 1.00 | 18.27 O |
| ATOM | 12202 | N | GLY | B | 267 | −63.516 | −22.607 | −19.444 | 1.00 | 17.43 N |
| ATOM | 12203 | CA | GLY | B | 267 | −63.316 | −24.013 | −19.789 | 1.00 | 16.98 C |
| ATOM | 12206 | C | GLY | B | 267 | −62.253 | −24.683 | −18.947 | 1.00 | 16.55 C |
| ATOM | 12207 | O | GLY | B | 267 | −62.360 | −25.859 | −18.609 | 1.00 | 16.37 O |
| ATOM | 12209 | N | VAL | B | 268 | −61.215 | −23.939 | −18.608 | 1.00 | 16.30 N |
| ATOM | 12210 | CA | VAL | B | 268 | −60.160 | −24.500 | −17.794 | 1.00 | 16.23 C |
| ATOM | 12212 | CB | VAL | B | 268 | −58.893 | −23.651 | −17.840 | 1.00 | 15.68 C |
| ATOM | 12214 | CG1 | VAL | B | 268 | −57.857 | −24.194 | −16.894 | 1.00 | 15.01 C |
| ATOM | 12218 | CG2 | VAL | B | 268 | −58.361 | −23.674 | −19.235 | 1.00 | 15.01 C |
| ATOM | 12222 | C | VAL | B | 268 | −60.654 | −24.718 | −16.374 | 1.00 | 16.86 C |
| ATOM | 12223 | O | VAL | B | 268 | −60.421 | −25.784 | −15.813 | 1.00 | 16.93 O |
| ATOM | 12225 | N | ALA | B | 269 | −61.362 | −23.733 | −15.817 | 1.00 | 17.64 N |
| ATOM | 12226 | CA | ALA | B | 269 | −61.911 | −23.838 | −14.461 | 1.00 | 18.46 C |
| ATOM | 12228 | CB | ALA | B | 269 | −60.958 | −23.215 | −13.472 | 1.00 | 18.15 C |
| ATOM | 12232 | C | ALA | B | 269 | −63.312 | −23.213 | −14.340 | 1.00 | 19.34 C |
| ATOM | 12233 | O | ALA | B | 269 | −63.448 | −22.030 | −14.047 | 1.00 | 19.78 O |
| ATOM | 12235 | N | PHE | B | 270 | −64.347 | −24.028 | −14.529 | 1.00 | 20.34 N |
| ATOM | 12236 | CA | PHE | B | 270 | −65.724 | −23.535 | −14.631 | 1.00 | 21.21 C |
| ATOM | 12238 | CB | PHE | B | 270 | −66.564 | −24.483 | −15.482 | 1.00 | 21.34 C |
| ATOM | 12241 | CG | PHE | B | 270 | −67.083 | −25.667 | −14.718 | 1.00 | 22.46 C |
| ATOM | 12242 | CD1 | PHE | B | 270 | −68.294 | −25.596 | −14.039 | 1.00 | 23.19 C |
| ATOM | 12244 | CE1 | PHE | B | 270 | −68.756 | −26.672 | −13.315 | 1.00 | 23.27 C |
| ATOM | 12246 | CZ | PHE | B | 270 | −68.003 | −27.836 | −13.258 | 1.00 | 23.35 C |
| ATOM | 12248 | CE2 | PHE | B | 270 | −66.794 | −27.918 | −13.932 | 1.00 | 22.73 C |
| ATOM | 12250 | CD2 | PHE | B | 270 | −66.340 | −26.843 | −14.646 | 1.00 | 22.88 C |
| ATOM | 12252 | C | PHE | B | 270 | −66.464 | −23.366 | −13.316 | 1.00 | 21.98 C |
| ATOM | 12253 | O | PHE | B | 270 | −67.408 | −22.583 | −13.268 | 1.00 | 21.93 O |
| ATOM | 12255 | N | GLU | B | 271 | −66.102 | −24.126 | −12.275 | 1.00 | 23.01 N |
| ATOM | 12256 | CA | GLU | B | 271 | −66.929 | −24.142 | −11.037 | 1.00 | 23.99 C |
| ATOM | 12258 | CB | GLU | B | 271 | −66.679 | −25.353 | −10.113 | 1.00 | 24.25 C |
| ATOM | 12261 | CG | GLU | B | 271 | −65.286 | −25.877 | −10.092 | 1.00 | 26.22 C |
| ATOM | 12264 | CD | GLU | B | 271 | −65.013 | −26.914 | −11.183 | 1.00 | 29.01 C |
| ATOM | 12265 | OE1 | GLU | B | 271 | −65.563 | −28.032 | −11.090 | 1.00 | 31.36 O |
| ATOM | 12266 | OE2 | GLU | B | 271 | −64.232 | −26.622 | −12.121 | 1.00 | 30.98 O |
| ATOM | 12267 | C | GLU | B | 271 | −66.795 | −22.831 | −10.281 | 1.00 | 23.90 C |
| ATOM | 12268 | O | GLU | B | 271 | −65.702 | −22.296 | −10.181 | 1.00 | 24.29 O |
| ATOM | 12270 | N | PRO | B | 272 | −67.913 | −22.316 | −9.745 | 1.00 | 24.09 N |
| ATOM | 12271 | CA | PRO | B | 272 | −68.005 | −20.885 | −9.428 | 1.00 | 24.11 C |
| ATOM | 12273 | CB | PRO | B | 272 | −69.380 | −20.751 | −8.751 | 1.00 | 24.03 C |
| ATOM | 12276 | CG | PRO | B | 272 | −70.083 | −22.069 | −8.997 | 1.00 | 24.12 C |
| ATOM | 12279 | CD | PRO | B | 272 | −69.013 | −23.083 | −9.132 | 1.00 | 23.99 C |
| ATOM | 12282 | C | PRO | B | 272 | −66.900 | −20.386 | −8.501 | 1.00 | 24.28 C |

TABLE 16-7-continued

Coordinates of *P. tremuloides* IspS

| ATOM | 12283 | O | PRO | B | 272 | −66.421 | −19.261 | −8.676 | 1.00 | 24.40 | O |
|---|---|---|---|---|---|---|---|---|---|---|---|
| ATOM | 12284 | N | GLN | B | 273 | −66.480 | −21.222 | −7.547 | 1.00 | 24.20 | N |
| ATOM | 12285 | CA | GLN | B | 273 | −65.500 | −20.809 | −6.551 | 1.00 | 24.20 | C |
| ATOM | 12287 | CB | GLN | B | 273 | −65.437 | −21.840 | −5.426 | 1.00 | 24.42 | C |
| ATOM | 12290 | CG | GLN | B | 273 | −64.750 | −23.176 | −5.775 | 1.00 | 25.17 | C |
| ATOM | 12293 | CD | GLN | B | 273 | −65.717 | −24.334 | −6.007 | 1.00 | 26.13 | C |
| ATOM | 12294 | OE1 | GLN | B | 273 | −66.857 | −24.141 | −6.453 | 1.00 | 27.46 | O |
| ATOM | 12295 | NE2 | GLN | B | 273 | −65.251 | −25.554 | −5.721 | 1.00 | 25.05 | N |
| ATOM | 12298 | C | GLN | B | 273 | −64.086 | −20.546 | −7.088 | 1.00 | 24.27 | C |
| ATOM | 12299 | O | GLN | B | 273 | −63.221 | −20.151 | −6.329 | 1.00 | 24.32 | O |
| ATOM | 12301 | N | TYR | B | 274 | −63.842 | −20.759 | −8.380 | 1.00 | 24.59 | N |
| ATOM | 12302 | CA | TYR | B | 274 | −62.509 | −20.551 | −8.962 | 1.00 | 24.85 | C |
| ATOM | 12304 | CB | TYR | B | 274 | −62.129 | −21.724 | −9.880 | 1.00 | 24.62 | C |
| ATOM | 12307 | CG | TYR | B | 274 | −62.009 | −23.054 | −9.184 | 1.00 | 24.35 | C |
| ATOM | 12308 | CD1 | TYR | B | 274 | −61.395 | −23.169 | −7.946 | 1.00 | 24.62 | C |
| ATOM | 12310 | CE1 | TYR | B | 274 | −61.280 | −24.391 | −7.314 | 1.00 | 25.10 | C |
| ATOM | 12312 | CZ | TYR | B | 274 | −61.771 | −25.525 | −7.920 | 1.00 | 24.92 | C |
| ATOM | 12313 | OH | TYR | B | 274 | −61.661 | −26.748 | −7.299 | 1.00 | 24.73 | O |
| ATOM | 12315 | CE2 | TYR | B | 274 | −62.366 | −25.437 | −9.150 | 1.00 | 24.76 | C |
| ATOM | 12317 | CD2 | TYR | B | 274 | −62.477 | −24.203 | −9.779 | 1.00 | 24.70 | C |
| ATOM | 12319 | C | TYR | B | 274 | −62.409 | −19.235 | −9.745 | 1.00 | 25.27 | C |
| ATOM | 12320 | O | TYR | B | 274 | −61.956 | −19.210 | −10.895 | 1.00 | 25.42 | O |
| ATOM | 12322 | N | SER | B | 275 | −62.808 | −18.134 | −9.121 | 1.00 | 25.40 | N |
| ATOM | 12323 | CA | SER | B | 275 | −62.755 | −16.849 | −9.802 | 1.00 | 25.43 | C |
| ATOM | 12325 | CB | SER | B | 275 | −63.615 | −15.814 | −9.071 | 1.00 | 25.53 | C |
| ATOM | 12328 | OG | SER | B | 275 | −65.006 | −16.068 | −9.291 | 1.00 | 25.52 | O |
| ATOM | 12330 | C | SER | B | 275 | −61.300 | −16.403 | −9.948 | 1.00 | 25.36 | C |
| ATOM | 12331 | O | SER | B | 275 | −60.885 | −15.903 | −10.996 | 1.00 | 25.17 | O |
| ATOM | 12333 | N | ASP | B | 276 | −60.517 | −16.617 | −8.901 | 1.00 | 25.41 | N |
| ATOM | 12334 | CA | ASP | B | 276 | −59.095 | −16.353 | −8.979 | 1.00 | 25.42 | C |
| ATOM | 12336 | CB | ASP | B | 276 | −58.390 | −16.794 | −7.712 | 1.00 | 25.44 | C |
| ATOM | 12339 | CG | ASP | B | 276 | −58.728 | −15.925 | −6.558 | 1.00 | 26.32 | C |
| ATOM | 12340 | OD1 | ASP | B | 276 | −59.302 | −14.857 | −6.818 | 1.00 | 27.50 | O |
| ATOM | 12341 | OD2 | ASP | B | 276 | −58.442 | −16.299 | −5.398 | 1.00 | 30.16 | O |
| ATOM | 12342 | C | ASP | B | 276 | −58.495 | −17.069 | −10.157 | 1.00 | 25.20 | C |
| ATOM | 12343 | O | ASP | B | 276 | −57.745 | −16.461 | −10.929 | 1.00 | 25.66 | O |
| ATOM | 12345 | N | CYS | B | 277 | −58.814 | −18.353 | −10.305 | 1.00 | 24.60 | N |
| ATOM | 12346 | CA | CYS | B | 277 | −58.228 | −19.110 | −11.391 | 1.00 | 24.30 | C |
| ATOM | 12348 | CB | CYS | B | 277 | −58.684 | −20.561 | −11.392 | 1.00 | 24.28 | C |
| ATOM | 12351 | SG | CYS | B | 277 | −57.737 | −21.574 | −12.569 | 1.00 | 23.82 | S |
| ATOM | 12353 | C | CYS | B | 277 | −58.593 | −18.448 | −12.698 | 1.00 | 24.09 | C |
| ATOM | 12354 | O | CYS | B | 277 | −57.727 | −18.013 | −13.450 | 1.00 | 23.87 | O |
| ATOM | 12356 | N | ARG | B | 278 | −59.893 | −18.329 | −12.933 | 1.00 | 24.22 | N |
| ATOM | 12357 | CA | ARG | B | 278 | −60.400 | −17.746 | −14.171 | 1.00 | 23.98 | C |
| ATOM | 12359 | CB | ARG | B | 278 | −61.917 | −17.556 | −14.123 | 1.00 | 23.93 | C |
| ATOM | 12362 | CG | ARG | B | 278 | −62.662 | −18.871 | −14.283 | 1.00 | 24.07 | C |
| ATOM | 12365 | CD | ARG | B | 278 | −64.132 | −18.670 | −14.607 | 1.00 | 24.48 | C |
| ATOM | 12368 | NE | ARG | B | 278 | −64.874 | −18.141 | −13.472 | 1.00 | 23.75 | N |
| ATOM | 12370 | CZ | ARG | B | 278 | −65.254 | −18.856 | −12.419 | 1.00 | 23.72 | C |
| ATOM | 12371 | NH1 | ARG | B | 278 | −64.973 | −20.149 | −12.326 | 1.00 | 22.86 | N |
| ATOM | 12374 | NH2 | ARG | B | 278 | −65.927 | −18.262 | −11.443 | 1.00 | 25.08 | N |
| ATOM | 12377 | C | ARG | B | 278 | −59.701 | −16.453 | −14.491 | 1.00 | 23.56 | C |
| ATOM | 12378 | O | ARG | B | 278 | −59.296 | −16.265 | −15.628 | 1.00 | 23.87 | O |
| ATOM | 12380 | N | ASN | B | 279 | −59.512 | −15.593 | −13.495 | 1.00 | 23.24 | N |
| ATOM | 12381 | CA | ASN | B | 279 | −58.854 | −14.301 | −13.734 | 1.00 | 23.48 | C |
| ATOM | 12383 | CB | ASN | B | 279 | −59.055 | −13.340 | −12.574 | 1.00 | 24.05 | C |
| ATOM | 12386 | CG | ASN | B | 279 | −60.510 | −13.017 | −12.346 | 1.00 | 26.58 | C |
| ATOM | 12387 | OD1 | ASN | B | 279 | −61.378 | −13.310 | −13.189 | 1.00 | 28.96 | O |
| ATOM | 12388 | ND2 | ASN | B | 279 | −60.799 | −12.416 | −11.194 | 1.00 | 30.30 | N |
| ATOM | 12391 | C | ASN | B | 279 | −57.376 | −14.404 | −14.027 | 1.00 | 22.58 | C |
| ATOM | 12392 | O | ASN | B | 279 | −56.903 | −13.749 | −14.941 | 1.00 | 22.73 | O |
| ATOM | 12394 | N | SER | B | 280 | −56.648 | −15.205 | −13.251 | 1.00 | 21.62 | N |
| ATOM | 12395 | CA | SER | B | 280 | −55.243 | −15.483 | −13.550 | 1.00 | 20.73 | C |
| ATOM | 12397 | CB | SER | B | 280 | −54.696 | −16.597 | −12.659 | 1.00 | 20.85 | C |
| ATOM | 12400 | OG | SER | B | 280 | −53.805 | −16.099 | −11.683 | 1.00 | 21.55 | O |
| ATOM | 12402 | C | SER | B | 280 | −55.091 | −15.896 | −15.004 | 1.00 | 20.04 | C |
| ATOM | 12403 | O | SER | B | 280 | −54.293 | −15.312 | −15.738 | 1.00 | 19.87 | O |
| ATOM | 12405 | N | VAL | B | 281 | −55.875 | −16.893 | −15.413 | 1.00 | 19.24 | N |
| ATOM | 12406 | CA | VAL | B | 281 | −55.720 | −17.491 | −16.720 | 1.00 | 18.77 | C |
| ATOM | 12408 | CB | VAL | B | 281 | −56.482 | −18.834 | −16.815 | 1.00 | 18.74 | C |
| ATOM | 12410 | CG1 | VAL | B | 281 | −56.467 | −19.404 | −18.251 | 1.00 | 18.34 | C |
| ATOM | 12414 | CG2 | VAL | B | 281 | −55.863 | −19.844 | −15.848 | 1.00 | 18.13 | C |
| ATOM | 12418 | C | VAL | B | 281 | −56.142 | −16.486 | −17.787 | 1.00 | 18.89 | C |
| ATOM | 12419 | O | VAL | B | 281 | −55.483 | −16.364 | −18.832 | 1.00 | 18.75 | O |
| ATOM | 12421 | N | ALA | B | 282 | −57.210 | −15.739 | −17.505 | 1.00 | 18.85 | N |
| ATOM | 12422 | CA | ALA | B | 282 | −57.709 | −14.723 | −18.439 | 1.00 | 18.80 | C |
| ATOM | 12424 | CB | ALA | B | 282 | −59.051 | −14.191 | −17.991 | 1.00 | 18.32 | C |
| ATOM | 12428 | C | ALA | B | 282 | −56.718 | −13.576 | −18.615 | 1.00 | 18.94 | C |

TABLE 16-7-continued

Coordinates of *P. tremuloides* IspS

| ATOM | 12429 | O | ALA | B | 282 | −56.582 | −13.021 | −19.700 | 1.00 | 19.16 | O |
|---|---|---|---|---|---|---|---|---|---|---|---|
| ATOM | 12431 | N | LYS | B | 283 | −56.022 | −13.211 | −17.553 | 1.00 | 19.24 | N |
| ATOM | 12432 | CA | LYS | B | 283 | −55.037 | −12.145 | −17.658 | 1.00 | 19.62 | C |
| ATOM | 12434 | CB | LYS | B | 283 | −54.649 | −11.615 | −16.276 | 1.00 | 19.68 | C |
| ATOM | 12437 | CG | LYS | B | 283 | −55.779 | −10.923 | −15.518 | 1.00 | 19.95 | C |
| ATOM | 12440 | CD | LYS | B | 283 | −55.265 | −10.398 | −14.196 | 1.00 | 21.72 | C |
| ATOM | 12443 | CE | LYS | B | 283 | −56.364 | −10.236 | −13.164 | 1.00 | 23.83 | C |
| ATOM | 12446 | NZ | LYS | B | 283 | −56.129 | −9.003 | −12.351 | 1.00 | 24.72 | N |
| ATOM | 12450 | C | LYS | B | 283 | −53.802 | −12.643 | −18.396 | 1.00 | 19.77 | C |
| ATOM | 12451 | O | LYS | B | 283 | −53.237 | −11.929 | −19.208 | 1.00 | 20.05 | O |
| ATOM | 12453 | N | MET | B | 284 | −53.387 | −13.871 | −18.117 | 1.00 | 19.88 | N |
| ATOM | 12454 | CA | MET | B | 284 | −52.136 | −14.367 | −18.652 | 1.00 | 19.90 | C |
| ATOM | 12456 | CB | MET | B | 284 | −51.719 | −15.676 | −17.960 | 1.00 | 20.08 | C |
| ATOM | 12459 | CG | MET | B | 284 | −51.125 | −15.505 | −16.560 | 1.00 | 20.62 | C |
| ATOM | 12462 | SD | MET | B | 284 | −49.782 | −14.295 | −16.485 | 1.00 | 23.69 | S |
| ATOM | 12463 | CE | MET | B | 284 | −50.600 | −12.872 | −15.754 | 1.00 | 23.82 | C |
| ATOM | 12467 | C | MET | B | 284 | −52.257 | −14.572 | −20.145 | 1.00 | 19.82 | C |
| ATOM | 12468 | O | MET | B | 284 | −51.326 | −14.269 | −20.889 | 1.00 | 20.21 | O |
| ATOM | 12470 | N | PHE | B | 285 | −53.401 | −15.088 | −20.579 | 1.00 | 19.72 | N |
| ATOM | 12471 | CA | PHE | B | 285 | −53.620 | −15.428 | −21.986 | 1.00 | 19.66 | C |
| ATOM | 12473 | CB | PHE | B | 285 | −54.863 | −16.324 | −22.114 | 1.00 | 20.09 | C |
| ATOM | 12476 | CG | PHE | B | 285 | −54.986 | −17.077 | −23.427 | 1.00 | 21.18 | C |
| ATOM | 12477 | CD1 | PHE | B | 285 | −53.877 | −17.362 | −24.232 | 1.00 | 22.86 | C |
| ATOM | 12479 | CE1 | PHE | B | 285 | −54.013 | −18.070 | −25.424 | 1.00 | 22.58 | C |
| ATOM | 12481 | CZ | PHE | B | 285 | −55.254 | −18.518 | −25.806 | 1.00 | 23.49 | C |
| ATOM | 12483 | CE2 | PHE | B | 285 | −56.365 | −18.254 | −25.002 | 1.00 | 23.36 | C |
| ATOM | 12485 | CD2 | PHE | B | 285 | −56.222 | −17.551 | −23.823 | 1.00 | 21.76 | C |
| ATOM | 12487 | C | PHE | B | 285 | −53.781 | −14.148 | −22.781 | 1.00 | 19.18 | C |
| ATOM | 12488 | O | PHE | B | 285 | −53.333 | −14.046 | −23.914 | 1.00 | 18.98 | O |
| ATOM | 12490 | N | SER | B | 286 | −54.410 | −13.161 | −22.164 | 1.00 | 18.92 | N |
| ATOM | 12491 | CA | SER | B | 286 | −54.488 | −11.843 | −22.753 | 1.00 | 19.15 | C |
| ATOM | 12493 | CB | SER | B | 286 | −55.292 | −10.894 | −21.863 | 1.00 | 19.38 | C |
| ATOM | 12496 | OG | SER | B | 286 | −56.684 | −11.180 | −21.957 | 1.00 | 20.24 | O |
| ATOM | 12498 | C | SER | B | 286 | −53.106 | −11.267 | −23.032 | 1.00 | 18.91 | C |
| ATOM | 12499 | O | SER | B | 286 | −52.894 | −10.668 | −24.087 | 1.00 | 19.48 | O |
| ATOM | 12501 | N | PHE | B | 287 | −52.172 | −11.446 | −22.102 | 1.00 | 18.48 | N |
| ATOM | 12502 | CA | PHE | B | 287 | −50.768 | −11.065 | −22.339 | 1.00 | 18.30 | C |
| ATOM | 12504 | CB | PHE | B | 287 | −49.958 | −11.035 | −21.044 | 1.00 | 18.27 | C |
| ATOM | 12507 | CG | PHE | B | 287 | −50.040 | −9.740 | −20.324 | 1.00 | 18.59 | C |
| ATOM | 12508 | CD1 | PHE | B | 287 | −49.375 | −8.624 | −20.813 | 1.00 | 20.02 | C |
| ATOM | 12510 | CE1 | PHE | B | 287 | −49.456 | −7.410 | −20.152 | 1.00 | 20.57 | C |
| ATOM | 12512 | CZ | PHE | B | 287 | −50.208 | −7.308 | −18.985 | 1.00 | 20.02 | C |
| ATOM | 12514 | CE2 | PHE | B | 287 | −50.869 | −8.417 | −18.503 | 1.00 | 19.78 | C |
| ATOM | 12516 | CD2 | PHE | B | 287 | −50.781 | −9.623 | −19.164 | 1.00 | 19.05 | C |
| ATOM | 12518 | C | PHE | B | 287 | −50.067 | −11.978 | −23.339 | 1.00 | 18.01 | C |
| ATOM | 12519 | O | PHE | B | 287 | −49.374 | −11.498 | −24.229 | 1.00 | 18.00 | O |
| ATOM | 12521 | N | VAL | B | 288 | −50.236 | −13.286 | −23.194 | 1.00 | 17.69 | N |
| ATOM | 12522 | CA | VAL | B | 288 | −49.720 | −14.206 | −24.197 | 1.00 | 17.66 | C |
| ATOM | 12524 | CB | VAL | B | 288 | −50.168 | −15.649 | −23.930 | 1.00 | 17.37 | C |
| ATOM | 12526 | CG1 | VAL | B | 288 | −49.937 | −16.529 | −25.134 | 1.00 | 16.24 | C |
| ATOM | 12530 | CG2 | VAL | B | 288 | −49.414 | −16.185 | −22.758 | 1.00 | 17.21 | C |
| ATOM | 12534 | C | VAL | B | 288 | −50.081 | −13.761 | −25.633 | 1.00 | 18.08 | C |
| ATOM | 12535 | O | VAL | B | 288 | −49.207 | −13.710 | −26.492 | 1.00 | 18.08 | O |
| ATOM | 12537 | N | THR | B | 289 | −51.327 | −13.396 | −25.895 | 1.00 | 18.42 | N |
| ATOM | 12538 | CA | THR | B | 289 | −51.683 | −13.001 | −27.256 | 1.00 | 19.33 | C |
| ATOM | 12540 | CB | THR | B | 289 | −53.171 | −12.736 | −27.401 | 1.00 | 19.35 | C |
| ATOM | 12542 | OG1 | THR | B | 289 | −53.573 | −11.895 | −26.321 | 1.00 | 21.59 | O |
| ATOM | 12544 | CG2 | THR | B | 289 | −53.973 | −14.046 | −27.350 | 1.00 | 19.09 | C |
| ATOM | 12548 | C | THR | B | 289 | −50.901 | −11.766 | −27.723 | 1.00 | 19.71 | C |
| ATOM | 12549 | O | THR | B | 289 | −50.469 | −11.707 | −28.891 | 1.00 | 19.88 | O |
| ATOM | 12551 | N | ILE | B | 290 | −50.689 | −10.796 | −26.829 | 1.00 | 19.94 | N |
| ATOM | 12552 | CA | ILE | B | 290 | −49.943 | −9.585 | −27.225 | 1.00 | 20.39 | C |
| ATOM | 12554 | CB | ILE | B | 290 | −50.069 | −8.410 | −26.221 | 1.00 | 20.50 | C |
| ATOM | 12556 | CG1 | ILE | B | 290 | −51.510 | −8.137 | −25.823 | 1.00 | 21.25 | C |
| ATOM | 12559 | CD1 | ILE | B | 290 | −51.650 | −6.854 | −25.002 | 1.00 | 21.58 | C |
| ATOM | 12563 | CG2 | ILE | B | 290 | −49.546 | −7.134 | −26.853 | 1.00 | 20.39 | C |
| ATOM | 12567 | C | ILE | B | 290 | −48.434 | −9.840 | −27.438 | 1.00 | 20.45 | C |
| ATOM | 12568 | O | ILE | B | 290 | −47.853 | −9.317 | −28.393 | 1.00 | 20.76 | O |
| ATOM | 12570 | N | ILE | B | 291 | −47.808 | −10.616 | −26.546 | 1.00 | 20.21 | N |
| ATOM | 12571 | CA | ILE | B | 291 | −46.375 | −10.869 | −26.618 | 1.00 | 19.87 | C |
| ATOM | 12573 | CB | ILE | B | 291 | −45.840 | −11.603 | −25.407 | 1.00 | 19.79 | C |
| ATOM | 12575 | CG1 | ILE | B | 291 | −46.205 | −10.879 | −24.102 | 1.00 | 19.71 | C |
| ATOM | 12578 | CD1 | ILE | B | 291 | −45.326 | −9.734 | −23.748 | 1.00 | 19.77 | C |
| ATOM | 12582 | CG2 | ILE | B | 291 | −44.336 | −11.747 | −25.516 | 1.00 | 18.91 | C |
| ATOM | 12586 | C | ILE | B | 291 | −46.134 | −11.735 | −27.825 | 1.00 | 20.44 | C |
| ATOM | 12587 | O | ILE | B | 291 | −45.233 | −11.481 | −28.600 | 1.00 | 20.35 | O |
| ATOM | 12589 | N | ASP | B | 292 | −46.965 | −12.751 | −28.005 | 1.00 | 21.33 | N |
| ATOM | 12590 | CA | ASP | B | 292 | −46.915 | −13.563 | −29.228 | 1.00 | 22.13 | C |

TABLE 16-7-continued

Coordinates of *P. tremuloides* IspS

| ATOM | 12592 | CB  | ASP | B | 292 | −48.120 | −14.508 | −29.316 | 1.00 | 22.40 | C |
| ATOM | 12595 | CG  | ASP | B | 292 | −47.847 | −15.741 | −30.160 | 1.00 | 23.47 | C |
| ATOM | 12596 | OD1 | ASP | B | 292 | −46.852 | −15.765 | −30.923 | 1.00 | 24.83 | O |
| ATOM | 12597 | OD2 | ASP | B | 292 | −48.637 | −16.707 | −30.038 | 1.00 | 25.22 | O |
| ATOM | 12598 | C   | ASP | B | 292 | −46.856 | −12.716 | −30.507 | 1.00 | 22.28 | C |
| ATOM | 12599 | O   | ASP | B | 292 | −46.088 | −13.033 | −31.399 | 1.00 | 22.73 | O |
| ATOM | 12601 | N   | ASP | B | 293 | −47.656 | −11.658 | −30.611 | 1.00 | 22.22 | N |
| ATOM | 12602 | CA  | ASP | B | 293 | −47.630 | −10.828 | −31.822 | 1.00 | 22.43 | C |
| ATOM | 12604 | CB  | ASP | B | 293 | −48.840 | −9.894  | −31.885 | 1.00 | 23.03 | C |
| ATOM | 12607 | CG  | ASP | B | 293 | −50.157 | −10.644 | −31.959 | 1.00 | 24.69 | C |
| ATOM | 12608 | OD1 | ASP | B | 293 | −50.113 | −11.900 | −32.025 | 1.00 | 28.66 | O |
| ATOM | 12609 | OD2 | ASP | B | 293 | −51.231 | −9.986  | −31.930 | 1.00 | 23.57 | O |
| ATOM | 12610 | C   | ASP | B | 293 | −46.354 | −9.997  | −31.921 | 1.00 | 21.94 | C |
| ATOM | 12611 | O   | ASP | B | 293 | −45.898 | −9.674  | −33.019 | 1.00 | 22.31 | O |
| ATOM | 12613 | N   | ILE | B | 294 | −45.783 | −9.643  | −30.780 | 1.00 | 21.05 | N |
| ATOM | 12614 | CA  | ILE | B | 294 | −44.513 | −8.941  | −30.770 | 1.00 | 20.53 | C |
| ATOM | 12616 | CB  | ILE | B | 294 | −44.166 | −8.448  | −29.344 | 1.00 | 20.42 | C |
| ATOM | 12618 | CG1 | ILE | B | 294 | −45.150 | −7.349  | −28.945 | 1.00 | 19.66 | C |
| ATOM | 12621 | CD1 | ILE | B | 294 | −45.057 | −6.956  | −27.536 | 1.00 | 18.81 | C |
| ATOM | 12625 | CG2 | ILE | B | 294 | −42.726 | −7.924  | −29.253 | 1.00 | 19.99 | C |
| ATOM | 12629 | C   | ILE | B | 294 | −43.416 | −9.845  | −31.343 | 1.00 | 20.44 | C |
| ATOM | 12630 | O   | ILE | B | 294 | −42.650 | −9.431  | −32.205 | 1.00 | 20.17 | O |
| ATOM | 12632 | N   | TYR | B | 295 | −43.355 | −11.088 | −30.886 | 1.00 | 20.65 | N |
| ATOM | 12633 | CA  | TYR | B | 295 | −42.313 | −12.008 | −31.353 | 1.00 | 20.76 | C |
| ATOM | 12635 | CB  | TYR | B | 295 | −42.145 | −13.198 | −30.412 | 1.00 | 20.29 | C |
| ATOM | 12638 | CG  | TYR | B | 295 | −41.393 | −12.926 | −29.129 | 1.00 | 17.92 | C |
| ATOM | 12639 | CD1 | TYR | B | 295 | −40.117 | −13.409 | −28.936 | 1.00 | 17.62 | C |
| ATOM | 12641 | CE1 | TYR | B | 295 | −39.427 | −13.195 | −27.747 | 1.00 | 17.12 | C |
| ATOM | 12643 | CZ  | TYR | B | 295 | −40.022 | −12.493 | −26.730 | 1.00 | 16.61 | C |
| ATOM | 12644 | OH  | TYR | B | 295 | −39.357 | −12.281 | −25.528 | 1.00 | 14.46 | O |
| ATOM | 12646 | CE2 | TYR | B | 295 | −41.296 | −12.008 | −26.911 | 1.00 | 16.82 | C |
| ATOM | 12648 | CD2 | TYR | B | 295 | −41.972 | −12.235 | −28.102 | 1.00 | 16.39 | C |
| ATOM | 12650 | C   | TYR | B | 295 | −42.619 | −12.519 | −32.749 | 1.00 | 21.65 | C |
| ATOM | 12651 | O   | TYR | B | 295 | −41.698 | −12.751 | −33.540 | 1.00 | 22.13 | O |
| ATOM | 12653 | N   | ASP | B | 296 | −43.905 | −12.677 | −33.049 | 1.00 | 22.47 | N |
| ATOM | 12654 | CA  | ASP | B | 296 | −44.327 | −13.316 | −34.285 | 1.00 | 23.52 | C |
| ATOM | 12656 | CB  | ASP | B | 296 | −45.761 | −13.851 | −34.185 | 1.00 | 23.99 | C |
| ATOM | 12659 | CG  | ASP | B | 296 | −46.134 | −14.744 | −35.369 | 1.00 | 26.22 | C |
| ATOM | 12660 | OD1 | ASP | B | 296 | −45.508 | −15.832 | −35.538 | 1.00 | 27.70 | O |
| ATOM | 12661 | OD2 | ASP | B | 296 | −47.052 | −14.348 | −36.128 | 1.00 | 28.78 | O |
| ATOM | 12662 | C   | ASP | B | 296 | −44.228 | −12.392 | −35.478 | 1.00 | 23.68 | C |
| ATOM | 12663 | O   | ASP | B | 296 | −43.673 | −12.784 | −36.502 | 1.00 | 24.01 | O |
| ATOM | 12665 | N   | VAL | B | 297 | −44.765 | −11.178 | −35.364 | 1.00 | 23.90 | N |
| ATOM | 12666 | CA  | VAL | B | 297 | −44.801 | −10.273 | −36.524 | 1.00 | 23.99 | C |
| ATOM | 12668 | CB  | VAL | B | 297 | −46.251 | −10.003 | −36.973 | 1.00 | 23.87 | C |
| ATOM | 12670 | CG1 | VAL | B | 297 | −46.949 | −11.310 | −37.197 | 1.00 | 23.75 | C |
| ATOM | 12674 | CG2 | VAL | B | 297 | −47.002 | −9.136  | −35.966 | 1.00 | 23.05 | C |
| ATOM | 12678 | C   | VAL | B | 297 | −44.060 | −8.940  | −36.383 | 1.00 | 24.27 | C |
| ATOM | 12679 | O   | VAL | B | 297 | −43.485 | −8.465  | −37.342 | 1.00 | 23.84 | O |
| ATOM | 12681 | N   | TYR | B | 298 | −44.058 | −8.347  | −35.199 | 1.00 | 24.87 | N |
| ATOM | 12682 | CA  | TYR | B | 298 | −43.760 | −6.926  | −35.078 | 1.00 | 25.67 | C |
| ATOM | 12684 | CB  | TYR | B | 298 | −44.656 | −6.294  | −34.010 | 1.00 | 26.06 | C |
| ATOM | 12687 | CG  | TYR | B | 298 | −44.520 | −4.789  | −33.932 | 1.00 | 27.95 | C |
| ATOM | 12688 | CD1 | TYR | B | 298 | −45.097 | −3.968  | −34.901 | 1.00 | 29.74 | C |
| ATOM | 12690 | CE1 | TYR | B | 298 | −44.982 | −2.574  | −34.843 | 1.00 | 29.93 | C |
| ATOM | 12692 | CZ  | TYR | B | 298 | −44.282 | −1.991  | −33.806 | 1.00 | 29.96 | C |
| ATOM | 12693 | OH  | TYR | B | 298 | −44.165 | −.631   | −33.746 | 1.00 | 30.01 | O |
| ATOM | 12695 | CE2 | TYR | B | 298 | −43.697 | −2.777  | −32.829 | 1.00 | 30.39 | C |
| ATOM | 12697 | CD2 | TYR | B | 298 | −43.811 | −4.181  | −32.899 | 1.00 | 29.96 | C |
| ATOM | 12699 | C   | TYR | B | 298 | −42.318 | −6.592  | −34.755 | 1.00 | 25.76 | C |
| ATOM | 12700 | O   | TYR | B | 298 | −41.696 | −5.830  | −35.470 | 1.00 | 26.54 | O |
| ATOM | 12702 | N   | GLY | B | 299 | −41.798 | −7.111  | −33.653 | 1.00 | 25.89 | N |
| ATOM | 12703 | CA  | GLY | B | 299 | −40.473 | −6.706  | −33.167 | 1.00 | 25.78 | C |
| ATOM | 12706 | C   | GLY | B | 299 | −39.346 | −7.341  | −33.951 | 1.00 | 25.52 | C |
| ATOM | 12707 | O   | GLY | B | 299 | −39.513 | −8.410  | −34.525 | 1.00 | 26.04 | O |
| ATOM | 12709 | N   | THR | B | 300 | −38.196 | −6.685  | −33.990 | 1.00 | 25.32 | N |
| ATOM | 12710 | CA  | THR | B | 300 | −37.063 | −7.237  | −34.716 | 1.00 | 25.16 | C |
| ATOM | 12712 | CB  | THR | B | 300 | −36.088 | −6.164  | −35.295 | 1.00 | 25.08 | C |
| ATOM | 12714 | OG1 | THR | B | 300 | −35.191 | −5.710  | −34.281 | 1.00 | 25.07 | O |
| ATOM | 12716 | CG2 | THR | B | 300 | −36.833 | −4.978  | −35.875 | 1.00 | 25.08 | C |
| ATOM | 12720 | C   | THR | B | 300 | −36.324 | −8.139  | −33.771 | 1.00 | 25.13 | C |
| ATOM | 12721 | O   | THR | B | 300 | −36.335 | −7.950  | −32.570 | 1.00 | 25.28 | O |
| ATOM | 12723 | N   | LEU | B | 301 | −35.662 | −9.129  | −34.332 | 1.00 | 25.50 | N |
| ATOM | 12724 | CA  | LEU | B | 301 | −34.918 | −10.093 | −33.538 | 1.00 | 25.42 | C |
| ATOM | 12726 | CB  | LEU | B | 301 | −34.148 | −11.020 | −34.479 | 1.00 | 25.17 | C |
| ATOM | 12729 | CG  | LEU | B | 301 | −33.624 | −12.338 | −33.941 | 1.00 | 24.95 | C |
| ATOM | 12731 | CD1 | LEU | B | 301 | −34.715 | −13.233 | −33.437 | 1.00 | 24.42 | C |
| ATOM | 12735 | CD2 | LEU | B | 301 | −32.900 | −12.998 | −35.080 | 1.00 | 26.50 | C |

TABLE 16-7-continued

Coordinates of *P. tremuloides* IspS

| ATOM | 12739 | C   | LEU | B | 301 | −33.995 | −9.425  | −32.485 | 1.00 | 25.54 | C |
|------|-------|-----|-----|---|-----|---------|---------|---------|------|-------|---|
| ATOM | 12740 | O   | LEU | B | 301 | −33.843 | −9.959  | −31.394 | 1.00 | 25.35 | O |
| ATOM | 12742 | N   | ASP | B | 302 | −33.417 | −8.257  | −32.782 | 1.00 | 25.68 | N |
| ATOM | 12743 | CA  | ASP | B | 302 | −32.598 | −7.550  | −31.774 | 1.00 | 26.02 | C |
| ATOM | 12745 | CB  | ASP | B | 302 | −31.800 | −6.377  | −32.378 | 1.00 | 26.37 | C |
| ATOM | 12748 | CG  | ASP | B | 302 | −30.563 | −6.833  | −33.167 | 1.00 | 28.27 | C |
| ATOM | 12749 | OD1 | ASP | B | 302 | −29.508 | −6.156  | −33.048 | 1.00 | 29.05 | O |
| ATOM | 12750 | OD2 | ASP | B | 302 | −30.652 | −7.852  | −33.910 | 1.00 | 31.04 | O |
| ATOM | 12751 | C   | ASP | B | 302 | −33.472 | −7.037  | −30.630 | 1.00 | 25.69 | C |
| ATOM | 12752 | O   | ASP | B | 302 | −33.110 | −7.142  | −29.447 | 1.00 | 25.90 | O |
| ATOM | 12754 | N   | GLU | B | 303 | −34.622 | −6.473  | −30.993 | 1.00 | 25.04 | N |
| ATOM | 12755 | CA  | GLU | B | 303 | −35.600 | −6.029  | −30.011 | 1.00 | 24.33 | C |
| ATOM | 12757 | CB  | GLU | B | 303 | −36.783 | −5.346  | −30.697 | 1.00 | 24.20 | C |
| ATOM | 12760 | CG  | GLU | B | 303 | −36.399 | −4.109  | −31.466 | 1.00 | 24.23 | C |
| ATOM | 12763 | CD  | GLU | B | 303 | −37.589 | −3.382  | −32.063 | 1.00 | 24.23 | C |
| ATOM | 12764 | OE1 | GLU | B | 303 | −38.496 | −4.065  | −32.604 | 1.00 | 22.66 | O |
| ATOM | 12765 | OE2 | GLU | B | 303 | −37.592 | −2.121  | −31.995 | 1.00 | 23.93 | O |
| ATOM | 12766 | C   | GLU | B | 303 | −36.103 | −7.212  | −29.193 | 1.00 | 23.87 | C |
| ATOM | 12767 | O   | GLU | B | 303 | −36.396 | −7.058  | −28.011 | 1.00 | 23.59 | O |
| ATOM | 12769 | N   | LEU | B | 304 | −36.204 | −8.383  | −29.825 | 1.00 | 23.39 | N |
| ATOM | 12770 | CA  | LEU | B | 304 | −36.766 | −9.570  | −29.166 | 1.00 | 23.23 | C |
| ATOM | 12772 | CB  | LEU | B | 304 | −37.180 | −10.624 | −30.208 | 1.00 | 22.83 | C |
| ATOM | 12775 | CG  | LEU | B | 304 | −38.381 | −10.217 | −31.074 | 1.00 | 22.06 | C |
| ATOM | 12777 | CD1 | LEU | B | 304 | −38.822 | −11.321 | −32.037 | 1.00 | 20.11 | C |
| ATOM | 12781 | CD2 | LEU | B | 304 | −39.551 | −9.800  | −30.163 | 1.00 | 21.94 | C |
| ATOM | 12785 | C   | LEU | B | 304 | −35.810 | −10.147 | −28.106 | 1.00 | 23.37 | C |
| ATOM | 12786 | O   | LEU | B | 304 | −36.248 | −10.785 | −27.141 | 1.00 | 23.22 | O |
| ATOM | 12788 | N   | GLU | B | 305 | −34.514 | −9.892  | −28.283 | 1.00 | 23.30 | N |
| ATOM | 12789 | CA  | GLU | B | 305 | −33.512 | −10.308 | −27.324 | 1.00 | 23.18 | C |
| ATOM | 12791 | CB  | GLU | B | 305 | −32.114 | −10.176 | −27.899 | 1.00 | 23.58 | C |
| ATOM | 12794 | CG  | GLU | B | 305 | −31.832 | −11.142 | −29.047 | 1.00 | 25.27 | C |
| ATOM | 12797 | CD  | GLU | B | 305 | −31.306 | −12.488 | −28.585 | 1.00 | 27.91 | C |
| ATOM | 12798 | OE1 | GLU | B | 305 | −30.946 | −13.303 | −29.470 | 1.00 | 29.87 | O |
| ATOM | 12799 | OE2 | GLU | B | 305 | −31.244 | −12.728 | −27.351 | 1.00 | 29.28 | O |
| ATOM | 12800 | C   | GLU | B | 305 | −33.633 | −9.440  | −26.104 | 1.00 | 22.52 | C |
| ATOM | 12801 | O   | GLU | B | 305 | −33.793 | −9.956  | −25.005 | 1.00 | 23.39 | O |
| ATOM | 12803 | N   | LEU | B | 306 | −33.576 | −8.124  | −26.274 | 1.00 | 21.51 | N |
| ATOM | 12804 | CA  | LEU | B | 306 | −33.715 | −7.224  | −25.114 | 1.00 | 20.70 | C |
| ATOM | 12806 | CB  | LEU | B | 306 | −33.899 | −5.764  | −25.544 | 1.00 | 20.59 | C |
| ATOM | 12809 | CG  | LEU | B | 306 | −32.769 | −5.065  | −26.293 | 1.00 | 20.12 | C |
| ATOM | 12811 | CD1 | LEU | B | 306 | −32.992 | −3.576  | −26.203 | 1.00 | 19.89 | C |
| ATOM | 12815 | CD2 | LEU | B | 306 | −31.402 | −5.437  | −25.739 | 1.00 | 19.81 | C |
| ATOM | 12819 | C   | LEU | B | 306 | −34.896 | −7.645  | −24.237 | 1.00 | 19.91 | C |
| ATOM | 12820 | O   | LEU | B | 306 | −34.771 | −7.778  | −23.031 | 1.00 | 19.53 | O |
| ATOM | 12822 | N   | PHE | B | 307 | −36.030 | −7.883  | −24.872 | 1.00 | 19.48 | N |
| ATOM | 12823 | CA  | PHE | B | 307 | −37.231 | −8.267  | −24.170 | 1.00 | 19.36 | C |
| ATOM | 12825 | CB  | PHE | B | 307 | −38.400 | −8.406  | −25.138 | 1.00 | 19.54 | C |
| ATOM | 12828 | CG  | PHE | B | 307 | −39.729 | −8.296  | −24.482 | 1.00 | 19.66 | C |
| ATOM | 12829 | CD1 | PHE | B | 307 | −40.365 | −7.079  | −24.400 | 1.00 | 21.03 | C |
| ATOM | 12831 | CE1 | PHE | B | 307 | −41.590 | −6.968  | −23.787 | 1.00 | 21.62 | C |
| ATOM | 12833 | CZ  | PHE | B | 307 | −42.182 | −8.072  | −23.248 | 1.00 | 20.25 | C |
| ATOM | 12835 | CE2 | PHE | B | 307 | −41.553 | −9.292  | −23.329 | 1.00 | 20.07 | C |
| ATOM | 12837 | CD2 | PHE | B | 307 | −40.338 | −9.400  | −23.939 | 1.00 | 19.62 | C |
| ATOM | 12839 | C   | PHE | B | 307 | −37.039 | −9.577  | −23.443 | 1.00 | 19.22 | C |
| ATOM | 12840 | O   | PHE | B | 307 | −37.354 | −9.684  | −22.260 | 1.00 | 19.50 | O |
| ATOM | 12842 | N   | THR | B | 308 | −36.532 | −10.583 | −24.143 | 1.00 | 18.96 | N |
| ATOM | 12843 | CA  | THR | B | 308 | −36.321 | −11.874 | −23.511 | 1.00 | 18.84 | C |
| ATOM | 12845 | CB  | THR | B | 308 | −35.774 | −12.879 | −24.490 | 1.00 | 18.62 | C |
| ATOM | 12847 | OG1 | THR | B | 308 | −36.687 | −12.988 | −25.579 | 1.00 | 18.88 | O |
| ATOM | 12849 | CG2 | THR | B | 308 | −35.626 | −14.228 | −23.833 | 1.00 | 18.74 | C |
| ATOM | 12853 | C   | THR | B | 308 | −35.384 | −11.737 | −22.317 | 1.00 | 19.04 | C |
| ATOM | 12854 | O   | THR | B | 308 | −35.686 | −12.244 | −21.233 | 1.00 | 18.69 | O |
| ATOM | 12856 | N   | ASP | B | 309 | −34.264 | −11.031 | −22.511 | 1.00 | 19.36 | N |
| ATOM | 12857 | CA  | ASP | B | 309 | −33.335 | −10.751 | −21.421 | 1.00 | 19.65 | C |
| ATOM | 12859 | CB  | ASP | B | 309 | −32.121 | −9.983  | −21.942 | 1.00 | 19.92 | C |
| ATOM | 12862 | CG  | ASP | B | 309 | −31.171 | −9.536  | −20.814 | 1.00 | 23.51 | C |
| ATOM | 12863 | OD1 | ASP | B | 309 | −30.520 | −10.412 | −20.175 | 1.00 | 27.27 | O |
| ATOM | 12864 | OD2 | ASP | B | 309 | −31.076 | −8.299  | −20.561 | 1.00 | 27.40 | O |
| ATOM | 12865 | C   | ASP | B | 309 | −34.048 | −9.977  | −20.295 | 1.00 | 19.08 | C |
| ATOM | 12866 | O   | ASP | B | 309 | −33.912 | −10.308 | −19.124 | 1.00 | 18.55 | O |
| ATOM | 12868 | N   | ALA | B | 310 | −34.836 | −8.975  | −20.665 | 1.00 | 18.93 | N |
| ATOM | 12869 | CA  | ALA | B | 310 | −35.546 | −8.151  | −19.688 | 1.00 | 19.12 | C |
| ATOM | 12871 | CB  | ALA | B | 310 | −36.346 | −7.062  | −20.380 | 1.00 | 18.79 | C |
| ATOM | 12875 | C   | ALA | B | 310 | −36.462 | −8.965  | −18.784 | 1.00 | 19.36 | C |
| ATOM | 12876 | O   | ALA | B | 310 | −36.560 | −8.696  | −17.577 | 1.00 | 19.58 | O |
| ATOM | 12878 | N   | VAL | B | 311 | −37.143 | −9.942  | −19.370 | 1.00 | 19.61 | N |
| ATOM | 12879 | CA  | VAL | B | 311 | −37.996 | −10.845 | −18.611 | 1.00 | 19.68 | C |
| ATOM | 12881 | CB  | VAL | B | 311 | −38.867 | −11.682 | −19.555 | 1.00 | 19.46 | C |

TABLE 16-7-continued

Coordinates of *P. tremuloides* IspS

| ATOM | 12883 | CG1 | VAL | B | 311 | −39.948 | −10.825 | −20.123 | 1.00 | 18.49 | C |
|---|---|---|---|---|---|---|---|---|---|---|---|
| ATOM | 12887 | CG2 | VAL | B | 311 | −39.469 | −12.863 | −18.843 | 1.00 | 19.31 | C |
| ATOM | 12891 | C | VAL | B | 311 | −37.161 | −11.726 | −17.673 | 1.00 | 20.46 | C |
| ATOM | 12892 | O | VAL | B | 311 | −37.479 | −11.843 | −16.494 | 1.00 | 20.25 | O |
| ATOM | 12894 | N | GLU | B | 312 | −36.085 | −12.317 | −18.189 | 1.00 | 21.67 | N |
| ATOM | 12895 | CA | GLU | B | 312 | −35.198 | −13.168 | −17.384 | 1.00 | 22.65 | C |
| ATOM | 12897 | CB | GLU | B | 312 | −34.056 | −13.708 | −18.239 | 1.00 | 23.03 | C |
| ATOM | 12900 | CG | GLU | B | 312 | −34.454 | −14.764 | −19.261 | 1.00 | 24.88 | C |
| ATOM | 12903 | CD | GLU | B | 312 | −33.335 | −15.077 | −20.267 | 1.00 | 27.34 | C |
| ATOM | 12904 | OE1 | GLU | B | 312 | −33.485 | −16.057 | −21.028 | 1.00 | 29.07 | O |
| ATOM | 12905 | OE2 | GLU | B | 312 | −32.316 | −14.342 | −20.313 | 1.00 | 28.63 | O |
| ATOM | 12906 | C | GLU | B | 312 | −34.598 | −12.443 | −16.167 | 1.00 | 23.09 | C |
| ATOM | 12907 | O | GLU | B | 312 | −34.506 | −13.007 | −15.082 | 1.00 | 23.04 | O |
| ATOM | 12909 | N | ARG | B | 313 | −34.186 | −11.199 | −16.335 | 1.00 | 23.67 | N |
| ATOM | 12910 | CA | ARG | B | 313 | −33.590 | −10.486 | −15.222 | 1.00 | 24.60 | C |
| ATOM | 12912 | CB | ARG | B | 313 | −32.609 | −9.436 | −15.735 | 1.00 | 25.26 | C |
| ATOM | 12915 | CG | ARG | B | 313 | −31.333 | −10.030 | −16.398 | 1.00 | 27.83 | C |
| ATOM | 12918 | CD | ARG | B | 313 | −30.289 | −8.943 | −16.754 | 1.00 | 31.87 | C |
| ATOM | 12921 | NE | ARG | B | 313 | −30.922 | −7.793 | −17.430 | 1.00 | 35.71 | N |
| ATOM | 12923 | CZ | ARG | B | 313 | −31.341 | −6.661 | −16.837 | 1.00 | 38.42 | C |
| ATOM | 12924 | NH1 | ARG | B | 313 | −31.189 | −6.452 | −15.522 | 1.00 | 39.15 | N |
| ATOM | 12927 | NH2 | ARG | B | 313 | −31.919 | −5.711 | −17.576 | 1.00 | 39.25 | N |
| ATOM | 12930 | C | ARG | B | 313 | −34.638 | −9.879 | −14.280 | 1.00 | 24.67 | C |
| ATOM | 12931 | O | ARG | B | 313 | −34.359 | −9.645 | −13.117 | 1.00 | 24.09 | O |
| ATOM | 12933 | N | TRP | B | 314 | −35.843 | −9.635 | −14.781 | 1.00 | 25.60 | N |
| ATOM | 12934 | CA | TRP | B | 314 | −36.971 | −9.180 | −13.951 | 1.00 | 26.20 | C |
| ATOM | 12936 | CB | TRP | B | 314 | −37.488 | −10.339 | −13.097 | 1.00 | 25.90 | C |
| ATOM | 12939 | CG | TRP | B | 314 | −38.912 | −10.184 | −12.662 | 1.00 | 23.93 | C |
| ATOM | 12940 | CD1 | TRP | B | 314 | −39.355 | −9.854 | −11.424 | 1.00 | 22.76 | C |
| ATOM | 12942 | NE1 | TRP | B | 314 | −40.727 | −9.804 | −11.412 | 1.00 | 21.93 | N |
| ATOM | 12944 | CE2 | TRP | B | 314 | −41.189 | −10.107 | −12.659 | 1.00 | 20.38 | C |
| ATOM | 12945 | CD2 | TRP | B | 314 | −40.074 | −10.352 | −13.473 | 1.00 | 21.17 | C |
| ATOM | 12946 | CE3 | TRP | B | 314 | −40.277 | −10.684 | −14.811 | 1.00 | 20.19 | C |
| ATOM | 12948 | CZ3 | TRP | B | 314 | −41.549 | −10.766 | −15.280 | 1.00 | 19.79 | C |
| ATOM | 12950 | CH2 | TRP | B | 314 | −42.640 | −10.512 | −14.445 | 1.00 | 21.00 | C |
| ATOM | 12952 | CZ2 | TRP | B | 314 | −42.474 | −10.179 | −13.130 | 1.00 | 20.60 | C |
| ATOM | 12954 | C | TRP | B | 314 | −36.620 | −7.966 | −13.076 | 1.00 | 27.57 | C |
| ATOM | 12955 | O | TRP | B | 314 | −36.890 | −7.935 | −11.870 | 1.00 | 27.56 | O |
| ATOM | 12957 | N | ASP | B | 315 | −36.039 | −6.959 | −13.718 | 1.00 | 29.12 | N |
| ATOM | 12958 | CA | ASP | B | 315 | −35.452 | −5.822 | −13.027 | 1.00 | 30.46 | C |
| ATOM | 12960 | CB | ASP | B | 315 | −33.935 | −5.796 | −13.315 | 1.00 | 30.84 | C |
| ATOM | 12963 | CG | ASP | B | 315 | −33.227 | −4.551 | −12.772 | 1.00 | 32.75 | C |
| ATOM | 12964 | OD1 | ASP | B | 315 | −33.747 | −3.904 | −11.830 | 1.00 | 35.67 | O |
| ATOM | 12965 | OD2 | ASP | B | 315 | −32.128 | −4.222 | −13.295 | 1.00 | 34.91 | O |
| ATOM | 12966 | C | ASP | B | 315 | −36.157 | −4.592 | −13.557 | 1.00 | 31.10 | C |
| ATOM | 12967 | O | ASP | B | 315 | −35.888 | −4.157 | −14.674 | 1.00 | 31.35 | O |
| ATOM | 12969 | N | VAL | B | 316 | −37.088 | −4.044 | −12.781 | 1.00 | 32.06 | N |
| ATOM | 12970 | CA | VAL | B | 316 | −37.864 | −2.896 | −13.262 | 1.00 | 32.65 | C |
| ATOM | 12972 | CB | VAL | B | 316 | −39.016 | −2.510 | −12.334 | 1.00 | 32.45 | C |
| ATOM | 12974 | CG1 | VAL | B | 316 | −39.911 | −1.499 | −13.012 | 1.00 | 32.15 | C |
| ATOM | 12978 | CG2 | VAL | B | 316 | −38.490 | −1.960 | −11.040 | 1.00 | 32.91 | C |
| ATOM | 12982 | C | VAL | B | 316 | −36.964 | −1.692 | −13.442 | 1.00 | 33.43 | C |
| ATOM | 12983 | O | VAL | B | 316 | −37.228 | −.854 | −14.294 | 1.00 | 33.74 | O |
| ATOM | 12985 | N | ASN | B | 317 | −35.881 | −1.628 | −12.663 | 1.00 | 34.29 | N |
| ATOM | 12986 | CA | ASN | B | 317 | −34.937 | −.510 | −12.730 | 1.00 | 34.63 | C |
| ATOM | 12988 | CB | ASN | B | 317 | −33.995 | −.526 | −11.505 | 1.00 | 34.50 | C |
| ATOM | 12991 | CG | ASN | B | 317 | −34.692 | −.084 | −10.201 | 1.00 | 34.08 | C |
| ATOM | 12992 | OD1 | ASN | B | 317 | −35.198 | 1.042 | −10.104 | 1.00 | 33.72 | O |
| ATOM | 12993 | ND2 | ASN | B | 317 | −34.690 | −.961 | −9.193 | 1.00 | 31.22 | N |
| ATOM | 12996 | C | ASN | B | 317 | −34.124 | −.481 | −14.029 | 1.00 | 35.21 | C |
| ATOM | 12997 | O | ASN | B | 317 | −33.196 | .296 | −14.127 | 1.00 | 35.52 | O |
| ATOM | 12999 | N | ALA | B | 318 | −34.470 | −1.318 | −15.013 | 1.00 | 35.89 | N |
| ATOM | 13000 | CA | ALA | B | 318 | −33.757 | −1.382 | −16.299 | 1.00 | 36.48 | C |
| ATOM | 13002 | CB | ALA | B | 318 | −32.727 | −2.508 | −16.253 | 1.00 | 36.49 | C |
| ATOM | 13006 | C | ALA | B | 318 | −34.695 | −1.525 | −17.534 | 1.00 | 37.02 | C |
| ATOM | 13007 | O | ALA | B | 318 | −34.297 | −1.984 | −18.616 | 1.00 | 36.52 | O |
| ATOM | 13009 | N | ILE | B | 319 | −35.952 | −1.137 | −17.339 | 1.00 | 37.76 | N |
| ATOM | 13010 | CA | ILE | B | 319 | −36.848 | −.733 | −18.424 | 1.00 | 38.08 | C |
| ATOM | 13012 | CB | ILE | B | 319 | −37.926 | .247 | −17.893 | 1.00 | 38.11 | C |
| ATOM | 13014 | CG1 | ILE | B | 319 | −39.110 | −.495 | −17.293 | 1.00 | 38.08 | C |
| ATOM | 13017 | CD1 | ILE | B | 319 | −40.068 | .451 | −16.596 | 1.00 | 38.27 | C |
| ATOM | 13021 | CG2 | ILE | B | 319 | −38.408 | 1.189 | −18.996 | 1.00 | 37.84 | C |
| ATOM | 13025 | C | ILE | B | 319 | −36.134 | .053 | −19.516 | 1.00 | 38.29 | C |
| ATOM | 13026 | O | ILE | B | 319 | −36.192 | −.324 | −20.677 | 1.00 | 38.68 | O |
| ATOM | 13028 | N | ASN | B | 320 | −35.460 | 1.141 | −19.125 | 1.00 | 38.36 | N |
| ATOM | 13029 | CA | ASN | B | 320 | −34.977 | 2.168 | −20.074 | 1.00 | 38.17 | C |
| ATOM | 13031 | CB | ASN | B | 320 | −34.278 | 3.331 | −19.331 | 1.00 | 38.16 | C |
| ATOM | 13034 | CG | ASN | B | 320 | −35.258 | 4.207 | −18.514 | 1.00 | 37.87 | C |

TABLE 16-7-continued

Coordinates of *P. tremuloides* IspS

| ATOM | 13035 | OD1 | ASN | B | 320 | −36.366 | 4.542 | −18.955 | 1.00 | 36.50 | O |
|---|---|---|---|---|---|---|---|---|---|---|---|
| ATOM | 13036 | ND2 | ASN | B | 320 | −34.827 | 4.589 | −17.322 | 1.00 | 38.12 | N |
| ATOM | 13039 | C | ASN | B | 320 | −34.082 | 1.643 | −21.206 | 1.00 | 37.78 | C |
| ATOM | 13040 | O | ASN | B | 320 | −33.856 | 2.332 | −22.181 | 1.00 | 37.76 | O |
| ATOM | 13042 | N | ASP | B | 321 | −33.600 | .416 | −21.083 | 1.00 | 37.46 | N |
| ATOM | 13043 | CA | ASP | B | 321 | −32.852 | −.224 | −22.162 | 1.00 | 37.25 | C |
| ATOM | 13045 | CB | ASP | B | 321 | −32.091 | −1.467 | −21.629 | 1.00 | 37.83 | C |
| ATOM | 13048 | CG | ASP | B | 321 | −31.351 | −1.207 | −20.285 | 1.00 | 39.33 | C |
| ATOM | 13049 | OD1 | ASP | B | 321 | −31.247 | −.021 | −19.871 | 1.00 | 40.72 | O |
| ATOM | 13050 | OD2 | ASP | B | 321 | −30.887 | −2.199 | −19.648 | 1.00 | 39.62 | O |
| ATOM | 13051 | C | ASP | B | 321 | −33.764 | −.636 | −23.339 | 1.00 | 35.99 | C |
| ATOM | 13052 | O | ASP | B | 321 | −33.273 | −.904 | −24.436 | 1.00 | 35.87 | O |
| ATOM | 13054 | N | LEU | B | 322 | −35.076 | −.674 | −23.111 | 1.00 | 34.66 | N |
| ATOM | 13055 | CA | LEU | B | 322 | −36.024 | −1.263 | −24.061 | 1.00 | 33.77 | C |
| ATOM | 13057 | CB | LEU | B | 322 | −37.180 | −1.961 | −23.327 | 1.00 | 33.65 | C |
| ATOM | 13060 | CG | LEU | B | 322 | −36.994 | −3.260 | −22.544 | 1.00 | 32.41 | C |
| ATOM | 13062 | CD1 | LEU | B | 322 | −38.223 | −3.482 | −21.693 | 1.00 | 31.54 | C |
| ATOM | 13066 | CD2 | LEU | B | 322 | −36.769 | −4.432 | −23.460 | 1.00 | 30.73 | C |
| ATOM | 13070 | C | LEU | B | 322 | −36.670 | −.243 | −24.982 | 1.00 | 33.32 | C |
| ATOM | 13071 | O | LEU | B | 322 | −36.910 | .893 | −24.570 | 1.00 | 33.37 | O |
| ATOM | 13073 | N | PRO | B | 323 | −37.005 | −.667 | −26.218 | 1.00 | 32.72 | N |
| ATOM | 13074 | CA | PRO | B | 323 | −37.856 | .068 | −27.126 | 1.00 | 32.42 | C |
| ATOM | 13076 | CB | PRO | B | 323 | −38.239 | −.985 | −28.158 | 1.00 | 32.28 | C |
| ATOM | 13079 | CG | PRO | B | 323 | −37.098 | −1.849 | −28.231 | 1.00 | 32.46 | C |
| ATOM | 13082 | CD | PRO | B | 323 | −36.498 | −1.891 | −26.857 | 1.00 | 32.79 | C |
| ATOM | 13085 | C | PRO | B | 323 | −39.115 | .576 | −26.453 | 1.00 | 32.50 | C |
| ATOM | 13086 | O | PRO | B | 323 | −39.655 | −.083 | −25.550 | 1.00 | 32.46 | O |
| ATOM | 13087 | N | ASP | B | 324 | −39.590 | 1.725 | −26.923 | 1.00 | 32.44 | N |
| ATOM | 13088 | CA | ASP | B | 324 | −40.729 | 2.387 | −26.318 | 1.00 | 32.44 | C |
| ATOM | 13090 | CB | ASP | B | 324 | −41.059 | 3.678 | −27.071 | 1.00 | 32.91 | C |
| ATOM | 13093 | CG | ASP | B | 324 | −40.241 | 4.873 | −26.576 | 1.00 | 34.17 | C |
| ATOM | 13094 | OD1 | ASP | B | 324 | −39.507 | 4.728 | −25.562 | 1.00 | 35.83 | O |
| ATOM | 13095 | OD2 | ASP | B | 324 | −40.351 | 5.960 | −27.196 | 1.00 | 35.42 | O |
| ATOM | 13096 | C | ASP | B | 324 | −41.967 | 1.504 | −26.186 | 1.00 | 31.78 | C |
| ATOM | 13097 | O | ASP | B | 324 | −42.546 | 1.440 | −25.102 | 1.00 | 31.77 | O |
| ATOM | 13099 | N | TYR | B | 325 | −42.368 | .821 | −27.258 | 1.00 | 30.99 | N |
| ATOM | 13100 | CA | TYR | B | 325 | −43.519 | −.086 | −27.167 | 1.00 | 30.49 | C |
| ATOM | 13102 | CB | TYR | B | 325 | −43.941 | −.640 | −28.536 | 1.00 | 30.28 | C |
| ATOM | 13105 | CG | TYR | B | 325 | −43.027 | −1.688 | −29.134 | 1.00 | 30.25 | C |
| ATOM | 13106 | CD1 | TYR | B | 325 | −41.917 | −1.332 | −29.893 | 1.00 | 29.81 | C |
| ATOM | 13108 | CE1 | TYR | B | 325 | −41.089 | −2.300 | −30.449 | 1.00 | 29.74 | C |
| ATOM | 13110 | CZ | TYR | B | 325 | −41.371 | −3.643 | −30.258 | 1.00 | 30.22 | C |
| ATOM | 13111 | OH | TYR | B | 325 | −40.565 | −4.625 | −30.805 | 1.00 | 31.28 | O |
| ATOM | 13113 | CE2 | TYR | B | 325 | −42.466 | −4.015 | −29.519 | 1.00 | 30.23 | C |
| ATOM | 13115 | CD2 | TYR | B | 325 | −43.288 | −3.038 | −28.963 | 1.00 | 30.49 | C |
| ATOM | 13117 | C | TYR | B | 325 | −43.284 | −1.221 | −26.168 | 1.00 | 30.14 | C |
| ATOM | 13118 | O | TYR | B | 325 | −44.219 | −1.638 | −25.483 | 1.00 | 30.19 | O |
| ATOM | 13120 | N | MET | B | 326 | −42.048 | −1.700 | −26.060 | 1.00 | 29.74 | N |
| ATOM | 13121 | CA | MET | B | 326 | −41.755 | −2.820 | −25.155 | 1.00 | 29.82 | C |
| ATOM | 13123 | CB | MET | B | 326 | −40.461 | −3.541 | −25.549 | 1.00 | 29.69 | C |
| ATOM | 13126 | CG | MET | B | 326 | −40.650 | −4.510 | −26.686 | 1.00 | 28.83 | C |
| ATOM | 13129 | SD | MET | B | 326 | −39.123 | −5.272 | −27.204 | 1.00 | 26.99 | S |
| ATOM | 13130 | CE | MET | B | 326 | −39.761 | −6.499 | −28.328 | 1.00 | 29.13 | C |
| ATOM | 13134 | C | MET | B | 326 | −41.696 | −2.402 | −23.683 | 1.00 | 29.92 | C |
| ATOM | 13135 | O | MET | B | 326 | −42.032 | −3.204 | −22.801 | 1.00 | 29.75 | O |
| ATOM | 13137 | N | LYS | B | 327 | −41.251 | −1.166 | −23.429 | 1.00 | 29.68 | N |
| ATOM | 13138 | CA | LYS | B | 327 | −41.318 | −.578 | −22.088 | 1.00 | 29.46 | C |
| ATOM | 13140 | CB | LYS | B | 327 | −41.016 | .921 | −22.114 | 1.00 | 29.93 | C |
| ATOM | 13143 | CG | LYS | B | 327 | −39.572 | 1.305 | −21.951 | 1.00 | 31.63 | C |
| ATOM | 13146 | CD | LYS | B | 327 | −39.410 | 2.803 | −22.249 | 1.00 | 34.93 | C |
| ATOM | 13149 | CE | LYS | B | 327 | −37.986 | 3.291 | −22.021 | 1.00 | 36.86 | C |
| ATOM | 13152 | NZ | LYS | B | 327 | −37.642 | 4.436 | −22.917 | 1.00 | 37.83 | N |
| ATOM | 13156 | C | LYS | B | 327 | −42.708 | −.752 | −21.531 | 1.00 | 28.46 | C |
| ATOM | 13157 | O | LYS | B | 327 | −42.879 | −1.314 | −20.461 | 1.00 | 28.54 | O |
| ATOM | 13159 | N | LEU | B | 328 | −43.696 | −.258 | −22.268 | 1.00 | 27.39 | N |
| ATOM | 13160 | CA | LEU | B | 328 | −45.056 | −.216 | −21.785 | 1.00 | 26.79 | C |
| ATOM | 13162 | CB | LEU | B | 328 | −45.946 | .519 | −22.773 | 1.00 | 26.68 | C |
| ATOM | 13165 | CG | LEU | B | 328 | −47.265 | 1.034 | −22.212 | 1.00 | 26.00 | C |
| ATOM | 13167 | CD1 | LEU | B | 328 | −47.010 | 1.964 | −21.036 | 1.00 | 24.88 | C |
| ATOM | 13171 | CD2 | LEU | B | 328 | −48.051 | 1.740 | −23.308 | 1.00 | 24.55 | C |
| ATOM | 13175 | C | LEU | B | 328 | −45.560 | −1.628 | −21.587 | 1.00 | 26.70 | C |
| ATOM | 13176 | O | LEU | B | 328 | −46.110 | −1.983 | −20.543 | 1.00 | 27.03 | O |
| ATOM | 13178 | N | CYS | B | 329 | −45.341 | −2.453 | −22.591 | 1.00 | 26.39 | N |
| ATOM | 13179 | CA | CYS | B | 329 | −45.750 | −3.843 | −22.524 | 1.00 | 26.12 | C |
| ATOM | 13181 | CB | CYS | B | 329 | −45.382 | −4.526 | −23.838 | 1.00 | 26.47 | C |
| ATOM | 13184 | SG | CYS | B | 329 | −45.857 | −6.236 | −23.880 | 1.00 | 30.60 | S |
| ATOM | 13186 | C | CYS | B | 329 | −45.124 | −4.568 | −21.319 | 1.00 | 24.45 | C |
| ATOM | 13187 | O | CYS | B | 329 | −45.829 | −5.105 | −20.486 | 1.00 | 23.93 | O |

TABLE 16-7-continued

Coordinates of *P. tremuloides* IspS

| ATOM | 13189 | N   | PHE | B | 330 | −43.801 | −4.553  | −21.228 | 1.00 | 23.30 | N |
|------|-------|-----|-----|---|-----|---------|---------|---------|------|-------|---|
| ATOM | 13190 | CA  | PHE | B | 330 | −43.087 | −5.220  | −20.141 | 1.00 | 22.47 | C |
| ATOM | 13192 | CB  | PHE | B | 330 | −41.575 | −5.019  | −20.267 | 1.00 | 22.42 | C |
| ATOM | 13195 | CG  | PHE | B | 330 | −40.800 | −5.518  | −19.076 | 1.00 | 22.37 | C |
| ATOM | 13196 | CD1 | PHE | B | 330 | −40.502 | −6.864  | −18.940 | 1.00 | 22.47 | C |
| ATOM | 13198 | CE1 | PHE | B | 330 | −39.799 | −7.339  | −17.836 | 1.00 | 21.64 | C |
| ATOM | 13200 | CZ  | PHE | B | 330 | −39.379 | −6.472  | −16.866 | 1.00 | 21.50 | C |
| ATOM | 13202 | CE2 | PHE | B | 330 | −39.659 | −5.122  | −16.983 | 1.00 | 21.92 | C |
| ATOM | 13204 | CD2 | PHE | B | 330 | −40.374 | −4.648  | −18.084 | 1.00 | 22.29 | C |
| ATOM | 13206 | C   | PHE | B | 330 | −43.524 | −4.739  | −18.765 | 1.00 | 21.87 | C |
| ATOM | 13207 | O   | PHE | B | 330 | −43.779 | −5.552  | −17.875 | 1.00 | 21.98 | O |
| ATOM | 13209 | N   | LEU | B | 331 | −43.594 | −3.427  | −18.573 | 1.00 | 20.88 | N |
| ATOM | 13210 | CA  | LEU | B | 331 | −43.997 | −2.894  | −17.276 | 1.00 | 20.25 | C |
| ATOM | 13212 | CB  | LEU | B | 331 | −43.927 | −1.354  | −17.257 | 1.00 | 20.06 | C |
| ATOM | 13215 | CG  | LEU | B | 331 | −44.124 | −.628   | −15.912 | 1.00 | 19.21 | C |
| ATOM | 13217 | CD1 | LEU | B | 331 | −43.542 | −1.408  | −14.737 | 1.00 | 18.78 | C |
| ATOM | 13221 | CD2 | LEU | B | 331 | −43.555 | .770    | −15.957 | 1.00 | 15.75 | C |
| ATOM | 13225 | C   | LEU | B | 331 | −45.398 | −3.408  | −16.902 | 1.00 | 19.99 | C |
| ATOM | 13226 | O   | LEU | B | 331 | −45.606 | −3.860  | −15.771 | 1.00 | 19.67 | O |
| ATOM | 13228 | N   | ALA | B | 332 | −46.336 | −3.373  | −17.860 | 1.00 | 19.56 | N |
| ATOM | 13229 | CA  | ALA | B | 332 | −47.695 | −3.882  | −17.629 | 1.00 | 19.24 | C |
| ATOM | 13231 | CB  | ALA | B | 332 | −48.528 | −3.802  | −18.891 | 1.00 | 18.58 | C |
| ATOM | 13235 | C   | ALA | B | 332 | −47.637 | −5.321  | −17.108 | 1.00 | 19.23 | C |
| ATOM | 13236 | O   | ALA | B | 332 | −48.235 | −5.650  | −16.079 | 1.00 | 19.18 | O |
| ATOM | 13238 | N   | LEU | B | 333 | −46.891 | −6.162  | −17.816 | 1.00 | 19.16 | N |
| ATOM | 13239 | CA  | LEU | B | 333 | −46.727 | −7.554  | −17.438 | 1.00 | 19.08 | C |
| ATOM | 13241 | CB  | LEU | B | 333 | −45.830 | −8.260  | −18.462 | 1.00 | 18.97 | C |
| ATOM | 13244 | CG  | LEU | B | 333 | −45.511 | −9.758  | −18.307 | 1.00 | 19.18 | C |
| ATOM | 13246 | CD1 | LEU | B | 333 | −46.779 | −10.611 | −18.121 | 1.00 | 18.09 | C |
| ATOM | 13250 | CD2 | LEU | B | 333 | −44.676 | −10.262 | −19.499 | 1.00 | 17.17 | C |
| ATOM | 13254 | C   | LEU | B | 333 | −46.111 | −7.616  | −16.042 | 1.00 | 19.16 | C |
| ATOM | 13255 | O   | LEU | B | 333 | −46.629 | −8.279  | −15.137 | 1.00 | 18.97 | O |
| ATOM | 13257 | N   | TYR | B | 334 | −45.013 | −6.887  | −15.884 | 1.00 | 19.23 | N |
| ATOM | 13258 | CA  | TYR | B | 334 | −44.212 | −6.906  | −14.664 | 1.00 | 19.33 | C |
| ATOM | 13260 | CB  | TYR | B | 334 | −43.092 | −5.873  | −14.785 | 1.00 | 19.43 | C |
| ATOM | 13263 | CG  | TYR | B | 334 | −42.190 | −5.748  | −13.596 | 1.00 | 19.44 | C |
| ATOM | 13264 | CD1 | TYR | B | 334 | −41.006 | −6.464  | −13.524 | 1.00 | 20.60 | C |
| ATOM | 13266 | CE1 | TYR | B | 334 | −40.148 | −6.347  | −12.442 | 1.00 | 20.77 | C |
| ATOM | 13268 | CZ  | TYR | B | 334 | −40.474 | −5.503  | −11.417 | 1.00 | 21.51 | C |
| ATOM | 13269 | OH  | TYR | B | 334 | −39.628 | −5.387  | −10.353 | 1.00 | 21.42 | O |
| ATOM | 13271 | CE2 | TYR | B | 334 | −41.646 | −4.768  | −11.466 | 1.00 | 22.15 | C |
| ATOM | 13273 | CD2 | TYR | B | 334 | −42.495 | −4.892  | −12.565 | 1.00 | 20.55 | C |
| ATOM | 13275 | C   | TYR | B | 334 | −45.065 | −6.614  | −13.443 | 1.00 | 19.37 | C |
| ATOM | 13276 | O   | TYR | B | 334 | −44.980 | −7.337  | −12.441 | 1.00 | 19.94 | O |
| ATOM | 13278 | N   | ASN | B | 335 | −45.888 | −5.565  | −13.527 | 1.00 | 18.83 | N |
| ATOM | 13279 | CA  | ASN | B | 335 | −46.784 | −5.236  | −12.443 | 1.00 | 18.37 | C |
| ATOM | 13281 | CB  | ASN | B | 335 | −47.452 | −3.896  | −12.675 | 1.00 | 18.52 | C |
| ATOM | 13284 | CG  | ASN | B | 335 | −46.493 | −2.742  | −12.518 | 1.00 | 19.27 | C |
| ATOM | 13285 | OD1 | ASN | B | 335 | −45.421 | −2.906  | −11.953 | 1.00 | 21.25 | O |
| ATOM | 13286 | ND2 | ASN | B | 335 | −46.872 | −1.566  | −13.022 | 1.00 | 19.24 | N |
| ATOM | 13289 | C   | ASN | B | 335 | −47.812 | −6.333  | −12.291 | 1.00 | 18.22 | C |
| ATOM | 13290 | O   | ASN | B | 335 | −47.966 | −6.891  | −11.207 | 1.00 | 18.53 | O |
| ATOM | 13292 | N   | THR | B | 336 | −48.481 | −6.697  | −13.379 | 1.00 | 17.95 | N |
| ATOM | 13293 | CA  | THR | B | 336 | −49.525 | −7.728  | −13.301 | 1.00 | 17.61 | C |
| ATOM | 13295 | CB  | THR | B | 336 | −49.980 | −8.204  | −14.676 | 1.00 | 17.36 | C |
| ATOM | 13297 | OG1 | THR | B | 336 | −50.249 | −7.065  | −15.500 | 1.00 | 17.02 | O |
| ATOM | 13299 | CG2 | THR | B | 336 | −51.228 | −9.044  | −14.551 | 1.00 | 16.07 | C |
| ATOM | 13303 | C   | THR | B | 336 | −49.065 | −8.941  | −12.501 | 1.00 | 17.75 | C |
| ATOM | 13304 | O   | THR | B | 336 | −49.788 | −9.429  | −11.621 | 1.00 | 18.09 | O |
| ATOM | 13306 | N   | ILE | B | 337 | −47.859 | −9.411  | −12.785 | 1.00 | 17.69 | N |
| ATOM | 13307 | CA  | ILE | B | 337 | −47.384 | −10.630 | −12.165 | 1.00 | 17.74 | C |
| ATOM | 13309 | CB  | ILE | B | 337 | −46.228 | −11.245 | −12.949 | 1.00 | 17.40 | C |
| ATOM | 13311 | CG1 | ILE | B | 337 | −46.795 | −11.865 | −14.227 | 1.00 | 18.44 | C |
| ATOM | 13314 | CD1 | ILE | B | 337 | −45.767 | −12.192 | −15.300 | 1.00 | 19.26 | C |
| ATOM | 13318 | CG2 | ILE | B | 337 | −45.568 | −12.320 | −12.152 | 1.00 | 16.25 | C |
| ATOM | 13322 | C   | ILE | B | 337 | −47.053 | −10.395 | −10.699 | 1.00 | 18.32 | C |
| ATOM | 13323 | O   | ILE | B | 337 | −47.497 | −11.175 | −9.838  | 1.00 | 18.06 | O |
| ATOM | 13325 | N   | ASN | B | 338 | −46.321 | −9.311  | −10.404 | 1.00 | 18.89 | N |
| ATOM | 13326 | CA  | ASN | B | 338 | −45.985 | −8.978  | −9.007  | 1.00 | 19.49 | C |
| ATOM | 13328 | CB  | ASN | B | 338 | −45.189 | −7.690  | −8.917  | 1.00 | 19.43 | C |
| ATOM | 13331 | CG  | ASN | B | 338 | −43.789 | −7.836  | −9.444  | 1.00 | 20.83 | C |
| ATOM | 13332 | OD1 | ASN | B | 338 | −43.292 | −8.954  | −9.634  | 1.00 | 21.52 | O |
| ATOM | 13333 | ND2 | ASN | B | 338 | −43.124 | −6.697  | −9.676  | 1.00 | 22.32 | N |
| ATOM | 13336 | C   | ASN | B | 338 | −47.229 | −8.835  | −8.146  | 1.00 | 20.05 | C |
| ATOM | 13337 | O   | ASN | B | 338 | −47.182 | −9.055  | −6.953  | 1.00 | 19.81 | O |
| ATOM | 13339 | N   | GLU | B | 339 | −48.337 | −8.459  | −8.770  | 1.00 | 20.81 | N |
| ATOM | 13340 | CA  | GLU | B | 339 | −49.589 | −8.347  | −8.086  | 1.00 | 21.81 | C |
| ATOM | 13342 | CB  | GLU | B | 339 | −50.563 | −7.544  | −8.933  | 1.00 | 22.69 | C |

TABLE 16-7-continued

Coordinates of *P. tremuloides* IspS

| ATOM | 13345 | CG | GLU | B | 339 | −51.240 | −6.422 | −8.148 | 1.00 | 27.28 | C |
|---|---|---|---|---|---|---|---|---|---|---|---|
| ATOM | 13348 | CD | GLU | B | 339 | −52.571 | −5.959 | −8.768 | 1.00 | 32.79 | C |
| ATOM | 13349 | OE1 | GLU | B | 339 | −52.761 | −4.713 | −8.897 | 1.00 | 36.20 | O |
| ATOM | 13350 | OE2 | GLU | B | 339 | −53.416 | −6.837 | −9.114 | 1.00 | 34.35 | O |
| ATOM | 13351 | C | GLU | B | 339 | −50.170 | −9.732 | −7.762 | 1.00 | 21.59 | C |
| ATOM | 13352 | O | GLU | B | 339 | −50.690 | −9.946 | −6.666 | 1.00 | 21.38 | O |
| ATOM | 13354 | N | ILE | B | 340 | −50.094 | −10.676 | −8.700 | 1.00 | 21.48 | N |
| ATOM | 13355 | CA | ILE | B | 340 | −50.486 | −12.049 | −8.384 | 1.00 | 21.27 | C |
| ATOM | 13357 | CB | ILE | B | 340 | −50.437 | −12.990 | −9.603 | 1.00 | 21.17 | C |
| ATOM | 13359 | CG1 | ILE | B | 340 | −51.478 | −12.589 | −10.643 | 1.00 | 20.99 | C |
| ATOM | 13362 | CD1 | ILE | B | 340 | −51.245 | −13.202 | −12.017 | 1.00 | 19.72 | C |
| ATOM | 13366 | CG2 | ILE | B | 340 | −50.702 | −14.444 | −9.177 | 1.00 | 21.09 | C |
| ATOM | 13370 | C | ILE | B | 340 | −49.557 | −12.585 | −7.278 | 1.00 | 21.40 | C |
| ATOM | 13371 | O | ILE | B | 340 | −50.023 | −13.238 | −6.334 | 1.00 | 21.74 | O |
| ATOM | 13373 | N | ALA | B | 341 | −48.256 | −12.301 | −7.380 | 1.00 | 20.90 | N |
| ATOM | 13374 | CA | ALA | B | 341 | −47.312 | −12.721 | −6.349 | 1.00 | 20.62 | C |
| ATOM | 13376 | CB | ALA | B | 341 | −45.922 | −12.260 | −6.694 | 1.00 | 20.53 | C |
| ATOM | 13380 | C | ALA | B | 341 | −47.720 | −12.195 | −4.969 | 1.00 | 20.59 | C |
| ATOM | 13381 | O | ALA | B | 341 | −47.606 | −12.901 | −3.950 | 1.00 | 20.57 | O |
| ATOM | 13383 | N | TYR | B | 342 | −48.208 | −10.958 | −4.949 | 1.00 | 20.62 | N |
| ATOM | 13384 | CA | TYR | B | 342 | −48.600 | −10.303 | −3.707 | 1.00 | 20.59 | C |
| ATOM | 13386 | CB | TYR | B | 342 | −48.790 | −8.792 | −3.907 | 1.00 | 20.05 | C |
| ATOM | 13389 | CG | TYR | B | 342 | −49.309 | −8.143 | −2.674 | 1.00 | 18.29 | C |
| ATOM | 13390 | CD1 | TYR | B | 342 | −48.443 | −7.683 | −1.698 | 1.00 | 17.62 | C |
| ATOM | 13392 | CE1 | TYR | B | 342 | −48.914 | −7.111 | −.518 | 1.00 | 17.91 | C |
| ATOM | 13394 | CZ | TYR | B | 342 | −50.285 | −7.005 | −.298 | 1.00 | 18.18 | C |
| ATOM | 13395 | OH | TYR | B | 342 | −50.763 | −6.433 | .877 | 1.00 | 16.00 | O |
| ATOM | 13397 | CE2 | TYR | B | 342 | −51.169 | −7.467 | −1.275 | 1.00 | 18.10 | C |
| ATOM | 13399 | CD2 | TYR | B | 342 | −50.670 | −8.037 | −2.450 | 1.00 | 17.67 | C |
| ATOM | 13401 | C | TYR | B | 342 | −49.863 | −10.928 | −3.118 | 1.00 | 21.48 | C |
| ATOM | 13402 | O | TYR | B | 342 | −49.960 | −11.089 | −1.913 | 1.00 | 20.91 | O |
| ATOM | 13404 | N | ASP | B | 343 | −50.832 | −11.273 | −3.959 | 1.00 | 22.93 | N |
| ATOM | 13405 | CA | ASP | B | 343 | −52.048 | −11.925 | −3.470 | 1.00 | 24.30 | C |
| ATOM | 13407 | CB | ASP | B | 343 | −53.010 | −12.282 | −4.608 | 1.00 | 24.59 | C |
| ATOM | 13410 | CG | ASP | B | 343 | −53.577 | −11.060 | −5.334 | 1.00 | 26.66 | C |
| ATOM | 13411 | OD1 | ASP | B | 343 | −53.619 | −9.936 | −4.756 | 1.00 | 28.24 | O |
| ATOM | 13412 | OD2 | ASP | B | 343 | −54.004 | −11.247 | −6.506 | 1.00 | 29.56 | O |
| ATOM | 13413 | C | ASP | B | 343 | −51.660 | −13.208 | −2.761 | 1.00 | 24.97 | C |
| ATOM | 13414 | O | ASP | B | 343 | −52.128 | −13.495 | −1.658 | 1.00 | 24.95 | O |
| ATOM | 13416 | N | ASN | B | 344 | −50.792 | −13.973 | −3.413 | 1.00 | 25.90 | N |
| ATOM | 13417 | CA | ASN | B | 344 | −50.322 | −15.252 | −2.884 | 1.00 | 26.59 | C |
| ATOM | 13419 | CB | ASN | B | 344 | −49.623 | −16.043 | −3.978 | 1.00 | 26.74 | C |
| ATOM | 13422 | CG | ASN | B | 344 | −50.594 | −16.639 | −4.933 | 1.00 | 28.21 | C |
| ATOM | 13423 | OD1 | ASN | B | 344 | −51.080 | −17.737 | −4.688 | 1.00 | 32.10 | O |
| ATOM | 13424 | ND2 | ASN | B | 344 | −50.923 | −15.916 | −6.016 | 1.00 | 28.40 | N |
| ATOM | 13427 | C | ASN | B | 344 | −49.421 | −15.146 | −1.655 | 1.00 | 26.78 | C |
| ATOM | 13428 | O | ASN | B | 344 | −49.424 | −16.053 | −.821 | 1.00 | 27.06 | O |
| ATOM | 13430 | N | LEU | B | 345 | −48.647 | −14.067 | −1.533 | 1.00 | 26.74 | N |
| ATOM | 13431 | CA | LEU | B | 345 | −47.970 | −13.793 | −.261 | 1.00 | 26.59 | C |
| ATOM | 13433 | CB | LEU | B | 345 | −47.005 | −12.618 | −.396 | 1.00 | 26.25 | C |
| ATOM | 13436 | CG | LEU | B | 345 | −46.046 | −12.376 | .764 | 1.00 | 24.65 | C |
| ATOM | 13438 | CD1 | LEU | B | 345 | −45.258 | −13.621 | 1.115 | 1.00 | 22.50 | C |
| ATOM | 13442 | CD2 | LEU | B | 345 | −45.119 | −11.251 | .387 | 1.00 | 23.54 | C |
| ATOM | 13446 | C | LEU | B | 345 | −49.004 | −13.503 | .840 | 1.00 | 27.00 | C |
| ATOM | 13447 | O | LEU | B | 345 | −48.903 | −14.014 | 1.947 | 1.00 | 26.93 | O |
| ATOM | 13449 | N | LYS | B | 346 | −50.008 | −12.697 | .518 | 1.00 | 27.54 | N |
| ATOM | 13450 | CA | LYS | B | 346 | −51.012 | −12.300 | 1.491 | 1.00 | 27.96 | C |
| ATOM | 13452 | CB | LYS | B | 346 | −51.998 | −11.288 | .889 | 1.00 | 28.13 | C |
| ATOM | 13455 | CG | LYS | B | 346 | −52.822 | −10.527 | 1.926 | 1.00 | 28.70 | C |
| ATOM | 13458 | CD | LYS | B | 346 | −53.781 | −9.526 | 1.281 | 1.00 | 29.73 | C |
| ATOM | 13461 | CE | LYS | B | 346 | −55.205 | −10.063 | 1.133 | 1.00 | 31.17 | C |
| ATOM | 13464 | NZ | LYS | B | 346 | −55.839 | −9.661 | −.171 | 1.00 | 32.83 | N |
| ATOM | 13468 | C | LYS | B | 346 | −51.788 | −13.498 | 1.984 | 1.00 | 28.31 | C |
| ATOM | 13469 | O | LYS | B | 346 | −52.074 | −13.600 | 3.177 | 1.00 | 28.52 | O |
| ATOM | 13471 | N | ASP | B | 347 | −52.149 | −14.396 | 1.075 | 1.00 | 28.56 | N |
| ATOM | 13472 | CA | ASP | B | 347 | −53.102 | −15.441 | 1.427 | 1.00 | 29.11 | C |
| ATOM | 13474 | CB | ASP | B | 347 | −54.068 | −15.736 | .268 | 1.00 | 29.50 | C |
| ATOM | 13477 | CG | ASP | B | 347 | −54.902 | −14.500 | −.150 | 1.00 | 31.04 | C |
| ATOM | 13478 | OD1 | ASP | B | 347 | −54.961 | −13.500 | .616 | 1.00 | 31.35 | O |
| ATOM | 13479 | OD2 | ASP | B | 347 | −55.496 | −14.534 | −1.261 | 1.00 | 33.39 | O |
| ATOM | 13480 | C | ASP | B | 347 | −52.403 | −16.699 | 1.891 | 1.00 | 28.79 | C |
| ATOM | 13481 | O | ASP | B | 347 | −52.824 | −17.321 | 2.854 | 1.00 | 29.02 | O |
| ATOM | 13483 | N | LYS | B | 348 | −51.326 | −17.068 | 1.222 | 1.00 | 28.74 | N |
| ATOM | 13484 | CA | LYS | B | 348 | −50.612 | −18.293 | 1.564 | 1.00 | 28.84 | C |
| ATOM | 13486 | CB | LYS | B | 348 | −50.290 | −19.101 | .299 | 1.00 | 29.24 | C |
| ATOM | 13489 | CG | LYS | B | 348 | −51.513 | −19.470 | −.576 | 1.00 | 30.97 | C |
| ATOM | 13492 | CD | LYS | B | 348 | −51.051 | −20.300 | −1.803 | 1.00 | 33.66 | C |
| ATOM | 13495 | CE | LYS | B | 348 | −52.033 | −20.244 | −2.989 | 1.00 | 34.52 | C |

TABLE 16-7-continued

| | | | | | | | | | | |
|---|---|---|---|---|---|---|---|---|---|---|
| ATOM | 13498 | NZ | LYS | B | 348 | −53.445 | −20.542 | −2.607 | 1.00 | 35.61 N |
| ATOM | 13502 | C | LYS | B | 348 | −49.330 | −18.029 | 2.358 | 1.00 | 27.97 C |
| ATOM | 13503 | O | LYS | B | 348 | −48.763 | −18.948 | 2.925 | 1.00 | 27.88 O |
| ATOM | 13505 | N | GLY | B | 349 | −48.874 | −16.785 | 2.403 | 1.00 | 27.21 N |
| ATOM | 13506 | CA | GLY | B | 349 | −47.625 | −16.473 | 3.075 | 1.00 | 26.87 C |
| ATOM | 13509 | C | GLY | B | 349 | −46.437 | −17.227 | 2.514 | 1.00 | 26.71 C |
| ATOM | 13510 | O | GLY | B | 349 | −45.576 | −17.669 | 3.271 | 1.00 | 26.65 O |
| ATOM | 13512 | N | GLU | B | 350 | −46.409 | −17.390 | 1.191 | 1.00 | 26.61 N |
| ATOM | 13513 | CA | GLU | B | 350 | −45.263 | −17.953 | .470 | 1.00 | 26.43 C |
| ATOM | 13515 | CB | GLU | B | 350 | −45.624 | −19.310 | −.128 | 1.00 | 26.85 C |
| ATOM | 13518 | CG | GLU | B | 350 | −45.685 | −20.453 | .888 | 1.00 | 29.63 C |
| ATOM | 13521 | CD | GLU | B | 350 | −44.304 | −21.036 | 1.227 | 1.00 | 34.21 C |
| ATOM | 13522 | OE1 | GLU | B | 350 | −43.417 | −21.045 | .328 | 1.00 | 36.93 O |
| ATOM | 13523 | OE2 | GLU | B | 350 | −44.106 | −21.498 | 2.384 | 1.00 | 35.89 O |
| ATOM | 13524 | C | GLU | B | 350 | −44.900 | −16.981 | −.637 | 1.00 | 25.49 C |
| ATOM | 13525 | O | GLU | B | 350 | −45.774 | −16.312 | −1.181 | 1.00 | 25.35 O |
| ATOM | 13527 | N | ASN | B | 351 | −43.616 | −16.866 | −.955 | 1.00 | 24.74 N |
| ATOM | 13528 | CA | ASN | B | 351 | −43.206 | −16.046 | −2.090 | 1.00 | 24.47 C |
| ATOM | 13530 | CB | ASN | B | 351 | −41.851 | −15.369 | −1.867 | 1.00 | 24.94 C |
| ATOM | 13533 | CG | ASN | B | 351 | −41.428 | −14.489 | −3.062 | 1.00 | 26.98 C |
| ATOM | 13534 | OD1 | ASN | B | 351 | −41.976 | −14.605 | −4.170 | 1.00 | 28.96 O |
| ATOM | 13535 | ND2 | ASN | B | 351 | −40.457 | −13.601 | −2.834 | 1.00 | 29.55 N |
| ATOM | 13538 | C | ASN | B | 351 | −43.095 | −16.918 | −3.303 | 1.00 | 23.33 C |
| ATOM | 13539 | O | ASN | B | 351 | −42.120 | −17.641 | −3.429 | 1.00 | 23.47 O |
| ATOM | 13541 | N | ILE | B | 352 | −44.060 | −16.823 | −4.208 | 1.00 | 22.09 N |
| ATOM | 13542 | CA | ILE | B | 352 | −44.048 | −17.644 | −5.410 | 1.00 | 21.22 C |
| ATOM | 13544 | CB | ILE | B | 352 | −45.452 | −18.213 | −5.675 | 1.00 | 21.23 C |
| ATOM | 13546 | CG1 | ILE | B | 352 | −46.464 | −17.080 | −5.913 | 1.00 | 21.11 C |
| ATOM | 13549 | CD1 | ILE | B | 352 | −47.346 | −17.305 | −7.126 | 1.00 | 20.33 C |
| ATOM | 13553 | CG2 | ILE | B | 352 | −45.875 | −19.116 | −4.519 | 1.00 | 19.79 C |
| ATOM | 13557 | C | ILE | B | 352 | −43.508 | −16.947 | −6.689 | 1.00 | 20.88 C |
| ATOM | 13558 | O | ILE | B | 352 | −43.486 | −17.553 | −7.758 | 1.00 | 20.76 O |
| ATOM | 13560 | N | LEU | B | 353 | −43.030 | −15.705 | −6.574 | 1.00 | 20.44 N |
| ATOM | 13561 | CA | LEU | B | 353 | −42.603 | −14.907 | −7.750 | 1.00 | 19.84 C |
| ATOM | 13563 | CB | LEU | B | 353 | −42.055 | −13.527 | −7.325 | 1.00 | 19.67 C |
| ATOM | 13566 | CG | LEU | B | 353 | −42.003 | −12.339 | −8.311 | 1.00 | 18.47 C |
| ATOM | 13568 | CD1 | LEU | B | 353 | −43.306 | −12.083 | −9.008 | 1.00 | 17.03 C |
| ATOM | 13572 | CD2 | LEU | B | 353 | −41.604 | −11.064 | −7.597 | 1.00 | 17.08 C |
| ATOM | 13576 | C | LEU | B | 353 | −41.587 | −15.628 | −8.633 | 1.00 | 19.81 C |
| ATOM | 13577 | O | LEU | B | 353 | −41.720 | −15.596 | −9.851 | 1.00 | 19.55 O |
| ATOM | 13579 | N | PRO | B | 354 | −40.578 | −16.299 | −8.024 | 1.00 | 20.01 N |
| ATOM | 13580 | CA | PRO | B | 354 | −39.571 | −17.010 | −8.822 | 1.00 | 19.73 C |
| ATOM | 13582 | CB | PRO | B | 354 | −38.781 | −17.796 | −7.779 | 1.00 | 19.55 C |
| ATOM | 13585 | CG | PRO | B | 354 | −38.928 | −17.037 | −6.542 | 1.00 | 19.61 C |
| ATOM | 13588 | CD | PRO | B | 354 | −40.289 | −16.413 | −6.578 | 1.00 | 19.90 C |
| ATOM | 13591 | C | PRO | B | 354 | −40.187 | −17.971 | −9.804 | 1.00 | 19.87 C |
| ATOM | 13592 | O | PRO | B | 354 | −39.693 | −18.103 | −10.918 | 1.00 | 20.08 O |
| ATOM | 13593 | N | TYR | B | 355 | −41.264 | −18.636 | −9.387 | 1.00 | 20.14 N |
| ATOM | 13594 | CA | TYR | B | 355 | −41.909 | −19.665 | −10.216 | 1.00 | 20.24 C |
| ATOM | 13596 | CB | TYR | B | 355 | −42.878 | −20.520 | −9.394 | 1.00 | 20.40 C |
| ATOM | 13599 | CG | TYR | B | 355 | −42.189 | −21.153 | −8.214 | 1.00 | 21.82 C |
| ATOM | 13600 | CD1 | TYR | B | 355 | −41.119 | −21.999 | −8.412 | 1.00 | 22.86 C |
| ATOM | 13602 | CE1 | TYR | B | 355 | −40.457 | −22.564 | −7.353 | 1.00 | 25.07 C |
| ATOM | 13604 | CZ | TYR | B | 355 | −40.850 | −22.285 | −6.053 | 1.00 | 25.58 C |
| ATOM | 13605 | OH | TYR | B | 355 | −40.153 | −22.887 | −5.020 | 1.00 | 27.33 O |
| ATOM | 13607 | CE2 | TYR | B | 355 | −41.918 | −21.433 | −5.815 | 1.00 | 23.93 C |
| ATOM | 13609 | CD2 | TYR | B | 355 | −42.577 | −20.867 | −6.900 | 1.00 | 23.10 C |
| ATOM | 13611 | C | TYR | B | 355 | −42.625 | −19.001 | −11.361 | 1.00 | 19.67 C |
| ATOM | 13612 | O | TYR | B | 355 | −42.455 | −19.405 | −12.510 | 1.00 | 19.75 O |
| ATOM | 13614 | N | LEU | B | 356 | −43.385 | −17.954 | −11.030 | 1.00 | 18.97 N |
| ATOM | 13615 | CA | LEU | B | 356 | −44.180 | −17.205 | −12.004 | 1.00 | 18.26 C |
| ATOM | 13617 | CB | LEU | B | 356 | −45.039 | −16.157 | −11.293 | 1.00 | 18.03 C |
| ATOM | 13620 | CG | LEU | B | 356 | −46.056 | −16.727 | −10.312 | 1.00 | 18.13 C |
| ATOM | 13622 | CD1 | LEU | B | 356 | −46.691 | −15.613 | −9.500 | 1.00 | 19.37 C |
| ATOM | 13626 | CD2 | LEU | B | 356 | −47.106 | −17.521 | −11.046 | 1.00 | 17.93 C |
| ATOM | 13630 | C | LEU | B | 356 | −43.298 | −16.536 | −13.056 | 1.00 | 17.76 C |
| ATOM | 13631 | O | LEU | B | 356 | −43.598 | −16.567 | −14.259 | 1.00 | 16.93 O |
| ATOM | 13633 | N | THR | B | 357 | −42.201 | −15.949 | −12.600 | 1.00 | 17.56 N |
| ATOM | 13634 | CA | THR | B | 357 | −41.335 | −15.215 | −13.501 | 1.00 | 17.63 C |
| ATOM | 13636 | CB | THR | B | 357 | −40.438 | −14.236 | −12.759 | 1.00 | 17.69 C |
| ATOM | 13638 | OG1 | THR | B | 357 | −39.530 | −14.974 | −11.934 | 1.00 | 18.39 O |
| ATOM | 13640 | CG2 | THR | B | 357 | −41.288 | −13.242 | −11.927 | 1.00 | 16.47 C |
| ATOM | 13644 | C | THR | B | 357 | −40.477 | −16.145 | −14.356 | 1.00 | 17.55 C |
| ATOM | 13645 | O | THR | B | 357 | −40.154 | −15.793 | −15.498 | 1.00 | 17.17 O |
| ATOM | 13647 | N | LYS | B | 358 | −40.127 | −17.321 | −13.824 | 1.00 | 17.37 N |
| ATOM | 13648 | CA | LYS | B | 358 | −39.462 | −18.337 | −14.649 | 1.00 | 17.55 C |
| ATOM | 13650 | CB | LYS | B | 358 | −39.030 | −19.542 | −13.827 | 1.00 | 17.87 C |
| ATOM | 13653 | CG | LYS | B | 358 | −38.450 | −20.718 | −14.640 | 1.00 | 18.75 C |

TABLE 16-7-continued

Coordinates of *P. tremuloides* IspS

| ATOM | 13656 | CD | LYS | B | 358 | −37.013 | −20.497 | −15.112 | 1.00 | 20.18 | C |
|---|---|---|---|---|---|---|---|---|---|---|---|
| ATOM | 13659 | CE | LYS | B | 358 | −36.361 | −21.843 | −15.457 | 1.00 | 21.49 | C |
| ATOM | 13662 | NZ | LYS | B | 358 | −35.189 | −21.702 | −16.361 | 1.00 | 22.89 | N |
| ATOM | 13666 | C | LYS | B | 358 | −40.403 | −18.777 | −15.754 | 1.00 | 17.43 | C |
| ATOM | 13667 | O | LYS | B | 358 | −40.031 | −18.775 | −16.926 | 1.00 | 17.52 | O |
| ATOM | 13669 | N | ALA | B | 359 | −41.633 | −19.120 | −15.384 | 1.00 | 17.42 | N |
| ATOM | 13670 | CA | ALA | B | 359 | −42.654 | −19.471 | −16.359 | 1.00 | 17.52 | C |
| ATOM | 13672 | CB | ALA | B | 359 | −44.011 | −19.434 | −15.738 | 1.00 | 17.16 | C |
| ATOM | 13676 | C | ALA | B | 359 | −42.585 | −18.521 | −17.531 | 1.00 | 18.18 | C |
| ATOM | 13677 | O | ALA | B | 359 | −42.513 | −18.956 | −18.675 | 1.00 | 18.50 | O |
| ATOM | 13679 | N | TRP | B | 360 | −42.556 | −17.223 | −17.245 | 1.00 | 19.14 | N |
| ATOM | 13680 | CA | TRP | B | 360 | −42.526 | −16.206 | −18.301 | 1.00 | 19.77 | C |
| ATOM | 13682 | CB | TRP | B | 360 | −42.922 | −14.837 | −17.746 | 1.00 | 20.15 | C |
| ATOM | 13685 | CG | TRP | B | 360 | −44.377 | −14.653 | −17.813 | 1.00 | 20.50 | C |
| ATOM | 13686 | CD1 | TRP | B | 360 | −45.259 | −14.729 | −16.788 | 1.00 | 22.15 | C |
| ATOM | 13688 | NE1 | TRP | B | 360 | −46.536 | −14.533 | −17.248 | 1.00 | 22.84 | N |
| ATOM | 13690 | CE2 | TRP | B | 360 | −46.487 | −14.348 | −18.603 | 1.00 | 21.68 | C |
| ATOM | 13691 | CD2 | TRP | B | 360 | −45.134 | −14.418 | −18.987 | 1.00 | 20.85 | C |
| ATOM | 13692 | CE3 | TRP | B | 360 | −44.802 | −14.253 | −20.334 | 1.00 | 21.21 | C |
| ATOM | 13694 | CZ3 | TRP | B | 360 | −45.821 | −14.025 | −21.245 | 1.00 | 20.75 | C |
| ATOM | 13696 | CH2 | TRP | B | 360 | −47.166 | −13.961 | −20.827 | 1.00 | 21.21 | C |
| ATOM | 13698 | CZ2 | TRP | B | 360 | −47.515 | −14.123 | −19.516 | 1.00 | 20.97 | C |
| ATOM | 13700 | C | TRP | B | 360 | −41.215 | −16.110 | −19.081 | 1.00 | 19.96 | C |
| ATOM | 13701 | O | TRP | B | 360 | −41.242 | −15.791 | −20.271 | 1.00 | 19.94 | O |
| ATOM | 13703 | N | ALA | B | 361 | −40.089 | −16.368 | −18.420 | 1.00 | 20.14 | N |
| ATOM | 13704 | CA | ALA | B | 361 | −38.790 | −16.437 | −19.102 | 1.00 | 20.41 | C |
| ATOM | 13706 | CB | ALA | B | 361 | −37.676 | −16.581 | −18.102 | 1.00 | 20.67 | C |
| ATOM | 13710 | C | ALA | B | 361 | −38.763 | −17.618 | −20.041 | 1.00 | 20.55 | C |
| ATOM | 13711 | O | ALA | B | 361 | −38.330 | −17.510 | −21.187 | 1.00 | 20.76 | O |
| ATOM | 13713 | N | ASP | B | 362 | −39.230 | −18.749 | −19.534 | 1.00 | 20.57 | N |
| ATOM | 13714 | CA | ASP | B | 362 | −39.360 | −19.965 | −20.326 | 1.00 | 20.97 | C |
| ATOM | 13716 | CB | ASP | B | 362 | −39.984 | −21.082 | −19.470 | 1.00 | 21.39 | C |
| ATOM | 13719 | CG | ASP | B | 362 | −38.938 | −21.902 | −18.693 | 1.00 | 22.80 | C |
| ATOM | 13720 | OD1 | ASP | B | 362 | −38.836 | −23.109 | −18.970 | 1.00 | 28.57 | O |
| ATOM | 13721 | OD2 | ASP | B | 362 | −38.210 | −21.384 | −17.825 | 1.00 | 22.78 | O |
| ATOM | 13722 | C | ASP | B | 362 | −40.179 | −19.748 | −21.618 | 1.00 | 20.66 | C |
| ATOM | 13723 | O | ASP | B | 362 | −39.740 | −20.141 | −22.701 | 1.00 | 20.69 | O |
| ATOM | 13725 | N | LEU | B | 363 | −41.346 | −19.110 | −21.501 | 1.00 | 20.22 | N |
| ATOM | 13726 | CA | LEU | B | 363 | −42.245 | −18.885 | −22.648 | 1.00 | 19.82 | C |
| ATOM | 13728 | CB | LEU | B | 363 | −43.592 | −18.327 | −22.164 | 1.00 | 19.11 | C |
| ATOM | 13731 | CG | LEU | B | 363 | −44.644 | −17.945 | −23.209 | 1.00 | 17.02 | C |
| ATOM | 13733 | CD1 | LEU | B | 363 | −44.829 | −19.033 | −24.214 | 1.00 | 16.20 | C |
| ATOM | 13737 | CD2 | LEU | B | 363 | −45.979 | −17.618 | −22.586 | 1.00 | 14.21 | C |
| ATOM | 13741 | C | LEU | B | 363 | −41.633 | −17.950 | −23.706 | 1.00 | 20.76 | C |
| ATOM | 13742 | O | LEU | B | 363 | −41.656 | −18.235 | −24.910 | 1.00 | 21.00 | O |
| ATOM | 13744 | N | CYS | B | 364 | −41.088 | −16.826 | −23.253 | 1.00 | 21.42 | N |
| ATOM | 13745 | CA | CYS | B | 364 | −40.427 | −15.884 | −24.147 | 1.00 | 21.67 | C |
| ATOM | 13747 | CB | CYS | B | 364 | −39.969 | −14.639 | −23.376 | 1.00 | 21.86 | C |
| ATOM | 13750 | SG | CYS | B | 364 | −41.327 | −13.638 | −22.722 | 1.00 | 23.36 | S |
| ATOM | 13752 | C | CYS | B | 364 | −39.229 | −16.547 | −24.835 | 1.00 | 21.52 | C |
| ATOM | 13753 | O | CYS | B | 364 | −39.010 | −16.323 | −26.037 | 1.00 | 21.67 | O |
| ATOM | 13755 | N | ASN | B | 365 | −38.454 | −17.352 | −24.095 | 1.00 | 20.83 | N |
| ATOM | 13756 | CA | ASN | B | 365 | −37.306 | −18.025 | −24.713 | 1.00 | 20.65 | C |
| ATOM | 13758 | CB | ASN | B | 365 | −36.425 | −18.756 | −23.691 | 1.00 | 20.74 | C |
| ATOM | 13761 | CG | ASN | B | 365 | −35.330 | −17.865 | −23.100 | 1.00 | 20.53 | C |
| ATOM | 13762 | OD1 | ASN | B | 365 | −34.553 | −17.229 | −23.830 | 1.00 | 18.26 | O |
| ATOM | 13763 | ND2 | ASN | B | 365 | −35.252 | −17.841 | −21.763 | 1.00 | 20.69 | N |
| ATOM | 13766 | C | ASN | B | 365 | −37.756 | −18.987 | −25.811 | 1.00 | 20.43 | C |
| ATOM | 13767 | O | ASN | B | 365 | −36.998 | −19.253 | −26.759 | 1.00 | 20.11 | O |
| ATOM | 13769 | N | ALA | B | 366 | −38.987 | −19.492 | −25.667 | 1.00 | 20.01 | N |
| ATOM | 13770 | CA | ALA | B | 366 | −39.618 | −20.340 | −26.665 | 1.00 | 19.70 | C |
| ATOM | 13772 | CB | ALA | B | 366 | −40.766 | −21.113 | −26.045 | 1.00 | 19.53 | C |
| ATOM | 13776 | C | ALA | B | 366 | −40.099 | −19.494 | −27.838 | 1.00 | 19.74 | C |
| ATOM | 13777 | O | ALA | B | 366 | −39.846 | −19.824 | −28.989 | 1.00 | 19.61 | O |
| ATOM | 13779 | N | PHE | B | 367 | −40.791 | −18.399 | −27.553 | 1.00 | 19.99 | N |
| ATOM | 13780 | CA | PHE | B | 367 | −41.138 | −17.446 | −28.606 | 1.00 | 20.36 | C |
| ATOM | 13782 | CB | PHE | B | 367 | −41.805 | −16.194 | −28.026 | 1.00 | 20.62 | C |
| ATOM | 13785 | CG | PHE | B | 367 | −43.200 | −16.403 | −27.537 | 1.00 | 21.75 | C |
| ATOM | 13786 | CD1 | PHE | B | 367 | −44.136 | −17.071 | −28.315 | 1.00 | 23.00 | C |
| ATOM | 13788 | CE1 | PHE | B | 367 | −45.435 | −17.242 | −27.874 | 1.00 | 23.60 | C |
| ATOM | 13790 | CZ | PHE | B | 367 | −45.819 | −16.731 | −26.648 | 1.00 | 23.64 | C |
| ATOM | 13792 | CE2 | PHE | B | 367 | −44.901 | −16.049 | −25.871 | 1.00 | 23.56 | C |
| ATOM | 13794 | CD2 | PHE | B | 367 | −43.599 | −15.883 | −26.316 | 1.00 | 22.91 | C |
| ATOM | 13796 | C | PHE | B | 367 | −39.906 | −16.986 | −29.393 | 1.00 | 20.19 | C |
| ATOM | 13797 | O | PHE | B | 367 | −39.934 | −16.903 | −30.615 | 1.00 | 19.98 | O |
| ATOM | 13799 | N | LEU | B | 368 | −38.839 | −16.659 | −28.675 | 1.00 | 20.24 | N |
| ATOM | 13800 | CA | LEU | B | 368 | −37.629 | −16.161 | −29.298 | 1.00 | 20.31 | C |
| ATOM | 13802 | CB | LEU | B | 368 | −36.569 | −15.900 | −28.232 | 1.00 | 20.27 | C |

TABLE 16-7-continued

Coordinates of *P. tremuloides* IspS

| ATOM | 13805 | CG | LEU | B | 368 | −35.235 | −15.313 | −28.694 | 1.00 | 20.12 C |
|---|---|---|---|---|---|---|---|---|---|---|
| ATOM | 13807 | CD1 | LEU | B | 368 | −35.417 | −14.069 | −29.592 | 1.00 | 20.05 C |
| ATOM | 13811 | CD2 | LEU | B | 368 | −34.409 | −14.987 | −27.465 | 1.00 | 18.60 C |
| ATOM | 13815 | C | LEU | B | 368 | −37.122 | −17.179 | −30.295 | 1.00 | 20.53 C |
| ATOM | 13816 | O | LEU | B | 368 | −36.844 | −16.844 | −31.446 | 1.00 | 20.49 O |
| ATOM | 13818 | N | GLN | B | 369 | −37.032 | −18.426 | −29.832 | 1.00 | 20.80 N |
| ATOM | 13819 | CA | GLN | B | 369 | −36.565 | −19.557 | −30.638 | 1.00 | 20.90 C |
| ATOM | 13821 | CB | GLN | B | 369 | −36.614 | −20.857 | −29.815 | 1.00 | 20.98 C |
| ATOM | 13824 | CG | GLN | B | 369 | −36.343 | −22.159 | −30.576 | 1.00 | 20.75 C |
| ATOM | 13827 | CD | GLN | B | 369 | −34.946 | −22.238 | −31.126 | 1.00 | 20.29 C |
| ATOM | 13828 | OE1 | GLN | B | 369 | −34.718 | −21.984 | −32.305 | 1.00 | 20.17 O |
| ATOM | 13829 | NE2 | GLN | B | 369 | −33.996 | −22.581 | −30.272 | 1.00 | 20.33 N |
| ATOM | 13832 | C | GLN | B | 369 | −37.365 | −19.718 | −31.910 | 1.00 | 21.04 C |
| ATOM | 13833 | O | GLN | B | 369 | −36.803 | −20.097 | −32.929 | 1.00 | 20.82 O |
| ATOM | 13835 | N | GLU | B | 370 | −38.668 | −19.453 | −31.863 | 1.00 | 21.80 N |
| ATOM | 13836 | CA | GLU | B | 370 | −39.480 | −19.512 | −33.087 | 1.00 | 22.73 C |
| ATOM | 13838 | CB | GLU | B | 370 | −40.996 | −19.518 | −32.801 | 1.00 | 23.18 C |
| ATOM | 13841 | CG | GLU | B | 370 | −41.449 | −20.608 | −31.809 | 1.00 | 25.92 C |
| ATOM | 13844 | CD | GLU | B | 370 | −42.927 | −21.064 | −31.957 | 1.00 | 29.74 C |
| ATOM | 13845 | OE1 | GLU | B | 370 | −43.840 | −20.191 | −32.101 | 1.00 | 30.13 O |
| ATOM | 13846 | OE2 | GLU | B | 370 | −43.156 | −22.316 | −31.892 | 1.00 | 31.94 O |
| ATOM | 13847 | C | GLU | B | 370 | −39.079 | −18.358 | −34.016 | 1.00 | 22.62 C |
| ATOM | 13848 | O | GLU | B | 370 | −38.933 | −18.565 | −35.221 | 1.00 | 22.53 O |
| ATOM | 13850 | N | ALA | B | 371 | −38.864 | −17.166 | −33.456 | 1.00 | 22.65 N |
| ATOM | 13851 | CA | ALA | B | 371 | −38.427 | −16.023 | −34.254 | 1.00 | 22.95 C |
| ATOM | 13853 | CB | ALA | B | 371 | −38.375 | −14.753 | −33.424 | 1.00 | 22.97 C |
| ATOM | 13857 | C | ALA | B | 371 | −37.070 | −16.296 | −34.891 | 1.00 | 23.13 C |
| ATOM | 13858 | O | ALA | B | 371 | −36.900 | −16.063 | −36.091 | 1.00 | 23.38 O |
| ATOM | 13860 | N | LYS | B | 372 | −36.113 | −16.804 | −34.107 | 1.00 | 23.15 N |
| ATOM | 13861 | CA | LYS | B | 372 | −34.776 | −17.102 | −34.640 | 1.00 | 23.10 C |
| ATOM | 13863 | CB | LYS | B | 372 | −33.808 | −17.633 | −33.575 | 1.00 | 22.85 C |
| ATOM | 13866 | CG | LYS | B | 372 | −33.414 | −16.616 | −32.514 | 1.00 | 24.28 C |
| ATOM | 13869 | CD | LYS | B | 372 | −31.973 | −16.806 | −31.969 | 1.00 | 26.34 C |
| ATOM | 13872 | CE | LYS | B | 372 | −31.919 | −17.407 | −30.544 | 1.00 | 27.84 C |
| ATOM | 13875 | NZ | LYS | B | 372 | −31.673 | −16.405 | −29.458 | 1.00 | 27.93 N |
| ATOM | 13879 | C | LYS | B | 372 | −34.887 | −18.093 | −35.790 | 1.00 | 23.16 C |
| ATOM | 13880 | O | LYS | B | 372 | −34.231 | −17.920 | −36.804 | 1.00 | 23.73 O |
| ATOM | 13882 | N | TRP | B | 373 | −35.720 | −19.122 | −35.658 | 1.00 | 23.11 N |
| ATOM | 13883 | CA | TRP | B | 373 | −35.844 | −20.094 | −36.742 | 1.00 | 22.99 C |
| ATOM | 13885 | CB | TRP | B | 373 | −36.746 | −21.274 | −36.370 | 1.00 | 22.71 C |
| ATOM | 13888 | CG | TRP | B | 373 | −36.081 | −22.343 | −35.562 | 1.00 | 20.71 C |
| ATOM | 13889 | CD1 | TRP | B | 373 | −34.770 | −22.740 | −35.623 | 1.00 | 19.89 C |
| ATOM | 13891 | NE1 | TRP | B | 373 | −34.540 | −23.757 | −34.734 | 1.00 | 19.05 N |
| ATOM | 13893 | CE2 | TRP | B | 373 | −35.715 | −24.050 | −34.090 | 1.00 | 18.91 C |
| ATOM | 13894 | CD2 | TRP | B | 373 | −36.707 | −23.184 | −34.599 | 1.00 | 18.41 C |
| ATOM | 13895 | CE3 | TRP | B | 373 | −38.007 | −23.288 | −34.105 | 1.00 | 15.66 C |
| ATOM | 13897 | CZ3 | TRP | B | 373 | −38.271 | −24.216 | −33.130 | 1.00 | 15.41 C |
| ATOM | 13899 | CH2 | TRP | B | 373 | −37.276 | −25.069 | −32.647 | 1.00 | 16.33 C |
| ATOM | 13901 | CZ2 | TRP | B | 373 | −35.994 | −25.005 | −33.112 | 1.00 | 17.53 C |
| ATOM | 13903 | C | TRP | B | 373 | −36.374 | −19.416 | −37.991 | 1.00 | 23.59 C |
| ATOM | 13904 | O | TRP | B | 373 | −35.878 | −19.653 | −39.096 | 1.00 | 23.60 O |
| ATOM | 13906 | N | LEU | B | 374 | −37.374 | −18.559 | −37.801 | 1.00 | 24.32 N |
| ATOM | 13907 | CA | LEU | B | 374 | −38.008 | −17.859 | −38.915 | 1.00 | 24.66 C |
| ATOM | 13909 | CB | LEU | B | 374 | −39.181 | −17.019 | −38.428 | 1.00 | 24.85 C |
| ATOM | 13912 | CG | LEU | B | 374 | −40.112 | −16.449 | −39.496 | 1.00 | 25.45 C |
| ATOM | 13914 | CD1 | LEU | B | 374 | −41.002 | −17.535 | −40.070 | 1.00 | 24.83 C |
| ATOM | 13918 | CD2 | LEU | B | 374 | −40.959 | −15.293 | −38.885 | 1.00 | 26.92 C |
| ATOM | 13922 | C | LEU | B | 374 | −37.009 | −16.975 | −39.618 | 1.00 | 24.64 C |
| ATOM | 13923 | O | LEU | B | 374 | −36.934 | −16.992 | −40.830 | 1.00 | 24.33 O |
| ATOM | 13925 | N | TYR | B | 375 | −36.232 | −16.220 | −38.850 | 1.00 | 25.09 N |
| ATOM | 13926 | CA | TYR | B | 375 | −35.283 | −15.274 | −39.433 | 1.00 | 25.71 C |
| ATOM | 13928 | CB | TYR | B | 375 | −34.534 | −14.479 | −38.349 | 1.00 | 25.91 C |
| ATOM | 13931 | CG | TYR | B | 375 | −33.536 | −13.468 | −38.892 | 1.00 | 27.11 C |
| ATOM | 13932 | CD1 | TYR | B | 375 | −33.950 | −12.200 | −39.305 | 1.00 | 27.98 C |
| ATOM | 13934 | CE1 | TYR | B | 375 | −33.039 | −11.271 | −39.811 | 1.00 | 28.61 C |
| ATOM | 13936 | CZ | TYR | B | 375 | −31.693 | −11.605 | −39.904 | 1.00 | 29.13 C |
| ATOM | 13937 | OH | TYR | B | 375 | −30.790 | −10.685 | −40.397 | 1.00 | 29.83 O |
| ATOM | 13939 | CE2 | TYR | B | 375 | −31.256 | −12.863 | −39.501 | 1.00 | 28.79 C |
| ATOM | 13941 | CD2 | TYR | B | 375 | −32.177 | −13.783 | −38.995 | 1.00 | 28.03 C |
| ATOM | 13943 | C | TYR | B | 375 | −34.305 | −16.036 | −40.301 | 1.00 | 25.64 C |
| ATOM | 13944 | O | TYR | B | 375 | −34.201 | −15.788 | −41.503 | 1.00 | 25.74 O |
| ATOM | 13946 | N | ASN | B | 376 | −33.635 | −17.000 | −39.685 | 1.00 | 25.73 N |
| ATOM | 13947 | CA | ASN | B | 376 | −32.599 | −17.777 | −40.346 | 1.00 | 25.78 C |
| ATOM | 13949 | CB | ASN | B | 376 | −31.739 | −18.497 | −39.303 | 1.00 | 25.73 C |
| ATOM | 13952 | CG | ASN | B | 376 | −31.155 | −17.565 | −38.273 | 1.00 | 25.13 C |
| ATOM | 13953 | OD1 | ASN | B | 376 | −30.491 | −16.590 | −38.601 | 1.00 | 25.53 O |
| ATOM | 13954 | ND2 | ASN | B | 376 | −31.389 | −17.874 | −37.013 | 1.00 | 24.64 N |
| ATOM | 13957 | C | ASN | B | 376 | −33.126 | −18.824 | −41.332 | 1.00 | 26.04 C |

TABLE 16-7-continued

Coordinates of *P. tremuloides* IspS

| ATOM | 13958 | O   | ASN | B | 376 | −32.343 | −19.644 | −41.807 | 1.00 | 26.36 | O |
|------|-------|-----|-----|---|-----|---------|---------|---------|------|-------|---|
| ATOM | 13960 | N   | LYS | B | 377 | −34.428 | −18.824 | −41.632 | 1.00 | 26.16 | N |
| ATOM | 13961 | CA  | LYS | B | 377 | −35.012 | −19.811 | −42.552 | 1.00 | 26.27 | C |
| ATOM | 13963 | CB  | LYS | B | 377 | −34.575 | −19.538 | −44.010 | 1.00 | 26.51 | C |
| ATOM | 13966 | CG  | LYS | B | 377 | −35.470 | −18.561 | −44.802 | 1.00 | 28.01 | C |
| ATOM | 13969 | CD  | LYS | B | 377 | −34.629 | −17.592 | −45.667 | 1.00 | 29.99 | C |
| ATOM | 13972 | CE  | LYS | B | 377 | −35.493 | −16.605 | −46.465 | 1.00 | 31.02 | C |
| ATOM | 13975 | NZ  | LYS | B | 377 | −36.420 | −15.819 | −45.589 | 1.00 | 32.17 | N |
| ATOM | 13979 | C   | LYS | B | 377 | −34.647 | −21.243 | −42.150 | 1.00 | 25.93 | C |
| ATOM | 13980 | O   | LYS | B | 377 | −34.380 | −22.084 | −43.003 | 1.00 | 25.82 | O |
| ATOM | 13982 | N   | SER | B | 378 | −34.637 | −21.522 | −40.852 | 1.00 | 25.65 | N |
| ATOM | 13983 | CA  | SER | B | 378 | −34.324 | −22.860 | −40.385 | 1.00 | 25.54 | C |
| ATOM | 13985 | CB  | SER | B | 378 | −34.132 | −22.877 | −38.882 | 1.00 | 25.41 | C |
| ATOM | 13988 | OG  | SER | B | 378 | −32.905 | −22.269 | −38.570 | 1.00 | 25.67 | O |
| ATOM | 13990 | C   | SER | B | 378 | −35.412 | −23.838 | −40.790 | 1.00 | 25.62 | C |
| ATOM | 13991 | O   | SER | B | 378 | −36.495 | −23.435 | −41.199 | 1.00 | 25.70 | O |
| ATOM | 13993 | N   | THR | B | 379 | −35.108 | −25.129 | −40.690 | 1.00 | 25.66 | N |
| ATOM | 13994 | CA  | THR | B | 379 | −36.038 | −26.175 | −41.097 | 1.00 | 25.55 | C |
| ATOM | 13996 | CB  | THR | B | 379 | −35.788 | −26.635 | −42.546 | 1.00 | 25.59 | C |
| ATOM | 13998 | OG1 | THR | B | 379 | −34.391 | −26.899 | −42.736 | 1.00 | 25.46 | O |
| ATOM | 14000 | CG2 | THR | B | 379 | −36.255 | −25.574 | −43.528 | 1.00 | 25.88 | C |
| ATOM | 14004 | C   | THR | B | 379 | −35.886 | −27.348 | −40.160 | 1.00 | 25.45 | C |
| ATOM | 14005 | O   | THR | B | 379 | −35.372 | −28.393 | −40.548 | 1.00 | 25.70 | O |
| ATOM | 14007 | N   | PRO | B | 380 | −36.335 | −27.179 | −38.915 | 1.00 | 25.37 | N |
| ATOM | 14008 | CA  | PRO | B | 380 | −36.144 | −28.182 | −37.876 | 1.00 | 25.22 | C |
| ATOM | 14010 | CB  | PRO | B | 380 | −36.500 | −27.437 | −36.583 | 1.00 | 25.19 | C |
| ATOM | 14013 | CG  | PRO | B | 380 | −36.643 | −26.021 | −36.955 | 1.00 | 25.83 | C |
| ATOM | 14016 | CD  | PRO | B | 380 | −37.025 | −25.998 | −38.390 | 1.00 | 25.71 | C |
| ATOM | 14019 | C   | PRO | B | 380 | −37.052 | −29.379 | −38.009 | 1.00 | 24.82 | C |
| ATOM | 14020 | O   | PRO | B | 380 | −38.143 | −29.280 | −38.575 | 1.00 | 24.84 | O |
| ATOM | 14021 | N   | THR | B | 381 | −36.607 | −30.493 | −37.436 | 1.00 | 24.42 | N |
| ATOM | 14022 | CA  | THR | B | 381 | −37.386 | −31.712 | −37.429 | 1.00 | 23.99 | C |
| ATOM | 14024 | CB  | THR | B | 381 | −36.614 | −32.873 | −36.789 | 1.00 | 23.99 | C |
| ATOM | 14026 | OG1 | THR | B | 381 | −36.339 | −32.575 | −35.418 | 1.00 | 24.02 | O |
| ATOM | 14028 | CG2 | THR | B | 381 | −35.302 | −33.117 | −37.524 | 1.00 | 23.76 | C |
| ATOM | 14032 | C   | THR | B | 381 | −38.649 | −31.461 | −36.636 | 1.00 | 23.78 | C |
| ATOM | 14033 | O   | THR | B | 381 | −38.700 | −30.548 | −35.813 | 1.00 | 23.89 | O |
| ATOM | 14035 | N   | PHE | B | 382 | −39.672 | −32.267 | −36.889 | 1.00 | 23.53 | N |
| ATOM | 14036 | CA  | PHE | B | 382 | −40.905 | −32.204 | −36.105 | 1.00 | 22.97 | C |
| ATOM | 14038 | CB  | PHE | B | 382 | −41.870 | −33.305 | −36.527 | 1.00 | 22.89 | C |
| ATOM | 14041 | CG  | PHE | B | 382 | −43.079 | −33.394 | −35.655 | 1.00 | 22.26 | C |
| ATOM | 14042 | CD1 | PHE | B | 382 | −44.189 | −32.601 | −35.910 | 1.00 | 21.65 | C |
| ATOM | 14044 | CE1 | PHE | B | 382 | −45.300 | −32.672 | −35.099 | 1.00 | 20.87 | C |
| ATOM | 14046 | CZ  | PHE | B | 382 | −45.310 | −33.534 | −34.016 | 1.00 | 20.36 | C |
| ATOM | 14048 | CE2 | PHE | B | 382 | −44.204 | −34.317 | −33.744 | 1.00 | 20.52 | C |
| ATOM | 14050 | CD2 | PHE | B | 382 | −43.098 | −34.243 | −34.556 | 1.00 | 21.17 | C |
| ATOM | 14052 | C   | PHE | B | 382 | −40.677 | −32.329 | −34.605 | 1.00 | 22.69 | C |
| ATOM | 14053 | O   | PHE | B | 382 | −41.341 | −31.657 | −33.834 | 1.00 | 22.44 | O |
| ATOM | 14055 | N   | ASP | B | 383 | −39.764 | −33.205 | −34.191 | 1.00 | 22.52 | N |
| ATOM | 14056 | CA  | ASP | B | 383 | −39.491 | −33.375 | −32.765 | 1.00 | 22.50 | C |
| ATOM | 14058 | CB  | ASP | B | 383 | −38.531 | −34.525 | −32.527 | 1.00 | 22.43 | C |
| ATOM | 14061 | CG  | ASP | B | 383 | −39.174 | −35.863 | −32.711 | 1.00 | 22.71 | C |
| ATOM | 14062 | OD1 | ASP | B | 383 | −40.359 | −35.945 | −33.074 | 1.00 | 22.89 | O |
| ATOM | 14063 | OD2 | ASP | B | 383 | −38.470 | −36.856 | −32.492 | 1.00 | 25.17 | O |
| ATOM | 14064 | C   | ASP | B | 383 | −38.954 | −32.116 | −32.091 | 1.00 | 22.43 | C |
| ATOM | 14065 | O   | ASP | B | 383 | −39.438 | −31.758 | −31.014 | 1.00 | 22.40 | O |
| ATOM | 14067 | N   | ASP | B | 384 | −37.966 | −31.464 | −32.713 | 1.00 | 22.37 | N |
| ATOM | 14068 | CA  | ASP | B | 384 | −37.422 | −30.191 | −32.213 | 1.00 | 22.61 | C |
| ATOM | 14070 | CB  | ASP | B | 384 | −36.317 | −29.648 | −33.124 | 1.00 | 22.82 | C |
| ATOM | 14073 | CG  | ASP | B | 384 | −34.963 | −30.208 | −32.807 | 1.00 | 23.40 | C |
| ATOM | 14074 | OD1 | ASP | B | 384 | −34.847 | −30.973 | −31.832 | 1.00 | 25.33 | O |
| ATOM | 14075 | OD2 | ASP | B | 384 | −34.009 | −29.891 | −33.545 | 1.00 | 24.26 | O |
| ATOM | 14076 | C   | ASP | B | 384 | −38.482 | −29.113 | −32.130 | 1.00 | 22.56 | C |
| ATOM | 14077 | O   | ASP | B | 384 | −38.598 | −28.429 | −31.108 | 1.00 | 22.48 | O |
| ATOM | 14079 | N   | TYR | B | 385 | −39.227 | −28.963 | −33.227 | 1.00 | 22.36 | N |
| ATOM | 14080 | CA  | TYR | B | 385 | −40.170 | −27.870 | −33.402 | 1.00 | 22.18 | C |
| ATOM | 14082 | CB  | TYR | B | 385 | −40.738 | −27.867 | −34.812 | 1.00 | 22.05 | C |
| ATOM | 14085 | CG  | TYR | B | 385 | −41.818 | −26.834 | −35.019 | 1.00 | 22.60 | C |
| ATOM | 14086 | CD1 | TYR | B | 385 | −41.493 | −25.553 | −35.437 | 1.00 | 23.64 | C |
| ATOM | 14088 | CE1 | TYR | B | 385 | −42.462 | −24.580 | −35.630 | 1.00 | 25.00 | C |
| ATOM | 14090 | CZ  | TYR | B | 385 | −43.788 | −24.882 | −35.410 | 1.00 | 26.86 | C |
| ATOM | 14091 | OH  | TYR | B | 385 | −44.734 | −23.883 | −35.622 | 1.00 | 28.48 | O |
| ATOM | 14093 | CE2 | TYR | B | 385 | −44.149 | −26.171 | −34.980 | 1.00 | 25.95 | C |
| ATOM | 14095 | CD2 | TYR | B | 385 | −43.158 | −27.133 | −34.790 | 1.00 | 23.94 | C |
| ATOM | 14097 | C   | TYR | B | 385 | −41.319 | −27.986 | −32.446 | 1.00 | 22.13 | C |
| ATOM | 14098 | O   | TYR | B | 385 | −41.703 | −27.017 | −31.808 | 1.00 | 22.95 | O |
| ATOM | 14100 | N   | PHE | B | 386 | −41.899 | −29.169 | −32.380 | 1.00 | 21.80 | N |
| ATOM | 14101 | CA  | PHE | B | 386 | −43.048 | −29.394 | −31.525 | 1.00 | 21.62 | C |

TABLE 16-7-continued

Coordinates of *P. tremuloides* IspS

| ATOM | 14103 | CB | PHE | B | 386 | −43.624 | −30.795 | −31.768 | 1.00 | 21.73 | C |
|---|---|---|---|---|---|---|---|---|---|---|---|
| ATOM | 14106 | CG | PHE | B | 386 | −44.834 | −31.104 | −30.952 | 1.00 | 21.27 | C |
| ATOM | 14107 | CD1 | PHE | B | 386 | −46.034 | −30.447 | −31.196 | 1.00 | 22.55 | C |
| ATOM | 14109 | CE1 | PHE | B | 386 | −47.164 | −30.732 | −30.448 | 1.00 | 23.14 | C |
| ATOM | 14111 | CZ | PHE | B | 386 | −47.095 | −31.699 | −29.446 | 1.00 | 23.20 | C |
| ATOM | 14113 | CE2 | PHE | B | 386 | −45.896 | −32.358 | −29.208 | 1.00 | 21.57 | C |
| ATOM | 14115 | CD2 | PHE | B | 386 | −44.781 | −32.057 | −29.959 | 1.00 | 20.29 | C |
| ATOM | 14117 | C | PHE | B | 386 | −42.630 | −29.226 | −30.073 | 1.00 | 21.34 | C |
| ATOM | 14118 | O | PHE | B | 386 | −43.353 | −28.639 | −29.284 | 1.00 | 21.44 | O |
| ATOM | 14120 | N | GLY | B | 387 | −41.447 | −29.725 | −29.736 | 1.00 | 20.84 | N |
| ATOM | 14121 | CA | GLY | B | 387 | −40.935 | −29.618 | −28.387 | 1.00 | 20.57 | C |
| ATOM | 14124 | C | GLY | B | 387 | −40.854 | −28.186 | −27.916 | 1.00 | 20.26 | C |
| ATOM | 14125 | O | GLY | B | 387 | −40.930 | −27.908 | −26.724 | 1.00 | 20.86 | O |
| ATOM | 14127 | N | ASN | B | 388 | −40.691 | −27.268 | −28.852 | 1.00 | 19.81 | N |
| ATOM | 14128 | CA | ASN | B | 388 | −40.758 | −25.853 | −28.536 | 1.00 | 19.51 | C |
| ATOM | 14130 | CB | ASN | B | 388 | −39.877 | −25.086 | −29.508 | 1.00 | 19.42 | C |
| ATOM | 14133 | CG | ASN | B | 388 | −39.593 | −23.700 | −29.045 | 1.00 | 19.26 | C |
| ATOM | 14134 | OD1 | ASN | B | 388 | −38.916 | −23.513 | −28.038 | 1.00 | 18.93 | O |
| ATOM | 14135 | ND2 | ASN | B | 388 | −40.105 | −22.709 | −29.774 | 1.00 | 17.99 | N |
| ATOM | 14138 | C | ASN | B | 388 | −42.200 | −25.320 | −28.604 | 1.00 | 19.41 | C |
| ATOM | 14139 | O | ASN | B | 388 | −42.591 | −24.447 | −27.833 | 1.00 | 19.58 | O |
| ATOM | 14141 | N | ALA | B | 389 | −42.989 | −25.848 | −29.532 | 1.00 | 19.11 | N |
| ATOM | 14142 | CA | ALA | B | 389 | −44.313 | −25.307 | −29.808 | 1.00 | 18.87 | C |
| ATOM | 14144 | CB | ALA | B | 389 | −44.897 | −25.949 | −31.060 | 1.00 | 18.87 | C |
| ATOM | 14148 | C | ALA | B | 389 | −45.264 | −25.460 | −28.634 | 1.00 | 18.51 | C |
| ATOM | 14149 | O | ALA | B | 389 | −45.916 | −24.511 | −28.262 | 1.00 | 18.33 | O |
| ATOM | 14151 | N | TRP | B | 390 | −45.344 | −26.652 | −28.054 | 1.00 | 18.73 | N |
| ATOM | 14152 | CA | TRP | B | 390 | −46.258 | −26.887 | −26.935 | 1.00 | 18.74 | C |
| ATOM | 14154 | CB | TRP | B | 390 | −46.389 | −28.377 | −26.569 | 1.00 | 18.75 | C |
| ATOM | 14157 | CG | TRP | B | 390 | −45.166 | −29.122 | −26.019 | 1.00 | 18.46 | C |
| ATOM | 14158 | CD1 | TRP | B | 390 | −44.390 | −30.001 | −26.705 | 1.00 | 18.75 | C |
| ATOM | 14160 | NE1 | TRP | B | 390 | −43.417 | −30.519 | −25.897 | 1.00 | 17.56 | N |
| ATOM | 14162 | CE2 | TRP | B | 390 | −43.559 | −30.005 | −24.642 | 1.00 | 16.67 | C |
| ATOM | 14163 | CD2 | TRP | B | 390 | −44.661 | −29.124 | −24.674 | 1.00 | 17.50 | C |
| ATOM | 14164 | CE3 | TRP | B | 390 | −45.008 | −28.448 | −23.505 | 1.00 | 18.38 | C |
| ATOM | 14166 | CZ3 | TRP | B | 390 | −44.251 | −28.685 | −22.347 | 1.00 | 18.34 | C |
| ATOM | 14168 | CH2 | TRP | B | 390 | −43.164 | −29.573 | −22.361 | 1.00 | 16.75 | C |
| ATOM | 14170 | CZ2 | TRP | B | 390 | −42.805 | −30.234 | −23.495 | 1.00 | 15.75 | C |
| ATOM | 14172 | C | TRP | B | 390 | −45.861 | −26.066 | −25.727 | 1.00 | 18.91 | C |
| ATOM | 14173 | O | TRP | B | 390 | −46.707 | −25.691 | −24.919 | 1.00 | 19.02 | O |
| ATOM | 14175 | N | LYS | B | 391 | −44.570 | −25.787 | −25.612 | 1.00 | 18.95 | N |
| ATOM | 14176 | CA | LYS | B | 391 | −44.085 | −24.810 | −24.643 | 1.00 | 18.85 | C |
| ATOM | 14178 | CB | LYS | B | 391 | −42.544 | −24.888 | −24.508 | 1.00 | 19.52 | C |
| ATOM | 14181 | CG | LYS | B | 391 | −42.023 | −25.373 | −23.143 | 1.00 | 21.17 | C |
| ATOM | 14184 | CD | LYS | B | 391 | −40.516 | −25.689 | −23.191 | 1.00 | 22.87 | C |
| ATOM | 14187 | CE | LYS | B | 391 | −40.251 | −27.159 | −23.508 | 1.00 | 23.91 | C |
| ATOM | 14190 | NZ | LYS | B | 391 | −38.938 | −27.354 | −24.191 | 1.00 | 25.44 | N |
| ATOM | 14194 | C | LYS | B | 391 | −44.537 | −23.400 | −25.032 | 1.00 | 17.57 | C |
| ATOM | 14195 | O | LYS | B | 391 | −44.937 | −22.629 | −24.180 | 1.00 | 17.66 | O |
| ATOM | 14197 | N | SER | B | 392 | −44.490 | −23.068 | −26.314 | 1.00 | 16.65 | N |
| ATOM | 14198 | CA | SER | B | 392 | −44.879 | −21.718 | −26.764 | 1.00 | 16.27 | C |
| ATOM | 14200 | CB | SER | B | 392 | −44.241 | −21.375 | −28.119 | 1.00 | 16.22 | C |
| ATOM | 14203 | OG | SER | B | 392 | −44.937 | −21.969 | −29.207 | 1.00 | 15.94 | O |
| ATOM | 14205 | C | SER | B | 392 | −46.384 | −21.504 | −26.866 | 1.00 | 15.87 | C |
| ATOM | 14206 | O | SER | B | 392 | −46.825 | −20.395 | −27.093 | 1.00 | 15.56 | O |
| ATOM | 14208 | N | SER | B | 393 | −47.167 | −22.568 | −26.724 | 1.00 | 15.92 | N |
| ATOM | 14209 | CA | SER | B | 393 | −48.629 | −22.474 | −26.718 | 1.00 | 15.80 | C |
| ATOM | 14211 | CB | SER | B | 393 | −49.240 | −23.867 | −26.630 | 1.00 | 15.78 | C |
| ATOM | 14214 | OG | SER | B | 393 | −49.025 | −24.426 | −25.348 | 1.00 | 15.00 | O |
| ATOM | 14216 | C | SER | B | 393 | −49.097 | −21.646 | −25.533 | 1.00 | 15.94 | C |
| ATOM | 14217 | O | SER | B | 393 | −50.115 | −20.948 | −25.599 | 1.00 | 15.60 | O |
| ATOM | 14219 | N | SER | B | 394 | −48.296 | −21.740 | −24.471 | 1.00 | 16.14 | N |
| ATOM | 14220 | CA | SER | B | 394 | −48.487 | −21.091 | −23.177 | 1.00 | 16.31 | C |
| ATOM | 14222 | CB | SER | B | 394 | −49.062 | −19.662 | −23.271 | 1.00 | 16.18 | C |
| ATOM | 14225 | OG | SER | B | 394 | −50.472 | −19.649 | −23.358 | 1.00 | 16.57 | O |
| ATOM | 14227 | C | SER | B | 394 | −49.316 | −22.006 | −22.297 | 1.00 | 16.34 | C |
| ATOM | 14228 | O | SER | B | 394 | −49.822 | −21.595 | −21.261 | 1.00 | 16.47 | O |
| ATOM | 14230 | N | GLY | B | 395 | −49.403 | −23.268 | −22.702 | 1.00 | 16.55 | N |
| ATOM | 14231 | CA | GLY | B | 395 | −50.103 | −24.282 | −21.927 | 1.00 | 16.79 | C |
| ATOM | 14234 | C | GLY | B | 395 | −49.543 | −24.391 | −20.534 | 1.00 | 16.80 | C |
| ATOM | 14235 | O | GLY | B | 395 | −50.222 | −24.083 | −19.556 | 1.00 | 16.74 | O |
| ATOM | 14237 | N | PRO | B | 396 | −48.291 | −24.824 | −20.430 | 1.00 | 17.07 | N |
| ATOM | 14238 | CA | PRO | B | 396 | −47.698 | −24.930 | −19.103 | 1.00 | 17.18 | C |
| ATOM | 14240 | CB | PRO | B | 396 | −46.273 | −25.399 | −19.386 | 1.00 | 17.09 | C |
| ATOM | 14243 | CG | PRO | B | 396 | −46.087 | −25.237 | −20.874 | 1.00 | 17.77 | C |
| ATOM | 14246 | CD | PRO | B | 396 | −47.424 | −25.390 | −21.470 | 1.00 | 17.20 | C |
| ATOM | 14249 | C | PRO | B | 396 | −47.707 | −23.615 | −18.313 | 1.00 | 17.17 | C |
| ATOM | 14250 | O | PRO | B | 396 | −47.921 | −23.644 | −17.089 | 1.00 | 17.10 | O |

TABLE 16-7-continued

Coordinates of *P. tremuloides* IspS

| ATOM | 14251 | N | LEU | B | 397 | −47.499 | −22.475 | −18.983 | 1.00 | 17.04 | N |
|---|---|---|---|---|---|---|---|---|---|---|---|
| ATOM | 14252 | CA | LEU | B | 397 | −47.513 | −21.183 | −18.261 | 1.00 | 16.77 | C |
| ATOM | 14254 | CB | LEU | B | 397 | −47.116 | −19.969 | −19.135 | 1.00 | 16.84 | C |
| ATOM | 14257 | CG | LEU | B | 397 | −47.145 | −18.576 | −18.458 | 1.00 | 16.91 | C |
| ATOM | 14259 | CD1 | LEU | B | 397 | −46.577 | −18.641 | −17.096 | 1.00 | 18.36 | C |
| ATOM | 14263 | CD2 | LEU | B | 397 | −46.373 | −17.515 | −19.196 | 1.00 | 16.88 | C |
| ATOM | 14267 | C | LEU | B | 397 | −48.894 | −20.988 | −17.682 | 1.00 | 16.24 | C |
| ATOM | 14268 | O | LEU | B | 397 | −49.051 | −20.710 | −16.494 | 1.00 | 16.09 | O |
| ATOM | 14270 | N | GLN | B | 398 | −49.902 | −21.173 | −18.515 | 1.00 | 15.72 | N |
| ATOM | 14271 | CA | GLN | B | 398 | −51.262 | −21.093 | −18.024 | 1.00 | 15.49 | C |
| ATOM | 14273 | CB | GLN | B | 398 | −52.267 | −21.387 | −19.120 | 1.00 | 15.51 | C |
| ATOM | 14276 | CG | GLN | B | 398 | −52.371 | −20.275 | −20.118 | 1.00 | 16.12 | C |
| ATOM | 14279 | CD | GLN | B | 398 | −53.436 | −20.545 | −21.114 | 1.00 | 17.86 | C |
| ATOM | 14280 | OE1 | GLN | B | 398 | −54.509 | −21.028 | −20.757 | 1.00 | 20.99 | O |
| ATOM | 14281 | NE2 | GLN | B | 398 | −53.170 | −20.239 | −22.374 | 1.00 | 18.31 | N |
| ATOM | 14284 | C | GLN | B | 398 | −51.471 | −22.040 | −16.873 | 1.00 | 15.03 | C |
| ATOM | 14285 | O | GLN | B | 398 | −51.974 | −21.638 | −15.843 | 1.00 | 15.21 | O |
| ATOM | 14287 | N | LEU | B | 399 | −51.065 | −23.291 | −17.022 | 1.00 | 14.72 | N |
| ATOM | 14288 | CA | LEU | B | 399 | −51.361 | −24.254 | −15.978 | 1.00 | 14.65 | C |
| ATOM | 14290 | CB | LEU | B | 399 | −51.201 | −25.688 | −16.475 | 1.00 | 14.44 | C |
| ATOM | 14293 | CG | LEU | B | 399 | −52.250 | −26.191 | −17.478 | 1.00 | 14.28 | C |
| ATOM | 14295 | CD1 | LEU | B | 399 | −51.907 | −27.633 | −17.846 | 1.00 | 15.50 | C |
| ATOM | 14299 | CD2 | LEU | B | 399 | −53.713 | −26.077 | −16.986 | 1.00 | 10.96 | C |
| ATOM | 14303 | C | LEU | B | 399 | −50.554 | −23.995 | −14.704 | 1.00 | 14.88 | C |
| ATOM | 14304 | O | LEU | B | 399 | −51.100 | −24.161 | −13.618 | 1.00 | 15.21 | O |
| ATOM | 14306 | N | ILE | B | 400 | −49.291 | −23.562 | −14.810 | 1.00 | 14.91 | N |
| ATOM | 14307 | CA | ILE | B | 400 | −48.532 | −23.174 | −13.607 | 1.00 | 14.89 | C |
| ATOM | 14309 | CB | ILE | B | 400 | −47.158 | −22.574 | −13.907 | 1.00 | 15.19 | C |
| ATOM | 14311 | CG1 | ILE | B | 400 | −46.189 | −23.674 | −14.353 | 1.00 | 16.76 | C |
| ATOM | 14314 | CD1 | ILE | B | 400 | −44.777 | −23.162 | −14.716 | 1.00 | 18.19 | C |
| ATOM | 14318 | CG2 | ILE | B | 400 | −46.603 | −21.906 | −12.665 | 1.00 | 13.65 | C |
| ATOM | 14322 | C | ILE | B | 400 | −49.288 | −22.137 | −12.819 | 1.00 | 14.77 | C |
| ATOM | 14323 | O | ILE | B | 400 | −49.485 | −22.302 | −11.632 | 1.00 | 15.36 | O |
| ATOM | 14325 | N | PHE | B | 401 | −49.717 | −21.071 | −13.486 | 1.00 | 14.59 | N |
| ATOM | 14326 | CA | PHE | B | 401 | −50.491 | −20.001 | −12.844 | 1.00 | 14.22 | C |
| ATOM | 14328 | CB | PHE | B | 401 | −50.825 | −18.900 | −13.845 | 1.00 | 14.12 | C |
| ATOM | 14331 | CG | PHE | B | 401 | −49.803 | −17.790 | −13.872 | 1.00 | 13.83 | C |
| ATOM | 14332 | CD1 | PHE | B | 401 | −50.012 | −16.623 | −13.173 | 1.00 | 12.77 | C |
| ATOM | 14334 | CE1 | PHE | B | 401 | −49.074 | −15.629 | −13.189 | 1.00 | 13.09 | C |
| ATOM | 14336 | CZ | PHE | B | 401 | −47.906 | −15.781 | −13.902 | 1.00 | 12.96 | C |
| ATOM | 14338 | CE2 | PHE | B | 401 | −47.684 | −16.928 | −14.592 | 1.00 | 12.86 | C |
| ATOM | 14340 | CD2 | PHE | B | 401 | −48.622 | −17.932 | −14.574 | 1.00 | 13.30 | C |
| ATOM | 14342 | C | PHE | B | 401 | −51.765 | −20.478 | −12.212 | 1.00 | 14.26 | C |
| ATOM | 14343 | O | PHE | B | 401 | −52.184 | −19.944 | −11.207 | 1.00 | 13.90 | O |
| ATOM | 14345 | N | ALA | B | 402 | −52.377 | −21.480 | −12.828 | 1.00 | 15.09 | N |
| ATOM | 14346 | CA | ALA | B | 402 | −53.641 | −22.054 | −12.364 | 1.00 | 15.76 | C |
| ATOM | 14348 | CB | ALA | B | 402 | −54.264 | −22.899 | −13.454 | 1.00 | 15.57 | C |
| ATOM | 14352 | C | ALA | B | 402 | −53.417 | −22.896 | −11.129 | 1.00 | 16.63 | C |
| ATOM | 14353 | O | ALA | B | 402 | −54.284 | −22.970 | −10.259 | 1.00 | 17.00 | O |
| ATOM | 14355 | N | TYR | B | 403 | −52.253 | −23.544 | −11.060 | 1.00 | 17.50 | N |
| ATOM | 14356 | CA | TYR | B | 403 | −51.885 | −24.317 | −9.894 | 1.00 | 17.86 | C |
| ATOM | 14358 | CB | TYR | B | 403 | −50.486 | −24.911 | −10.038 | 1.00 | 17.73 | C |
| ATOM | 14361 | CG | TYR | B | 403 | −50.006 | −25.576 | −8.764 | 1.00 | 18.24 | C |
| ATOM | 14362 | CD1 | TYR | B | 403 | −50.401 | −26.867 | −8.436 | 1.00 | 18.12 | C |
| ATOM | 14364 | CE1 | TYR | B | 403 | −49.971 | −27.476 | −7.273 | 1.00 | 18.07 | C |
| ATOM | 14366 | CZ | TYR | B | 403 | −49.145 | −26.790 | −6.409 | 1.00 | 18.62 | C |
| ATOM | 14367 | OH | TYR | B | 403 | −48.727 | −27.383 | −5.244 | 1.00 | 17.70 | O |
| ATOM | 14369 | CE2 | TYR | B | 403 | −48.748 | −25.499 | −6.703 | 1.00 | 18.93 | C |
| ATOM | 14371 | CD2 | TYR | B | 403 | −49.177 | −24.901 | −7.876 | 1.00 | 18.88 | C |
| ATOM | 14373 | C | TYR | B | 403 | −51.966 | −23.461 | −8.630 | 1.00 | 18.48 | C |
| ATOM | 14374 | O | TYR | B | 403 | −52.494 | −23.908 | −7.616 | 1.00 | 18.66 | O |
| ATOM | 14376 | N | PHE | B | 404 | −51.468 | −22.232 | −8.682 | 1.00 | 18.91 | N |
| ATOM | 14377 | CA | PHE | B | 404 | −51.400 | −21.430 | −7.468 | 1.00 | 19.53 | C |
| ATOM | 14379 | CB | PHE | B | 404 | −50.395 | −20.325 | −7.644 | 1.00 | 19.35 | C |
| ATOM | 14382 | CG | PHE | B | 404 | −49.014 | −20.808 | −7.799 | 1.00 | 18.79 | C |
| ATOM | 14383 | CD1 | PHE | B | 404 | −48.311 | −21.246 | −6.701 | 1.00 | 17.67 | C |
| ATOM | 14385 | CE1 | PHE | B | 404 | −47.001 | −21.683 | −6.832 | 1.00 | 18.44 | C |
| ATOM | 14387 | CZ | PHE | B | 404 | −46.384 | −21.688 | −8.078 | 1.00 | 18.44 | C |
| ATOM | 14389 | CE2 | PHE | B | 404 | −47.083 | −21.245 | −9.190 | 1.00 | 18.79 | C |
| ATOM | 14391 | CD2 | PHE | B | 404 | −48.396 | −20.805 | −9.047 | 1.00 | 18.90 | C |
| ATOM | 14393 | C | PHE | B | 404 | −52.733 | −20.817 | −7.072 | 1.00 | 20.49 | C |
| ATOM | 14394 | O | PHE | B | 404 | −52.925 | −20.389 | −5.924 | 1.00 | 19.95 | O |
| ATOM | 14396 | N | ALA | B | 405 | −53.636 | −20.756 | −8.043 | 1.00 | 21.92 | N |
| ATOM | 14397 | CA | ALA | B | 405 | −54.918 | −20.106 | −7.872 | 1.00 | 23.09 | C |
| ATOM | 14399 | CB | ALA | B | 405 | −55.333 | −19.426 | −9.167 | 1.00 | 23.15 | C |
| ATOM | 14403 | C | ALA | B | 405 | −55.959 | −21.113 | −7.446 | 1.00 | 24.23 | C |
| ATOM | 14404 | O | ALA | B | 405 | −57.003 | −20.726 | −6.925 | 1.00 | 24.33 | O |
| ATOM | 14406 | N | VAL | B | 406 | −55.657 | −22.399 | −7.662 | 1.00 | 25.80 | N |

TABLE 16-7-continued

Coordinates of P. tremuloides IspS

| ATOM | 14407 | CA | VAL | B | 406 | −56.569 | −23.511 | −7.355 | 1.00 | 26.88 | C |
|---|---|---|---|---|---|---|---|---|---|---|---|
| ATOM | 14409 | CB | VAL | B | 406 | −56.640 | −24.514 | −8.512 | 1.00 | 26.64 | C |
| ATOM | 14411 | CG1 | VAL | B | 406 | −57.132 | −25.854 | −8.012 | 1.00 | 27.24 | C |
| ATOM | 14415 | CG2 | VAL | B | 406 | −57.547 | −23.986 | −9.593 | 1.00 | 26.45 | C |
| ATOM | 14419 | C | VAL | B | 406 | −56.161 | −24.266 | −6.094 | 1.00 | 27.91 | C |
| ATOM | 14420 | O | VAL | B | 406 | −56.932 | −24.345 | −5.155 | 1.00 | 28.28 | O |
| ATOM | 14422 | N | VAL | B | 407 | −54.954 | −24.825 | −6.087 | 1.00 | 29.25 | N |
| ATOM | 14423 | CA | VAL | B | 407 | −54.443 | −25.573 | −4.941 | 1.00 | 30.16 | C |
| ATOM | 14425 | CB | VAL | B | 407 | −53.128 | −26.276 | −5.279 | 1.00 | 30.04 | C |
| ATOM | 14427 | CG1 | VAL | B | 407 | −52.482 | −26.831 | −4.032 | 1.00 | 30.42 | C |
| ATOM | 14431 | CG2 | VAL | B | 407 | −53.378 | −27.376 | −6.280 | 1.00 | 30.14 | C |
| ATOM | 14435 | C | VAL | B | 407 | −54.208 | −24.646 | −3.755 | 1.00 | 31.34 | C |
| ATOM | 14436 | O | VAL | B | 407 | −53.535 | −23.618 | −3.876 | 1.00 | 31.46 | O |
| ATOM | 14438 | N | GLN | B | 408 | −54.753 | −25.032 | −2.604 | 1.00 | 32.63 | N |
| ATOM | 14439 | CA | GLN | B | 408 | −54.727 | −24.191 | −1.417 | 1.00 | 33.51 | C |
| ATOM | 14441 | CB | GLN | B | 408 | −55.891 | −24.572 | −.514 | 1.00 | 33.84 | C |
| ATOM | 14444 | CG | GLN | B | 408 | −56.161 | −23.548 | .577 | 1.00 | 35.49 | C |
| ATOM | 14447 | CD | GLN | B | 408 | −57.623 | −23.161 | .656 | 1.00 | 37.61 | C |
| ATOM | 14448 | OE1 | GLN | B | 408 | −58.519 | −24.006 | .501 | 1.00 | 38.23 | O |
| ATOM | 14449 | NE2 | GLN | B | 408 | −57.876 | −21.874 | .893 | 1.00 | 38.64 | N |
| ATOM | 14452 | C | GLN | B | 408 | −53.399 | −24.274 | −.647 | 1.00 | 33.72 | C |
| ATOM | 14453 | O | GLN | B | 408 | −52.852 | −23.253 | −.204 | 1.00 | 33.52 | O |
| ATOM | 14455 | N | ASN | B | 409 | −52.889 | −25.491 | −.490 | 1.00 | 33.95 | N |
| ATOM | 14456 | CA | ASN | B | 409 | −51.642 | −25.707 | .226 | 1.00 | 34.16 | C |
| ATOM | 14458 | CB | ASN | B | 409 | −51.865 | −26.665 | 1.391 | 1.00 | 34.25 | C |
| ATOM | 14461 | CG | ASN | B | 409 | −52.756 | −26.069 | 2.459 | 1.00 | 34.39 | C |
| ATOM | 14462 | OD1 | ASN | B | 409 | −52.269 | −25.577 | 3.480 | 1.00 | 34.40 | O |
| ATOM | 14463 | ND2 | ASN | B | 409 | −54.070 | −26.089 | 2.222 | 1.00 | 34.12 | N |
| ATOM | 14466 | C | ASN | B | 409 | −50.582 | −26.244 | −.709 | 1.00 | 34.12 | C |
| ATOM | 14467 | O | ASN | B | 409 | −50.578 | −27.422 | −1.046 | 1.00 | 34.41 | O |
| ATOM | 14469 | N | ILE | B | 410 | −49.681 | −25.369 | −1.127 | 1.00 | 34.07 | N |
| ATOM | 14470 | CA | ILE | B | 410 | −48.699 | −25.718 | −2.138 | 1.00 | 34.08 | C |
| ATOM | 14472 | CB | ILE | B | 410 | −48.138 | −24.455 | −2.840 | 1.00 | 34.15 | C |
| ATOM | 14474 | CG1 | ILE | B | 410 | −47.274 | −23.610 | −1.891 | 1.00 | 34.26 | C |
| ATOM | 14477 | CD1 | ILE | B | 410 | −47.216 | −22.139 | −2.249 | 1.00 | 34.10 | C |
| ATOM | 14481 | CG2 | ILE | B | 410 | −49.290 | −23.634 | −3.404 | 1.00 | 34.49 | C |
| ATOM | 14485 | C | ILE | B | 410 | −47.586 | −26.553 | −1.533 | 1.00 | 33.93 | C |
| ATOM | 14486 | O | ILE | B | 410 | −47.181 | −26.317 | −.405 | 1.00 | 33.80 | O |
| ATOM | 14488 | N | LYS | B | 411 | −47.123 | −27.546 | −2.285 | 1.00 | 34.12 | N |
| ATOM | 14489 | CA | LYS | B | 411 | −46.012 | −28.395 | −1.874 | 1.00 | 34.45 | C |
| ATOM | 14491 | CB | LYS | B | 411 | −46.414 | −29.873 | −1.907 | 1.00 | 34.67 | C |
| ATOM | 14494 | CG | LYS | B | 411 | −47.850 | −30.130 | −1.460 | 1.00 | 35.79 | C |
| ATOM | 14497 | CD | LYS | B | 411 | −48.102 | −31.586 | −1.052 | 1.00 | 37.60 | C |
| ATOM | 14500 | CE | LYS | B | 411 | −49.450 | −31.728 | −.309 | 1.00 | 38.80 | C |
| ATOM | 14503 | NZ | LYS | B | 411 | −49.568 | −32.992 | .488 | 1.00 | 39.20 | N |
| ATOM | 14507 | C | LYS | B | 411 | −44.843 | −28.132 | −2.810 | 1.00 | 34.33 | C |
| ATOM | 14508 | O | LYS | B | 411 | −45.038 | −27.956 | −4.006 | 1.00 | 34.14 | O |
| ATOM | 14510 | N | LYS | B | 412 | −43.631 | −28.102 | −2.265 | 1.00 | 34.50 | N |
| ATOM | 14511 | CA | LYS | B | 412 | −42.460 | −27.688 | −3.042 | 1.00 | 34.69 | C |
| ATOM | 14513 | CB | LYS | B | 412 | −41.242 | −27.398 | −2.154 | 1.00 | 35.13 | C |
| ATOM | 14516 | CG | LYS | B | 412 | −41.205 | −25.960 | −1.613 | 1.00 | 36.90 | C |
| ATOM | 14519 | CD | LYS | B | 412 | −40.079 | −25.749 | −.588 | 1.00 | 38.57 | C |
| ATOM | 14522 | CE | LYS | B | 412 | −40.546 | −24.852 | .555 | 1.00 | 39.55 | C |
| ATOM | 14525 | NZ | LYS | B | 412 | −39.491 | −24.644 | 1.587 | 1.00 | 40.83 | N |
| ATOM | 14529 | C | LYS | B | 412 | −42.075 | −28.687 | −4.103 | 1.00 | 34.13 | C |
| ATOM | 14530 | O | LYS | B | 412 | −41.468 | −28.308 | −5.093 | 1.00 | 34.21 | O |
| ATOM | 14532 | N | GLU | B | 413 | −42.408 | −29.958 | −3.910 | 1.00 | 33.54 | N |
| ATOM | 14533 | CA | GLU | B | 413 | −42.095 | −30.949 | −4.933 | 1.00 | 33.19 | C |
| ATOM | 14535 | CB | GLU | B | 413 | −41.886 | −32.335 | −4.330 | 1.00 | 33.44 | C |
| ATOM | 14538 | CG | GLU | B | 413 | −43.127 | −33.037 | −3.807 | 1.00 | 34.37 | C |
| ATOM | 14541 | CD | GLU | B | 413 | −42.834 | −34.490 | −3.499 | 1.00 | 35.56 | C |
| ATOM | 14542 | OE1 | GLU | B | 413 | −42.662 | −35.264 | −4.471 | 1.00 | 35.30 | O |
| ATOM | 14543 | OE2 | GLU | B | 413 | −42.751 | −34.847 | −2.297 | 1.00 | 36.69 | O |
| ATOM | 14544 | C | GLU | B | 413 | −43.157 | −30.965 | −6.029 | 1.00 | 32.47 | C |
| ATOM | 14545 | O | GLU | B | 413 | −42.846 | −31.232 | −7.193 | 1.00 | 32.28 | O |
| ATOM | 14547 | N | GLU | B | 414 | −44.403 | −30.676 | −5.652 | 1.00 | 31.58 | N |
| ATOM | 14548 | CA | GLU | B | 414 | −45.482 | −30.512 | −6.614 | 1.00 | 30.99 | C |
| ATOM | 14550 | CB | GLU | B | 414 | −46.781 | −30.101 | −5.927 | 1.00 | 30.98 | C |
| ATOM | 14553 | CG | GLU | B | 414 | −47.732 | −31.245 | −5.642 | 1.00 | 31.82 | C |
| ATOM | 14556 | CD | GLU | B | 414 | −49.100 | −30.774 | −5.138 | 1.00 | 34.29 | C |
| ATOM | 14557 | OE1 | GLU | B | 414 | −49.258 | −29.581 | −4.777 | 1.00 | 35.53 | O |
| ATOM | 14558 | OE2 | GLU | B | 414 | −50.036 | −31.603 | −5.101 | 1.00 | 36.44 | O |
| ATOM | 14559 | C | GLU | B | 414 | −45.104 | −29.455 | −7.628 | 1.00 | 30.59 | C |
| ATOM | 14560 | O | GLU | B | 414 | −45.169 | −29.687 | −8.828 | 1.00 | 30.37 | O |
| ATOM | 14562 | N | ILE | B | 415 | −44.684 | −28.295 | −7.140 | 1.00 | 30.49 | N |
| ATOM | 14563 | CA | ILE | B | 415 | −44.367 | −27.177 | −8.028 | 1.00 | 30.40 | C |
| ATOM | 14565 | CB | ILE | B | 415 | −44.412 | −25.797 | −7.320 | 1.00 | 30.40 | C |
| ATOM | 14567 | CG1 | ILE | B | 415 | −43.235 | −25.589 | −6.388 | 1.00 | 30.36 | C |

TABLE 16-7-continued

Coordinates of *P. tremuloides* IspS

| ATOM | 14570 | CD1 | ILE | B | 415 | −43.373 | −24.313 | −5.611 | 1.00 | 31.01 | C |
|------|-------|-----|-----|---|-----|---------|---------|--------|------|-------|---|
| ATOM | 14574 | CG2 | ILE | B | 415 | −45.686 | −25.644 | −6.523 | 1.00 | 30.85 | C |
| ATOM | 14578 | C | ILE | B | 415 | −43.037 | −27.347 | −8.730 | 1.00 | 30.12 | C |
| ATOM | 14579 | O | ILE | B | 415 | −42.870 | −26.865 | −9.840 | 1.00 | 30.42 | O |
| ATOM | 14581 | N | GLU | B | 416 | −42.095 | −28.030 | −8.099 | 1.00 | 29.75 | N |
| ATOM | 14582 | CA | GLU | B | 416 | −40.799 | −28.249 | −8.719 | 1.00 | 29.70 | C |
| ATOM | 14584 | CB | GLU | B | 416 | −39.825 | −28.777 | −7.690 | 1.00 | 30.02 | C |
| ATOM | 14587 | CG | GLU | B | 416 | −38.386 | −28.426 | −7.948 | 1.00 | 31.20 | C |
| ATOM | 14590 | CD | GLU | B | 416 | −37.523 | −28.839 | −6.776 | 1.00 | 32.91 | C |
| ATOM | 14591 | OE1 | GLU | B | 416 | −38.008 | −28.723 | −5.632 | 1.00 | 32.37 | O |
| ATOM | 14592 | OE2 | GLU | B | 416 | −36.377 | −29.294 | −6.994 | 1.00 | 35.31 | O |
| ATOM | 14593 | C | GLU | B | 416 | −40.917 | −29.222 | −9.890 | 1.00 | 29.24 | C |
| ATOM | 14594 | O | GLU | B | 416 | −40.121 | −29.177 | −10.835 | 1.00 | 28.86 | O |
| ATOM | 14596 | N | ASN | B | 417 | −41.915 | −30.097 | −9.819 | 1.00 | 28.81 | N |
| ATOM | 14597 | CA | ASN | B | 417 | −42.252 | −30.960 | −10.941 | 1.00 | 28.66 | C |
| ATOM | 14599 | CB | ASN | B | 417 | −43.165 | −32.105 | −10.503 | 1.00 | 28.72 | C |
| ATOM | 14602 | CG | ASN | B | 417 | −42.379 | −33.285 | −9.973 | 1.00 | 29.78 | C |
| ATOM | 14603 | OD1 | ASN | B | 417 | −41.887 | −34.108 | −10.744 | 1.00 | 30.39 | O |
| ATOM | 14604 | ND2 | ASN | B | 417 | −42.223 | −33.358 | −8.653 | 1.00 | 31.45 | N |
| ATOM | 14607 | C | ASN | B | 417 | −42.888 | −30.183 | −12.067 | 1.00 | 28.32 | C |
| ATOM | 14608 | O | ASN | B | 417 | −42.611 | −30.456 | −13.232 | 1.00 | 27.95 | O |
| ATOM | 14610 | N | LEU | B | 418 | −43.740 | −29.217 | −11.713 | 1.00 | 28.23 | N |
| ATOM | 14611 | CA | LEU | B | 418 | −44.349 | −28.313 | −12.697 | 1.00 | 27.92 | C |
| ATOM | 14613 | CB | LEU | B | 418 | −45.298 | −27.320 | −12.023 | 1.00 | 27.48 | C |
| ATOM | 14616 | CG | LEU | B | 418 | −46.636 | −27.896 | −11.553 | 1.00 | 27.02 | C |
| ATOM | 14618 | CD1 | LEU | B | 418 | −47.393 | −26.882 | −10.691 | 1.00 | 26.70 | C |
| ATOM | 14622 | CD2 | LEU | B | 418 | −47.499 | −28.355 | −12.720 | 1.00 | 25.90 | C |
| ATOM | 14626 | C | LEU | B | 418 | −43.275 | −27.567 | −13.491 | 1.00 | 28.20 | C |
| ATOM | 14627 | O | LEU | B | 418 | −43.310 | −27.541 | −14.733 | 1.00 | 27.90 | O |
| ATOM | 14629 | N | GLN | B | 419 | −42.308 | −26.995 | −12.770 | 1.00 | 28.43 | N |
| ATOM | 14630 | CA | GLN | B | 419 | −41.170 | −26.315 | −13.395 | 1.00 | 28.72 | C |
| ATOM | 14632 | CB | GLN | B | 419 | −40.223 | −25.746 | −12.347 | 1.00 | 28.81 | C |
| ATOM | 14635 | CG | GLN | B | 419 | −40.592 | −24.332 | −11.946 | 1.00 | 30.14 | C |
| ATOM | 14638 | CD | GLN | B | 419 | −39.535 | −23.671 | −11.092 | 1.00 | 32.05 | C |
| ATOM | 14639 | OE1 | GLN | B | 419 | −39.246 | −22.477 | −11.257 | 1.00 | 33.88 | O |
| ATOM | 14640 | NE2 | GLN | B | 419 | −38.948 | −24.437 | −10.170 | 1.00 | 31.84 | N |
| ATOM | 14643 | C | GLN | B | 419 | −40.390 | −27.179 | −14.370 | 1.00 | 28.83 | C |
| ATOM | 14644 | O | GLN | B | 419 | −39.922 | −26.668 | −15.386 | 1.00 | 28.72 | O |
| ATOM | 14646 | N | LYS | B | 420 | −40.265 | −28.475 | −14.067 | 1.00 | 29.21 | N |
| ATOM | 14647 | CA | LYS | B | 420 | −39.613 | −29.451 | −14.968 | 1.00 | 29.26 | C |
| ATOM | 14649 | CB | LYS | B | 420 | −38.924 | −30.555 | −14.143 | 1.00 | 29.42 | C |
| ATOM | 14652 | CG | LYS | B | 420 | −37.800 | −30.052 | −13.207 | 1.00 | 30.58 | C |
| ATOM | 14655 | CD | LYS | B | 420 | −37.373 | −31.113 | −12.151 | 1.00 | 32.35 | C |
| ATOM | 14658 | CE | LYS | B | 420 | −36.572 | −30.506 | −10.955 | 1.00 | 33.05 | C |
| ATOM | 14661 | NZ | LYS | B | 420 | −36.520 | −31.368 | −9.702 | 1.00 | 32.62 | N |
| ATOM | 14665 | C | LYS | B | 420 | −40.579 | −30.057 | −16.021 | 1.00 | 28.96 | C |
| ATOM | 14666 | O | LYS | B | 420 | −40.216 | −30.965 | −16.753 | 1.00 | 28.66 | O |
| ATOM | 14668 | N | TYR | B | 421 | −41.804 | −29.543 | −16.088 | 1.00 | 29.01 | N |
| ATOM | 14669 | CA | TYR | B | 421 | −42.777 | −29.893 | −17.134 | 1.00 | 29.16 | C |
| ATOM | 14671 | CB | TYR | B | 421 | −42.209 | −29.602 | −18.534 | 1.00 | 29.48 | C |
| ATOM | 14674 | CG | TYR | B | 421 | −41.968 | −28.127 | −18.773 | 1.00 | 31.04 | C |
| ATOM | 14675 | CD1 | TYR | B | 421 | −43.018 | −27.219 | −18.716 | 1.00 | 32.54 | C |
| ATOM | 14677 | CE1 | TYR | B | 421 | −42.815 | −25.878 | −18.914 | 1.00 | 33.35 | C |
| ATOM | 14679 | CZ | TYR | B | 421 | −41.556 | −25.413 | −19.193 | 1.00 | 34.56 | C |
| ATOM | 14680 | OH | TYR | B | 421 | −41.377 | −24.066 | −19.384 | 1.00 | 37.99 | O |
| ATOM | 14682 | CE2 | TYR | B | 421 | −40.490 | −26.278 | −19.267 | 1.00 | 33.56 | C |
| ATOM | 14684 | CD2 | TYR | B | 421 | −40.702 | −27.638 | −19.051 | 1.00 | 32.75 | C |
| ATOM | 14686 | C | TYR | B | 421 | −43.345 | −31.311 | −17.042 | 1.00 | 28.60 | C |
| ATOM | 14687 | O | TYR | B | 421 | −43.395 | −32.046 | −18.025 | 1.00 | 28.49 | O |
| ATOM | 14689 | N | HIS | B | 422 | −43.808 | −31.662 | −15.846 | 1.00 | 28.18 | N |
| ATOM | 14690 | CA | HIS | B | 422 | −44.507 | −32.919 | −15.594 | 1.00 | 27.66 | C |
| ATOM | 14692 | CB | HIS | B | 422 | −45.082 | −32.914 | −14.180 | 1.00 | 27.73 | C |
| ATOM | 14695 | CG | HIS | B | 422 | −45.500 | −34.264 | −13.685 | 1.00 | 28.14 | C |
| ATOM | 14696 | ND1 | HIS | B | 422 | −44.597 | −35.195 | −13.217 | 1.00 | 29.15 | N |
| ATOM | 14698 | CE1 | HIS | B | 422 | −45.247 | −36.277 | −12.829 | 1.00 | 29.50 | C |
| ATOM | 14700 | NE2 | HIS | B | 422 | −46.539 | −36.078 | −13.022 | 1.00 | 28.69 | N |
| ATOM | 14702 | CD2 | HIS | B | 422 | −46.724 | −34.827 | −13.552 | 1.00 | 27.24 | C |
| ATOM | 14704 | C | HIS | B | 422 | −45.650 | −33.164 | −16.575 | 1.00 | 27.29 | C |
| ATOM | 14705 | O | HIS | B | 422 | −46.463 | −32.269 | −16.853 | 1.00 | 26.86 | O |
| ATOM | 14707 | N | ASP | B | 423 | −45.712 | −34.402 | −17.060 | 1.00 | 26.96 | N |
| ATOM | 14708 | CA | ASP | B | 423 | −46.772 | −34.883 | −17.952 | 1.00 | 26.78 | C |
| ATOM | 14710 | CB | ASP | B | 423 | −46.792 | −36.413 | −17.939 | 1.00 | 27.01 | C |
| ATOM | 14713 | CG | ASP | B | 423 | −45.594 | −37.018 | −18.646 | 1.00 | 28.21 | C |
| ATOM | 14714 | OD1 | ASP | B | 423 | −45.100 | −36.378 | −19.602 | 1.00 | 31.33 | O |
| ATOM | 14715 | OD2 | ASP | B | 423 | −45.153 | −38.130 | −18.262 | 1.00 | 28.39 | O |
| ATOM | 14716 | C | ASP | B | 423 | −48.187 | −34.383 | −17.651 | 1.00 | 26.21 | C |
| ATOM | 14717 | O | ASP | B | 423 | −49.015 | −34.336 | −18.556 | 1.00 | 26.75 | O |
| ATOM | 14719 | N | ILE | B | 424 | −48.463 | −34.042 | −16.391 | 1.00 | 25.11 | N |

TABLE 16-7-continued

Coordinates of *P. tremuloides* IspS

| ATOM | 14720 | CA | ILE | B | 424 | −49.773 | −33.553 | −15.956 | 1.00 | 23.82 | C |
|---|---|---|---|---|---|---|---|---|---|---|---|
| ATOM | 14722 | CB | ILE | B | 424 | −49.798 | −33.310 | −14.439 | 1.00 | 23.67 | C |
| ATOM | 14724 | CG1 | ILE | B | 424 | −51.196 | −32.990 | −13.938 | 1.00 | 22.97 | C |
| ATOM | 14727 | CD1 | ILE | B | 424 | −51.220 | −32.693 | −12.465 | 1.00 | 22.06 | C |
| ATOM | 14731 | CG2 | ILE | B | 424 | −48.859 | −32.171 | −14.065 | 1.00 | 24.35 | C |
| ATOM | 14735 | C | ILE | B | 424 | −50.102 | −32.265 | −16.669 | 1.00 | 23.08 | C |
| ATOM | 14736 | O | ILE | B | 424 | −51.265 | −32.025 | −17.023 | 1.00 | 22.99 | O |
| ATOM | 14738 | N | ILE | B | 425 | −49.082 | −31.436 | −16.886 | 1.00 | 22.22 | N |
| ATOM | 14739 | CA | ILE | B | 425 | −49.282 | −30.199 | −17.633 | 1.00 | 21.61 | C |
| ATOM | 14741 | CB | ILE | B | 425 | −48.796 | −28.959 | −16.848 | 1.00 | 21.18 | C |
| ATOM | 14743 | CG1 | ILE | B | 425 | −47.279 | −28.853 | −16.804 | 1.00 | 19.47 | C |
| ATOM | 14746 | CD1 | ILE | B | 425 | −46.850 | −27.581 | −16.140 | 1.00 | 18.00 | C |
| ATOM | 14750 | CG2 | ILE | B | 425 | −49.357 | −28.977 | −15.428 | 1.00 | 20.75 | C |
| ATOM | 14754 | C | ILE | B | 425 | −48.665 | −30.255 | −19.033 | 1.00 | 21.73 | C |
| ATOM | 14755 | O | ILE | B | 425 | −49.100 | −29.523 | −19.912 | 1.00 | 21.75 | O |
| ATOM | 14757 | N | SER | B | 426 | −47.686 | −31.134 | −19.258 | 1.00 | 21.74 | N |
| ATOM | 14758 | CA | SER | B | 426 | −47.016 | −31.174 | −20.560 | 1.00 | 21.53 | C |
| ATOM | 14760 | CB | SER | B | 426 | −45.639 | −31.876 | −20.516 | 1.00 | 21.66 | C |
| ATOM | 14763 | OG | SER | B | 426 | −45.724 | −33.281 | −20.405 | 1.00 | 22.19 | O |
| ATOM | 14765 | C | SER | B | 426 | −47.922 | −31.798 | −21.582 | 1.00 | 21.19 | C |
| ATOM | 14766 | O | SER | B | 426 | −47.950 | −31.358 | −22.721 | 1.00 | 21.37 | O |
| ATOM | 14768 | N | ARG | B | 427 | −48.692 | −32.800 | −21.177 | 1.00 | 20.91 | N |
| ATOM | 14769 | CA | ARG | B | 427 | −49.532 | −33.504 | −22.143 | 1.00 | 20.78 | C |
| ATOM | 14771 | CB | ARG | B | 427 | −50.038 | −34.840 | −21.616 | 1.00 | 20.94 | C |
| ATOM | 14774 | CG | ARG | B | 427 | −49.006 | −35.887 | −21.874 | 1.00 | 22.76 | C |
| ATOM | 14777 | CD | ARG | B | 427 | −49.158 | −37.101 | −21.025 | 1.00 | 26.75 | C |
| ATOM | 14780 | NE | ARG | B | 427 | −47.960 | −37.927 | −21.185 | 1.00 | 29.36 | N |
| ATOM | 14782 | CZ | ARG | B | 427 | −47.574 | −38.887 | −20.352 | 1.00 | 30.25 | C |
| ATOM | 14783 | NH1 | ARG | B | 427 | −48.293 | −39.179 | −19.266 | 1.00 | 30.27 | N |
| ATOM | 14786 | NH2 | ARG | B | 427 | −46.447 | −39.547 | −20.611 | 1.00 | 31.25 | N |
| ATOM | 14789 | C | ARG | B | 427 | −50.646 | −32.650 | −22.668 | 1.00 | 20.07 | C |
| ATOM | 14790 | O | ARG | B | 427 | −50.724 | −32.466 | −23.866 | 1.00 | 20.13 | O |
| ATOM | 14792 | N | PRO | B | 428 | −51.482 | −32.091 | −21.786 | 1.00 | 19.38 | N |
| ATOM | 14793 | CA | PRO | B | 428 | −52.533 | −31.202 | −22.264 | 1.00 | 19.05 | C |
| ATOM | 14795 | CB | PRO | B | 428 | −53.046 | −30.547 | −20.990 | 1.00 | 19.13 | C |
| ATOM | 14798 | CG | PRO | B | 428 | −52.696 | −31.476 | −19.918 | 1.00 | 19.55 | C |
| ATOM | 14801 | CD | PRO | B | 428 | −51.443 | −32.161 | −20.319 | 1.00 | 19.20 | C |
| ATOM | 14804 | C | PRO | B | 428 | −52.016 | −30.135 | −23.227 | 1.00 | 18.84 | C |
| ATOM | 14805 | O | PRO | B | 428 | −52.688 | −29.802 | −24.205 | 1.00 | 18.73 | O |
| ATOM | 14806 | N | SER | B | 429 | −50.828 | −29.608 | −22.964 | 1.00 | 18.57 | N |
| ATOM | 14807 | CA | SER | B | 429 | −50.208 | −28.679 | −23.899 | 1.00 | 18.64 | C |
| ATOM | 14809 | CB | SER | B | 429 | −48.960 | −28.086 | −23.291 | 1.00 | 18.46 | C |
| ATOM | 14812 | OG | SER | B | 429 | −49.141 | −27.980 | −21.911 | 1.00 | 19.08 | O |
| ATOM | 14814 | C | SER | B | 429 | −49.877 | −29.315 | −25.260 | 1.00 | 18.52 | C |
| ATOM | 14815 | O | SER | B | 429 | −49.886 | −28.633 | −26.276 | 1.00 | 19.02 | O |
| ATOM | 14817 | N | HIS | B | 430 | −49.579 | −30.606 | −25.297 | 1.00 | 18.29 | N |
| ATOM | 14818 | CA | HIS | B | 430 | −49.457 | −31.273 | −26.583 | 1.00 | 18.25 | C |
| ATOM | 14820 | CB | HIS | B | 430 | −49.085 | −32.765 | −26.467 | 1.00 | 18.40 | C |
| ATOM | 14823 | CG | HIS | B | 430 | −47.753 | −33.024 | −25.806 | 1.00 | 19.41 | C |
| ATOM | 14824 | ND1 | HIS | B | 430 | −46.776 | −32.055 | −25.657 | 1.00 | 19.55 | N |
| ATOM | 14826 | CE1 | HIS | B | 430 | −45.729 | −32.576 | −25.043 | 1.00 | 17.77 | C |
| ATOM | 14828 | NE2 | HIS | B | 430 | −45.981 | −33.849 | −24.800 | 1.00 | 18.52 | N |
| ATOM | 14830 | CD2 | HIS | B | 430 | −47.232 | −34.160 | −25.277 | 1.00 | 19.19 | C |
| ATOM | 14832 | C | HIS | B | 430 | −50.789 | −31.105 | −27.306 | 1.00 | 17.93 | C |
| ATOM | 14833 | O | HIS | B | 430 | −50.816 | −30.599 | −28.417 | 1.00 | 18.54 | O |
| ATOM | 14835 | N | ILE | B | 431 | −51.897 | −31.479 | −26.665 | 1.00 | 17.34 | N |
| ATOM | 14836 | CA | ILE | B | 431 | −53.217 | −31.372 | −27.301 | 1.00 | 16.58 | C |
| ATOM | 14838 | CB | ILE | B | 431 | −54.400 | −31.738 | −26.375 | 1.00 | 16.53 | C |
| ATOM | 14840 | CG1 | ILE | B | 431 | −54.225 | −33.123 | −25.728 | 1.00 | 16.06 | C |
| ATOM | 14843 | CD1 | ILE | B | 431 | −54.069 | −34.212 | −26.698 | 1.00 | 16.05 | C |
| ATOM | 14847 | CG2 | ILE | B | 431 | −55.701 | −31.666 | −27.149 | 1.00 | 15.49 | C |
| ATOM | 14851 | C | ILE | B | 431 | −53.431 | −29.949 | −27.748 | 1.00 | 16.35 | C |
| ATOM | 14852 | O | ILE | B | 431 | −53.856 | −29.712 | −28.860 | 1.00 | 16.74 | O |
| ATOM | 14854 | N | PHE | B | 432 | −53.110 | −29.003 | −26.881 | 1.00 | 16.15 | N |
| ATOM | 14855 | CA | PHE | B | 432 | −53.353 | −27.577 | −27.145 | 1.00 | 16.19 | C |
| ATOM | 14857 | CB | PHE | B | 432 | −52.811 | −26.776 | −25.956 | 1.00 | 16.36 | C |
| ATOM | 14860 | CG | PHE | B | 432 | −53.007 | −25.295 | −26.043 | 1.00 | 16.54 | C |
| ATOM | 14861 | CD1 | PHE | B | 432 | −53.869 | −24.708 | −26.946 | 1.00 | 16.55 | C |
| ATOM | 14863 | CE1 | PHE | B | 432 | −54.007 | −23.334 | −26.974 | 1.00 | 17.89 | C |
| ATOM | 14865 | CZ | PHE | B | 432 | −53.305 | −22.538 | −26.080 | 1.00 | 17.96 | C |
| ATOM | 14867 | CE2 | PHE | B | 432 | −52.461 | −23.114 | −25.169 | 1.00 | 17.30 | C |
| ATOM | 14869 | CD2 | PHE | B | 432 | −52.323 | −24.482 | −25.151 | 1.00 | 17.54 | C |
| ATOM | 14871 | C | PHE | B | 432 | −52.726 | −27.104 | −28.452 | 1.00 | 15.93 | C |
| ATOM | 14872 | O | PHE | B | 432 | −53.398 | −26.525 | −29.303 | 1.00 | 15.63 | O |
| ATOM | 14874 | N | ARG | B | 433 | −51.438 | −27.387 | −28.594 | 1.00 | 15.79 | N |
| ATOM | 14875 | CA | ARG | B | 433 | −50.674 | −27.044 | −29.778 | 1.00 | 15.74 | C |
| ATOM | 14877 | CB | ARG | B | 433 | −49.196 | −27.279 | −29.470 | 1.00 | 15.68 | C |
| ATOM | 14880 | CG | ARG | B | 433 | −48.259 | −27.218 | −30.665 | 1.00 | 16.39 | C |

TABLE 16-7-continued

Coordinates of *P. tremuloides* IspS

| ATOM | 14883 | CD | ARG | B | 433 | −48.348 | −25.919 | −31.388 | 1.00 | 16.27 | C |
| ATOM | 14886 | NE | ARG | B | 433 | −47.969 | −24.850 | −30.492 | 1.00 | 17.34 | N |
| ATOM | 14888 | CZ | ARG | B | 433 | −48.210 | −23.565 | −30.703 | 1.00 | 17.89 | C |
| ATOM | 14889 | NH1 | ARG | B | 433 | −48.834 | −23.142 | −31.803 | 1.00 | 16.79 | N |
| ATOM | 14892 | NH2 | ARG | B | 433 | −47.805 | −22.701 | −29.792 | 1.00 | 18.53 | N |
| ATOM | 14895 | C | ARG | B | 433 | −51.114 | −27.852 | −31.011 | 1.00 | 15.85 | C |
| ATOM | 14896 | O | ARG | B | 433 | −51.197 | −27.328 | −32.120 | 1.00 | 15.40 | O |
| ATOM | 14898 | N | LEU | B | 434 | −51.381 | −29.134 | −30.813 | 1.00 | 16.18 | N |
| ATOM | 14899 | CA | LEU | B | 434 | −51.794 | −29.986 | −31.902 | 1.00 | 16.58 | C |
| ATOM | 14901 | CB | LEU | B | 434 | −51.802 | −31.453 | −31.468 | 1.00 | 16.79 | C |
| ATOM | 14904 | CG | LEU | B | 434 | −50.408 | −32.055 | −31.232 | 1.00 | 17.49 | C |
| ATOM | 14906 | CD1 | LEU | B | 434 | −50.486 | −33.548 | −30.864 | 1.00 | 16.63 | C |
| ATOM | 14910 | CD2 | LEU | B | 434 | −49.511 | −31.836 | −32.467 | 1.00 | 18.00 | C |
| ATOM | 14914 | C | LEU | B | 434 | −53.158 | −29.559 | −32.423 | 1.00 | 17.07 | C |
| ATOM | 14915 | O | LEU | B | 434 | −53.333 | −29.442 | −33.633 | 1.00 | 17.44 | O |
| ATOM | 14917 | N | CYS | B | 435 | −54.118 | −29.308 | −31.532 | 1.00 | 17.23 | N |
| ATOM | 14918 | CA | CYS | B | 435 | −55.419 | −28.778 | −31.947 | 1.00 | 17.44 | C |
| ATOM | 14920 | CB | CYS | B | 435 | −56.301 | −28.529 | −30.746 | 1.00 | 17.38 | C |
| ATOM | 14923 | SG | CYS | B | 435 | −56.825 | −29.993 | −29.971 | 1.00 | 17.90 | S |
| ATOM | 14925 | C | CYS | B | 435 | −55.295 | −27.460 | −32.696 | 1.00 | 17.78 | C |
| ATOM | 14926 | O | CYS | B | 435 | −55.978 | −27.232 | −33.701 | 1.00 | 17.44 | O |
| ATOM | 14928 | N | ASN | B | 436 | −54.442 | −26.585 | −32.178 | 1.00 | 18.31 | N |
| ATOM | 14929 | CA | ASN | B | 436 | −54.248 | −25.267 | −32.769 | 1.00 | 19.14 | C |
| ATOM | 14931 | CB | ASN | B | 436 | −53.392 | −24.394 | −31.844 | 1.00 | 19.31 | C |
| ATOM | 14934 | CG | ASN | B | 436 | −52.984 | −23.068 | −32.478 | 1.00 | 20.07 | C |
| ATOM | 14935 | OD1 | ASN | B | 436 | −53.456 | −22.686 | −33.555 | 1.00 | 22.72 | O |
| ATOM | 14936 | ND2 | ASN | B | 436 | −52.099 | −22.356 | −31.800 | 1.00 | 20.90 | N |
| ATOM | 14939 | C | ASN | B | 436 | −53.615 | −25.345 | −34.157 | 1.00 | 19.51 | C |
| ATOM | 14940 | O | ASN | B | 436 | −54.173 | −24.840 | −35.131 | 1.00 | 19.79 | O |
| ATOM | 14942 | N | ASP | B | 437 | −52.446 | −25.965 | −34.245 | 1.00 | 19.85 | N |
| ATOM | 14943 | CA | ASP | B | 437 | −51.754 | −26.058 | −35.517 | 1.00 | 20.01 | C |
| ATOM | 14945 | CB | ASP | B | 437 | −50.340 | −26.638 | −35.331 | 1.00 | 20.00 | C |
| ATOM | 14948 | CG | ASP | B | 437 | −49.397 | −25.675 | −34.557 | 1.00 | 21.23 | C |
| ATOM | 14949 | OD1 | ASP | B | 437 | −49.902 | −24.749 | −33.877 | 1.00 | 22.90 | O |
| ATOM | 14950 | OD2 | ASP | B | 437 | −48.149 | −25.821 | −34.632 | 1.00 | 22.18 | O |
| ATOM | 14951 | C | ASP | B | 437 | −52.629 | −26.838 | −36.512 | 1.00 | 20.00 | C |
| ATOM | 14952 | O | ASP | B | 437 | −52.678 | −26.491 | −37.695 | 1.00 | 20.02 | O |
| ATOM | 14954 | N | LEU | B | 438 | −53.372 | −27.836 | −36.021 | 1.00 | 20.02 | N |
| ATOM | 14955 | CA | LEU | B | 438 | −54.352 | −28.558 | −36.858 | 1.00 | 20.18 | C |
| ATOM | 14957 | CB | LEU | B | 438 | −55.144 | −29.593 | −36.049 | 1.00 | 19.88 | C |
| ATOM | 14960 | CG | LEU | B | 438 | −54.699 | −31.050 | −36.142 | 1.00 | 18.97 | C |
| ATOM | 14962 | CD1 | LEU | B | 438 | −55.537 | −31.869 | −35.200 | 1.00 | 18.86 | C |
| ATOM | 14966 | CD2 | LEU | B | 438 | −54.818 | −31.585 | −37.550 | 1.00 | 16.23 | C |
| ATOM | 14970 | C | LEU | B | 438 | −55.358 | −27.644 | −37.564 | 1.00 | 20.60 | C |
| ATOM | 14971 | O | LEU | B | 438 | −55.717 | −27.889 | −38.712 | 1.00 | 20.30 | O |
| ATOM | 14973 | N | ALA | B | 439 | −55.825 | −26.620 | −36.853 | 1.00 | 21.39 | N |
| ATOM | 14974 | CA | ALA | B | 439 | −56.802 | −25.654 | −37.377 | 1.00 | 21.96 | C |
| ATOM | 14976 | CB | ALA | B | 439 | −57.306 | −24.741 | −36.242 | 1.00 | 21.77 | C |
| ATOM | 14980 | C | ALA | B | 439 | −56.214 | −24.805 | −38.494 | 1.00 | 22.47 | C |
| ATOM | 14981 | O | ALA | B | 439 | −56.850 | −24.559 | −39.517 | 1.00 | 22.13 | O |
| ATOM | 14983 | N | SER | B | 440 | −54.983 | −24.370 | −38.282 | 1.00 | 23.40 | N |
| ATOM | 14984 | CA | SER | B | 440 | −54.337 | −23.428 | −39.169 | 1.00 | 24.40 | C |
| ATOM | 14986 | CB | SER | B | 440 | −53.423 | −22.529 | −38.342 | 1.00 | 24.44 | C |
| ATOM | 14989 | OG | SER | B | 440 | −52.994 | −23.206 | −37.166 | 1.00 | 25.19 | O |
| ATOM | 14991 | C | SER | B | 440 | −53.544 | −24.103 | −40.289 | 1.00 | 25.15 | C |
| ATOM | 14992 | O | SER | B | 440 | −53.093 | −23.424 | −41.210 | 1.00 | 25.24 | O |
| ATOM | 14994 | N | ALA | B | 441 | −53.392 | −25.428 | −40.222 | 1.00 | 25.99 | N |
| ATOM | 14995 | CA | ALA | B | 441 | −52.488 | −26.160 | −41.119 | 1.00 | 26.53 | C |
| ATOM | 14997 | CB | ALA | B | 441 | −52.532 | −27.655 | −40.830 | 1.00 | 26.26 | C |
| ATOM | 15001 | C | ALA | B | 441 | −52.726 | −25.903 | −42.608 | 1.00 | 27.31 | C |
| ATOM | 15002 | O | ALA | B | 441 | −51.811 | −25.489 | −43.310 | 1.00 | 27.26 | O |
| ATOM | 15004 | N | SER | B | 442 | −53.940 | −26.134 | −43.098 | 1.00 | 28.45 | N |
| ATOM | 15005 | CA | SER | B | 442 | −54.138 | −26.138 | −44.545 | 1.00 | 29.47 | C |
| ATOM | 15007 | CB | SER | B | 442 | −55.477 | −26.769 | −44.936 | 1.00 | 29.40 | C |
| ATOM | 15010 | OG | SER | B | 442 | −56.454 | −25.784 | −45.181 | 1.00 | 30.36 | O |
| ATOM | 15012 | C | SER | B | 442 | −53.966 | −24.731 | −45.125 | 1.00 | 30.22 | C |
| ATOM | 15013 | O | SER | B | 442 | −53.304 | −24.562 | −46.139 | 1.00 | 30.26 | O |
| ATOM | 15015 | N | ALA | B | 443 | −54.537 | −23.729 | −44.467 | 1.00 | 31.38 | N |
| ATOM | 15016 | CA | ALA | B | 443 | −54.308 | −22.333 | −44.835 | 1.00 | 32.22 | C |
| ATOM | 15018 | CB | ALA | B | 443 | −55.057 | −21.410 | −43.893 | 1.00 | 32.28 | C |
| ATOM | 15022 | C | ALA | B | 443 | −52.820 | −21.992 | −44.818 | 1.00 | 33.12 | C |
| ATOM | 15023 | O | ALA | B | 443 | −52.302 | −21.419 | −45.766 | 1.00 | 33.24 | O |
| ATOM | 15025 | N | GLU | B | 444 | −52.136 | −22.351 | −43.736 | 1.00 | 34.43 | N |
| ATOM | 15026 | CA | GLU | B | 444 | −50.711 | −22.033 | −43.582 | 1.00 | 35.35 | C |
| ATOM | 15028 | CB | GLU | B | 444 | −50.237 | −22.271 | −42.134 | 1.00 | 35.46 | C |
| ATOM | 15031 | CG | GLU | B | 444 | −50.757 | −21.227 | −41.126 | 1.00 | 36.42 | C |
| ATOM | 15034 | CD | GLU | B | 444 | −50.178 | −21.376 | −39.708 | 1.00 | 37.82 | C |
| ATOM | 15035 | OE1 | GLU | B | 444 | −49.965 | −22.506 | −39.224 | 1.00 | 37.92 | O |

TABLE 16-7-continued

| | | | | | | | | | | |
|---|---|---|---|---|---|---|---|---|---|---|
| ATOM | 15036 | OE2 | GLU | B | 444 | −49.955 | −20.344 | −39.049 | 1.00 | 40.09 O |
| ATOM | 15037 | C | GLU | B | 444 | −49.840 | −22.794 | −44.594 | 1.00 | 35.87 C |
| ATOM | 15038 | O | GLU | B | 444 | −48.870 | −22.239 | −45.107 | 1.00 | 35.85 O |
| ATOM | 15040 | N | ILE | B | 445 | −50.193 | −24.048 | −44.883 | 1.00 | 36.63 N |
| ATOM | 15041 | CA | ILE | B | 445 | −49.517 | −24.837 | −45.928 | 1.00 | 37.21 C |
| ATOM | 15043 | CB | ILE | B | 445 | −49.854 | −26.366 | −45.832 | 1.00 | 37.15 C |
| ATOM | 15045 | CG1 | ILE | B | 445 | −49.181 | −26.991 | −44.609 | 1.00 | 36.85 C |
| ATOM | 15048 | CD1 | ILE | B | 445 | −49.867 | −28.244 | −44.102 | 1.00 | 36.62 C |
| ATOM | 15052 | CG2 | ILE | B | 445 | −49.416 | −27.120 | −47.093 | 1.00 | 36.66 C |
| ATOM | 15056 | C | ILE | B | 445 | −49.933 | −24.289 | −47.290 | 1.00 | 37.88 C |
| ATOM | 15057 | O | ILE | B | 445 | −50.926 | −24.733 | −47.874 | 1.00 | 38.20 O |
| ATOM | 15059 | N | ALA | B | 446 | −49.175 | −23.314 | −47.785 | 1.00 | 38.56 N |
| ATOM | 15060 | CA | ALA | B | 446 | −49.544 | −22.575 | −48.992 | 1.00 | 39.03 C |
| ATOM | 15062 | CB | ALA | B | 446 | −49.833 | −23.522 | −50.169 | 1.00 | 39.19 C |
| ATOM | 15066 | C | ALA | B | 446 | −50.768 | −21.740 | −48.685 | 1.00 | 39.42 C |
| ATOM | 15067 | O | ALA | B | 446 | −51.866 | −22.288 | −48.742 | 1.00 | 39.26 O |
| ATOM | 15069 | N | ARG | B | 447 | −50.650 | −20.443 | −48.361 | 1.00 | 40.06 N |
| ATOM | 15070 | CA | ARG | B | 447 | −49.426 | −19.589 | −48.361 | 1.00 | 40.54 C |
| ATOM | 15072 | CB | ARG | B | 447 | −49.276 | −18.901 | −46.986 | 1.00 | 40.70 C |
| ATOM | 15075 | CG | ARG | B | 447 | −50.121 | −17.634 | −46.836 | 1.00 | 41.82 C |
| ATOM | 15078 | CD | ARG | B | 447 | −50.292 | −17.234 | −45.377 | 1.00 | 42.99 C |
| ATOM | 15081 | NE | ARG | B | 447 | −51.628 | −17.546 | −44.864 | 1.00 | 44.22 N |
| ATOM | 15083 | CZ | ARG | B | 447 | −51.924 | −17.766 | −43.580 | 1.00 | 46.00 C |
| ATOM | 15084 | NH1 | ARG | B | 447 | −50.977 | −17.730 | −42.633 | 1.00 | 46.34 N |
| ATOM | 15087 | NH2 | ARG | B | 447 | −53.184 | −18.039 | −43.236 | 1.00 | 46.39 N |
| ATOM | 15090 | C | ARG | B | 447 | −48.095 | −20.208 | −48.837 | 1.00 | 40.35 C |
| ATOM | 15091 | O | ARG | B | 447 | −47.897 | −20.403 | −50.038 | 1.00 | 40.95 O |
| ATOM | 15093 | N | GLY | B | 448 | −47.170 | −20.442 | −47.918 | 1.00 | 39.87 N |
| ATOM | 15094 | CA | GLY | B | 448 | −46.020 | −21.306 | −48.162 | 1.00 | 39.52 C |
| ATOM | 15097 | C | GLY | B | 448 | −45.258 | −21.517 | −46.865 | 1.00 | 39.26 C |
| ATOM | 15098 | O | GLY | B | 448 | −44.071 | −21.842 | −46.885 | 1.00 | 39.15 O |
| ATOM | 15100 | N | GLU | B | 449 | −45.966 | −21.344 | −45.742 | 1.00 | 38.85 N |
| ATOM | 15101 | CA | GLU | B | 449 | −45.365 | −21.215 | −44.426 | 1.00 | 38.45 C |
| ATOM | 15103 | CB | GLU | B | 449 | −46.288 | −20.472 | −43.444 | 1.00 | 38.76 C |
| ATOM | 15106 | CG | GLU | B | 449 | −46.346 | −18.943 | −43.636 | 1.00 | 40.34 C |
| ATOM | 15109 | CD | GLU | B | 449 | −47.486 | −18.257 | −42.839 | 1.00 | 42.09 C |
| ATOM | 15110 | OE1 | GLU | B | 449 | −47.897 | −18.787 | −41.780 | 1.00 | 43.23 O |
| ATOM | 15111 | OE2 | GLU | B | 449 | −47.972 | −17.184 | −43.274 | 1.00 | 42.13 O |
| ATOM | 15112 | C | GLU | B | 449 | −45.073 | −22.600 | −43.906 | 1.00 | 37.54 C |
| ATOM | 15113 | O | GLU | B | 449 | −45.810 | −23.553 | −44.167 | 1.00 | 37.34 O |
| ATOM | 15115 | N | THR | B | 450 | −43.986 | −22.688 | −43.159 | 1.00 | 36.47 N |
| ATOM | 15116 | CA | THR | B | 450 | −43.459 | −23.950 | −42.702 | 1.00 | 35.65 C |
| ATOM | 15118 | CB | THR | B | 450 | −42.017 | −24.105 | −43.245 | 1.00 | 35.81 C |
| ATOM | 15120 | OG1 | THR | B | 450 | −41.593 | −25.465 | −43.109 | 1.00 | 37.67 O |
| ATOM | 15122 | CG2 | THR | B | 450 | −41.029 | −23.152 | −42.538 | 1.00 | 36.21 C |
| ATOM | 15126 | C | THR | B | 450 | −43.528 | −24.084 | −41.166 | 1.00 | 34.22 C |
| ATOM | 15127 | O | THR | B | 450 | −43.165 | −25.127 | −40.619 | 1.00 | 34.00 O |
| ATOM | 15129 | N | ALA | B | 451 | −44.024 | −23.034 | −40.495 | 1.00 | 32.69 N |
| ATOM | 15130 | CA | ALA | B | 451 | −44.144 | −22.974 | −39.026 | 1.00 | 31.28 C |
| ATOM | 15132 | CB | ALA | B | 451 | −43.952 | −21.546 | −38.545 | 1.00 | 31.06 C |
| ATOM | 15136 | C | ALA | B | 451 | −45.495 | −23.500 | −38.547 | 1.00 | 29.97 C |
| ATOM | 15137 | O | ALA | B | 451 | −46.337 | −22.735 | −38.082 | 1.00 | 30.08 O |
| ATOM | 15139 | N | ASN | B | 452 | −45.690 | −24.809 | −38.656 | 1.00 | 28.19 N |
| ATOM | 15140 | CA | ASN | B | 452 | −46.935 | −25.444 | −38.272 | 1.00 | 26.73 C |
| ATOM | 15142 | CB | ASN | B | 452 | −47.929 | −25.339 | −39.422 | 1.00 | 26.45 C |
| ATOM | 15145 | CG | ASN | B | 452 | −49.311 | −25.832 | −39.057 | 1.00 | 25.38 C |
| ATOM | 15146 | OD1 | ASN | B | 452 | −49.608 | −27.004 | −39.195 | 1.00 | 24.57 O |
| ATOM | 15147 | ND2 | ASN | B | 452 | −50.171 | −24.928 | −38.618 | 1.00 | 24.44 N |
| ATOM | 15150 | C | ASN | B | 452 | −46.631 | −26.889 | −37.952 | 1.00 | 26.05 C |
| ATOM | 15151 | O | ASN | B | 452 | −45.930 | −27.544 | −38.695 | 1.00 | 26.21 O |
| ATOM | 15153 | N | SER | B | 453 | −47.131 | −27.388 | −36.834 | 1.00 | 25.30 N |
| ATOM | 15154 | CA | SER | B | 453 | −46.843 | −28.760 | −36.432 | 1.00 | 24.72 C |
| ATOM | 15156 | CB | SER | B | 453 | −47.638 | −29.139 | −35.174 | 1.00 | 24.81 C |
| ATOM | 15159 | OG | SER | B | 453 | −47.143 | −28.455 | −34.031 | 1.00 | 24.36 O |
| ATOM | 15161 | C | SER | B | 453 | −47.111 | −29.770 | −37.543 | 1.00 | 24.12 C |
| ATOM | 15162 | O | SER | B | 453 | −46.325 | −30.679 | −37.743 | 1.00 | 24.33 O |
| ATOM | 15164 | N | VAL | B | 454 | −48.202 | −29.606 | −38.272 | 1.00 | 23.57 N |
| ATOM | 15165 | CA | VAL | B | 454 | −48.546 | −30.541 | −39.328 | 1.00 | 23.27 C |
| ATOM | 15167 | CB | VAL | B | 454 | −50.001 | −30.361 | −39.795 | 1.00 | 23.06 C |
| ATOM | 15169 | CG1 | VAL | B | 454 | −50.363 | −31.385 | −40.829 | 1.00 | 22.41 C |
| ATOM | 15173 | CG2 | VAL | B | 454 | −50.946 | −30.489 | −38.622 | 1.00 | 22.80 C |
| ATOM | 15177 | C | VAL | B | 454 | −47.581 | −30.473 | −40.521 | 1.00 | 23.83 C |
| ATOM | 15178 | O | VAL | B | 454 | −47.370 | −31.493 | −41.175 | 1.00 | 24.48 O |
| ATOM | 15180 | N | SER | B | 455 | −46.981 | −29.309 | −40.803 | 1.00 | 23.99 N |
| ATOM | 15181 | CA | SER | B | 455 | −45.978 | −29.198 | −41.881 | 1.00 | 24.22 C |
| ATOM | 15183 | CB | SER | B | 455 | −45.577 | −27.767 | −42.111 | 1.00 | 24.02 C |
| ATOM | 15186 | OG | SER | B | 455 | −46.655 | −27.098 | −42.689 | 1.00 | 25.57 O |
| ATOM | 15188 | C | SER | B | 455 | −44.708 | −29.949 | −41.582 | 1.00 | 24.65 C |

TABLE 16-7-continued

Coordinates of *P. tremuloides* IspS

| ATOM | 15189 | O | SER | B | 455 | −44.211 | −30.700 | −42.417 | 1.00 | 25.23 | O |
| ATOM | 15191 | N | CYS | B | 456 | −44.151 | −29.700 | −40.405 | 1.00 | 24.82 | N |
| ATOM | 15192 | CA | CYS | B | 456 | −43.024 | −30.462 | −39.935 | 1.00 | 24.81 | C |
| ATOM | 15194 | CB | CYS | B | 456 | −42.765 | −30.170 | −38.470 | 1.00 | 24.92 | C |
| ATOM | 15197 | SG | CYS | B | 456 | −42.139 | −28.541 | −38.190 | 1.00 | 25.18 | S |
| ATOM | 15199 | C | CYS | B | 456 | −43.304 | −31.938 | −40.124 | 1.00 | 24.84 | C |
| ATOM | 15200 | O | CYS | B | 456 | −42.507 | −32.634 | −40.728 | 1.00 | 25.34 | O |
| ATOM | 15202 | N | TYR | B | 457 | −44.442 | −32.421 | −39.644 | 1.00 | 24.75 | N |
| ATOM | 15203 | CA | TYR | B | 457 | −44.735 | −33.838 | −39.778 | 1.00 | 24.85 | C |
| ATOM | 15205 | CB | TYR | B | 457 | −46.069 | −34.197 | −39.142 | 1.00 | 24.64 | C |
| ATOM | 15208 | CG | TYR | B | 457 | −46.057 | −35.537 | −38.451 | 1.00 | 24.00 | C |
| ATOM | 15209 | CD1 | TYR | B | 457 | −45.846 | −35.635 | −37.083 | 1.00 | 24.19 | C |
| ATOM | 15211 | CE1 | TYR | B | 457 | −45.848 | −36.873 | −36.436 | 1.00 | 23.72 | C |
| ATOM | 15213 | CZ | TYR | B | 457 | −46.059 | −38.025 | −37.170 | 1.00 | 23.27 | C |
| ATOM | 15214 | OH | TYR | B | 457 | −46.063 | −39.244 | −36.554 | 1.00 | 22.94 | O |
| ATOM | 15216 | CE2 | TYR | B | 457 | −46.268 | −37.961 | −38.528 | 1.00 | 23.68 | C |
| ATOM | 15218 | CD2 | TYR | B | 457 | −46.265 | −36.711 | −39.163 | 1.00 | 24.16 | C |
| ATOM | 15220 | C | TYR | B | 457 | −44.676 | −34.267 | −41.251 | 1.00 | 25.30 | C |
| ATOM | 15221 | O | TYR | B | 457 | −43.965 | −35.208 | −41.584 | 1.00 | 24.94 | O |
| ATOM | 15223 | N | MET | B | 458 | −45.388 | −33.569 | −42.134 | 1.00 | 26.02 | N |
| ATOM | 15224 | CA | MET | B | 458 | −45.207 | −33.775 | −43.585 | 1.00 | 26.76 | C |
| ATOM | 15226 | CB | MET | B | 458 | −45.913 | −32.685 | −44.407 | 1.00 | 26.84 | C |
| ATOM | 15229 | CG | MET | B | 458 | −47.419 | −32.720 | −44.429 | 1.00 | 27.32 | C |
| ATOM | 15232 | SD | MET | B | 458 | −48.092 | −31.238 | −45.229 | 1.00 | 27.76 | S |
| ATOM | 15233 | CE | MET | B | 458 | −47.283 | −31.311 | −46.830 | 1.00 | 26.95 | C |
| ATOM | 15237 | C | MET | B | 458 | −43.723 | −33.759 | −43.996 | 1.00 | 27.06 | C |
| ATOM | 15238 | O | MET | B | 458 | −43.192 | −34.746 | −44.485 | 1.00 | 26.94 | O |
| ATOM | 15240 | N | ARG | B | 459 | −43.069 | −32.624 | −43.800 | 1.00 | 27.58 | N |
| ATOM | 15241 | CA | ARG | B | 459 | −41.720 | −32.419 | −44.289 | 1.00 | 28.38 | C |
| ATOM | 15243 | CB | ARG | B | 459 | −41.313 | −30.965 | −44.041 | 1.00 | 28.96 | C |
| ATOM | 15246 | CG | ARG | B | 459 | −39.862 | −30.642 | −44.328 | 1.00 | 31.93 | C |
| ATOM | 15249 | CD | ARG | B | 459 | −39.656 | −29.139 | −44.480 | 1.00 | 36.88 | C |
| ATOM | 15252 | NE | ARG | B | 459 | −40.318 | −28.349 | −43.427 | 1.00 | 41.70 | N |
| ATOM | 15254 | CZ | ARG | B | 459 | −39.890 | −28.241 | −42.161 | 1.00 | 45.68 | C |
| ATOM | 15255 | NH1 | ARG | B | 459 | −38.795 | −28.899 | −41.751 | 1.00 | 48.08 | N |
| ATOM | 15258 | NH2 | ARG | B | 459 | −40.566 | −27.489 | −41.284 | 1.00 | 45.92 | N |
| ATOM | 15261 | C | ARG | B | 459 | −40.717 | −33.401 | −43.672 | 1.00 | 28.03 | C |
| ATOM | 15262 | O | ARG | B | 459 | −39.829 | −33.881 | −44.356 | 1.00 | 28.13 | O |
| ATOM | 15264 | N | THR | B | 460 | −40.882 | −33.711 | −42.393 | 1.00 | 27.88 | N |
| ATOM | 15265 | CA | THR | B | 460 | −40.002 | −34.635 | −41.664 | 1.00 | 27.75 | C |
| ATOM | 15267 | CB | THR | B | 460 | −40.240 | −34.502 | −40.134 | 1.00 | 27.79 | C |
| ATOM | 15269 | OG1 | THR | B | 460 | −39.805 | −33.209 | −39.689 | 1.00 | 27.98 | O |
| ATOM | 15271 | CG2 | THR | B | 460 | −39.519 | −35.589 | −39.356 | 1.00 | 27.46 | C |
| ATOM | 15275 | C | THR | B | 460 | −40.171 | −36.114 | −42.045 | 1.00 | 27.72 | C |
| ATOM | 15276 | O | THR | B | 460 | −39.211 | −36.857 | −42.069 | 1.00 | 27.60 | O |
| ATOM | 15278 | N | LYS | B | 461 | −41.398 | −36.538 | −42.313 | 1.00 | 28.05 | N |
| ATOM | 15279 | CA | LYS | B | 461 | −41.701 | −37.929 | −42.649 | 1.00 | 28.25 | C |
| ATOM | 15281 | CB | LYS | B | 461 | −42.972 | −38.381 | −41.914 | 1.00 | 28.32 | C |
| ATOM | 15284 | CG | LYS | B | 461 | −42.767 | −38.763 | −40.453 | 1.00 | 28.57 | C |
| ATOM | 15287 | CD | LYS | B | 461 | −42.569 | −40.271 | −40.299 | 1.00 | 29.79 | C |
| ATOM | 15290 | CE | LYS | B | 461 | −41.913 | −40.651 | −38.970 | 1.00 | 30.32 | C |
| ATOM | 15293 | NZ | LYS | B | 461 | −42.651 | −40.184 | −37.749 | 1.00 | 30.60 | N |
| ATOM | 15297 | C | LYS | B | 461 | −41.876 | −38.139 | −44.155 | 1.00 | 28.50 | C |
| ATOM | 15298 | O | LYS | B | 461 | −42.071 | −39.269 | −44.598 | 1.00 | 28.58 | O |
| ATOM | 15300 | N | GLY | B | 462 | −41.818 | −37.057 | −44.933 | 1.00 | 28.79 | N |
| ATOM | 15301 | CA | GLY | B | 462 | −41.978 | −37.114 | −46.385 | 1.00 | 29.04 | C |
| ATOM | 15304 | C | GLY | B | 462 | −43.333 | −37.610 | −46.853 | 1.00 | 29.39 | C |
| ATOM | 15305 | O | GLY | B | 462 | −43.410 | −38.452 | −47.738 | 1.00 | 29.53 | O |
| ATOM | 15307 | N | ILE | B | 463 | −44.406 | −37.081 | −46.270 | 1.00 | 29.91 | N |
| ATOM | 15308 | CA | ILE | B | 463 | −45.764 | −37.552 | −46.572 | 1.00 | 30.27 | C |
| ATOM | 15310 | CB | ILE | B | 463 | −46.333 | −38.444 | −45.433 | 1.00 | 30.13 | C |
| ATOM | 15312 | CG1 | ILE | B | 463 | −46.308 | −37.706 | −44.092 | 1.00 | 30.22 | C |
| ATOM | 15315 | CD1 | ILE | B | 463 | −46.983 | −38.462 | −42.965 | 1.00 | 30.14 | C |
| ATOM | 15319 | CG2 | ILE | B | 463 | −45.558 | −39.740 | −45.340 | 1.00 | 29.85 | C |
| ATOM | 15323 | C | ILE | B | 463 | −46.775 | −36.429 | −46.881 | 1.00 | 30.75 | C |
| ATOM | 15324 | O | ILE | B | 463 | −46.595 | −35.270 | −46.495 | 1.00 | 30.52 | O |
| ATOM | 15326 | N | SER | B | 464 | −47.842 | −36.822 | −47.581 | 1.00 | 31.33 | N |
| ATOM | 15327 | CA | SER | B | 464 | −48.951 | −35.944 | −47.952 | 1.00 | 31.68 | C |
| ATOM | 15329 | CB | SER | B | 464 | −49.948 | −36.709 | −48.830 | 1.00 | 32.02 | C |
| ATOM | 15332 | OG | SER | B | 464 | −50.547 | −37.793 | −48.123 | 1.00 | 32.84 | O |
| ATOM | 15334 | C | SER | B | 464 | −49.705 | −35.396 | −46.747 | 1.00 | 31.62 | C |
| ATOM | 15335 | O | SER | B | 464 | −49.897 | −36.097 | −45.747 | 1.00 | 31.69 | O |
| ATOM | 15337 | N | GLU | B | 465 | −50.165 | −34.153 | −46.874 | 1.00 | 31.42 | N |
| ATOM | 15338 | CA | GLU | B | 465 | −50.881 | −33.466 | −45.803 | 1.00 | 31.20 | C |
| ATOM | 15340 | CB | GLU | B | 465 | −51.465 | −32.141 | −46.324 | 1.00 | 31.33 | C |
| ATOM | 15343 | CG | GLU | B | 465 | −52.441 | −31.455 | −45.359 | 1.00 | 31.42 | C |
| ATOM | 15346 | CD | GLU | B | 465 | −52.768 | −30.006 | −45.712 | 1.00 | 31.30 | C |
| ATOM | 15347 | OE1 | GLU | B | 465 | −52.325 | −29.490 | −46.765 | 1.00 | 30.56 | O |

TABLE 16-7-continued

Coordinates of *P. tremuloides* IspS

| ATOM | 15348 | OE2 | GLU | B | 465 | −53.487 | −29.380 | −44.906 | 1.00 | 31.84 | O |
|------|-------|-----|-----|---|-----|---------|---------|---------|------|-------|---|
| ATOM | 15349 | C   | GLU | B | 465 | −51.985 | −34.325 | −45.202 | 1.00 | 30.97 | C |
| ATOM | 15350 | O   | GLU | B | 465 | −52.175 | −34.327 | −43.992 | 1.00 | 30.72 | O |
| ATOM | 15352 | N   | GLU | B | 466 | −52.709 | −35.052 | −46.055 | 1.00 | 30.98 | N |
| ATOM | 15353 | CA  | GLU | B | 466 | −53.865 | −35.833 | −45.618 | 1.00 | 30.65 | C |
| ATOM | 15355 | CB  | GLU | B | 466 | −54.553 | −36.541 | −46.788 | 1.00 | 30.62 | C |
| ATOM | 15358 | CG  | GLU | B | 466 | −55.733 | −37.401 | −46.336 | 1.00 | 31.50 | C |
| ATOM | 15361 | CD  | GLU | B | 466 | −56.353 | −38.240 | −47.446 | 1.00 | 33.14 | C |
| ATOM | 15362 | OE1 | GLU | B | 466 | −56.512 | −37.736 | −48.581 | 1.00 | 34.40 | O |
| ATOM | 15363 | OE2 | GLU | B | 466 | −56.699 | −39.413 | −47.173 | 1.00 | 33.21 | O |
| ATOM | 15364 | C   | GLU | B | 466 | −53.477 | −36.851 | −44.564 | 1.00 | 30.17 | C |
| ATOM | 15365 | O   | GLU | B | 466 | −54.215 | −37.049 | −43.606 | 1.00 | 30.46 | O |
| ATOM | 15367 | N   | LEU | B | 467 | −52.333 | −37.506 | −44.726 | 1.00 | 29.59 | N |
| ATOM | 15368 | CA  | LEU | B | 467 | −51.953 | −38.540 | −43.769 | 1.00 | 29.19 | C |
| ATOM | 15370 | CB  | LEU | B | 467 | −51.640 | −39.869 | −44.476 | 1.00 | 29.27 | C |
| ATOM | 15373 | CG  | LEU | B | 467 | −50.356 | −40.081 | −45.268 | 1.00 | 29.84 | C |
| ATOM | 15375 | CD1 | LEU | B | 467 | −49.341 | −40.761 | −44.357 | 1.00 | 31.06 | C |
| ATOM | 15379 | CD2 | LEU | B | 467 | −50.589 | −40.920 | −46.523 | 1.00 | 29.47 | C |
| ATOM | 15383 | C   | LEU | B | 467 | −50.865 | −38.092 | −42.794 | 1.00 | 28.54 | C |
| ATOM | 15384 | O   | LEU | B | 467 | −50.490 | −38.834 | −41.894 | 1.00 | 28.28 | O |
| ATOM | 15386 | N   | ALA | B | 468 | −50.388 | −36.862 | −42.962 | 1.00 | 28.04 | N |
| ATOM | 15387 | CA  | ALA | B | 468 | −49.682 | −36.158 | −41.893 | 1.00 | 27.54 | C |
| ATOM | 15389 | CB  | ALA | B | 468 | −48.922 | −34.970 | −42.435 | 1.00 | 27.34 | C |
| ATOM | 15393 | C   | ALA | B | 468 | −50.711 | −35.698 | −40.865 | 1.00 | 27.17 | C |
| ATOM | 15394 | O   | ALA | B | 468 | −50.482 | −35.801 | −39.662 | 1.00 | 27.40 | O |
| ATOM | 15396 | N   | THR | B | 469 | −51.841 | −35.182 | −41.349 | 1.00 | 26.57 | N |
| ATOM | 15397 | CA  | THR | B | 469 | −52.957 | −34.795 | −40.490 | 1.00 | 25.87 | C |
| ATOM | 15399 | CB  | THR | B | 469 | −54.130 | −34.297 | −41.328 | 1.00 | 25.53 | C |
| ATOM | 15401 | OG1 | THR | B | 469 | −53.737 | −33.111 | −42.025 | 1.00 | 24.99 | O |
| ATOM | 15403 | CG2 | THR | B | 469 | −55.316 | −33.993 | −40.453 | 1.00 | 24.62 | C |
| ATOM | 15407 | C   | THR | B | 469 | −53.412 | −35.988 | −39.669 | 1.00 | 25.95 | C |
| ATOM | 15408 | O   | THR | B | 469 | −53.551 | −35.925 | −38.450 | 1.00 | 25.80 | O |
| ATOM | 15410 | N   | GLU | B | 470 | −53.618 | −37.091 | −40.367 | 1.00 | 26.06 | N |
| ATOM | 15411 | CA  | GLU | B | 470 | −54.043 | −38.344 | −39.756 | 1.00 | 26.10 | C |
| ATOM | 15413 | CB  | GLU | B | 470 | −54.057 | −39.436 | −40.848 | 1.00 | 26.60 | C |
| ATOM | 15416 | CG  | GLU | B | 470 | −55.038 | −40.587 | −40.646 | 1.00 | 28.01 | C |
| ATOM | 15419 | CD  | GLU | B | 470 | −54.553 | −41.897 | −41.286 | 1.00 | 29.05 | C |
| ATOM | 15420 | OE1 | GLU | B | 470 | −54.298 | −41.930 | −42.515 | 1.00 | 27.96 | O |
| ATOM | 15421 | OE2 | GLU | B | 470 | −54.435 | −42.892 | −40.536 | 1.00 | 30.42 | O |
| ATOM | 15422 | C   | GLU | B | 470 | −53.148 | −38.746 | −38.557 | 1.00 | 25.28 | C |
| ATOM | 15423 | O   | GLU | B | 470 | −53.629 | −39.266 | −37.556 | 1.00 | 25.08 | O |
| ATOM | 15425 | N   | SER | B | 471 | −51.850 | −38.497 | −38.654 | 1.00 | 24.70 | N |
| ATOM | 15426 | CA  | SER | B | 471 | −50.930 | −38.906 | −37.599 | 1.00 | 24.26 | C |
| ATOM | 15428 | CB  | SER | B | 471 | −49.494 | −38.842 | −38.085 | 1.00 | 24.11 | C |
| ATOM | 15431 | OG  | SER | B | 471 | −49.315 | −39.693 | −39.186 | 1.00 | 23.98 | O |
| ATOM | 15433 | C   | SER | B | 471 | −51.085 | −38.029 | −36.377 | 1.00 | 23.92 | C |
| ATOM | 15434 | O   | SER | B | 471 | −51.240 | −38.530 | −35.270 | 1.00 | 24.09 | O |
| ATOM | 15436 | N   | VAL | B | 472 | −51.032 | −36.719 | −36.582 | 1.00 | 23.48 | N |
| ATOM | 15437 | CA  | VAL | B | 472 | −51.279 | −35.774 | −35.510 | 1.00 | 23.15 | C |
| ATOM | 15439 | CB  | VAL | B | 472 | −51.377 | −34.332 | −36.045 | 1.00 | 23.03 | C |
| ATOM | 15441 | CG1 | VAL | B | 472 | −51.739 | −33.347 | −34.929 | 1.00 | 21.74 | C |
| ATOM | 15445 | CG2 | VAL | B | 472 | −50.067 | −33.945 | −36.728 | 1.00 | 22.27 | C |
| ATOM | 15449 | C   | VAL | B | 472 | −52.572 | −36.192 | −34.830 | 1.00 | 23.49 | C |
| ATOM | 15450 | O   | VAL | B | 472 | −52.663 | −36.276 | −33.614 | 1.00 | 23.29 | O |
| ATOM | 15452 | N   | MET | B | 473 | −53.573 | −36.508 | −35.626 | 1.00 | 24.34 | N |
| ATOM | 15453 | CA  | MET | B | 473 | −54.850 | −36.901 | −35.070 | 1.00 | 24.93 | C |
| ATOM | 15455 | CB  | MET | B | 473 | −55.816 | −37.266 | −36.190 | 1.00 | 25.09 | C |
| ATOM | 15458 | CG  | MET | B | 473 | −57.191 | −36.788 | −35.912 | 1.00 | 26.94 | C |
| ATOM | 15461 | SD  | MET | B | 473 | −57.328 | −35.035 | −36.251 | 1.00 | 29.69 | S |
| ATOM | 15462 | CE  | MET | B | 473 | −58.316 | −35.080 | −37.775 | 1.00 | 29.12 | C |
| ATOM | 15466 | C   | MET | B | 473 | −54.668 | −38.072 | −34.100 | 1.00 | 25.00 | C |
| ATOM | 15467 | O   | MET | B | 473 | −55.135 | −38.018 | −32.963 | 1.00 | 24.78 | O |
| ATOM | 15469 | N   | ASN | B | 474 | −53.965 | −39.110 | −34.556 | 1.00 | 25.30 | N |
| ATOM | 15470 | CA  | ASN | B | 474 | −53.681 | −40.293 | −33.738 | 1.00 | 25.55 | C |
| ATOM | 15472 | CB  | ASN | B | 474 | −53.143 | −41.439 | −34.601 | 1.00 | 25.82 | C |
| ATOM | 15475 | CG  | ASN | B | 474 | −54.243 | −42.137 | −35.402 | 1.00 | 27.62 | C |
| ATOM | 15476 | OD1 | ASN | B | 474 | −54.238 | −42.102 | −36.638 | 1.00 | 29.33 | O |
| ATOM | 15477 | ND2 | ASN | B | 474 | −55.196 | −42.780 | −34.697 | 1.00 | 28.58 | N |
| ATOM | 15480 | C   | ASN | B | 474 | −52.711 | −40.034 | −32.592 | 1.00 | 25.20 | C |
| ATOM | 15481 | O   | ASN | B | 474 | −52.711 | −40.773 | −31.621 | 1.00 | 25.71 | O |
| ATOM | 15483 | N   | LEU | B | 475 | −51.883 | −38.999 | −32.704 | 1.00 | 24.65 | N |
| ATOM | 15484 | CA  | LEU | B | 475 | −50.987 | −38.595 | −31.614 | 1.00 | 24.04 | C |
| ATOM | 15486 | CB  | LEU | B | 475 | −49.939 | −37.626 | −32.142 | 1.00 | 23.88 | C |
| ATOM | 15489 | CG  | LEU | B | 475 | −48.837 | −37.285 | −31.164 | 1.00 | 23.70 | C |
| ATOM | 15491 | CD1 | LEU | B | 475 | −47.936 | −38.471 | −31.004 | 1.00 | 23.97 | C |
| ATOM | 15495 | CD2 | LEU | B | 475 | −48.088 | −36.104 | −31.679 | 1.00 | 23.99 | C |
| ATOM | 15499 | C   | LEU | B | 475 | −51.747 | −37.940 | −30.453 | 1.00 | 23.65 | C |
| ATOM | 15500 | O   | LEU | B | 475 | −51.323 | −38.014 | −29.299 | 1.00 | 23.74 | O |

TABLE 16-7-continued

Coordinates of *P. tremuloides* IspS

| ATOM | 15502 | N | ILE | B | 476 | −52.858 | −37.282 | −30.766 | 1.00 | 23.15 | N |
|---|---|---|---|---|---|---|---|---|---|---|---|
| ATOM | 15503 | CA | ILE | B | 476 | −53.728 | −36.711 | −29.742 | 1.00 | 22.50 | C |
| ATOM | 15505 | CB | ILE | B | 476 | −54.779 | −35.755 | −30.359 | 1.00 | 22.27 | C |
| ATOM | 15507 | CG1 | ILE | B | 476 | −54.099 | −34.508 | −30.910 | 1.00 | 20.55 | C |
| ATOM | 15510 | CD1 | ILE | B | 476 | −55.000 | −33.671 | −31.693 | 1.00 | 19.19 | C |
| ATOM | 15514 | CG2 | ILE | B | 476 | −55.817 | −35.363 | −29.336 | 1.00 | 22.15 | C |
| ATOM | 15518 | C | ILE | B | 476 | −54.398 | −37.849 | −28.985 | 1.00 | 22.40 | C |
| ATOM | 15519 | O | ILE | B | 476 | −54.316 | −37.900 | −27.767 | 1.00 | 22.32 | O |
| ATOM | 15521 | N | ASP | B | 477 | −55.023 | −38.777 | −29.708 | 1.00 | 22.37 | N |
| ATOM | 15522 | CA | ASP | B | 477 | −55.616 | −39.975 | −29.090 | 1.00 | 22.55 | C |
| ATOM | 15524 | CB | ASP | B | 477 | −55.996 | −41.007 | −30.151 | 1.00 | 22.67 | C |
| ATOM | 15527 | CG | ASP | B | 477 | −57.262 | −40.636 | −30.892 | 1.00 | 24.93 | C |
| ATOM | 15528 | OD1 | ASP | B | 477 | −57.690 | −39.458 | −30.818 | 1.00 | 28.87 | O |
| ATOM | 15529 | OD2 | ASP | B | 477 | −57.847 | −41.523 | −31.549 | 1.00 | 27.92 | O |
| ATOM | 15530 | C | ASP | B | 477 | −54.675 | −40.622 | −28.083 | 1.00 | 22.10 | C |
| ATOM | 15531 | O | ASP | B | 477 | −55.048 | −40.877 | −26.938 | 1.00 | 21.83 | O |
| ATOM | 15533 | N | GLU | B | 478 | −53.444 | −40.867 | −28.510 | 1.00 | 21.73 | N |
| ATOM | 15534 | CA | GLU | B | 478 | −52.472 | −41.506 | −27.645 | 1.00 | 21.69 | C |
| ATOM | 15536 | CB | GLU | B | 478 | −51.233 | −41.920 | −28.437 | 1.00 | 21.97 | C |
| ATOM | 15539 | CG | GLU | B | 478 | −50.786 | −43.360 | −28.150 | 1.00 | 24.18 | C |
| ATOM | 15542 | CD | GLU | B | 478 | −51.793 | −44.429 | −28.618 | 1.00 | 27.03 | C |
| ATOM | 15543 | OE1 | GLU | B | 478 | −51.599 | −45.627 | −28.285 | 1.00 | 29.15 | O |
| ATOM | 15544 | OE2 | GLU | B | 478 | −52.770 | −44.080 | −29.323 | 1.00 | 28.37 | O |
| ATOM | 15545 | C | GLU | B | 478 | −52.107 | −40.608 | −26.449 | 1.00 | 20.97 | C |
| ATOM | 15546 | O | GLU | B | 478 | −51.928 | −41.110 | −25.316 | 1.00 | 21.15 | O |
| ATOM | 15548 | N | THR | B | 479 | −52.031 | −39.291 | −26.687 | 1.00 | 19.82 | N |
| ATOM | 15549 | CA | THR | B | 479 | −51.787 | −38.319 | −25.604 | 1.00 | 18.59 | C |
| ATOM | 15551 | CB | THR | B | 479 | −51.587 | −36.897 | −26.129 | 1.00 | 17.95 | C |
| ATOM | 15553 | OG1 | THR | B | 479 | −50.291 | −36.779 | −26.712 | 1.00 | 17.43 | O |
| ATOM | 15555 | CG2 | THR | B | 479 | −51.654 | −35.938 | −25.009 | 1.00 | 17.90 | C |
| ATOM | 15559 | C | THR | B | 479 | −52.927 | −38.342 | −24.580 | 1.00 | 18.16 | C |
| ATOM | 15560 | O | THR | B | 479 | −52.695 | −38.339 | −23.383 | 1.00 | 18.06 | O |
| ATOM | 15562 | N | TRP | B | 480 | −54.160 | −38.390 | −25.057 | 1.00 | 17.77 | N |
| ATOM | 15563 | CA | TRP | B | 480 | −55.301 | −38.493 | −24.169 | 1.00 | 17.54 | C |
| ATOM | 15565 | CB | TRP | B | 480 | −56.605 | −38.464 | −24.970 | 1.00 | 17.49 | C |
| ATOM | 15568 | CG | TRP | B | 480 | −57.239 | −37.099 | −25.028 | 1.00 | 17.53 | C |
| ATOM | 15569 | CD1 | TRP | B | 480 | −57.150 | −36.186 | −26.041 | 1.00 | 17.04 | C |
| ATOM | 15571 | NE1 | TRP | B | 480 | −57.857 | −35.067 | −25.721 | 1.00 | 16.57 | N |
| ATOM | 15573 | CE2 | TRP | B | 480 | −58.423 | −35.236 | −24.484 | 1.00 | 16.41 | C |
| ATOM | 15574 | CD2 | TRP | B | 480 | −58.055 | −36.498 | −24.020 | 1.00 | 16.68 | C |
| ATOM | 15575 | CE3 | TRP | B | 480 | −58.507 | −36.914 | −22.765 | 1.00 | 16.92 | C |
| ATOM | 15577 | CZ3 | TRP | B | 480 | −59.300 | −36.076 | −22.039 | 1.00 | 16.97 | C |
| ATOM | 15579 | CH2 | TRP | B | 480 | −59.654 | −34.823 | −22.524 | 1.00 | 16.91 | C |
| ATOM | 15581 | CZ2 | TRP | B | 480 | −59.223 | −34.383 | −23.742 | 1.00 | 16.89 | C |
| ATOM | 15583 | C | TRP | B | 480 | −55.232 | −39.760 | −23.334 | 1.00 | 17.75 | C |
| ATOM | 15584 | O | TRP | B | 480 | −55.582 | −39.747 | −22.164 | 1.00 | 17.74 | O |
| ATOM | 15586 | N | LYS | B | 481 | −54.784 | −40.861 | −23.933 | 1.00 | 18.09 | N |
| ATOM | 15587 | CA | LYS | B | 481 | −54.721 | −42.124 | −23.210 | 1.00 | 18.10 | C |
| ATOM | 15589 | CB | LYS | B | 481 | −54.277 | −43.282 | −24.115 | 1.00 | 18.01 | C |
| ATOM | 15592 | CG | LYS | B | 481 | −55.311 | −43.803 | −25.114 | 1.00 | 16.89 | C |
| ATOM | 15595 | CD | LYS | B | 481 | −54.613 | −44.663 | −26.199 | 1.00 | 15.83 | C |
| ATOM | 15598 | CE | LYS | B | 481 | −55.587 | −45.500 | −27.025 | 1.00 | 14.74 | C |
| ATOM | 15601 | NZ | LYS | B | 481 | −55.119 | −45.725 | −28.413 | 1.00 | 12.34 | N |
| ATOM | 15605 | C | LYS | B | 481 | −53.750 | −41.970 | −22.054 | 1.00 | 18.46 | C |
| ATOM | 15606 | O | LYS | B | 481 | −53.976 | −42.494 | −20.969 | 1.00 | 18.44 | O |
| ATOM | 15608 | N | LYS | B | 482 | −52.662 | −41.252 | −22.279 | 1.00 | 18.80 | N |
| ATOM | 15609 | CA | LYS | B | 482 | −51.727 | −41.019 | −21.192 | 1.00 | 19.58 | C |
| ATOM | 15611 | CB | LYS | B | 482 | −50.425 | −40.424 | −21.727 | 1.00 | 20.03 | C |
| ATOM | 15614 | CG | LYS | B | 482 | −49.499 | −41.500 | −22.277 | 1.00 | 22.03 | C |
| ATOM | 15617 | CD | LYS | B | 482 | −48.706 | −41.063 | −23.506 | 1.00 | 24.87 | C |
| ATOM | 15620 | CE | LYS | B | 482 | −47.908 | −42.268 | −24.066 | 1.00 | 26.65 | C |
| ATOM | 15623 | NZ | LYS | B | 482 | −47.287 | −41.996 | −25.408 | 1.00 | 28.80 | N |
| ATOM | 15627 | C | LYS | B | 482 | −52.363 | −40.156 | −20.096 | 1.00 | 19.56 | C |
| ATOM | 15628 | O | LYS | B | 482 | −52.367 | −40.537 | −18.926 | 1.00 | 19.19 | O |
| ATOM | 15630 | N | MET | B | 483 | −52.922 | −39.013 | −20.483 | 1.00 | 20.00 | N |
| ATOM | 15631 | CA | MET | B | 483 | −53.677 | −38.165 | −19.552 | 1.00 | 20.37 | C |
| ATOM | 15633 | CB | MET | B | 483 | −54.426 | −37.057 | −20.295 | 1.00 | 20.25 | C |
| ATOM | 15636 | CG | MET | B | 483 | −53.529 | −35.951 | −20.807 | 1.00 | 20.52 | C |
| ATOM | 15639 | SD | MET | B | 483 | −54.461 | −34.483 | −21.225 | 1.00 | 20.47 | S |
| ATOM | 15640 | CE | MET | B | 483 | −55.361 | −35.084 | −22.649 | 1.00 | 22.07 | C |
| ATOM | 15644 | C | MET | B | 483 | −54.668 | −38.981 | −18.741 | 1.00 | 20.72 | C |
| ATOM | 15645 | O | MET | B | 483 | −54.809 | −38.779 | −17.543 | 1.00 | 20.37 | O |
| ATOM | 15647 | N | ASN | B | 484 | −55.345 | −39.910 | −19.403 | 1.00 | 21.57 | N |
| ATOM | 15648 | CA | ASN | B | 484 | −56.339 | −40.731 | −18.744 | 1.00 | 22.46 | C |
| ATOM | 15650 | CB | ASN | B | 484 | −57.042 | −41.631 | −19.765 | 1.00 | 22.23 | C |
| ATOM | 15653 | CG | ASN | B | 484 | −58.118 | −40.900 | −20.576 | 1.00 | 21.61 | C |
| ATOM | 15654 | OD1 | ASN | B | 484 | −58.412 | −39.722 | −20.362 | 1.00 | 20.25 | O |
| ATOM | 15655 | ND2 | ASN | B | 484 | −58.720 | −41.622 | −21.510 | 1.00 | 20.80 | N |

TABLE 16-7-continued

Coordinates of *P. tremuloides* IspS

| ATOM | 15658 | C | ASN | B | 484 | −55.723 | −41.555 | −17.598 | 1.00 | 23.83 | C |
|---|---|---|---|---|---|---|---|---|---|---|---|
| ATOM | 15659 | O | ASN | B | 484 | −56.262 | −41.591 | −16.484 | 1.00 | 23.76 | O |
| ATOM | 15661 | N | LYS | B | 485 | −54.585 | −42.190 | −17.868 | 1.00 | 25.69 | N |
| ATOM | 15662 | CA | LYS | B | 485 | −53.854 | −42.937 | −16.843 | 1.00 | 27.11 | C |
| ATOM | 15664 | CB | LYS | B | 485 | −52.679 | −43.712 | −17.447 | 1.00 | 27.13 | C |
| ATOM | 15667 | CG | LYS | B | 485 | −52.073 | −44.755 | −16.489 | 1.00 | 28.85 | C |
| ATOM | 15670 | CD | LYS | B | 485 | −51.643 | −46.082 | −17.187 | 1.00 | 31.17 | C |
| ATOM | 15673 | CE | LYS | B | 485 | −50.150 | −46.132 | −17.555 | 1.00 | 32.11 | C |
| ATOM | 15676 | NZ | LYS | B | 485 | −49.291 | −46.282 | −16.344 | 1.00 | 33.08 | N |
| ATOM | 15680 | C | LYS | B | 485 | −53.370 | −42.035 | −15.701 | 1.00 | 28.37 | C |
| ATOM | 15681 | O | LYS | B | 485 | −53.288 | −42.481 | −14.563 | 1.00 | 28.59 | O |
| ATOM | 15683 | N | GLU | B | 486 | −53.083 | −40.766 | −15.980 | 1.00 | 29.89 | N |
| ATOM | 15684 | CA | GLU | B | 486 | −52.683 | −39.849 | −14.910 | 1.00 | 31.09 | C |
| ATOM | 15686 | CB | GLU | B | 486 | −52.174 | −38.511 | −15.470 | 1.00 | 31.55 | C |
| ATOM | 15689 | CG | GLU | B | 486 | −51.059 | −37.851 | −14.643 | 1.00 | 32.69 | C |
| ATOM | 15692 | CD | GLU | B | 486 | −49.785 | −38.689 | −14.605 | 1.00 | 34.51 | C |
| ATOM | 15693 | OE1 | GLU | B | 486 | −49.104 | −38.682 | −13.557 | 1.00 | 36.35 | O |
| ATOM | 15694 | OE2 | GLU | B | 486 | −49.476 | −39.368 | −15.611 | 1.00 | 34.55 | O |
| ATOM | 15695 | C | GLU | B | 486 | −53.836 | −39.615 | −13.939 | 1.00 | 31.70 | C |
| ATOM | 15696 | O | GLU | B | 486 | −53.684 | −39.868 | −12.750 | 1.00 | 31.90 | O |
| ATOM | 15698 | N | LYS | B | 487 | −54.983 | −39.164 | −14.453 | 1.00 | 32.71 | N |
| ATOM | 15699 | CA | LYS | B | 487 | −56.177 | −38.856 | −13.629 | 1.00 | 33.57 | C |
| ATOM | 15701 | CB | LYS | B | 487 | −57.343 | −38.402 | −14.519 | 1.00 | 33.54 | C |
| ATOM | 15704 | CG | LYS | B | 487 | −58.703 | −38.196 | −13.823 | 1.00 | 33.45 | C |
| ATOM | 15707 | CD | LYS | B | 487 | −58.686 | −37.024 | −12.866 | 1.00 | 33.71 | C |
| ATOM | 15710 | CE | LYS | B | 487 | −59.906 | −36.996 | −11.931 | 1.00 | 34.48 | C |
| ATOM | 15713 | NZ | LYS | B | 487 | −61.123 | −36.378 | −12.526 | 1.00 | 35.03 | N |
| ATOM | 15717 | C | LYS | B | 487 | −56.626 | −40.046 | −12.802 | 1.00 | 34.60 | C |
| ATOM | 15718 | O | LYS | B | 487 | −57.126 | −39.892 | −11.681 | 1.00 | 34.55 | O |
| ATOM | 15720 | N | LEU | B | 488 | −56.453 | −41.233 | −13.371 | 1.00 | 35.94 | N |
| ATOM | 15721 | CA | LEU | B | 488 | −56.878 | −42.451 | −12.723 | 1.00 | 37.00 | C |
| ATOM | 15723 | CB | LEU | B | 488 | −57.280 | −43.489 | −13.778 | 1.00 | 36.90 | C |
| ATOM | 15726 | CG | LEU | B | 488 | −58.081 | −44.714 | −13.312 | 1.00 | 37.52 | C |
| ATOM | 15728 | CD1 | LEU | B | 488 | −58.758 | −44.536 | −11.946 | 1.00 | 38.76 | C |
| ATOM | 15732 | CD2 | LEU | B | 488 | −59.121 | −45.084 | −14.346 | 1.00 | 38.42 | C |
| ATOM | 15736 | C | LEU | B | 488 | −55.786 | −42.980 | −11.803 | 1.00 | 38.02 | C |
| ATOM | 15737 | O | LEU | B | 488 | −56.063 | −43.315 | −10.653 | 1.00 | 38.19 | O |
| ATOM | 15739 | N | GLY | B | 489 | −54.550 | −43.016 | −12.298 | 1.00 | 39.44 | N |
| ATOM | 15740 | CA | GLY | B | 489 | −53.441 | −43.710 | −11.621 | 1.00 | 40.62 | C |
| ATOM | 15743 | C | GLY | B | 489 | −52.563 | −42.837 | −10.740 | 1.00 | 41.76 | C |
| ATOM | 15744 | O | GLY | B | 489 | −51.357 | −42.703 | −10.988 | 1.00 | 41.83 | O |
| ATOM | 15746 | N | GLY | B | 490 | −53.183 | −42.230 | −9.726 | 1.00 | 43.10 | N |
| ATOM | 15747 | CA | GLY | B | 490 | −52.481 | −41.538 | −8.636 | 1.00 | 43.82 | C |
| ATOM | 15750 | C | GLY | B | 490 | −51.131 | −40.924 | −8.967 | 1.00 | 44.31 | C |
| ATOM | 15751 | O | GLY | B | 490 | −50.084 | −41.560 | −8.831 | 1.00 | 44.25 | O |
| ATOM | 15753 | N | SER | B | 491 | −51.161 | −39.672 | −9.396 | 1.00 | 44.87 | N |
| ATOM | 15754 | CA | SER | B | 491 | −49.939 | −38.892 | −9.575 | 1.00 | 45.22 | C |
| ATOM | 15756 | CB | SER | B | 491 | −50.224 | −37.723 | −10.537 | 1.00 | 45.34 | C |
| ATOM | 15759 | OG | SER | B | 491 | −51.411 | −37.032 | −10.166 | 1.00 | 45.38 | O |
| ATOM | 15761 | C | SER | B | 491 | −49.419 | −38.389 | −8.203 | 1.00 | 45.14 | C |
| ATOM | 15762 | O | SER | B | 491 | −49.896 | −38.824 | −7.140 | 1.00 | 45.11 | O |
| ATOM | 15764 | N | LEU | B | 492 | −48.429 | −37.491 | −8.227 | 1.00 | 44.77 | N |
| ATOM | 15765 | CA | LEU | B | 492 | −48.046 | −36.752 | −7.018 | 1.00 | 44.31 | C |
| ATOM | 15767 | CB | LEU | B | 492 | −46.726 | −35.971 | −7.188 | 1.00 | 44.55 | C |
| ATOM | 15770 | CG | LEU | B | 492 | −45.530 | −36.546 | −7.972 | 1.00 | 45.73 | C |
| ATOM | 15772 | CD1 | LEU | B | 492 | −44.373 | −35.556 | −7.859 | 1.00 | 46.25 | C |
| ATOM | 15776 | CD2 | LEU | B | 492 | −45.084 | −37.972 | −7.530 | 1.00 | 46.14 | C |
| ATOM | 15780 | C | LEU | B | 492 | −49.151 | −35.760 | −6.703 | 1.00 | 43.30 | C |
| ATOM | 15781 | O | LEU | B | 492 | −49.315 | −35.370 | −5.555 | 1.00 | 43.49 | O |
| ATOM | 15783 | N | PHE | B | 493 | −49.903 | −35.367 | −7.735 | 1.00 | 42.05 | N |
| ATOM | 15784 | CA | PHE | B | 493 | −50.822 | −34.239 | −7.668 | 1.00 | 41.03 | C |
| ATOM | 15786 | CB | PHE | B | 493 | −50.913 | −33.549 | −9.028 | 1.00 | 40.81 | C |
| ATOM | 15789 | CG | PHE | B | 493 | −49.696 | −32.771 | −9.408 | 1.00 | 38.96 | C |
| ATOM | 15790 | CD1 | PHE | B | 493 | −49.651 | −31.408 | −9.233 | 1.00 | 37.06 | C |
| ATOM | 15792 | CE1 | PHE | B | 493 | −48.543 | −30.697 | −9.603 | 1.00 | 36.41 | C |
| ATOM | 15794 | CZ | PHE | B | 493 | −47.471 | −31.341 | −10.158 | 1.00 | 35.87 | C |
| ATOM | 15796 | CE2 | PHE | B | 493 | −47.507 | −32.690 | −10.343 | 1.00 | 36.39 | C |
| ATOM | 15798 | CD2 | PHE | B | 493 | −48.612 | −33.400 | −9.977 | 1.00 | 37.36 | C |
| ATOM | 15800 | C | PHE | B | 493 | −52.240 | −34.603 | −7.268 | 1.00 | 40.76 | C |
| ATOM | 15801 | O | PHE | B | 493 | −52.686 | −35.733 | −7.419 | 1.00 | 40.35 | O |
| ATOM | 15803 | N | ALA | B | 494 | −52.943 | −33.584 | −6.790 | 1.00 | 40.72 | N |
| ATOM | 15804 | CA | ALA | B | 494 | −54.355 | −33.658 | −6.471 | 1.00 | 40.68 | C |
| ATOM | 15806 | CB | ALA | B | 494 | −54.786 | −32.362 | −5.770 | 1.00 | 40.70 | C |
| ATOM | 15810 | C | ALA | B | 494 | −55.175 | −33.851 | −7.744 | 1.00 | 40.59 | C |
| ATOM | 15811 | O | ALA | B | 494 | −55.013 | −33.099 | −8.716 | 1.00 | 40.95 | O |
| ATOM | 15813 | N | LYS | B | 495 | −56.071 | −34.835 | −7.733 | 1.00 | 40.12 | N |
| ATOM | 15814 | CA | LYS | B | 495 | −57.000 | −35.047 | −8.854 | 1.00 | 39.67 | C |
| ATOM | 15816 | CB | LYS | B | 495 | −58.008 | −36.166 | −8.520 | 1.00 | 39.98 | C |

TABLE 16-7-continued

Coordinates of *P. tremuloides* IspS

| ATOM | 15819 | CG | LYS | B | 495 | −57.388 | −37.590 | −8.496 | 1.00 | 40.57 | C |
| ATOM | 15822 | CD | LYS | B | 495 | −58.468 | −38.688 | −8.419 | 1.00 | 41.18 | C |
| ATOM | 15825 | CE | LYS | B | 495 | −57.878 | −40.065 | −8.132 | 1.00 | 41.28 | C |
| ATOM | 15828 | NZ | LYS | B | 495 | −58.736 | −41.159 | −8.671 | 1.00 | 41.39 | N |
| ATOM | 15832 | C | LYS | B | 495 | −57.717 | −33.752 | −9.333 | 1.00 | 38.82 | C |
| ATOM | 15833 | O | LYS | B | 495 | −57.847 | −33.535 | −10.537 | 1.00 | 38.70 | O |
| ATOM | 15835 | N | PRO | B | 496 | −58.169 | −32.890 | −8.397 | 1.00 | 37.71 | N |
| ATOM | 15836 | CA | PRO | B | 496 | −58.701 | −31.551 | −8.687 | 1.00 | 36.80 | C |
| ATOM | 15838 | CB | PRO | B | 496 | −58.820 | −30.937 | −7.304 | 1.00 | 36.94 | C |
| ATOM | 15841 | CG | PRO | B | 496 | −59.255 | −32.073 | −6.483 | 1.00 | 37.90 | C |
| ATOM | 15844 | CD | PRO | B | 496 | −58.534 | −33.294 | −7.030 | 1.00 | 37.86 | C |
| ATOM | 15847 | C | PRO | B | 496 | −57.845 | −30.625 | −9.536 | 1.00 | 35.57 | C |
| ATOM | 15848 | O | PRO | B | 496 | −58.389 | −29.693 | −10.139 | 1.00 | 35.93 | O |
| ATOM | 15849 | N | PHE | B | 497 | −56.527 | −30.836 | −9.546 | 1.00 | 33.52 | N |
| ATOM | 15850 | CA | PHE | B | 497 | −55.654 | −30.083 | −10.439 | 1.00 | 31.34 | C |
| ATOM | 15852 | CB | PHE | B | 497 | −54.355 | −29.710 | −9.750 | 1.00 | 30.86 | C |
| ATOM | 15855 | CG | PHE | B | 497 | −53.394 | −28.989 | −10.634 | 1.00 | 29.04 | C |
| ATOM | 15856 | CD1 | PHE | B | 497 | −53.639 | −27.700 | −11.022 | 1.00 | 27.89 | C |
| ATOM | 15858 | CE1 | PHE | B | 497 | −52.752 | −27.028 | −11.834 | 1.00 | 27.39 | C |
| ATOM | 15860 | CZ | PHE | B | 497 | −51.599 | −27.653 | −12.259 | 1.00 | 27.40 | C |
| ATOM | 15862 | CE2 | PHE | B | 497 | −51.341 | −28.941 | −11.877 | 1.00 | 27.44 | C |
| ATOM | 15864 | CD2 | PHE | B | 497 | −52.236 | −29.604 | −11.074 | 1.00 | 28.18 | C |
| ATOM | 15866 | C | PHE | B | 497 | −55.390 | −30.870 | −11.714 | 1.00 | 30.24 | C |
| ATOM | 15867 | O | PHE | B | 497 | −55.301 | −30.266 | −12.786 | 1.00 | 30.39 | O |
| ATOM | 15869 | N | VAL | B | 498 | −55.295 | −32.200 | −11.630 | 1.00 | 28.50 | N |
| ATOM | 15870 | CA | VAL | B | 498 | −55.076 | −32.983 | −12.854 | 1.00 | 27.54 | C |
| ATOM | 15872 | CB | VAL | B | 498 | −54.778 | −34.472 | −12.611 | 1.00 | 27.34 | C |
| ATOM | 15874 | CG1 | VAL | B | 498 | −56.027 | −35.194 | −12.262 | 1.00 | 28.14 | C |
| ATOM | 15878 | CG2 | VAL | B | 498 | −53.731 | −34.649 | −11.530 | 1.00 | 27.04 | C |
| ATOM | 15882 | C | VAL | B | 498 | −56.277 | −32.857 | −13.784 | 1.00 | 26.60 | C |
| ATOM | 15883 | O | VAL | B | 498 | −56.129 | −32.864 | −14.995 | 1.00 | 26.33 | O |
| ATOM | 15885 | N | GLU | B | 499 | −57.468 | −32.731 | −13.214 | 1.00 | 25.87 | N |
| ATOM | 15886 | CA | GLU | B | 499 | −58.662 | −32.484 | −14.022 | 1.00 | 25.20 | C |
| ATOM | 15888 | CB | GLU | B | 499 | −59.975 | −32.639 | −13.206 | 1.00 | 25.26 | C |
| ATOM | 15891 | CG | GLU | B | 499 | −61.287 | −32.694 | −14.028 | 1.00 | 25.16 | C |
| ATOM | 15894 | CD | GLU | B | 499 | −61.422 | −33.922 | −14.973 | 1.00 | 26.79 | C |
| ATOM | 15895 | OE1 | GLU | B | 499 | −60.607 | −34.880 | −14.928 | 1.00 | 26.39 | O |
| ATOM | 15896 | OE2 | GLU | B | 499 | −62.379 | −33.926 | −15.785 | 1.00 | 27.83 | O |
| ATOM | 15897 | C | GLU | B | 499 | −58.542 | −31.097 | −14.641 | 1.00 | 24.27 | C |
| ATOM | 15898 | O | GLU | B | 499 | −58.819 | −30.948 | −15.832 | 1.00 | 24.32 | O |
| ATOM | 15900 | N | THR | B | 500 | −58.098 | −30.093 | −13.882 | 1.00 | 22.90 | N |
| ATOM | 15901 | CA | THR | B | 500 | −58.027 | −28.764 | −14.487 | 1.00 | 22.29 | C |
| ATOM | 15903 | CB | THR | B | 500 | −57.908 | −27.592 | −13.488 | 1.00 | 22.43 | C |
| ATOM | 15905 | OG1 | THR | B | 500 | −56.536 | −27.259 | −13.274 | 1.00 | 22.65 | O |
| ATOM | 15907 | CG2 | THR | B | 500 | −58.614 | −27.899 | −12.183 | 1.00 | 22.84 | C |
| ATOM | 15911 | C | THR | B | 500 | −56.940 | −28.671 | −15.565 | 1.00 | 21.20 | C |
| ATOM | 15912 | O | THR | B | 500 | −57.120 | −27.939 | −16.536 | 1.00 | 21.06 | O |
| ATOM | 15914 | N | ALA | B | 501 | −55.845 | −29.414 | −15.422 | 1.00 | 19.88 | N |
| ATOM | 15915 | CA | ALA | B | 501 | −54.906 | −29.574 | −16.537 | 1.00 | 19.24 | C |
| ATOM | 15917 | CB | ALA | B | 501 | −53.704 | −30.393 | −16.115 | 1.00 | 19.22 | C |
| ATOM | 15921 | C | ALA | B | 501 | −55.581 | −30.226 | −17.757 | 1.00 | 18.68 | C |
| ATOM | 15922 | O | ALA | B | 501 | −55.427 | −29.768 | −18.881 | 1.00 | 18.32 | O |
| ATOM | 15924 | N | ILE | B | 502 | −56.324 | −31.300 | −17.523 | 1.00 | 18.11 | N |
| ATOM | 15925 | CA | ILE | B | 502 | −57.023 | −31.988 | −18.591 | 1.00 | 17.68 | C |
| ATOM | 15927 | CB | ILE | B | 502 | −57.750 | −33.251 | −18.059 | 1.00 | 17.63 | C |
| ATOM | 15929 | CG1 | ILE | B | 502 | −56.713 | −34.350 | −17.769 | 1.00 | 18.16 | C |
| ATOM | 15932 | CD1 | ILE | B | 502 | −57.253 | −35.645 | −17.115 | 1.00 | 17.02 | C |
| ATOM | 15936 | CG2 | ILE | B | 502 | −58.756 | −33.762 | −19.063 | 1.00 | 16.93 | C |
| ATOM | 15940 | C | ILE | B | 502 | −57.990 | −31.030 | −19.289 | 1.00 | 17.50 | C |
| ATOM | 15941 | O | ILE | B | 502 | −58.153 | −31.071 | −20.512 | 1.00 | 17.62 | O |
| ATOM | 15943 | N | ASN | B | 503 | −58.604 | −30.139 | −18.524 | 1.00 | 17.23 | N |
| ATOM | 15944 | CA | ASN | B | 503 | −59.545 | −29.184 | −19.102 | 1.00 | 17.07 | C |
| ATOM | 15946 | CB | ASN | B | 503 | −60.184 | −28.327 | −18.016 | 1.00 | 17.21 | C |
| ATOM | 15949 | CG | ASN | B | 503 | −61.155 | −29.094 | −17.176 | 1.00 | 17.29 | C |
| ATOM | 15950 | OD1 | ASN | B | 503 | −61.721 | −30.097 | −17.609 | 1.00 | 16.66 | O |
| ATOM | 15951 | ND2 | ASN | B | 503 | −61.365 | −28.621 | −15.958 | 1.00 | 19.16 | N |
| ATOM | 15954 | C | ASN | B | 503 | −58.920 | −28.270 | −20.149 | 1.00 | 16.59 | C |
| ATOM | 15955 | O | ASN | B | 503 | −59.611 | −27.811 | −21.071 | 1.00 | 16.67 | O |
| ATOM | 15957 | N | LEU | B | 504 | −57.629 | −27.992 | −20.014 | 1.00 | 15.79 | N |
| ATOM | 15958 | CA | LEU | B | 504 | −56.948 | −27.204 | −21.031 | 1.00 | 15.44 | C |
| ATOM | 15960 | CB | LEU | B | 504 | −55.530 | −26.865 | −20.609 | 1.00 | 15.07 | C |
| ATOM | 15963 | CG | LEU | B | 504 | −54.933 | −25.837 | −21.552 | 1.00 | 14.21 | C |
| ATOM | 15965 | CD1 | LEU | B | 504 | −54.246 | −24.726 | −20.800 | 1.00 | 14.21 | C |
| ATOM | 15969 | CD2 | LEU | B | 504 | −54.000 | −26.538 | −22.462 | 1.00 | 14.27 | C |
| ATOM | 15973 | C | LEU | B | 504 | −56.954 | −27.933 | −22.375 | 1.00 | 15.59 | C |
| ATOM | 15974 | O | LEU | B | 504 | −57.177 | −27.323 | −23.414 | 1.00 | 15.30 | O |
| ATOM | 15976 | N | ALA | B | 505 | −56.732 | −29.242 | −22.341 | 1.00 | 15.89 | N |
| ATOM | 15977 | CA | ALA | B | 505 | −56.914 | −30.073 | −23.514 | 1.00 | 16.23 | C |

TABLE 16-7-continued

Coordinates of *P. tremuloides* IspS

| ATOM | 15979 | CB | ALA | B | 505 | −56.608 | −31.483 | −23.188 | 1.00 | 16.05 | C |
|---|---|---|---|---|---|---|---|---|---|---|---|
| ATOM | 15983 | C | ALA | B | 505 | −58.352 | −29.955 | −24.010 | 1.00 | 16.69 | C |
| ATOM | 15984 | O | ALA | B | 505 | −58.598 | −29.738 | −25.204 | 1.00 | 16.88 | O |
| ATOM | 15986 | N | ARG | B | 506 | −59.300 | −30.071 | −23.090 | 1.00 | 16.88 | N |
| ATOM | 15987 | CA | ARG | B | 506 | −60.709 | −29.972 | −23.457 | 1.00 | 17.20 | C |
| ATOM | 15989 | CB | ARG | B | 506 | −61.630 | −30.170 | −22.248 | 1.00 | 17.34 | C |
| ATOM | 15992 | CG | ARG | B | 506 | −61.549 | −31.537 | −21.614 | 1.00 | 17.46 | C |
| ATOM | 15995 | CD | ARG | B | 506 | −62.837 | −31.917 | −20.962 | 1.00 | 17.48 | C |
| ATOM | 15998 | NE | ARG | B | 506 | −62.783 | −33.280 | −20.435 | 1.00 | 18.37 | N |
| ATOM | 16000 | CZ | ARG | B | 506 | −62.404 | −33.613 | −19.201 | 1.00 | 19.03 | C |
| ATOM | 16001 | NH1 | ARG | B | 506 | −62.008 | −32.690 | −18.324 | 1.00 | 18.83 | N |
| ATOM | 16004 | NH2 | ARG | B | 506 | −62.415 | −34.892 | −18.841 | 1.00 | 19.72 | N |
| ATOM | 16007 | C | ARG | B | 506 | −61.038 | −28.646 | −24.114 | 1.00 | 17.32 | C |
| ATOM | 16008 | O | ARG | B | 506 | −61.754 | −28.622 | −25.111 | 1.00 | 17.41 | O |
| ATOM | 16010 | N | GLN | B | 507 | −60.540 | −27.543 | −23.564 | 1.00 | 17.59 | N |
| ATOM | 16011 | CA | GLN | B | 507 | −60.864 | −26.233 | −24.139 | 1.00 | 18.05 | C |
| ATOM | 16013 | CB | GLN | B | 507 | −60.382 | −25.090 | −23.258 | 1.00 | 18.16 | C |
| ATOM | 16016 | CG | GLN | B | 507 | −60.798 | −23.709 | −23.764 | 1.00 | 17.57 | C |
| ATOM | 16019 | CD | GLN | B | 507 | −62.291 | −23.508 | −23.723 | 1.00 | 17.42 | C |
| ATOM | 16020 | OE1 | GLN | B | 507 | −62.953 | −23.959 | −22.800 | 1.00 | 17.55 | O |
| ATOM | 16021 | NE2 | GLN | B | 507 | −62.832 | −22.823 | −24.722 | 1.00 | 17.56 | N |
| ATOM | 16024 | C | GLN | B | 507 | −60.258 | −26.060 | −25.521 | 1.00 | 18.49 | C |
| ATOM | 16025 | O | GLN | B | 507 | −60.855 | −25.413 | −26.380 | 1.00 | 18.73 | O |
| ATOM | 16027 | N | SER | B | 508 | −59.066 | −26.619 | −25.724 | 1.00 | 18.85 | N |
| ATOM | 16028 | CA | SER | B | 508 | −58.427 | −26.621 | −27.037 | 1.00 | 19.07 | C |
| ATOM | 16030 | CB | SER | B | 508 | −57.108 | −27.364 | −26.969 | 1.00 | 19.04 | C |
| ATOM | 16033 | OG | SER | B | 508 | −56.304 | −26.772 | −25.979 | 1.00 | 20.10 | O |
| ATOM | 16035 | C | SER | B | 508 | −59.305 | −27.296 | −28.065 | 1.00 | 19.12 | C |
| ATOM | 16036 | O | SER | B | 508 | −59.438 | −26.827 | −29.187 | 1.00 | 19.00 | O |
| ATOM | 16038 | N | HIS | B | 509 | −59.905 | −28.409 | −27.674 | 1.00 | 19.26 | N |
| ATOM | 16039 | CA | HIS | B | 509 | −60.814 | −29.095 | −28.559 | 1.00 | 19.33 | C |
| ATOM | 16041 | CB | HIS | B | 509 | −61.275 | −30.412 | −27.959 | 1.00 | 19.30 | C |
| ATOM | 16044 | CG | HIS | B | 509 | −60.263 | −31.501 | −28.067 | 1.00 | 18.71 | C |
| ATOM | 16045 | ND1 | HIS | B | 509 | −59.941 | −32.089 | −29.267 | 1.00 | 18.57 | N |
| ATOM | 16047 | CE1 | HIS | B | 509 | −59.020 | −33.012 | −29.064 | 1.00 | 19.07 | C |
| ATOM | 16049 | NE2 | HIS | B | 509 | −58.738 | −33.044 | −27.774 | 1.00 | 18.52 | N |
| ATOM | 16051 | CD2 | HIS | B | 509 | −59.499 | −32.105 | −27.129 | 1.00 | 18.43 | C |
| ATOM | 16053 | C | HIS | B | 509 | −62.017 | −28.251 | −28.878 | 1.00 | 19.60 | C |
| ATOM | 16054 | O | HIS | B | 509 | −62.491 | −28.286 | −29.969 | 1.00 | 19.68 | O |
| ATOM | 16056 | N | CYS | B | 510 | −62.540 | −27.502 | −27.932 | 1.00 | 20.12 | N |
| ATOM | 16057 | CA | CYS | B | 510 | −63.748 | −26.738 | −28.216 | 1.00 | 20.63 | C |
| ATOM | 16059 | CB | CYS | B | 510 | −64.493 | −26.492 | −26.915 | 1.00 | 20.70 | C |
| ATOM | 16062 | SG | CYS | B | 510 | −64.856 | −28.020 | −26.065 | 1.00 | 22.93 | S |
| ATOM | 16064 | C | CYS | B | 510 | −63.465 | −25.422 | −28.950 | 1.00 | 20.55 | C |
| ATOM | 16065 | O | CYS | B | 510 | −64.338 | −24.881 | −29.622 | 1.00 | 20.16 | O |
| ATOM | 16067 | N | THR | B | 511 | −62.236 | −24.933 | −28.827 | 1.00 | 20.89 | N |
| ATOM | 16068 | CA | THR | B | 511 | −61.833 | −23.654 | −29.378 | 1.00 | 21.32 | C |
| ATOM | 16070 | CB | THR | B | 511 | −60.682 | −23.107 | −28.550 | 1.00 | 20.76 | C |
| ATOM | 16072 | OG1 | THR | B | 511 | −61.208 | −22.619 | −27.324 | 1.00 | 19.50 | O |
| ATOM | 16074 | CG2 | THR | B | 511 | −59.961 | −21.994 | −29.253 | 1.00 | 19.79 | C |
| ATOM | 16078 | C | THR | B | 511 | −61.417 | −23.735 | −30.851 | 1.00 | 23.11 | C |
| ATOM | 16079 | O | THR | B | 511 | −61.910 | −22.992 | −31.694 | 1.00 | 22.75 | O |
| ATOM | 16081 | N | TYR | B | 512 | −60.501 | −24.646 | −31.152 | 1.00 | 25.46 | N |
| ATOM | 16082 | CA | TYR | B | 512 | −59.867 | −24.704 | −32.462 | 1.00 | 27.09 | C |
| ATOM | 16084 | CB | TYR | B | 512 | −58.397 | −25.107 | −32.327 | 1.00 | 27.16 | C |
| ATOM | 16087 | CG | TYR | B | 512 | −57.598 | −24.056 | −31.582 | 1.00 | 27.26 | C |
| ATOM | 16088 | CD1 | TYR | B | 512 | −57.300 | −22.834 | −32.182 | 1.00 | 28.18 | C |
| ATOM | 16090 | CE1 | TYR | B | 512 | −56.583 | −21.844 | −31.511 | 1.00 | 27.98 | C |
| ATOM | 16092 | CZ | TYR | B | 512 | −56.164 | −22.068 | −30.226 | 1.00 | 27.72 | C |
| ATOM | 16093 | OH | TYR | B | 512 | −55.462 | −21.072 | −29.584 | 1.00 | 27.09 | O |
| ATOM | 16095 | CE2 | TYR | B | 512 | −56.453 | −23.281 | −29.602 | 1.00 | 27.52 | C |
| ATOM | 16097 | CD2 | TYR | B | 512 | −57.171 | −24.262 | −30.278 | 1.00 | 26.68 | C |
| ATOM | 16099 | C | TYR | B | 512 | −60.633 | −25.623 | −33.382 | 1.00 | 28.79 | C |
| ATOM | 16100 | O | TYR | B | 512 | −61.050 | −25.179 | −34.444 | 1.00 | 28.98 | O |
| ATOM | 16102 | N | HIS | B | 513 | −60.789 | −26.893 | −32.991 | 1.00 | 31.06 | N |
| ATOM | 16103 | CA | HIS | B | 513 | −61.865 | −27.800 | −33.492 | 1.00 | 33.07 | C |
| ATOM | 16105 | CB | HIS | B | 513 | −62.740 | −28.208 | −32.265 | 1.00 | 33.66 | C |
| ATOM | 16108 | CG | HIS | B | 513 | −64.181 | −28.602 | −32.535 | 1.00 | 34.73 | C |
| ATOM | 16109 | ND1 | HIS | B | 513 | −65.035 | −27.903 | −33.367 | 1.00 | 35.70 | N |
| ATOM | 16111 | CE1 | HIS | B | 513 | −66.234 | −28.464 | −33.343 | 1.00 | 35.40 | C |
| ATOM | 16113 | NE2 | HIS | B | 513 | −66.206 | −29.469 | −32.491 | 1.00 | 35.10 | N |
| ATOM | 16115 | CD2 | HIS | B | 513 | −64.943 | −29.565 | −31.956 | 1.00 | 35.07 | C |
| ATOM | 16117 | C | HIS | B | 513 | −62.692 | −27.179 | −34.623 | 1.00 | 34.03 | C |
| ATOM | 16118 | O | HIS | B | 513 | −63.003 | −27.848 | −35.627 | 1.00 | 34.55 | O |
| ATOM | 16120 | N | ASN | B | 514 | −63.047 | −25.906 | −34.444 | 1.00 | 34.65 | N |
| ATOM | 16121 | CA | ASN | B | 514 | −63.713 | −25.123 | −35.483 | 1.00 | 35.15 | C |
| ATOM | 16123 | CB | ASN | B | 514 | −63.845 | −23.643 | −35.070 | 1.00 | 35.01 | C |
| ATOM | 16126 | CG | ASN | B | 514 | −64.704 | −23.456 | −33.820 | 1.00 | 33.48 | C |

TABLE 16-7-continued

Coordinates of *P. tremuloides* IspS

| ATOM | 16127 | OD1 | ASN | B | 514 | −64.787 | −24.343 | −32.968 | 1.00 | 30.92 | O |
|---|---|---|---|---|---|---|---|---|---|---|---|
| ATOM | 16128 | ND2 | ASN | B | 514 | −65.327 | −22.295 | −33.703 | 1.00 | 32.16 | N |
| ATOM | 16131 | C | ASN | B | 514 | −63.192 | −25.274 | −36.942 | 1.00 | 36.08 | C |
| ATOM | 16132 | O | ASN | B | 514 | −62.010 | −25.051 | −37.254 | 1.00 | 35.69 | O |
| ATOM | 16134 | N | GLY | B | 515 | −64.119 | −25.765 | −37.772 | 1.00 | 37.15 | N |
| ATOM | 16135 | CA | GLY | B | 515 | −64.224 | −25.493 | −39.177 | 1.00 | 37.94 | C |
| ATOM | 16138 | C | GLY | B | 515 | −65.269 | −24.384 | −39.284 | 1.00 | 39.01 | C |
| ATOM | 16139 | O | GLY | B | 515 | −64.904 | −23.286 | −39.702 | 1.00 | 39.58 | O |
| ATOM | 16141 | N | ASP | B | 516 | −66.550 | −24.585 | −38.909 | 1.00 | 39.95 | N |
| ATOM | 16142 | CA | ASP | B | 516 | −67.167 | −25.810 | −38.349 | 1.00 | 40.65 | C |
| ATOM | 16144 | CB | ASP | B | 516 | −67.296 | −25.652 | −36.836 | 1.00 | 41.09 | C |
| ATOM | 16147 | CG | ASP | B | 516 | −66.318 | −26.511 | −36.063 | 1.00 | 43.63 | C |
| ATOM | 16148 | OD1 | ASP | B | 516 | −65.697 | −27.434 | −36.662 | 1.00 | 45.83 | O |
| ATOM | 16149 | OD2 | ASP | B | 516 | −66.152 | −26.246 | −34.843 | 1.00 | 47.12 | O |
| ATOM | 16150 | C | ASP | B | 516 | −68.603 | −26.067 | −38.853 | 1.00 | 40.78 | C |
| ATOM | 16151 | O | ASP | B | 516 | −69.134 | −25.301 | −39.660 | 1.00 | 41.28 | O |
| ATOM | 16153 | N | ALA | B | 517 | −69.222 | −27.141 | −38.349 | 1.00 | 40.66 | N |
| ATOM | 16154 | CA | ALA | B | 517 | −70.675 | −27.396 | −38.468 | 1.00 | 40.60 | C |
| ATOM | 16156 | CB | ALA | B | 517 | −71.422 | −26.622 | −37.359 | 1.00 | 40.27 | C |
| ATOM | 16160 | C | ALA | B | 517 | −71.295 | −27.106 | −39.862 | 1.00 | 40.79 | C |
| ATOM | 16161 | O | ALA | B | 517 | −70.654 | −27.296 | −40.899 | 1.00 | 40.67 | O |
| ATOM | 16163 | N | HIS | B | 518 | −72.562 | −26.696 | −39.874 | 1.00 | 41.13 | N |
| ATOM | 16164 | CA | HIS | B | 518 | −73.162 | −26.033 | −41.039 | 1.00 | 41.60 | C |
| ATOM | 16166 | CB | HIS | B | 518 | −74.446 | −26.756 | −41.480 | 1.00 | 42.24 | C |
| ATOM | 16169 | CG | HIS | B | 518 | −74.207 | −28.179 | −41.910 | 1.00 | 45.54 | C |
| ATOM | 16170 | ND1 | HIS | B | 518 | −73.441 | −28.509 | −43.012 | 1.00 | 48.51 | N |
| ATOM | 16172 | CE1 | HIS | B | 518 | −73.392 | −29.825 | −43.140 | 1.00 | 48.79 | C |
| ATOM | 16174 | NE2 | HIS | B | 518 | −74.092 | −30.364 | −42.156 | 1.00 | 49.12 | N |
| ATOM | 16176 | CD2 | HIS | B | 518 | −74.608 | −29.357 | −41.369 | 1.00 | 48.28 | C |
| ATOM | 16178 | C | HIS | B | 518 | −73.377 | −24.545 | −40.686 | 1.00 | 40.84 | C |
| ATOM | 16179 | O | HIS | B | 518 | −74.487 | −23.997 | −40.769 | 1.00 | 40.60 | O |
| ATOM | 16181 | N | THR | B | 519 | −72.261 | −23.932 | −40.275 | 1.00 | 40.10 | N |
| ATOM | 16182 | CA | THR | B | 519 | −72.143 | −22.521 | −39.878 | 1.00 | 39.39 | C |
| ATOM | 16184 | CB | THR | B | 519 | −72.561 | −22.263 | −38.393 | 1.00 | 39.40 | C |
| ATOM | 16186 | OG1 | THR | B | 519 | −71.823 | −23.131 | −37.517 | 1.00 | 39.55 | O |
| ATOM | 16188 | CG2 | THR | B | 519 | −74.074 | −22.460 | −38.178 | 1.00 | 38.98 | C |
| ATOM | 16192 | C | THR | B | 519 | −70.654 | −22.164 | −40.059 | 1.00 | 38.81 | C |
| ATOM | 16193 | O | THR | B | 519 | −69.800 | −23.050 | −40.067 | 1.00 | 38.48 | O |
| ATOM | 16195 | N | SER | B | 520 | −70.338 | −20.881 | −40.199 | 1.00 | 38.19 | N |
| ATOM | 16196 | CA | SER | B | 520 | −68.959 | −20.453 | −40.521 | 1.00 | 37.77 | C |
| ATOM | 16198 | CB | SER | B | 520 | −68.983 | −18.976 | −40.960 | 1.00 | 37.76 | C |
| ATOM | 16201 | OG | SER | B | 520 | −68.760 | −18.106 | −39.870 | 1.00 | 38.49 | O |
| ATOM | 16203 | C | SER | B | 520 | −67.974 | −20.724 | −39.340 | 1.00 | 37.24 | C |
| ATOM | 16204 | O | SER | B | 520 | −68.394 | −21.267 | −38.320 | 1.00 | 36.89 | O |
| ATOM | 16206 | N | PRO | B | 521 | −66.671 | −20.350 | −39.472 | 1.00 | 36.96 | N |
| ATOM | 16207 | CA | PRO | B | 521 | −65.692 | −20.638 | −38.396 | 1.00 | 36.80 | C |
| ATOM | 16209 | CB | PRO | B | 521 | −64.320 | −20.354 | −39.041 | 1.00 | 36.68 | C |
| ATOM | 16212 | CG | PRO | B | 521 | −64.599 | −19.593 | −40.309 | 1.00 | 37.19 | C |
| ATOM | 16215 | CD | PRO | B | 521 | −66.091 | −19.469 | −40.507 | 1.00 | 37.10 | C |
| ATOM | 16218 | C | PRO | B | 521 | −65.915 | −19.763 | −37.168 | 1.00 | 36.68 | C |
| ATOM | 16219 | O | PRO | B | 521 | −66.233 | −20.289 | −36.105 | 1.00 | 36.90 | O |
| ATOM | 16220 | N | ASP | B | 522 | −65.744 | −18.445 | −37.298 | 1.00 | 36.61 | N |
| ATOM | 16221 | CA | ASP | B | 522 | −66.373 | −17.528 | −36.347 | 1.00 | 36.58 | C |
| ATOM | 16223 | CB | ASP | B | 522 | −65.938 | −16.070 | −36.543 | 1.00 | 36.82 | C |
| ATOM | 16226 | CG | ASP | B | 522 | −64.456 | −15.846 | −36.243 | 1.00 | 37.94 | C |
| ATOM | 16227 | OD1 | ASP | B | 522 | −63.848 | −16.627 | −35.473 | 1.00 | 39.62 | O |
| ATOM | 16228 | OD2 | ASP | B | 522 | −63.891 | −14.876 | −36.790 | 1.00 | 39.40 | O |
| ATOM | 16229 | C | ASP | B | 522 | −67.836 | −17.718 | −36.681 | 1.00 | 36.12 | C |
| ATOM | 16230 | O | ASP | B | 522 | −68.150 | −18.306 | −37.702 | 1.00 | 35.98 | O |
| ATOM | 16232 | N | GLU | B | 523 | −68.732 | −17.249 | −35.830 | 1.00 | 35.69 | N |
| ATOM | 16233 | CA | GLU | B | 523 | −70.152 | −17.605 | −35.927 | 1.00 | 35.46 | C |
| ATOM | 16235 | CB | GLU | B | 523 | −70.703 | −17.560 | −37.379 | 1.00 | 35.51 | C |
| ATOM | 16238 | CG | GLU | B | 523 | −70.535 | −16.175 | −38.061 | 1.00 | 36.11 | C |
| ATOM | 16241 | CD | GLU | B | 523 | −70.854 | −16.136 | −39.572 | 1.00 | 36.72 | C |
| ATOM | 16242 | OE1 | GLU | B | 523 | −71.848 | −16.767 | −40.013 | 1.00 | 37.20 | O |
| ATOM | 16243 | OE2 | GLU | B | 523 | −70.101 | −15.452 | −40.314 | 1.00 | 35.53 | O |
| ATOM | 16244 | C | GLU | B | 523 | −70.440 | −18.943 | −35.216 | 1.00 | 34.97 | C |
| ATOM | 16245 | O | GLU | B | 523 | −71.557 | −19.148 | −34.765 | 1.00 | 35.02 | O |
| ATOM | 16247 | N | LEU | B | 524 | −69.462 | −19.846 | −35.099 | 1.00 | 34.59 | N |
| ATOM | 16248 | CA | LEU | B | 524 | −69.503 | −20.832 | −34.004 | 1.00 | 34.45 | C |
| ATOM | 16250 | CB | LEU | B | 524 | −68.735 | −22.136 | −34.286 | 1.00 | 34.21 | C |
| ATOM | 16253 | CG | LEU | B | 524 | −69.530 | −23.434 | −34.508 | 1.00 | 33.92 | C |
| ATOM | 16255 | CD1 | LEU | B | 524 | −68.657 | −24.627 | −34.227 | 1.00 | 32.21 | C |
| ATOM | 16259 | CD2 | LEU | B | 524 | −70.794 | −23.520 | −33.641 | 1.00 | 34.06 | C |
| ATOM | 16263 | C | LEU | B | 524 | −68.901 | −20.162 | −32.791 | 1.00 | 34.38 | C |
| ATOM | 16264 | O | LEU | B | 524 | −69.535 | −20.067 | −31.741 | 1.00 | 34.49 | O |
| ATOM | 16266 | N | THR | B | 525 | −67.670 | −19.688 | −32.958 | 1.00 | 34.30 | N |
| ATOM | 16267 | CA | THR | B | 525 | −66.913 | −19.073 | −31.874 | 1.00 | 34.23 | C |

TABLE 16-7-continued

Coordinates of *P. tremuloides* IspS

| ATOM | 16269 | CB  | THR | B | 525 | −65.570 | −18.524 | −32.380 | 1.00 | 34.04 | C |
|------|-------|-----|-----|---|-----|---------|---------|---------|------|-------|---|
| ATOM | 16271 | OG1 | THR | B | 525 | −64.894 | −19.549 | −33.112 | 1.00 | 33.83 | O |
| ATOM | 16273 | CG2 | THR | B | 525 | −64.689 | −18.087 | −31.227 | 1.00 | 33.37 | C |
| ATOM | 16277 | C   | THR | B | 525 | −67.702 | −17.960 | −31.184 | 1.00 | 34.46 | C |
| ATOM | 16278 | O   | THR | B | 525 | −67.684 | −17.858 | −29.955 | 1.00 | 34.57 | O |
| ATOM | 16280 | N   | ARG | B | 526 | −68.401 | −17.144 | −31.969 | 1.00 | 34.54 | N |
| ATOM | 16281 | CA  | ARG | B | 526 | −69.200 | −16.056 | −31.418 | 1.00 | 34.60 | C |
| ATOM | 16283 | CB  | ARG | B | 526 | −69.571 | −15.059 | −32.513 | 1.00 | 35.04 | C |
| ATOM | 16286 | CG  | ARG | B | 526 | −70.256 | −13.800 | −32.013 | 1.00 | 37.13 | C |
| ATOM | 16289 | CD  | ARG | B | 526 | −70.143 | −12.656 | −33.026 | 1.00 | 39.87 | C |
| ATOM | 16292 | NE  | ARG | B | 526 | −70.353 | −13.075 | −34.420 | 1.00 | 42.28 | N |
| ATOM | 16294 | CZ  | ARG | B | 526 | −71.543 | −13.292 | −35.000 | 1.00 | 44.26 | C |
| ATOM | 16295 | NH1 | ARG | B | 526 | −72.685 | −13.159 | −34.320 | 1.00 | 44.66 | N |
| ATOM | 16298 | NH2 | ARG | B | 526 | −71.593 | −13.658 | −36.279 | 1.00 | 44.49 | N |
| ATOM | 16301 | C   | ARG | B | 526 | −70.448 | −16.593 | −30.735 | 1.00 | 33.91 | C |
| ATOM | 16302 | O   | ARG | B | 526 | −70.848 | −16.074 | −29.704 | 1.00 | 33.74 | O |
| ATOM | 16304 | N   | LYS | B | 527 | −71.048 | −17.637 | −31.306 | 1.00 | 33.39 | N |
| ATOM | 16305 | CA  | LYS | B | 527 | −72.240 | −18.252 | −30.722 | 1.00 | 33.15 | C |
| ATOM | 16307 | CB  | LYS | B | 527 | −72.837 | −19.332 | −31.639 | 1.00 | 33.42 | C |
| ATOM | 16310 | CG  | LYS | B | 527 | −73.898 | −18.804 | −32.609 | 1.00 | 34.55 | C |
| ATOM | 16313 | CD  | LYS | B | 527 | −74.643 | −19.919 | −33.358 | 1.00 | 35.43 | C |
| ATOM | 16316 | CE  | LYS | B | 527 | −75.230 | −19.383 | −34.667 | 1.00 | 36.11 | C |
| ATOM | 16319 | NZ  | LYS | B | 527 | −76.076 | −20.372 | −35.384 | 1.00 | 37.04 | N |
| ATOM | 16323 | C   | LYS | B | 527 | −71.925 | −18.865 | −29.378 | 1.00 | 32.36 | C |
| ATOM | 16324 | O   | LYS | B | 527 | −72.589 | −18.584 | −28.387 | 1.00 | 32.56 | O |
| ATOM | 16326 | N   | ARG | B | 528 | −70.909 | −19.713 | −29.358 | 1.00 | 31.53 | N |
| ATOM | 16327 | CA  | ARG | B | 528 | −70.502 | −20.401 | −28.138 | 1.00 | 30.77 | C |
| ATOM | 16329 | CB  | ARG | B | 528 | −69.283 | −21.286 | −28.414 | 1.00 | 30.55 | C |
| ATOM | 16332 | CG  | ARG | B | 528 | −69.624 | −22.519 | −29.252 | 1.00 | 29.48 | C |
| ATOM | 16335 | CD  | ARG | B | 528 | −68.418 | −23.417 | −29.493 | 1.00 | 28.05 | C |
| ATOM | 16338 | NE  | ARG | B | 528 | −68.811 | −24.774 | −29.880 | 1.00 | 26.55 | N |
| ATOM | 16340 | CZ  | ARG | B | 528 | −67.968 | −25.719 | −30.288 | 1.00 | 25.87 | C |
| ATOM | 16341 | NH1 | ARG | B | 528 | −66.668 | −25.472 | −30.385 | 1.00 | 26.33 | N |
| ATOM | 16344 | NH2 | ARG | B | 528 | −68.424 | −26.920 | −30.615 | 1.00 | 25.49 | N |
| ATOM | 16347 | C   | ARG | B | 528 | −70.225 | −19.415 | −27.004 | 1.00 | 30.42 | C |
| ATOM | 16348 | O   | ARG | B | 528 | −70.721 | −19.582 | −25.885 | 1.00 | 30.30 | O |
| ATOM | 16350 | N   | VAL | B | 529 | −69.455 | −18.376 | −27.307 | 1.00 | 29.96 | N |
| ATOM | 16351 | CA  | VAL | B | 529 | −69.194 | −17.312 | −26.342 | 1.00 | 29.47 | C |
| ATOM | 16353 | CB  | VAL | B | 529 | −68.261 | −16.227 | −26.932 | 1.00 | 29.40 | C |
| ATOM | 16355 | CG1 | VAL | B | 529 | −68.269 | −14.968 | −26.081 | 1.00 | 29.18 | C |
| ATOM | 16359 | CG2 | VAL | B | 529 | −66.845 | −16.782 | −27.062 | 1.00 | 28.90 | C |
| ATOM | 16363 | C   | VAL | B | 529 | −70.516 | −16.723 | −25.841 | 1.00 | 28.98 | C |
| ATOM | 16364 | O   | VAL | B | 529 | −70.759 | −16.682 | −24.641 | 1.00 | 28.97 | O |
| ATOM | 16366 | N   | LEU | B | 530 | −71.384 | −16.308 | −26.752 | 1.00 | 28.54 | N |
| ATOM | 16367 | CA  | LEU | B | 530 | −72.709 | −15.824 | −26.353 | 1.00 | 28.23 | C |
| ATOM | 16369 | CB  | LEU | B | 530 | −73.631 | −15.604 | −27.559 | 1.00 | 28.09 | C |
| ATOM | 16372 | CG  | LEU | B | 530 | −73.767 | −14.150 | −28.007 | 1.00 | 28.15 | C |
| ATOM | 16374 | CD1 | LEU | B | 530 | −72.412 | −13.570 | −28.406 | 1.00 | 27.99 | C |
| ATOM | 16378 | CD2 | LEU | B | 530 | −74.784 | −14.034 | −29.150 | 1.00 | 28.85 | C |
| ATOM | 16382 | C   | LEU | B | 530 | −73.389 | −16.767 | −25.367 | 1.00 | 27.88 | C |
| ATOM | 16383 | O   | LEU | B | 530 | −73.932 | −16.319 | −24.363 | 1.00 | 28.11 | O |
| ATOM | 16385 | N   | SER | B | 531 | −73.352 | −18.066 | −25.652 | 1.00 | 27.28 | N |
| ATOM | 16386 | CA  | SER | B | 531 | −74.081 | −19.049 | −24.849 | 1.00 | 26.68 | C |
| ATOM | 16388 | CB  | SER | B | 531 | −74.209 | −20.363 | −25.612 | 1.00 | 26.68 | C |
| ATOM | 16391 | OG  | SER | B | 531 | −72.970 | −21.033 | −25.681 | 1.00 | 26.67 | O |
| ATOM | 16393 | C   | SER | B | 531 | −73.410 | −19.312 | −23.514 | 1.00 | 26.20 | C |
| ATOM | 16394 | O   | SER | B | 531 | −74.076 | −19.550 | −22.511 | 1.00 | 25.86 | O |
| ATOM | 16396 | N   | VAL | B | 532 | −72.085 | −19.281 | −23.512 | 1.00 | 25.86 | N |
| ATOM | 16397 | CA  | VAL | B | 532 | −71.320 | −19.562 | −22.306 | 1.00 | 25.51 | C |
| ATOM | 16399 | CB  | VAL | B | 532 | −69.891 | −20.055 | −22.651 | 1.00 | 25.34 | C |
| ATOM | 16401 | CG1 | VAL | B | 532 | −68.955 | −19.932 | −21.460 | 1.00 | 24.01 | C |
| ATOM | 16405 | CG2 | VAL | B | 532 | −69.950 | −21.484 | −23.158 | 1.00 | 24.95 | C |
| ATOM | 16409 | C   | VAL | B | 532 | −71.271 | −18.357 | −21.373 | 1.00 | 25.52 | C |
| ATOM | 16410 | O   | VAL | B | 532 | −71.377 | −18.523 | −20.164 | 1.00 | 25.82 | O |
| ATOM | 16412 | N   | ILE | B | 533 | −71.137 | −17.158 | −21.935 | 1.00 | 25.39 | N |
| ATOM | 16413 | CA  | ILE | B | 533 | −70.875 | −15.954 | −21.151 | 1.00 | 25.48 | C |
| ATOM | 16415 | CB  | ILE | B | 533 | −69.666 | −15.185 | −21.732 | 1.00 | 25.30 | C |
| ATOM | 16417 | CG1 | ILE | B | 533 | −68.375 | −15.928 | −21.451 | 1.00 | 24.91 | C |
| ATOM | 16420 | CD1 | ILE | B | 533 | −68.118 | −16.120 | −19.989 | 1.00 | 25.00 | C |
| ATOM | 16424 | CG2 | ILE | B | 533 | −69.553 | −13.797 | −21.130 | 1.00 | 25.81 | C |
| ATOM | 16428 | C   | ILE | B | 533 | −72.065 | −14.983 | −21.030 | 1.00 | 25.77 | C |
| ATOM | 16429 | O   | ILE | B | 533 | −72.537 | −14.707 | −19.928 | 1.00 | 25.77 | O |
| ATOM | 16431 | N   | THR | B | 534 | −72.541 | −14.442 | −22.142 | 1.00 | 25.98 | N |
| ATOM | 16432 | CA  | THR | B | 534 | −73.446 | −13.295 | −22.064 | 1.00 | 26.31 | C |
| ATOM | 16434 | CB  | THR | B | 534 | −73.094 | −12.253 | −23.143 | 1.00 | 26.21 | C |
| ATOM | 16436 | OG1 | THR | B | 534 | −72.914 | −12.909 | −24.397 | 1.00 | 26.72 | O |
| ATOM | 16438 | CG2 | THR | B | 534 | −71.795 | −11.535 | −22.781 | 1.00 | 25.97 | C |
| ATOM | 16442 | C   | THR | B | 534 | −74.961 | −13.621 | −22.064 | 1.00 | 26.50 | C |

TABLE 16-7-continued

Coordinates of *P. tremuloides* IspS

| ATOM | 16443 | O | THR | B | 534 | −75.713 | −12.974 | −21.344 | 1.00 | 26.67 | O |
|---|---|---|---|---|---|---|---|---|---|---|---|
| ATOM | 16445 | N | GLU | B | 535 | −75.410 | −14.616 | −22.829 | 1.00 | 26.55 | N |
| ATOM | 16446 | CA | GLU | B | 535 | −76.851 | −14.892 | −22.961 | 1.00 | 26.50 | C |
| ATOM | 16448 | CB | GLU | B | 535 | −77.197 | −15.197 | −24.426 | 1.00 | 26.68 | C |
| ATOM | 16451 | CG | GLU | B | 535 | −77.226 | −13.936 | −25.296 | 1.00 | 27.68 | C |
| ATOM | 16454 | CD | GLU | B | 535 | −78.193 | −14.014 | −26.475 | 1.00 | 28.75 | C |
| ATOM | 16455 | OE1 | GLU | B | 535 | −79.370 | −13.588 | −26.330 | 1.00 | 27.72 | O |
| ATOM | 16456 | OE2 | GLU | B | 535 | −77.762 | −14.492 | −27.549 | 1.00 | 30.06 | O |
| ATOM | 16457 | C | GLU | B | 535 | −77.355 | −16.019 | −22.056 | 1.00 | 26.19 | C |
| ATOM | 16458 | O | GLU | B | 535 | −77.021 | −17.171 | −22.279 | 1.00 | 26.15 | O |
| ATOM | 16460 | N | PRO | B | 536 | −78.186 | −15.697 | −21.047 | 1.00 | 26.05 | N |
| ATOM | 16461 | CA | PRO | B | 536 | −78.692 | −16.763 | −20.196 | 1.00 | 26.05 | C |
| ATOM | 16463 | CB | PRO | B | 536 | −79.495 | −16.018 | −19.118 | 1.00 | 25.87 | C |
| ATOM | 16466 | CG | PRO | B | 536 | −79.140 | −14.621 | −19.239 | 1.00 | 25.88 | C |
| ATOM | 16469 | CD | PRO | B | 536 | −78.760 | −14.402 | −20.660 | 1.00 | 26.21 | C |
| ATOM | 16472 | C | PRO | B | 536 | −79.608 | −17.717 | −20.943 | 1.00 | 26.14 | C |
| ATOM | 16473 | O | PRO | B | 536 | −80.173 | −17.359 | −21.973 | 1.00 | 25.99 | O |
| ATOM | 16474 | N | ILE | B | 537 | −79.746 | −18.924 | −20.411 | 1.00 | 26.38 | N |
| ATOM | 16475 | CA | ILE | B | 537 | −80.662 | −19.905 | −20.960 | 1.00 | 26.58 | C |
| ATOM | 16477 | CB | ILE | B | 537 | −80.443 | −21.292 | −20.333 | 1.00 | 26.47 | C |
| ATOM | 16479 | CG1 | ILE | B | 537 | −79.023 | −21.789 | −20.600 | 1.00 | 26.38 | C |
| ATOM | 16482 | CD1 | ILE | B | 537 | −78.709 | −23.102 | −19.907 | 1.00 | 26.40 | C |
| ATOM | 16486 | CG2 | ILE | B | 537 | −81.430 | −22.300 | −20.890 | 1.00 | 26.71 | C |
| ATOM | 16490 | C | ILE | B | 537 | −82.072 | −19.420 | −20.657 | 1.00 | 26.93 | C |
| ATOM | 16491 | O | ILE | B | 537 | −82.347 | −18.965 | −19.545 | 1.00 | 26.81 | O |
| ATOM | 16493 | N | LEU | B | 538 | −82.963 | −19.491 | −21.641 | 1.00 | 27.36 | N |
| ATOM | 16494 | CA | LEU | B | 538 | −84.309 | −18.984 | −21.439 | 1.00 | 27.68 | C |
| ATOM | 16496 | CB | LEU | B | 538 | −85.181 | −19.094 | −22.698 | 1.00 | 27.75 | C |
| ATOM | 16499 | CG | LEU | B | 538 | −84.782 | −18.291 | −23.949 | 1.00 | 27.47 | C |
| ATOM | 16501 | CD1 | LEU | B | 538 | −85.992 | −18.109 | −24.844 | 1.00 | 27.11 | C |
| ATOM | 16505 | CD2 | LEU | B | 538 | −84.164 | −16.933 | −23.621 | 1.00 | 26.99 | C |
| ATOM | 16509 | C | LEU | B | 538 | −84.919 | −19.752 | −20.288 | 1.00 | 28.01 | C |
| ATOM | 16512 | N | PRO | B | 539 | −85.645 | −19.046 | −19.421 | 1.00 | 28.69 | N |
| ATOM | 16513 | CA | PRO | B | 539 | −86.028 | −19.631 | −18.152 | 1.00 | 29.05 | C |
| ATOM | 16515 | CB | PRO | B | 539 | −86.640 | −18.452 | −17.397 | 1.00 | 29.08 | C |
| ATOM | 16518 | CG | PRO | B | 539 | −87.144 | −17.548 | −18.447 | 1.00 | 28.86 | C |
| ATOM | 16521 | CD | PRO | B | 539 | −86.298 | −17.748 | −19.660 | 1.00 | 28.62 | C |
| ATOM | 16524 | C | PRO | B | 539 | −87.035 | −20.767 | −18.259 | 1.00 | 29.51 | C |
| ATOM | 16525 | O | PRO | B | 539 | −87.665 | −20.970 | −19.297 | 1.00 | 29.23 | O |
| ATOM | 16526 | N | PHE | B | 540 | −87.164 | −21.500 | −17.159 | 1.00 | 30.25 | N |
| ATOM | 16527 | CA | PHE | B | 540 | −88.089 | −22.613 | −17.070 | 1.00 | 30.56 | C |
| ATOM | 16529 | CB | PHE | B | 540 | −87.971 | −23.297 | −15.708 | 1.00 | 30.73 | C |
| ATOM | 16532 | CG | PHE | B | 540 | −88.848 | −24.499 | −15.567 | 1.00 | 30.49 | C |
| ATOM | 16533 | CD1 | PHE | B | 540 | −89.910 | −24.505 | −14.683 | 1.00 | 30.32 | C |
| ATOM | 16535 | CE1 | PHE | B | 540 | −90.718 | −25.614 | −14.568 | 1.00 | 30.59 | C |
| ATOM | 16537 | CZ | PHE | B | 540 | −90.475 | −26.722 | −15.346 | 1.00 | 30.55 | C |
| ATOM | 16539 | CE2 | PHE | B | 540 | −89.420 | −26.720 | −16.234 | 1.00 | 30.68 | C |
| ATOM | 16541 | CD2 | PHE | B | 540 | −88.619 | −25.617 | −16.342 | 1.00 | 30.43 | C |
| ATOM | 16543 | C | PHE | B | 540 | −89.507 | −22.120 | −17.257 | 1.00 | 30.76 | C |
| ATOM | 16544 | O | PHE | B | 540 | −89.967 | −21.257 | −16.508 | 1.00 | 30.59 | O |
| ATOM | 16546 | N | GLU | B | 541 | −90.184 | −22.677 | −18.259 | 1.00 | 31.13 | N |
| ATOM | 16547 | CA | GLU | B | 541 | −91.553 | −22.289 | −18.608 | 1.00 | 31.45 | C |
| ATOM | 16549 | CB | GLU | B | 541 | −91.525 | −21.186 | −19.680 | 1.00 | 31.60 | C |
| ATOM | 16552 | CG | GLU | B | 541 | −92.860 | −20.454 | −19.911 | 1.00 | 32.56 | C |
| ATOM | 16555 | CD | GLU | B | 541 | −93.773 | −21.133 | −20.935 | 1.00 | 33.64 | C |
| ATOM | 16556 | OE1 | GLU | B | 541 | −93.261 | −21.922 | −21.771 | 1.00 | 35.06 | O |
| ATOM | 16557 | OE2 | GLU | B | 541 | −95.002 | −20.868 | −20.901 | 1.00 | 32.44 | O |
| ATOM | 16558 | C | GLU | B | 541 | −92.326 | −23.510 | −19.105 | 1.00 | 31.31 | C |
| ATOM | 16559 | O | GLU | B | 541 | −92.860 | −24.286 | −18.310 | 1.00 | 31.30 | O |
| ATOM | 16562 | MG | MG | C | 1 | −42.844 | 11.427 | 13.309 | 1.00 | 46.29 | MG |
| ATOM | 16561 | MG | MG | C | 2 | −46.615 | −18.454 | −33.231 | 1.00 | 48.45 | MG |
| ATOM | 16563 | O | HOH | E | 1 | −50.507 | −5.408 | −4.491 | 1.00 | 17.42 | O |
| ATOM | 16566 | O | HOH | E | 2 | −64.748 | −36.007 | −11.725 | 1.00 | 2.00 | O |
| ATOM | 16569 | O | HOH | E | 3 | −40.643 | −2.220 | −34.996 | 1.00 | 2.00 | O |
| ATOM | 16572 | O | HOH | E | 4 | −36.090 | −9.757 | −37.074 | 1.00 | 17.20 | O |
| ATOM | 16575 | O | HOH | E | 5 | −46.117 | −37.662 | −22.916 | 1.00 | 17.03 | O |
| ATOM | 16578 | O | HOH | E | 6 | −49.541 | 35.476 | 6.921 | 1.00 | 14.03 | O |
| ATOM | 16581 | O | HOH | E | 7 | −32.288 | 27.572 | 16.443 | 1.00 | 13.16 | O |
| ATOM | 16584 | O | HOH | E | 8 | −50.706 | 10.207 | −15.061 | 1.00 | 18.73 | O |
| ATOM | 16587 | O | HOH | E | 9 | −77.188 | 36.767 | −9.218 | 1.00 | 8.05 | O |
| ATOM | 16590 | O | HOH | E | 10 | −90.260 | −31.248 | −21.071 | 1.00 | 2.00 | O |
| ATOM | 16593 | O | HOH | E | 11 | −70.920 | −33.414 | −3.884 | 1.00 | 9.35 | O |
| ATOM | 16596 | O | HOH | E | 12 | −37.761 | −21.294 | −9.249 | 1.00 | 25.78 | O |
| ATOM | 16599 | O | HOH | E | 13 | −76.050 | 23.855 | −18.293 | 1.00 | 2.00 | O |
| ATOM | 16602 | O | HOH | E | 14 | −76.876 | −19.575 | −22.856 | 1.00 | 19.25 | O |
| ATOM | 16605 | O | HOH | E | 15 | −40.936 | 11.629 | −24.832 | 1.00 | 22.29 | O |

TABLE 16-7-continued

| | | | Coordinates of *P. tremuloides* IspS | | | | | | |
|---|---|---|---|---|---|---|---|---|---|
| ATOM | 16608 | O | HOH | E | 16 | −85.551 | 34.832 | 3.260 | 1.00 25.14 O |
| ATOM | 16611 | O | HOH | E | 17 | −56.825 | 31.771 | −7.464 | 1.00 17.27 O |
| ATOM | 16614 | O | HOH | E | 18 | −76.222 | 39.261 | −.613 | 1.00 25.47 O |

Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention, which are obvious to those skilled in the relevant fields, are intended to be within the scope of the following claims.

We claim:

1. An isolated host cell comprising a heterologous polynucleotide sequence encoding an isoprene synthase variant in operable combination with a promoter, wherein said isoprene synthase variant comprises one or more amino acid substitution(s) at one or more amino acid residues corresponding to a poplar isoprene synthase having the sequence of SEQ ID NO: 120, wherein said substitution(s) are selected from the group consisting of V10M, F12S, T15A, E18G, V58I, V58F, L70Q, L70R, L70V, L70T, T71P, V79L, E89D, G94A, S119F, F120L, G127R, E175V, T212I, S257A, R262G, A266G, F280L, N297K, F305L, L319M, E323K, A328T, D342E, A359T, K366N, E368D, L374M, S396T, V418S, K438N, H440R, T442A, I449V, A469S, K500R, K505Q, G507S, S509N, F511Y, and N532K; and
wherein the variant is capable of more effectively converting dimethylallyl diphosphate (DMAPP) to isoprene, as compared to an isoprene synthase variant without a substitution.

2. The host cell of claim 1 wherein at least one amino acid substitution is a L70R substitution.

3. The host cell of claim 1 wherein at least one amino acid substitution is a G507S substitution.

4. The host cell of claim 1 wherein the variant comprises one of more amino acid substitutions selected from the group consisting of G127R/F511Y, L70Q/G94A/R262G/F305L, F12S/T15A/E18G/N297K, S396T/T442I, V10M/E323K, F120L/A266G, K438N/K500R, V79L/S509N, E175V/S257A/E368D/A469S, T71P/L374M, F280L/H440R, E89D/H440R, V58F/A328T/N532K, S119F/D342E/I449V, and K366N/G507S.

5. The host cell of claim 1 wherein the polynucleotide sequence is contained within a plasmid.

6. The host cell of claim 5 wherein the polynucleotide sequence is integrated into a chromosome of the host cell.

7. The host cell of claim 1 wherein the host is selected from the group consisting of gram-positive bacterial cells, gram-negative bacterial cells, filamentous fungal cells, and yeast cells.

8. The host cell of claim 1 wherein the host is selected from the group consisting of Escherichia sp. (E. coli), Panteoa sp. (P. citrea), Bacillus sp. (B. subtilis), Saccharomyces sp. (S. cerevisia), Yarrowia sp. (Y. lipolytica), and Trichoderma (T. reesei).

9. The host cell of claim 1 wherein the host cell is cultured in a medium comprising a carbon source selected from the group consisting of glucose, glycerol, glycerine, dihydroxyacetone, yeast extract, biomass, molasses, sucrose, and oil.

10. The host cell of claim 1 wherein the host cell further comprises a heterologous or native nucleic acid encoding an isopentenyl-diphosphate delta-isomerase (IDI) polypeptide or a heterologous or native nucleic acid encoding a 1-Deoxyxylulose-5-phosphate synthase (DXS) polypeptide, optionally in combination with the native 1-deoxy-D-xylulose-5-phosphate (DXP) pathway.

11. The host cell of claim 1 wherein the host cell further comprises one or more nucleic acids encoding an IDI polypeptide and a DXS polypeptide.

12. The host cell of claim 1 wherein the host cell comprises one vector encoding the isoprene synthase variant, the IDI polypeptide, and the DXS polypeptide.

13. The host cell of claim 12 wherein the host cell further comprises a nucleic acid encoding a mevalonate (MVA) pathway polypeptide selected from the group consisting of an MVA pathway polypeptide from Saccharomyces cerevisia and Enterococcus faecalis.

14. The host cell of claim 1 wherein the host cell further comprises one or more nucleic acids encoding an MVA pathway polypeptide and a DXS polypeptide and wherein one vector encodes the isoprene synthase variant, the MVA pathway polypeptide, and the DXS polypeptide.

15. The host cell of claim 14 wherein the host cell further comprises one or more nucleic acids encoding a DXS polypeptide, an IDI polypeptide, or one or more of the rest of the DXP pathway polypeptides, and a MVA pathway polypeptide.

16. The host cell of claim 1 wherein the host cell further comprises one or more nucleic acid(s) encoding an MVA pathway polypeptide.

17. The host cell of claim 16 wherein the host cell further comprises one or more nucleic acids encoding an IDI polypeptide.

18. A method of producing isoprene, comprising:
(a) culturing the host cells of claim 1 under suitable culture conditions for production of isoprene; and
(b) producing the isoprene.

19. The method of claim 18 further comprising (c) recovering the isoprene.

20. The method of claim 19 further comprising (d) polymerizing isoprene.

21. The host cell of claim 1 wherein the host cell further comprises a heterologous or native nucleic acid encoding an isopentenyl-diposhpate delta-isomerase (IDI) polypeptide and a heterologous or native nucleic acid encoding a 1-Deoxyxylulose-5-phosphate synthase (DXS) polypeptide, optionally in combination with the native 1-deoxy-D-xylulose-5-phospahte (DXP) pathway.

* * * * *

SEQUENCE LISTING

<160> NUMBER OF SEQ ID NOS: 167

<210> SEQ ID NO 1
<211> LENGTH: 1695
<212> TYPE: DNA
<213> ORGANISM: Artificial Sequence
<220> FEATURE:
<223> OTHER INFORMATION: Synthetic Construct

<400> SEQUENCE: 1

```
atgtgtgcga cctcttctca atttactcag attaccgagc ataattcccg tcgttccgca      60
aactatcagc caaacctgtg gaatttcgaa ttcctgcaat ccctggagaa cgacctgaaa     120
gtggaaaagc tggaggagaa agcgaccaaa ctggaggaag aagttcgctg catgatcaac     180
cgtgtagaca cccagccgct gtccctgctg gagctgatcg acgatgtgca gcgcctgggt     240
ctgacctaca aatttgaaaa agacatcatt aaagccctgg aaaacatcgt actgctggac     300
gaaaacaaaa agaacaaatc tgacctgcac gcaaccgctc tgtcttccg tctgctgcgt     360 cagcacggtt tcgaggtttc tcaggatgtt tttgagcgtt tcaaggataa agaaggtggt     420
ttcagcggtg aactgaaagg tgacgtccaa ggcctgctga gcctgtatga agcgtcttac     480 ctgggttcg agggtgagaa cctgctggag gaggcgcgta cctttccat cacccacctg     540 aagaacaacc tgaaagaagg cattaatacc aaggttgcag aacaagtgag ccacgccctg     600
gaactgccat atcaccagcg tctgcaccgt ctggaggcac gttggttcct ggataaatac     660
gaaccgaaag aaccgcatca ccagctgctg ctggagctgg cgaagctgga ttttaacatg     720
gtacagaccc tgcaccagaa agagctgcaa gatctgtccc gctggtggac cgagatgggc     780
ctggctagca aactggattt tgtacgcgac cgcctgatgg aagtttattt ctgggcactg     840
ggtatggcgc cagacccgca gtttggtgaa tgtcgcaaag ctgttactaa aatgtttggt     900
ctggtgacga tcatcgatga cgtgtatgac gtttatggca ctctggacga actgcaactg     960
ttcaccgatg ctgtagagcg ctgggacgtt aacgctatta cacccctgcc ggactatatg    1020
aaactgtgtt tcctggcact gtacaacacc gttaacgaca cgtcctattc tattctgaaa    1080
gagaaaggtc ataacaacct gtcctatctg acgaaaagct ggcgtgaact gtgcaaagcc    1140
tttctgcaag aggcgaaatg gtccaacaac aaaattatcc cggctttctc caagtacctg    1200
gaaaacgcca gcgtttcctc ctccggtgta gcgctgctgg cgccgtctta cttttccgta    1260
tgccagcagc aggaagacat ctccgaccac gcgctgcgtt ccctgaccga cttccatggt    1320
ctggtgcgtt ctagctgcgt tatcttccgc ctgtgcaacg atctggccac ctctgcggcg    1380
gagctggaac gtggcgagac taccaattct atcattagct acatgcacga aaacgatggt    1440
accagcgagg aacaggcccg cgaagaactg cgtaaactga tcgacgccga atggaaaaag    1500
```

-continued

```
atgaatcgtg aacgcgttag cgactccacc ctgctgccta aagcgttcat ggaaatcgca    1560
gttaacatgg cacgtgtttc ccactgcacc taccagtatg cgatggtct gggtcgccca     1620 gactacgcga ctgaaaaccg catcaaactg ctgctgattg accctttccc gattaaccag    1680
ctgatgtatg tctaa                                                      1695
```

<210> SEQ ID NO 2
<211> LENGTH: 564
<212> TYPE: PRT
<213> ORGANISM: Peuraria sp.

<400> SEQUENCE: 2

```
Met Cys Ala Thr Ser Ser Gln Phe Thr Gln Ile Thr Glu His Asn Ser
 1               5                  10                  15

Arg Arg Ser Ala Asn Tyr Gln Pro Asn Leu Trp Asn Phe Glu Phe Leu
            20                  25                  30

Gln Ser Leu Glu Asn Asp Leu Lys Val Glu Lys Leu Glu Glu Lys Ala
        35                  40                  45

Thr Lys Leu Glu Glu Glu Val Arg Cys Met Ile Asn Arg Val Asp Thr
    50                  55                  60

Gln Pro Leu Ser Leu Leu Glu Leu Ile Asp Asp Val Gln Arg Leu Gly
65                  70                  75                  80

Leu Thr Tyr Lys Phe Glu Lys Asp Ile Ile Lys Ala Leu Glu Asn Ile
                85                  90                  95

Val Leu Leu Asp Glu Asn Lys Lys Asn Lys Ser Asp Leu His Ala Thr
            100                 105                 110

Ala Leu Ser Phe Arg Leu Leu Arg Gln His Gly Phe Glu Val Ser Gln
        115                 120                 125

Asp Val Phe Glu Arg Phe Lys Asp Lys Glu Gly Gly Phe Ser Gly Glu
    130                 135                 140

Leu Lys Gly Asp Val Gln Gly Leu Leu Ser Leu Tyr Glu Ala Ser Tyr
145                 150                 155                 160

Leu Gly Phe Glu Gly Glu Asn Leu Leu Glu Glu Ala Arg Thr Phe Ser
                165                 170                 175

Ile Thr His Leu Lys Asn Asn Leu Lys Glu Gly Ile Asn Thr Lys Val
            180                 185                 190

Ala Glu Gln Val Ser His Ala Leu Glu Leu Pro Tyr His Gln Arg Leu
        195                 200                 205

His Arg Leu Glu Ala Arg Trp Phe Leu Asp Lys Tyr Glu Pro Lys Glu
    210                 215                 220

Pro His His Gln Leu Leu Leu Glu Leu Ala Lys Leu Asp Phe Asn Met
225                 230                 235                 240

Val Gln Thr Leu His Gln Lys Glu Leu Gln Asp Leu Ser Arg Trp Trp
                245                 250                 255

Thr Glu Met Gly Leu Ala Ser Lys Leu Asp Phe Val Arg Asp Arg Leu
            260                 265                 270

Met Glu Val Tyr Phe Trp Ala Leu Gly Met Ala Pro Asp Pro Gln Phe
        275                 280                 285

Gly Glu Cys Arg Lys Ala Val Thr Lys Met Phe Gly Leu Val Thr Ile
    290                 295                 300

Ile Asp Asp Val Tyr Asp Val Tyr Gly Thr Leu Asp Glu Leu Gln Leu
305                 310                 315                 320

Phe Thr Asp Ala Val Glu Arg Trp Asp Val Asn Ala Ile Asn Thr Leu
                325                 330                 335
```

```
Pro Asp Tyr Met Lys Leu Cys Phe Leu Ala Leu Tyr Asn Thr Val Asn
            340                 345                 350

Asp Thr Ser Tyr Ser Ile Leu Lys Glu Lys Gly His Asn Asn Leu Ser
        355                 360                 365

Tyr Leu Thr Lys Ser Trp Arg Glu Leu Cys Lys Ala Phe Leu Gln Glu
    370                 375                 380

Ala Lys Trp Ser Asn Asn Lys Ile Ile Pro Ala Phe Ser Lys Tyr Leu
385                 390                 395                 400

Glu Asn Ala Ser Val Ser Ser Gly Val Ala Leu Leu Ala Pro Ser
                405                 410                 415

Tyr Phe Ser Val Cys Gln Gln Gln Glu Asp Ile Ser Asp His Ala Leu
            420                 425                 430

Arg Ser Leu Thr Asp Phe His Gly Leu Val Arg Ser Ser Cys Val Ile
        435                 440                 445

Phe Arg Leu Cys Asn Asp Leu Ala Thr Ser Ala Ala Glu Leu Glu Arg
    450                 455                 460

Gly Glu Thr Thr Asn Ser Ile Ile Ser Tyr Met His Glu Asn Asp Gly
465                 470                 475                 480

Thr Ser Glu Glu Gln Ala Arg Glu Glu Leu Arg Lys Leu Ile Asp Ala
                485                 490                 495

Glu Trp Lys Lys Met Asn Arg Glu Arg Val Ser Asp Ser Thr Leu Leu
            500                 505                 510

Pro Lys Ala Phe Met Glu Ile Ala Val Asn Met Ala Arg Val Ser His
        515                 520                 525

Cys Thr Tyr Gln Tyr Gly Asp Gly Leu Gly Arg Pro Asp Tyr Ala Thr
    530                 535                 540

Glu Asn Arg Ile Lys Leu Leu Leu Ile Asp Pro Phe Pro Ile Asn Gln
545                 550                 555                 560

Leu Met Tyr Val

<210> SEQ ID NO 3
<211> LENGTH: 37
<212> TYPE: DNA
<213> ORGANISM: Artificial Sequence
<220> FEATURE:
<223> OTHER INFORMATION: Synthetic Construct

<400> SEQUENCE: 3
cgtgagatca tatgtgtgcg acctcttctc aatttac                          37

<210> SEQ ID NO 4
<211> LENGTH: 38
<212> TYPE: DNA
<213> ORGANISM: Artificial Sequence
<220> FEATURE:
<223> OTHER INFORMATION: Synthetic Construct

<400> SEQUENCE: 4
cggtcgacgg atccctgcag ttagacatac atcagctg                         38

<210> SEQ ID NO 5
<211> LENGTH: 41
<212> TYPE: DNA
<213> ORGANISM: Artificial Sequence
<220> FEATURE:
<223> OTHER INFORMATION: Synthetic Construct

<400> SEQUENCE: 5
catatgaaag cttgtatcga ttaaataagg aggaataaac c                     41
```

<210> SEQ ID NO 6
<211> LENGTH: 1680
<212> TYPE: DNA
<213> ORGANISM: Poplus alba x tremula

<400> SEQUENCE: 6

| | |
|---|---|
| atgtgctctg tttctaccga gaacgtttcc ttcactgaga cggaaaccga ggcacgtcgt | 60 |
| agcgcgaact acgagccgaa tagctgggac tacgatttcc tgctgtcttc cgatactgac | 120 |
| gaatctattg aggtgtacaa agacaaagca agaaactgg aggctgaagt gcgccgcgaa | 180 |
| attaacaacg agaaagctga attcctgact ctgctggagc tgatcgataa cgtacagcgc | 240 |
| ctgggtctgg gttaccgctt cgaatctgat atccgtcgcg cactggatcg tttcgtaagc | 300 |
| agcggcggtt tcgatggcgt gaccaaaacg agcctgcacg ctaccgcgct gtccttccgt | 360 |
| ctgctgcgtc agcacggctt cgaagtttct caggaagcat tctccggttt caaagatcaa | 420 |
| aacggtaact tcctggaaaa cctgaaagaa gacactaagg cgatcctgag cctgtatgag | 480 |
| gcaagctttc tggccctgga gggtgagaac atcctggatg aggcgcgcgt attcgccatc | 540 |
| tcccatctga aagagctgtc tgaagagaaa atcggtaagg aactggcaga gcaggttaat | 600 |
| cacgcactgg aactgccgct gcatcgtcgt acccagcgtc tggaggcggt ttggtccatc | 660 |
| gaagcgtacc gcaaaaagga ggatgctaac caggttctgc tggaactggc catcctggac | 720 |
| tacaacatga tccagtccgt ttaccagcgt gatctgcgtg aaacctcccg ttggtggcgc | 780 |
| cgtgtgggcc tggcgaccaa actgcacttc gctaaggacc gcctgattga gtcttttttac | 840 |
| tgggcagtcg gcgttgcgtt cgaacctcag tattctgact gccgtaacag cgttgcgaaa | 900 |
| atgttcagct tcgttactat tatcgacgac atctacgacg tttacggtac tctggacgag | 960 |
| ctggaactgt ttaccgacgc tgtcgaacgt tgggatgtta acgccatcaa cgatctgcct | 1020 |
| gactacatga aactgtgctt cctggcactg tataacacga tcaacgaaat tgcatacgac | 1080 |
| aacctgaaag acaaaggtga aaacatcctg ccgtacctga ctaaagcgtg gcggatctg | 1140 |
| tgtaacgctt ttctgcaaga agcgaaatgg ctgtataaca atccactcc gacctttgac | 1200 |
| gattatttcg gcaatgcctg gaaatccagc tctggcccgc tgcaactgat cttcgcttat | 1260 |
| tttgcggttg tccaaaacat caaaaaggag gaaattgaaa acctgcaaaa ataccacgat | 1320 |
| atcattagcc gtccttctca tatctttcgc ctgtgcaacg acctggcaag cgcgtccgca | 1380 |
| gagatcgcac gtggcgaaac cgctaactct gtttcctgct acatgcgcac caagggcatt | 1440 |
| tccgaagagc tggcaaccga gagcgtaatg aatctgatcg acgaaacctg taagaaaatg | 1500 |
| aacaaagaaa aactgggtgg ctccctgttc gctaaaccgt tcgtagagac tgctattaac | 1560 |
| ctggcacgtc agagccactg cacctaccac aatggtgacg cacatactag cccggatgaa | 1620 |
| ctgactcgta acgtgtact gtctgttatc accgaaccga ttctgccgtt cgaacgttaa | 1680 |

<210> SEQ ID NO 7
<211> LENGTH: 559
<212> TYPE: PRT
<213> ORGANISM: Poplus alba x tremula

<400> SEQUENCE: 7

Met Cys Ser Val Ser Thr Glu Asn Val Ser Phe Thr Glu Thr Glu Thr
1               5                   10                  15

Glu Ala Arg Arg Ser Ala Asn Tyr Glu Pro Asn Ser Trp Asp Tyr Asp
            20                  25                  30

```
Phe Leu Leu Ser Ser Asp Thr Asp Glu Ser Ile Glu Val Tyr Lys Asp
            35                  40                  45

Lys Ala Lys Lys Leu Glu Ala Glu Val Arg Arg Glu Ile Asn Asn Glu
 50                  55                  60

Lys Ala Glu Phe Leu Thr Leu Leu Glu Leu Ile Asp Asn Val Gln Arg
 65                  70                  75                  80

Leu Gly Leu Gly Tyr Arg Phe Glu Ser Asp Ile Arg Arg Ala Leu Asp
                85                  90                  95

Arg Phe Val Ser Ser Gly Gly Phe Asp Gly Val Thr Lys Thr Ser Leu
                100                 105                 110

His Ala Thr Ala Leu Ser Phe Arg Leu Leu Arg Gln His Gly Phe Glu
            115                 120                 125

Val Ser Gln Glu Ala Phe Ser Gly Phe Lys Asp Gln Asn Gly Asn Phe
130                 135                 140

Leu Glu Asn Leu Lys Glu Asp Thr Lys Ala Ile Leu Ser Leu Tyr Glu
145                 150                 155                 160

Ala Ser Phe Leu Ala Leu Glu Gly Glu Asn Ile Leu Asp Glu Ala Arg
                165                 170                 175

Val Phe Ala Ile Ser His Leu Lys Glu Leu Ser Glu Glu Lys Ile Gly
                180                 185                 190

Lys Glu Leu Ala Glu Gln Val Asn His Ala Leu Glu Leu Pro Leu His
            195                 200                 205

Arg Arg Thr Gln Arg Leu Glu Ala Val Trp Ser Ile Glu Ala Tyr Arg
            210                 215                 220

Lys Lys Glu Asp Ala Asn Gln Val Leu Leu Glu Leu Ala Ile Leu Asp
225                 230                 235                 240

Tyr Asn Met Ile Gln Ser Val Tyr Gln Arg Asp Leu Arg Glu Thr Ser
                245                 250                 255

Arg Trp Trp Arg Arg Val Gly Leu Ala Thr Lys Leu His Phe Ala Lys
            260                 265                 270

Asp Arg Leu Ile Glu Ser Phe Tyr Trp Ala Val Gly Val Ala Phe Glu
            275                 280                 285

Pro Gln Tyr Ser Asp Cys Arg Asn Ser Val Ala Lys Met Phe Ser Phe
        290                 295                 300

Val Thr Ile Ile Asp Asp Ile Tyr Asp Val Tyr Gly Thr Leu Asp Glu
305                 310                 315                 320

Leu Glu Leu Phe Thr Asp Ala Val Glu Arg Trp Asp Val Asn Ala Ile
                325                 330                 335

Asn Asp Leu Pro Asp Tyr Met Lys Leu Cys Phe Leu Ala Leu Tyr Asn
            340                 345                 350

Thr Ile Asn Glu Ile Ala Tyr Asp Asn Leu Lys Asp Lys Gly Glu Asn
            355                 360                 365

Ile Leu Pro Tyr Leu Thr Lys Ala Trp Ala Asp Leu Cys Asn Ala Phe
370                 375                 380

Leu Gln Glu Ala Lys Trp Leu Tyr Asn Lys Ser Thr Pro Thr Phe Asp
385                 390                 395                 400

Asp Tyr Phe Gly Asn Ala Trp Lys Ser Ser Gly Pro Leu Gln Leu
                405                 410                 415

Ile Phe Ala Tyr Phe Ala Val Val Gln Asn Ile Lys Lys Glu Glu Ile
                420                 425                 430

Glu Asn Leu Gln Lys Tyr His Asp Ile Ile Ser Arg Pro Ser His Ile
            435                 440                 445

Phe Arg Leu Cys Asn Asp Leu Ala Ser Ala Ser Ala Glu Ile Ala Arg
```

```
                450              455              460
Gly Glu Thr Ala Asn Ser Val Ser Cys Tyr Met Arg Thr Lys Gly Ile
465              470              475              480

Ser Glu Glu Leu Ala Thr Glu Ser Val Met Asn Leu Ile Asp Glu Thr
                485              490              495

Cys Lys Lys Met Asn Lys Glu Lys Leu Gly Gly Ser Leu Phe Ala Lys
                500              505              510

Pro Phe Val Glu Thr Ala Ile Asn Leu Ala Arg Gln Ser His Cys Thr
            515              520              525

Tyr His Asn Gly Asp Ala His Thr Ser Pro Asp Glu Leu Thr Arg Lys
        530              535              540

Arg Val Leu Ser Val Ile Thr Glu Pro Ile Leu Pro Phe Glu Arg
545              550              555
```

<210> SEQ ID NO 8
<211> LENGTH: 22
<212> TYPE: DNA
<213> ORGANISM: Artificial Sequence
<220> FEATURE:
<223> OTHER INFORMATION: Synthetic Construct

<400> SEQUENCE: 8
gagaaaatcg gtaaggaact gg                                          22

<210> SEQ ID NO 9
<211> LENGTH: 13
<212> TYPE: PRT
<213> ORGANISM: Artificial Sequence
<220> FEATURE:
<223> OTHER INFORMATION: Synthetic Construct

<400> SEQUENCE: 9

Leu Ala Ser Ala Ser Ala Glu Ile Ala Arg Gly Glu Thr
1               5                   10

<210> SEQ ID NO 10
<211> LENGTH: 39
<212> TYPE: DNA
<213> ORGANISM: Artificial Sequence
<220> FEATURE:
<223> OTHER INFORMATION: Synthetic Construct

<400> SEQUENCE: 10
ctggaggaag aagttcgctc catgatcaac cgtgtagac                         39

<210> SEQ ID NO 11
<211> LENGTH: 47
<212> TYPE: DNA
<213> ORGANISM: Artificial Sequence
<220> FEATURE:
<223> OTHER INFORMATION: Synthetic Construct

<400> SEQUENCE: 11
cgccagaccc gcagtttggt gaatctcgca aagctgttac taaaatg               47

<210> SEQ ID NO 12
<211> LENGTH: 41
<212> TYPE: DNA
<213> ORGANISM: Artificial Sequence
<220> FEATURE:
<223> OTHER INFORMATION: Synthetic Construct

<400> SEQUENCE: 12
cgccgtctta cttttccgta tcccagcagc aggaagacat c               41

<210> SEQ ID NO 13
<211> LENGTH: 42
<212> TYPE: DNA
<213> ORGANISM: Artificial Sequence
<220> FEATURE:
<223> OTHER INFORMATION: Synthetic Construct

<400> SEQUENCE: 13
catggtctgg tgcgttctag ctccgttatc ttccgcctgt gc              42

<210> SEQ ID NO 14
<211> LENGTH: 41
<212> TYPE: DNA
<213> ORGANISM: Artificial Sequence
<220> FEATURE:
<223> OTHER INFORMATION: Synthetic Construct

<400> SEQUENCE: 14
gatgtcttcc tgctgctggg atacggaaaa gtaagacggc g               41

<210> SEQ ID NO 15
<211> LENGTH: 28
<212> TYPE: DNA
<213> ORGANISM: Artificial Sequence
<220> FEATURE:
<223> OTHER INFORMATION: Synthetic Construct

<400> SEQUENCE: 15
gatcaagctt aaccggaatt gccagctg                              28

<210> SEQ ID NO 16
<211> LENGTH: 33
<212> TYPE: DNA
<213> ORGANISM: Artificial Sequence
<220> FEATURE:
<223> OTHER INFORMATION: Synthetic Construct

<400> SEQUENCE: 16
gatccgatcg tcagaagaac tcgtcaagaa ggc                        33

<210> SEQ ID NO 17
<211> LENGTH: 35
<212> TYPE: DNA
<213> ORGANISM: Artificial Sequence
<220> FEATURE:
<223> OTHER INFORMATION: Synthetic Construct

<400> SEQUENCE: 17
ccaaactgca cttcgctcgt gaccgcctga ttgag                      35

<210> SEQ ID NO 18
<211> LENGTH: 30
<212> TYPE: DNA
<213> ORGANISM: Artificial Sequence
<220> FEATURE:
<223> OTHER INFORMATION: Synthetic Construct

<400> SEQUENCE: 18
atctttcgcc tgtgcgacga cctggcaagc                            30

<210> SEQ ID NO 19
<211> LENGTH: 45
<212> TYPE: DNA
<213> ORGANISM: Artificial Sequence

```
<220> FEATURE:
<223> OTHER INFORMATION: Synthetic Construct

<400> SEQUENCE: 19
tgaatctgat cgacgaaacc tggaagaaaa tgaacaaaga aaaac              45

<210> SEQ ID NO 20
<211> LENGTH: 60
<212> TYPE: DNA
<213> ORGANISM: Artificial Sequence
<220> FEATURE:
<223> OTHER INFORMATION: Synthetic Construct

<400> SEQUENCE: 20
gatcatgcat tcgcccttag gaggtaaaaa aacatgtgtg cgacctcttc tcaatttact    60

<210> SEQ ID NO 21
<211> LENGTH: 38
<212> TYPE: DNA
<213> ORGANISM: Artificial Sequence
<220> FEATURE:
<223> OTHER INFORMATION: Synthetic Construct

<400> SEQUENCE: 21
cggtcgacgg atccctgcag ttagacatac atcagctg                     38

<210> SEQ ID NO 22
<211> LENGTH: 5679
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 3895
<223> OTHER INFORMATION: n = A,T,C or G

<400> SEQUENCE: 22
aagggcgaat tctgcagata tccatcacac tggcggccgc tcgagcatgc atctagaggg    60
cccaattcgc cctatagtga gtcgtattac aattcactgg ccgtcgtttt acaacgtcgt   120
gactgggaaa accctggcgt tacccaactt aatcgccttg cagcacatcc ccctttcgcc   180
agctggcgta atagcgaaga ggcccgcacc gatcgccctt cccaacagtt gcgcagcctg   240
aatggcgaat ggacgcgccc tgtagcggcg cattaagcgc ggcgggtgtg gtggttacgc   300
gcagcgtgac cgctacactt gccagcgccc tagcgcccgc tcctttcgct ttcttccctt   360
cctttctcgc cacgttcgcc ggctttcccc gtcaagctct aaatcggggg ctccctttag   420
ggttccgatt tagtgcttta cggcacctcg accccaaaaa acttgattag ggtgatggtt   480
cacgtagtgg gccatcgccc tgatagacgg ttttccgccc tttgacgttg gagtccacgt   540
tctttaatag tggactcttg ttccaaactg gaacaacact caaccctatc tcggtctatt   600
cttttgattt ataagggatt ttgccgattt cggcctattg gttaaaaaat gagctgattt   660
aacaaaaatt taacgcgaat tttaacaaaa ttcagggcgc aagggctgct aaaggaagcg   720
gaacacgtag aaagccagtc cgcagaaacg gtgctgaccc cggatgaatg tcagctactg   780
ggctatctgg acaagggaaa acgcaagcgc aaagagaaag caggtagctt gcagtgggct   840
tacatggcga tagctagact gggcggtttt atggacagca agcgaaccgg aattgccagc   900
tggggcgccc tctggtaagg ttgggaagcc ctgcaaagta aactggatgg ctttcttgcc   960
gccaaggatc tgatggcgca ggggatcaag atctgatcaa gagacaggat gaggatcgtt  1020
```

```
tcgcatgatt gaacaagatg gattgcacgc aggttctccg gccgcttggg tggagaggct   1080
attcggctat gactgggcac aacagacaat cggctgctct gatgccgccg tgttccggct   1140
gtcagcgcag gggcgcccgg ttcttttttgt caagaccgac ctgtccggtg ccctgaatga   1200
actgcaggac gaggcagcgc ggctatcgtg gctggccacg acgggcgttc cttgcgcagc   1260
tgtgctcgac gttgtcactg aagcgggaag ggactggctg ctattgggcg aagtgccggg   1320
gcaggatctc ctgtcatccc accttgctcc tgccgagaaa gtatccatca tggctgatgc   1380
aatgcggcgg ctgcatacgc ttgatccggc tacctgccca ttcgaccacc aagcgaaaca   1440
tcgcatcgag cgagcacgta ctcggatgga agccggtctt gtcgatcagg atgatctgga   1500
cgaagagcat caggggctcg cgccagccga actgttcgcc aggctcaagg cgcgcatgcc   1560
cgacggcgag gatctcgtcg tgacccatgg cgatgcctgc ttgccgaata tcatggtgga   1620
aaatggccgc ttttctggat tcatcgactg tggccggctg ggtgtggcgg accgctatca   1680
ggacatagcg ttggctaccc gtgatattgc tgaagagctt ggcggcgaat gggctgaccg   1740
cttcctcgtg ctttacggta tcgccgctcc cgattcgcag cgcatcgcct tctatcgcct   1800
tcttgacgag ttcttctgaa ttgaaaaagg aagagtatga gtattcaaca tttccgtgtc   1860
gcccttattc cctttttgc ggcattttgc cttcctgttt ttgctcaccc agaaacgctg   1920
gtgaaagtaa aagatgctga agatcagttg ggtgcacgag tgggttacat cgaactggat   1980
ctcaacagcg gtaagatcct tgagagtttt cgccccgaag aacgttttcc aatgatgagc   2040
acttttaaag ttctgctatg tggcgcggta ttatcccgta ttgacgccgg caagagcaa    2100 ctcggtcgcc gcatacacta ttctcagaat gacttggttg agtactcacc agtcacagaa   2160
aagcatctta cggatggcat gacagtaaga gaattatgca gtgctgccat aaccatgagt   2220
gataacactg cggccaactt acttctgaca acgatcggag gaccgaagga gctaaccgct   2280
tttttgcaca acatggggga tcatgtaact cgccttgatc gttgggaacc ggagctgaat   2340
gaagccatac caaacgacga gcgtgacacc acgatgcctg tagcaatggc aacaacgttg   2400
cgcaaactat taactggcga actacttact ctagcttccc ggcaacaatt aatagactgg   2460
atggaggcgg ataaagttgc aggaccactt ctgcgctcgg cccttccggc tggctggttt   2520
attgctgata atctggagc cggtgagcgt gggtctcgcg gtatcattgc agcactgggg   2580
ccagatggta agccctcccg tatcgtagtt atctacacga cggggagtca ggcaactatg   2640
gatgaacgaa atagacagat cgctgagata ggtgcctcac tgattaagca ttggtaactg   2700
tcagaccaag tttactcata tatactttag attgatttaa aacttcattt ttaatttaaa   2760
aggatctagg tgaagatcct ttttgataat ctcatgacca aaatccctta acgtgagttt   2820
tcgttccact gagcgtcaga ccccgtagaa aagatcaaag gatcttcttg agatcctttt   2880
tttctgcgcg taatctgctg cttgcaaaca aaaaaaccac cgctaccagc ggtggtttgt   2940
ttgccggatc aagagctacc aactcttttt ccgaaggtaa ctggcttcag cagagcgcag   3000
ataccaaata ctgttcttct agtgtagccg tagttaggcc accacttcaa gaactctgta   3060
gcaccgccta catacctcgc tctgctaatc ctgttaccag tggctgctgc cagtggcgat   3120
aagtcgtgtc ttaccgggtt ggactcaaga cgatagttac cggataaggc gcagcggtcg   3180
ggctgaacgg ggggttcgtg cacacagccc agcttggagc gaacgaccta caccgaactg   3240
agatacctac agcgtgagct atgagaaagc gccacgcttc ccgaagggag aaaggcggac   3300
aggtatccgg taagcggcag ggtcggaaca ggagagcgca cgagggagct tccagggggga  3360 aacgcctggt atctttatag tcctgtcggg tttcgccacc tctgacttga gcgtcgattt   3420
```

```
ttgtgatgct cgtcaggggg gcggagccta tggaaaaacg ccagcaacgc ggcctttta      3480 cggttcctgg cctttgctg gccttttgct cacatgttct ttcctgcgtt atccctgat      3540 tctgtggata accgtattac cgcctttgag tgagctgata ccgctcgccg cagccgaacg      3600
accgagcgca gcgagtcagt gagcgaggaa gcggaagagc gcccaatacg caaaccgcct      3660
ctccccgcgc gttggccgat tcattaatgc agctggcacg acaggtttcc cgactggaaa      3720
gcgggcagtg agcgcaacgc aattaatgtg agttagctca ctcattaggc accccaggct      3780
ttacacttta tgcttccggc tcgtatgttg tgtggaattg tgagcggata acaatttcac      3840
acaggaaaca gctatgacca tgattacgcc aagcttggta ccgagctcgg atccnctagt      3900
aacggccgcc agtgtgctgg aattcgccct tgatcatgca ttcgcccttaa ggaggtaaaa      3960 aaacatgtgt gcgacctctt ctcaatttac tcagattacc gagcataatt cccgtcgttc      4020
cgcaaactat cagccaaacc tgtggaattt cgaattcctg caatccctgg agaacgacct      4080
gaaagtggaa aagctggagg agaaagcgac caaactggag gaagaagttc gctgcatgat      4140
caaccgtgta gacacccagc cgctgtccct gctggagctg atcgacgatg tgcagcgcct      4200
gggtctgacc tacaaatttg aaaaagacat cattaaagcc ctggaaaaca tcgtactgct      4260
ggacgaaaac aaaaagaaca atctgacct gcacgcaacc gctctgtctt tccgtctgct      4320
gcgtcagcac ggtttcgagg tttctcagga tgttttgag cgtttcaagg ataaagaagg      4380
tggtttcagc ggtgaactga aggtgacgt ccaaggcctg ctgagcctgt atgaagcgtc      4440
ttacctgggt ttcgagggtg agaacctgct ggaggaggcg cgtaccttt ccatcaccca      4500 cctgaagaac aacctgaaag aaggcattaa taccaaggtt gcagaacaag tgagccacgc      4560
cctggaactg ccatatcacc agcgtctgca ccgtctggag gcacgttggt tcctggataa      4620
atacgaaccg aaagaaccgc atcaccagct gctgctggag ctggcgaagc tggattttaa      4680
catggtacag accctgcacc agaaagagct gcaagatctg tcccgctggt ggaccgagat      4740
gggcctggct agcaaactgg attttgtacg cgaccgcctg atggaagttt atttctgggc      4800
actgggtatg gcgccagacc cgcagttttgg tgaatgtcgc aaagctgtta ctaaaatgtt      4860
tggtctggtg acgatcatcg atgacgtgta tgacgtttat ggcactctgg acgaactgca      4920
actgttcacc gatgctgtag agcgctggga cgttaacgct attaacaccc tgccggacta      4980
tatgaaactg tgtttcctgg cactgtacaa caccgttaac gacacgtcct attctattct      5040
gaaagagaaa ggtcataaca acctgtccta tctgacgaaa agctggcgtg aactgtgcaa      5100
agcctttctg caagaggcga atggtccaa caacaaaatt atcccggctt ctccaagta      5160 cctggaaaac gccagcgttt cctcctccgg tgtagcgctg ctggcgccgt cttactttc      5220 cgtatgccag cagcaggaag acatctccga ccacgcgctg cgttccctga ccgacttcca      5280
tggtctggtg cgttctagct gcgttatctt ccgcctgtgc aacgatctgg ccacctctgc      5340
ggcggagctg gaacgtggcg agactaccaa ttctatcatt agctacatgc acgaaaacga      5400
tggtaccagc gaggaacagg cccgcgaaga actgcgtaaa ctgatcgacg ccgaatggaa      5460
aaagatgaat cgtgaacgcg ttagcgactc caccctgctg cctaaagcgt tcatggaaat      5520
cgcagttaac atggcacgtg tttcccactg cacctaccag tatggcgatg gtctgggtcg      5580
cccagactac gcgactgaaa accgcatcaa actgctgctg attgacccctt tcccgattaa      5640 ccagctgatg tatgtctaac tgcagggatc cgtcgaccg                           5679

<210> SEQ ID NO 23
```

<211> LENGTH: 6974
<212> TYPE: DNA
<213> ORGANISM: Artificial Sequence
<220> FEATURE:
<223> OTHER INFORMATION: Synthetic Construct

<400> SEQUENCE: 23

| | | | | | |
|---|---|---|---|---|---|
| gtgcggccgc | aagcttgtcg | acggagctcg | aattcggatc | cctgcagtta | gacatacatc | 60 |
| agctggttaa | tcgggaaagg | gtcaatcagc | agcagtttga | tgcggttttc | agtcgcgtag | 120 |
| tctgggcgac | ccagaccatc | gccatactgg | taggtgcagt | gggaaacacg | tgccatgtta | 180 |
| actgcgattt | ccatgaacgc | tttaggcagc | agggtggagt | cgctaacgcg | ttcacgattc | 240 |
| atcttttcc | attcggcgtc | gatcagttta | cgcagttctt | cgcgggcctg | ttcctcgctg | 300 |
| gtaccatcgt | tttcgtgcat | gtagctaatg | atagaattgg | tagtctcgcc | acgttccagc | 360 |
| tccgccgcag | aggtggccag | atcgttgcac | aggcggaaga | taacgcagct | agaacgcacc | 420 |
| agaccatgga | agtcggtcag | ggaacgcagc | gcgtggtcgg | agatgtcttc | ctgctgctgg | 480 |
| catacggaaa | agtaagacgg | cgccagcagc | gctacaccgg | aggaggaaac | gctggcgttt | 540 |
| tccaggtact | tggagaaagc | cgggataatt | ttgttgttgg | accatttcgc | ctcttgcaga | 600 |
| aaggctttgc | acagttcacg | ccagcttttc | gtcagatagg | acaggttgtt | atgacctttc | 660 |
| tctttcagaa | tagaatagga | cgtgtcgtta | acggtgttgt | acagtgccag | gaaacacagt | 720 |
| ttcatatagt | ccggcagggt | gttaatagcg | ttaacgtccc | agcgctctac | agcatcggtg | 780 |
| aacagttgca | gttcgtccag | agtgccataa | acgtcataca | cgtcatcgat | gatcgtcacc | 840 |
| agaccaaaca | ttttagtaac | agctttgcga | cattcaccaa | actgcgggtc | tggcgccata | 900 |
| cccagtgccc | agaaataaac | ttccatcagg | cggtcgcgta | caaaatccag | tttgctagcc | 960 |
| aggcccatct | cggtccacca | gcgggacaga | tcttgcagct | ctttctggtg | cagggtctgt | 1020 |
| accatgttaa | aatccagctt | cgccagctcc | agcagcagct | ggtgatgcgg | ttctttcggt | 1080 |
| tcgtatttat | ccaggaacca | acgtgcctcc | agacggtgca | gacgctggtg | atatggcagt | 1140 |
| tccagggcgt | ggctcacttg | ttctgcaacc | ttggtattaa | tgccttcttt | caggttgttc | 1200 |
| ttcaggtggg | tgatggaaaa | ggtacgcgcc | tcctccagca | ggttctcacc | ctcgaaaccc | 1260 |
| aggtaagacg | cttcatacag | gctcagcagg | ccttggacgt | cacctttcag | ttcaccgctg | 1320 |
| aaaccacctt | ctttatcctt | gaaacgctca | aaaacatcct | gagaaacctc | gaaaccgtgc | 1380 |
| tgacgcagca | gacggaaaga | cagagcggtt | gcgtgcaggt | cagatttgtt | cttttttgttt | 1440 |
| tcgtccagca | gtacgatgtt | ttccagggct | ttaatgatgt | ctttttcaaa | tttgtaggtc | 1500 |
| agacccaggc | gctgcacatc | gtcgatcagc | tccagcaggg | acagcggctg | ggtgtctaca | 1560 |
| cggttgatca | tgcagcgaac | ttcttcctcc | agtttggtcg | cttttctcctc | cagcttttcc | 1620 |
| actttcaggt | cgttctccag | ggattgcagg | aattcgaaat | tccacaggtt | tggctgatag | 1680 |
| tttgcggaac | gacgggaatt | atgctcggta | atctgagtaa | attgagaaga | ggtcgcacac | 1740 |
| atggtatatc | tccttcttaa | agttaaacaa | aattatttct | agaggggaat | tgttatccgc | 1800 |
| tcacaattcc | cctatagtga | gtcgtattaa | tttcgcggga | tcgagatctc | gatcctctac | 1860 |
| gccgacgca | tcgtggccgg | catcaccggc | gccacaggtg | cggttgctgg | cgcctatatc | 1920 |
| gccgacatca | ccgatgggga | agatcgggct | cgccacttcg | ggctcatgag | cgcttgtttc | 1980 |
| ggcgtgggta | tggtggcagg | ccccgtggcc | ggggactgt | tgggcgccat | ctccttgcat | 2040 |
| gcaccattcc | ttgcggcggc | ggtgctcaac | ggcctcaacc | tactactggg | ctgcttccta | 2100 |
| atgcaggagt | cgcataaggg | agagcgtcga | gatcccggac | accatcgaat | ggcgcaaaac | 2160 |

```
ctttcgcggt atggcatgat agcgcccgga agagagtcaa ttcagggtgg tgaatgtgaa    2220
accagtaacg ttatacgatg tcgcagagta tgccggtgtc tcttatcaga ccgtttcccg    2280
cgtggtgaac caggccagcc acgtttctgc gaaaacgcgg gaaaaagtgg aagcggcgat    2340
ggcggagctg aattacattc ccaaccgcgt ggcacaacaa ctggcgggca acagtcgtt    2400
gctgattggc gttgccacct ccagtctggc cctgcacgcg ccgtcgcaaa ttgtcgcggc    2460
gattaaatct cgcgccgatc aactgggtgc cagcgtggtg gtgtcgatgg tagaacgaag    2520
cggcgtcgaa gcctgtaaag cggcggtgca caatcttctc gcgcaacgcg tcagtgggct    2580
gatcattaac tatccgctgg atgaccagga tgccattgct gtggaagctg cctgcactaa    2640
tgttccggcg ttatttcttg atgtctctga ccagacaccc atcaacagta ttattttctc    2700
ccatgaagac ggtacgcgac tgggcgtgga gcatctggtc gcattgggtc accagcaaat    2760
cgcgctgtta gcgggcccat taagttctgt ctcggcgcgt ctgcgtctgg ctggctggca    2820
taaatatctc actcgcaatc aaattcagcc gatagcggaa cgggaaggcg actggagtgc    2880
catgtccggt tttcaacaaa ccatgcaaat gctgaatgag ggcatcgttc ccactgcgat    2940
gctggttgcc aacgatcaga tggcgctggg cgcaatgcgc gccattaccg agtccgggct    3000
gcgcgttggt gcggatatct cggtagtggg atacgacgat accgaagaca gctcatgtta    3060
tatcccgccg ttaaccacca tcaaacagga ttttcgcctg ctggggcaaa ccagcgtgga    3120
ccgcttgctg caactctctc agggccaggc ggtgaagggc aatcagctgt tgcccgtctc    3180
actggtgaaa agaaaaacca ccctggcgcc caatacgcaa accgcctctc cccgcgcgtt    3240
ggccgattca ttaatgcagc tggcacgaca ggtttcccga ctggaaagcg ggcagtgagc    3300
gcaacgcaat taatgtaagt tagctcactc attaggcacc gggatctcga ccgatgccct    3360
tgagagcctt caacccagtc agctccttcc ggtgggcgcg gggcatgact atcgtcgccg    3420
cacttatgac tgtcttcttt atcatgcaac tcgtaggaca ggtgccggca gcgctctggg    3480
tcattttcgg cgaggaccgc tttcgctgga gcgcgacgat gatcggcctg tcgcttgcgg    3540
tattcggaat cttgcacgcc ctcgctcaag ccttcgtcac tggtcccgcc accaaacgtt    3600
tcggcgagaa gcaggccatt atcgccggca tggcggcccc acgggtgcgc atgatcgtgc    3660
tcctgtcgtt gaggacccgg ctaggctggc ggggttgcct tactggttag cagaatgaat    3720
caccgatacg cgagcgaacg tgaagcgact gctgctgcaa aacgtctgcg acctgagcaa    3780
caacatgaat ggtcttcggt ttccgtgttt cgtaaagtct ggaaacgcgg aagtcagcgc    3840
cctgcaccat tatgttccgg atctgcatcg caggatgctg ctggctaccc tgtggaacac    3900
ctacatctgt attaacgaag cgctggcatt gaccctgagt gattttctc tggtcccgcc    3960
gcatccatac cgccagttgt ttaccctcac aacgttccag taaccgggca tgttcatcat    4020
cagtaacccg tatcgtgagc atcctctctc gtttcatcgg tatcattacc cccatgaaca    4080
gaaatccccc ttacacggag gcatcagtga ccaaacagga aaaaaccgcc cttaacatgg    4140
cccgctttat cagaagccag acattaacgc ttctggagaa actcaacgag ctggacgcgg    4200
atgaacaggc agacatctgt gaatcgcttc acgaccacgc tgatgagctt taccgcagct    4260
gcctcgcgcg tttcggtgat gacgtgaaa acctctgaca catgcagctc ccggagacgg    4320
tcacagcttg tctgtaagcg gatgccggga gcagacaagc ccgtcagggc gcgtcagcgg    4380
gtgttggcgg gtgtcgggc gcagccatga cccagtcacg tagcgatagc ggagtgtata    4440
ctggcttaac tatgcggcat cagagcagat tgtactgaga gtgcaccata tatgcggtgt    4500
```

```
gaaataccgc acagatgcgt aaggagaaaa taccgcatca ggcgctcttc cgcttcctcg    4560
ctcactgact cgctgcgctc ggtcgttcgg ctgcggcgag cggtatcagc tcactcaaag    4620
gcggtaatac ggttatccac agaatcaggg gataacgcag gaaagaacat gtgagcaaaa    4680
ggccagcaaa aggccaggaa ccgtaaaaag gccgcgttgc tggcgttttt ccataggctc    4740
cgcccccctg acgagcatca caaaaatcga cgctcaagtc agaggtggcg aaacccgaca    4800
ggactataaa gataccaggc gtttccccct ggaagctccc tcgtgcgctc tcctgttccg    4860
accctgccgc ttaccggata cctgtccgcc tttctccctt cgggaagcgt ggcgctttct    4920
catagctcac gctgtaggta tctcagttcg gtgtaggtcg ttcgctccaa gctgggctgt    4980
gtgcacgaac cccccgttca gcccgaccgc tgcgccttat ccggtaacta tcgtcttgag    5040
tccaacccgg taagacacga cttatcgcca ctggcagcag ccactggtaa caggattagc    5100
agagcgaggt atgtaggcgg tgctacagag ttcttgaagt ggtggcctaa ctacggctac    5160
actagaagga cagtatttgg tatctgcgct ctgctgaagc cagttacctt cggaaaaaga    5220
gttggtagct cttgatccgg caaacaaacc accgctggta gcggtggttt ttttgtttgc    5280
aagcagcaga ttacgcgcag aaaaaaagga tctcaagaag atcctttgat cttttctacg    5340
gggtctgacg ctcagtggaa cgaaaactca cgttaaggga ttttggtcat gaacaataaa    5400
actgtctgct tacataaaca gtaatacaag gggtgttatg agccatattc aacgggaaac    5460
gtcttgctct aggccgcgat taaattccaa catggatgct gatttatatg ggtataaatg    5520
ggctcgcgat aatgtcgggc aatcaggtgc gacaatctat cgattgtatg ggaagcccga    5580
tgcgccagag ttgtttctga acatggcaa aggtagcgtt gccaatgatg ttacagatga    5640
gatggtcaga ctaaactggc tgacggaatt tatgcctctt ccgaccatca agcattttat    5700
ccgtactcct gatgatgcat ggttactcac cactgcgatc cccgggaaaa cagcattcca    5760
ggtattagaa gaatatcctg attcaggtga aaatattgtt gatgcgctgg cagtgttcct    5820
gcgccggttg cattcgattc ctgtttgtaa ttgtcctttt aacagcgatc gcgtatttcg    5880
tctcgctcag gcgcaatcac gaatgaataa cggtttggtt gatgcgagtg attttgatga    5940
cgagcgtaat ggctggcctg ttgaacaagt ctggaaagaa atgcataaac ttttgccatt    6000
ctcaccggat tcagtcgtca ctcatggtga tttctcactt gataacctta ttttttgacga    6060
ggggaaatta ataggttgta ttgatgttgg acgagtcgga atcgcagacc gataccagga    6120
tcttgccatc ctatggaact gcctcggtga gttttctcct tcattacaga aacggctttt    6180
tcaaaaatat ggtattgata atcctgatat gaataaattg cagtttcatt tgatgctcga    6240
tgagttttc taagaattaa ttcatgagcg gatacatatt tgaatgtatt tagaaaaata    6300
aacaaatagg ggttccgcgc acatttcccc gaaaagtgcc acctgaaatt gtaaacgtta    6360
atattttgtt aaaattcgcg ttaaattttt gttaaatcag ctcatttttt aaccaatagg    6420
ccgaaatcgg caaaatccct tataaatcaa aagaatagac cgagataggg ttgagtgttg    6480
ttccagtttg gaacaagagt ccactattaa agaacgtgga ctccaacgtc aaagggcgaa    6540
aaaccgtcta tcagggcgat ggcccactac gtgaaccatc accctaatca agttttttgg    6600
ggtcgaggtg ccgtaaagca ctaaatcgga acccctaaagg agcccccga tttagagctt    6660
gacggggaaa gccggcgaac gtggcgagaa aggaaggga gaaagcgaaa ggagcgggcg    6720
ctagggcgct ggcaagtgta gcggtcacgc tgcgcgtaac caccacaccc gccgcgctta    6780
atgcgccgct acagggcgcg tcccattcgc caatccggat atagttcctc ctttcagcaa    6840
aaaacccctc aagacccgtt tagaggcccc aaggggttat gctagttatt gctcagcggt    6900
```
ggcagcagcc aactcagctt cctttcgggc tttgttagca gccggatctc agtggtggtg       6960
gtggtggtgc tcga                                                        6974

<210> SEQ ID NO 24
<211> LENGTH: 39
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 19, 20
<223> OTHER INFORMATION: n = A,T,C or G

<400> SEQUENCE: 24
cataattccc gtcgttccnn saactatcag ccaaacctg                             39

<210> SEQ ID NO 25
<211> LENGTH: 41
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 22, 23
<223> OTHER INFORMATION: n = A,T,C or G

<400> SEQUENCE: 25
cataattccc gtcgttccgc annstatcag ccaaacctgt g                          41

<210> SEQ ID NO 26
<211> LENGTH: 41
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 18, 19
<223> OTHER INFORMATION: n = A,T,C or G

<400> SEQUENCE: 26
cccgtcgttc cgcaaacnns cagccaaacc tgtggaattt c                          41

<210> SEQ ID NO 27
<211> LENGTH: 38
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 18, 19
<223> OTHER INFORMATION: n = A,T,C or G

<400> SEQUENCE: 27
gtcgttccgc aaactatnns ccaaacctgt ggaatttc                              38

<210> SEQ ID NO 28
<211> LENGTH: 39
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 19, 20

-continued

<223> OTHER INFORMATION: n = A,T,C or G

<400> SEQUENCE: 28
ctggattttg tacgcgacnn sctgatggaa gtttatttc        39

<210> SEQ ID NO 29
<211> LENGTH: 38
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 19, 20
<223> OTHER INFORMATION: n = A,T,C or G

<400> SEQUENCE: 29
ctgatggaag tttatttcnn sgcactgggt atggcgcc        38

<210> SEQ ID NO 30
<211> LENGTH: 40
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 20, 21
<223> OTHER INFORMATION: n = A,T,C or G

<400> SEQUENCE: 30
caaagctgtt actaaaatgn nsggtctggt gacgatcatc        40

<210> SEQ ID NO 31
<211> LENGTH: 38
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 18, 19
<223> OTHER INFORMATION: n = A,T,C or G

<400> SEQUENCE: 31
ctaaaatgtt tggtctgnns acgatcatcg atgacgtg        38

<210> SEQ ID NO 32
<211> LENGTH: 41
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 22, 23
<223> OTHER INFORMATION: n = A,T,C or G

<400> SEQUENCE: 32
gaaaacgcca gcgtttcctc cnnsggtgta gcgctgctgg c        41

<210> SEQ ID NO 33
<211> LENGTH: 23
<212> TYPE: DNA
<213> ORGANISM: Artificial Sequence
<220> FEATURE:
<223> OTHER INFORMATION: Synthetic Construct

<400> SEQUENCE: 33
caccatgcgt tgtagcgtgt cca                                           23

<210> SEQ ID NO 34
<211> LENGTH: 52
<212> TYPE: DNA
<213> ORGANISM: Artificial Sequence
<220> FEATURE:
<223> OTHER INFORMATION: Synthetic Construct

<400> SEQUENCE: 34
gggcccgttt aaactttaac tagactctgc agttagcgtt caaacggcag aa           52

<210> SEQ ID NO 35
<211> LENGTH: 37
<212> TYPE: DNA
<213> ORGANISM: Artificial Sequence
<220> FEATURE:
<223> OTHER INFORMATION: Synthetic Construct

<400> SEQUENCE: 35
gaaggagata tacatatgag cgtgtccacc gaaaatg                            37

<210> SEQ ID NO 36
<211> LENGTH: 37
<212> TYPE: DNA
<213> ORGANISM: Artificial Sequence
<220> FEATURE:
<223> OTHER INFORMATION: Synthetic Construct

<400> SEQUENCE: 36
cattttcggt ggacacgctc atatgtatat ctccttc                            37

<210> SEQ ID NO 37
<211> LENGTH: 38
<212> TYPE: DNA
<213> ORGANISM: Artificial Sequence
<220> FEATURE:
<223> OTHER INFORMATION: Synthetic Construct

<400> SEQUENCE: 37
gaaggagata tacatatggt gtccaccgaa aatgtgtc                           38

<210> SEQ ID NO 38
<211> LENGTH: 38
<212> TYPE: DNA
<213> ORGANISM: Artificial Sequence
<220> FEATURE:
<223> OTHER INFORMATION: Synthetic Construct

<400> SEQUENCE: 38
gacacatttt cggtggacac catatgtata tctccttc                           38

<210> SEQ ID NO 39
<211> LENGTH: 38
<212> TYPE: DNA
<213> ORGANISM: Artificial Sequence
<220> FEATURE:
<223> OTHER INFORMATION: Synthetic Construct

<400> SEQUENCE: 39
gaaggagata tacatatgac cgaaaatgtg tctttcac                           38

<210> SEQ ID NO 40
<211> LENGTH: 38
<212> TYPE: DNA

```
<213> ORGANISM: Artificial Sequence
<220> FEATURE:
<223> OTHER INFORMATION: Synthetic Construct

<400> SEQUENCE: 40
gtgaaagaca cattttcggt catatgtata tctccttc                    38

<210> SEQ ID NO 41
<211> LENGTH: 38
<212> TYPE: DNA
<213> ORGANISM: Artificial Sequence
<220> FEATURE:
<223> OTHER INFORMATION: Synthetic Construct

<400> SEQUENCE: 41
gaaggagata tacatatgaa tgtgtctttc accgaaac                    38

<210> SEQ ID NO 42
<211> LENGTH: 38
<212> TYPE: DNA
<213> ORGANISM: Artificial Sequence
<220> FEATURE:
<223> OTHER INFORMATION: Synthetic Construct

<400> SEQUENCE: 42
gtttcggtga aagacacatt catatgtata tctccttc                    38

<210> SEQ ID NO 43
<211> LENGTH: 36
<212> TYPE: DNA
<213> ORGANISM: Artificial Sequence
<220> FEATURE:
<223> OTHER INFORMATION: Synthetic Construct

<400> SEQUENCE: 43
gaaggagata tacatatgga agctcgtcgt tctgcg                      36

<210> SEQ ID NO 44
<211> LENGTH: 36
<212> TYPE: DNA
<213> ORGANISM: Artificial Sequence
<220> FEATURE:
<223> OTHER INFORMATION: Synthetic Construct

<400> SEQUENCE: 44
cgcagaacga cgagcttcca tatgtatatc tccttc                      36

<210> SEQ ID NO 45
<211> LENGTH: 30
<212> TYPE: DNA
<213> ORGANISM: Artificial Sequence
<220> FEATURE:
<223> OTHER INFORMATION: Synthetic Construct

<400> SEQUENCE: 45
gaaggagata tacatatgcg ttgtagcgtg                             30

<210> SEQ ID NO 46
<211> LENGTH: 60
<212> TYPE: DNA
<213> ORGANISM: Artificial Sequence
<220> FEATURE:
<223> OTHER INFORMATION: Synthetic Construct

<400> SEQUENCE: 46
cccgcgctta ctcgaggccc tgaaaataca ggttttcgcg ttcaaacggc agaatcggtt    60
```

<210> SEQ ID NO 47
<211> LENGTH: 35
<212> TYPE: DNA
<213> ORGANISM: Artificial Sequence
<220> FEATURE:
<223> OTHER INFORMATION: Synthetic Construct

<400> SEQUENCE: 47
gaaactgaaa cccatatgga agctcgtcgt tctgc                          35

<210> SEQ ID NO 48
<211> LENGTH: 43
<212> TYPE: DNA
<213> ORGANISM: Artificial Sequence
<220> FEATURE:
<223> OTHER INFORMATION: Synthetic Construct

<400> SEQUENCE: 48
gcatgctcga gcggccgctt ttaatcaaac atcctgccaa ctc                 43

<210> SEQ ID NO 49
<211> LENGTH: 37
<212> TYPE: DNA
<213> ORGANISM: Artificial Sequence
<220> FEATURE:
<223> OTHER INFORMATION: Synthetic Construct

<400> SEQUENCE: 49
gatcgaaggg cgatcgtgtc acagtctggc gaaaccg                        37

<210> SEQ ID NO 50
<211> LENGTH: 43
<212> TYPE: DNA
<213> ORGANISM: Artificial Sequence
<220> FEATURE:
<223> OTHER INFORMATION: Synthetic Construct

<400> SEQUENCE: 50
ctgaattctg cagatatctg tttttccact cttcgttcac ttt                 43

<210> SEQ ID NO 51
<211> LENGTH: 33
<212> TYPE: DNA
<213> ORGANISM: Artificial Sequence
<220> FEATURE:
<223> OTHER INFORMATION: Synthetic Construct

<400> SEQUENCE: 51
tctagagggc ccaagaaaaa tgccccgctt acg                            33

<210> SEQ ID NO 52
<211> LENGTH: 111
<212> TYPE: DNA
<213> ORGANISM: Artificial Sequence
<220> FEATURE:
<223> OTHER INFORMATION: Synthetic Construct

<400> SEQUENCE: 52
gatcgcggcc gcgcccttga cgatgccaca tcctgagcaa ataattcaac cactaattgt     60
gagcggataa cacaaggagg aaacagctat gtcattaccg ttcttaactt c             111

<210> SEQ ID NO 53
<211> LENGTH: 75
<212> TYPE: DNA

<213> ORGANISM: Artificial Sequence
<220> FEATURE:
<223> OTHER INFORMATION: Synthetic Construct

<400> SEQUENCE: 53

```
gatcgggccc caagaaaaaa ggcacgtcat ctgacgtgcc ttttttattt gtagacgcgt      60
tgttatagca ttcta                                                      75
```

<210> SEQ ID NO 54
<211> LENGTH: 81
<212> TYPE: DNA
<213> ORGANISM: Artificial Sequence
<220> FEATURE:
<223> OTHER INFORMATION: Synthetic Construct

<400> SEQUENCE: 54

```
aaagtagccg aagatgacgg tttgtcacat ggagttggca ggatgtttga ttaaaagcaa      60
ttaaccctca ctaaagggcg g                                                81
```

<210> SEQ ID NO 55
<211> LENGTH: 160
<212> TYPE: DNA
<213> ORGANISM: Artificial Sequence
<220> FEATURE:
<223> OTHER INFORMATION: Synthetic Construct

<400> SEQUENCE: 55

```
agagtgttca ccaaaaataa taacctttcc cggtgcagaa gttaagaacg gtaatgacat      60
agctgtttcc tccttgtgtt atccgctcac aattagtggt tgaattattt gctcaggatg     120
tggcatcgtc aagggctaat acgactcact atagggctcg                           160
```

<210> SEQ ID NO 56
<211> LENGTH: 445
<212> TYPE: DNA
<213> ORGANISM: Artificial Sequence
<220> FEATURE:
<223> OTHER INFORMATION: Synthetic Construct

<400> SEQUENCE: 56

```
aaagaccgac caagcgacgt ctgagagctc cctggcgaat tcggtaccaa taaaagagct      60
ttattttcat gatctgtgtg ttggttttg tgtgcggcgc ggaagttcct attctctaga     120
aagtatagga acttcctcga gccctatagt gagtcgtatt aaattcatat aaaaaacata    180
cagataacca tctgcggtga taaattatct ctggcggtgt tgacataaat accactggcg    240
gtgatactga gcacatcagc aggacgcact gaccaccatg aaggtgcaaa ggaggtaaaa    300
aaacatggta tcctgttctg cgccgggtaa gatttacctg ttcggtgaac acgccgtagt    360
ttatggcgaa actgcaattg cgtgtgcggt ggaactgcgt acccgtgttc gcgcggaact    420
caatgactct atcactattc agagc                                         445
```

<210> SEQ ID NO 57
<211> LENGTH: 445
<212> TYPE: DNA
<213> ORGANISM: Artificial Sequence
<220> FEATURE:
<223> OTHER INFORMATION: Synthetic Construct

<400> SEQUENCE: 57

```
aaagaccgac caagcgacgt ctgagagctc cctggcgaat tcggtaccaa taaaagagct      60
ttattttcat gatctgtgtg ttggttttg tgtgcggcgc ggaagttcct attctctaga     120
```

```
aagtatagga acttcctcga gccctatagt gagtcgtatt aaattcatat aaaaaacata    180
cagataacca tctgcggtga taaattatct ctggcggtgt tgacctaaat accactggcg    240
gtgatactga gcacatcagc aggacgcact gaccaccatg aaggtgcaaa ggaggtaaaa    300
aaacatggta tcctgttctg cgccgggtaa gatttacctg ttcggtgaac acgccgtagt    360
ttatggcgaa actgcaattg cgtgtgcggt ggaactgcgt acccgtgttc gcgcggaact    420
caatgactct atcactattc agagc                                         445
```

<210> SEQ ID NO 58
<211> LENGTH: 442
<212> TYPE: DNA
<213> ORGANISM: Artificial Sequence
<220> FEATURE:
<223> OTHER INFORMATION: Synthetic Construct

<400> SEQUENCE: 58

```
aaagaccgac caagcgacgt ctgagagctc cctggcgaat tcggtaccaa taaaagagct     60
ttattttcat gatctgtgtg ttggtttttg tgtgcggcgc ggaagttcct attctctaga    120
aagtatagga acttcctcga gccctatagt gagtcgtatt aaattcatat aaaaaacata    180
cagataacca tctgcggtga taaattatct ctggcggtgt tgacctaaat accactggcg    240
gtgatactga gcacatcagc aggacgcact gaccaccatg aaggtgcaaa ggtaaaaaaa    300
catggtatcc tgttctgcgc cgggtaagat ttacctgttc ggtgaacacg ccgtagttta    360
tggcgaaact gcaattgcgt gtgcggtgga actgcgtacc cgtgttcgcg cggaactcaa    420
tgactctatc actattcaga gc                                            442
```

<210> SEQ ID NO 59
<211> LENGTH: 445
<212> TYPE: DNA
<213> ORGANISM: Artificial Sequence
<220> FEATURE:
<223> OTHER INFORMATION: Synthetic Construct

<400> SEQUENCE: 59

```
aaagaccgac caagcgacgt ctgagagctc cctggcgaat tcggtaccaa taaaagagct     60
ttattttcat gatctgtgtg ttggtttttg tgtgcggcgc ggaagttcct attctctaga    120
aagtatagga acttcctcga gccctatagt gagtcgtatt aaattcatat aaaaaacata    180
cagataacca tctgcggtga taaattatct ctggcggtgt tgacgtaaat accactggcg    240
gtgatactga gcacatcagc aggacgcact gaccaccatg aaggtgcaaa ggaggtaaaa    300
aaacatggta tcctgttctg cgccgggtaa gatttacctg ttcggtgaac acgccgtagt    360
ttatggcgaa actgcaattg cgtgtgcggt ggaactgcgt acccgtgttc gcgcggaact    420
caatgactct atcactattc agagc                                         445
```

<210> SEQ ID NO 60
<211> LENGTH: 81
<212> TYPE: DNA
<213> ORGANISM: Artificial Sequence
<220> FEATURE:
<223> OTHER INFORMATION: Synthetic Construct

<400> SEQUENCE: 60

```
aaagtagccg aagatgacgg tttgtcacat ggagttggca ggatgtttga ttaaaagcaa     60
ttaaccctca ctaaagggcg g                                              81
```

<210> SEQ ID NO 61
<211> LENGTH: 22
<212> TYPE: DNA
<213> ORGANISM: Artificial Sequence
<220> FEATURE:
<223> OTHER INFORMATION: Synthetic Construct

<400> SEQUENCE: 61
gctctgaata gtgatagagt ca                                              22

<210> SEQ ID NO 62
<211> LENGTH: 199
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 112
<223> OTHER INFORMATION: n = A,T,C or G

<400> SEQUENCE: 62
taaatcttac ccggcgcaga acaggatacc atgttttttt acctcctttg caccttcatg      60
gtggtcagtg cgtcctgctg atgtgctcag tatcaccgcc agtggtattt angtcaacac    120
cgccagagat aatttatcac cgcagatggt tatctgtatg ttttttatat gaatttaata    180
cgactcacta tagggctcg                                                 199

<210> SEQ ID NO 63
<211> LENGTH: 24
<212> TYPE: DNA
<213> ORGANISM: Artificial Sequence
<220> FEATURE:
<223> OTHER INFORMATION: Synthetic Construct

<400> SEQUENCE: 63
aaagaccgac caagcgacgt ctga                                            24

<210> SEQ ID NO 64
<211> LENGTH: 22
<212> TYPE: DNA
<213> ORGANISM: Artificial Sequence
<220> FEATURE:
<223> OTHER INFORMATION: Synthetic Construct

<400> SEQUENCE: 64
caccatggta tcctgttctg cg                                              22

<210> SEQ ID NO 65
<211> LENGTH: 22
<212> TYPE: DNA
<213> ORGANISM: Artificial Sequence
<220> FEATURE:
<223> OTHER INFORMATION: Synthetic Construct

<400> SEQUENCE: 65
ttaatctact ttcagacctt gc                                              22

<210> SEQ ID NO 66
<211> LENGTH: 37
<212> TYPE: DNA
<213> ORGANISM: Artificial Sequence
<220> FEATURE:
<223> OTHER INFORMATION: Synthetic Construct

<400> SEQUENCE: 66
aggaggtggt ctcaaatgac tgccgacaac aatagta       37

<210> SEQ ID NO 67
<211> LENGTH: 50
<212> TYPE: DNA
<213> ORGANISM: Artificial Sequence
<220> FEATURE:
<223> OTHER INFORMATION: Synthetic Construct

<400> SEQUENCE: 67
aggaggtggt ctcagcgctc tgcagttata gcattctatg aatttgcctg       50

<210> SEQ ID NO 68
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 16, 17
<223> OTHER INFORMATION: n = A,T,C or G

<400> SEQUENCE: 68
gaaaaagcag aatttnnkac cctgctggaa ctg       33

<210> SEQ ID NO 69
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 17, 18
<223> OTHER INFORMATION: n = A,T,C or G

<400> SEQUENCE: 69
cagttccagc agggtmnnaa attctgcttt ttc       33

<210> SEQ ID NO 70
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 16, 17
<223> OTHER INFORMATION: n = A,T,C or G

<400> SEQUENCE: 70
gagtctgata tccgtnnkgc gctggatcgc ttc       33

<210> SEQ ID NO 71
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 17, 18
<223> OTHER INFORMATION: n = A,T,C or G

<400> SEQUENCE: 71
gaagcgatcc agcgcmnnac ggatatcaga ctc       33

```
<210> SEQ ID NO 72
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 16, 17
<223> OTHER INFORMATION: n = A,T,C or G

<400> SEQUENCE: 72
tcccgttggt ggcgtnnkgt gggtctggcg acc                                33

<210> SEQ ID NO 73
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 17, 18
<223> OTHER INFORMATION: n = A,T,C or G

<400> SEQUENCE: 73
ggtcgccaga cccacmnnac gccaccaacg gga                                33

<210> SEQ ID NO 74
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 16, 17
<223> OTHER INFORMATION: n = A,T,C or G

<400> SEQUENCE: 74
tccgtcgcaa aaatgnnktc tttcgtaacc att                                33

<210> SEQ ID NO 75
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 17, 18
<223> OTHER INFORMATION: n = A,T,C or G

<400> SEQUENCE: 75
aatggttacg aaagamnnca tttttgcgac gga                                33

<210> SEQ ID NO 76
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 16, 17
<223> OTHER INFORMATION: n = A,T,C or G

<400> SEQUENCE: 76
gcaaaaatgt tttctnnkgt aaccattatc gac                                33
```

```
<210> SEQ ID NO 77
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 17, 18
<223> OTHER INFORMATION: n = A,T,C or G

<400> SEQUENCE: 77
gtcgataatg gttacmnnag aaaacatttt tgc                               33

<210> SEQ ID NO 78
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 16, 17
<223> OTHER INFORMATION: n = A,T,C or G

<400> SEQUENCE: 78
aaaatgtttt ctttcnnkac cattatcgac gat                               33

<210> SEQ ID NO 79
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 17, 18
<223> OTHER INFORMATION: n = A,T,C or G

<400> SEQUENCE: 79
atcgtcgata atggtmnnga agaaaacat ttt                                33

<210> SEQ ID NO 80
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 16, 17
<223> OTHER INFORMATION: n = A,T,C or G

<400> SEQUENCE: 80
gacctgtgca acgctnnkct gcaagaagcc aag                               33

<210> SEQ ID NO 81
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 17, 18
<223> OTHER INFORMATION: n = A,T,C or G

<400> SEQUENCE: 81
```
cttggcttct tgcagmnnag cgttgcacag gtc                           33

<210> SEQ ID NO 82
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 16, 17
<223> OTHER INFORMATION: n = A,T,C or G

<400> SEQUENCE: 82
gcatggaaat cctctnnkgg cccgctgcaa ctg                           33

<210> SEQ ID NO 83
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 17, 18
<223> OTHER INFORMATION: n = A,T,C or G

<400> SEQUENCE: 83
cagttgcagc gggccmnnag aggatttcca tgc                           33

<210> SEQ ID NO 84
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 16, 17
<223> OTHER INFORMATION: n = A,T,C or G

<400> SEQUENCE: 84
tcttctggcc cgctgnnkct ggtgttcgct tac                           33

<210> SEQ ID NO 85
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 17, 18
<223> OTHER INFORMATION: n = A,T,C or G

<400> SEQUENCE: 85
gtaagcgaac accagmnnca gcgggccaga aga                           33

<210> SEQ ID NO 86
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 16, 17
<223> OTHER INFORMATION: n = A,T,C or G

<400> SEQUENCE: 86

```
ggcccgctgc aactgnnktt cgcttacttc gct                          33
```

<210> SEQ ID NO 87
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 17, 18
<223> OTHER INFORMATION: n = A,T,C or G

<400> SEQUENCE: 87

```
agcgaagtaa gcgaamnnca gttgcagcgg gcc                          33
```

<210> SEQ ID NO 88
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 16, 17
<223> OTHER INFORMATION: n = A,T,C or G

<400> SEQUENCE: 88

```
caaaaatacc atgacnnkat ctctcgtcct tcc                          33
```

<210> SEQ ID NO 89
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 17, 18
<223> OTHER INFORMATION: n = A,T,C or G

<400> SEQUENCE: 89

```
ggaaggacga gagatmnngt catggtattt ttg                          33
```

<210> SEQ ID NO 90
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 16, 17
<223> OTHER INFORMATION: n = A,T,C or G

<400> SEQUENCE: 90

```
cgtccttccc atatcnnkcg tctgtgcaat gac                          33
```

<210> SEQ ID NO 91
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 17, 18
<223> OTHER INFORMATION: n = A,T,C or G

```
<400> SEQUENCE: 91
gtcattgcac agacgmnnga tatgggaagg acg                              33

<210> SEQ ID NO 92
<211> LENGTH: 33
<212> TYPE: DNA
<213> ORGANISM: Artificial Sequence
<220> FEATURE:
<223> OTHER INFORMATION: Synthetic Construct

<400> SEQUENCE: 92
gaaggagata tacatatgac cgaagctcgt cgt                              33

<210> SEQ ID NO 93
<211> LENGTH: 33
<212> TYPE: DNA
<213> ORGANISM: Artificial Sequence
<220> FEATURE:
<223> OTHER INFORMATION: Synthetic Construct

<400> SEQUENCE: 93
acgacgagct tcggtcatat gtatatctcc ttc                              33

<210> SEQ ID NO 94
<211> LENGTH: 33
<212> TYPE: DNA
<213> ORGANISM: Artificial Sequence
<220> FEATURE:
<223> OTHER INFORMATION: Synthetic Construct

<400> SEQUENCE: 94
gaaggagata tacatatgga aaccgaagct cgt                              33

<210> SEQ ID NO 95
<211> LENGTH: 33
<212> TYPE: DNA
<213> ORGANISM: Artificial Sequence
<220> FEATURE:
<223> OTHER INFORMATION: Synthetic Construct

<400> SEQUENCE: 95
acgagcttcg gtttccatat gtatatctcc ttc                              33

<210> SEQ ID NO 96
<211> LENGTH: 33
<212> TYPE: DNA
<213> ORGANISM: Artificial Sequence
<220> FEATURE:
<223> OTHER INFORMATION: Synthetic Construct

<400> SEQUENCE: 96
gaaggagata tacatatgac tgaaaccgaa gct                              33

<210> SEQ ID NO 97
<211> LENGTH: 33
<212> TYPE: DNA
<213> ORGANISM: Artificial Sequence
<220> FEATURE:
<223> OTHER INFORMATION: Synthetic Construct

<400> SEQUENCE: 97
agcttcggtt tcagtcatat gtatatctcc ttc                              33

<210> SEQ ID NO 98
<211> LENGTH: 33
```

```
<212> TYPE: DNA
<213> ORGANISM: Artificial Sequence
<220> FEATURE:
<223> OTHER INFORMATION: Synthetic Construct

<400> SEQUENCE: 98
gaaggagata tacatatgga aactgaaacc gaa                                   33

<210> SEQ ID NO 99
<211> LENGTH: 33
<212> TYPE: DNA
<213> ORGANISM: Artificial Sequence
<220> FEATURE:
<223> OTHER INFORMATION: Synthetic Construct

<400> SEQUENCE: 99
ttcggtttca gtttccatat gtatatctcc ttc                                   33

<210> SEQ ID NO 100
<211> LENGTH: 33
<212> TYPE: DNA
<213> ORGANISM: Artificial Sequence
<220> FEATURE:
<223> OTHER INFORMATION: Synthetic Construct

<400> SEQUENCE: 100
gaaggagata tacatatgac cgaaactgaa acc                                   33

<210> SEQ ID NO 101
<211> LENGTH: 33
<212> TYPE: DNA
<213> ORGANISM: Artificial Sequence
<220> FEATURE:
<223> OTHER INFORMATION: Synthetic Construct

<400> SEQUENCE: 101
ggtttcagtt tcggtcatat gtatatctcc ttc                                   33

<210> SEQ ID NO 102
<211> LENGTH: 39
<212> TYPE: DNA
<213> ORGANISM: Artificial Sequence
<220> FEATURE:
<223> OTHER INFORMATION: Synthetic Construct

<400> SEQUENCE: 102
agaaggagat ataccatgga agctcgtcgt tccgcaaac                             39

<210> SEQ ID NO 103
<211> LENGTH: 39
<212> TYPE: DNA
<213> ORGANISM: Artificial Sequence
<220> FEATURE:
<223> OTHER INFORMATION: Synthetic Construct

<400> SEQUENCE: 103
gtttgcggaa cgacgagctt ccatggtata tctccttct                             39

<210> SEQ ID NO 104
<211> LENGTH: 33
<212> TYPE: DNA
<213> ORGANISM: Artificial Sequence
<220> FEATURE:
<223> OTHER INFORMATION: Synthetic Construct

<400> SEQUENCE: 104
```

```
agaaggagat ataccatgga gcataattcc cgt                                      33

<210> SEQ ID NO 105
<211> LENGTH: 33
<212> TYPE: DNA
<213> ORGANISM: Artificial Sequence
<220> FEATURE:
<223> OTHER INFORMATION: Synthetic Construct

<400> SEQUENCE: 105
acgggaatta tgctccatgg tatatctcct tct                                      33

<210> SEQ ID NO 106
<211> LENGTH: 33
<212> TYPE: DNA
<213> ORGANISM: Artificial Sequence
<220> FEATURE:
<223> OTHER INFORMATION: Synthetic Construct

<400> SEQUENCE: 106
gaaggagata tacatatgga aacgcgtcgt tct                                      33

<210> SEQ ID NO 107
<211> LENGTH: 33
<212> TYPE: DNA
<213> ORGANISM: Artificial Sequence
<220> FEATURE:
<223> OTHER INFORMATION: Synthetic Construct

<400> SEQUENCE: 107
agaacgacgc gtttccatat gtatatctcc ttc                                      33

<210> SEQ ID NO 108
<211> LENGTH: 23
<212> TYPE: DNA
<213> ORGANISM: Artificial Sequence
<220> FEATURE:
<223> OTHER INFORMATION: Synthetic Construct

<400> SEQUENCE: 108
cggtgaactg aaaggtgacg tcc                                                 23

<210> SEQ ID NO 109
<211> LENGTH: 25
<212> TYPE: DNA
<213> ORGANISM: Artificial Sequence
<220> FEATURE:
<223> OTHER INFORMATION: Synthetic Construct

<400> SEQUENCE: 109
ggacgttaac gctattaaca ccctg                                               25

<210> SEQ ID NO 110
<211> LENGTH: 22
<212> TYPE: DNA
<213> ORGANISM: Artificial Sequence
<220> FEATURE:
<223> OTHER INFORMATION: Synthetic Construct

<400> SEQUENCE: 110
cacatcgtcg atcagctcca gc                                                  22

<210> SEQ ID NO 111
<211> LENGTH: 24
<212> TYPE: DNA
<213> ORGANISM: Artificial Sequence
```

<220> FEATURE:
<223> OTHER INFORMATION: Synthetic Construct

<400> SEQUENCE: 111
ggtcgtcaga ctgtcgatga agcc                                       24

<210> SEQ ID NO 112
<211> LENGTH: 39
<212> TYPE: DNA
<213> ORGANISM: Artificial Sequence
<220> FEATURE:
<223> OTHER INFORMATION: Synthetic Construct

<400> SEQUENCE: 112
gcttatgaat tctgtgcgac ctcttctcaa tttactcag                       39

<210> SEQ ID NO 113
<211> LENGTH: 38
<212> TYPE: DNA
<213> ORGANISM: Artificial Sequence
<220> FEATURE:
<223> OTHER INFORMATION: Synthetic Construct

<400> SEQUENCE: 113
gcttataagc ttagacatac atcagctggt taatcggg                        38

<210> SEQ ID NO 114
<211> LENGTH: 21
<212> TYPE: DNA
<213> ORGANISM: Artificial Sequence
<220> FEATURE:
<223> OTHER INFORMATION: Synthetic Construct

<400> SEQUENCE: 114
ctcctccagc aggttctcac c                                          21

<210> SEQ ID NO 115
<211> LENGTH: 52
<212> TYPE: DNA
<213> ORGANISM: Artificial Sequence
<220> FEATURE:
<223> OTHER INFORMATION: Synthetic Construct

<400> SEQUENCE: 115
gggcccgttt aaactttaac tagactctgc agttagcgtt caaacggcag aa         52

<210> SEQ ID NO 116
<211> LENGTH: 25
<212> TYPE: DNA
<213> ORGANISM: Artificial Sequence
<220> FEATURE:
<223> OTHER INFORMATION: Synthetic Construct

<400> SEQUENCE: 116
caccatgcgt cgttctgcga actac                                      25

<210> SEQ ID NO 117
<211> LENGTH: 25
<212> TYPE: DNA
<213> ORGANISM: Artificial Sequence
<220> FEATURE:
<223> OTHER INFORMATION: Synthetic Construct

<400> SEQUENCE: 117
caccatgcgt cgttctgcga actac                                      25

```
<210> SEQ ID NO 118
<211> LENGTH: 596
<212> TYPE: PRT
<213> ORGANISM: Artificial Sequence
<220> FEATURE:
<223> OTHER INFORMATION: Synthetic Construct

<400> SEQUENCE: 118
```

| | | | | | | | | | | | | | | |
|---|---|---|---|---|---|---|---|---|---|---|---|---|---|---|
| Met | Arg | Gly | Ser | His | His | His | His | His | Gly | Met | Ala | Ser | Met | Thr |
| 1 | | | | 5 | | | | | 10 | | | | | 15 |

| | | | | | | | | | | | | | | |
|---|---|---|---|---|---|---|---|---|---|---|---|---|---|---|
| Gly | Gly | Gln | Gln | Met | Gly | Arg | Asp | Leu | Tyr | Asp | Asp | Asp | Lys | Asp |
| | | | 20 | | | | | 25 | | | | | 30 | |

| | | | | | | | | | | | | | | |
|---|---|---|---|---|---|---|---|---|---|---|---|---|---|---|
| His | Pro | Phe | Thr | Met | Arg | Cys | Ser | Val | Ser | Thr | Glu | Asn | Val | Ser | Phe |
| | | | 35 | | | | | 40 | | | | | 45 | | |

| | | | | | | | | | | | | | | |
|---|---|---|---|---|---|---|---|---|---|---|---|---|---|---|
| Thr | Glu | Thr | Glu | Thr | Glu | Ala | Arg | Arg | Ser | Ala | Asn | Tyr | Glu | Pro | Asn |
| | 50 | | | | | 55 | | | | | 60 | | | | |

| | | | | | | | | | | | | | | | |
|---|---|---|---|---|---|---|---|---|---|---|---|---|---|---|---|
| Ser | Trp | Asp | Tyr | Asp | Tyr | Leu | Leu | Ser | Ser | Asp | Thr | Asp | Glu | Ser | Ile |
| 65 | | | | | 70 | | | | | 75 | | | | | 80 |

| | | | | | | | | | | | | | | |
|---|---|---|---|---|---|---|---|---|---|---|---|---|---|---|
| Glu | Val | Tyr | Lys | Asp | Lys | Ala | Lys | Lys | Leu | Glu | Ala | Glu | Val | Arg | Arg |
| | | | | 85 | | | | | 90 | | | | | 95 | |

| | | | | | | | | | | | | | |
|---|---|---|---|---|---|---|---|---|---|---|---|---|---|
| Glu | Ile | Asn | Asn | Glu | Lys | Ala | Glu | Phe | Leu | Thr | Leu | Leu | Glu | Leu | Ile |
| | | | | 100 | | | | | 105 | | | | | 110 | |

| | | | | | | | | | | | | | |
|---|---|---|---|---|---|---|---|---|---|---|---|---|---|
| Asp | Asn | Val | Gln | Arg | Leu | Gly | Leu | Gly | Tyr | Arg | Phe | Glu | Ser | Asp | Ile |
| | | | 115 | | | | | 120 | | | | | 125 | | |

| | | | | | | | | | | | | | |
|---|---|---|---|---|---|---|---|---|---|---|---|---|---|
| Arg | Gly | Ala | Leu | Asp | Arg | Phe | Val | Ser | Ser | Gly | Gly | Phe | Asp | Ala | Val |
| 130 | | | | | 135 | | | | | 140 | | | | | |

| | | | | | | | | | | | | | | | |
|---|---|---|---|---|---|---|---|---|---|---|---|---|---|---|---|
| Thr | Lys | Thr | Ser | Leu | His | Gly | Thr | Ala | Leu | Ser | Phe | Arg | Leu | Leu | Arg |
| 145 | | | | | 150 | | | | | 155 | | | | | 160 |

| | | | | | | | | | | | | | | |
|---|---|---|---|---|---|---|---|---|---|---|---|---|---|---|
| Gln | His | Gly | Phe | Glu | Val | Ser | Gln | Glu | Ala | Phe | Ser | Gly | Phe | Lys | Asp |
| | | | | 165 | | | | | 170 | | | | | 175 | |

| | | | | | | | | | | | | | | |
|---|---|---|---|---|---|---|---|---|---|---|---|---|---|---|
| Gln | Asn | Gly | Asn | Phe | Leu | Glu | Asn | Leu | Lys | Glu | Asp | Ile | Lys | Ala | Ile |
| | | | 180 | | | | | 185 | | | | | 190 | | |

| | | | | | | | | | | | | | | |
|---|---|---|---|---|---|---|---|---|---|---|---|---|---|---|
| Leu | Ser | Leu | Tyr | Glu | Ala | Ser | Phe | Leu | Ala | Leu | Glu | Gly | Glu | Asn | Ile |
| | | 195 | | | | | 200 | | | | | 205 | | | |

| | | | | | | | | | | | | | | |
|---|---|---|---|---|---|---|---|---|---|---|---|---|---|---|
| Leu | Asp | Glu | Ala | Lys | Val | Phe | Ala | Ile | Ser | His | Leu | Lys | Glu | Leu | Ser |
| | 210 | | | | | 215 | | | | | 220 | | | | |

| | | | | | | | | | | | | | | | |
|---|---|---|---|---|---|---|---|---|---|---|---|---|---|---|---|
| Glu | Glu | Lys | Ile | Gly | Lys | Glu | Leu | Ala | Glu | Gln | Val | Asn | His | Ala | Leu |
| 225 | | | | | 230 | | | | | 235 | | | | | 240 |

| | | | | | | | | | | | | | | |
|---|---|---|---|---|---|---|---|---|---|---|---|---|---|---|
| Glu | Leu | Pro | Leu | His | Arg | Arg | Thr | Gln | Arg | Leu | Glu | Ala | Val | Trp | Ser |
| | | | 245 | | | | | 250 | | | | | 255 | | |

| | | | | | | | | | | | | | | |
|---|---|---|---|---|---|---|---|---|---|---|---|---|---|---|
| Ile | Glu | Ala | Tyr | Arg | Lys | Lys | Glu | Asp | Ala | Asn | Gln | Val | Leu | Leu | Glu |
| | | | 260 | | | | | 265 | | | | | 270 | | |

| | | | | | | | | | | | | | | |
|---|---|---|---|---|---|---|---|---|---|---|---|---|---|---|
| Leu | Ala | Ile | Leu | Asp | Tyr | Asn | Met | Ile | Gln | Ser | Val | Tyr | Gln | Arg | Asp |
| | | 275 | | | | | 280 | | | | | 285 | | | |

| | | | | | | | | | | | | | | |
|---|---|---|---|---|---|---|---|---|---|---|---|---|---|---|
| Leu | Arg | Glu | Thr | Ser | Arg | Trp | Trp | Arg | Arg | Val | Gly | Leu | Ala | Thr | Lys |
| | 290 | | | | | 295 | | | | | 300 | | | | |

| | | | | | | | | | | | | | | | |
|---|---|---|---|---|---|---|---|---|---|---|---|---|---|---|---|
| Leu | His | Phe | Ala | Arg | Asp | Arg | Leu | Ile | Glu | Ser | Phe | Tyr | Trp | Ala | Val |
| 305 | | | | | 310 | | | | | 315 | | | | | 320 |

| | | | | | | | | | | | | | | |
|---|---|---|---|---|---|---|---|---|---|---|---|---|---|---|
| Gly | Val | Ala | Phe | Glu | Pro | Gln | Tyr | Ser | Asp | Cys | Arg | Asn | Ser | Val | Ala |
| | | | 325 | | | | | 330 | | | | | 335 | | |

| | | | | | | | | | | | | | | |
|---|---|---|---|---|---|---|---|---|---|---|---|---|---|---|
| Lys | Met | Phe | Ser | Phe | Val | Thr | Ile | Ile | Asp | Asp | Ile | Tyr | Asp | Val | Tyr |
| | | | 340 | | | | | 345 | | | | | 350 | | |

| | | | | | | | | | | | | | | |
|---|---|---|---|---|---|---|---|---|---|---|---|---|---|---|
| Gly | Thr | Leu | Asp | Glu | Leu | Glu | Leu | Phe | Thr | Asp | Ala | Val | Glu | Arg | Trp |
| | | 355 | | | | | 360 | | | | | 365 | | | |

Asp Val Asn Ala Ile Asn Asp Leu Pro Asp Tyr Met Lys Leu Cys Phe
370                 375                 380

Leu Ala Leu Tyr Asn Thr Ile Asn Glu Ile Ala Tyr Asp Asn Leu Lys
385                 390                 395                 400

Asp Lys Gly Glu Asn Ile Leu Pro Tyr Leu Thr Lys Ala Trp Ala Asp
            405                 410                 415

Leu Cys Asn Ala Phe Leu Gln Glu Ala Lys Trp Leu Tyr Asn Lys Ser
            420                 425                 430

Thr Pro Thr Phe Asp Asp Tyr Phe Gly Asn Ala Trp Lys Ser Ser Ser
            435                 440                 445

Gly Pro Leu Gln Leu Val Phe Ala Tyr Phe Ala Val Gln Asn Ile
450                 455                 460

Lys Lys Glu Glu Ile Glu Asn Leu Gln Lys Tyr His Asp Thr Ile Ser
465                 470                 475                 480

Arg Pro Ser His Ile Phe Arg Leu Cys Asn Asp Leu Ala Ser Ala Ser
            485                 490                 495

Ala Glu Ile Ala Arg Gly Glu Thr Ala Asn Ser Val Ser Cys Tyr Met
            500                 505                 510

Arg Thr Lys Gly Ile Ser Glu Glu Leu Ala Thr Glu Ser Val Met Asn
515                 520                 525

Leu Ile Asp Glu Thr Trp Lys Lys Met Asn Lys Glu Lys Leu Gly Gly
530                 535                 540

Ser Leu Phe Ala Lys Pro Phe Val Glu Thr Ala Ile Asn Leu Ala Arg
545                 550                 555                 560

Gln Ser His Cys Thr Tyr His Asn Gly Asp Ala His Thr Ser Pro Asp
            565                 570                 575

Glu Leu Thr Arg Lys Arg Val Leu Ser Val Ile Thr Glu Pro Ile Leu
            580                 585                 590

Pro Phe Glu Arg
        595

<210> SEQ ID NO 119
<211> LENGTH: 7424
<212> TYPE: DNA
<213> ORGANISM: Artificial Sequence
<220> FEATURE:
<223> OTHER INFORMATION: Synthetic Construct

<400> SEQUENCE: 119
aagggcgagc tcaacgatcc ggctgctaac aaagcccgaa aggaagctga gttggctgct      60
gccaccgctg agcaataact agcataaccc cttggggcct ctaaacgggt cttgaggagt     120
ttttgctga aggaggaac tatatccgga tatcccgcaa gaggcccggc agtaccggca       180
taaccaagcc tatgcctaca gcatccaggg tgacggtgcc gaggatgacg atgagcgcat    240
tgttagattt catacacggt gcctgactgc gttagcaatt taactgtgat aaactaccgc    300
attaaagctt atcgatgata agctgtcaaa catgagaatt aattcttgaa gacgaaaggg    360
cctcgtgata cgcctatttt tataggttaa tgtcatgata ataatggttt cttagacgtc    420
aggtggcact tttcggggaa atgtgcgcgg aacccctatt tgtttatttt tctaaataca    480
ttcaaatatg tatccgctca tgagacaata accctgataa atgcttcaat aatattgaaa    540
aaggaagagt atgattgaac aagatggatt gcacgcaggt tctccggccg cttgggtgga    600
gaggctattc ggctatgact gggcacaact gacaatcggc tgctctgatg ccgccgtgtt    660
ccggctgtca gcgcaggggc gcccggttct ttttgtcaag accgacctgt ccggtgccct    720

```
gaatgaactg caggacgagg cagcgcggct atcgtggctg gccacgacgg gcgttccttg    780
cgcagctgtg ctcgacgttg tcactgaagc gggaagggac tggctgctat tgggcgaagt    840
gccggggcag gatctcctgt catctcacct tgctcctgcc gagaaagtat ccatcatggc    900
tgatgcaatg cggcggctgc atacgcttga tccggctacc tgcccattcg accaccaagc    960
gaaacatcgc atcgagcggg cacgtactcg gatggaagcc ggtcttgtcg atcaggatga   1020
tctggacgaa gagcatcagg ggctcgcgcc agccgaactg ttcgccaggc tcaaggcgcg   1080
catgcccgac ggcgaggatc tcgtcgtgac acatggcgat gcctgcttgc cgaatatcat   1140
ggtggaaaat ggccgctttt ctggattcat cgactgtggc cggctgggtg tggcggaccg   1200
ctatcaggac atagcgttgg ctacccgtga tattgctgaa gagcttggcg gcgaatgggc   1260
tgaccgcttc ctcgtgcttt acggtatcgc cgctcccgat tcgcagcgca tcgccttcta   1320
tcgccttctt gacgagttct tctgagcggg actctggggt tcgaaatgac cgaccaagcg   1380
acgcctaact gtcagaccaa gtttactcat atatacttta gattgattta aaacttcatt   1440
tttaatttaa aaggatctag gtgaagatcc tttttgataa tctcatgacc aaaatcccct   1500
aacgtgagtt ttcgttccac tgagcgtcag accccgtaga aaagatcaaa ggatcttctt   1560
gagatccttt ttttctgcgc gtaatctgct gcttgcaaac aaaaaaacca ccgctaccag   1620
cggtggtttg tttgccggat caagagctac caactctttt tccgaaggta actggcttca   1680
gcagagcgca gataccaaat actgtccttc tagtgtagcc gtagttaggc caccacttca   1740
agaactctgt agcaccgcct acatacctcg ctctgctaat cctgttacca gtggctgctg   1800
ccagtggcga taagtcgtgt cttaccgggt tggactcaag acgatagtta ccggataagg   1860
cgcagcggtc gggctgaacg gggggttcgt gcacacagcc cagcttggag cgaacgacct   1920
acaccgaact gagatacccta cagcgtgagc tatgagaaag cgccacgctt cccgaaggga   1980
gaaaggcgga caggtatccg gtaagcggca gggtcggaac aggagagcgc acgagggagc   2040
ttccaggggg aaacgcctgg tatctttata gtcctgtcgg gtttcgccac ctctgacttg   2100
agcgtcgatt tttgtgatgc tcgtcagggg ggcggagcct atggaaaaac gccagcaacg   2160
cggccttttt acggttcctg gccttttgct ggccttttgc tcacatgttc tttcctgcgt   2220
tatcccctga ttctgtggat aaccgtatta ccgcctttga gtgagctgat accgctcgcc   2280
gcagccgaac gaccgagcgc agcgagtcag tgagcgagga agcggaagag cgcctgatgc   2340
ggtattttct ccttacgcat ctgtgcggta tttcacaccg caatggtgca ctctcagtac   2400
aatctgctct gatgccgcat agttaagcca gtatacactc cgctatcgct acgtgactgg   2460
gtcatggctg cgccccgaca cccgccaaca cccgctgacg cgccctgacg ggcttgtctg   2520
ctcccggcat ccgcttacag acaagctgtg accgtctccg ggagctgcat gtgtcagagg   2580
ttttcaccgt catcaccgaa acgcgcgagg cagctgcggt aaagctcatc agcgtggtcg   2640
tgaagcgatt cacagatgtc tgcctgttca tccgcgtcca gctcgttgag tttctccaga   2700
agcgttaatg tctggcttct gataaagcgg gccatgttaa gggcggtttt ttcctgtttg   2760
gtcactgatg cctccgtgta agggggattt ctgttcatgg ggtaatgat accgatgaaa   2820
cgagagagga tgctcacgat acgggttact gatgatgaac atgcccggtt actggaacgt   2880
tgtgagggta acaactggcg gtatggatg cggcggacc agagaaaaat cactcagggt   2940
caatgccagc gcttcgttaa tacagatgta ggtgttccac agggtagcca gcagcatcct   3000
gcgatgcaga tccggaacat aatggtgcag gcgctgact tccgcgtttc cagactttac   3060
gaaacacgga aaccgaagac cattcatgtt gttgctcagg tcgcagacgt tttgcagcag   3120
```

```
cagtcgcttc acgttcgctc gcgtatcggt gattcattct gctaaccagt aaggcaaccc    3180
cgccagccta gccgggtcct caacgacagg agcacgatca tgcgcacccg tggccaggac    3240
ccaacgctgc ccgagatgcg ccgcgtgcgg ctgctggaga tggcggacgc gatggatatg    3300
ttctgccaag ggttggtttg cgcattcaca gttctccgca agaattgatt ggctccaatt    3360
cttggagtgg tgaatccgtt agcgaggtgc cgccggcttc cattcaggtc gaggtggccc    3420
ggctccatgc accgcgacgc aacgcgggga ggcagacaag gtatagggcg cgcctacaa     3480 tccatgccaa cccgttccat gtgctcgccg aggcggcata aatcgccgtg acgatcagcg    3540
gtccaatgat cgaagttagg ctggtaagag ccgcgagcga tccttgaagc tgtccctgat    3600
ggtcgtcatc tacctgcctg acagcatgg cctgcaacgc gggcatcccg atgccgccgg     3660
aagcgagaag aatcataatg gggaaggcca tccagcctcg cgtcgcgaac gccagcaaga    3720
cgtagcccag cgcgtcggcc gccatgccgg cgataatggc ctgcttctcg ccgaaacgtt    3780
tggtggcggg accagtgacg aaggcttgag cgagggcgtg caagattccg aataccgcaa    3840
gcgacaggcc gatcatcgtc gcgctccagc gaaagcggtc ctcgccgaaa atgacccaga    3900
gcgctgccgg cacctgtcct acgagttgca tgataaagaa gacagtcata agtgcggcga    3960
cgatagtcat gccccgcgcc caccggaagg agctgactgg gttgaaggct ctcaagggca    4020
tcggtcgaga tcccggtgcc taatgagtga gctaacttac attaattgcg ttgcgctcac    4080
tgcccgcttt ccagtcggga aacctgtcgt gccagctgca ttaatgaatc ggccaacgcg    4140
cggggagagg cggtttgcgt attgggcgcc agggtggttt ttcttttcac cagtgagacg    4200
ggcaacagct gattgcccct caccgcctgg ccctgagaga gttgcagcaa gcggtccacg    4260 ctggttttgcc ccagcaggcg aaaatcctgt ttgatggtgg ttaacggcgg gatataacat    4320
gagctgtctt cggtatcgtc gtatcccact accgagatat ccgcaccaac gcgcagcccg    4380
gactcggtaa tggcgcgcat tgcgcccagc gccatctgat cgttggcaac cagcatcgca    4440
gtgggaacga tgccctcatt cagcatttgc atggtttgtt gaaaaccgga catggcactc    4500
cagtcgcctt cccgttccgc tatcggctga atttgattgc gagtgagata tttatgccag    4560
ccagccagac gcagacgcgc cgagacagaa cttaatgggc ccgctaacag cgcgatttgc    4620
tggtgaccca atgcgaccag atgctccacg cccagtcgcg taccgtcttc atgggagaaa    4680
ataatactgt tgatgggtgt ctggtcagag acatcaagaa ataacgccgg aacattagtg    4740
caggcagctt ccacagcaat ggcatcctgg tcatccagcg atagttaat gatcagccca     4800 ctgacgcgtt gcgcgagaag attgtgcacc gccgctttac aggcttcgac gccgcttcgt    4860
tctaccatcg acaccaccac gctggcaccc agttgatcgg cgcgagattt aatcgccgcg    4920
acaatttgcg acgcgcgtg cagggccaga ctggaggtgg caacgccaat cagcaacgac     4980
tgtttgcccg ccagttgttg tgccacgcgg ttgggaatgt aattcagctc cgccatcgcc    5040
gcttccactt tttcccgcgt tttcgcagaa acgtggctgg cctggttcac cacgcgggaa    5100
acggtctgat aagagacacc ggcatactct gcgacatcgt ataacgttac tggtttcaca    5160
ttcaccaccc tgaattgact ctcttccggg cgctatcatg ccataccgcg aaaggttttg    5220
cgccattcga tggtgtccgg gatctcgacg ctctccctta tgcgactcct gcattaggaa    5280
gcagcccagt agtaggttga ggccgttgag caccgccgcc gcaaggaatg gtgcatgcaa    5340
ggagatggcg cccaacagtc ccccggccac ggggcctgcc accatacccca gccgaaaca    5400 agcgctcatg agcccgaagt ggcgagcccg atcttcccca tcggtgatgt cggcgatata    5460
```

-continued

```
ggcgccagca accgcacctg tgcgccggt gatgccggcc acgatgcgtc cggcgtagag    5520
gatcgagatc tcgatcccgc gaaattaata cgactcacta tagggaatt gtgagcggat    5580
aacaattccc ctctagaaat aattttgttt aactttaaga aggagatata catatgcggg    5640
gttctcatca tcatcatcat catggtatgg ctagcatgac tggtggacag caaatgggtc    5700
gggatctgta cgacgatgac gataaggatc atcccttcac catgcgttgt agcgtgtcca    5760
ccgaaaatgt gtctttcacc gaaactgaaa ccgaagctcg tcgttctgcg aactacgaac    5820
ctaacagctg ggactatgat tacctgctgt cctccgacac ggacgagtcc atcgaagtat    5880
acaaagacaa agcgaaaaag ctggaagccg aagttcgtcg cgagattaat aacgaaaaag    5940
cagaatttct gaccctgctg gaactgattg acaacgtcca gcgcctgggc ctgggttacc    6000
gtttcgagtc tgatatccgt ggtgcgctgg atcgcttcgt ttcctccggc ggcttcgatg    6060
cggtaaccaa gacttccctg cacggtacgg cactgtcttt ccgtctgctg cgtcaacacg    6120
gttttgaggt ttctcaggaa gcgttcagcg gcttcaaaga ccaaaacggc aacttcctgg    6180
agaacctgaa ggaagatatc aaagctatcc tgagcctgta cgaggccagc ttcctggctc    6240
tggaaggcga aaacatcctg gacgaggcga aggttttcgc aatctctcat ctgaaagaac    6300
tgtctgaaga aaagatcggt aaagagctgg cagaacaggt gaaccatgca ctggaactgc    6360
cactgcatcg ccgtactcag cgtctggaag cagtatggtc tatcgaggcc taccgtaaaa    6420
aggaggacgc gaatcaggtt ctgctggagc tggcaattct ggattacaac atgatccagt    6480
ctgtatacca gcgtgatctg cgtgaaacgt cccgttggtg gcgtcgtgtg ggtctggcga    6540
ccaaactgca ctttgctcgt gaccgcctga ttgagagctt ctactgggcc gtgggtgtag    6600
cattcgaacc gcaatactcc gactgccgta actccgtcgc aaaaatgttt tctttcgtaa    6660
ccattatcga cgatatctac gatgtatacg gcaccctgga cgaactggag ctgtttactg    6720
atgcagttga gcgttgggac gtaaacgcca tcaacgacct gccggattac atgaaactgt    6780
gctttctggc tctgtataac actattaacg aaatcgccta cgacaacctg aaagataaag    6840
gtgagaacat cctgccgtat ctgaccaaag cctgggctga cctgtgcaac gctttcctgc    6900
aagaagccaa gtggctgtac aacaaatcta ctccgacctt tgacgactac ttcggcaacg    6960
catggaaatc ctcttctggc ccgctgcaac tggtgttcgc ttacttcgct gtcgtgcaga    7020
acattaaaaa ggaagagatc gaaaacctgc aaaaatacca tgacaccatc tctcgtcctt    7080
cccatatctt ccgtctgtgc aatgacctgg ctagcgcgtc tgcggaaatt gcgcgtggtg    7140
aaaccgcaaa tagcgtttct tgttacatgc gcactaaagg tatctccgaa gaactggcta    7200
ccgaaagcgt gatgaatctg atcgatgaaa cctggaaaaa gatgaacaag gaaaaactgg    7260
gtggtagcct gttcgcgaaa ccgttcgtgg aaaccgcgat caacctggca cgtcaatctc    7320
actgcacta tcataacggc gacgcgcata cctctccgga tgagctgacc cgcaaacgcg    7380
ttctgtctgt aatcactgaa ccgattctgc cgtttgaacg ctaa                    7424
```

<210> SEQ ID NO 120
<211> LENGTH: 560
<212> TYPE: PRT
<213> ORGANISM: Poplus alba v tremula

<400> SEQUENCE: 120

```
Met Arg Cys Ser Val Ser Thr Glu Asn Val Ser Phe Thr Glu Thr Glu
 1               5                  10                  15
Thr Glu Ala Arg Arg Ser Ala Asn Tyr Glu Pro Asn Ser Trp Asp Tyr
            20                  25                  30
```

```
Asp Tyr Leu Leu Ser Ser Asp Thr Asp Glu Ser Ile Glu Val Tyr Lys
         35                  40                  45

Asp Lys Ala Lys Lys Leu Glu Ala Glu Val Arg Arg Glu Ile Asn Asn
 50                  55                  60

Glu Lys Ala Glu Phe Leu Thr Leu Leu Glu Leu Ile Asp Asn Val Gln
 65                  70                  75                  80

Arg Leu Gly Leu Gly Tyr Arg Phe Glu Ser Asp Ile Arg Gly Ala Leu
                 85                  90                  95

Asp Arg Phe Val Ser Ser Gly Gly Phe Asp Ala Val Thr Lys Thr Ser
                100                 105                 110

Leu His Gly Thr Ala Leu Ser Phe Arg Leu Leu Arg Gln His Gly Phe
                115                 120                 125

Glu Val Ser Gln Glu Ala Phe Ser Gly Phe Lys Asp Gln Asn Gly Asn
                130                 135                 140

Phe Leu Glu Asn Leu Lys Glu Asp Ile Lys Ala Ile Leu Ser Leu Tyr
145                 150                 155                 160

Glu Ala Ser Phe Leu Ala Leu Glu Gly Glu Asn Ile Leu Asp Glu Ala
                165                 170                 175

Lys Val Phe Ala Ile Ser His Leu Lys Glu Leu Ser Glu Glu Lys Ile
                180                 185                 190

Gly Lys Glu Leu Ala Glu Gln Val Asn His Ala Leu Glu Leu Pro Leu
                195                 200                 205

His Arg Arg Thr Gln Arg Leu Glu Ala Val Trp Ser Ile Glu Ala Tyr
                210                 215                 220

Arg Lys Lys Glu Asp Ala Asn Gln Val Leu Leu Glu Leu Ala Ile Leu
225                 230                 235                 240

Asp Tyr Asn Met Ile Gln Ser Val Tyr Gln Arg Asp Leu Arg Glu Thr
                245                 250                 255

Ser Arg Trp Trp Arg Arg Val Gly Leu Ala Thr Lys Leu His Phe Ala
                260                 265                 270

Arg Asp Arg Leu Ile Glu Ser Phe Tyr Trp Ala Val Gly Val Ala Phe
                275                 280                 285

Glu Pro Gln Tyr Ser Asp Cys Arg Asn Ser Val Ala Lys Met Phe Ser
                290                 295                 300

Phe Val Thr Ile Ile Asp Asp Ile Tyr Asp Val Tyr Gly Thr Leu Asp
305                 310                 315                 320

Glu Leu Glu Leu Phe Thr Asp Ala Val Glu Arg Trp Asp Val Asn Ala
                325                 330                 335

Ile Asn Asp Leu Pro Asp Tyr Met Lys Leu Cys Phe Leu Ala Leu Tyr
                340                 345                 350

Asn Thr Ile Asn Glu Ile Ala Tyr Asp Asn Leu Lys Asp Lys Gly Glu
                355                 360                 365

Asn Ile Leu Pro Tyr Leu Thr Lys Ala Trp Ala Asp Leu Cys Asn Ala
                370                 375                 380

Phe Leu Gln Glu Ala Lys Trp Leu Tyr Asn Lys Ser Thr Pro Thr Phe
385                 390                 395                 400

Asp Asp Tyr Phe Gly Asn Ala Trp Lys Ser Ser Gly Pro Leu Gln
                405                 410                 415

Leu Val Phe Ala Tyr Phe Ala Val Val Gln Asn Ile Lys Lys Glu Glu
                420                 425                 430

Ile Glu Asn Leu Gln Lys Tyr His Asp Thr Ile Ser Arg Pro Ser His
                435                 440                 445
```

```
Ile Phe Arg Leu Cys Asn Asp Leu Ala Ser Ala Ala Glu Ile Ala
        450                 455                 460
Arg Gly Glu Thr Ala Asn Ser Val Ser Cys Tyr Met Arg Thr Lys Gly
465                 470                 475                 480
Ile Ser Glu Glu Leu Ala Thr Glu Ser Val Met Asn Leu Ile Asp Glu
                485                 490                 495
Thr Trp Lys Lys Met Asn Lys Glu Lys Leu Gly Gly Ser Leu Phe Ala
                500                 505                 510
Lys Pro Phe Val Glu Thr Ala Ile Asn Leu Ala Arg Gln Ser His Cys
                515                 520                 525
Thr Tyr His Asn Gly Asp Ala His Thr Ser Pro Asp Glu Leu Thr Arg
        530                 535                 540
Lys Arg Val Leu Ser Val Ile Thr Glu Pro Ile Leu Pro Phe Glu Arg
545                 550                 555                 560

<210> SEQ ID NO 121
<211> LENGTH: 6957
<212> TYPE: DNA
<213> ORGANISM: Artificial Sequence
<220> FEATURE:
<223> OTHER INFORMATION: Synthetic Construct

<400> SEQUENCE: 121
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcggggggc tccctttagg     180
gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta agggattt tgccgatttc ggcctattgg ttaaaaaatg agctgattta      420
acaaaaattt aacgcgaatt ttaacaaaat attaacgttt acaatttcag gtggcacttt     480
tcggggaaat gtgcgcggaa cccctatttg tttattttc taaatacatt caaatatgta      540
tccgctcatg aattaattct tagaaaaact catcgagcat caaatgaaac tgcaatttat     600
tcatatcagg attatcaata ccatattttt gaaaaagccg tttctgtaat gaaggagaaa     660
actcaccgag gcagttccat aggatggcaa gatcctggta tcggtctgcg attccgactc     720
gtccaacatc aatacaacct attaatttcc cctcgtcaaa ataaggtta tcaagtgaga     780 aatcaccatg agtgacgact gaatccggtg agaatggcaa aagtttatgc atttctttcc     840
agacttgttc aacaggccag ccattacgct cgtcatcaaa atcactcgca tcaaccaaac     900
cgttattcat tcgtgattgc gcctgagcga cgaaatac gcgatcgctg ttaaaaggac     960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa aatcccttaa    1440
```

```
cgtgagtttt cgttccactg agcgtcagac cccgtagaaa agatcaaagg atcttcttga    1500 gatcctttt tttctgcgcgt aatctgctgc ttgcaaacaa aaaaaccacc gctaccagcg    1560
gtggtttgtt tgccggatca agagctacca actctttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata gtcgtgtct taccggggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc gaagggaga    1920 aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcagggggg cggagcctat ggaaaaacgc cagcaacgcg    2100
gcctttttac ggttcctggc cttttgctgg ccttttgctc acatgttctt tcctgcgtta    2160 tccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280 tatttttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
```

```
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa agacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatgcgttgt agcgtgtcca ccgaaaatgt    5100
gtctttcacc gaaactgaaa ccgaagctcg tcgttctgcg aactacgaac ctaacagctg    5160
ggactatgat tacctgctgt cctccgacac ggacgagtcc atcgaagtat acaaagacaa    5220
agcgaaaaag ctggaagccg aagttcgtcg cgagattaat aacgaaaaag cagaatttct    5280
gaccctgctg gaactgattg acaacgtcca gcgcctgggc ctgggttacc gtttcgagtc    5340
tgatatccgt ggtgcgctgg atcgcttcgt ttcctccggc ggcttcgatg cggtaaccaa    5400
gacttccctg cacggtacgg cactgtcttt ccgtctgctg cgtcaacacg ttttgaggt    5460
ttctcaggaa gcgttcagcg gcttcaaaga ccaaaacggc aacttcctgg agaacctgaa    5520
ggaagatatc aaagctatcc tgagcctgta cgaggccagc ttcctggctc tggaaggcga    5580
aaacatcctg gacgaggcga aggttttcgc aatctctcat ctgaaagaac tgtctgaaga    5640
aaagatcggt aaagagctgg cagaacaggt gaaccatgca ctggaactgc cactgcatcg    5700
ccgtactcag cgtctggaag cagtatggtc tatcgaggcc taccgtaaaa aggaggacgc    5760
gaatcaggtt ctgctggagc tggcaattct ggattacaac atgatccagt ctgtatacca    5820
gcgtgatctg cgtgaaacgt cccgttggtg gcgtcgtgtg ggtctggcga ccaaactgca    5880
ctttgctcgt gaccgcctga ttgagagctt ctactgggcc gtgggtgtag cattcgaacc    5940
gcaatactcc gactgccgta actccgtcgc aaaaatgttt tctttcgtaa ccattatcga    6000
cgatatctac gatgtatacg gcaccctgga cgaactggag ctgtttactg atgcagttga    6060
gcgttgggac gtaaacgcca tcaacgacct gccggattac atgaaactgt gctttctggc    6120
tctgtataac actattaacg aaatcgccta cgacaacctg aaagataaag gtgagaacat    6180
```

-continued

```
cctgccgtat ctgaccaaag cctgggctga cctgtgcaac gctttcctgc aagaagccaa    6240
gtggctgtac aacaaatcta ctccgacctt tgacgactac ttcggcaacg catggaaatc    6300
ctcttctggc ccgctgcaac tggtgttcgc ttacttcgct gtcgtgcaga acattaaaaa    6360
ggaagagatc gaaacctgc aaaaatacca tgacaccatc tctcgtcctt cccatatctt    6420
ccgtctgtgc aatgacctgg ctagcgcgtc tgcggaaatt gcgcgtggtg aaaccgcaaa    6480 tagcgttttct tgttacatgc gcactaaagg tatctccgaa gaactggcta ccgaaagcgt    6540
gatgaatctg atcgatgaaa cctggaaaaa gatgaacaag gaaaaactgg gtggtagcct    6600
gttcgcgaaa ccgttcgtgg aaaccgcgat caacctggca cgtcaatctc actgcactta    6660
tcataacggc gacgcgcata cctctccgga tgagctgacc cgcaaacgcg ttctgtctgt    6720
aatcactgaa ccgattctgc cgtttgaacg ctaaggatcc gaattcgagc tccgtcgaca    6780
agcttgcggc cgcactcgag caccaccacc accaccactg agatccggct gctaacaaag    6840
cccgaaagga agctgagttg gctgctgcca ccgctgagca ataactagca taaccccttg    6900
gggcctctaa acgggtcttg agggttttt tgctgaaagg aggaactata tccggat       6957
```

<210> SEQ ID NO 122
<211> LENGTH: 544
<212> TYPE: PRT
<213> ORGANISM: Artificial Sequence
<220> FEATURE:
<223> OTHER INFORMATION: Synthetic Construct

<400> SEQUENCE: 122

```
Met Glu Ala Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
```

```
            225                 230                 235                 240
Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
                260                 265                 270

Glu Pro Gln Tyr Ser Asp Cys Arg Asn Ser Val Ala Lys Met Phe Ser
                275                 280                 285

Phe Val Thr Ile Ile Asp Asp Ile Tyr Asp Val Tyr Gly Thr Leu Asp
                290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
                340                 345                 350

Asn Ile Leu Pro Tyr Leu Thr Lys Ala Trp Ala Asp Leu Cys Asn Ala
                355                 360                 365

Phe Leu Gln Glu Ala Lys Trp Leu Tyr Asn Lys Ser Thr Pro Thr Phe
                370                 375                 380

Asp Asp Tyr Phe Gly Asn Ala Trp Lys Ser Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
                420                 425                 430

Ile Phe Arg Leu Cys Asn Asp Leu Ala Ser Ala Ser Ala Glu Ile Ala
                435                 440                 445

Arg Gly Glu Thr Ala Asn Ser Val Ser Cys Tyr Met Arg Thr Lys Gly
                450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Gly Ser Leu Phe Ala
                485                 490                 495

Lys Pro Phe Val Glu Thr Ala Ile Asn Leu Ala Arg Gln Ser His Cys
                500                 505                 510

Thr Tyr His Asn Gly Asp Ala His Thr Ser Pro Asp Glu Leu Thr Arg
                515                 520                 525

Lys Arg Val Leu Ser Val Ile Thr Glu Pro Ile Leu Pro Phe Glu Arg
530                 535                 540
```

<210> SEQ ID NO 123
<211> LENGTH: 6909
<212> TYPE: DNA
<213> ORGANISM: Artificial Sequence
<220> FEATURE:
<223> OTHER INFORMATION: Synthetic Construct

<400> SEQUENCE: 123
tggcgaatgg gacgcgccct gtagcggcgc attaagcgcg gcgggtgtgg tggttacgcg    60
cagcgtgacc gctacacttg ccagcgccct agcgcccgct cctttcgctt tcttcccttc   120
ctttctcgcc acgttcgccg gctttccccg tcaagctcta aatcggggc tccctttagg   180 gttccgattt agtgctttac ggcacctcga ccccaaaaaa cttgattagg gtgatggttc   240
acgtagtggg ccatcgccct gatagacggt ttttcgccct ttgacgttgg agtccacgtt   300

```
ctttaatagt ggactcttgt tccaaactgg aacaacactc aaccctatct cggtctattc    360
ttttgattta taagggatttt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttattttttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttcttttcc    840 agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actcttttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980 ccaggggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280 tatttttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
```

```
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtcccgga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttcccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
```

```
ttttgtttaa ctttaagaag gagatataca tatggaagct cgtcgttctg cgaactacga    5100
acctaacagc tgggactatg attacctgct gtcctccgac acggacgagt ccatcgaagt    5160
atacaaagac aaagcgaaaa agctggaagc cgaagttcgt cgcgagatta ataacgaaaa    5220
agcagaattt ctgaccctgc tggaactgat tgacaacgtc cagcgcctgg gcctgggtta    5280
ccgtttcgag tctgatatcc gtggtgcgct ggatcgcttc gtttcctccg gcggcttcga    5340
tgcggtaacc aagacttccc tgcacggtac ggcactgtct ttccgtctgc tgcgtcaaca    5400
cggttttgag gtttctcagg aagcgttcag cggcttcaaa gaccaaaacg gcaacttcct    5460
ggagaacctg aaggaagata tcaaagctat cctgagcctg tacgaggcca gcttcctggc    5520
tctggaaggc gaaaacatcc tggacgaggc gaaggttttc gcaatctctc atctgaaaga    5580
actgtctgaa gaaagatcg gtaaagagct ggcagaacag gtgaaccatg cactggaact    5640
gccactgcat cgccgtactc agcgtctgga agcagtatgg tctatcgagg cctaccgtaa    5700
aaaggaggac gcgaatcagg ttctgctgga gctggcaatt ctggattaca acatgatcca    5760
gtctgtatac cagcgtgatc tgcgtgaaac gtcccgttgg tggcgtcgtg tgggtctggc    5820
gaccaaactg cactttgctc gtgaccgcct gattgagagc ttctactggg ccgtgggtgt    5880
agcattcgaa ccgcaatact ccgactgccg taactccgtc gcaaaaatgt ttctttcgt    5940 aaccattatc gacgatatct acgatgtata cggcaccctg gacgaactgg agctgtttac    6000
tgatgcagtt gagcgttggg acgtaaacgc catcaacgac ctgccggatt acatgaaact    6060
gtgctttctg gctctgtata acactattaa cgaaatcgcc tacgacaacc tgaaagataa    6120
aggtgagaac atcctgccgt atctgaccaa agcctgggct gacctgtgca acgctttcct    6180
gcaagaagcc aagtggctgt acaacaaatc tactccgacc tttgacgact acttcggcaa    6240
cgcatggaaa tcctcttctg gcccgctgca actggtgttc gcttacttcg ctgtcgtgca    6300
gaacattaaa aaggaagaga tcgaaaacct gcaaaaatac catgacacca tctctcgtcc    6360
ttcccatatc ttccgtctgt gcaatgacct ggctagcgcg tctgcggaaa ttgcgcgtgg    6420
tgaaaccgca aatagcgttt cttgttacat gcgcactaaa ggtatctccg aagaactggc    6480
taccgaaagc gtgatgaatc tgatcgatga aacctggaaa aagatgaaca aggaaaaact    6540
gggtggtagc ctgttcgcga aaccgttcgt ggaaaccgcg atcaacctgg cacgtcaatc    6600
tcactgcact tatcataacg cgacgcgca tacctctccg gatgagctga cccgcaaacg    6660
cgttctgtct gtaatcactg aaccgattct gccgtttgaa cgctaaggat ccgaattcga    6720
gctccgtcga caagcttgcg gccgcactcg agcaccacca ccaccaccac tgagatccgg    6780
ctgctaacaa agcccgaaag gaagctgagt tggctgctgc caccgctgag caataactag    6840
cataacccct tggggcctct aaacgggtct tgaggggttt tttgctgaaa ggaggaacta    6900
tatccggat                                                            6909
```

<210> SEQ ID NO 124
<211> LENGTH: 558
<212> TYPE: PRT
<213> ORGANISM: Artificial Sequence
<220> FEATURE:
<223> OTHER INFORMATION: Synthetic Construct

<400> SEQUENCE: 124

Met Ser Val Ser Thr Glu Asn Val Ser Phe Thr Glu Thr Glu Thr Glu
1               5                   10                  15

Ala Arg Arg Ser Ala Asn Tyr Glu Pro Asn Ser Trp Asp Tyr Asp Tyr
            20                  25                  30

-continued

```
Leu Leu Ser Ser Asp Thr Asp Glu Ser Ile Glu Val Tyr Lys Asp Lys
            35                  40                  45

Ala Lys Lys Leu Glu Ala Glu Val Arg Arg Glu Ile Asn Asn Glu Lys
 50                  55                  60

Ala Glu Phe Leu Thr Leu Leu Glu Leu Ile Asp Asn Val Gln Arg Leu
 65                  70                  75                  80

Gly Leu Gly Tyr Arg Phe Glu Ser Asp Ile Arg Gly Ala Leu Asp Arg
                 85                  90                  95

Phe Val Ser Ser Gly Gly Phe Asp Ala Val Thr Lys Thr Ser Leu His
                100                 105                 110

Gly Thr Ala Leu Ser Phe Arg Leu Leu Arg Gln His Gly Phe Glu Val
                115                 120                 125

Ser Gln Glu Ala Phe Ser Gly Phe Lys Asp Gln Asn Gly Asn Phe Leu
130                 135                 140

Glu Asn Leu Lys Glu Asp Ile Lys Ala Ile Leu Ser Leu Tyr Glu Ala
145                 150                 155                 160

Ser Phe Leu Ala Leu Glu Gly Glu Asn Ile Leu Asp Glu Ala Lys Val
                165                 170                 175

Phe Ala Ile Ser His Leu Lys Glu Leu Ser Glu Lys Ile Gly Lys
                180                 185                 190

Glu Leu Ala Glu Gln Val Asn His Ala Leu Glu Leu Pro Leu His Arg
                195                 200                 205

Arg Thr Gln Arg Leu Glu Ala Val Trp Ser Ile Glu Ala Tyr Arg Lys
210                 215                 220

Lys Glu Asp Ala Asn Gln Val Leu Leu Glu Leu Ala Ile Leu Asp Tyr
225                 230                 235                 240

Asn Met Ile Gln Ser Val Tyr Gln Arg Asp Leu Arg Glu Thr Ser Arg
                245                 250                 255

Trp Trp Arg Arg Val Gly Leu Ala Thr Lys Leu His Phe Ala Arg Asp
                260                 265                 270

Arg Leu Ile Glu Ser Phe Tyr Trp Ala Val Gly Val Ala Phe Glu Pro
                275                 280                 285

Gln Tyr Ser Asp Cys Arg Asn Ser Val Ala Lys Met Phe Ser Phe Val
                290                 295                 300

Thr Ile Ile Asp Asp Ile Tyr Asp Val Tyr Gly Thr Leu Asp Glu Leu
305                 310                 315                 320

Glu Leu Phe Thr Asp Ala Val Glu Arg Trp Asp Val Asn Ala Ile Asn
                325                 330                 335

Asp Leu Pro Asp Tyr Met Lys Leu Cys Phe Leu Ala Leu Tyr Asn Thr
                340                 345                 350

Ile Asn Glu Ile Ala Tyr Asp Asn Leu Lys Asp Lys Gly Glu Asn Ile
                355                 360                 365

Leu Pro Tyr Leu Thr Lys Ala Trp Ala Asp Leu Cys Asn Ala Phe Leu
370                 375                 380

Gln Glu Ala Lys Trp Leu Tyr Asn Lys Ser Thr Pro Thr Phe Asp Asp
385                 390                 395                 400

Tyr Phe Gly Asn Ala Trp Lys Ser Ser Gly Pro Leu Gln Leu Val
                405                 410                 415

Phe Ala Tyr Phe Ala Val Val Gln Asn Ile Lys Lys Glu Glu Ile Glu
                420                 425                 430

Asn Leu Gln Lys Tyr His Asp Thr Ile Ser Arg Pro Ser His Ile Phe
                435                 440                 445
```

Arg Leu Cys Asn Asp Leu Ala Ser Ala Ser Ala Glu Ile Ala Arg Gly
    450                 455                 460

Glu Thr Ala Asn Ser Val Ser Cys Tyr Met Arg Thr Lys Gly Ile Ser
465                 470                 475                 480

Glu Glu Leu Ala Thr Glu Ser Val Met Asn Leu Ile Asp Glu Thr Trp
                485                 490                 495

Lys Lys Met Asn Lys Glu Lys Leu Gly Gly Ser Leu Phe Ala Lys Pro
            500                 505                 510

Phe Val Glu Thr Ala Ile Asn Leu Ala Arg Gln Ser His Cys Thr Tyr
        515                 520                 525

His Asn Gly Asp Ala His Thr Ser Pro Asp Glu Leu Thr Arg Lys Arg
    530                 535                 540

Val Leu Ser Val Ile Thr Glu Pro Ile Leu Pro Phe Glu Arg
545                 550                 555

<210> SEQ ID NO 125
<211> LENGTH: 6951
<212> TYPE: DNA
<213> ORGANISM: Artificial Sequence
<220> FEATURE:
<223> OTHER INFORMATION: Synthetic Construct

<400> SEQUENCE: 125
tggcgaatgg gacgcgccct gtagcggcgc attaagcgcg gcgggtgtgg tggttacgcg     60
cagcgtgacc gctacacttg ccagcgccct agcgcccgct cctttcgctt tcttcccttc    120
ctttctcgcc acgttcgccg gctttccccg tcaagctcta atcggggggc tccctttagg    180
gttccgattt agtgctttac ggcacctcga ccccaaaaaa cttgattagg gtgatggttc    240
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta agggatttt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttatttttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga cgaaatac gcgatcgctg ttaaaaggac    960
aattacaaac aggaatcgaa tgcaaccggc gcaggaacac tgccagcgca tcaacaatat   1020
tttcacctga tcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440

```
cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actcttttc cgaaggtaac tggcttcagc     1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata gtcgtgtct taccggggtg gactcaagac gatagttacc ggataaggcg     1800
cagcggtcgg gctaacggg gggttcgtgc acacagccca gcttggagcg aacgacctac      1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcagggggg cggagcctat ggaaaaacgc cagcaacgcg    2100
gccttttac ggttcctggc cttttgctgg ccttttgctc acatgttctt tcctgcgtta     2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tatttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
```

```
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccgaaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa agacaccgg     4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatgagcgtg tccaccgaaa atgtgtcttt    5100
caccgaaact gaaaccgaag ctcgtcgttc tgcgaactac gaacctaaca gctgggacta    5160
tgattacctg ctgtcctccg acacggacga gtccatcgaa gtatacaaag acaaagcgaa    5220
aaagctggaa gccgaagttc gtcgcgagat taataacgaa aaagcagaat ttctgaccct    5280
gctggaactg attgacaacg tccagcgcct gggcctgggt taccgtttcg agtctgatat    5340
ccgtggtgcg ctggatcgct tcgtttcctc cggcggcttc gatgcggtaa ccaagacttc    5400
cctgcacggt acggcactgt cttttccgtct gctgcgtcaa cacggttttg aggtttctca    5460
ggaagcgttc agcggcttca agaccaaaaa cggcaacttc ctggagaacc tgaaggaaga    5520
tatcaaagct atcctgagcc tgtacgaggc cagcttcctg gctctggaag cgaaaaacat    5580
cctggacgag gcgaaggttt tcgcaatctc tcatctgaaa gaactgtctg aagaaaagat    5640
cggtaaagag ctgcagaac aggtgaacca tgcactggaa ctgccactgc atcgccgtac    5700
tcagcgtctg gaagcagtat ggtctatcga ggcctaccgt aaaaaggagg acgcgaatca    5760
ggttctgctg gagctggcaa ttctggatta caacatgatc cagtctgtat accagcgtga    5820
tctgcgtgaa acgtcccgtt ggtggcgtcg tgtgggtctg gcgaccaaac tgcactttgc    5880
tcgtgaccgc ctgattgaga gcttctactg ggccgtgggt gtagcattcg aaccgcaata    5940
ctccgactgc cgtaactccg tcgcaaaaat gttttctttc gtaaccatta tcgacgatat    6000
ctacgatgta tacggcaccc tggacgaact ggagctgttt actgatgcag ttgagcgttg    6060
ggacgtaaac gccatcaacg acctgccgga ttacatgaaa ctgtgctttc tggctctgta    6120
taacactatt aacgaaatcg cctacgacaa cctgaaagat aaaggtgaga acatcctgcc    6180
```

```
gtatctgacc aaagcctggg ctgacctgtg caacgctttc ctgcaagaag ccaagtggct    6240
gtacaacaaa tctactccga cctttgacga ctacttcggc aacgcatgga atcctcttc     6300 tggcccgctg caactggtgt tcgcttactt cgctgtcgtg cagaacatta aaaggaaga    6360 gatcgaaaac ctgcaaaaat accatgacac catctctcgt ccttcccata tcttccgtct    6420
gtgcaatgac ctggctagcg cgtctgcgga aattgcgcgt ggtgaaaccg caaatagcgt    6480
ttcttgttac atgcgcacta aaggtatctc cgaagaactg gctaccgaaa gcgtgatgaa    6540
tctgatcgat gaaacctgga aaagatgaa caaggaaaaa ctgggtggta gcctgttcgc     6600
gaaaccgttc gtggaaaccg cgatcaacct ggcacgtcaa tctcactgca cttatcataa    6660
cggcgacgcg catacctctc cggatgagct gacccgcaaa cgcgttctgt ctgtaatcac    6720
tgaaccgatt ctgccgtttg aacgctaagg atccgaattc gagctccgtc gacaagcttg    6780
cggccgcact cgagcaccac caccaccacc actgagatcc ggctgctaac aaagcccgaa    6840
aggaagctga gttggctgct gccaccgctg agcataact agcataaccc cttggggcct    6900
ctaaacgggt cttgaggggt ttttgctga aggaggaac tatatccgga t               6951
```

<210> SEQ ID NO 126
<211> LENGTH: 557
<212> TYPE: PRT
<213> ORGANISM: Artificial Sequence
<220> FEATURE:
<223> OTHER INFORMATION: Synthetic Construct

<400> SEQUENCE: 126

```
Met Val Ser Thr Glu Asn Val Ser Phe Thr Glu Thr Glu Thr Glu Ala
1               5                   10                  15

Arg Arg Ser Ala Asn Tyr Glu Pro Asn Ser Trp Asp Tyr Asp Tyr Leu
            20                  25                  30

Leu Ser Ser Asp Thr Asp Glu Ser Ile Glu Val Tyr Lys Asp Lys Ala
        35                  40                  45

Lys Lys Leu Glu Ala Glu Val Arg Arg Glu Ile Asn Asn Glu Lys Ala
    50                  55                  60

Glu Phe Leu Thr Leu Leu Glu Leu Ile Asp Asn Val Gln Arg Leu Gly
65                  70                  75                  80

Leu Gly Tyr Arg Phe Glu Ser Asp Ile Arg Gly Ala Leu Asp Arg Phe
                85                  90                  95

Val Ser Ser Gly Gly Phe Asp Ala Val Thr Lys Thr Ser Leu His Gly
            100                 105                 110

Thr Ala Leu Ser Phe Arg Leu Leu Arg Gln His Gly Phe Glu Val Ser
        115                 120                 125

Gln Glu Ala Phe Ser Gly Phe Lys Asp Gln Asn Gly Asn Phe Leu Glu
    130                 135                 140

Asn Leu Lys Glu Asp Ile Lys Ala Ile Leu Ser Leu Tyr Glu Ala Ser
145                 150                 155                 160

Phe Leu Ala Leu Glu Gly Glu Asn Ile Leu Asp Glu Ala Lys Val Phe
                165                 170                 175

Ala Ile Ser His Leu Lys Glu Leu Ser Glu Glu Lys Ile Gly Lys Glu
            180                 185                 190

Leu Ala Glu Gln Val Asn His Ala Leu Glu Leu Pro Leu His Arg Arg
        195                 200                 205

Thr Gln Arg Leu Glu Ala Val Trp Ser Ile Glu Ala Tyr Arg Lys Lys
    210                 215                 220

Glu Asp Ala Asn Gln Val Leu Leu Glu Leu Ala Ile Leu Asp Tyr Asn
```

```
            225                 230                 235                 240
Met Ile Gln Ser Val Tyr Gln Arg Asp Leu Arg Glu Thr Ser Arg Trp
                245                 250                 255

Trp Arg Arg Val Gly Leu Ala Thr Lys Leu His Phe Ala Arg Asp Arg
                260                 265                 270

Leu Ile Glu Ser Phe Tyr Trp Ala Val Gly Val Ala Phe Glu Pro Gln
                275                 280                 285

Tyr Ser Asp Cys Arg Asn Ser Val Ala Lys Met Phe Ser Phe Val Thr
                290                 295                 300

Ile Ile Asp Asp Ile Tyr Asp Val Tyr Gly Thr Leu Asp Glu Leu Glu
305                 310                 315                 320

Leu Phe Thr Asp Ala Val Glu Arg Trp Asp Val Asn Ala Ile Asn Asp
                325                 330                 335

Leu Pro Asp Tyr Met Lys Leu Cys Phe Leu Ala Leu Tyr Asn Thr Ile
                340                 345                 350

Asn Glu Ile Ala Tyr Asp Asn Leu Lys Asp Lys Gly Glu Asn Ile Leu
                355                 360                 365

Pro Tyr Leu Thr Lys Ala Trp Ala Asp Leu Cys Asn Ala Phe Leu Gln
                370                 375                 380

Glu Ala Lys Trp Leu Tyr Asn Lys Ser Thr Pro Thr Phe Asp Asp Tyr
385                 390                 395                 400

Phe Gly Asn Ala Trp Lys Ser Ser Gly Pro Leu Gln Leu Val Phe
                405                 410                 415

Ala Tyr Phe Ala Val Val Gln Asn Ile Lys Lys Glu Ile Glu Asn
                420                 425                 430

Leu Gln Lys Tyr His Asp Thr Ile Ser Arg Pro Ser His Ile Phe Arg
                435                 440                 445

Leu Cys Asn Asp Leu Ala Ser Ala Ser Ala Glu Ile Ala Arg Gly Glu
                450                 455                 460

Thr Ala Asn Ser Val Ser Cys Tyr Met Arg Thr Lys Gly Ile Ser Glu
465                 470                 475                 480

Glu Leu Ala Thr Glu Ser Val Met Asn Leu Ile Asp Glu Thr Trp Lys
                485                 490                 495

Lys Met Asn Lys Glu Lys Leu Gly Gly Ser Leu Phe Ala Lys Pro Phe
                500                 505                 510

Val Glu Thr Ala Ile Asn Leu Ala Arg Gln Ser His Cys Thr Tyr His
                515                 520                 525

Asn Gly Asp Ala His Thr Ser Pro Asp Glu Leu Thr Arg Lys Arg Val
                530                 535                 540

Leu Ser Val Ile Thr Glu Pro Ile Leu Pro Phe Glu Arg
545                 550                 555

<210> SEQ ID NO 127
<211> LENGTH: 6948
<212> TYPE: DNA
<213> ORGANISM: Artificial Sequence
<220> FEATURE:
<223> OTHER INFORMATION: Synthetic Construct

<400> SEQUENCE: 127
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tcccttagg      180 gttccgattt agtgctttac ggcacctcga ccccaaaaaa cttgattagg gtgatggttc     240
```

```
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta tagggatttt tgccgatttc ggcctattgg ttaaaaaatg agctgattta    420
acaaaatttt aacgcgaatt ttaacaaaat attaacgttt acaatttcag gtggcacttt    480
tcggggaaat gtgcgcggaa cccctatttg tttatttttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttcttcc    840 agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga tcaggatat tcttctaata cctggaatgc tgttttcccg gggatcgcag    1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actcttttc cgaaggtaac tggcttcagc    1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata gtcgtgtct taccgggttg gactcaagac gatagttacc ggataaggcg    1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt cctgcgtta    2160 tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280 tatttctcc ttacgcatct gtgcggtatt tcacaccgca tatatggtgc actctcagta    2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
```

```
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagactttta    3000 cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa agacacaccgg   4560 catactctgc gacatcgtat aacgttactg gtttcacatt caccaccctg aattgactct    4620
cttccgggcg ctatcatgcc ataccgcgaa aggttttgcg ccattcgatg tgtccggga     4680 tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttcccccatc ggtgatgtcg gcgatatagg cgccagcaac cgcacctgtg    4920
gcgccggtga tgccggccac gatgcgtccg gcgtagagga tcgagatctc gatcccgcga    4980
```

```
aattaatacg actcactata ggggaattgt gagcggataa caattcccct ctagaaataa    5040
ttttgtttaa ctttaagaag gagatataca tatggtgtcc accgaaaatg tgtctttcac    5100
cgaaactgaa accgaagctc gtcgttctgc gaactacgaa cctaacagct gggactatga    5160
ttacctgctg tcctccgaca cggacgagtc catcgaagta tacaaagaca aagcgaaaaa    5220
gctggaagcc gaagttcgtc gcgagattaa taacgaaaaa gcagaatttc tgaccctgct    5280
ggaactgatt gacaacgtcc agcgcctggg cctgggttac cgtttcgagt ctgatatccg    5340
tggtgcgctg gatcgcttcg tttcctccgg cggcttcgat gcggtaacca agacttccct    5400
gcacggtacg gcactgtctt ccgtctgctg cgtcaacac ggttttgagg tttctcagga    5460
agcgttcagc ggcttcaaag accaaaacgg caacttcctg gagaacctga aggaagatat    5520
caaagctatc ctgagcctgt acgaggccag cttcctggct ctggaaggcg aaaacatcct    5580
ggacgaggcg aaggttttcg caatctctca tctgaaagaa ctgtctgaag aaaagatcgg    5640
taaagagctg gcagaacagg tgaaccatgc actggaactg ccactgcatc gccgtactca    5700
gcgtctggaa gcagtatggt ctatcgaggc ctaccgtaaa aaggaggacg cgaatcaggt    5760
tctgctggag ctggcaattc tggattacaa catgatccag tctgtatacc agcgtgatct    5820
gcgtgaaacg tcccgttggt ggcgtcgtgt gggtctggcg accaaactgc actttgctcg    5880
tgaccgcctg attgagagct ctactgggc cgtgggtgta gcattcgaac cgcaatactc    5940
cgactgccgt aactccgtcg caaaaatgtt ttctttcgta accattatcg acgatatcta    6000
cgatgtatac ggcaccctgg acgaactgga gctgtttact gatgcagttg agcgttggga    6060
cgtaaacgcc atcaacgacc tgccggatta catgaaactg tgctttctgg ctctgtataa    6120
cactattaac gaaatcgcct acgacaacct gaaagataaa ggtgagaaca tcctgccgta    6180
tctgaccaaa gcctgggctg acctgtgcaa cgctttcctg caagaagcca gtggctgta    6240 caacaaatct actccgacct ttgacgacta cttcggcaac gcatggaaat cctcttctgg    6300
cccgctgcaa ctggtgttcg cttacttcgc tgtcgtgcag aacattaaaa aggaagagat    6360
cgaaaacctg caaaaatacc atgacaccat ctctcgtcct tcccatatct tccgtctgtg    6420
caatgacctg gctagcgcgt ctgcggaaat tgcgcgtggt gaaaccgcaa atagcgtttc    6480
ttgttacatg cgcactaaag gtatctccga agaactggct accgaaagcg tgatgaatct    6540
gatcgatgaa acctggaaaa agatgaacaa ggaaaaactg ggtggtagcc tgttcgcgaa    6600
accgttcgtg gaaaccgcga tcaacctggc acgtcaatct cactgcactt atcataacgg    6660
cgacgcgcat acctctccgg atgagctgac ccgcaaacgc gttctgtctg taatcactga    6720
accgattctg ccgtttgaac gctaaggatc cgaattcgag ctccgtcgac aagcttgcgg    6780
ccgcactcga gcaccaccac caccaccact gagatccggc tgctaacaaa gcccgaaagg    6840
aagctgagtt ggctgctgcc accgctgagc aataactagc ataacccctt ggggcctcta    6900
aacgggtctt gagggttttt ttgctgaaag gaggaactat atccggat              6948
```

<210> SEQ ID NO 128
<211> LENGTH: 555
<212> TYPE: PRT
<213> ORGANISM: Artificial Sequence
<220> FEATURE:
<223> OTHER INFORMATION: Synthetic Construct

<400> SEQUENCE: 128

Met Thr Glu Asn Val Ser Phe Thr Glu Thr Glu Thr Glu Ala Arg Arg
1               5                   10                  15

-continued

```
Ser Ala Asn Tyr Glu Pro Asn Ser Trp Asp Tyr Asp Tyr Leu Leu Ser
                20              25                  30

Ser Asp Thr Asp Glu Ser Ile Glu Val Tyr Lys Asp Lys Ala Lys Lys
            35              40                  45

Leu Glu Ala Glu Val Arg Arg Glu Ile Asn Asn Glu Lys Ala Glu Phe
50                      55                  60

Leu Thr Leu Leu Glu Leu Ile Asp Asn Val Gln Arg Leu Gly Leu Gly
65                  70                  75                  80

Tyr Arg Phe Glu Ser Asp Ile Arg Gly Ala Leu Asp Arg Phe Val Ser
                85                  90                  95

Ser Gly Gly Phe Asp Ala Val Thr Lys Thr Ser Leu His Gly Thr Ala
            100                 105                 110

Leu Ser Phe Arg Leu Leu Arg Gln His Gly Phe Glu Val Ser Gln Glu
                115                 120                 125

Ala Phe Ser Gly Phe Lys Asp Gln Asn Gly Asn Phe Leu Glu Asn Leu
130                 135                 140

Lys Glu Asp Ile Lys Ala Ile Leu Ser Leu Tyr Glu Ala Ser Phe Leu
145                 150                 155                 160

Ala Leu Glu Gly Glu Asn Ile Leu Asp Glu Ala Lys Val Phe Ala Ile
                165                 170                 175

Ser His Leu Lys Glu Leu Ser Glu Glu Lys Ile Gly Lys Glu Leu Ala
                180                 185                 190

Glu Gln Val Asn His Ala Leu Glu Leu Pro Leu His Arg Arg Thr Gln
                195                 200                 205

Arg Leu Glu Ala Val Trp Ser Ile Glu Ala Tyr Arg Lys Lys Glu Asp
                210                 215                 220

Ala Asn Gln Val Leu Leu Glu Leu Ala Ile Leu Asp Tyr Asn Met Ile
225                 230                 235                 240

Gln Ser Val Tyr Gln Arg Asp Leu Arg Glu Thr Ser Arg Trp Trp Arg
                245                 250                 255

Arg Val Gly Leu Ala Thr Lys Leu His Phe Ala Arg Asp Arg Leu Ile
                260                 265                 270

Glu Ser Phe Tyr Trp Ala Val Gly Val Ala Phe Glu Pro Gln Tyr Ser
                275                 280                 285

Asp Cys Arg Asn Ser Val Ala Lys Met Phe Ser Phe Val Thr Ile Ile
290                 295                 300

Asp Asp Ile Tyr Asp Val Tyr Gly Thr Leu Asp Glu Leu Glu Leu Phe
305                 310                 315                 320

Thr Asp Ala Val Glu Arg Trp Asp Val Asn Ala Ile Asn Asp Leu Pro
                325                 330                 335

Asp Tyr Met Lys Leu Cys Phe Leu Ala Leu Tyr Asn Thr Ile Asn Glu
                340                 345                 350

Ile Ala Tyr Asp Asn Leu Lys Asp Lys Gly Glu Asn Ile Leu Pro Tyr
                355                 360                 365

Leu Thr Lys Ala Trp Ala Asp Leu Cys Asn Ala Phe Leu Gln Glu Ala
                370                 375                 380

Lys Trp Leu Tyr Asn Lys Ser Thr Pro Thr Phe Asp Asp Tyr Phe Gly
385                 390                 395                 400

Asn Ala Trp Lys Ser Ser Gly Pro Leu Gln Leu Val Phe Ala Tyr
                405                 410                 415

Phe Ala Val Val Gln Asn Ile Lys Lys Glu Glu Ile Glu Asn Leu Gln
                420                 425                 430
```

```
Lys Tyr His Asp Thr Ile Ser Arg Pro Ser His Ile Phe Arg Leu Cys
        435                 440                 445

Asn Asp Leu Ala Ser Ala Ser Ala Glu Ile Ala Arg Gly Glu Thr Ala
450                 455                 460

Asn Ser Val Ser Cys Tyr Met Arg Thr Lys Gly Ile Ser Glu Leu
465                 470                 475                 480

Ala Thr Glu Ser Val Met Asn Leu Ile Asp Glu Thr Trp Lys Lys Met
                485                 490                 495

Asn Lys Glu Lys Leu Gly Gly Ser Leu Phe Ala Lys Pro Phe Val Glu
                500                 505                 510

Thr Ala Ile Asn Leu Ala Arg Gln Ser His Cys Thr Tyr His Asn Gly
            515                 520                 525

Asp Ala His Thr Ser Pro Asp Glu Leu Thr Arg Lys Arg Val Leu Ser
            530                 535                 540

Val Ile Thr Glu Pro Ile Leu Pro Phe Glu Arg
545                 550                 555

<210> SEQ ID NO 129
<211> LENGTH: 6942
<212> TYPE: DNA
<213> ORGANISM: Artificial Sequence
<220> FEATURE:
<223> OTHER INFORMATION: Synthetic Construct

<400> SEQUENCE: 129
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcggggggc tccctttagg     180
gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta agggatttt tgccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg aattaattct tagaaaaact catcgagcat caaatgaaac tgcaatttat     600
tcatatcagg attatcaata ccatattttt gaaaaagccg tttctgtaat gaaggagaaa     660
actcaccgag gcagttccat aggatggcaa gatcctggta tcggtctgcg attccgactc     720
gtccaacatc aatacaacct attaatttcc cctcgtcaaa aataaggtta tcaagtgaga     780
aatcaccatg agtgacgact gaatccggtg agaatggcaa aagtttatgc atttctttcc     840
agacttgttc aacaggccag ccattacgct cgtcatcaaa atcactcgca tcaaccaaac     900
cgttattcat tcgtgattgc gcctgagcga cgaaatac gcgatcgctg ttaaaaggac     960
aattacaaac aggaatcgaa tgcaaccggc gcaggaacac tgccagcgca tcaacaatat    1020
tttcacctga atcaggatat tcttctaata cctggaatgc tgtttttccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
```

```
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actcttttc cgaaggtaac tggcttcagc    1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gataccctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100 gccttttac ggttcctggc cttttgctgg cctttgctc acatgttctt tcctgcgtta     2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag gtggtttttc ttttcacca gtgagacggg caacagctga ttgcccttca    3660
ccgcctggcc ctgagagagt tgcagcaagc ggtccacgct ggtttgcccc agcaggcgaa   3720
```

```
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatgaccgaa aatgtgtctt tcaccgaaac   5100
tgaaaccgaa gctcgtcgtt ctgcgaacta cgaacctaac agctgggact atgattacct   5160
gctgtcctcc gacacggacg agtccatcga agtatacaaa gacaaagcga aaagctgga   5220
agccgaagtt cgtcgcgaga ttaataacga aaaagcagaa tttctgaccc tgctggaact   5280
gattgacaac gtccagcgcc tgggcctggg ttaccgtttc gagtctgata tccgtggtgc   5340
gctggatcgc ttcgtttcct ccggcggctt cgatgcggta accaagactt ccctgcacgg   5400
tacggcactg tcttttccgtc tgctgcgtca cacggttttt gaggtttctc aggaagcgtt   5460
cagcggcttc aaagaccaaa acggcaactt cctggagaac ctgaaggaag atatcaaagc   5520
tatcctgagc ctgtacgagg ccagcttcct ggctctggaa ggcgaaaaca tcctggacga   5580
ggcgaaggtt ttcgcaatct ctcatctgaa agaactgtct gaagaaaaga tcggtaaaga   5640
gctggcagaa caggtgaacc atgcactgga actgccactg catcgccgta ctcagcgtct   5700
ggaagcagta tggtctatcg aggcctaccg taaaaaggag gacgcgaatc aggttctgct   5760
ggagctggca attctggatt acaacatgat ccagtctgta taccagcgtg atctgcgtga   5820
aacgtcccgt tggtggcgtc gtgtgggtct ggcgaccaaa ctgcactttg ctcgtgaccg   5880
cctgattgag agcttctact gggccgtggg tgtagcattc gaaccgcaat actccgactg   5940
ccgtaactcc gtcgcaaaaa tgttttcttt cgtaaccatt atcgacgata tctacgatgt   6000
atacggcacc ctgacgaac tggagctgtt tactgatgca gttgagcgtt gggacgtaaa   6060
cgccatcaac gacctgccgg attacatgaa actgtgcttt ctggctctgt ataacactat   6120
```

```
taacgaaatc gcctacgaca acctgaaaga taaaggtgag aacatcctgc cgtatctgac    6180
caaagcctgg gctgacctgt gcaacgcttt cctgcaagaa gccaagtggc tgtacaacaa    6240
atctactccg acctttgacg actacttcgg caacgcatgg aaatcctctt ctggcccgct    6300
gcaactggtg ttcgcttact cgctgtcgt gcagaacatt aaaaaggaag agatcgaaaa    6360
cctgcaaaaa taccatgaca ccatctctcg tccttcccat atcttccgtc tgtgcaatga    6420
cctggctagc gcgtctgcgg aaattgcgcg tggtgaaacc gcaaatagcg tttcttgtta    6480
catgcgcact aaaggtatct ccgaagaact ggctaccgaa agcgtgatga atctgatcga    6540
tgaaacctgg aaaagatga acaaggaaaa actgggtggt agcctgttcg cgaaaccgtt    6600
cgtggaaacc gcgatcaacc tggcacgtca atctcactgc acttatcata acggcgacgc    6660
gcatacctct ccggatgagc tgacccgcaa acgcgttctg tctgtaatca ctgaaccgat    6720
tctgccgttt gaacgctaag gatccgaatt cgagctccgt cgacaagctt gcggccgcac    6780
tcgagcacca ccaccaccac cactgagatc cggctgctaa caaagcccga aaggaagctg    6840
agttggctgc tgccaccgct gagcaataac tagcataacc ccttggggcc tctaaacggg    6900
tcttgagggg ttttttgctg aaaggaggaa ctatatccgg at                      6942
```

<210> SEQ ID NO 130
<211> LENGTH: 553
<212> TYPE: PRT
<213> ORGANISM: Artificial Sequence
<220> FEATURE:
<223> OTHER INFORMATION: Synthetic Construct

<400> SEQUENCE: 130

```
Met Asn Val Ser Phe Thr Glu Thr Glu Thr Glu Ala Arg Arg Ser Ala
 1               5                  10                  15

Asn Tyr Glu Pro Asn Ser Trp Asp Tyr Asp Tyr Leu Leu Ser Ser Asp
            20                  25                  30

Thr Asp Glu Ser Ile Glu Val Tyr Lys Asp Lys Ala Lys Lys Leu Glu
        35                  40                  45

Ala Glu Val Arg Arg Glu Ile Asn Asn Glu Lys Ala Glu Phe Leu Thr
    50                  55                  60

Leu Leu Glu Leu Ile Asp Asn Val Gln Arg Leu Gly Leu Gly Tyr Arg
65                  70                  75                  80

Phe Glu Ser Asp Ile Arg Gly Ala Leu Asp Arg Phe Val Ser Ser Gly
                85                  90                  95

Gly Phe Asp Ala Val Thr Lys Thr Ser Leu His Gly Thr Ala Leu Ser
            100                 105                 110

Phe Arg Leu Leu Arg Gln His Gly Phe Glu Val Ser Gln Glu Ala Phe
        115                 120                 125

Ser Gly Phe Lys Asp Gln Asn Gly Asn Phe Leu Glu Asn Leu Lys Glu
    130                 135                 140

Asp Ile Lys Ala Ile Leu Ser Leu Tyr Glu Ala Ser Phe Leu Ala Leu
145                 150                 155                 160

Glu Gly Glu Asn Ile Leu Asp Glu Ala Lys Val Phe Ala Ile Ser His
                165                 170                 175

Leu Lys Glu Leu Ser Glu Glu Lys Ile Gly Lys Glu Leu Ala Glu Gln
            180                 185                 190

Val Asn His Ala Leu Glu Leu Pro Leu His Arg Arg Thr Gln Arg Leu
        195                 200                 205

Glu Ala Val Trp Ser Ile Glu Ala Tyr Arg Lys Lys Glu Asp Ala Asn
```

```
                210                 215                 220
Gln Val Leu Leu Glu Leu Ala Ile Leu Asp Tyr Asn Met Ile Gln Ser
225                 230                 235                 240

Val Tyr Gln Arg Asp Leu Arg Glu Thr Ser Arg Trp Trp Arg Arg Val
                245                 250                 255

Gly Leu Ala Thr Lys Leu His Phe Ala Arg Asp Arg Leu Ile Glu Ser
                260                 265                 270

Phe Tyr Trp Ala Val Gly Val Ala Phe Glu Pro Gln Tyr Ser Asp Cys
                275                 280                 285

Arg Asn Ser Val Ala Lys Met Phe Ser Phe Val Thr Ile Ile Asp Asp
                290                 295                 300

Ile Tyr Asp Val Tyr Gly Thr Leu Asp Glu Leu Glu Leu Phe Thr Asp
305                 310                 315                 320

Ala Val Glu Arg Trp Asp Val Asn Ala Ile Asn Asp Leu Pro Asp Tyr
                325                 330                 335

Met Lys Leu Cys Phe Leu Ala Leu Tyr Asn Thr Ile Asn Glu Ile Ala
                340                 345                 350

Tyr Asp Asn Leu Lys Asp Lys Gly Glu Asn Ile Leu Pro Tyr Leu Thr
                355                 360                 365

Lys Ala Trp Ala Asp Leu Cys Asn Ala Phe Leu Gln Glu Ala Lys Trp
                370                 375                 380

Leu Tyr Asn Lys Ser Thr Pro Thr Phe Asp Asp Tyr Phe Gly Asn Ala
385                 390                 395                 400

Trp Lys Ser Ser Ser Gly Pro Leu Gln Leu Val Phe Ala Tyr Phe Ala
                405                 410                 415

Val Val Gln Asn Ile Lys Lys Glu Glu Ile Glu Asn Leu Gln Lys Tyr
                420                 425                 430

His Asp Thr Ile Ser Arg Pro Ser His Ile Phe Arg Leu Cys Asn Asp
                435                 440                 445

Leu Ala Ser Ala Ser Ala Glu Ile Ala Arg Gly Glu Thr Ala Asn Ser
                450                 455                 460

Val Ser Cys Tyr Met Arg Thr Lys Gly Ile Ser Glu Glu Leu Ala Thr
465                 470                 475                 480

Glu Ser Val Met Asn Leu Ile Asp Glu Thr Trp Lys Lys Met Asn Lys
                485                 490                 495

Glu Lys Leu Gly Gly Ser Leu Phe Ala Lys Pro Phe Val Glu Thr Ala
                500                 505                 510

Ile Asn Leu Ala Arg Gln Ser His Cys Thr Tyr His Asn Gly Asp Ala
                515                 520                 525

His Thr Ser Pro Asp Glu Leu Thr Arg Lys Arg Val Leu Ser Val Ile
                530                 535                 540

Thr Glu Pro Ile Leu Pro Phe Glu Arg
545                 550
```

<210> SEQ ID NO 131
<211> LENGTH: 6936
<212> TYPE: DNA
<213> ORGANISM: Artificial Sequence
<220> FEATURE:
<223> OTHER INFORMATION: Synthetic Construct

<400> SEQUENCE: 131
tggcgaatgg gacgcgccct gtagcggcgc attaagcgcg gcgggtgtgg tggttacgcg    60
cagcgtgacc gctacacttg ccagcgccct agcgcccgct cctttcgctt tcttcccttc   120

```
ctttctcgcc acgttcgccg gctttccccg tcaagctcta atcgggggc tccctttagg      180
gttccgattt agtgctttac ggcacctcga ccccaaaaaa cttgattagg gtgatggttc      240
acgtagtggg ccatcgccct gatagacggt ttttcgccct ttgacgttgg agtccacgtt      300
ctttaatagt ggactcttgt tccaaactgg aacaacactc aaccctatct cggtctattc      360
ttttgattta taagggattt tgccgatttc ggcctattgg ttaaaaaatg agctgattta      420
acaaaaattt aacgcgaatt ttaacaaaat attaacgttt acaatttcag gtggcacttt      480
tcggggaaat gtgcgcggaa cccctatttg tttattttc taaatacatt caaatatgta      540
tccgctcatg aattaattct tagaaaaact catcgagcat caaatgaaac tgcaatttat      600
tcatatcagg attatcaata ccatattttt gaaaaagccg tttctgtaat gaaggagaaa      660
actcaccgag gcagttccat aggatggcaa gatcctggta tcggtctgcg attccgactc      720
gtccaacatc aatacaacct attaatttcc cctcgtcaaa aataaggtta tcaagtgaga      780
aatcaccatg agtgacgact gaatccggtg agaatggcaa aagtttatgc atttctttcc      840
agacttgttc aacaggccag ccattacgct cgtcatcaaa atcactcgca tcaaccaaac      900
cgttattcat tcgtgattgc gcctgagcga cgaaatac gcgatcgctg ttaaaaggac       960
aattacaaac aggaatcgaa tgcaaccggc gcaggaacac tgccagcgca tcaacaatat     1020
tttcacctga atcaggatat tcttctaata cctggaatgc tgttttcccg gggatcgcag     1080
tggtgagtaa ccatgcatca tcaggagtac ggataaaatg cttgatgtc ggaagaggca      1140
taaattccgt cagccagttt agtctgacca tctcatctgt aacatcattg gcaacgctac     1200
ctttgccatg tttcagaaac aactctggcg catcgggctt cccatacaat cgatagattg     1260
tcgcacctga ttgcccgaca ttatcgcgag cccatttata cccatataaa tcagcatcca     1320
tgttggaatt taatcgcggc ctagagcaag acgtttcccg ttgaatatgg ctcataacac     1380
cccttgtatt actgtttatg taagcagaca gttttattgt tcatgaccaa aatcccttaa     1440
cgtgagtttt cgttccactg agcgtcagac cccgtagaaa agatcaaagg atcttcttga     1500
gatcctttt ttctgcgcgt aatctgctgc ttgcaaacaa aaaaaccacc gctaccagcg      1560
gtggtttgtt tgccggatca agagctacca actctttttc cgaaggtaac tggcttcagc     1620
agagcgcaga taccaaatac tgtccttcta gtgtagccgt agttaggcca ccacttcaag     1680
aactctgtag caccgcctac atacctcgct ctgctaatcc tgttaccagt ggctgctgcc     1740
agtggcgata agtcgtgtct taccgggttg gactcaagac gatagttacc ggataaggcg     1800
cagcggtcgg gctgaacggg gggttcgtgc acacagccca gcttggagcg aacgacctac     1860
accgaactga gatacctaca gcgtgagcta tgagaaagcg ccacgcttcc gaagggaga      1920
aaggcggaca ggtatccggt aagcggcagg gtcggaacag gagagcgcac gagggagctt     1980
ccagggggaa acgcctggta tctttatagt cctgtcgggt ttcgccacct ctgacttgag     2040
cgtcgatttt tgtgatgctc gtcagggggg cggagcctat ggaaaaacgc cagcaacgcg     2100
gccttttac ggttcctggc cttttgctgg ccttttgctc acatgttctt tcctgcgtta      2160
tccctgatt ctgtggataa ccgtattacc gcctttgagt gagctgatac cgctcgccgc      2220
agccgaacga ccgagcgcag cgagtcagtg agcgaggaag cggaagagcg cctgatgcgg     2280
tattttctcc ttacgcatct gtgcggtatt tcacaccgca tatatggtgc actctcagta     2340
caatctgctc tgatgccgca tagttaagcc agtatacact ccgctatcgc tacgtgactg     2400
ggtcatggct gcgccccgac acccgccaac acccgctgac gcgccctgac gggcttgtct     2460
gctcccggca tccgcttaca gacaagctgt gaccgtctcc gggagctgca tgtgtcagag     2520
```

-continued

```
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
```

```
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatgaatgtg tctttcaccg aaactgaaac    5100
cgaagctcgt cgttctgcga actacgaacc taacagctgg gactatgatt acctgctgtc    5160
ctccgacacg gacgagtcca tcgaagtata caaagacaaa gcgaaaaagc tggaagccga    5220
agttcgtcgc gagattaata cgaaaaagc agaatttctg accctgctgg aactgattga    5280
caacgtccag cgcctgggcc tgggttaccg tttcgagtct gatatccgtg gtgcgctgga    5340
tcgcttcgtt tcctccggcg gcttcgatgc ggtaaccaag acttccctgc acggtacggc    5400
actgtctttc cgtctgctgc gtcaacacgt ttttgaggtt tctcaggaag cgttcagcgg    5460
cttcaaagac caaaacggca acttcctgga gaacctgaag gaagatatca aagctatcct    5520
gagcctgtac gaggccagct tcctggctct ggaaggcgaa aacatcctgg acgaggcgaa    5580
ggttttcgca atctctcatc tgaaagaact gtctgaagaa aagatcggta aagagctggc    5640
agaacaggtg aaccatgcac tggaactgcc actgcatcgc cgtactcagc gtctggaagc    5700
agtatggtct atcgaggcct accgtaaaaa ggaggacgcg aatcaggttc tgctggagct    5760
ggcaattctg gattacaaca tgatccagtc tgtataccag cgtgatctgc gtgaaacgtc    5820
ccgttggtgg cgtcgtgtgg gtctggcgac caaactgcac tttgctcgtg accgcctgat    5880
tgagagcttc tactgggccg tgggtgtagc attcgaaccg caatactccg actgccgtaa    5940
ctccgtcgca aaaatgtttt ctttcgtaac cattatcgac gatatctacg atgtatacgg    6000
caccctggac gaactggagc tgtttactga tgcagttgag cgttgggacg taaacgccat    6060
caacgacctg ccggattaca tgaaactgtg ctttctggct ctgtataaca ctattaacga    6120
aatcgcctac gacaacctga agataaagg tgagaacatc ctgccgtatc tgaccaaagc    6180
ctgggctgac ctgtgcaacg ctttcctgca agaagccaag tggctgtaca acaaatctac    6240
tccgaccttt gacgactact cggcaacgc atggaaatcc tcttctggcc cgctgcaact    6300
ggtgttcgct tacttcgctg tcgtgcagaa cattaaaaag gaagagatcg aaaacctgca    6360
aaaataccat gacaccatct ctcgtccttc ccatatcttc cgtctgtgca atgacctggc    6420
tagcgcgtct gcggaaattg cgcgtggtga accgcaaaat agcgtttctt gttacatgcg    6480
cactaaaggt atctccgaag aactggctac cgaaagcgtg atgaatctga tcgatgaaac    6540
ctggaaaaag atgaacaagg aaaaactggg tggtagcctg ttcgcgaaac cgttcgtgga    6600
aaccgcgatc aacctggcac gtcaatctca ctgcacttat cataacggcg acgcgcatac    6660
ctctccggat gagctgaccc gcaaacgcgt tctgtctgta atcactgaac cgattctgcc    6720
gtttgaacgc taaggatccg aattcgagct ccgtcgacaa gcttgcggcc gcactcgagc    6780
accaccacca ccaccactga gatccggctg ctaacaaagc ccgaaaggaa gctgagttgg    6840
ctgctgccac cgctgagcaa taactagcat aaccccttgg ggcctctaaa cgggtcttga    6900
ggggttttt gctgaaagga ggaactatat ccggat                              6936
```

<210> SEQ ID NO 132
<211> LENGTH: 559
<212> TYPE: PRT
<213> ORGANISM: Artificial Sequence
<220> FEATURE:
<223> OTHER INFORMATION: Synthetic Construct

<400> SEQUENCE: 132

-continued

```
Met Glu Ala Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
 50                  55                  60

Arg Leu Gly Leu Gly Tyr Arg Phe Glu Ser Asp Ile Arg Gly Ala Leu
 65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
            115                 120                 125

Phe Leu Glu Asn Leu Lys Glu Asp Ile Lys Ala Ile Leu Ser Leu Tyr
130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
            195                 200                 205

Arg Lys Lys Glu Asp Ala Asn Gln Val Leu Leu Glu Leu Ala Ile Leu
210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
            275                 280                 285

Phe Val Thr Ile Ile Asp Asp Ile Tyr Asp Val Tyr Gly Thr Leu Asp
            290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
            355                 360                 365

Phe Leu Gln Glu Ala Lys Trp Leu Tyr Asn Lys Ser Thr Pro Thr Phe
370                 375                 380

Asp Asp Tyr Phe Gly Asn Ala Trp Lys Ser Ser Ser Gly Pro Leu Gln
385                 390                 395                 400

Leu Val Phe Ala Tyr Phe Ala Val Val Gln Asn Ile Lys Lys Glu Glu
                405                 410                 415
```

```
Ile Glu Asn Leu Gln Lys Tyr His Asp Thr Ile Ser Arg Pro Ser His
        420                 425                 430
Ile Phe Arg Leu Cys Asn Asp Leu Ala Ser Ala Ser Ala Glu Ile Ala
        435                 440                 445
Arg Gly Glu Thr Ala Asn Ser Val Ser Cys Tyr Met Arg Thr Lys Gly
        450                 455                 460
Ile Ser Glu Glu Leu Ala Thr Glu Ser Val Met Asn Leu Ile Asp Glu
465                 470                 475                 480
Thr Trp Lys Lys Met Asn Lys Glu Lys Leu Gly Gly Ser Leu Phe Ala
                485                 490                 495
Lys Pro Phe Val Glu Thr Ala Ile Asn Leu Ala Arg Gln Ser His Cys
            500                 505                 510
Thr Tyr His Asn Gly Asp Ala His Thr Ser Pro Asp Glu Leu Thr Arg
        515                 520                 525
Lys Arg Val Leu Ser Val Ile Thr Glu Pro Ile Leu Pro Phe Glu Arg
530                 535                 540
Glu Asn Leu Tyr Phe Gln Gly Leu Glu His His His His His His
545                 550                 555

<210> SEQ ID NO 133
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 133
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tccctttagg      180 gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta agggattt tgccgatttc ggcctattgg ttaaaaaatg agctgattta      420
acaaaaattt aacgcgaatt ttaacaaaat attaacgttt acaatttcag gtggcacttt     480
tcggggaaat gtgcgcggaa cccctatttg tttattttc taaatacatt caaatatgta      540
tccgctcatg aattaattct tagaaaaact catcgagcat caaatgaaac tgcaatttat     600
tcatatcagg attatcaata ccatatttt gaaaaagccg tttctgtaat gaaggagaaa      660
actcaccgag gcagttccat aggatggcaa gatcctggta tcggtctgcg attccgactc     720
gtccaacatc aatacaacct attaatttcc cctcgtcaaa aataaggtta tcaagtgaga     780
aatcaccatg agtgacgact gaatccggtg agaatggcaa aagtttatgc atttcttcc      840 agacttgttc aacaggccag ccattacgct cgtcatcaaa atcactcgca tcaaccaaac     900
cgttattcat tcgtgattgc gcctgagcga cgaaatac gcgatcgctg ttaaaaggac       960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
```

```
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa atcccttaa    1440 cgtgagtttt cgttccactg agcgtcagac cccgtagaaa agatcaaagg atcttcttga   1500
gatccttttt ttctgcgcgt aatctgctgc ttgcaaacaa aaaaccacc gctaccagcg    1560 gtggtttgtt tgccggatca agagctacca actcttttc cgaaggtaac tggcttcagc    1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980 ccaggggaa acgcctggta tctttatagt cctgtcgggt ttcgccacct ctgacttgag    2040
cgtcgatttt tgtgatgctc gtcaggggg cggagcctat ggaaaaacgc cagcaacgcg    2100 gccttttac ggttcctggc cttttgctgg ccttttgctc acatgttctt tcctgcgtta    2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280 tatttctcc ttacgcatct gtgcggtatt tcacaccgca tatatggtgc actctcagta    2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca acaagctgt gaccgtctcc gggagctgca tgtgtcagag    2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg gccatgtta agggcggttt tttcctgttt    2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtgggccgc    3180 catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
```

```
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccgacgcg agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttcccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatggaagct cgtcgttctg cgaactacga   5100
acctaacagc tgggactatg attacctgct gtcctccgac acggacgagt ccatcgaagt   5160
atacaaagac aaagcgaaaa agctggaagc cgaagttcgt cgcgagatta ataacgaaaa   5220
agcagaattt ctgaccctgc tggaactgat tgacaacgtc agcgcctggg gcctgggtta   5280
ccgtttcgag tctgatatcc gtggtgcgct ggatcgcttc gtttcctccg gcggcttcga   5340
tgcggtaacc aagacttccc tgcacggtac ggcactgtct ttccgtctgc tgcgtcaaca   5400
cggttttgag gtttctcagg aagcgttcag cggcttcaaa gaccaaaacg gcaacttcct   5460
ggagaacctg aaggaagata tcaaagctat cctgagcctg tacgaggcca gcttcctggc   5520
tctggaaggc gaaaacatcc tggacgaggc gaaggttttc gcaatctctc atctgaaaga   5580
actgtctgaa gaaagatcg gtaaagagct ggcagaacag gtgaaccatg cactggaact   5640
gccactgcat cgccgtactc agcgtctgga agcagtatgg tctatcgagg cctaccgtaa   5700
aaaggaggac gcgaatcagg ttctgctgga gctggcaatt ctggattaca acatgatcca   5760
gtctgtatac cagcgtgatc tgcgtgaaac gtcccgttgg tggcgtcgtg tgggtctggc   5820
gaccaaactg cactttgctc gtgaccgcct gattgagagc ttctactggg ccgtgggtgt   5880
agcattcgaa ccgcaatact ccgactgccg taactccgtc gcaaaaatgt tttctttcgt   5940
aaccattatc gacgatatct acgatgtata cggcaccctg gacgaactgg agctgtttac   6000
```

```
tgatgcagtt gagcgttggg acgtaaacgc catcaacgac ctgccggatt acatgaaact    6060
gtgctttctg gctctgtata acactattaa cgaaatcgcc tacgacaacc tgaaagataa    6120
aggtgagaac atcctgccgt atctgaccaa agcctgggct gacctgtgca acgctttcct    6180
gcaagaagcc aagtggctgt acaacaaatc tactccgacc tttgacgact acttcggcaa    6240
cgcatggaaa tcctcttctg gcccgctgca actggtgttc gcttacttcg ctgtcgtgca    6300
gaacattaaa aaggaagaga tcgaaaacct gcaaaaatac catgacacca tctctcgtcc    6360
ttcccatatc ttccgtctgt gcaatgacct ggctagcgcg tctgcggaaa ttgcgcgtgg    6420
tgaaaccgca aatagcgttt cttgttacat gcgcactaaa ggtatctccg aagaactggc    6480
taccgaaagc gtgatgaatc tgatcgatga acctggaaa aagatgaaca aggaaaaact    6540
gggtggtagc ctgttcgcga aaccgttcgt ggaaaccgcg atcaacctgg cacgtcaatc    6600
tcactgcact tatcataacg gcgacgcgca tacctctccg gatgagctga cccgcaaacg    6660
cgttctgtct gtaatcactg aaccgattct gccgtttgaa cgcgaaaacc tgtatttca    6720 gggcctcgag caccaccacc accaccactg agatccggct gctaacaaag cccgaaagga    6780
agctgagttg ctgctgcca ccgctgagca taactagca taaccccttg gggcctctaa    6840
acgggtcttg aggggttttt tgctgaaagg aggaactata tccggat                  6887
```

<210> SEQ ID NO 134
<211> LENGTH: 575
<212> TYPE: PRT
<213> ORGANISM: Artificial Sequence
<220> FEATURE:
<223> OTHER INFORMATION: Synthetic Construct

<400> SEQUENCE: 134

```
Met Arg Cys Ser Val Ser Thr Glu Asn Val Ser Phe Thr Glu Thr Glu
 1               5                   10                  15

Thr Glu Ala Arg Arg Ser Ala Asn Tyr Glu Pro Asn Ser Trp Asp Tyr
            20                  25                  30

Asp Tyr Leu Leu Ser Ser Asp Thr Asp Glu Ser Ile Glu Val Tyr Lys
        35                  40                  45

Asp Lys Ala Lys Lys Leu Glu Ala Glu Val Arg Arg Glu Ile Asn Asn
    50                  55                  60

Glu Lys Ala Glu Phe Leu Thr Leu Leu Glu Leu Ile Asp Asn Val Gln
65                  70                  75                  80

Arg Leu Gly Leu Gly Tyr Arg Phe Glu Ser Asp Ile Arg Gly Ala Leu
                85                  90                  95

Asp Arg Phe Val Ser Ser Gly Gly Phe Asp Ala Val Thr Lys Thr Ser
            100                 105                 110

Leu His Gly Thr Ala Leu Ser Phe Arg Leu Leu Arg Gln His Gly Phe
        115                 120                 125

Glu Val Ser Gln Glu Ala Phe Ser Gly Phe Lys Asp Gln Asn Gly Asn
    130                 135                 140

Phe Leu Glu Asn Leu Lys Glu Asp Ile Lys Ala Ile Leu Ser Leu Tyr
145                 150                 155                 160

Glu Ala Ser Phe Leu Ala Leu Glu Gly Glu Asn Ile Leu Asp Glu Ala
                165                 170                 175

Lys Val Phe Ala Ile Ser His Leu Lys Glu Leu Ser Glu Glu Lys Ile
            180                 185                 190

Gly Lys Glu Leu Ala Glu Gln Val Asn His Ala Leu Glu Leu Pro Leu
        195                 200                 205
```

His Arg Arg Thr Gln Arg Leu Glu Ala Val Trp Ser Ile Glu Ala Tyr
210                 215                 220

Arg Lys Lys Glu Asp Ala Asn Gln Val Leu Leu Glu Leu Ala Ile Leu
225                 230                 235                 240

Asp Tyr Asn Met Ile Gln Ser Val Tyr Gln Arg Asp Leu Arg Glu Thr
                245                 250                 255

Ser Arg Trp Trp Arg Arg Val Gly Leu Ala Thr Lys Leu His Phe Ala
            260                 265                 270

Arg Asp Arg Leu Ile Glu Ser Phe Tyr Trp Ala Val Gly Val Ala Phe
        275                 280                 285

Glu Pro Gln Tyr Ser Asp Cys Arg Asn Ser Val Ala Lys Met Phe Ser
290                 295                 300

Phe Val Thr Ile Ile Asp Asp Ile Tyr Asp Val Tyr Gly Thr Leu Asp
305                 310                 315                 320

Glu Leu Glu Leu Phe Thr Asp Ala Val Glu Arg Trp Asp Val Asn Ala
                325                 330                 335

Ile Asn Asp Leu Pro Asp Tyr Met Lys Leu Cys Phe Leu Ala Leu Tyr
            340                 345                 350

Asn Thr Ile Asn Glu Ile Ala Tyr Asp Asn Leu Lys Asp Lys Gly Glu
        355                 360                 365

Asn Ile Leu Pro Tyr Leu Thr Lys Ala Trp Ala Asp Leu Cys Asn Ala
370                 375                 380

Phe Leu Gln Glu Ala Lys Trp Leu Tyr Asn Lys Ser Thr Pro Thr Phe
385                 390                 395                 400

Asp Asp Tyr Phe Gly Asn Ala Trp Lys Ser Ser Gly Pro Leu Gln
                405                 410                 415

Leu Val Phe Ala Tyr Phe Ala Val Val Gln Asn Ile Lys Lys Glu Glu
            420                 425                 430

Ile Glu Asn Leu Gln Lys Tyr His Asp Thr Ile Ser Arg Pro Ser His
        435                 440                 445

Ile Phe Arg Leu Cys Asn Asp Leu Ala Ser Ala Ser Ala Glu Ile Ala
450                 455                 460

Arg Gly Glu Thr Ala Asn Ser Val Ser Cys Tyr Met Arg Thr Lys Gly
465                 470                 475                 480

Ile Ser Glu Glu Leu Ala Thr Glu Ser Val Met Asn Leu Ile Asp Glu
                485                 490                 495

Thr Trp Lys Lys Met Asn Lys Glu Lys Leu Gly Gly Ser Leu Phe Ala
            500                 505                 510

Lys Pro Phe Val Glu Thr Ala Ile Asn Leu Ala Arg Gln Ser His Cys
        515                 520                 525

Thr Tyr His Asn Gly Asp Ala His Thr Ser Pro Asp Glu Leu Thr Arg
530                 535                 540

Lys Arg Val Leu Ser Val Ile Thr Glu Pro Ile Leu Pro Phe Glu Arg
545                 550                 555                 560

Glu Asn Leu Tyr Phe Gln Gly Leu Glu His His His His His His
                565                 570                 575

<210> SEQ ID NO 135
<211> LENGTH: 6935
<212> TYPE: DNA
<213> ORGANISM: Artificial Sequence
<220> FEATURE:
<223> OTHER INFORMATION: Synthetic Construct

<400> SEQUENCE: 135

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcggggc tcccctttagg     180 gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta aagggatttt tgccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttattttc taaatacatt caaatatgta     540
tccgctcatg aattaattct tagaaaaact catcgagcat caaatgaaac tgcaatttat     600
tcatatcagg attatcaata ccatattttt gaaaaagccg tttctgtaat gaaggagaaa     660
actcaccgag gcagttccat aggatggcaa gatcctggta tcggtctgcg attccgactc     720
gtccaacatc aatacaacct attaatttcc cctcgtcaaa ataaggtta tcaagtgaga     780 aatcaccatg agtgacgact gaatccggtg agaatggcaa aagtttatgc atttcttttcc     840 agacttgttc aacaggccag ccattacgct cgtcatcaaa atcactcgca tcaaccaaac     900
cgttattcat cgtgattgc gcctgagcga cgaaatac gcgatcgctg ttaaaaggac     960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa aatcccttaa    1440
cgtgagtttt cgttccactg agcgtcagac cccgtagaaa agatcaaagg atcttcttga    1500 gatcctttt ttctgcgcgt aatctgctgc ttgcaaacaa aaaaaccacc gctaccagcg    1560
gtggtttgtt tgccggatca agagctacca actcttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata agtcgtgtct taccgggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980 ccaggggggaa acgcctggta tctttatagt cctgtcgggt ttcgccacct ctgacttgag    2040
cgtcgatttt tgtgatgctc gtcaggggg cggagcctat ggaaaaacgc cagcaacgcg    2100 gccttttta c ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
```

```
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aaggggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccgagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtcccggga    4680 tctcgacgct ctcccttatg cgactcctgc attaggaagc agcccagtag taggttgagg    4740
```

-continued

| | |
|---|---|
| ccgttgagca ccgccgccgc aaggaatggt gcatgcaagg agatggcgcc aacagtccc | 4800 |
| ccggccacgg ggcctgccac catacccacg ccgaaacaag cgctcatgag cccgaagtgg | 4860 |
| cgagcccgat cttccccatc ggtgatgtcg gcgatatagg cgccagcaac cgcacctgtg | 4920 |
| gcgccggtga tgccgccac gatgcgtccg gcgtagagga tcgagatctc gatcccgcga | 4980 |
| aattaatacg actcactata ggggaattgt gagcggataa caattcccct ctagaaataa | 5040 |
| ttttgtttaa ctttaagaag gagatataca tatgcgttgt agcgtgtcca ccgaaaatgt | 5100 |
| gtctttcacc gaaactgaaa ccgaagctcg tcgttctgcg aactacgaac ctaacagctg | 5160 |
| ggactatgat tacctgctgt cctccgacac ggacgagtcc atcgaagtat acaaagacaa | 5220 |
| agcgaaaaag ctggaagccg aagttcgtcg cgagattaat aacgaaaaag cagaatttct | 5280 |
| gaccctgctg gaactgattg acaacgtcca gcgcctgggc ctgggttacc gtttcgagtc | 5340 |
| tgatatccgt ggtgcgctgg atcgcttcgt ttcctccggc ggcttcgatg cggtaaccaa | 5400 |
| gacttccctg cacggtacgg cactgtcttt ccgtctgctg cgtcaacacg gttttgaggt | 5460 |
| ttctcaggaa gcgttcagcg gcttcaaaga ccaaaacggc aacttcctgg agaacctgaa | 5520 |
| ggaagatatc aaagctatcc tgagcctgta cgaggccagc ttcctggctc tggaaggcga | 5580 |
| aaacatcctg gacgaggcga aggttttcgc aatctctcat ctgaaagaac tgtctgaaga | 5640 |
| aaagatcggt aaagagctgg cagaacaggt gaaccatgca ctggaactgc cactgcatcg | 5700 |
| ccgtactcag cgtctggaag cagtatggtc tatcgaggcc taccgtaaaa aggaggacgc | 5760 |
| gaatcaggtt ctgctggagc tggcaattct ggattacaac atgatccagt ctgtatacca | 5820 |
| gcgtgatctg cgtgaaacgt cccgttggtg gcgtcgtgtg ggtctggcga ccaaactgca | 5880 |
| ctttgctcgt gaccgcctga ttgagagctt ctactgggcc gtgggtgtag cattcgaacc | 5940 |
| gcaatactcc gactgccgta actccgtcgc aaaaatgttt tctttcgtaa ccattatcga | 6000 |
| cgatatctac gatgtatacg gcaccctgga cgaactggag ctgtttactg atgcagttga | 6060 |
| gcgttgggac gtaaacgcca tcaacgacct gccggattac atgaaactgt gctttctggc | 6120 |
| tctgtataac actattaacg aaatcgccta cgacaacctg aaagataaag gtgagaacat | 6180 |
| cctgccgtat ctgaccaaag cctgggctga cctgtgcaac gctttcctgc aagaagccaa | 6240 |
| gtggctgtac aacaaatcta ctccgacctt tgacgactac ttcggcaacg catggaaatc | 6300 |
| ctcttctggc ccgctgcaac tggtgttcgc ttacttcgct gtcgtgcaga acattaaaaa | 6360 |
| ggaagagatc gaaaacctgc aaaaatacca tgacaccatc tctcgtcctt cccatatctt | 6420 |
| ccgtctgtgc aatgacctgg ctagcgcgtc tgcggaaatt gcgcgtggtg aaaccgcaaa | 6480 |
| tagcgttcct tgttacatgc gcactaaagg tatctccgaa gaactggcta ccgaaagcgt | 6540 |
| gatgaatctg atcgatgaaa cctggaaaaa gatgaacaag gaaaaactgg gtggtagcct | 6600 |
| gttcgcgaaa ccgttcgtgg aaaccgcgat caacctggca cgtcaatctc actgcactta | 6660 |
| tcataacggc gacgcgcata cctctccgga tgagctgacc cgcaaacgcg ttctgtctgt | 6720 |
| aatcactgaa ccgattctgc cgtttgaacg cgaaaacctg tattttcagg gcctcgagca | 6780 |
| ccaccaccac caccactgag atccggctgc taacaaagcc cgaaaggaag ctgagttggc | 6840 |
| tgctgccacc gctgagcaat aactagcata accccttggg gcctctaaac gggtcttgag | 6900 |
| gggttttttg ctgaaaggag gaactatatc cggat | 6935 |

<210> SEQ ID NO 136
<211> LENGTH: 545
<212> TYPE: PRT
<213> ORGANISM: Artificial Sequence
<220> FEATURE:
<223> OTHER INFORMATION: Synthetic Construct

<400> SEQUENCE: 136

```
Met Thr Glu Ala Arg Arg Ser Ala Asn Tyr Glu Pro Asn Ser Trp Asp
1               5                   10                  15

Tyr Asp Tyr Leu Leu Ser Ser Asp Thr Asp Glu Ser Ile Glu Val Tyr
            20                  25                  30

Lys Asp Lys Ala Lys Lys Leu Glu Ala Glu Val Arg Arg Glu Ile Asn
        35                  40                  45

Asn Glu Lys Ala Glu Phe Leu Thr Leu Leu Glu Leu Ile Asp Asn Val
50                  55                  60

Gln Arg Leu Gly Leu Gly Tyr Arg Phe Glu Ser Asp Ile Arg Gly Ala
65                  70                  75                  80

Leu Asp Arg Phe Val Ser Ser Gly Gly Phe Asp Ala Val Thr Lys Thr
                85                  90                  95

Ser Leu His Gly Thr Ala Leu Ser Phe Arg Leu Leu Arg Gln His Gly
            100                 105                 110

Phe Glu Val Ser Gln Glu Ala Phe Ser Gly Phe Lys Asp Gln Asn Gly
        115                 120                 125

Asn Phe Leu Glu Asn Leu Lys Glu Asp Ile Lys Ala Ile Leu Ser Leu
130                 135                 140

Tyr Glu Ala Ser Phe Leu Ala Leu Glu Gly Glu Asn Ile Leu Asp Glu
145                 150                 155                 160

Ala Lys Val Phe Ala Ile Ser His Leu Lys Glu Leu Ser Glu Glu Lys
                165                 170                 175

Ile Gly Lys Glu Leu Ala Glu Gln Val Asn His Ala Leu Glu Leu Pro
            180                 185                 190

Leu His Arg Arg Thr Gln Arg Leu Glu Ala Val Trp Ser Ile Glu Ala
        195                 200                 205

Tyr Arg Lys Lys Glu Asp Ala Asn Gln Val Leu Leu Glu Leu Ala Ile
210                 215                 220

Leu Asp Tyr Asn Met Ile Gln Ser Val Tyr Gln Arg Asp Leu Arg Glu
225                 230                 235                 240

Thr Ser Arg Trp Trp Arg Arg Val Gly Leu Ala Thr Lys Leu His Phe
                245                 250                 255

Ala Arg Asp Arg Leu Ile Glu Ser Phe Tyr Trp Ala Val Gly Val Ala
            260                 265                 270

Phe Glu Pro Gln Tyr Ser Asp Cys Arg Asn Ser Val Ala Lys Met Phe
        275                 280                 285

Ser Phe Val Thr Ile Ile Asp Asp Ile Tyr Asp Val Tyr Gly Thr Leu
290                 295                 300

Asp Glu Leu Glu Leu Phe Thr Asp Ala Val Glu Arg Trp Asp Val Asn
305                 310                 315                 320

Ala Ile Asn Asp Leu Pro Asp Tyr Met Lys Leu Cys Phe Leu Ala Leu
                325                 330                 335

Tyr Asn Thr Ile Asn Glu Ile Ala Tyr Asp Asn Leu Lys Asp Lys Gly
            340                 345                 350

Glu Asn Ile Leu Pro Tyr Leu Thr Lys Ala Trp Ala Asp Leu Cys Asn
        355                 360                 365

Ala Phe Leu Gln Glu Ala Lys Trp Leu Tyr Asn Lys Ser Thr Pro Thr
370                 375                 380

Phe Asp Asp Tyr Phe Gly Asn Ala Trp Lys Ser Ser Ser Gly Pro Leu
385                 390                 395                 400
```

```
Gln Leu Val Phe Ala Tyr Phe Ala Val Val Gln Asn Ile Lys Lys Glu
            405                 410                 415

Glu Ile Glu Asn Leu Gln Lys Tyr His Asp Thr Ile Ser Arg Pro Ser
        420                 425                 430

His Ile Phe Arg Leu Cys Asn Asp Leu Ala Ser Ala Ser Ala Glu Ile
    435                 440                 445

Ala Arg Gly Glu Thr Ala Asn Ser Val Ser Cys Tyr Met Arg Thr Lys
450                 455                 460

Gly Ile Ser Glu Glu Leu Ala Thr Glu Ser Val Met Asn Leu Ile Asp
465                 470                 475                 480

Glu Thr Trp Lys Lys Met Asn Lys Glu Lys Leu Gly Gly Ser Leu Phe
                485                 490                 495

Ala Lys Pro Phe Val Glu Thr Ala Ile Asn Leu Ala Arg Gln Ser His
            500                 505                 510

Cys Thr Tyr His Asn Gly Asp Ala His Thr Ser Pro Asp Glu Leu Thr
        515                 520                 525

Arg Lys Arg Val Leu Ser Val Ile Thr Glu Pro Ile Leu Pro Phe Glu
    530                 535                 540

Arg
545

<210> SEQ ID NO 137
<211> LENGTH: 6912
<212> TYPE: DNA
<213> ORGANISM: Artificial Sequence
<220> FEATURE:
<223> OTHER INFORMATION: Synthetic Construct

<400> SEQUENCE: 137
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tccctttagg      180 gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta taagggattt tgccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg aattaattct tagaaaaact catcgagcat caaatgaaac tgcaatttat     600
tcatatcagg attatcaata ccatattttt gaaaagccg tttctgtaat gaaggagaaa      660
actcaccgag gcagttccat aggatggcaa gatcctggta tcggtctgcg attccgactc     720
gtccaacatc aatacaacct attaatttcc cctcgtcaaa aataaggtta tcaagtgaga     780
aatcaccatg agtgacgact gaatccggtg agaatggcaa aagtttatgc atttctttcc     840
agacttgttc aacaggccag ccattacgct cgtcatcaaa atcactcgca tcaaccaaac     900
cgttattcat tcgtgattgc gcctgagcga acgaaatac gcgatcgctg ttaaaaggac       960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
```

-continued

```
taaattccgt cagccagttt agtctgacca tctcatctgt aacatcattg gcaacgctac     1200
ctttgccatg tttcagaaac aactctggcg catcgggctt cccatacaat cgatagattg     1260
tcgcacctga ttgcccgaca ttatcgcgag cccatttata cccatataaa tcagcatcca     1320
tgttggaatt taatcgcggc ctagagcaag acgtttcccg ttgaatatgg ctcataacac     1380
cccttgtatt actgtttatg taagcagaca gttttattgt tcatgaccaa aatcccttaa     1440
cgtgagtttt cgttccactg agcgtcagac cccgtagaaa agatcaaagg atcttcttga     1500 gatcctttt ttctgcgcgt aatctgctgc ttgcaaacaa aaaaaccacc gctaccagcg     1560
gtggtttgtt tgccggatca agagctacca actcttttc cgaaggtaac tggcttcagc     1620
agagcgcaga taccaaatac tgtccttcta gtgtagccgt agttaggcca ccacttcaag     1680
aactctgtag caccgcctac atacctcgct ctgctaatcc tgttaccagt ggctgctgcc     1740
agtggcgata agtcgtgtct taccgggttg gactcaagac gatagttacc ggataaggcg     1800
cagcggtcgg gctgaacggg gggttcgtgc acacagccca gcttggagcg aacgacctac     1860
accgaactga gatacctaca gcgtgagcta tgagaaagcg ccacgcttcc cgaagggaga     1920
aaggcggaca ggtatccggt aagcggcagg gtcggaacag gagagcgcac gagggagctt     1980
ccagggggaa acgcctggta tctttatagt cctgtcgggt ttcgccacct ctgacttgag     2040
cgtcgatttt tgtgatgctc gtcaggggg cggagcctat ggaaaaacgc cagcaacgcg     2100 gccttttac ggttcctggc cttttgctgg ccttttgctc acatgttctt tcctgcgtta     2160
tcccctgatt ctgtggataa ccgtattacc gcctttgagt gagctgatac cgctcgccgc     2220
agccgaacga ccgagcgcag cgagtcagtg agcgaggaag cggaagagcg cctgatgcgg     2280
tattttctcc ttacgcatct gtgcggtatt tcacaccgca tatatggtgc actctcagta     2340
caatctgctc tgatgccgca tagttaagcc agtatacact ccgctatcgc tacgtgactg     2400
ggtcatggct gcgccccgac acccgccaac acccgctgac gcgccctgac gggcttgtct     2460
gctcccggca tccgcttaca gacaagctgt gaccgtctcc gggagctgca tgtgtcagag     2520
gttttcaccg tcatcaccga aacgcgcgag gcagctgcgg taaagctcat cagcgtggtc     2580
gtgaagcgat tcacagatgt ctgcctgttc atccgcgtcc agctcgttga gtttctccag     2640
aagcgttaat gtctggcttc tgataaagcg ggccatgtta agggcggttt tttcctgttt     2700
ggtcactgat gcctccgtgt aagggggatt tctgttcatg ggggtaatga taccgatgaa     2760
acgagagagg atgctcacga tacgggttac tgatgatgaa catgcccggt tactggaacg     2820
ttgtgagggt aaacaactgg cggtatggat gcggcgggac cagagaaaaa tcactcaggg     2880
tcaatgccag cgcttcgtta atacagatgt aggtgttcca cagggtagcc agcagcatcc     2940
tgcgatgcag atccggaaca taatggtgca gggcgctgac ttccgcgttt ccagacttta     3000
cgaaacacgg aaaccgaaga ccattcatgt tgttgctcag gtcgcagacg ttttgcagca     3060
gcagtcgctt cacgttcgct cgcgtatcgg tgattcattc tgctaaccag taaggcaacc     3120
ccgccagcct agccgggtcc tcaacgacag gagcacgatc atgcgcaccc gtggggccgc     3180
catgccggcg ataatggcct gcttctcgcc gaaacgtttg gtggcgggac cagtgacgaa     3240
ggcttgagcg agggcgtgca agattccgaa taccgcaagc gacaggccga tcatcgtcgc     3300
gctccagcga aagcggtcct cgccgaaaat gacccagagc gctgccggca cctgtcctac     3360
gagttgcatg ataaagaaga cagtcataag tgcggcgacg atagtcatgc ccgcgccca     3420 ccggaaggag ctgactgggt tgaaggctct caagggcatc ggtcgagatc ccggtgccta     3480
atgagtgagc taacttacat taattgcgtt gcgctcactg cccgctttcc agtcgggaaa     3540
```

```
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacgcggga tataacatga gctgtcttcg gtatcgtcgt     3780
atcccactac cgagatatcc gcaccaacgc gcagcccgga ctcggtaatg cgcgcattg     3840 cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa cttaagaag gagatataca tatgaccgaa gctcgtcgtt ctgcgaacta    5100
cgaacctaac agctgggact atgattacct gctgtcctcc gacacggacg agtccatcga    5160
agtatacaaa gacaaagcga aaagctgga agccgaagtt cgtcgcgaga ttaataacga    5220
aaaagcagaa tttctgaccc tgctggaact gattgacaac gtccagcgcc tgggcctggg    5280
ttaccgtttc gagtctgata tccgtggtgc gctggatcgc ttcgtttcct ccggcggctt    5340
cgatgcggta accaagactt ccctgcacgg tacggcactg tctttccgtc tgctgcgtca    5400
acacggtttt gaggtttctc aggaagcgtt cagcggcttc aaagaccaaa acggcaactt    5460
cctggagaac ctgaaggaag atatcaaagc tatcctgagc ctgtacgagg ccagcttcct    5520
ggctctggaa ggcgaaaaca tcctggacga ggcgaaggtt ttcgcaatct ctcatctgaa    5580
agaactgtct gaagaaaaga tcggtaaaga gctggcagaa caggtgaacc atgcactgga    5640
actgccactg catcgccgta ctcagcgtct ggaagcagta tggtctatcg aggcctaccg    5700
taaaaaggag gacgcgaatc aggttctgct ggagctggca attctggatt acaacatgat    5760
ccagtctgta taccagcgtg atctgcgtga aacgtcccgt tggtggcgtc gtgtgggtct    5820
ggcgaccaaa ctgcactttg ctcgtgaccg cctgattgag agcttctact gggccgtggg    5880
```

```
tgtagcattc gaaccgcaat actccgactg ccgtaactcc gtcgcaaaaa tgttttcttt   5940
cgtaaccatt atcgacgata tctacgatgt atacggcacc ctggacgaac tggagctgtt   6000
tactgatgca gttgagcgtt gggacgtaaa cgccatcaac gacctgccgg attacatgaa   6060
actgtgcttt ctggctctgt ataacactat taacgaaatc gcctacgaca acctgaaaga   6120
taaaggtgag aacatcctgc cgtatctgac caaagcctgg gctgacctgt gcaacgcttt   6180
cctgcaagaa gccaagtggc tgtacaacaa atctactccg acctttgacg actacttcgg   6240
caacgcatgg aaatcctctt ctggcccgct gcaactggtg ttcgcttact tcgctgtcgt   6300
gcagaacatt aaaaaggaag agatcgaaaa cctgcaaaaa taccatgaca ccatctctcg   6360
tccttcccat atcttccgtc tgtgcaatga cctggctagc gcgtctgcgg aaattgcgcg   6420
tggtgaaacc gcaaatagcg tttcttgtta catgcgcact aaaggtatct ccgaagaact   6480
ggctaccgaa agcgtgatga atctgatcga tgaaacctgg aaaaagatga acaaggaaaa   6540
actgggtggt agcctgttcg cgaaaccgtt cgtggaaacc gcgatcaacc tggcacgtca   6600
atctcactgc acttatcata acggcgacgc gcatacctct ccggatgagc tgacccgcaa   6660
acgcgttctg tctgtaatca ctgaaccgat tctgccgttt gaacgctaag gatccgaatt   6720
cgagctccgt cgacaagctt gcggccgcac tcgagcacca ccaccaccac cactgagatc   6780
cggctgctaa caaagcccga aaggaagctg agttggctgc tgccaccgct gagcaataac   6840
tagcataacc ccttggggcc tctaaacggg tcttgagggg ttttttgctg aaaggaggaa   6900
ctatatccgg at                                                        6912
```

```
<210> SEQ ID NO 138
<211> LENGTH: 546
<212> TYPE: PRT
<213> ORGANISM: Artificial Sequence
<220> FEATURE:
<223> OTHER INFORMATION: Synthetic Construct

<400> SEQUENCE: 138

Met Glu Thr Glu Ala Arg Arg Ser Ala Asn Tyr Glu Pro Asn Ser Trp
1               5                   10                  15

Asp Tyr Asp Tyr Leu Leu Ser Ser Asp Thr Asp Glu Ser Ile Glu Val
            20                  25                  30

Tyr Lys Asp Lys Ala Lys Lys Leu Glu Ala Glu Val Arg Arg Glu Ile
        35                  40                  45

Asn Asn Glu Lys Ala Glu Phe Leu Thr Leu Leu Glu Leu Ile Asp Asn
    50                  55                  60

Val Gln Arg Leu Gly Leu Gly Tyr Arg Phe Glu Ser Asp Ile Arg Gly
65                  70                  75                  80

Ala Leu Asp Arg Phe Val Ser Ser Gly Gly Phe Asp Ala Val Thr Lys
                85                  90                  95

Thr Ser Leu His Gly Thr Ala Leu Ser Phe Arg Leu Leu Arg Gln His
            100                 105                 110

Gly Phe Glu Val Ser Gln Glu Ala Phe Ser Gly Phe Lys Asp Gln Asn
        115                 120                 125

Gly Asn Phe Leu Glu Asn Leu Lys Glu Asp Ile Lys Ala Ile Leu Ser
    130                 135                 140

Leu Tyr Glu Ala Ser Phe Leu Ala Leu Glu Gly Glu Asn Ile Leu Asp
145                 150                 155                 160

Glu Ala Lys Val Phe Ala Ile Ser His Leu Lys Glu Leu Ser Glu Glu
                165                 170                 175
```

```
Lys Ile Gly Lys Glu Leu Ala Glu Gln Val Asn His Ala Leu Glu Leu
            180                 185                 190

Pro Leu His Arg Arg Thr Gln Arg Leu Glu Ala Val Trp Ser Ile Glu
        195                 200                 205

Ala Tyr Arg Lys Lys Glu Asp Ala Asn Gln Val Leu Leu Glu Leu Ala
    210                 215                 220

Ile Leu Asp Tyr Asn Met Ile Gln Ser Val Tyr Gln Arg Asp Leu Arg
225                 230                 235                 240

Glu Thr Ser Arg Trp Trp Arg Val Gly Leu Ala Thr Lys Leu His
                245                 250                 255

Phe Ala Arg Asp Arg Leu Ile Glu Ser Phe Tyr Trp Ala Val Gly Val
                260                 265                 270

Ala Phe Glu Pro Gln Tyr Ser Asp Cys Arg Asn Ser Val Ala Lys Met
        275                 280                 285

Phe Ser Phe Val Thr Ile Ile Asp Ile Tyr Asp Val Tyr Gly Thr
    290                 295                 300

Leu Asp Glu Leu Glu Leu Phe Thr Asp Ala Val Glu Arg Trp Asp Val
305                 310                 315                 320

Asn Ala Ile Asn Asp Leu Pro Asp Tyr Met Lys Leu Cys Phe Leu Ala
                325                 330                 335

Leu Tyr Asn Thr Ile Asn Glu Ile Ala Tyr Asp Asn Leu Lys Asp Lys
                340                 345                 350

Gly Glu Asn Ile Leu Pro Tyr Leu Thr Lys Ala Trp Ala Asp Leu Cys
            355                 360                 365

Asn Ala Phe Leu Gln Glu Ala Lys Trp Leu Tyr Asn Lys Ser Thr Pro
        370                 375                 380

Thr Phe Asp Asp Tyr Phe Gly Asn Ala Trp Lys Ser Ser Gly Pro
385                 390                 395                 400

Leu Gln Leu Val Phe Ala Tyr Phe Ala Val Val Gln Asn Ile Lys Lys
                405                 410                 415

Glu Glu Ile Glu Asn Leu Gln Lys Tyr His Asp Thr Ile Ser Arg Pro
            420                 425                 430

Ser His Ile Phe Arg Leu Cys Asn Asp Leu Ala Ser Ala Ser Ala Glu
        435                 440                 445

Ile Ala Arg Gly Glu Thr Ala Asn Ser Val Ser Cys Tyr Met Arg Thr
450                 455                 460

Lys Gly Ile Ser Glu Glu Leu Ala Thr Glu Ser Val Met Asn Leu Ile
465                 470                 475                 480

Asp Glu Thr Trp Lys Lys Met Asn Lys Glu Lys Leu Gly Gly Ser Leu
                485                 490                 495

Phe Ala Lys Pro Phe Val Glu Thr Ala Ile Asn Leu Ala Arg Gln Ser
            500                 505                 510

His Cys Thr Tyr His Asn Gly Asp Ala His Thr Ser Pro Asp Glu Leu
        515                 520                 525

Thr Arg Lys Arg Val Leu Ser Val Ile Thr Glu Pro Ile Leu Pro Phe
530                 535                 540

Glu Arg
545

<210> SEQ ID NO 139
<211> LENGTH: 6915
<212> TYPE: DNA
<213> ORGANISM: Artificial Sequence
<220> FEATURE:
<223> OTHER INFORMATION: Synthetic Construct
```

<400> SEQUENCE: 139

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
cttctcgcc acgttcgccg gctttccccg tcaagctcta aatcggggc tcccttagg       180
gttccgattt agtgctttac ggcacctcga ccccaaaaaa cttgattagg gtgatggttc     240
acgtagtggg ccatcgccct gatagacggt ttttcgccct tgacgttgg agtccacgtt     300
ctttaatagt ggactcttgt tccaaactgg aacaacactc aaccctatct cggtctattc     360
ttttgattta taggattt tgccgatttc ggcctattgg ttaaaaatg agctgattta       420
acaaaatt aacgcgaatt ttaacaaaat attaacgttt acaatttcag gtggcactttt     480
tcggggaaat gtgcgcggaa cccctatttg tttattttc taaatacatt caaatatgta     540
tccgctcatg aattaattct tagaaaaact catcgagcat caaatgaaac tgcaatttat     600
tcatatcagg attatcaata ccatatttt gaaaagccg tttctgtaat gaaggagaaa      660
actcaccgag gcagttccat aggatggcaa gatcctggta tcggtctgcg attccgactc     720
gtccaacatc aatacaacct attaatttcc cctcgtcaaa aataaggtta tcaagtgaga     780
aatcaccatg agtgacgact gaatccggtg agaatggcaa aagtttatgc atttctttcc     840
agacttgttc aacaggccag ccattacgct cgtcatcaaa atcactcgca tcaaccaaac     900
cgttattcat tcgtgattgc gcctgagcga gacgaaatac gcgatcgctg ttaaaaggac     960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa atcccttaa    1440
cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actcttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata agtcgtgtct taccgggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc gaagggaga    1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcagggggg cggagcctat ggaaaaacgc cagcaacgcg    2100
gcctttttac ggttcctggc cttttgctgg cctttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
```

```
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
```

```
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatggaaacc gaagctcgtc gttctgcgaa   5100
ctacgaacct aacagctggg actatgatta cctgctgtcc tccgacacgg acgagtccat   5160
cgaagtatac aaagacaaag cgaaaaagct ggaagccgaa gttcgtcgcg agattaataa   5220
cgaaaaagca gaatttctga ccctgctgga actgattgac aacgtccagc gcctgggcct   5280
gggttaccgt ttcgagtctg atatccgtgg tgcgctggat cgcttcgttt cctccggcgg   5340
cttcgatgcg gtaaccaaga cttccctgca cggtacggca ctgtctttcc gtctgctgcg   5400
tcaacacggt tttgaggttt ctcaggaagc gttcagcggc ttcaaagacc aaaacggcaa   5460
cttcctggag aacctgaagg aagatatcaa agctatcctg agcctgtacg aggccagctt   5520
cctggctctg gaaggcgaaa acatcctgga cgaggcgaag gttttcgcaa tctctcatct   5580
gaaagaactg tctgaagaaa agatcggtaa agagctggca gaacaggtga accatgcact   5640
ggaactgcca ctgcatcgcc gtactcagcg tctggaagca gtatggtcta tcgaggccta   5700
ccgtaaaaag gaggacgcga atcaggttct gctggagctg gcaattctgg attacaacat   5760
gatccagtct gtataccagc gtgatctgcg tgaaacgtcc cgttggtggc gtcgtgtggg   5820
tctggcgacc aaaactgcact tgctcgtga ccgcctgatt gagagcttct actgggccgt   5880
gggtgtagca ttcgaaccgc aatactccga ctgccgtaac tccgtcgcaa aaatgttttc   5940
tttcgtaacc attatcgacg atatctacga tgtatacggc ccctggacg aactggagct   6000 gtttactgat gcagttgagc gttgggacgt aaacgccatc aacgacctgc cggattacat   6060
gaaactgtgc tttctggctc tgtataacac tattaacgaa atcgcctacg acaacctgaa   6120
agataaaggt gagaacatcc tgccgtatct gaccaaagcc tgggctgacc tgtgcaacgc   6180
tttcctgcaa gaagccaagt ggctgtacaa caaatctact ccgaccttg acgactactt   6240 cggcaacgca tggaaatcct cttctggccc gctgcaactg gtgttcgctt acttcgctgt   6300
cgtgcagaac attaaaaagg aagagatcga aacctgcaa aaataccatg acaccatctc   6360
tcgtccttcc catatcttcc gtctgtgcaa tgacctggct agcgcgtctg cggaaattgc   6420
gcgtggtgaa accgcaaata gcgtttcttg ttacatgcgc actaaaggta tctccgaaga   6480
actggctacc gaaagcgtga tgaatctgat cgatgaaacc tggaaaaaga tgaacaagga   6540
aaaactgggt ggtagcctgt tcgcgaaacc gttcgtggaa accgcgatca acctggcacg   6600
tcaatctcac tgcacttatc ataacggcga cgcgcatacc tctccggatg agctgaccccg   6660 caaacgcgtt ctgtctgtaa tcactgaacc gattctgccg tttgaacgct aaggatccga   6720
attcgagctc cgtcgacaag cttgcggccg cactcgagca ccaccaccac caccactgag   6780
atccggctgc taacaaagcc cgaaaggaag ctgagttggc tgctgccacc gctgagcaat   6840
aactagcata acccccttggg gcctctaaac gggtcttgag gggttttttg ctgaaaggag   6900
gaactatatc cggat   6915
```

<210> SEQ ID NO 140

<211> LENGTH: 547
<212> TYPE: PRT
<213> ORGANISM: Artificial Sequence
<220> FEATURE:
<223> OTHER INFORMATION: Synthetic Construct

<400> SEQUENCE: 140

Met Thr Glu Thr Glu Ala Arg Arg Ser Ala Asn Tyr Glu Pro Asn Ser
1               5                   10                  15

Trp Asp Tyr Asp Tyr Leu Leu Ser Ser Asp Thr Asp Glu Ser Ile Glu
            20                  25                  30

Val Tyr Lys Asp Lys Ala Lys Lys Leu Glu Ala Glu Val Arg Arg Glu
        35                  40                  45

Ile Asn Asn Glu Lys Ala Glu Phe Leu Thr Leu Leu Glu Leu Ile Asp
    50                  55                  60

Asn Val Gln Arg Leu Gly Leu Gly Tyr Arg Phe Glu Ser Asp Ile Arg
65                  70                  75                  80

Gly Ala Leu Asp Arg Phe Val Ser Ser Gly Gly Phe Asp Ala Val Thr
                85                  90                  95

Lys Thr Ser Leu His Gly Thr Ala Leu Ser Phe Arg Leu Leu Arg Gln
            100                 105                 110

His Gly Phe Glu Val Ser Gln Glu Ala Phe Ser Gly Phe Lys Asp Gln
        115                 120                 125

Asn Gly Asn Phe Leu Glu Asn Leu Lys Glu Asp Ile Lys Ala Ile Leu
    130                 135                 140

Ser Leu Tyr Glu Ala Ser Phe Leu Ala Leu Glu Gly Glu Asn Ile Leu
145                 150                 155                 160

Asp Glu Ala Lys Val Phe Ala Ile Ser His Leu Lys Glu Leu Ser Glu
                165                 170                 175

Glu Lys Ile Gly Lys Glu Leu Ala Glu Gln Val Asn His Ala Leu Glu
            180                 185                 190

Leu Pro Leu His Arg Arg Thr Gln Arg Leu Glu Ala Val Trp Ser Ile
        195                 200                 205

Glu Ala Tyr Arg Lys Lys Glu Asp Ala Asn Gln Val Leu Leu Glu Leu
    210                 215                 220

Ala Ile Leu Asp Tyr Asn Met Ile Gln Ser Val Tyr Gln Arg Asp Leu
225                 230                 235                 240

Arg Glu Thr Ser Arg Trp Trp Arg Arg Val Gly Leu Ala Thr Lys Leu
                245                 250                 255

His Phe Ala Arg Asp Arg Leu Ile Glu Ser Phe Tyr Trp Ala Val Gly
            260                 265                 270

Val Ala Phe Glu Pro Gln Tyr Ser Asp Cys Arg Asn Ser Val Ala Lys
        275                 280                 285

Met Phe Ser Phe Val Thr Ile Ile Asp Asp Ile Tyr Asp Val Tyr Gly
    290                 295                 300

Thr Leu Asp Glu Leu Glu Leu Phe Thr Asp Ala Val Glu Arg Trp Asp
305                 310                 315                 320

Val Asn Ala Ile Asn Asp Leu Pro Asp Tyr Met Lys Leu Cys Phe Leu
                325                 330                 335

Ala Leu Tyr Asn Thr Ile Asn Glu Ile Ala Tyr Asp Asn Leu Lys Asp
            340                 345                 350

Lys Gly Glu Asn Ile Leu Pro Tyr Leu Thr Lys Ala Trp Ala Asp Leu
        355                 360                 365

Cys Asn Ala Phe Leu Gln Glu Ala Lys Trp Leu Tyr Asn Lys Ser Thr
    370                 375                 380

Pro Thr Phe Asp Asp Tyr Phe Gly Asn Ala Trp Lys Ser Ser Gly
385                 390                 395                 400

Pro Leu Gln Leu Val Phe Ala Tyr Phe Ala Val Val Gln Asn Ile Lys
            405                 410                 415

Lys Glu Glu Ile Glu Asn Leu Gln Lys Tyr His Asp Thr Ile Ser Arg
        420                 425                 430

Pro Ser His Ile Phe Arg Leu Cys Asn Asp Leu Ala Ser Ala Ser Ala
            435                 440                 445

Glu Ile Ala Arg Gly Glu Thr Ala Asn Ser Val Ser Cys Tyr Met Arg
        450                 455                 460

Thr Lys Gly Ile Ser Glu Glu Leu Ala Thr Glu Ser Val Met Asn Leu
465                 470                 475                 480

Ile Asp Glu Thr Trp Lys Lys Met Asn Lys Glu Lys Leu Gly Gly Ser
            485                 490                 495

Leu Phe Ala Lys Pro Phe Val Glu Thr Ala Ile Asn Leu Ala Arg Gln
            500                 505                 510

Ser His Cys Thr Tyr His Asn Gly Asp Ala His Thr Ser Pro Asp Glu
        515                 520                 525

Leu Thr Arg Lys Arg Val Leu Ser Val Ile Thr Glu Pro Ile Leu Pro
        530                 535                 540

Phe Glu Arg
545

<210> SEQ ID NO 141
<211> LENGTH: 6918
<212> TYPE: DNA
<213> ORGANISM: Artificial Sequence
<220> FEATURE:
<223> OTHER INFORMATION: Synthetic Construct

<400> SEQUENCE: 141
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcggggggc tccctttagg     180
gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta taaggatttt gccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg aattaattct tagaaaaact catcgagcat caaatgaaac tgcaatttat     600
tcatatcagg attatcaata ccatattttt gaaaaagccg tttctgtaat gaaggagaaa     660
actcaccgag gcagttccat aggatggcaa gatcctggta tcggtctgcg attccgactc     720
gtccaacatc aatacaacct attaatttcc cctcgtcaaa ataaggtta tcaagtgaga     780 aatcaccatg agtgacgact gaatccggtg agaatggcaa aagtttatgc atttctttcc     840
agacttgttc aacaggccag ccattacgct cgtcatcaaa atcactcgca tcaaccaaac     900
cgttattcat tcgtgattgc gcctgagcga cgaaatac gcgatcgctg ttaaaaggac     960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080

```
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa aatcccttaa    1440
cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actcttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata gtcgtgtct taccggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980 ccaggggaa acgcctggta tctttatagt cctgtcgggt ttcgccacct ctgacttgag    2040
cgtcgatttt tgtgatgctc gtcaggggg cggagcctat ggaaaaacgc cagcaacgcg    2100 gccttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt ttcctgtttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
```

```
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatgactgaa accgaagctc gtcgttctgc   5100
gaactacgaa cctaacagct gggactatga ttacctgctg tcctccgaca cggacgagtc   5160
catcgaagta tacaaagaca agcgaaaaa gctggaagcc gaagttcgtc gcgagattaa   5220
taacgaaaaa gcagaatttc tgaccctgct ggaactgatt gacaacgtcc agcgcctggg   5280
cctgggttac cgtttcgagt ctgatatccg tggtgcgctg gatcgcttcg tttcctccgg   5340
cggcttcgat gcggtaacca agacttccct gcacggtacg gcactgtctt tccgtctgct   5400
gcgtcaacac ggttttgagg tttctcagga agcgttcagc ggcttcaaag accaaaacgg   5460
caacttcctg gagaacctga aggaagatat caaagctatc ctgagcctgt acgaggccag   5520
cttcctggct ctgaaggcg aaaacatcct ggacgaggcg aaggttttcg caatctctca   5580
tctgaaagaa ctgtctgaag aaaagatcgg taaagagctg gcagaacagg tgaaccatgc   5640
actggaactg ccactgcatc gccgtactca gcgtctggaa gcagtatggt ctatcgaggc   5700
ctaccgtaaa aaggaggacg cgaatcaggt tctgctggag ctggcaattc tggattacaa   5760
catgatccag tctgtatacc agcgtgatct gcgtgaaacg tcccgttggt ggcgtcgtgt   5820
```

-continued

```
gggtctggcg accaaactgc actttgctcg tgaccgcctg attgagagct tctactgggc    5880
cgtgggtgta gcattcgaac cgcaatactc cgactgccgt aactccgtcg caaaaatgtt    5940
ttctttcgta accattatcg acgatatcta cgatgtatac ggcaccctgg acgaactgga    6000
gctgttyact gatgcagttg agcgttggga cgtaaacgcc atcaacgacc tgccggatta    6060
catgaaactg tgctttctgg ctctgtataa cactattaac gaaatcgcct acgacaacct    6120
gaaagataaa ggtgagaaca tcctgccgta tctgaccaaa gcctgggctg acctgtgcaa    6180
cgctttcctg caagaagcca gtggctgta caacaaatct actccgacct tgacgacta     6240
cttcggcaac gcatggaaat cctcttctgg cccgctgcaa ctggtgttcg cttacttcgc    6300
tgtcgtgcag aacattaaaa aggaagagat cgaaaacctg caaaaatacc atgacaccat    6360
ctctcgtcct tcccatatct ccgtctgtg caatgacctg gctagcgcgt ctgcggaaat     6420
tgcgcgtggt gaaaccgcaa atagcgtttc ttgttacatg cgcactaaag gtatctccga    6480
agaactggct accgaaagcg tgatgaatct gatcgatgaa acctggaaaa agatgaacaa    6540
ggaaaaactg ggtggtagcc tgttcgcgaa accgttcgtg gaaaccgcga tcaacctggc    6600
acgtcaatct cactgcactt atcataacgg cgacgcgcat acctctccgg atgagctgac    6660
ccgcaaacgc gttctgtctg taatcactga accgattctg ccgtttgaac gctaaggatc    6720
cgaattcgag ctccgtcgac aagcttgcgg ccgcactcga gcaccaccac caccaccact    6780
gagatccggc tgctaacaaa gcccgaaagg aagctgagtt ggctgctgcc accgctgagc    6840
aataactagc ataaccccct tggggcctcta acgggtctt gagggttttt tgctgaaag    6900
gaggaactat atccggat                                                  6918
```

<210> SEQ ID NO 142
<211> LENGTH: 548
<212> TYPE: PRT
<213> ORGANISM: Artificial Sequence
<220> FEATURE:
<223> OTHER INFORMATION: Synthetic Construct

<400> SEQUENCE: 142

```
Met Glu Thr Glu Thr Glu Ala Arg Arg Ser Ala Asn Tyr Glu Pro Asn
  1               5                  10                  15

Ser Trp Asp Tyr Asp Tyr Leu Leu Ser Ser Asp Thr Asp Glu Ser Ile
             20                  25                  30

Glu Val Tyr Lys Asp Lys Ala Lys Lys Leu Glu Ala Glu Val Arg Arg
         35                  40                  45

Glu Ile Asn Asn Glu Lys Ala Glu Phe Leu Thr Leu Leu Glu Leu Ile
     50                  55                  60

Asp Asn Val Gln Arg Leu Gly Leu Gly Tyr Arg Phe Glu Ser Asp Ile
 65                  70                  75                  80

Arg Gly Ala Leu Asp Arg Phe Val Ser Ser Gly Gly Phe Asp Ala Val
                 85                  90                  95

Thr Lys Thr Ser Leu His Gly Thr Ala Leu Ser Phe Arg Leu Leu Arg
            100                 105                 110

Gln His Gly Phe Glu Val Ser Gln Glu Ala Phe Ser Gly Phe Lys Asp
        115                 120                 125

Gln Asn Gly Asn Phe Leu Glu Asn Leu Lys Glu Asp Ile Lys Ala Ile
    130                 135                 140

Leu Ser Leu Tyr Glu Ala Ser Phe Leu Ala Leu Glu Gly Glu Asn Ile
145                 150                 155                 160
```

Leu Asp Glu Ala Lys Val Phe Ala Ile Ser His Leu Lys Glu Leu Ser
            165                 170                 175

Glu Glu Lys Ile Gly Lys Glu Leu Ala Glu Gln Val Asn His Ala Leu
        180                 185                 190

Glu Leu Pro Leu His Arg Arg Thr Gln Arg Leu Glu Ala Val Trp Ser
    195                 200                 205

Ile Glu Ala Tyr Arg Lys Lys Glu Asp Ala Asn Gln Val Leu Leu Glu
210                 215                 220

Leu Ala Ile Leu Asp Tyr Asn Met Ile Gln Ser Val Tyr Gln Arg Asp
225                 230                 235                 240

Leu Arg Glu Thr Ser Arg Trp Trp Arg Val Gly Leu Ala Thr Lys
            245                 250                 255

Leu His Phe Ala Arg Asp Arg Leu Ile Glu Ser Phe Tyr Trp Ala Val
            260                 265                 270

Gly Val Ala Phe Glu Pro Gln Tyr Ser Asp Cys Arg Asn Ser Val Ala
        275                 280                 285

Lys Met Phe Ser Phe Val Thr Ile Ile Asp Asp Ile Tyr Asp Val Tyr
    290                 295                 300

Gly Thr Leu Asp Glu Leu Glu Leu Phe Thr Asp Ala Val Glu Arg Trp
305                 310                 315                 320

Asp Val Asn Ala Ile Asn Asp Leu Pro Asp Tyr Met Lys Leu Cys Phe
                325                 330                 335

Leu Ala Leu Tyr Asn Thr Ile Asn Glu Ile Ala Tyr Asp Asn Leu Lys
            340                 345                 350

Asp Lys Gly Glu Asn Ile Leu Pro Tyr Leu Thr Lys Ala Trp Ala Asp
        355                 360                 365

Leu Cys Asn Ala Phe Leu Gln Glu Ala Lys Trp Leu Tyr Asn Lys Ser
    370                 375                 380

Thr Pro Thr Phe Asp Asp Tyr Phe Gly Asn Ala Trp Lys Ser Ser Ser
385                 390                 395                 400

Gly Pro Leu Gln Leu Val Phe Ala Tyr Phe Ala Val Val Gln Asn Ile
                405                 410                 415

Lys Lys Glu Glu Ile Glu Asn Leu Gln Lys Tyr His Asp Thr Ile Ser
            420                 425                 430

Arg Pro Ser His Ile Phe Arg Leu Cys Asn Asp Leu Ala Ser Ala Ser
        435                 440                 445

Ala Glu Ile Ala Arg Gly Glu Thr Ala Asn Ser Val Ser Cys Tyr Met
    450                 455                 460

Arg Thr Lys Gly Ile Ser Glu Glu Leu Ala Thr Glu Ser Val Met Asn
465                 470                 475                 480

Leu Ile Asp Glu Thr Trp Lys Lys Met Asn Lys Glu Lys Leu Gly Gly
                485                 490                 495

Ser Leu Phe Ala Lys Pro Phe Val Glu Thr Ala Ile Asn Leu Ala Arg
            500                 505                 510

Gln Ser His Cys Thr Tyr His Asn Gly Asp Ala His Thr Ser Pro Asp
        515                 520                 525

Glu Leu Thr Arg Lys Arg Val Leu Ser Val Ile Thr Glu Pro Ile Leu
    530                 535                 540

Pro Phe Glu Arg
545

<210> SEQ ID NO 143
<211> LENGTH: 6921
<212> TYPE: DNA

<213> ORGANISM: Artificial Sequence
<220> FEATURE:
<223> OTHER INFORMATION: Synthetic Construct

<400> SEQUENCE: 143

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta aatcggggc tcccttagg      180
gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta tagggatttt tgccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg aattaattct tagaaaaact catcgagcat caaatgaaac tgcaatttat     600
tcatatcagg attatcaata ccatattttt gaaaaagccg tttctgtaat gaaggagaaa     660
actcaccgag gcagttccat aggatggcaa gatcctggta tcggtctgcg attccgactc     720
gtccaacatc aatacaacct attaatttcc cctcgtcaaa ataaggtta tcaagtgaga     780
aatcaccatg agtgacgact gaatccggtg agaatggcaa aagtttatgc atttctttcc     840
agacttgttc aacaggccag ccattacgct cgtcatcaaa atcactcgca tcaaccaaac     900
cgttattcat tcgtgattgc gcctgagcga acgaaatac gcgatcgctg ttaaaaggac     960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa aatcccttaa    1440
cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actctttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata gtcgtgtct taccgggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcagggggg cggagcctat ggaaaaacgc cagcaacgcg    2100
gcctttttac ggttcctggc cttttgctgg ccttttgctc acatgttctt tcctgcgtta    2160
tccctgatt ctgtggataa ccgtattacc gcctttgagt gagctgatac cgctcgccgc    2220
```

```
agccgaacga ccgagcgcag cgagtcagtg agcgaggaag cggaagagcg cctgatgcgg     2280
tattttctcc ttacgcatct gtgcggtatt tcacaccgca tatatggtgc actctcagta     2340
caatctgctc tgatgccgca tagttaagcc agtatacact ccgctatcgc tacgtgactg     2400
ggtcatggct gcgcccgac acccgccaac acccgctgac gcgccctgac gggcttgtct      2460
gctcccggca tccgcttaca gacaagctgt gaccgtctcc gggagctgca tgtgtcagag     2520
gttttcaccg tcatcaccga aacgcgcgag gcagctgcgg taaagctcat cagcgtggtc     2580
gtgaagcgat tcacagatgt ctgcctgttc atccgcgtcc agctcgttga gtttctccag     2640
aagcgttaat gtctggcttc tgataaagcg ggccatgtta agggcggttt tttcctgttt     2700
ggtcactgat gcctccgtgt aaggggggatt tctgttcatg ggggtaatga taccgatgaa    2760
acgagagagg atgctcacga tacgggttac tgatgatgaa catgcccggt tactggaacg     2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc     2940
tgcgatgcag atccggaaca taatggtgca gggcgctgac ttccgcgttt ccagacttta     3000
cgaaacacgg aaaccgaaga ccattcatgt tgttgctcag gtcgcagacg ttttgcagca     3060
gcagtcgctt cacgttcgct cgcgtatcgg tgattcattc tgctaaccag taaggcaacc     3120
ccgccagcct agccgggtcc tcaacgacag gagcacgatc atgcgcaccc gtggggccgc     3180
catgccggcg ataatggcct gcttctcgcc gaaacgtttg gtggcgggac cagtgacgaa     3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac     3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa     3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca     3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt     3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca     3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgca aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
```

```
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatggaaact gaaaccgaag ctcgtcgttc    5100
tgcgaactac gaacctaaca gctgggacta tgattacctg ctgtcctccg acacggacga    5160
gtccatcgaa gtatacaaag acaaagcgaa aaagctggaa gccgaagttc gtcgcgagat    5220
taataacgaa aaagcagaat ttctgaccct gctggaactg attgacaacg tccagcgcct    5280
gggcctgggt taccgtttcg agtctgatat ccgtggtgcg ctggatcgct tcgtttcctc    5340
cggcggcttc gatgcggtaa ccaagacttc cctgcacggt acggcactgt ctttccgtct    5400
gctgcgtcaa cacggttttg aggtttctca ggaagcgttc agcggcttca agaccaaaa    5460
cggcaacttc ctggagaacc tgaaggaaga tatcaaagct atcctgagcc tgtacgaggc    5520
cagcttcctg gctctggaag gcgaaaacat cctggacgag gcgaaggttt tcgcaatctc    5580
tcatctgaaa gaactgtctg aagaaagat cggtaaagag ctggcagaac aggtgaacca    5640
tgcactggaa ctgccactgc atcgccgtac tcagcgtctg gaagcagtat ggtctatcga    5700
ggcctaccgt aaaaggagg acgcgaatca ggttctgctg gagctggcaa ttctggatta    5760
caacatgatc cagtctgtat accagcgtga tctgcgtgaa acgtcccgtt ggtggcgtcg    5820
tgtgggtctg gcgaccaaac tgcactttgc tcgtgaccgc ctgattgaga gcttctactg    5880
ggccgtgggt gtagcattcg aaccgcaata ctccgactgc cgtaactccg tcgcaaaaat    5940
gttttctttc gtaaccatta tcgacgatat ctacgatgta tacggcaccc tggacgaact    6000
ggagctgttt actgatgcag ttgagcgttg ggacgtaaac gccatcaacg acctgccgga    6060
ttacatgaaa ctgtgctttt tggctctgta taacactatt aacgaaatcg cctacgacaa    6120
cctgaaagat aaaggtgaga acatcctgcc gtatctgacc aaagcctggg ctgacctgtg    6180
caacgctttc ctgcaagaag ccaagtggct gtacaacaaa tctactccga cctttgacga    6240
ctacttcggc aacgcatgga atcctcttc tggcccgctg caactggtgt tcgcttactt    6300
cgctgtcgtg cagaacatta aaaggaaga gatcgaaaac ctgcaaaaat accatgacac    6360
catctctcgt ccttcccata tcttccgtct gtgcaatgac ctggctagcg cgtctgcgga    6420
aattgcgcgt ggtgaaaccg caaatagcgt ttcttgttac atgcgcacta aggtatctc    6480
cgaagaactg gctaccgaaa gcgtgatgaa tctgatcgat gaaacctgga aaagatgaa    6540
caaggaaaaa ctgggtggta gcctgttcgc gaaaccgttc gtggaaaccg cgatcaacct    6600
ggcacgtcaa tctcactgca cttatcataa cggcgacgcg catacctctc cggatgagct    6660
gacccgcaaa cgcgttctgt ctgtaatcac tgaaccgatt ctgccgtttg aacgctaagg    6720
atccgaattc gagctccgtc gacaagcttg cggccgcact cgagcaccac caccaccacc    6780
actgagatcc ggctgctaac aaagcccgaa aggaagctga gttggctgct gccaccgctg    6840
agcaataact agcataaccc cttggggcct ctaaacgggt cttgaggggt tttttgctga    6900
aaggaggaac tatatccgga t    6921
```

<210> SEQ ID NO 144
<211> LENGTH: 549
<212> TYPE: PRT
<213> ORGANISM: Artificial Sequence
<220> FEATURE:
<223> OTHER INFORMATION: Synthetic Construct

<400> SEQUENCE: 144

```
Met Thr Glu Thr Glu Thr Glu Ala Arg Arg Ser Ala Asn Tyr Glu Pro
1               5                   10                  15

Asn Ser Trp Asp Tyr Asp Tyr Leu Leu Ser Ser Asp Thr Asp Glu Ser
            20                  25                  30

Ile Glu Val Tyr Lys Asp Lys Ala Lys Lys Leu Glu Ala Glu Val Arg
        35                  40                  45

Arg Glu Ile Asn Asn Glu Lys Ala Glu Phe Leu Thr Leu Leu Glu Leu
    50                  55                  60

Ile Asp Asn Val Gln Arg Leu Gly Leu Gly Tyr Arg Phe Glu Ser Asp
65                  70                  75                  80

Ile Arg Gly Ala Leu Asp Arg Phe Val Ser Ser Gly Gly Phe Asp Ala
                85                  90                  95

Val Thr Lys Thr Ser Leu His Gly Thr Ala Leu Ser Phe Arg Leu Leu
            100                 105                 110

Arg Gln His Gly Phe Glu Val Ser Gln Glu Ala Phe Ser Gly Phe Lys
        115                 120                 125

Asp Gln Asn Gly Asn Phe Leu Glu Asn Leu Lys Glu Asp Ile Lys Ala
    130                 135                 140

Ile Leu Ser Leu Tyr Glu Ala Ser Phe Leu Ala Leu Glu Gly Glu Asn
145                 150                 155                 160

Ile Leu Asp Glu Ala Lys Val Phe Ala Ile Ser His Leu Lys Glu Leu
                165                 170                 175

Ser Glu Glu Lys Ile Gly Lys Glu Leu Ala Glu Gln Val Asn His Ala
            180                 185                 190

Leu Glu Leu Pro Leu His Arg Arg Thr Gln Arg Leu Glu Ala Val Trp
        195                 200                 205

Ser Ile Glu Ala Tyr Arg Lys Lys Glu Asp Ala Asn Gln Val Leu Leu
    210                 215                 220

Glu Leu Ala Ile Leu Asp Tyr Asn Met Ile Gln Ser Val Tyr Gln Arg
225                 230                 235                 240

Asp Leu Arg Glu Thr Ser Arg Trp Trp Arg Arg Val Gly Leu Ala Thr
                245                 250                 255

Lys Leu His Phe Ala Arg Asp Arg Leu Ile Glu Ser Phe Tyr Trp Ala
            260                 265                 270

Val Gly Val Ala Phe Glu Pro Gln Tyr Ser Asp Cys Arg Asn Ser Val
        275                 280                 285

Ala Lys Met Phe Ser Phe Val Thr Ile Ile Asp Asp Ile Tyr Asp Val
    290                 295                 300

Tyr Gly Thr Leu Asp Glu Leu Glu Leu Phe Thr Asp Ala Val Glu Arg
305                 310                 315                 320

Trp Asp Val Asn Ala Ile Asn Asp Leu Pro Asp Tyr Met Lys Leu Cys
                325                 330                 335

Phe Leu Ala Leu Tyr Asn Thr Ile Asn Glu Ile Ala Tyr Asp Asn Leu
            340                 345                 350

Lys Asp Lys Gly Glu Asn Ile Leu Pro Tyr Leu Thr Lys Ala Trp Ala
        355                 360                 365
```

```
Asp Leu Cys Asn Ala Phe Leu Gln Glu Ala Lys Trp Leu Tyr Asn Lys
    370                 375                 380

Ser Thr Pro Thr Phe Asp Asp Tyr Phe Gly Asn Ala Trp Lys Ser Ser
385                 390                 395                 400

Ser Gly Pro Leu Gln Leu Val Phe Ala Tyr Phe Ala Val Val Gln Asn
                405                 410                 415

Ile Lys Lys Glu Glu Ile Glu Asn Leu Gln Lys Tyr His Asp Thr Ile
            420                 425                 430

Ser Arg Pro Ser His Ile Phe Arg Leu Cys Asn Asp Leu Ala Ser Ala
        435                 440                 445

Ser Ala Glu Ile Ala Arg Gly Glu Thr Ala Asn Ser Val Ser Cys Tyr
    450                 455                 460

Met Arg Thr Lys Gly Ile Ser Glu Glu Leu Ala Thr Glu Ser Val Met
465                 470                 475                 480

Asn Leu Ile Asp Glu Thr Trp Lys Lys Met Asn Lys Glu Lys Leu Gly
                485                 490                 495

Gly Ser Leu Phe Ala Lys Pro Phe Val Glu Thr Ala Ile Asn Leu Ala
                500                 505                 510

Arg Gln Ser His Cys Thr Tyr His Asn Gly Asp Ala His Thr Ser Pro
            515                 520                 525

Asp Glu Leu Thr Arg Lys Arg Val Leu Ser Val Ile Thr Glu Pro Ile
        530                 535                 540

Leu Pro Phe Glu Arg
545
```

<210> SEQ ID NO 145
<211> LENGTH: 6924
<212> TYPE: DNA
<213> ORGANISM: Artificial Sequence
<220> FEATURE:
<223> OTHER INFORMATION: Synthetic Construct

<400> SEQUENCE: 145

```
tggcgaatgg gacgcgccct gtagcggcgc attaagcgcg gcgggtgtgg tggttacgcg    60
cagcgtgacc gctacacttg ccagcgccct agcgcccgct cctttcgctt tcttcccttc   120
ctttctcgcc acgttcgccg gctttccccg tcaagctcta atcgggggc tccctttagg   180
gttccgattt agtgctttac ggcacctcga ccccaaaaaa cttgattagg gtgatggttc   240
acgtagtggg ccatcgccct gatagacggt ttttcgccct tgacgttgg agtccacgtt   300
ctttaatagt ggactcttgt tccaaactgg aacaacactc aaccctatct cggtctattc   360
ttttgattta agggatttt tgccgatttc ggcctattgg ttaaaaaatg agctgattta   420
acaaaaattt aacgcgaatt ttaacaaaat attaacgttt acaatttcag gtggcacttt   480
tcggggaaat gtgcgcggaa cccctatttg tttattttc taaatacatt caaatatgta   540
tccgctcatg aattaattct tagaaaaact catcgagcat caaatgaaac tgcaattat   600
tcatatcagg attatcaata ccatatttt gaaaaagccg tttctgtaat gaaggagaaa   660
actcaccgag gcagttccat aggatggcaa gatcctggta tcggtctgcg attccgactc   720
gtccaacatc aatacaacct attaatttcc cctcgtcaaa aataaggtta tcaagtgaga   780
aatcaccatg agtgacgact gaatccggtg agaatggcaa aagtttatgc atttctttcc   840
agacttgttc aacaggccag ccattacgct cgtcatcaaa atcactcgca tcaaccaaac   900
cgttattcat tcgtgattgc gcctgagcga gacgaaatac gcgatcgctg ttaaaaggac   960
```

```
aattacaaac aggaatcgaa tgcaaccggc gcaggaacac tgccagcgca tcaacaatat       1020
tttcacctga atcaggatat tcttctaata cctggaatgc tgttttcccg gggatcgcag       1080
tggtgagtaa ccatgcatca tcaggagtac ggataaaatg cttgatggtc ggaagaggca       1140
taaattccgt cagccagttt agtctgacca tctcatctgt aacatcattg caacgctac        1200 ctttgccatg tttcagaaac aactctggcg catcgggctt cccatacaat cgatagattg       1260
tcgcacctga ttgcccgaca ttatcgcgag cccatttata cccatataaa tcagcatcca       1320
tgttggaatt taatcgcggc ctagagcaag acgtttcccg ttgaatatgg ctcataacac       1380
cccttgtatt actgtttatg taagcagaca gttttattgt tcatgaccaa aatcccttaa       1440
cgtgagtttt cgttccactg agcgtcagac cccgtagaaa agatcaaagg atcttcttga      1500
gatccttttt ttctgcgcgt aatctgctgc ttgcaaacaa aaaaaccacc gctaccagcg       1560
gtggtttgtt tgccggatca agagctacca actcttttc cgaaggtaac tggcttcagc       1620
agagcgcaga taccaaatac tgtccttcta gtgtagccgt agttaggcca ccacttcaag       1680
aactctgtag caccgcctac atacctcgct ctgctaatcc tgttaccagt ggctgctgcc       1740
agtggcgata gtcgtgtct taccggggttg gactcaagac gatagttacc ggataaggcg      1800
cagcggtcgg gctgaacggg gggttcgtgc acacagccca gcttggagcg aacgacctac       1860
accgaactga gatacctaca gcgtgagcta tgagaaagcg ccacgcttcc cgaagggaga      1920
aaggcggaca ggtatccggt aagcggcagg gtcggaacag gagagcgcac gagggagctt      1980
ccagggggaa acgcctggta tctttatagt cctgtcgggt ttcgccacct ctgacttgag      2040
cgtcgatttt tgtgatgctc gtcagggggg cggagcctat ggaaaaacgc cagcaacgcg      2100 gccttttac ggttcctggc cttttgctgg ccttttgctc acatgttctt cctgcgtta        2160 tcccctgatt ctgtggataa ccgtattacc gcctttgagt gagctgatac cgctcgccgc      2220
agccgaacga ccgagcgcag cgagtcagtg agcgaggaag cggaagagcg cctgatgcgg      2280
tattttctcc ttacgcatct gtgcggtatt tcacaccgca tatatggtgc actctcagta      2340
caatctgctc tgatgccgca tagttaagcc agtatacact ccgctatcgc tacgtgactg      2400
ggtcatggct gcgccccgac acccgccaac acccgctgac gcgccctgac gggcttgtct      2460
gctcccggca tccgcttaca gacaagctgt gaccgtctcc gggagctgca tgtgtcagag      2520
gttttcaccg tcatcaccga aacgcgcgag gcagctgcgg taaagctcat cagcgtggtc      2580
gtgaagcgat tcacagatgt ctgcctgttc atccgcgtcc agctcgttga gtttctccag      2640
aagcgttaat gtctggcttc tgataaagcg ggccatgtta agggcggttt ttcctgtttt      2700
ggtcactgat gcctccgtgt aagggggatt tctgttcatg ggggtaatga taccgatgaa      2760
acgagagagg atgctcacga tacgggttac tgatgatgaa catgcccggt tactggaacg      2820
ttgtgagggt aaacaactgg cggtatggat gcggcgggac cagagaaaaa tcactcaggg      2880
tcaatgccag cgcttcgtta atacagatgt aggtgttcca cagggtagcc agcagcatcc      2940
tgcgatgcag atccggaaca taatggtgca gggcgctgac ttccgcgttt ccagacttta      3000
cgaaacacgg aaaccgaaga ccattcatgt tgttgctcag gtcgcagacg ttttgcagca      3060
gcagtcgctt cacgttcgct cgcgtatcgg tgattcattc tgctaaccag taaggcaacc      3120
ccgccagcct agccgggtcc tcaacgacag gagcacgatc atgcgcaccc gtgggccgc      3180 catgccggcg ataatggcct gcttctcgcc gaaacgtttg gtggcgggac cagtgacgaa      3240
ggcttgagcg agggcgtgca agattccgaa taccgcaagc gacaggccga tcatcgtcgc      3300
gctccagcga aagcggtcct cgccgaaaat gacccagagc gctgccggca cctgtcctac      3360
```

```
gagttgcatg ataaagaaga cagtcataag tgcggcgacg atagtcatgc cccgcgccca   3420
ccggaaggag ctgactgggt tgaaggctct caagggcatc ggtcgagatc cggtgcctc    3480 atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg cgcgcattg    3840 cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tgtaccgaa actgaaaccg aagctcgtcg    5100
ttctgcgaac tacgaaccta acagctggga ctatgattac ctgctgtcct ccgacacgga   5160
cgagtccatc gaagtataca agacaaagc gaaaagctg gaagccgaag ttcgtcgcga    5220
gattaataac gaaaaagcag aatttctgac cctgctggaa ctgattgaca acgtccagcg   5280
cctgggcctg ggttaccgtt tcgagtctga tatccgtggt gcgctggatc gcttcgtttc   5340
ctccggcggc ttcgatgcgg taaccaagac ttccctgcac ggtacggcac tgtcttttccg   5400 tctgctgcgt caaacacggtt ttgaggtttc tcaggaagcg ttcagcggct tcaaagacca   5460
aaacggcaac ttcctggaga acctgaagga agatatcaaa gctatcctga gcctgtacga   5520
ggccagcttc ctggctctgg aaggcgaaaa catcctggac gaggcgaagg ttttcgcaat   5580
ctctcatctg aaagaactgt ctgaagaaaa gatcggtaaa gagctggcag aacaggtgaa   5640
ccatgcactg gaactgccac tgcatcgccg tactcagcgt ctggaagcag tatggtctat   5700
```

```
cgaggcctac cgtaaaaagg aggacgcgaa tcaggttctg ctggagctgg caattctgga   5760
ttacaacatg atccagtctg tataccagcg tgatctgcgt gaaacgtccc gttggtggcg   5820
tcgtgtgggt ctggcgacca aactgcactt tgctcgtgac cgcctgattg agagcttcta   5880
ctgggccgtg ggtgtagcat tcgaaccgca atactccgac tgccgtaact ccgtcgcaaa   5940
aatgttttct ttcgtaacca ttatcgacga tatctacgat gtatacggca ccctggacga   6000
actggagctg tttactgatg cagttgagcg ttgggacgta aacgccatca acgacctgcc   6060
ggattacatg aaactgtgct ttctggctct gtataacact attaacgaaa tcgcctacga   6120
caacctgaaa gataaaggtg agaacatcct gccgtatctg accaaagcct gggctgacct   6180
gtgcaacgct ttcctgcaag aagccaagtg gctgtacaac aaatctactc cgacctttga   6240
cgactacttc ggcaacgcat ggaaatcctc ttctggcccg ctgcaactgg tgttcgctta   6300
cttcgctgtc gtgcagaaca ttaaaaagga agagatcgaa acctgcaaa ataccatga    6360
caccatctct cgtccttccc atatcttccg tctgtgcaat gacctggcta gcgcgtctgc   6420
ggaaattgcg cgtggtgaaa ccgcaaatag cgtttcttgt tacatgcgca ctaaaggtat   6480
ctccgaagaa ctggctaccg aaagcgtgat gaatctgatc gatgaaacct ggaaaaagat   6540
gaacaaggaa aaactgggtg gtagcctgtt cgcgaaaccg ttcgtggaaa ccgcgatcaa   6600
cctggcacgt caatctcact gcacttatca taacggcgac gcgcataccc tccggatga   6660
gctgaccccg aaacgcgttc tgtctgtaat cactgaaccg attctgccgt ttgaacgcta   6720
aggatccgaa ttcgagctcc gtcgacaagc ttgcggccgc actcgagcac caccaccacc   6780
accactgaga tccggctgct aacaaagccc gaaaggaagc tgagttggct gctgccaccg   6840
ctgagcaata actagcataa ccccttgggg cctctaaacg ggtcttgagg ggttttttgc   6900
tgaaaggagg aactatatcc ggat                                         6924
```

<210> SEQ ID NO 146
<211> LENGTH: 544
<212> TYPE: PRT
<213> ORGANISM: Artificial Sequence
<220> FEATURE:
<223> OTHER INFORMATION: Synthetic Construct

<400> SEQUENCE: 146

```
Met Glu Thr Arg Arg Ser Ala Asn Tyr Glu Pro Asn Ser Trp Asp Tyr
  1               5                  10                  15

Asp Tyr Leu Leu Ser Ser Asp Thr Asp Glu Ser Ile Glu Val His Lys
             20                  25                  30

Asp Lys Ala Lys Lys Leu Glu Ala Glu Val Arg Arg Glu Ile Asn Asn
         35                  40                  45

Glu Lys Ala Glu Phe Leu Thr Leu Leu Glu Leu Ile Asp Asn Val Gln
     50                  55                  60

Arg Leu Gly Leu Gly Tyr Arg Phe Glu Ser Asp Ile Arg Arg Ala Leu
 65                  70                  75                  80

Asp Arg Phe Val Ser Ser Gly Gly Phe Asp Gly Val Thr Lys Thr Ser
                 85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140
```

```
Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Ser His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
        275                 280                 285

Phe Val Thr Ile Ile Asp Asp Ile Tyr Asp Val Tyr Gly Thr Leu Asp
290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
        355                 360                 365

Phe Leu Gln Glu Ala Lys Trp Leu Tyr Asn Lys Ser Thr Pro Thr Phe
370                 375                 380

Asp Asp Tyr Phe Gly Asn Ala Trp Lys Ser Ser Gly Pro Leu Gln
385                 390                 395                 400

Leu Ile Phe Ala Tyr Phe Ala Val Val Gln Asn Ile Lys Lys Glu Glu
                405                 410                 415

Ile Glu Asn Leu Gln Lys Tyr His Asp Ile Ile Ser Arg Pro Ser His
            420                 425                 430

Ile Phe Arg Leu Cys Asn Asp Leu Ala Ser Ala Ser Ala Glu Ile Ala
        435                 440                 445

Arg Gly Glu Thr Ala Asn Ser Val Ser Cys Tyr Met Arg Thr Lys Gly
450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Gly Ser Leu Phe Ala
                485                 490                 495

Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
        515                 520                 525

Lys Arg Val Leu Ser Val Ile Thr Glu Pro Ile Leu Pro Phe Glu Arg
530                 535                 540

<210> SEQ ID NO 147
<211> LENGTH: 6909
<212> TYPE: DNA
```

<213> ORGANISM: Artificial Sequence
<220> FEATURE:
<223> OTHER INFORMATION: Synthetic Construct

<400> SEQUENCE: 147

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tcccctttagg     180
gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta taggggattt tgccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg aattaattct tagaaaaact catcgagcat caaatgaaac tgcaatttat     600
tcatatcagg attatcaata ccatattttt gaaaaagccg tttctgtaat gaaggagaaa     660
actcaccgag gcagttccat aggatggcaa gatcctggta tcggtctgcg attccgactc     720
gtccaacatc aatacaacct attaatttcc cctcgtcaaa ataaggttat caagtgaga     780
aatcaccatg agtgacgact gaatccggtg agaatggcaa aagtttatgc atttcttcc      840
agacttgttc aacaggccag ccattacgct cgtcatcaaa atcactcgca tcaaccaaac     900
cgttattcat tcgtgattgc gcctgagcga acgaaatac gcgatcgctg ttaaaaggac      960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa atcccttaa     1440
cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actcttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata gtcgtgtct taccggggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcaggggg cggagcctat ggaaaaacgc cagcaacgcg    2100
gcctttttac ggttcctggc cttttgctgg ccttttgctc acatgttctt tcctgcgtta    2160
tcccctgatt ctgtggataa ccgtattacc gcctttgagt gagctgatac cgctcgccgc    2220
```

```
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aaggggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccgaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
```

-continued

```
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa cttaagaag gagatataca tatggaaacg cgtcgttctg cgaactacga    5100
acctaacagc tgggactatg attacctgct gtcctccgac acggacgagt ccatcgaagt    5160
acacaaagac aaagcgaaaa agctggaagc cgaagttcgt cgcgagatta ataacgaaaa    5220
agcagaattt ctgaccctgc tggaactgat tgacaacgtc cagcgcctgg gcctgggtta    5280
ccgtttcgag tctgatatcc gtcgtgcgct ggatcgcttc gtttcctccg gcggcttcga    5340
tggcgtaacc aagacttccc tgcacggtac ggcactgtct ttccgtctgc tgcgtcaaca    5400
cggttttgag gtttctcagg aagcgttcag cggcttcaaa gaccaaaacg gcaacttcct    5460
ggagaacctg aaggaagata tcaaagctat cctgagcctg tacgaggcca gcttcctggc    5520
tctggaaggc gaaaacatcc tggacgaggc gaaggttttc gcaatctctc atctgaaaga    5580
actgtctgaa gaaaagatcg gtaaagagct ggcagaacag gtgtcccatg cactggaact    5640
gccactgcat cgccgtactc agcgtctgga agcagtatgg tctatcgagg cctaccgtaa    5700
aaaggaggac gcgaaccagg ttctgctgga gctggcaatt ctggattaca acatgatcca    5760
gtctgtatac cagcgtgatc tgcgtgaaac gtcccgttgg tggcgtcgtg tgggtctggc    5820
gaccaaactg cactttgctc gtgaccgcct gattgagagc ttctactggg ccgtgggtgt    5880
agcattcgaa ccgcaatact ccgactgccg taactccgtc gcaaaaatgt ttctttcgt    5940
aaccattatc gacgatatct acgatgtata cggcaccctg gacgaactgg agctgtttac    6000
tgatgcagtt gagcgttggg acgtaaacgc catcaacgac ctgccggatt acatgaaact    6060
gtgctttctg gctctgtata acactattaa cgaaatcgcc tacgacaacc tgaaagataa    6120
aggtgagaac atcctgccgt atctgaccaa agcctgggct gacctgtgca acgctttcct    6180
gcaagaagcc aagtggctgt acaacaaatc tactccgacc tttgacgact acttcggcaa    6240
cgcatggaaa tcctcttctg gcccgctgca actgatcttc gcttacttcg ctgtcgtgca    6300
gaacattaaa aaggaagaga tcgaaaacct gcaaaaatac catgacatca tctctcgtcc    6360
ttccatatc ttccgtctgt gcaatgacct ggctagcgcg tctgcggaaa ttgcgcgtgg    6420
tgaaaccgca aatagcgttt cttgttacat gcgcactaaa ggtatctccg aagaactggc    6480
taccgaaagc gtgatgaatc tgatcgatga aacctggaaa aagatgaaca aggaaaaact    6540
gggtggtagc ctgttcgcga aaccgttcgt ggaaaccgcg atcaacctgg cacgtcaatc    6600
tcactgcact tatcataacg gcgacgcgca tacctctccg gatgagctga cccgcaaacg    6660
cgttctgtct gtaatcactg aaccgattct gccgtttgaa cgctaaggat ccgaattcga    6720
gctccgtcga caagcttgcg gccgcactcg agcaccacca ccaccaccac tgagatccgg    6780
ctgctaacaa agcccgaaag gaagctgagt tggctgctgc caccgctgag caataactag    6840
cataacccct tggggcctct aaacgggtct tgaggggttt tttgctgaaa ggaggaacta    6900
tatccggat                                                            6909
```

-continued

```
<210> SEQ ID NO 148
<211> LENGTH: 544
<212> TYPE: PRT
<213> ORGANISM: Artificial Sequence
<220> FEATURE:
<223> OTHER INFORMATION: Synthetic Construct

<400> SEQUENCE: 148

Met Glu Thr Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Arg Ala Leu
65                  70                  75                  80

Asp Arg Phe Val Ser Ser Gly Gly Phe Asp Ala Val Thr Lys Thr Ser
                85                  90                  95

Leu His Ala Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Asp Leu Ala Glu Gln Val Asn His Ala Leu Glu Leu Pro Leu
            180                 185                 190

His Arg Arg Thr Gln Arg Leu Glu Ala Val Leu Ser Ile Glu Ala Tyr
        195                 200                 205

Arg Lys Lys Glu Asp Ala Asp Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
        275                 280                 285

Phe Val Thr Ile Ile Asp Asp Ile Tyr Asp Val Tyr Gly Thr Leu Asp
    290                 295                 300

Glu Leu Glu Leu Phe Thr Asn Ala Val Glu Arg Trp Asp Val Asn Ala
305                 310                 315                 320

Ile Asp Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Glu Lys Gly Glu
            340                 345                 350

Asn Ile Leu Pro Tyr Leu Thr Lys Ala Trp Ala Asp Leu Cys Asn Ala
        355                 360                 365
```

```
Phe Leu Gln Glu Ala Lys Trp Leu Tyr Asn Lys Ser Thr Pro Thr Phe
        370                 375                 380
Asp Glu Tyr Phe Gly Asn Ala Trp Lys Ser Ser Gly Pro Leu Gln
385                 390                 395                 400
Leu Val Phe Ala Tyr Phe Ala Val Val Gln Asn Ile Lys Lys Glu Glu
                405                 410                 415
Ile Glu Asn Leu Gln Lys Tyr His Asp Ile Ile Ser Arg Pro Ser His
                420                 425                 430
Ile Phe Arg Leu Cys Asn Asp Leu Ala Ser Ala Ser Ala Glu Ile Ala
                435                 440                 445
Arg Gly Glu Thr Ala Asn Ser Val Ser Cys Tyr Met Arg Thr Lys Gly
        450                 455                 460
Ile Ser Glu Glu Leu Ala Thr Glu Ser Val Met Asn Leu Ile Asp Glu
465                 470                 475                 480
Thr Trp Lys Lys Met Asn Lys Glu Lys Leu Gly Gly Ser Leu Phe Ala
                485                 490                 495
Lys Pro Phe Val Glu Thr Ala Ile Asn Leu Ala Arg Gln Ser His Cys
                500                 505                 510
Thr Tyr His Asn Gly Asp Ala His Thr Ser Pro Asp Glu Leu Thr Arg
                515                 520                 525
Lys Arg Val Leu Ser Val Ile Thr Glu Pro Ile Leu Pro Phe Glu Arg
        530                 535                 540

<210> SEQ ID NO 149
<211> LENGTH: 6909
<212> TYPE: DNA
<213> ORGANISM: Artificial Sequence
<220> FEATURE:
<223> OTHER INFORMATION: Synthetic Construct

<400> SEQUENCE: 149
```

| | | | | | |
|---|---|---|---|---|---|
| tggcgaatgg | gacgcgccct | gtagcggcgc | attaagcgcg | gcgggtgtgg | tggttacgcg | 60 |
| cagcgtgacc | gctacacttg | ccagcgccct | agcgcccgct | cctttcgctt | tcttcccttc | 120 |
| ctttctcgcc | acgttcgccg | gctttccccg | tcaagctcta | aatcgggggc | tccctttagg | 180 |
| gttccgattt | agtgctttac | ggcacctcga | ccccaaaaaa | cttgattagg | gtgatggttc | 240 |
| acgtagtggg | ccatcgccct | gatagacggt | ttttcgccct | ttgacgttgg | agtccacgtt | 300 |
| ctttaatagt | ggactcttgt | tccaaactgg | aacaacactc | aaccctatct | cggtctattc | 360 |
| ttttgattta | taagggattt | tgccgatttc | ggcctattgg | ttaaaaaatg | agctgattta | 420 |
| acaaaaattt | aacgcgaatt | ttaacaaaat | attaacgttt | acaatttcag | gtggcacttt | 480 |
| tcggggaaat | gtgcgcggaa | cccctatttg | tttatttttc | taaatacatt | caaatatgta | 540 |
| tccgctcatg | aattaattct | tagaaaaact | catcgagcat | caaatgaaac | tgcaatttat | 600 |
| tcatatcagg | attatcaata | ccatattttt | gaaaaagccg | tttctgtaat | gaaggagaaa | 660 |
| actcaccgag | gcagttccat | aggatggcaa | gatcctggta | tcggtctgcg | attccgactc | 720 |
| gtccaacatc | aatacaacct | attaatttcc | cctcgtcaaa | aataaggtta | tcaagtgaga | 780 |
| aatcaccatg | agtgacgact | gaatccggtg | agaatggcaa | aagtttatgc | atttctttcc | 840 |
| agacttgttc | aacaggccag | ccattacgct | cgtcatcaaa | atcactcgca | tcaaccaaac | 900 |
| cgttattcat | tcgtgattgc | gcctgagcga | gacgaaatac | gcgatcgctg | ttaaaaggac | 960 |
| aattacaaac | aggaatcgaa | tgcaaccggc | gcaggaacac | tgccagcgca | tcaacaatat | 1020 |
| tttcacctga | atcaggatat | tcttctaata | cctggaatgc | tgttttcccg | gggatcgcag | 1080 |

```
tggtgagtaa ccatgcatca tcaggagtac ggataaaatg cttgatggtc ggaagaggca  1140
taaattccgt cagccagttt agtctgacca tctcatctgt aacatcattg gcaacgctac  1200
ctttgccatg tttcagaaac aactctggcg catcgggctt cccatacaat cgatagattg  1260
tcgcacctga ttgcccgaca ttatcgcgag cccatttata cccatataaa tcagcatcca  1320
tgttggaatt taatcgcggc ctagagcaag acgtttcccg ttgaatatgg ctcataacac  1380
cccttgtatt actgtttatg taagcagaca gtttattgt tcatgaccaa aatcccttaa   1440
cgtgagtttt cgttccactg agcgtcagac cccgtagaaa agatcaaagg atcttcttga  1500
gatccttttt ttctgcgcgt aatctgctgc ttgcaaacaa aaaaaccacc gctaccagcg  1560
gtggtttgtt tgccggatca agagctacca actcttttc cgaaggtaac tggcttcagc   1620
agagcgcaga taccaaatac tgtccttcta gtgtagccgt agttaggcca ccacttcaag  1680
aactctgtag caccgcctac atacctcgct ctgctaatcc tgttaccagt ggctgctgcc  1740
agtggcgata agtcgtgtct taccggggttg actcaagac gatagttacc ggataaggcg   1800
cagcggtcgg gctgaacggg gggttcgtgc acacagccca gcttggagcg aacgacctac  1860
accgaactga gatacctaca gcgtgagcta tgagaaagcg ccacgcttcc cgaagggaga  1920
aaggcggaca ggtatccggt aagcggcagg gtcggaacag gagagcgcac gagggagctt  1980
ccaggggggaa acgcctggta tctttatagt cctgtcgggt ttcgccacct ctgacttgag  2040
cgtcgatttt tgtgatgctc gtcaggggg cggagcctat ggaaaaacgc cagcaacgcg   2100
gccttttac ggttcctggc cttttgctgg ccttttgctc acatgttctt tcctgcgtta    2160
tcccctgatt ctgtggataa ccgtattacc gcctttgagt gagctgatac cgctcgccgc  2220
agccgaacga ccgagcgcag cgagtcagtg agcgaggaag cggaagagcg cctgatgcgg  2280
tattttctcc ttacgcatct gtgcggtatt tcacaccgca tatatggtgc actctcagta  2340
caatctgctc tgatgccgca tagttaagcc agtatacact ccgctatcgc tacgtgactg  2400
ggtcatggct gcgccccgac acccgccaac acccgctgac gcgccctgac gggcttgtct  2460
gctcccggca tccgcttaca gacaagctgt gaccgtctcc gggagctgca tgtgtcagag  2520
gttttcaccg tcatcaccga aacgcgcgag gcagctgcgg taaagctcat cagcgtggtc  2580
gtgaagcgat tcacagatgt ctgcctgttc atccgcgtcc agctcgttga gtttctccag  2640
aagcgttaat gtctggcttc tgataaagcg ggccatgtta agggcggttt ttcctgtttt  2700
ggtcactgat gcctccgtgt aagggggatt tctgttcatg ggggtaatga taccgatgaa  2760
acgagagagg atgctcacga tacgggttac tgatgatgaa catgcccggt tactggaacg  2820
ttgtgagggt aaacaactgg cggtatggat gcggcgggac cagagaaaaa tcactcaggg  2880
tcaatgccag cgcttcgtta atacagatgt aggtgttcca cagggtagcc agcagcatcc  2940
tgcgatgcag atccggaaca taatggtgca gggcgctgac ttccgcgttt ccagacttta  3000
cgaaacacga aaaccgaaga ccattcatgt tgttgctcag gtcgcagacg ttttgcagca  3060
gcagtcgctt cacgttcgct cgcgtatcgg tgattcattc tgctaaccag taaggcaacc  3120
ccgccagcct agccgggtcc tcaacgacag gagcacgatc atgcgcaccc gtggggccgc  3180
catgccggcg ataatggcct gcttctcgcc gaaacgtttg gtggcgggac cagtgacgaa  3240
ggcttgagcg agggcgtgca agattccgaa taccgcaagc gacaggccga tcatcgtcgc  3300
gctccagcga aagcggtcct cgccgaaaat gacccagagc gctgccggca cctgtcctac  3360
gagttgcatg ataaagaaga cagtcataag tgcggcgacg atagtcatgc cccgcgccca  3420
```

```
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacgcggga tataacatga gctgtcttcg gtatcgtcgt    3780
atcccactac cgagatatcc gcaccaacgc gcagcccgga ctcggtaatg cgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccgaaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
tttgtttaa ctttaagaag gagatataca tatggaaacg cgtcgttctg cgaactacga    5100
acctaacagc tgggactatg attacctgct gtcctccgac acggacgagt ccatcgaagt    5160
atacaaagac aaagcgaaaa agctggaagc cgaagttcgt cgcgagatta ataacgaaaa    5220
agcagaattt ctgaccctgc tggaactgat tgacaacgtc cagcgcctgg gcctgggtta    5280
ccgtttcgag tctgatatcc gtcgtgcgct ggatcgcttc gtttcctccg gcggcttcga    5340
tgcggtaacc aagacttccc tgcacgcgac ggcactgtct ttccgtctgc tgcgtcaaca    5400
cggttttgag gtttctcagg aagcgttcag cggcttcaaa gaccaaaacg gcaacttcct    5460
ggagaacctg aaggaagata tcaaagctat cctgagcctg tacgaggcca gcttcctggc    5520
tctggaaggc gaaaacatcc tggacgaggc gaaggttttc gcaatctctc atctgaaaga    5580
actgtctgaa gaaaagatcg gtaaagatct ggcagaacag gtgaaccatg cactggaact    5640
gccactgcat cgccgtactc agcgtctgga agcagtactg tctatcgagg cctaccgtaa    5700
aaaggaggac gcggatcagg ttctgctgga gctggcaatt ctggattaca acatgatcca    5760
gtctgtatac cagcgtgatc tgcgtgaaac gtcccgttgg tggcgtcgtg tgggtctggc    5820
```

-continued

```
gaccaaactg cactttgctc gtgaccgcct gattgagagc ttctactggg ccgtgggtgt      5880
agcattcgaa ccgcaatact ccgactgccg taactccgtc gcaaaaatgt tttctttcgt      5940
aaccattatc gacgatatct acgatgtata cggcaccctg gacgaactgg agctgtttac      6000
taacgcagtt gagcgttggg acgtaaacgc catcgacgat ctgccggatt acatgaaact      6060
gtgctttctg gctctgtata acactattaa cgaaatcgcc tacgacaacc tgaaagaaaa      6120
aggtgagaac atcctgccgt atctgaccaa agcctgggct gacctgtgca acgctttcct      6180
gcaagaagcc aagtggctgt acaacaaatc tactccgacc tttgacgaat acttcggcaa      6240
cgcatggaaa tcctcttctg gcccgctgca actggtgttc gcttacttcg ctgtcgtgca      6300
gaacattaaa aaggaagaga tcgaaaacct gcaaaaatac catgacatca tctctcgtcc      6360
ttcccatatc ttccgtctgt gcaatgacct ggctagcgcg tctgcggaaa ttgcgcgtgg      6420
tgaaaccgca aatagcgttt cttgttacat gcgcactaaa ggtatctccg aagaactggc      6480
taccgaaagc gtgatgaatc tgatcgatga aacctggaaa aagatgaaca aggaaaaact      6540
gggtggtagc ctgttcgcga aaccgttcgt ggaaaccgcg atcaacctgg cacgtcaatc      6600
tcactgcact tatcataacg cgacgcgca tacctctccg gatgagctga cccgcaaacg      6660
cgttctgtct gtaatcactg aaccgattct gccgtttgaa cgctaaggat ccgaattcga      6720
gctccgtcga caagcttgcg gccgcactcg agcaccacca ccaccaccac tgagatccgg      6780
ctgctaacaa agcccgaaag gaagctgagt tggctgctgc caccgctgag caataactag      6840
cataacccct tggggcctct aaacgggtct tgaggggttt tttgctgaaa ggaggaacta      6900
tatccggat                                                              6909
```

<210> SEQ ID NO 150
<211> LENGTH: 551
<212> TYPE: PRT
<213> ORGANISM: Artificial Sequence
<220> FEATURE:
<223> OTHER INFORMATION: Synthetic Construct

<400> SEQUENCE: 150

```
Met Glu Ala Arg Arg Ser Ala Asn Tyr Gln Pro Asn Leu Trp Asn Phe
  1               5                  10                  15

Glu Phe Leu Gln Ser Leu Glu Asn Asp Leu Lys Val Glu Lys Leu Glu
             20                  25                  30

Glu Lys Ala Thr Lys Leu Glu Glu Glu Val Arg Cys Met Ile Asn Arg
         35                  40                  45

Val Asp Thr Gln Pro Leu Ser Leu Leu Glu Leu Ile Asp Asp Val Gln
     50                  55                  60

Arg Leu Gly Leu Thr Tyr Lys Phe Glu Lys Asp Ile Ile Lys Ala Leu
 65                  70                  75                  80

Glu Asn Ile Val Leu Leu Asp Glu Asn Lys Lys Asn Lys Ser Asp Leu
                 85                  90                  95

His Ala Thr Ala Leu Ser Phe Arg Leu Leu Arg Gln His Gly Phe Glu
            100                 105                 110

Val Ser Gln Asp Val Phe Glu Arg Phe Lys Asp Lys Glu Gly Gly Phe
        115                 120                 125

Ser Gly Glu Leu Lys Gly Asp Val Gln Gly Leu Leu Ser Leu Tyr Glu
    130                 135                 140

Ala Ser Tyr Leu Gly Phe Glu Gly Glu Asn Leu Leu Glu Glu Ala Arg
145                 150                 155                 160
```

-continued

Thr Phe Ser Ile Thr His Leu Lys Asn Asn Leu Lys Glu Gly Ile Asn
            165                 170                 175

Thr Lys Val Ala Glu Gln Val Ser His Ala Leu Glu Leu Pro Tyr His
        180                 185                 190

Gln Arg Leu His Arg Leu Glu Ala Arg Trp Phe Leu Asp Lys Tyr Glu
    195                 200                 205

Pro Lys Glu Pro His His Gln Leu Leu Glu Leu Ala Lys Leu Asp
210                 215                 220

Phe Asn Met Val Gln Thr Leu His Gln Lys Glu Leu Gln Asp Leu Ser
225                 230                 235                 240

Arg Trp Trp Thr Glu Met Gly Leu Ala Ser Lys Leu Asp Phe Val Arg
                245                 250                 255

Asp Arg Leu Met Glu Val Tyr Phe Trp Ala Leu Gly Met Ala Pro Asp
            260                 265                 270

Pro Gln Phe Gly Glu Cys Arg Lys Ala Val Thr Lys Met Phe Gly Leu
        275                 280                 285

Val Thr Ile Ile Asp Asp Val Tyr Asp Val Tyr Gly Thr Leu Asp Glu
    290                 295                 300

Leu Gln Leu Phe Thr Asp Ala Val Glu Arg Trp Asp Val Asn Ala Ile
305                 310                 315                 320

Asn Thr Leu Pro Asp Tyr Met Lys Leu Cys Phe Leu Ala Leu Tyr Asn
                325                 330                 335

Thr Val Asn Asp Thr Ser Tyr Ser Ile Leu Lys Glu Lys Gly His Asn
            340                 345                 350

Asn Leu Ser Tyr Leu Thr Lys Ser Trp Arg Glu Leu Cys Lys Ala Phe
        355                 360                 365

Leu Gln Glu Ala Lys Trp Ser Asn Asn Lys Ile Ile Pro Ala Phe Ser
    370                 375                 380

Lys Tyr Leu Glu Asn Ala Ser Val Ser Ser Gly Val Ala Leu Leu
385                 390                 395                 400

Ala Pro Ser Tyr Phe Ser Val Cys Gln Gln Gln Glu Asp Ile Ser Asp
                405                 410                 415

His Ala Leu Arg Ser Leu Thr Asp Phe His Gly Leu Val Arg Ser Ser
            420                 425                 430

Cys Val Ile Phe Arg Leu Cys Asn Asp Leu Ala Thr Ser Ala Ala Glu
        435                 440                 445

Leu Glu Arg Gly Glu Thr Thr Asn Ser Ile Ile Ser Tyr Met His Glu
    450                 455                 460

Asn Asp Gly Thr Ser Glu Glu Gln Ala Arg Glu Glu Leu Arg Lys Leu
465                 470                 475                 480

Ile Asp Ala Glu Trp Lys Lys Met Asn Arg Glu Arg Val Ser Asp Ser
                485                 490                 495

Thr Leu Leu Pro Lys Ala Phe Met Glu Ile Ala Val Asn Met Ala Arg
            500                 505                 510

Val Ser His Cys Thr Tyr Gln Tyr Gly Asp Gly Leu Gly Arg Pro Asp
        515                 520                 525

Tyr Ala Thr Glu Asn Arg Ile Lys Leu Leu Leu Ile Asp Pro Phe Pro
    530                 535                 540

Ile Asn Gln Leu Met Tyr Val
545                 550

<210> SEQ ID NO 151
<211> LENGTH: 6935
<212> TYPE: DNA

<213> ORGANISM: Artificial Sequence
<220> FEATURE:
<223> OTHER INFORMATION: Synthetic Construct

<400> SEQUENCE: 151

```
tcgagcacca ccaccaccac cactgagatc cggctgctaa caaagcccga aaggaagctg      60
agttggctgc tgccaccgct gagcaataac tagcataacc ccttgggggcc tctaaacggg    120
tcttgagggg ttttttgctg aaaggaggaa ctatatccgg attggcgaat gggacgcgcc    180
ctgtagcggc gcattaagcg cggcgggtgt ggtggttacg cgcagcgtga ccgctacact    240
tgccagcgcc ctagcgcccg ctcctttcgc tttcttccct cctttctcg ccacgttcgc     300
cggctttccc cgtcaagctc taaatcgggg ctcccttta gggttccgat ttagtgcttt     360
acggcacctc gaccccaaaa aacttgatta gggtgatggt tcacgtagtg gccatcgcc     420
ctgatagacg gtttttcgcc ctttgacgtt ggagtccacg ttctttaata gtggactctt    480
gttccaaact ggaacaacac tcaaccctat ctcggtctat tcttttgatt tataagggat    540
tttgccgatt tcggcctatt ggttaaaaaa tgagctgatt taacaaaaat ttaacgcgaa    600
ttttaacaaa atattaacgt ttacaatttc aggtggcact tttcggggaa atgtgcgcgg    660
aacccctatt tgtttatttt tctaaataca ttcaaatatg tatccgctca tgaattaatt    720
cttagaaaaa ctcatcgagc atcaaatgaa actgcaattt attcatatca ggattatcaa    780
taccatattt ttgaaaaagc cgtttctgta atgaaggaga aaactcaccg aggcagttcc    840
ataggatggc aagatcctgg tatcggtctg cgattccgac tcgtccaaca tcaatacaac    900
ctattaattt cccctcgtca aaataaggt tatcaagtga aaatcacca tgagtgacga      960
ctgaatccgg tgagaatggc aaaagtttat gcatttcttt ccagacttgt tcaacaggcc   1020
agccattacg ctcgtcatca aaatcactcg catcaaccaa accgttattc attcgtgatt   1080
gcgcctgagc gagacgaaat acgcgatcgc tgttaaaagg acaattacaa acaggaatcg   1140
aatgcaaccg gcgcaggaac actgccagcg catcaacaat attttcacct gaatcaggat   1200
attcttctaa tacctggaat gctgttttcc cggggatcgc agtggtgagt aaccatgcat   1260
catcaggagt acggataaaa tgcttgatgg tcggaagagg cataaattcc gtcagccagt   1320
ttagtctgac catctcatct gtaacatcat tggcaacgct accttttgcca tgtttcagaa   1380
acaactctgg cgcatcgggc ttcccataca atcgatagat tgtcgcacct gattgcccga   1440
cattatcgcg agcccattta tacccatata atcagcatc catgttggaa tttaatcgcg    1500
gcctagagca agacgtttcc cgttgaatat ggctcataac accccttgta ttactgttta   1560
tgtaagcaga cagtttttatt gttcatgacc aaaatccctt aacgtgagtt ttcgttccac   1620
tgagcgtcag accccgtaga aaagatcaaa ggatcttctt gagatccttt ttttctgcgc   1680
gtaatctgct gcttgcaaac aaaaaaacca ccgctaccag cggtggtttg tttgccggat   1740
caagagctac caactctttt tccgaaggta actggcttca gcagagcgca gataccaaat   1800
actgtccttc tagtgtagcc gtagttaggc caccacttca agaactctgt agcaccgcct   1860
acatacctcg ctctgctaat cctgttacca gtggctgctg ccagtggcga taagtcgtgt   1920
cttaccgggt tggactcaag acgatagtta ccggataagg cgcagcggtc gggctgaacg   1980
gggggttcgt gcacacagcc cagcttggag cgaacgacct acaccgaact gagatacta    2040
cagcgtgagc tatgagaaag cgccacgctt cccgaaggga aaaggcgga caggtatccg    2100
gtaagcggca gggtcggaac aggagagcgc acgagggagc ttccagggg aaacgcctgg    2160
tatctttata gtcctgtcgg gtttcgccac ctctgacttg agcgtcgatt tttgtgatgc   2220
```

```
tcgtcagggg ggcggagcct atggaaaaac gccagcaacg cggccttttt acggttcctg   2280
gccttttgct ggccttttgc tcacatgttc tttcctgcgt tatcccctga ttctgtggat   2340
aaccgtatta ccgcctttga gtgagctgat accgctcgcc gcagccgaac gaccgagcgc   2400
agcgagtcag tgagcgagga agcggaagag cgcctgatgc ggtattttct ccttacgcat   2460
ctgtgcggta tttcacaccg catatatggt gcactctcag tacaatctgc tctgatgccg   2520
catagttaag ccagtataca ctccgctatc gctacgtgac tgggtcatgg ctgcgccccg   2580
acacccgcca cacccgctg acgcgccctg acgggcttgt ctgctcccgg catccgctta   2640
cagacaagct gtgaccgtct ccgggagctg catgtgtcag aggttttcac cgtcatcacc   2700
gaaacgcgcg aggcagctgc ggtaaagctc atcagcgtgg tcgtgaagcg attcacagat   2760
gtctgcctgt tcatccgcgt ccagctcgtt gagtttctcc agaagcgtta atgtctggct   2820
tctgataaag cgggccatgt taagggcggt ttttcctgt ttggtcactg atgcctccgt   2880
gtaaggggga tttctgttca tgggggtaat gataccgatg aaacgagaga ggatgctcac   2940
gatacgggtt actgatgatg aacatgcccg gttactggaa cgttgtgagg gtaaacaact   3000
ggcggtatgg atgcggcggg accagagaaa aatcactcag ggtcaatgcc agcgcttcgt   3060
taatacagat gtaggtgttc cacagggtag ccagcagcat cctgcgatgc agatccggaa   3120
cataatggtg cagggcgctg acttccgcgt ttccagactt tacgaaacac ggaaaccgaa   3180
gaccattcat gttgttgctc aggtcgcaga cgttttgcag cagcagtcgc ttcacgttcg   3240
ctcgcgtatc ggtgattcat tctgctaacc agtaaggcaa ccccgccagc ctagccgggt   3300
cctcaacgac aggagcacga tcatgcgcac ccgtggggcc gccatgccgg cgataatggc   3360
ctgcttctcg ccgaaacgtt tggtggcggg accagtgacg aaggcttgag cgagggcgtg   3420
caagattccg aataccgcaa gcgacaggcc gatcatcgtc gcgctccagc gaaagcggtc   3480
ctcgccgaaa atgacccaga gcgctgccgg cacctgtcct acgagttgca tgataaagaa   3540
gacagtcata agtgcggcga cgatagtcat gccccgcgcc caccggaagg agctgactgg   3600
gttgaaggct ctcaagggca tcggtcgaga tcccggtgcc taatgagtga gctaacttac   3660
attaattgcg ttgcgctcac tgcccgcttt ccagtcggga aacctgtcgt gccagctgca   3720
ttaatgaatc ggccaacgcg cggggagagg cggtttgcgt attgggcgcc agggtggttt   3780
ttcttttcac cagtgagacg ggcaacagct gattgccctt caccgcctgg ccctgagaga   3840
gttgcagcaa gcggtccacg ctggtttgcc ccagcaggcg aaaatcctgt ttgatggtgg   3900 ttaacgcgg gatataacat gagctgtctt cggtatcgtc gtatcccact accgagatat   3960
ccgcaccaac gcgcagcccg gactcggtaa tggcgcgcat tgcgcccagc gccatctgat   4020
cgttggcaac cagcatcgca gtgggaacga tgccctcatt cagcatttgc atggtttgtt   4080
gaaaaccgga catggcactc cagtcgcctt cccgttccgc tatcggctga atttgattgc   4140
gagtgagata tttatgccag ccagccagac gcagacgcgc cgagacagaa cttaatgggc   4200
ccgctaacag cgcgatttgc tggtgaccca atgcgaccag atgctccacg cccagtcgcg   4260
taccgtcttc atgggagaaa ataatactgt tgatgggtgt ctggtcagag acatcaagaa   4320
ataacgccgg aacattagtg caggcagctt ccacagcaat ggcatcctgg tcatccagcg   4380
gatagttaat gatcagccca ctgacgcgtt gcgcgagaag attgtgcacc gccgctttac   4440
aggcttcgac gccgcttcgt tctaccatcg acaccaccac gctggcaccc agttgatcgg   4500
cgcgagattt aatcgccgcg acaatttgcg acggcgcgtg cagggccaga ctggaggtgg   4560
```

```
caacgccaat cagcaacgac tgtttgcccg ccagttgttg tgccacgcgg ttgggaatgt    4620
aattcagctc cgccatcgcc gcttccactt tttcccgcgt tttcgcagaa acgtggctgg    4680
cctggttcac cacgcgggaa acggtctgat aagagacacc ggcatactct gcgacatcgt    4740
ataacgttac tggtttcaca ttcaccaccc tgaattgact ctcttccggg cgctatcatg    4800
ccataccgcg aaaggttttg cgccattcga tggtgtccgg gatctcgacg ctctccctta    4860
tgcgactcct gcattaggaa gcagcccagt agtaggttga ggcgttgag caccgccgcc      4920 gcaaggaatg gtgcatgcaa ggagatggcg cccaacagtc ccccggccac ggggcctgcc    4980 accatacccca cgccgaaaca agcgctcatg agcccgaagt ggcgagcccg atcttcccca   5040
tcggtgatgt cggcgatata ggcgccagca accgcacctg tggcgccggt gatgccggcc    5100
acgatgcgtc cggcgtagag gatcgagatc tcgatcccgc gaaattaata cgactcacta    5160 tagggggaatt gtgagcggat aacaattccc ctctagaaat aattttgttt aactttaaga   5220
aggagatata ccatggaagc tcgtcgttcc gcaaactatc agccaaacct gtggaatttc    5280
gaattcctgc aatccctgga gaacgacctg aaagtggaaa agctggagga gaaagcgacc    5340
aaactggagg aagaagttcg ctgcatgatc aaccgtgtag acacccagcc gctgtccctg    5400
ctggagctga tcgacgatgt gcagcgcctg ggtctgacct acaaatttga aaagacatc     5460 attaaagccc tggaaaacat cgtactgctg gacgaaaaca aaagaacaa atctgacctg     5520 cacgcaaccg ctctgtcttt ccgtctgctg cgtcagcacg tttcgaggt ttctcaggat      5580 gttttgagc gtttcaagga taaagaaggt ggtttcagcg gtgaactgaa aggtgacgtc      5640
caaggcctgc tgagcctgta tgaagcgtct tacctgggtt tcgagggtga aacctgctg      5700 gaggaggcgc gtacctttc catcacccac ctgaagaaca acctgaaaga aggcattaat      5760
accaaggttg cagaacaagt gagccacgcc ctggaactgc catatcacca gcgtctgcac    5820
cgtctggagg cacgttggtt cctggataaa tacgaaccga agaaccgca tcaccagctg      5880 ctgctggagc tggcgaagct ggattttaac atggtacaga ccctgcacca gaaagagctg    5940
caagatctgt cccgctggtg gaccgagatg ggcctggcta gcaaactgga ttttgtacgc    6000
gaccgcctga tggaagttta tttctgggca ctgggtatgg cgccagaccc gcagtttggt    6060
gaatgtcgca aagctgttac taaaatgttt ggtctggtga cgatcatcga tgacgtgtat    6120
gacgtttatg gcactctgga cgaactgcaa ctgttcaccg atgctgtaga gcgctgggac    6180
gttaacgcta ttaacaccct gccggactat atgaaactgt gtttcctggc actgtacaac    6240
accgttaacg acacgtccta ttctattctg aaagagaaag gtcataacaa cctgtcctat    6300
ctgacgaaaa gctggcgtga actgtgcaaa gcctttctgc aagaggcgaa atggtccaac    6360
aacaaaatta tcccggcttt ctccaagtac ctggaaaacg ccagcgtttc ctcctccggt    6420
gtagcgctgc tggcgccgtc ttacttttcc gtatgccagc agcaggaaga catctccgac    6480
cacgcgctgc gttccctgac cgacttccat ggtctggtgc gttctagctg cgttatcttc    6540
cgcctgtgca acgatctggc cacctctgcg gcggagctgg aacgtggcga gactaccaat    6600
tctatcatta gctacatgca cgaaaacgat ggtaccagcg aggaacaggc ccgcgaagaa    6660
ctgcgtaaac tgatcgacgc cgaatggaaa aagatgaatc gtgaacgcgt tagcgactcc    6720
accctgctgc ctaaagcgtt catggaaatc gcagttaaca tggcacgtgt ttcccactgc    6780
acctaccagt atggcgatgg tctgggtcgc ccagactacg cgactgaaaa ccgcatcaaa    6840
ctgctgctga ttgaccctttt cccgattaac cagctgatgt atgtctaact gcagggatcc    6900
gaattcgagc tccgtcgaca agcttgcggc cgcac                               6935
```

<210> SEQ ID NO 152
<211> LENGTH: 553
<212> TYPE: PRT
<213> ORGANISM: Artificial Sequence
<220> FEATURE:
<223> OTHER INFORMATION: Synthetic Construct

<400> SEQUENCE: 152

```
Met Glu His Asn Ser Arg Arg Ser Ala Asn Tyr Gln Pro Asn Leu Trp
 1               5                  10                  15

Asn Phe Glu Phe Leu Gln Ser Leu Glu Asn Asp Leu Lys Val Glu Lys
             20                  25                  30

Leu Glu Glu Lys Ala Thr Lys Leu Glu Glu Val Arg Cys Met Ile
         35                  40                  45

Asn Arg Val Asp Thr Gln Pro Leu Ser Leu Leu Glu Leu Ile Asp Asp
 50                  55                  60

Val Gln Arg Leu Gly Leu Thr Tyr Lys Phe Glu Lys Asp Ile Ile Lys
 65                  70                  75                  80

Ala Leu Glu Asn Ile Val Leu Asp Glu Asn Lys Lys Asn Lys Ser
                 85                  90                  95

Asp Leu His Ala Thr Ala Leu Ser Phe Arg Leu Leu Arg Gln His Gly
             100                 105                 110

Phe Glu Val Ser Gln Asp Val Phe Glu Arg Phe Lys Asp Lys Glu Gly
         115                 120                 125

Gly Phe Ser Gly Glu Leu Lys Gly Asp Val Gln Gly Leu Leu Ser Leu
     130                 135                 140

Tyr Glu Ala Ser Tyr Leu Gly Phe Glu Gly Glu Asn Leu Leu Glu Glu
145                 150                 155                 160

Ala Arg Thr Phe Ser Ile Thr His Leu Lys Asn Asn Leu Lys Glu Gly
                 165                 170                 175

Ile Asn Thr Lys Val Ala Glu Gln Val Ser His Ala Leu Glu Leu Pro
             180                 185                 190

Tyr His Gln Arg Leu His Arg Leu Glu Ala Arg Trp Phe Leu Asp Lys
         195                 200                 205

Tyr Glu Pro Lys Glu Pro His His Gln Leu Leu Glu Leu Ala Lys
     210                 215                 220

Leu Asp Phe Asn Met Val Gln Thr Leu His Gln Lys Glu Leu Gln Asp
225                 230                 235                 240

Leu Ser Arg Trp Trp Thr Glu Met Gly Leu Ala Ser Lys Leu Asp Phe
                 245                 250                 255

Val Arg Asp Arg Leu Met Glu Val Tyr Phe Trp Ala Leu Gly Met Ala
             260                 265                 270

Pro Asp Pro Gln Phe Gly Glu Cys Arg Lys Ala Val Thr Lys Met Phe
         275                 280                 285

Gly Leu Val Thr Ile Ile Asp Asp Val Tyr Asp Val Tyr Gly Thr Leu
     290                 295                 300

Asp Glu Leu Gln Leu Phe Thr Asp Ala Val Glu Arg Trp Asp Val Asn
305                 310                 315                 320

Ala Ile Asn Thr Leu Pro Asp Tyr Met Lys Leu Cys Phe Leu Ala Leu
                 325                 330                 335

Tyr Asn Thr Val Asn Asp Thr Ser Tyr Ser Ile Leu Lys Glu Lys Gly
             340                 345                 350

His Asn Asn Leu Ser Tyr Leu Thr Lys Ser Trp Arg Glu Leu Cys Lys
         355                 360                 365
```

```
Ala Phe Leu Gln Glu Ala Lys Trp Ser Asn Asn Lys Ile Ile Pro Ala
        370                 375                 380

Phe Ser Lys Tyr Leu Glu Asn Ala Ser Val Ser Ser Ser Gly Val Ala
385                 390                 395                 400

Leu Leu Ala Pro Ser Tyr Phe Ser Val Cys Gln Gln Gln Glu Asp Ile
                405                 410                 415

Ser Asp His Ala Leu Arg Ser Leu Thr Asp Phe His Gly Leu Val Arg
            420                 425                 430

Ser Ser Cys Val Ile Phe Arg Leu Cys Asn Asp Leu Ala Thr Ser Ala
        435                 440                 445

Ala Glu Leu Glu Arg Gly Glu Thr Thr Asn Ser Ile Ile Ser Tyr Met
450                 455                 460

His Glu Asn Asp Gly Thr Ser Glu Glu Gln Ala Arg Glu Glu Leu Arg
465                 470                 475                 480

Lys Leu Ile Asp Ala Glu Trp Lys Lys Met Asn Arg Glu Arg Val Ser
                485                 490                 495

Asp Ser Thr Leu Leu Pro Lys Ala Phe Met Glu Ile Ala Val Asn Met
                500                 505                 510

Ala Arg Val Ser His Cys Thr Tyr Gln Tyr Gly Asp Gly Leu Gly Arg
            515                 520                 525

Pro Asp Tyr Ala Thr Glu Asn Arg Ile Lys Leu Leu Leu Ile Asp Pro
        530                 535                 540

Phe Pro Ile Asn Gln Leu Met Tyr Val
545                 550

<210> SEQ ID NO 153
<211> LENGTH: 6941
<212> TYPE: DNA
<213> ORGANISM: Artificial Sequence
<220> FEATURE:
<223> OTHER INFORMATION: Synthetic Construct

<400> SEQUENCE: 153
tcgagcacca ccaccaccac cactgagatc cggctgctaa caaagcccga aggaagctg      60
agttggctgc tgccaccgct gagcaataac tagcataacc ccttgggcc tctaaacggg     120
tcttgagggg ttttttgctg aaaggaggaa ctatatccgg attggcgaat gggacgcgcc     180
ctgtagcggc gcattaagcg cggcgggtgt ggtggttacg cgcagcgtga ccgctacact     240
tgccagcgcc ctagcgcccg ctcctttcgc tttcttccct cctttctcg ccacgttcgc     300
cggctttccc cgtcaagctc taaatcgggg ctcccttta gggttccgat ttagtgcttt     360
acggcacctc gaccccaaaa aacttgatta gggtgatggt tcacgtagtg gccatcgcc     420
ctgatagacg ttttcgcc ctttgacgtt ggagtccacg ttctttaata gtggactctt     480
gttccaaact ggaacaacac tcaaccctat ctcggtctat tctttgatt tataagggat     540
tttgccgatt tcggcctatt ggttaaaaaa tgagctgatt taacaaaaat ttaacgcgaa     600
ttttaacaaa atattaacgt ttacaatttc aggtggcact tttcggggaa atgtgcgcgg     660
aacccctatt tgtttatttt tctaaataca ttcaaatatg tatccgctca tgaattaatt     720
cttagaaaaa ctcatcgagc atcaaatgaa actgcaattt attcatatca ggattatcaa     780
taccatattt ttgaaaaagc cgtttctgta atgaaggaga aaactcaccg aggcagttcc     840
ataggatggc aagatcctgg tatcggtctg cgattccgac tcgtccaaca tcaatacaac     900
ctattaattt ccctcgtca aaataaggt tatcaagtga gaaatcacca tgagtgacga     960
```

```
ctgaatccgg tgagaatggc aaaagtttat gcatttcttt ccagacttgt tcaacaggcc    1020
agccattacg ctcgtcatca aaatcactcg catcaaccaa accgttattc attcgtgatt    1080
gcgcctgagc gagacgaaat acgcgatcgc tgttaaaagg acaattacaa acaggaatcg    1140
aatgcaaccg cgcaggaac actgccagcg catcaacaat attttcacct gaatcaggat    1200
attcttctaa tacctggaat gctgttttcc cggggatcgc agtggtgagt aaccatgcat    1260
catcaggagt acgataaaa tgcttgatgg tcggaagagg cataaattcc gtcagccagt    1320
ttagtctgac catctcatct gtaacatcat tggcaacgct acctttgcca tgtttcagaa    1380
acaactctgg cgcatcgggc ttcccataca atcgatagat tgtcgcacct gattgcccga    1440
cattatcgcg agcccattta tacccatata atcagcatc catgttggaa tttaatcgcg    1500
gcctagagca agacgtttcc cgttgaatat ggctcataac accccttgta ttactgttta    1560
tgtaagcaga cagttttatt gttcatgacc aaaatccctt aacgtgagtt ttcgttccac    1620
tgagcgtcag accccgtaga aaagatcaaa ggatcttctt gagatccttt ttttctgcgc    1680
gtaatctgct gcttgcaaac aaaaaaacca ccgctaccag cggtggtttg tttgccggat    1740
caagagctac caactctttt tccgaaggta actggcttca gcagagcgca gataccaaat    1800
actgtccttc tagtgtagcc gtagttaggc caccacttca agaactctgt agcaccgcct    1860
acatacctcg ctctgctaat cctgttacca gtggctgctg ccagtggcga taagtcgtgt    1920
cttaccgggt tggactcaag acgatagtta ccggataagg cgcagcggtc gggctgaacg    1980
gggggttcgt gcacacagcc cagcttggag cgaacgacct acaccgaact gagatacccta    2040 cagcgtgagc tatgagaaag cgccacgctt cccgaaggga gaaaggcgga caggtatccg    2100
gtaagcggca gggtcggaac aggagagcgc acgagggagc ttccagggga aaacgcctgg    2160
tatctttata gtcctgtcgg gtttcgccac ctctgacttg agcgtcgatt tttgtgatgc    2220
tcgtcagggg ggcggagcct atggaaaaac gccagcaacg cggccttttt acggttcctg    2280
gccttttgct ggccttttgc tcacatgttc tttcctgcgt tatcccctga ttctgtggat    2340
aaccgtatta ccgcctttga gtgagctgat accgctcgcc gcagccgaac gaccgagcgc    2400
agcgagtcag tgagcgagga agcggaagag cgcctgatgc ggtattttct ccttacgcat    2460
ctgtgcggta tttcacaccg catatatggt gcactctcag tacaatctgc tctgatgccg    2520
catagttaag ccagtataca ctccgctatc gctacgtgac tgggtcatgg ctgcgccccg    2580
acacccgcca cacccgctg acgcgccctg acgggcttgt ctgctcccgg catccgctta    2640
cagacaagct gtgaccgtct ccgggagctg catgtgtcag aggttttcac cgtcatcacc    2700
gaaacgcgcg aggcagctgc ggtaaagctc atcagcgtgg tcgtgaagcg attcacagat    2760
gtctgcctgt tcatccgcgt ccagctcgtt gagtttctcc agaagcgtta atgtctggct    2820
tctgataaag cgggccatgt taagggcggt ttttcctgt ttggtcactg atgcctccgt    2880
gtaaggggga tttctgttca tgggggtaat gataccgatg aaacgagaga ggatgctcac    2940
gatacgggtt actgatgatg aacatgcccg gttactggaa cgttgtgagg gtaaacaact    3000
ggcggtatgg atgcggcggg accagagaaa aatcactcag ggtcaatgcc agcgcttcgt    3060
taatacagat gtaggtgttc cacagggtag ccagcagcat cctgcgatgc agatccggaa    3120
cataatggtg cagggcgctg acttccgcgt ttccagactt tacgaaacac ggaaaccgaa    3180
gaccattcat gttgttgctc aggtcgcaga cgttttgcag cagcagtcgc ttcacgttcg    3240
ctcgcgtatc ggtgattcat tctgctaacc agtaaggcaa ccccgccagc ctagccgggt    3300
cctcaacgac aggagcacga tcatgcgcac ccgtggggcc gccatgccgg cgataatggc    3360
```

```
ctgcttctcg ccgaaacgtt tggtggcggg accagtgacg aaggcttgag cgagggcgtg    3420
caagattccg aataccgcaa gcgacaggcc gatcatcgtc gcgctccagc gaaagcggtc    3480
ctcgccgaaa atgacccaga gcgctgccgg cacctgtcct acgagttgca tgataaagaa    3540
gacagtcata agtgcggcga cgatagtcat gccccgcgcc caccggaagg agctgactgg    3600
gttgaaggct ctcaagggca tcggtcgaga tcccggtgcc taatgagtga gctaacttac    3660
attaattgcg ttgcgctcac tgcccgcttt ccagtcggga aacctgtcgt gccagctgca    3720
ttaatgaatc ggccaacgcg cggggagagg cggtttgcgt attgggcgcc agggtggttt    3780
ttcttttcac cagtgagacg ggcaacagct gattgccctt caccgcctgg ccctgagaga    3840
gttgcagcaa gcggtccacg ctggtttgcc ccagcaggcg aaaatcctgt ttgatggtgg    3900
ttaacggcgg gatataacat gagctgtctt cggtatcgtc gtatcccact accgagatat    3960
ccgcaccaac gcgcagcccg gactcggtaa tggcgcgcat tgcgcccagc gccatctgat    4020
cgttggcaac cagcatcgca gtgggaacga tgccctcatt cagcatttgc atggtttgtt    4080
gaaaaccgga catggcactc cagtcgcctt cccgttccgc tatcggctga atttgattgc    4140
gagtgagata tttatgccag ccagccagac gcagacgcgc cgagacagaa cttaatgggc    4200
ccgctaacag cgcgatttgc tggtgaccca atgcgaccag atgctccacg cccagtcgcg    4260
taccgtcttc atgggagaaa ataatactgt tgatgggtgt ctggtcagag acatcaagaa    4320
ataacgccgg aacattagtg caggcagctt ccacagcaat ggcatcctgg tcatccagcg    4380
gatagttaat gatcagccca ctgacgcgtt gcgcgagaag attgtgcacc gccgctttac    4440
aggcttcgac gccgcttcgt tctaccatcg acaccaccac gctggcaccc agttgatcgg    4500
cgcgagattt aatcgccgcg acaatttgcg acggcgcgtg cagggccaga ctggaggtgg    4560
caacgccaat cagcaacgac tgtttgcccg ccagttgttg tgccacgcgg ttgggaatgt    4620
aattcagctc cgccatcgcc gcttccactt tttcccgcgt tttcgcagaa acgtggctgg    4680
cctggttcac cacgcgggaa acggtctgat aagagacacc ggcatactct gcgacatcgt    4740
ataacgttac tggtttcaca ttcaccaccc tgaattgact ctcttccggg cgctatcatg    4800
ccataccgcg aaaggttttg cgccattcga tggtgtccgg gatctcgacg ctctccctta    4860
tgcgactcct gcattaggaa gcagcccagt agtaggttga ggccgttgag caccgccgcc    4920
gcaaggaatg gtgcatgcaa ggagatggcg cccaacagtc ccccggccac ggggcctgcc    4980 accatacccca cgccgaaaca agcgctcatg agcccgaagt ggcgagcccg atcttcccca    5040
tcggtgatgt cggcgatata ggcgccagca accgcacctg tggcgccggt gatgccggcc    5100
acgatgcgtc cggcgtagag gatcgagatc tcgatcccgc gaaattaata cgactcacta    5160 tagggggaatt gtgagcggat aacaattccc ctctagaaat aattttgttt aactttaaga    5220
aggagatata ccatggagca taattcccgt cgttccgcaa actatcagcc aaacctgtgg    5280
aatttcgaat tcctgcaatc cctggagaac gacctgaaag tggaaaagct ggaggagaaa    5340
gcgaccaaac tggaggaaga agttcgctgc atgatcaacc gtgtagacac ccagccgctg    5400
tccctgctgg agctgatcga cgatgtgcag cgcctgggtc tgacctacaa atttgaaaaa    5460
gacatcatta aagcccctgga aaacatcgta ctgctggacg aaaacaaaaa gaacaaatct    5520
gacctgcacg caaccgctct gtctttccgt ctgctgcgtc agcacggttt cgaggtttct    5580
caggatgttt ttgagcgttt caaggataaa gaaggtggtt tcagcggtga actgaaaggt    5640
gacgtccaag gcctgctgag cctgtatgaa gcgtcttacc tgggtttcga gggtgagaac    5700
```

-continued

| | |
|---|---|
| ctgctggagg aggcgcgtac cttttccatc acccacctga agaacaacct gaaagaaggc | 5760 |
| attaatacca aggttgcaga acaagtgagc cacgccctgg aactgccata tcaccagcgt | 5820 |
| ctgcaccgtc tggaggcacg ttggttcctg gataaatacg aaccgaaaga accgcatcac | 5880 |
| cagctgctgc tggagctggc gaagctggat tttaacatgg tacagaccct gcaccagaaa | 5940 |
| gagctgcaag atctgtcccg ctggtggacc gagatgggcc tggctagcaa actggatttt | 6000 |
| gtacgcgacc gcctgatgga agtttatttc tgggcactgg gtatggcgcc agacccgcag | 6060 |
| tttggtgaat gtcgcaaagc tgttactaaa atgtttggtc tggtgacgat catcgatgac | 6120 |
| gtgtatgacg tttatggcac tctggacgaa ctgcaactgt tcaccgatgc tgtagagcgc | 6180 |
| tgggacgtta acgctattaa caccctgccg gactatatga actgtgtttt cctggcactg | 6240 |
| tacaacaccg ttaacgacac gtcctattct attctgaaag agaaaggtca taacaacctg | 6300 |
| tcctatctga cgaaaagctg gcgtgaactg tgcaaagcct tctgcaagag ggcgaaatgg | 6360 |
| tccaacaaca aaattatccc ggctttctcc aagtacctgg aaaacgccag cgtttcctcc | 6420 |
| tccggtgtag cgctgctggc gccgtcttac ttttccgtat gccagcagca ggaagacatc | 6480 |
| tccgaccacg cgctgcgttc cctgaccgac ttccatggtc tggtgcgttc tagctgcgtt | 6540 |
| atcttccgcc tgtgcaacga tctggccacc tctgcggcgg agctggaacg tggcgagact | 6600 |
| accaattcta tcattagcta catgcacgaa aacgatggta ccagcgagga acaggcccgc | 6660 |
| gaagaactgc gtaaactgat cgacgccgaa tggaaaaaga tgaatcgtga acgcgttagc | 6720 |
| gactccaccc tgctgcctaa agcgttcatg gaaatcgcag ttaacatggc acgtgtttcc | 6780 |
| cactgcacct accagtatgg cgatggtctg ggtcgcccag actacgcgac tgaaaaccgc | 6840 |
| atcaaactgc tgctgattga cccttcccg attaaccagc tgatgtatgt ctaactgcag | 6900 |
| ggatccgaat tcgagctccg tcgacaagct tgcggccgca c | 6941 |

<210> SEQ ID NO 154
<211> LENGTH: 4352
<212> TYPE: DNA
<213> ORGANISM: Artificial Sequence
<220> FEATURE:
<223> OTHER INFORMATION: Synthetic Construct

<400> SEQUENCE: 154

| | |
|---|---|
| tagaaaaact catcgagcat caaatgaaac tgcaatttat tcatatcagg attatcaata | 60 |
| ccatatttt gaaaaagccg tttctgtaat gaaggagaaa actcaccgag gcagttccat | 120 |
| aggatggcaa gatcctggta tcggtctgcg attccgactc gtccaacatc aatacaacct | 180 |
| attaatttcc cctcgtcaaa aataaggtta tcaagtgaga atcaccatg agtgacgact | 240 |
| gaatccggtg agaatggcaa aagtttatgc atttctttcc agacttgttc aacaggccag | 300 |
| ccattacgct cgtcatcaaa atcactcgca tcaaccaaac cgttattcat tcgtgattgc | 360 |
| gcctgagcga ggcgaaatac gcgatcgctg ttaaaaggac aattacaaac aggaatcgag | 420 |
| tgcaaccggc gcaggaacac tgccagcgca tcaacaatat tttcacctga atcaggatat | 480 |
| tcttctaata cctggaacgc tgttttttccg gggatcgcag tggtgagtaa ccatgcatca | 540 |
| tcaggagtac ggataaaatg cttgatggtc ggaagtggca taaattccgt cagccagttt | 600 |
| agtctgacca tctcatctgt aacatcattg gcaacgctac ctttgccatg tttcagaaac | 660 |
| aactctggcg catcgggctt cccatacaag cgatagattg tcgcacctga ttgcccgaca | 720 |
| ttatcgcgag cccatttata cccatataaa tcagcatcca tgttggaatt taatcgcggc | 780 |
| ctcgacgttt cccgttgaat atggctcata ttcttccttt ttcaatatta ttgaagcatt | 840 |

-continued

```
tatcagggtt attgtctcat gagcggatac atatttgaat gtatttagaa aaataaacaa      900
ataggggtca gtgttacaac caattaacca attctgaaca ttatcgcgag cccatttata      960
cctgaatatg gctcataaca ccccttgttt gcctggcggc agtagcgcgg tggtcccacc     1020
tgaccccatg ccgaactcag aagtgaaacg ccgtagcgcc gatggtagtg tggggactcc     1080
ccatgcgaga gtagggaact gccaggcatc aaataaaacg aaaggctcag tcgaaagact     1140
gggcctttcg cccgggctaa ttaggggtg tcgcccttc gattgacgct gcagttagac       1200
atacatcagc tggttaatcg ggaaagggtc aatcagcagc agtttgatgc ggttttcagt     1260
cgcgtagtct gggcgaccca gaccatcgcc atactggtag gtgcagtggg aaacacgtgc     1320
catgttaact gcgatttcca tgaacgcttt aggcagcagg gtggagtcgc taacgcgttc     1380
acgattcatc ttttccatt cggcgtcgat cagtttacgc agttcttcgc gggcctgttc      1440
ctcgctggta ccatcgtttt cgtgcatgta gctaatgata gaattggtag tctcgccacg     1500
ttccagctcc gccgcagagg tggccagatc gttgcacagg cggaagataa cgcagctaga     1560
acgcaccaga ccatggaagt cggtcaggga acgcagcgcg tggtcggaga tgtcttcctg     1620
ctgctggcat acggaaaagt aagacggcgc cagcagcgct acaccggagg aggaaacgct     1680
ggcgttttcc aggtacttgg agaaagccgg gataattttg ttgttggacc atttcgcctc     1740
ttgcagaaag gctttgcaca gttcacgcca gcttttcgtc agataggaca ggttgttatg     1800
accttctct ttcagaatag aataggacgt gtcgttaacg gtgttgtaca gtgccaggaa      1860
acacagtttc atatagtccg gcagggtgtt aatagcgtta acgtcccagc gctctacagc     1920
atcggtgaac agttgcagtt cgtccagagt gccataaacg tcatacacgt catcgatgat     1980
cgtcaccaga ccaaacattt tagtaacagc tttgcgacat tcaccaaact gcgggtctgg     2040
cgccataccc agtgcccaga aataaacttc catcaggcgg tcgcgtacaa aatccagttt     2100
gctagccagg cccatctcgg tccaccagcg ggacagatct tgcagctctt tctggtgcag     2160
ggtctgtacc atgttaaaat ccagcttcgc cagctccagc agcagctggt gatgcggttc     2220
tttcggttcg tatttatcca ggaaccaacg tgcctccaga cggtcagac gctggtgata    2280
tggcagttcc agggcgtggc tcacttgttc tgcaaccttg gtattaatgc cttctttcag     2340
gttgttcttc aggtgggtga tggaaaaggt acgcgcctcc tccagcaggt tctcaccctc     2400
gaaacccagg taagacgctt catacaggct cagcaggcct tggacgtcac ctttcagttc     2460
accgctgaaa ccaccttctt tatccttgaa acgctcaaaa acatcctgag aaacctcgaa     2520
accgtgctga cgcagcagac ggaaagacag agccggttgcg tgcaggtcag atttgttctt   2580
tttgttttcg tccagcagta cgatgttttc cagggctttta atgatgtctt tttcaaattt   2640
gtaggtcaga cccaggcgct gcacatcgtc gatcagctcc agcagggaca gcggctgggt     2700
gtctacacgg ttgatcatgc agcgaacttc ttcctccagt ttggtcgctt ctcctccag     2760
cttttccact ttcaggtcgt tctccaggga ttgcaggaat tcgaaattcc acaggtttgg     2820
ctgatagttt gcggaacgac gggaattatg ctcggtaatc tgagtaaatt gagaagaggt     2880
cgcacacatg ttcagcgaca agggcgacac aaaatttatt ctaaatgcat aataaatact     2940
gataacatct tatagtttgt attatatttt gtattatcgt tgcatgtat aattttgata     3000
tcaaaaactg attttcccctt tattattttc gagatttatt ttcttaattc tctttaacaa    3060
actagaaata ttgtatatac aaaaaatcat aaataataga tgaatagttt aattataggt     3120
gttcatcaat cgaaaaagca acgtatctta tttaaagtgc gttgcttttt tctcatttat     3180
```

| | |
|---|---|
| aaggttaaat aattctcata tatcaagcaa agtgacaggc gcccttaaat attctgacaa | 3240 |
| atgctctttc cctaaactcc ccccataaaa aaacccgccg aagcgggttt ttacgttatt | 3300 |
| tgcggattaa cgattactcg ttatcagaac cgcccagggg gcccgagctt aagactggcc | 3360 |
| gtcgttttac aacacagaaa gagtttgtag aaacgcaaaa aggccatccg tcaggggcct | 3420 |
| tctgcttagt ttgatgcctg gcagttccct actctcgcct tccgcttcct cgctcactga | 3480 |
| ctcgctgcgc tcggtcgttc ggctgcggcg agcggtatca gctcactcaa aggcggtaat | 3540 |
| acggttatcc acagaatcag gggataacgc aggaaagaac atgtgagcaa aaggccagca | 3600 |
| aaaggccagg aaccgtaaaa aggccgcgtt gctggcgttt ttccataggc tccgcccccc | 3660 |
| tgacgagcat cacaaaaatc gacgctcaag tcagaggtgg cgaaacccga caggactata | 3720 |
| aagataccag gcgtttcccc ctggaagctc cctcgtgcgc tctcctgttc cgaccctgcc | 3780 |
| gcttaccgga tacctgtccg cctttctccc ttcgggaagc gtggcgcttt ctcatagctc | 3840 |
| acgctgtagg tatctcagtt cggtgtaggt cgttcgctcc aagctgggct gtgtgcacga | 3900 |
| accccccgtt cagcccgacc gctgcgcctt atccggtaac tatcgtcttg agtccaaccc | 3960 |
| ggtaagacac gacttatcgc cactggcagc agccactggt aacaggatta gcagagcgag | 4020 |
| gtatgtaggc ggtgctacag agttcttgaa gtggtgggct aactacggct acactagaag | 4080 |
| aacagtattt ggtatctgcg ctctgctgaa gccagttacc ttcggaaaaa gagttggtag | 4140 |
| ctcttgatcc ggcaaacaaa ccaccgctgg tagcggtggt ttttttgttt gcaagcagca | 4200 |
| gattacgcgc agaaaaaaag gatctcaaga agatcctttg atcttttcta cggggtctga | 4260 |
| cgctcagtgg aacgacgcgc gcgtaactca cgttaaggga ttttggtcat gagcttgcgc | 4320 |
| cgtcccgtca agtcagcgta atgctctgct tt | 4352 |

<210> SEQ ID NO 155
<211> LENGTH: 6080
<212> TYPE: DNA
<213> ORGANISM: Artificial Sequence
<220> FEATURE:
<223> OTHER INFORMATION: Synthetic Construct

<400> SEQUENCE: 155

| | |
|---|---|
| gtttgacagc ttatcatcga ctgcacggtg caccaatgct tctggcgtca ggcagccatc | 60 |
| ggaagctgtg gtatggctgt gcaggtcgta aatcactgca taattcgtgt cgctcaaggc | 120 |
| gcactcccgt tctggataat gttttttgcg ccgacatcat aacggttctg gcaaatattc | 180 |
| tgaaatgagc tgttgacaat taatcatccg gctcgtataa tgtgtggaat tgtgagcgga | 240 |
| taacaatttc acacaggaaa cagcgccgct gagaaaaagc gaagcggcac tgctctttaa | 300 |
| caatttatca gacaatctgt gtgggcactc gaccggaatt atcgattaac tttattatta | 360 |
| aaaattaaag aggtatatat taatgtatcg attaaataag gaggaataaa ccatgtgtgc | 420 |
| gacctcttct caatttactc agattaccga gcataattcc cgtcgttccg caaactatca | 480 |
| gccaaacctg tggaatttcg aattcctgca atccctggag aacgacctga agtggaaaa | 540 |
| gctggaggag aaagcgacca aactggagga agaagttcgc tgcatgatca accgtgtaga | 600 |
| cacccagccg ctgtccctgc tggagctgat cgacgatgtg cagcgcctgg gtctgaccta | 660 |
| caaatttgaa aaagacatca ttaaagccct ggaaaacatc gtactgctgg acgaaaacaa | 720 |
| aaagaacaaa tctgacctgc acgcaaccgc tctgtctttc cgtctgctgc gtcagcacgg | 780 |
| tttcgaggtt tctcaggatg ttttttgagcg tttcaaggat aaagaaggtg gtttcagcgg | 840 |
| tgaactgaaa ggtgacgtcc aaggcctgct gagcctgtat gaagcgtctt acctgggttt | 900 |

```
cgagggtgag aacctgctgg aggaggcgcg tacctttttcc atcacccacc tgaagaacaa    960
cctgaaagaa ggcattaata ccaaggttgc agaacaagtg agccacgccc tggaactgcc   1020
atatcaccag cgtctgcacc gtctggaggc acgttggttc ctggataaat acgaaccgaa   1080
agaaccgcat caccagctgc tgctggagct ggcgaagctg gattttaaca tggtacagac   1140
cctgcaccag aaagagctgc aagatctgtc ccgctggtgg accgagatgg gcctggctag   1200
caaactggat tttgtacgcg accgcctgat ggaagtttat ttctgggcac tgggtatggc   1260
gccagacccg cagtttggtg aatgtcgcaa agctgttact aaaatgtttg gtctggtgac   1320
gatcatcgat gacgtgtatg acgtttatgg cactctggac gaactgcaac tgttcaccga   1380
tgctgtagag cgctgggacg ttaacgctat taacaccctg ccggactata tgaaactgtg   1440
tttcctggca ctgtacaaca ccgttaacga cacgtcctat tctattctga agagaaaagg   1500
tcataacaac ctgtcctatc tgacgaaaag ctggcgtgaa ctgtgcaaag cctttctgca   1560
agaggcgaaa tggtccaaca acaaaattat cccggctttc tccaagtacc tggaaaacgc   1620
cagcgttttcc tcctccggtg tagcgctgct ggcgccgtct tacttttccg tatgccagca   1680
gcaggaagac atctccgacc acgcgctgcg ttccctgacc gacttccatg gtctggtgcg   1740
ttctagctgc gttatcttcc gcctgtgcaa cgatctggcc acctctgcgg cggagctgga   1800
acgtggcgag actaccaatt ctatcattag ctacatgcac gaaaacgatg gtaccagcga   1860
ggaacaggcc cgcgaagaac tgcgtaaact gatcgacgcc gaatggaaaa agatgaatcg   1920
tgaacgcgtt agcgactcca ccctgctgcc taaagcgttc atggaaatcg cagttaacat   1980
ggcacgtgtt tcccactgca cctaccagta tggcgatggt ctgggtcgcc agactacgc   2040
gactgaaaac cgcatcaaac tgctgctgat tgacccttc ccgattaacc agctgatgta   2100
tgtctaactg cagctggtac catatgggaa ttcgaagctt tctagaacaa aaactcatct   2160
cagaagagga tctgaatagc gccgtcgacc atcatcatca tcatcattga gtttaaacgg   2220
tctccagctt ggctgttttg gcggatgaga gaagattttc agcctgatac agattaaatc   2280
agaacgcaga agcggtctga taaaacagaa tttgcctggc ggcagtagcg cggtggtccc   2340
acctgacccc atgccgaact cagaagtgaa acgccgtagc gccgatggta gtgtggggtc   2400
tccccatgcg agagtaggga actgccaggc atcaaataaa acgaaaggct cagtcgaaag   2460
actgggcctt tcgttttatc tgttgtttgt cggtgaacgc tctcctgagt aggacaaatc   2520
cgccgggagc ggatttgaac gttgcgaagc aacggcccgg agggtggcgg caggacgcc   2580
cgccataaac tgccaggcat caaattaagc agaaggccat cctgacggat ggcctttttg   2640
cgtttctaca aactcttttt gtttattttt ctaaatacat tcaaatatgt atccgctcat   2700
gagacaataa ccctgataaa tgcttcaata atattgaaaa aggaagagta tgagtattca   2760
acatttccgt gtcgccctta ttccctttt tgcggcattt tgccttcctg ttttgctca   2820
cccagaaacg ctggtgaaag taaaagatgc tgaagatcag ttgggtgcac gagtgggtta   2880
catcgaactg gatctcaaca gcggtaagat ccttgagagt tttcgccccg aagaacgttt   2940
tccaatgatg agcacttta aagttctgct atgtggcgcg gtattatccc gtgttgacgc   3000
cgggcaagag caactcggtc gccgcataca ctattctcag aatgacttgg ttgagtactc   3060
accagtcaca gaaaagcatc ttacggatgg catgacagta agagaattat gcagtgctgc   3120
cataaccatg agtgataaca ctgcggccaa cttacttctg acaacgatcg gaggaccgaa   3180
ggagctaacc gcttttttgc acaacatggg ggatcatgta actcgccttg atcgttggga   3240
```

```
accggagctg aatgaagcca taccaaacga cgagcgtgac accacgatgc ctgtagcaat    3300
ggcaacaacg ttgcgcaaac tattaactgg cgaactactt actctagctt cccggcaaca    3360
attaatagac tggatggagg cggataaagt tgcaggacca cttctgcgct cggcccttcc    3420
ggctggctgg tttattgctg ataaatctgg agccggtgag cgtgggtctc gcggtatcat    3480
tgcagcactg gggccagatg gtaagccctc ccgtatcgta gttatctaca cgacggggag    3540
tcaggcaact atggatgaac gaaatagaca gatcgctgag ataggtgcct cactgattaa    3600
gcattggtaa ctgtcagacc aagtttactc atatatactt tagattgatt taaaacttca    3660
tttttaattt aaaaggatct aggtgaagat cctttttgat aatctcatga ccaaaatccc    3720
ttaacgtgag ttttcgttcc actgagcgtc agaccccgta gaaaagatca aggatcttc    3780
ttgagatcct ttttttctgc gcgtaatctg ctgcttgcaa acaaaaaaac caccgctacc    3840
agcggtggtt tgtttgccgg atcaagagct accaactctt tttccgaagg taactggctt    3900
cagcagagcg cagataccaa atactgtcct tctagtgtag ccgtagttag gccaccactt    3960
caagaactct gtagcaccgc ctacatacct cgctctgcta atcctgttac cagtggctgc    4020
tgccagtggc gataagtcgt gtcttaccgg gttggactca agacgatagt taccggataa    4080
ggcgcagcgg tcgggctgaa cggggggttc gtgcacacag cccagcttgg agcgaacgac    4140
ctacaccgaa ctgagatacc tacagcgtga gctatgagaa agcgccacgc ttcccgaagg    4200
gagaaaggcg gacaggtatc cggtaagcgg cagggtcgga acaggagagc gcacgaggga    4260
gcttccaggg ggaaacgcct ggtatcttta tagtcctgtc gggtttcgcc acctctgact    4320
tgagcgtcga ttttttgtgat gctcgtcagg ggggcggagc ctatggaaaa acgccagcaa    4380
cgcggccttt ttacggttcc tggccttttg ctggcctttt gctcacatgt tctttcctgc    4440
gttatcccct gattctgtgg ataaccgtat taccgccttt gagtgagctg ataccgctcg    4500
ccgcagccga acgaccgagc gcagcgagtc agtgagcgag gaagcggaag agcgcctgat    4560
gcggtatttt ctccttacgc atctgtgcgg tatttcacac cgcatatggt gcactctcag    4620
tacaatctgc tctgatgccg catagttaag ccagtataca ctccgctatc gctacgtgac    4680
tgggtcatgg ctgcgccccg acacccgcca cacccgctg acgcgccctg acgggcttgt    4740
ctgctcccgg catccgctta cagacaagct gtgaccgtct ccgggagctg catgtgtcag    4800
aggttttcac cgtcatcacc gaaacgcgcg aggcagcaga tcaattcgcg cgcgaaggcg    4860
aagcggcatg catttacgtt gacaccatcg aatggtgcaa aacctttcgc ggtatggcat    4920
gatagcgccc ggaagagagt caattcaggg tggtgaatgt gaaaccagta acgttatacg    4980
atgtcgcaga gtatgccggt gtctcttatc agaccgtttc ccgcgtggtg aaccaggcca    5040
gccacgtttc tgcgaaaacg cgggaaaaag tggaagcggc gatggcggag ctgaattaca    5100
ttcccaaccg cgtggcacaa caactggcgg caaacagtc gttgctgatt ggcgttgcca    5160
cctccagtct ggccctgcac gcgccgtcgc aaattgtcgc ggcgattaaa tctcgcgccg    5220
atcaactggg tgccagcgtg gtggtgtcga tggtagaacg aagcggcgtc gaagcctgta    5280
aagcggcggt gcacaatctt ctcgcgcaac gcgtcagtgg gctgatcatt aactatccgc    5340
tggatgacca ggatgccatt gctgtggaag ctgcctgcac taatgttccg gcgttatttc    5400
ttgatgtctc tgaccagaca cccatcaaca gtattatttt ctcccatgaa gacggtacgc    5460
gactgggcgt ggagcatctg gtcgcattgg gtcaccagca atcgcgctg ttagcgggcc    5520
cattaagttc tgtctcggcg cgtctgcgtc tggctggctg cataaatat ctcactcgca    5580
atcaaattca gccgatagcg gaacgggaag gcgactggag tgccatgtcc ggttttcaac    5640
```

```
aaaccatgca aatgctgaat gagggcatcg ttcccactgc gatgctggtt gccaacgatc    5700
agatggcgct gggcgcaatg cgcgccatta ccgagtccgg gctgcgcgtt ggtgcggata    5760
tctcggtagt gggatacgac gataccgaag acagctcatg ttatatcccg ccgtcaacca    5820
ccatcaaaca ggattttcgc ctgctggggc aaaccagcgt ggaccgcttg ctgcaactct    5880
ctcagggcca ggcggtgaag ggcaatcagc tgttgcccgt ctcactggtg aaaagaaaaa    5940
ccaccctggc gcccaatacg caaaccgcct ctccccgcgc gttggccgat tcattaatgc    6000
agctggcacg acaggtttcc cgactggaaa gcgggcagtg agcgcaacgc aattaatgtg    6060
agttagcgcg aattgatctg                                                6080

<210> SEQ ID NO 156
<211> LENGTH: 6646
<212> TYPE: DNA
<213> ORGANISM: Artificial Sequence
<220> FEATURE:
<223> OTHER INFORMATION: Synthetic Construct

<400> SEQUENCE: 156
ccgacaccat cgaatggtgc aaaacctttc gcggtatggc atgatagcgc ccggaagaga      60
gtcaattcag ggtggtgaat gtgaaaccag taacgttata cgatgtcgca gagtatgccg     120
gtgtctctta tcagaccgtt tcccgcgtgg tgaaccaggc cagccacgtt tctgcgaaaa     180
cgcgggaaaa agtggaagcg gcgatggcgg agctgaatta cattcccaac cgcgtggcac     240
aacaactggc gggcaaacag tcgttgctga ttggcgttgc cacctccagt ctggccctgc     300
acgcgccgtc gcaaattgtc gcggcgatta atctcgcgc gatcaactg ggtgccagcg     360 tggtggtgtc gatggtagaa cgaagcggcg tcgaagcctg taaagcggcg gtgcacaatc     420
ttctcgcgca acgcgtcagt gggctgatca ttaactatcc gctggatgac caggatgcca     480
ttgctgtgga agctgcctgc actaatgttc cggcgttatt tcttgatgtc tctgaccaga     540
cacccatcaa cagtattatt ttctcccatg aagacggtac gcgactgggc gtggagcatc     600
tggtcgcatt gggtcaccag caaatcgcgc tgttagcggg cccattaagt tctgtctcgg     660
cgcgtctgcg tctggctggc tggcataaat atctcactcg caatcaaatt cagccgatag     720
cggaacggga aggcgactgg agtgccatgt ccggttttca acaaaccatg caaatgctga     780
atgagggcat cgttcccact gcgatgctgg ttgccaacga tcagatggcg ctgggcgcaa     840
tgcgcgccat taccgagtcc gggctgcgcg ttggtgcgga tatctcggta gtgggatacg     900
acgataccga agacagctca tgttatatcc gccgttaac caccatcaaa caggattttc     960
gcctgctggg gcaaaccagc gtggaccgct tgctgcaact ctctcagggc caggcggtga    1020
agggcaatca gctgttgccc gtctcactgg tgaaaagaaa aaccaccctg gcgcccaata    1080
cgcaaaccgc ctctccccgc gcgttggccg attcattaat gcagctggca cgacaggttt    1140
cccgactgga aagcgggcag tgagcgcaac gcaattaatg taagttagct cactcattag    1200
gcacaattct catgtttgac agcttatcat cgactgcacg gtgcaccaat gcttctggcg    1260
tcaggcagcc atcggaagct gtggtatggc tgtgcaggtc gtaaatcact gcataattcg    1320
tgtcgctcaa ggcgcactcc cgttctggat aatgttttt gcgccgacat cataacggtt    1380
ctggcaaata ttctgaaatg agctgttgac aattaatcat cggctcgtat aatgtgtgga    1440
attgtgagcg gataacaatt tcacacagga aacagccagt ccgttaggt gttttcacga    1500 gcacttcacc aacaaggacc atagcatatg aaaatcgaag aaggtaaact ggtaatctgg    1560
```

-continued

```
attaacggcg ataaaggcta taacggtctc gctgaagtcg gtaagaaatt cgagaaagat    1620
accggaatta aagtcaccgt tgagcatccg gataaactgg aagagaaatt cccacaggtt    1680
gcggcaactg gcgatggccc tgacattatc ttctgggcac acgaccgctt tggtggctac    1740
gctcaatctg gcctgttggc tgaaatcacc ccggacaaag cgttccagga caagctgtat    1800
ccgtttacct gggatgccgt acgttacaac ggcaagctga ttgcttaccc gatcgctgtt    1860
gaagcgttat cgctgattta taacaaagat ctgctgccga acccgccaaa aacctgggaa    1920
gagatcccgg cgctggataa agaactgaaa gcgaaaggta gagcgcgct gatgttcaac    1980
ctgcaagaac cgtacttcac ctggccgctg attgctgctg acggggggtta tgcgttcaag    2040
tatgaaaacg gcaagtacga cattaaagac gtgggcgtgg ataacgctgg cgcgaaagcg    2100
ggtctgacct tcctggttga cctgattaaa aacaaacaca tgaatgcaga caccgattac    2160
tccatcgcag aagctgcctt taataaaggc gaaacagcga tgaccatcaa cggcccgtgg    2220
gcatggtcca catcgacac cagcaaagtg aattatggtg taacggtact gccgaccttc    2280
aagggtcaac catccaaacc gttcgttggc gtgctgagcg caggtattaa cgccgccagt    2340
ccgaacaaag agctggcaaa agagttcctc gaaaactatc tgctgactga tgaaggtctg    2400
gaagcggtta ataagacaa accgctgggt gccgtagcgc tgaagtctta cgaggaagag    2460
ttggtgaaag atccgcggat tgccgccact atggaaaacg cccagaaagg tgaaatcatg    2520
ccgaacatcc cgcagatgtc cgcttctggg tatgccgtgc gtactgcggt gatcaacgcc    2580
gccagcggtc gtcagactgt cgatgaagcc ctgaaagacg cgcagactaa ttcgagctcg    2640
aacaacaaca caataacaa taacaacaac ctcgggatcg agggaaggat ttcagaattc    2700
ggatcctcta gagtcgacct gcaggcaagc ttggcactgg ccgtcgtttt acaacgtcgt    2760
gactgggaaa accctggcgt tacccaactt aatcgccttg cagcacatcc ccctttcgcc    2820
agctggcgta atagcgaaga ggcccgcacc gatcgccctt cccaacagtt gcgcagcctg    2880
aatggcgaat ggcagcttgg ctgttttggc ggatgagata gattttcag cctgatacag    2940
attaaatcag aacgcagaag cggtctgata aaacagaatt gcctggcgg cagtagcgcg    3000
gtggtcccac ctgaccccat gccgaactca gaagtgaaac gccgtagcgc cgatggtagt    3060
gtgggtctc cccatgcgag agtagggaac tgccaggcat caaataaaac gaaaggctca    3120
gtcgaaagac tgggcctttc gttttatctg ttgtttgtcg gtgaacgctc tcctgagtag    3180
gacaaatccg ccgggagcgg atttgaacgt tgcgaagcaa cggcccggag ggtggcgggc    3240
aggacgcccg ccataaactg ccaggcatca aattaagcag aaggccatcc tgacggatgg    3300
cctttttgcg tttctacaaa ctcttttttgt ttatttttct aaatacattc aaatatgtat    3360
ccgctcatga caataaacc ctgataaatg cttcaataat attgaaaaag gaagagtatg    3420
agtattcaac atttccgtgt cgcccttatt ccctttttttg cggcattttg ccttcctgtt    3480
tttgctcacc cagaaacgct ggtgaaagta aaagatgctg aagatcagtt gggtgcacga    3540
gtgggttaca tcgaactgga tctcaacagc ggtaagatcc ttgagagttt cgccccgaa    3600
gaacgttctc caatgatgag cacttttaaa gttctgctat gtggcgcggt attatcccgt    3660
gttgacgccg gcaagagca actcggtcgc cgcatacact attctcagaa tgacttggtt    3720
gagtactcac cagtcacaga aaagcatctt acggatggca tgacagtaag agaattatgc    3780
agtgctgcca taaccatgag tgataacact gcggccaact tacttctgac aacgatcgga    3840
ggaccgaagg agctaaccgc ttttttgcac aacatggggg atcatgtaac tcgccttgat    3900
cgttgggaac cggagctgaa tgaagccata ccaaacgacg agcgtgacac cacgatgcct    3960
```

```
gtagcaatgg caacaacgtt gcgcaaacta ttaactggcg aactacttac tctagcttcc    4020
cggcaacaat taatagactg gatggaggcg gataaagttg caggaccact tctgcgctcg    4080
gcccttccgg ctggctggtt tattgctgat aaatctggag ccggtgagcg tgggtctcgc    4140
ggtatcattg cagcactggg gccagatggt aagccctccc gtatcgtagt tatctacacg    4200
acggggagtc aggcaactat ggatgaacga aatagacaga tcgctgagat aggtgcctca    4260
ctgattaagc attggtaact gtcagaccaa gtttactcat atatacttta gattgattta    4320
ccccggttga taatcagaaa agccccaaaa acaggaagat tgtataagca aatatttaaa    4380
ttgtaaacgt taatattttg ttaaaattcg cgttaaattt ttgttaaatc agctcatttt    4440
ttaaccaata ggccgaaatc ggcaaaatcc cttataaatc aaaagaatag accgagatag    4500
ggttgagtgt tgttccagtt tggaacaaga gtccactatt aaagaacgtg gactccaacg    4560
tcaaagggcg aaaaaccgtc tatcagggcg atggcccact acgtgaacca tcacccaaat    4620
caagtttttt ggggtcgagg tgccgtaaag cactaaatcg gaaccctaaa gggagccccc    4680
gatttagagc ttgacgggga agccggcga acgtggcgag aaaggaaggg aagaaagcga    4740
aaggagcggg cgctagggcg ctggcaagtg tagcggtcac gctgcgcgta accaccacac    4800
ccgccgcgct taatgcgccg ctacagggcg cgtaaaagga tctaggtgaa gatcctttt    4860 gataatctca tgaccaaaat cccttaacgt gagttttcgt tccactgagc gtcagacccc    4920
gtagaaaaga tcaaaggatc ttcttgagat cctttttttc tgcgcgtaat ctgctgcttg    4980
caaacaaaaa aaccaccgct accagcggtg gtttgtttgc cggatcaaga gctaccaact    5040 cttttccga aggtaactgg cttcagcaga gcgcagatac caaatactgt ccttctagtg    5100
tagccgtagt taggccacca cttcaagaac tctgtagcac cgcctacata cctcgctctg    5160
ctaatcctgt taccagtggc tgctgccagt ggcgataagt cgtgtcttac cgggttggac    5220
tcaagacgat agttaccgga taaggcgcag cggtcgggct gaacggggg ttcgtgcaca    5280 cagcccagct tggagcgaac gacctacacc gaactgagat acctacagcg tgagctatga    5340
gaaagcgcca cgcttcccga agggagaaag gcggacaggt atccggtaag cggcagggtc    5400
ggaacaggag agcgcacgag ggagcttcca ggggggaaacg cctggtatct ttatagtcct    5460
gtcgggtttc gccacctctg acttgagcgt cgatttttgt gatgctcgtc aggggggcgg    5520
agcctatgga aaaacgccag caacgcggcc tttttacggt tcctggcctt ttgctggcct    5580
tttgctcaca tgttctttcc tgcgttatcc cctgattctg tggataaccg tattaccgcc    5640
tttgagtgag ctgataccgc tcgccgcagc cgaacgaccg agcgcagcga gtcagtgagc    5700
gaggaagcgg aagagcgcct gatgcggtat tttctcctta cgcatctgtg cggtatttca    5760
caccgcatat atggtgcact ctcagtacaa tctgctctga tgccgcatag ttaagccagt    5820
atacactccg ctatcgctac gtgactgggt catggctgcg ccccgacacc cgccaacacc    5880
cgctgacgcg ccctgacggg cttgtctgct cccggcatcc gcttacagac aagctgtgac    5940
cgtctccggg agctgcatgt gtcagaggtt ttcaccgtca tcaccgaaac gcgcgaggca    6000
gctgcggtaa agctcatcag cgtggtcgtg cagcgattca cagatgtctg cctgttcatc    6060
cgcgtccagc tcgttgagtt tctccagaag cgttaatgtc tggcttctga taaagcgggc    6120
catgttaagg gcggtttttt cctgtttggt cactgatgcc tccgtgtaag ggggatttct    6180
gttcatgggg gtaatgatac cgatgaaacg agagaggatg ctcacgatac gggttactga    6240
tgatgaacat gcccggttac tggaacgttg tgagggtaaa caactggcgg tatggatgcg    6300
```

| | |
|---|---|
| gcgggaccag agaaaaatca ctcagggtca atgccagcgc ttcgttaata cagatgtagg | 6360 |
| tgttccacag ggtagccagc agcatcctgc gatgcagatc cggaacataa tggtgcaggg | 6420 |
| cgctgacttc cgcgttttcca gactttacga acacggaaa ccgaagacca ttcatgttgt | 6480 |
| tgctcaggtc gcagacgttt tgcagcagca gtcgcttcac gttcgctcgc gtatcggtga | 6540 |
| ttcattctgc taaccagtaa ggcaaccccg ccagcctagc cgggtcctca acgacaggag | 6600 |
| cacgatcatg cgcacccgtg gccaggaccc aacgctgccc gaaatt | 6646 |

<210> SEQ ID NO 157
<211> LENGTH: 8310
<212> TYPE: DNA
<213> ORGANISM: Artificial Sequence
<220> FEATURE:
<223> OTHER INFORMATION: Synthetic Construct

<400> SEQUENCE: 157

| | |
|---|---|
| ccgacaccat cgaatggtgc aaaacctttc gcggtatggc atgatagcgc ccggaagaga | 60 |
| gtcaattcag ggtggtgaat gtgaaaccag taacgttata cgatgtcgca gagtatgccg | 120 |
| gtgtctctta tcagaccgtt tcccgcgtgg tgaaccaggc cagccacgtt tctgcgaaaa | 180 |
| cgcgggaaaa agtggaagcg gcgatggcgg agctgaatta cattcccaac cgcgtggcac | 240 |
| aacaactggc gggcaaacag tcgttgctga ttggcgttgc cacctccagt ctggccctgc | 300 |
| acgcgccgtc gcaaattgtc gcggcgatta atctcgcgc cgatcaactg ggtgccagcg | 360 |
| tggtggtgtc gatggtagaa cgaagcggcg tcgaagcctg taaagcggcg gtgcacaatc | 420 |
| ttctcgcgca acgcgtcagt gggctgatca ttaactatcc gctggatgac caggatgcca | 480 |
| ttgctgtgga agctgcctgc actaatgttc cggcgttatt tcttgatgtc tctgaccaga | 540 |
| cacccatcaa cagtattatt ttctcccatg aagacggtac gcgactgggc gtggagcatc | 600 |
| tggtcgcatt gggtcaccag caaatcgcgc tgttagcggg cccattaagt tctgtctcgg | 660 |
| cgcgtctgcg tctggctggc tggcataaat atctcactcg caatcaaatt cagccgatag | 720 |
| cggaacggga aggcgactgg agtgccatgt ccggttttca acaaaccatg caaatgctga | 780 |
| atgagggcat cgttcccact gcgatgctgg ttgccaacga tcagatggcg ctgggcgcaa | 840 |
| tgcgcgccat taccgagtcc gggctgcgcg ttggtgcgga tatctcggta gtgggatacg | 900 |
| acgataccga agacagctca tgttatatcc cgccgttaac caccatcaaa caggattttc | 960 |
| gcctgctggg gcaaaccagc gtggaccgct tgctgcaact ctctcagggc caggcggtga | 1020 |
| agggcaatca gctgttgccc gtctcactgg tgaaaagaaa aaccaccctg gcgcccaata | 1080 |
| cgcaaaccgc ctctccccgc gcgttggccg attcattaat gcagctggca cgacaggttt | 1140 |
| cccgactgga aagcgggcag tgagcgcaac gcaattaatg taagttagct cactcattag | 1200 |
| gcacaattct catgtttgac agcttatcat cgactgcacg gtgcaccaat gcttctggcg | 1260 |
| tcaggcagcc atcggaagct gtggtatggc tgtgcaggtc gtaaatcact gcataattcg | 1320 |
| tgtcgctcaa ggcgcactcc cgttctggat aatgtttttt gcgccgacat cataacggtt | 1380 |
| ctggcaaata ttctgaaatg agctgttgac aattaatcat cggctcgtat aatgtgtgga | 1440 |
| attgtgagcg gataacaatt tcacacagga aacagccagt ccgtttaggt gttttcacga | 1500 |
| gcacttcacc aacaaggacc atagcatatg aaaatcgaag aaggtaaact ggtaatctgg | 1560 |
| attaacggcg ataaaggcta taacggtctc gctgaagtcg gtaagaaatt cgagaaagat | 1620 |
| accggaatta aagtcaccgt tgagcatccg gataaactgg aagagaaatt cccacaggtt | 1680 |
| gcggcaactg gcgatggccc tgacattatc ttctgggcac acgaccgctt tggtggctac | 1740 |

```
gctcaatctg gcctgttggc tgaaatcacc ccggacaaag cgttccagga caagctgtat    1800
ccgtttacct gggatgccgt acgttacaac ggcaagctga ttgcttaccc gatcgctgtt    1860
gaagcgttat cgctgattta taacaaagat ctgctgccga acccgccaaa aacctgggaa    1920
gagatcccgg cgctggataa agaactgaaa gcgaaggta agagcgcgct gatgttcaac    1980
ctgcaagaac cgtacttcac ctggccgctg attgctgctg acggggtta tgcgttcaag    2040 tatgaaaacg gcaagtacga cattaaagac gtgggcgtgg ataacgctgg cgcgaaagcg    2100
ggtctgacct tcctggttga cctgattaaa aacaaacaca tgaatgcaga caccgattac    2160
tccatcgcag aagctgcctt taataaaggc gaaacagcga tgaccatcaa cggcccgtgg    2220
gcatggtcca acatcgacac cagcaaagtg aattatggtg taacggtact gccgaccttc    2280
aagggtcaac catccaaacc gttcgttggc gtgctgagcg caggtattaa cgccgccagt    2340
ccgaacaaag agctggcaaa agagttcctc gaaaactatc tgctgactga tgaaggtctg    2400
gaagcggtta ataaagacaa accgctgggt gccgtagcgc tgaagtctta cgaggaagag    2460
ttggtgaaag atccgcggat tgccgccact atggaaaacg cccagaaagg tgaaatcatg    2520
ccgaacatcc cgcagatgtc cgcttttctgg tatgccgtgc gtactgcggt gatcaacgcc    2580
gccagcggtc gtcagactgt cgatgaagcc ctgaaagacg cgcagactaa ttcgagctcg    2640
aacaacaaca caataacaa taacaacaac ctcgggatcg agggaaggat ttcagaattc    2700
tgtgcgacct cttctcaatt tactcagatt accgagcata attccgtcg ttccgcaaac    2760 tatcagccaa acctgtggaa tttcgaattc ctgcaatccc tggagaacga cctgaaagtg    2820
gaaaagctgg aggagaaagc gaccaaactg gaggaagaag ttcgctgcat gatcaaccgt    2880
gtagacaccc agccgctgtc cctgctggag ctgatcgacg atgtgcagcg cctgggtctg    2940
acctacaaat ttgaaaaaga catcattaaa gccctggaaa acatcgtact gctggacgaa    3000
aacaaaaaga acaaatctga cctgcacgca accgctctgt ctttccgtct gctgcgtcag    3060
cacggtttcg aggtttctca ggatgttttt gagcgtttca aggataaaga aggtggtttc    3120
agcggtgaac tgaaaggtga cgtccaaggc ctgctgagcc tgtatgaagc gtcttacctg    3180
ggtttcgagg gtgagaacct gctggaggag gcgcgtacct tttccatcac ccacctgaag    3240
aacaacctga agaaggcat taataccaag gttgcagaac aagtgagcca cgccctggaa    3300
ctgccatatc accagcgtct gcaccgtctg gaggcacgtt ggttcctgga taaatacgaa    3360
ccgaaagaac cgcatcacca gctgctgctg gagctggcga agctggattt taacatggta    3420
cagaccctgc accagaaaga gctgcaagat ctgtcccgct ggtggaccga gatgggcctg    3480
gctagcaaac tggattttgt acgcgaccgc ctgatggaag tttatttctg ggcactgggt    3540
atggcgccag acccgcagtt tggtgaatgt cgcaaagctg ttactaaaat gtttggtctg    3600
gtgacgatca tcgatgacgt gtatgacgtt tatggcactc tggacgaact gcaactgttc    3660
accgatgctg tagagcgctg ggacgttaac gctattaaca ccctgccgga ctatatgaaa    3720
ctgtgtttcc tggcactgta caacaccgtt aacgacacgt cctattctat tctgaaagag    3780
aaaggtcata caacctgtc ctatctgacg aaaagctggc gtgaactgtg caaagccttt    3840
ctgcaagagg cgaaatggtc caacaacaaa attatcccgg cttttctccaa gtacctggaa    3900 aacgccagcg tttcctcctc cggtgtagcg ctgctggcgc cgtcttactt tccgtatgc    3960 cagcagcagg aagacatctc cgaccacgcg ctgcgttccc tgaccgactt ccatggtctg    4020
gtgcgttcta gctgcgttat cttccgcctg tgcaacgatc tggccacctc tgcggcggag    4080
```

```
ctggaacgtg gcgagactac caattctatc attagctaca tgcacgaaaa cgatggtacc   4140
agcgaggaac aggcccgcga agaactgcgt aaactgatcg acgccgaatg gaaaaagatg   4200
aatcgtgaac gcgttagcga ctccaccctg ctgcctaaag cgttcatgga aatcgcagtt   4260
aacatggcac gtgtttccca ctgcacctac cagtatggcg atggtctggg tcgcccagac   4320
tacgcgactg aaaaccgcat caaactgctg ctgattgacc cttttcccgat taaccagctg   4380
atgtatgtct aagcttggca ctggccgtcg ttttacaacg tcgtgactgg gaaaaccctg   4440
gcgttaccca acttaatcgc cttgcagcac atccccccttt cgccagctgg cgtaatagcg   4500
aagaggcccg caccgatcgc ccttcccaac agttgcgcag cctgaatggc gaatggcagc   4560
ttggctgttt tggcggatga gataagattt tcagcctgat acagattaaa tcagaacgca   4620
gaagcggtct gataaaacag aatttgcctg gcggcagtag cgcggtggtc ccacctgacc   4680
ccatgccgaa ctcagaagtg aaacgccgta gcgccgatgg tagtgtgggg tctccccatg   4740
cgagagtagg gaactgccag gcatcaaata aaacgaaagg ctcagtcgaa agactgggcc   4800
tttcgtttta tctgttgttt gtcggtgaac gctctcctga gtaggacaaa tccgccggga   4860
gcggatttga cgttgcgaa gcaacggccc ggagggtggc gggcaggacg cccgccataa   4920
actgccaggc atcaaattaa gcagaaggcc atcctgacgg atggccttt tgcgtttcta   4980
caaactcttt tgtttatttt ttctaaatac attcaaatat gtatccgctc atgagacaat   5040
aaccctgata aatgcttcaa taatattgaa aaaggaagag tatgagtatt caacatttcc   5100
gtgtcgccct tattccctttt tttgcggcat tttgccttcc tgttttttgct cacccagaaa   5160
cgctggtgaa agtaaaagat gctgaagatc agttgggtgc acgagtgggt tacatcgaac   5220
tggatctcaa cagcggtaag atccttgaga gttttcgccc cgaagaacgt tctccaatga   5280
tgagcacttt taaagttctg ctatgtggcg cggtattatc ccgtgttgac gccgggcaag   5340
agcaactcgg tcgccgcata cactattctc agaatgactt ggttgagtac tcaccagtca   5400
cagaaaagca tcttacggat ggcatgacag taagagaatt atgcagtgct gccataacca   5460
tgagtgataa cactgcggcc aacttacttc tgacaacgat cggaggaccg aaggagctaa   5520
ccgctttttt gcacaacatg ggggatcatg taactcgcct tgatcgttgg aaccggagc   5580
tgaatgaagc cataccaaac gacgagcgtg acaccacgat gcctgtagca atggcaacaa   5640
cgttgcgcaa actattaact ggcgaactac ttactctagc ttcccggcaa caattaatag   5700
actggatgga ggcggataaa gttgcaggac cacttctgcg ctcggccctt ccggctggct   5760
ggtttattgc tgataaatct ggagccggtg agcgtgggtc tcgcggtatc attgcagcac   5820
tggggccaga tggtaagccc tcccgtatcg tagttatcta cacgacgggg agtcaggcaa   5880
ctatggatga acgaaataga cagatcgctg agataggtgc ctcactgatt aagcattggt   5940
aactgtcaga ccaagtttac tcatatatac tttagattga tttaccccgg ttgataatca   6000
gaaaagcccc aaaaacagga agattgtata agcaaatatt taaattgtaa acgttaatat   6060
tttgttaaaa ttcgcgttaa attttttgtta aatcagctca ttttttaacc aataggccga   6120
aatcggcaaa atcccttata aatcaaaaga atagaccgag atagggttga gtgttgttcc   6180
agtttggaac aagagtccac tattaaagaa cgtggactcc aacgtcaaag ggcgaaaaac   6240
cgtctatcag ggcgatggcc cactacgtga accatcaccc aaatcaagtt ttttggggtc   6300
gaggtgccgt aaagcactaa atcggaaccc taaagggagc cccgatttta gagcttgacg   6360
gggaagccg cgaacgtgg cgagaaagga agggaagaaa gcgaaggag cgggcgctag   6420
ggcgctggca agtgtagcgg tcacgctgcg cgtaaccacc acacccgccg cgcttaatgc   6480
```

```
gccgctacag ggcgcgtaaa aggatctagg tgaagatcct ttttgataat ctcatgacca    6540
aaatccctta acgtgagttt tcgttccact gagcgtcaga ccccgtagaa agatcaaag     6600 gatcttcttg agatccttttt tttctgcgcg taatctgctg cttgcaaaca aaaaaaccac   6660
cgctaccagc ggtggtttgt ttgccggatc aagagctacc aactctttt ccgaaggtaa    6720 ctggcttcag cagagcgcag ataccaaata ctgtccttct agtgtagccg tagttaggcc   6780
accacttcaa gaactctgta gcaccgccta catcctcgc tctgctaatc ctgttaccag    6840
tggctgctgc cagtggcgat aagtcgtgtc ttaccgggtt ggactcaaga cgatagttac   6900
cggataaggc gcagcggtcg ggctgaacgg ggggttcgtg cacacagccc agcttggagc   6960
gaacgaccta caccgaactg agatacctac agcgtgagct atgagaaagc gccacgcttc   7020
ccgaagggag aaaggcggac aggtatccgg taagcggcag ggtcggaaca ggagagcgca   7080
cgagggagct tccaggggga aacgcctggt atctttatag tcctgtcggg tttcgccacc   7140
tctgacttga gcgtcgattt ttgtgatgct cgtcaggggg gcggagccta tggaaaaacg   7200
ccagcaacgc ggcctttttt cggttcctgg ccttttgctg gccttttgct cacatgttct   7260
ttcctgcgtt atcccctgat tctgtggata accgtattac cgcctttgag tgagctgata   7320
ccgctcgccg cagccgaacg accgagcgca gcgagtcagt gagcgaggaa gcggaagagc   7380
gcctgatgcg gtattttctc cttacgcatc tgtgcggtat ttcacaccgc atatatggtg   7440
cactctcagt acaatctgct ctgatgccgc atagttaagc cagtatacac tccgctatcg   7500
ctacgtgact gggtcatggc tgcgccccga cacccgccaa cacccgctga cgcgccctga   7560
cgggcttgtc tgctcccggc atccgcttac agacaagctg tgaccgtctc cgggagctgc   7620
atgtgtcaga ggttttcacc gtcatcaccg aaacgcgcga ggcagctgcg gtaaagctca   7680
tcagcgtggt cgtgcagcga ttcacagatg tctgcctgtt catccgcgtc cagctcgttg   7740
agtttctcca gaagcgttaa tgtctggctt ctgataaagc gggccatgtt aagggcggtt   7800
ttttcctgtt tggtcactga tgcctccgtg taaggggat ttctgttcat gggggtaatg    7860
ataccgatga acgagagag gatgctcacg atacgggtta ctgatgatga acatgcccgg   7920
ttactggaac gttgtgaggg taaacaactg gcggtatgga tgcggcggga ccagagaaaa   7980
atcactcagg gtcaatgcca gcgcttcgtt aatacagatg taggtgttcc acagggtagc   8040
cagcagcatc ctgcgatgca gatccggaac ataatggtgc agggcgctga cttccgcgtt   8100
tccagacttt acgaaacacg gaaaccgaag accattcatg ttgttgctca ggtcgcagac   8160
gttttgcagc agcagtcgct tcacgttcgc tcgcgtatcg gtgattcatt ctgctaacca   8220
gtaaggcaac cccgccagcc tagccgggtc ctcaacgaca ggagcacgat catgcgcacc   8280
cgtggccagg acccaacgct gcccgaaatt                                     8310
```

<210> SEQ ID NO 158
<211> LENGTH: 560
<212> TYPE: PRT
<213> ORGANISM: Populus tremuloides

<400> SEQUENCE: 158

Met Arg Cys Ser Val Ser Thr Glu Asn Val Ser Phe Ser Glu Thr Glu
1               5                   10                  15

Thr Glu Thr Arg Arg Ser Ala Asn Tyr Glu Pro Asn Ser Trp Asp Tyr
            20                  25                  30

Asp Tyr Leu Leu Ser Ser Asp Thr Asp Glu Ser Ile Glu Val His Lys
        35                  40                  45

```
Asp Lys Ala Lys Lys Leu Glu Ala Glu Val Arg Arg Glu Ile Asn Asn
 50                  55                  60

Glu Lys Ala Glu Phe Leu Thr Leu Leu Glu Leu Ile Asp Asn Val Gln
 65                  70                  75                  80

Arg Leu Gly Leu Gly Tyr Arg Phe Glu Ser Asp Ile Arg Arg Ala Leu
                 85                  90                  95

Asp Arg Phe Val Ser Ser Gly Gly Phe Asp Gly Val Thr Lys Thr Ser
                100                 105                 110

Leu His Gly Thr Ala Leu Ser Phe Arg Leu Leu Arg Gln His Gly Phe
            115                 120                 125

Glu Val Ser Gln Glu Ala Phe Ser Gly Phe Lys Asp Gln Asn Gly Asn
130                 135                 140

Phe Leu Glu Asn Leu Lys Glu Asp Ile Lys Ala Ile Leu Ser Leu Tyr
145                 150                 155                 160

Glu Ala Ser Phe Leu Ala Leu Glu Gly Glu Asn Ile Leu Asp Glu Ala
                165                 170                 175

Lys Val Phe Ala Ile Ser His Leu Lys Glu Leu Ser Glu Glu Lys Ile
                180                 185                 190

Gly Lys Glu Leu Ala Glu Gln Val Ser His Ala Leu Glu Leu Pro Leu
            195                 200                 205

His Arg Arg Thr Gln Arg Leu Glu Ala Val Trp Ser Ile Glu Ala Tyr
        210                 215                 220

Arg Lys Lys Glu Asp Ala Asn Gln Val Leu Leu Glu Leu Ala Ile Leu
225                 230                 235                 240

Asp Tyr Asn Met Ile Gln Ser Val Tyr Gln Arg Asp Leu Arg Glu Thr
                245                 250                 255

Ser Arg Trp Trp Arg Arg Val Gly Leu Ala Thr Lys Leu His Phe Ala
                260                 265                 270

Arg Asp Arg Leu Ile Glu Ser Phe Tyr Trp Ala Val Gly Val Ala Phe
            275                 280                 285

Glu Pro Gln Tyr Ser Asp Cys Arg Asn Ser Val Ala Lys Met Phe Ser
290                 295                 300

Phe Val Thr Ile Ile Asp Asp Ile Tyr Asp Val Tyr Gly Thr Leu Asp
305                 310                 315                 320

Glu Leu Glu Leu Phe Thr Asp Ala Val Glu Arg Trp Asp Val Asn Ala
                325                 330                 335

Ile Asn Asp Leu Pro Asp Tyr Met Lys Leu Cys Phe Leu Ala Leu Tyr
                340                 345                 350

Asn Thr Ile Asn Glu Ile Ala Tyr Asp Asn Leu Lys Asp Lys Gly Glu
            355                 360                 365

Asn Ile Leu Pro Tyr Leu Thr Lys Ala Trp Ala Asp Leu Cys Asn Ala
370                 375                 380

Phe Leu Gln Glu Ala Lys Trp Leu Tyr Asn Lys Ser Thr Pro Thr Phe
385                 390                 395                 400

Asp Asp Tyr Phe Gly Asn Ala Trp Lys Ser Ser Gly Pro Leu Gln
                405                 410                 415

Leu Ile Phe Ala Tyr Phe Ala Val Val Gln Asn Ile Lys Lys Glu Glu
                420                 425                 430

Ile Glu Asn Leu Gln Lys Tyr His Asp Ile Ile Ser Arg Pro Ser His
            435                 440                 445

Ile Phe Arg Leu Cys Asn Asp Leu Ala Ser Ala Ser Ala Glu Ile Ala
450                 455                 460
```

-continued

Arg Gly Glu Thr Ala Asn Ser Val Ser Cys Tyr Met Arg Thr Lys Gly
465                 470                 475                 480

Ile Ser Glu Glu Leu Ala Thr Glu Ser Val Met Asn Leu Ile Asp Glu
            485                 490                 495

Thr Trp Lys Lys Met Asn Lys Gly Lys Leu Gly Gly Ser Leu Phe Ala
        500                 505                 510

Lys Pro Phe Val Glu Thr Ala Ile Asn Leu Ala Arg Gln Ser His Cys
        515                 520                 525

Thr Tyr His Asn Gly Asp Ala His Thr Ser Pro Asp Glu Leu Thr Arg
        530                 535                 540

Lys Arg Val Leu Ser Val Ile Thr Glu Pro Ile Leu Pro Phe Glu Arg
545                 550                 555                 560

<210> SEQ ID NO 159
<211> LENGTH: 6957
<212> TYPE: DNA
<213> ORGANISM: Artificial Sequence
<220> FEATURE:
<223> OTHER INFORMATION: Synthetic Construct

<400> SEQUENCE: 159
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcggggggc tccctttagg     180
gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta tagggatttt tgccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg aattaattct tagaaaaact catcgagcat caaatgaaac tgcaatttat     600
tcatatcagg attatcaata ccatatttttt gaaaagccg tttctgtaat gaaggagaaa     660
actcaccgag gcagttccat aggatggcaa gatcctggta tcggtctgcg attccgactc     720
gtccaacatc aatacaacct attaatttcc cctcgtcaaa aataaggtta tcaagtgaga     780
aatcaccatg agtgacgact gaatccggtg agaatggcaa aagtttatgc atttctttcc     840
agacttgttc aacaggccag ccattacgct cgtcatcaaa atcactcgca tcaaccaaac     900
cgttattcat tcgtgattgc gcctgagcga gacgaaatac gcgatcgctg ttaaaaggac     960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa atcccttaa    1440 cgtgagtttt cgttccactg agcgtcagac cccgtagaaa agatcaaagg atcttcttga    1500 gatcctttt ttctgcgcgt aatctgctgc ttgcaaacaa aaaaaccacc gctaccagcg    1560

```
gtggtttgtt tgccggatca agagctacca actcttttc  cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata agtcgtgtct taccggggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980 ccaggggaa  acgcctggta tctttatagt cctgtcgggt ttcgccacct ctgacttgag    2040
cgtcgatttt tgtgatgctc gtcagggggg cggagcctat ggaaaaacgc cagcaacgcg    2100
gcctttttac ggttcctggc cttttgctgg cctttgctc  acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc ccgcgcccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
```

-continued

```
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatgcgttgt agcgtgtcca ccgaaaatgt    5100
gtctttctct gaaactgaaa ccgaaacgcg tcgttctgcg aactacgaac ctaacagctg    5160
ggactatgat tacctgctgt cctccgacac ggacgagtcc atcgaagtac acaaagacaa    5220
agcgaaaaag ctggaagccg aagttcgtcg cgagattaat aacgaaaaag cagaatttct    5280
gaccctgctg gaactgattg acaacgtcca gcgcctgggc ctgggttacc gtttcgagtc    5340
tgatatccgt cgtgcgctgg atcgcttcgt ttcctccggc ggcttcgatg gcgtaaccaa    5400
gacttccctg cacggtacgg cactgtcttt ccgtctgctg cgtcaacacg ttttgaggt    5460
ttctcaggaa gcgttcagcg gcttcaaaga ccaaaacggc aacttcctgg agaacctgaa    5520
ggaagatatc aaagctatcc tgagcctgta cgaggccagc ttcctggctc tggaaggcga    5580
aaacatcctg gacgaggcga aggttttcgc aatctctcat ctgaaagaac tgtctgaaga    5640
aaagatcggt aaagagctgg cagaacaggt gtcccatgca ctggaactgc cactgcatcg    5700
ccgtactcag cgtctggaag cagtatggtc tatcgaggcc taccgtaaaa aggaggacgc    5760
gaaccaggtt ctgctggagc tggcaattct ggattacaac atgatccagt ctgtatacca    5820
gcgtgatctg cgtgaaacgt cccgttggtg gcgtcgtgtg ggtctggcga ccaaactgca    5880
ctttgctcgt gaccgcctga ttgagagctt ctactgggcc gtgggtgtag cattcgaacc    5940
gcaatactcc gactgccgta actccgtcgc aaaaatgttt tctttcgtaa ccattatcga    6000
cgatatctac gatgtatacg gcaccctgga cgaactggag ctgtttactg atgcagttga    6060
gcgttgggac gtaaacgcca tcaacgacct gccggattac atgaaactgt gctttctggc    6120
tctgtataac actattaacg aaatcgccta cgacaacctg aaagataaag gtgagaacat    6180
cctgccgtat ctgaccaaag cctgggctga cctgtgcaac gctttcctgc aagaagccaa    6240
gtggctgtac aacaaatcta ctccgacctt tgacgactac ttcggcaacg catggaaatc    6300
```

-continued

```
ctcttctggc cgctgcaac tgatcttcgc ttacttcgct gtcgtgcaga acattaaaaa    6360
ggaagagatc gaaaacctgc aaaaatacca tgacatcatc tctcgtcctt cccatatctt    6420
ccgtctgtgc aatgacctgg ctagcgcgtc tgcggaaatt gcgcgtggtg aaaccgcaaa    6480
tagcgttcct tgttacatgc gcactaaagg tatctccgaa gaactggcta ccgaaagcgt    6540
gatgaatctg atcgatgaaa cctggaaaaa gatgaacaag gaaaactgg gtggtagcct     6600 gttcgcgaaa ccgttcgtgg aaaccgcgat caacctggca cgtcaatctc actgcactta    6660
tcataacggc gacgcgcata cctctccgga tgagctgacc cgcaaacgcg ttctgtctgt    6720
aatcactgaa ccgattctgc cgtttgaacg ctaaggatcc gaattcgagc tccgtcgaca    6780
agcttgcggc cgcactcgag caccaccacc accaccactg agatccggct gctaacaaag    6840
cccgaaagga agctgagttg gctgctgcca ccgctgagca ataactagca taacccttg      6900 gggcctctaa acgggtcttg agggttttt tgctgaaagg aggaactata tccggat         6957
```

<210> SEQ ID NO 160
<211> LENGTH: 560
<212> TYPE: PRT
<213> ORGANISM: Populus trichocharpa

<400> SEQUENCE: 160

```
Met Arg Cys Ser Val Ser Thr Glu Asn Val Ser Phe Thr Glu Thr Glu
 1               5                  10                  15

Thr Glu Thr Arg Arg Ser Ala Asn Tyr Glu Pro Asn Ser Trp Asp Tyr
                20                  25                  30

Asp Tyr Leu Leu Ser Ser Asp Thr Asp Glu Ser Ile Glu Val Tyr Lys
            35                  40                  45

Asp Lys Ala Lys Lys Leu Glu Ala Glu Val Arg Arg Glu Ile Asn Asn
        50                  55                  60

Glu Lys Ala Glu Phe Leu Thr Leu Leu Glu Leu Ile Asp Asn Val Gln
 65                  70                  75                  80

Arg Leu Gly Leu Gly Tyr Arg Phe Glu Ser Asp Ile Arg Arg Ala Leu
                85                  90                  95

Asp Arg Phe Val Ser Ser Gly Gly Phe Asp Ala Val Thr Lys Thr Ser
            100                 105                 110

Leu His Ala Thr Ala Leu Ser Phe Arg Leu Leu Arg Gln His Gly Phe
        115                 120                 125

Glu Val Ser Gln Glu Ala Phe Ser Gly Phe Lys Asp Gln Asn Gly Asn
    130                 135                 140

Phe Leu Glu Asn Leu Lys Glu Asp Ile Lys Ala Ile Leu Ser Leu Tyr
145                 150                 155                 160

Glu Ala Ser Phe Leu Ala Leu Glu Gly Glu Asn Ile Leu Asp Glu Ala
                165                 170                 175

Lys Val Phe Ala Ile Ser His Leu Lys Glu Leu Ser Glu Glu Lys Ile
            180                 185                 190

Gly Lys Asp Leu Ala Glu Gln Val Asn His Ala Leu Glu Leu Pro Leu
        195                 200                 205

His Arg Arg Thr Gln Arg Leu Glu Ala Val Leu Ser Ile Glu Ala Tyr
    210                 215                 220

Arg Lys Lys Glu Asp Ala Asp Gln Val Leu Leu Glu Leu Ala Ile Leu
225                 230                 235                 240

Asp Tyr Asn Met Ile Gln Ser Val Tyr Gln Arg Asp Leu Arg Glu Thr
                245                 250                 255
```

```
Ser Arg Trp Trp Arg Arg Val Gly Leu Ala Thr Lys Leu His Phe Ala
        260                 265                 270

Arg Asp Arg Leu Ile Glu Ser Phe Tyr Trp Ala Val Gly Val Ala Phe
            275                 280                 285

Glu Pro Gln Tyr Ser Asp Cys Arg Asn Ser Val Ala Lys Met Phe Ser
        290                 295                 300

Phe Val Thr Ile Ile Asp Asp Ile Tyr Asp Val Tyr Gly Thr Leu Asp
305                 310                 315                 320

Glu Leu Glu Leu Phe Thr Asn Ala Val Glu Arg Trp Asp Val Asn Ala
                325                 330                 335

Ile Asp Asp Leu Pro Asp Tyr Met Lys Leu Cys Phe Leu Ala Leu Tyr
            340                 345                 350

Asn Thr Ile Asn Glu Ile Ala Tyr Asp Asn Leu Lys Glu Lys Gly Glu
        355                 360                 365

Asn Ile Leu Pro Tyr Leu Thr Lys Ala Trp Ala Asp Leu Cys Asn Ala
    370                 375                 380

Phe Leu Gln Glu Ala Lys Trp Leu Tyr Asn Lys Ser Thr Pro Thr Phe
385                 390                 395                 400

Asp Glu Tyr Phe Gly Asn Ala Trp Lys Ser Ser Gly Pro Leu Gln
                405                 410                 415

Leu Val Phe Ala Tyr Phe Ala Val Val Gln Asn Ile Lys Lys Glu Glu
            420                 425                 430

Ile Glu Asn Leu Gln Lys Tyr His Asp Ile Ile Ser Arg Pro Ser His
        435                 440                 445

Ile Phe Arg Leu Cys Asn Asp Leu Ala Ser Ala Ser Ala Glu Ile Ala
    450                 455                 460

Arg Gly Glu Thr Ala Asn Ser Val Ser Cys Tyr Met Arg Thr Lys Gly
465                 470                 475                 480

Ile Ser Glu Glu Leu Ala Thr Glu Ser Val Met Asn Leu Ile Asp Glu
                485                 490                 495

Thr Trp Lys Lys Met Asn Lys Glu Lys Leu Gly Gly Ser Leu Phe Ala
            500                 505                 510

Lys Pro Phe Val Glu Thr Ala Ile Asn Leu Ala Arg Gln Ser His Cys
        515                 520                 525

Thr Tyr His Asn Gly Asp Ala His Thr Ser Pro Asp Glu Leu Thr Arg
    530                 535                 540

Lys Arg Val Leu Ser Val Ile Thr Glu Pro Ile Leu Pro Phe Glu Arg
545                 550                 555                 560

<210> SEQ ID NO 161
<211> LENGTH: 6963
<212> TYPE: DNA
<213> ORGANISM: Artificial Sequence
<220> FEATURE:
<223> OTHER INFORMATION: Synthetic Construct

<400> SEQUENCE: 161
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tccctttagg      180 gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aacccatctc ggtctattc      360
```

-continued

```
ttttgattta taagggattt tgccgatttc ggcctattgg ttaaaaaatg agctgattta      420
acaaaaattt aacgcgaatt ttaacaaaat attaacgttt acaatttcag gtggcacttt      480
tcggggaaat gtgcgcggaa cccctatttg tttattttc taaatacatt caaatatgta       540
tccgctcatg aattaattct tagaaaaact catcgagcat caaatgaaac tgcaatttat      600
tcatatcagg attatcaata ccatattttt gaaaaagccg tttctgtaat gaaggagaaa      660
actcaccgag gcagttccat aggatggcaa gatcctggta tcggtctgcg attccgactc     720
gtccaacatc aatacaacct attaatttcc cctcgtcaaa aataaggtta tcaagtgaga     780
aatcaccatg agtgacgact gaatccggtg agaatggcaa aagtttatgc atttcttcc      840 agacttgttc aacaggccag ccattacgct cgtcatcaaa atcactcgca tcaaccaaac     900
cgttattcat tcgtgattgc gcctgagcga acgaaatac gcgatcgctg ttaaaaggac      960
aattacaaac aggaatcgaa tgcaaccggc gcaggaacac tgccagcgca tcaacaatat     1020
tttcacctga atcaggatat tcttctaata cctggaatgc tgttttcccg gggatcgcag     1080
tggtgagtaa ccatgcatca tcaggagtac ggataaaatg cttgatggtc ggaagaggca     1140
taaattccgt cagccagttt agtctgacca tctcatctgt aacatcattg gcaacgctac     1200
ctttgccatg tttcagaaac aactctgcg catcgggctt cccatacaat cgatagattg       1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac     1380
cccttgtatt actgtttatg taagcagaca gttttattgt tcatgaccaa aatcccttaa     1440
cgtgagtttt cgttccactg agcgtcagac cccgtagaaa agatcaaagg atcttcttga    1500 gatcctttt ttctgcgcgt aatctgctgc ttgcaaacaa aaaaaccacc gctaccagcg       1560 gtggttgtt tgccggatca agagctacca actctttttc cgaaggtaac tggcttcagc      1620
agagcgcaga taccaaatac tgtccttcta gtgtagccgt agttaggcca ccacttcaag     1680
aactctgtag caccgcctac atacctcgct ctgctaatcc tgttaccagt ggctgctgcc     1740
agtggcgata agtcgtgtct taccgggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga     1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcagggggg cggagcctat ggaaaaacgc cagcaacgcg     2100
gcctttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg     2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt     2700
ggtcactgat gcctccgtgt aagggggatt tctgttcatg ggggtaatga taccgatgaa    2760
```

```
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttcccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatgcatatg cgttgtagcg tgtccaccga    5100
```

```
aaatgtgtct ttcaccgaaa ctgaaaccga aacgcgtcgt tctgcgaact acgaacctaa    5160
cagctgggac tatgattacc tgctgtcctc cgacacggac gagtccatcg aagtatacaa    5220
agacaaagcg aaaaagctgg aagccgaagt tcgtcgcgag attaataacg aaaaagcaga    5280
atttctgacc ctgctggaac tgattgacaa cgtccagcgc ctgggcctgg gttaccgttt    5340
cgagtctgat atccgtcgtg cgctggatcg cttcgtttcc tccggcggct tcgatgcggt    5400
aaccaagact tccctgcacg cgacggcact gtctttccgt ctgctgcgtc aacacggttt    5460
tgaggtttct caggaagcgt tcagcggctt caaagaccaa aacggcaact tcctggagaa    5520
cctgaaggaa gatatcaaag ctatcctgag cctgtacgag gccagcttcc tggctctgga    5580
aggcgaaaac atcctggacg aggcgaaggt tttcgcaatc tctcatctga agaactgtc     5640
tgaagaaaag atcggtaaag atctggcaga acaggtgaac catgcactgg aactgccact    5700
gcatcgccgt actcagcgtc tggaagcagt actgtctatc gaggcctacc gtaaaaagga    5760
ggacgcggat caggttctgc tggagctggc aattctggat tacaacatga tccagtctgt    5820
ataccagcgt gatctgcgtg aaacgtcccg ttggtggcgt cgtgtgggtc tggcgaccaa    5880
actgcacttt gctcgtgacc gcctgattga gagcttctac tgggccgtgg gtgtagcatt    5940
cgaaccgcaa tactccgact gccgtaactc cgtcgcaaaa atgttttctt tcgtaaccat    6000
tatcgacgat atctacgatg tatacggcac cctggacgaa ctggagctgt ttactaacgc    6060
agttgagcgt tgggacgtaa acgccatcga cgatctgccg gattacatga aactgtgctt    6120
tctggctctg tataacacta ttaacgaaat cgcctacgac aacctgaaag aaaaaggtga    6180
gaacatcctg ccgtatctga ccaaagcctg ggctgacctg tgcaacgctt tcctgcaaga    6240
agccaagtgg ctgtacaaca atctactcc gacctttgac gaatacttcg caacgcatg     6300
gaaatcctct tctggcccgc tgcaactggt gttcgcttac ttcgctgtcg tgcagaacat    6360
taaaaaggaa gagatcgaaa acctgcaaaa ataccatgac atcatctctc gtccttccca    6420
tatcttccgt ctgtgcaatg acctggctag cgcgtctgcg gaaattgcgc gtggtgaaac    6480
cgcaaatagc gtttcttgtt acatgcgcac taaaggtatc tccgaagaac tggctaccga    6540
aagcgtgatg aatctgatcg atgaaacctg gaaaaagatg aacaaggaaa actgggtgg    6600
tagcctgttc gcgaaaccgt tcgtggaaac cgcgatcaac ctggcacgtc aatctcactg    6660
cacttatcat aacggcgacg cgcataccct ccggatgag ctgaccccgca aacgcgttct    6720
gtctgtaatc actgaaccga ttctgccgtt tgaacgctaa ggatccgaat tcgagctccg    6780
tcgacaagct tgcggccgca ctcgagcacc accaccacca ccactgagat ccggctgcta    6840
acaaagcccg aaaggaagct gagttggctg ctgccaccgc tgagcaataa ctagcataac    6900
cccttggggc ctctaaacgg gtcttgaggg gttttttgct gaaaggagga actatatccg    6960
gat                                                                    6963
```

<210> SEQ ID NO 162
<211> LENGTH: 578
<212> TYPE: PRT
<213> ORGANISM: Artificial Sequence
<220> FEATURE:
<223> OTHER INFORMATION: Synthetic Construct

<400> SEQUENCE: 162

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

```
His Pro Phe Thr Met Arg Arg Ser Ala Asn Tyr Glu Pro Asn Ser Trp
        35                  40                  45

Asp Tyr Asp Tyr Leu Leu Ser Ser Asp Thr Asp Glu Ser Ile Glu Val
    50                  55                  60

Tyr Lys Asp Lys Ala Lys Lys Leu Glu Ala Glu Val Arg Arg Glu Ile
65                  70                  75                  80

Asn Asn Glu Lys Ala Glu Phe Leu Thr Leu Leu Glu Leu Ile Asp Asn
                85                  90                  95

Val Gln Arg Leu Gly Leu Gly Tyr Arg Phe Glu Ser Asp Ile Arg Gly
                100                 105                 110

Ala Leu Asp Arg Phe Val Ser Ser Gly Gly Phe Asp Ala Val Thr Lys
                115                 120                 125

Thr Ser Leu His Gly Thr Ala Leu Ser Phe Arg Leu Leu Arg Gln His
                130                 135                 140

Gly Phe Glu Val Ser Gln Glu Ala Phe Ser Gly Phe Lys Asp Gln Asn
145                 150                 155                 160

Gly Asn Phe Leu Glu Asn Leu Lys Glu Asp Ile Lys Ala Ile Leu Ser
                165                 170                 175

Leu Tyr Glu Ala Ser Phe Leu Ala Leu Glu Gly Glu Asn Ile Leu Asp
                180                 185                 190

Glu Ala Lys Val Phe Ala Ile Ser His Leu Lys Glu Leu Ser Glu Glu
                195                 200                 205

Lys Ile Gly Lys Glu Leu Ala Glu Gln Val Asn His Ala Leu Glu Leu
210                 215                 220

Pro Leu His Arg Arg Thr Gln Arg Leu Glu Ala Val Trp Ser Ile Glu
225                 230                 235                 240

Ala Tyr Arg Lys Lys Glu Asp Ala Asn Gln Val Leu Leu Glu Leu Ala
                245                 250                 255

Ile Leu Asp Tyr Asn Met Ile Gln Ser Val Tyr Gln Arg Asp Leu Arg
                260                 265                 270

Glu Thr Ser Arg Trp Trp Arg Arg Val Gly Leu Ala Thr Lys Leu His
                275                 280                 285

Phe Ala Arg Asp Arg Leu Ile Glu Ser Phe Tyr Trp Ala Val Gly Val
                290                 295                 300

Ala Phe Glu Pro Gln Tyr Ser Asp Cys Arg Asn Ser Val Ala Lys Met
305                 310                 315                 320

Phe Ser Phe Val Thr Ile Ile Asp Asp Ile Tyr Asp Val Tyr Gly Thr
                325                 330                 335

Leu Asp Glu Leu Glu Leu Phe Thr Asp Ala Val Glu Arg Trp Asp Val
                340                 345                 350

Asn Ala Ile Asn Asp Leu Pro Asp Tyr Met Lys Leu Cys Phe Leu Ala
                355                 360                 365

Leu Tyr Asn Thr Ile Asn Glu Ile Ala Tyr Asp Asn Leu Lys Asp Lys
                370                 375                 380

Gly Glu Asn Ile Leu Pro Tyr Leu Thr Lys Ala Trp Ala Asp Leu Cys
385                 390                 395                 400

Asn Ala Phe Leu Gln Glu Ala Lys Trp Leu Tyr Asn Lys Ser Thr Pro
                405                 410                 415

Thr Phe Asp Asp Tyr Phe Gly Asn Ala Trp Lys Ser Ser Ser Gly Pro
                420                 425                 430

Leu Gln Leu Val Phe Ala Tyr Phe Ala Val Val Gln Asn Ile Lys Lys
                435                 440                 445
```

| | | | | | | | | | | | | | | |
|---|---|---|---|---|---|---|---|---|---|---|---|---|---|---|
|Glu|Glu|Ile|Glu|Asn|Leu|Gln|Lys|Tyr|His|Asp|Thr|Ile|Ser|Arg|Pro|
| |450| | | |455| | | |460| | | | | |
|Ser|His|Ile|Phe|Arg|Leu|Cys|Asn|Asp|Leu|Ala|Ser|Ala|Ser|Ala|Glu|
|465| | | | |470| | | | |475| | | | |480|
|Ile|Ala|Arg|Gly|Glu|Thr|Ala|Asn|Ser|Val|Ser|Cys|Tyr|Met|Arg|Thr|
| | | | |485| | | | |490| | | | |495| |
|Lys|Gly|Ile|Ser|Glu|Glu|Leu|Ala|Thr|Glu|Ser|Val|Met|Asn|Leu|Ile|
| | | |500| | | | |505| | | | |510| | |
|Asp|Glu|Thr|Trp|Lys|Lys|Met|Asn|Lys|Glu|Lys|Leu|Gly|Gly|Ser|Leu|
| | |515| | | | |520| | | | |525| | | |
|Phe|Ala|Lys|Pro|Phe|Val|Glu|Thr|Ala|Ile|Asn|Leu|Ala|Arg|Gln|Ser|
| |530| | | | |535| | | | |540| | | | |
|His|Cys|Thr|Tyr|His|Asn|Gly|Asp|Ala|His|Thr|Ser|Pro|Asp|Glu|Leu|
|545| | | | |550| | | | |555| | | | |560|
|Thr|Arg|Lys|Arg|Val|Leu|Ser|Val|Ile|Thr|Glu|Pro|Ile|Leu|Pro|Phe|
| | | | |565| | | | |570| | | | |575| |
|Glu|Arg| | | | | | | | | | | | | | |

<210> SEQ ID NO 163
<211> LENGTH: 7370
<212> TYPE: DNA
<213> ORGANISM: Artificial Sequence
<220> FEATURE:
<223> OTHER INFORMATION: Synthetic Construct

<400> SEQUENCE: 163

```
aagggcgagc tcaacgatcc ggctgctaac aaagcccgaa aggaagctga gttggctgct      60
gccaccgctg agcaataact agcataaccc cttggggcct ctaaacgggt cttgaggagt     120
ttttgctga aggaggaac tatatccgga tatcccgcaa gaggcccggc agtaccggca      180
taaccaagcc tatgcctaca gcatccaggg tgacggtgcc gaggatgacg atgagcgcat     240
tgttagattt catacacggt gcctgactgc gttagcaatt taactgtgat aaactaccgc     300
attaaagctt atcgatgata agctgtcaaa catgagaatt aattcttgaa gacgaaaggg     360
cctcgtgata cgcctatttt tataggttaa tgtcatgata ataatggttt cttagacgtc     420
aggtggcact tttcggggaa atgtgcgcgg aacccctatt tgtttatttt tctaaataca     480
ttcaaatatg tatccgctca tgagacaata accctgataa atgcttcaat aatattgaaa     540
aaggaagagt atgattgaac aagatggatt gcacgcaggt tctccggccg cttgggtgga     600
gaggctattc ggctatgact gggcacaact gacaatcggc tgctctgatg ccgccgtgtt     660
ccggctgtca gcgcaggggc gcccggttct ttttgtcaag accgacctgt ccggtgccct     720
gaatgaactg caggacgagg cagcgcggct atcgtggctg gccacgacgg gcgttccttg     780
cgcagctgtg ctcgacgttg tcactgaagc gggaagggac tggctgctat tgggcgaagt     840
gccggggcag gatctcctgt catctcacct tgctcctgcc gagaaagtat ccatcatggc     900
tgatgcaatg cggcggctgc atacgcttga tccggctacc tgcccattcg accaccaagc     960
gaaacatcgc atcgagcggg cacgtactcg gatggaagcc ggtcttgtcg atcaggatga    1020
tctggacgaa gagcatcagg ggctcgcgcc agccgaactg ttcgccaggc tcaaggcgcg    1080
catgcccgac ggcgaggatc tcgtcgtgac acatggcgat gcctgcttgc cgaatatcat    1140
ggtggaaaat ggccgctttt ctggattcat cgactgtggc cggctgggtg tggcggaccg    1200
ctatcaggac atagcgttgg ctacccgtga tattgctgaa gagcttggcg gcgaatgggc    1260
tgaccgcttc ctcgtgcttt acggtatcgc cgctcccgat tcgcagcgca tcgccttcta    1320
```

-continued

```
tcgccttctt gacgagttct tctgagcggg actctggggt tcgaaatgac cgaccaagcg    1380
acgcctaact gtcagaccaa gtttactcat atatacttta gattgattta aaacttcatt    1440
tttaatttaa aaggatctag gtgaagatcc ttttttgataa tctcatgacc aaaatcccctt   1500 aacgtgagtt ttcgttccac tgagcgtcag accccgtaga aaagatcaaa ggatcttctt    1560
gagatccttt ttttctgcgc gtaatctgct gcttgcaaac aaaaaaacca ccgctaccag    1620
cggtggtttg tttgccggat caagagctac caactctttt tccgaaggta actggcttca    1680
gcagagcgca gataccaaat actgtccttc tagtgtagcc gtagttaggc caccacttca    1740
agaactctgt agcaccgcct acatacctcg ctctgctaat cctgttacca gtggctgctg    1800
ccagtggcga taagtcgtgt cttaccgggt tggactcaag acgatagtta ccggataagg    1860
cgcagcggtc gggctgaacg gggggttcgt gcacacagcc cagcttggag cgaacgacct    1920
acaccgaact gagataccta cagcgtgagc tatgagaaag cgccacgctt cccgaaggga    1980
gaaaggcgga caggtatccg gtaagcggca gggtcggaac aggagagcgc acgagggagc    2040 ttccagggggg aaacgcctgg tatctttata gtcctgtcgg gtttcgccac ctctgacttg    2100
agcgtcgatt tttgtgatgc tcgtcagggg gcggagcct  atggaaaaac gccagcaacg    2160 cggcctttttt acggttcctg gccttttgct ggccttttgc tcacatgttc tttcctgcgt    2220
tatcccctga ttctgtggat aaccgtatta ccgcctttga gtgagctgat accgctcgcc    2280
gcagccgaac gaccgagcgc agcgagtcag tgagcgagga agcggaagag cgcctgatgc    2340
ggtattttct ccttacgcat ctgtgcggta tttcacaccg caatggtgca ctctcagtac    2400
aatctgctct gatgccgcat agttaagcca gtatacactc cgctatcgct acgtgactgg    2460
gtcatggctg cgccccgaca cccgccaaca cccgctgacg cgccctgacg ggcttgtctg    2520
ctcccggcat ccgcttacag acaagctgtg accgtctccg ggagctgcat gtgtcagagg    2580
ttttcaccgt catcaccgaa acgcgcgagg cagctgcggt aaagctcatc agcgtggtcg    2640
tgaagcgatt cacagatgtc tgcctgttca tccgcgtcca gctcgttgag tttctccaga    2700
agcgttaatg tctggcttct gataaagcgg gccatgttaa gggcggtttt ttcctgtttg    2760
gtcactgatg cctccgtgta agggggattt ctgttcatgg gggtaatgat accgatgaaa    2820
cgagagagga tgctcacgat acgggttact gatgatgaac atgcccggtt actggaacgt    2880
tgtgagggta acaactggc ggtatggatg cggcgggacc agagaaaaat cactcagggt     2940
caatgccagc gcttcgttaa tacagatgta ggtgttccac agggtagcca gcagcatcct    3000
gcgatgcaga tccggaacat aatggtgcag gcgctgact tccgcgtttc cagactttac     3060
gaaacacgga aaccgaagac cattcatgtt gttgctcagg tcgcagacgt tttgcagcag    3120
cagtcgcttc acgttcgctc gcgtatcggt gattcattct gctaaccagt aaggcaaccc    3180
cgccagccta gccgggtcct caacgacagg agcacgatca tgcgcacccg tggccaggac    3240
ccaacgctgc ccgagatgcg ccgcgtgcgg ctgctggaga tggcggacgc gatggatatg    3300
ttctgccaag ggttggtttg cgcattcaca gttctccgca agaattgatt ggctccaatt    3360
cttggagtgg tgaatccgtt agcgaggtgc cgccggcttc cattcaggtc gaggtggccc    3420
ggctccatgc accgcgacgc aacgcgggga ggcagacaag gtatagggcg cgcctacaa    3480 tccatgccaa cccgttccat gtgctcgccg aggcggcata aatcgccgtg acgatcagcg    3540
gtccaatgat cgaagttagg ctggtaagag ccgcgagcga tccttgaagc tgtccctgat    3600
ggtcgtcatc tacctgcctg gacagcatgg cctgcaacgc gggcatcccg atgccgccgg    3660
```

```
aagcgagaag aatcataatg gggaaggcca tccagcctcg cgtcgcgaac gccagcaaga    3720
cgtagcccag cgcgtcggcc gccatgccgg cgataatggc ctgcttctcg ccgaaacgtt    3780
tggtggcggg accagtgacg aaggcttgag cgagggcgtg caagattccg aataccgcaa    3840
gcgacaggcc gatcatcgtc gcgctccagc gaaagcggtc ctcgccgaaa atgacccaga    3900
gcgctgccgg cacctgtcct acgagttgca tgataaagaa gacagtcata agtgcggcga    3960
cgatagtcat gccccgcgcc caccggaagg agctgactgg gttgaaggct ctcaagggca    4020
tcggtcgaga tcccggtgcc taatgagtga gctaacttac attaattgcg ttgcgctcac    4080
tgcccgcttt ccagtcggga aacctgtcgt gccagctgca ttaatgaatc ggccaacgcg    4140
cggggagagg cggtttgcgt attgggcgcc agggtggttt ttcttttcac cagtgagacg    4200
ggcaacagct gattgccctt caccgcctgg ccctgagaga gttgcagcaa gcggtccacg    4260
ctggtttgcc ccagcaggcg aaaatcctgt ttgatggtgg ttaacggcgg gatataacat    4320
gagctgtctt cggtatcgtc gtatcccact accgagatat ccgcaccaac gcgcagcccg    4380
gactcggtaa tggcgcgcat gccgcccagc gccatctgat cgttggcaac cagcatcgca    4440
gtgggaacga tgccctcatt cagcatttgc atggtttgtt gaaaaccgga catggcactc    4500
cagtcgcctt cccgttccgc tatcggctga atttgattgc gagtgagata tttatgccag    4560
ccagccagac gcagacgcgc cgagacagaa cttaatgggc ccgctaacag cgcgatttgc    4620
tggtgaccca atgcgaccag atgctccacg cccagtcgcg taccgtcttc atgggagaaa    4680
ataatactgt tgatgggtgt ctggtcagag acatcaagaa ataacgccgg aacattagtg    4740
caggcagctt ccacagcaat ggcatcctgg tcatccagcg atagttaat gatcagccca     4800 ctgacgcgtt gcgcgagaag attgtgcacc gccgctttac aggcttcgac gccgcttcgt    4860
tctaccatcg acaccaccac gctggcaccc agttgatcgg cgcgagattt aatcgccgcg    4920
acaatttgcg acggcgcgtg cagggccaga ctggaggtgg caacgccaat cagcaacgac    4980
tgtttgcccg ccagttgttg tgccacgcgg ttgggaatgt aattcagctc cgccatcgcc    5040
gcttccactt ttttcccgcgt tttcgcagaa acgtggctgg cctggttcac cacgcgggaa    5100
acggtctgat aagagacacc ggcatactct gcgacatcgt ataacgttac tggtttcaca    5160
ttcaccaccc tgaattgact ctcttccggg cgctatcatg ccataccgcg aaaggttttg    5220
cgccattcga tggtgtccgg gatctcgacg ctctccctta tgcgactcct gcattaggaa    5280
gcagcccagt agtaggttga ggccgttgag caccgccgcc gcaaggaatg gtgcatgcaa    5340
ggagatggcg cccaacagtc ccccggccac ggggcctgcc accataccca cgccgaaaca    5400
agcgctcatg agcccgaagt ggcgagcccg atcttcccca tcggtgatgt cggcgatata    5460
ggcgccagca accgcacctg tggcgccggt gatgccggcc acgatgcgtc cggcgtagag    5520
gatcgagatc tcgatcccgc gaaattaata cgactcacta tagggggaatt gtgagcggat    5580 aacaattccc ctctagaaat aattttgttt aactttaaga aggagatata catatgcggg    5640
gttctcatca tcatcatcat catggtatgg ctagcatgac tggtggacag caaatgggtc    5700
gggatctgta cgacgatgac gataaggatc atcccttcac catgcgtcgt tctgcgaact    5760
acgaacctaa cagctgggac tatgattacc tgctgtcctc cgacacggac gagtccatcg    5820
aagtatacaa agacaaagcg aaaaagctgg aagccgaagt tcgtcgcgag attaataacg    5880
aaaaagcaga atttctgacc ctgctggaac tgattgacaa cgtccagcgc ctgggcctgg    5940
gttaccgttt cgagtctgat atccgtggtg cgctggatcg cttcgtttcc tccggcggct    6000
tcgatgcggt aaccaagact tccctgcacg gtacggcact gtctttccgt ctgctgcgtc    6060
```

```
aacacggttt tgaggtttct caggaagcgt tcagcggctt caaagaccaa aacggcaact    6120
tcctggagaa cctgaaggaa gatatcaaag ctatcctgag cctgtacgag gccagcttcc    6180
tggctctgga aggcgaaaac atcctggacg aggcgaaggt tttcgcaatc tctcatctga    6240
aagaactgtc tgaagaaaag atcggtaaag agctggcaga acaggtgaac catgcactgg    6300
aactgccact gcatcgccgt actcagcgtc tggaagcagt atggtctatc gaggcctacc    6360
gtaaaaagga ggacgcgaat caggttctgc tggagctggc aattctggat acaacatga    6420 tccagtctgt ataccagcgt gatctgcgtg aaacgtcccg ttggtggcgt cgtgtgggtc    6480
tggcgaccaa actgcacttt gctcgtgacc gcctgattga gagcttctac tgggccgtgg    6540
gtgtagcatt cgaaccgcaa tactccgact gccgtaactc cgtcgcaaaa atgttttctt    6600
tcgtaaccat tatcgacgat atctacgatg tatacggcac cctggacgaa ctggagctgt    6660
ttactgatgc agttgagcgt tgggacgtaa acgccatcaa cgacctgccg gattacatga    6720
aactgtgctt tctggctctg tataacacta ttaacgaaat cgcctacgac aacctgaaag    6780
ataaaggtga gaacatcctg ccgtatctga ccaaagcctg gctgacctg tgcaacgctt    6840 tcctgcaaga agccaagtgg ctgtacaaca atctactcc gacctttgac gactacttcg    6900
gcaacgcatg gaaatcctct tctggcccgc tgcaactggt gttcgcttac ttcgctgtcg    6960
tgcagaacat taaaaaggaa gagatcgaaa acctgcaaaa ataccatgac accatctctc    7020
gtccttccca tatcttccgt ctgtgcaatg acctggctag cgcgtctgcg gaaattgcgc    7080
gtggtgaaac cgcaaatagc gtttcttgtt acatgcgcac taaaggtatc tccgaagaac    7140
tggctaccga aagcgtgatg aatctgatcg atgaaacctg gaaaaagatg aacaaggaaa    7200
aactgggtgg tagcctgttc gcgaaaccgt tcgtggaaac cgcgatcaac ctggcacgtc    7260
aatctcactg cacttatcat aacggcgacg cgcataccctc tccggatgag ctgacccgca    7320
aacgcgttct gtctgtaatc actgaaccga ttctgccgtt tgaacgctaa                7370
```

<210> SEQ ID NO 164
<211> LENGTH: 578
<212> TYPE: PRT
<213> ORGANISM: Artificial Sequence
<220> FEATURE:
<223> OTHER INFORMATION: Synthetic Construct

<400> SEQUENCE: 164

```
Met Arg Gly Ser His His His His His His Gly Met Ala Ser Met Thr
 1               5                  10                  15

Gly Gly Gln Gln Met Gly Arg Asp Leu Tyr Asp Asp Asp Lys Asp
            20                  25                  30

His Pro Phe Thr Met Arg Arg Ser Ala Asn Tyr Glu Pro Asn Ser Trp
        35                  40                  45

Asp Tyr Asp Tyr Leu Leu Ser Ser Asp Thr Asp Glu Ser Ile Glu Val
    50                  55                  60

His Lys Asp Lys Ala Lys Lys Leu Glu Ala Glu Val Arg Arg Glu Ile
65                  70                  75                  80

Asn Asn Glu Lys Ala Glu Phe Leu Thr Leu Leu Glu Leu Ile Asp Asn
                85                  90                  95

Val Gln Arg Leu Gly Leu Gly Tyr Arg Phe Glu Ser Asp Ile Arg Arg
            100                 105                 110

Ala Leu Asp Arg Phe Val Ser Ser Gly Gly Phe Asp Gly Val Thr Lys
        115                 120                 125
```

```
Thr Ser Leu His Gly Thr Ala Leu Ser Phe Arg Leu Arg Gln His
    130                 135                 140
Gly Phe Glu Val Ser Gln Glu Ala Phe Ser Gly Phe Lys Asp Gln Asn
145                 150                 155                 160
Gly Asn Phe Leu Glu Asn Leu Lys Glu Asp Ile Lys Ala Ile Leu Ser
                165                 170                 175
Leu Tyr Glu Ala Ser Phe Leu Ala Leu Glu Gly Glu Asn Ile Leu Asp
            180                 185                 190
Glu Ala Lys Val Phe Ala Ile Ser His Leu Lys Glu Leu Ser Glu Glu
        195                 200                 205
Lys Ile Gly Lys Glu Leu Ala Glu Gln Val Ser His Ala Leu Glu Leu
    210                 215                 220
Pro Leu His Arg Arg Thr Gln Arg Leu Glu Ala Val Trp Ser Ile Glu
225                 230                 235                 240
Ala Tyr Arg Lys Lys Glu Asp Ala Asn Gln Val Leu Glu Leu Ala
                245                 250                 255
Ile Leu Asp Tyr Asn Met Ile Gln Ser Val Tyr Gln Arg Asp Leu Arg
                260                 265                 270
Glu Thr Ser Arg Trp Trp Arg Arg Val Gly Leu Ala Thr Lys Leu His
            275                 280                 285
Phe Ala Arg Asp Arg Leu Ile Glu Ser Phe Tyr Trp Ala Val Gly Val
        290                 295                 300
Ala Phe Glu Pro Gln Tyr Ser Asp Cys Arg Asn Ser Val Ala Lys Met
305                 310                 315                 320
Phe Ser Phe Val Thr Ile Ile Asp Asp Ile Tyr Asp Val Tyr Gly Thr
                325                 330                 335
Leu Asp Glu Leu Glu Leu Phe Thr Asp Ala Val Glu Arg Trp Asp Val
            340                 345                 350
Asn Ala Ile Asn Asp Leu Pro Asp Tyr Met Lys Leu Cys Phe Leu Ala
        355                 360                 365
Leu Tyr Asn Thr Ile Asn Glu Ile Ala Tyr Asp Asn Leu Lys Asp Lys
    370                 375                 380
Gly Glu Asn Ile Leu Pro Tyr Leu Thr Lys Ala Trp Ala Asp Leu Cys
385                 390                 395                 400
Asn Ala Phe Leu Gln Glu Ala Lys Trp Leu Tyr Asn Lys Ser Thr Pro
                405                 410                 415
Thr Phe Asp Asp Tyr Phe Gly Asn Ala Trp Lys Ser Ser Gly Pro
            420                 425                 430
Leu Gln Leu Ile Phe Ala Tyr Phe Ala Val Val Gln Asn Ile Lys Lys
        435                 440                 445
Glu Glu Ile Glu Asn Leu Gln Lys Tyr His Asp Ile Ile Ser Arg Pro
    450                 455                 460
Ser His Ile Phe Arg Leu Cys Asn Asp Leu Ala Ser Ala Ser Ala Glu
465                 470                 475                 480
Ile Ala Arg Gly Glu Thr Ala Asn Ser Val Ser Cys Tyr Met Arg Thr
                485                 490                 495
Lys Gly Ile Ser Glu Glu Leu Ala Thr Glu Ser Val Met Asn Leu Ile
            500                 505                 510
Asp Glu Thr Trp Lys Lys Met Asn Lys Glu Lys Leu Gly Gly Ser Leu
        515                 520                 525
Phe Ala Lys Pro Phe Val Glu Thr Ala Ile Asn Leu Ala Arg Gln Ser
    530                 535                 540
His Cys Thr Tyr His Asn Gly Asp Ala His Thr Ser Pro Asp Glu Leu
```

```
545                 550                 555                 560
Thr Arg Lys Arg Val Leu Ser Val Ile Thr Glu Pro Ile Leu Pro Phe
                565                 570                 575
Glu Arg

<210> SEQ ID NO 165
<211> LENGTH: 7370
<212> TYPE: DNA
<213> ORGANISM: Artificial Sequence
<220> FEATURE:
<223> OTHER INFORMATION: Synthetic Construct

<400> SEQUENCE: 165
cgtcgttctg cgaactacga acctaacagc tgggactatg attacctgct gtcctccgac      60
acggacgagt ccatcgaagt acacaaagac aaagcgaaaa agctggaagc cgaagttcgt     120
cgcgagatta ataacgaaaa agcagaattt ctgaccctgc tggaactgat tgacaacgtc     180
cagcgcctgg gcctgggtta ccgtttcgag tctgatatcc gtcgtgcgct ggatcgcttc     240
gtttcctccg gcggcttcga tggcgtaacc aagacttccc tgcacggtac ggcactgtct     300
ttccgtctgc tgcgtcaaca cggttttgag gtttctcagg aagcgttcag cggcttcaaa     360
gaccaaaacg gcaacttcct ggagaacctg aaggaagata tcaaagctat cctgagcctg     420
tacgaggcca gcttcctggc tctggaaggc gaaacatcc tggacgaggc gaaggttttc     480
gcaatctctc atctgaaaga actgtctgaa gaaaagatcg gtaaagagct ggcagaacag     540
gtgtcccatg cactggaact gccactgcat cgccgtactc agcgtctgga agcagtatgg     600
tctatcgagg cctaccgtaa aaaggaggac gcgaaccagg ttctgctgga gctggcaatt     660
ctggattaca acatgatcca gtctgtatac cagcgtgatc tgcgtgaaac gtcccgttgg     720
tggcgtcgtg tgggtctggc gaccaaactg cactttgctc gtgaccgcct gattgagagc     780
ttctactggg ccgtgggtgt agcattcgaa ccgcaatact ccgactgccg taactccgtc     840
gcaaaaatgt tttctttcgt aaccattatc gacgatatct acgatgtata cggcaccctg     900
gacgaactgg agctgtttac tgatgcagtt gagcgttggg acgtaaacgc catcaacgac     960
ctgccggatt acatgaaact gtgctttctg gctctgtata acactattaa cgaaatcgcc    1020
tacgacaacc tgaaagataa aggtgagaac atcctgccgt atctgaccaa agcctgggct    1080
gacctgtgca acgctttcct gcaagaagcc aagtggctgt acaacaaatc tactccgacc    1140
tttgacgact acttcggcaa cgcatggaaa tcctcttctg gcccgctgca actgatcttc    1200
gcttacttcg ctgtcgtgca gaacattaaa aggaagaga tcgaaaacct gcaaaaatac    1260
catgacatca tctctcgtcc ttcccatatc ttccgtctgt gcaatgacct ggctagcgcg    1320
tctgcggaaa ttgcgcgtgg tgaaaccgca aatagcgttt cttgttacat gcgcactaaa    1380
ggtatctccg aagaactggc taccgaaagc gtgatgaatc tgatcgatga acctggaaa    1440
aagatgaaca aggaaaaact gggtggtagc ctgttcgcga aaccgttcgt ggaaaccgcg    1500
atcaacctgg cacgtcaatc tcactgcact tatcataacg cgacgcgca tacctctccg    1560
gatgagctga cccgcaaacg cgttctgtct gtaatcactg aaccgattct gccgtttgaa    1620
cgctaaaagg gcgagctcaa cgatccggct gctaacaaag cccgaaagga agctgagttg    1680
gctgctgcca ccgctgagca ataactagca tanaccccttg gggcctctaa acgggtcttg    1740
aggagttttt tgctgaaagg aggaactata tccggatatc ccgcaagagg cccggcagta    1800
ccggcataac caagcctatg cctacagcat ccagggtgac ggtgccgagg atgacgatga    1860
```

-continued

```
gcgcattgtt agatttcata cacggtgcct gactgcgtta gcaatttaac tgtgataaac    1920
taccgcatta aagcttatcg atgataagct gtcaaacatg agaattaatt cttgaagacg    1980
aaagggcctc gtgatacgcc tatttttata ggttaatgtc atgataataa tggtttctta    2040
gacgtcaggt ggcacttttc ggggaaatgt gcgcggaacc cctatttgtt tattttctta    2100
aatacattca aatatgtatc cgctcatgag acaataaccc tgataaatgc ttcaataata    2160
ttgaaaaagg aagagtatga ttgaacaaga tggattgcac gcaggttctc cggccgcttg    2220
ggtggagagg ctattcggct atgactgggc acaactgaca atcggctgct ctgatgccgc    2280
cgtgttccgg ctgtcagcgc aggggcgccc ggttcttttt gtcaagaccg acctgtccgg    2340
tgccctgaat gaactgcagg acgaggcagc gcggctatcg tggctggcca cgacgggcgt    2400
tccttgcgca gctgtgctcg acgttgtcac tgaagcggga agggactggc tgctattggg    2460
cgaagtgccg gggcaggatc tcctgtcatc tcaccttgct cctgccgaga agtatccat    2520 catggctgat gcaatgcggc ggctgcatac gcttgatccg gctacctgcc cattcgacca    2580
ccaagcgaaa catcgcatcg agcgggcacg tactcggatg aagccggtc ttgtcgatca    2640 ggatgatctg gacgaagagc atcaggggct cgcgccagcc gaactgttcg ccaggctcaa    2700
ggcgcgcatg cccgacggcg aggatctcgt cgtgacacat ggcgatgcct gcttgccgaa    2760
tatcatggtg aaaatggcc gcttttctgg attcatcgac tgtggccggc tgggtgtggc    2820
ggaccgctat caggacatag cgttggctac ccgtgatatt gctgaagagc ttggcggcga    2880
atgggctgac cgcttcctcg tgctttacgg tatcgccgct cccgattcgc agcgcatcgc    2940
cttctatcgc cttcttgacg agttcttctg agcgggactc tggggttcga atgaccgac    3000 caagcgacgc ctaactgtca gaccaagttt actcatatat actttagatt gatttaaaac    3060 ttcatttta atttaaaagg atctaggtga agatccttt tgataatctc atgaccaaaa    3120
tcccttaacg tgagttttcg ttccactgag cgtcagaccc cgtagaaaag atcaaggat    3180 cttcttgaga tccttttttt ctgcgcgtaa tctgctgctt gcaaacaaaa aaaccaccgc    3240
taccagcggt ggtttgtttg ccggatcaag agctaccaac tcttttccg aaggtaactg    3300 gcttcagcag agcgcagata ccaaatactg tccttctagt gtagccgtag ttaggccacc    3360
acttcaagaa ctctgtagca ccgcctacat acctcgctct gctaatcctg ttaccagtgg    3420
ctgctgccag tggcgataag tcgtgtctta ccgggttgga ctcaagacga tagttaccgg    3480
ataaggcgca gcggtcgggc tgaacggggg gttcgtgcac acagcccagc ttggagcgaa    3540
cgacctacac cgaactgaga tacctacagc gtgagctatg agaaagcgcc acgcttcccg    3600
aagggagaaa ggcggacagg tatccggtaa gcggcagggt cggaacagga gagcgcacga    3660
gggagcttcc aggggggaaac gcctggtatc tttatagtcc tgtcgggttt cgccacctct    3720
gacttgagcg tcgatttttg tgatgctcgt caggggggcg gagcctatgg aaaaacgcca    3780
gcaacgcggc cttttttacgg ttcctggcct tttgctggcc ttttgctcac atgttctttc    3840
ctgcgttatc ccctgattct gtggataacc gtattaccgc ctttgagtga gctgataccg    3900
ctcgccgcag ccgaacgacc gagcgcagcg agtcagtgag cgaggaagcg gaagagcgcc    3960
tgatgcggta ttttctcctt acgcatctgt gcggtatttc acaccgcaat ggtgcactct    4020
cagtacaatc tgctctgatg ccgcatagtt aagccagtat acactccgct atcgctacgt    4080
gactgggtca tggctgcgcc ccgacacccg ccaacacccg ctgacgcgcc ctgacgggct    4140
tgtctgctcc cggcatccgc ttacagacaa gctgtgaccg tctccgggag ctgcatgtgt    4200
cagaggtttt caccgtcatc accgaaacgc gcgaggcagc tgcggtaaag ctcatcagcg    4260
```

```
tggtcgtgaa gcgattcaca gatgtctgcc tgttcatccg cgtccagctc gttgagtttc    4320
tccagaagcg ttaatgtctg gcttctgata aagcgggcca tgttaagggc ggttttttcc    4380
tgtttggtca ctgatgcctc cgtgtaaggg ggatttctgt tcatgggggt aatgataccg    4440
atgaaacgag agaggatgct cacgatacgg gttactgatg atgaacatgc ccggttactg    4500
gaacgttgtg agggtaaaca actggcggta tggatgcggc gggaccagag aaaaatcact    4560
cagggtcaat gccagcgctt cgttaataca gatgtaggtg ttccacaggg tagccagcag    4620
catcctgcga tgcagatccg gaacataatg gtgcagggcg ctgacttccg cgtttccaga    4680
ctttacgaaa cacggaaacc gaagaccatt catgttgttg ctcaggtcgc agacgttttg    4740
cagcagcagt cgcttcacgt tcgctcgcgt atcggtgatt cattctgcta accagtaagg    4800
caaccccgcc agcctagccg ggtcctcaac gacaggagca cgatcatgcg cacccgtggc    4860
caggacccaa cgctgcccga gatgcgccgc gtgcggctgc tggagatggc ggacgcgatg    4920
gatatgttct gccaagggtt ggtttgcgca ttcacagttc tccgcaagaa ttgattggct    4980
ccaattcttg gagtggtgaa tccgttagcg aggtgccgcc ggcttccatt caggtcgagg    5040
tggcccggct ccatgcaccg cgacgcaacg cggggaggca gacaaggtat agggcggcgc    5100
ctacaatcca tgccaacccg ttccatgtgc tcgccgaggc ggcataaatc gccgtgacga    5160
tcagcggtcc aatgatcgaa gttaggctgg taagagccgc gagcgatcct tgaagctgtc    5220
cctgatggtc gtcatctacc tgcctggaca gcatggcctg caacgcgggc atcccgatgc    5280
cgccggaagc gagaagaatc ataatgggga aggccatcca gcctcgcgtc gcgaacgcca    5340
gcaagacgta gcccagcgcg tcggccgcca tgccggcgat aatggcctgc ttctcgccga    5400
aacgtttggt ggcgggacca gtgacgaagg cttgagcgag ggcgtgcaag attccgaata    5460
ccgcaagcga caggccgatc atcgtcgcgc tccagcgaaa gcggtcctcg ccgaaaatga    5520
cccagagcgc tgccggcacc tgtcctacga gttgcatgat aaagaagaca gtcataagtg    5580
cggcgacgat agtcatgccc cgcgcccacc ggaaggagct gactgggttg aaggctctca    5640
agggcatcgg tcgagatccc ggtgcctaat gagtgagcta acttacatta attgcgttgc    5700
gctcactgcc cgctttccag tcgggaaacc tgtcgtgcca gctgcattaa tgaatcggcc    5760
aacgcgcggg gagaggcggt ttgcgtattg ggcgccaggg tggtttttct tttcaccagt    5820
gagacgggca acagctgatt gcccttcacc gcctggccct gagagagttg cagcaagcgg    5880
tccacgctgg tttgccccag caggcgaaaa tcctgtttga tggtggttaa cggcgggata    5940
taacatgagc tgtcttcggt atcgtcgtat cccactaccg agatatccgc accaacgcgc    6000
agcccggact cggtaatggc gcgcattgcg cccagcgcca tctgatcgtt ggcaaccagc    6060
atcgcagtgg gaacgatgcc ctcattcagc atttgcatgg tttgttgaaa ccggacatg    6120 gcactccagt cgccttcccg ttccgctatc ggctgaattt gattgcgagt gagatattta    6180
tgccagccag ccagacgcag acgcgccgag acagaactta atgggcccgc taacagcgcg    6240
atttgctggt gacccaatgc gaccagatgc tccacgccca gtcgcgtacc gtcttcatgg    6300
gagaaaataa tactgttgat gggtgtctgg tcagagacat caagaaataa cgccggaaca    6360
ttagtgcagg cagcttccac agcaatggca tcctggtcat ccagcggata gttaatgatc    6420
agcccactga cgcgttgcgc gagaagattg tgcaccgccg ctttacaggc ttcgacgccg    6480
cttcgttcta ccatcgacac caccacgctg cacccagtt gatcggcgcg agatttaatc    6540
gccgcgacaa tttgcgacgg cgcgtgcagg gccagactgg aggtggcaac gccaatcagc    6600
```

```
aacgactgtt tgcccgccag ttgttgtgcc acgcggttgg gaatgtaatt cagctccgcc    6660
atcgccgctt ccacttttc ccgcgttttc gcagaaacgt ggctggcctg gttcaccacg    6720
cgggaaacgg tctgataaga gacaccggca tactctgcga catcgtataa cgttactggt    6780
ttcacattca ccaccctgaa ttgactctct tccgggcgct atcatgccat accgcgaaag    6840
gttttgcgcc attcgatggt gtccgggatc tcgacgctct cccttatgcg actcctgcat    6900
taggaagcag cccagtagta ggttgaggcc gttgagcacc gccgccgcaa ggaatggtgc    6960
atgcaaggag atggcgccca acagtccccc ggccacgggg cctgccacca tacccacgcc    7020
gaaacaagcg ctcatgagcc cgaagtggcg agcccgatct tccccatcgg tgatgtcggc    7080
gatataggcg ccagcaaccg cacctgtggc gccggtgatg ccggccacga tgcgtccggc    7140
gtagaggatc gagatctcga tcccgcgaaa ttaatacgac tcactatagg ggaattgtga    7200
gcggataaca attcccctct agaaataatt ttgtttaact ttaagaagga gatatacata    7260
tgcggggttc tcatcatcat catcatcatg gtatggctag catgactggt ggacagcaaa    7320
tgggtcggga tctgtacgac gatgacgata aggatcatcc cttcaccatg              7370
```

<210> SEQ ID NO 166
<211> LENGTH: 578
<212> TYPE: PRT
<213> ORGANISM: Artificial Sequence
<220> FEATURE:
<223> OTHER INFORMATION: Synthetic Construct

<400> SEQUENCE: 166

Met Arg Gly Ser His His His His His Gly Met Ala Ser Met Thr
1               5                   10                  15

Gly Gly Gln Gln Met Gly Arg Asp Leu Tyr Asp Asp Asp Lys Asp
            20                  25                  30

His Pro Phe Thr Met Arg Arg Ser Ala Asn Tyr Glu Pro Asn Ser Trp
        35                  40                  45

Asp Tyr Asp Tyr Leu Leu Ser Ser Asp Thr Asp Glu Ser Ile Glu Val
    50                  55                  60

Tyr Lys Asp Lys Ala Lys Lys Leu Glu Ala Glu Val Arg Arg Glu Ile
65                  70                  75                  80

Asn Asn Glu Lys Ala Glu Phe Leu Thr Leu Leu Glu Leu Ile Asp Asn
                85                  90                  95

Val Gln Arg Leu Gly Leu Gly Tyr Arg Phe Glu Ser Asp Ile Arg Arg
            100                 105                 110

Ala Leu Asp Arg Phe Val Ser Ser Gly Gly Phe Asp Ala Val Thr Lys
        115                 120                 125

Thr Ser Leu His Ala Thr Ala Leu Ser Phe Arg Leu Leu Arg Gln His
    130                 135                 140

Gly Phe Glu Val Ser Gln Glu Ala Phe Ser Gly Phe Lys Asp Gln Asn
145                 150                 155                 160

Gly Asn Phe Leu Glu Asn Leu Lys Glu Asp Ile Lys Ala Ile Leu Ser
                165                 170                 175

Leu Tyr Glu Ala Ser Phe Leu Ala Leu Glu Gly Glu Asn Ile Leu Asp
            180                 185                 190

Glu Ala Lys Val Phe Ala Ile Ser His Leu Lys Glu Leu Ser Glu Glu
        195                 200                 205

Lys Ile Gly Lys Asp Leu Ala Glu Gln Val Asn His Ala Leu Glu Leu
    210                 215                 220

Pro Leu His Arg Arg Thr Gln Arg Leu Glu Ala Val Leu Ser Ile Glu

```
             225                 230                 235                 240
Ala Tyr Arg Lys Lys Glu Asp Ala Asp Gln Val Leu Glu Leu Ala
                245                 250                 255

Ile Leu Asp Tyr Asn Met Ile Gln Ser Val Tyr Gln Arg Asp Leu Arg
                260                 265                 270

Glu Thr Ser Arg Trp Trp Arg Val Gly Leu Ala Thr Lys Leu His
            275                 280                 285

Phe Ala Arg Asp Arg Leu Ile Glu Ser Phe Tyr Trp Ala Val Gly Val
            290                 295                 300

Ala Phe Glu Pro Gln Tyr Ser Asp Cys Arg Asn Ser Val Ala Lys Met
305                 310                 315                 320

Phe Ser Phe Val Thr Ile Asp Asp Ile Tyr Asp Val Tyr Gly Thr
                325                 330                 335

Leu Asp Glu Leu Glu Leu Phe Thr Asn Ala Val Glu Arg Trp Asp Val
                340                 345                 350

Asn Ala Ile Asp Asp Leu Pro Asp Tyr Met Lys Leu Cys Phe Leu Ala
                355                 360                 365

Leu Tyr Asn Thr Ile Asn Glu Ile Ala Tyr Asp Asn Leu Lys Glu Lys
            370                 375                 380

Gly Glu Asn Ile Leu Pro Tyr Leu Thr Lys Ala Trp Ala Asp Leu Cys
385                 390                 395                 400

Asn Ala Phe Leu Gln Glu Ala Lys Trp Leu Tyr Asn Lys Ser Thr Pro
                405                 410                 415

Thr Phe Asp Glu Tyr Phe Gly Asn Ala Trp Lys Ser Ser Gly Pro
                420                 425                 430

Leu Gln Leu Val Phe Ala Tyr Phe Ala Val Val Gln Asn Ile Lys Lys
            435                 440                 445

Glu Glu Ile Glu Asn Leu Gln Lys Tyr His Asp Ile Ile Ser Arg Pro
            450                 455                 460

Ser His Ile Phe Arg Leu Cys Asn Asp Leu Ala Ser Ala Ser Ala Glu
465                 470                 475                 480

Ile Ala Arg Gly Glu Thr Ala Asn Ser Val Ser Cys Tyr Met Arg Thr
                485                 490                 495

Lys Gly Ile Ser Glu Glu Leu Ala Thr Glu Ser Val Met Asn Leu Ile
            500                 505                 510

Asp Glu Thr Trp Lys Lys Met Asn Lys Glu Lys Leu Gly Gly Ser Leu
            515                 520                 525

Phe Ala Lys Pro Phe Val Glu Thr Ala Ile Asn Leu Ala Arg Gln Ser
            530                 535                 540

His Cys Thr Tyr His Asn Gly Asp Ala His Thr Ser Pro Asp Glu Leu
545                 550                 555                 560

Thr Arg Lys Arg Val Leu Ser Val Ile Thr Glu Pro Ile Leu Pro Phe
                565                 570                 575

Glu Arg

<210> SEQ ID NO 167
<211> LENGTH: 7370
<212> TYPE: DNA
<213> ORGANISM: Artificial Sequence
<220> FEATURE:
<223> OTHER INFORMATION: Synthetic Construct

<400> SEQUENCE: 167
cgtcgttctg cgaactacga acctaacagc tgggactatg attacctgct gtcctccgac      60
```

-continued

```
acggacgagt ccatcgaagt atacaaagac aaagcgaaaa agctggaagc cgaagttcgt      120
cgcgagatta ataacgaaaa agcagaattt ctgaccctgc tggaactgat tgacaacgtc      180
cagcgcctgg gcctgggtta ccgtttcgag tctgatatcc gtcgtgcgct ggatcgcttc      240
gtttcctccg gcggcttcga tgcggtaacc aagacttccc tgcacgcgac ggcactgtct      300
ttccgtctgc tgcgtcaaca cggttttgag gtttctcagg aagcgttcag cggcttcaaa      360
gaccaaaacg gcaacttcct ggagaacctg aaggaagata tcaaagctat cctgagcctg      420
tacgaggcca gcttcctggc tctggaaggc gaaaacatcc tggacgaggc gaaggttttc      480
gcaatctctc atctgaaaga actgtctgaa gaaaagatcg gtaaagatct ggcagaacag      540
gtgaaccatg cactggaact gccactgcat cgccgtactc agcgtctgga agcagtactg      600
tctatcgagg cctaccgtaa aaaggaggac gcggatcagg ttctgctgga gctggcaatt      660
ctggattaca acatgatcca gtctgtatac cagcgtgatc tgcgtgaaac gtcccgttgg      720
tggcgtcgtg tgggtctggc gaccaaactg cactttgctc gtgaccgcct gattgagagc      780
ttctactggg ccgtgggtgt agcattcgaa ccgcaatact ccgactgccg taactccgtc      840
gcaaaaatgt tttctttcgt aaccattatc gacgatatct acgatgtata cggcaccctg      900
gacgaactgg agctgtttac taacgcagtt gagcgttggg acgtaaacgc catcgacgat      960
ctgccggatt acatgaaact gtgctttctg gctctgtata acactattaa cgaaatcgcc     1020
tacgacaacc tgaaagaaaa aggtgagaac atcctgccgt atctgaccaa agcctgggct     1080
gacctgtgca acgctttcct gcaagaagcc aagtggctgt acaacaaatc tactccgacc     1140
tttgacgaat acttcggcaa cgcatggaaa tcctcttctg gcccgctgca actggtgttc     1200
gcttacttcg ctgtcgtgca gaacattaaa aaggaagaga tcgaaaacct gcaaaaatac     1260
catgacatca tctctcgtcc ttcccatatc ttccgtctgt gcaatgacct ggctagcgcg     1320
tctgcggaaa ttgcgcgtgg tgaaaccgca atagcgtttc cttgttacat gcgcactaaa     1380
ggtatctccg aagaactggc taccgaaagc gtgatgaatc tgatcgatga aacctggaaa     1440
aagatgaaca aggaaaaact gggtggtagc ctgttcgcga accgttcgt ggaaaccgcg      1500 atcaacctgg cacgtcaatc tcactgcact tatcataacg gcgacgcgca tacctctccg     1560
gatgagctga cccgcaaacg cgttctgtct gtaatcactg aaccgattct gccgtttgaa     1620
cgctaaaagg gcgagctcaa cgatccggct gctaacaaag cccgaaagga agctgagttg     1680
gctgctgcca ccgctgagca ataactagca taacccttg gggcctctaa cgggtcttg      1740 aggagttttt tgctgaaagg aggaactata tccggatatc ccgcaagagg cccggcagta     1800
ccggcataac caagcctatg cctacagcat ccagggtgac ggtgccgagg atgacgatga     1860
gcgcattgtt agatttcata cacggtgcct gactgcgtta gcaatttaac tgtgataaac     1920
taccgcatta agcttatcg atgataagct gtcaaacatg agaattaatt cttgaagacg     1980
aaagggcctc gtgatacgcc tatttttata ggttaatgtc atgataataa tggtttctta     2040
gacgtcaggt ggcactttc ggggaaatgt gcgcggaacc cctatttgtt tattttcta      2100 aatacattca aatatgtatc cgctcatgag acaataaccc tgataaatgc ttcaataata     2160
ttgaaaaagg aagagtatga ttgaacaaga tggattgcac gcaggttctc cggccgcttg     2220
ggtggagagg ctattcggct atgactgggc acaactgaca atcggctgct ctgatgccgc     2280
cgtgttccgg ctgtcagcgc aggggcgccc ggttcttttt gtcaagaccg acctgtccgg     2340
tgccctgaat gaactgcagg acgaggcagc gcggctatcg tggctggcca cgacgggcgt     2400
tccttgcgca gctgtgctcg acgttgtcac tgaagcggga agggactggc tgctattggg     2460
```

```
cgaagtgccg gggcaggatc tcctgtcatc tcaccttgct cctgccgaga aagtatccat    2520
catggctgat gcaatgcggc ggctgcatac gcttgatccg gctacctgcc cattcgacca    2580
ccaagcgaaa catcgcatcg agcgggcacg tactcggatg gaagccggtc ttgtcgatca    2640
ggatgatctg gacgaagagc atcaggggct cgcgccagcc gaactgttcg ccaggctcaa    2700
ggcgcgcatg cccgacggcg aggatctcgt cgtgacacat ggcgatgcct gcttgccgaa    2760
tatcatggtg gaaaatggcc gcttttctgg attcatcgac tgtggccggc tgggtgtggc    2820
ggaccgctat caggacatag cgttggctac ccgtgatatt gctgaagagc ttggcggcga    2880
atgggctgac cgcttcctcg tgctttacgg tatcgccgct cccgattcgc agcgcatcgc    2940
cttctatcgc cttcttgacg agttcttctg agcgggactc tggggttcga atgaccgac     3000 caagcgacgc ctaactgtca gaccaagttt actcatatat actttagatt gatttaaaac    3060
ttcattttta atttaaaagg atctaggtga agatcctttt tgataatctc atgaccaaaa    3120
tcccttaacg tgagttttcg ttccactgag cgtcagaccc cgtagaaaag atcaaaggat    3180
cttcttgaga tcctttttt ctgcgcgtaa tctgctgctt gcaaacaaaa aaaccaccgc    3240
taccagcggt ggtttgtttg ccggatcaag agctaccaac tcttttccg aaggtaactg    3300 gcttcagcag agcgcagata ccaaatactg tccttctagt gtagccgtag ttaggccacc    3360
acttcaagaa ctctgtagca ccgcctacat acctcgctct gctaatcctg ttaccagtgg    3420
ctgctgccag tggcgataag tcgtgtctta ccgggttgga ctcaagacga tagttaccgg    3480
ataaggcgca gcggtcgggc tgaacggggg gttcgtgcac acagcccagc ttggagcgaa    3540
cgacctacac cgaactgaga tacctacagc gtgagctatg agaaagcgcc acgcttcccg    3600
aagggagaaa ggcggacagg tatccggtaa gcggcagggt cggaacagga gagcgcacga    3660
gggagcttcc agggggaaac gcctggtatc tttatagtcc tgtcgggttt cgccacctct    3720
gacttgagcg tcgatttttg tgatgctcgt caggggggcg gagcctatgg aaaaacgcca    3780
gcaacgcggc cttttacgg ttcctggcct tttgctggcc ttttgctcac atgttctttc    3840
ctgcgttatc ccctgattct gtggataacc gtattaccgc ctttgagtga gctgataccg    3900
ctcgccgcag ccgaacgacc gagcgcagcg agtcagtgag cgaggaagcg gaagagcgcc    3960
tgatgcggta ttttctcctt acgcatctgt gcggtatttc acaccgcaat ggtgcactct    4020
cagtacaatc tgctctgatg ccgcatagtt aagccagtat acactccgct atcgctacgt    4080
gactgggtca tggctgcgcc ccgacacccg ccaacacccg ctgacgcgcc ctgacgggct    4140
tgtctgctcc cggcatccgc ttacagacaa gctgtgaccg tctccgggag ctgcatgtgt    4200
cagaggtttt caccgtcatc accgaaacgc gcgaggcagc tgcggtaaag ctcatcagcg    4260
tggtcgtgaa gcgattcaca gatgtctgcc tgttcatccg cgtccagctc gttgagtttc    4320
tccagaagcg ttaatgtctg gcttctgata aagcgggcca tgttaagggc ggttttttcc    4380
tgtttggtca ctgatgcctc cgtgtaaggg ggatttctgt tcatgggggt aatgataccg    4440
atgaaacgag agaggatgct cacgatacgg gttactgatg atgaacatgc ccggttactg    4500
gaacgttgtg agggtaaaca actggcggta tggatgcggc gggaccagag aaaaatcact    4560
cagggtcaat gccagcgctt cgttaataca gatgtaggtg ttccacaggg tagccagcag    4620
catcctgcga tgcagatccg gaacataatg gtgcagggcg ctgacttccg cgtttccaga    4680
ctttacgaaa cacggaaacc gaagaccatt catgttgttg ctcaggtcgc agacgttttg    4740
cagcagcagt cgcttcacgt tcgctcgcgt atcggtgatt cattctgcta accagtaagg    4800
```

```
caaccccgcc agcctagccg ggtcctcaac gacaggagca cgatcatgcg cacccgtggc   4860
caggacccaa cgctgcccga gatgcgccgc gtgcggctgc tggagatggc ggacgcgatg   4920
gatatgttct gccaagggtt ggtttgcgca ttcacagttc tccgcaagaa ttgattggct   4980
ccaattcttg gagtggtgaa tccgttagcg aggtgccgcc ggcttccatt caggtcgagg   5040
tggcccggct ccatgcaccg cgacgcaacg cggggaggca gacaaggtat agggcggcgc   5100
ctacaatcca tgccaacccg ttccatgtgc tcgccgaggc ggcataaatc gccgtgacga   5160
tcagcggtcc aatgatcgaa gttaggctgg taagagccgc gagcgatcct tgaagctgtc   5220
cctgatggtc gtcatctacc tgcctggaca gcatggcctg caacgcgggc atcccgatgc   5280
cgccggaagc gagaagaatc ataatgggga aggccatcca gcctcgcgtc gcgaacgcca   5340
gcaagacgta gcccagcgcg tcggccgcca tgccggcgat aatggcctgc ttctcgccga   5400
aacgtttggt ggcgggacca gtgacgaagg cttgagcgag ggcgtgcaag attccgaata   5460
ccgcaagcga caggccgatc atcgtcgcgc tccagcgaaa gcggtcctcg ccgaaaatga   5520
cccagagcgc tgccggcacc tgtcctacga gttgcatgat aaagaagaca gtcataagtg   5580
cggcgacgat agtcatgccc cgcgcccacc ggaaggagct gactgggttg aaggctctca   5640
agggcatcgg tcgagatccc ggtgcctaat gagtgagcta acttacatta attgcgttgc   5700
gctcactgcc cgctttccag tcgggaaacc tgtcgtgcca gctgcattaa tgaatcggcc   5760
aacgcgcggg gagaggcggt ttgcgtattg ggcgccaggg tggttttct tttcaccagt    5820
gagacgggca acagctgatt gcccttcacc gcctggccct gagagagttg cagcaagcgg   5880
tccacgctgg tttgccccag caggcgaaaa tcctgtttga tggtggttaa cggcgggata   5940
taacatgagc tgtcttcggt atcgtcgtat cccactaccg agatatccgc accaacgcgc   6000
agcccggact cggtaatggc gcgcattgcg cccagcgcca tctgatcgtt ggcaaccagc   6060
atcgcagtgg gaacgatgcc ctcattcagc atttgcatgg tttgttgaaa accggacatg   6120
gcactccagt cgccttcccg ttccgctatc ggctgaattt gattgcgagt gagatattta   6180
tgccagccag ccagacgcag acgcgccgag acagaactta atgggcccgc taacagcgcg   6240
atttgctggt gacccaatgc gaccagatgc tccacgccca gtcgcgtacc gtcttcatgg   6300
gagaaaataa tactgttgat gggtgtctgg tcagagacat caagaaataa cgccggaaca   6360
ttagtgcagg cagcttccac agcaatggca tcctggtcat ccagcggata gttaatgatc   6420
agcccactga cgcgttgcgc gagaagattg tgcaccgccg ctttacaggc ttcgacgccg   6480
cttcgttcta ccatcgacac caccacgctg cacccagtt gatcggcgcg agatttaatc    6540
gccgcgacaa tttgcgacgg cgcgtgcagg ccagactgg aggtggcaac gccaatcagc    6600
aacgactgtt tgcccgccag ttgttgtgcc acgcggttgg gaatgtaatt cagctccgcc   6660
atcgccgctt ccacttttc ccgcgttttc gcagaaacgt ggctggcctg gttcaccacg    6720
cgggaaacgg tctgataaga gacaccggca tactctgcga catcgtataa cgttactggt   6780
ttcacattca ccaccctgaa ttgactctct tccgggcgct atcatgccat accgcgaaag   6840
gttttgcgcc attcgatggt gtccgggatc tcgacgctct cccttatgcg actcctgcat   6900
taggaagcag cccagtagta ggttgaggcc gttgagcacc gccgcgcaa ggaatggtgc     6960
atgcaaggag atggcgccca acagtccccc ggccacgggg cctgccacca tacccacgcc   7020
gaaacaagcg ctcatgagcc cgaagtggcg agcccgatct tccccatcgg tgatgtcggc   7080
gatataggcg ccagcaaccg cacctgtggc gccggtgatg ccggccacga tgcgtccggc   7140
gtagaggatc gagatctcga tcccgcgaaa ttaatacgac tcactatagg ggaattgtga   7200
```

```
gcggataaca attccctct agaaataatt ttgtttaact ttaagaagga gatatacata    7260
tgcggggttc tcatcatcat catcatcatg gtatggctag catgactggt ggacagcaaa    7320
tgggtcggga tctgtacgac gatgacgata aggatcatcc cttcaccatg              7370
```